United States Patent
Wiles et al.

(10) Patent No.: US 11,718,626 B2
(45) Date of Patent: Aug. 8, 2023

(54) MACROCYCLIC COMPOUNDS FOR TREATMENT OF MEDICAL DISORDERS

(71) Applicant: Achillion Pharmaceuticals, Inc., Boston, MA (US)

(72) Inventors: Jason Allan Wiles, Madison, CT (US); Avinash S. Phadke, Branford, CT (US); Dawei Chen, Guilford, CT (US); Venkat Rao Gadhachanda, Hamden, CT (US); Joel Charles Barrish, Richboro, CT (US); Atul Agarwal, Hamden, CT (US); Kyle J. Eastman, New Haven, CT (US)

(73) Assignee: Achillion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 17/314,155

(22) Filed: May 7, 2021

(65) Prior Publication Data
US 2021/0300934 A1 Sep. 30, 2021

Related U.S. Application Data

(60) Division of application No. 16/555,930, filed on Aug. 29, 2019, now Pat. No. 11,053,253, which is a continuation of application No. PCT/US2018/020531, filed on Mar. 1, 2018.

(60) Provisional application No. 62/500,287, filed on May 2, 2017, provisional application No. 62/466,252, filed on Mar. 2, 2017, provisional application No. 62/465,600, filed on Mar. 1, 2017.

(51) Int. Cl.
| | | |
|---|---|---|
| *C07D 487/08* | (2006.01) | |
| *C07D 498/08* | (2006.01) | |
| *C07D 513/08* | (2006.01) | |
| *C07D 487/18* | (2006.01) | |
| *A61P 7/00* | (2006.01) | |
| *A61P 31/12* | (2006.01) | |
| *A61P 7/02* | (2006.01) | |

(52) U.S. Cl.
CPC .............. *C07D 487/08* (2013.01); *A61P 7/00* (2018.01); *A61P 7/02* (2018.01); *A61P 31/12* (2018.01); *C07D 487/18* (2013.01); *C07D 498/08* (2013.01); *C07D 513/08* (2013.01)

(58) Field of Classification Search
CPC ... C07D 487/08; C07D 487/18; C07D 498/08
See application file for complete search history.

(56) References Cited

U.S. PATENT DOCUMENTS

| | | |
|---|---|---|
| 6,489,476 B1 | 12/2002 | Dang et al. |
| 6,653,340 B1 | 11/2003 | Babu et al. |
| 7,629,340 B2 | 12/2009 | Schmitz et al. |
| 8,524,716 B2 | 9/2013 | Raboisson et al. |
| 9,085,555 B2 | 7/2015 | Altmann et al. |
| 9,421,240 B2 | 8/2016 | Francois et al. |
| 9,468,661 B2 | 10/2016 | Altmann et al. |
| 9,598,446 B2 | 3/2017 | Gadhachanda et al. |
| 9,643,986 B2 | 5/2017 | Wiles et al. |
| 9,663,543 B2 | 5/2017 | Wiles et al. |
| 9,695,205 B2 | 7/2017 | Wiles et al. |
| 9,732,103 B2 | 8/2017 | Wiles et al. |
| 9,732,104 B2 | 8/2017 | Gadhachanda et al. |
| 9,758,537 B2 | 9/2017 | Wiles et al. |
| 9,796,741 B2 | 10/2017 | Gadhachanda et al. |
| 9,828,396 B2 | 11/2017 | Wiles et al. |
| 10,000,516 B2 | 6/2018 | Wiles et al. |
| 10,005,802 B2 | 6/2018 | Wiles et al. |
| 10,011,612 B2 | 7/2018 | Wiles et al. |
| 10,081,645 B2 | 9/2018 | Wiles et al. |
| 10,087,203 B2 | 10/2018 | Wiles et al. |
| 10,092,547 B2 | 10/2018 | Wiles et al. |
| 10,092,584 B2 | 10/2018 | Wiles et al. |
| 10,100,072 B2 | 10/2018 | Wiles et al. |
| 10,106,563 B2 | 10/2018 | Wiles et al. |
| 10,138,225 B2 | 11/2018 | Wiles et al. |
| 10,189,869 B2 | 1/2019 | Gadhachanda et al. |
| 10,253,053 B2 | 4/2019 | Wiles et al. |
| 10,287,301 B2 | 5/2019 | Wiles et al. |
| 10,301,336 B2 | 5/2019 | Wiles et al. |
| 10,370,394 B2 | 8/2019 | Wiles et al. |
| 10,385,097 B2 | 8/2019 | Wiles et al. |

(Continued)

FOREIGN PATENT DOCUMENTS

| | | |
|---|---|---|
| CN | 103402996 A | 11/2013 |
| EA | 201890594 A1 | 8/2018 |

(Continued)

OTHER PUBLICATIONS

"Are There Any Treatments for ALS?" WebMD, <https://www.webmd.com/brain/understanding-als-treatment#1>, retrieved on May 3, 2019 (8 pages).

"Arteriosclerosis/atherosclerosis," Mayo Clinic, <https://www.mayoclinic.org/diseases-conditions/arteriosclerosis-atherosclerosis/diagnosis-treatment/drc-20350575>, retrieved on Apr. 24, 2018 (10 pages).

"Cancer," MedLine Plus, <http://www.nlm.nih.gov/medlineplus/cancer.html>, retrieved Jul. 6, 2007 (10 pages).

(Continued)

*Primary Examiner* — Susanna Moore
(74) *Attorney, Agent, or Firm* — Clark & Elbing LLP

(57) ABSTRACT

Macrocyclic Complement Factor D inhibitors, pharmaceutical compositions, and uses thereof, as well as processes for their manufacture are provided. The compounds provided include Formula I, Formula II, Formula III, Formula IV, Formula V, Formula VI, Formula VII, and Formula VIII or a pharmaceutically acceptable salt, prodrug, isotopic analog, N-oxide, or isolated isomer thereof, optionally in a pharmaceutically acceptable composition. The inhibitors described herein target Factor D and inhibit or regulate the complement cascade.

21 Claims, 4 Drawing Sheets

(56) References Cited

U.S. PATENT DOCUMENTS

| | | |
|---|---|---|
| 10,428,094 B2 | 10/2019 | Wiles et al. |
| 10,428,095 B2 | 10/2019 | Wiles et al. |
| 10,464,956 B2 | 11/2019 | Wiles et al. |
| 10,550,140 B2 | 2/2020 | Wiles et al. |
| 10,660,876 B2 | 5/2020 | Wiles et al. |
| 10,662,175 B2 | 5/2020 | Wiles et al. |
| 10,807,952 B2 | 10/2020 | Wiles et al. |
| 10,822,352 B2 | 11/2020 | Wiles et al. |
| 10,906,887 B2 | 2/2021 | Wiles et al. |
| 10,919,884 B2 | 2/2021 | Wiles et al. |
| 11,001,600 B2 | 5/2021 | Wiles et al. |
| 11,053,253 B2 | 7/2021 | Wiles et al. |
| 11,084,800 B2 | 8/2021 | Wiles et al. |
| 11,407,738 B2 | 8/2022 | Wiles et al. |
| 11,447,465 B2 | 9/2022 | Wiles et al. |
| 2002/0133004 A1 | 9/2002 | Sekiyama et al. |
| 2005/0228000 A1 | 10/2005 | Smallheer et al. |
| 2005/0267108 A1 | 12/2005 | Hsieh et al. |
| 2007/0155712 A1 | 7/2007 | Zahn et al. |
| 2008/0075720 A1 | 3/2008 | Holers et al. |
| 2008/0075728 A1 | 3/2008 | Newman |
| 2008/0108691 A1 | 5/2008 | Hamann et al. |
| 2010/0041628 A1 | 2/2010 | Enomoto et al. |
| 2011/0280808 A1 | 11/2011 | Kroth et al. |
| 2012/0231471 A1 | 9/2012 | Sato et al. |
| 2012/0295884 A1 | 11/2012 | Altmann et al. |
| 2013/0296377 A1 | 11/2013 | Adams et al. |
| 2013/0344073 A1 | 12/2013 | Schwaeble et al. |
| 2014/0371133 A1 | 12/2014 | Francois et al. |
| 2015/0141455 A1 | 5/2015 | Altmann et al. |
| 2015/0148374 A1 | 5/2015 | Hommel et al. |
| 2015/0191462 A1 | 7/2015 | Hommel et al. |
| 2015/0239837 A1 | 8/2015 | Wiles et al. |
| 2015/0239838 A1 | 8/2015 | Phadke et al. |
| 2015/0239868 A1 | 8/2015 | Pais et al. |
| 2015/0239893 A1 | 8/2015 | Wang et al. |
| 2015/0239894 A1 | 8/2015 | Gadhachanda et al. |
| 2015/0239895 A1 | 8/2015 | Gadhachanda et al. |
| 2015/0239919 A1 | 8/2015 | Gadhachanda et al. |
| 2015/0239920 A1 | 8/2015 | Gadhachanda et al. |
| 2015/0239921 A1 | 8/2015 | Wiles et al. |
| 2015/0269868 A1 | 9/2015 | Carney et al. |
| 2015/0322060 A1 | 11/2015 | Flohr et al. |
| 2015/0368271 A1 | 12/2015 | Su et al. |
| 2016/0015810 A1 | 1/2016 | Deschatelets et al. |
| 2016/0024079 A1 | 1/2016 | Adams et al. |
| 2016/0361329 A1 | 12/2016 | Wiles et al. |
| 2016/0362398 A1 | 12/2016 | Wiles et al. |
| 2016/0362399 A1 | 12/2016 | Wiles et al. |
| 2016/0362432 A1 | 12/2016 | Wiles et al. |
| 2016/0362433 A1 | 12/2016 | Wiles et al. |
| 2017/0056428 A1 | 3/2017 | Wiles et al. |
| 2017/0057950 A1 | 3/2017 | Wiles et al. |
| 2017/0057983 A1 | 3/2017 | Wiles et al. |
| 2017/0057993 A1 | 3/2017 | Wiles et al. |
| 2017/0066783 A1 | 3/2017 | Wiles et al. |
| 2017/0189410 A1 | 7/2017 | Gadhachanda et al. |
| 2017/0226142 A1 | 8/2017 | Wiles et al. |
| 2017/0260219 A1 | 9/2017 | Wiles et al. |
| 2017/0298084 A1 | 10/2017 | Wiles et al. |
| 2017/0298085 A1 | 10/2017 | Wiles et al. |
| 2018/0022766 A1 | 1/2018 | Wiles et al. |
| 2018/0022767 A1 | 1/2018 | Wiles et al. |
| 2018/0030075 A1 | 2/2018 | Wiles et al. |
| 2018/0072762 A1 | 3/2018 | Wiles et al. |
| 2018/0177761 A1 | 6/2018 | Wiles et al. |
| 2018/0179185 A1 | 6/2018 | Wiles et al. |
| 2018/0179186 A1 | 6/2018 | Wiles et al. |
| 2018/0179236 A1 | 6/2018 | Wiles et al. |
| 2018/0186782 A1 | 7/2018 | Wiles et al. |
| 2018/0201580 A1 | 7/2018 | Wiles et al. |
| 2018/0305375 A1 | 10/2018 | Wiles et al. |
| 2019/0023729 A1 | 1/2019 | Wiles et al. |
| 2019/0031692 A1 | 1/2019 | Wiles et al. |
| 2019/0038623 A1 | 2/2019 | Huang et al. |
| 2019/0048033 A1 | 2/2019 | Wiles et al. |
| 2019/0085005 A1 | 3/2019 | Wiles et al. |
| 2019/0144473 A1 | 5/2019 | Gadhachanda et al. |
| 2019/0211033 A1 | 7/2019 | Wiles et al. |
| 2019/0382376 A1 | 12/2019 | Wiles et al. |
| 2020/0002347 A1 | 1/2020 | Wiles et al. |
| 2020/0062790 A1 | 2/2020 | Wiles et al. |
| 2020/0071301 A1 | 3/2020 | Wiles et al. |
| 2020/0101071 A1 | 4/2020 | Huang et al. |
| 2020/0262818 A1 | 8/2020 | Wiles et al. |
| 2021/0332026 A1 | 10/2021 | Phadke et al. |
| 2022/0079943 A1 | 3/2022 | Huang et al. |

FOREIGN PATENT DOCUMENTS

| | | |
|---|---|---|
| JP | 2014-506877 A | 3/2014 |
| JP | 2015-522005 A | 8/2015 |
| JP | 2015-522006 A | 8/2015 |
| JP | 2015-522007 A | 8/2015 |
| JP | 2015-522008 A | 8/2015 |
| JP | 2015-522062 A | 8/2015 |
| JP | 2017-511815 A | 4/2017 |
| JP | 6400738 B2 | 10/2018 |
| JP | 2018-199714 A | 12/2018 |
| JP | 6537532 B2 | 7/2019 |
| JP | 6688352 B2 | 4/2020 |
| WO | WO-93/20099 A2 | 10/1993 |
| WO | WO-95/29697 A1 | 11/1995 |
| WO | WO-99/48492 A1 | 9/1999 |
| WO | WO-2004/007501 A1 | 1/2004 |
| WO | WO-2004/045518 A2 | 6/2004 |
| WO | WO-2004/111041 A1 | 12/2004 |
| WO | WO-2008/047831 A1 | 4/2008 |
| WO | WO-2009/091826 A2 | 7/2009 |
| WO | WO-2011/057158 A1 | 5/2011 |
| WO | WO-2012/093101 A1 | 7/2012 |
| WO | WO-2012/177782 A1 | 12/2012 |
| WO | WO-2013/166436 A1 | 11/2013 |
| WO | WO-2013/192345 A1 | 12/2013 |
| WO | WO-2014/002051 A2 | 1/2014 |
| WO | WO-2014/002052 A1 | 1/2014 |
| WO | WO-2014/002053 A1 | 1/2014 |
| WO | WO-2014/002054 A1 | 1/2014 |
| WO | WO-2014/002057 A1 | 1/2014 |
| WO | WO-2014/002058 A2 | 1/2014 |
| WO | WO-2014/002059 A1 | 1/2014 |
| WO | WO-2014/005150 A1 | 1/2014 |
| WO | WO-2014/009833 A2 | 1/2014 |
| WO | WO-2014/037480 A1 | 3/2014 |
| WO | WO-2014/116880 A1 | 7/2014 |
| WO | WO-2015/008861 A1 | 1/2015 |
| WO | WO-2015/130784 A1 | 9/2015 |
| WO | WO-2015/130795 A1 | 9/2015 |
| WO | WO-2015/130806 A1 | 9/2015 |
| WO | WO-2015/130830 A1 | 9/2015 |
| WO | WO-2015/130838 A1 | 9/2015 |
| WO | WO-2015/130842 A2 | 9/2015 |
| WO | WO-2015/130845 A1 | 9/2015 |
| WO | WO-2015/130854 A1 | 9/2015 |
| WO | WO-2017/035348 A1 | 3/2017 |
| WO | WO-2017/035349 A1 | 3/2017 |
| WO | WO-2017/035351 A1 | 3/2017 |
| WO | WO-2017/035352 A1 | 3/2017 |
| WO | WO-2017/035353 A1 | 3/2017 |
| WO | WO-2017/035355 A1 | 3/2017 |
| WO | WO-2017/035357 A1 | 3/2017 |
| WO | WO-2017/035360 A1 | 3/2017 |
| WO | WO-2017/035361 A1 | 3/2017 |
| WO | WO-2017/035362 A1 | 3/2017 |
| WO | WO-2017/035401 A1 | 3/2017 |
| WO | WO-2017/035405 A1 | 3/2017 |
| WO | WO-2017/035408 A1 | 3/2017 |
| WO | WO-2017/035409 A1 | 3/2017 |
| WO | WO-2017/035411 A1 | 3/2017 |
| WO | WO-2017/035413 A2 | 3/2017 |
| WO | WO-2017/035415 A1 | 3/2017 |
| WO | WO-2017/035417 A1 | 3/2017 |
| WO | WO-2017/035418 A1 | 3/2017 |
| WO | WO-2017/098328 A2 | 6/2017 |

(56) References Cited

FOREIGN PATENT DOCUMENTS

| WO | WO-2017/136395 A1 | 8/2017 |
|---|---|---|
| WO | WO-2018/005552 A1 | 1/2018 |
| WO | WO-2018/160889 A1 | 9/2018 |
| WO | WO-2018/160891 A1 | 9/2018 |
| WO | WO-2018/160892 A1 | 9/2018 |
| WO | WO-2019/028284 A1 | 2/2019 |
| WO | WO-2019/070714 A1 | 4/2019 |
| WO | WO-2020/069024 A1 | 4/2020 |
| WO | WO-2020/109343 A1 | 6/2020 |
| WO | WO-2021/021909 A1 | 2/2021 |

OTHER PUBLICATIONS

"Dermatomyositis," Mayo Clinic, <https://www.mayoclinic.org/diseases-conditions/dermatomyositis/diagnosis-treatment/drc-20353192>, retrieved on Aug. 1, 2017 (7 pages).
"History of Changes for Study: NCT03053102—A Treatment Study of ACH-0144471 in Patients With Paroxysmal Nocturnal Hemoglobinuria (PNH)," U.S. National Library of Medicine, available at: <https://clinicaltrials.gov/ct2/history/NCT03053102?V_4=View#StudyPageTop>, submitted Jun. 6, 2017, retrieved Mar. 9, 2021 (3 pages).
"NCT03472885—A Treatment Study of ACH-0144471 in Patients With Paroxysmal Nocturnal Hemoglobinuria (PNH) With Inadequate Response to Eculizumab (PNH)," U.S. National Library of Medicine, available at: <https://clinicaltrials.gov/ct2/show/NCT03472885>, first posted Mar. 21, 2018, last update posted Dec. 3, 2019, retrieved Mar. 27, 2020 (7 pages).
"Reperfusion injury," Wikipedia, <https://en.wikipedia.org/wiki/Reperfusion_injury>, retrieved Apr. 30, 2020 (8 pages).
"Treatment for Multiple Sclerosis," WebMD, <https://www.webmd.com/multiple-sclerosis/ms-treatment#1>, retrieved on May 3, 2019 (24 pages).
"What Are the Treatments for Cirrhosis?," WebMD, <https://www.webmd.com/digestive-disorders/understanding-cirrhosis-treatment#1>, retrieved May 3, 2019 (15 pages).
"What is Cardiovascular Disease?" American Heart Association, <https://www.heart.org/en/health-topics/consumer-healthcare/what-is-cardiovascular-disease>, dated May 31, 2017 (4 pages).
Airey et al., "A Convenient Preparation of Thieno[3,2-c]pyrazole," Synthesis. 46: 96-100 (2014).
Armand, "Fatty liver disease: What it is and what to do about it," Harvard Health Publishing, <https://www.health.harvard.edu/blog/fatty-liver-disease-what-it-is-and-what-to-do-about-it-2019011015746>, dated Jan. 10, 2019, retrieved May 2, 2019 (3 pages).
Barraclough et al., "Synthesis of (2S,3R)- and (2S,3S)-[3-$^2$H$_1$]-proline via highly selective hydrolysis of a silyl enol ether," Tetrahedron Letters. 46(1): 4653-4655 (2005).
Barraclough et al., "Two separate and distinct syntheses of stereospecifically deuterated samples of (2S)-proline," Org Biomol Chem. 4(8):1483-1491 (2006).
Carter, "Complement Activation: An Emerging Player in the Pathogenesis of Cardiovascular Disease," Scientifica. 2012:402783 (2012) (14 pages).
CAS RN 1236228-05-9, dated Aug. 16, 2010 (1 page).
CAS RN 1236251-51-6, dated Aug. 17, 2010 (2 pages).
CAS RN 1270608-88-2, dated 2019 (1 page).
CAS RN 1277041-86-7, dated Apr. 8, 2011 (2 pages).
Cole et al. "Structure of 3,4-Dichloroisocoumarin-Inhibited Factor D," Acta Crystallogr D Biol Crystallogr. 54(Pt 5): 711-717 (1998).
Compound Summary for CID 1129904, PubChem. <https://pubchem.ncbi.nlm.nih.gov/compound/1129904> retrieved Jul. 14, 2020, created Jul. 10, 2005 (10 pages).
Compound Summary for CID 118324207, PubChem, <https://pubchem.ncbi.nlm.nih.gov/compound/118324207>, dated Feb. 23, 2016, retrieved on Jul. 14, 2020 (8 pages).
Compound Summary for CID 123543544, PubChem, <https://pubchem.ncbi.nlm.nih.gov/compound/123543544>, created on Jan. 25, 2017, retrieved on Jul. 13, 2020 (8 pages).
Compound Summary for CID 134222466, PubChem, <https://pubchem.ncbi.nlm.nih.gov/compound/134222466>, created on Jun. 23, 2018, retrieved on Jul. 14, 2020 (11 pages).
Compound Summary for CID 59912842, PubChem, <https://pubchem.ncbi.nlm.nih.gov/compound/59912842>, created Aug. 20, 2012, retrieved Jul. 14, 2020 (9 pages).
Database Registry Chemical Abstracts Service, Columbus, Ohio, Accession No. RN1236248-20-6, Entered STN: Aug. 16, 2010 (1 page).
Database Registry Chemical Abstracts Service, Columbus, Ohio, Accession No. RN1380849-41-1, Entered STN: Jul. 3, 2012 (2 pages).
De Luca et al., "HIV-1 integrase strand-transfer inhibitors: Design, synthesis and molecular modeling investigation," Eur J Med Chem. 46(2): 756-764 (2011).
DeZern et al., "Paroxysmal nocturnal hemoglobinuria: a complement-mediated hemolytic anemia," available in PMC Dec. 30, 2015, published in final edited form as: Hematol Oncol Clin North Am. 29(3):479-94 (2015) (18 pages).
Donthiri et al., "Copper-Catalyzed C—H Functionalization of Pyridines and Isoquinolines with Vinyl Azides: Synthesis of Imidazo Heterocycles," J Org Chem. 79(22): 11277-11284 (2014).
Dormoy et al., "Synthesis of N-t-Butoxycarbonyl-4,4-dideuterio-L-proline," Synthesis. 1: 81-82 (1986).
Ellis-Pegler et al., "An Orally Administered Small Molecule Factor D Inhibitor (ACH-4471) for Treatment of PNH and Complement Diseases: Preliminary Phase 1 Results In Healthy Volunteers," European Hematology Association. Abstract LB2250, available <https://library.ehaweb.org/eha/2016/21st/135361/roderick.b.ellis-pegler.an.orally.administered.small.molecule.factor.d.html> (2016) (2 pages).
Ellis-Pegler et al., "An Orally Administered Small Molecule Factor D Inhibitor (ACH-4471) for Treatment of PNH, C3G and Complement-Mediated Diseases: Interim Phase 1 Results In Healthy Volunteers," European Hematology Association, Copenhagen 21st Congress, Jun. 9-12, Abstract ID: EHA-4145 (2016).
Gadhachanda et al., CAplus Database Summary Sheet for Document No. 164:507515, Accession No. 2016:627420, CAplus on STN. (2016) (6 pages).
Gavrilaki et al., "275 Small Molecule Factor D Inhibitors Block Complement Activation in Paroxysmal Nocturnal Hemoglobinuria and Atypical Hemolytic Uremic Syndrome," ASH 57th Annual Meeting & Exposition, Session: 101. Dec. 6, 2015 (2 pages).
Golub et al., "Molecular classification of cancer: class discovery and class prediction by gene expression monitoring," Science. 286(5439):531-537 (1999) (8 pages).
Haddrill, "Stargardt's Disease (Fundus Flavimaculatus)," All About Vision, <https://www.allaboutvision.com/conditions/stargardts.htm#article-section-2>, retrieved May 3, 2019 (5 pages).
Hecker et al., "Liver-Targeted Prodrugs of 2'-C-Methyladenosine for Therapy of Hepatitis C Virus Infection," J Med Chem. 50(16): 3891-3896 (2007).
Hruby et al., "$^{13}$C Nuclear Magnetic Resonance Studies of the Peptide Hormones Oxytocin, Arginine Vasopressin, Isotocin, Mesotocin, Glumitocin, Aspartocin, Related Analogues, and Diastereoisomers. Use of Specifically Deuterated Hormone Derivatives for Assignments and Effects of Structural Changes on $^{13}$C NMR Chemical Shifts in Peptides," J Am Chem Soc. 101(1): 202-212 (1979).
International Search Report and Written Opinion for International Application No. PCT/US2015/017523, dated May 14, 2015 (7 pages).
International Search Report and Written Opinion for International Application No. PCT/US2015/017538, dated May 14, 2015 (8 pages).
International Search Report and Written Opinion for International Application No. PCT/US2015/017554, dated May 14, 2015 (7 pages).
International Search Report and Written Opinion for International Application No. PCT/US2015/017583, dated May 27, 2015 (12 pages).

(56) References Cited

OTHER PUBLICATIONS

International Search Report and Written Opinion for International Application No. PCT/US2015/017593, dated Jun. 16, 2015 (6 pages).
International Search Report and Written Opinion for International Application No. PCT/US2015/017597, dated Jan. 29, 2016 (10 pages).
International Search Report and Written Opinion for International Application No. PCT/US2015/017600, dated May 27, 2015 (12 pages).
International Search Report and Written Opinion for International Application No. PCT/US2015/017609, dated May 29, 2015 (6 pages).
International Search Report and Written Opinion for International Application No. PCT/US2016/048688, dated Dec. 28, 2016 (11 pages).
International Search Report and Written Opinion for International Application No. PCT/US2016/048690, dated Dec. 28, 2016 (11 pages).
International Search Report and Written Opinion for International Application No. PCT/US2016/048693, dated Jan. 13, 2017 (11 pages).
International Search Report and Written Opinion for International Application No. PCT/US2016/048695, dated Dec. 30, 2016 (10 pages).
International Search Report and Written Opinion for International Application No. PCT/US2016/048696, dated Jan. 5, 2017 (10 pages).
International Search Report and Written Opinion for International Application No. PCT/US2016/048701, dated Jan. 10, 2017 (10 pages).
International Search Report and Written Opinion for International Application No. PCT/US2016/048704, dated Dec. 27, 2016 (7 pages).
International Search Report and Written Opinion for International Application No. PCT/US2016/048707, dated Jan. 5, 2017 (10 pages).
International Search Report and Written Opinion for International Application No. PCT/US2016/048709, dated Jan. 17, 2017 (9 pages).
International Search Report and Written Opinion for International Application No. PCT/US2016/048710, dated Jan. 5, 2017 (8 pages).
International Search Report and Written Opinion for International Application No. PCT/US2016/048779, dated Dec. 27, 2016 (8 pages).
International Search Report and Written Opinion for International Application No. PCT/US2016/048783, dated Feb. 3, 2017 (8 pages).
International Search Report and Written Opinion for International Application No. PCT/US2016/048787, dated Jan. 5, 2017 (13 pages).
International Search Report and Written Opinion for International Application No. PCT/US2016/048788, dated Jan. 5, 2017 (12 pages).
International Search Report and Written Opinion for International Application No. PCT/US2016/048793, dated Dec. 28, 2016 (8 pages).
International Search Report and Written Opinion for International Application No. PCT/US2016/048795, dated Feb. 17, 2017 (12 pages).
International Search Report and Written Opinion for International Application No. PCT/US2016/048797, dated Jan. 5, 2017 (12 pages).
International Search Report and Written Opinion for International Application No. PCT/US2016/048799, dated Nov. 15, 2016 (7 pages).
International Search Report and Written Opinion for International Application No. PCT/US2016/048800, dated Jan. 5, 2017 (12 pages).
International Search Report for International Application No. PCT/US18/20530, dated Jun. 25, 2018 (3 pages).
International Search Report for International Application No. PCT/US2018/020528, dated Apr. 24, 2018 (3 pages).
International Search Report for International Application No. PCT/US2018/20531, dated May 15, 2018 (3 pages).
International Search Report for International Application No. PCT/US2019/034210, dated Sep. 13, 2019 (4 pages).
International Search Report for International Application No. PCT/US2019/047252, dated Dec. 17, 2019 (4 pages).
International Search Report for International Application No. PCT/US2019/050065, dated Feb. 25, 2020 (4 pages).
International Search Report for International Application No. PCT/US2019/053012, dated Jan. 28, 2020 (4 pages).
International Search Report for International Application No. PCT/US2019/066999, dated Feb. 12, 2020 (3 pages).
Józsi, "Anti-Complement Autoantibodies in Membranoproliferative Glomerulonephritis and Dense Deposit Disease", *An Update on Glomerulopathies—Etiology and Pathogenesis*. Prof. Sharma Prabhakar, 31-46 (2011) (18 pages).
Kathuria, "Membranoproliferative Glomerulonephritis Medication," Medscape, <https://emedicine.medscape.com/article/240056-medication>, updated Jun. 23, 2016, retrieved May 3, 2019, (1 page).
Kinman, "COPD Drugs: A List of Medications to Help Relieve Your Symptoms," Healthline, <https://www.healthline.com/health/copd/drugs>, retrieved on May 3, 2019 (12 pages).
Kobayashi et al., "Carboxylation of alkynylsilanes with carbon dioxide mediated by cesium fluoride in DMSO," Org Biomol Chem. 11:3773-3775 (2013).
Komiya et al., CAplus Database Summary Sheet for Document No. 162:229476, Accession No. 2015:126147, CAplus on STN. (2015) (2 pages).
Kuang et al., "Synthesis of (Z)-1-bromo-1-alkenes and terminal alkynes from anti-2,3-dibromoalkanoic acids by microwave-induced reaction," Tetrahedron. 61(16):4043-4052 (2005).
Lala et al., "Role of nitric oxide in tumor progression: lessons from experimental tumors," Cancer Metastasis Rev. 17(1):91-106 (1998).
Lassmann, "What drives disease in multiple sclerosis: Inflammation or neurodegeneration?" Clinical and Experimental Neuroimmunology. 1:2-11 (2010).
MacKay et al., "Rapid Synthesis of the N-Methylwelwitindolinone Skeleton," Org Lett. 7(16):3421-4 (2005).
Noris et al., "Overview of Complement Activation and Regulation," Semin Nephrol. 33:479-492 (2013).
Office Action issued for Eurasian Patent Application No. 201992005, dated Oct. 23, 2020 (6 pages).
Okutani et al., "Conversion of Bromoalkenes into Alkynes by Wet Tetra-n-butylammonium Fluoride," J Org Chem. 74(1):442-444 (2009).
Oseini et al., "Therapies in Non-Alcoholic Steatohepatitis (NASH)," available in PMC Jan. 1, 2018, published in final edited form as: Liver Int. 37(Suppl 1):97-103 (2017) (15 pages).
Pandya et al., "Complement System in Lung Disease," Am J Respir Cell Mol Biol. 51(4):467-473 (2014).
Partial Supplementary European Search Report for European Application No. 18761960.6, dated Nov. 27, 2020 (12 pages).
Patel et al., "In Vitro Combination Studies of ACH-4471 with Eculizumab to Assess a Potential 'Switch' Treatment Approach for Paroxysmal Nocturnal Hemoglobinuria" 59th American Society of Hematology Annual Meeting and Exposition, Dec. 9-12, Atlanta, Georgia, Poster Abstract 2198 (2017).
Peifer et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors," J Med Chem. 51(13):3814-3824 (2008).
Pugsley et al., "Inhibitors of the complement system currently in development for cardiovascular disease," Cardiovasc Toxicol. 3(1):43-69 (2003).
Qu et al., "Recent Developments in Low Molecular Weight Complement Inhibitors," available in PMC, Dec. 1, 2010, published in final edited form as: Mol Immunol. 47(2-3):185-195 (2009) (25 pages).
Quesada et al., "One-pot conversion of activated alcohols into terminal alkynes using manganese dioxide in combination with the Bestmann-Ohira reagent," Tetrahedron Letters. 46:6473-6476 (2005).

(56) References Cited

OTHER PUBLICATIONS

Ricklin et al., "Complement in immune and inflammatory disorders: pathophysiological mechanisms," J Immunol. 190(8):3831-3838 (2013).
Rohrer et al., "Eliminating complement factor D reduces photoreceptor susceptibility to light-induced damage," Invest Ophthalmol Vis Sci. 48(11):5282-9 (2007).
Roth et al., "Further Improvements of the Synthesis of Alkynes from Aldehydes," Synthesis. 1:59-62 (2004).
Ruiz-Gómez et al., "Structure-Activity Relationships for Substrate-Based Inhibitors of Human Complement Factor B," J Med Chem. 52(19):6042-6052 (2009).
Salifu, "Chronic Glomerulonephritis Medication," Medscape, <https://emedicine.medscape.com/article/239392-medication>, updated Feb. 1, 2017, retrieved on May 2, 2019 (1 page).
Segers et al., "Complement Alternative Pathway Activation in Human Nonalcoholic Steatohepatitis," PLOS ONE. 9(10):e110053 (2014) (9 pages).
Stanton et al., "Complement Factor D in Age-Related Macular Degeneration," Invest Ophthalmol Vis Sci. 52(12):8828-8834 (2011) (15 pages).
Strobel et al., "Anti-factor B autoantibody in dense deposit disease," Mol Immunol. 47:1476-1483 (2010).
Tandon et al., "Substrate specificity of human prolyl-4-hydroxylase," Bioorg Med Chem Lett. 8(10):1139-1144 (1998).
Tang et al.,"Palladium-Catalyzed Carbonylative Sonogashira Coupling of Aryl Bromides via tert-Butyl Isocyanide Insertion," J Org Chem. 78(7):3170-3175 (2013).
Written Opinion for International Application No. PCT/US18/20528, dated Apr. 24, 2018 (6 pages).
Written Opinion for International Application No. PCT/US18/20530, dated Jun. 25, 2018 (6 pages).
Written Opinion for International Application No. PCT/US18/20531, dated May 15, 2018 (7 pages).
Written Opinion for International Application No. PCT/US19/47252, dated Dec. 17, 2019 (6 pages).
Written Opinion for International Application No. PCT/US19/50065, dated Feb. 25, 2020 (7 pages).
Written Opinion for International Application No. PCT/US19/53012, dated Jan. 28, 2020 (5 pages).
Written Opinion for International Application No. PCT/US19/66999, dated Feb. 12, 2020 (7 pages).
Yuan et al., "Small-molecule Factor D Inhibitors Selectively Block the Alternative Pathway of Complement in Paroxysmal Nocturnal Hemoglobinuria and Atypical Hemolytic Uremic Syndrome," Haematologica. 102(3):466-75 (2017).
Andrighetto et al., "Complement and Complement Targeting Therapies in Glomerular Diseases," Int J Mol Sci. 20(24):6336 (2019), available <https://www.ncbi.nlm.nih.gov/pmc/articles/PMC6940904/>, retrieved on May 26, 2022 (21 pages).
Gilkeson, "Complement-Targeted Therapies in Lupus," Curr Treat Options in Rheum. 1:10-18 (2015) (26 pages).
Hom et al., "Complement Inhibitors for Treatment of Geographic Atrophy and Advanced Nonexudative AMD," Retinal Physician. 16:28-31 (2019).
Kocinsky et al., "Abstract SaO018: Factor D inhibition with ACH-4471 to reduce complement alternative pathway hyperactivity and proteinuria in C3 glomerulopathy: preliminary proof of concept data," Nephrology Dialysis Transplantation. 33(Supplement 1):i322-3 (2018) (1 page).
Mantegazza et al., "Complement Inhibition for the Treatment of Myasthenia Gravis," Immunotargets Ther. 9:317-31 (2020), available <https://www.ncbi.nlm.nih.gov/pmc/articles/PMC7751298/>, retrieved on May 26, 2022 (24 pages).
Varelas et al., "Complement in Sickle Cell Disease: Are We Ready for Prime Time?," J Blood Med. 12:177-87 (2021), available <https://www.ncbi.nlm.nih.gov/pmc/articles/PMC8001680/>, retrieved on May 26, 2022 (19 pages).
Willows et al., "The role of complement in kidney disease," Clin Med (Lond). 20(2):156-60 (2020) (9 pages).
Extended European Search Report for European Application No. 19897806.6, dated Jul. 18, 2022 (12 pages).
Harris et al., "Developments in anti-complement therapy; from disease to clinical trial," Mol Immunol. 102:89-119 (Oct. 2018).

MACROCYCLIC COMPOUNDS FOR TREATMENT OF MEDICAL DISORDERS

FIELD OF THE INVENTION

This invention provides macrocyclic compounds to treat medical disorders, such as complement-mediated disorders.

BACKGROUND OF THE INVENTION

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells), and agglutination (clustering and binding of pathogens together).

The complement system has three pathways: classical, alternative, and lectin. Complement Factor D plays an early and central role in activation of the alternative pathway of the complement cascade. Activation of the alternative complement pathway is initiated by spontaneous hydrolysis of a thioester bond within C3 to produce C3($H_2O$), which associates with Factor B to form the C3($H_2O$)B complex. Complement Factor D acts to cleave Factor B within the C3($H_2O$)B complex to form Ba and Bb. The Bb fragment remains associated with C3($H_2O$) to form the alternative pathway C3 convertase C3($H_2O$)Bb. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement Factor H have a fivefold increased risk of macular degeneration and individuals with mutations in other complement factor genes also have an increased risk of AMD. Individuals with mutant Factor H also have increased levels of C-reactive protein, a marker of inflammation. Without adequate functioning Factor H, the alternative pathway of the complement cascade is overly activated leading to cellular damage.

Paroxysmal nocturnal hemoglobinuria (PNH) is a non-malignant, hematological disorder characterized by the expansion of hematopoietic stem cells and progeny mature blood cells that are deficient in some surface proteins. PNH erythrocytes are not capable of modulating their surface complement activation, which leads to the typical hallmark of PNH—the chronic activation of complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections.

Additional complement-mediated disorders include those classified under component 3 glomerulopathy (C3G). C3G is a recently defined entity comprised of dense deposit disease (DDD) and C3 glomerulonephritis (C3GN) which encompasses a population of chronic kidney diseases wherein elevated activity of the alternative complement pathway and terminal complement pathway results in glomerular deposits made solely of complement C3 and no immunoglobulin (Ig).

Immune-complex membranoproliferative glomerulonephritis (IC-MPGN) is a renal disease which shares many clinical, pathologic, genetic and laboratory features with C3G, and therefore can be considered a sister disease of C3G. In the majority of patients with IC-MPGN, an underlying disease or disorder—most commonly infections, autoimmune diseases, or monoclonal gammopathies—are identified to which the renal disease is secondary. Patients with idiopathic IC-MPGN can have low C3 and normal C4 levels, similar to those observed in C3G, as well as many of the same genetic or acquired factors that are associated with abnormal alternative pathway activity. Although there are current hypotheses suggesting that the majority of IC-MPGN is attributable to over activity of the classical pathway, those patients with a low C3 and a normal C4 are likely to have significant overactivity of the alternative pathway. IC-MPGN patients with a low C3 and a normal C4 may benefit from alternative pathway inhibition.

Other disorders that have been linked to the complement cascade include atypical hemolytic uremic syndrome (aHUS), hemolytic uremic syndrome (HUS), abdominal aortic aneurysm, hemodialysis complications, hemolytic anemia, or hemodialysis, neuromyelitis (NMO), myasthenia gravis (MG), fatty liver, nonalcoholic steatohepatitis (NASH), liver inflammation, cirrhosis, liver failure, dermatomyositis, and amyotrophic lateral sclerosis.

Factor D is an attractive target for inhibition or regulation of the complement cascade due to its early and essential role in the alternative complement pathway, and for its potential role in signal amplification within the classical and lectin complement pathways. Inhibition of Factor D effectively interrupts the pathway and attenuates the formation of the membrane attack complex.

While initial attempts have been made to develop inhibitors of Factor D, there are currently no clinically approved small molecule Factor D inhibitors. Examples of Factor D inhibitor compounds are described in the following disclosures.

Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D. Development of the Factor D inhibitor BCX1470 was discontinued due to lack of specificity and short half-life of the compound.

Novartis PCT patent publication WO2012/093101 titled "Indole compounds or analogues thereof useful for the treatment of age-related macular degeneration" describes certain Factor D inhibitors. Additional Factor D inhibitors are described in Novartis PCT patent publications WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, and WO2015/066241.

A paper published by Novartis titled "Structure-Based Library Design and Fragment Screening for the Identification of Reversible Complement Factor D Protease Inhibitors" (Vulpetti et al., J. Med. Chem. 10.1021/acs.jmedchem.6b01684) describes an in silico active site mapping for regions that contribute to a large fraction of binding energy using the Factor D crystal structure and NMR-based screening (structure-based drug design (SBDD) and fragment-based screening (FBD)). Another Novartis paper titled "Small-molecule factor D inhibitors targeting the alternative complement pathway" (Maibaum et al., Nat. Chem. Bio. 2016;12;1105) discloses small-molecule inhibitors designed by use of a structure-based design approach in combination with fragment-based screening.

Lifesci Pharmaceuticals PCT patent publication WO2017/098328 titled "Therapeutic Inhibitory Compounds" describes various Factor D inhibitors with variations in the central core ring heterocycle ring. PCT patent publication WO2018/015818 is also titled "Therapeutic Inhibitory Compounds" and describes Factor D inhibitors without cyclic central core.

Bristol-Myers Squibb PCT patent publication WO2004/045518 titled "Open chain prolyl urea-related modulators of androgen receptor function" describes open chain prolyl urea and thiourea related compounds for the treatment of androgen receptor-associated conditions, such as age-related diseases, for example, sarcopenia.

Japan Tobacco Inc. PCT patent publication WO1999/048492 titled "Amide derivatives and nociceptin antagonists" describes compounds with a proline-like core and aromatic sub stituents connected to the proline core through amide linkages useful for the treatment of pain.

Ferring B. V. and Yamanouchi Pharmaceutical Co. 1TD. PCT patent publication WO1993/020099 titled "CCK and/or gastrin receptor ligands" describes compounds with a proline-like core and heterocyclic substituents connected to the proline core through amide linkages for the treatment of, for example, gastric disorders or pain.

Alexion Pharmaceuticals PCT patent publication WO1995/029697 titled "Methods and compositions for the treatment of glomerulonephritis and other inflammatory diseases" discloses antibodies directed to C5 of the complement pathway for the treatment of glomerulonephritis and inflammatory conditions involving pathologic activation of the complement system. Alexion Pharmaceutical's anti-C5 antibody eculizumab (Soliris®) is currently the only complement-specific antibody on the market, and is the first and only approved treatment for paroxysmal nocturnal hemoglobinuria (PNH).

On Feb. 25, 2015, Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders" and U.S. patent application Ser. No. 14/630,959 titled "Factor D Inhibitors Useful for Treating Infectious Disorders."

Additional Complement Factor D inhibitors are described in U.S. Pat. Nos. 9,828,396; 9,695,205; 9,598,446; 9,732,103; 9,796,741; 9,732,104; 9,663,543; 9,758,537; and 9,643,986; International Publication Nos. WO 2015/130784; WO 2015/130795; WO 2015/130806; WO 2015/130830; WO 2015/130838; WO 2015/130842; WO 2015/130845; and WO 2015/130854; and U.S. Patent Publication Nos. US 2017-0298084; US 2016-0362398; US 2017-0189410; US 2017-0298085; US 2018-0030075; US 2016-0362399; US 2018-0022766; US 2016-0362433; US 2017-0260219; US 2016-0362432; US 2018-0022767; US 2016-0361329; and US 2017-0226142; all owned by Achillion Pharmaceuticals, Inc.

Given the wide variety of medical disorders that are caused by detrimental immune or inflammatory responses, new compounds are needed for medical treatment.

SUMMARY

This invention includes an active compound of Formula I, Formula II, Formula III, Formula IV, Formula V, Formula VI, Formula VII, or Formula VIII (described below) or a pharmaceutically acceptable salt, prodrug, isotopic analog, N-oxide, or isolated isomer thereof, optionally in a pharmaceutically acceptable composition, wherein each of the Formulas is a macrocyclic compound. In one embodiment, an active compound or its salt or composition, as described herein is used to treat a medical disorder which is an inflammatory or immune condition, a disorder mediated by the complement cascade (including a dysfunctional cascade), a disorder or abnormality of a cell that adversely affects the ability of the cell to engage in or respond to normal complement activity including the alternative complement pathway, or an undesired complement-mediated response to a medical treatment, such as surgery or other medical procedure or a pharmaceutical or biopharmaceutical drug administration, a blood transfusion, or other allogenic tissue or fluid administration.

These macrocyclic compounds can be used to treat such conditions in a host in need thereof, typically a human. The active compound may act as an inhibitor of the Complement Factor D cascade. In one embodiment, a method for the treatment of such a disorder is provided that includes the administration of an effective amount of a compound of Formula I, Formula II, Formula III, Formula IV, Formula V, Formula VI, Formula VII, or Formula VIII or a pharmaceutically acceptable salt, prodrug, isotopic analog, N-oxide, or isolated isomer thereof, optionally in a pharmaceutically acceptable composition, as described in more detail below.

In certain embodiments, compounds are provided that have minimal effect on BSEP (bile salt export pump protein) (e.g., with an $IC_{50}$ of greater than about 20, 30, 40, 50, 60, 75 or 100 µM or greater), or with a therapeutic index of BSEP relative to complement D inhibition (e.g., $IC_{50}$ inhibition of BSEP/$IC_{50}$ inhibition of complement D inhibitor), of about at least 50, 100, 200, 300, 400, 500, 750 or 1000 or greater). BSEP inhibition correlates with cholestatic drug-induced liver injury. Certain compounds of the present invention with low BSEP inhibition have at least one $R^{201}$.

In some embodiments, the compounds of the present invention exhibit minimal hydrolysis of the amide bond between the C ring and the B ring in vivo, for example, by including a proline that has a cis-substituent relative to the proline-carbonyl bond directed toward the B-ring. In certain embodiments, the cis-substituent is in the Q3 position or the Q2 position or is a group that bridges Q3 and Q2.

It has also been discovered that including a B-ring substituent in the position ortho to the amide (for example 2-(L1)-3-methyl-6-substituted-pyridine or 2-(L1)-3-cyclopropyl-6-substituted-pyridine) may decreases the potential for formation of reactive metabolites.

In one aspect of the invention, an $R^{301}$ acylated embodiment of an active compound of the invention is provided that exhibits extended half-life or other advantageous pharmacokinetic properties, which may be achieved by albumin stabilization in vivo. In certain embodiments, the acylated analogue can include several linking moieties in linear, branched or cyclic manner. In some embodiments, either one or a series of amino acids is used as a linker to a terminal fatty acid. In one non-limiting example a non-natural amino acid, 8-amino-3,6-dioxaoctanoic acid (one or several in sequence) is covalently bound to the selected complement D inhibitor of the present invention through a functional group such as a carboxylic acid, sulfonyl, hydroxyl or amino group. See generally Lau, et al., "Discovery of the Once-Weekly Glucagon-Like Peptide-1 (GLP-1) Analogue Semiglutide", *J. Med. Chem.*, 2015, 58, 7370-7380. In this embodiment, the 8-amino-3,6-dioxaoctanoic acid or similar molecule is covalently linked to an aliphatic acid, including but not limited to a $C_{16}$, $C_{18}$, $C_{20}$ aliphatic acid, or a dicarboxylic acid, including but not limited to a $C_8$, $C_{10}$, $C_{12}$, $C_{14}$, $C_{16}$, $C_{18}$ or $C_{20}$ diacid. One or more amino acids can also be used in the selected configuration to add length or functionality. More generally, nonlimiting embodiments include the use of a divalent linker moiety such as a dicarboxylic acid, amino acid, diamine, hydroxycarboxylic acid, hydroxyamine, di-hydroxy compound, or other compound that has at least two functional groups that can link the parent molecule with another linking moiety, and which may be albumin or other protein stabilized in vivo. In some embodiments, 2, 3, 4 or 5 linking moieties are covalently bound in sequence, branched or cyclic fashion to the parent compound. In some embodiments, an $R^{301}$ acyl group is located in a position of the active compound that does not significantly adversely affect the complement D inhibition of the molecule, for example, as (i) a substituent on the $R^{32}$ group or (ii) a substituent on a C-ring, such as proline, or as a substituent on a substituent on the C-ring, such as on an $R^1$, $R^2$ or $R^3$ substituent, including for example, on a bridged moiety such as a fused cyclopropyl on the proline ring. In certain embodiments, the acyl group has an aliphatic or heteroaliphatic carbon range of about $C_{12}$, $C_{14}$, $C_{16}$, $C_{18}$, $C_{20}$, $C_{22}$ or $C_{24}$.

In one embodiment, the disorder is associated with the alternative complement cascade pathway. In yet another embodiment, the disorder is associated with the complement classical pathway. In a further embodiment, the disorder is associated with the complement lectin pathway. Alternatively, the active compound or its salt or prodrug may act through a different mechanism of action than the complement cascade, or in particular as a Complement Factor D inhibitor, to treat the disorder described herein.

In one embodiment, a method for the treatment of C3 Glomerulonephritis (C3G) is provided that includes the administration of an effective amount of a compound to a host of Formula I, Formula II, Formula III, Formula IV, Formula V, Formula VI, Formula VII, or Formula VIII or a pharmaceutically acceptable salt, prodrug, isotopic analog, N-oxide, or isolated isomer thereof, optionally in a pharmaceutically acceptable composition. In one embodiment, a method for the treatment of paroxysmal nocturnal hemoglobinuria (PNH) is provided that includes the administration of an effective amount of a compound to a host of Formula I, Formula II, Formula III, Formula IV, Formula V, Formula VI, Formula VII, or Formula VIII or a pharmaceutically acceptable salt, prodrug, isotopic analog, N-oxide, or isolated isomer thereof, optionally in a pharmaceutically acceptable composition. In another embodiment, a method for the treatment of wet or dry age-related macular degeneration (AMD) in a host is provided that includes the administration of an effective amount of a compound of Formula I, Formula II, Formula III, Formula IV, Formula V, Formula VI, Formula VII, or Formula VIII, or a pharmaceutically acceptable salt, prodrug, isotopic analog, N-oxide, or isolated isomer thereof, optionally in a pharmaceutically acceptable composition. In another embodiment, a method for the treatment of rheumatoid arthritis in a host is provided that includes the administration of an effective amount of a compound of Formula I, Formula II, Formula III, Formula IV, Formula V, Formula VI, Formula VII, or Formula VIII or a pharmaceutically acceptable salt, prodrug, isotopic analog, N-oxide, or isolated isomer thereof, optionally in a pharmaceutically acceptable composition. In another embodiment, a method for the treatment of multiple sclerosis in a host is provided that includes the administration of an effective amount of a compound of Formula I, Formula II, Formula III, Formula IV, Formula V, Formula VI, Formula VII, or Formula VIII or a pharmaceutically acceptable salt, prodrug, isotopic analog, N-oxide, or isolated isomer thereof, optionally in a pharmaceutically acceptable composition.

In other embodiments, an active compound or its salt or prodrug as described herein can be used to treat fatty liver and conditions stemming from fatty liver, nonalcoholic steatohepatitis (NASH), liver inflammation, cirrhosis, and liver failure, dermatomyocitis, or amyotrophic lateral sclerosis.

The active compound or its pharmaceutically acceptable salt, prodrug, isotopic analog, N-oxide, or isolated isomer thereof, optionally in a pharmaceutically acceptable composition, as disclosed herein is also useful for administration in combination (in the same or a different dosage form) or alternation with a second pharmaceutical agent for use in ameliorating or reducing a side effect of the second pharmaceutical agent. For example, in one embodiment, the active compound may be used in combination with an adoptive cell transfer therapy to reduce an inflammatory response associated with such therapy, for example, a cytokine mediated response such as cytokine response syndrome. In one embodiment, the adoptive cell transfer therapy is a chimeric antigen receptor T-Cell (CAR T) or a dendritic cell used to treat a hematologic or solid tumor, for example, a B-cell related hematologic cancer. In one embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19. In one embodiment, the associated inflammatory response is a cytokine mediated response.

Another embodiment is provided that includes the administration of an effective amount of an active compound or a pharmaceutically acceptable salt, prodrug, isotopic analog, N-oxide, or isolated isomer thereof, optionally in a pharmaceutically acceptable composition to a host to treat an ocular, pulmonary, gastrointestinal, or other disorder that can benefit from topical or local delivery.

Any of the compounds described herein (Formula I, Formula II, Formula III, Formula IV, Formula V, Formula VI, Formula VII, or Formula VIII) can be administered to the eye in any desired form of administration, including via intravitreal, intrastromal, intracameral, sub-tenon, sub-retinal, retro-bulbar, peribulbar, suprachorodial, choroidal, sub-choroidal, conjunctival, subconjunctival, episcleral, posterior juxtascleralscleral, circumcorneal, and tear duct injections, or through a mucus, mucin, or a mucosal barrier, in an immediate or controlled release fashion. In certain embodiments, the active compound includes a lipophilic group, such as a lipophilic acyl group, which is delivered to the eye in a polymeric drug delivery system such as polylactic acid, polylactide-co-glycolide, polyglycolide or other erodible polymer, or a combination thereof, or in another type of lipophilic material for ocular delivery. In some embodiments, the lipophilic active molecule is more soluble in the polymeric or other form of delivery system than in ocular fluid.

In other embodiments of the invention, an active compound provided herein can be used to treat or prevent a disorder in a host mediated by Complement Factor D, or by an excessive or detrimental amount of the complement-C3 amplification loop of the complement pathway. As examples, the invention includes methods to treat or prevent complement associated disorders that are induced by antibody-antigen interactions, a component of an immune or autoimmune disorder or by ischemic injury. The invention also provides methods to decrease inflammation or an immune response, including an autoimmune response, where mediated or affected by Factor D.

In another embodiment, a method is provided for treating a host, typically a human, with a disorder mediated by the complement system, that includes administration of a prophylactic antibiotic or vaccine to reduce the possibility of a bacterial infection during the treatment using one of the compounds described herein. In certain embodiments, the host, typically a human, is given a prophylactic vaccine prior to, during or after treatment with one of the compounds described herein. In certain embodiments, the host, typically a human, is given a prophylactic antibiotic prior to, during or after treatment with one of the compounds described herein. In some embodiment, the infection is a meningococcal infection (e.g., septicemia and/or meningitis), an *Aspergillus* infection, or an infection due to an encapsulated organism, for example, *Streptococcus pneumoniae* or *Haemophilus influenza* type b (Hib), especially in children. In other embodiments, the vaccine or antibiotic is administered to the patient after contracting an infection due to, or concomitant with inhibition of the complement system.

The disclosure provides a compound of Formula I:

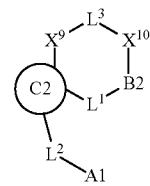

Formula I or a pharmaceutically acceptable salt, isotopic analog, prodrug, N-oxide, or isolated isomer thereof, optionally in a pharmaceutically acceptable carrier;

wherein:

C2 is

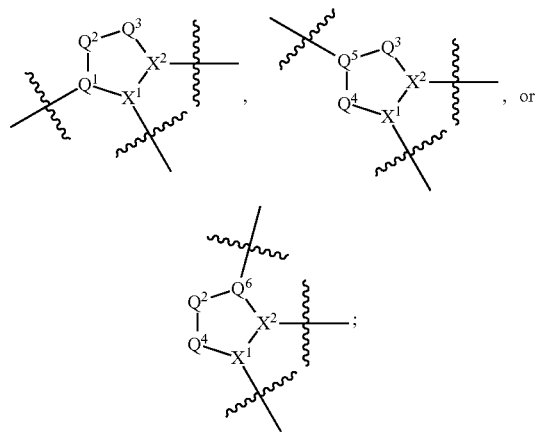

or C2 is

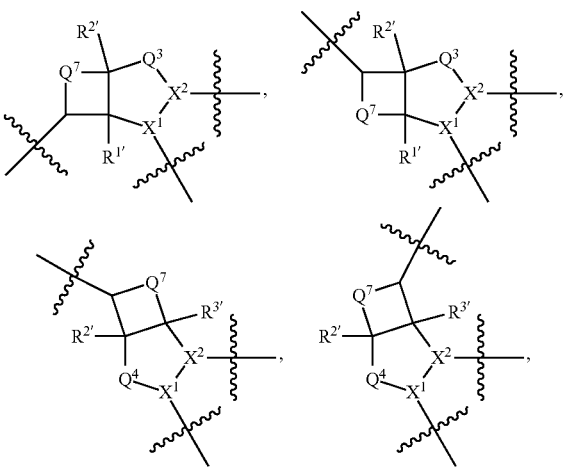

-continued

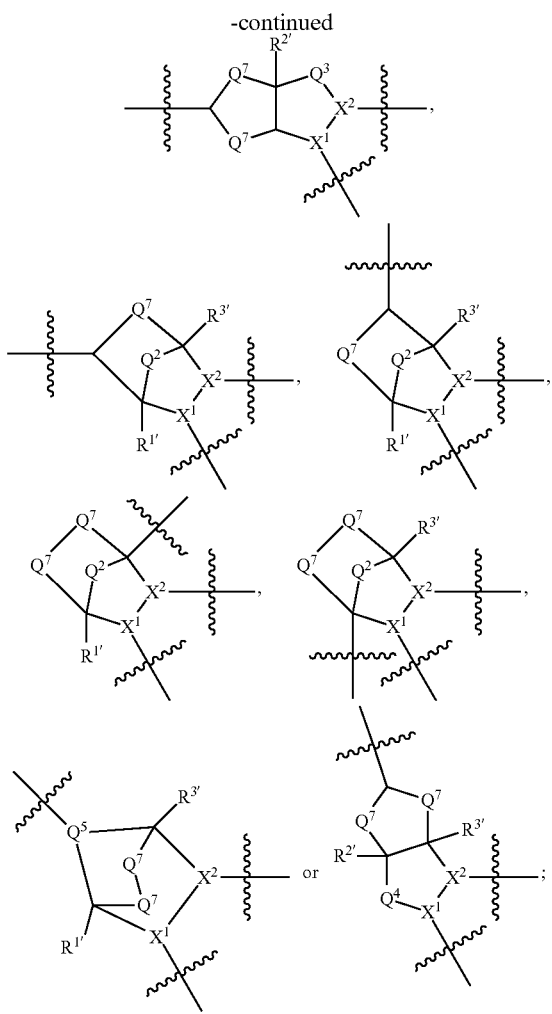

$Q^1$ is N or $C(R^1)$, wherein $Q^1$ is directly bound to $X^9$;

$Q^2$ is $C(R^2R^{2'})$, $C(R^2R^{2'})C(R^2R^{2'})$, $C(R^2R^{2'})C(R^2R^{2'})C(R^2R^{2'})$, $N(R^2)$, S, O, or $C(R^2R^{2'})O$;

$Q^3$ is $N(R^3)$, S, O, $C(R^3R^{3'})$, $C(R^3R^{3'})C(R^3R^{3'})$, or $C(R^3R^{3'})C(R^3R^{3'})C(R^3R^{3'})$;

$Q^4$ is $N(R^1)$, $C(R^1R^{1'})$, $C(R^1R^{1'})C(R^1R^{1'})$, $C(R^1R^{1'})C(R^1R^{1'})C(R^1R^{1'})$, S or O;

$Q^5$ is $C(R^2)$, N, or $C(R^2)O$, wherein $Q^5$ is directly bound to $X^9$;

$Q^6$ is N or $C(R^3)$, wherein $Q^6$ is directly bound to $X^9$;

$Q^7$ is bond, $N(R^9)$, O, S, $C(R^{54})_2$, $C(R^{54})_2C(R^{54})_2$;

$X^1$ and $X^2$ are independently N, CH, or CZ, wherein $X^1$ is directly bound to $L^2$ and $X^2$ is directly bound to $L^1$;

wherein $Q^1$, $Q^2$, $Q^3$, $Q^4$, $Q^5$, $Q^6$, $X^1$ and $X^2$ are selected such that a stable compound results, and for example, heteroatoms are not adjacent in the ring such that an unstable structure results nor is a substituent placed α, β or γ to a heteroatom in a manner that creates an unstable structure, as well known to those in this field;

Z is F, Cl, $NH_2$, $CH_3$, $CH_2D$, $CHD_2$, or $CD_3$;

$R^1$, $R^{1'}$, $R^2$, $R^{2'}$, $R^3$, and $R^{3'}$ are independently selected at each occurrence, as appropriate, and only where a stable compound results, from hydrogen, $R^{201}$, $R^{301}$, halogen (and specifically fluoro, chloro, and bromo), hydroxyl, nitro, cyano, amino, alkyl including $C_1$-$C_6$alkyl, alkenyl including $C_2$-$C_6$alkenyl, alkynyl including $C_2$-$C_6$alkynyl, alkoxy including $C_1$-$C_6$alkoxy, alkanoyl including $C_2$-$C_6$alkanoyl, thioalkyl including $C_1$-$C_6$alkylthio-, hydroxy$C_1$-$C_6$alkyl-, amino$C_1$-$C_6$alkyl-, -$C_0$-$C_4$alkylN$R^9R^{10}$, —C(O)O$R^9$, —OC(O)$R^9$, —N$R^9$C(O)$R^{10}$, —C(O)N$R^9R^{10}$, —OC(O)N$R^9R^{10}$, —N$R^9$C(O)O$R^{10}$, —OR', —NR'R'', haloalkyl including $C_1$-$C_6$haloalkyl, and haloalkoxy including $C_1$-$C_6$haloalkoxy;

or $R^1$ and $R^{1'}$ are taken together to form a 3- to 6-membered carbocyclic spiro ring or a 3- to 6-membered heterocyclic spiro ring containing 1 or 2 heteroatoms independently selected from N, O, and S;

or $R^3$ and $R^{3'}$ are taken together to form a 3- to 6-membered carbocyclic spiro ring or a 3- to 6-membered heterocyclic spiro ring containing 1 or 2 heteroatoms independently selected from N, O, and S;

or $R^2$ and $R^{2'}$ are taken together to form a 3- to 6-membered carbocyclic spiro ring or a 3- to 6-membered heterocyclic spiro ring;

wherein, each of the above spiro rings may be optionally substituted with 1 or more substituents independently selected from $R^{201}$, halogen (and in particular F), hydroxyl, cyano, —COOH, alkyl including $C_1$-$C_4$alkyl (including in particular methyl), alkenyl including $C_2$-$C_4$alkenyl, alkynyl including $C_2$-$C_4$alkynyl, alkoxy including $C_1$-$C_6$alkoxy, alkanoyl including $C_2$-$C_4$alkanoyl, hydroxy$C_1$-$C_4$alkyl, (mono- and di-alkylamino)$C_1$-$C_4$alkyl, -$C_0$-$C_4$alkyl($C_3$-$C_7$cycloalkyl), —O-alkyl($C_3$-$C_7$cycloalkyl), haloalkyl including $C_1$-$C_6$haloalkyl, and haloalkoxy including $C_1$-$C_6$haloalkoxy;

or $R^1$ and $R^2$ are taken together to form a 3-membered carbocyclic ring, a 4- to 6-membered carbocyclic or aryl ring, or a 4- to 6-membered heterocyclic or heteroaryl ring containing 1 or 2 heteroatoms independently selected from N, O, and S;

or $R^2$ and $R^3$ are taken together to form a 3- to 6-membered carbocyclic or aryl ring or a 3- to 6-membered heterocyclic or heteroaryl ring;

wherein each of which fused $R^1$ and $R^2$ or $R^2$ and $R^3$ rings or generally $R^1$, $R^2$, $R^3$, $R^{1'}$, $R^{2'}$, or $R^{3'}$, are optionally substituted with 1 or more substituents independently selected from $R^{201}$, halogen (and in particular F), hydroxyl, cyano, —COOH, alkyl including $C_1$-$C_4$alkyl (including in particular methyl), alkenyl including $C_2$-$C_4$alkenyl, alkynyl including $C_2$-$C_4$alkynyl, alkoxy including $C_1$-$C_4$alkoxy, alkanoyl including $C_2$-$C_4$alkanoyl, hydroxy$C_1$-$C_4$alkyl, (mono- and di-alkylamino)$C_0$-$C_4$alkyl, alkyl($C_3$-$C_7$cycloalkyl) including -$C_1$-$C_4$alkyl($C_3$-$C_7$cycloalkyl), —O-($C_3$-$C_7$cycloalkyl), haloalkyl including $C_1$-$C_6$haloalkyl, and haloalkoxy including $C_1$-$C_6$haloalkoxy;

or $R^1$ and $R^{1'}$ are taken together to form a carbonyl group;
or $R^2$ and $R^{2'}$ are taken together to form a carbonyl group;
or $R^3$ and $R^{3'}$ are taken together to form a carbonyl group;
or $R^1$ and $R^2$ are taken together to form a carbon-carbon double bond;
or $R^2$ and $R^3$ are taken together to form a carbon-carbon double bond;

R and R' are independently selected from H, $R^{201}$, alkyl, cycloalkyl, cycloalkylalkyl, heterocycle, heterocycloalkyl, aryl, arylalkyl, heteroaryl, and heteroarylalkyl;

in an alternative embodiment, R'' is selected from H, $R^{201}$, alkyl, cycloalkyl, cycloalkylalkyl, heterocycle, heterocycloalkyl, aryl, arylalkyl, heteroaryl, and heteroarylalkyl;

and where any of these groups may be further optionally substituted as that term is defined in the Terminology Section below, if desired to achieve the target effect, results in a stable compound that makes chemical sense to the skilled artisan, and the group is not redundant (i.e., as known in the art, alkyl substituted with alkyl is redundant; however, for example, alkoxy substituted with alkoxy is not redundant);
A1 is selected from:
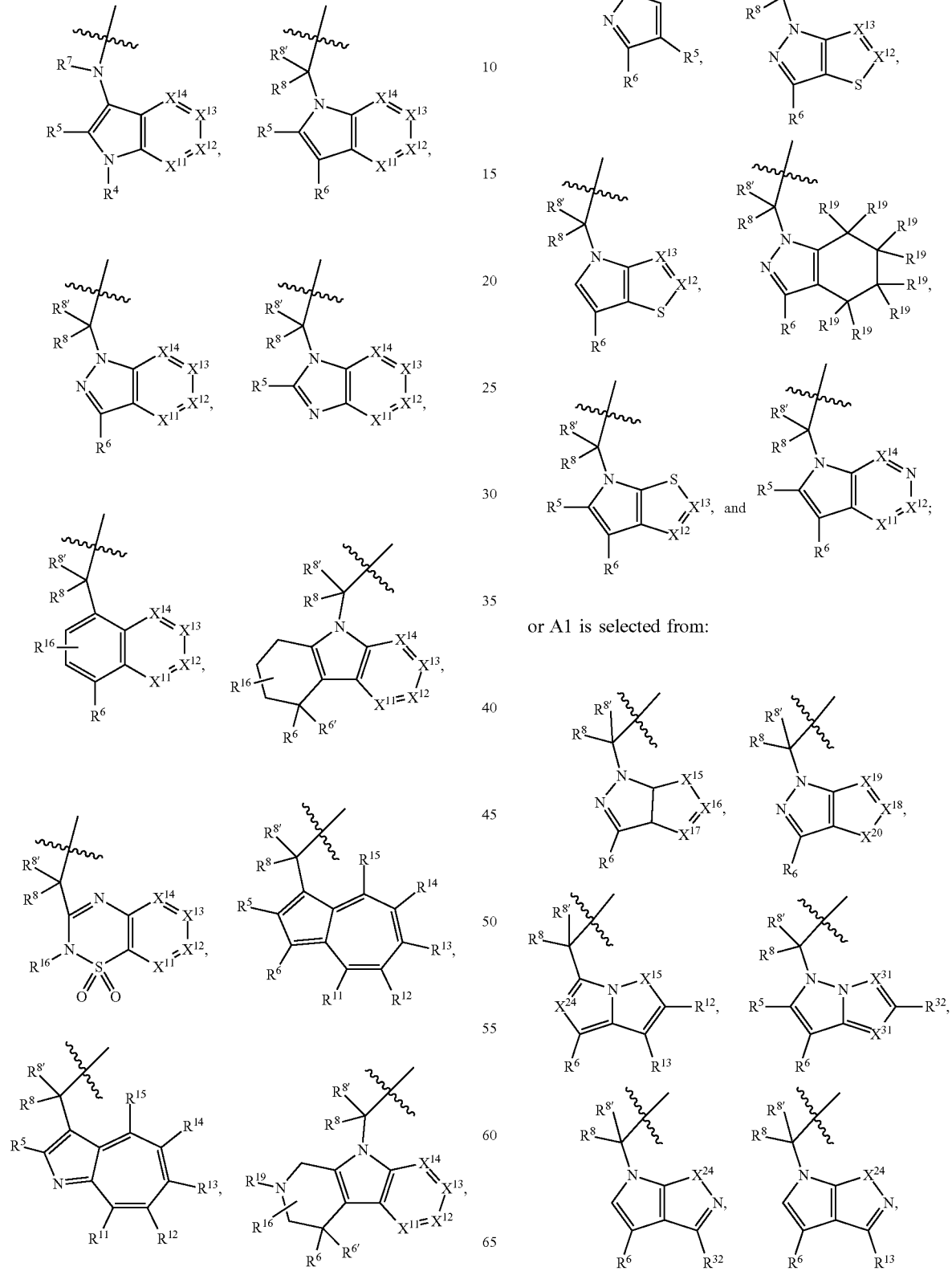
or A1 is selected from:
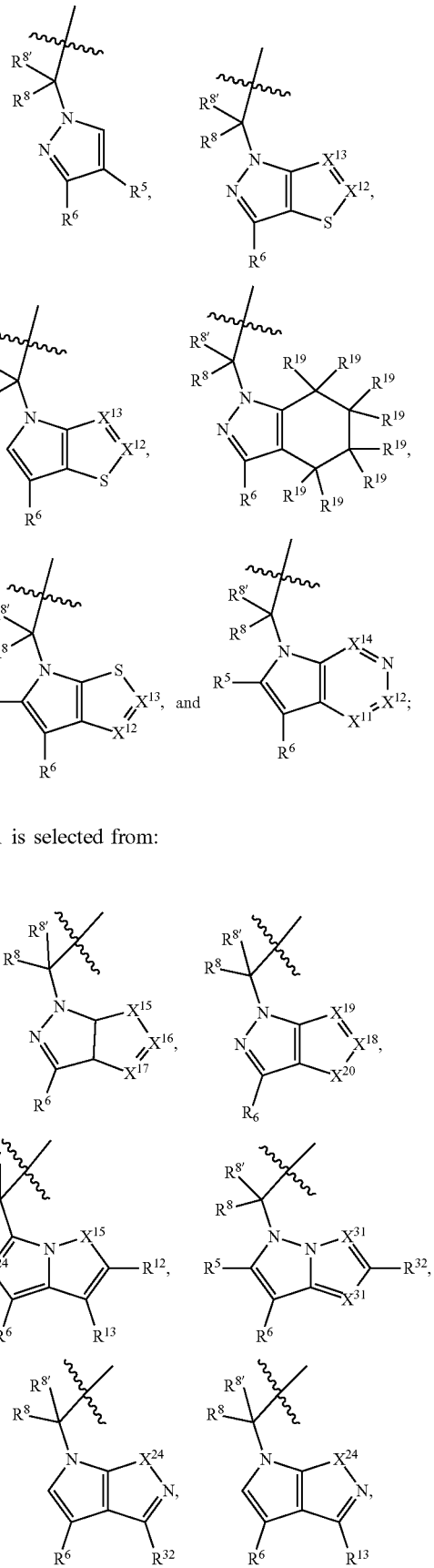

-continued
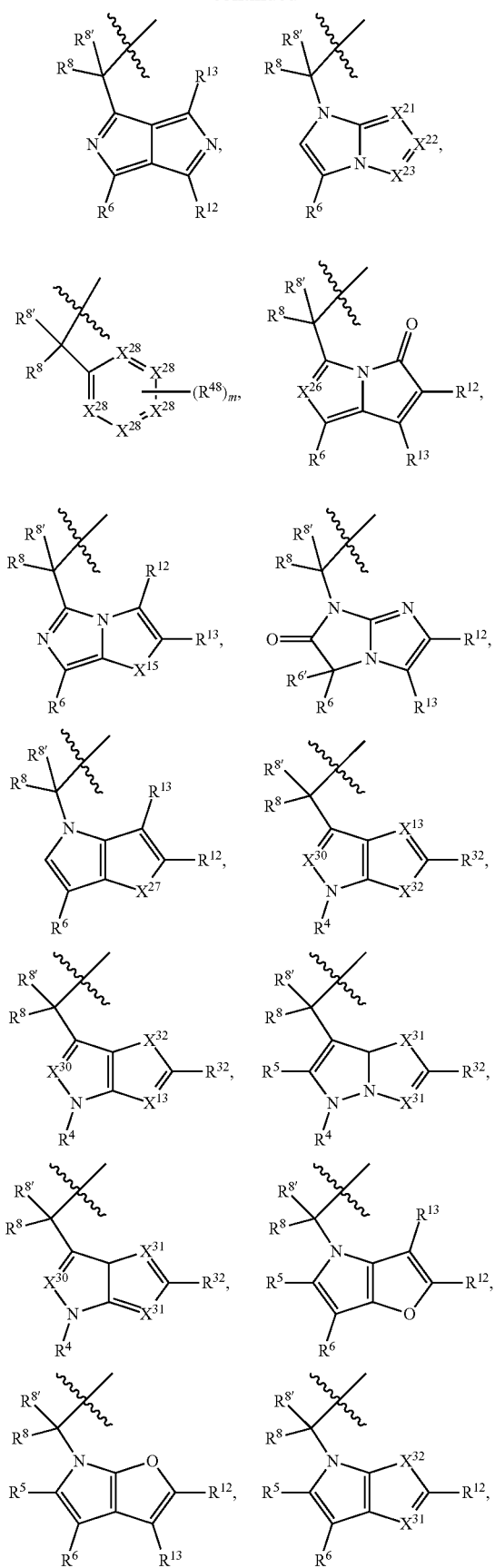
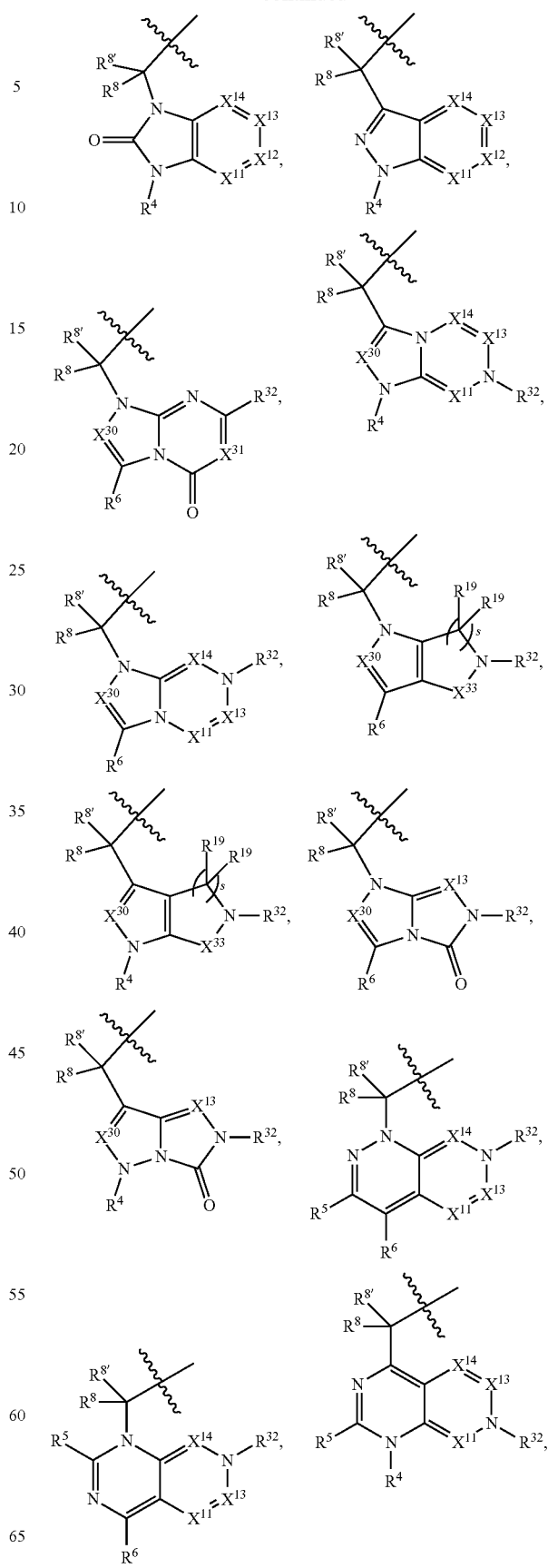

-continued
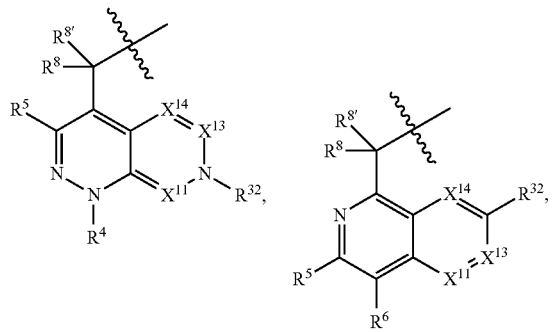
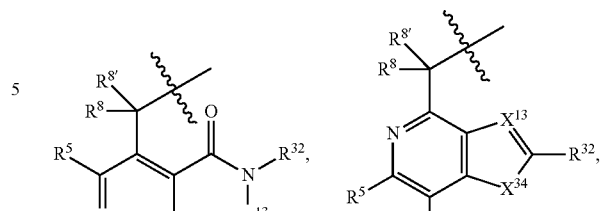
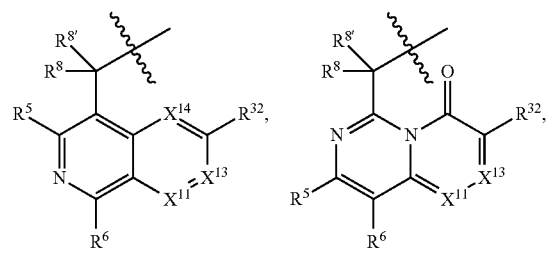
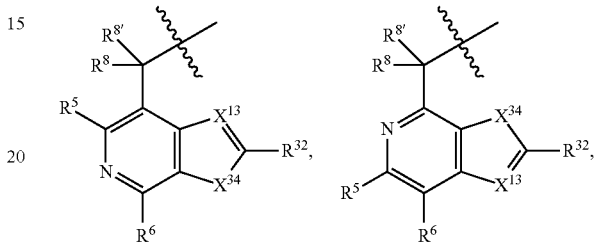
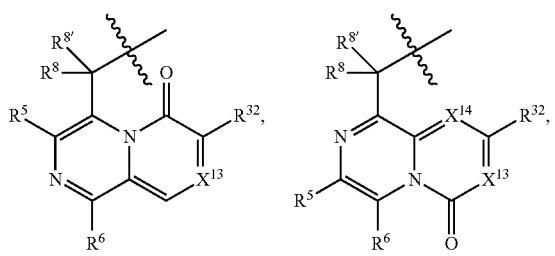
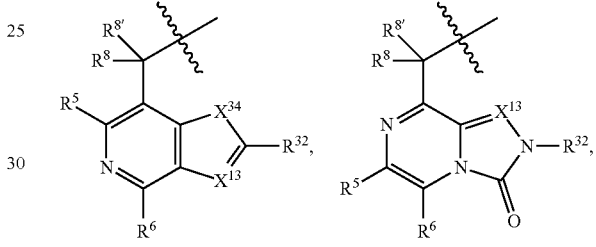
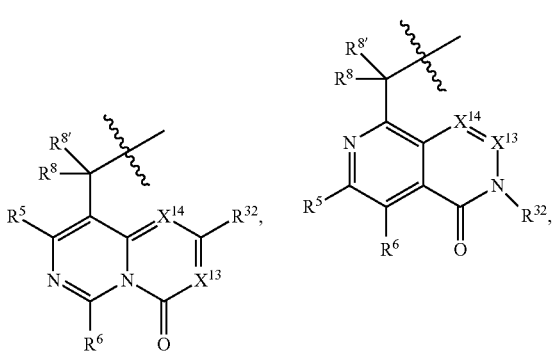
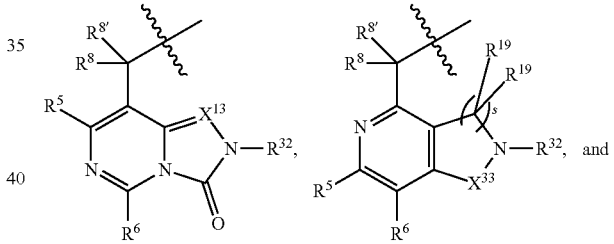
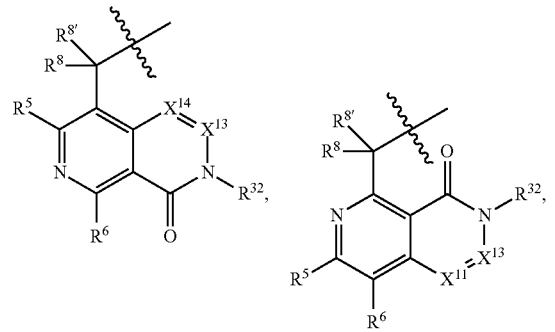
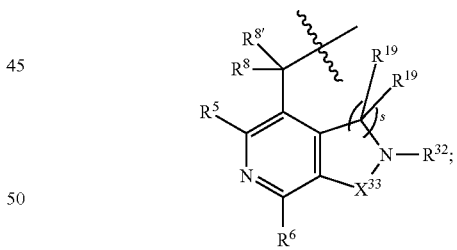
$L^1$ is a bond,
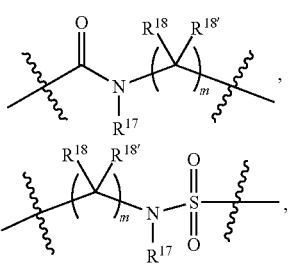

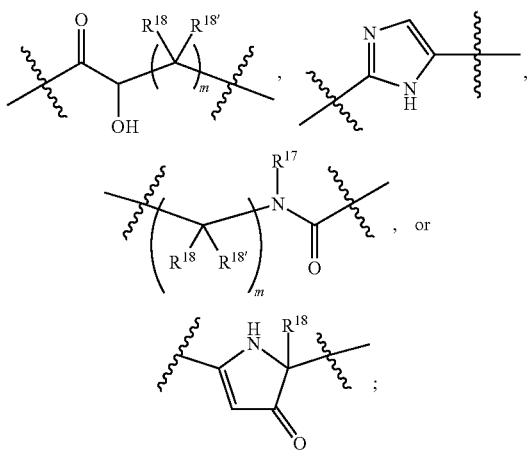

or L¹ is selected from:

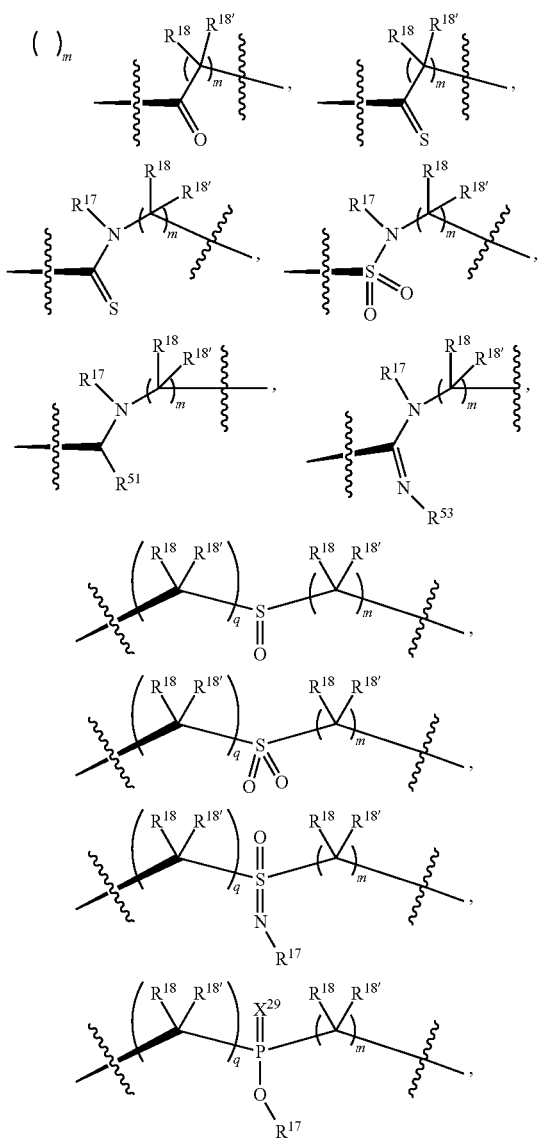

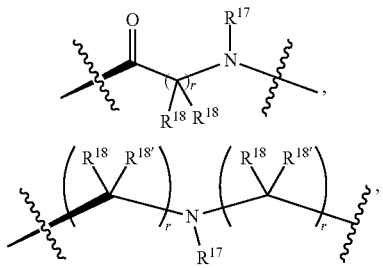

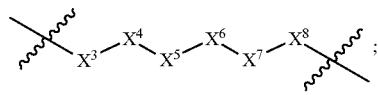

an optionally substituted monocyclic or bicyclic carbocycle; an optionally substituted monocyclic or bicyclic carbocyclic-oxy group; an optionally substituted monocyclic or bicyclic heterocycle having 1, 2, 3, or 4 heteroatoms independently selected from N, O, and S and from 4 to 7 ring atoms per ring, an optionally substituted -($C_0$-$C_4$alkyl)(aryl); an optionally substituted -($C_0$-$C_4$alkyl)(5-membered heteroaryl) selected from pyrrole, furan, thiophene, pyrazole, oxazole, isoxazole, thiazole and isothiazole or a substituted imidazole; an optionally substituted -($C_0$-$C_4$alkyl)(6-membered heteroaryl); an optionally substituted -($C_0$-$C_4$alkyl)(8-membered heteroaryl); an optionally substituted -($C_0$-$C_4$alkyl)(9-membered heteroaryl) selected from isoindole, indazole, purine, indolizine, benzothiophene, benzothiazole, benzoxazole, benzofuran, and furopyridine; and -($C_0$-$C_4$alkyl)(10-membered heteroaryl);

$L^2$ is —C(O)—, —C(S)—, —P(O)OH—, —S(O)—, —S(O)$_2$— or —C($R^{52}$)$_2$—;

$L^3$ is $X^3$, $X^4$, $X^5$, $X^6$, $X^7$, and $X^8$ are each independently selected from bond, —C($R^{52}$)$_2$—, —C($R^{52}$)$_2$C($R^{52}$)$_2$—, —C($R^{52}$)$_2$C($R^{52}$)$_2$C($R^{52}$)$_2$—, —C(O)—, —C(S)—, —P(O)OR$^9$—, —S(O)—, —S(O)$_2$—, —O—, —S—, $R^{201}$ in a divalent state, alkenylene, alkynylene, heterocycle, heteroalkylene, heteroalkynylene, heteroalkenylene, arylalkyl, heterocycloalkyl, heteroarylalkyl, aryl, heteroaryl, cycloalkyl, and —NR$^9$—, which moieties are used in any order that results in a stable compound, and makes chemical sense to the skilled artisan, each of which is considered independently disclosed;

or $X^3$, $X^4$, $X^5$, $X^6$, $X^7$, and $X^8$ are each independently selected from alkyl, bond, —C($R^{52}$)$_2$—, —C($R^{52}$)$_2$C($R^{52}$)$_2$—, —C($R^{52}$)$_2$C($R^{52}$)$_2$C($R^{52}$)$_2$—, —C(O)—, —C(S)—, —P(O)OR$^9$—, —S(O)—, —S(O)$_2$—, —O—, —S—, $R^{201}$ in a divalent state, alkenylene, alkynylene, heterocycle, heteroalkylene, heteroalkynylene, heteroalkenylene, arylalkyl, heterocycloalkyl, heteroarylalkyl, aryl, heteroaryl, cycloalkyl, and —NR$^9$—, which moieties are used in any order that results in a stable compound, and makes chemical sense to the skilled artisan, each of which is considered independently disclosed;

in an alternative embodiment $X^3$, $X^4$, $X^5$, $X^6$, $X^7$, or $X^8$ is —N=S(O)$_2$($R^{52}$)— or —S(O)$_2$($R^{52}$)=N—, for example

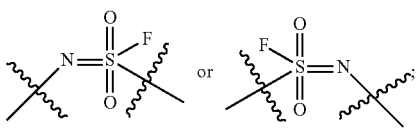

in an alternative embodiment $X^3$, $X^4$, $X^5$, $X^6$, $X^7$, or $X^8$ is —S(O)$_2$-heteroaryl- or -heteroaryl—S(O)$_2$, for example

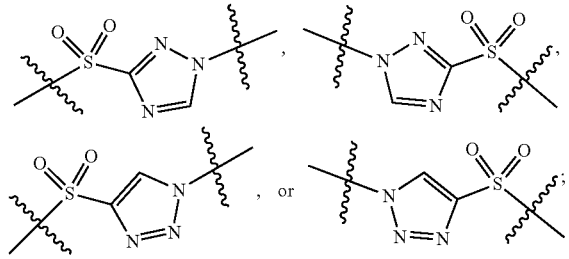

$X^9$ and $X^{10}$ are independently selected from —C(R$^{52}$)$_2$—, —C(R$^{52}$)$_2$O—, —C(R$^{52}$)$_2$NR$^9$—, —C(R$^{52}$)$_2$OC(O)—, —C(R$^{52}$)$_2$NR$^9$C(O)—, —O—, —S—, —C(O)—, —C(S)—, —P(O)OR$^9$—, —S(O)—, —S(O)$_2$—, alkenylene, alkynylene, R$^{201}$ in a divalent state, R$^{32}$ in a divalent state, and —NR$^9$—;

or $X^9$ and $X^{10}$ are independently selected from —CH$_2$O—, —CH$_2$N(H)—, —CH$_2$OC(O)—, —CH$_2$N(H)C(O)—, —CH$_2$N(CH$_3$)—, and —CH$_2$N(CH$_3$)C(O)—;

or $X^9$ and $X^{10}$ are independently selected from alkylene, —C(R$^{52}$)$_2$—, —C(R$^{52}$)$_2$O—, —C(R$^{52}$)$_2$NR$^9$—, —C(R$^{52}$)$_2$OC(O)—, —C(R$^{52}$)$_2$NR$^9$C(O)—, —O—, —S—, —C(O)—, —C(S)—, —P(O)OR$^9$—, —S(O)—, —S(O)$_2$—, alkenylene, alkynylene, R$^{201}$ in a divalent state, R$^{32}$ in a divalent state, —NR$^9$—, —CH$_2$O—, —CH$_2$N(H)—, —CH$_2$OC(O)—, —CH$_2$N(H)C(O)—, —CH$_2$N(CH$_3$)—, and —CH$_2$N(CH$_3$)C(O)—;

$X^{11}$ is N or CR$^{11}$;
$X^{12}$ is N or CR$^{12}$;
$X^{13}$ is N or CR$^{13}$;
$X^{14}$ is N or CR$^{14}$;
wherein no more than 2 of $X^{11}$, $X^{12}$, $X^{13}$, and $X^{14}$ are N;
$X^{15}$ is NH, O, or S;
$X^{16}$ is CR$^{12}$;
$X^{17}$ is N or CR$^{13}$;
$X^{18}$ is CR$^{12}$;
$X^{19}$ is N or CR$^{13}$;
$X^{20}$ is NH or O;
$X^{21}$ is N or CR$^{14}$;
$X^{22}$ is N or CR$^{13}$;
$X^{23}$ is CR$^{12}$;
$X^{24}$ is O or S;
$X^{26}$ is N or CR$^{41}$;
$X^{27}$ is CR$^{12}$, NH or O;
$X^{28}$ is N or CH;
$X^{30}$ is N or CR$^5$;
$X^{31}$ is N, C(R$^{54}$)$_2$ or CR$^{54}$;
$X^{32}$ is NH, C(R$^{54}$)$_2$ or CR$^{54}$;
$X^{33}$ is —CO— or —SO— or —SO$_2$—;
$X^{34}$ 1S CHR$^{13}$, NH, O, or S;
wherein no more than 2 of $X^{28}$ are N;

$R^4$, $R^5$, and $R^6$ are independently selected from hydrogen, -JCHO, -JC(O)NH$_2$, -JC$_2$-C$_6$alkanoyl, -JC(O)NH(CH$_3$), -J—COOH, -JP(O)(OR$^9$)$_2$, -JOC(O)R$^9$, -JC(O)OR$^9$, -JC(O)N(CH$_2$CH$_2$R$^9$)(R$^{10}$), -JNR$^9$C(O)R$^{10}$, -JSO$_2$NH$_2$, -JS(O)NH$_2$, -JC(CH$_2$)$_2$F, -JCH(CF$_3$)NH$_2$, -JC(O)C$_0$-C$_2$alkyl(C$_3$-C$_7$cycloalkyl), -JNR$^9$(alkanoyl including C$_2$-C$_6$alkanoyl), -JNR$^9$C(O)NR$^9$R$^{10}$, -JSO$_2$(C$_1$-C$_6$alkyl), -JSO$_2$(haloalkyl including C$_1$-C$_6$haloalkyl), -JSO$_2$NR$^7$R$^7$, -JSO=NH(C$_1$-C$_6$alkyl), -J-nitro, -J-halogen, -J-hydroxyl, -J-phenyl, a 5- to 6-membered heteroaryl, -J-cyano, -J-cyanoimino, -J-amino, -J-imino, -alkyl including C$_1$-C$_6$alkyl, -C$_0$-C$_4$alkyl(C$_3$-C$_7$heterocycloalkyl), -C$_0$-C$_4$alkyl(C$_3$-C$_7$cycloalkyl),

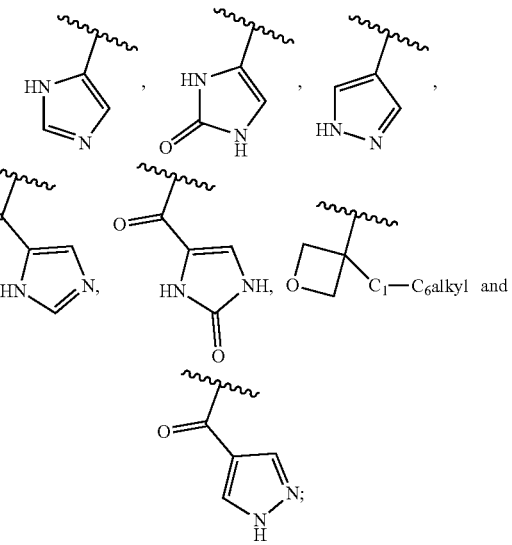

each of which $R^4$, $R^5$ and $R^6$ other than hydrogen, nitro, halogen, cyano, cyanoimino, and —CHO, is optionally substituted with one or more of amino, imino, halogen, hydroxyl, cyano, cyanoimino, alkyl including C$_1$-C$_6$alkyl, C$_1$-C$_6$alkoxy, -C$_0$-C$_2$alkyl(mono- and di-C$_1$-C$_4$alkylamino), haloalkyl including C$_1$-C$_6$haloalkyl, and haloalkoxy including C$_1$-C$_6$haloalkoxy;

$R^{6'}$ is hydrogen, halogen, hydroxyl, C$_1$-C$_4$alkyl, -C$_0$-C$_4$alkyl(C$_3$-C$_7$cycloalkyl), or C$_1$-C$_4$alkoxy;

or $R^6$ and $R^{6'}$ are taken together to form an oxo, vinyl, or imino group;

$R^7$ is hydrogen, alkyl including C$_1$-C$_6$alkyl, or -C$_0$-C$_4$alkyl(C$_3$-C$_7$cycloalkyl);

$R^8$ and $R^{8'}$ are independently selected from hydrogen, halogen, hydroxyl, alkyl including C$_1$-C$_6$alkyl, -C$_0$-C$_4$alkyl(C$_3$-C$_7$cycloalkyl), C$_1$-C$_6$alkoxy, and (C$_1$-C$_4$alkylamino)C$_0$-C$_2$alkyl;

or $R^8$ and $R^{8'}$ are taken together to form an oxo group;

or $R^8$ and $R^{8'}$ or taken together to form a 3-membered carbocyclic ring;

$R^9$ and $R^{10}$ are independently selected at each occurrence from hydrogen, alkyl including C$_1$-C$_6$alkyl, (C$_3$-C$_7$cycloalkyl)C$_0$-C$_4$alkyl, -C$_0$-C$_4$alkyl(C$_3$-C$_7$cycloalkyl), and —O-C$_0$-C$_4$alkyl(C$_3$-C$_7$cycloalkyl);

$R^{11}$, $R^{12}$, $R^{13}$, $R^{14}$, and $R^{15}$ are independently selected at each occurrence from hydrogen, $R^{201}$, $R^{301}$, halogen, hydroxyl, nitro, cyano, —O(PO)(OR$^9$)$_2$, —(PO)(OR$^9$)$_2$, alkyl including C$_1$-C$_6$alkyl, alkenyl including C$_2$-C$_6$alkenyl, alkynyl including C$_2$-C$_6$alkynyl, C$_2$-C$_6$alkenyl(aryl), C$_2$-C$_6$alkenyl(cycloalkyl), C$_2$-C$_6$alkenyl(heterocycle), C$_2$-C$_6$alkenyl(heteroaryl), alkynyl including C$_2$-C$_6$alkynyl, C$_2$-C$_6$alkynyl(aryl), C$_2$-C$_6$alkynyl(cycloalkyl), C$_2$-C$_6$alkynyl(heterocycle), C$_2$-C$_6$alkynyl(heteroaryl), alkanoyl including C$_2$-C$_6$alkanoyl, C$_1$-C$_6$alkoxy, thioalkyl including C$_1$-C$_6$thioalkyl, -C$_0$-C$_4$alkyl(mono- and di-alkyl amino), -C$_0$-C$_4$alkyl(C$_3$-C$_7$cycloalkyl), -C$_0$-C$_4$alkoxy(C$_3$-C$_7$cycloalkyl), haloalkyl including C$_1$-C$_6$haloalkyl, haloalkoxy including C$_1$-C$_6$haloalkoxy, amino, —COOH, -C$_0$-C$_4$alkyl(C$_3$-C$_7$cycloalkyl), C$_2$-C$_6$alkenyloxy, —C(O)OR$^9$, thioalkyl including C$_1$-C$_6$thioalkyl, -C$_0$-C$_4$alkylNR$^9$R$^{10}$, —C(O)NR$^9$R$^{10}$, —SO$_2$R$^9$, —SO$_2$NR$^9$R$^{10}$, —OC(O)R$^9$, —C(NR$^9$)NR$^9$R$^{10}$, and R$^{32}$, each of which other than hydrogen, halogen, hydroxyl, nitro, cyano, haloalkyl, and haloalkoxy is optionally substituted with one or more substituents independently selected from halogen, hydroxyl, nitro, cyano, amino, —COOH, —CONH$_2$ haloalkyl including C$_1$-C$_6$haloalkyl, haloalkoxy including C$_1$-C$_6$haloalkoxy, phenyl, 4- to 7-membered heterocycle containing 1, 2, or 3 heteroatoms independently selected from N, O, and S, each of which phenyl or 4- to 7-membered heterocycle is optionally substituted with one or more substituents independently selected from halogen, hydroxyl, nitro, cyano, alkyl including C$_1$-C$_6$alkyl, alkenyl including C$_2$-C$_6$alkenyl, alkanoyl including C$_2$-C$_6$alkanoyl, C$_1$-C$_6$alkoxy, (mono- and di-alkylamino)C$_0$-C$_4$alkyl, C$_1$-C$_6$alkylester, -C$_0$-C$_4$alkyl)(C$_3$-C$_7$cycloalkyl), haloalkyl including C$_1$-C$_6$haloalkyl, and haloalkoxy including C$_1$-C$_6$haloalkoxy;

R$^{16}$ is independently selected from hydrogen, halogen, hydroxyl, nitro, cyano, alkyl including C$_1$-C$_6$alkyl, alkenyl including C$_2$-C$_6$alkenyl, alkanoyl including C$_2$-C$_6$alkanoyl, C$_1$-C$_6$alkoxy, -C$_0$-C$_4$alkyl(mono- and di-C$_1$-C$_6$alkylamino), -C$_0$-C$_4$alkyl(C$_3$-C$_7$cycloalkyl), haloalkyl including C$_1$-C$_6$haloalkyl, and haloalkoxy including C$_1$-C$_6$haloalkoxy;

R$^{17}$ is hydrogen, alkyl including C$_1$-C$_6$alkyl, or -C$_0$-C$_4$alkyl(C$_3$-C$_7$cycloalkyl);

R$^{18}$ and R$^{18'}$ are independently selected from hydrogen, halogen, hydroxymethyl, and methyl;

R$^{19}$ is independently hydrogen, alkyl including C$_1$-C$_6$alkyl, alkenyl including C$_2$-C$_6$alkenyl, alkanoyl including C$_2$-C$_6$alkanoyl, —SO$_2$C$_1$-C$_6$alkyl, (mono- and di-alkylamino)C$_1$-C$_4$alkyl, -C$_0$-C$_4$alkyl(C$_3$-C$_7$cycloalkyl), -C$_0$-C$_4$alkyl(C$_3$-C$_7$heterocycloalkyl), -C$_0$-C$_4$alkyl(aryl), or C$_0$-C$_4$alkyl(heteroaryl), and wherein R$^{19}$ other than hydrogen is optionally substituted with one or more substituents independently selected from halogen, hydroxyl, amino, —COOH, and —C(O)OC$_1$-C$_4$alkyl;

R$^{21}$ and R$^{22}$ are independently selected from hydrogen, hydroxyl, cyano, amino, alkyl including C$_1$-C$_6$alkyl, haloalkyl including C$_1$-C$_6$haloalkyl, C$_1$-C$_6$alkoxy, (C$_3$-C$_7$cycloalkyl)C$_0$-C$_4$alkyl, (phenyl)C$_0$-C$_4$alkyl, -C$_1$-C$_4$alkylOC(O)OC$_1$-C$_6$alkyl, -C$_1$-C$_4$alkylOC(O)C$_1$-C$_6$alkyl, -C$_1$-C$_4$alkylC(O)OC$_1$-C$_6$alkyl, (4- to 7-membered heterocycloalkyl)C$_0$-C$_4$alkyl having 1, 2, or 3 heteroatoms independently selected from N, O, and S, and (5- or 6-membered unsaturated or aromatic heterocycle)C$_0$-C$_4$alkyl having 1, 2, or 3 heteroatoms independently selected from N, O, and S, and each R$^{21}$ and R$^{22}$ can be optionally substituted;

or R$^{21}$ and R$^{22}$ can be taken together to form a carbocyclic or heterocyclic ring;

R$^{23}$ is independently selected from alkyl including C$_1$-C$_6$alkyl, haloalkyl including C$_1$-C$_6$haloalkyl, (aryl)C$_0$-C$_4$alkyl, (C$_3$-C$_7$cycloalkyl)C$_0$-C$_4$alkyl, (phenyl)C$_0$-C$_4$alkyl, (4- to 7-membered heterocycloalkyl)C$_0$-C$_4$alkyl having 1, 2, or 3 heteroatoms independently selected from N, O, and S, and (5- or 6-membered unsaturated or aromatic heterocycle)C$_0$-C$_4$alkyl having 1, 2, or 3 heteroatoms independently selected from N, O, and S, wherein each R$^{23}$ can be optionally substituted;

or R$^{23}$ is hydrogen;

R$^{24}$ and R$^{25}$ are taken together with the nitrogen to which they are attached to form a 4- to 7-membered monocyclic heterocycloalkyl group, or a 6- to 10-membered bicyclic heterocyclic group having fused, spiro, or bridged rings, wherein each R$^{24}$ and R$^{25}$ can be optionally substituted;

R$^{32}$ is independently selected from hydrogen, aryl, heteroaryl; saturated heterocycle, and partially unsaturated heterocycle; wherein the aryl, heteroaryl; saturated heterocycle, and partially unsaturated heterocycle can be optionally substituted with any appropriate group including R$^{201}$;

or R$^{32}$ is independently selected from -C$_2$-C$_6$alkynylR$^{30}$, and each R$^{32}$ can be optionally substituted with any appropriate group including R$^{201}$; examples of R$^{32}$ include, but are not limited to,

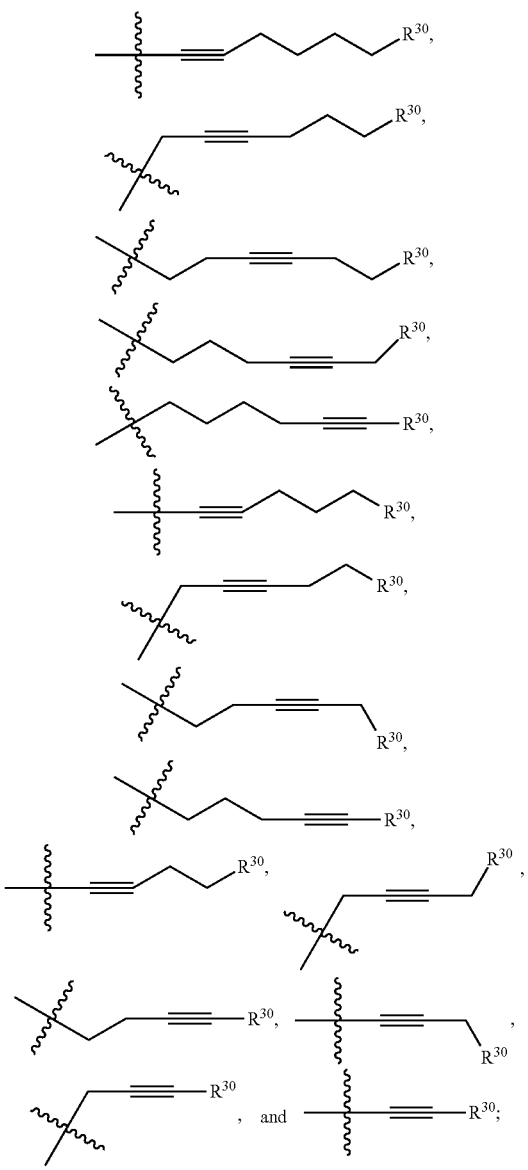

or R$^{32}$ is independently selected from C(O)NR$^{21}$R$^{71}$, C(O)NR$^{24}$R$^{25}$, —C(O)NR$^9$R$^{71}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, and —NR$^9$C(O)NR$^{24}$R$^{25}$, each of which can be optionally substituted with any appropriate group including R$^{201}$;

or $R^{32}$ is independently selected from $NR^{72}R^{73}$, $NR^9SO_2R^{73}$, and $N(SO_2R^9)CH_2C(O)R^{74}$ each of which can be optionally substituted with any appropriate group including $R^{201}$;

or $R^{32}$ is independently selected from $—OC(O)(CH_2)_{1-4}R^{21}$, $—OC(O)NR^{21}R^{22}$, $—OC(O)NR^{24}R^{25}$, $—OC(O)(C_{1-6}$alkyl or $C_{3-6}$cycloalkyl)(aryl), $—OC(O)(C_{1-6}$alkyl or $C_{3-6}$cycloalkyl)(heteroaryl), $—OC(O)(C_{1-6}$alkyl or $C_{3-6}$cycloalkyl)(heterocycle), $—OC(O)$(heteroaryl), $—OC(O)$(aryl), $—OC(O)(C_{1-6}$alkyl or $C_{3-6}$cycloalkyl), $—OC(O)NR^9(CH_2)_{1-4}P(O)(OR^{21})(OR^{22})$, $—C(O)(C_{1-6}$alkyl or $C_{3-6}$cycloalkyl)(aryl), $—C(O)(C_{1-6}$alkyl or $C_{3-6}$cycloalkyl)(heteroaryl), $—C(O)(C_{1-6}$alkyl or $C_{3-6}$cycloalkyl)(heterocycle), $—C(O)$(heteroaryl), $—C(O)$(heterocycle), $—C(O)$(aryl), $—C(O)(C_{1-6}$alkyl or $C_{3-6}$cycloalkyl) and $—C(O)(CH_2)S(O)R^{21}$, each of which can be optionally substituted with any appropriate group including $R^{201}$;

or $R^{32}$ is independently selected from $—O(CH_2)_{1-4}R^{23a}$, $—OC_2$-$C_4$alkenyl$R^{23a}$, $—OC_2$-$C_4$alkynyl$R^{23}$, $—O(CH_2)_{1-4}$paracyclophane, $—O(CH_2)_{1-4}P(O)R^{23b}R^{23b}$, $—O(CH_2)_{1-4}S(O)NR^{21}R^{22}$, $—O(CH_2)_{1-4}S(O)NR^{24}R^{25}$, $—O(CH_2)_{1-4}SO_2NR^{21}R^{22}$, $—O(CH_2)_{1-4}SO_2NR^{24}R^{25}$, $—O(C_3$-$C_7$cycloalkyl), $—O$(aryl), $—O$(heteroaryl), and '$O$(heterocycle) each of which can be optionally substituted with any appropriate group including $R^{201}$;

or $R^{32}$ is independently selected from $P(O)R^{75}R^{75}$, each of which can be optionally substituted with any appropriate group including $R^{201}$;

or $R^{32}$ is independently selected from

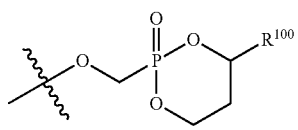

which can be optionally substituted with any appropriate group including $R^{201}$;

$R^{100}$ is aryl, heteroaryl, alkyl, cycloalkyl, heterocyclic, alkenyl or alkynyl;

$R^{23a}$ is independently selected at each occurrence from $(C_3$-$C_7$cycloalkyl), and each $R^{23a}$ can be optionally substituted;

$R^{23b}$ is independently selected at each occurrence from hydroxyl, $C_1$-$C_6$alkoxy, $C_1$-$C_6$alkyl, $(C_3$-$C_7$cycloalkyl)$C_0$-$C_4$alkyl, (phenyl)$C_0$-$C_4$alkyl, $—O(CH_2)_{2-4}O(CH_2)_{8-18}$, $—OC(R^{23c})_2OC(O)OR^{23d}$, $—OC(R^{23c})_2OC(O)R^{23d}$, an N-linked amino acid or an N-linked amino acid ester, and each $R^{23b}$ can be optionally substituted;

$R^{23c}$ is independently selected at each occurrence from hydrogen, $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl- or (aryl)$C_2$-$C_8$alkynyl; or two $R^{23c}$ groups can be taken together with the carbon that they are bonded to form a 3-6 membered heterocycloalkyl having 1, 2, or 3 heteroatoms independently selected from N, O, and S, or a 3- to 6-membered carbocyclic ring, and each $R^{23c}$ can be optionally substituted;

$R^{23d}$ is independently selected at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl or (aryl)$C_2$-$C_8$alkynyl, and each $R^{23d}$ can be optionally substituted;

$R^{71}$ is independently selected at each occurrence from hydroxyl, $C_1$-$C_6$alkoxy, $(C_3$-$C_7$cycloalkyl)$C_0$-$C_4$alkyl, (phenyl)$C_0$-$C_4$alkyl, $-C_1$-$C_4$alkylOC(O)OC_1$-$C_6$alkyl, $-C_1$-$C_4$alkylOC(O)C_1$-$C_6$alkyl, $-C_1$-$C_4$alkylC(O)OC_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S, and each can be optionally substituted;

$R^{72}$ is independently selected at each occurrence from aryl, heteroaryl, heterocycle, alkynyl, hydroxyl, $C_1$-$C_6$alkoxy, $(C_3$-$C_7$cycloalkyl)$C_0$-$C_4$alkyl, (aryl)$C_0$-$C_4$alkyl, (heterocycle)$C_0$-$C_4$alkyl, (heteroaryl)$C_0$-$C_4$alkyl, $-C_1$-$C_4$alkylOC(O)OC_1$-$C_6$alkyl, $-C_1$-$C_4$alkylOC(O)C_1$-$C_6$alkyl, $-C_1$-$C_4$alkylC(O)OC_1$-$C_6$alkyl, $—S(O)(O)(alkyl)$, $—S(O)(alkyl)$, $—S(O)(O)(heteroalkyl)$, $—S(O)(heteroalkyl)$, $—S(O)(O)(aryl)$, $—S(O)(aryl)$, $—S(O)(O)(heteroaryl)$, $—S(O)(heteroaryl)$, and in some embodiments is a (4- to 7-membered heterocycloalkyl)$C_0$-$C_4$alkyl having 1, 2, or 3 heteroatoms independently selected from N, O, and S, and (5- or 6-membered saturated or partially unsaturated heterocycle)$C_0$-$C_4$alkyl having 1, 2, or 3 heteroatoms independently selected from N, O, and S), each of which groups can be optionally substituted;

$R^{73}$ is independently selected at each occurrence from hydrogen, hydroxyl, cyano, amino, $C_1$-$C_6$alkyl, $C_1$-$C_6$haloalkyl, $C_1$-$C_6$alkoxy, $(C_3$-$C_7$cycloalkyl)$C_0$-$C_4$alkyl, (phenyl)$C_0$-$C_4$alkyl, $-C_1$-$C_4$alkylOC(O)OC_1$-$C_6$alkyl, $-C_1$-$C_4$alkylOC(O)C_1$-$C_6$alkyl, $-C_1$-$C_4$alkylC(O)OC_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S, each of which groups can be optionally substituted;

$R^{74}$ is an optionally substituted proline, and in one embodiment the proline is substituted with a $—C(O)NR^9R^{10}$;

$R^{75}$ is independently selected at each occurrence from hydroxyl, $C_1$-$C_6$alkoxy, $C_1$-$C_6$haloalkoxy, $C_1$-$C_6$alkyl, $(C_3$-$C_7$cycloalkyl)$C_0$-$C_4$alkyl-, (aryl)$C_0$-$C_4$alkyl-, $—O$-$C_0$-$C_4$alkyl(aryl), $—O$-$C_0$-$C_4$alkyl$(C_3$-$C_7$cycloalkyl), (4- to 7-membered heterocycloalkyl)$C_0$-$C_4$alkyl-$O$— having 1, 2, or 3 heteroatoms independently selected from N, O, and S; (5- or 6-membered unsaturated or aromatic heterocycle)$C_0$-$C_4$alkyl-$O$— having 1, 2, or 3 heteroatoms independently selected from N, O, and S; $—O(CH_2)_{2-4}O(CH_2)_{8-18}$, $—OC(R^{75a})_2OC(O)OR^{75b}$, $—OC(R^{75a})_2OC(O)R^{75b}$, $—NR^9R^{10}$, an N-linked amino acid or an N-linked amino acid ester and each $R^{75}$ can be optionally substituted;

$R^{75a}$ is independently selected at each occurrence from hydrogen, $C_1$-$C_8$alkyl, $C_2$-$C_8$alkenyl, $C_2$-$C_8$alkynyl, (aryl)$C_0$-$C_4$alkyl-, (aryl)$C_2$-$C_8$alkenyl- or (aryl)$C_2$-$C_8$alkynyl-;

or two $R^{75a}$ groups can be taken together with the carbon that they are bonded to form a 3-6 membered heterocycloalkyl having 1, 2, or 3 heteroatoms independently selected from N, O, and S, or a 3- to 6-membered carbocyclic ring;

$R^{75b}$ is independently selected at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl and (aryl)$C_2$-$C_8$alkynyl;

$R^{30}$ is independently selected at each occurrence from hydrogen, $C_1$-$C_6$alkyl, $C_1$-$C_6$haloalkyl, (aryl)$C_0$-$C_4$alkyl, $(C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S; (5- or 6-membered unsaturated or aromatic heterocycle)$C_0$-$C_4$alkyl having 1, 2, or 3 heteroatoms independently selected from N, O, and S; COOH, $Si(CH_3)_3$, $COOR^{30a}$, $C_2$-$C_6$alkanoyl, $—B(OH)_2$, $—C(O)(CH_2)_{1-4}S(O)R^{21}$, $—P(O)(OR^{21})(OR^{22})$, $—P(O)(OR^{21})R^{22}$, $—P(O)R^{21}R^{22}$, $—NR^9P(O)(NHR^{21})(NHR^{22})$, $—NR^9P(O)(OR^{21})(NHR^{22})$, —NR$^9$P(O)(OR$^{21}$)(OR$^{22}$), —C(S)R$^{21}$, —NR$^{21}$SO$_2$R$^{22}$, —NR$^9$S(O)NR$^{10}$R$^{22}$, —NR$^9$SO$_2$NR$^{10}$R$^{22}$, —SO$_2$NR$^9$COR$^{22}$, —SO$_2$NR$^9$CONR$^{21}$R$^{22}$, —NR$^{21}$SO$_2$R$^{22}$, —C(O)NR$^{21}$SO$_2$R$^{22}$, —C(NH$_2$)NR$^9$R$^{22}$, —C(NH$_2$)NR$^9$S(O)$_2$R$^{22}$, —NR$^9$C(O)OR$^{10}$, —NR$^9$OC(O)R$^{22}$, —(CH$_2$)$_{1\text{-}4}$C(O)NR$^{21}$R$^{22}$, —C(O)R$^{24}$R$^{25}$, —NR$^9$C(O)R$^{21}$, —C(O)R$^{21}$, —NR$^9$C(O)NR$^9$R$^{10}$, —NR$^9$C(O)NR$^{24}$R$^{25}$, —(CH$_2$)$_{1\text{-}4}$OC(O)R$^{21}$, each of which R$^{30}$ can be optionally substituted;

R$^{30a}$ is C$_1$-C$_6$alkyl, C$_2$-C$_6$alkenyl, C$_2$-C$_6$alkynyl, (C$_3$-C$_7$cycloalkyl)C$_0$-C$_4$alkyl-, (aryl)C$_0$-C$_4$alkyl-, (3- to 7-membered heterocycloalkyl)C$_0$-C$_4$alkyl- having 1, 2, or 3 heteroatoms independently selected from N, O, and S, and (5- or 6-membered unsaturated or aromatic heterocycle)C$_0$-C$_4$alkyl having 1, 2, or 3 heteroatoms independently selected from N, O, and S, each of which R$^{30a}$ can be optionally substituted;

R$^{41}$ is hydrogen, alkyl including C$_1$-C$_6$alkyl, or -(C$_0$-C$_2$alkyl)(C$_3$-C$_5$cycloalkyl);

R$^{54}$ is hydrogen, alkyl including C$_1$-C$_6$alkyl, alkenyl including C$_2$-C$_6$alkenyl, alkynyl including C$_2$-C$_6$alkynyl, C$_1$-C$_6$alkoxy, alkanoyl including C$_2$-C$_6$alkanoyl, thioalkyl including C$_1$-C$_6$thioalkyl, hydroxyC$_1$-C$_6$alkyl, aminoC$_1$-C$_6$alkyl, -C$_0$-C$_4$alkyl(C$_3$-C$_7$cycloalkyl), (phenyl)C$_0$-C$_4$alkyl-, (heterocycloalkyl)C$_0$-C$_4$alkyl and (heteroaryl)C$_0$-C$_4$alkyl-;

B2 is a heteroaryl, heterocycle, or aryl group directly bound to both L$^1$ and X$^{10}$ at two independent positions;

or B2 is a monocyclic or bicyclic carbocyclic; a monocyclic or bicyclic carbocyclic-oxy group; alkenyl including C$_2$-C$_6$alkenyl; alkynyl including C$_2$-C$_6$alkynyl; -(C$_0$-C$_4$alkyl)(aryl); -(C$_0$-C$_4$alkyl)(heteroaryl); or -(C$_0$-C$_4$alkyl)(biphenyl) directly bound to both L$^1$ and X$^{10}$ at two independent positions;

or B2 is a 6-membered aryl group fused to a 5-membered saturated cyclic group that optionally contains 1 or 2 heteroatoms independently selected from N or S directly bound to both L$^1$ and X$^{10}$ at two independent positions, wherein one of the CH$_2$ groups of the 5-membered cyclic group is optionally substituted by oxo (i.e., =O);

or B2 is an 8-membered monocyclic or bicyclic heteroaryl, a 9-membered monocyclic or bicyclic heteroaryl group, a 10-membered aryl, or a 10 membered heteroaryl group directly bound to both L$^1$ and X$^{10}$ at two independent positions;

or B2 is (optionally substituted alkyl)-(optionally substituted cycloalkyl), (optionally substituted alkenyl)-(optionally substituted cycloalkyl), or (optionally substituted alkynyl)-(optionally substituted cycloalkyl) directly bound to both L$^1$ and X$^{10}$ at two independent positions;

or B2 is alkyl;

wherein, each of which B2 is optionally substituted with one or more substituents independently selected from R$^{33}$, R$^{34}$, R$^{35}$, R$^{36}$, R$^{201}$, and R$^{48}$;

R$^{33}$ is independently selected from halogen, hydroxyl, —COOH, cyano, alkyl including C$_1$-C$_6$alkyl, alkanoyl including C$_2$-C$_6$alkanoyl, C$_1$-C$_6$alkoxy, -C$_0$-C$_4$alkylNR$^9$R$^{10}$, —SO$_2$R$^9$, haloalkyl including C$_1$-C$_6$haloalkyl, and haloalkoxy including C$_1$-C$_6$haloalkoxy;

R$^{34}$ is independently selected from nitro, alkenyl including C$_2$-C$_6$alkenyl, alkynyl including C$_2$-C$_6$alkynyl, thioalkyl including C$_1$-C$_6$thioalkyl, -JC$_3$-C$_7$cycloalkyl, —B(OH)$_2$, -JC(O)NR$^9$R$^{23}$, -JOSO$_2$OR$^{21}$, —C(O)(CH$_2$)$_{1\text{-}4}$S(O)R$^{21}$, —O(CH$_2$)$_{1\text{-}4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$_{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CORNR$^{21}$R$^{22}$, -JNR$^{21}$SO$_2$R$^{22}$, -JC(O)NR$^{21}$SO$_2$R$^{22}$, -JC(NH$_2$)=NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1\text{-}4}$C(O)NR$^{21}$R$^{22}$, -JC(O)R$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1\text{-}4}$OC(O)R$^{21}$, and -JC(O)OR$^{23}$; each of which R$^{34}$ is optionally substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, alkyl including C$_1$-C$_6$alkyl, -C$_0$-C$_4$alkyl(C$_3$-C$_7$cycloalkyl), C$_1$-C$_6$alkoxy, -C$_0$-C$_2$alkyl(mono- and di-C$_1$-C$_4$alkylamino), C$_1$-C$_6$alkylester, C$_1$-C$_4$alkylamino, C$_1$-C$_4$hydroxylalkyl, haloalkyl including C$_1$-C$_6$haloalkyl, and haloalkoxy including C$_1$-C$_6$haloalkoxy;

R$^{35}$ is independently selected from naphthyl, naphthyloxy, indanyl, (4- to 7-membered heterocycloalkyl)C$_0$-C$_4$alkyl containing 1 or 2 heteroatoms selected from N, O, and S, and bicyclic heterocycle containing 1, 2, or 3 heteroatoms independently selected from N, O, and S, and containing 4- to 7-ring atoms in each ring; each of which R$^{35}$ is optionally substituted with one or more substituents independently selected from halogen, hydroxyl, nitro, cyano, alkyl including C$_1$-C$_6$alkyl, alkenyl including C$_2$-C$_6$alkenyl, alkanoyl including C$_2$-C$_6$alkanoyl, C$_1$-C$_6$alkoxy, (mono- and di-alkylamino)C$_0$-C$_4$alkyl, C$_1$-C$_6$alkylester, -C$_0$-C$_4$alkyl(C$_3$-C$_7$cycloalkyl), —SO$_2$R$^9$, haloalkyl including C$_1$-C$_6$haloalkyl, and haloalkoxy including C$_1$-C$_6$haloalkoxy;

R$^{36}$ is independently selected from tetrazolyl, (phenyl)C$_0$-C$_2$alkyl, (phenyl)C$_1$-C$_6$alkoxy, phenoxy, and 5- or 6-membered heteroaryl containing 1, 2, or 3 heteroatoms independently selected from N, O, B, and S, each of which R$^{36}$ is optionally substituted with one or more substituents independently selected from halogen, hydroxyl, nitro, cyano, alkyl including C$_1$-C$_6$alkyl, alkenyl including C$_2$-C$_6$alkenyl, alkanoyl including C$_2$-C$_6$alkanoyl, C$_1$-C$_6$alkoxy, (mono- and di-alkylamino)C$_0$-C$_4$alkyl, C$_1$-C$_6$alkylester, -C$_0$-C$_4$alkyl(C$_3$-C$_7$cycloalkyl), —SO$_2$R$^9$, —OSi(CH$_3$)$_2$C(CH$_3$)$_3$, —Si(CH$_3$)$_2$C(CH$_3$)$_3$, haloalkyl including C$_1$-C$_6$haloalkyl, and haloalkoxy including C$_1$-C$_6$haloalkoxy;

R$^{48}$ is independently selected from hydrogen, halogen, hydroxyl, nitro, cyano, amino, alkyl including C$_1$-C$_6$alkyl, haloalkyl including C$_1$-C$_6$haloalkyl, alkenyl including C$_2$-C$_6$alkenyl, alkynyl including C$_2$-C$_6$alkynyl, thioalkyl including C$_1$-C$_6$thioalkyl, C$_1$-C$_6$alkoxy, -JC$_3$-C$_7$cycloalkyl, —B(OH)$_2$, -JC(O)NR$^9$R$^{23}$, -JOSO$_2$OR$^{21}$, —C(O)(CH$_2$)$_{1\text{-}4}$S(O)R$^{21}$, —O(CH$_2$)$_{1\text{-}4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)=NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1\text{-}4}$C(O)NR$^{21}$R$^{22}$, -JC(O)NR$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1\text{-}4}$OC(O)R$^{21}$, -JC(O)OR$^{23}$; S(O)=NHR$^{21}$, SF$_5$, JC(R$^9$)=NR$^{21}$', and SO$_2$OR$^{21}$;

R$^{51}$ is CH$_3$, CH$_2$F, CHF$_2$ or CF$_3$;

X$^{29}$ is O or S;

$R^{52}$ is independently selected from halo, hydrogen, or optionally substituted alkyl including $C_1$-$C_6$alkyl;

or two $R^{52}$ groups can be taken together to form a 3- to 6-membered carbocyclic spiro ring or a 3- to 6-membered heterocyclic spiro ring containing 1 or 2 heteroatoms independently selected from N, O, or S;

or two $R^{52}$ groups can be taken together to form an oxo or alkene group (e.g.

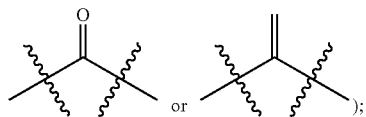

);

or $R^{52}$ is independently selected from halo, hydrogen, or optionally substituted alkyl including $C_1$-$C_6$alkyl, amino, hydroxyl, aminoalkyl, alkenyl, alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), alkanoyl, $C_1$-$C_6$alkoxy, $C_1$-$C_6$thioalkyl, -$C_0$-$C_4$alkyl(mono- and di-alkylamino), -$C_0$-$C_4$alkyl($C_3$-$C_7$cycloalkyl), -$C_0$-$C_4$alkoxy($C_3$-$C_7$cycloalkyl), haloalkyl, haloalkoxy, —COOH, -$C_0$-$C_4$alkyl($C_3$-$C_7$cycloalkyl), $C_2$-$C_6$alkenyloxy, —C(O)O$R^9$, -$C_0$-$C_4$alkylN$R^9R^{10}$, —C(O)N$R^9R^{10}$, —SO$_2R^9$, —SO$_2$N$R^9R^{10}$, —OC(O)$R^9$, $R^{201}$, and N($R^9$)C(O)$R^{10}$;

$R^{201}$ is selected from aminoalkyl-, alkylaminoalkyl-, heterocycloalkyl-, hydroxyalkyl, -alkyl—O-alkyl including —CH$_2$OCH$_3$, -alkyl—S-alkyl, -alkyl—N(alkyl)-alkyl, -alkyl—NH-alkyl, -aliphatic—O-aliphatic, -aliphatic—S-aliphatic, -aliphatic—N(aliphatic)-aliphatic, -aliphatic—NH-aliphatic, -aliphatic—O-heterocycle, -aliphatic—S-heterocycle, -aliphatic—N(aliphatic)-heterocycle, -aliphatic—NH-heterocycle, -alkyl—NHC(O)haloalkyl, -alkyl—N$R^9$C(O)haloalkyl, -alkyl—C(O)NHhaloalkyl, -alkyl—C(O)N$R^9$haloalkyl, -alkyl—NHC(O)haloalkyl, -alkyl—N$R^9$C(O)aliphatic, -alkyl—C(O)NHaliphatic, -alkyl—N$R^9$C(O)aliphatic, -alkyl—NHC(O)aliphatic, -substituted alkyl—N($R^9$)-substituted-alkyl, alkyl—O-haloalkyl, alkyl-heteroaryl, heteroaryl, heterocycle, alkyl-heterocycle, —N(aliphatic)$_2$; and wherein each $R^{201}$ can be optionally substituted as defined in the Terminology section below if it results in a stable compound that makes sense to the skilled artisan, and wherein each $R^{201}$ can be optionally substituted with $R^{301}$, which can be directly linked to $R^{201}$ or can be linked to $R^{201}$ through an amino, hydroxyl, thio, carboxyl acid, phosphate, phosphonate or sulfonate linkage as desired and appropriate;

J is independently selected from a covalent bond, alkylene including $C_1$-$C_4$alkylene, O—alkylene including —O$C_1$-$C_4$alkylene, alkenylene including $C_2$-$C_4$alkenylene, and alkynylene $C_2$-$C_4$alkynylene;

$R^{301}$ is selected from the following:

i. The residue of a fatty acid. Examples are short chain fatty acids with 3, 4, or 5 aliphatic carbons, medium-chain fatty acids with aliphatic tails of 6, 7, 8, 9, 10, 11 or 12 carbons, long chain fatty acids, which have aliphatic tails of 13, 14, 15, 16, 17, 18, 19, 20, 21 or 22 carbons, or a very long fatty acid, which has 22, 23, 24, 25, 26 27, or 28 or more aliphatic carbons. The aliphatic chain can be saturated, mono-unsaturated, di-unsaturated, tri-unsaturated, polyunsaturated, or alkynyl. Unsaturated fatty acids can be used in a cis or trans configuration, and include, but are not limited to oleic acid, Ω6 fatty acid such as linoleic acid, ω3 fatty acid such as α-linolenic acid, docosahexaenoic acid, stearidonic acid, eicosapentaenoic acid, docosapentaenoic acid, eicosatetraenoic acid, myristoleic acid, palmitoleic acid, sapienic acid, elaidic acid, vaccenic acid, gadoleic acid, eicosenoic acid, nervonic acid, eicosadienoic acid, docasadienoic acid, linolenic acid, t-linolenic acid, pinolenic acid, eleosteric acid, β-eleostearic acid, mead acid, eicosatrienoic acid, linoleic acid, linoelaidic acid, α-linolenic acid, arachidonic acid, erucic acid and docosahexaenoic acid. Nonlimiting examples of saturated fatty acids that can be used to provide the prodrugs of the present invention are caprylic acid, capric acid, lauric acid, myristic acid, palmitic acid, stearic acid, arachidic acid, behenic acid, lignoceric acid and cerotic acid.

ii. The residue of an amino acid that is naturally occurring or synthetic, and includes for example, α, β γ or δ amino acids. Naturally occurring amino acids include those found in proteins, e.g., glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In some embodiments, the amino acid is in the L-configuration. Alternatively, the amino acid can be used in the D-configuration or in a mixture of L- and D-. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. Additional amino acids include selenocysteine, pyrrolysine, N-formylmethionine, γ-aminobutyric acid (GABA), δ-aminolevulinic acid, aminobenzoic acid (including 4-aminobenzoic acid), aminoisobutyric acid, dehydroalanine, cystathionine, lanthionine, djenkolic acid, diaminopimelic acid, norvaline, alloisoleucine, t-leucine, α-amino-heptanoic acid, pipecolic acid, α, β-diaminopropionic acid, α,γ-diaminobutyric acid, ornithine, glutamic acid, allothreonine, homocysteine, β-aminobutyric acid, α-aminoisobutyric acid, isovaline, sarcosine, N-ethylglycine, N-propylglycine, N-isopropyl glycine, N-methyl alanine, N-ethyl alanine, N-methyl-β-alanine, isoserine, norleucine, homoserine, O-methyl-homoserine, O-ethyl-homoserine, homonorleucine, carboxyglutamic acid, hydroxyproline, hypusine, pyroglutamic acid, and a-hydroxy-y-aminobutyric acid.

iii. The residue of a non-naturally occurring amino acid with an extended length between the amino group and the carboxylic acid, which can be used either alone or as a linker to another prodrug moiety. Examples include amino acids wherein the amino and carboxylic acid are separated by an aliphatic or heteroaliphatic moiety (nonlimiting example is 8-amino-3,6-dioxaoctanoic acid), for example an alkyl, alkenyl, alkynyl, ethylene glycol, propylene glycol, alkylene glycol, or the like, moiety, e.g., with 3, 4, 5, 6, 7, 8, 9, 10, 11 or 12 or more straight, branched or cyclic atoms or moieties (e.g., alkylene glycol moieties), as appropriate to provide the desired properties. In some embodiments, the amino acid has one or more internal amine, carbonyl, carboxy, oxo, thio, phosphate or phosphonate moieties in the heteroaliphatic chain.

iv. The residue of one or a series of amino acids linked to a terminal fatty acid or to an end cap like hydrogen or alkyl. In one non-limiting example, 8-amino-3,6-dioxaoctanoic acid (one or several in sequence) is covalently bound to the selected complement D inhibitor of the present invention through a functional group such as a carboxylic acid, sulfonyl, hydroxyl or amino group. See generally Lau, et al., "Discovery of the Once-Weekly Glucagon-Like Peptide-1 (GLP-1) Analogue Semiglutide", *J. Med. Chem.*, 2015, 58, 7370-7380. The 8-amino-3,6-dioxaoctanoic acid is covalently linked to an aliphatic acid, including but not limited to a $C_{16}$, $C_{18}$, $C_{20}$ aliphatic acid, or a dicarboxylic acid, including but not limited to a $C_8$, $C_{10}$, $C_{12}$, $C_{14}$, $C_{16}$, $C_{18}$ or $C_{20}$ diacid. One or more amino acids can also be used in the selected configuration to add length or functionality.

v. $R^{301}$ can optionally be on any A, B, C, or R directly or through a difunctional linking moiety (e.g. divalent aliphatic, heteroaliphatic, heterocyclic, heteroaryl, aryl, or a heteroatom)

s is 1 or 2;

r is 1, 2 or 3;

q is 1, 2 or 3; and m is 0, 1, 2, or 3.

The disclosure provides a compound of Formula II:

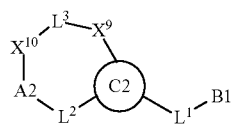

Formula II or a pharmaceutically acceptable salt, isotopic analog, prodrug, N-oxide, or isolated isomer thereof, optionally in a pharmaceutically acceptable carrier;

wherein:

A2 is selected from:

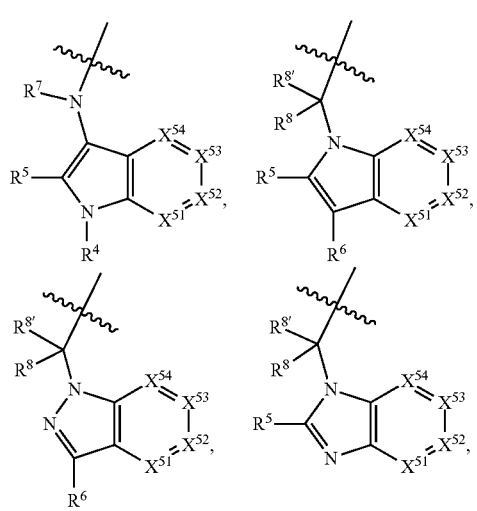

-continued

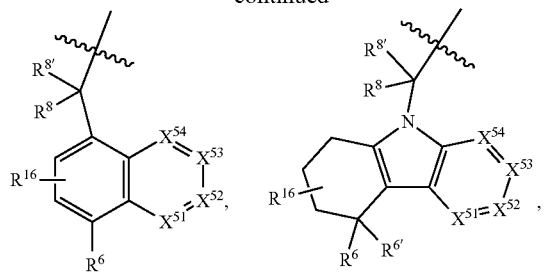

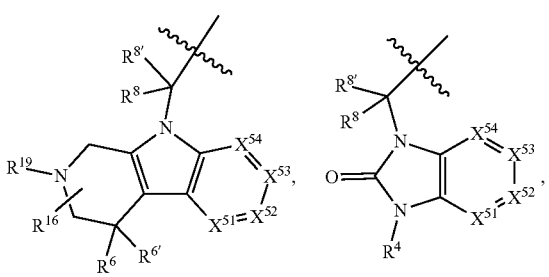

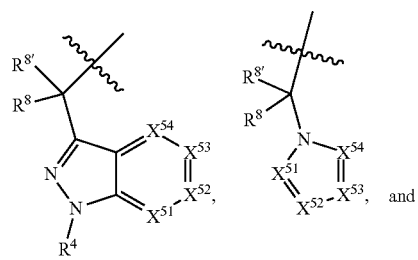

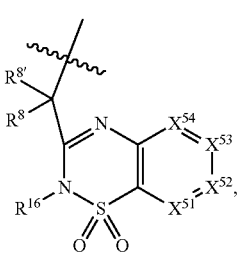

wherein $X^{51}$, $X^{52}$, $X^{53}$ and $X^{54}$ are selected from N, $CR^{13}$, and a carbon directly bound to $X^{10}$, and wherein one and only one of $X^{51}$, $X^{52}$, $X^{53}$ and $X^{54}$ is a carbon directly bound to $X^{10}$;

or A2 is selected from:

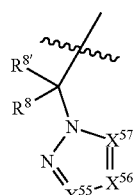

wherein $X^{55}$, $X^{56}$, and $X^{57}$ are selected from N, $CR^{13}$, $CR^5$, $CR^6$, and a carbon directly bound to $X^{10}$, and wherein one and only one of $X^{55}$, $X^{56}$, and $X^{57}$ is a carbon directly bound to $X^{10}$;

or A2 is A2' which is selected from:
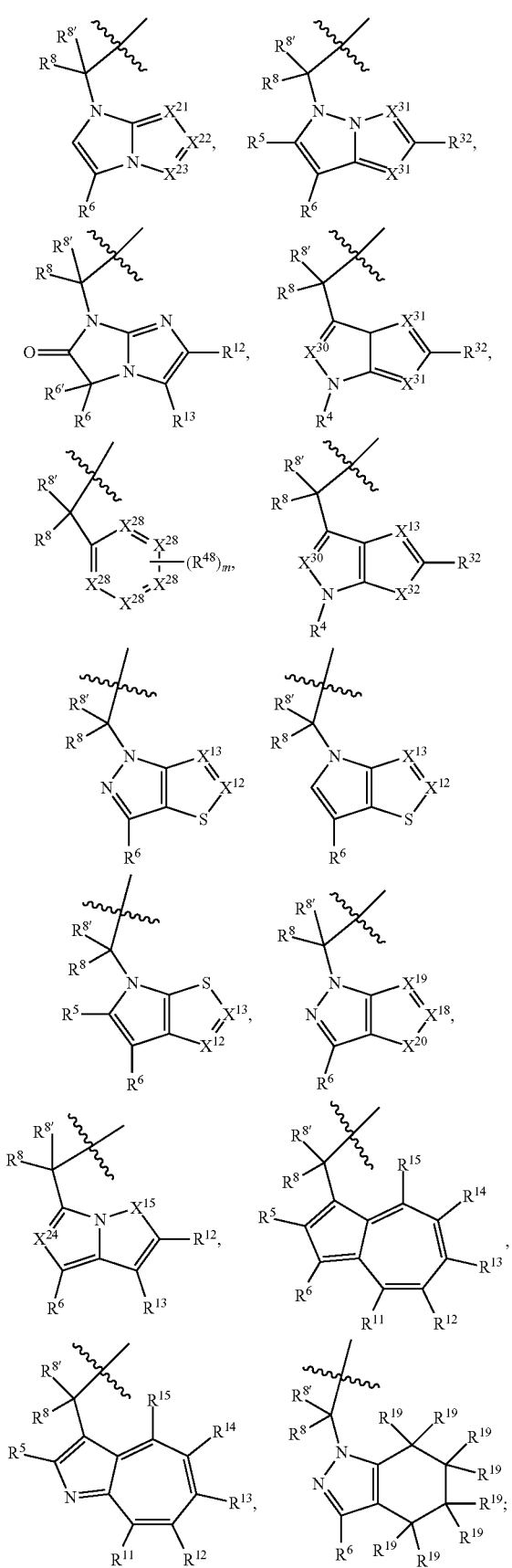
-continued
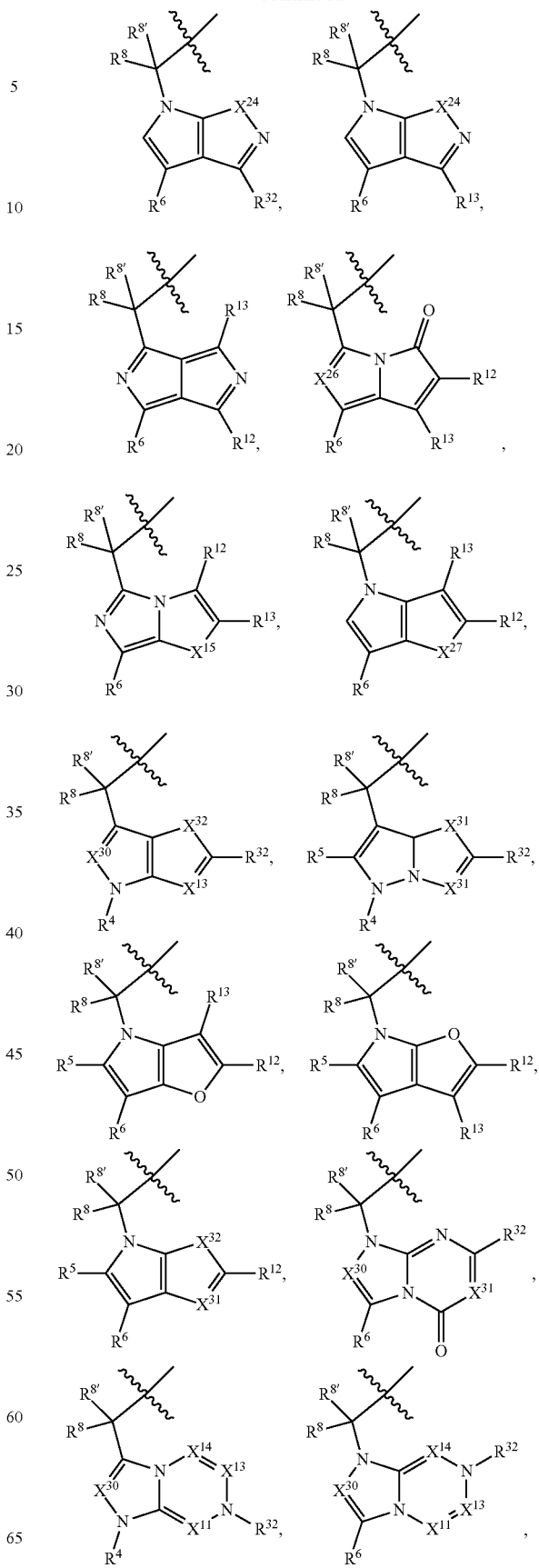

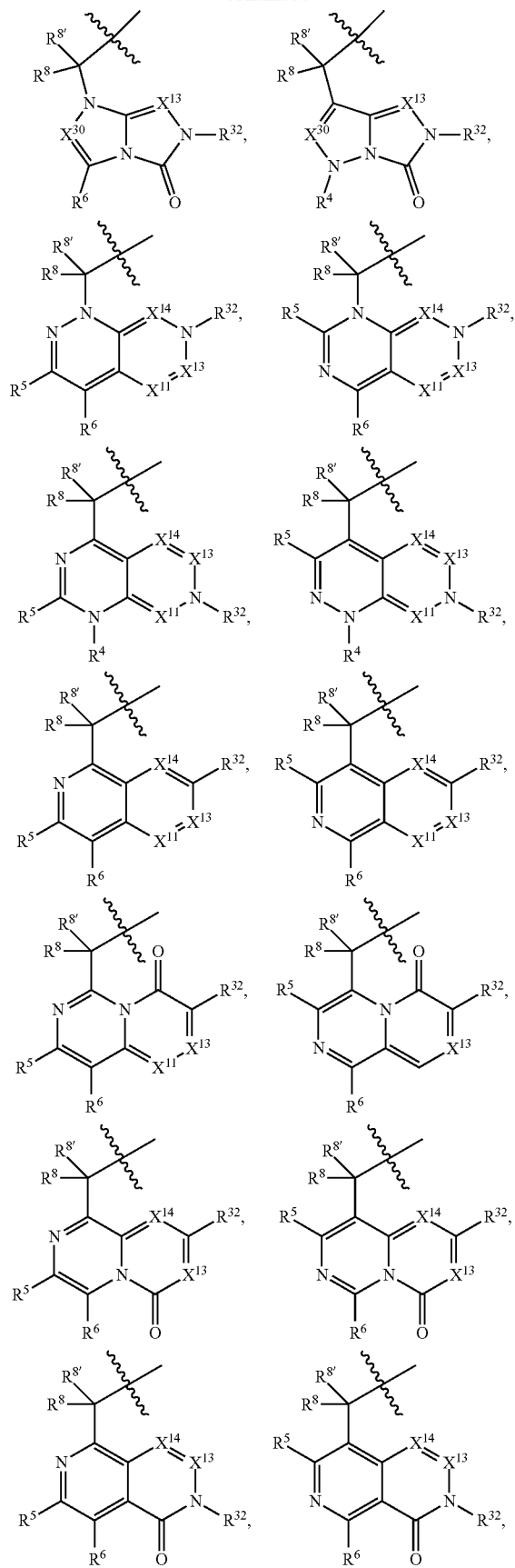
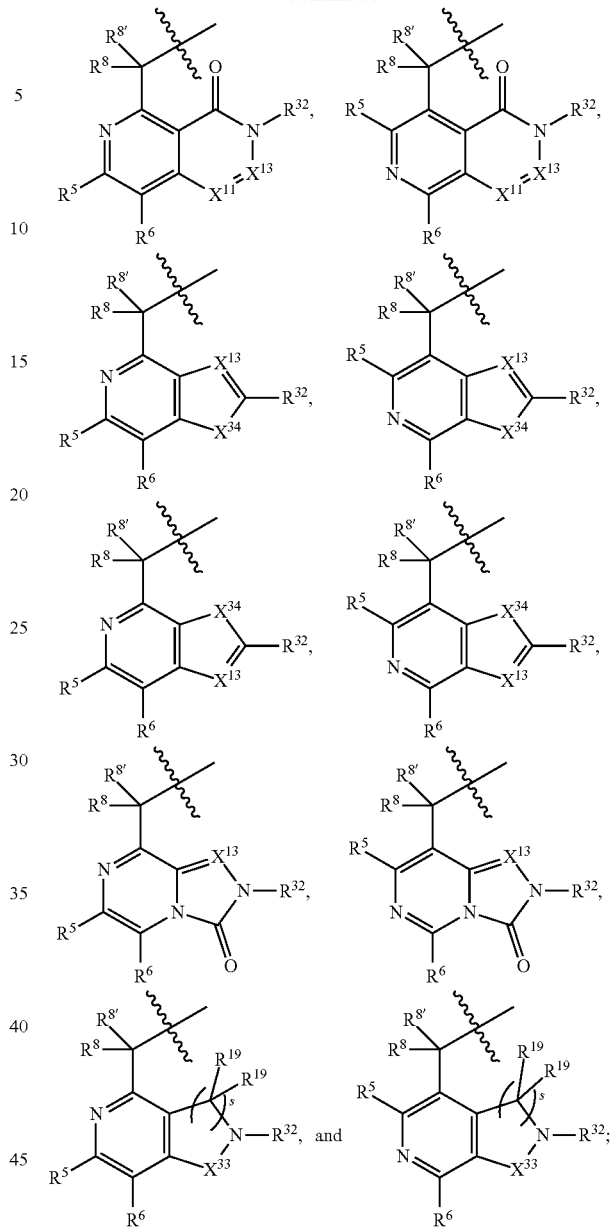

wherein each of which A2' has one and only one R group replaced with a direct bond to $X^{10}$;

wherein in one embodiment the R group replaced with a direct bond to $X^{10}$ is selected from $R^4$, $R^5$, $R^6$, $R^{11}$, $R^{12}$, $R^{13}$, $R^{14}$, $R^{15}$, $R^{19}$, $R^{32}$, and $R^{54}$;

B1 is a heteroaryl, heterocycle, or aryl group;

or B1 is a monocyclic or bicyclic carbocyclic; a monocyclic or bicyclic carbocyclic-oxy group; alkenyl including $C_2$-$C_6$alkenyl; alkynyl including $C_2$-$C_6$alkynyl; -($C_0$-$C_4$alkyl)(aryl); -($C_0$-$C_4$alkyl)(heteroaryl); or -($C_0$-$C_4$alkyl)(biphenyl);

or B1 is a 6-membered aryl group fused to a 5-membered saturated cyclic group that optionally contains 1 or 2 heteroatoms independently selected from N or S wherein one of the $CH_2$ groups of the 5-membered cyclic group is optionally substituted by oxo (i.e., =O);

or B1 is an 8-membered monocyclic or bicyclic heteroaryl, a 9-membered monocyclic or bicyclic heteroaryl group, a 10-membered aryl, or a 10 membered heteroaryl group;

or B1 is (optionally substituted alkyl)-(optionally substituted cycloalkyl), (optionally substituted alkenyl)-(optionally substituted cycloalkyl), or (optionally substituted alkynyl)-(optionally substituted cycloalkyl);

in an alternative embodiment, B1 is alkyl, alkyl(alkenyl), alkyl(alkynyl), or cycloalkyl(alkenyl);

wherein, each of which B1 is optionally substituted with one or more substituents independently selected from $R^{33}$, $R^{34}$, $R^{35}$, $R^{36}$, $R^{201}$, $R^{301}$, and $R^{48}$; and wherein each other variable is as defined herein.

The disclosure provides a compound of Formula III:

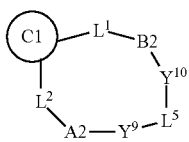

Formula III or a pharmaceutically acceptable salt, isotopic analog, prodrug, N-oxide, or isolated isomer thereof, optionally in a pharmaceutically acceptable carrier;
wherein:

A2 is as defined in Formula II except A2 is directly bound to $Y^9$ instead of $X^{10}$;

B2 is as defined in Formula I except B2 is directly bound to $Y^{10}$ instead of $X^{10}$;

$L^5$ is selected from $L^3$ and $L^4$;

$Y^9$ is selected from $X^9$ and $Z^9$;

$Y^{10}$ is selected from $X^{10}$ and $Z^{10}$;

wherein for compounds of Formula III at least one of the following is true:
a. $L^5$ is $L^4$;
b. $Y^9$ is $Z^9$; or
c. $Y^{10}$ is $Z^{10}$;

$Z^9$ is —CO—, —S(O)$_2$—, or —S(O)—;
$Z^{10}$ is —CO— or —S(O)—;
$L^4$ is

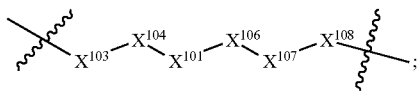

$X^{101}$ is selected from —CR$^{52a}$R$^{52}$—, —C(O)—, —C(S)—, —P(O)OR$^9$—, —S(O)—, —S(O)$_2$—, —O—, —S—, alkenylene, alkynylene, heterocycle, heteroalkylene, heteroalkynylene, heteroalkenylene, arylalkyl, heterocycloalkyl, heterocycloalkyl, heteroarylalkyl, aryl, heteroaryl, cycloalkyl, and —NR$^9$—, which moieties are used in any order that results in a stable compound, and makes chemical sense to the skilled artisan, each of which is considered independently disclosed;

$X^{103}$, $X^{104}$, $X^{106}$, $X^{107}$, and $X^{108}$ are each independently selected from bond, —C(R$^{52}$)$_2$—, —C(O)—, —C(S)—, —P(O)OR$^9$—, —S(O)—, —S(O)$_2$—, —O—, —5—, alkenylene, alkynylene, heterocycle, heteroalkylene, heteroalkynylene, heteroalkenylene, arylalkyl, heterocycloalkyl, heterocycloalkyl, heteroarylalkyl, aryl, heteroaryl, cycloalkyl, and —NR$^9$-, which moieties are used in any order that results in a stable compound, and makes chemical sense to the skilled artisan, each of which is considered independently disclosed; or in an alternative embodiment, $L^4$ is

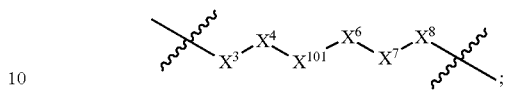

$R^{52a}$ is independently selected from $R^{201}$, halogen, hydroxyl, nitro, cyano, —O(PO)(OR$^9$)$_2$, —(PO)(OR$^9$)$_2$, alkyl including C$_1$-C$_6$alkyl, alkenyl including C$_2$-C$_6$alkenyl, alkynyl including C$_2$-C$_6$alkynyl, C$_2$-C$_6$alkenyl(aryl), C$_2$-C$_6$alkenyl(cycloalkyl), C$_2$-C$_6$alkenyl(heterocycle), C$_2$-C$_6$alkenyl(heteroaryl), C$_2$-C$_6$alkynyl(aryl), C$_2$-C$_6$alkynyl(cycloalkyl), C$_2$-C$_6$alkynyl(heterocycle), C$_2$-C$_6$alkynyl(heteroaryl), alkanoyl including C$_2$-C$_6$alkanoyl, C$_1$-C$_6$alkoxy, thioalkyl including C$_1$-C$_6$thioalkyl, -C$_0$-C$_4$alkyl(mono- and di-alkylamino), -C$_0$-C$_4$alkyl(C$_3$-C$_7$cycloalkyl), -C$_0$-C$_4$alkoxy(C$_3$-C$_7$cycloalkyl), haloalkyl including C$_1$-C$_6$haloalkyl, haloalkoxy including C$_1$-C$_6$haloalkoxy, amino, —COOH, -C$_0$-C$_4$alkyl(C$_3$-C$_7$cycloalkyl), C$_2$-C$_6$alkenyloxy, —C(O)OR$^9$, -C$_0$-C$_4$alkylNR$^9$R$^{10}$, —C(O)NR$^9$R$^{10}$, —SO$_2$R$^9$, —SO$_2$NR$^9$R$^{10}$, —OC(O)R$^9$, —C(NR)NR$^9$R$^{10}$;

or $R^{52a}$ and $R^{52}$ can be taken together to form a 3- to 6-membered carbocyclic spiro ring or a 3- to 6-membered heterocyclic spiro ring containing 1 or 2 heteroatoms independently selected from N, O, or S;

or $R^{52a}$ and $R^{52}$ are taken together to form an oxo or alkenyl group;

C1 is

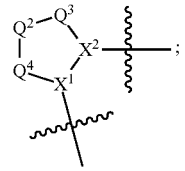

or C1 is selected from:

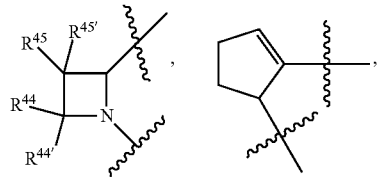

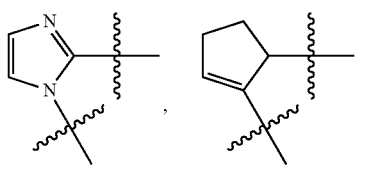

and

-continued
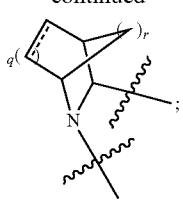
or C1 is selected from:
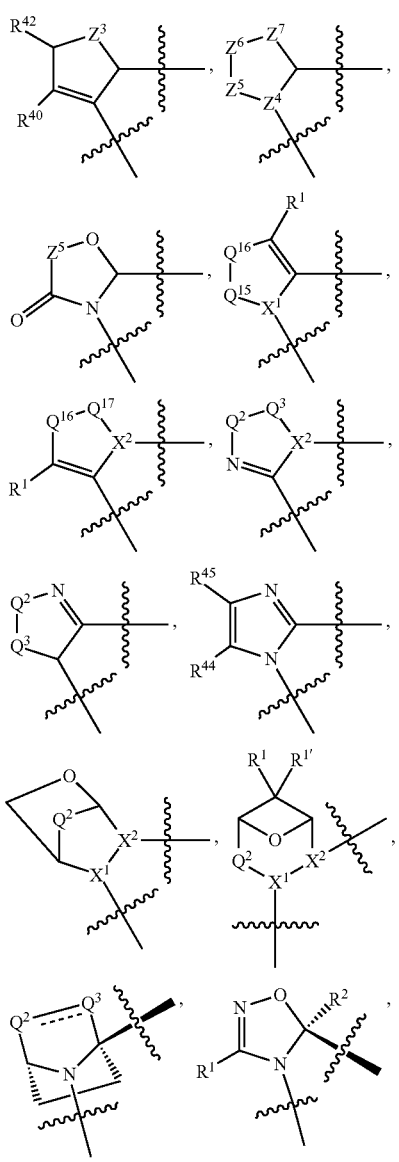
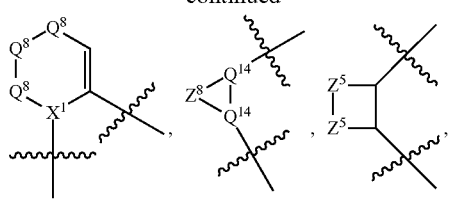
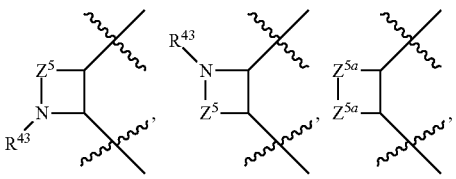
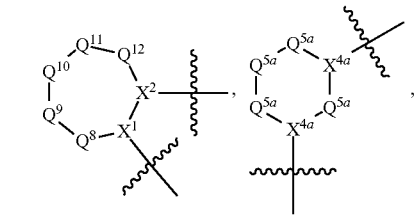
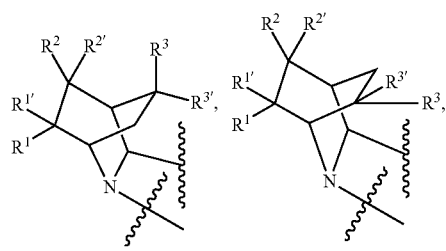
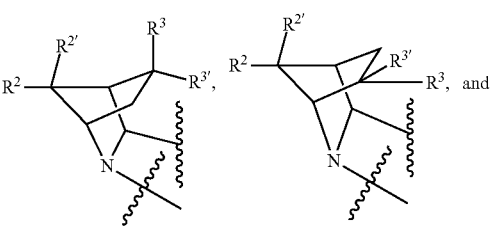
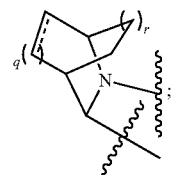
or C1 is selected from:
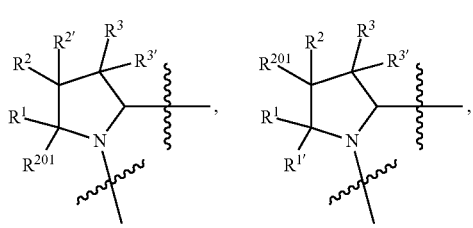

-continued

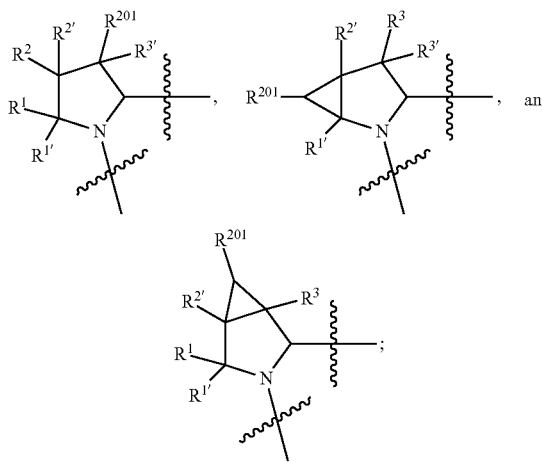

or C1 is selected from:

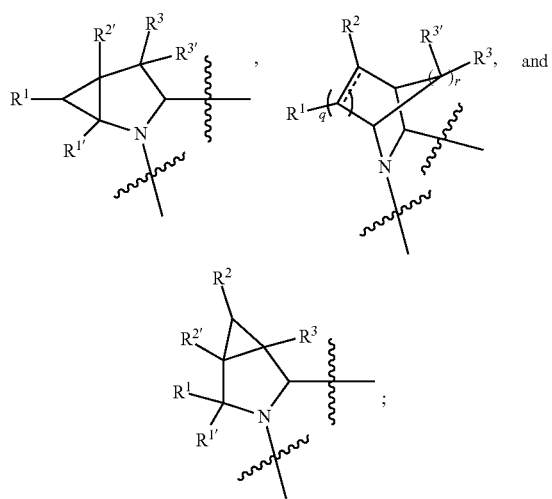

or C1 is selected from:

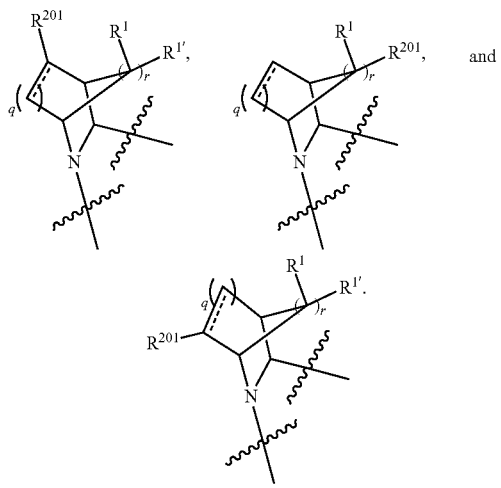

or C1 is selected from:

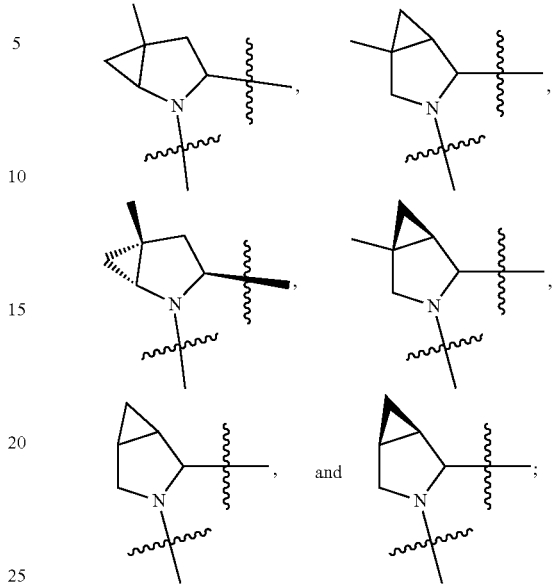

$R^{44}$, $R^{44'}$, $R^{45}$, $R^{45'}$ are independently selected at each occurrence, as appropriate, and only where a stable compound results, from hydrogen, $R^{201}$, halogen (and specifically fluoro, chloro, bromo), hydroxyl, nitro, cyano, amino, alkyl, including $C_1$-$C_6$alkyl; alkenyl, including $C_2$-$C_6$alkenyl; alkynyl, including $C_2$-$C_6$alkynyl; alkoxy, including $C_1$-$C_6$alkoxy; alkanoyl, including $C_2$-$C_6$alkanoyl; thioalkyl, including $C_1$-$C_6$alkylthio; hydroxy$C_1$-$C_6$alkyl; amino$C_1$-$C_6$alkyl; -$C_0$-$C_4$alkylNR$^9$R$^{10}$; —C(O)OR$^9$; —OC(O)R$^9$; —NR$^9$C(O)R$^{10}$; —C(O)NR$^9$R$^{10}$; —OC(O)NR$^9$R$^{10}$; —NR$^9$C(O)OR$^{10}$, haloalkyl including $C_1$-$C_6$haloalkyl, and haloalkoxy including $C_1$-$C_6$haloalkoxy;

or $R^{44}$ and $R^{44'}$, $R^{45}$ and $R^{45'}$, or two $R^{47}$ groups are taken together to form a carbonyl group;

or $R^{44}$ and $R^{44'}$, $R^{45}$ and $R^{45'}$, or $R^{46}$ and $R^{46'}$ are taken together to form an optionally substituted 3- to 6-membered carbocyclic spiro ring or a 3- to 6-membered heterocyclic spiro ring containing 1 or 2 heteroatoms independently selected from N, O, or S;

wherein, each of the above spiro rings may be optionally substituted with 1 or more substituents independently selected from $R^{201}$, halogen (and in particular F), hydroxyl, cyano, —COOH; alkyl, including $C_1$-$C_4$alkyl (including in particular methyl); alkenyl, including $C_2$-$C_4$alkenyl; alkynyl, including $C_2$-$C_4$alkynyl; alkoxy, including $C_1$-$C_6$alkoxy; alkanoyl, including $C_2$-$C_4$alkanoyl; hydroxy$C_1$-$C_4$alkyl, (mono- and di-alkylamino)$C_1$-$C_4$alkyl, -$C_0$-$C_4$alkyl($C_3$-$C_7$cycloalkyl), —O-alkyl($C_3$-$C_7$cycloalkyl), haloalkyl including $C_1$-$C_6$haloalkyl, and haloalkoxy including $C_1$-$C_6$haloalkoxy;

or $R^{44}$ and $R^{45}$ or $R^{44'}$ and $R^{45'}$ are taken together to form a 4- to 6-membered carbocyclic or aryl ring or a 4- to 6-membered heterocyclic or heteroaryl ring; each of which ring may be optionally substituted with 1 or more substituents;

each of which fused rings or generally $R^{44}$, $R^{44'}$, $R^{45}$, or $R^{45'}$ are optionally substituted with 1 or more substituents independently selected from $R^{201}$, halogen (and in particular F), hydroxyl, cyano, —COOH; alkyl, including $C_1$-$C_4$alkyl (including in particular methyl); alkenyl, including $C_2$-$C_4$alkenyl; alkynyl, including $C_2$-$C_4$alkynyl; alkoxy, including $C_1$-$C_4$alkoxy; alkanoyl, including $C_2$-$C_4$alkanoyl, hydroxyC$_1$-C$_4$alkyl, (mono- and di-alkylamino)C$_0$-C$_4$alkyl; alkyl(C$_3$-C$_7$cycloalkyl), including -C$_1$-C$_4$alkyl(C$_3$-C$_7$cycloalkyl); —O-(C$_3$-C$_7$cycloalkyl), haloalkyl including C$_1$-C$_6$haloalkyl, and haloalkoxy including C$_1$-C$_6$haloalkoxy;

Z$^4$ is N or CH;
Z$^5$ and Z$^6$ are C(R$^1$R$^{1'}$);
or Z$^4$ and Z$^5$ or Z$^5$ and Z$^6$ together are C=C;
Z$^7$ is SO or SO$_2$;
Z$^8$ is C(R$^1$R$^{1'}$) or N(R$^{43}$);
Z$^{5a}$ is C(R$^1$R$^{1'}$) or O;
Q$^{14}$ is N or CH;
Q$^{15}$ is N(R$^{47}$) or C(R$^{46}$R$^{46'}$);
Q$^{5a}$ is C(R$^{47}$R$^{47}$), N(R$^{47}$), O, S, SO, or SO$_2$;
Q$^{16}$ is N(R$^{47}$), C(R$^{46}$R$^{46'}$), S, or O;
Q$^{17}$ is C(R$^{46}$R$^{46'}$), S or N(R$^{47}$);
Q$^8$, Q$^9$, Q$^{10}$, Q$^{11}$ and Q$^{12}$ are each independently C(R$^2$R$^{2'}$), S, SO, SO$_2$, O, N(R$^2$), B(R$^{50}$), or Si(R$^{49}$)$_2$;

In a typical embodiment, no more than one heteroatom is in a three or four membered C3 and no more than one, two or three heteroatoms can be in a five, six or seven membered C3. It is in general known by those of skill in the art which combinations of several heteroatoms will not form a stable ring system. For example, those of skill in the art would understand that the C3 ring system would not normally contain an —O—O—, —O—S—, —Si—Si—, —B—B—, —B—Si—, bond;

R$^{40}$ is hydrogen, alkyl, cycloalkyl, cycloalkylalkyl, heterocycle, heterocycloalkyl, aryl, arylalkyl, heteroaryl, or heteroarylalkyl wherein each group can be optionally substituted;

R$^{42}$ is halo, hydroxy, C$_1$-C$_6$alkoxy, haloalkoxy including C$_1$-C$_6$haloalkoxy, —SH, or —S(alkyl);

R$^{43}$ is hydrogen, acyl, alkyl, cycloalkyl, cycloalkylalkyl, heterocycle, heterocycloalkyl, aryl, arylalkyl, heteroaryl, or heteroarylalkyl wherein each group can be optionally substituted;

R$^{46}$ and R$^{46'}$ are independently hydrogen, alkyl, cycloalkyl, cycloalkylalkyl, heterocycle, heterocycloalkyl, aryl, arylalkyl, heteroaryl, or heteroarylalkyl wherein each group can be optionally substituted;

R$^{47}$ is hydrogen, acyl, alkyl, cycloalkyl, cycloalkylalkyl, heterocycle, heterocycloalkyl, aryl, arylalkyl, heteroaryl, or heteroarylalkyl wherein each group can be optionally substituted;

R$^{49}$ is halo, hydrogen, alkyl, cycloalkyl, cycloalkylalkyl, heterocycle, heterocycloalkyl, aryl, arylalkyl, heteroaryl, or heteroarylalkyl wherein each group can be optionally substituted
or two R$^{49}$ groups are taken together to form a double bond that can be optionally substituted;

R$^{50}$ is hydroxy or C$_1$-C$_6$alkyoxy;
or X$^1$ and Q$^8$ or Q$^8$ and Q$^9$ or Q$^9$ and Q$^{10}$ or Q$^{10}$ and Q$^{11}$ or Q$^{11}$ and Q$^{12}$ or Q$^{12}$ and X$^2$ can form a carbon-carbon double bond;
or two Q$^{5a}$ groups or a X$^{4a}$ and a Q$^{5a}$ group can form a carbon-carbon double bond;
wherein each other variable is as defined herein; and
wherein all variables, including but not limited to X$^1$, X$^2$, X$^3$, X$^4$, X$^5$, X$^{5a}$, X$^6$, X$^7$, X$^8$, Q$^1$, Q$^2$, Q$^3$, Q$^4$, R$^1$, R$^{40}$, R$^{42}$, R$^{43}$, R$^{44}$, R$^{44'}$, R$^{45}$, and R$^{45'}$ are independently selected at each occurrence, as appropriate, and only where a stable compound results. For example, when C1 is a 7-membered ring and comprises silicon or boron, the ring will only comprise one Si(R$^{49}$)$_2$ or B(R$^{50}$) moiety. In addition, 3, 4, 5, 6 and 7-membered rings will not comprise —O—O— or —O—S— bonds;

The disclosure provides a compound of Formula IV:

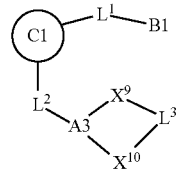

Formula IV or a pharmaceutically acceptable salt, isotopic analog, prodrug, N-oxide, or isolated isomer thereof, optionally in a pharmaceutically acceptable carrier; wherein:

A3 is selected from:

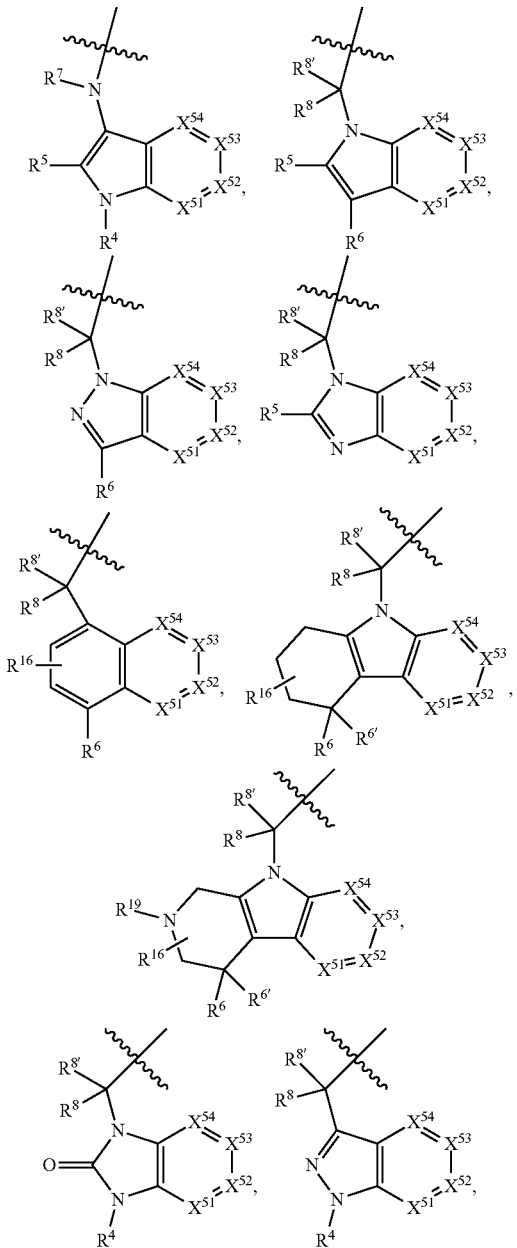

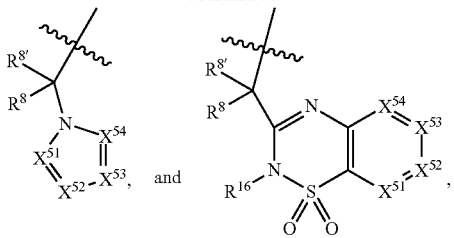

wherein $X^{51}$, $X^{52}$, $X^{53}$ and $X^{54}$ are selected from N, $CR^{13}$, a carbon directly bound to $X^9$, and a carbon directly bound to $X^{10}$, and wherein one and only one of $X^{51}$, $X^{52}$, $X^{53}$ and $X^{54}$ is a carbon directly bound to $X^9$, and wherein one and only one of $X^{51}$, $X^{52}$, $X^{53}$ and $X^{54}$ is a carbon directly bound to $X^{10}$, and wherein $X^9$ and $X^{10}$ are linked to $L^3$;

or A3 is selected from:

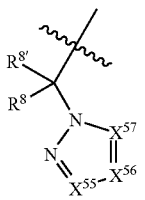

wherein $X^{55}$, $X^{56}$, and $X^{57}$ are selected from N, $CR^{13}$, $CR^5$, $CR^6$, a carbon directly bound to $X^9$, and a carbon directly bound to $X^{10}$, and wherein one and only one of $X^{55}$, $X^{56}$, and $X^{57}$ is a carbon directly bound to $X^9$, and wherein one and only one of $X^{55}$, $X^{56}$, and $X^{57}$ is a carbon directly bound to $X^{10}$, and wherein $X^9$ and $X^{10}$ are linked to $L^3$;

or A3 is A3' which is selected from:

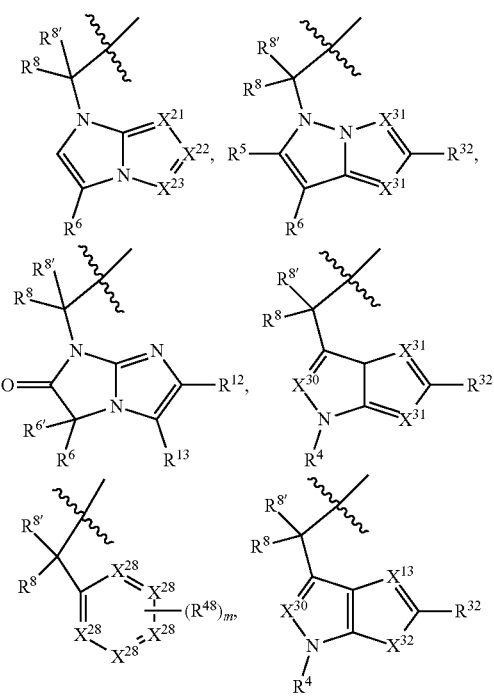

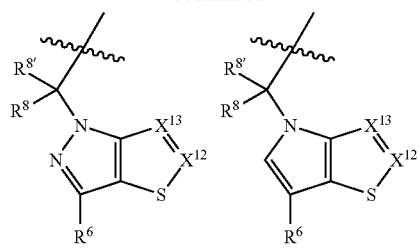

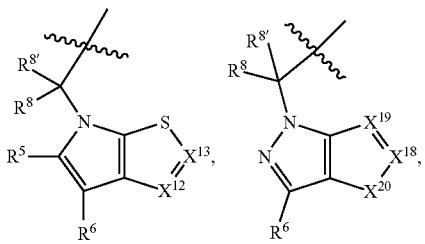

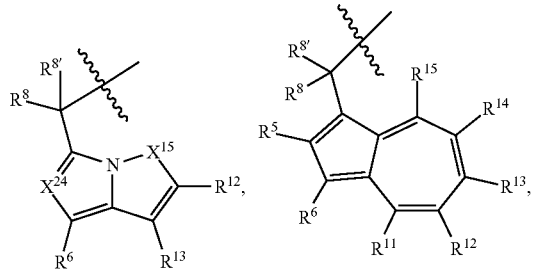

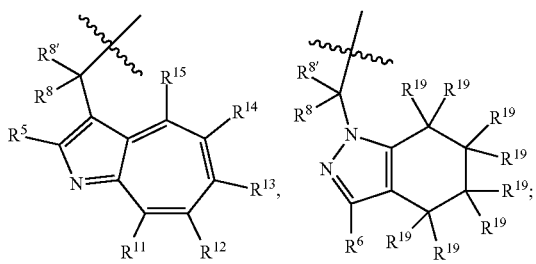

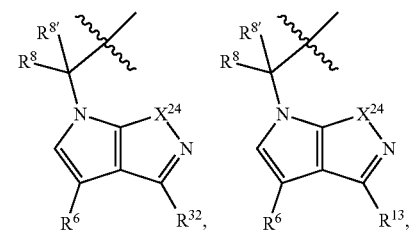

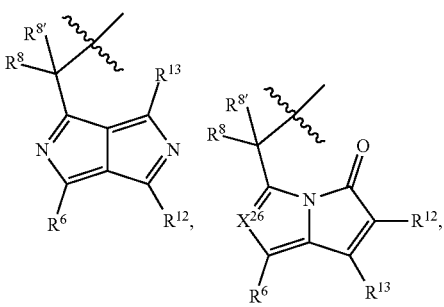

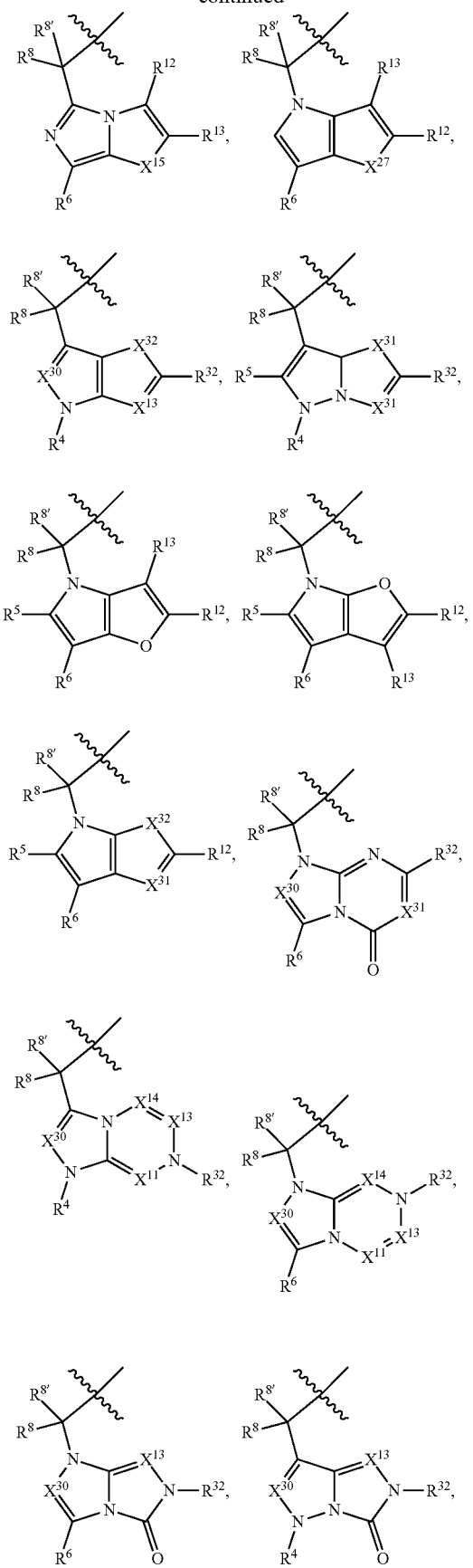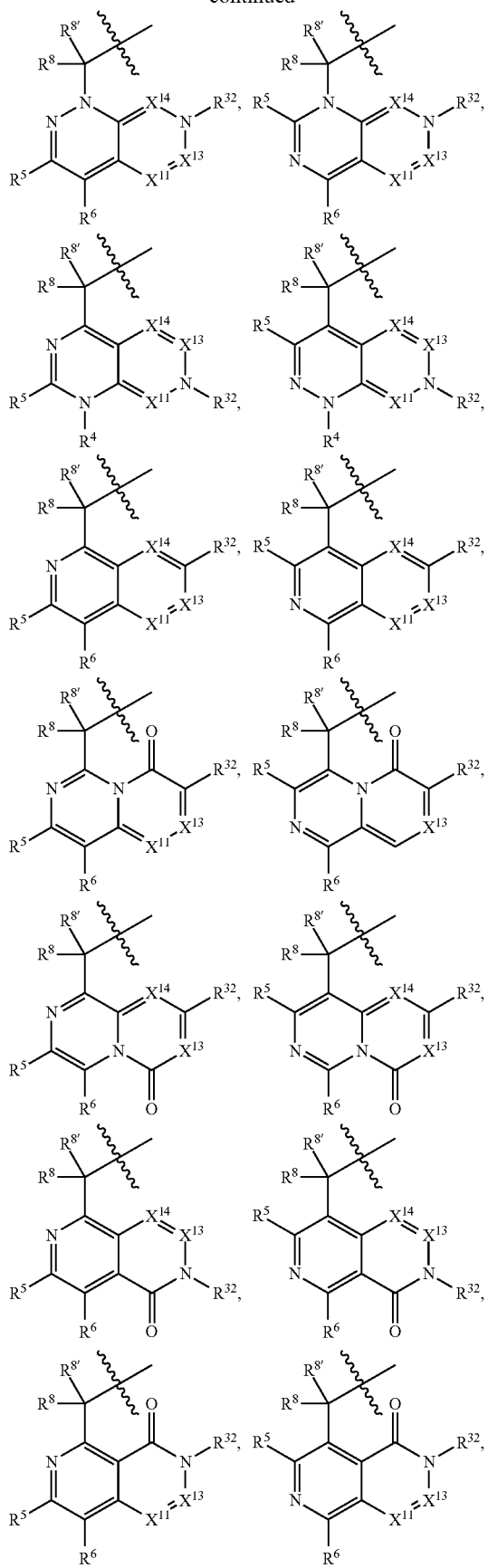

-continued

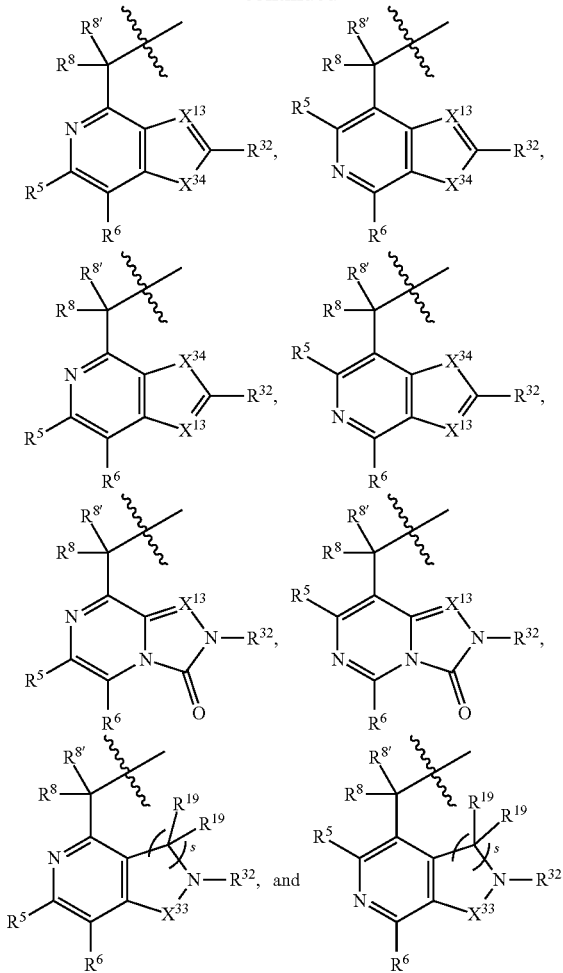

wherein each of which A3' has one R group replaced with a direct bond to $X^9$, and one R group replaced with a direct bond to $X^{10}$, and wherein $X^9$ and $X^{10}$ are linked to $L^3$; and wherein each other variable is as defined herein.

The disclosure provides a compound of Formula V:

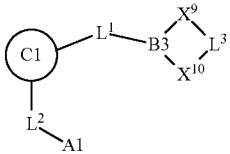

Formula V or a pharmaceutically acceptable salt, isotopic analog, prodrug, N-oxide, or isolated isomer thereof, optionally in a pharmaceutically acceptable carrier;
wherein:

B3 is a heteroaryl, heterocycle, or aryl group directly bound to $L^1$, $X^9$ and $X^{10}$ at three independent positions;

or B3 is a monocyclic or bicyclic carbocyclic; a monocyclic or bicyclic carbocyclic-oxy group; alkenyl including $C_2$-$C_6$alkenyl; alkynyl including $C_2$-$C_6$alkynyl; -($C_0$-$C_4$alkyl)(aryl); -($C_0$-$C_4$alkyl)(heteroaryl); or -($C_0$-$C_4$alkyl)(biphenyl) directly bound to $L^1$, $X^9$ and $X^{10}$ at three independent positions;

or B3 is a 6-membered aryl group fused to a 5-membered saturated cyclic group that optionally contains 1 or 2 heteroatoms independently selected from N or S directly bound to $L^1$, $X^9$ and $X^{10}$ at three independent positions, wherein one of the $CH_2$ groups of the 5-membered cyclic group is optionally substituted by oxo (i.e., $=O$);

or B3 is an 8-membered monocyclic or bicyclic heteroaryl, a 9-membered monocyclic or bicyclic heteroaryl group, a 10-membered aryl, or a 10 membered heteroaryl group directly bound to $L^1$, $X^9$ and $X^{10}$ at three independent positions;

or B3 is (optionally substituted alkyl)-(optionally substituted cycloalkyl), (optionally substituted alkenyl)-(optionally substituted cycloalkyl), or (optionally substituted alkynyl)-(optionally substituted cycloalkyl) directly bound to $L^1$, $X^9$ and $X^{10}$ at three independent positions;

wherein, each of which B3 is optionally substituted with one or more substituents independently selected from $R^{33}$, $R^{34}$, $R^{35}$, $R^{36}$, $R^{201}$, and $R^{48}$; and wherein each other variable is as defined herein.

The disclosure provides a compound of Formula VI:

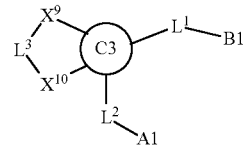

Formula VI or a pharmaceutically acceptable salt, isotopic analog, prodrug, N-oxide, or isolated isomer thereof, optionally in a pharmaceutically acceptable carrier;
wherein:

C3 is

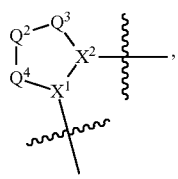

wherein one of $R^1$, $R^2$, $R^3$, $R^{1'}$, $R^{2'}$, or $R^{3'}$ is replaced with a direct bond to $X^9$, and wherein one of $R^1$, $R^2$, $R^3$, $R^{1'}$, $R^{2'}$, or $R^{3'}$ is replaced with a direct bond to $X^{10}$; and wherein each other variable is as defined herein.

The disclosure provides a compound of Formula VII:

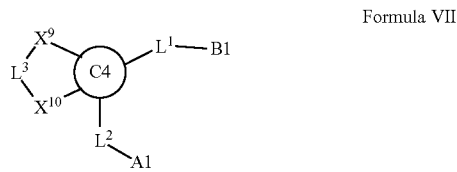

Formula VII or a pharmaceutically acceptable salt, isotopic analog, prodrug, N-oxide, or isolated isomer thereof, optionally in a pharmaceutically acceptable carrier;

wherein:
C4 is

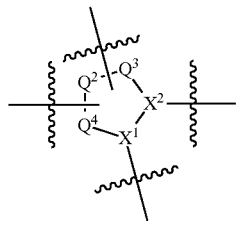

wherein C4 is directly bound to $X^9$, $X^{10}$, $L^1$, and $L^2$, wherein $X^9$ and/or $X^{10}$ can be directly bound to C4 (e.g. $Q^4$ is $CH_2$ and one H is replaced with a bond to $X^9$ or $X^{10}$), or $X^9$ and/or $X^{10}$ can be bound to a ring resulting from the cyclization of $R^1$, $R^2$, $R^3$, $R^{1'}$, $R^{2'}$, or $R^{3'}$, as defined herein; and wherein each other variable is as defined herein.

The present invention thus includes at least the following features:

a. a compound of Formula I, Formula II, Formula III, Formula IV, Formula V, Formula VI, Formula VII, or Formula VIII or a pharmaceutically acceptable salt, prodrug, isotopic analog, N-oxide, or isolated isomer thereof, optionally in a pharmaceutically acceptable composition, for use in treating or preventing a disorder listed in the Detailed Description, including but not limited to the development of fatty liver and conditions stemming from fatty liver, such as nonalcoholic steatohepatitis (NASH), liver inflammation, cirrhosis, or liver failure; dermatomyositis; amyotrophic lateral sclerosis; cytokine or inflammatory reactions in response to biotherapeutics (e.g. CAR T-cell therapy); paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

b. a pharmaceutically acceptable composition of a compound of Formula I, Formula II, Formula III, Formula IV, Formula V, Formula VI, Formula VII, or Formula VIII or its pharmaceutically acceptable salt, prodrug, isotopic analog, N-oxide, or isolated isomer thereof in a pharmaceutically acceptable carrier;

c. a compound selected from Formula I, Formula II, Formula III, Formula IV, Formula V, Formula VI, Formula VII, or Formula VIII or a pharmaceutically acceptable salt, prodrug, isotopic analog, N-oxide, or isolated isomer thereof, optionally in a pharmaceutically acceptable composition, for use in treating or preventing a disorder mediated by the complement pathway, and for example, cascade Factor D;

d. use of a compound of Formula I, Formula II, Formula III, Formula IV, Formula V, Formula VI, Formula VII, or Formula VIII as described herein, or a pharmaceutically acceptable salt, prodrug, isotopic analog, N-oxide, or isolated isomer thereof, optionally in a pharmaceutically acceptable composition, in the manufacture of a medicament for treating or preventing a disorder listed in the Detailed Description, including but not limited to the development of fatty liver and conditions stemming from fatty liver, such as nonalcoholic steatohepatitis (NASH), liver inflammation, cirrhosis, liver failure; dermatomyositis; amyotrophic lateral sclerosis; cytokine or inflammatory reactions in response to biotherapeutics (e.g. CAR T-cell therapy); paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

e. a process for manufacturing a medicament intended for the therapeutic use for treating or preventing a disorder listed in the Detailed Description, or generally for treating or preventing disorders mediated by complement cascade Factor D, characterized in that a compound selected from Formula I, Formula II, Formula III, Formula IV, Formula V, Formula VI, Formula VII, or Formula VIII or an embodiment of the active compound is used in the manufacture;

f. a compound selected from Formula I, Formula II, Formula III, Formula IV, Formula V, Formula VI, Formula VII, or Formula VIII or a salt thereof as described herein in substantially pure form (e.g., at least 90 or 95%):

g. a compound of Formula I, Formula II, Formula III, Formula IV, Formula V, Formula VI, Formula VII, or Formula VIII as described herein, or a pharmaceutically acceptable salt, prodrug, isotopic analog, N-oxide, or isolated isomer thereof, optionally in a carrier to form a pharmaceutically acceptable composition, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

h. For each of (a) through (g) above, and otherwise herein, each assembly of moieties in the Figures and each active compound made therefrom or its use is considered and deemed specifically and individually disclosed, as such depiction is for convenience of space only and not intended to describe a only a genus or even a subgenus for such indication.

DETAILED DESCRIPTION

I. Terminology

Figure 1A:
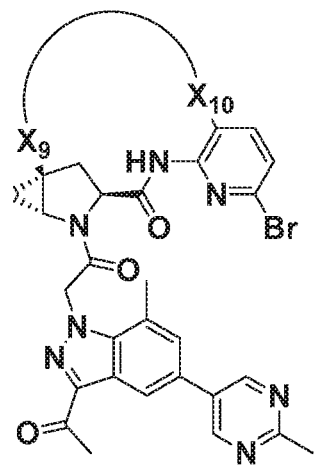
FIG. 1A is an example of a macrocyclic-containing compound where the C-ring and the B-ring are bridged.
Figure 1B:
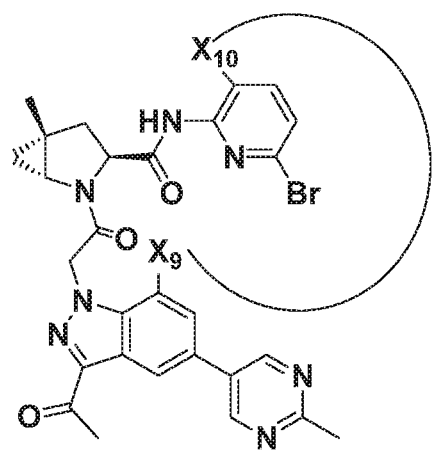
FIG. 1B is an example of a macrocyclic-containing compound where the B-ring and A-ring are bridged.
Figure 1C:
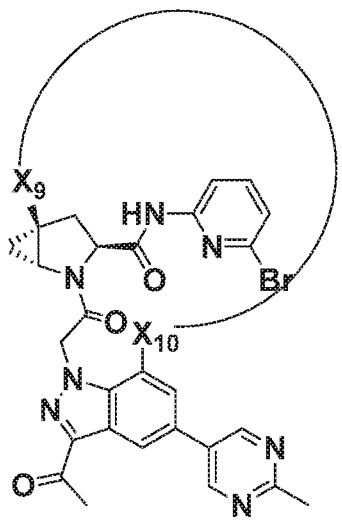
FIG. 1C is an example of a macrocyclic-containing compound where the C-ring and the A-ring are bridged.
Figure 1D:
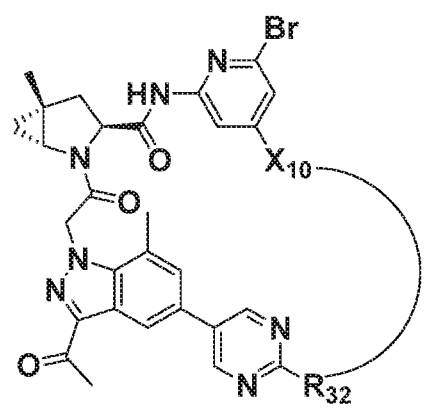
FIG. 1D is an example of a macrocyclic-containing compound where the $R^{32}$ moiety and the B-ring are bridged.
Figure 2:
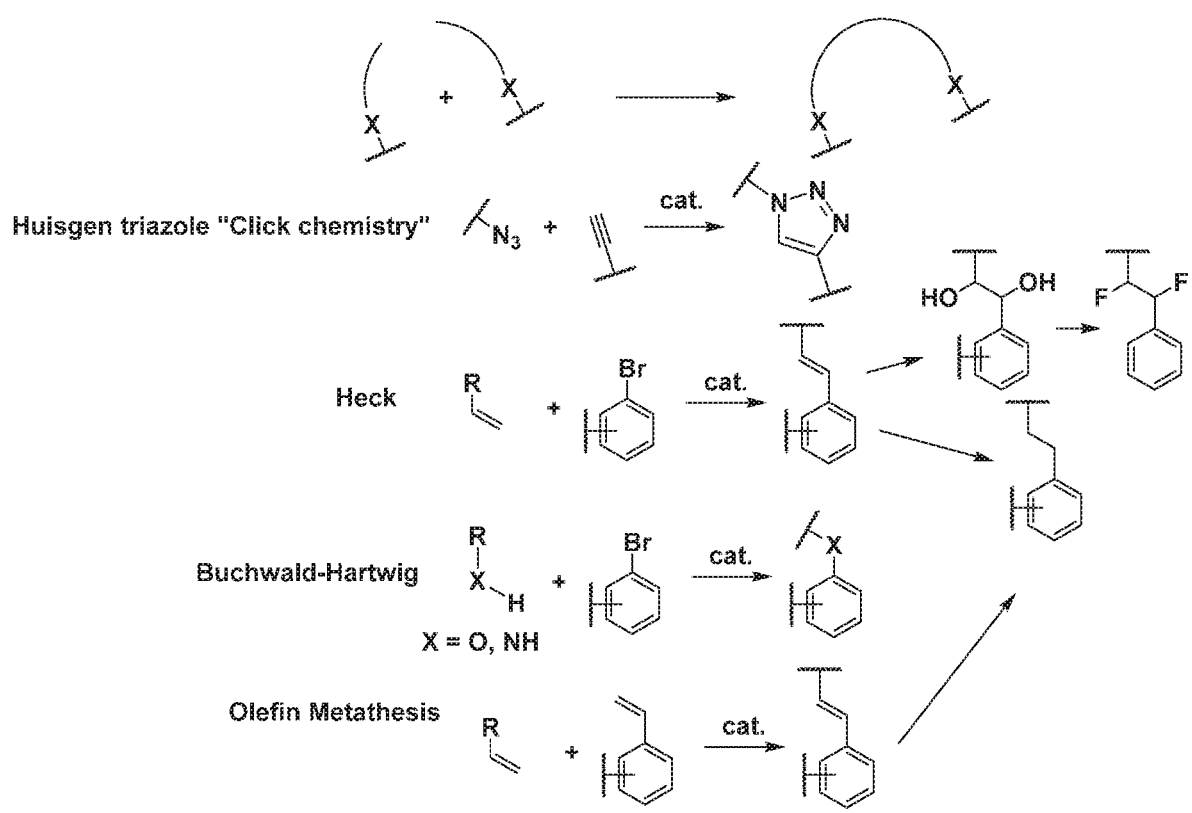
FIG. 2 is a schematic of examples of synthetic processes examples including Huisgen triazole "click chemistry", Heck coupling, Buchwald-Hartwig coupling, and olefin metathesis that can be used to create the bridge portion of the macrocycle.
Figure 3:
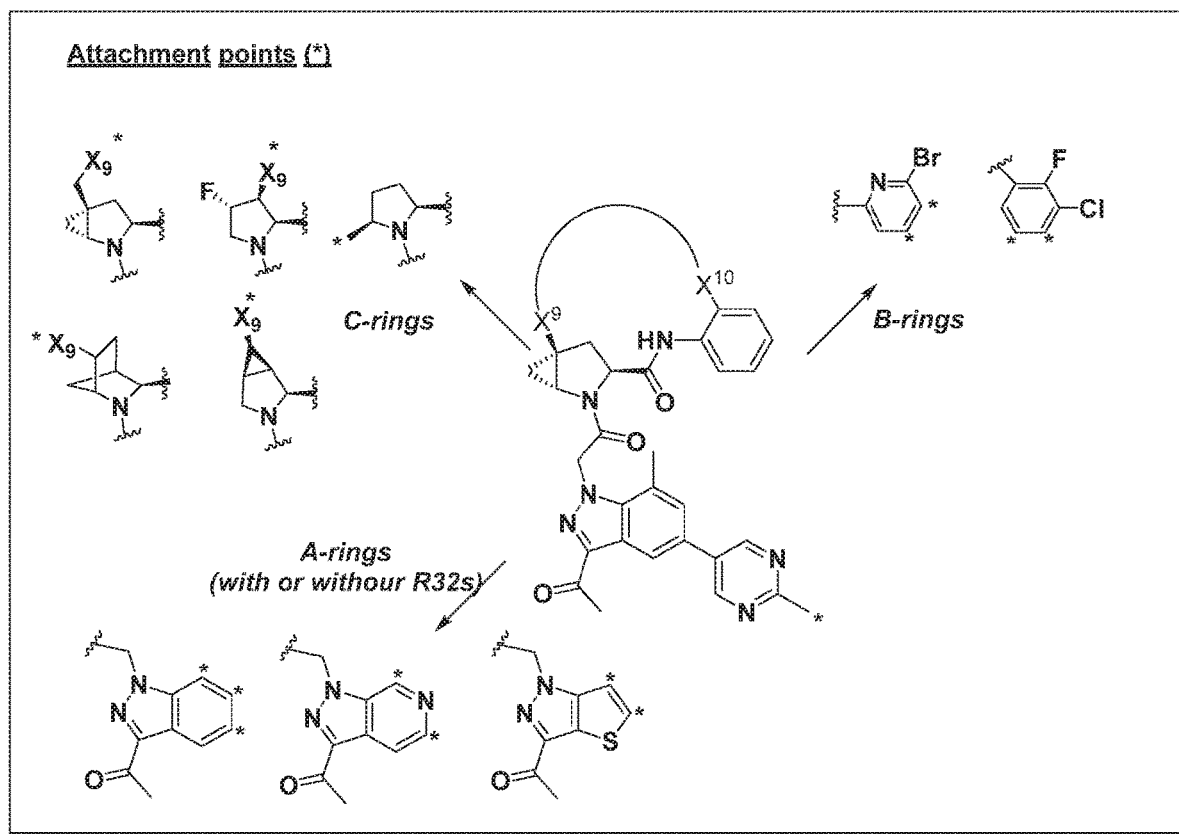
FIG. 3 is a schematic of the various potential points of attachment of the $R^{301}$ or macrocyclic functionality on an example of a compound where the C-ring and the B-ring are bridged through a macrocycle.
Figure 4:
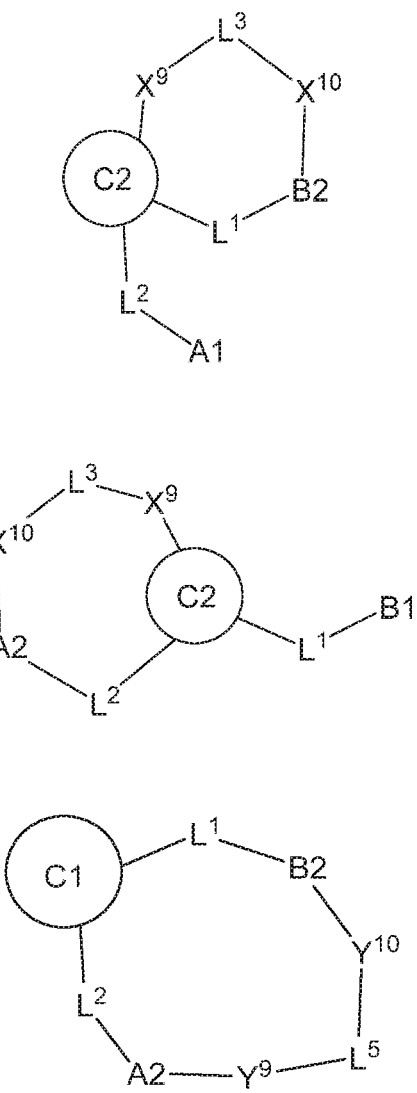
FIG. 4 depicts Formula I, Formula II, and Formula III.

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, tautomers, racemates and other isomers, such as rotamers, as if each is specifically described, unless otherwise indicated or otherwise excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula I, Formula II, Formula III, Formula IV, Formula V, Formula VI, Formula VII, or Formula VIII with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. In one embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may optionally be used anywhere in described structures that achieves the desired result. Alternatively or in addition, isotopes of carbon, e.g., $^{13}C$ and $^{14}C$, may be used. In one embodiment, the isotopic substitution is replacing hydrogen with a deuterium at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an a-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 80, 85, 90, 95 or 99% or more enriched in an isotope at any location of interest. In one embodiments deuterium is 80, 85, 90, 95 or 99% enriched at a desired location. Unless otherwise stated, the enrichment at any point is above natural abundance. And in an embodiment is enough to alter a detectable property of the drug in a human.

In one embodiment, the substitution of a hydrogen atom for a deuterium atom can be provided in any of A1, A2, A3, B1, B2, B3, C1, C2, C3, C4, L1, L2, or L3. In one embodiment, the substitution of a hydrogen atom for a deuterium atom occurs within any R group. In certain embodiment the R group is selected from any of R, R', $R^1$, $R^{1'}$, $R^2$, $R^{2'}$, $R^3$, $R^{3'}$, $R^4$, $R^5$, $R^6$, $R^{6'}$, $R^7$, $R^8$, $R^{8'}$, $R^9$, $R^{10}$, $R^{11}$, $R^{12}$, $R^{13}$, $R^{14}$, $R^{15}$, $R^{16}$, $R^{17}$, $R^{18}$, $R^{18'}$, $R^{19}$, $R^{21}$, $R^{22}$, $R^{23}$, $R^{24}$, $R^{25}$, $R^{30}$, $R^{31}$, $R^{32}$, $R^{33}$, $R^{34}$, $R^{35}$, $R^{36}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{52a}$, $R^{53}$, $R^{54}$, $R^{71}$, $R^{73}$, $R^{74}$, $R^{75}$, $R^{101}$, $R^{102}$, $R^{103}$, $R^{104}$, $R^{201}$, $R^{301}$, $R^{302}$, $R^{303}$, $R^{304}$, $R^{305}$, $R^{306}$, $R^{307}$, $R^{308}$, and $R^{309}$. For example, when any of R groups are, or contain for example through substitution, methyl, ethyl, or methoxy, the alkyl residue may be deuterated (in nonlimiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, $OCDH_2$, $OCD_2H$, or $OCD_3$ etc.). In certain other embodiments, an R group has a "'" or an "a" designation, which in one embodiment can be deuterated. In certain other embodiments, when two substituents of the central core ring are combined to form a cyclopropyl ring, the unsubstituted methylene carbon may be deuterated.

The compound of the present invention may form a solvate with solvents (including water). Therefore, in one embodiment, the invention includes a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A dash ("—") that is not between two letters or symbols is used to indicate a point of attachment for a substituent. For example, —(C=O)NH$_2$ is attached through carbon of the keto (C=O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., =O) then two hydrogens on the atom are replaced. For example a pyridyl group substituted by oxo is a pyridone. Combinations of substituents and/or variables are permissible only if such combinations result in stable compounds or useful synthetic intermediates.

A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Nonlimiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, alkyl including $C_1$-$C_6$alkyl, alkenyl including $C_2$-$C_6$alkenyl, alkynyl including $C_2$-$C_6$alkynyl, -$C_1$-$C_6$alkoxy, alkanoyl including $C_2$-$C_6$alkanoyl, $C_1$-$C_6$alkylester, (mono- and di-$C_1$-$C_6$alkylamino)$C_0$-$C_2$alkyl, haloalkyl including $C_1$-$C_6$haloalkyl, hydoxy$C_1$-$C_6$alkyl, ester, carbamate, urea, sulfonamide,-$C_1$-$C_6$alkyl(heterocyclo), $C_1$-$C_6$alkyl(heteroaryl), -$C_1$-$C_6$alkyl($C_3$-$C_7$cycloalkyl), O-$C_1$-$C_6$alkyl($C_3$-$C_7$cycloalkyl), B(OH)$_2$, phosphate, phosphonate and haloalkoxy including $C_1$-$C_6$haloalkoxy.

"Alkyl" is a branched or straight chain saturated aliphatic hydrocarbon group. In one embodiment, the alkyl contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, $C_1$-$C_4$, $C_1$-$C_5$ or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or -$C_0$-$C_4$alkyl($C_3$-$C_7$cycloalkyl), the indicated group, in this case cycloalkyl, is either directly bound by a single covalent bond (C0alkyl), or attached by an alkyl chain in this case 1, 2, 3, or 4 carbon atoms. Alkyls can also be attached via other groups such as heteroatoms as in —O-$C_0$-$C_4$alkyl ($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, 2,3-dimethylbutane, and hexyl. In one embodiment, the alkyl group is optionally substituted as described above. In one embodiment, trimethylsilyl can be used instead of t-butyl.

In one embodiment, when a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenloxy, haloalkyl, aminoalkyl, alkylene, alkenylene, alkynylene, etc. can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Nonlimiting examples are $C_2$-$C_8$alkenyl, $C_2$-$C_7$alkenyl, $C_2$-$C_6$alkenyl, $C_2$-$C_5$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described above.

As used herein a "squiggly" bond alkene

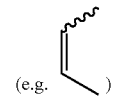

(e.g.                )

in a compound described herein means that the alkene can be in either the cis or trans stereoconfiguration or a mixture thereof. For example,

can be either

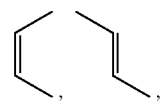

or a mixture thereof. Where a "squiggly" bond is used it is understood that both the cis, trans, and mixtures thereof are independently described. The structures are drawn with a "squiggly" bond simply to save space.

Unless inconsistent with the disclosure, in alternative embodiments, if desired by the skilled worker, an alkene can be alternatively in the cis or trans stereoconfiguration or a mixture thereof. For example, in one embodiment can be

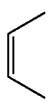

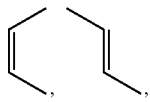

or a mixture thereof.

Unless inconsistent with the disclosure, in alternative embodiments, when a structure is drawn in either the cis or trans stereoconfiguration both the cis and trans stereoconfiguration are also considered separately and independently disclosed in each instance.

In one embodiment the stereoisomer is more than 75% cis or trans, more than 80% cis or trans, more than 85% cis or trans, 90% cis or trans, more than 95% cis or trans, or more than 99% cis or trans.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a divalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_5$alkylene, or $C_1$-$C_6$alkylene.

"Alkenylene" is a divalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a divalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

"Heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl—O-alkyl, alkyl-O-haloalkyl, etc.

"Alkanoyl" is an alkyl group as defined above covalently bound through a carbonyl (C=O) bridge. The carbonyl carbon is included in the number of carbons, that is $C_2$alkanoyl is a $CH_3(C=O)$— group. In one embodiment, the alkanoyl group is optionally substituted as described above.

"Alkylester" is an alkyl group as defined herein covalently bound through an ester linkage. The ester linkage may be in either orientation, e.g., a group of the formula —O(C=O)alkyl or a group of the formula —(C=O)Oalkyl.

"Amide" or "carboxamide" is —C(O)NR$^a$R$^b$ wherein R$^a$ and R$^b$ are each independently selected from hydrogen, alkyl, for example, alkyl including $C_1$-$C_6$alkyl, alkenyl, for example, $C_2$-$C_6$alkenyl, alkynyl, for example, $C_2$-$C_6$alkynyl, -$C_0$-$C_4$alkyl($C_3$-$C_7$cycloalkyl), -$C_0$-$C_4$alkyl ($C_3$-$C_7$heterocycloalkyl), -$C_0$-$C_4$alkyl(aryl), and -$C_0$-$C_4$alkyl(heteroaryl); or together with the nitrogen to which they are bonded, $R^a$ and $R^b$ can form a $C_3$-$C_7$ heterocyclic ring. In one embodiment, the $R^a$ and $R^b$ groups are each independently be optionally substituted as described herein.

"Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms.

"Carbocyclic-oxy group" is a monocyclic carbocyclic ring or a mono- or bi-cyclic carbocyclic group as defined above attached to the group it substitutes via an oxygen, —O—, linker.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Hydroxyalkyl" is an alkyl group as previously described, substituted with at least one hydroxyl subsitutuent.

"Aminoalkyl" is an alkyl group as previously described, substituted with at least one amino subsitutuent.

"Halo" or "halogen" indicates independently, any of fluoro, chloro, bromo or iodo.

"Aryl" indicates an aromatic group containing only carbon in the aromatic ring or rings. In one embodiment, the aryl group contains 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 4 to 7 or a 5 to 7-membered saturated or partially unsaturated cyclic group that optionally contains 1, 2 or 3 heteroatoms independently selected from N, O, B, P, Si and/or S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above.

The term "heterocycle," or "heterocyclic ring" as used herein refers to a saturated or a partially unsaturated (i.e., having one or more double and/or triple bonds within the ring without aromaticity) carbocyclic moiety of 3 to about 12, and more typically 3, 4, 5, 6, 7, 8 to 10 ring atoms in which at least one ring atom is a heteroatom selected from nitrogen, oxygen, phosphorus sulfur, silicon and boron, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, S, Si and B) or a bicycle having 6 to 10 ring members (4 to 9 carbon atoms and 1 to 6 heteroatoms selected from N, O, P, S, Si and B), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur, boron or silicon. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (=O) moieties are pyrimidinonyl and 1,1-dioxo-thiomorpholinyl. The heterocycle groups herein are optionally substituted independently with one or more substituents described herein, for example, 1, 2, or 3 substituents.

"Heterocyclicoxy group" is a monocyclic heterocyclic ring or a bicyclic heterocyclic group as described previously linked to the group it substitutes via an oxygen, —O—, linker.

"Heteroaryl" refers to a stable monocyclic, bicyclic, or multicyclic aromatic ring which contains from 1 to 3, or in some embodiments from 1, 2, or 3 heteroatoms selected from N, O, S, B or P with remaining ring atoms being carbon, or a stable bicyclic or tricyclic system containing at least one 5, 6, or 7 membered aromatic ring which contains from 1 to 3, or in some embodiments from 1 to 2, heteroatoms selected from N, O, S, B or P with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5, 6, or 7 ring atoms. In some embodiments bicyclic heteroaryl groups are 8- to 10-membered heteroaryl groups, that is, groups containing 8 or 10 ring atoms in which one 5, 6, or 7 member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein. "Heteroaryloxy" is a heteroaryl group as described bound to the group it substituted via an oxygen, —O—, linker.

"Heterocycloalkyl" is a fully saturated heterocycle as defined herein. It may have, for example, include 1, 2, 3, or 4 heteroatoms independently selected from N, S, O, Si and B with the remaining ring atoms being carbon. In a typical embodiment, nitrogen is the heteroatom. Monocyclic heterocycloalkyl groups typically have from 3 to about 8 ring atoms or from 4 to 6 ring atoms.

The term "mono- and/ or di-alkylamino" indicate a secondary or tertiary alkylamino group, wherein the alkyl groups are independently selected as defined herein. The point of attachment of the alkylamino group is on the nitrogen. Examples of mono- and di-alkylamino groups include ethylamino, dimethylamino, and methyl-propylamino.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" is a derivative of the disclosed compound in which the parent compound is modified by making inorganic and organic, pharmaceutically acceptable, acid or base addition salts thereof. The salts of the present compounds can be synthesized from a parent compound that contains a basic or acidic moiety by conventional chemical methods. Generally, such salts can be prepared by reacting free acid forms of these macrocyclic compounds with a stoichiometric amount of the appropriate base (such as Na, Ca, Mg, or K hydroxide, carbonate, bicarbonate, or the like), or by reacting free base forms of these macrocyclic compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include salts which are acceptable for human consumptionand the quaternary ammonium salts of the parent compound formed, for example, from inorganic or organic acids. Examples, of such salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, acceptable for human consumption, and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, including but not limited to by modulation of the Complement Factor D pathway or with a condition that is treatable with one of the compounds described herein. Typically the host is a human. A "patient" or "host" or "subject" also refers to for example, a mammal, primate (e.g., human), cows, sheep, goat, horse, dog, cat, rabbit, rat, mice, bird and the like.

A "prodrug" as used herein, means a compound which when administered to a host in vivo is converted into a parent drug described herein. As used herein, the term "parent drug" means any of the presently described chemical compounds herein. Prodrugs can be used to achieve any desired effect, including to enhance properties of the parent drug or to improve the pharmaceutic or pharmacokinetic properties of the parent, including to increase the half-life of the drug in vivo. Prodrug strategies provide choices in modulating the conditions for in vivo generation of the parent drug. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others. In certain embodiments, the prodrug renders the parent compound more lipophilic. In certain embodiments, a prodrug can be provided that has several prodrug moieties in linear, branched or cyclic manner. For example, nonlimiting embodiments include the use of a divalent linker moiety such as a dicarboxylic acid, amino acid, diamine, hydroxycarboxylic acid, hydroxyamine, di-hydroxy compound, or other compound that has at least two functional groups that can link the parent molecule with another prodrug moiety, and is typically biodegradable in vivo. In some embodiments, 2, 3, 4 or 5 prodrug biodegradable moieties are covalently bound in sequence, branched or cyclic fashion to the parent compound. Nonlimiting examples of prodrugs according to the present invention are formed with:

i. a carboxylic acid on the parent drug and a hydroxylated prodrug moiety to form an ester;
 ii. a carboxylic acid on the parent drug and an amine prodrug to form an amide;

iii. an amino on the parent drug and a carboxylic acid prodrug moiety to form an amide,
iv. an amino on the parent drug and a sulfonic acid to form a sulfonamide;
v. a sulfonic acid on the parent drug and an amino on the prodrug moiety to form a sulfonamide;
vi. a hydroxyl group on the parent drug and a carboxylic acid on the prodrug moiety to form an ester;
vii. a hydroxyl on the parent drug and a hydroxylated prodrug moiety to form an ether;
viii. a phosphonate on the parent drug and a hydroxylated prodrug moiety to form a phosphonate ester;
ix. a phosphoric acid on the parent drug and a hydroxylated prodrug moiety to form a phosphate ester;
x. a hydroxyl on the parent drug and a phosphonate on the prodrug to form a phosphonate ester;
xi. a hydroxyl on the parent drug and a phosphoric acid prodrug moiety to form a phosphate ester;
xii. a carboxylic acid on the parent drug and a prodrug of the structure HO—$(CH_2)_2$—S-($C_{2-24}$ aliphatic group), for example, HO—$(CH_2)_2$—O-($C_{2-24}$ alkyl group) to form an ester;
xiii. a carboxylic acid on the parent drug and a prodrug of the structure HO—$(CH_2)_2$—S-($C_{2-24}$ aliphatic group), for example, HO—$(CH_2)_2$—S-($C_{2-24}$ alkyl group) to form a thioester;
xiv. a hydroxyl on the parent drug and a prodrug of the structure HO—$(CH_2)_2$—O-($C_{2-24}$ aliphatic group), for example, HO—$(CH_2)_2$—O-($C_{2-24}$ alkyl group) to form an ether;
xv. a carboxylic acid on the parent drug and a prodrug of the structure HO—$(CH_2)_2$—S-($C_{2-24}$ aliphatic group), for example, HO—$(CH_2)_2$—S-($C_{2-24}$ alkyl group), to form a thioether; and
xvi. a carboxylic acid, amine or hydroxyl on the parent compound and a prodrug moiety that is a biodegradable polymer or oligomer including but not limited to polylactic acid, polylactide-co-glycolide, polyglycolide, polyethylene glycol, polyanhydride, polyester, polyamide or a peptide.

In one embodiment, a prodrug is provided by attaching a natural or non-natural amino acid to an appropriate functional moiety on the parent compound, for example, oxygen, nitrogen or sulfur, and typically oxygen or nitrogen, usually in a manner such that the amino acid can be cleaved in vivo to provide the parent drug. The amino acid can be used alone or covalently linked (straight, branched or cyclic) to one or more other prodrug moieties to modify the parent drug to achieve the desired performance, such as increased half-life, lipophilicity, or other drug delivery or pharmacokinetic properties. The amino acid can be any compound with an amino group and a carboxylic acid, which includes an aliphatic amino acid, alkyl amino acid, aromatic amino acid, heteroaliphatic amino acid, heteroallyl amino acid, or heterocyclic amino acid or heteroaryl amino acid.

"Providing a compound with at least one additional active agent," for example, in one embodiment can mean that the compound and the additional active agent(s) are provided simultaneously in a single dosage form, provided concomitantly in separate dosage forms, or provided in separate dosage forms for administration. In one embodiment, the compound administrations are separated by some amount of time that is within the time in which both the compound and the at least one additional active agent are within the blood stream of a patient. In certain embodiments the compound and the additional active agent need not be prescribed for a patient by the same medical care worker. In certain embodiments the additional active agent or agents need not require a prescription. Administration of the compound or the at least one additional active agent can occur via any appropriate route, for example, oral tablets, oral capsules, oral liquids, inhalation, injection, suppositories, parenteral, sublingual, buccal, intravenous, intraaortal, transdermal, polymeric controlled delivery, non-polymeric controlled delivery, nano or microparticles, liposomes, and/or topical contact. In one embodiment, the instructions for administration in a form of combination therapy is provided in the drug labeling.

A "therapeutically effective amount" of a pharmaceutical composition/combination of this invention means an amount effective, when administered to a host, provides a therapeutic benefit such as an amelioration of symptoms or reduction or diminution of the disease itself. In one embodiment, a therapeutically effective amount is an amount sufficient to prevent a significant increase or will significantly reduce the detectable level of Complement Factor D in the patient's blood, serum, or tissues.

DETAILED DESCRIPTION OF THE ACTIVE COMPOUNDS

Embodiments of "Alkyl"
In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.
In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.
Non-limiting examples of "alkyl" include: methyl, ethyl, propyl, butyl, pentyl, and hexyl.
Additional non-limiting examples of "alkyl" include: isopropyl, isobutyl, isopentyl, and isohexyl.
Additional non-limiting examples of "alkyl" include: sec-butyl, sec-pentyl, and sec-hexyl.
Additional non-limiting examples of "alkyl" include: tert-butyl, tert-pentyl, and tert-hexyl.
Additional non-limiting examples of "alkyl" include: neopentyl, 3-pentyl, and active pentyl.
In one embodiment "alkyl" is "substituted alkyl"
In one embodiment "alkenyl" is "substituted alkenyl"
In one embodiment "alkynyl" is "substituted alkynyl"

Embodiments of "Haloalkyl"

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.
In one embodiment "haloalkyl" has one carbon.
In one embodiment "haloalkyl" has one carbon and one halogen.
In one embodiment "haloalkyl" has one carbon and two halogens.
In one embodiment "haloalkyl" has one carbon and three halogens.
In one embodiment "haloalkyl" has two carbons.
In one embodiment "haloalkyl" has three carbons.
In one embodiment "haloalkyl" has four carbons.
In one embodiment "haloalkyl" has five carbons.
In one embodiment "haloalkyl" has six carbons.

Non-limiting examples of "haloalkyl" include:

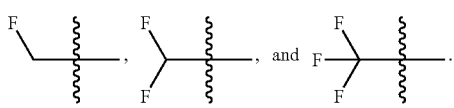

Additional non-limiting examples of "haloalkyl" include:

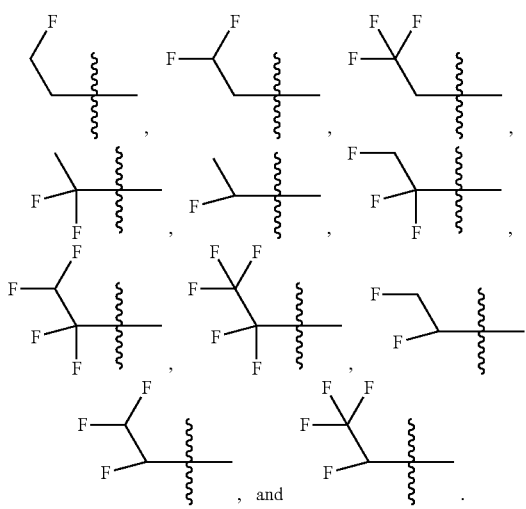

Additional non-limiting examples of "haloalkyl" include:

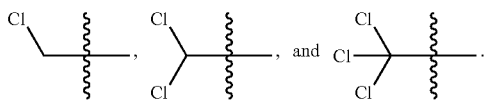

Additional non-limiting examples of "haloalkyl" include:

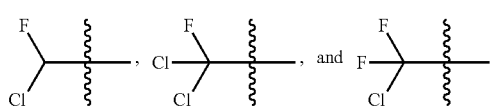

Embodiments of "Aryl"

In one embodiment "aryl" is a 6 carbon aromatic group (phenyl)

In one embodiment "aryl" is a 10 carbon aromatic group (napthyl)

In one embodiment "aryl" is "substituted aryl".

Embodiments of "Heteroaryl"

In one embodiment "heteroaryl" is a 5 membered aromatic group containing 1, 2, or 3, nitrogen atoms.

Non-limiting examples of 5 membered "heteroaryl" groups include pyrrole, furan, thiophene, pyrazole, imidazole, triazole, isoxazole, oxazole, oxadiazole, oxatriazole, isothiazole, thiazole, thiadiazole, and thiatriazole.

Additional non-limiting examples of 5 membered "heteroaryl" groups include:

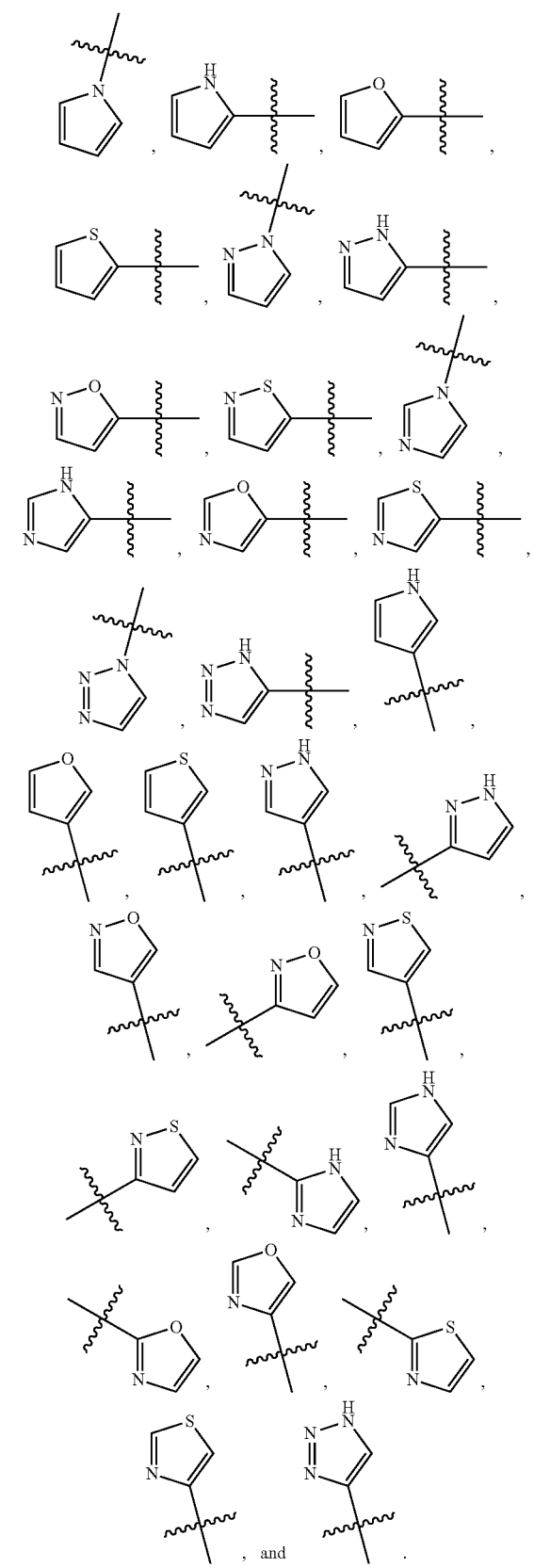

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

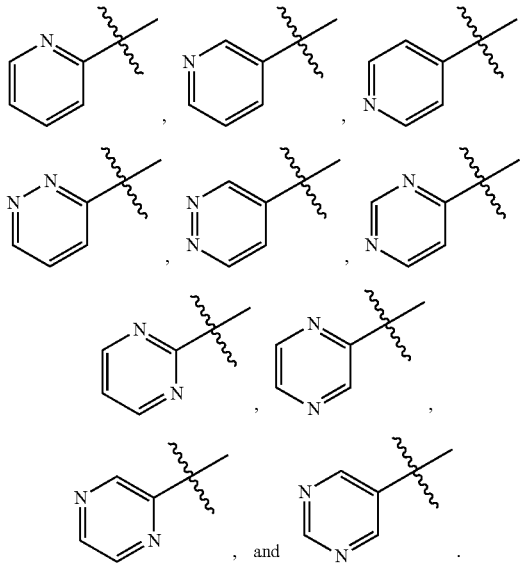

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

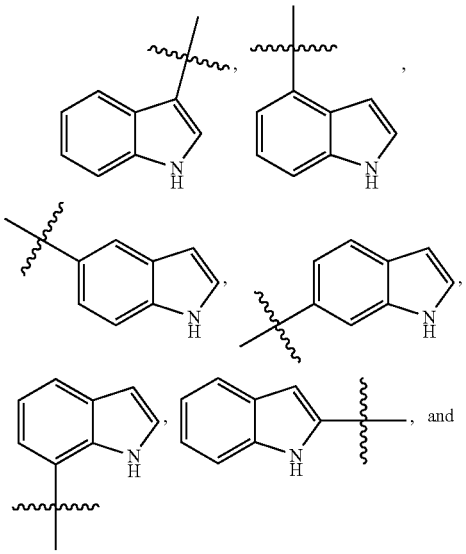

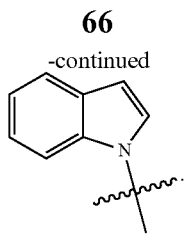

Additional non-limiting examples of "heteroaryl" groups that are bicyclic include:

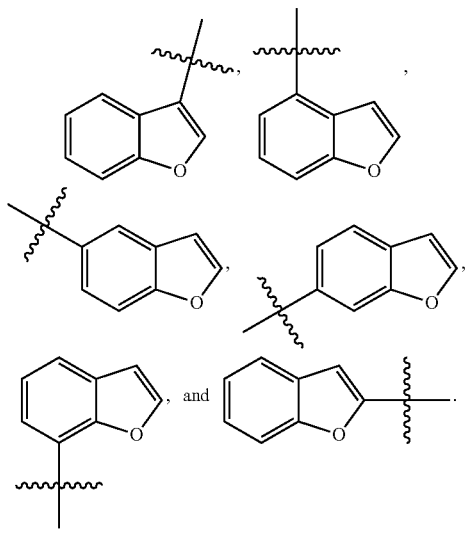

Additional non-limiting examples of "heteroaryl" groups that are bicyclic include:

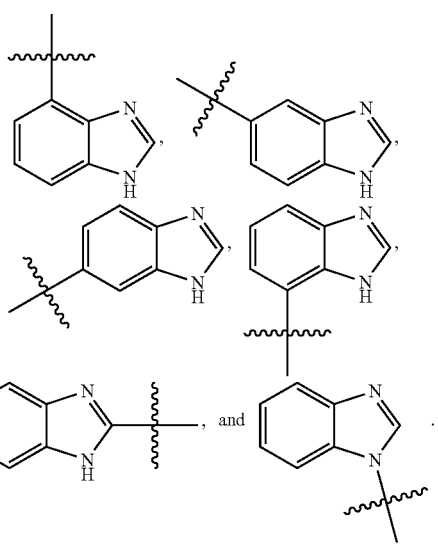

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

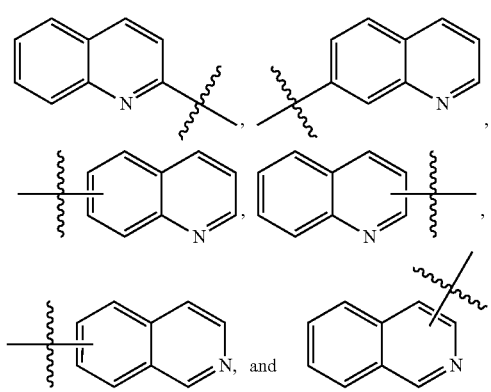

In one embodiment "heteroaryl" is "substituted heteroaryl"

Embodiments of "Cycloalkyl"

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.
In one embodiment "cycloalkyl" has three carbons.
In one embodiment "cycloalkyl" has four carbons.
In one embodiment "cycloalkyl" has five carbons.
In one embodiment "cycloalkyl" has six carbons.
In one embodiment "cycloalkyl" has seven carbons.
In one embodiment "cycloalkyl" has eight carbons.
In one embodiment "cycloalkyl" has nine carbons.
In one embodiment "cycloalkyl" has ten carbons.
Non-limiting examples of "cycloalkyl" include: cyclopropyl, cyclobutyl, cyclopentyl, cyclohexyl, cycloheptyl, cyclooctyl, and cyclodecyl.
In one embodiment "cycloalkyl" is a "substituted cycloalkyl"

Embodiments of "Heterocycle"

In one embodiment "heterocycle" refers to a cyclic ring with one nitrogen and 3, 4, 5, 6, 7, or 8 carbon atoms.
In one embodiment "heterocycle" refers to a cyclic ring with one nitrogen and one oxygen and 3, 4, 5, 6, 7, or 8 carbon atoms.
In one embodiment "heterocycle" refers to a cyclic ring with two nitrogens and 3, 4, 5, 6, 7, or 8 carbon atoms.
In one embodiment "heterocycle" refers to a cyclic ring with one oxygen and 3, 4, 5, 6, 7, or 8 carbon atoms.
In one embodiment "heterocycle" refers to a cyclic ring with one sulfur and 3, 4, 5, 6, 7, or 8 carbon atoms.
Non-limiting examples of "heterocycle" include aziridine, oxirane, thiirane, azetidine, 1,3-diazetidine, oxetane, and thietane.
Additional non-limiting examples of "heterocycle" include pyrrolidine, 3-pyrroline, 2-pyrroline, pyrazolidine, and imidazolidine.
Additional non-limiting examples of "heterocycle" include tetrahydrofuran, 1,3-dioxolane, tetrahydrothiophene, 1,2-oxathiolane, and 1,3-oxathiolane.
Additional non-limiting examples of "heterocycle" include piperidine, piperazine, tetrahydropyran, 1,4-dioxane, thiane, 1,3-dithiane, 1,4-dithiane, morpholine, and thiomorpholine.

Non-limiting examples of "heterocycle" also include:

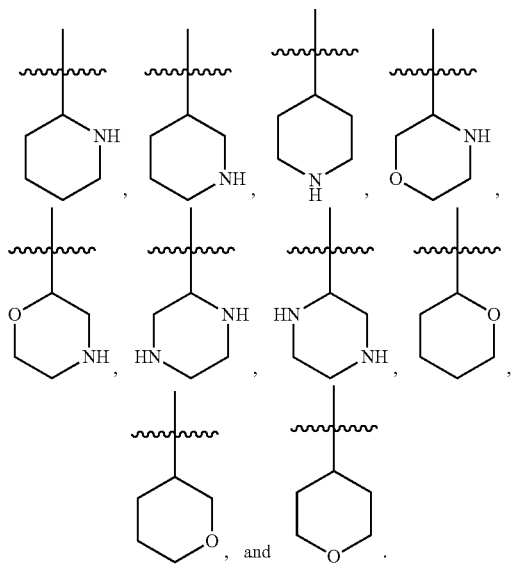

Additional non-limiting examples of "heterocycle" include:

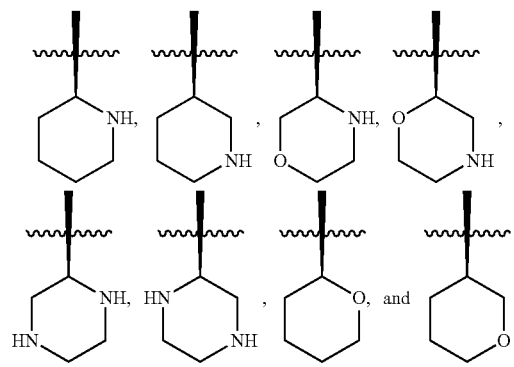

Additional non-limiting examples of "heterocycle" include:

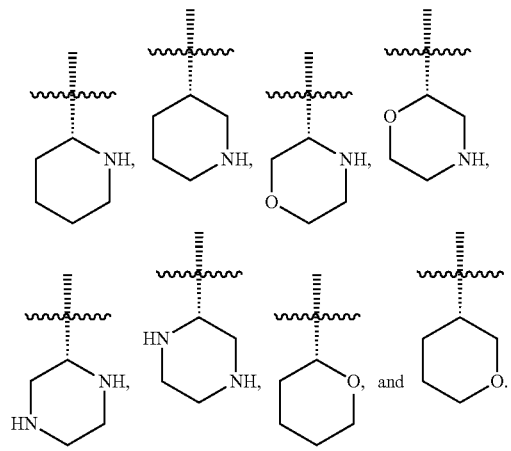

Non-limiting examples of "heterocycle" also include:

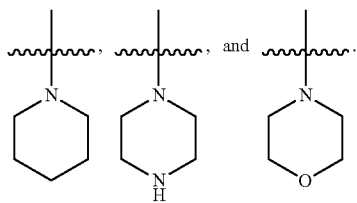

Non-limiting examples of "heterocycle" also include:

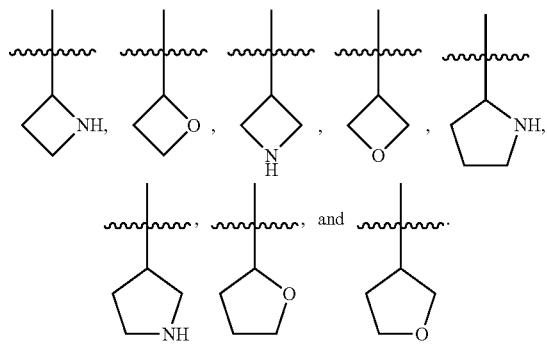

Additional non-limiting examples of "heterocycle" include:

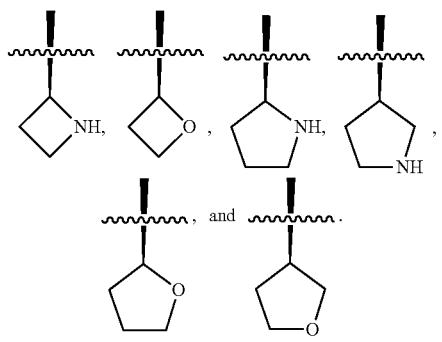

Additional non-limiting examples of "heterocycle" include:

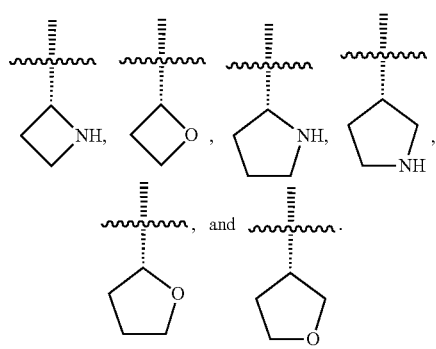

In one embodiment "heterocycle" is "substituted heterocycle".

Embodiments of A

In one embodiment A2 is selected from:

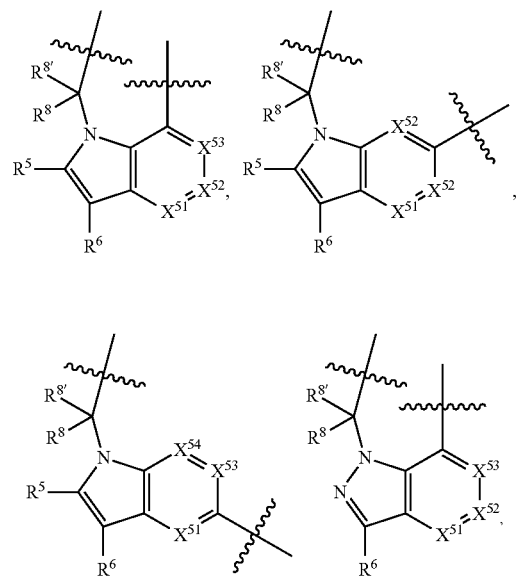

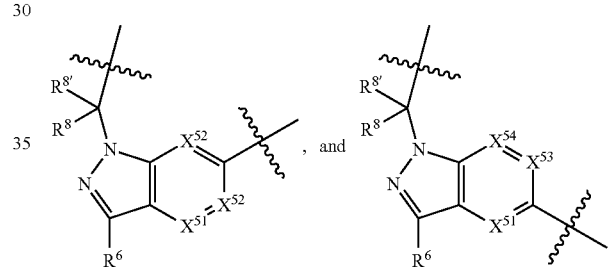

In one embodiment A3 is selected from:

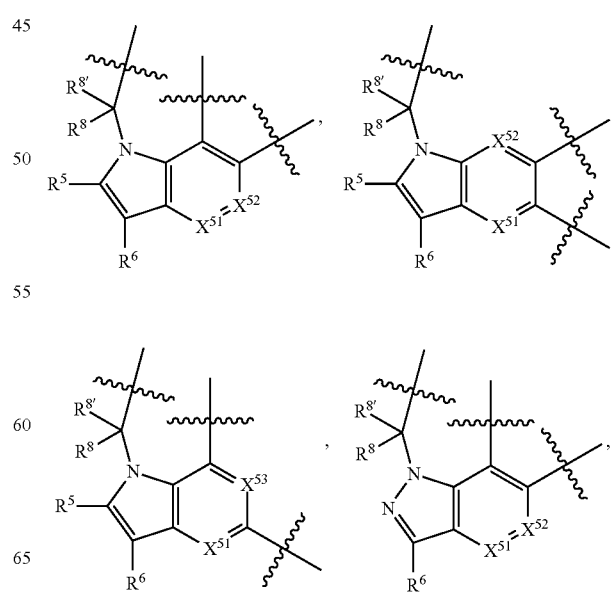

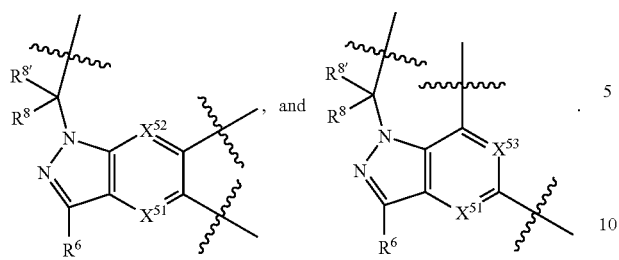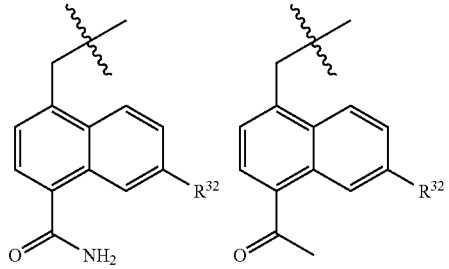
Non-limiting examples of A1 include:
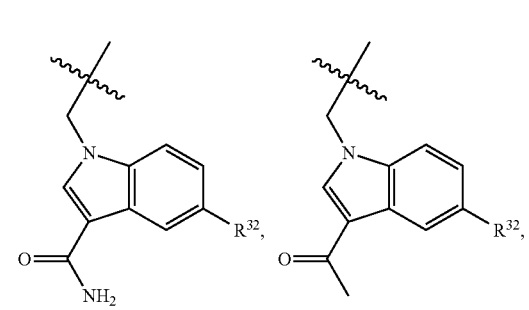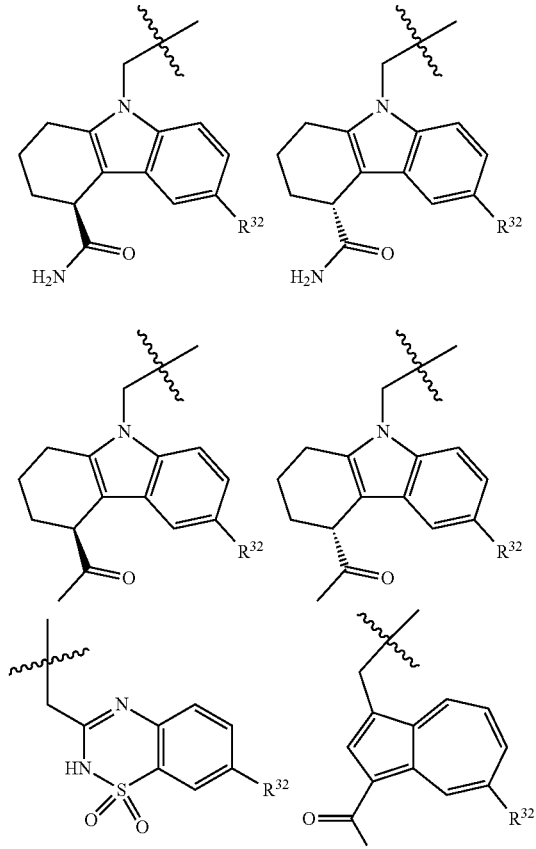
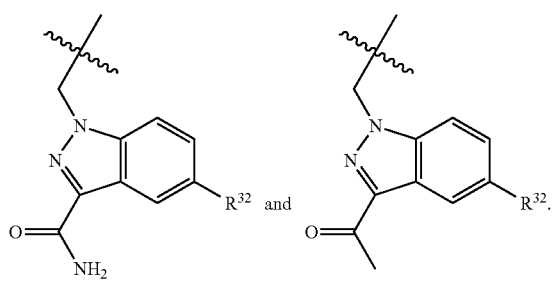
In one embodiment A1 is selected from:
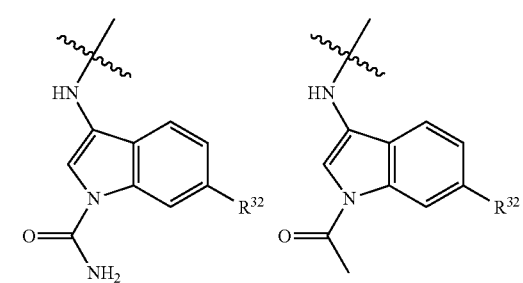
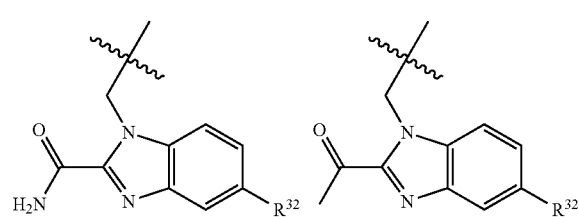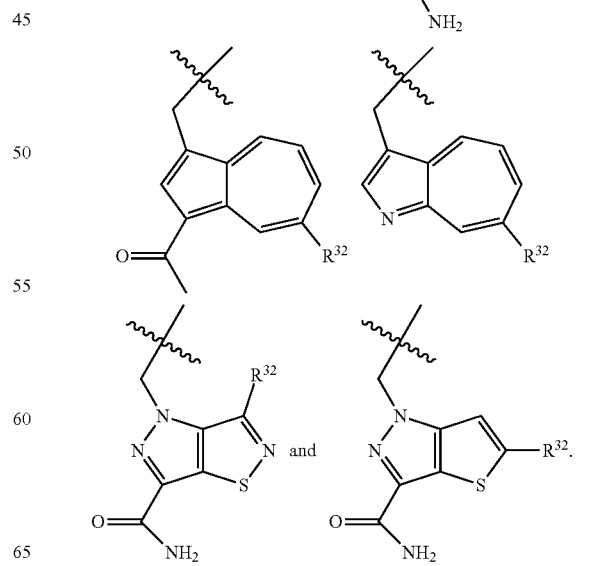

In one embodiment A1 is selected from:
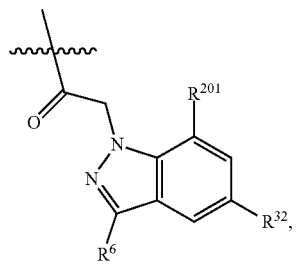
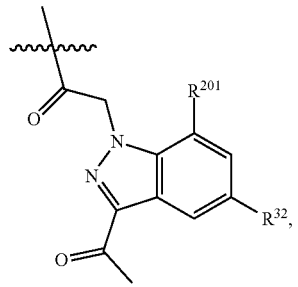
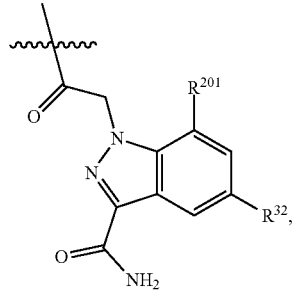
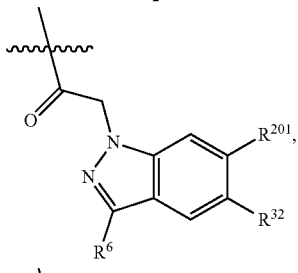
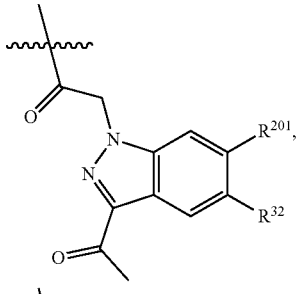
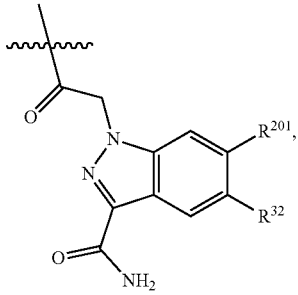
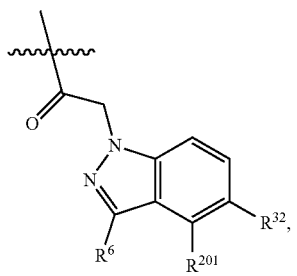
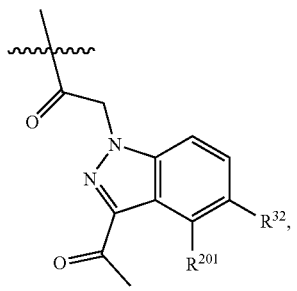
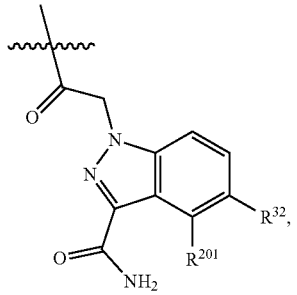
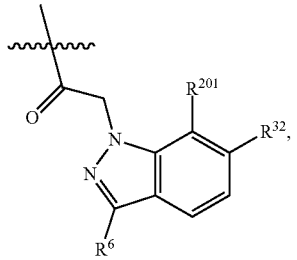
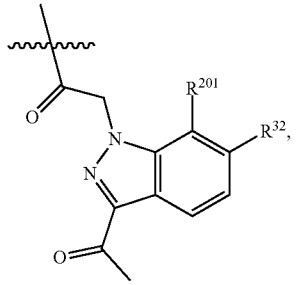
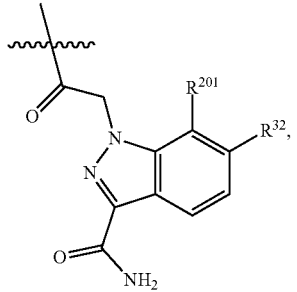

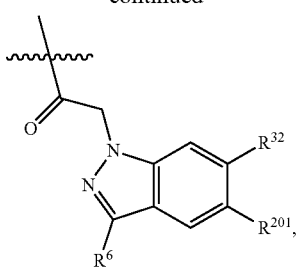
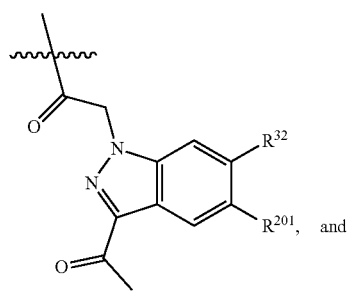
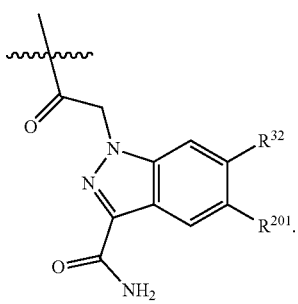
In one embodiment A is selected from:
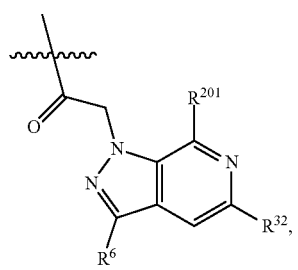
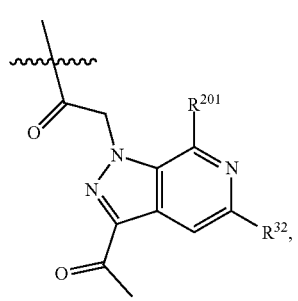
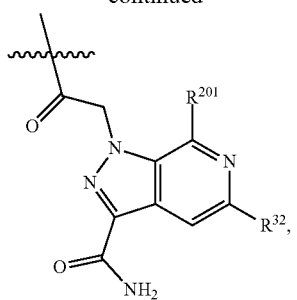
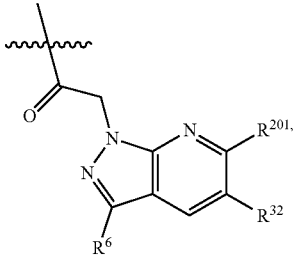
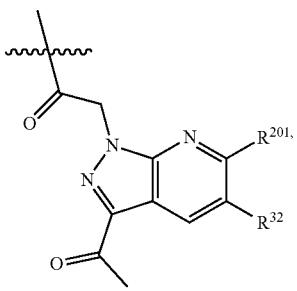
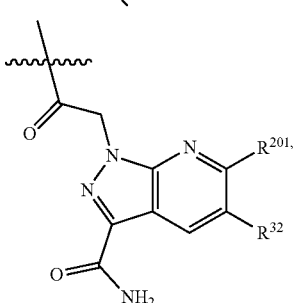
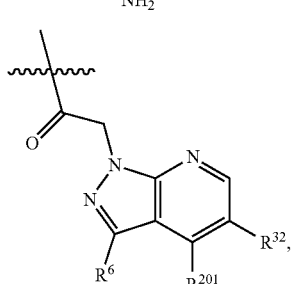
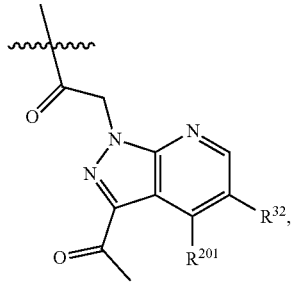

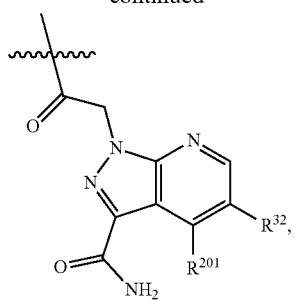
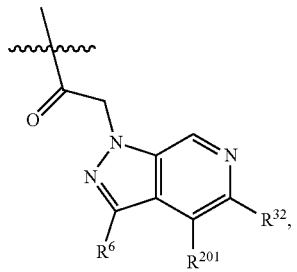
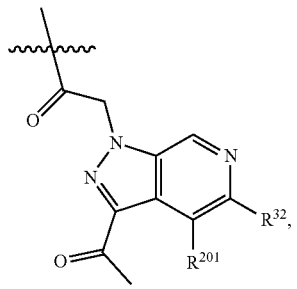
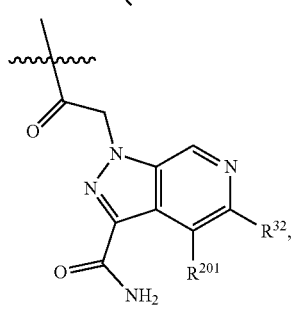
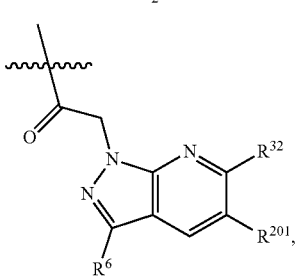
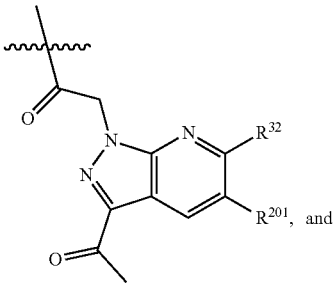
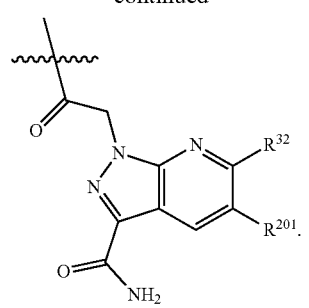
In one embodiment A is selected from:
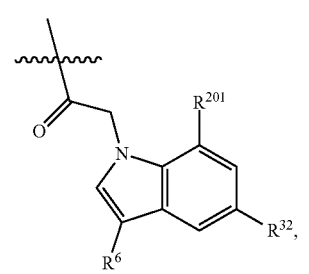
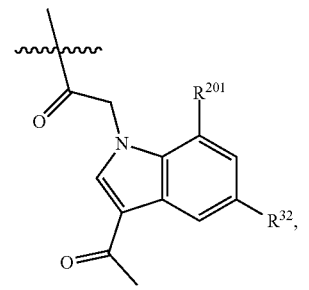
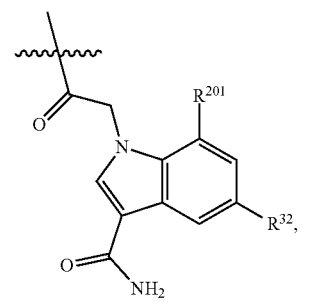
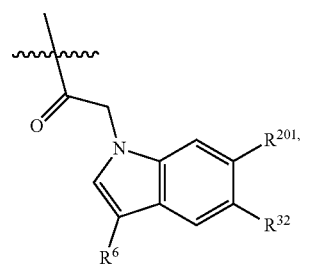

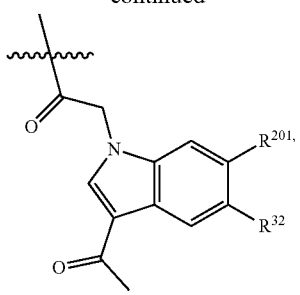
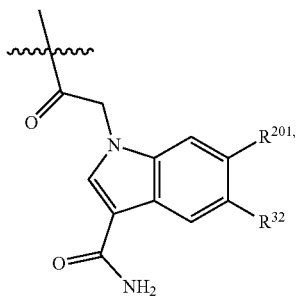
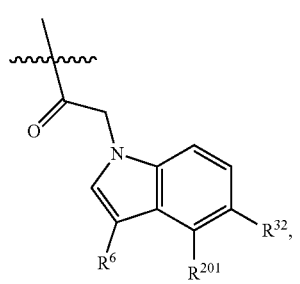
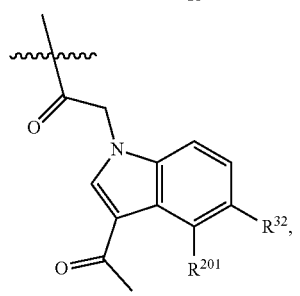
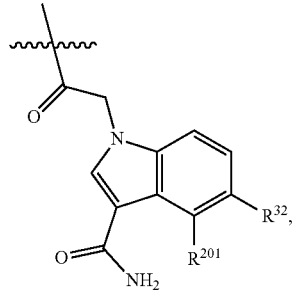
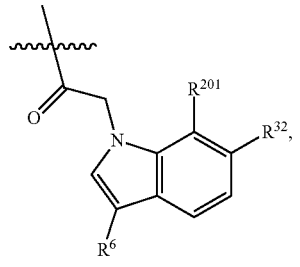
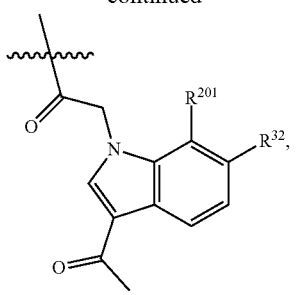
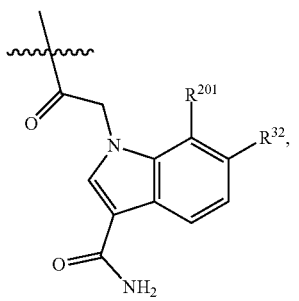
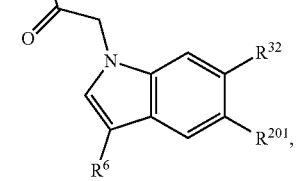
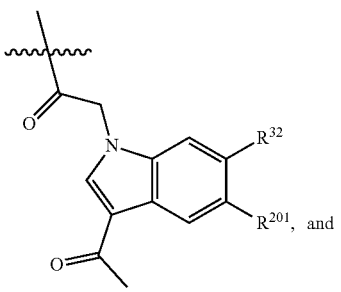
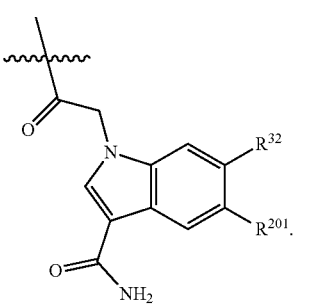

In one embodiment A is selected from:
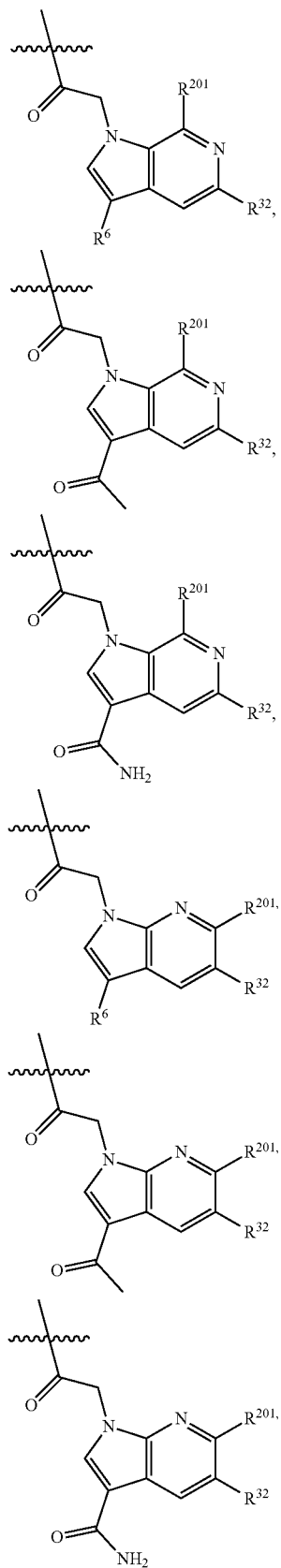
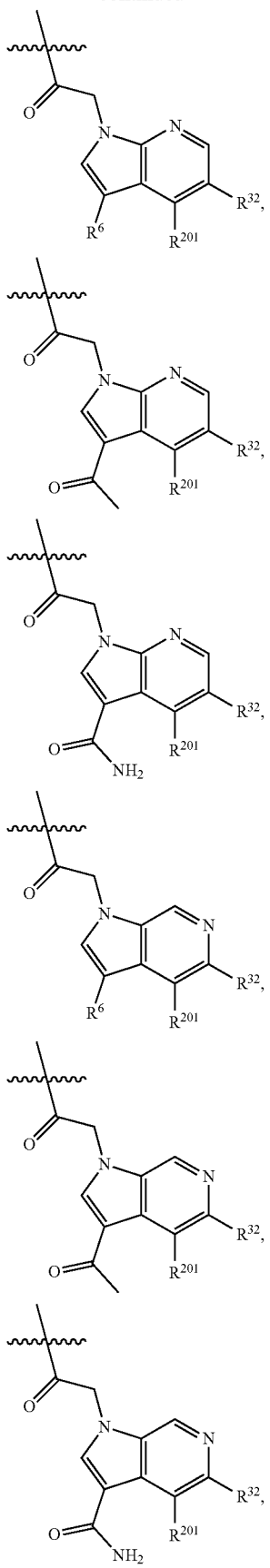

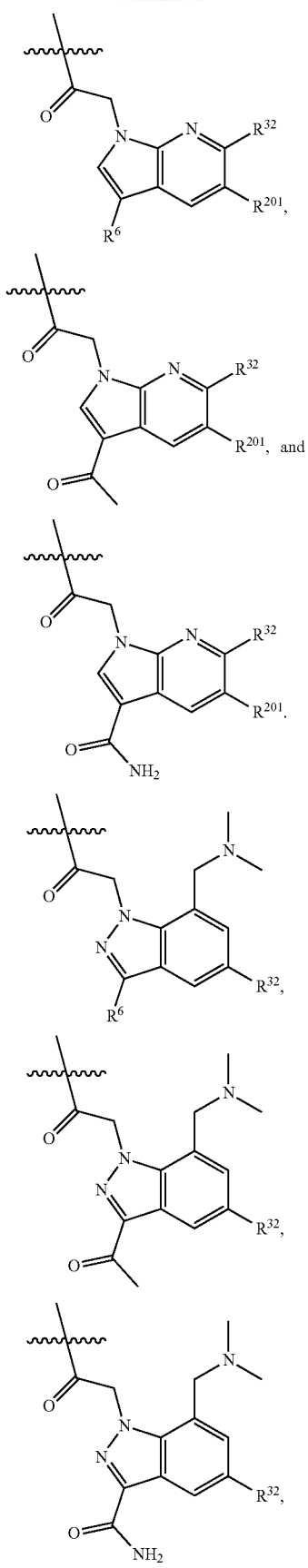
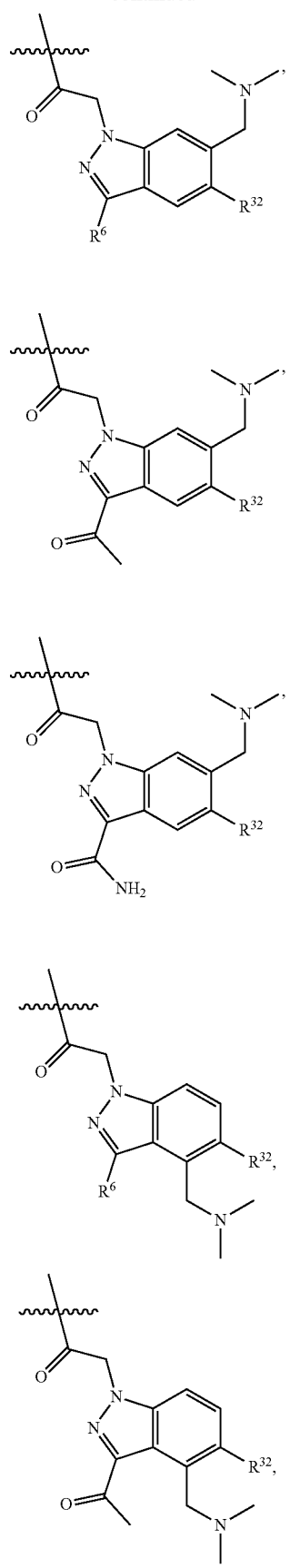

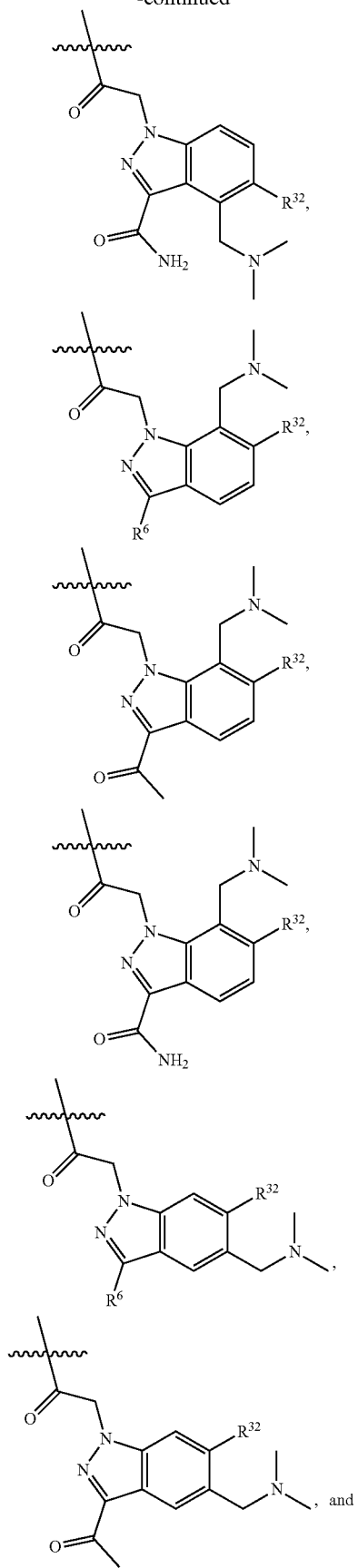
In one embodiment A is selected from:
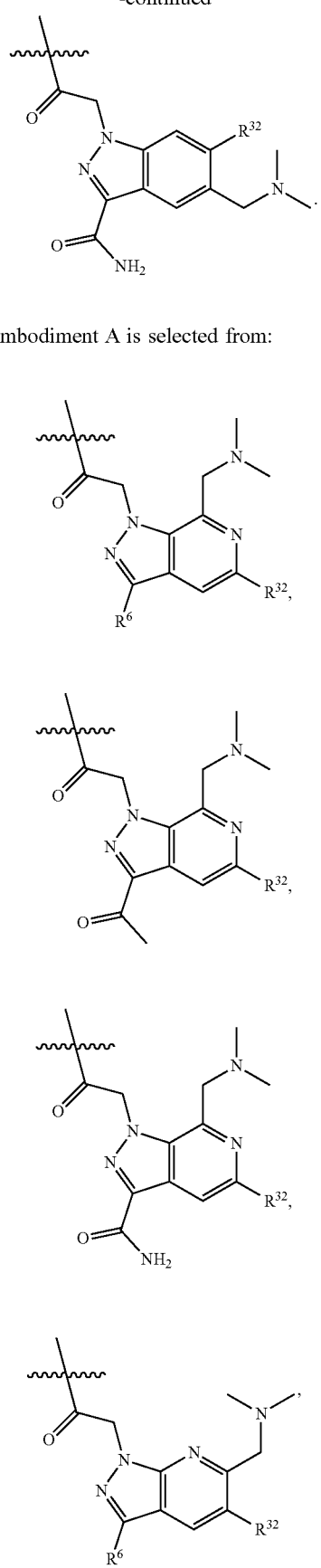

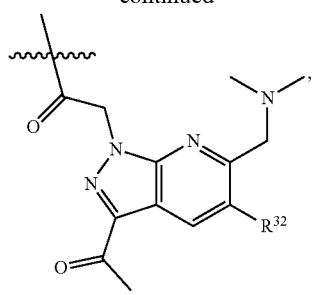
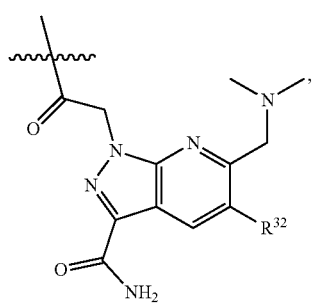
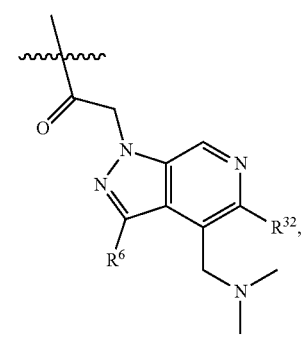
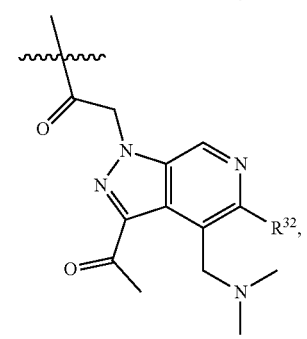
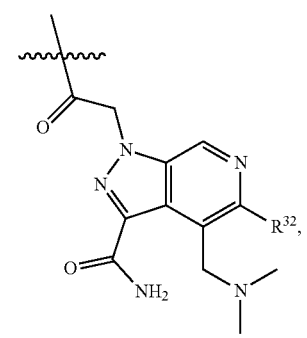
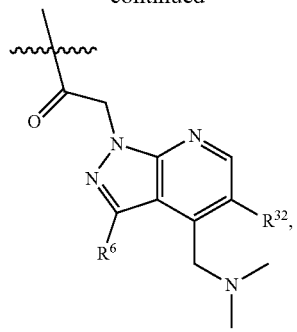
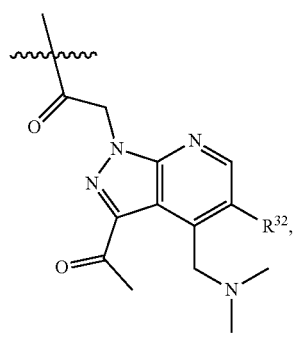
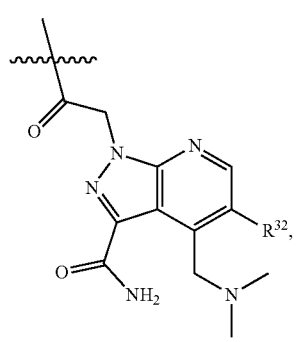
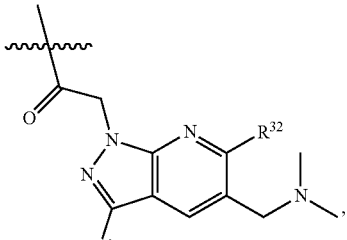
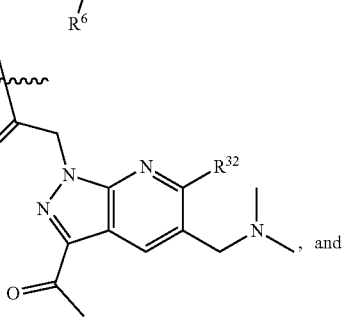

-continued
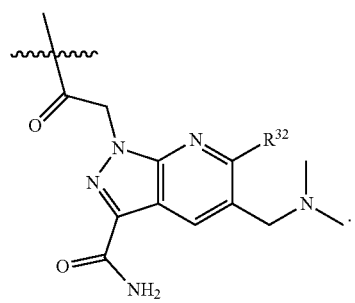
In one embodiment A is selected from:
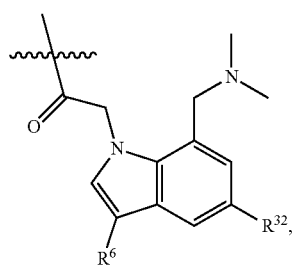
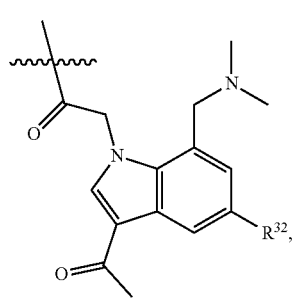
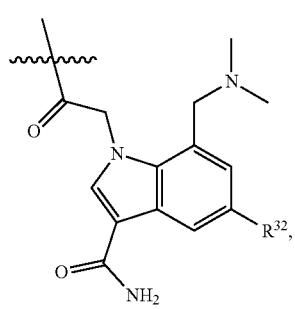
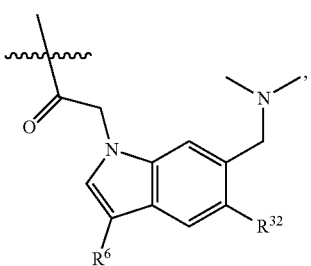
-continued
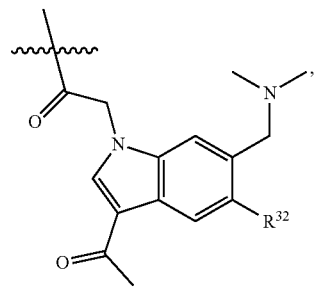
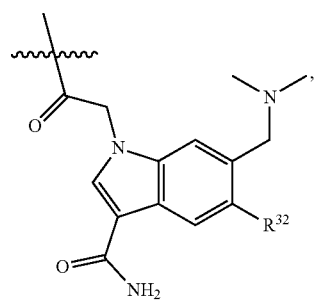
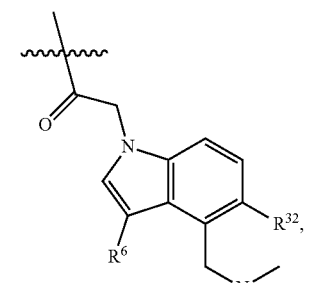
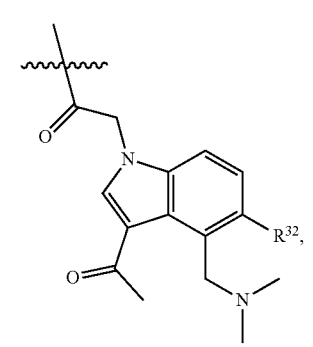
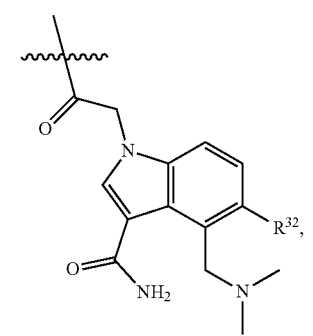

-continued
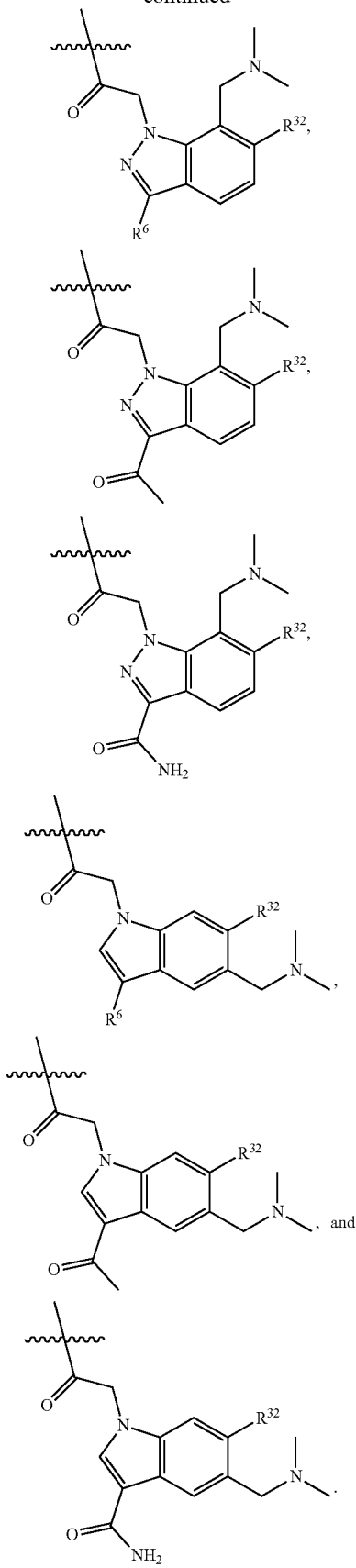
In one embodiment A is selected from:
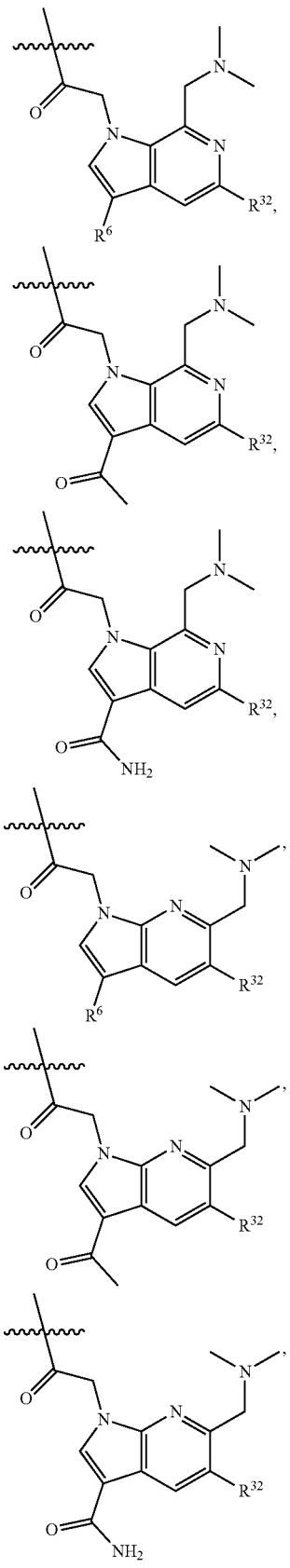

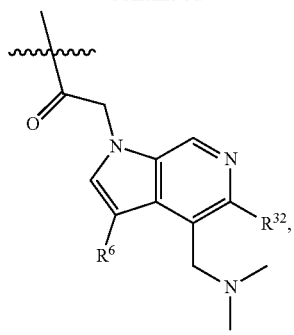
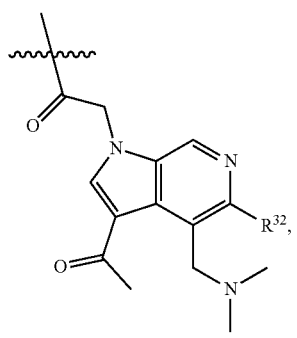
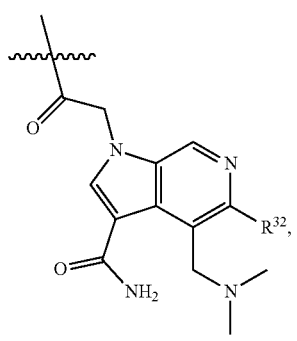
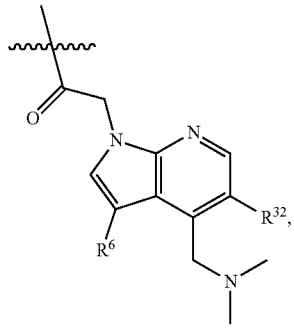
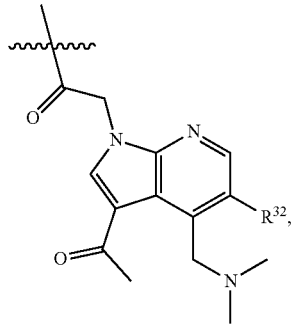
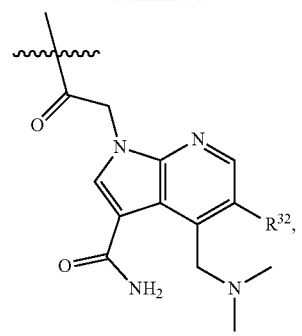
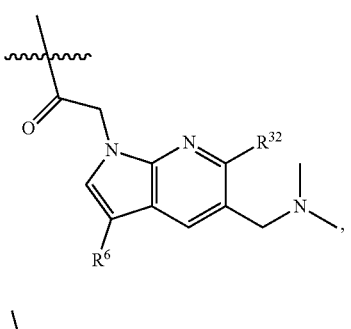
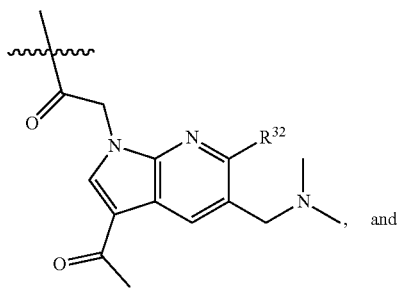
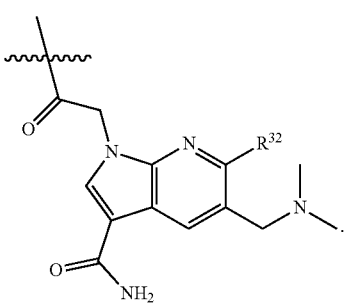
In one embodiment A1 is selected from:
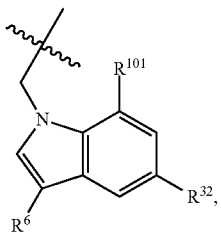 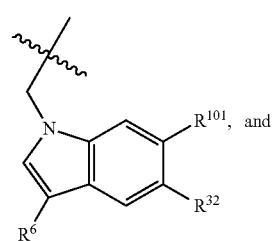

-continued
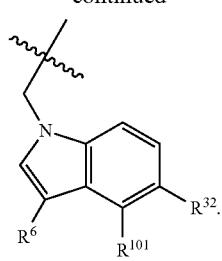
In one embodiment A1 is selected from:
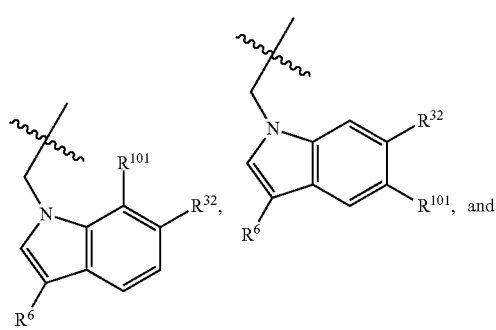
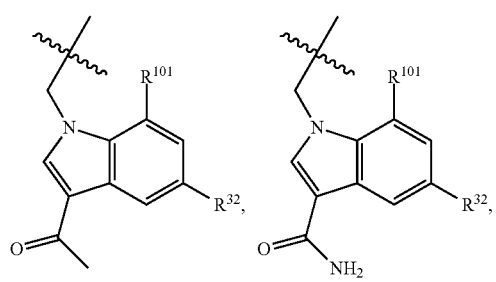
In one embodiment A1 is selected from:
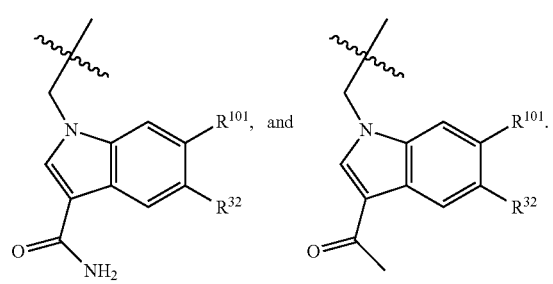
In one embodiment A1 is selected from:
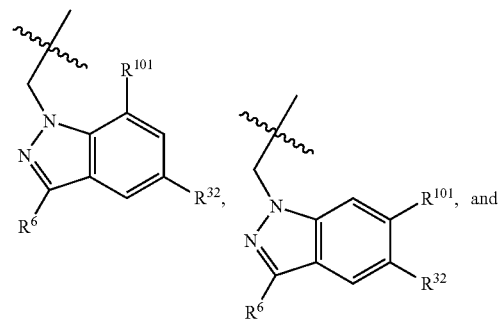
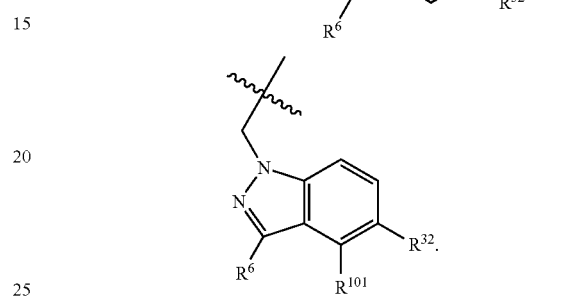
In one embodiment A1 is selected from:
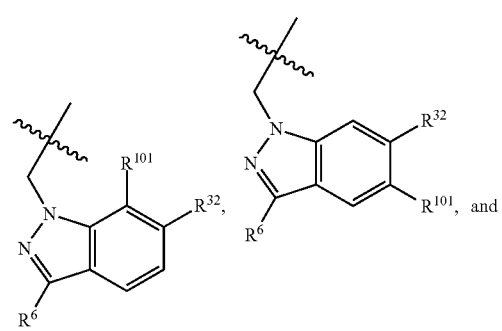
In one embodiment A1 is selected from:
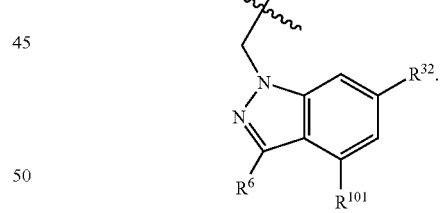
In one embodiment A1 is selected from:
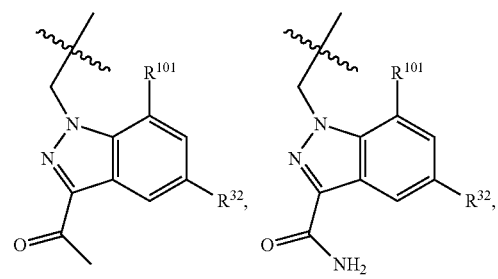

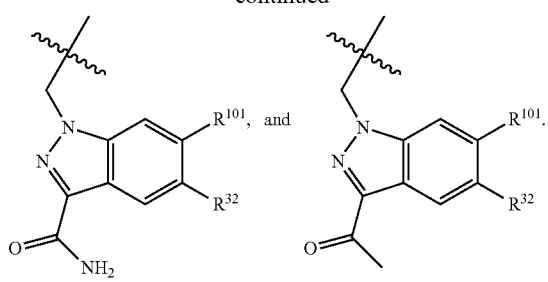, and 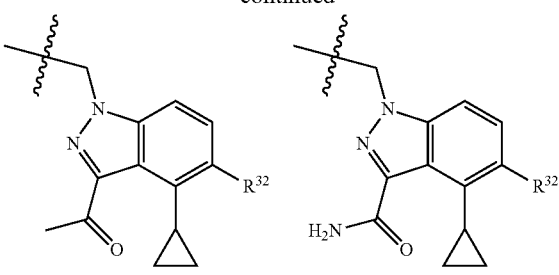
In the above embodiments and throughout this specification $R^{101}$ is $C_1$-$C_4$ alkyl or $C_3$-$C_7$ cycloalkyl.
In another embodiment A1 is selected from:
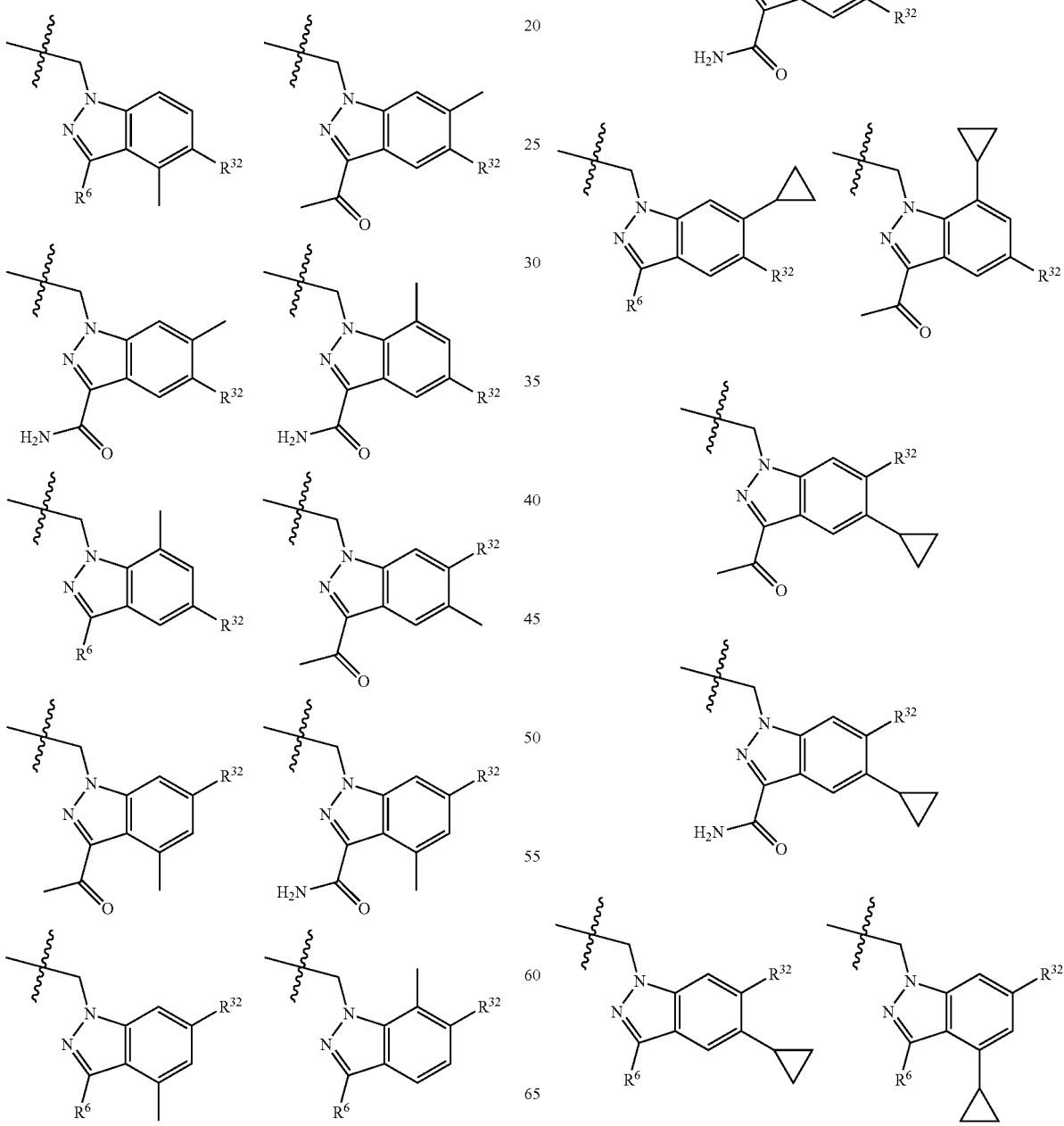

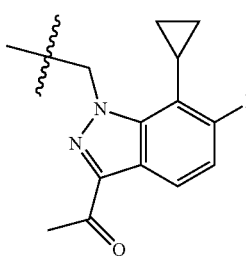
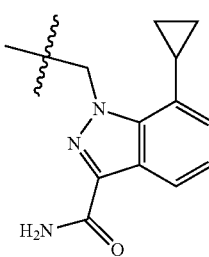
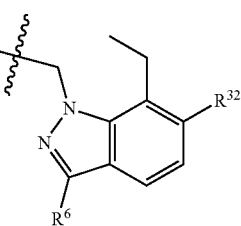
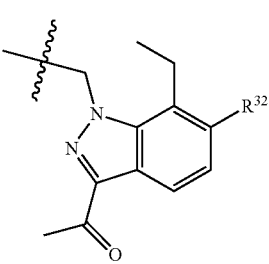
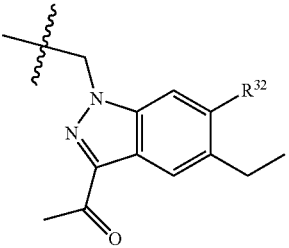
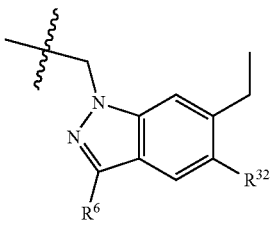
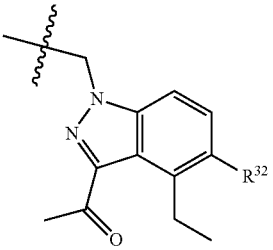
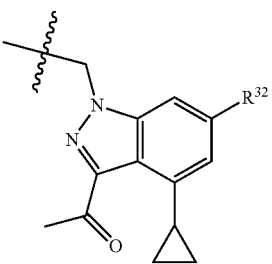

-continued

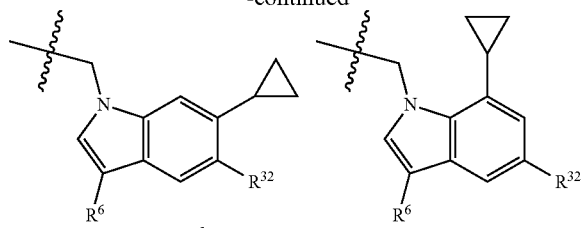
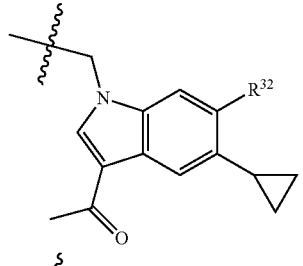
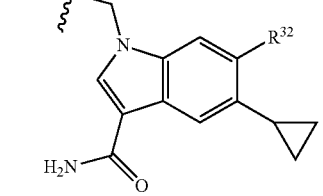
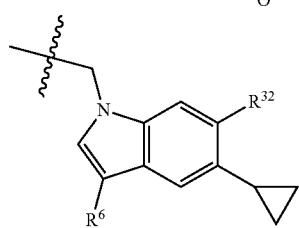
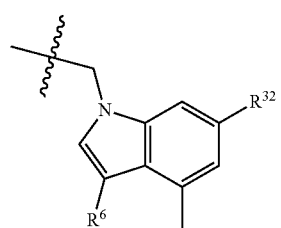
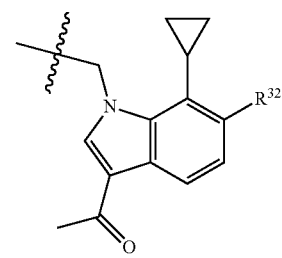
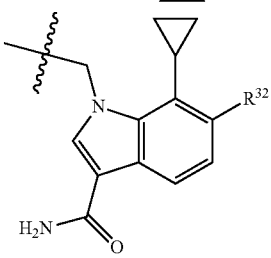
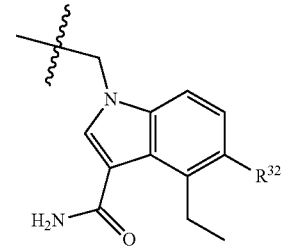
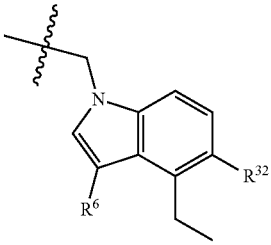
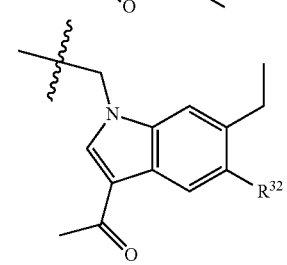
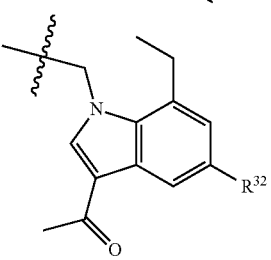
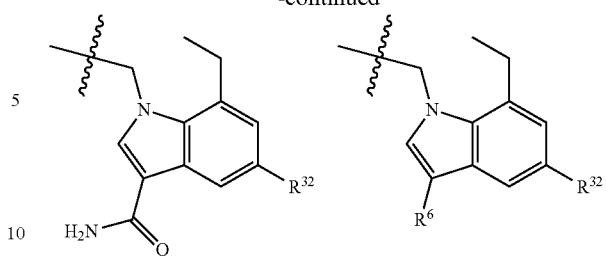
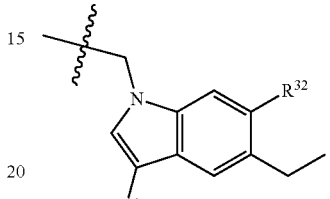
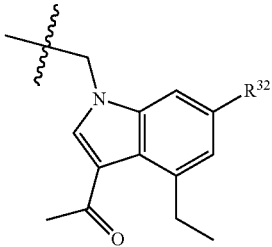
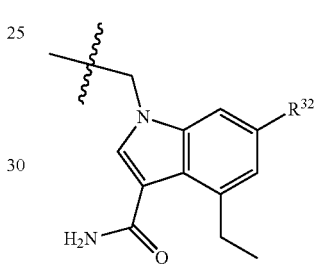
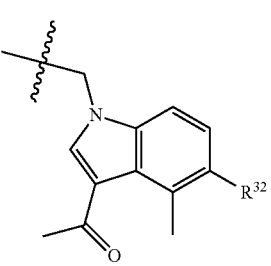
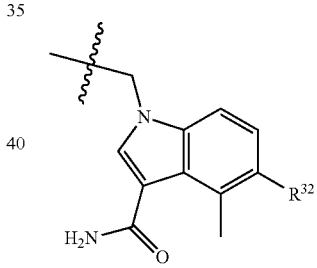
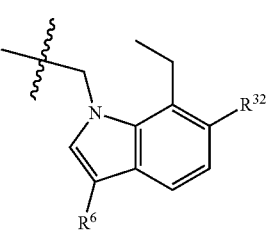
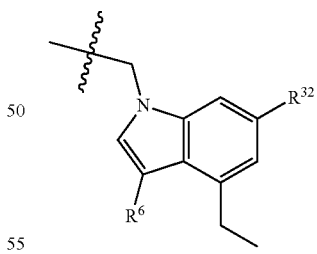
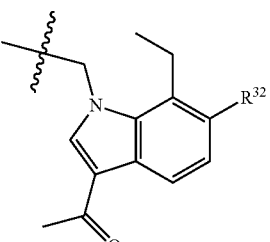
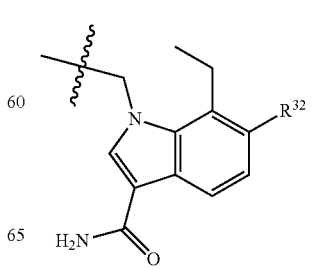
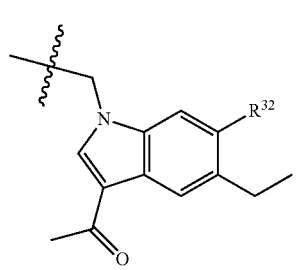

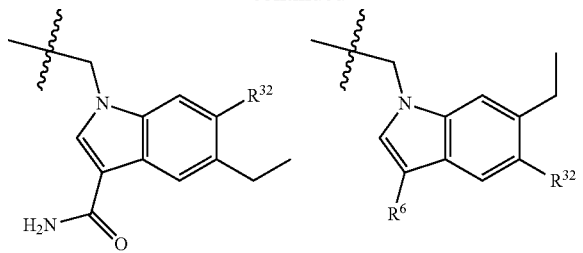
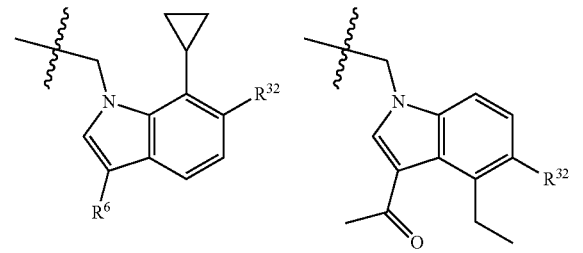
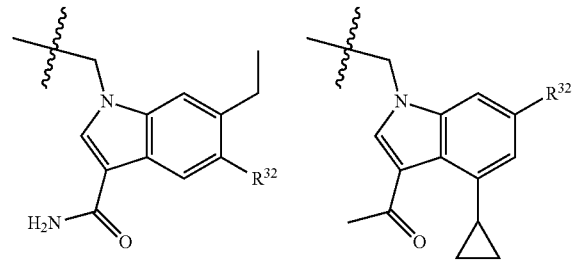
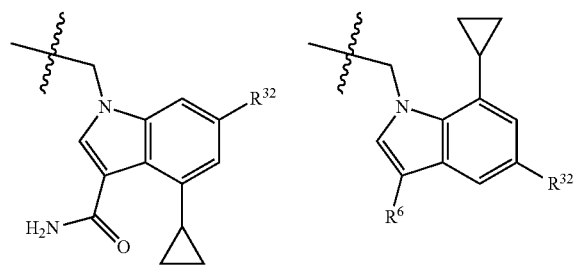
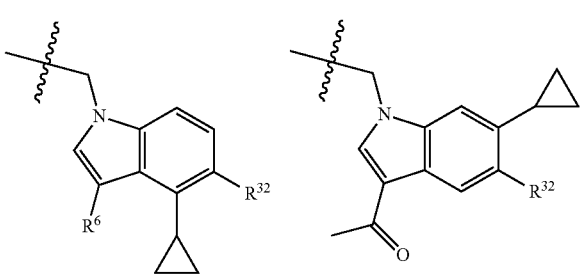
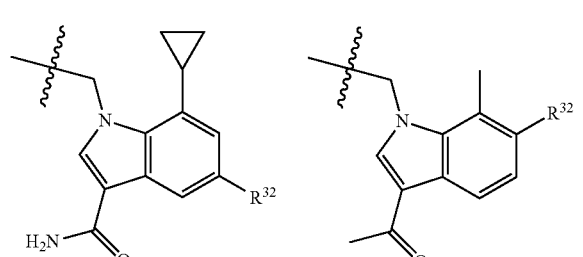
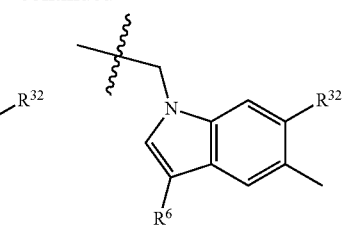
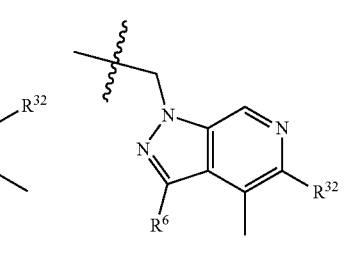
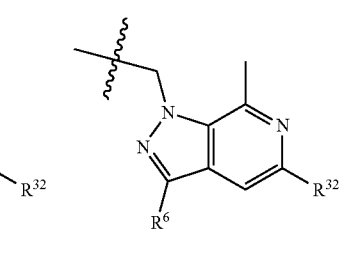
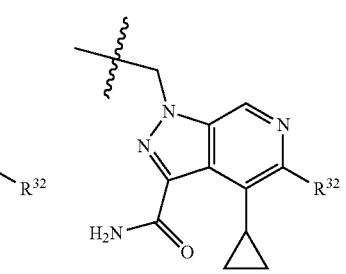
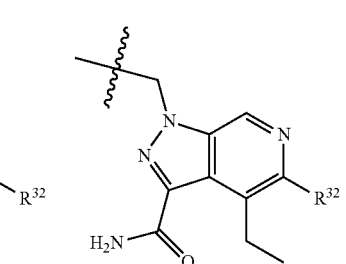

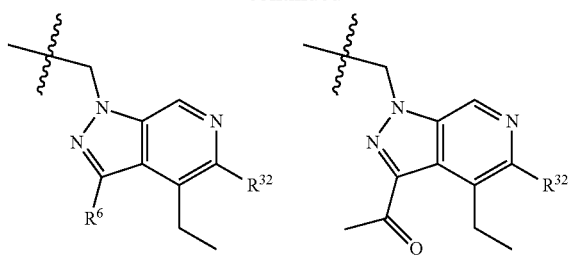
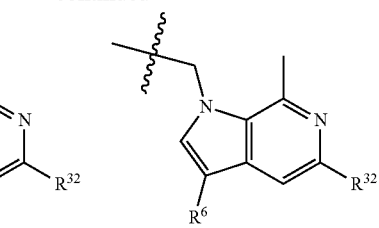
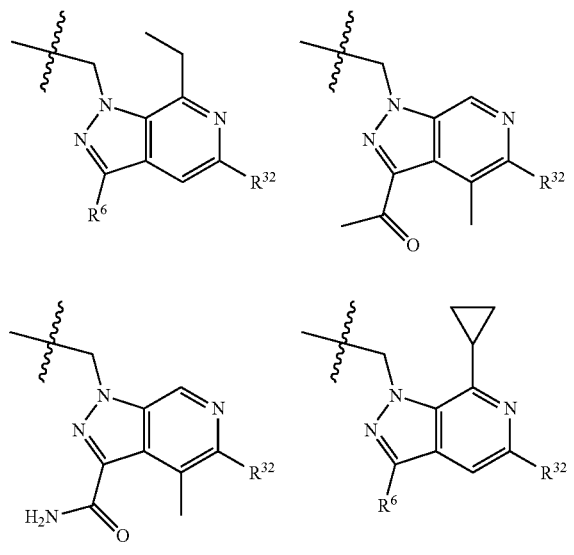
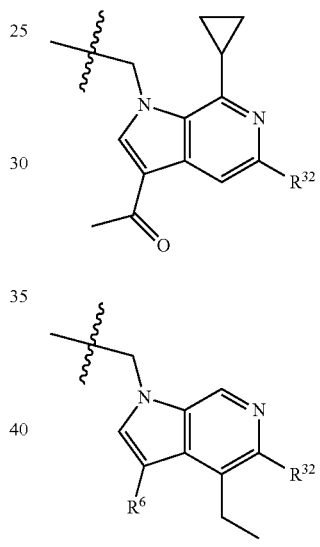
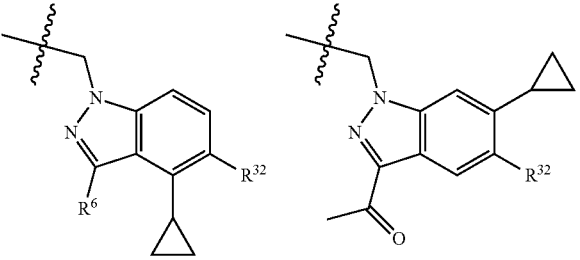
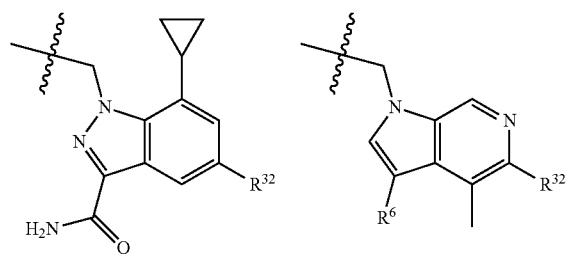

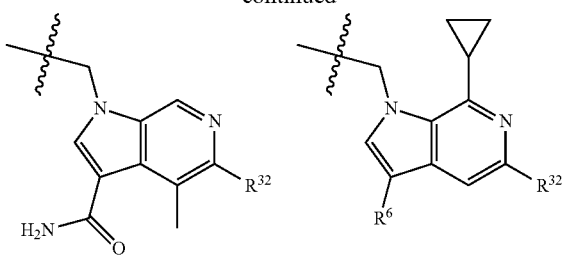
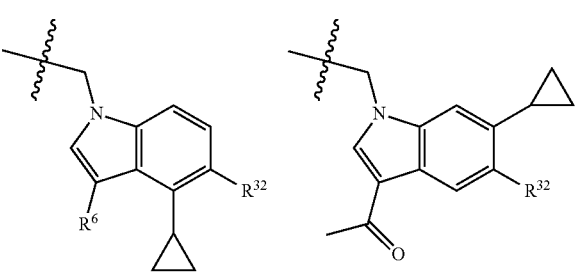
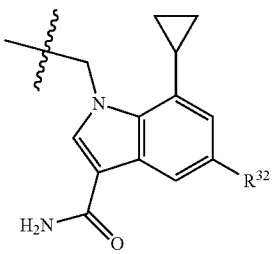
In one embodiment A1 is selected from:
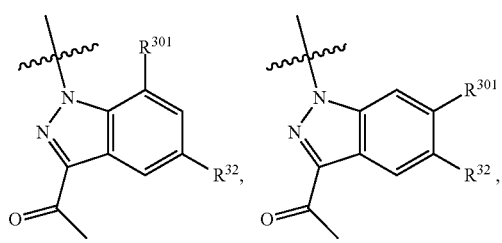
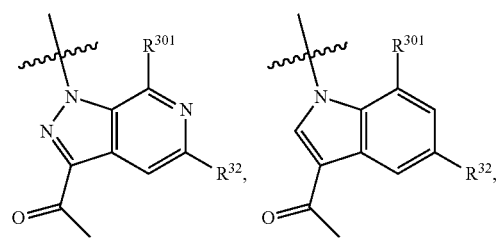
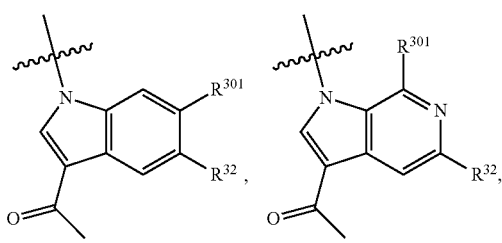
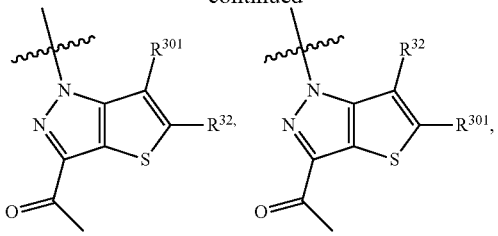
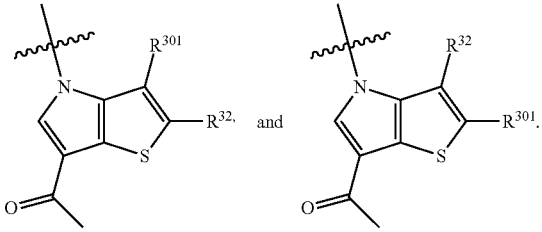
Additional non-limiting examples of A1 include:
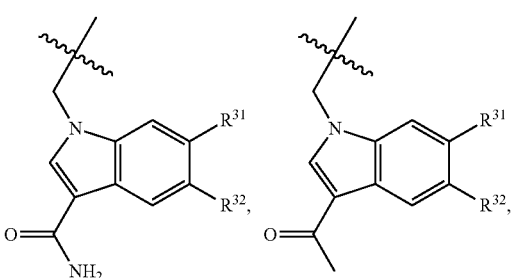
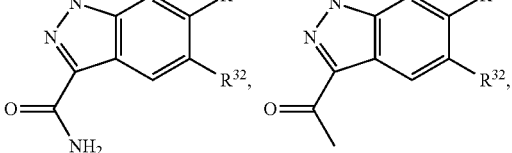
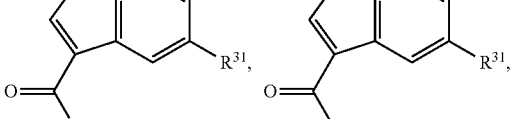
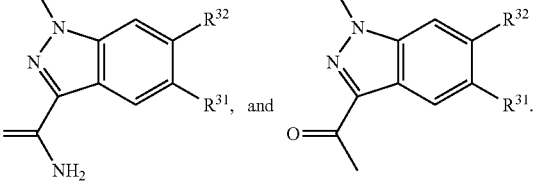

Additional non-limiting examples of A1 include:
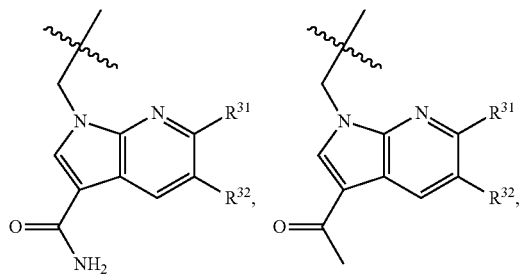
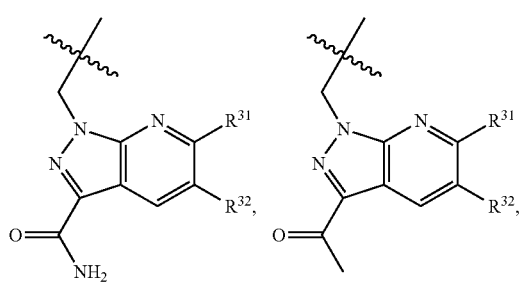
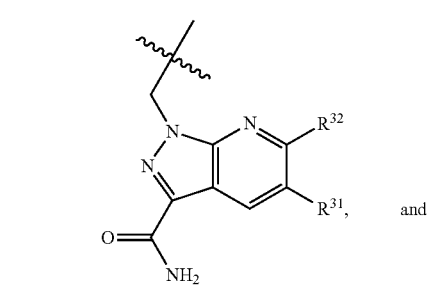
and
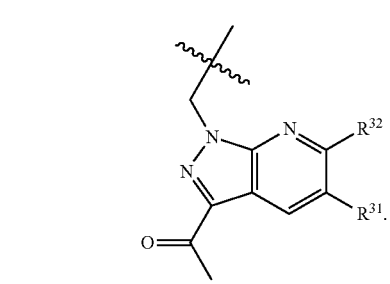
In another embodiment, A1 is selected from:
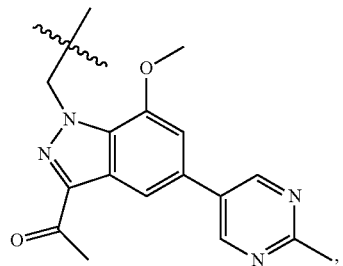
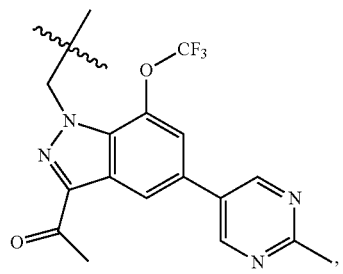
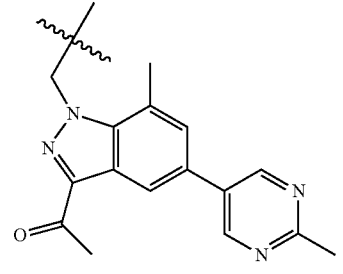
In another embodiment A1 is selected from:
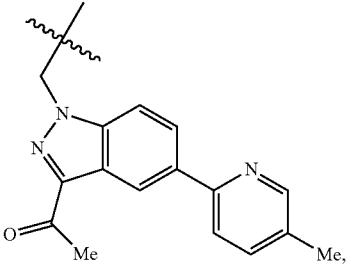
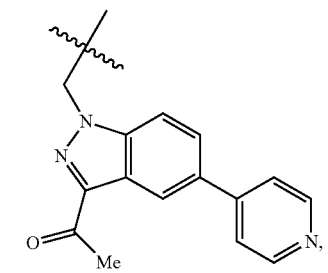

In an alternative embodiment A1 is selected from:
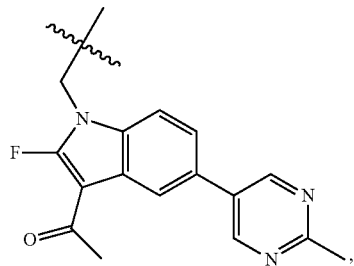,
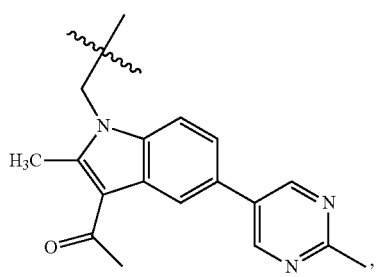,
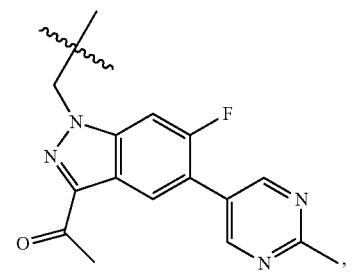,
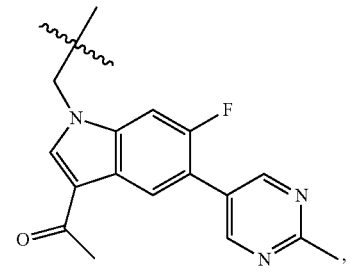,
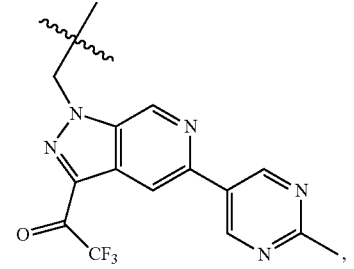,
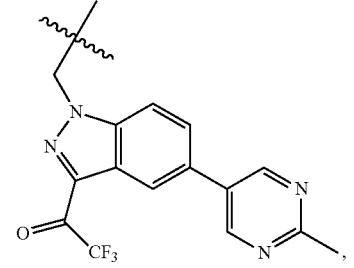,
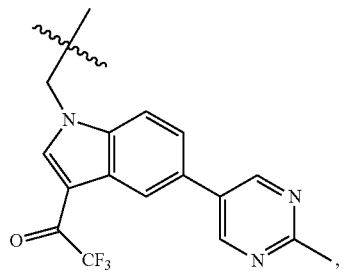,
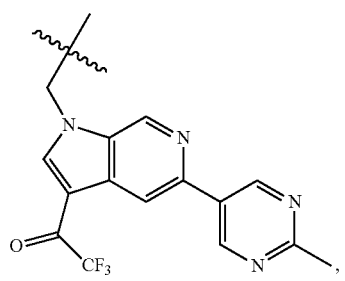,
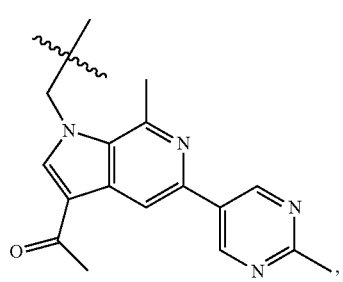,
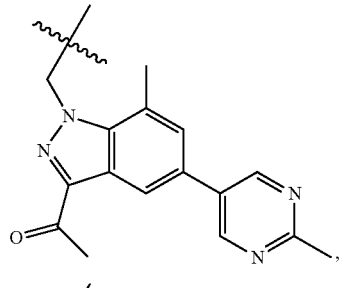,
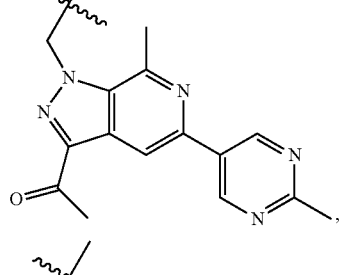,
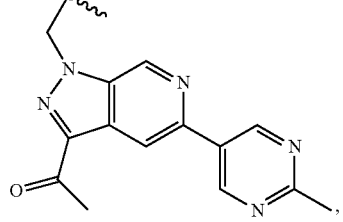,

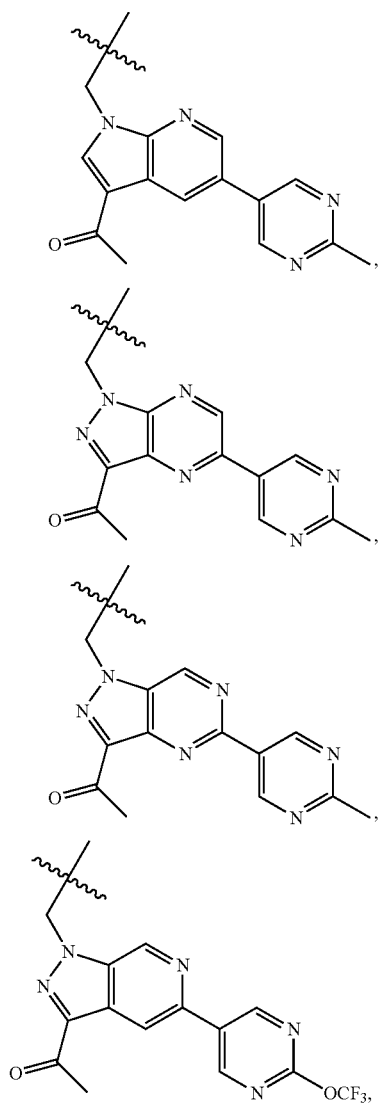
In one embodiment R$^{32}$ is selected from:
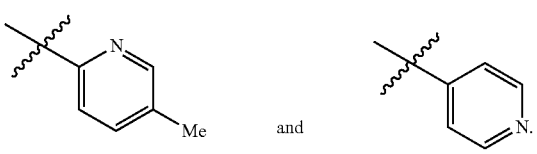 [SMILES: *c1ccc(C)cn1 ; *c1ccncc1]
Embodiments of B
In one additional alternative embodiment B is selected from:
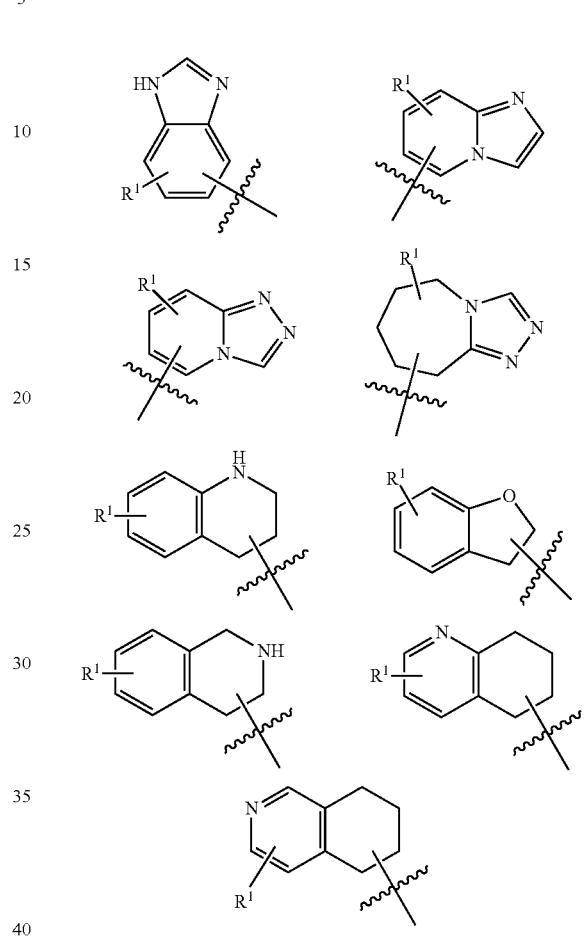
In one additional alternative embodiment R$^{36}$ is selected from:
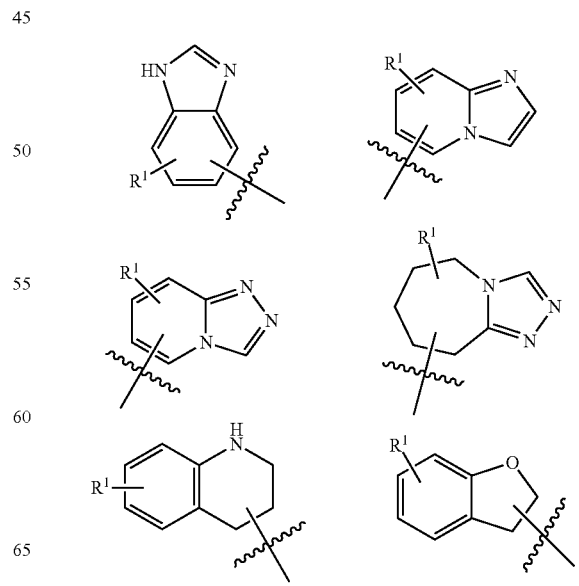

117
-continued
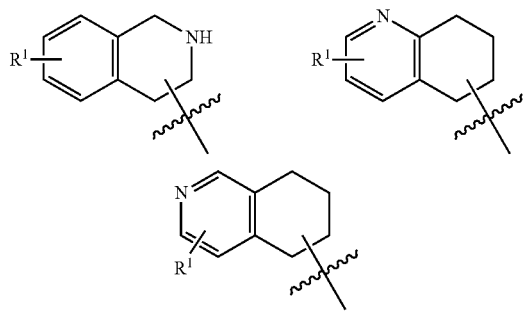
In one embodiment, B is selected from:
118
-continued
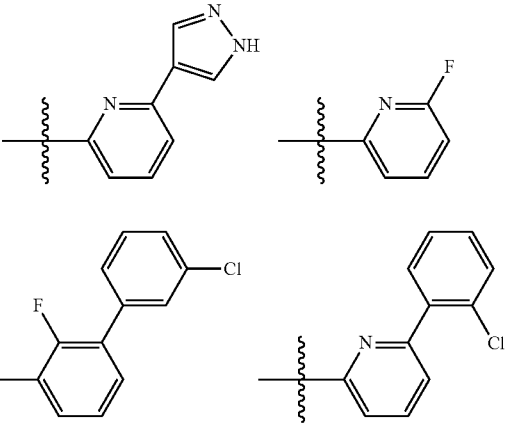
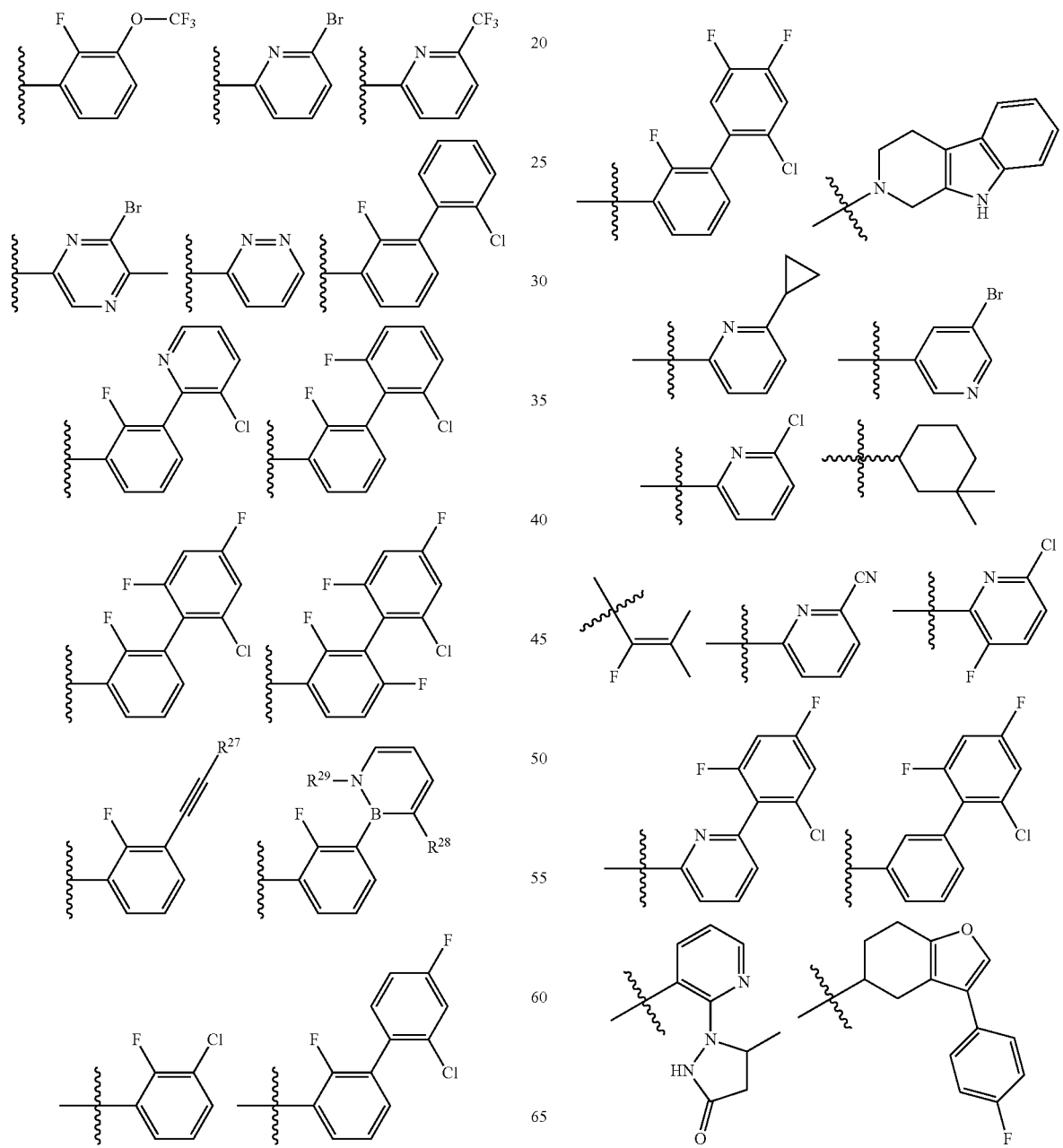

-continued
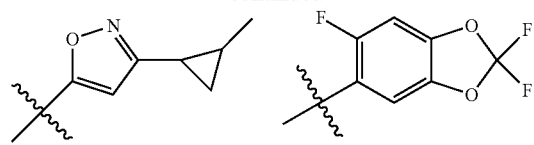
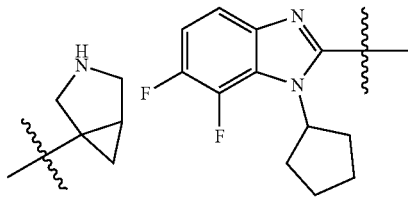
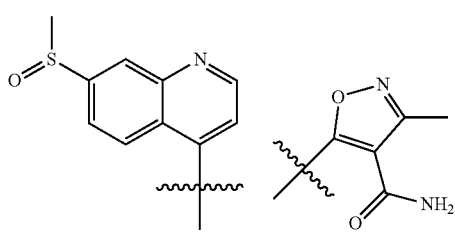
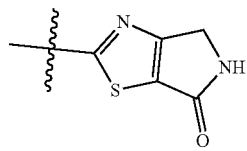
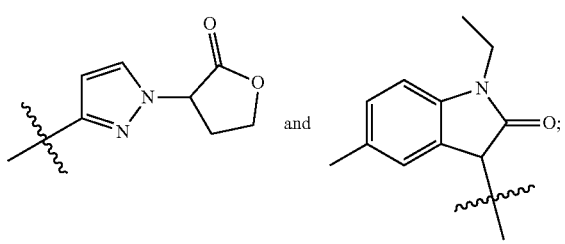
wherein $R^{27}$ is hydrogen, methyl, or trifluoromethyl; $R^{28}$ is hydrogen or halogen; and $R^{29}$ is hydrogen, methyl, trifluoromethyl, or —Si(CH$_3$)$_2$C(CH$_3$)$_3$.
In one embodiment, B is selected from:
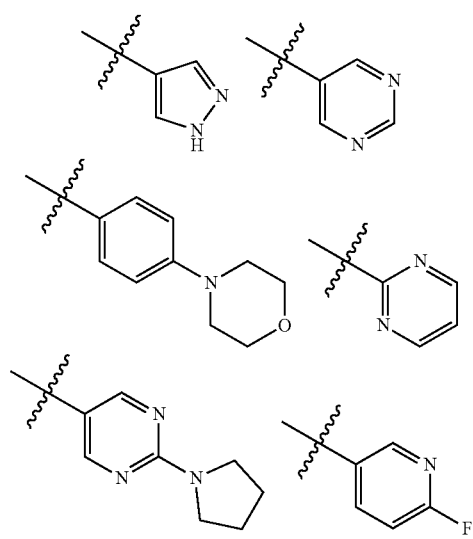
-continued
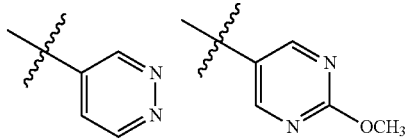
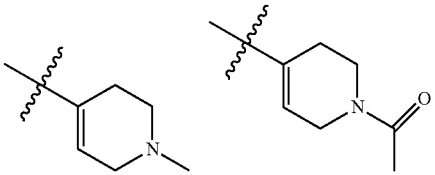
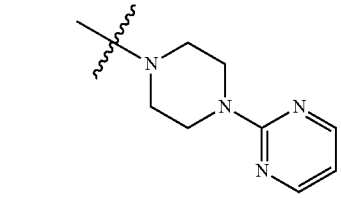
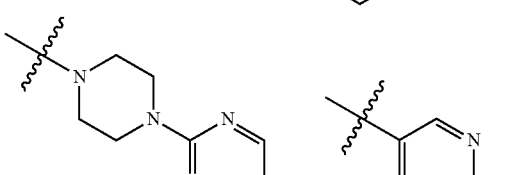
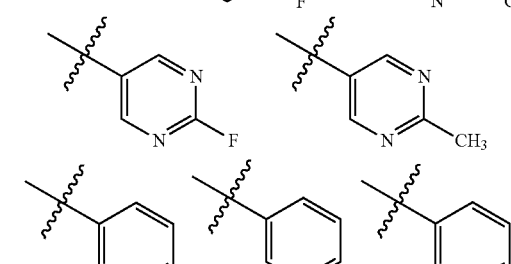
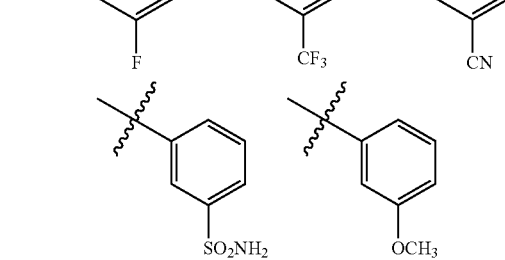
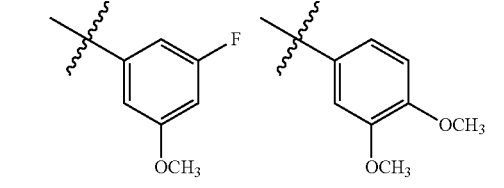
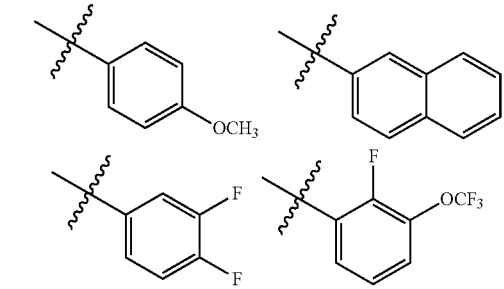

-continued
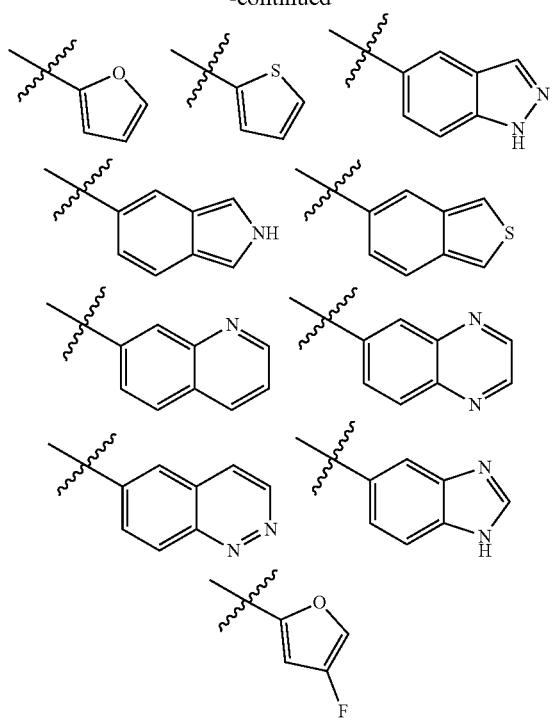
Examples of B moieties include, but are not limited to
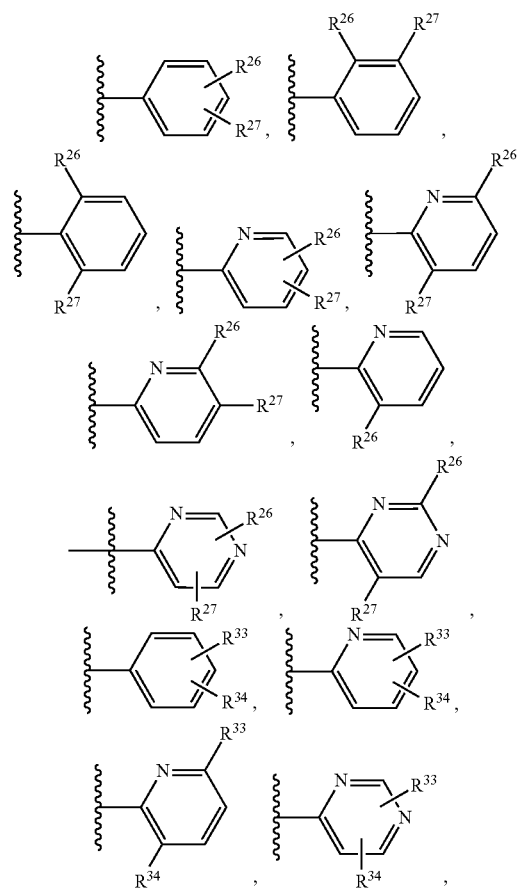
-continued
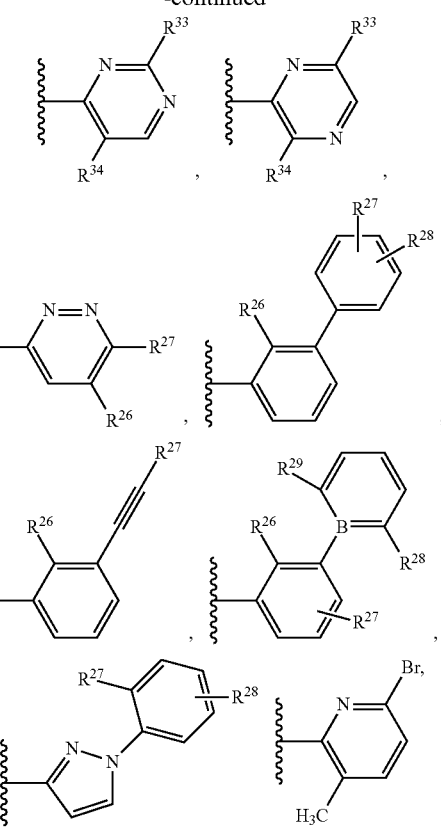

In one embodiment, B1 is selected from:
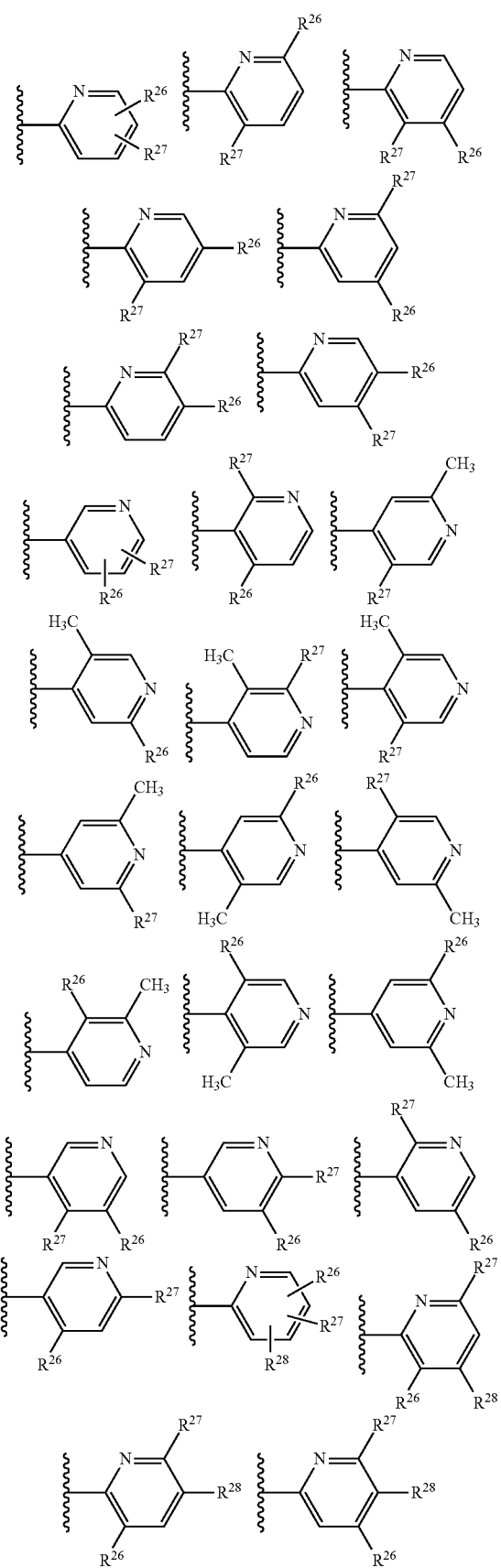
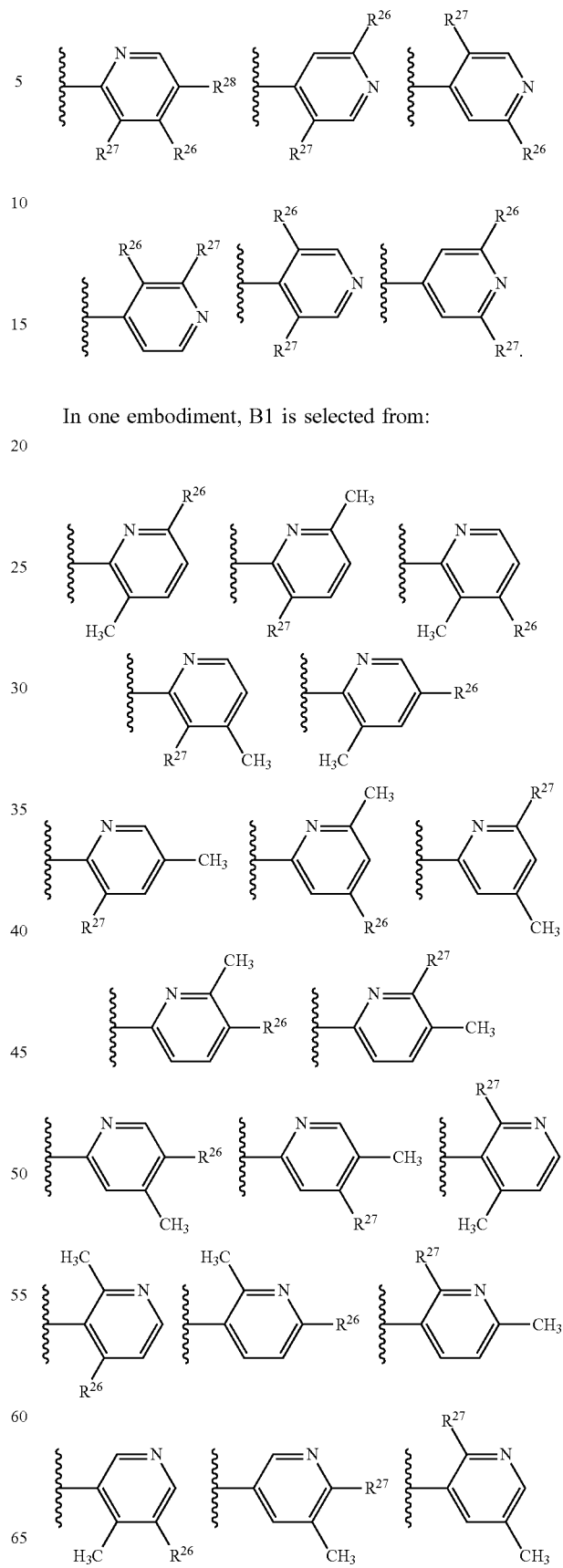
In one embodiment, B1 is selected from:

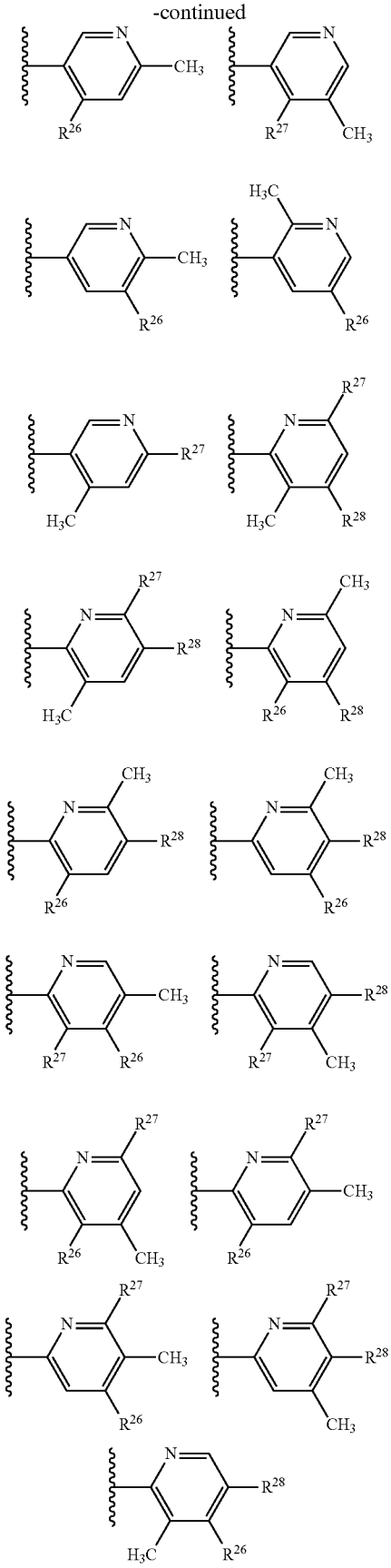
In one embodiment, B1 is selected from:
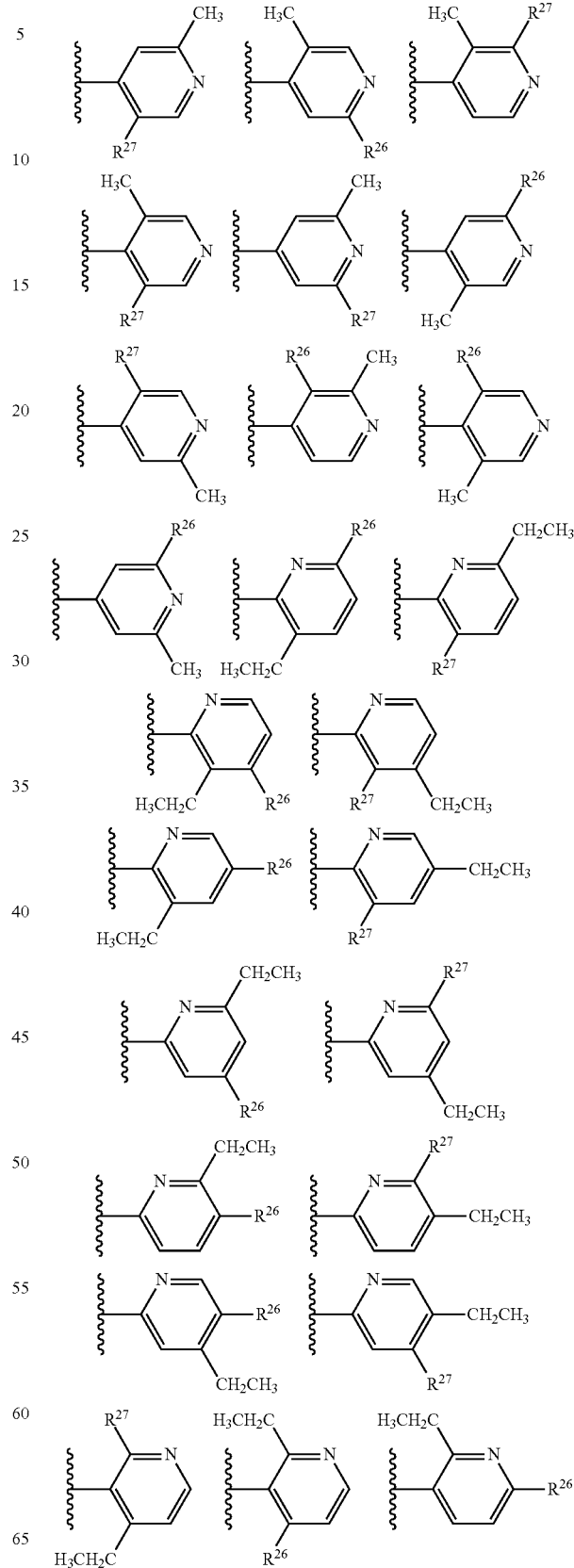

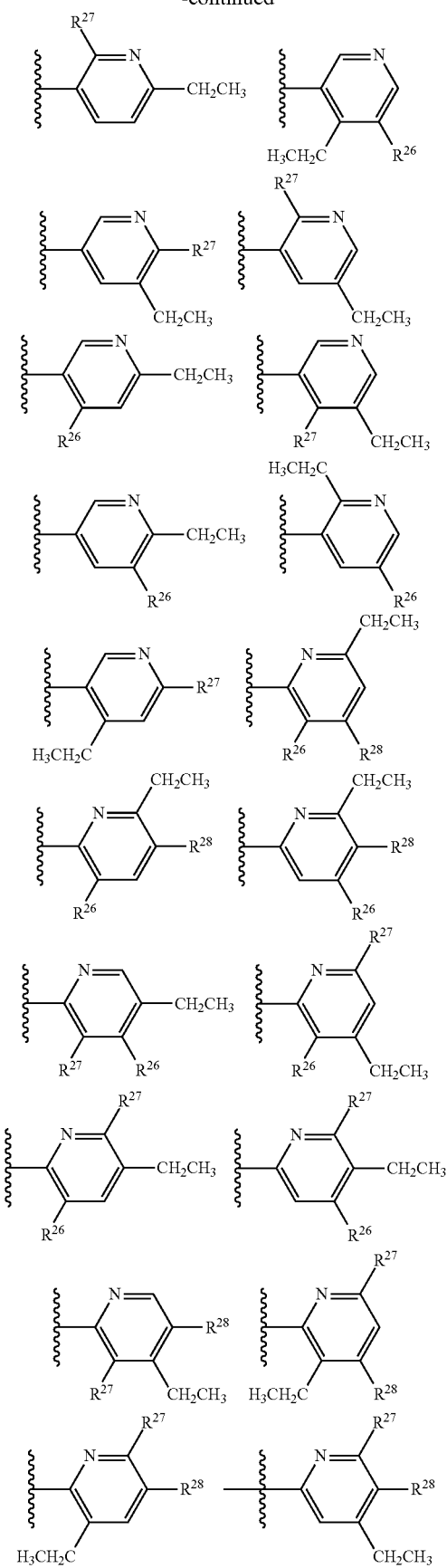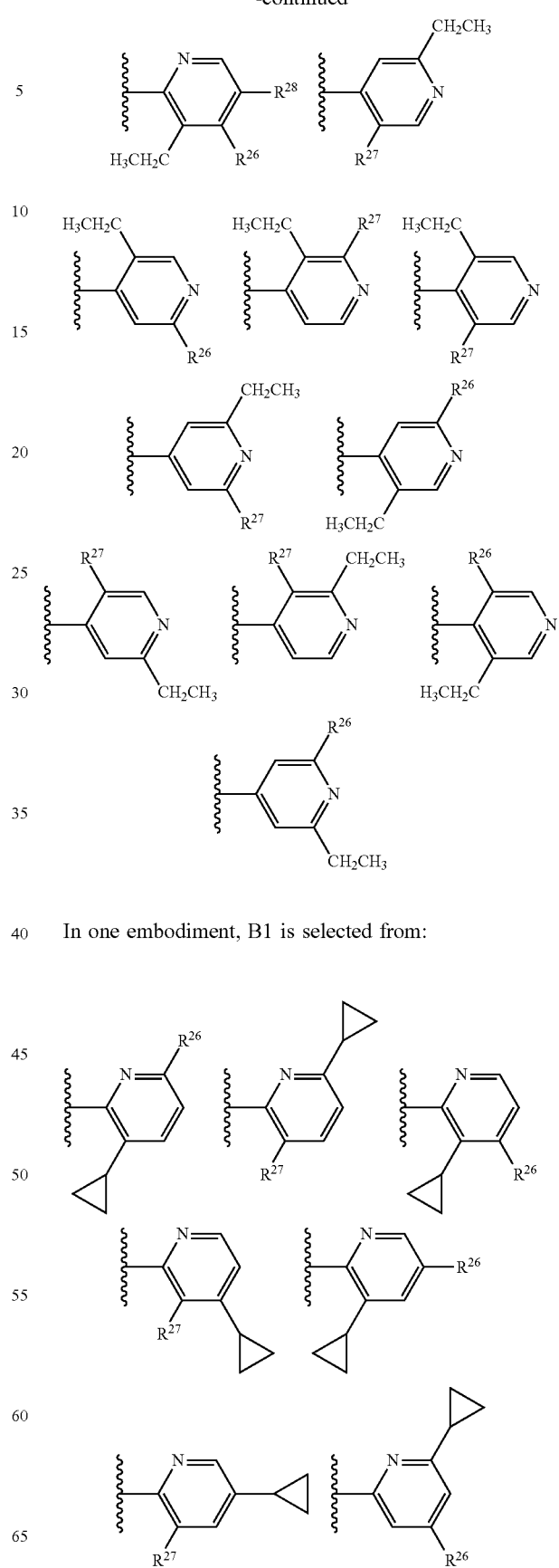
In one embodiment, B1 is selected from:
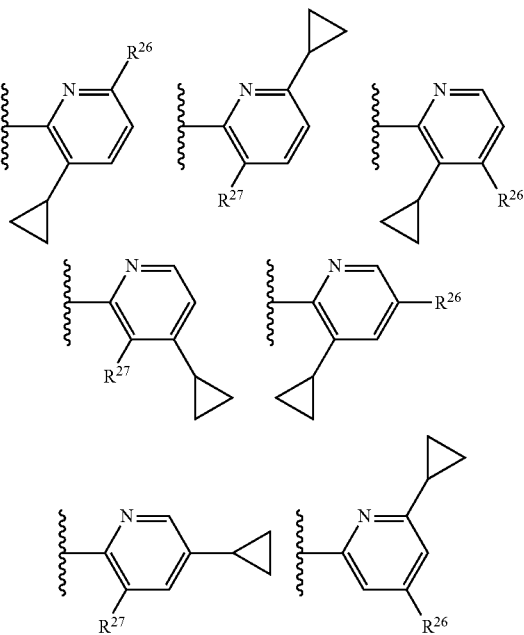

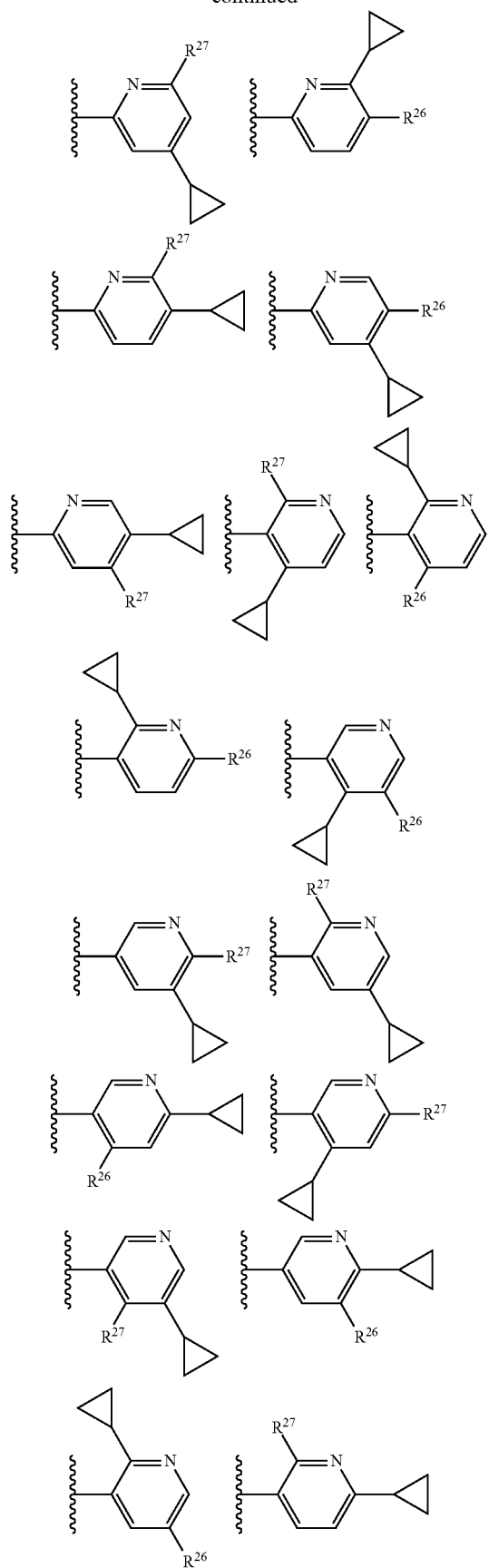
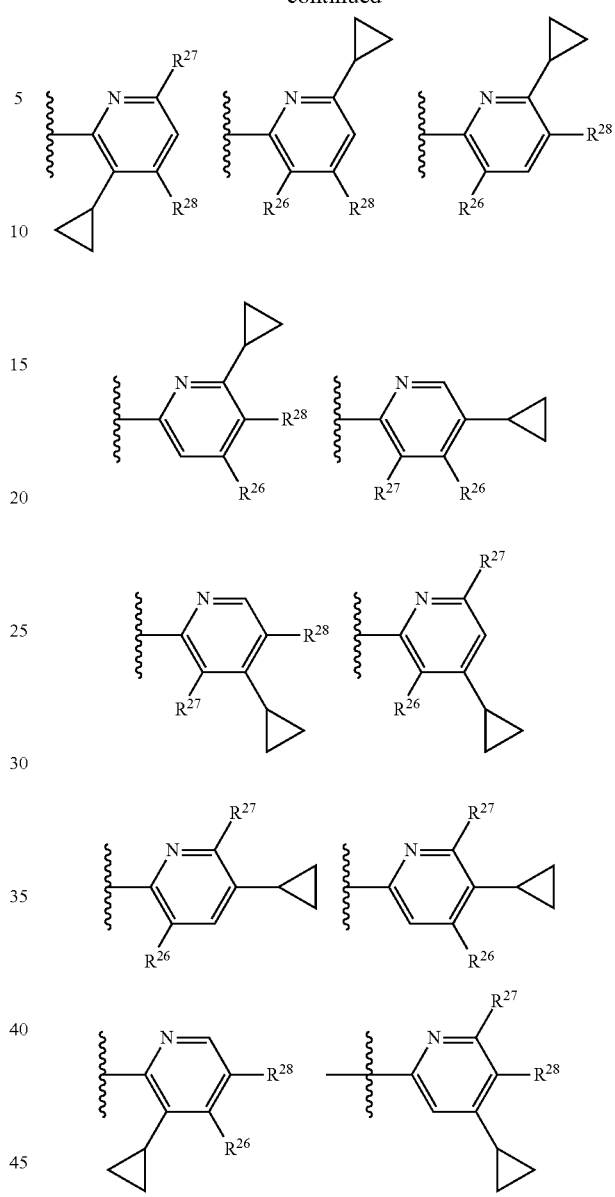
In one embodiment, B1 is selected from:
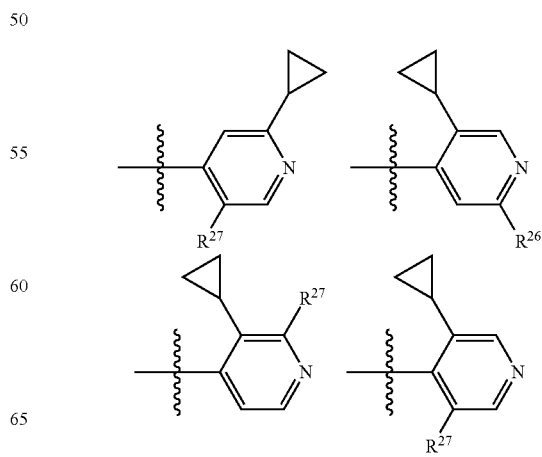

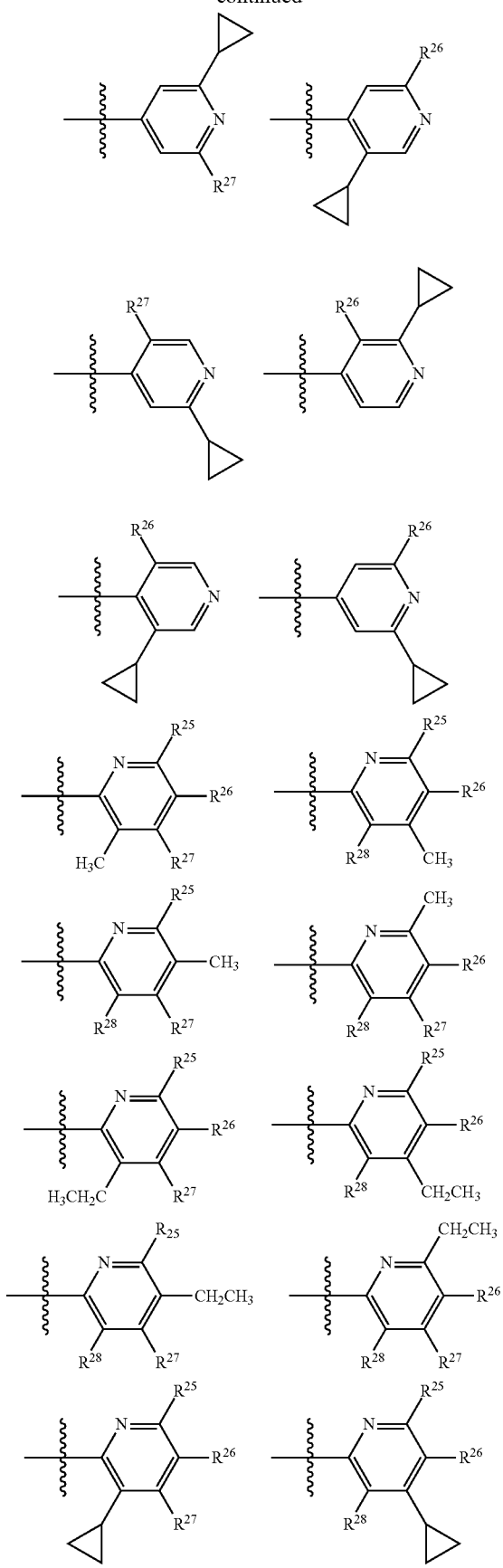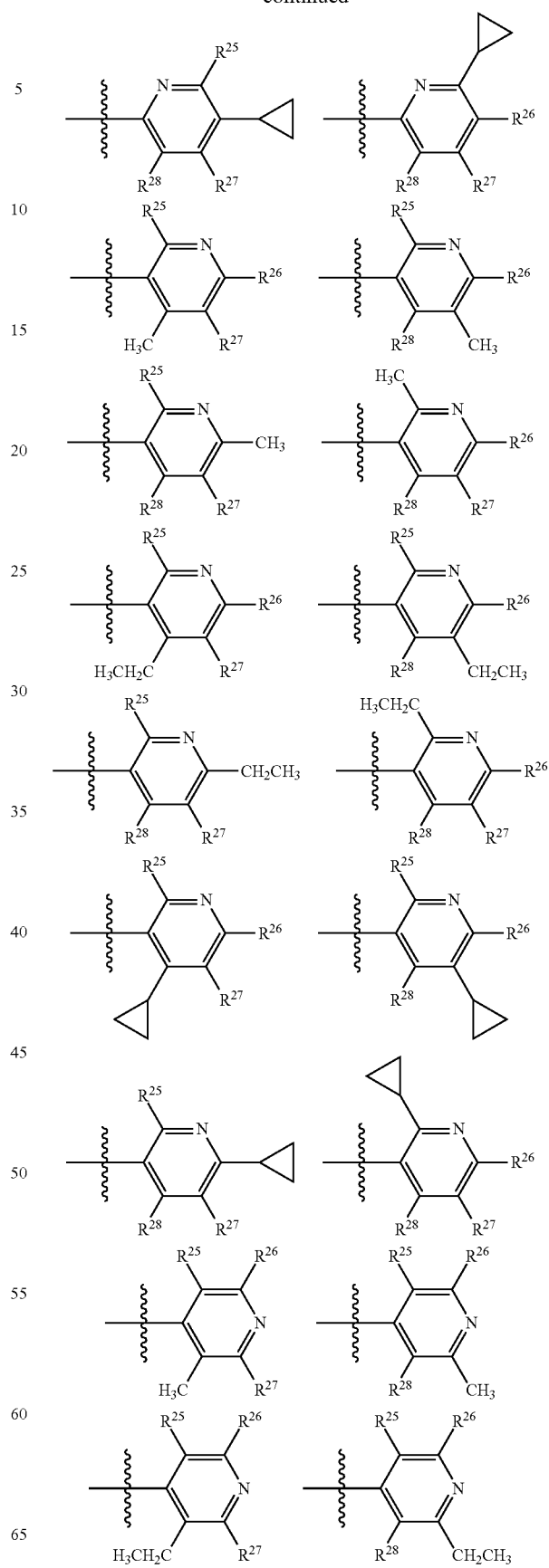

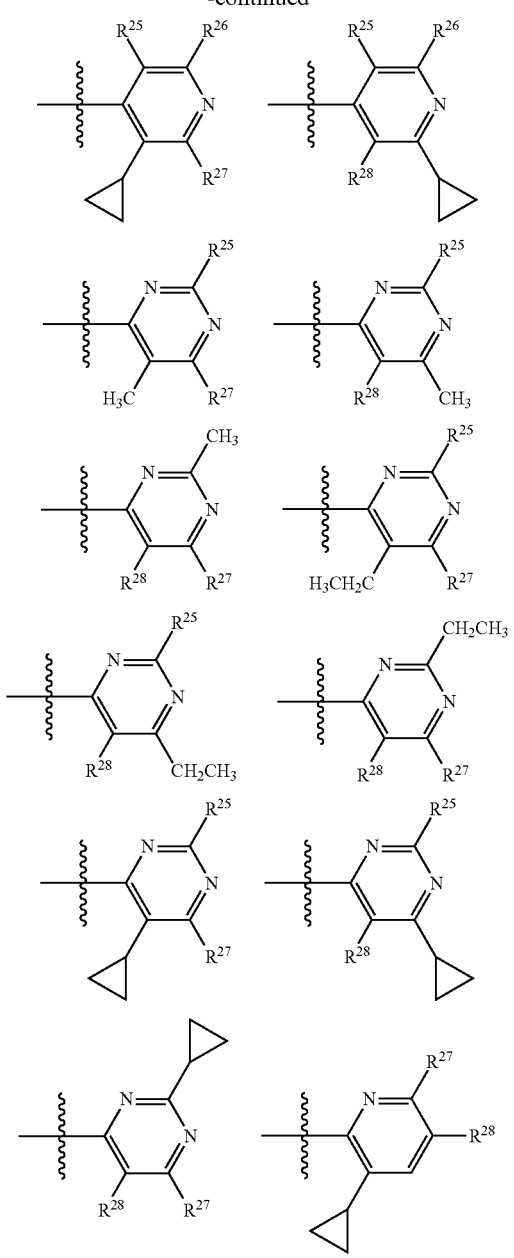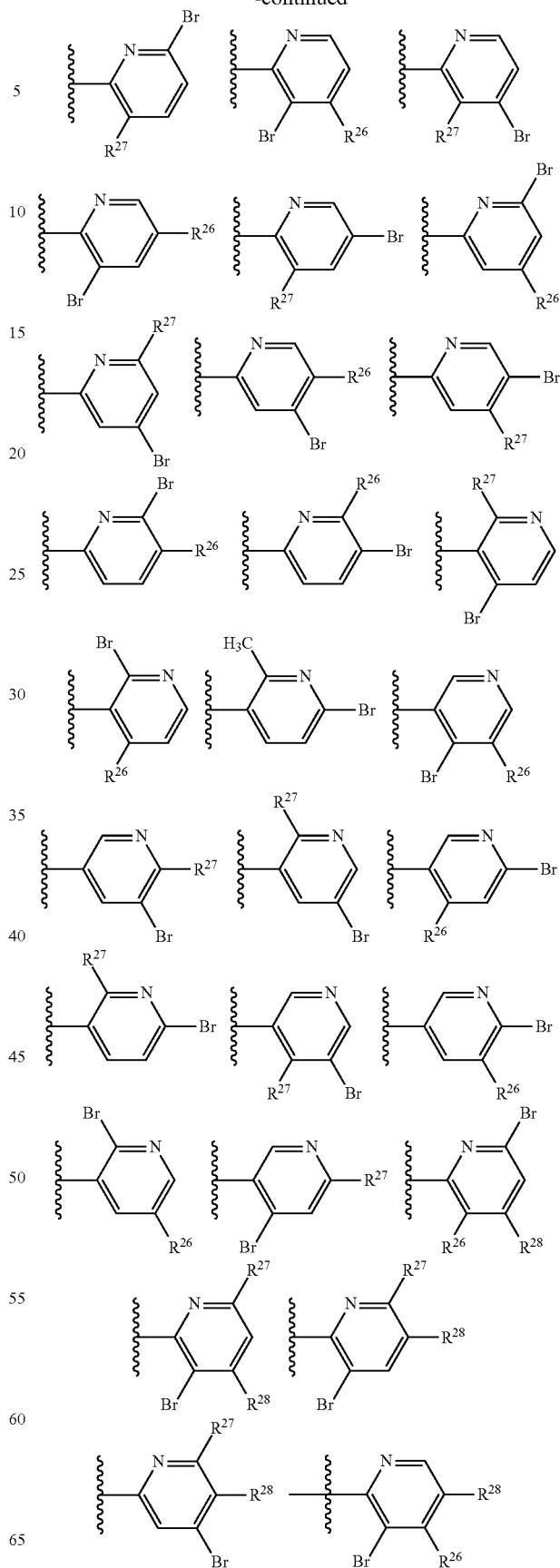
In one embodiment, B1 is selected from:

-continued
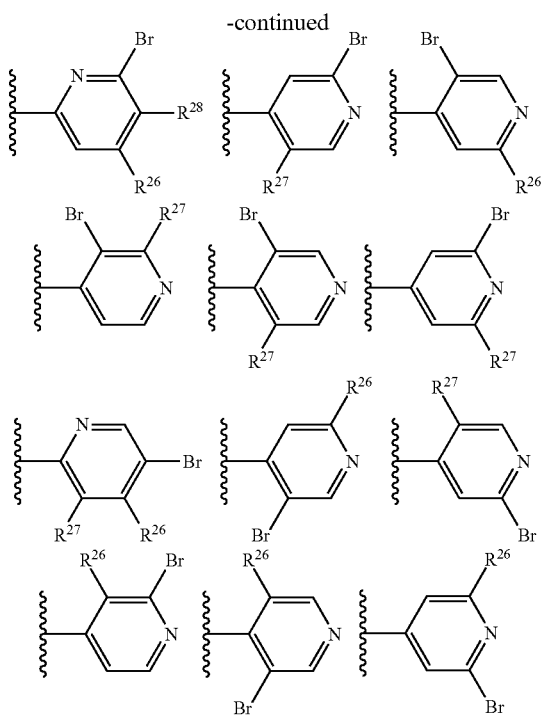
In one embodiment, B1 is selected from:
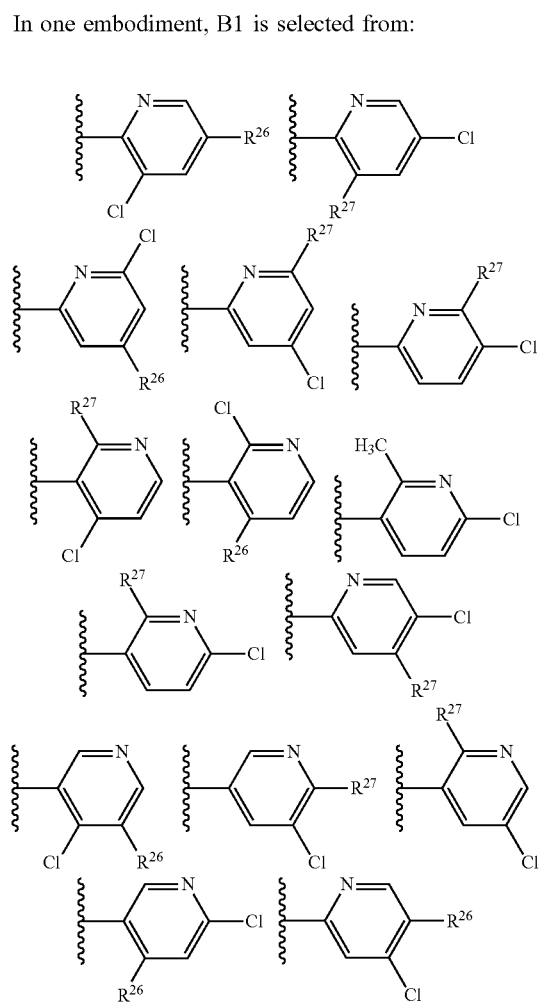
-continued
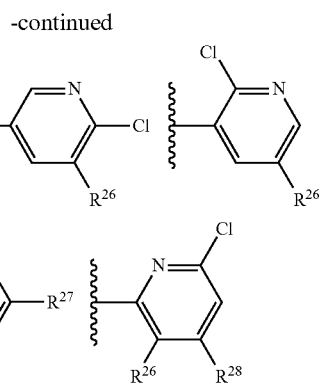
In one embodiment, B1 is selected from:
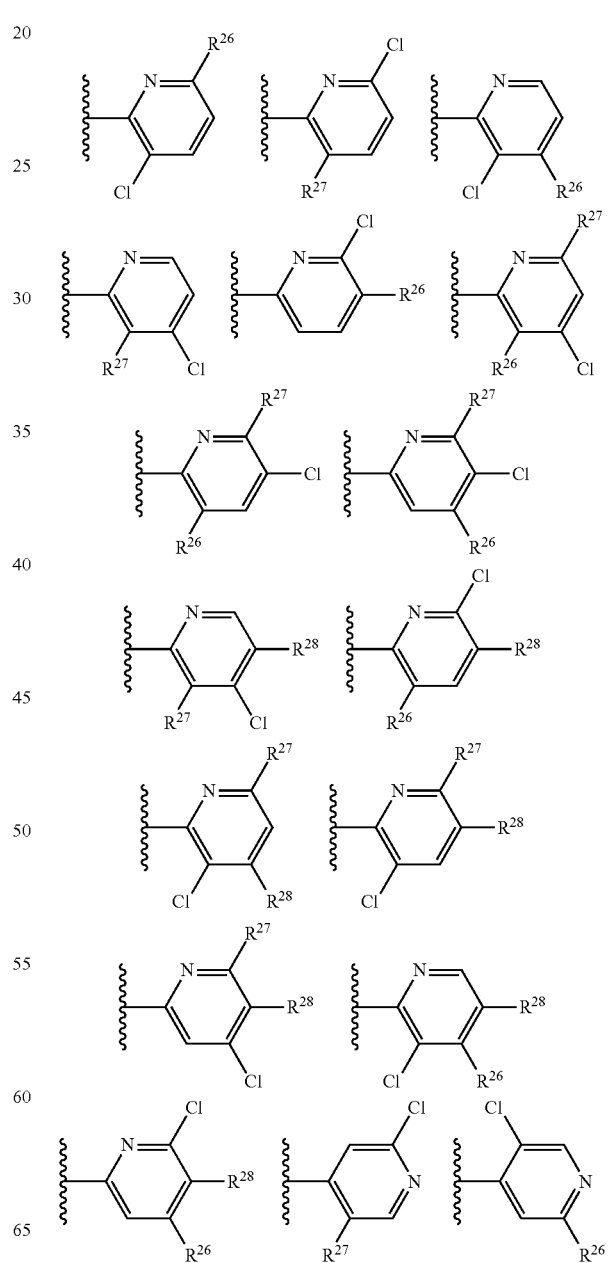

-continued
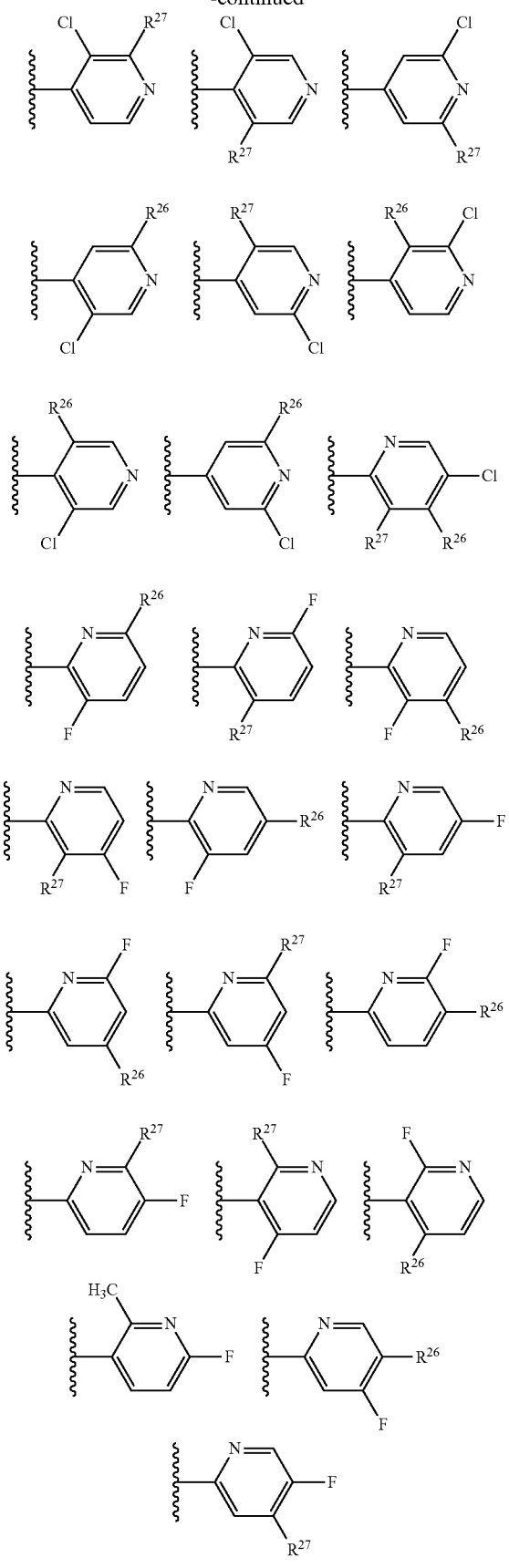
In one embodiment, B1 is selected from:
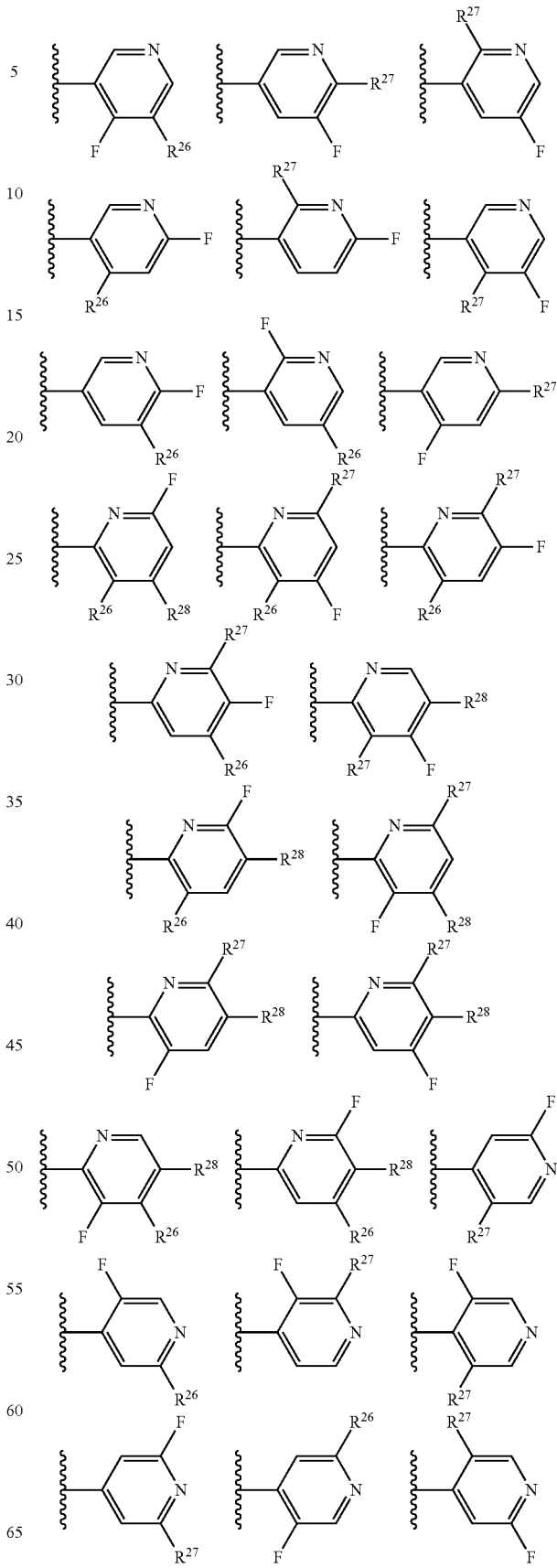

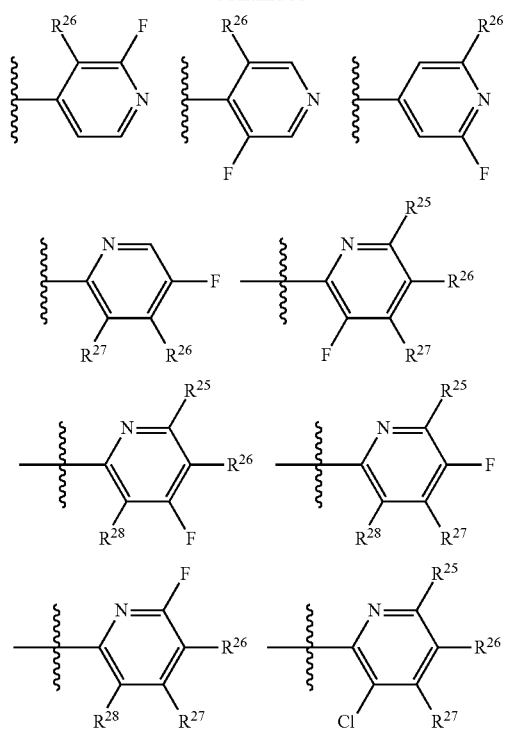
In one embodiment, B1 is selected from:
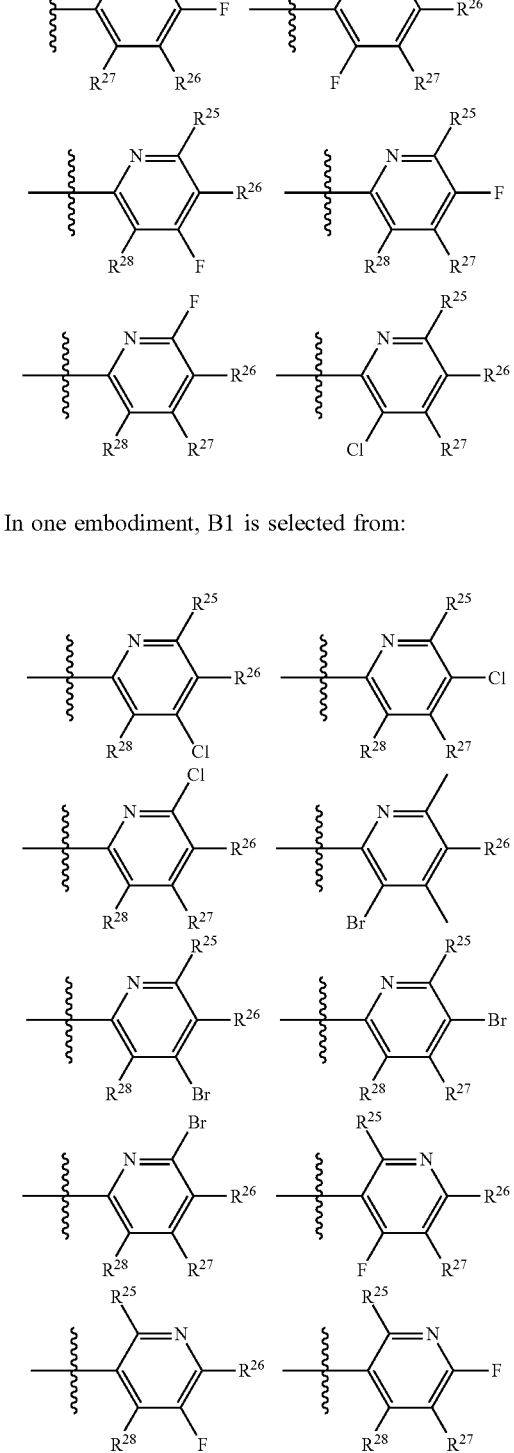
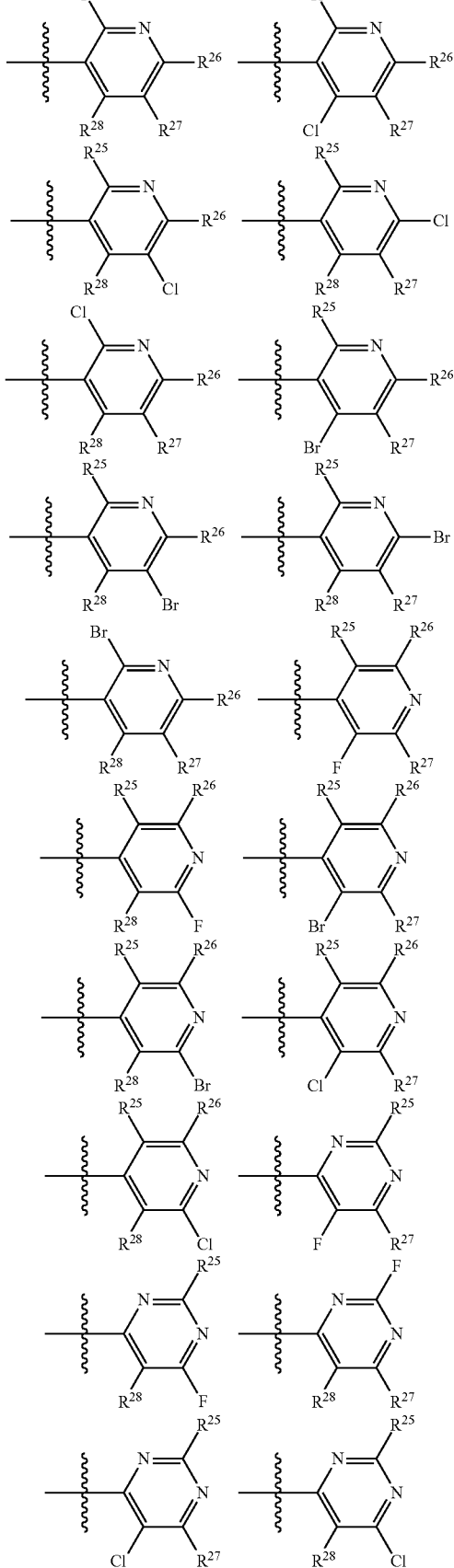

-continued
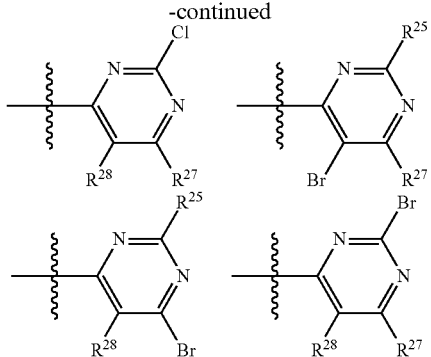
In one embodiment, B1 is selected from:
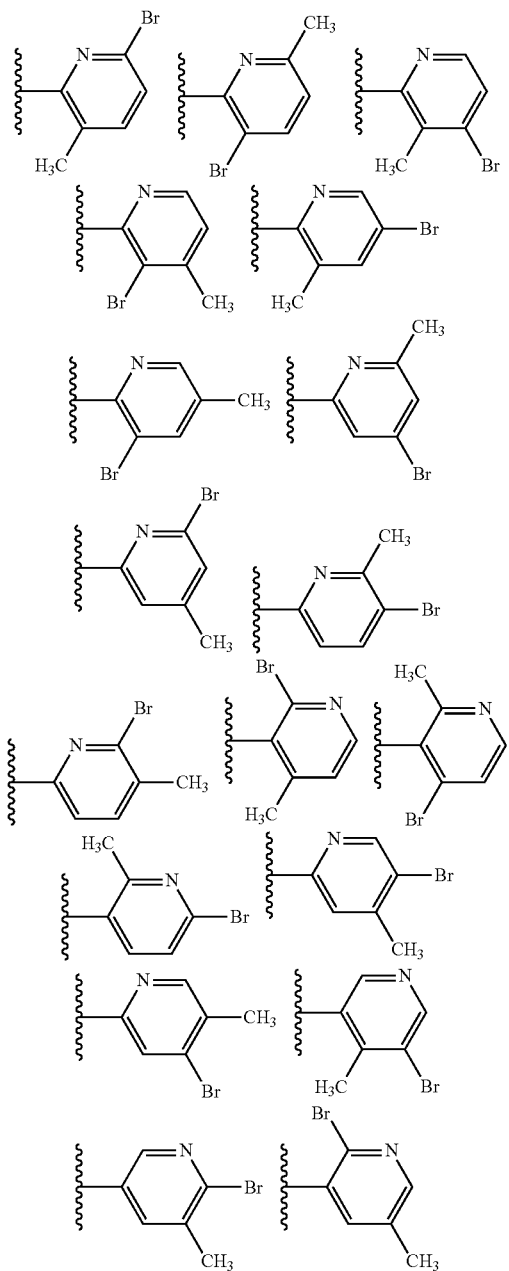
-continued
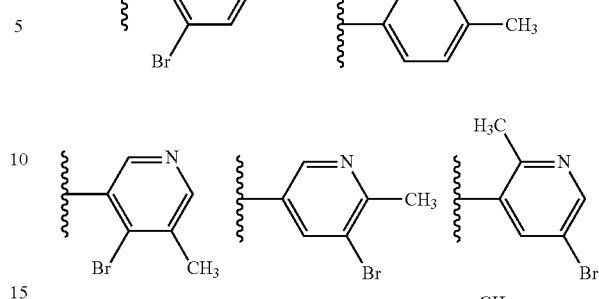
In one embodiment, B1 is selected from:
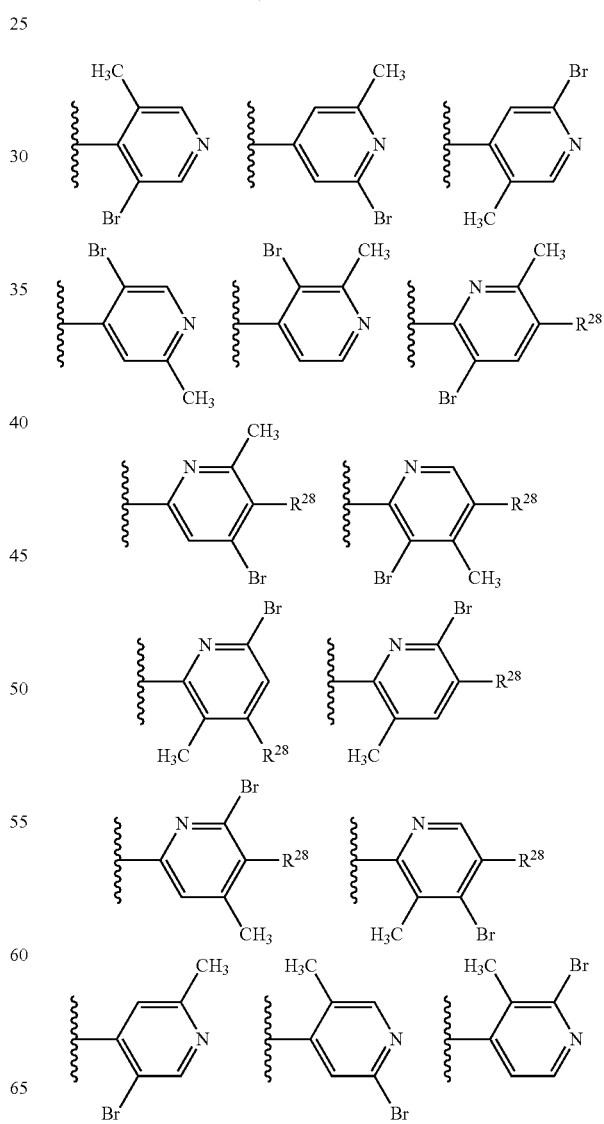

-continued
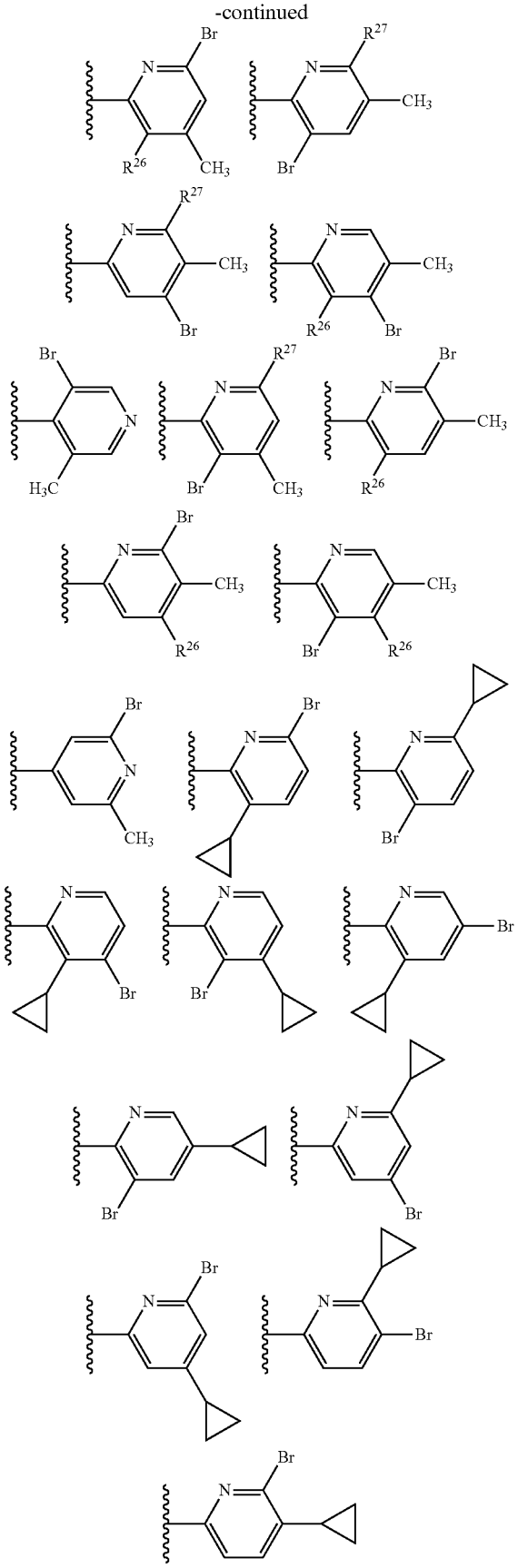
In one embodiment B1 is selected from:
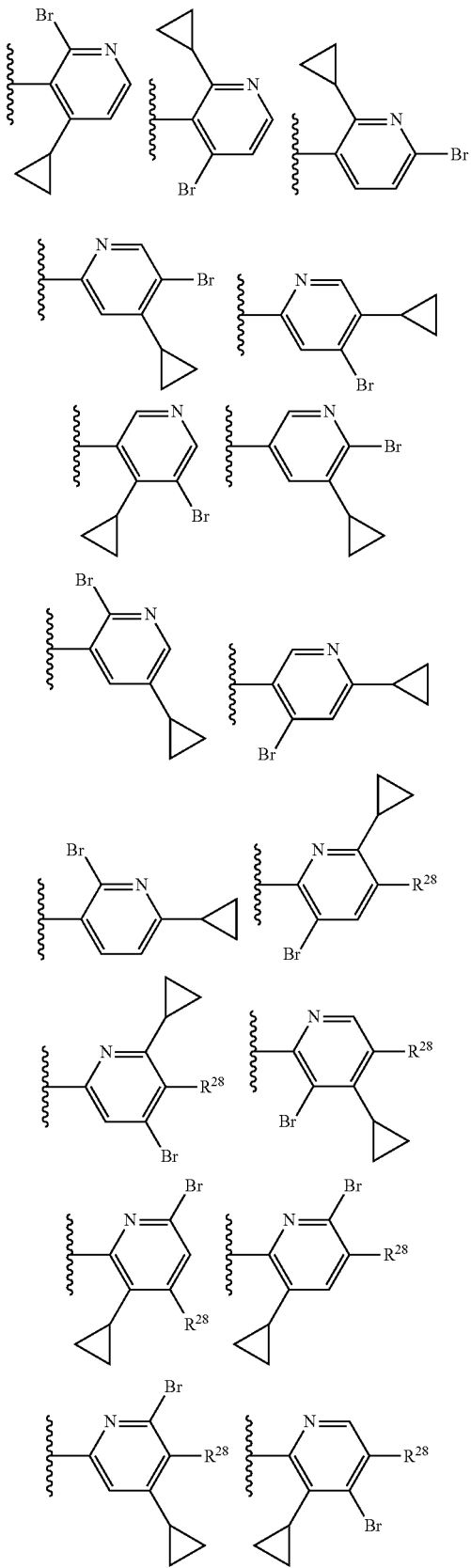

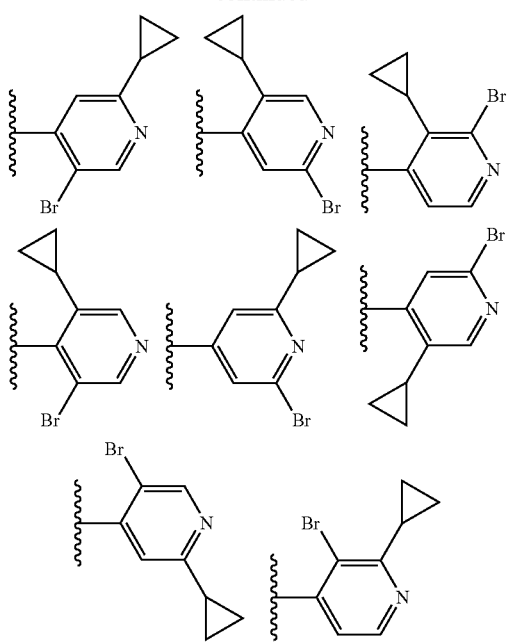
In one embodiment, B1 is selected from:
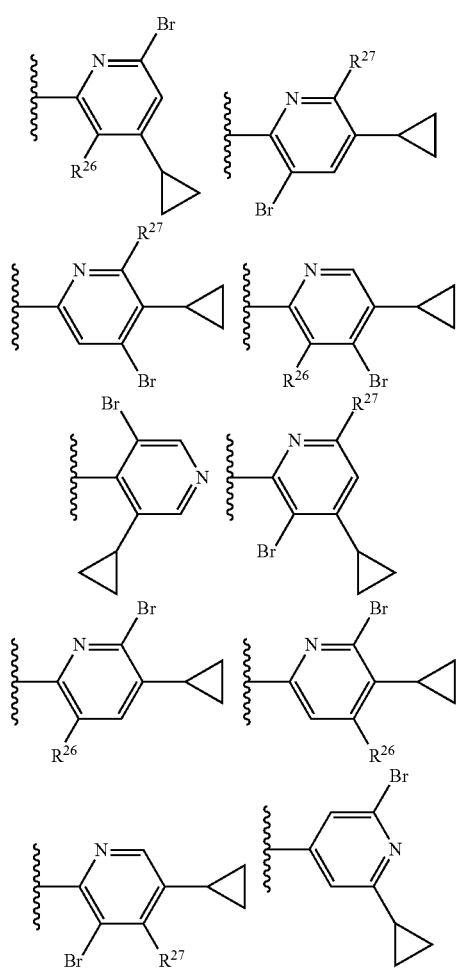
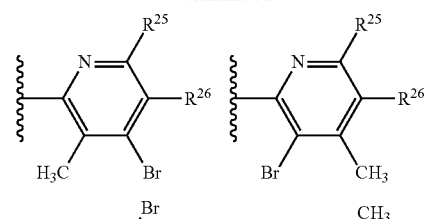
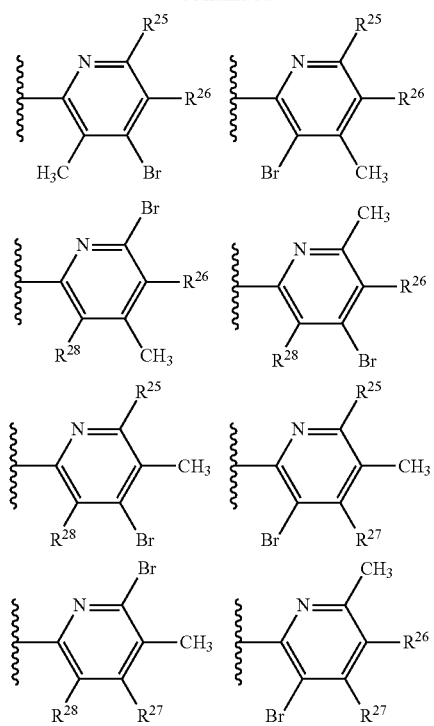

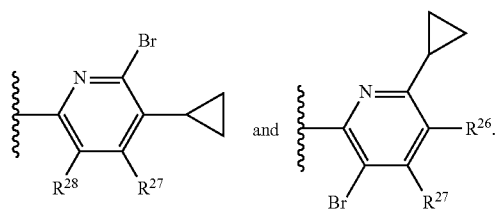
In one embodiment, B1 is selected from:
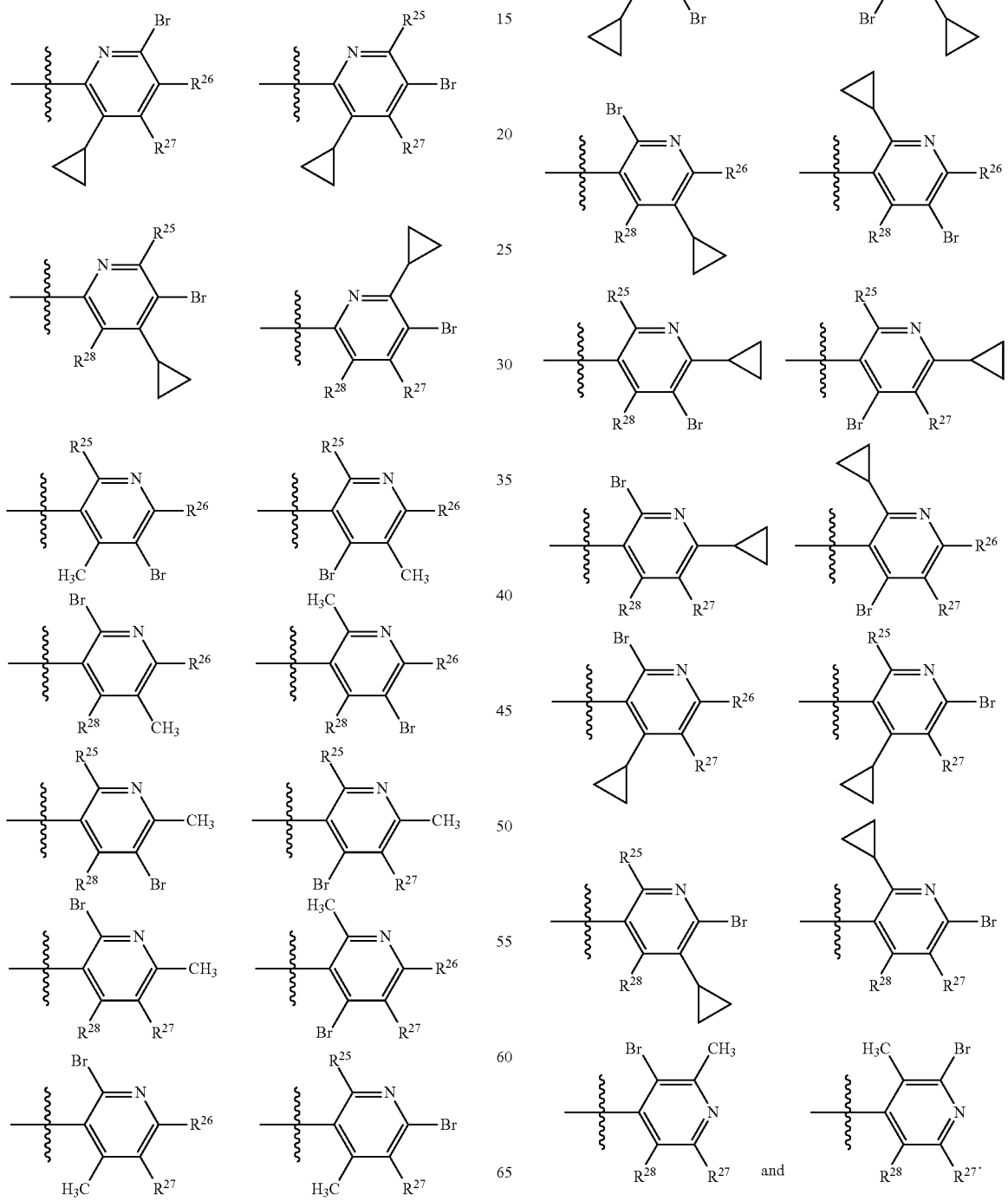

In one embodiment, B1 is selected from:
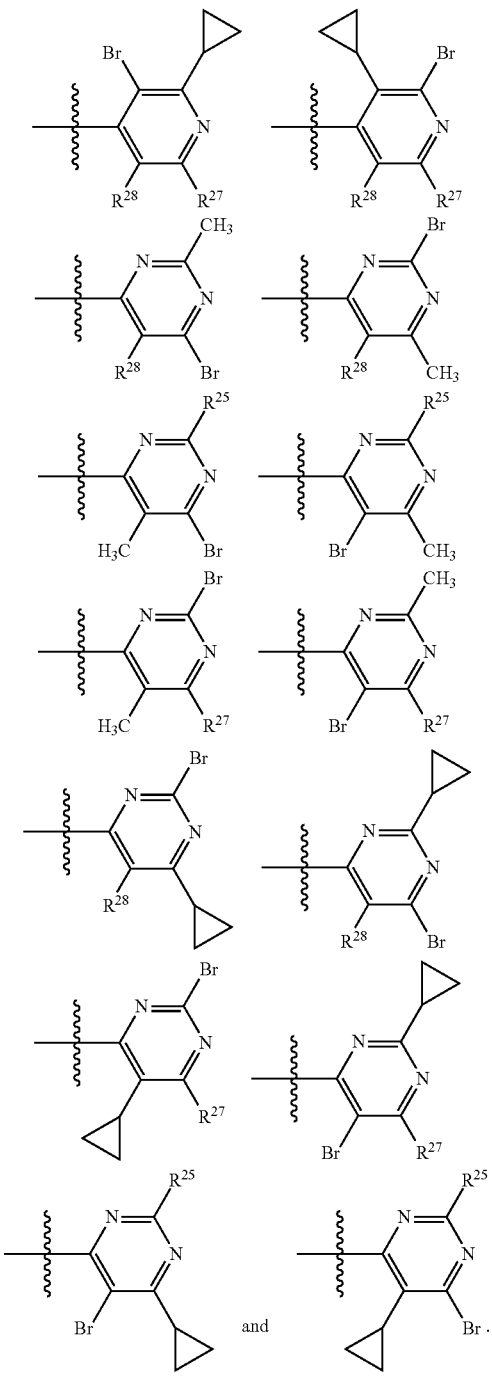
In one embodiment B1 is selected from:
-continued
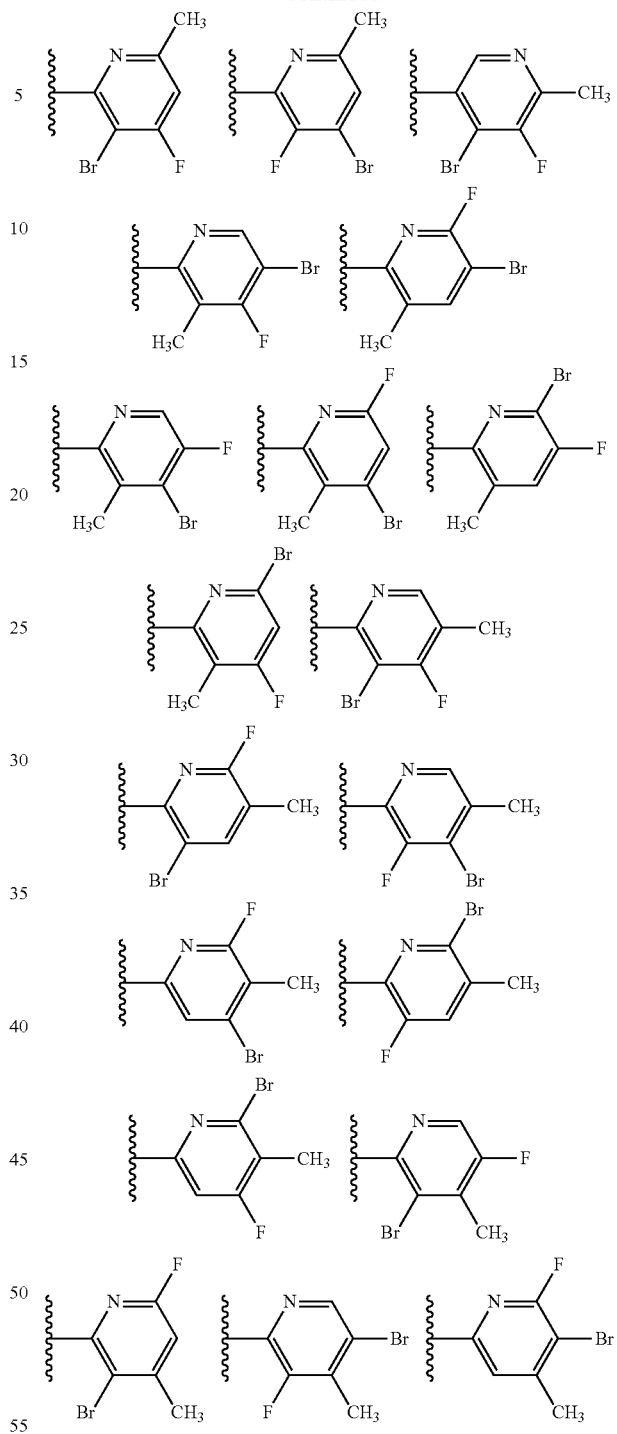
In one embodiment, B1 is selected from:
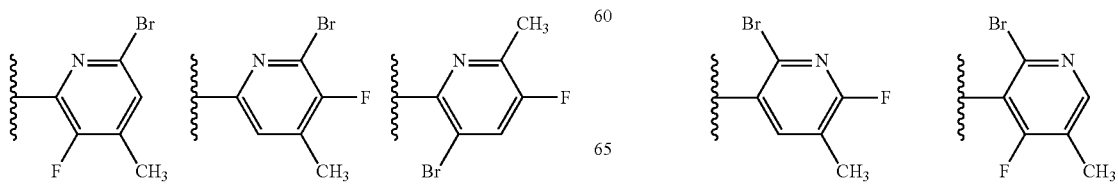

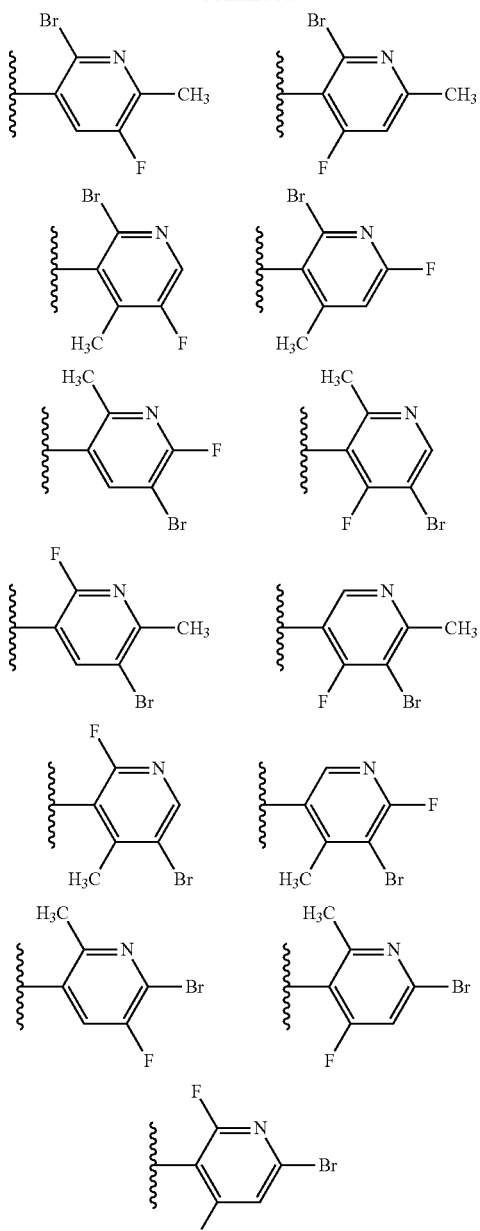
In one embodiment, B1 is selected from:
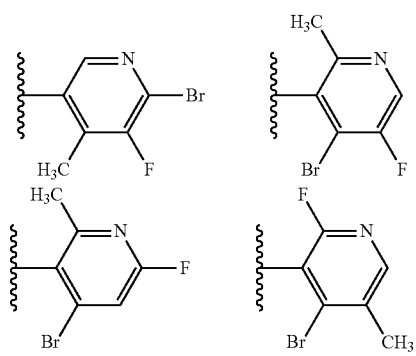
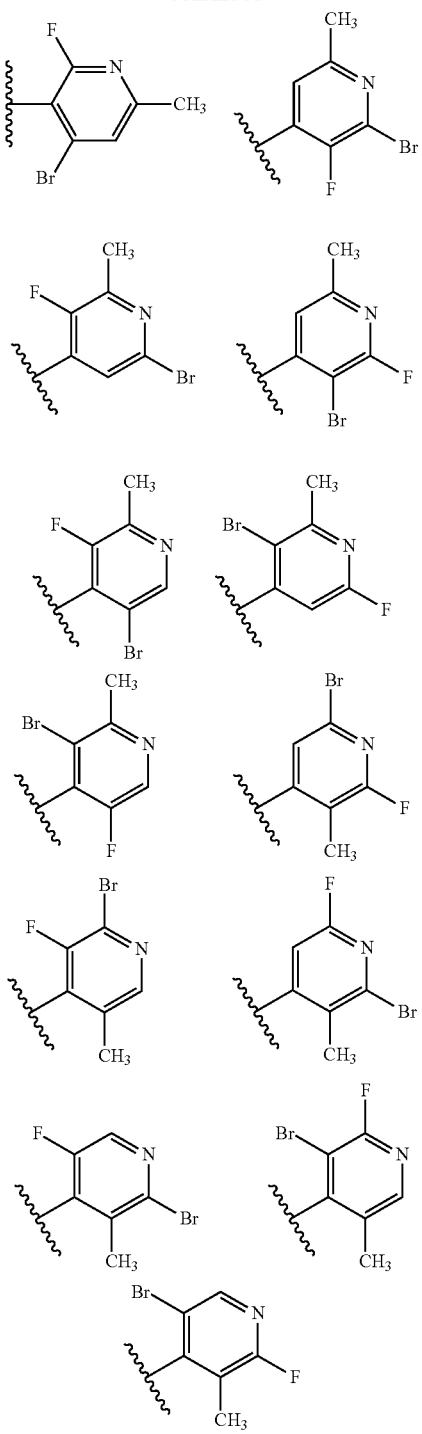
In one embodiment, B1 is selected from:
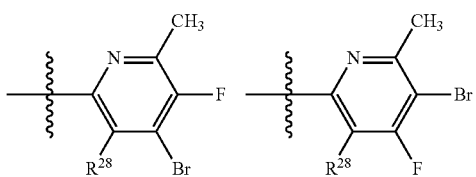

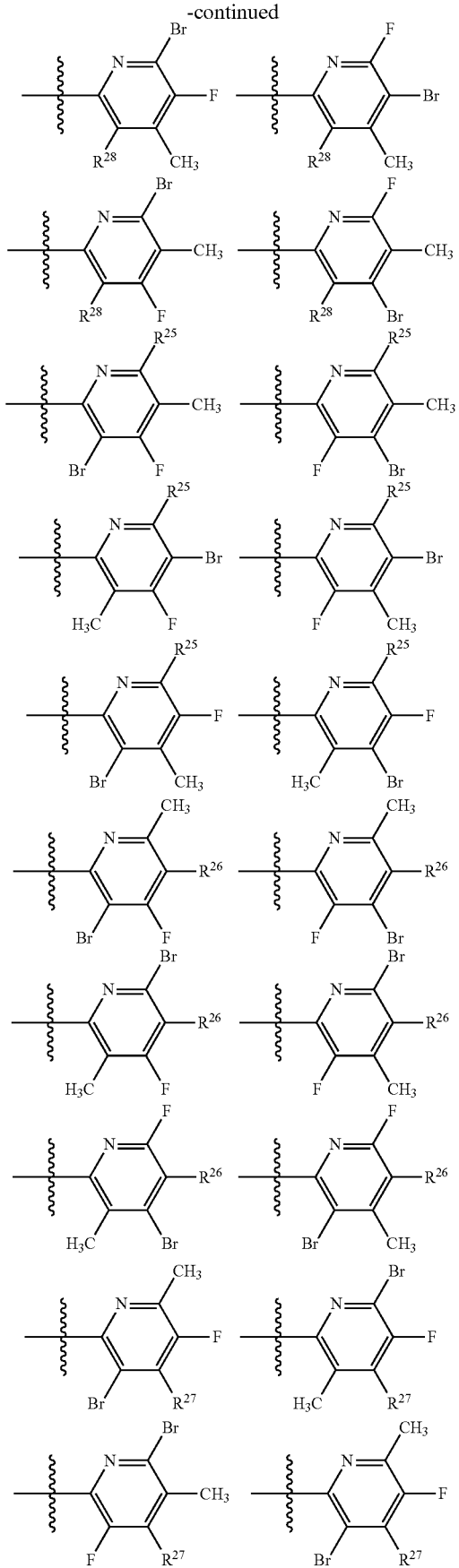
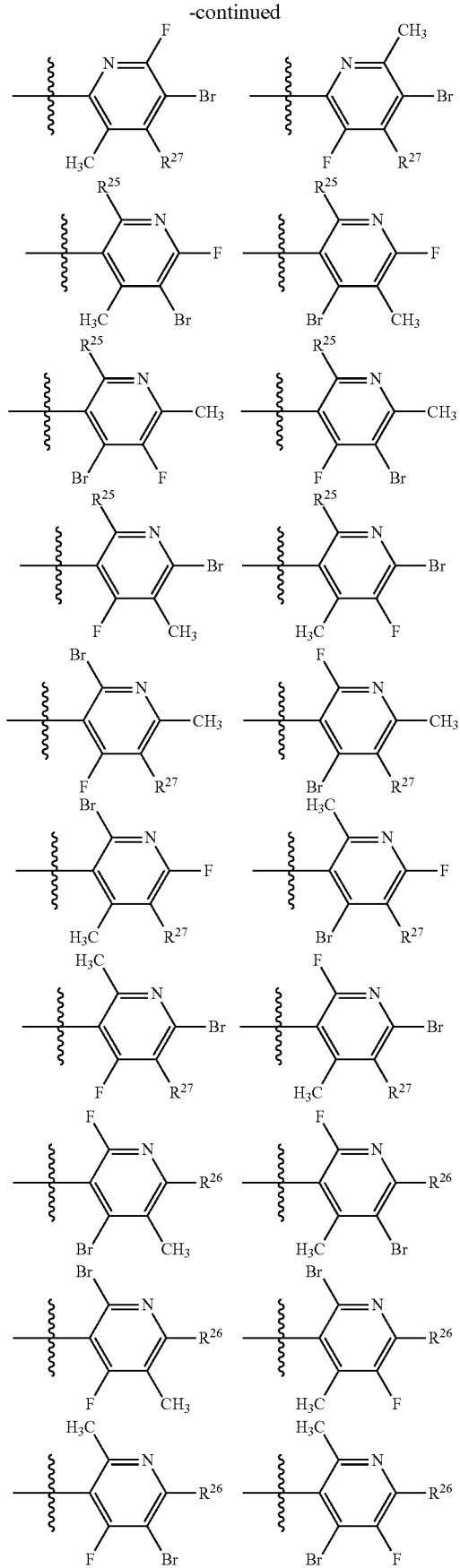

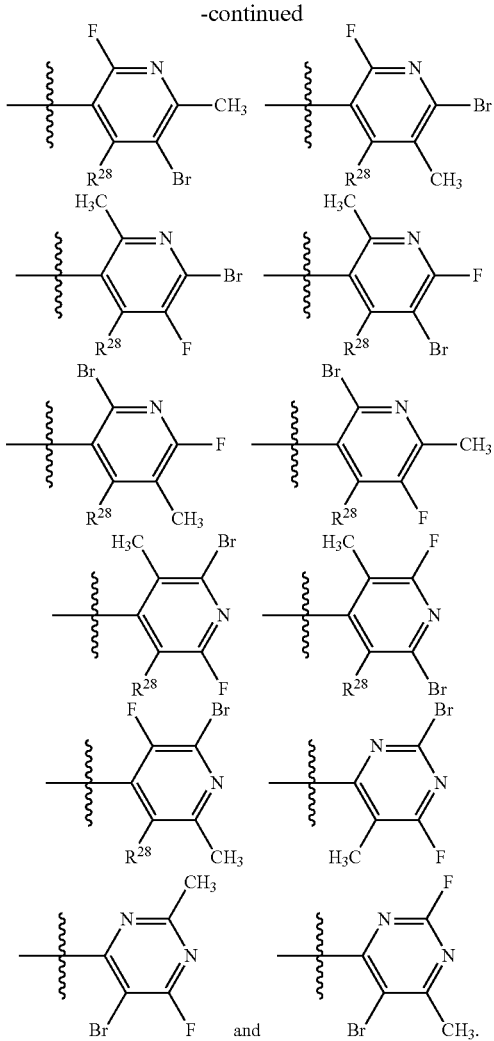
In one embodiment, B1 is selected from:
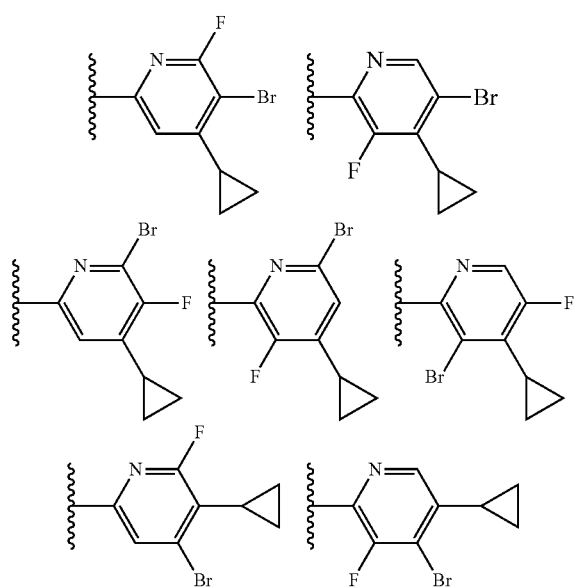
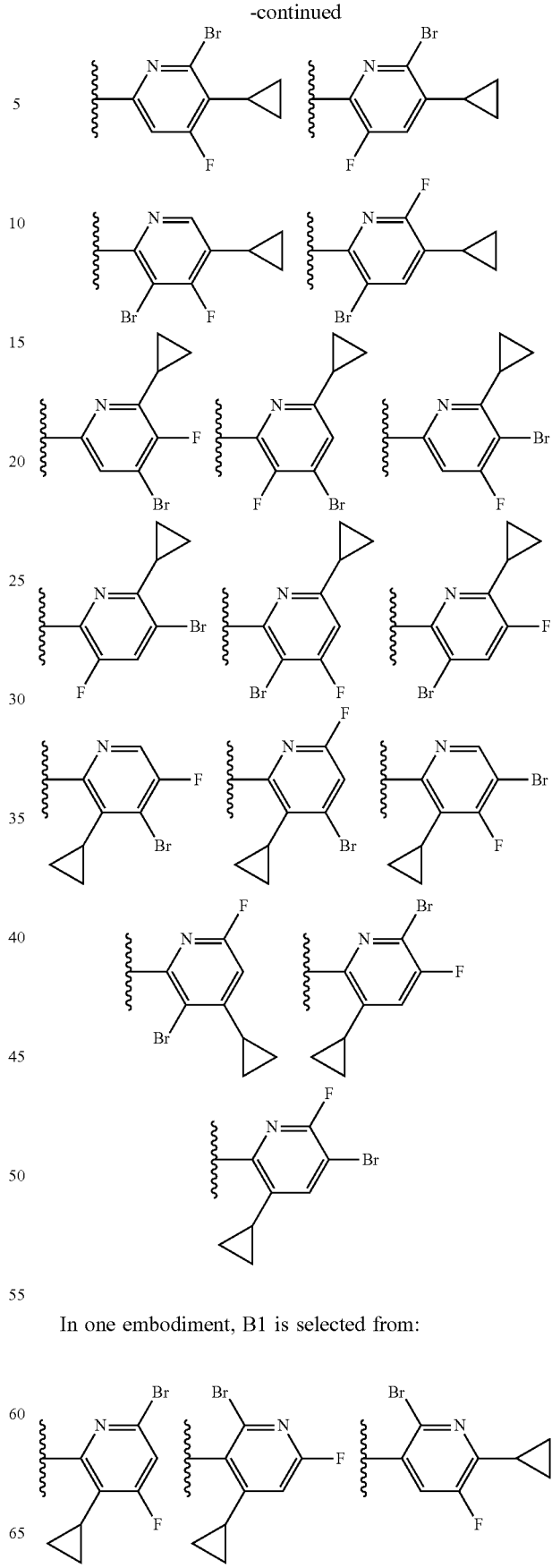
In one embodiment, B1 is selected from:

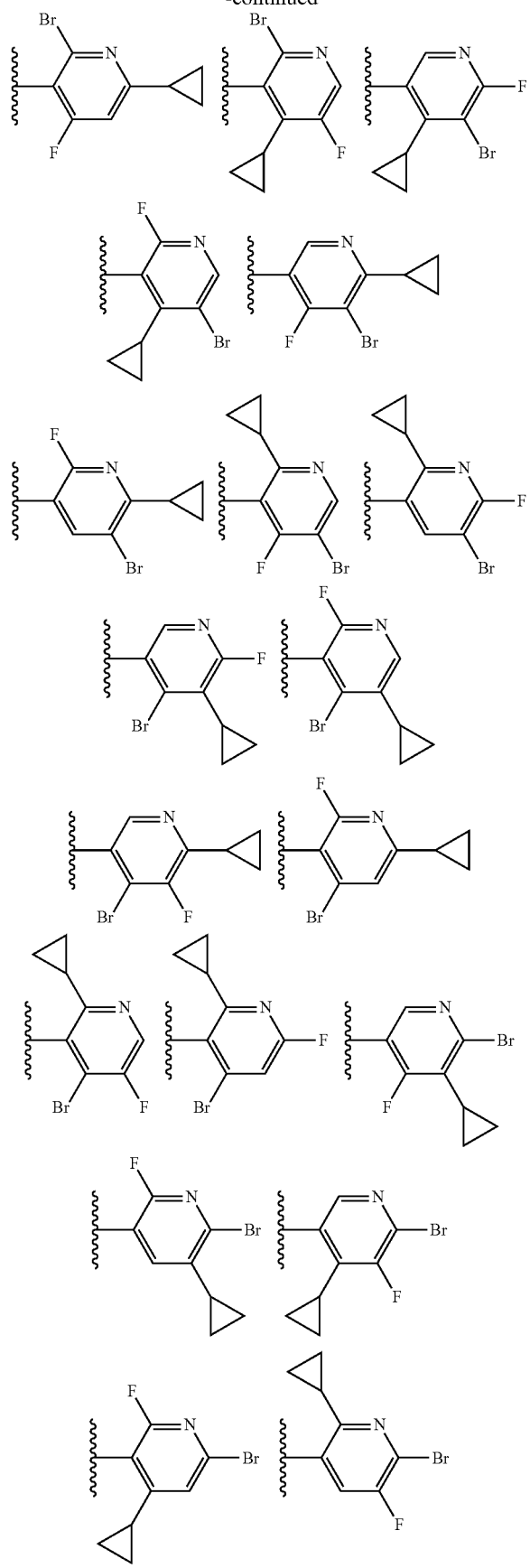
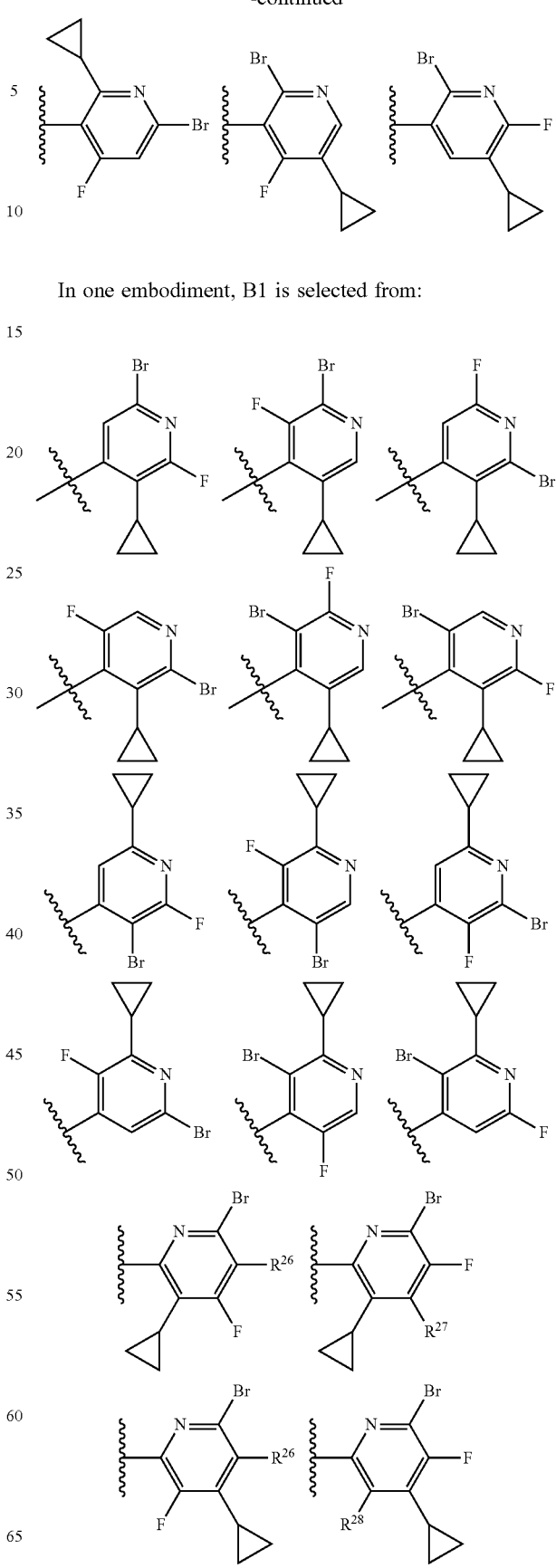
In one embodiment, B1 is selected from:

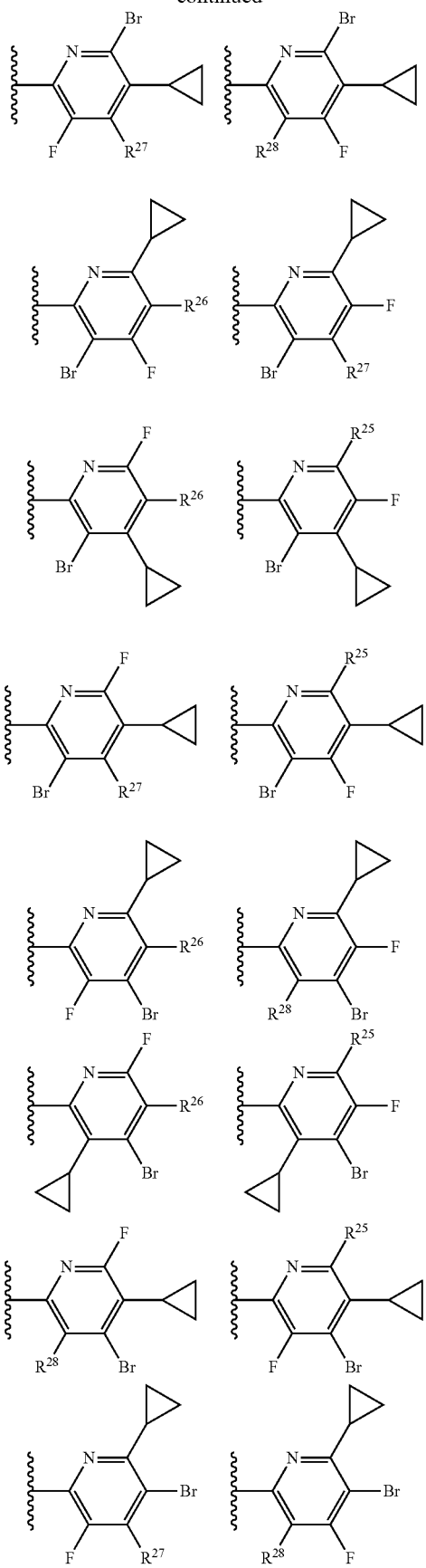
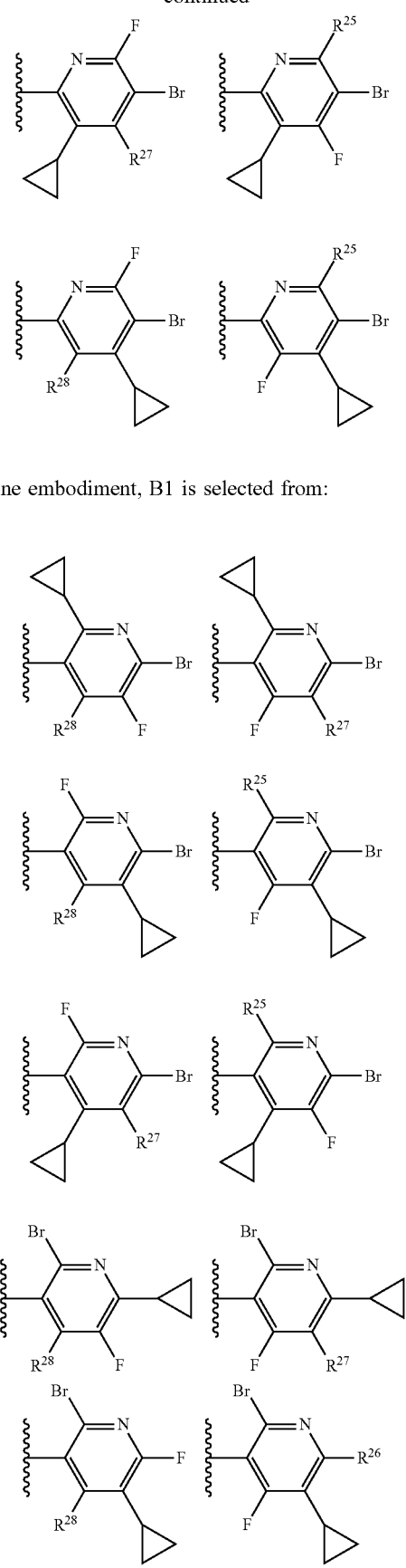
In one embodiment, B1 is selected from:

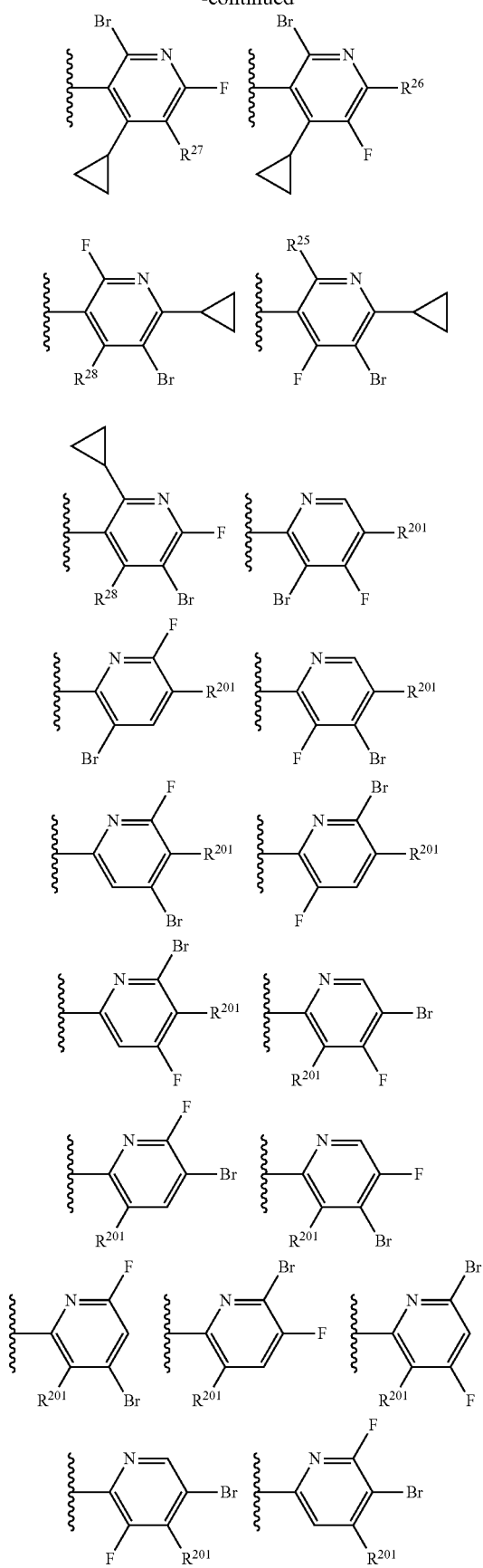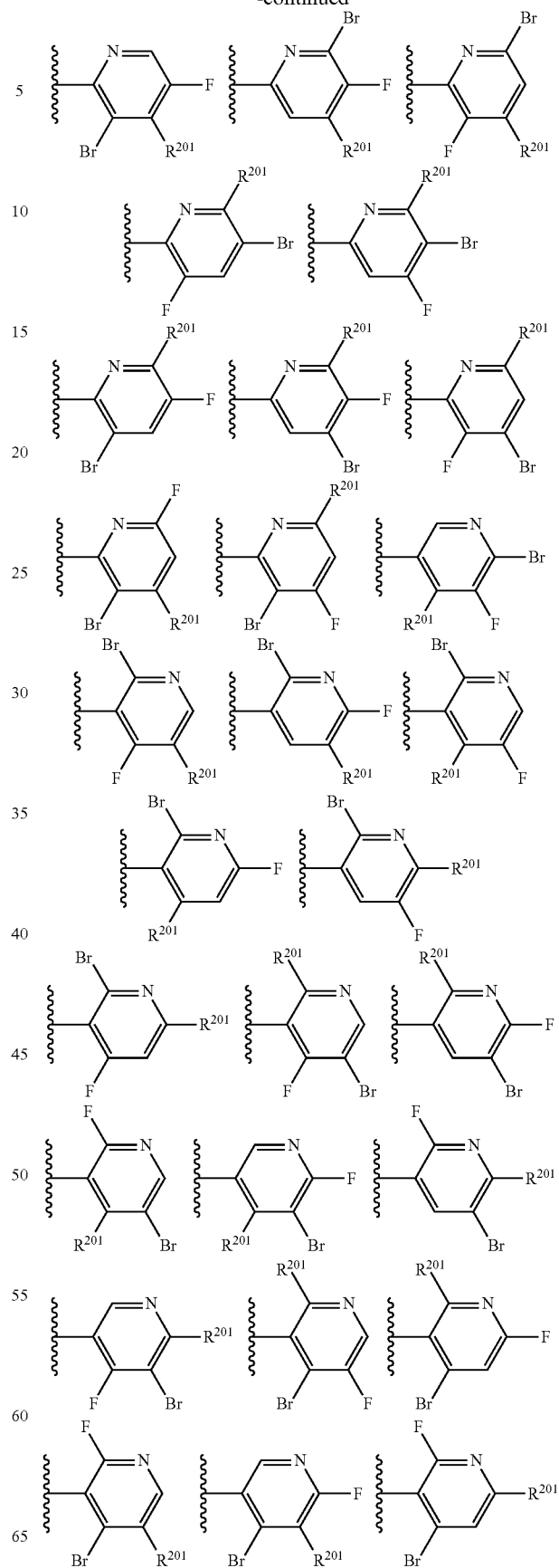

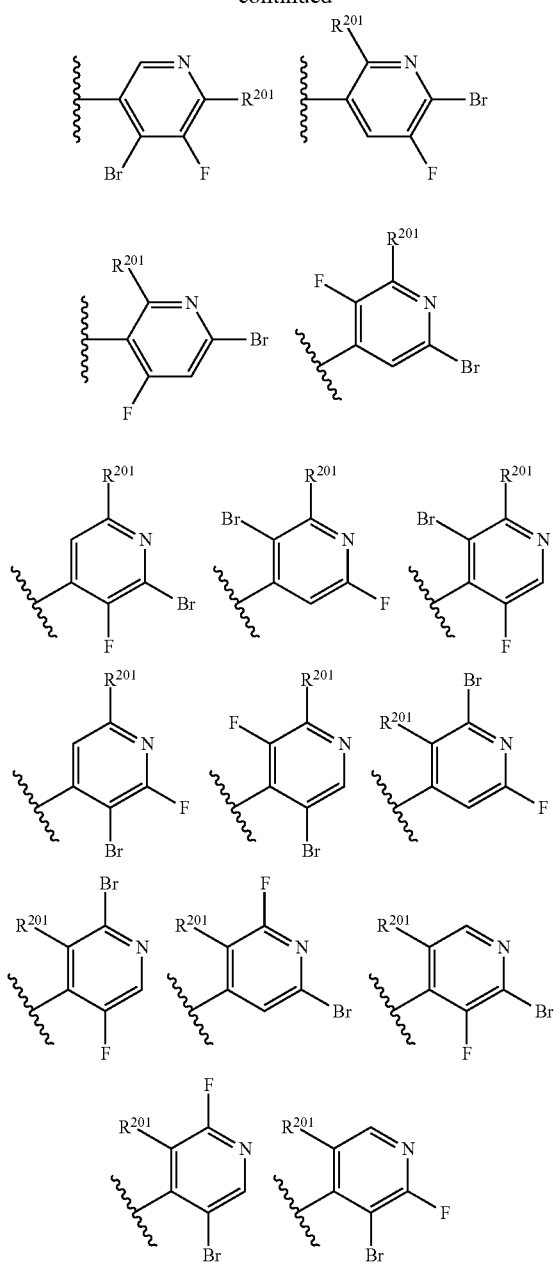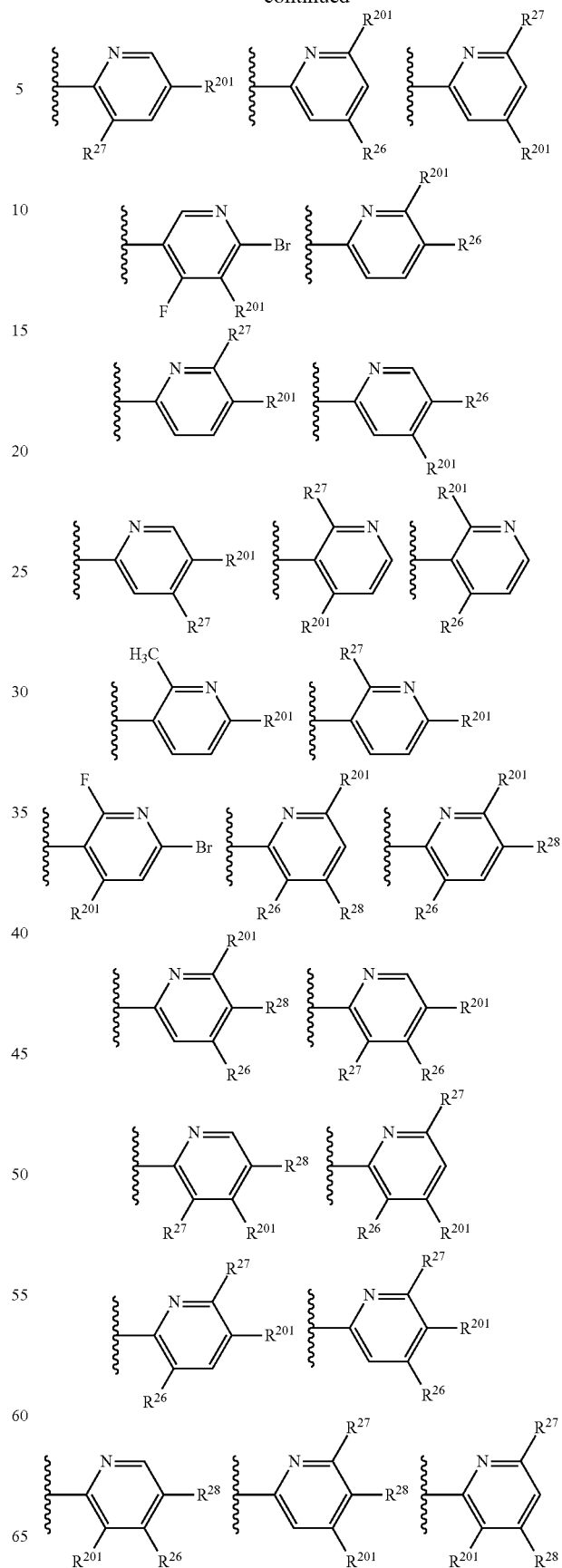
In one embodiment, B1 is selected from:
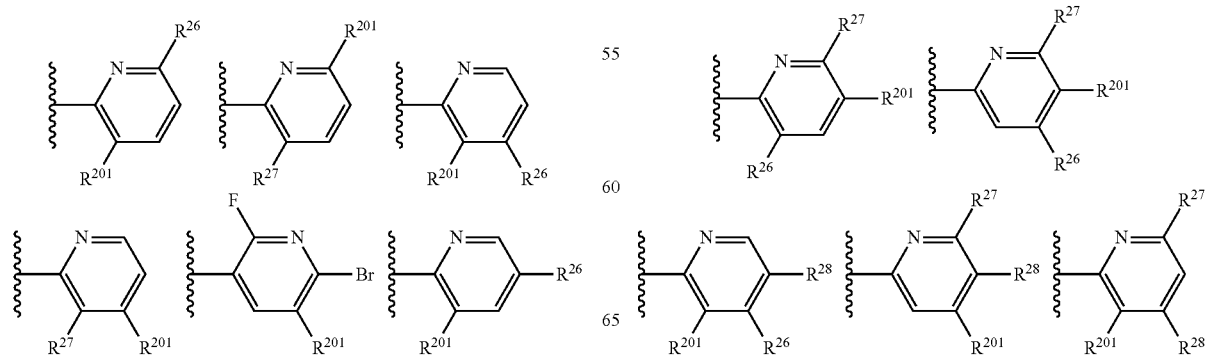

-continued
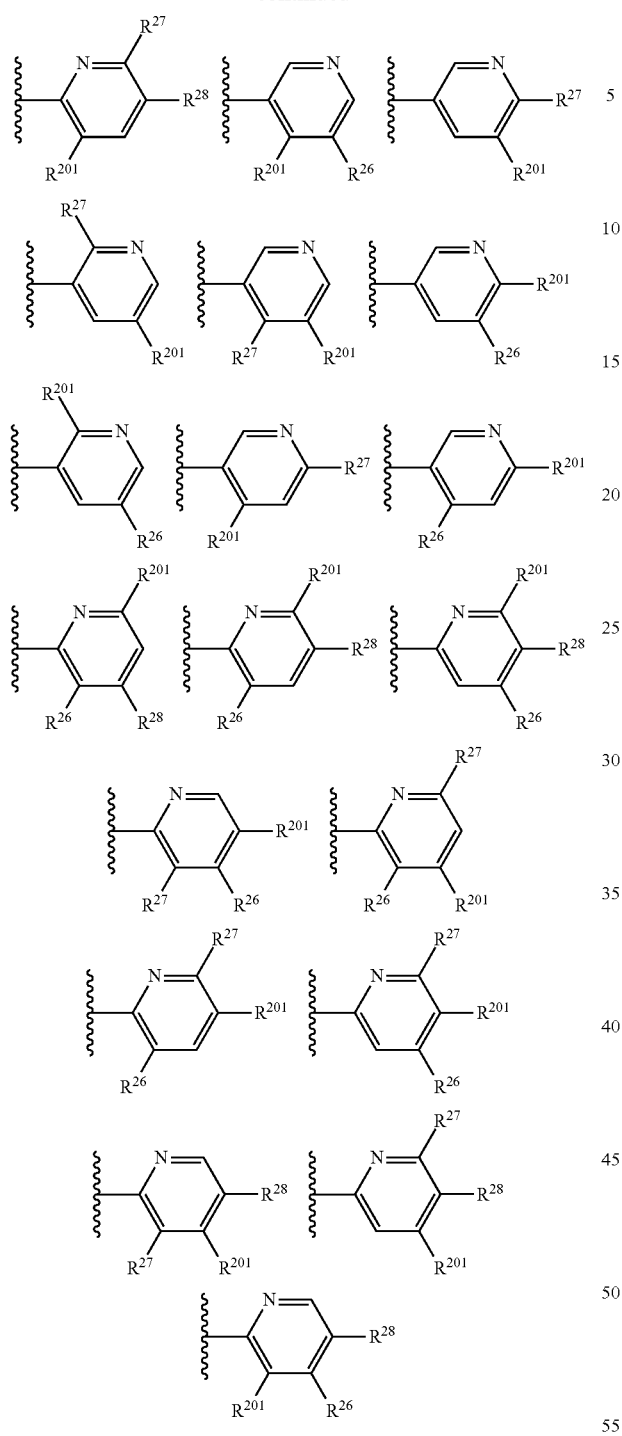
In one embodiment, B1 is selected from:
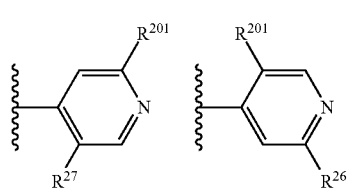
-continued
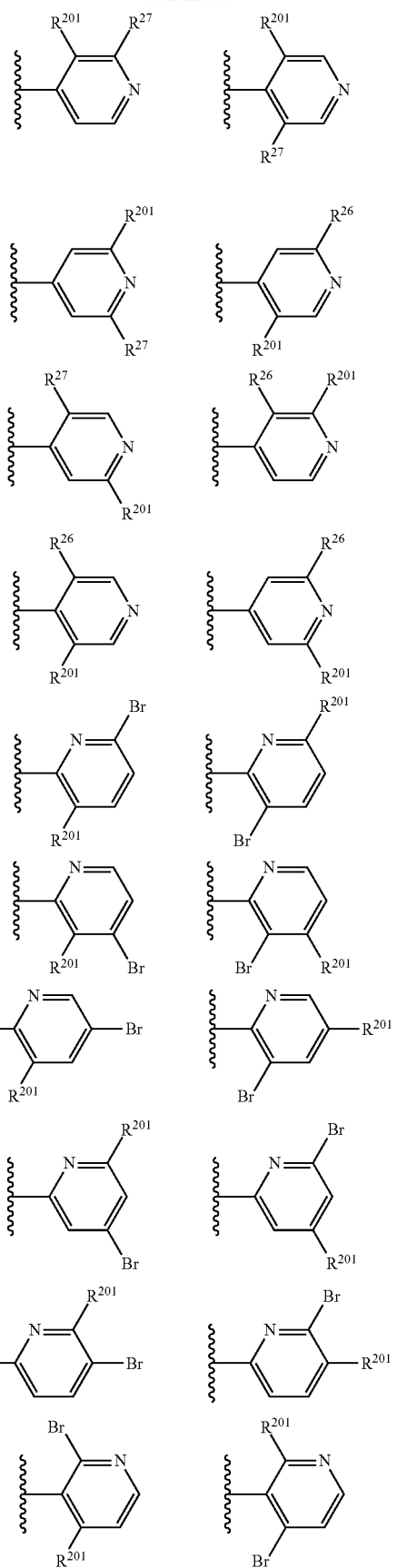

-continued
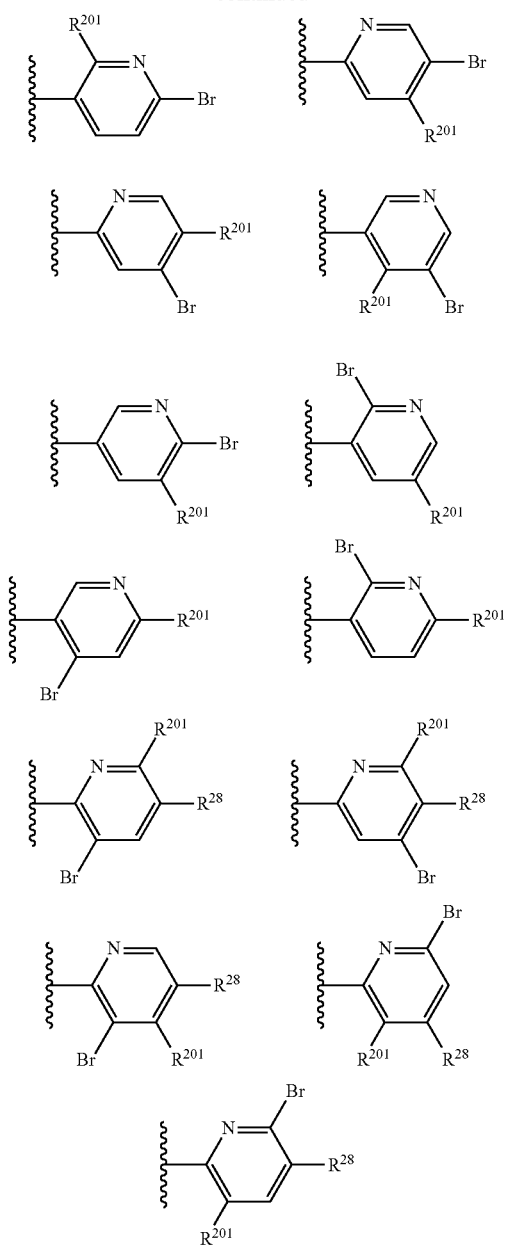
In one embodiment, B1 is selected from:
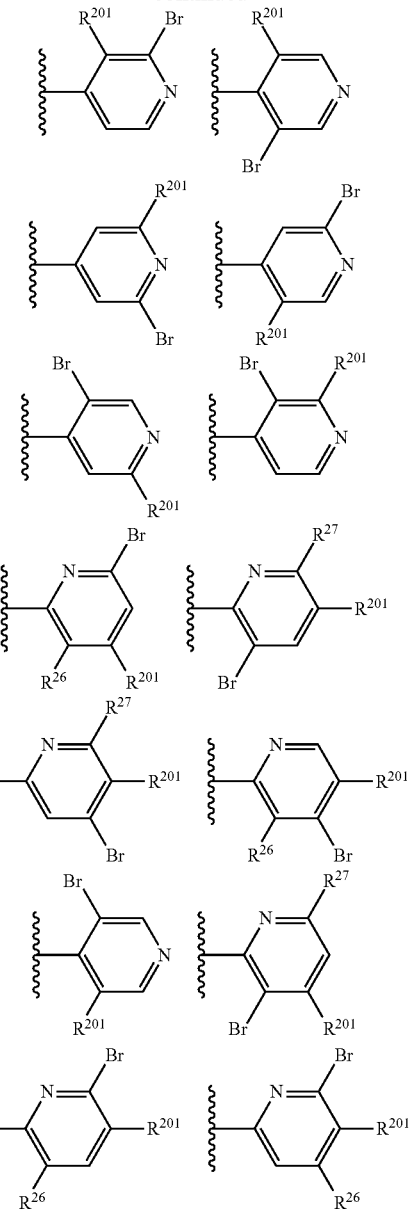
-continued
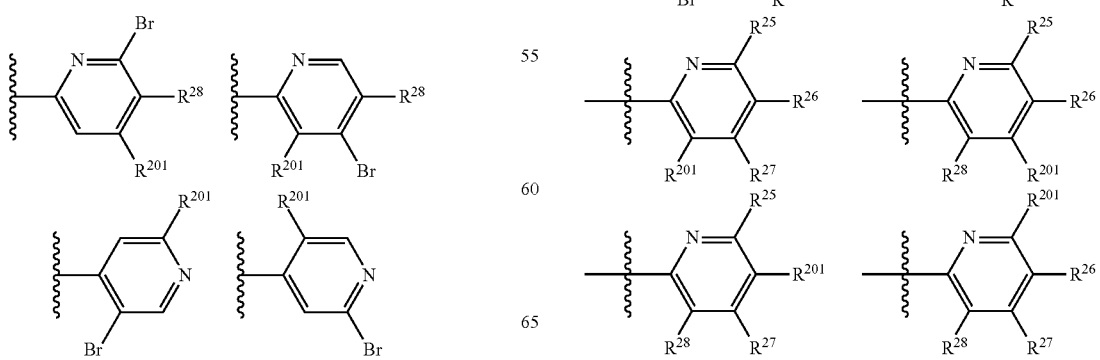

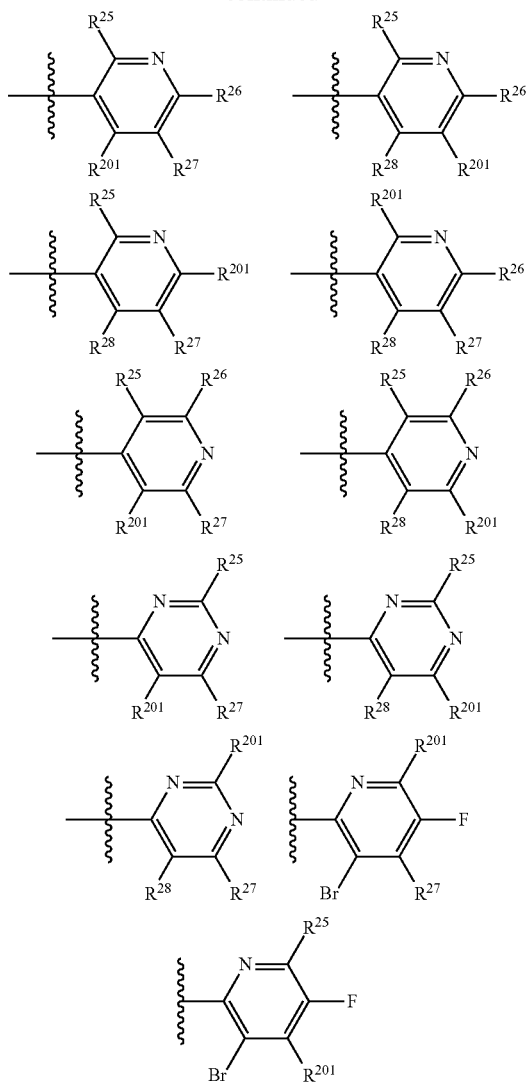
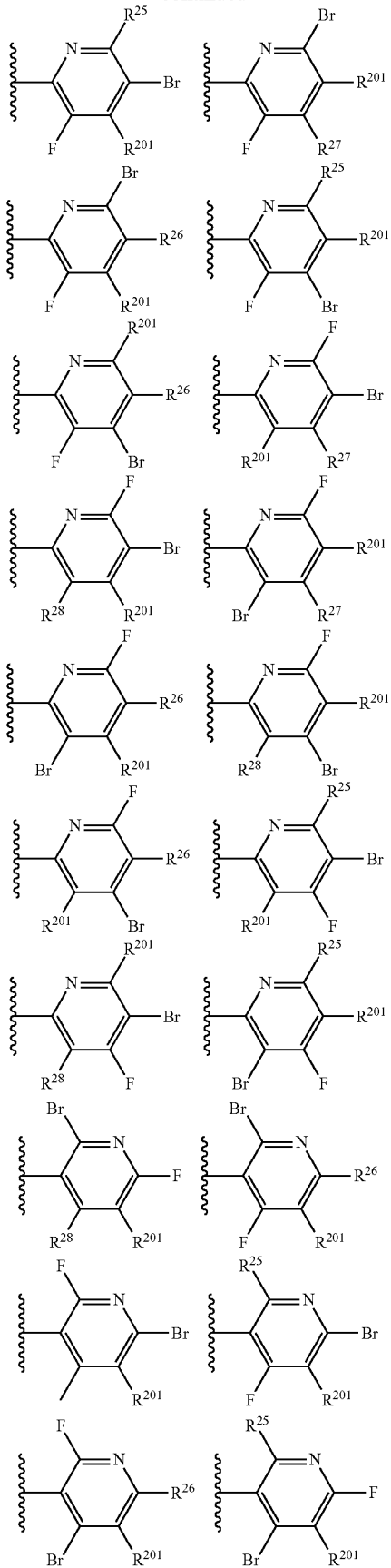
In one embodiment, B1 is selected from:

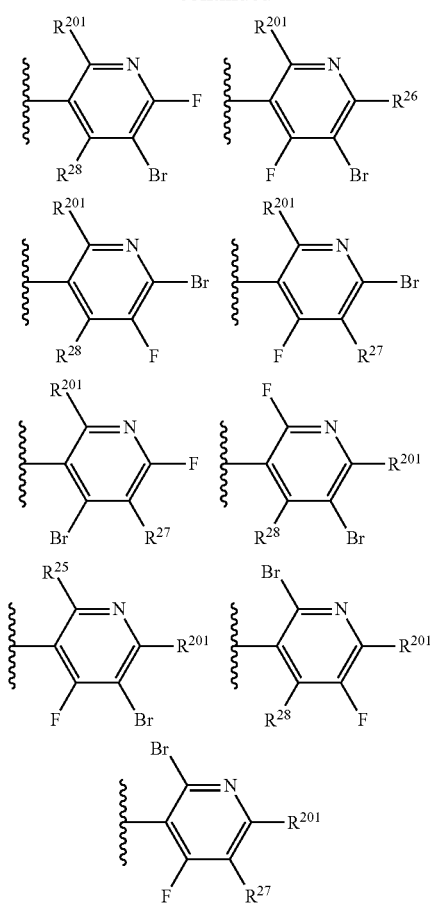
In one embodiment, B1 is selected from:
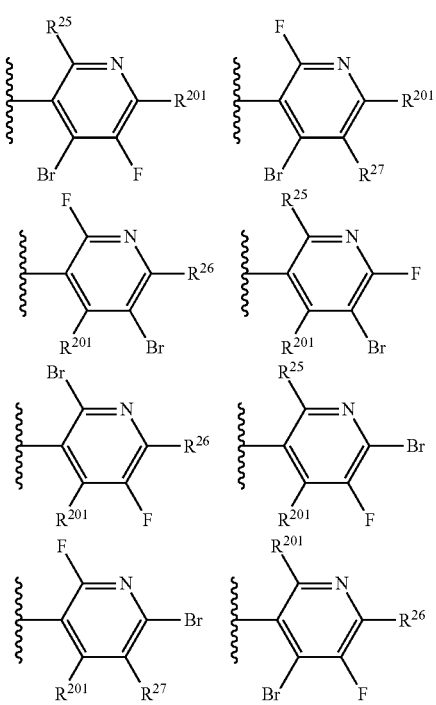
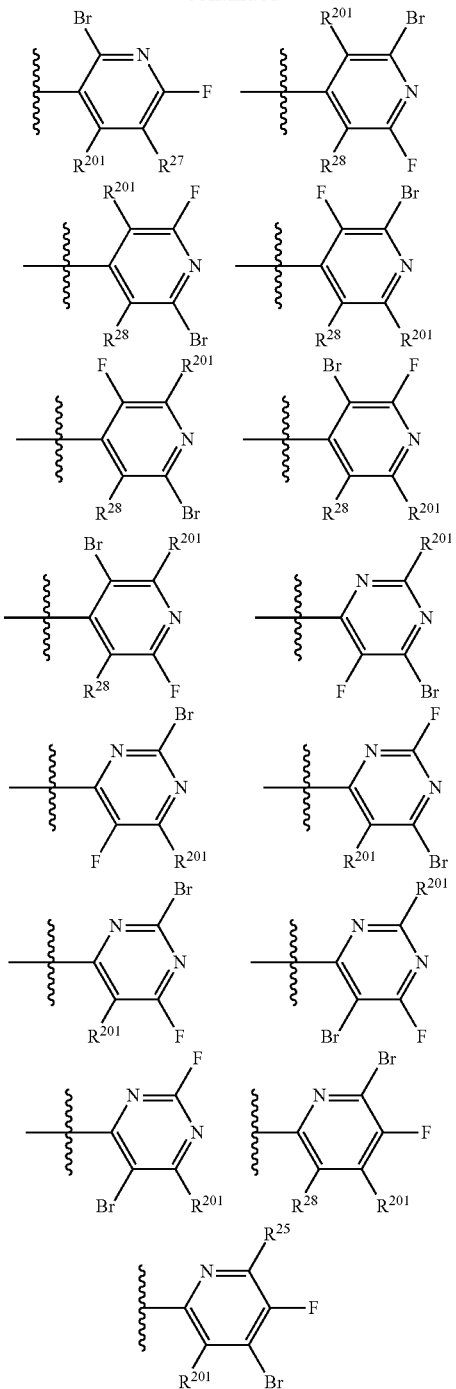
In one embodiment, B1 is selected from:
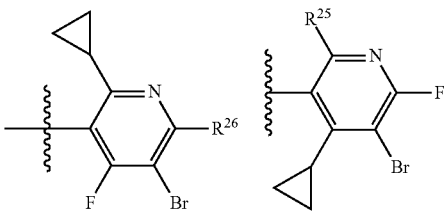

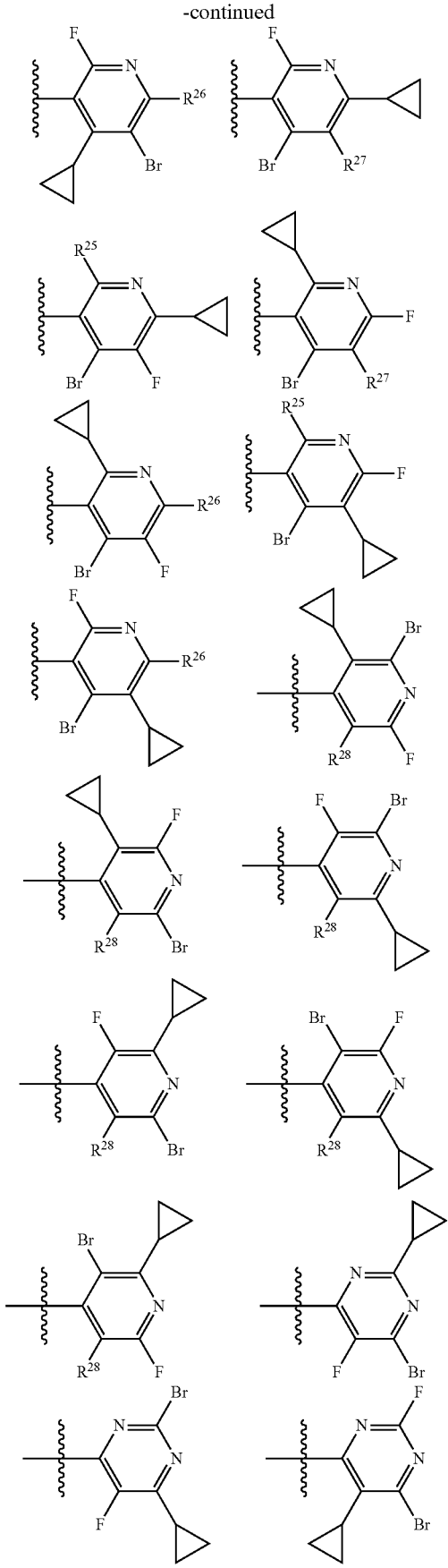
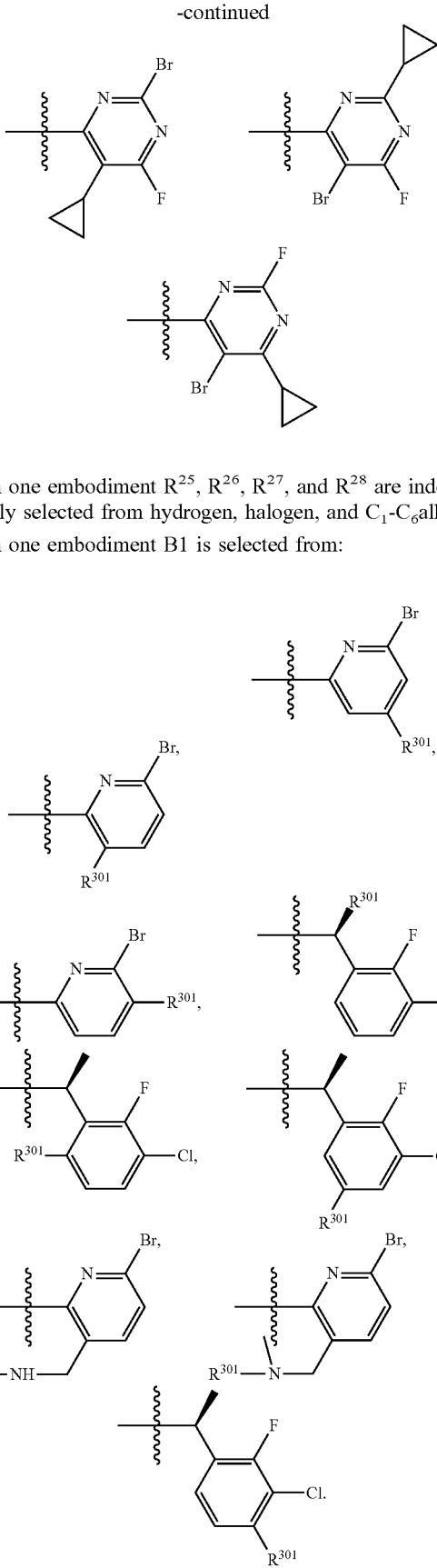
In one embodiment $R^{25}$, $R^{26}$, $R^{27}$, and $R^{28}$ are independently selected from hydrogen, halogen, and $C_1$-$C_6$alkyl.
In one embodiment B1 is selected from:

In another embodiment, B1 is selected from:
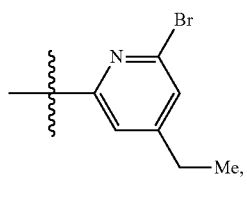 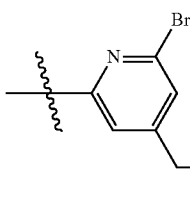
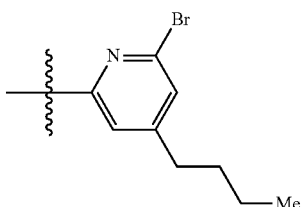 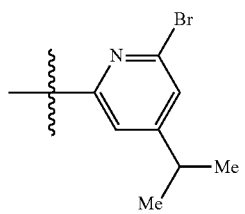
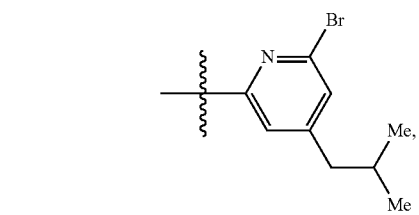
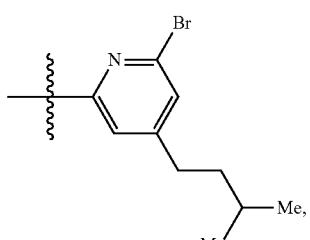 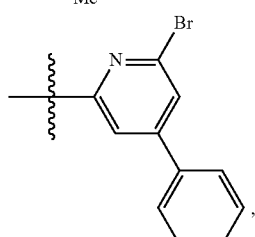
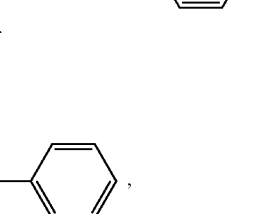
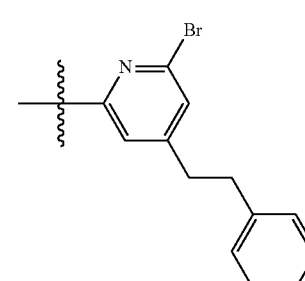 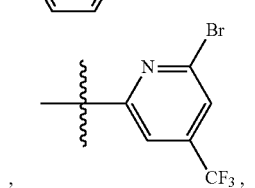
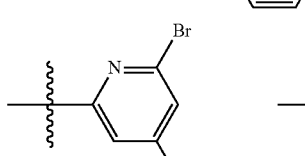 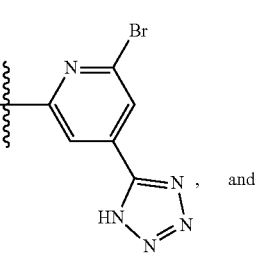, and
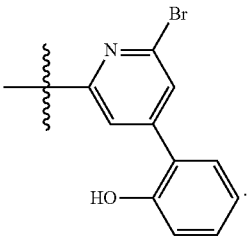.
In another embodiment, B1 is selected from:
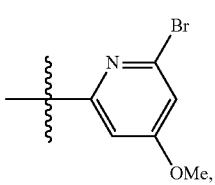, 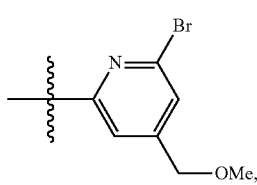
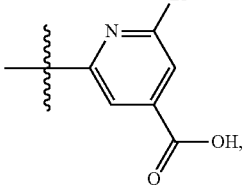, 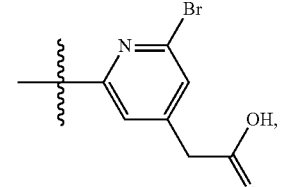
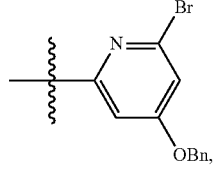, 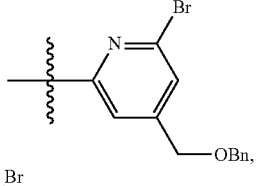
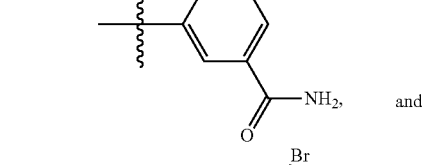 and
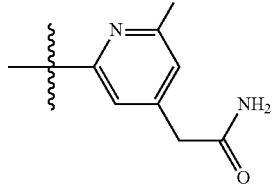.
In another embodiment, B1 is selected from:
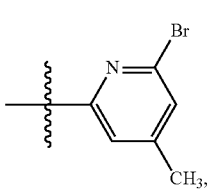 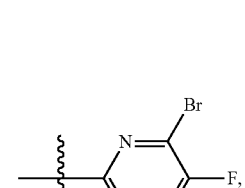

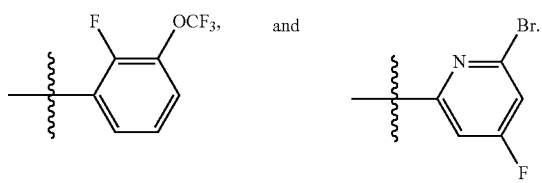 and
In another embodiment, B1 is selected from:
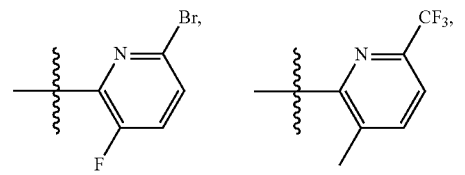
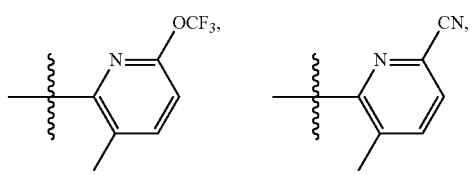
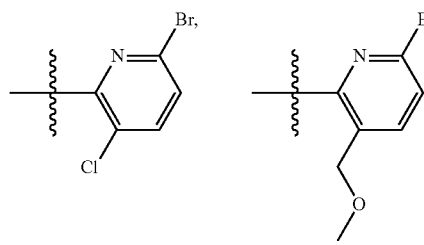 and 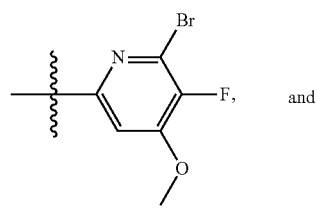
In another embodiment, B1 is selected from:
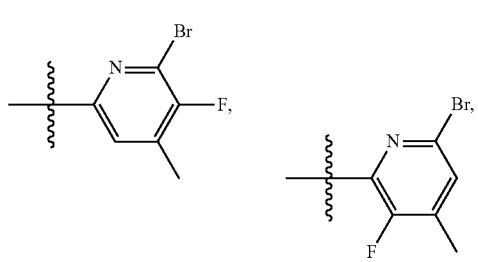
-continued
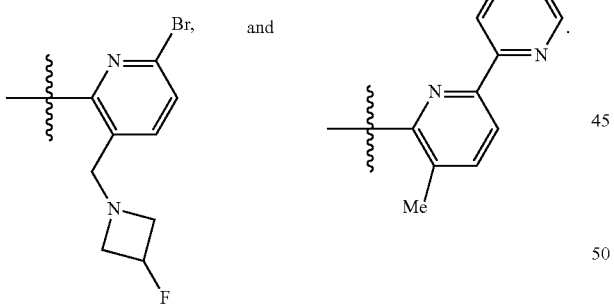 and
In another embodiment, B1 is selected from:
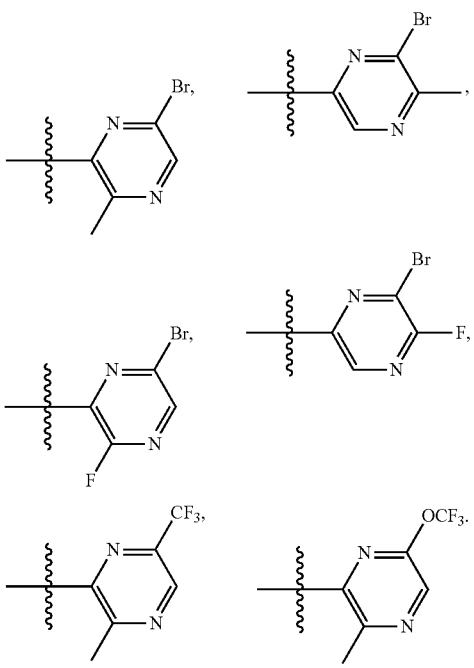
In an alternative embodiment, B1 is selected from:
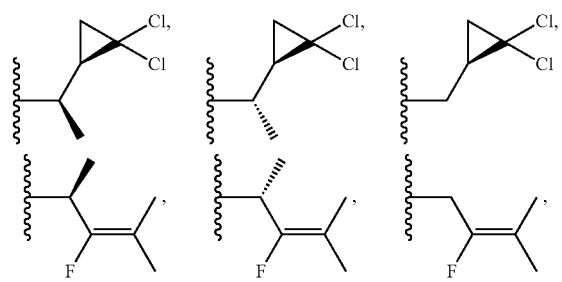

-continued

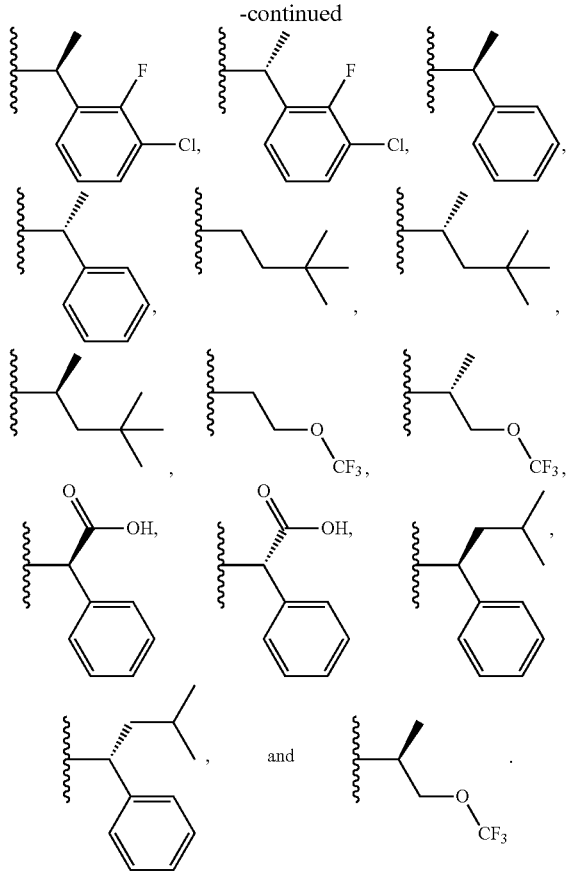

In another alternative embodiment, B1 is selected from:

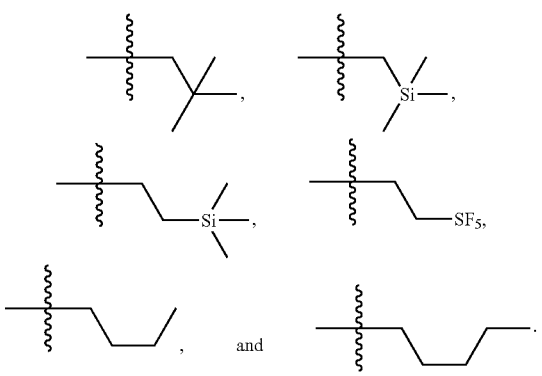

In another alternative embodiment, B4 is —alkyl-Si(alkyl)$_3$ or -alkyl-SF$_5$.

In another alternative embodiment, B1 is substituted with oxo. In this embodiment if the B ring is a nitrogen containing heteroaryl group then the nitrogen may also be substituted as defined herein. For example:

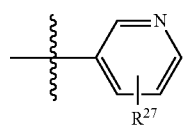

substituted with an oxo can be selected from the following compounds:

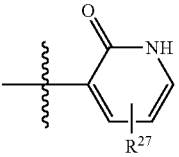

And examples of

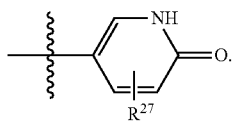

include:

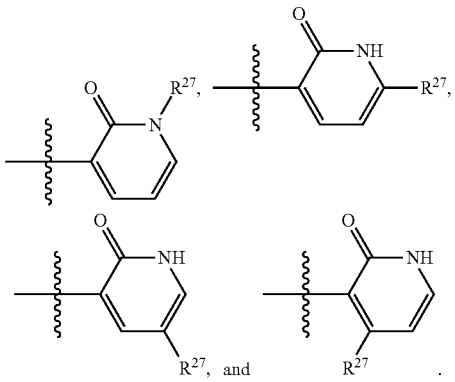

In another alternative embodiment, B1 is selected from:

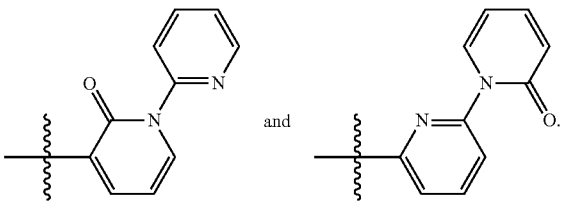 [SMILES: *c1cccn(-c2ccccn2)c1=O ; *c1cccc(-n2ccccc2=O)n1]

In another alternative embodiment, R$^{32}$ is a heteroaryl ring substituted with oxo as allowed by valence. In this embodiment if the R$^{32}$ ring is a nitrogen containing heteroaryl group then the nitrogen may also be substituted as defined herein. For example:

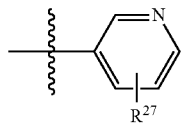

substituted with an oxo can be selected from the following compounds:
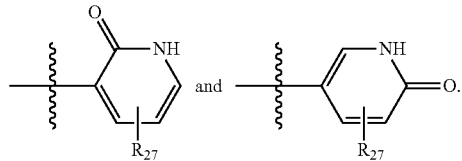
And examples of
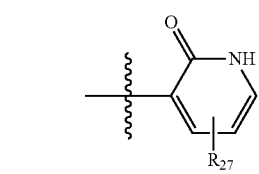
include:
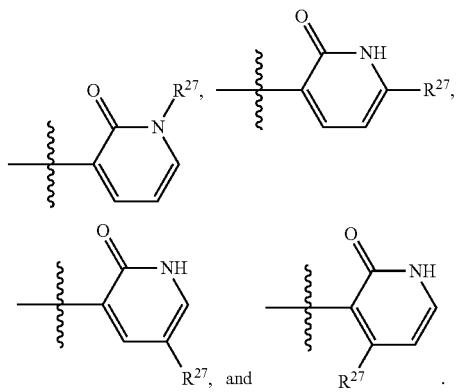
In another alternative embodiment, R³² is selected from:
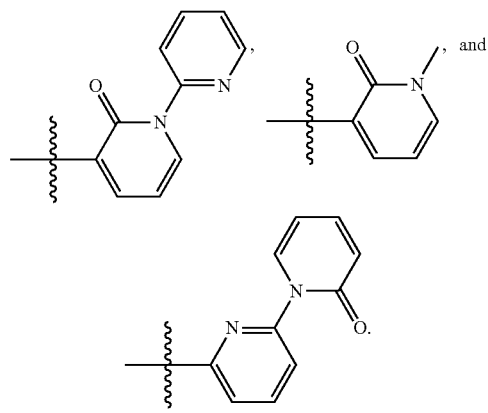
In another alternative embodiment, B1 is an alkyl group.
In another alternative embodiment, B1 is an alkenyl group.
Embodiments of C
In one embodiment C1 is selected from:
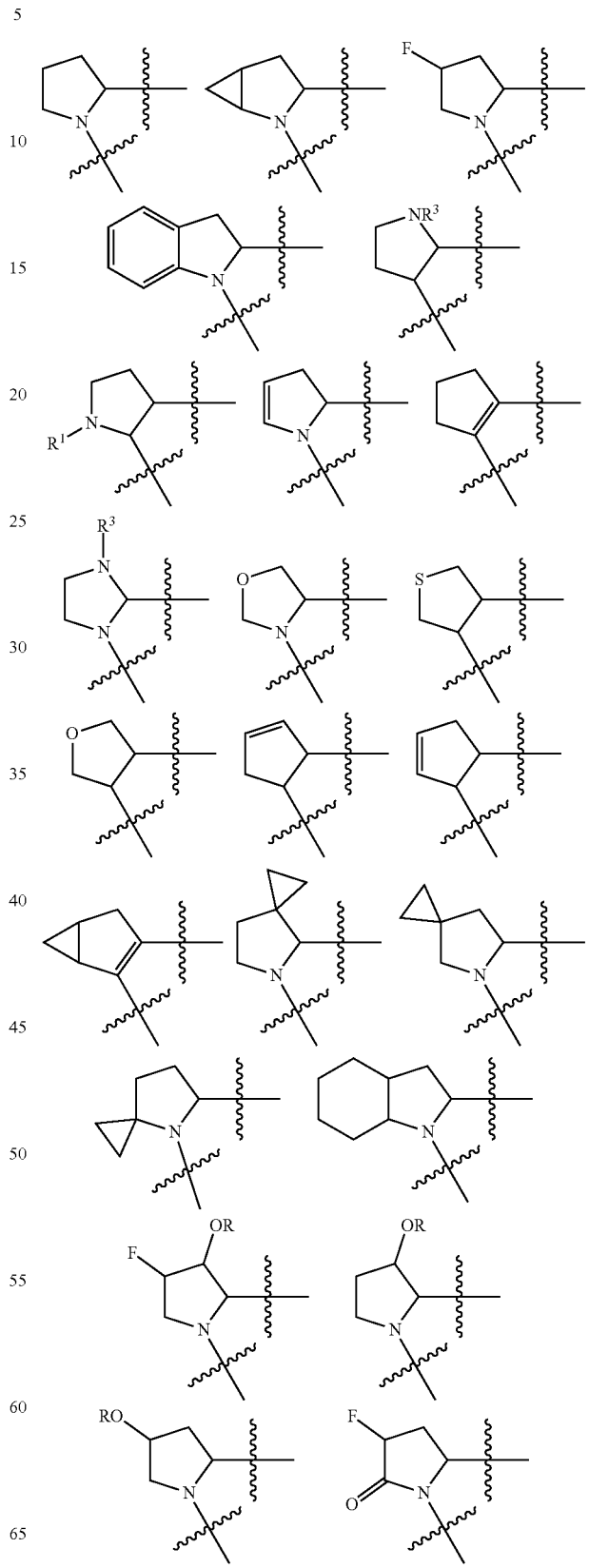

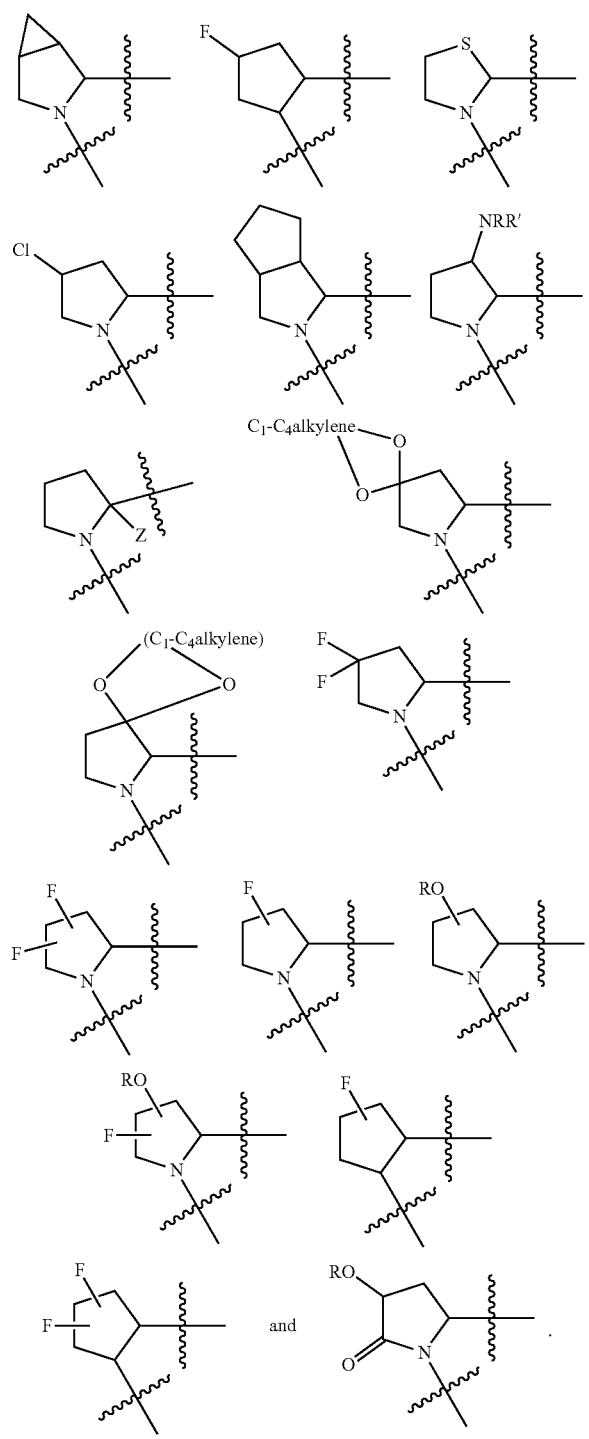
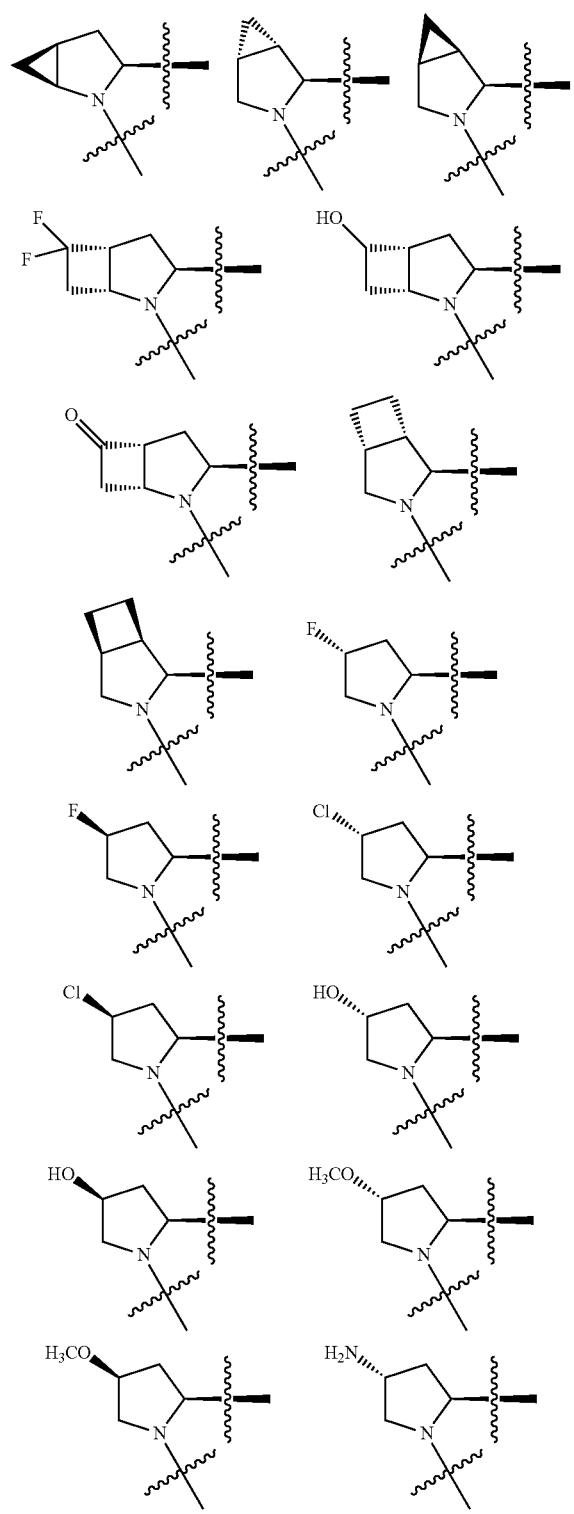
In one embodiment C1 is selected from:
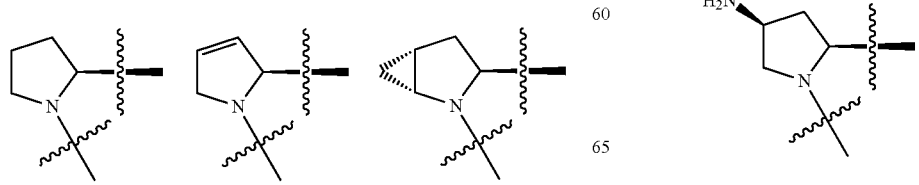
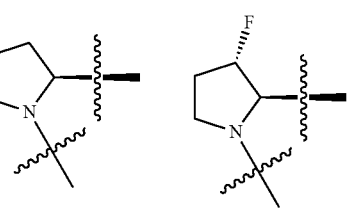

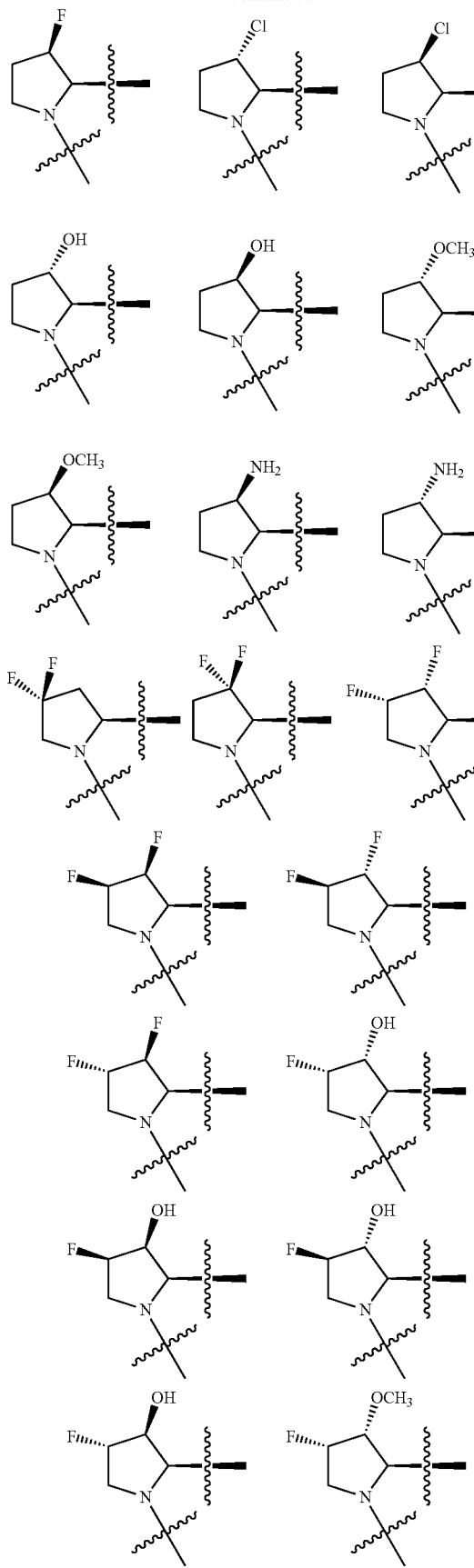
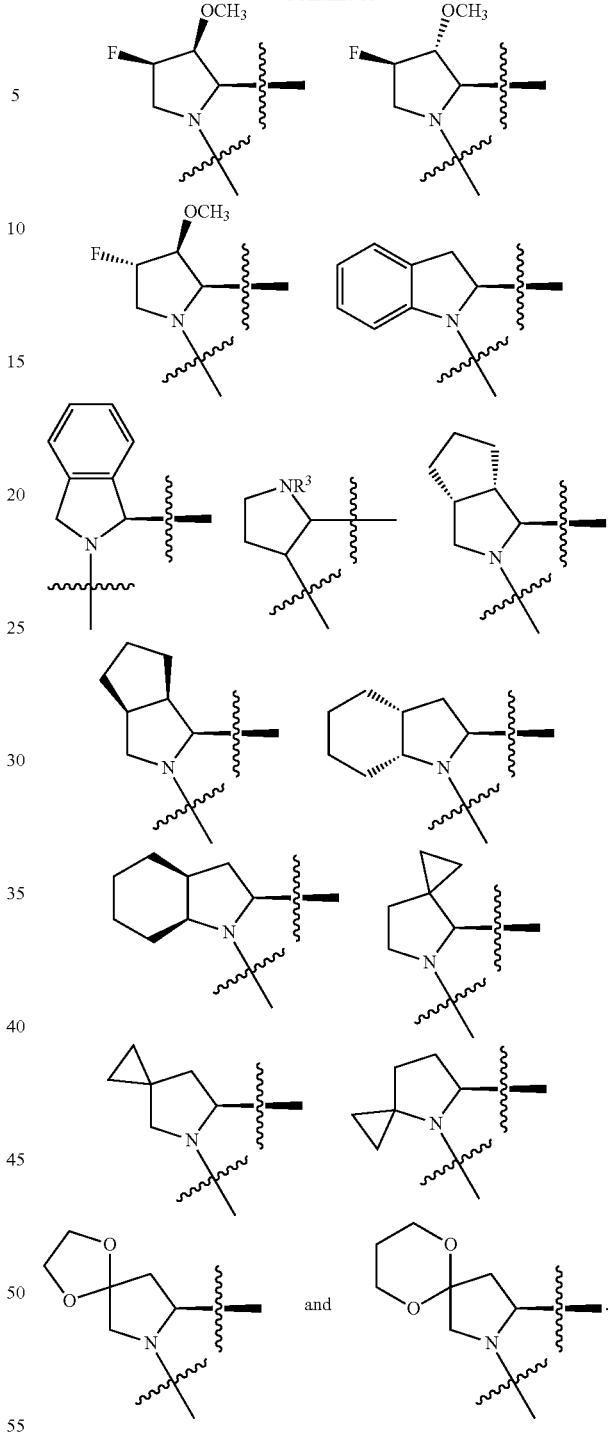

In one embodiment, a methyl group in a structure illustrated above can be replaced with a different alkyl group, as defined herein. In another embodiment, the fluoro atoms in the structures illustrated above can be replaced with any other halogen. Any of the structures illustrated above or otherwise can be optionally substituted with 0, 1, 2, 3, or 4, as appropriate, and independently, with an $R^{48}$ substituent.

Examples of central core small mimetics of a beta-turn, beta turn inducers, reverse turn mimetics and foldamer monomers include:

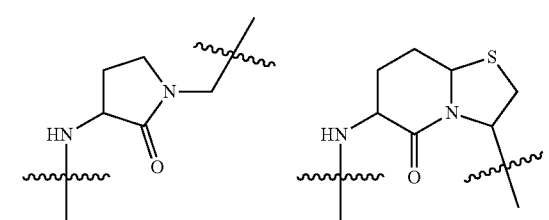
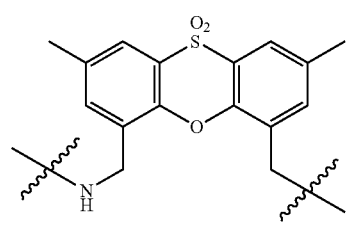
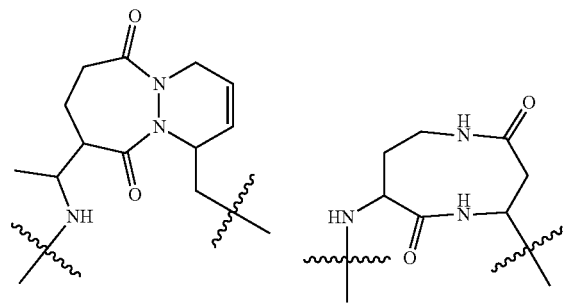
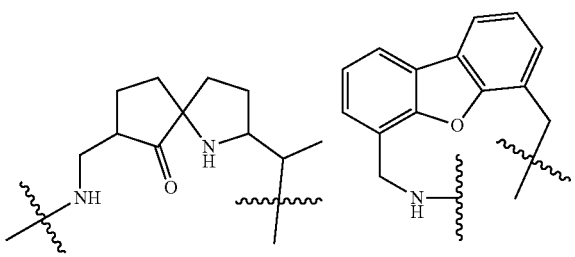
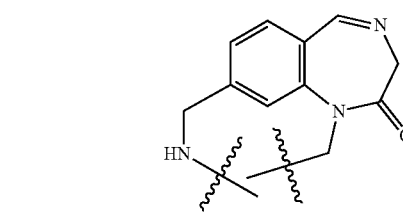
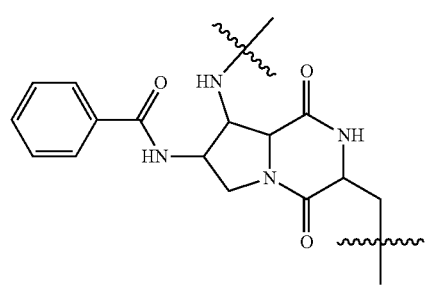
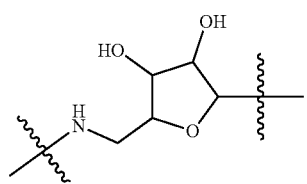
-continued
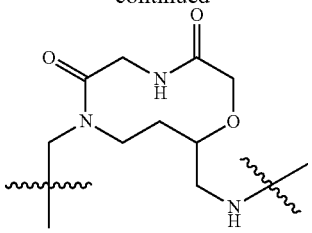
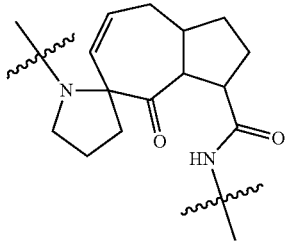
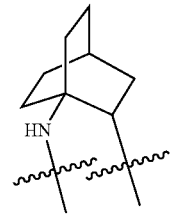
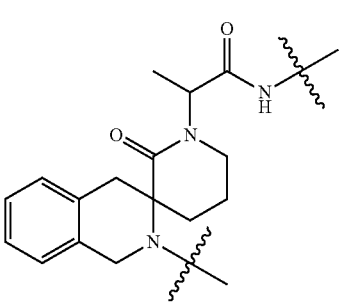
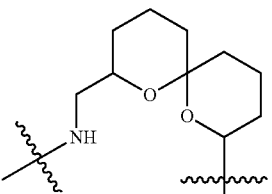
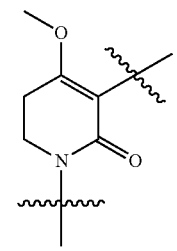
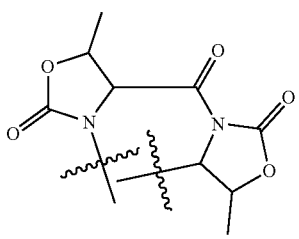
In one embodiment C is selected from:
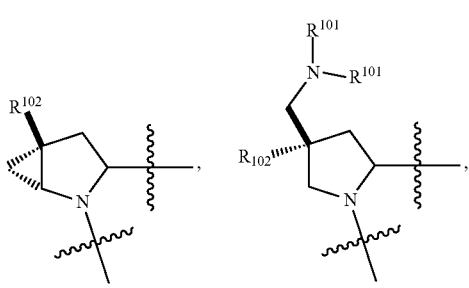

189
-continued
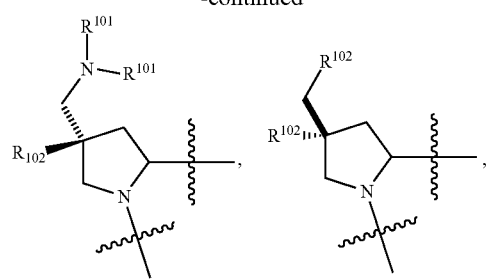
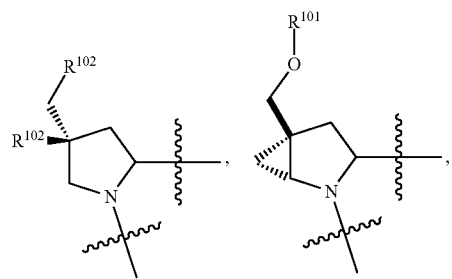
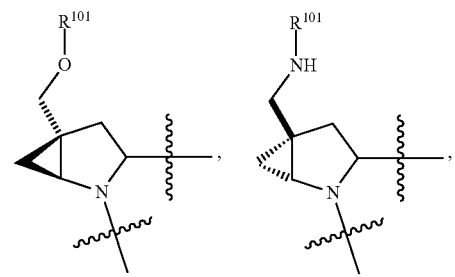
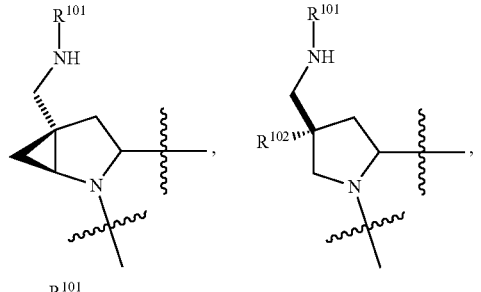
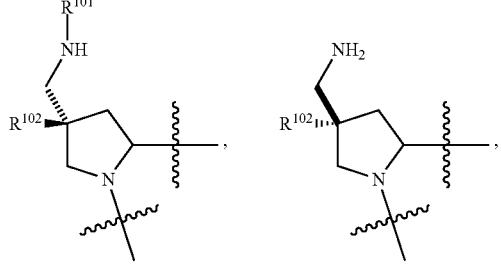
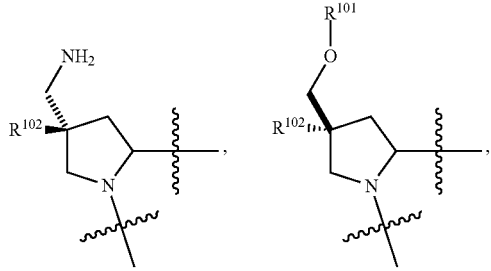
190
-continued
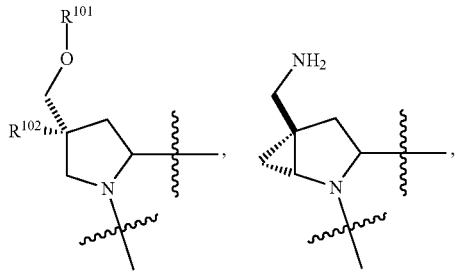
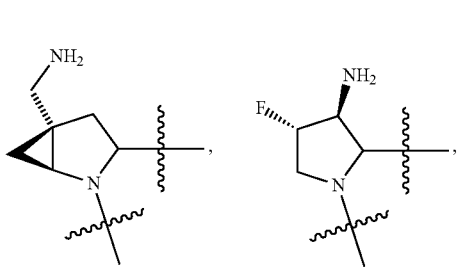
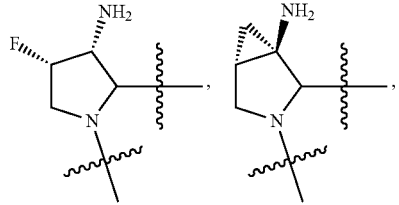
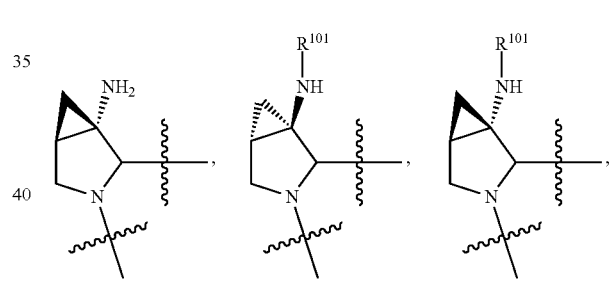
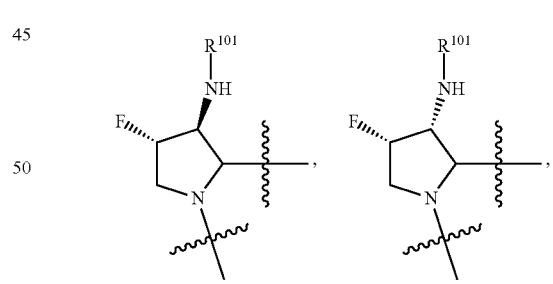
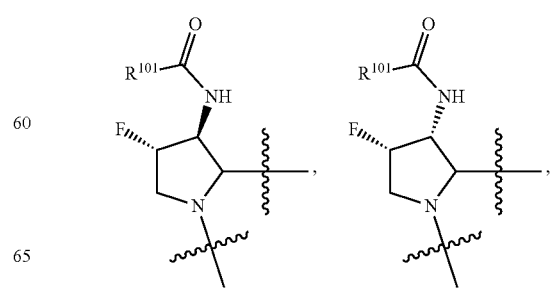

191
-continued
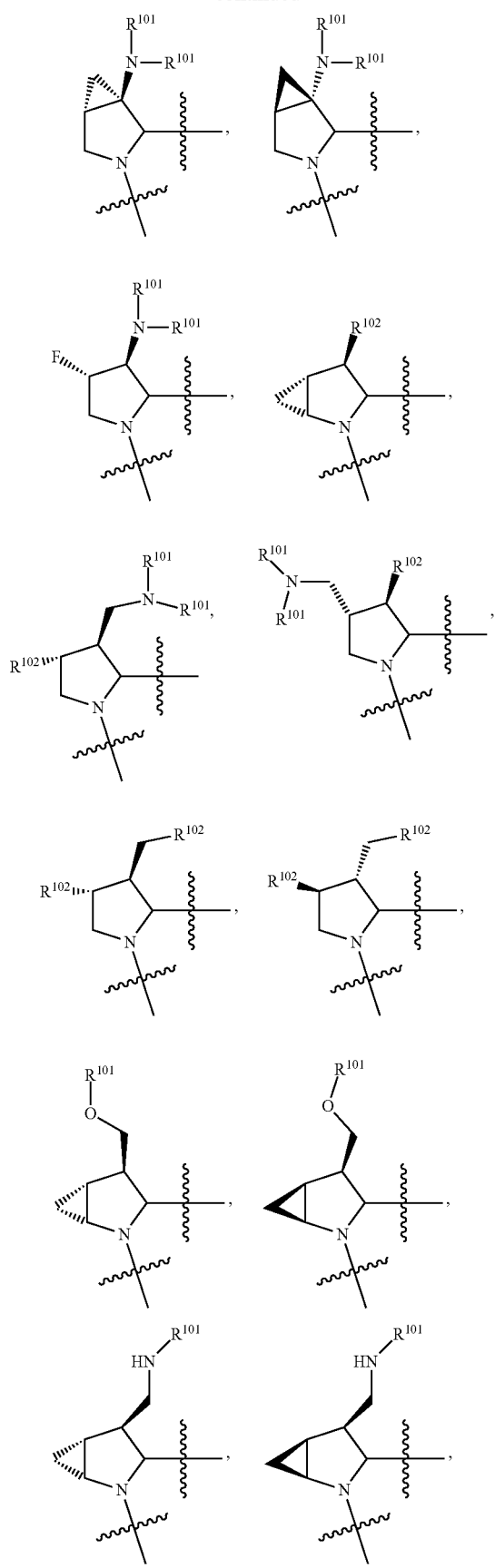
192
-continued
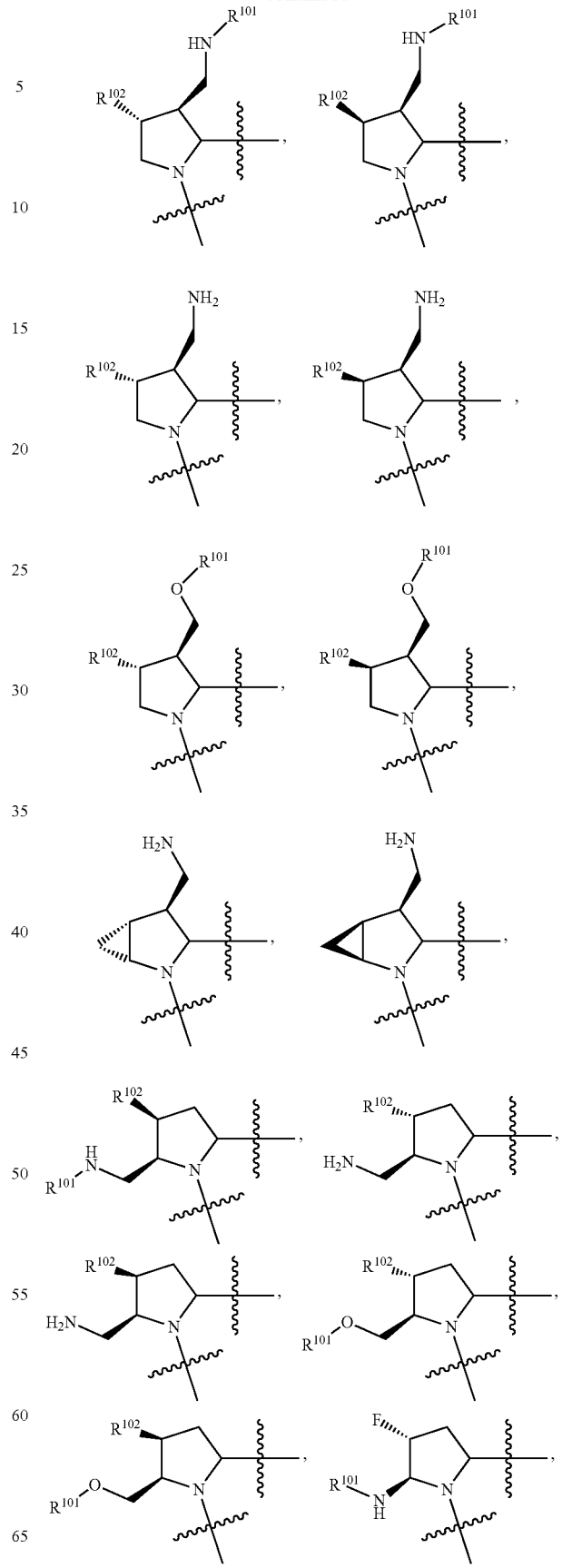

-continued
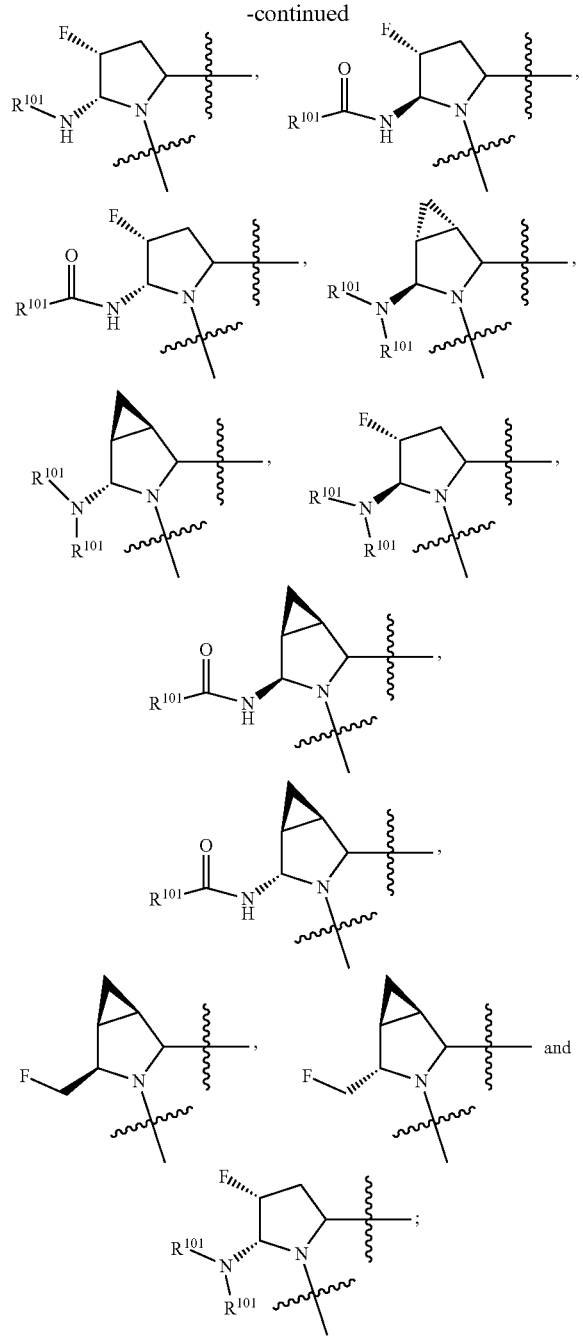
wherein:
R[101] is $C_1$-$C_4$ alkyl or $C_3$-$C_7$ cycloalkyl; and
R[102] is $C_1$-$C_4$ alkyl, fluorine, chlorine, or bromine.
In one embodiment C1 is selected from:
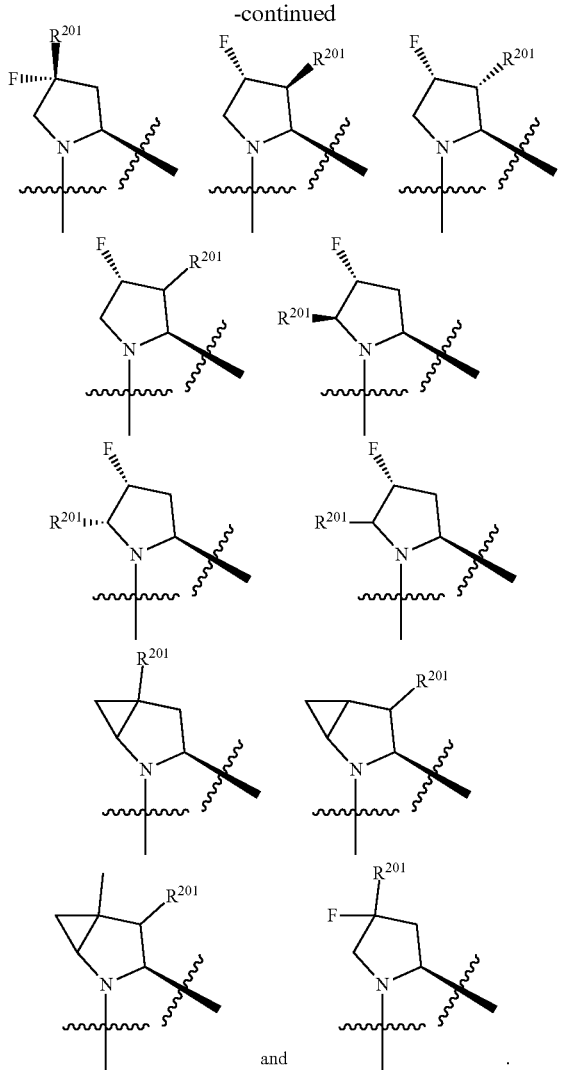
and
In one embodiment C1 is selected from:
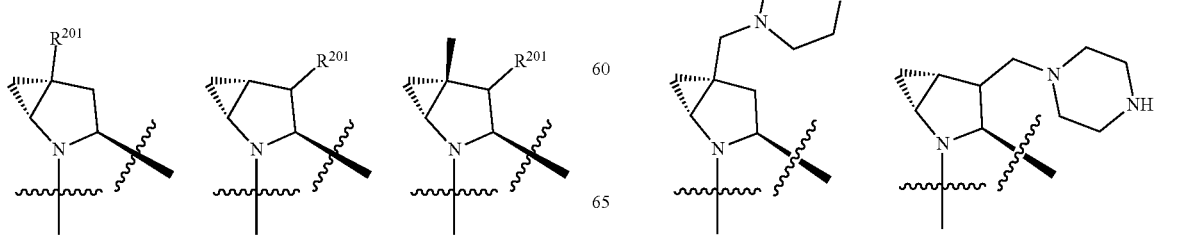

-continued
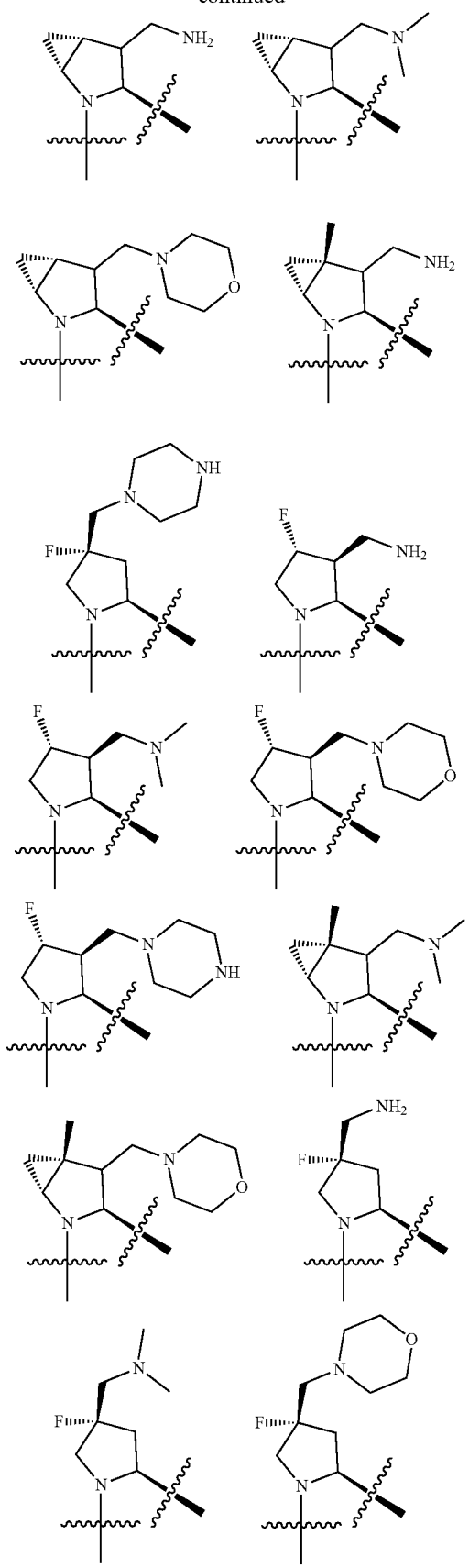
In one embodiment C1 is selected from:
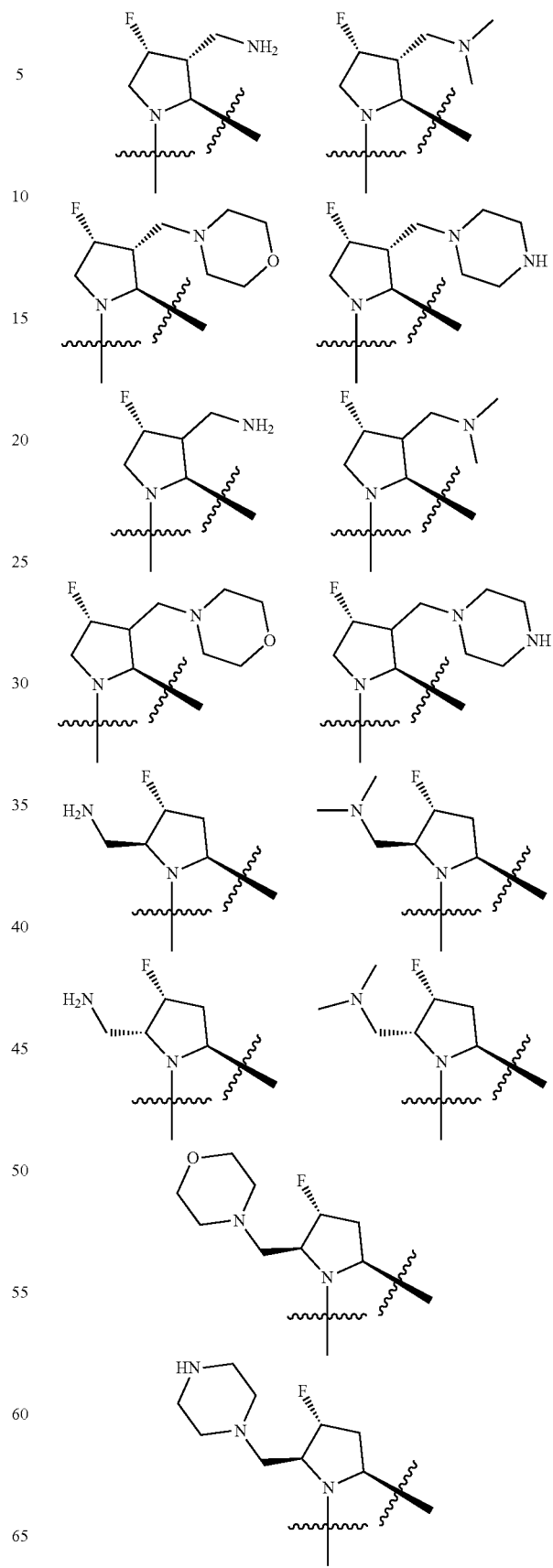

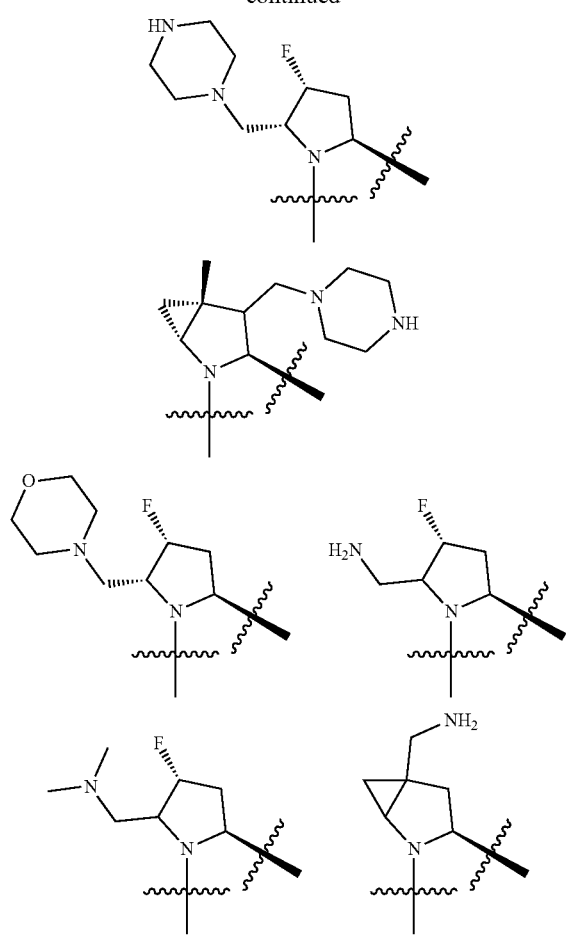
In one embodiment C1 is selected from:
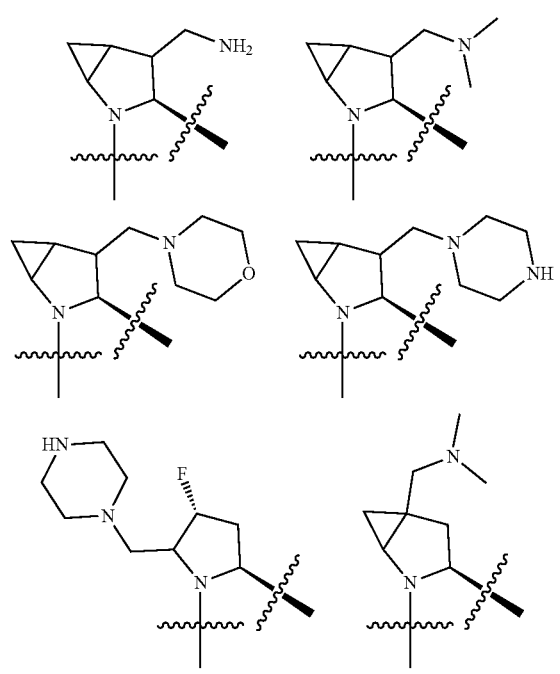
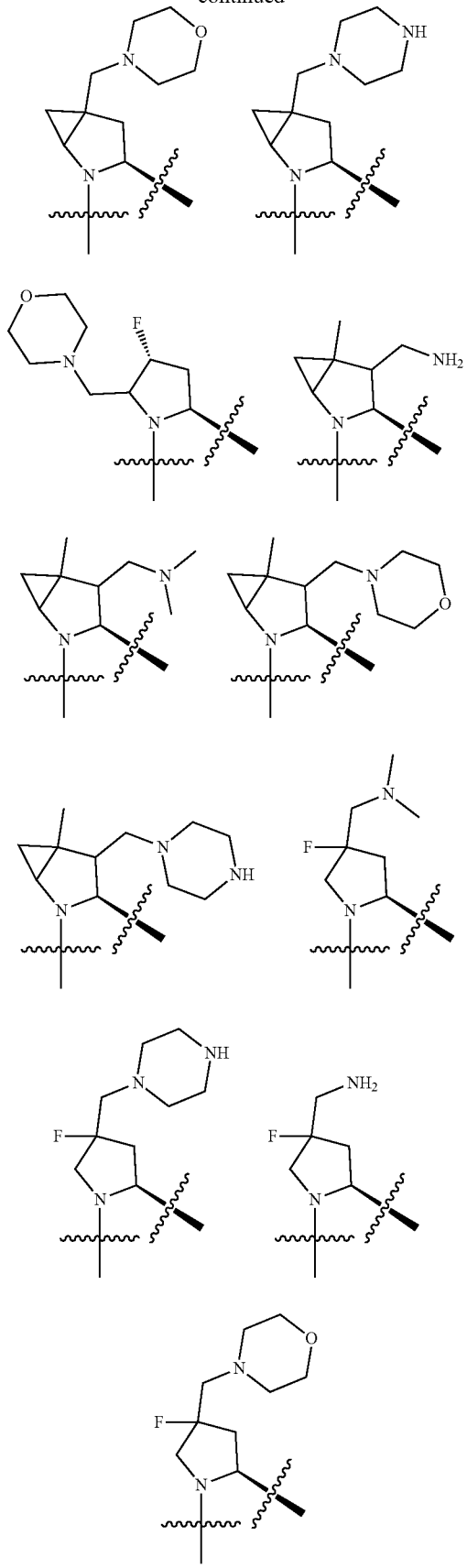

In one embodiment C is selected from:
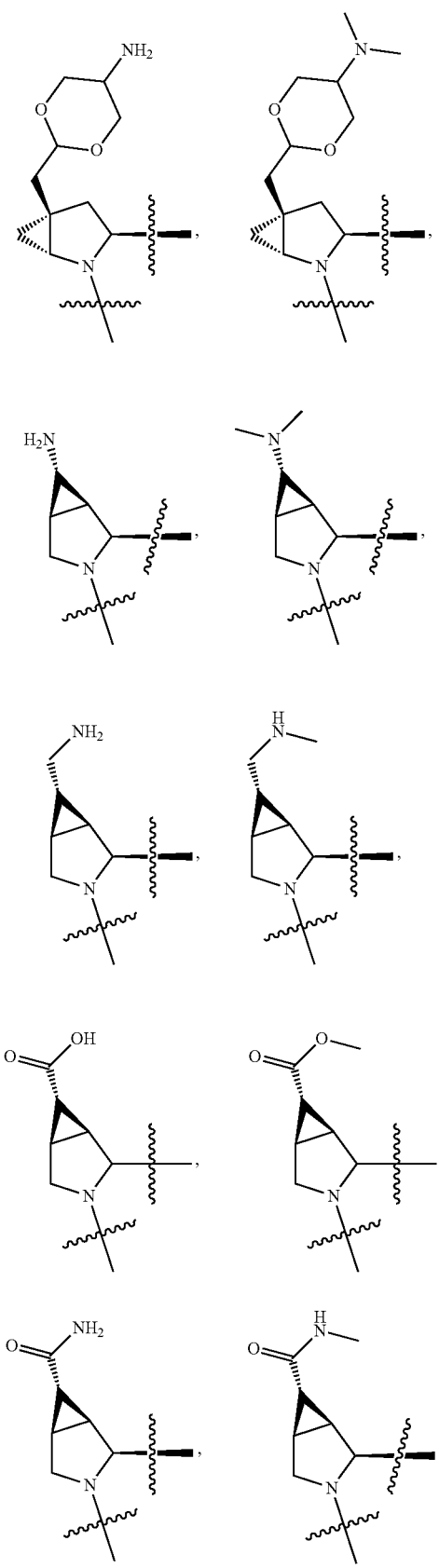
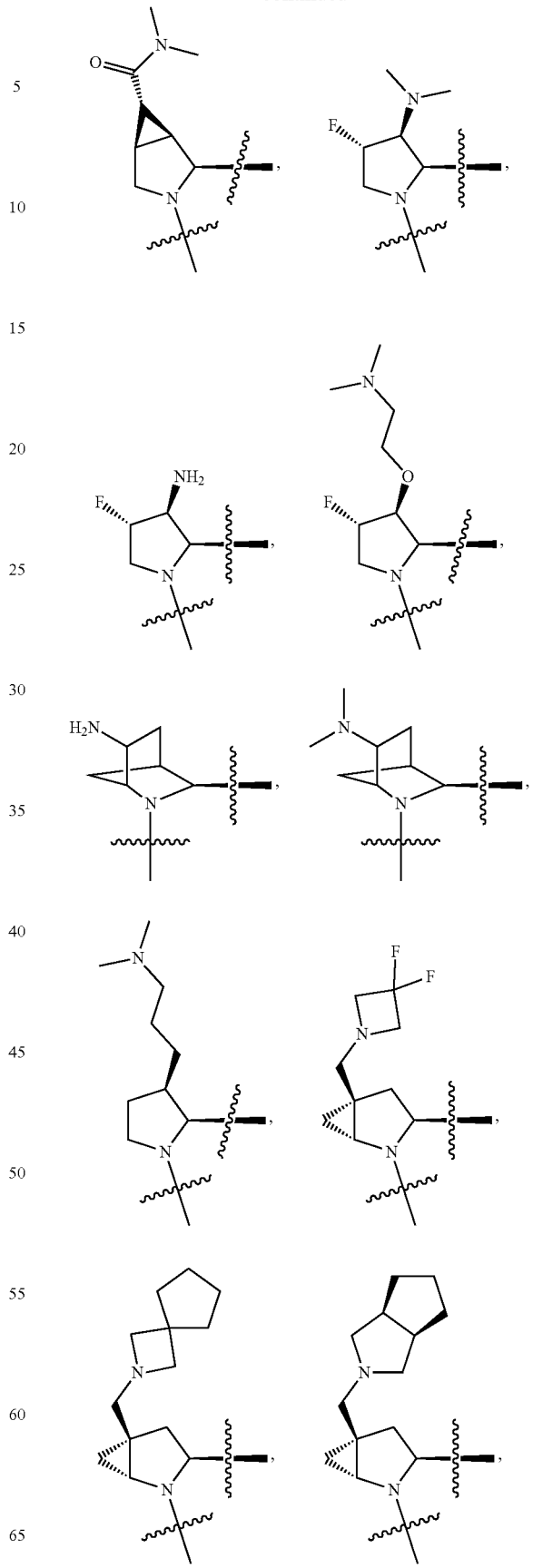
-continued

201
-continued
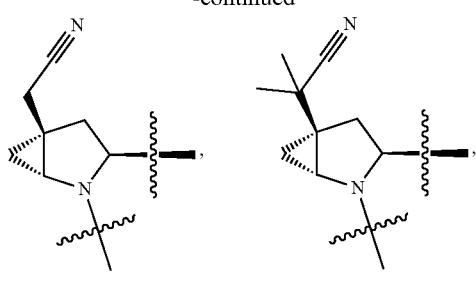
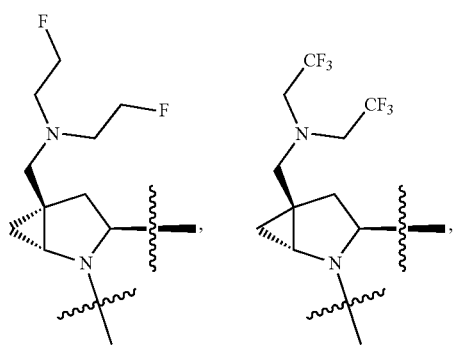
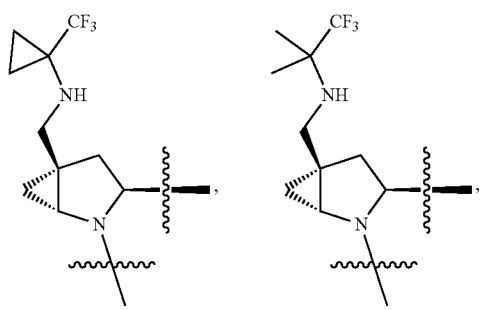
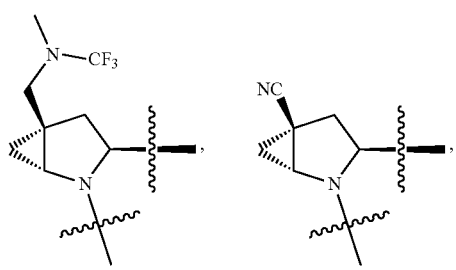
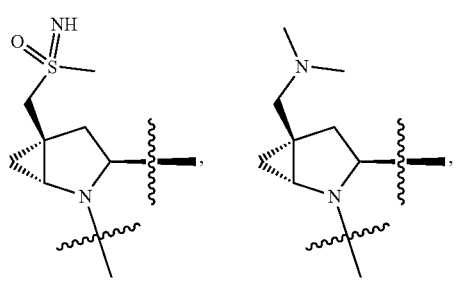
202
-continued
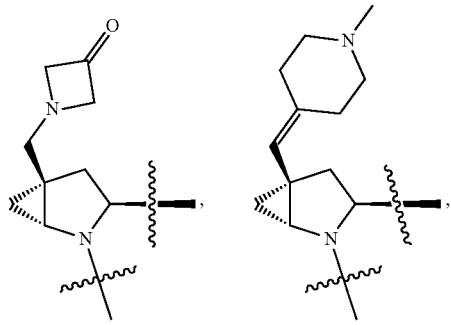
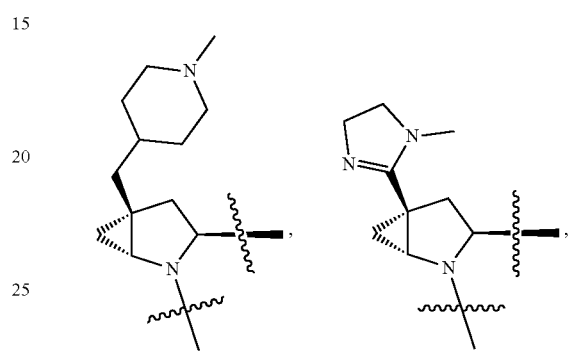
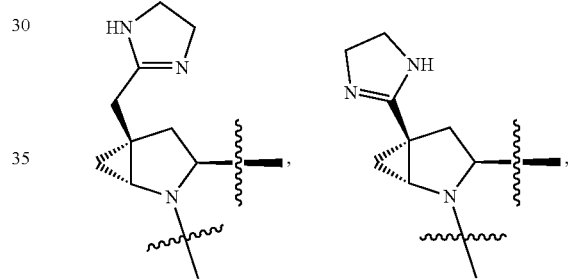
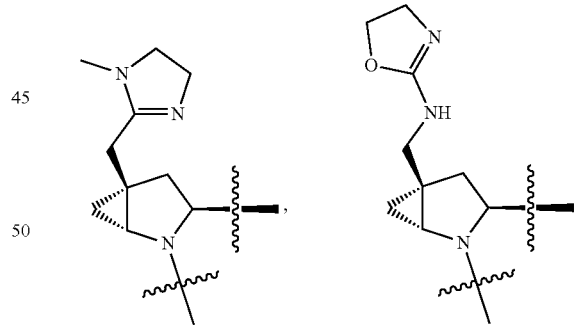
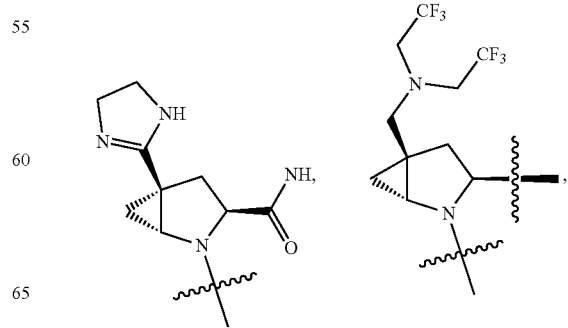

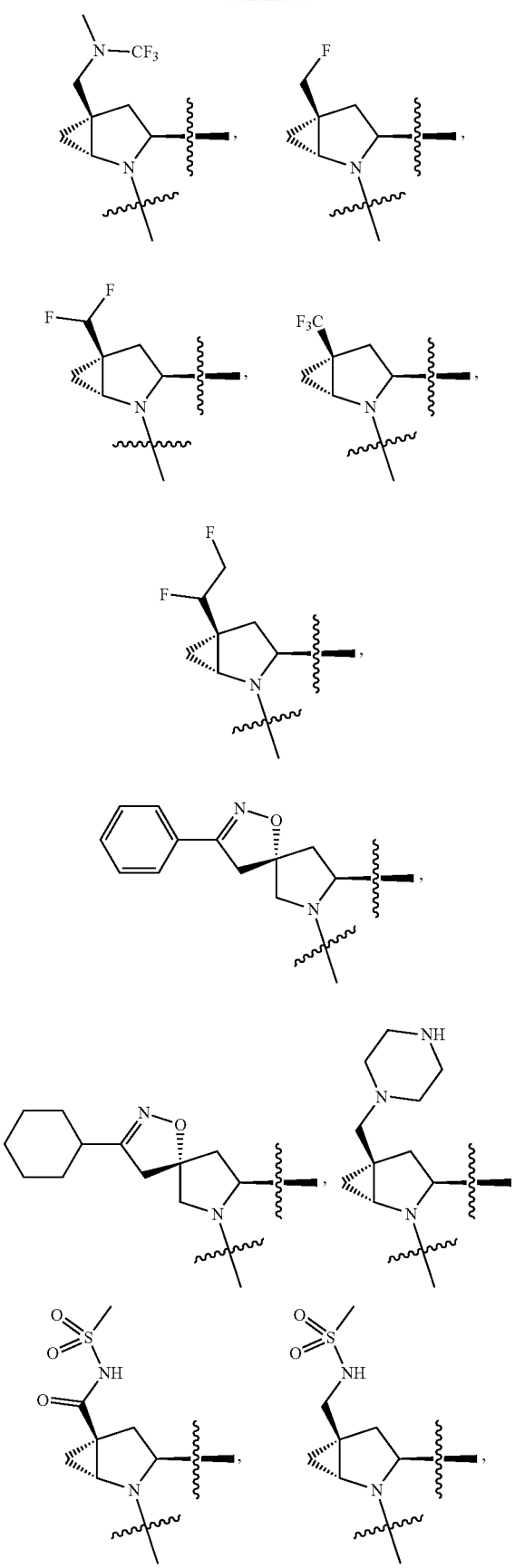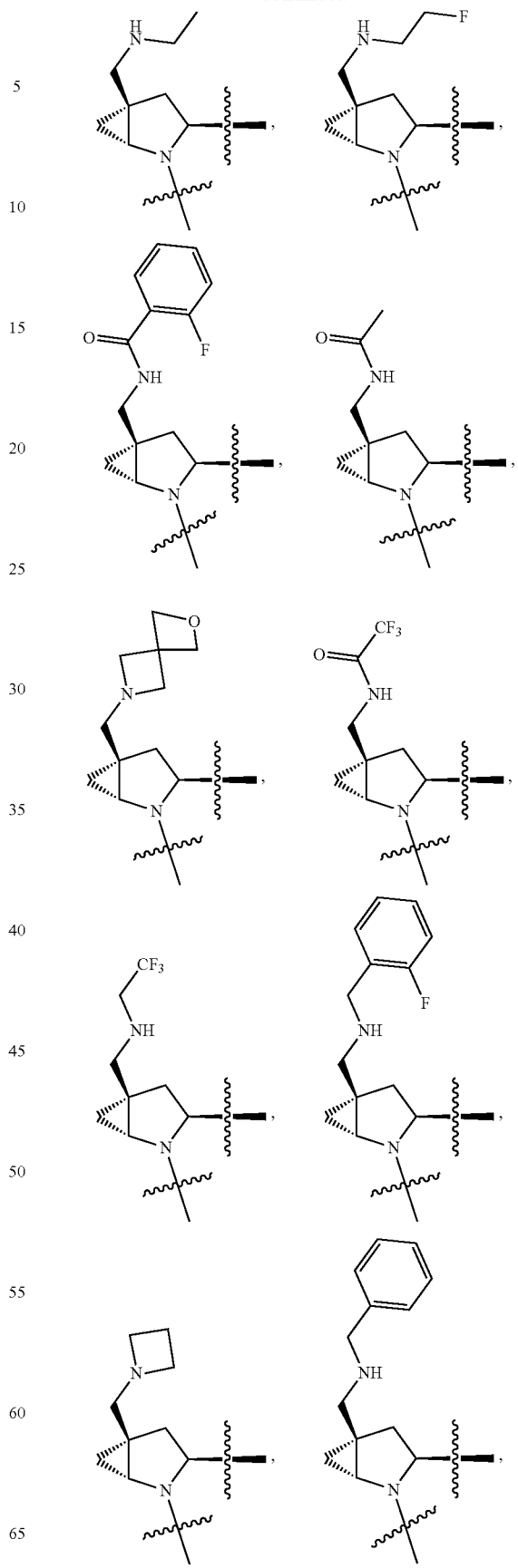

205
-continued
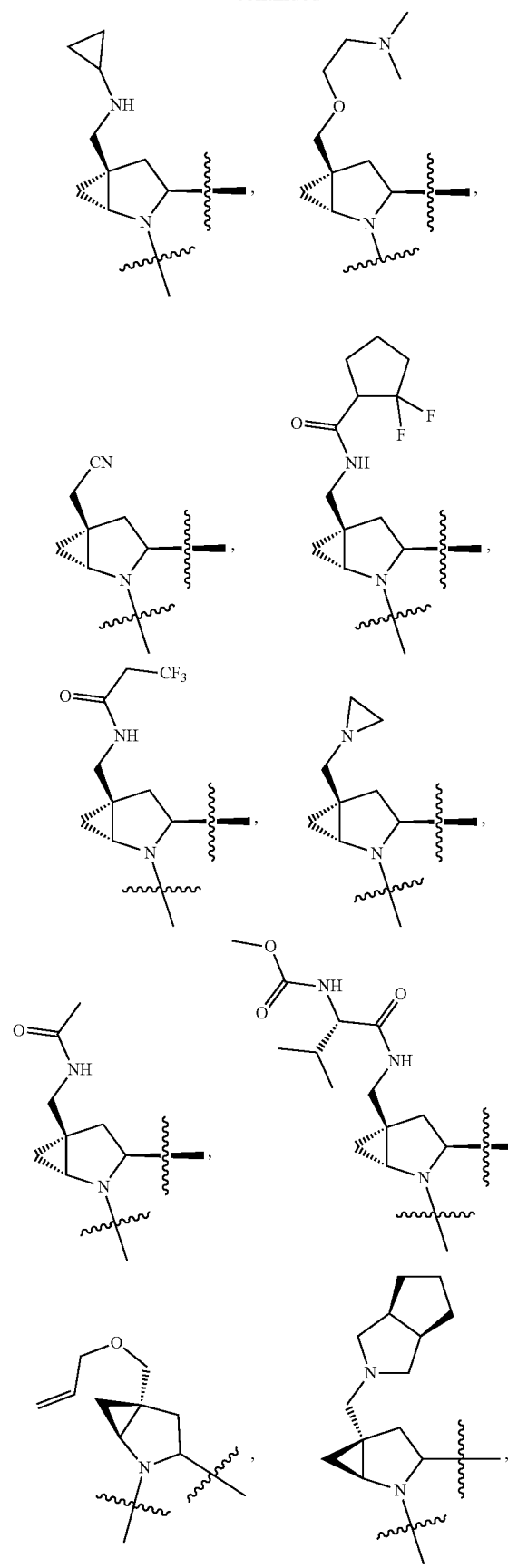
206
-continued
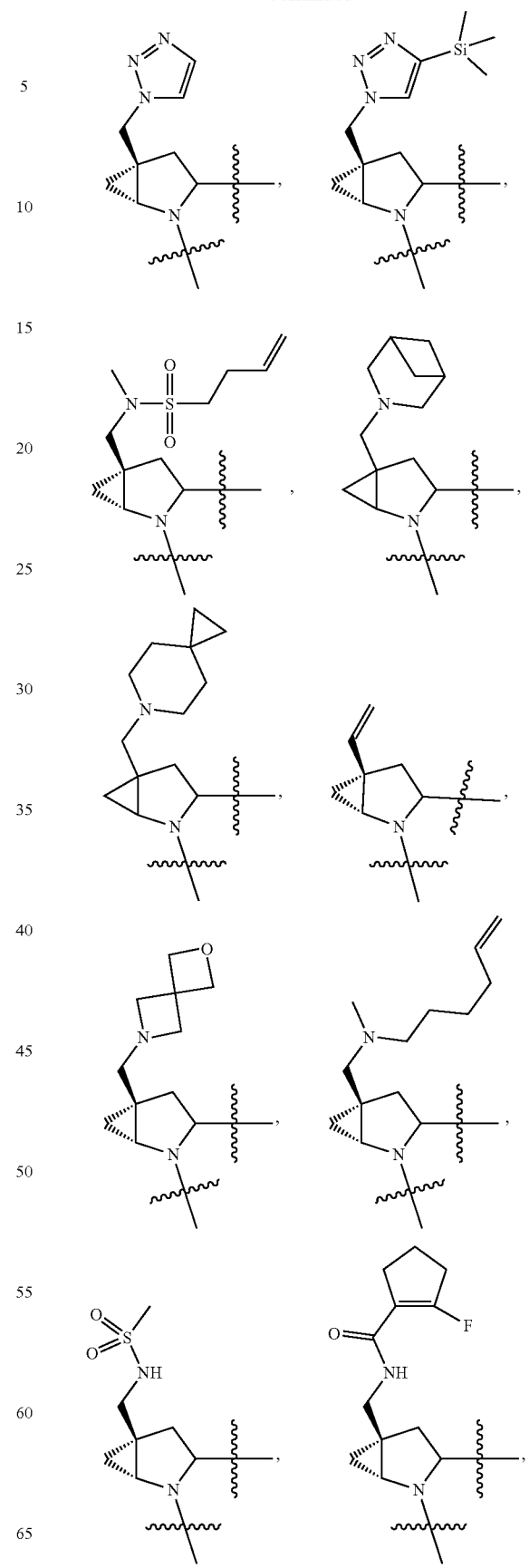

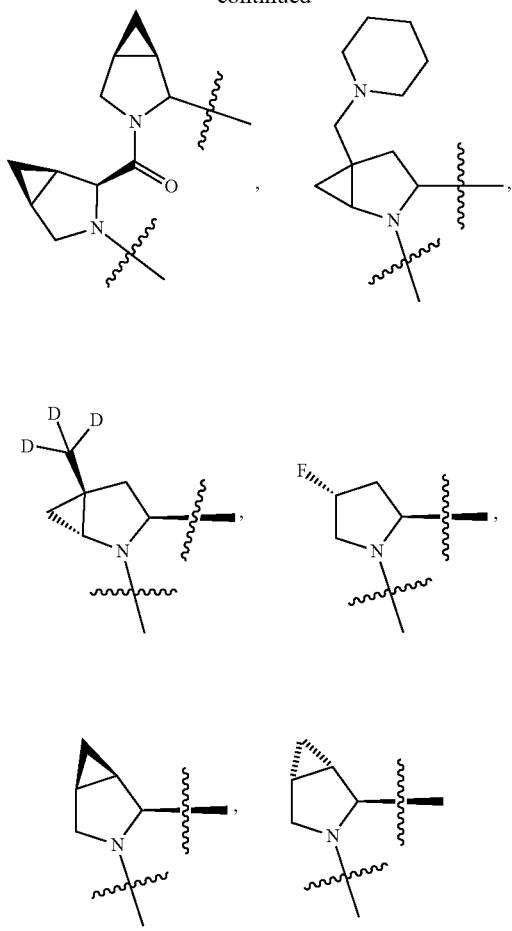
In one embodiment C is selected from:
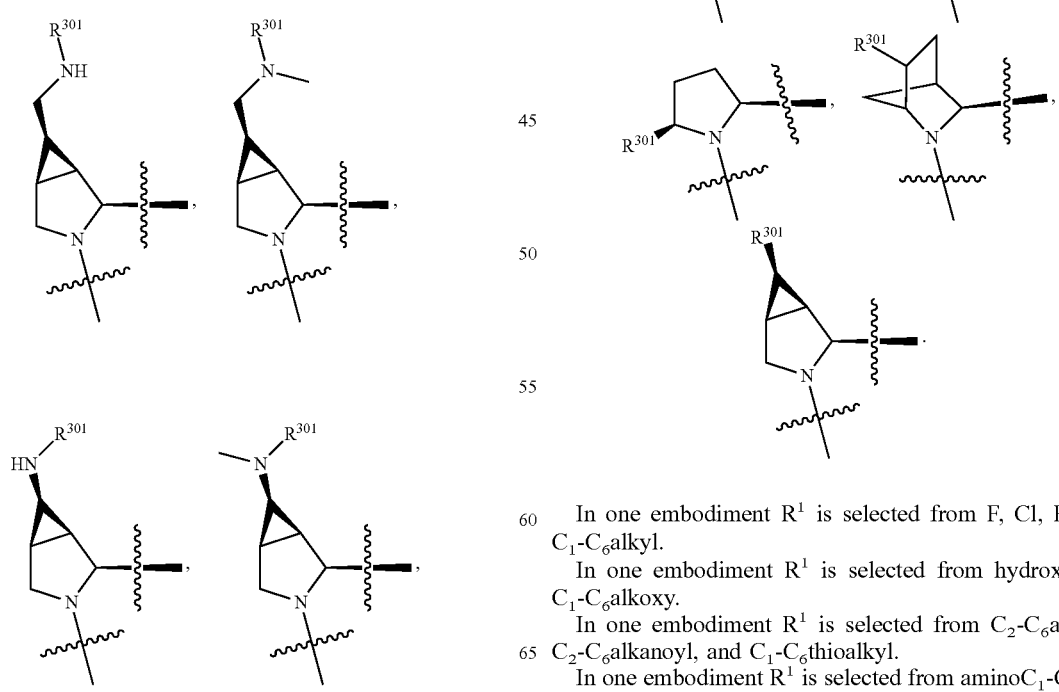
In one embodiment $R^1$ is selected from F, Cl, Br, and $C_1$-$C_6$alkyl.
In one embodiment $R^1$ is selected from hydroxyl and $C_1$-$C_6$alkoxy.
In one embodiment $R^1$ is selected from $C_2$-$C_6$alkynyl, $C_2$-$C_6$alkanoyl, and $C_1$-$C_6$thioalkyl.
In one embodiment $R^1$ is selected from amino$C_1$-$C_6$alkyl and -$C_0$-$C_4$alkylNR$^9$R$^{10}$.

Embodiments of L
In one embodiment L1 is selected from:
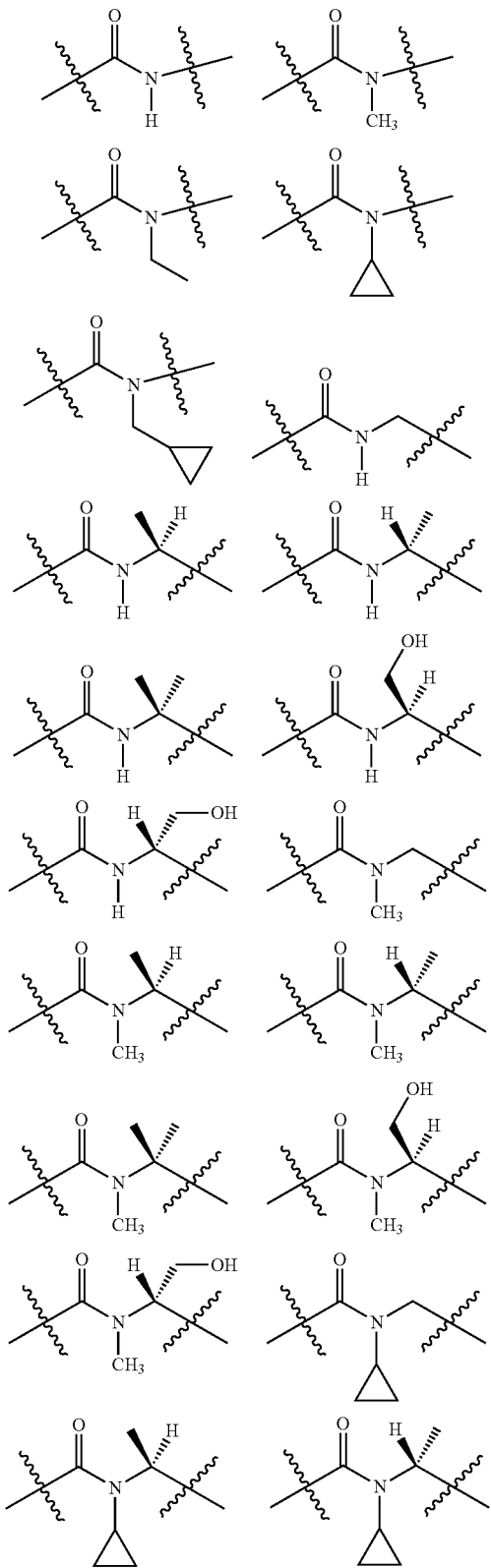
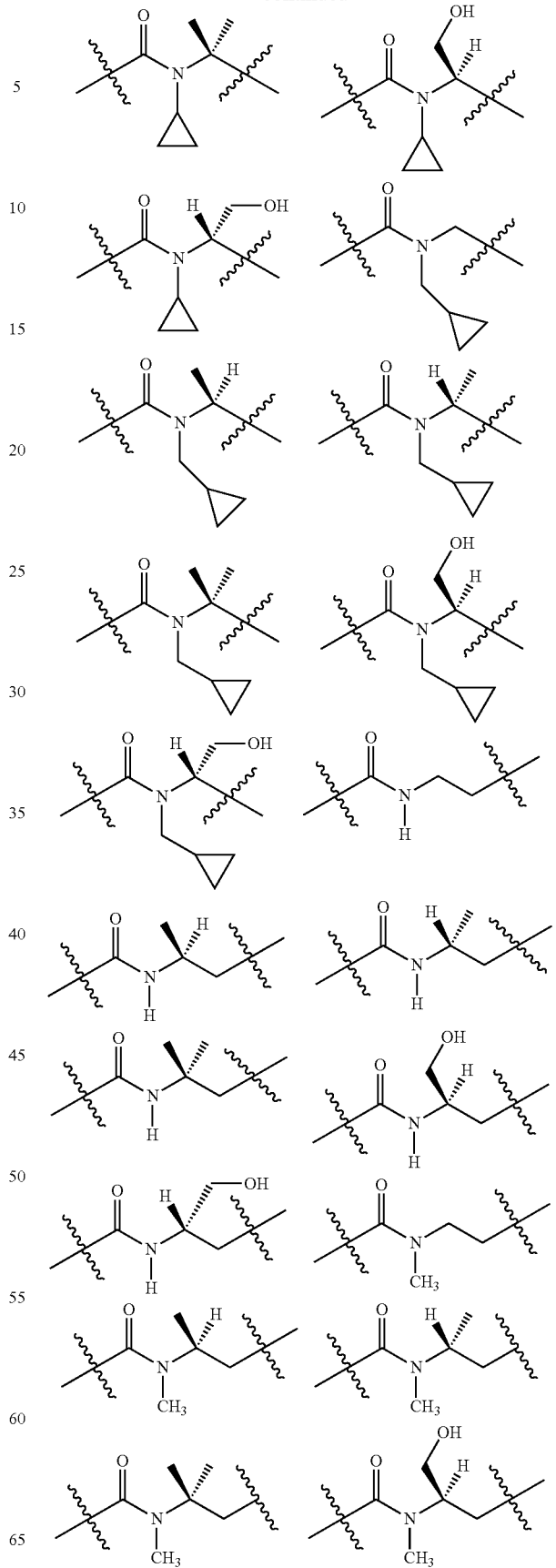

In one embodiment L1 is selected from:

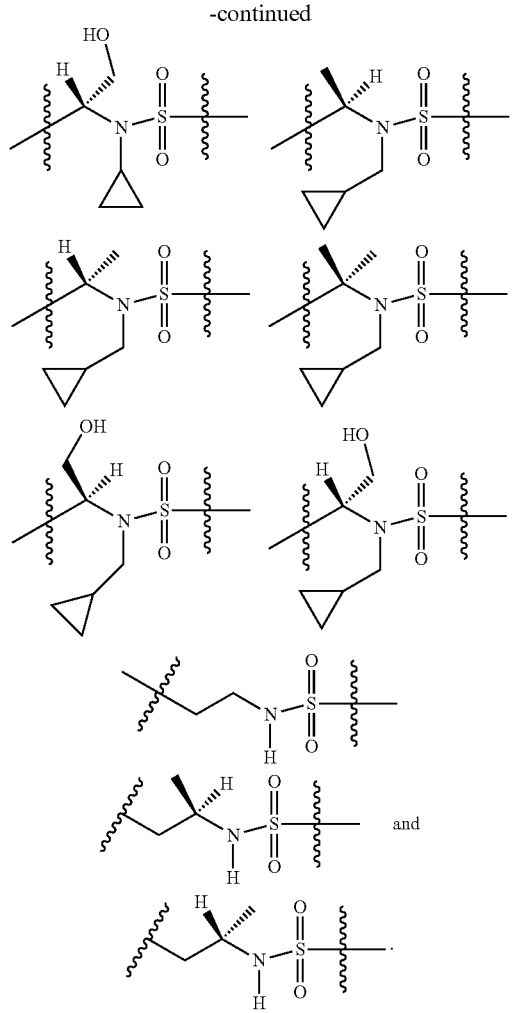
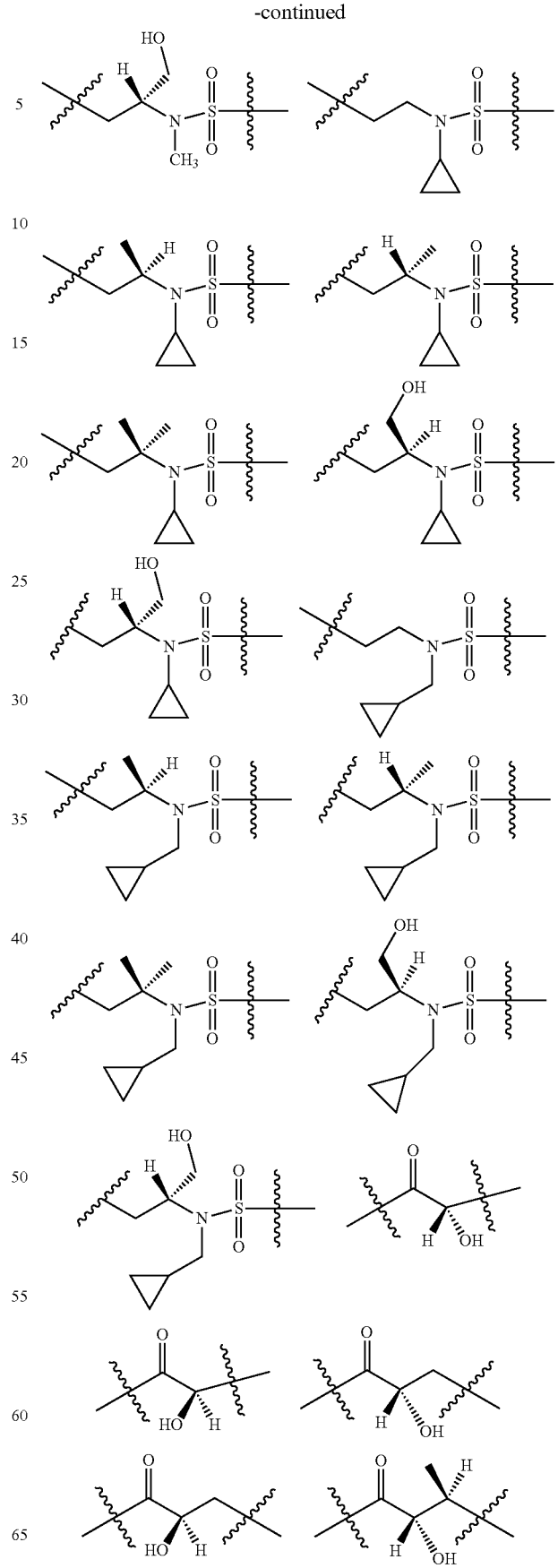
In one embodiment L1 is selected from:
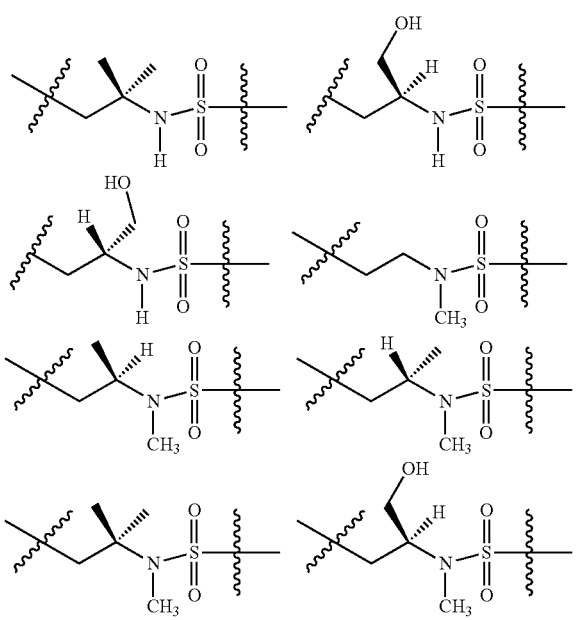

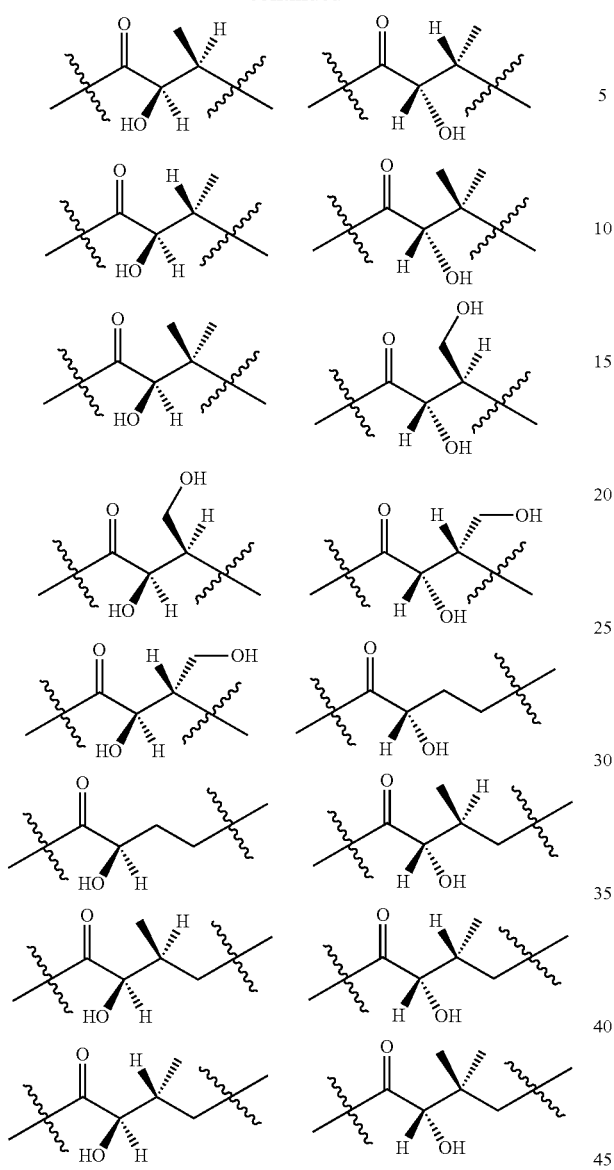
In one embodiment L1 is selected from:
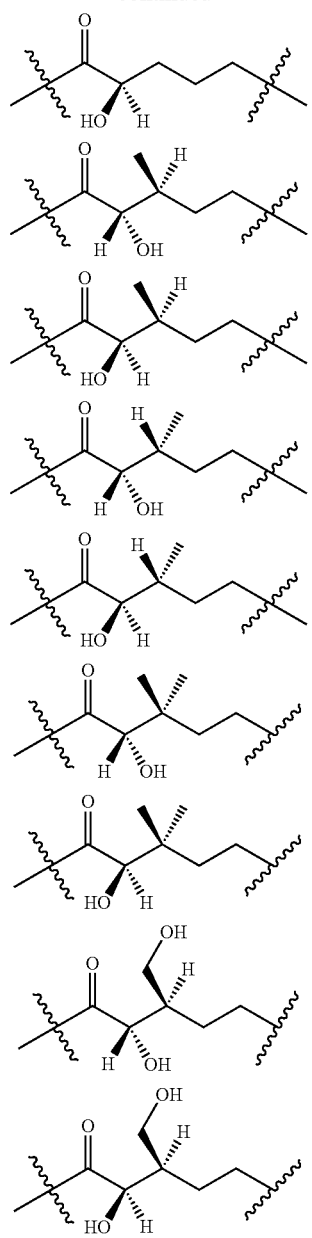
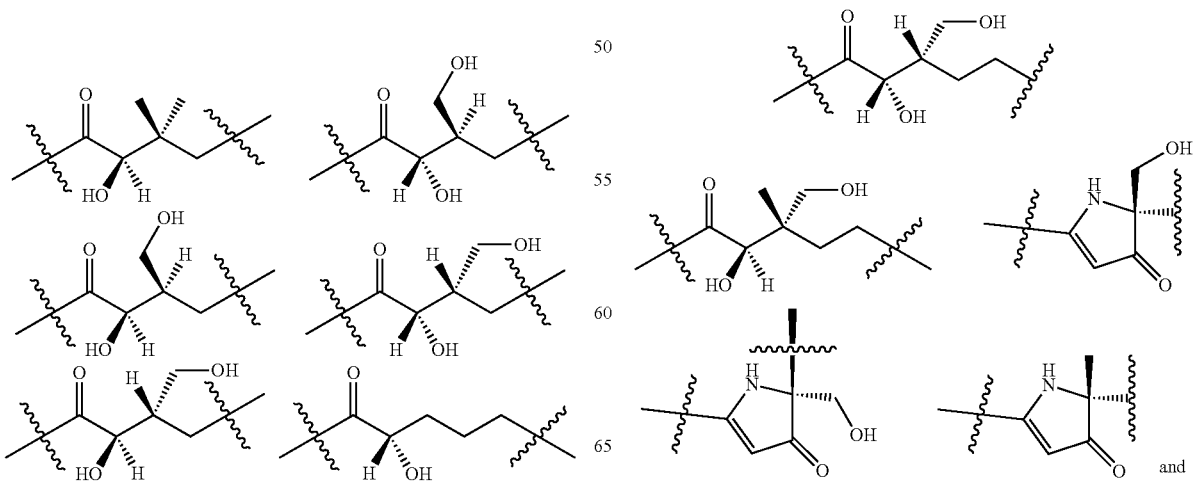
and

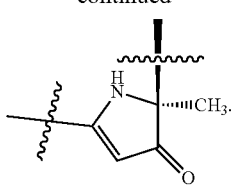
In one embodiment, the methyl groups in the structures illustrated above can be replaced with another alkyl group, as defined herein.
In one embodiment L1 is selected from:
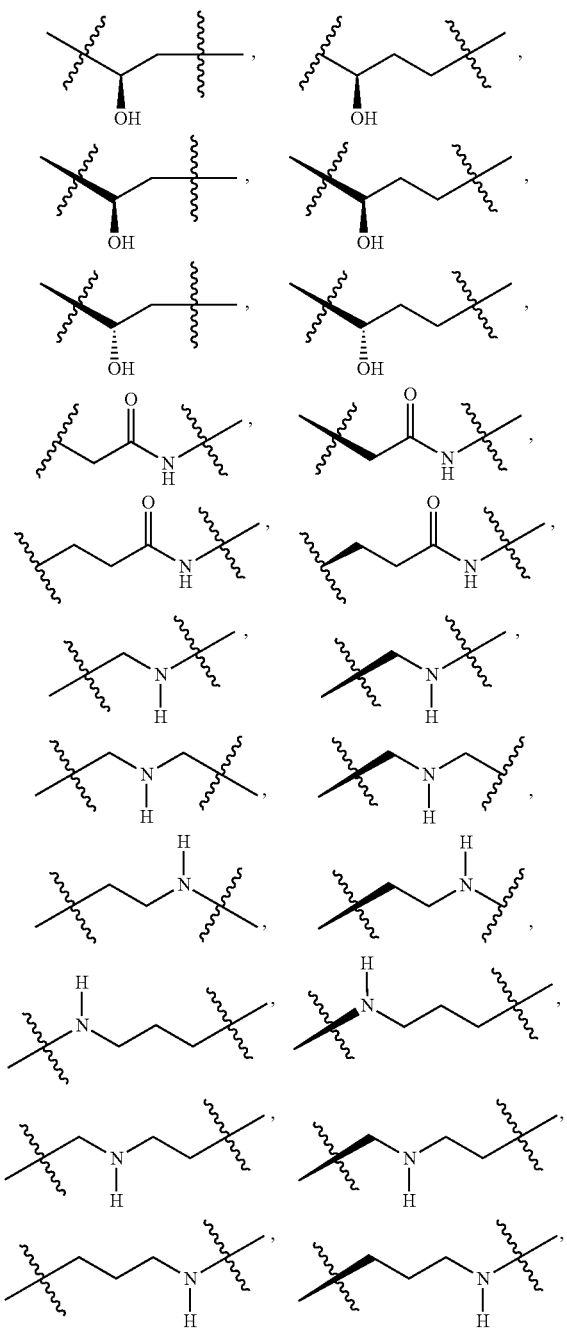
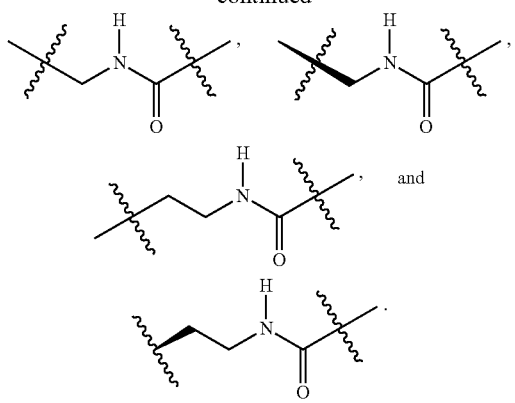
Non-limiting examples of L1 include:
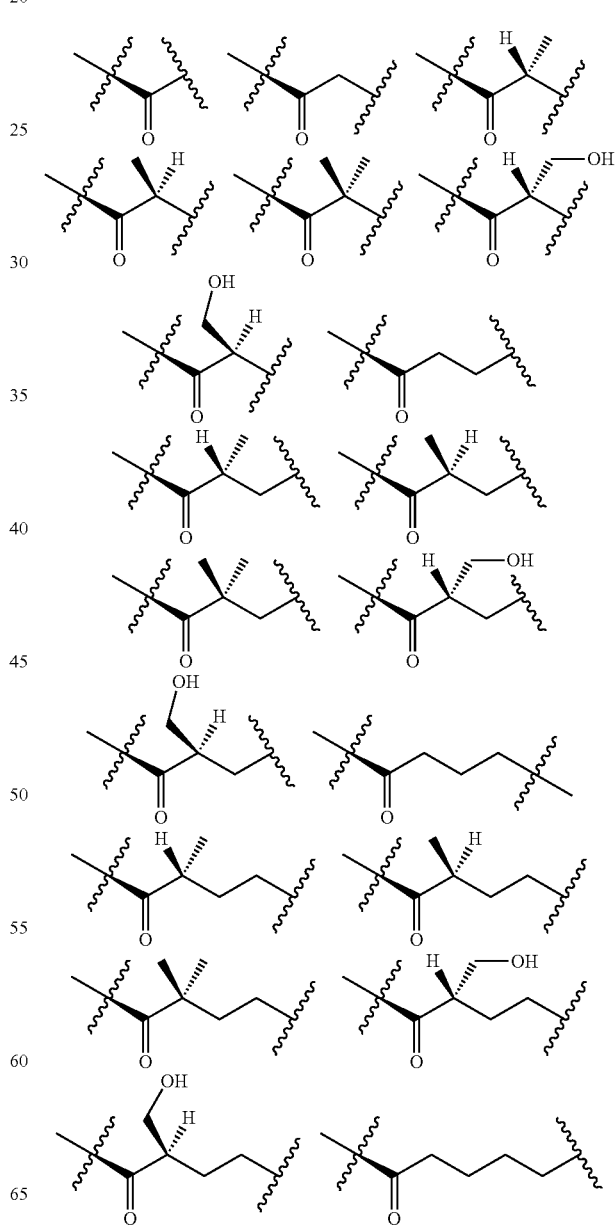

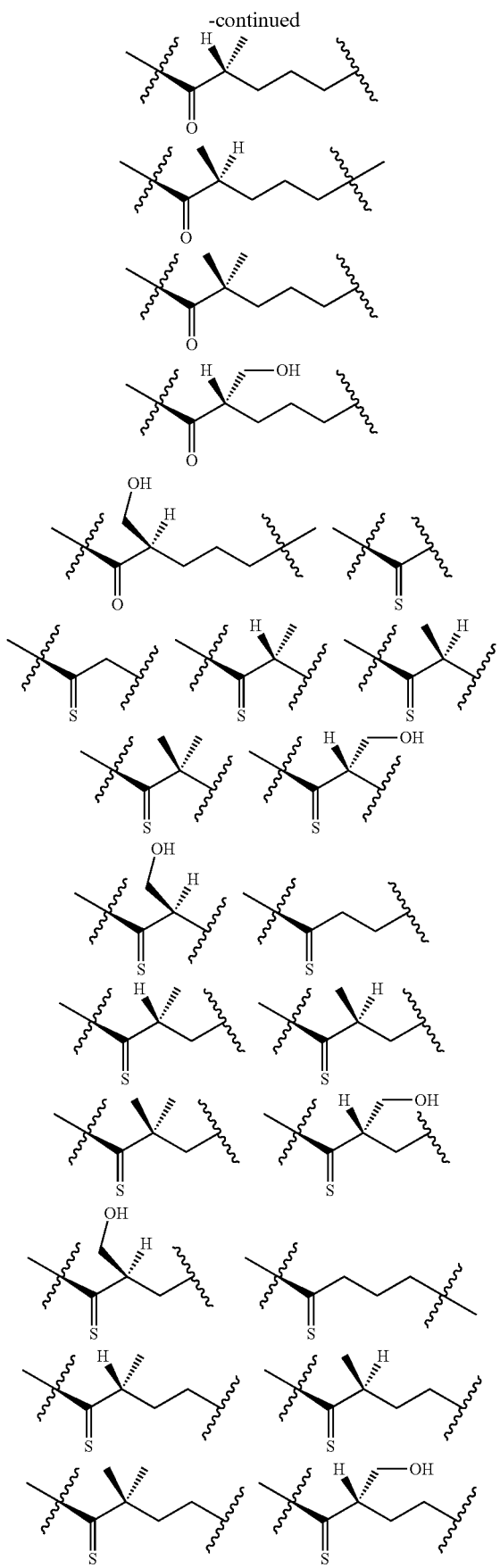
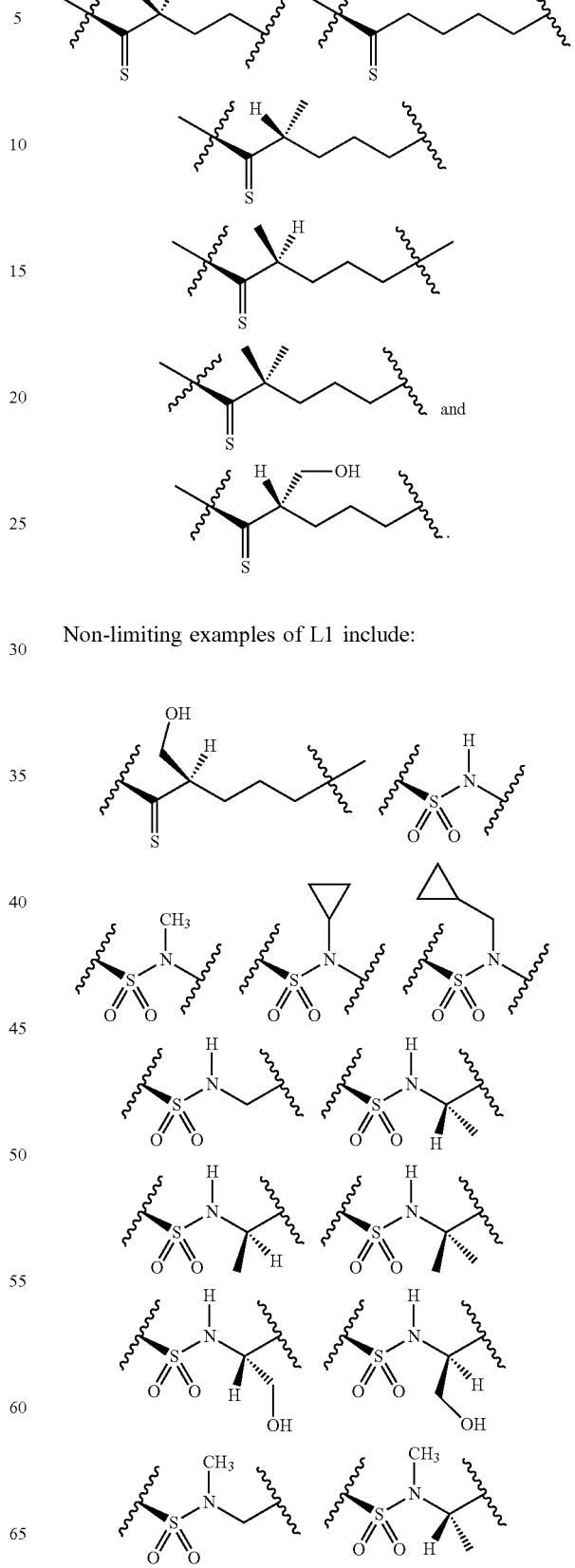
Non-limiting examples of L1 include:
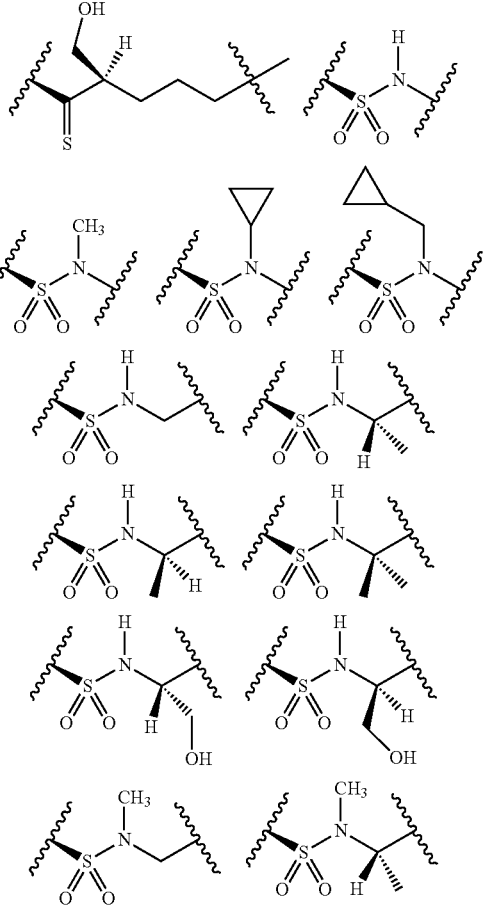

221
-continued
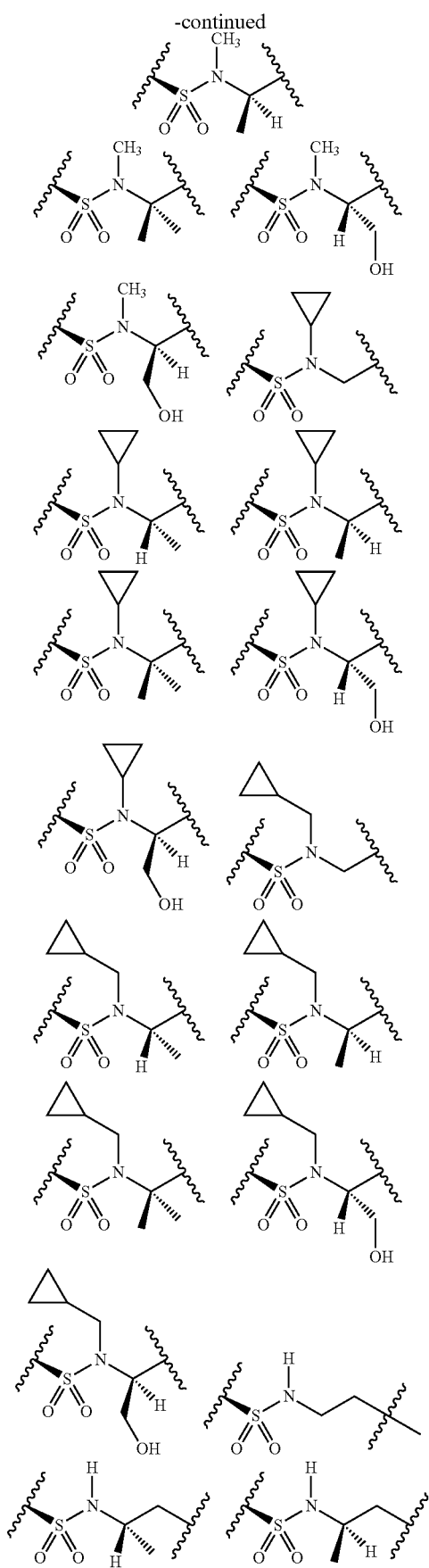
222
-continued
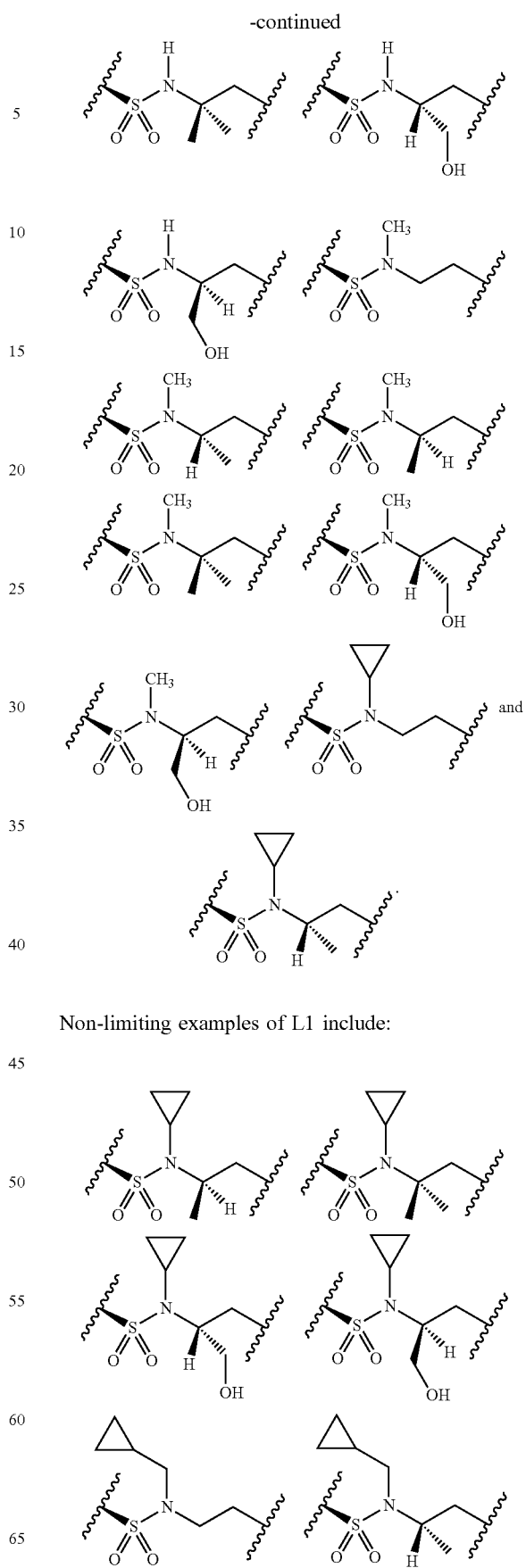
Non-limiting examples of L1 include:

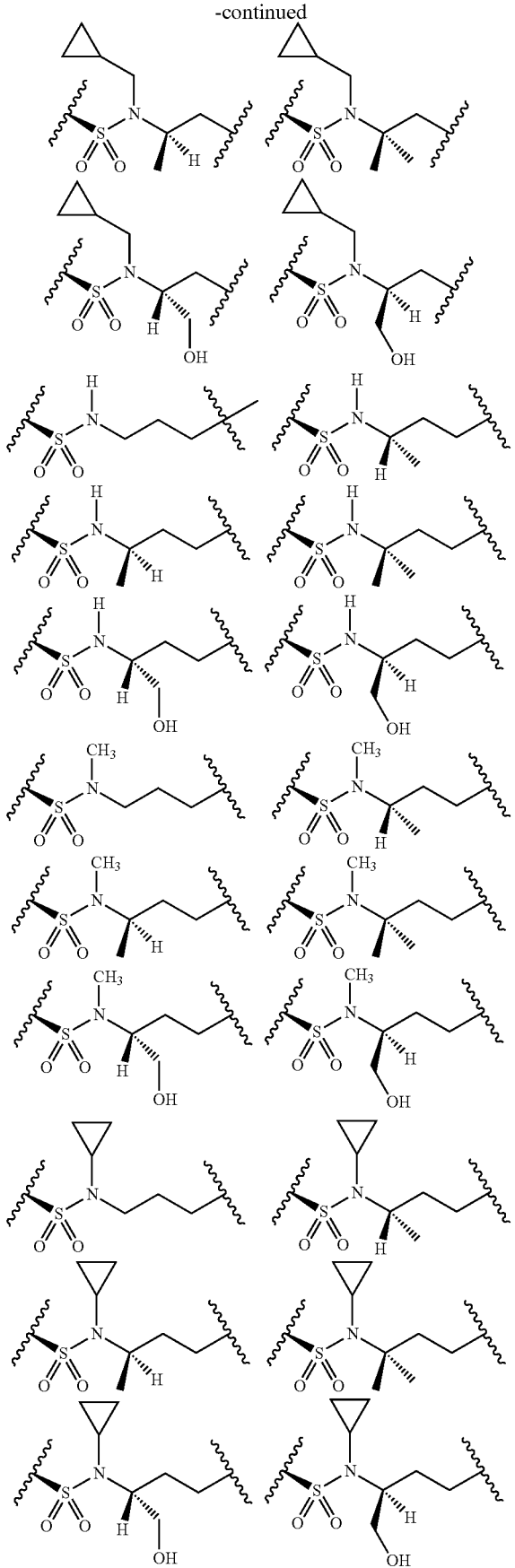
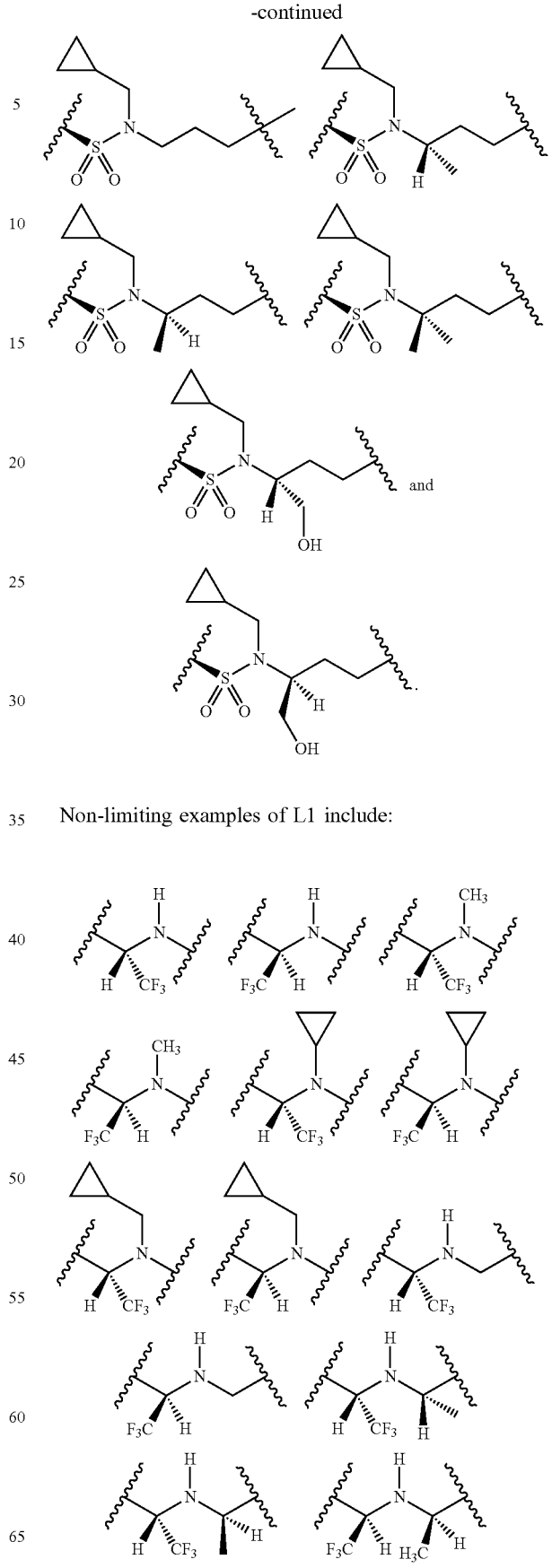
Non-limiting examples of L1 include:
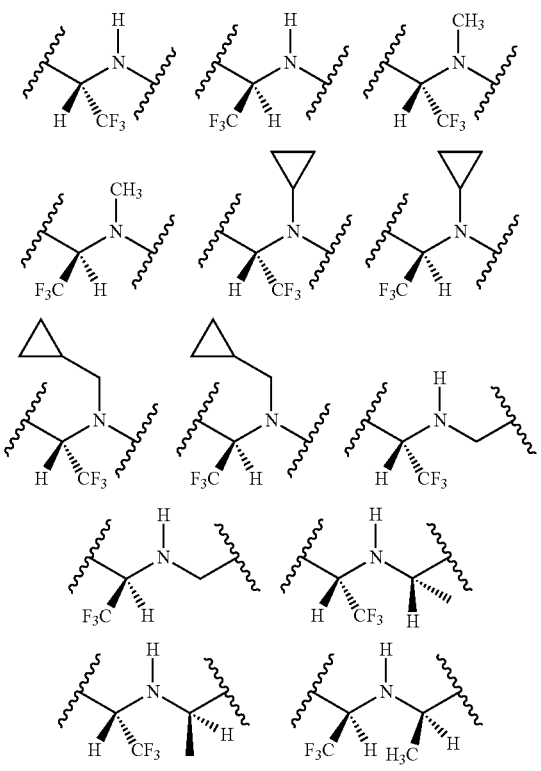

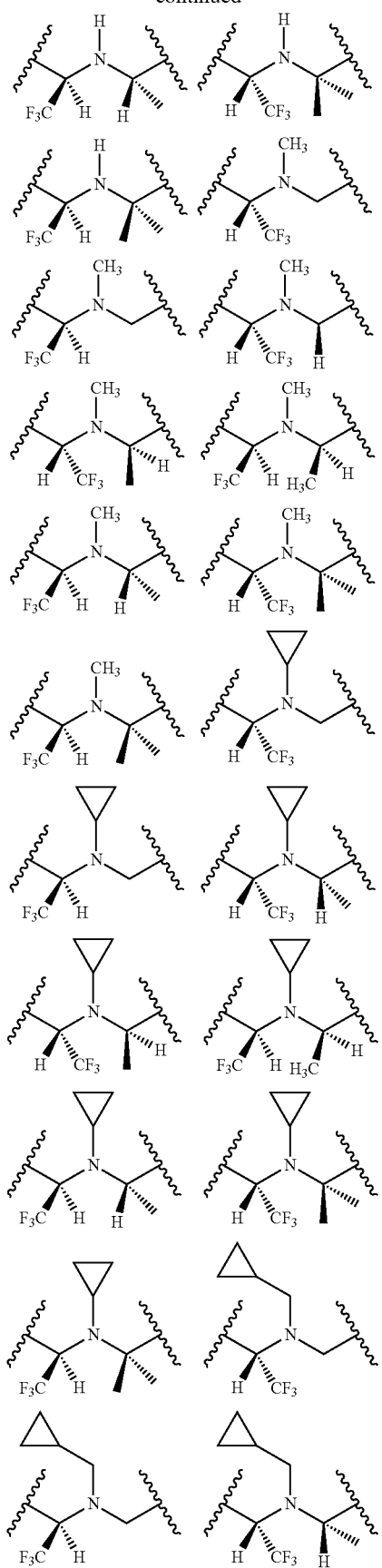
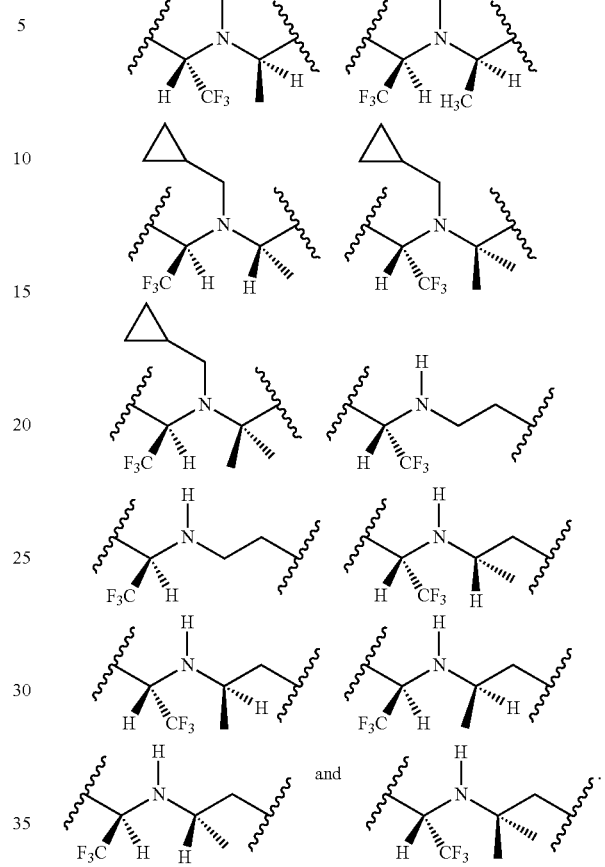
Non-limiting examples of L1 include:
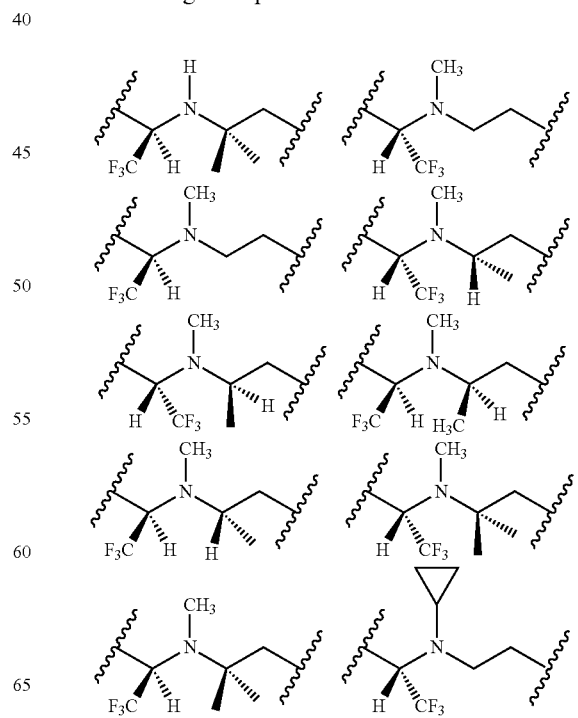

-continued

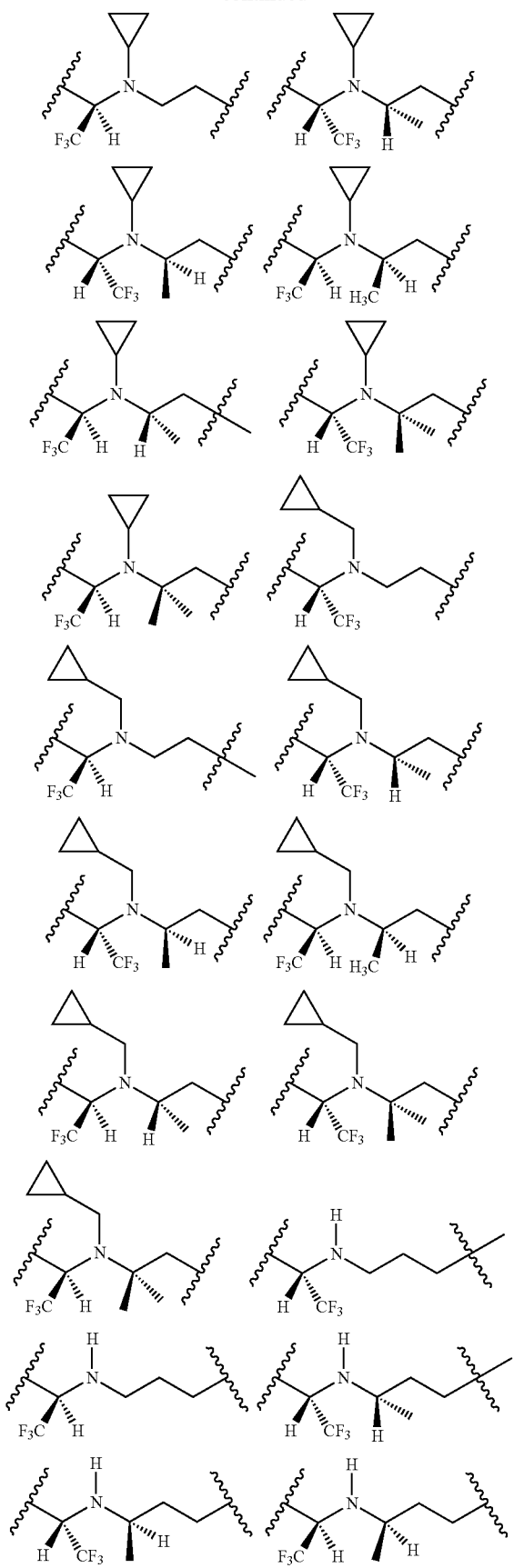

-continued

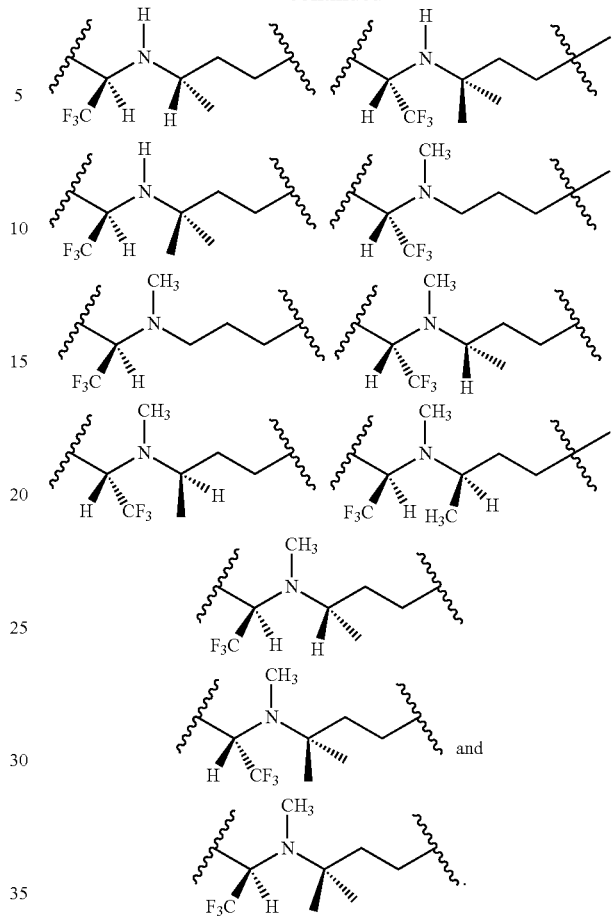

In one embodiment, the methyl groups in the structures illustrated above can be replaced with another alkyl or acyl, as defined herein. In another embodiment, the carbocyclic, heterocyclic, aryl or heteroaryl rings can be optionally substituted. As indicated above, any of the structures illustrated above or below can be optionally substituted with 0, 1, 2, 3, or 4, as appropriate, and independently, of an $R^{48}$ substituent.

In certain embodiment, L1 is a bond. In certain embodiments, if L1 is heterocyclic or heteroaryl, then B can be hydrogen.

Embodiments of $R^{201}$

In one embodiment $R^{201}$ is selected from —$(CH_2)_m$—O-heterocycle, —$(CH_2)_m$—NH-heterocycle, or —$(CH_2)_m$—$NR^9$-heterocycle;

In one embodiment $R^{201}$ is selected from —$(CH_2)_m$—$NR^9R^{10}$, —$(CH_2)_m$—$OR^9$, or —$(CH_2)_m$-heterocycle;

In one embodiment $R^{201}$ is selected from —$CH_2$—O-heterocycle, —$CH_2$—NH-heterocycle, or —$CH_2$—$NR^9$-heterocycle;

In one embodiment $R^{201}$ is selected from —$CH_2$—$NR^9R^{10}$, —$CH_2$—$OR^9$, or —$CH_2$-heterocycle;

In one embodiment $R^{201}$ is selected from —$(CH_2)_m$—$NH_2$, —$(CH_2)_m$—OH, or —$(CH_2$—$OC_1$-$C_6$alkyl;

In one embodiment $R^{201}$ is selected from:
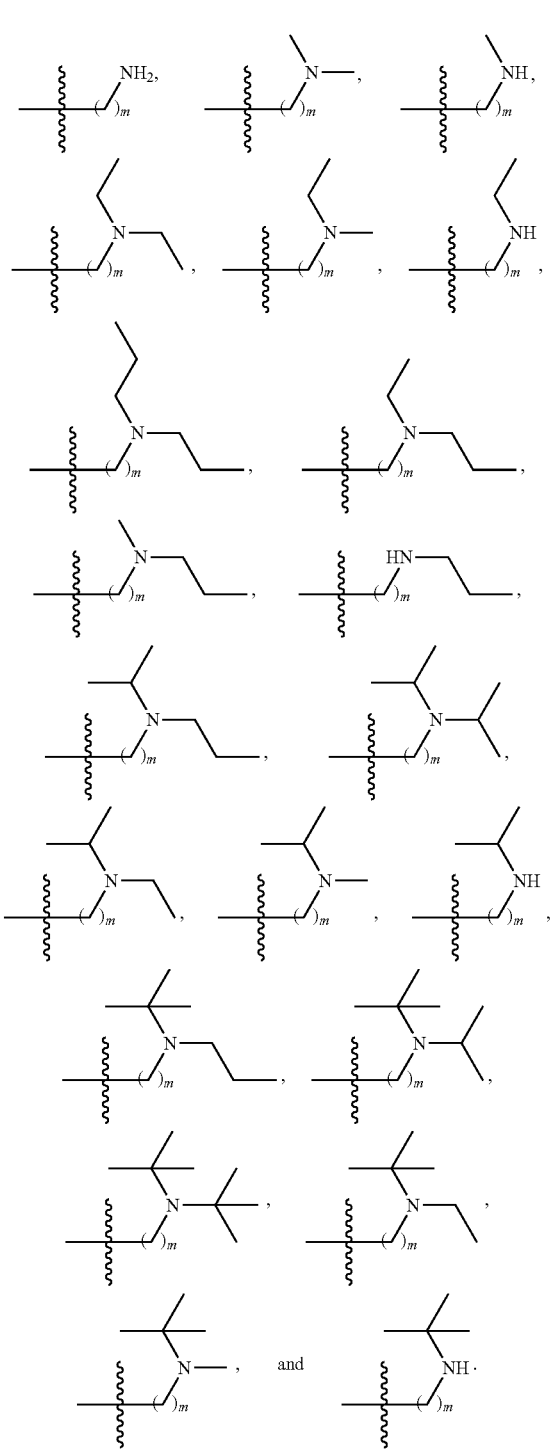
In one embodiment $R^{201}$ is selected from:
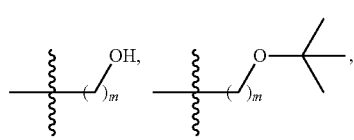
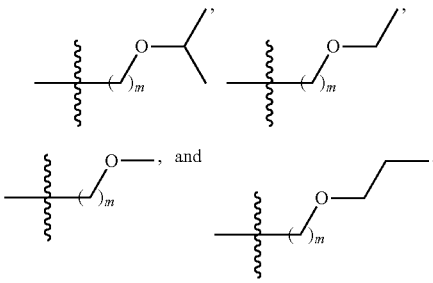
In one embodiment $R^{201}$ is selected from:
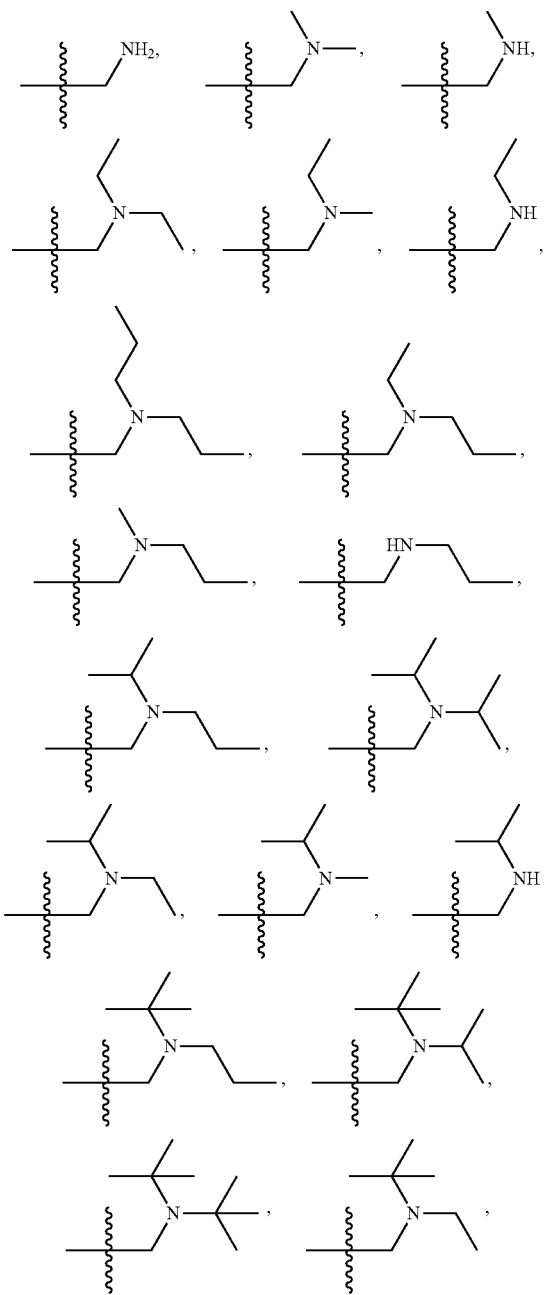

In one embodiment R²⁰¹ is selected from:

In one embodiment R²⁰¹ is selected from:

In one embodiment R²⁰¹ is selected from:

In one embodiment R²⁰¹ is selected from:

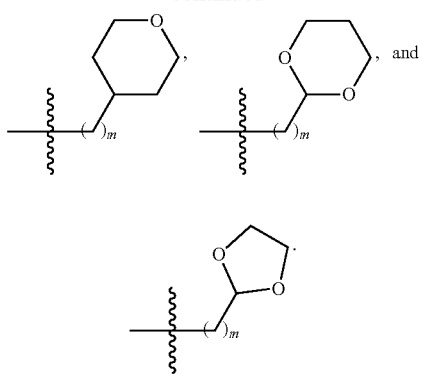
In one embodiment $R^{201}$ is selected from:
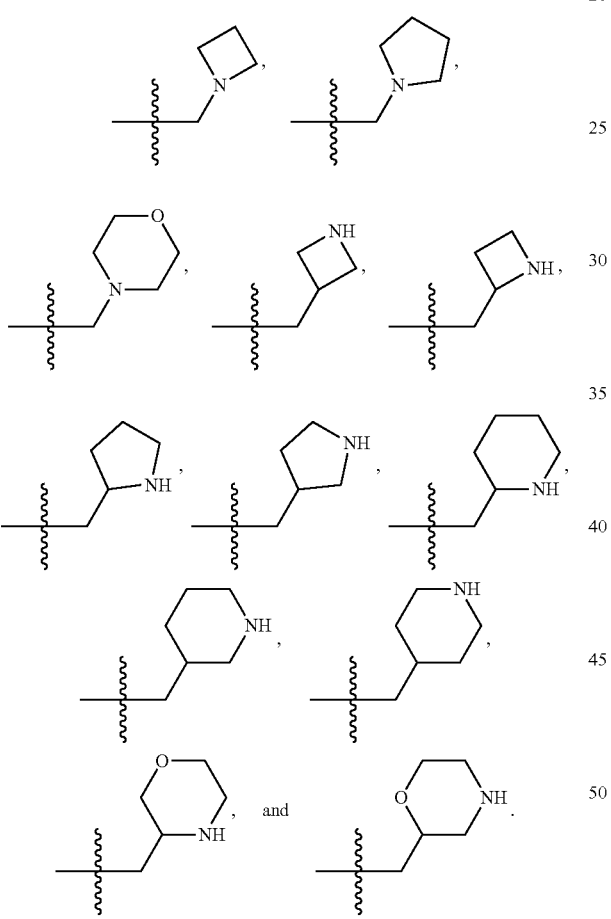
In one embodiment $R^{201}$ is selected from:
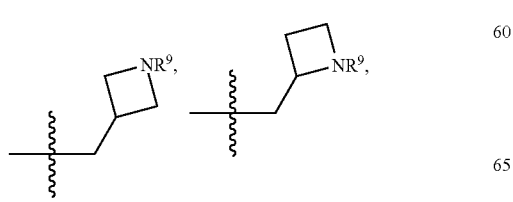
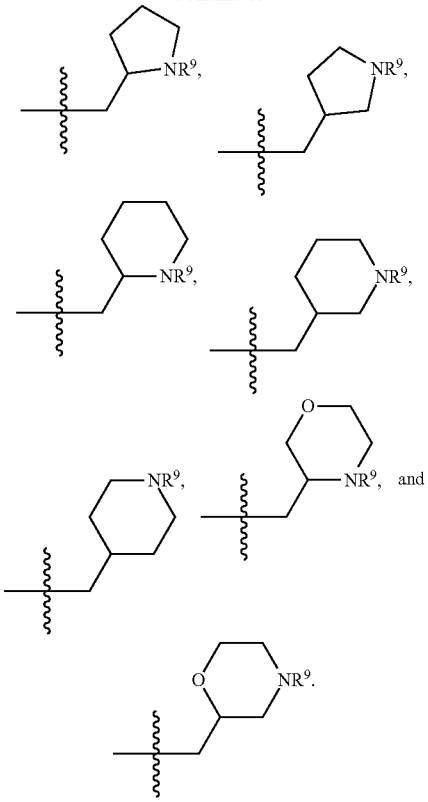
In one embodiment $R^{201}$ is selected from:
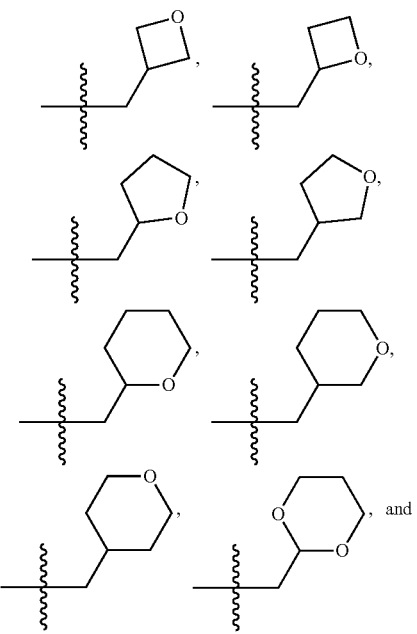
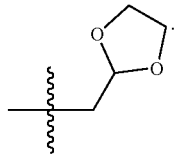

In one embodiment R$^{201}$ is selected from:
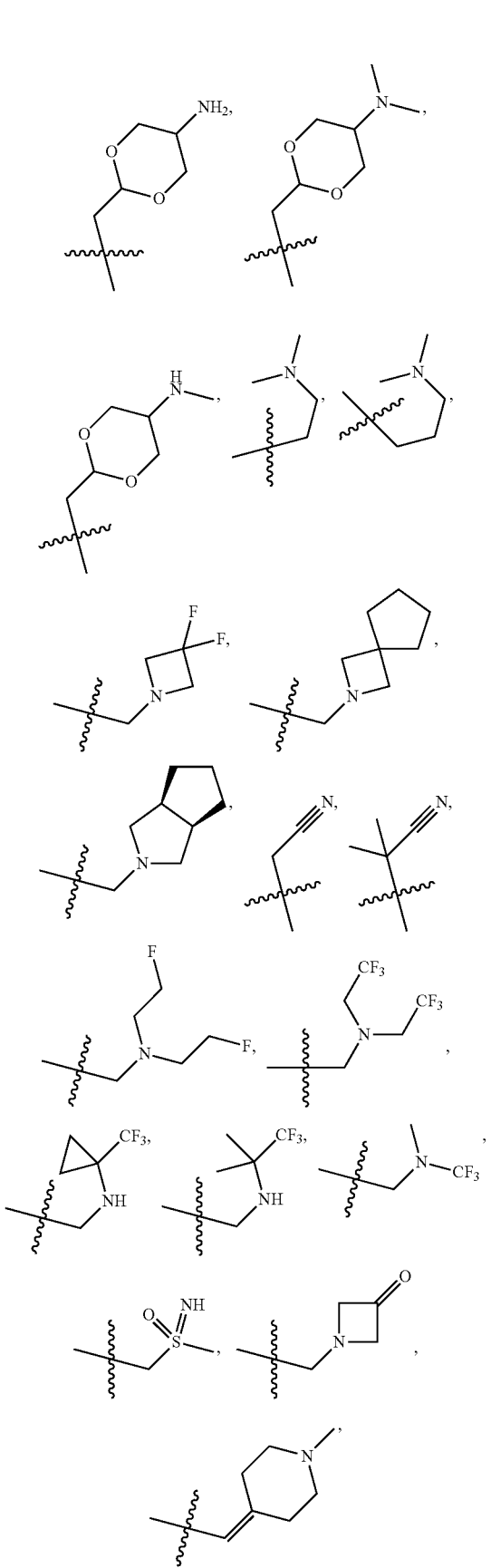
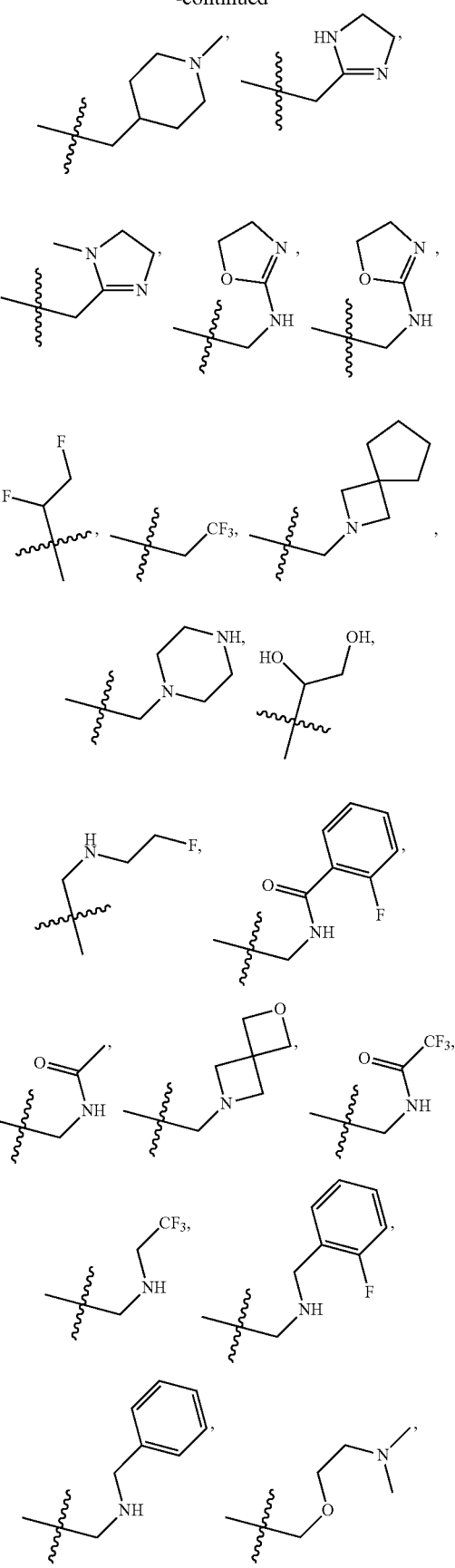

237

-continued

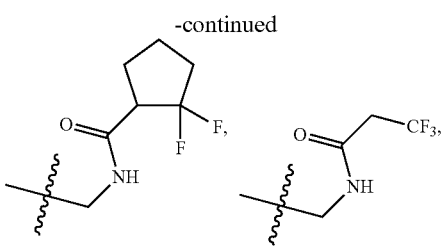

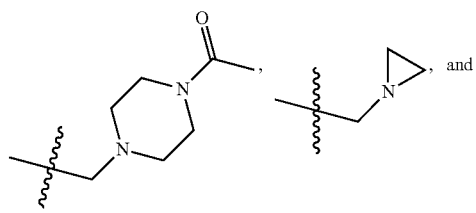

238

-continued

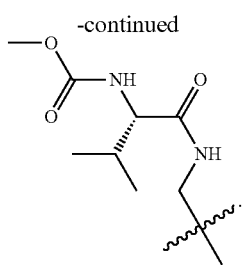

Embodiments of $R^{301}$

Examples of $R^{301}$ are provided below. In the compounds of the present invention, $R^{301}$ is monovalently attached to the molecule. The divalent species below are presented to illustrate that the $R^{301}$ can be linked at either point and the other is capped for example with H, alkyl, halogen, haloalkyl, aryl, heteroaryl, and heterocycle, each of which may be optionally substituted as described herein. In one embodiment $R^{301}$ is selected from:

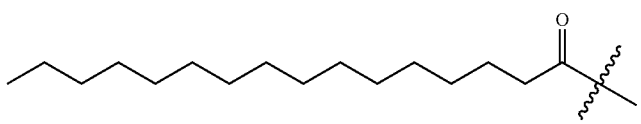

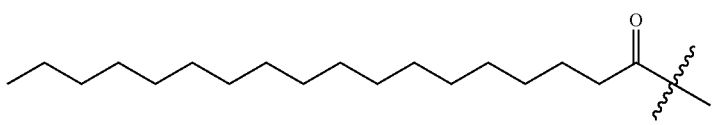

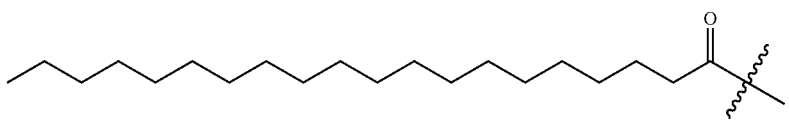

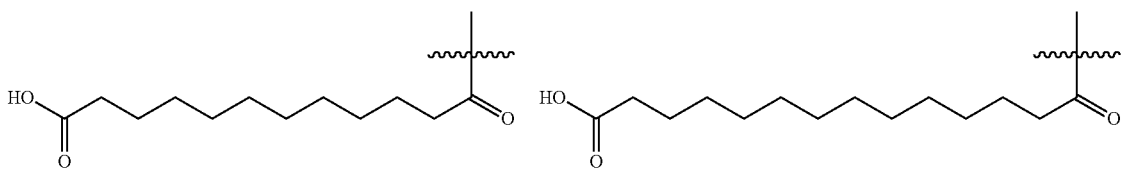

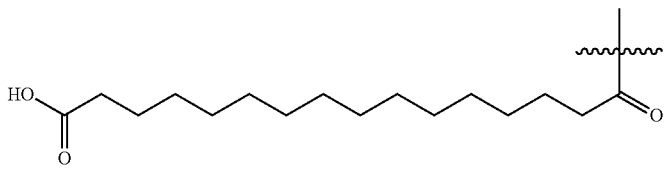

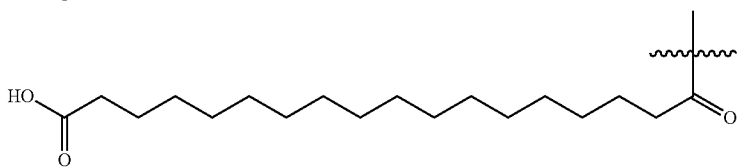

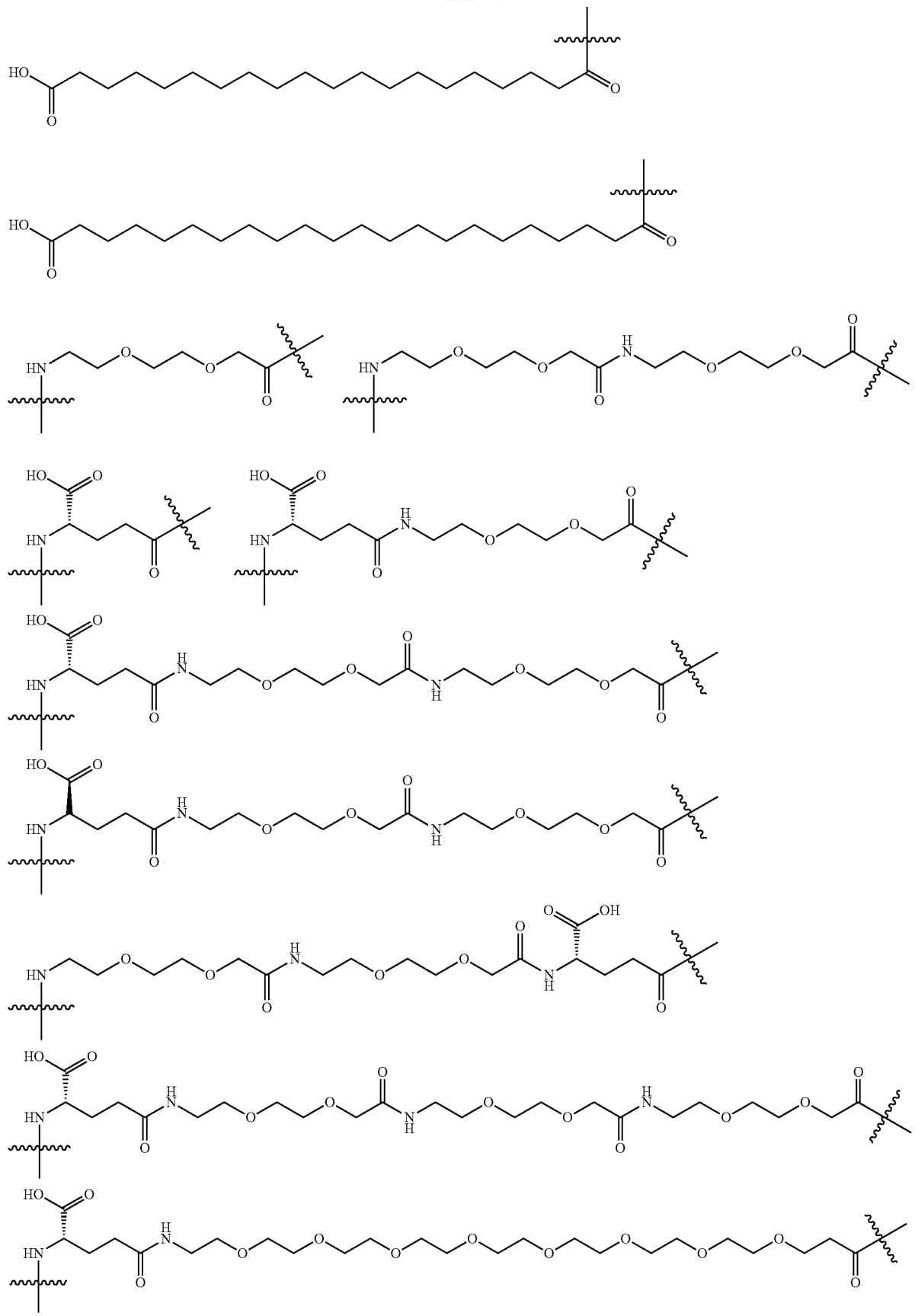

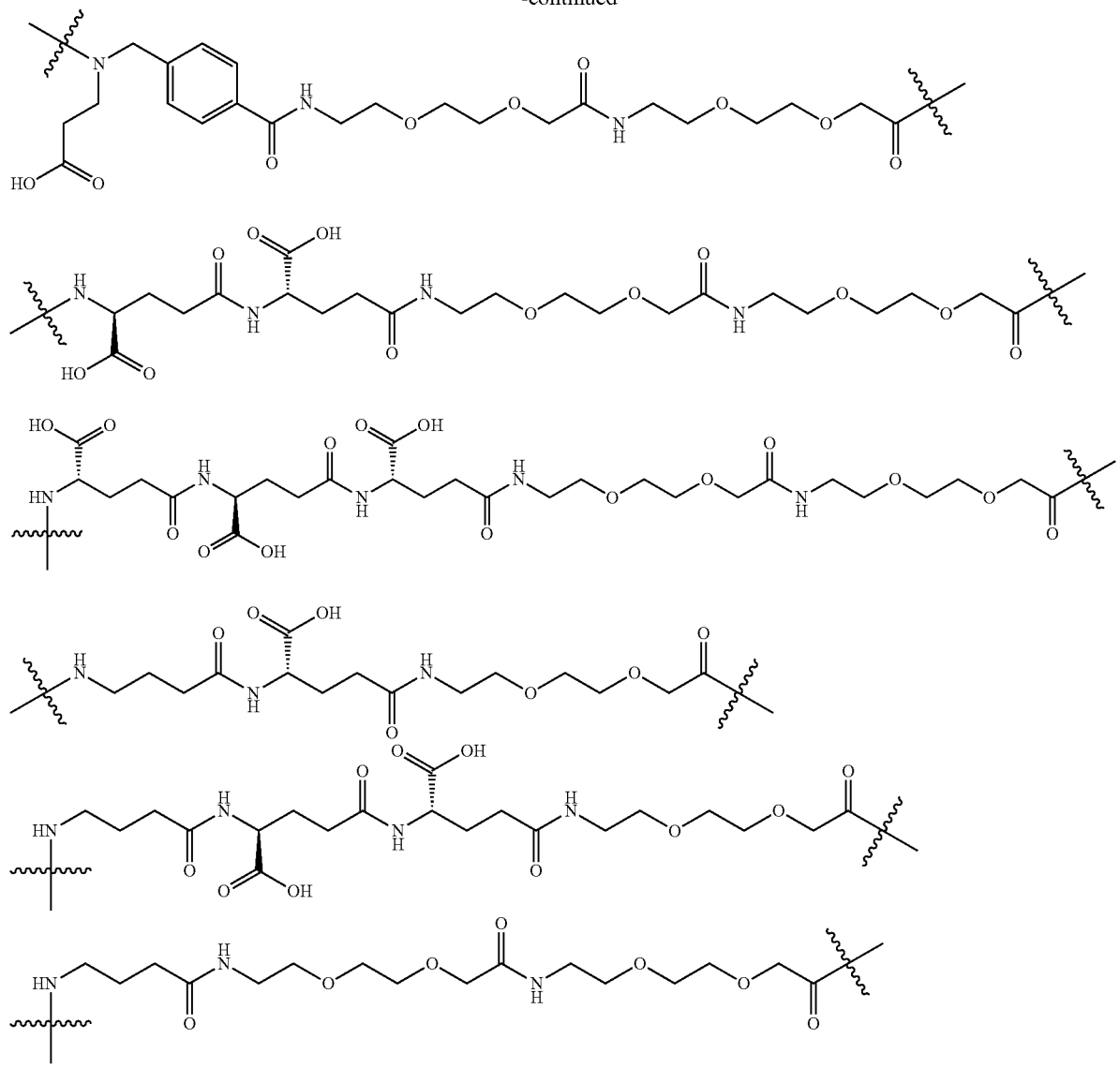
wherein if the moiety is shown as a divalent species, it can also be capped with a bioactive moiety or prodrug moiety.
In one embodiment $R^{301}$ is selected from:
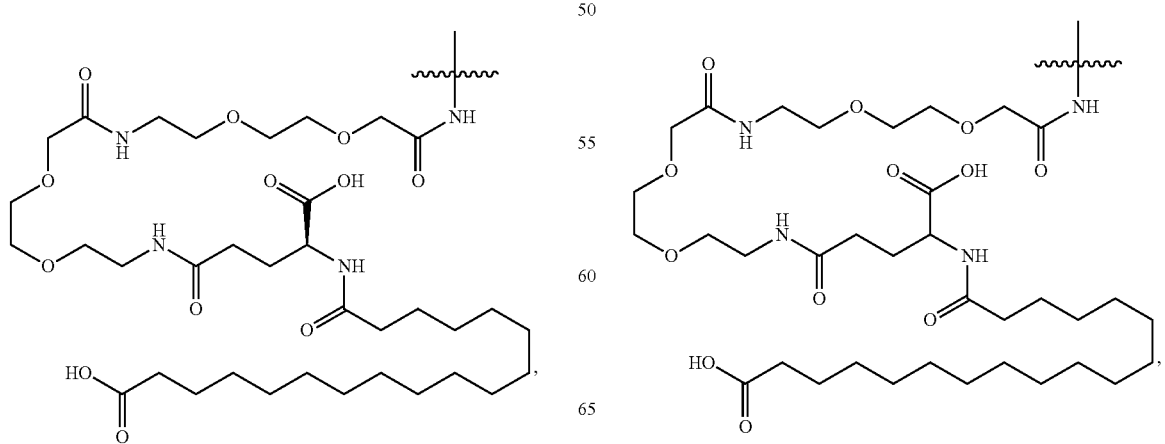
-continued

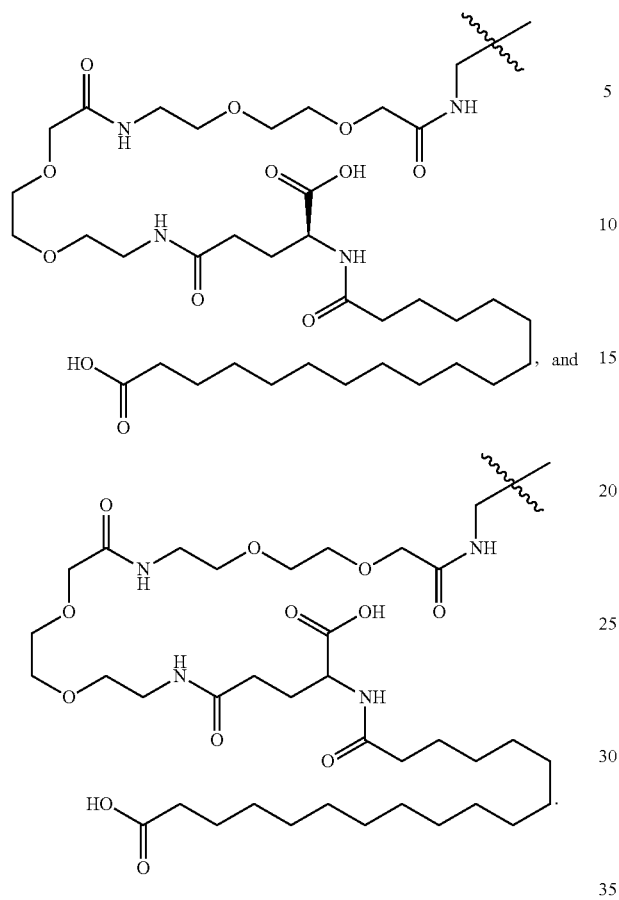, and
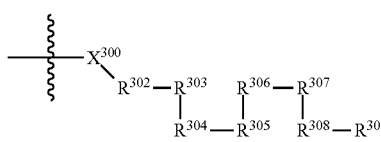.
In one embodiment $R^{301}$ is
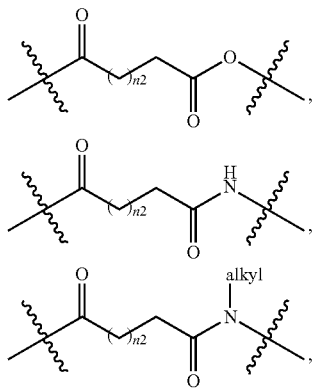;
wherein $R^{302}$, $R^{303}$, $R^{304}$, $R^{305}$, $R^{306}$, $R^{307}$, and $R^{308}$ are selected from: bond, polyethylene glycol, a natural amino acid, an unnatural amino acid,
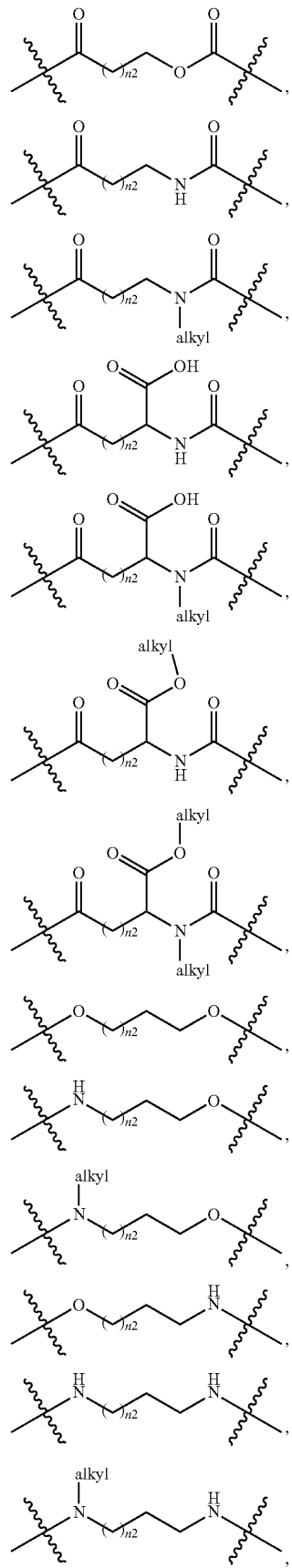

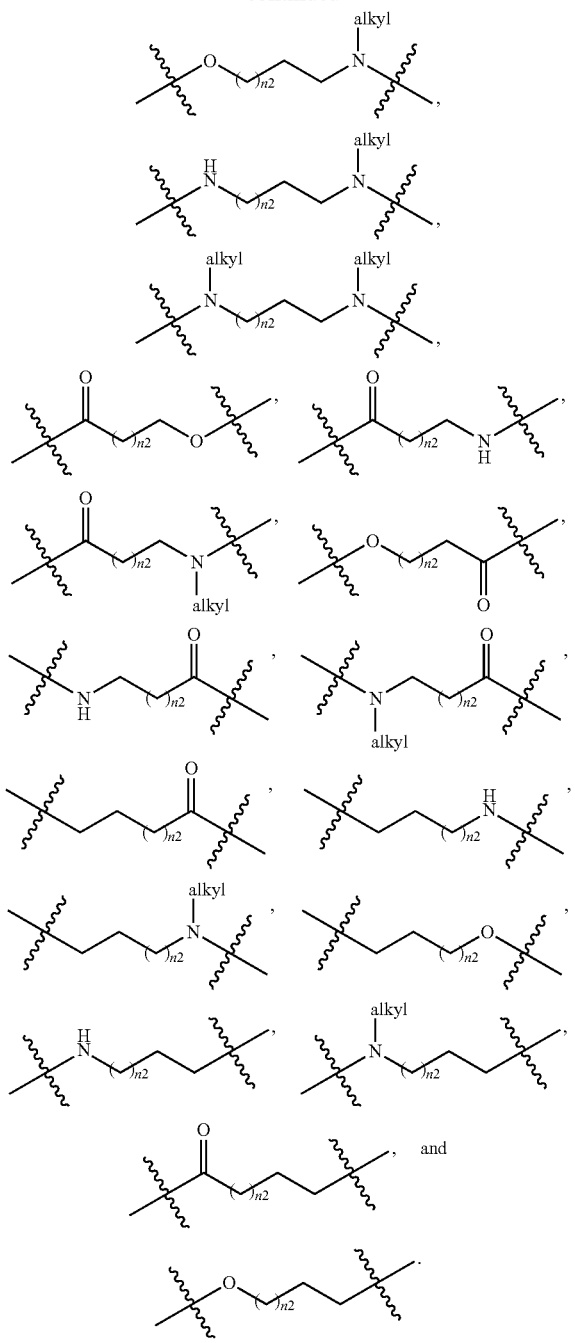

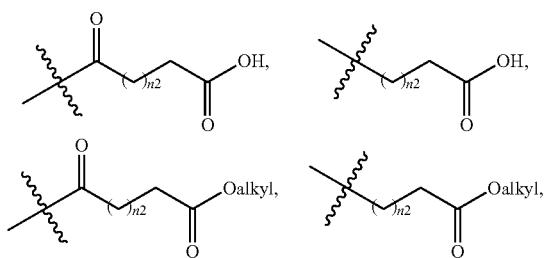

R³⁰⁹ is selected from: alkyl, hydrogen,

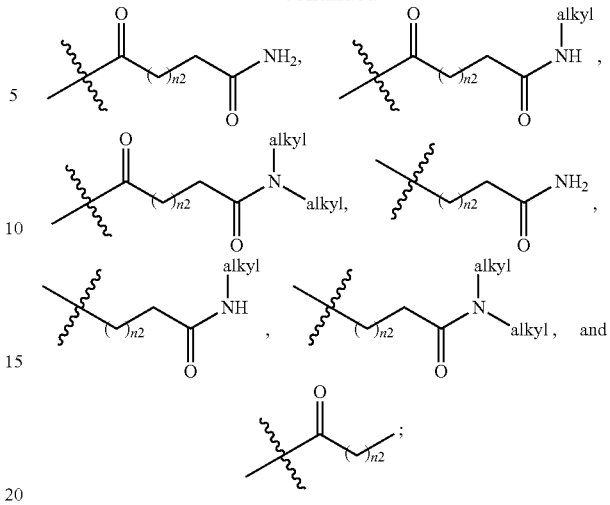

n2 is independently selected at each instance from 0, 1, 2, 3, 4, 5, 6, 7, 8, 9, 10, 11, 12, 13, 14, 15, 16, 17, 18, 19, and 20; and X³⁰⁰ is selected from bond, —NH—, —N(alkyl)-, O, —CH₂—O—, —CH₂—NH—, and —CH₂—N(alkyl).

In one embodiment only 1, 2, 3, 4, or 5 of R³⁰², R³⁰³, R³⁰⁴, R³⁰⁵, R³⁰⁶, R³⁰⁷, and R³⁰⁸ are selected to be bond.

In one embodiment none of R³⁰², R³⁰³, R³⁰⁴, R³⁰⁵, R³⁰⁶, R³⁰⁷, and R³⁰⁸ are selected to be bond.

In one embodiment only 1 of R³⁰², R³⁰³, R³⁰⁴, R³⁰⁵, R³⁰⁶, R³⁰⁷, and R³⁰⁸ are selected to be bond.

In one embodiment only 2 of R³⁰², R³⁰³, R³⁰⁴, R³⁰⁵, R³⁰⁶, R³⁰⁷, and R³⁰⁸ are selected to be bond.

In one embodiment only 3 of R³⁰², R³⁰³, R³⁰⁴, R³⁰⁵, R³⁰⁶, R³⁰⁷, and R³⁰⁸ are selected to be bond.

In one embodiment only 4 of R³⁰², R³⁰³, R³⁰⁴, R³⁰⁵, R³⁰⁶, R³⁰⁷, and R³⁰⁸ are selected to be bond.

In one embodiment only 5 of R³⁰², R³⁰³, R³⁰⁴, R³⁰⁵, R³⁰⁶, R³⁰⁷, and R³⁰⁸ are selected to be bond.

Non-limiting examples of compounds of the present invention with a R³⁰¹ group include:

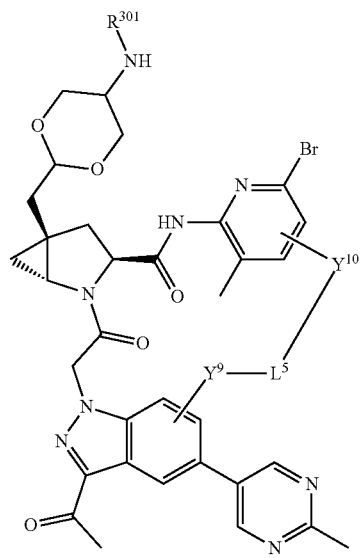

247
-continued
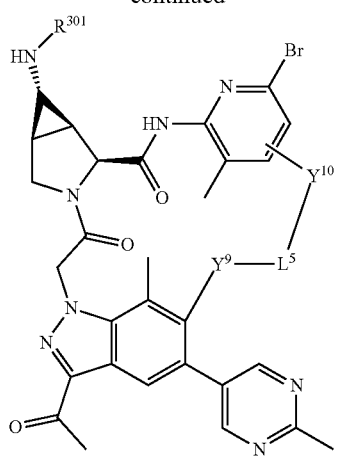
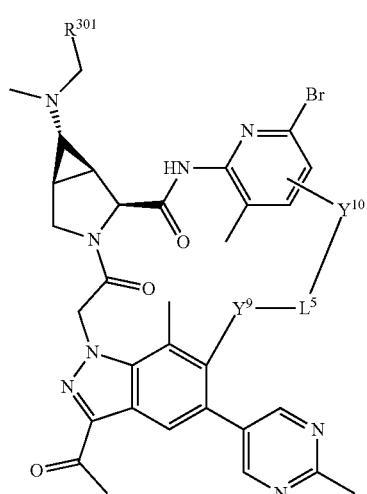
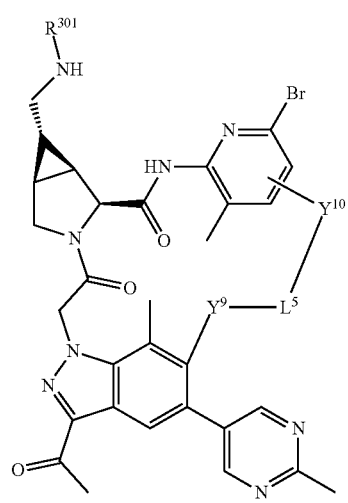
248
-continued
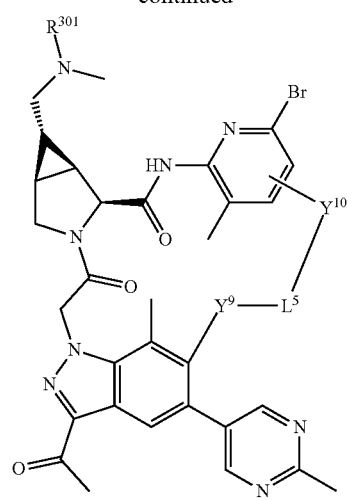
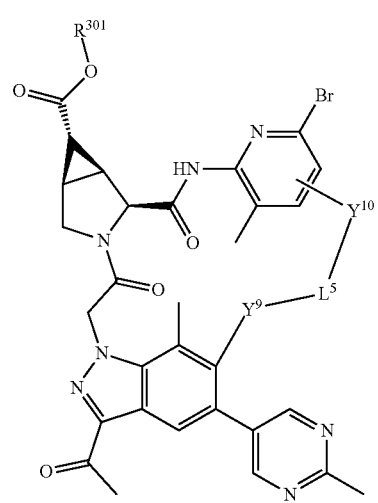
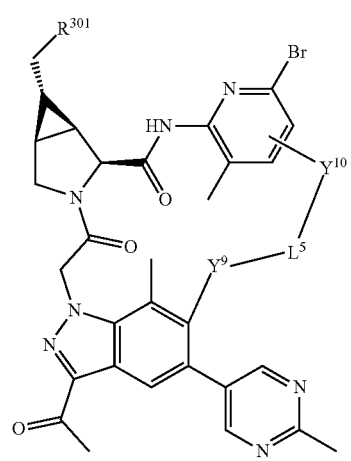

-continued
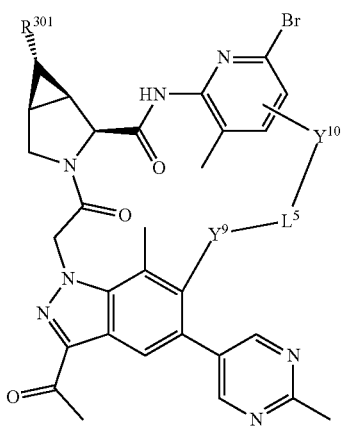
Non-limiting examples of compounds of the present invention with a $R^{301}$ group include:
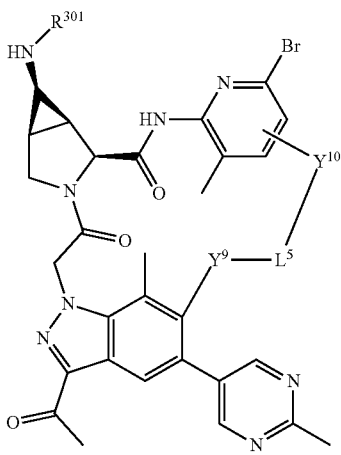
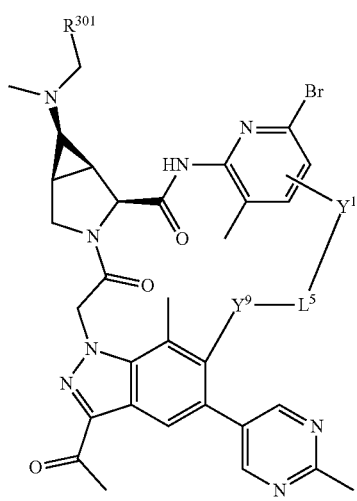
-continued
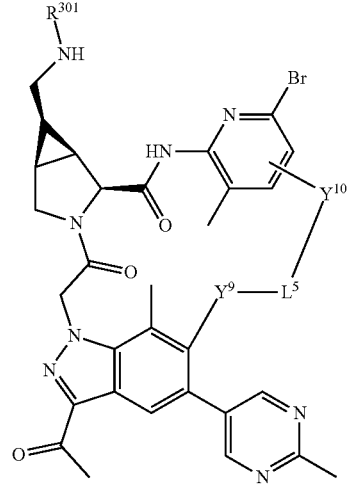
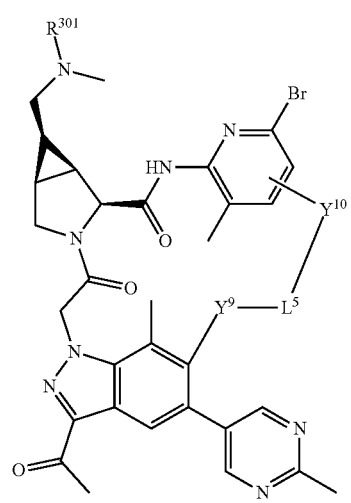
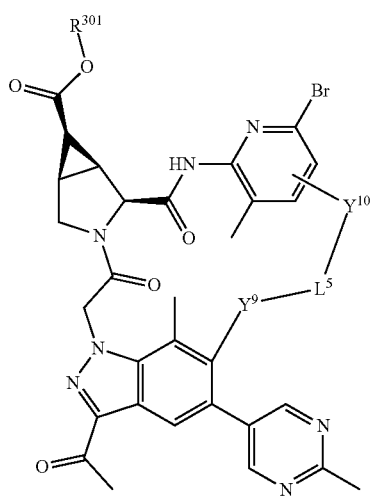

-continued
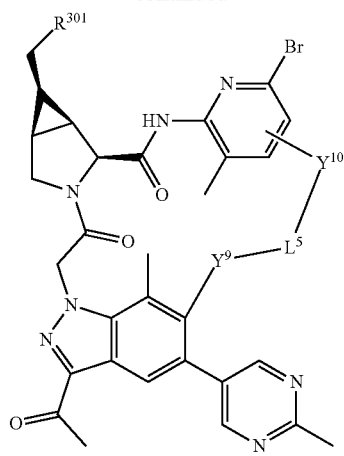
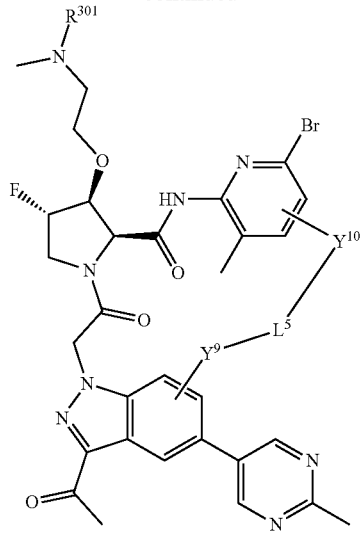
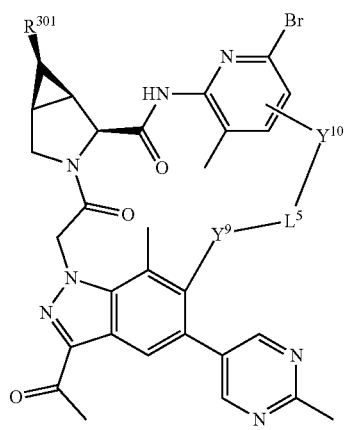
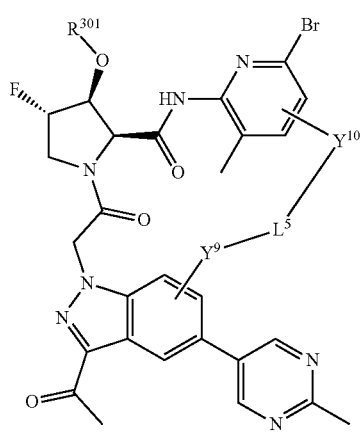
Non-limiting examples of compounds of the present invention with a R³⁰¹ group include:
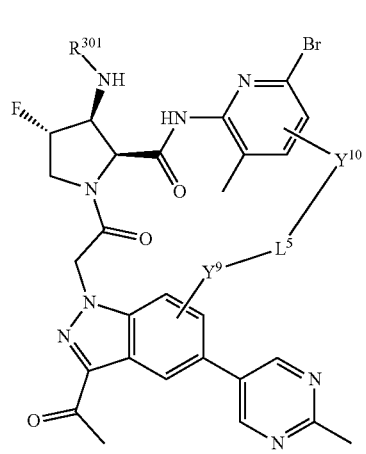
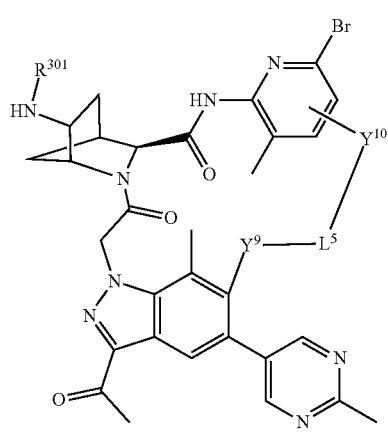

253
-continued
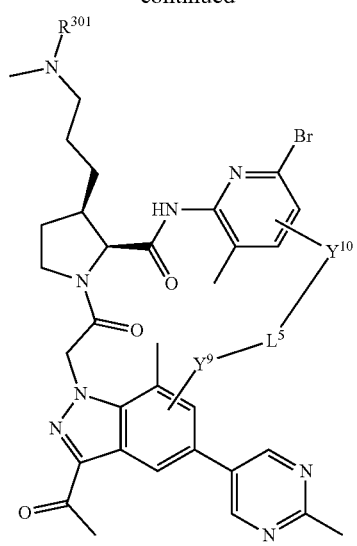
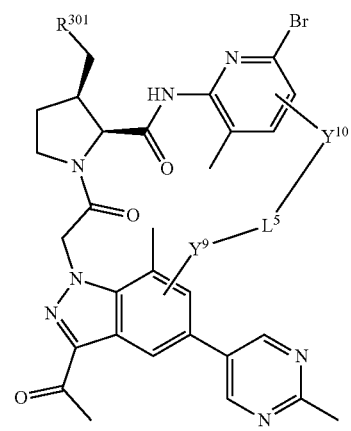
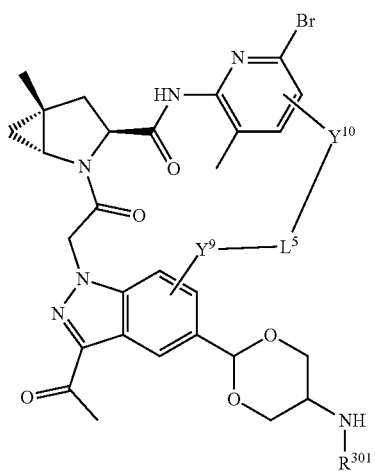
254
-continued
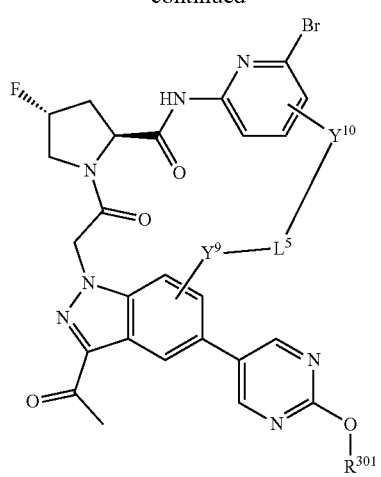
Non-limiting examples of compounds of the present invention with a $R^{301}$ group include:
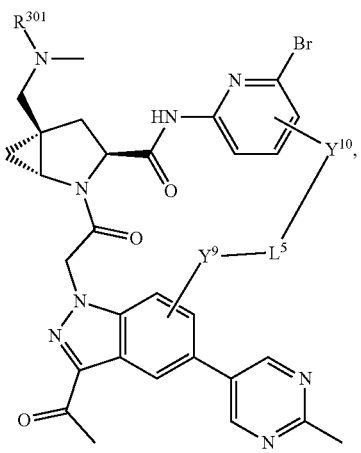
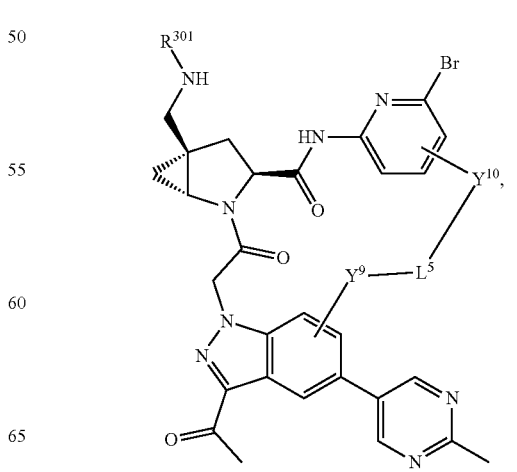

255
-continued
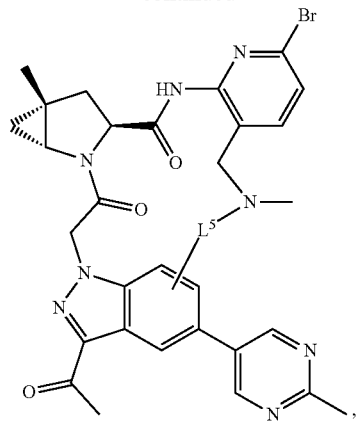
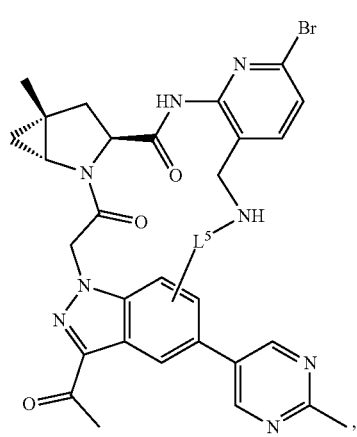
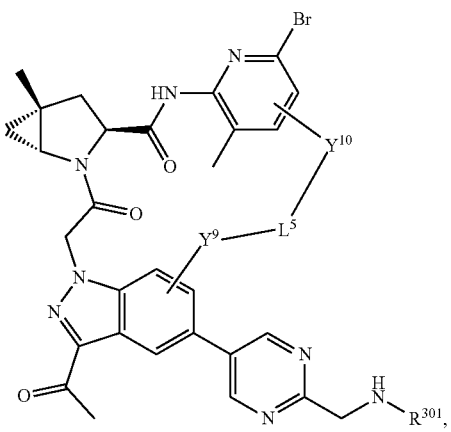
256
-continued
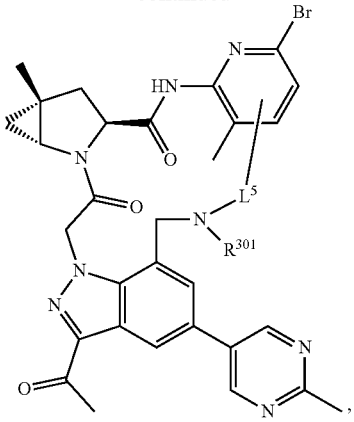
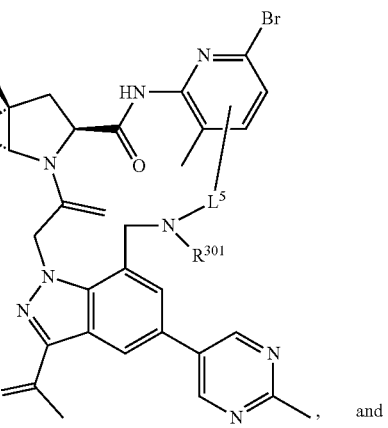
, and
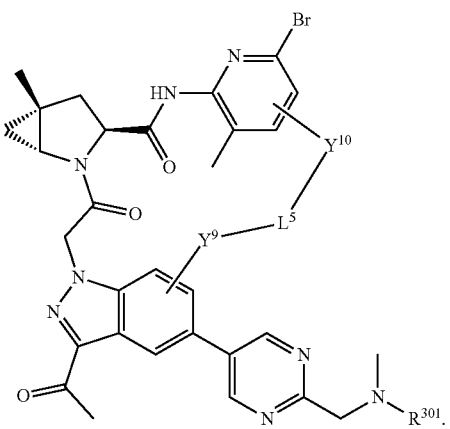

Non-limiting examples of compounds with an $R^{301}$ and/or $R^{201}$ substituent of the present invention include:
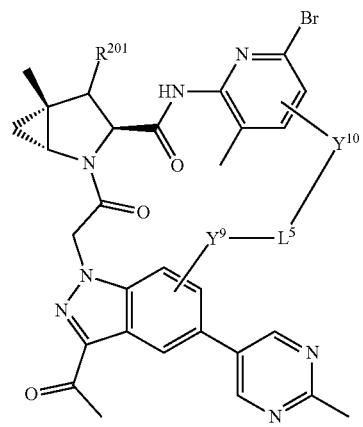
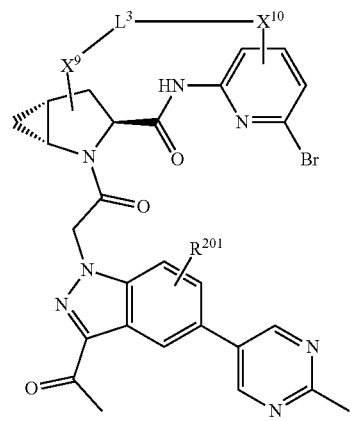
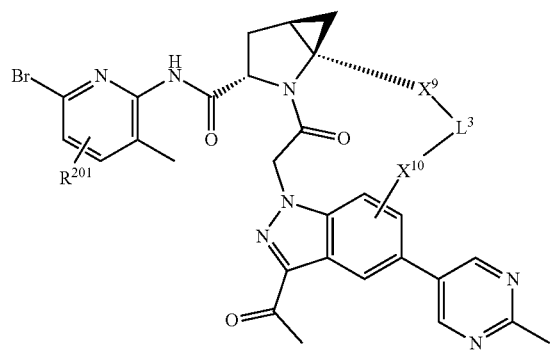
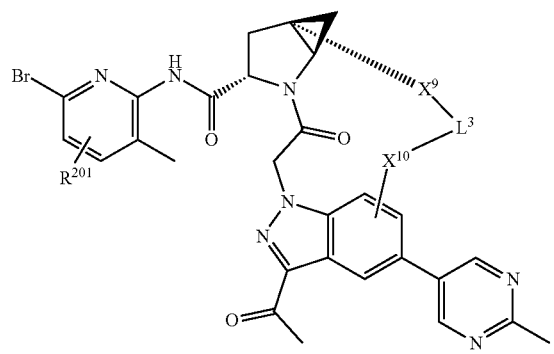
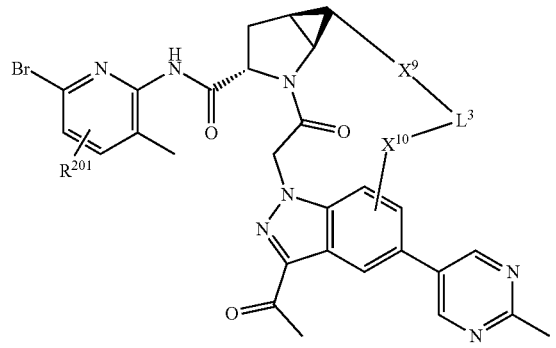
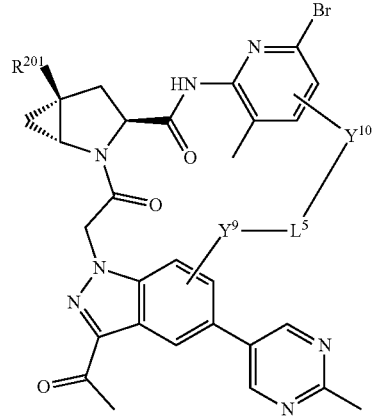
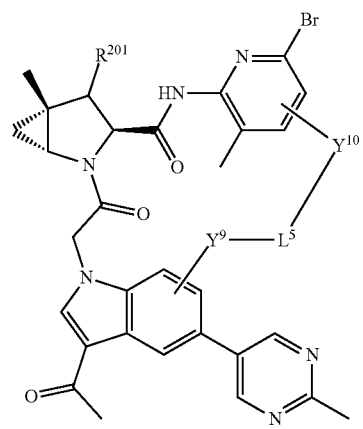
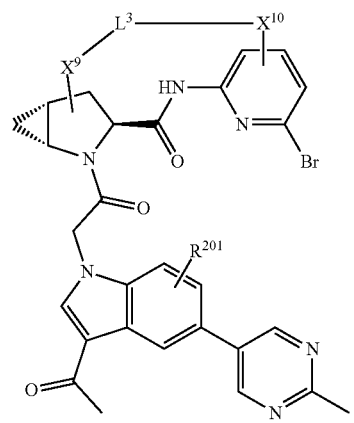

259 260
-continued
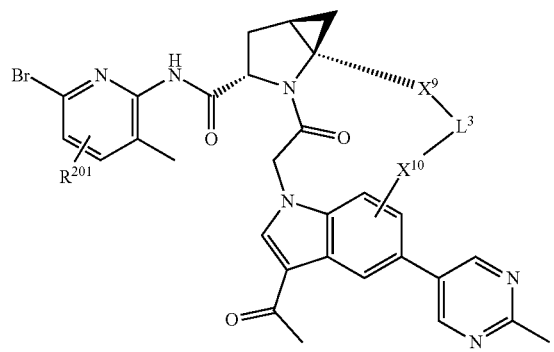
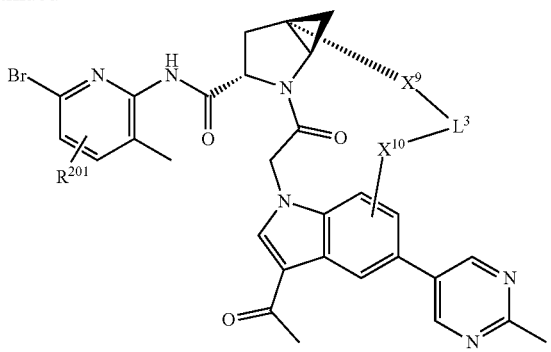
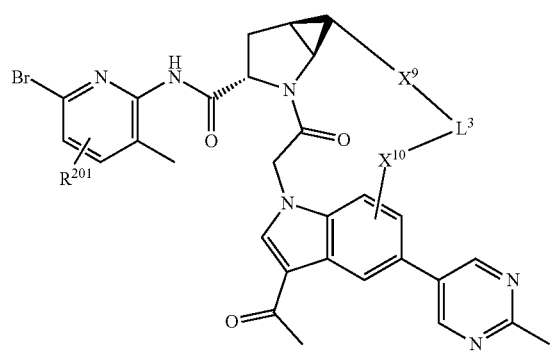
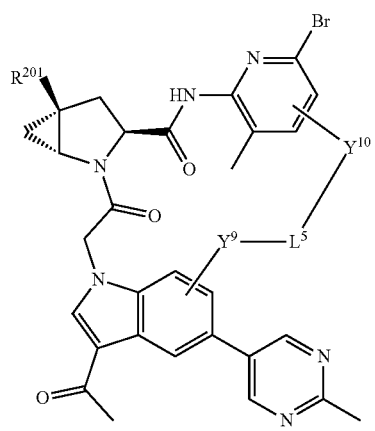
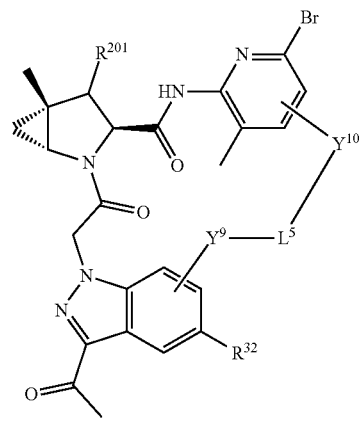
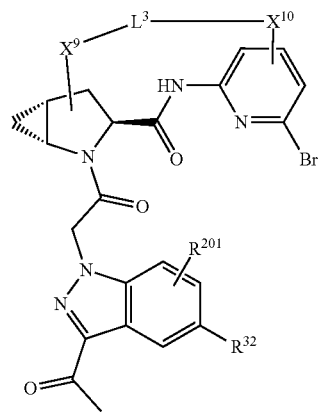
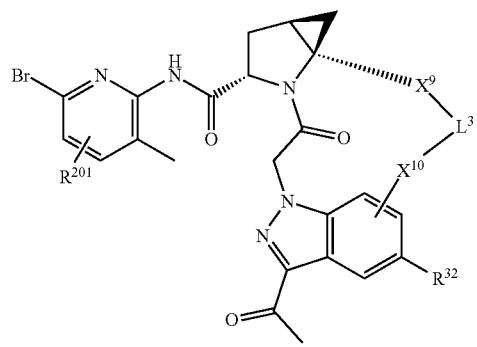
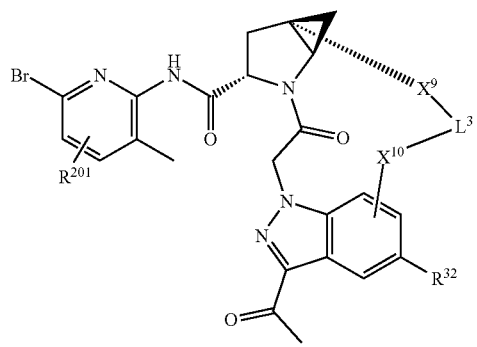

261
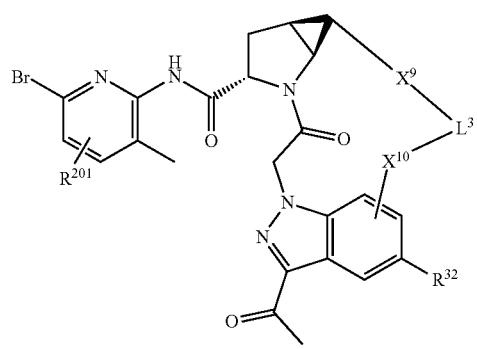
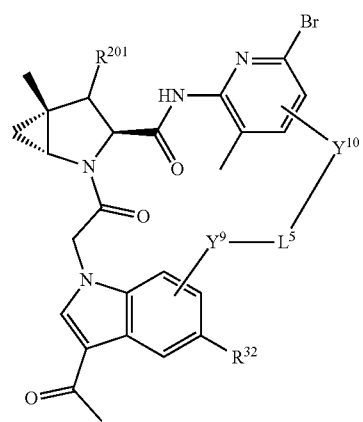
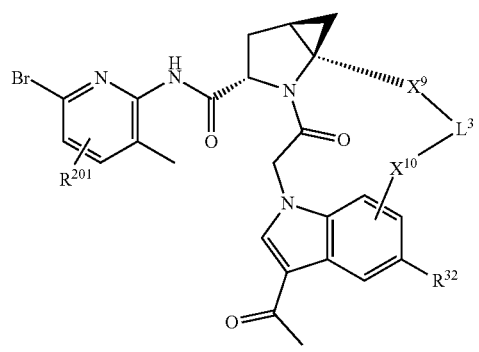
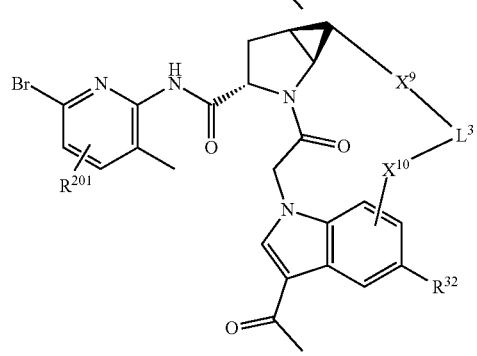
262
-continued
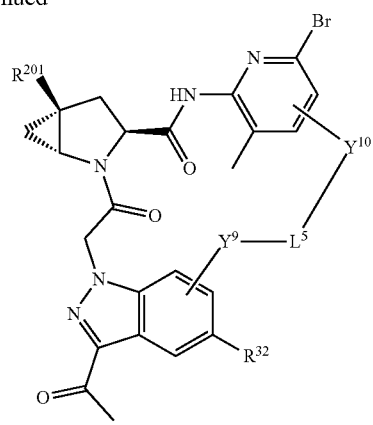
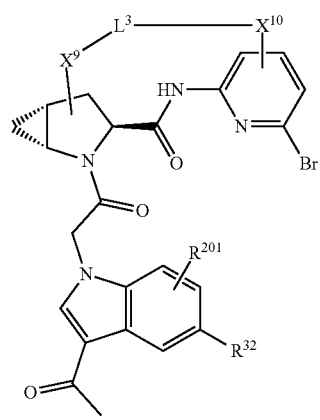
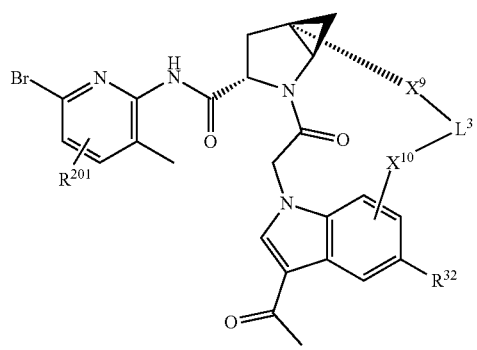
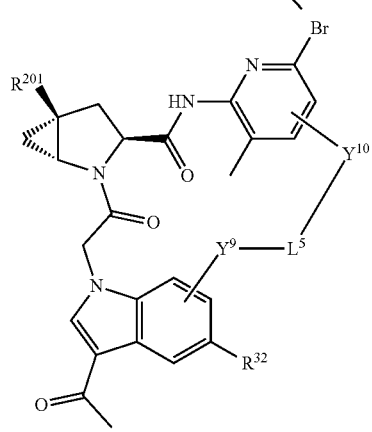

263
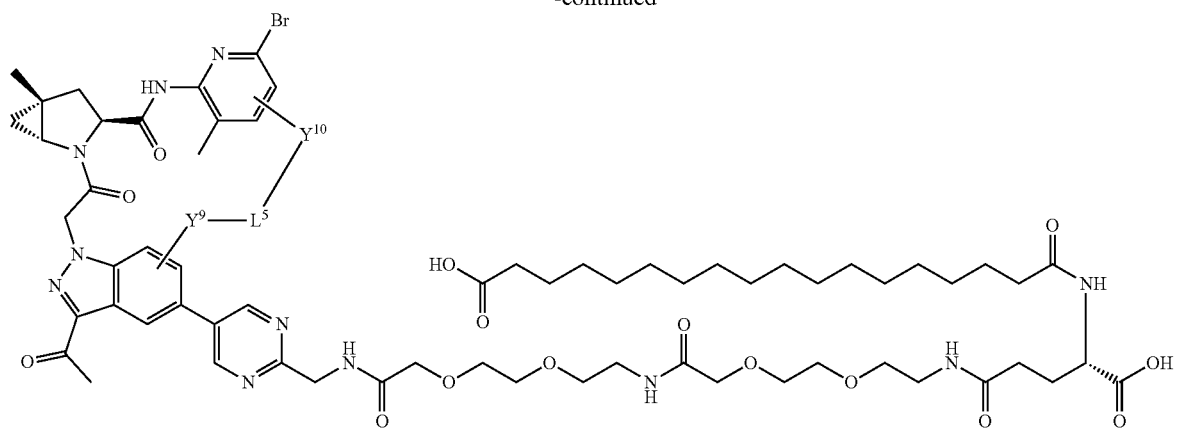
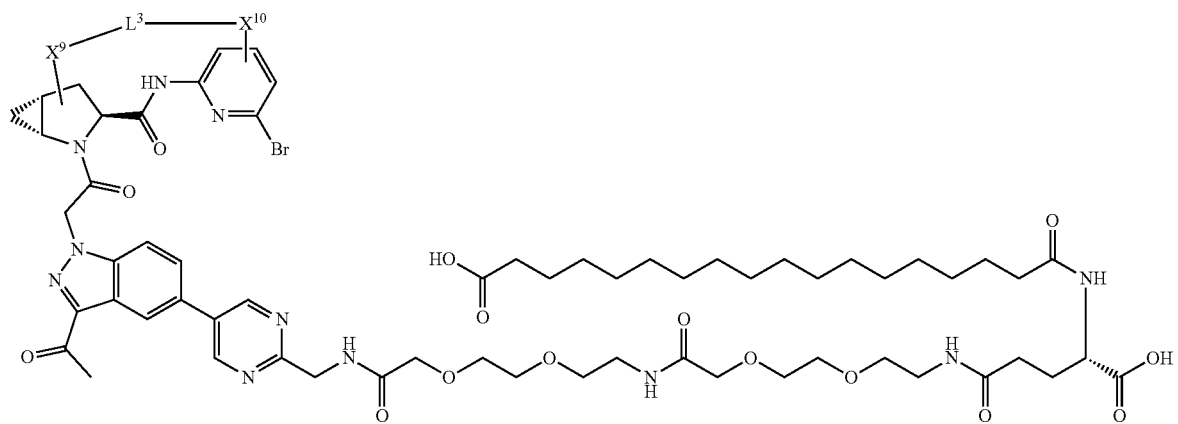
264
-continued
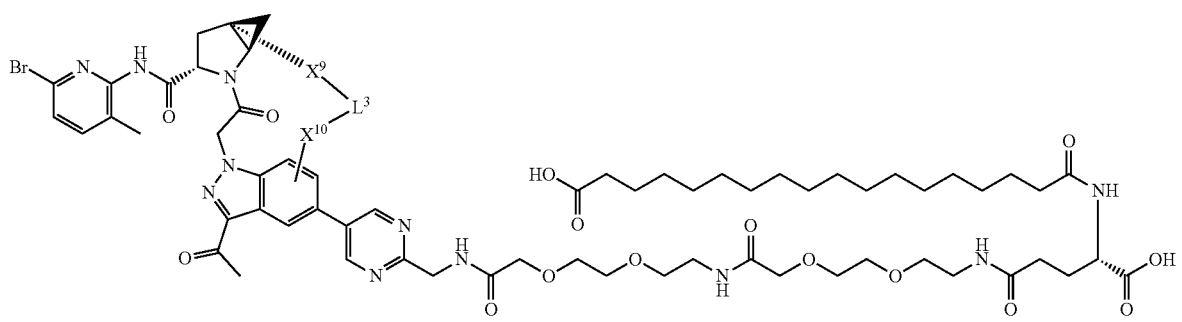

265
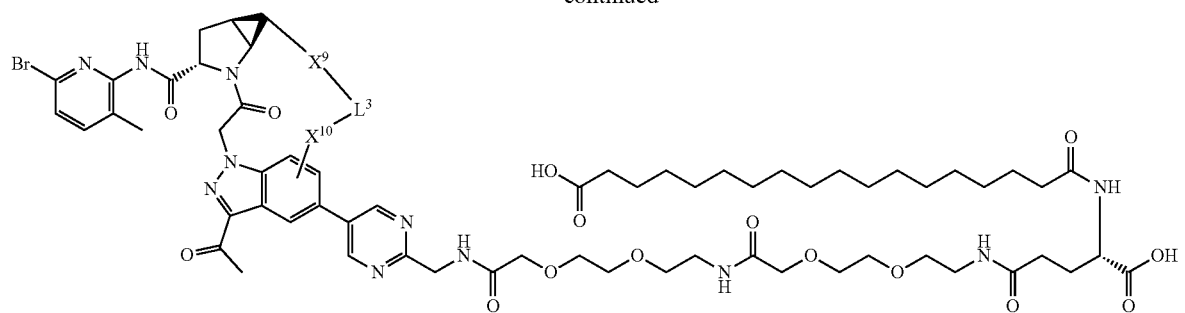
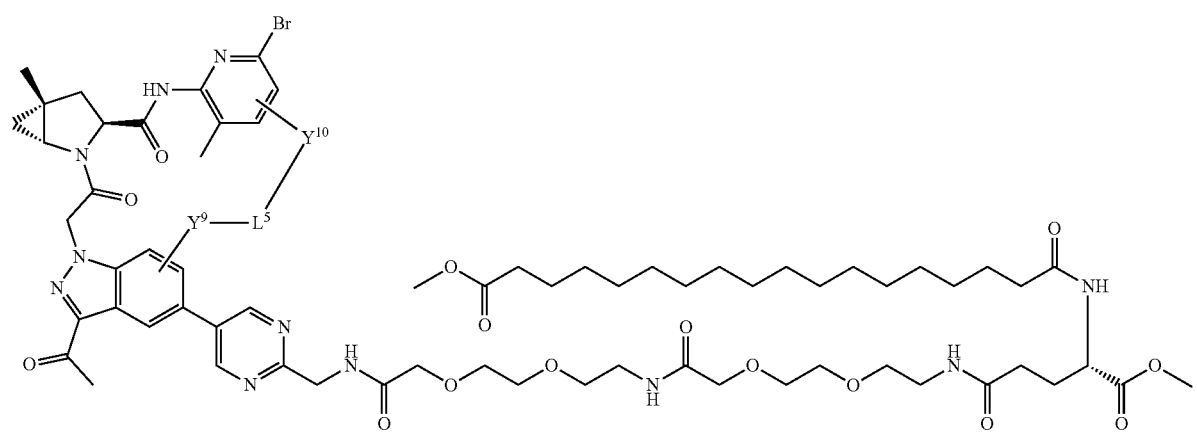
266
-continued
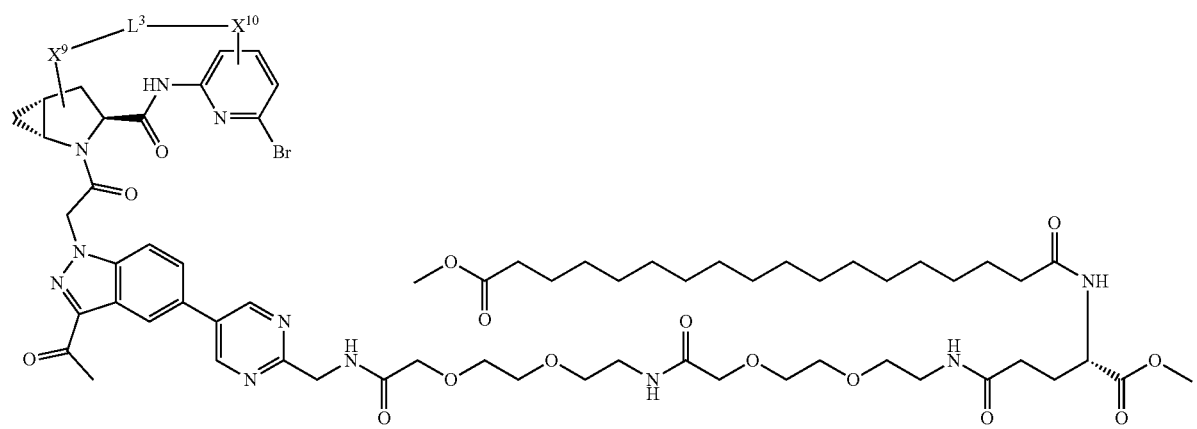
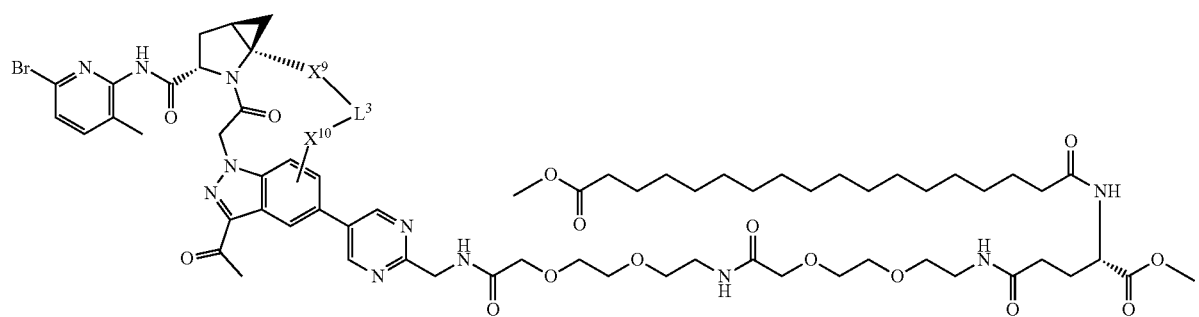

267
268
-continued
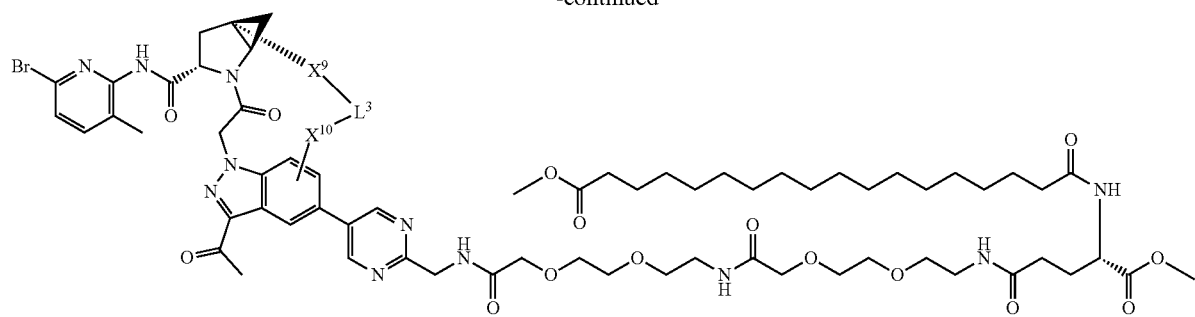
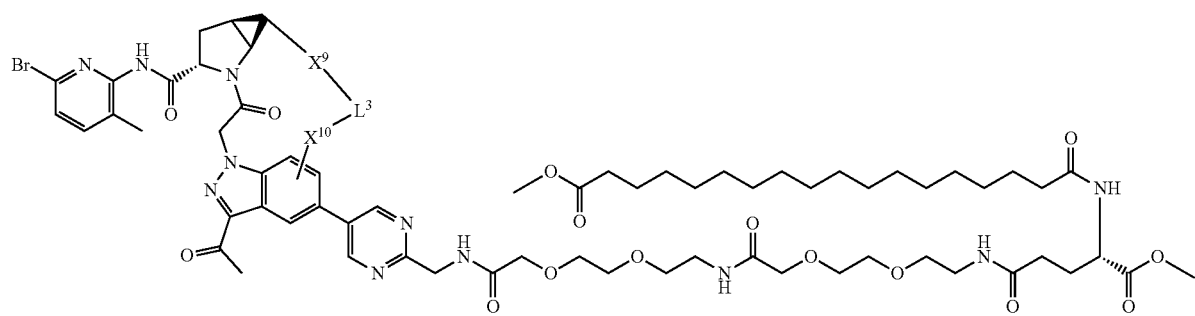
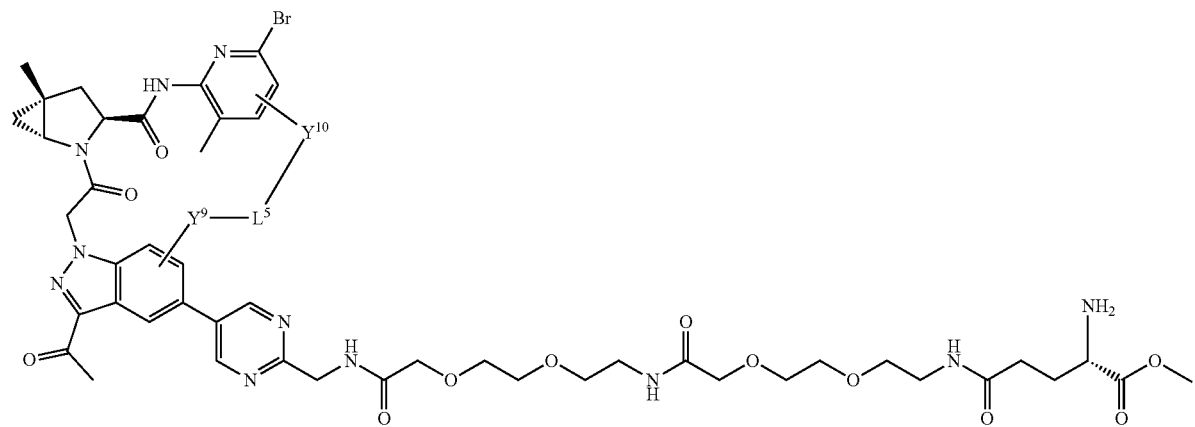
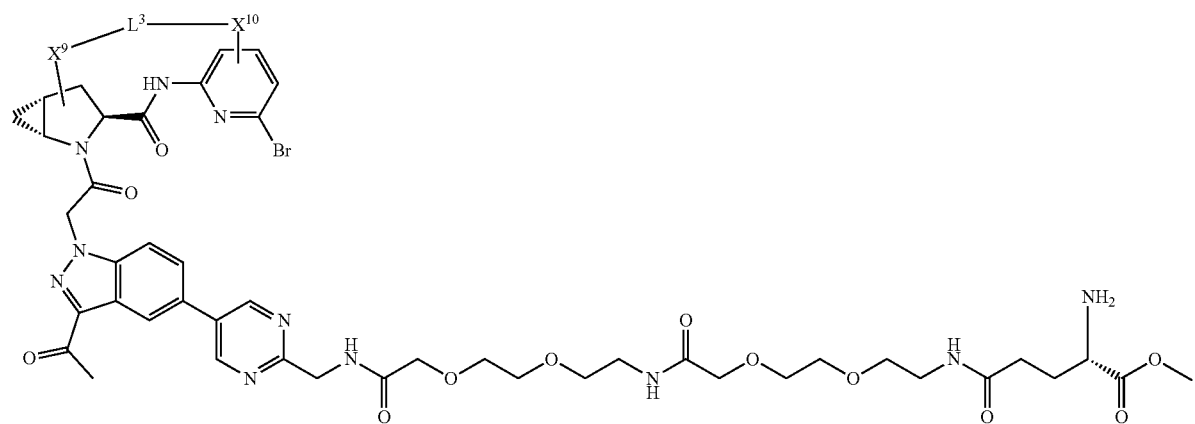

-continued
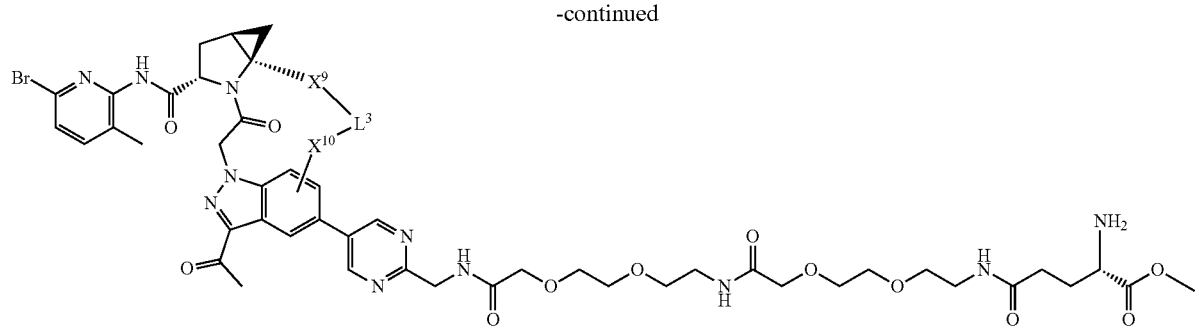
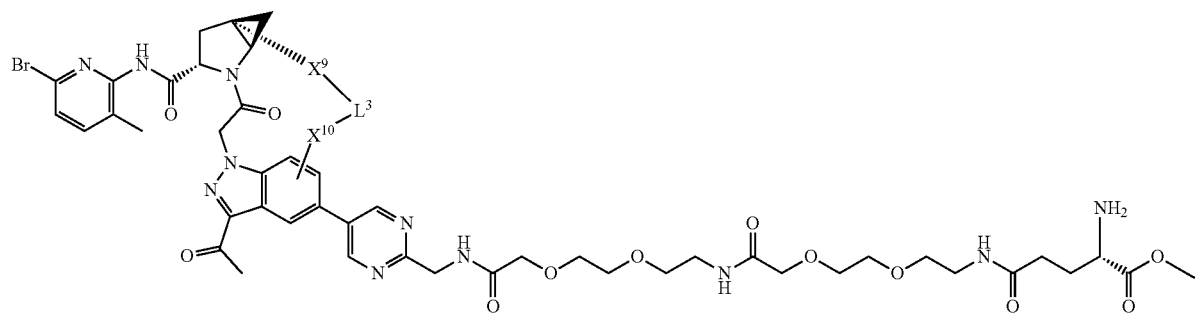
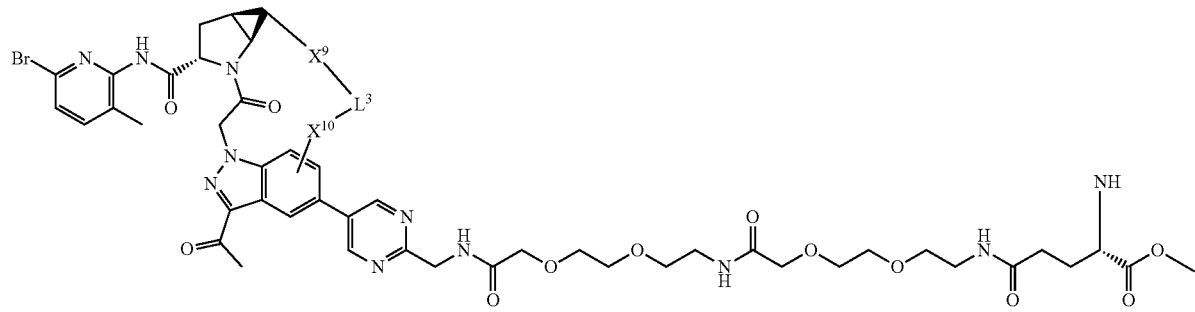
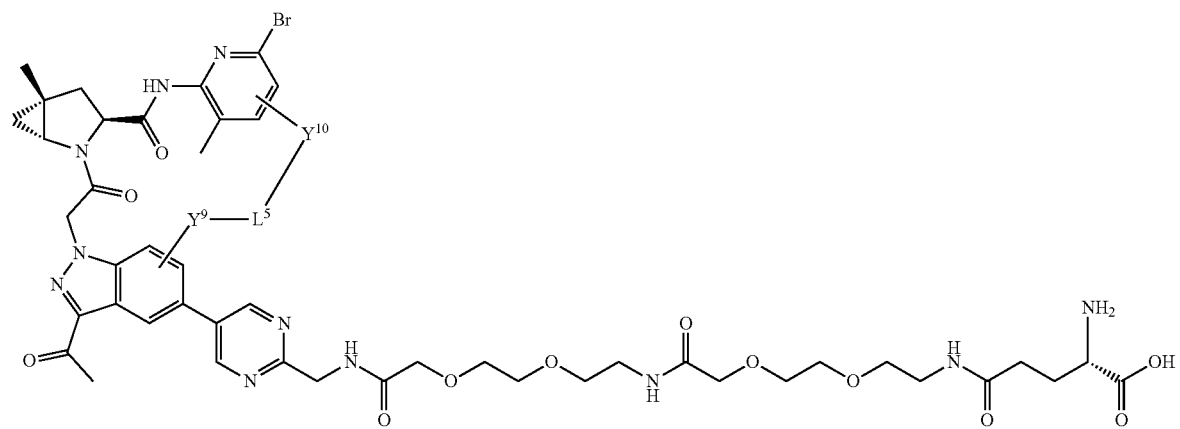

271
272
-continued
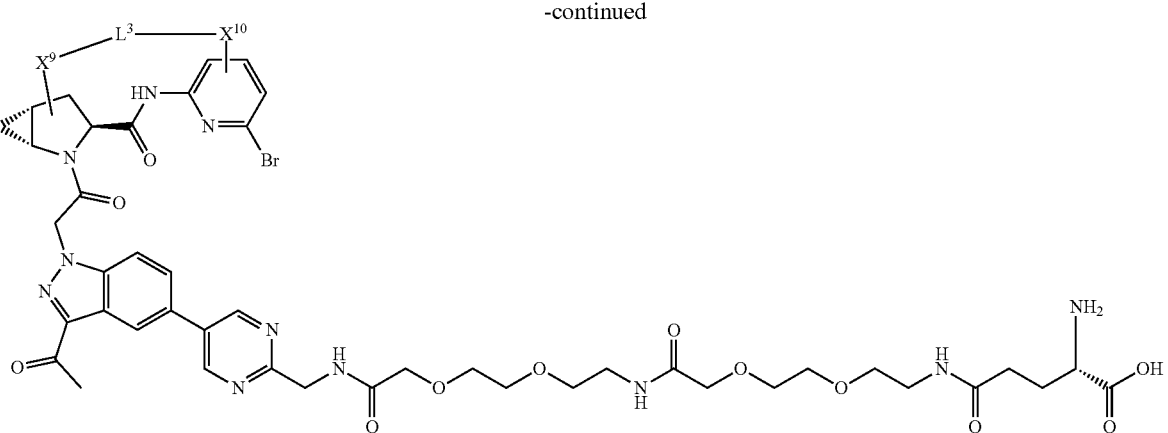
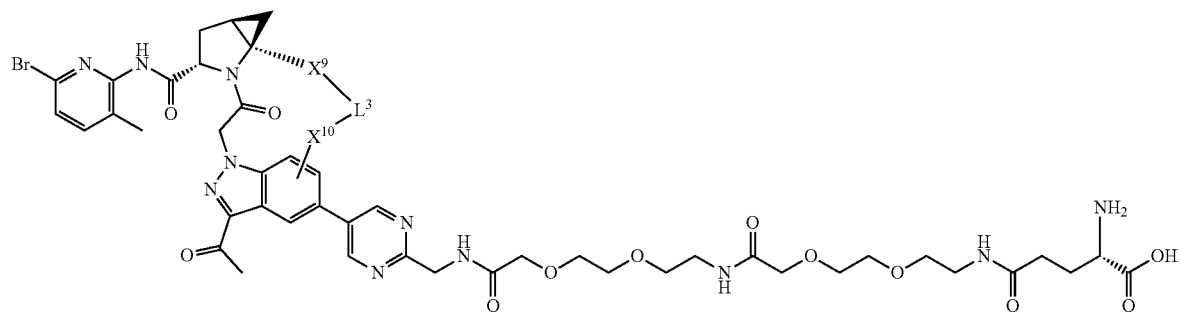
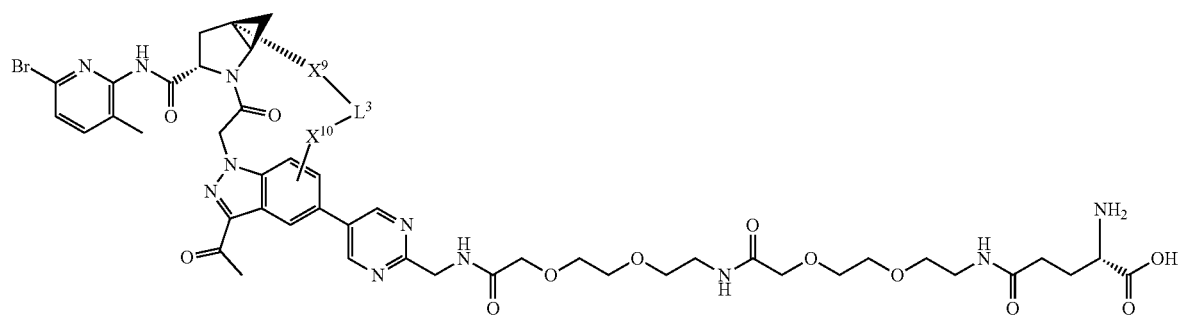
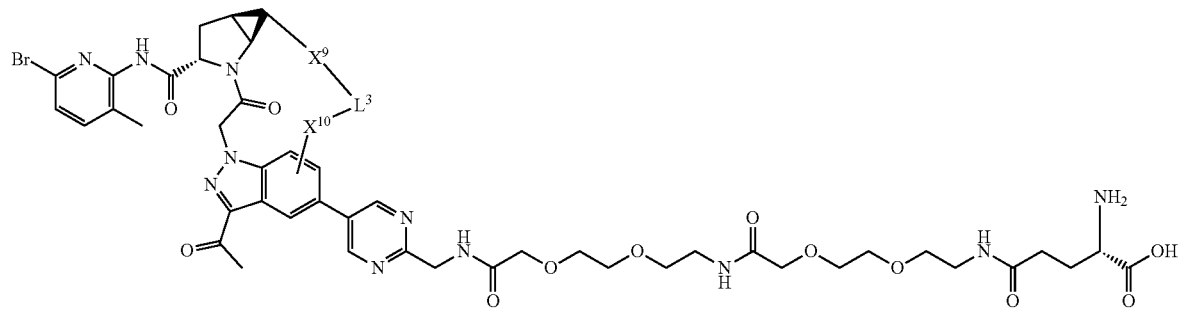

273
274
-continued
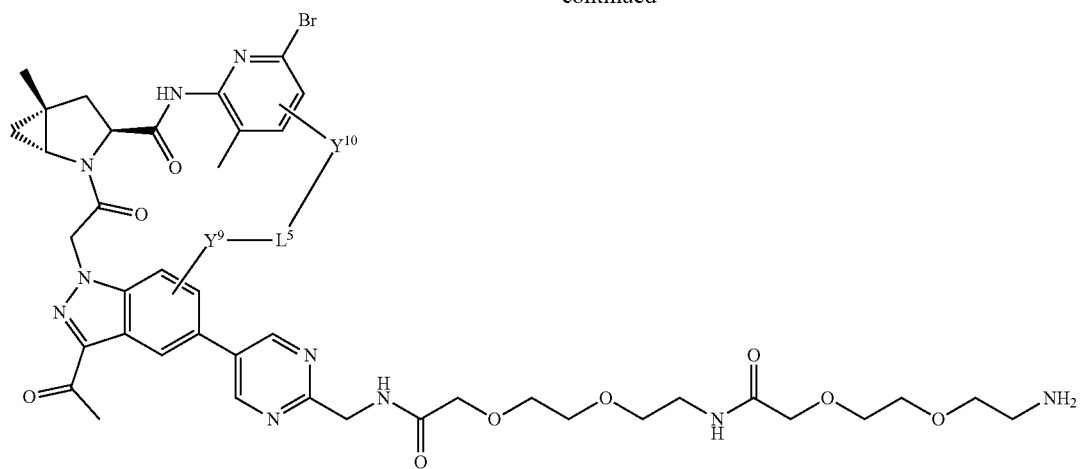
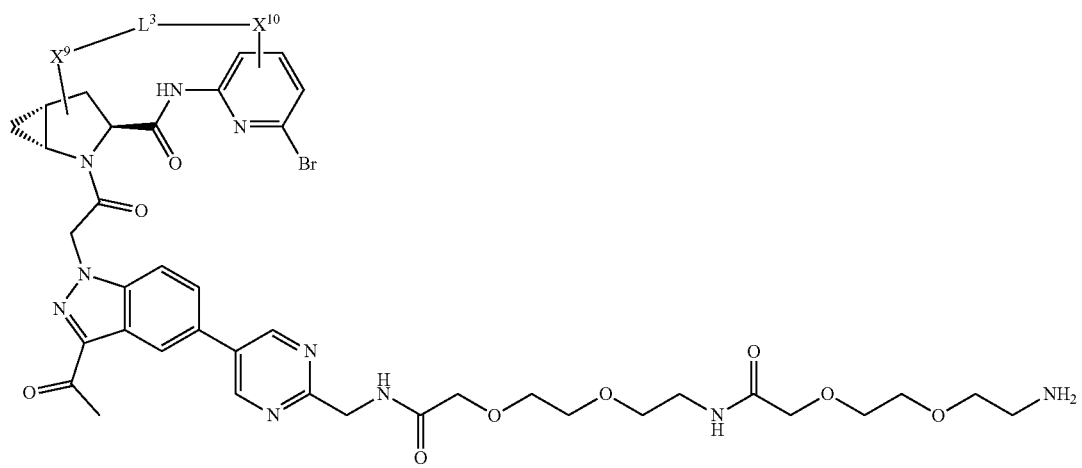
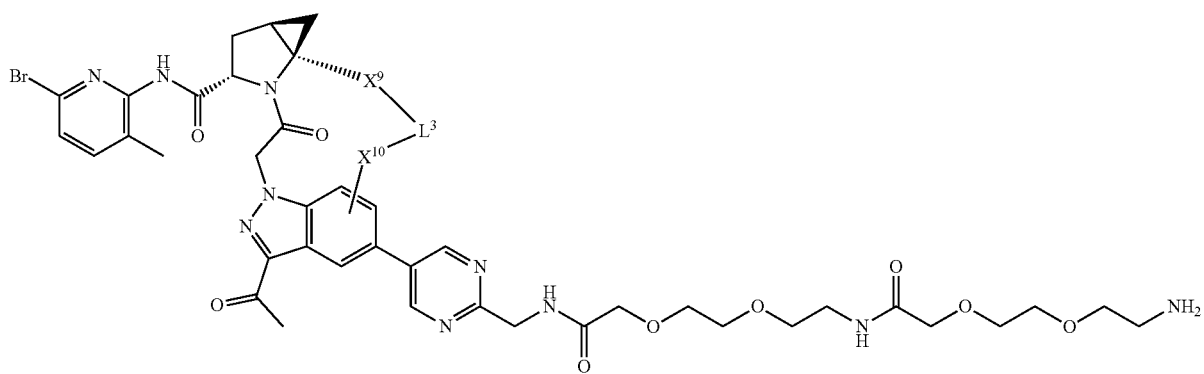
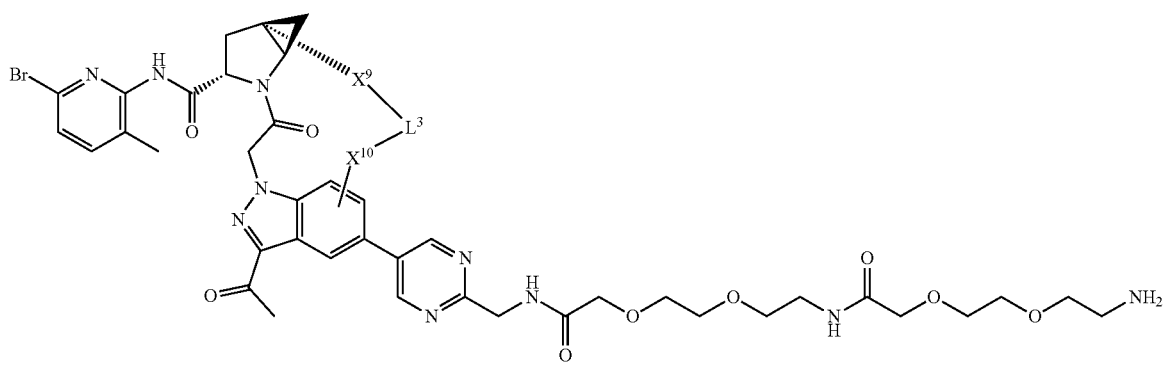

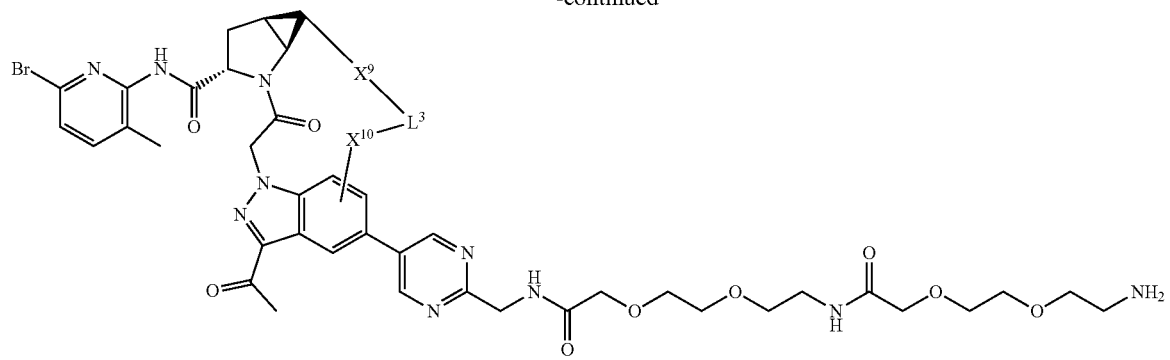
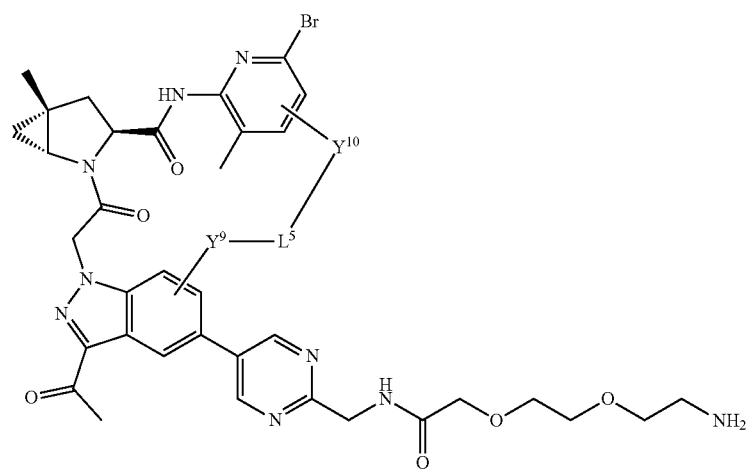
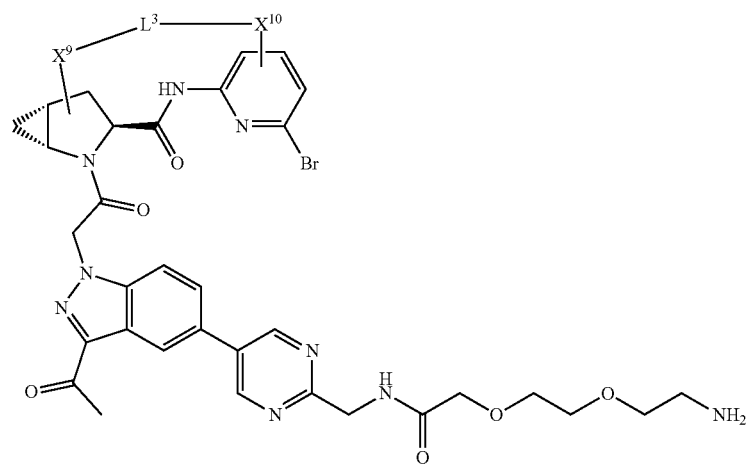
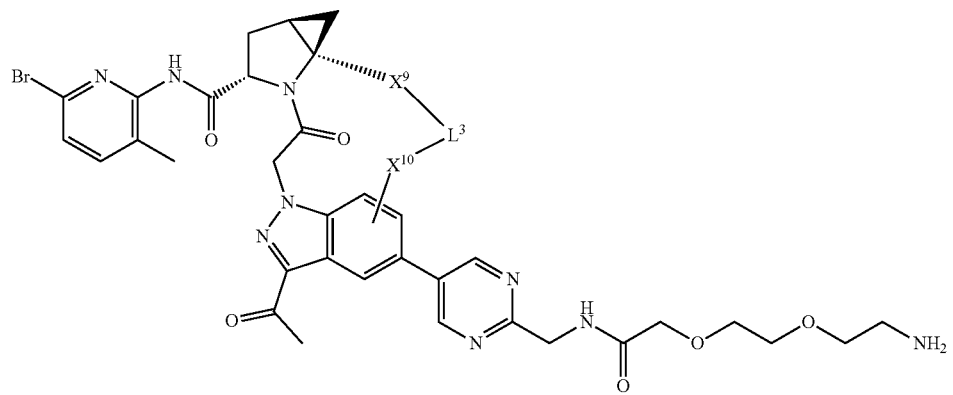

-continued
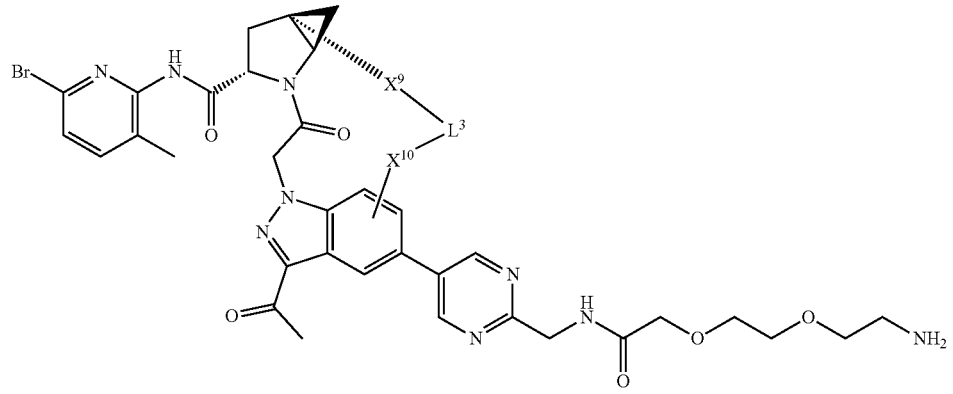
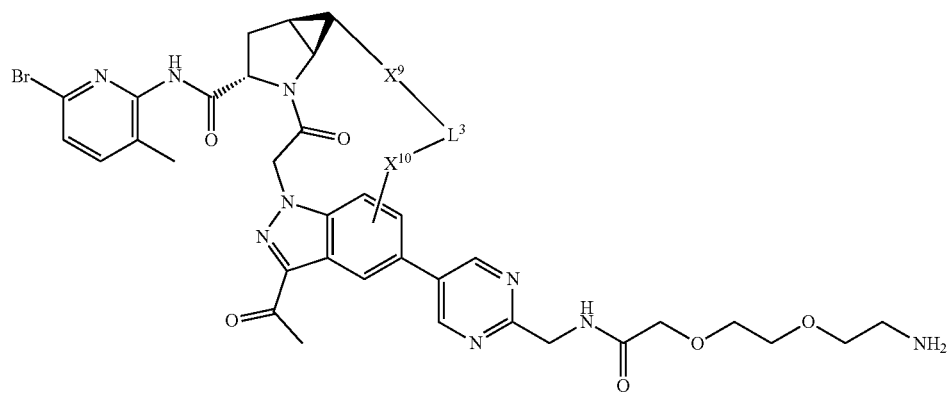
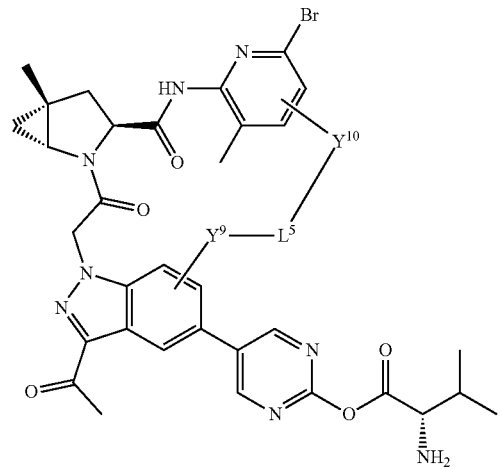
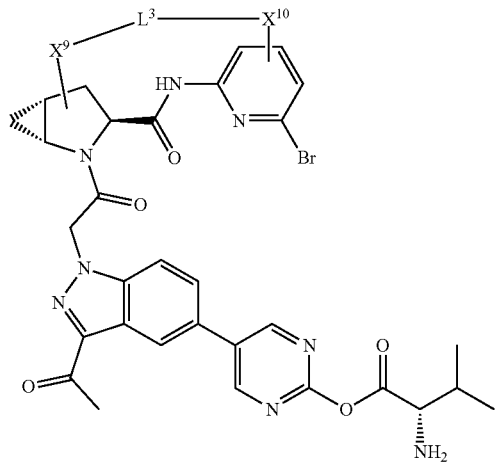
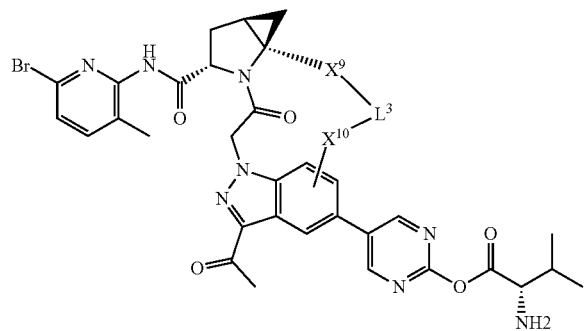
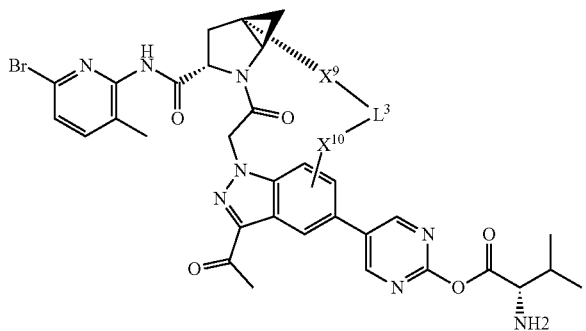

-continued
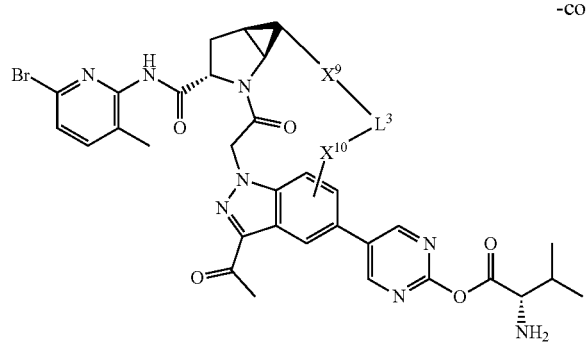
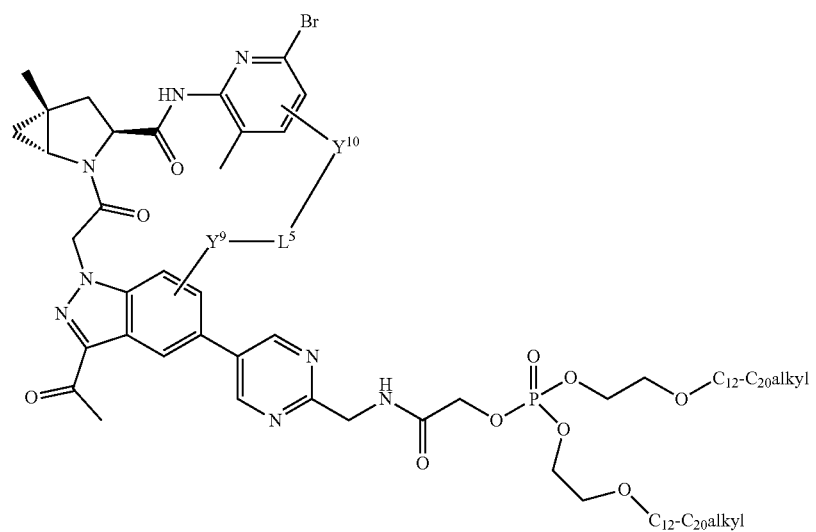
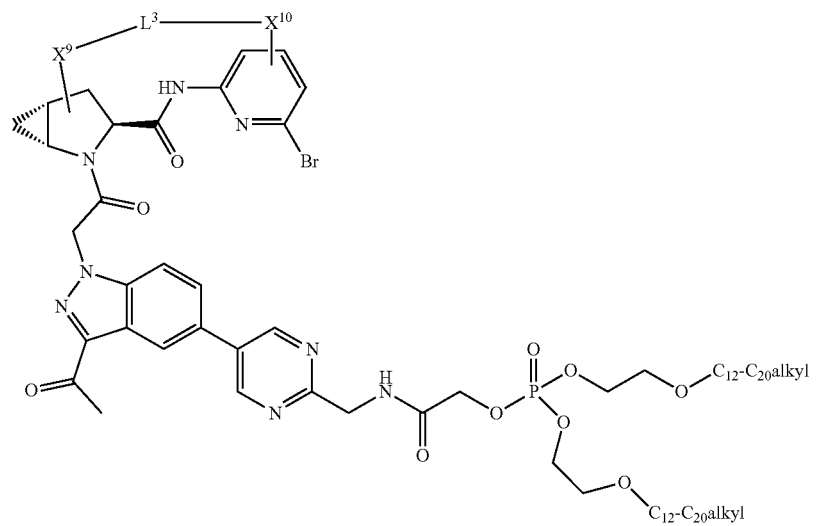

281
282
-continued
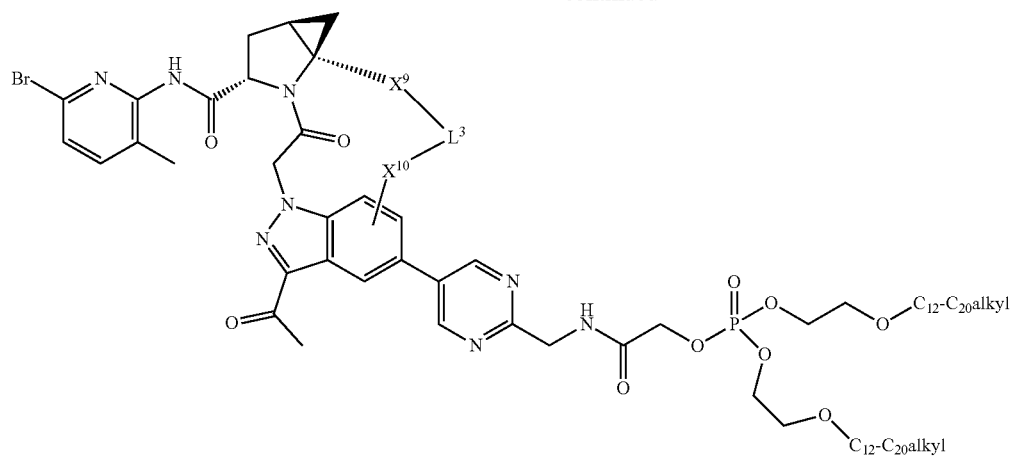
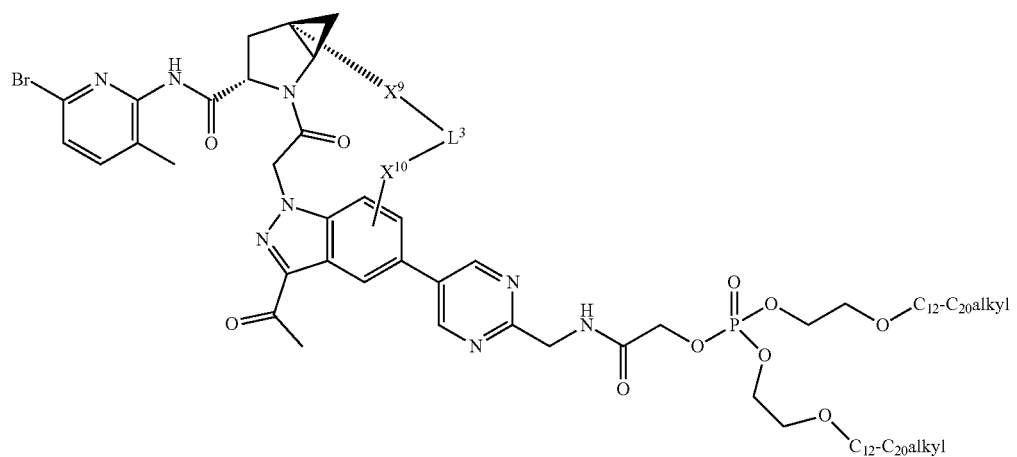
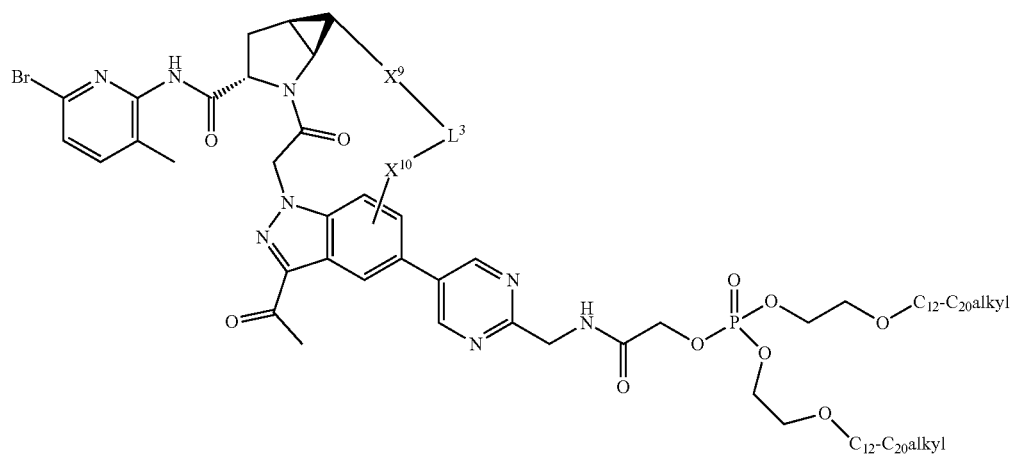

-continued
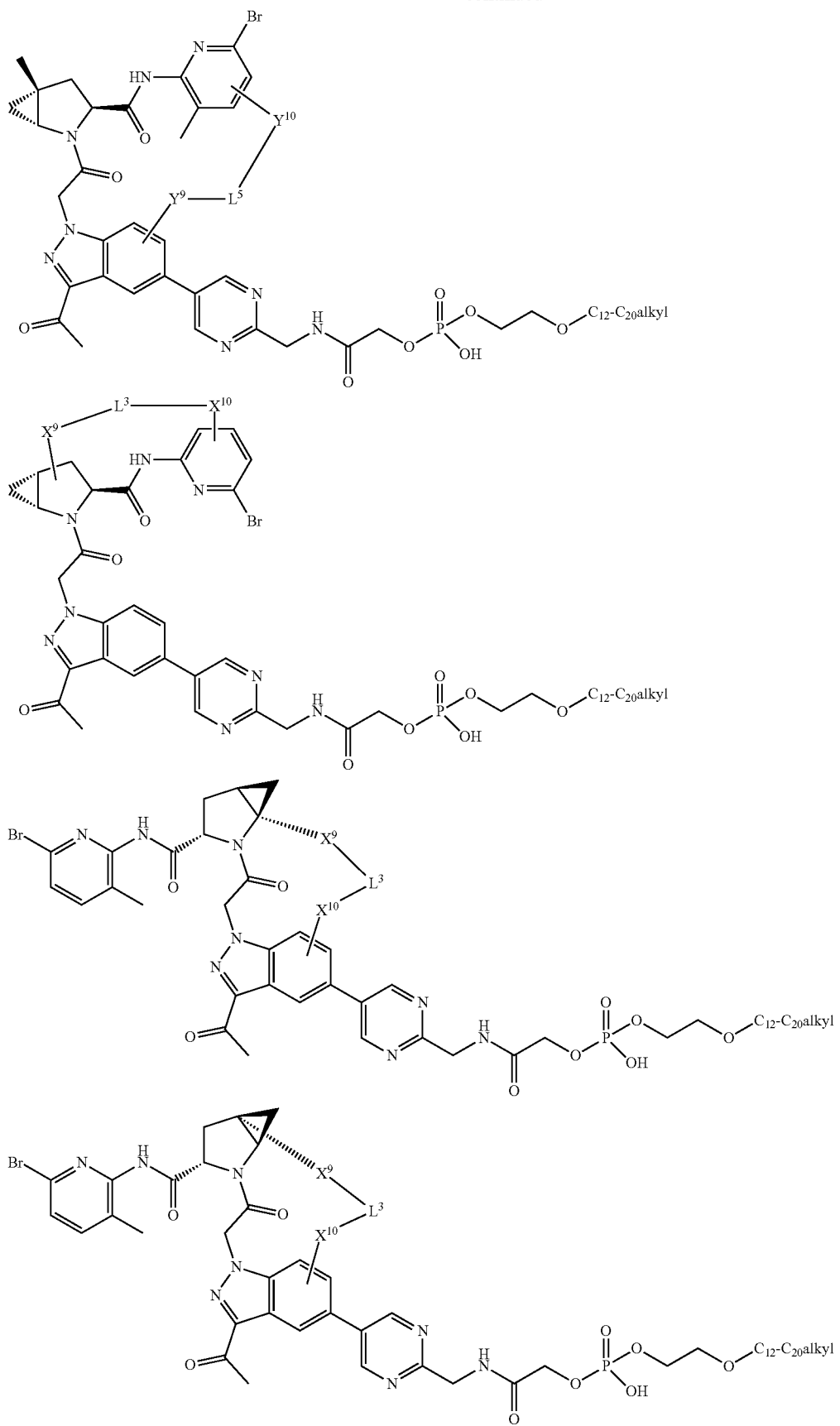

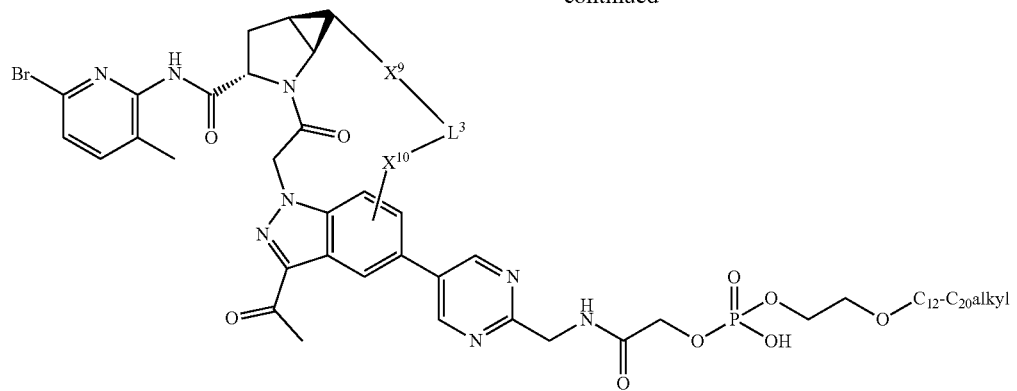
Non-limiting examples of compounds with an $R^{301}$ and/or $R^{201}$ substituent of the present invention include:
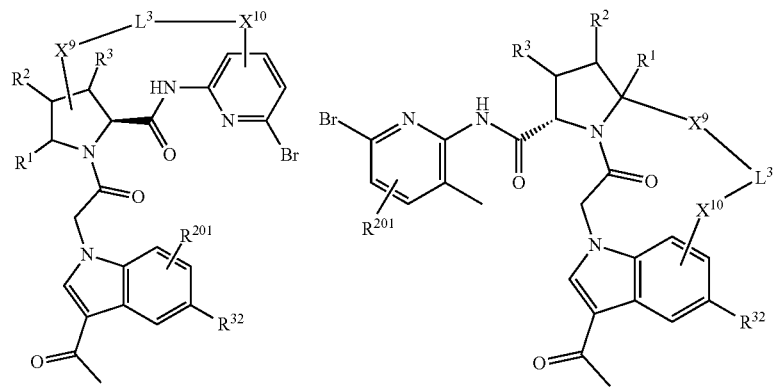
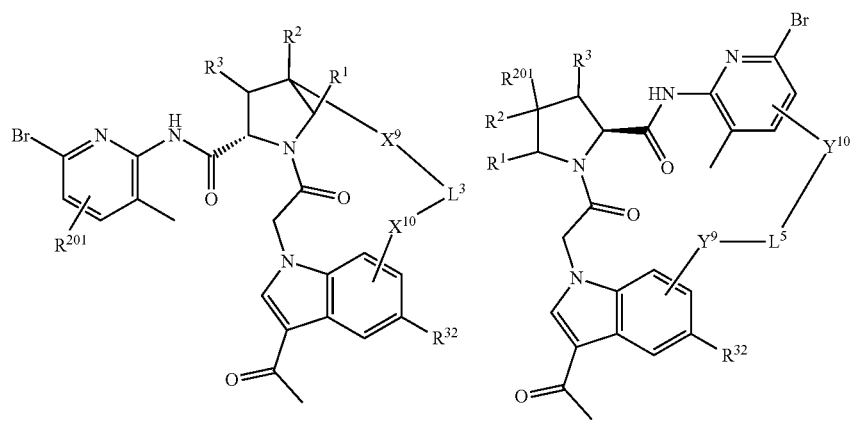

287
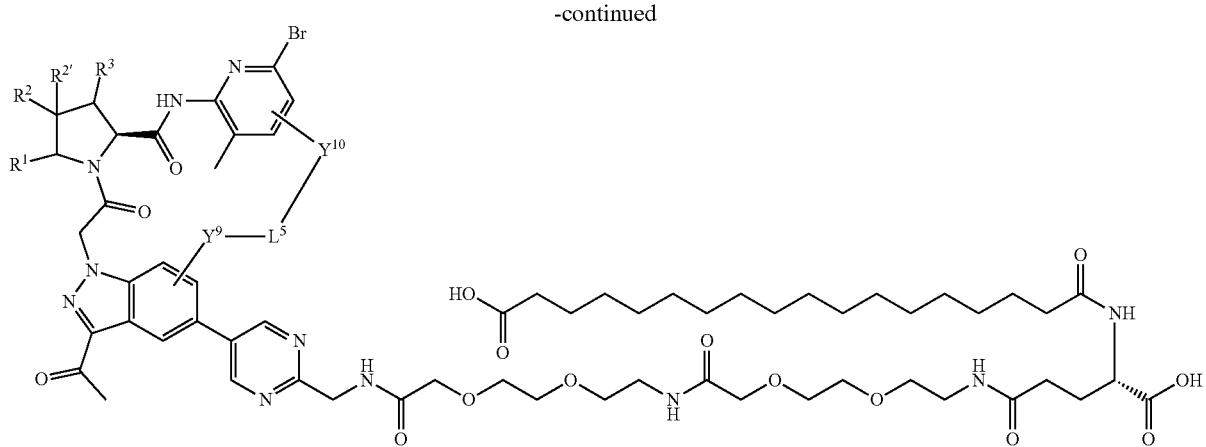
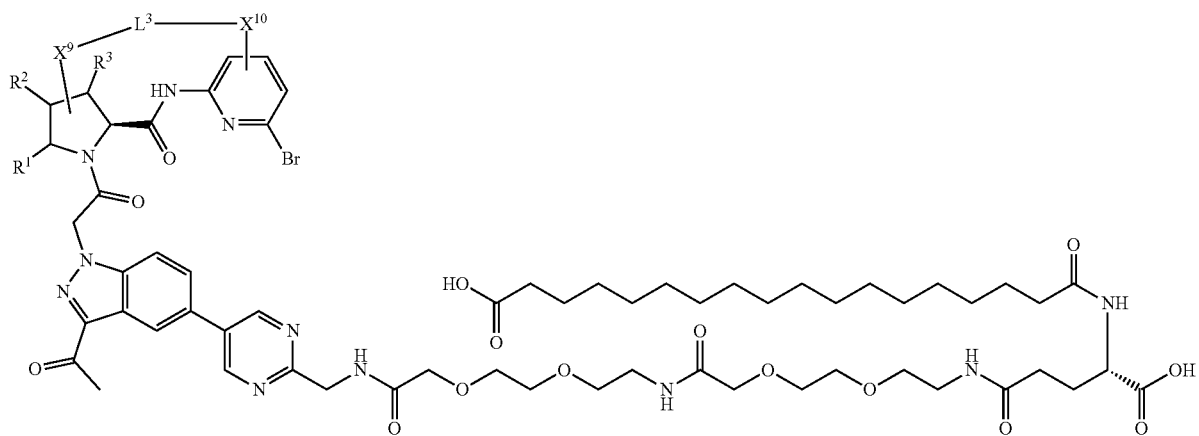
288
-continued
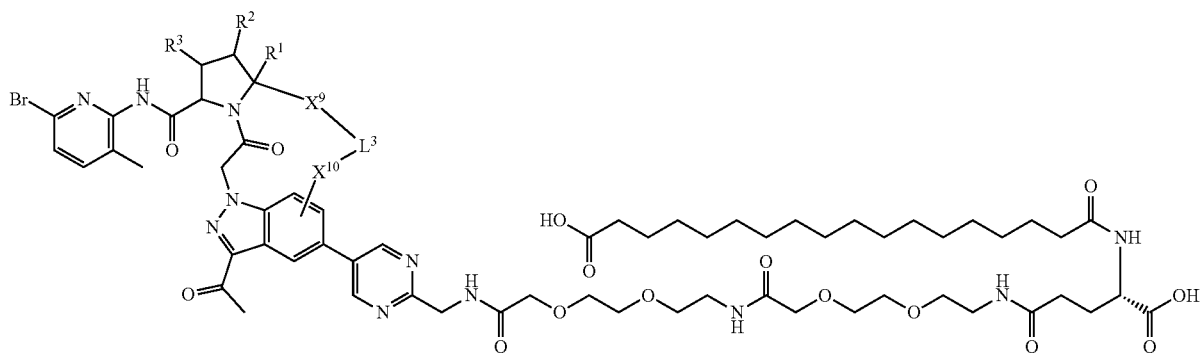
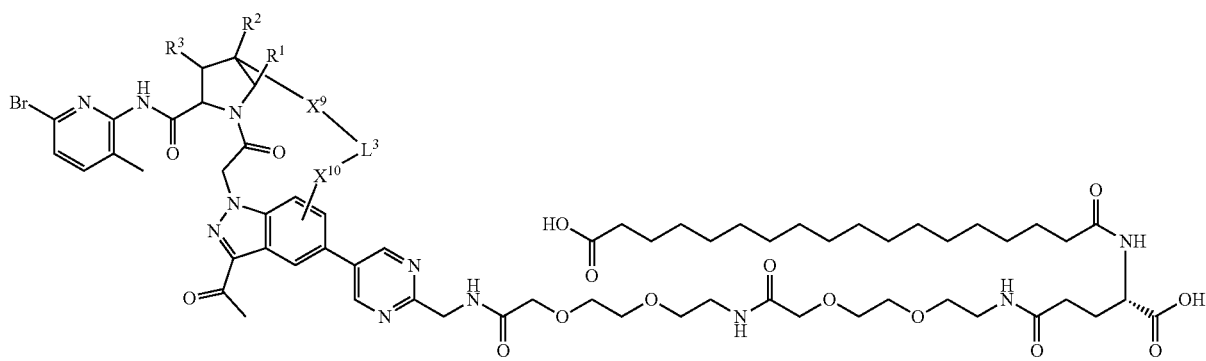

289
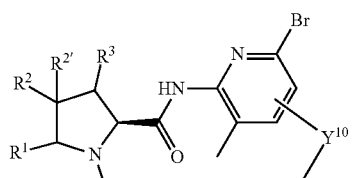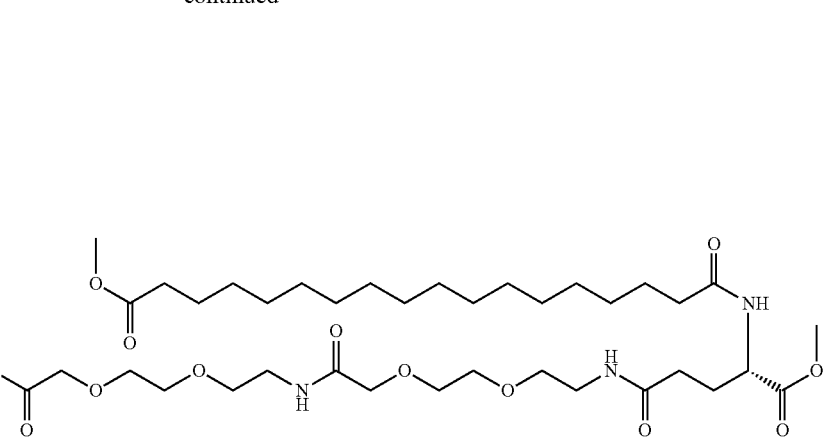
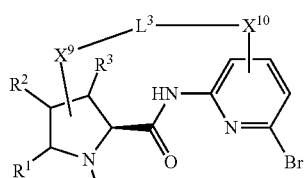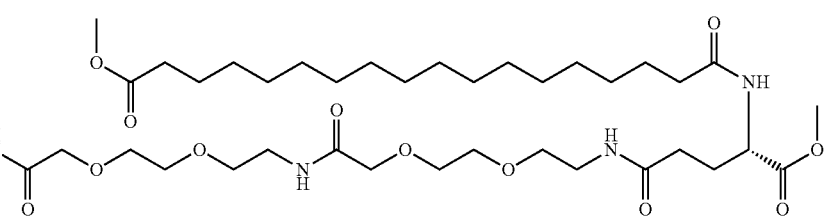
290
-continued
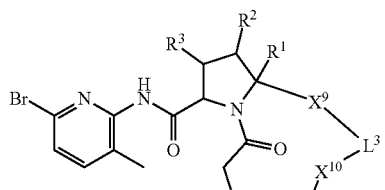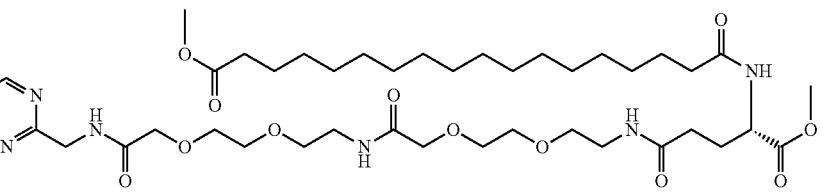
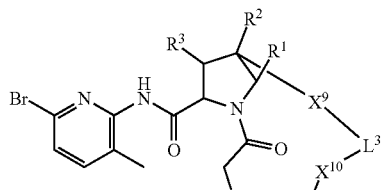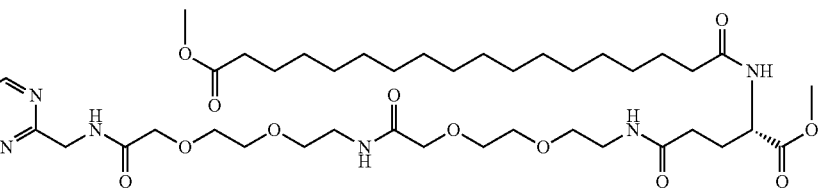

291
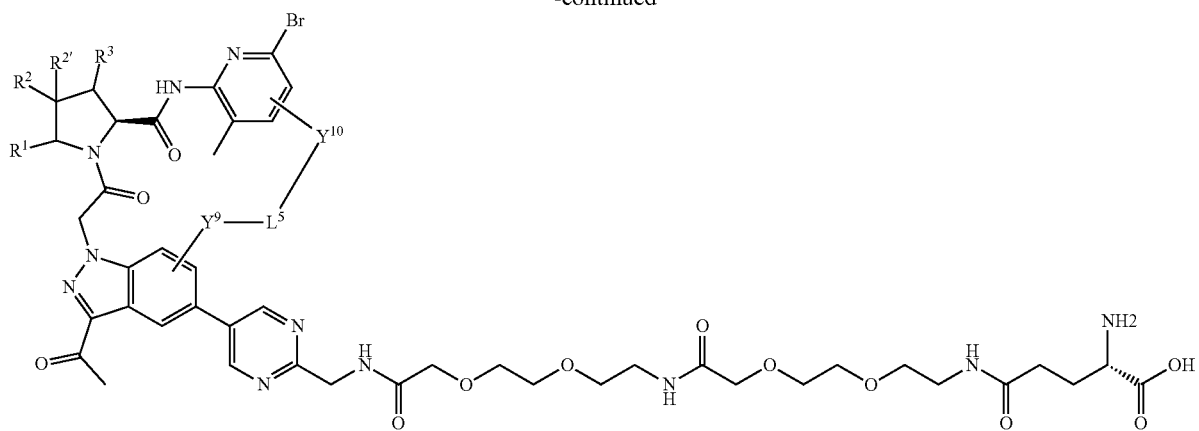
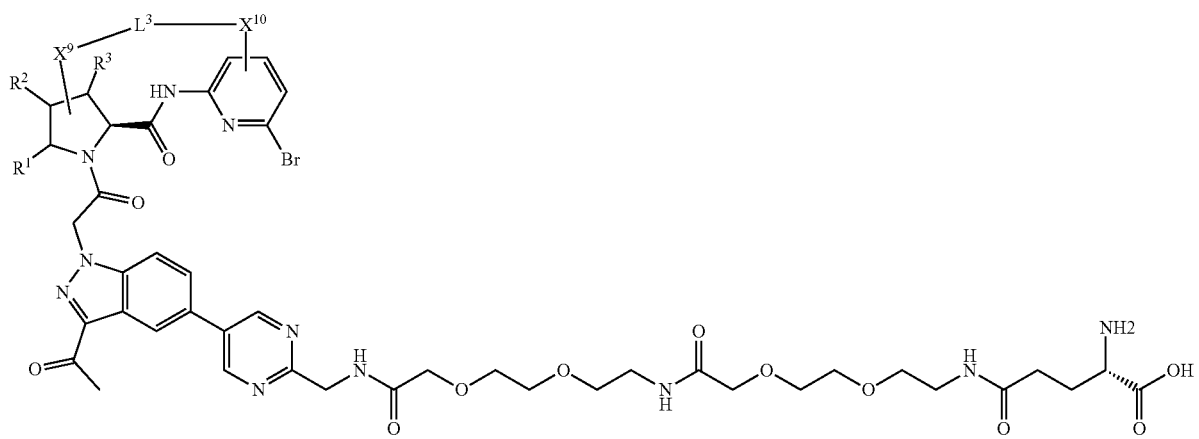
292
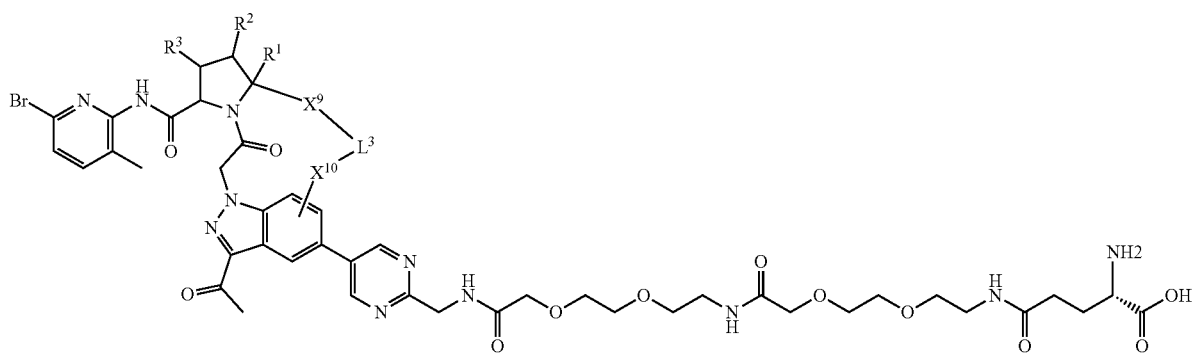
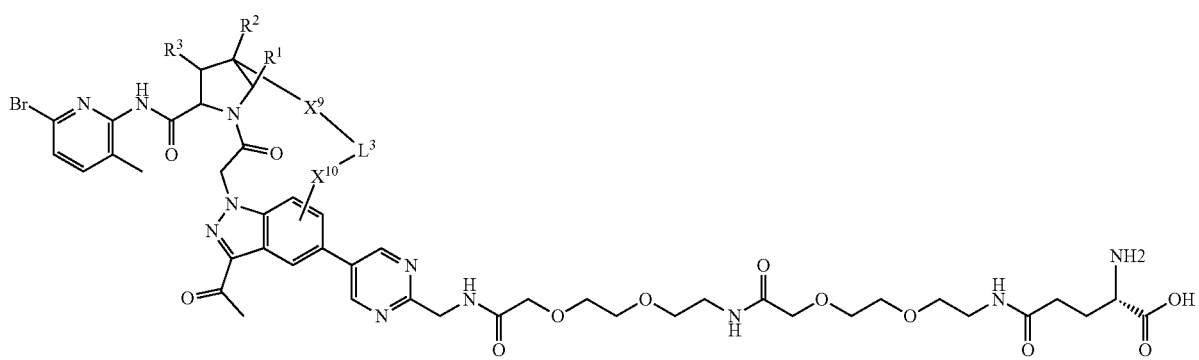

293
294
-continued
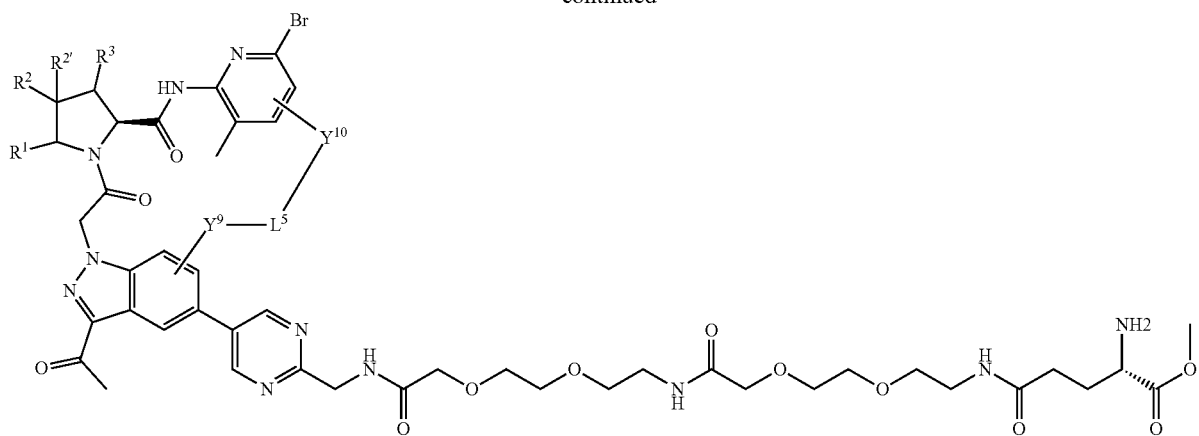
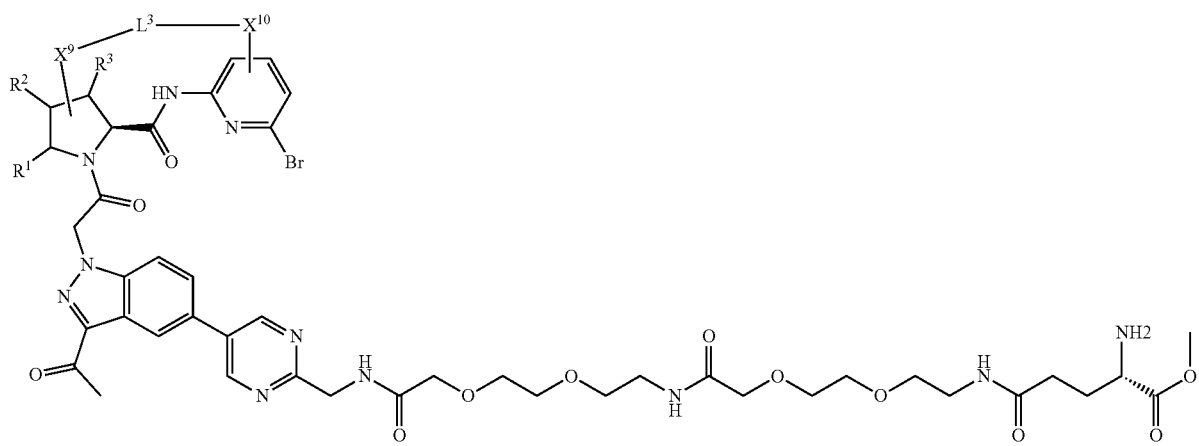
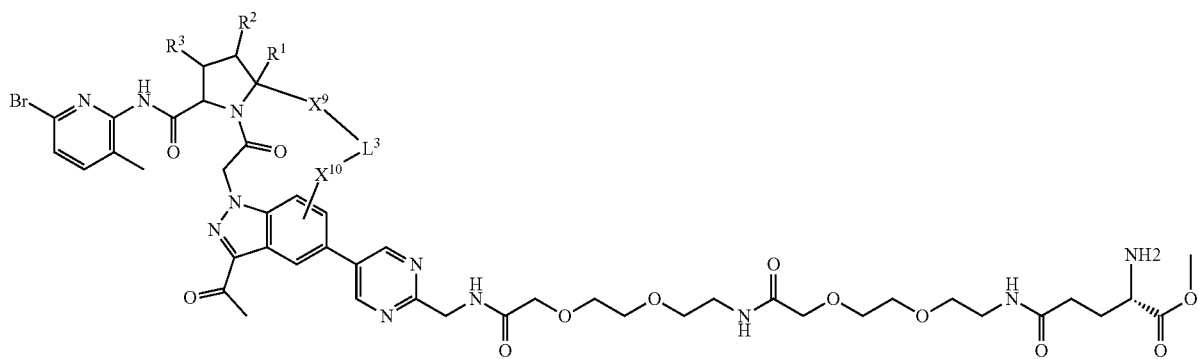
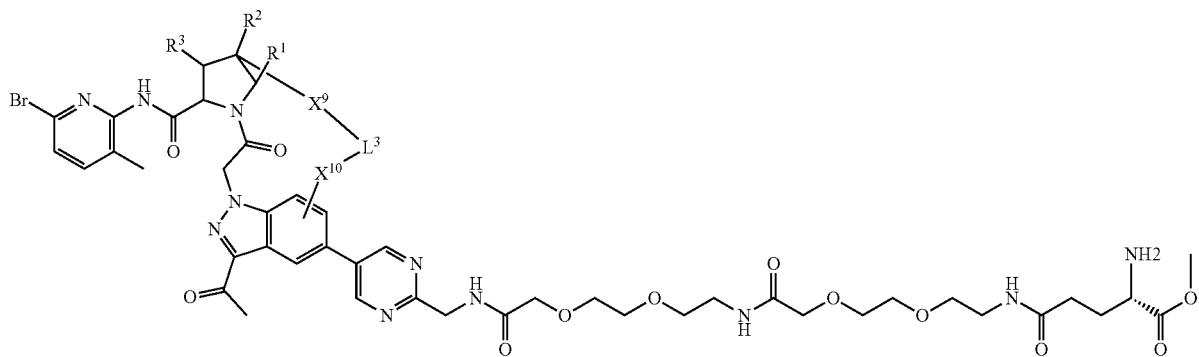

295
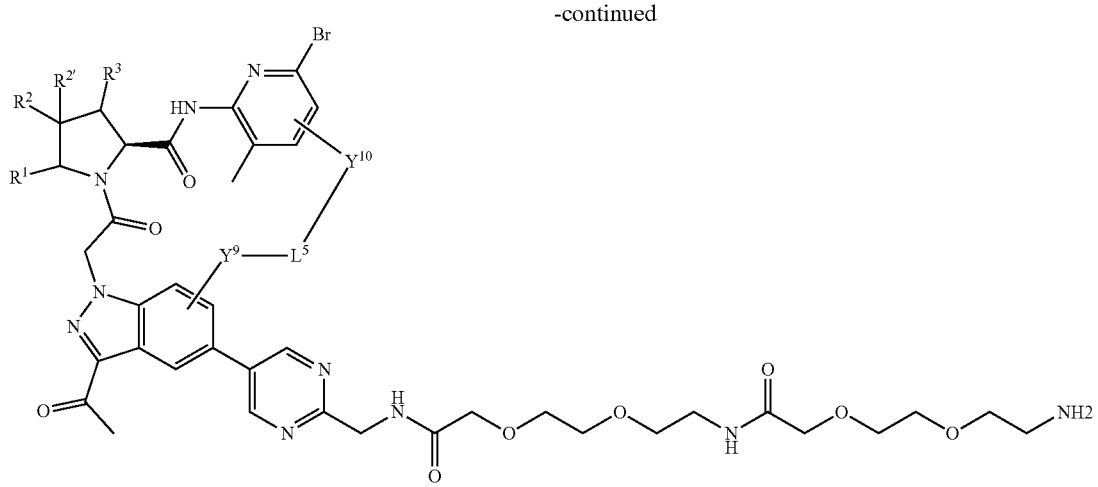
296
-continued
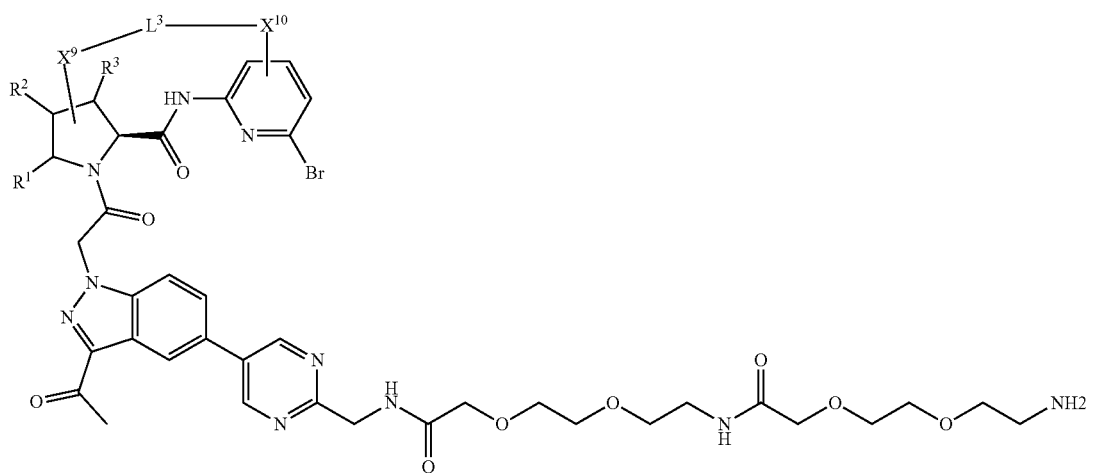
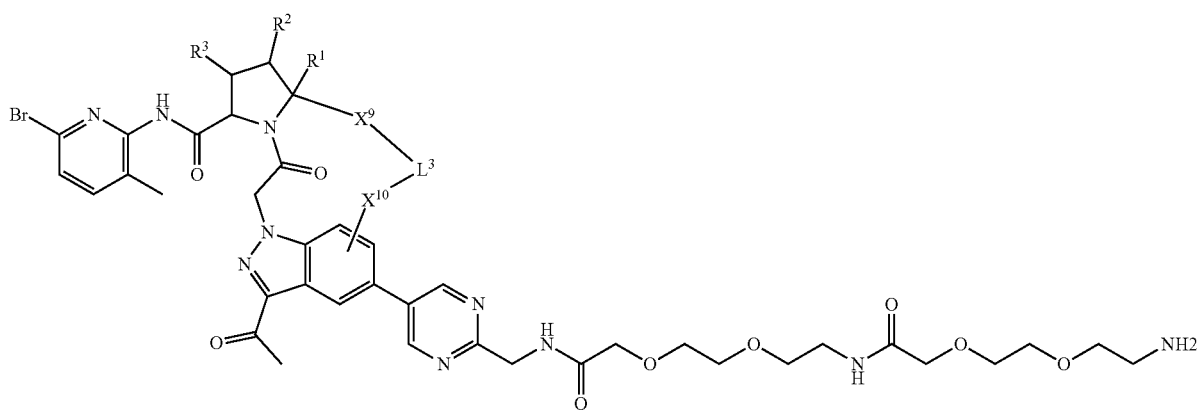

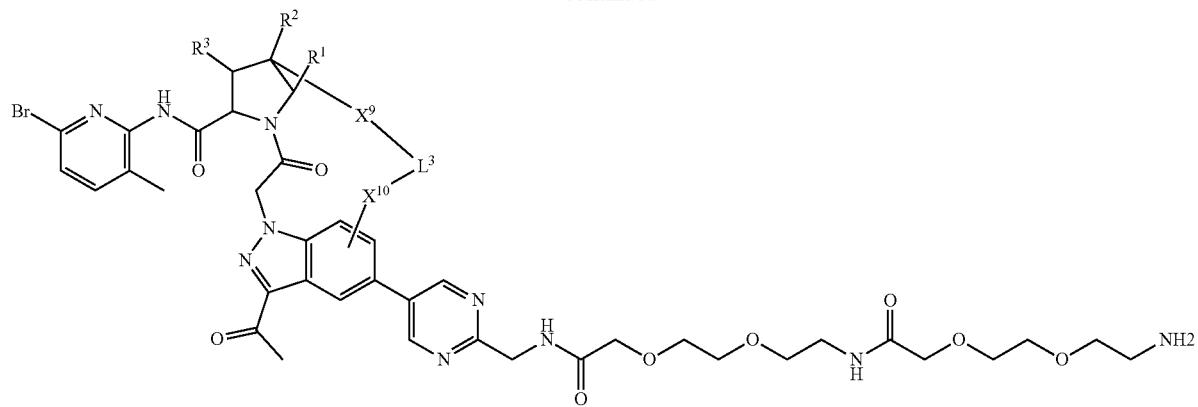
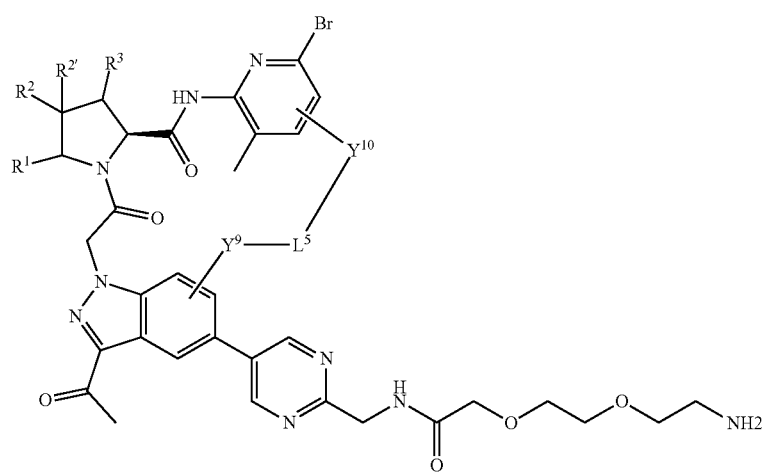
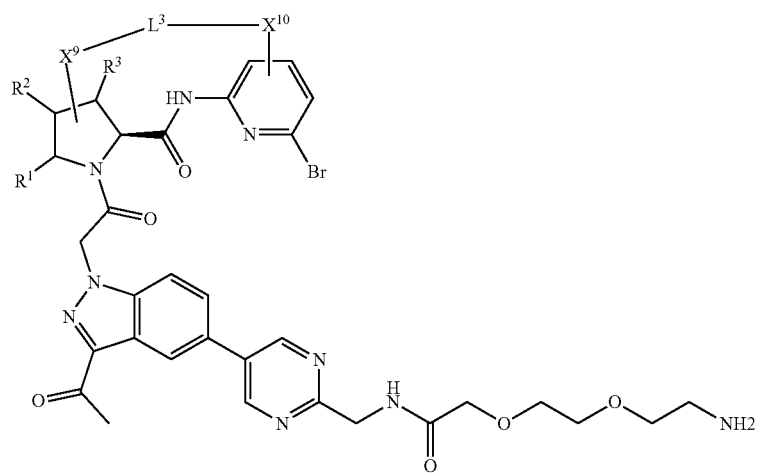

299 300
-continued
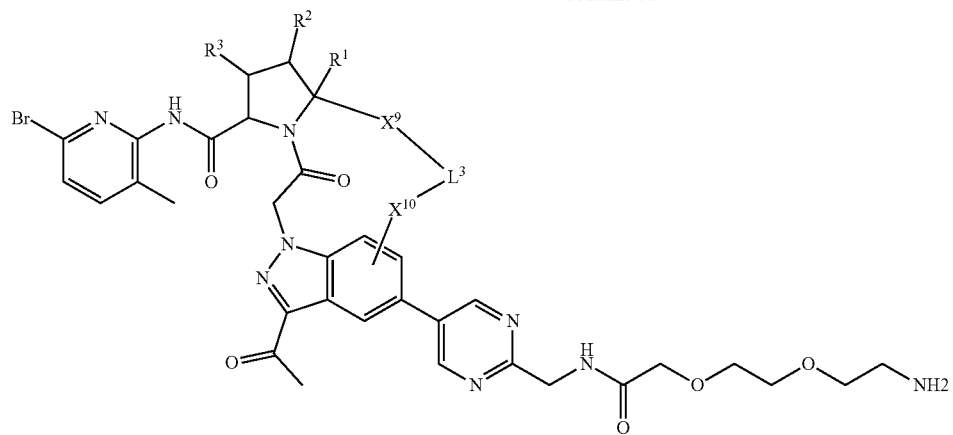
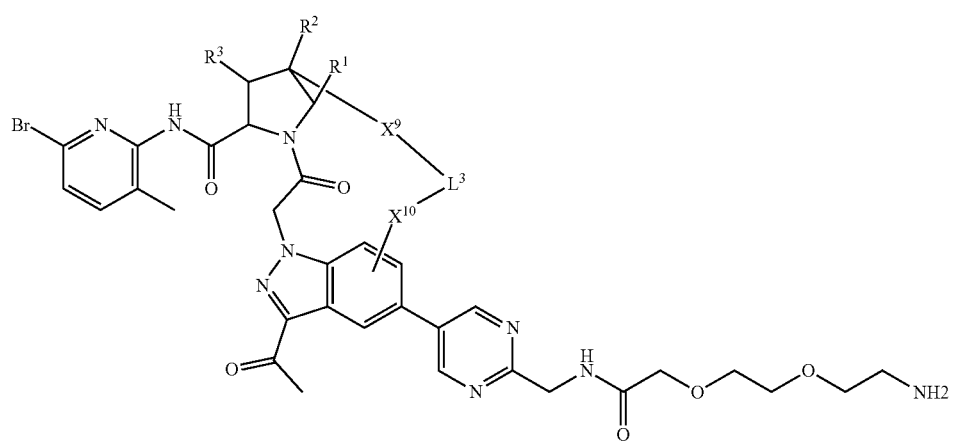
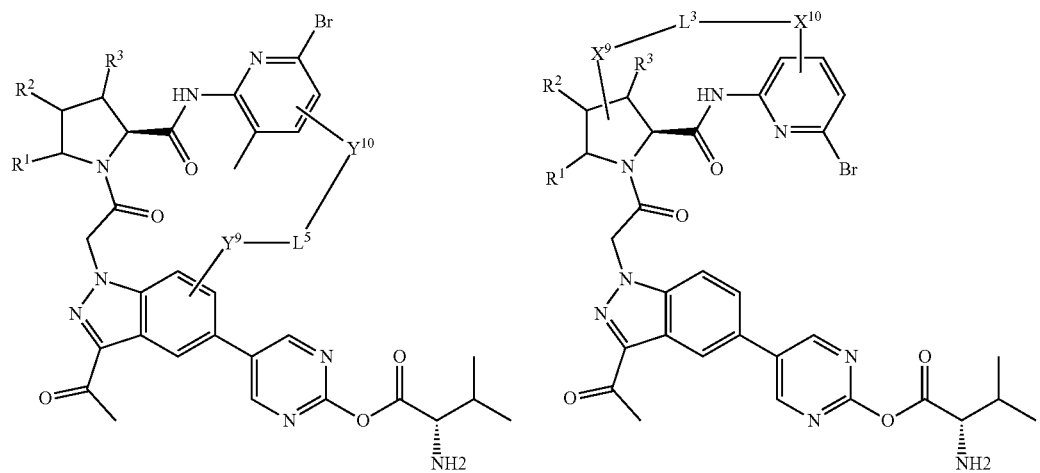

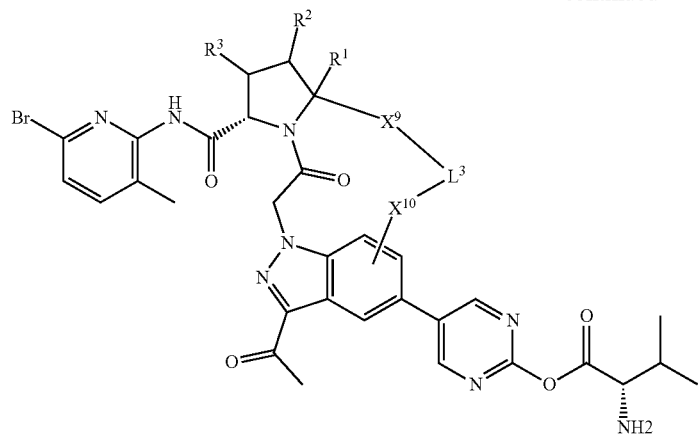
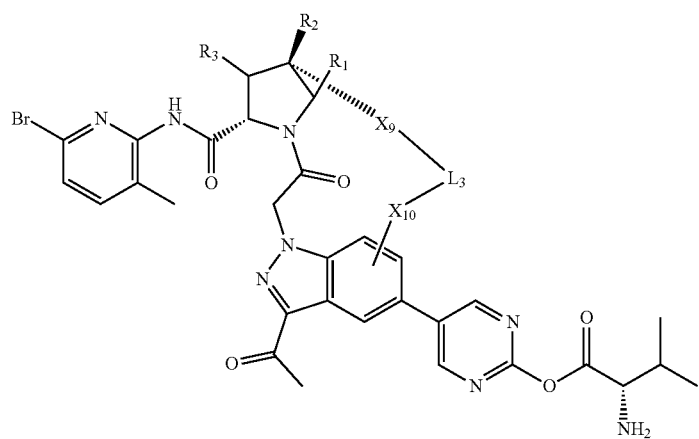
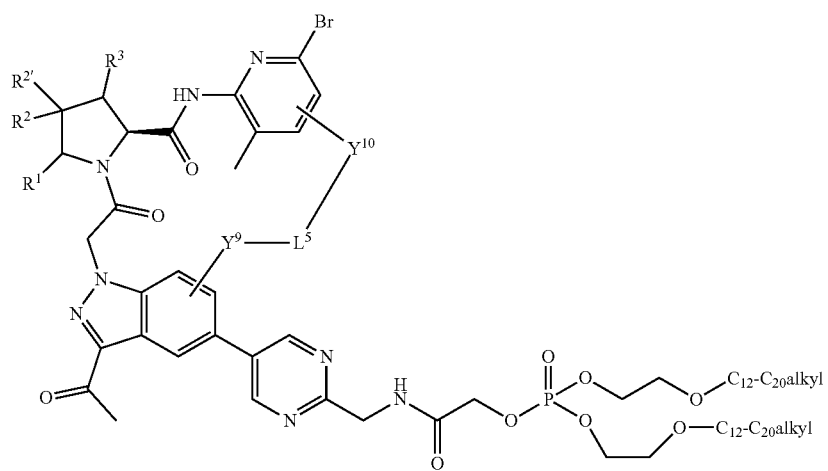

-continued
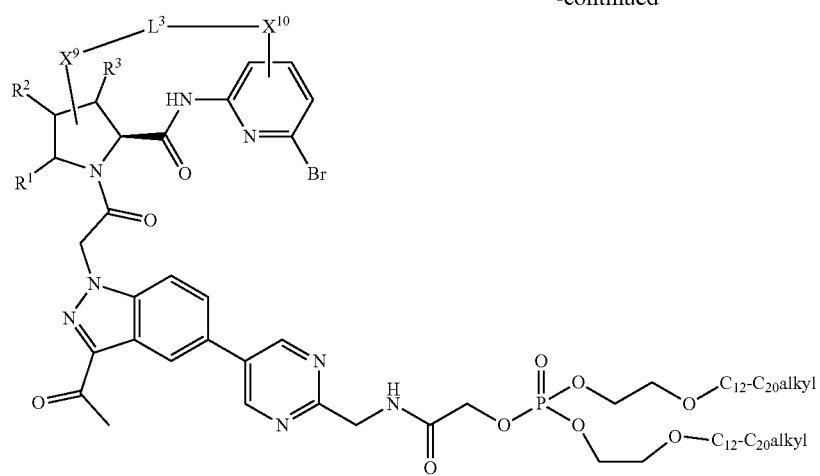
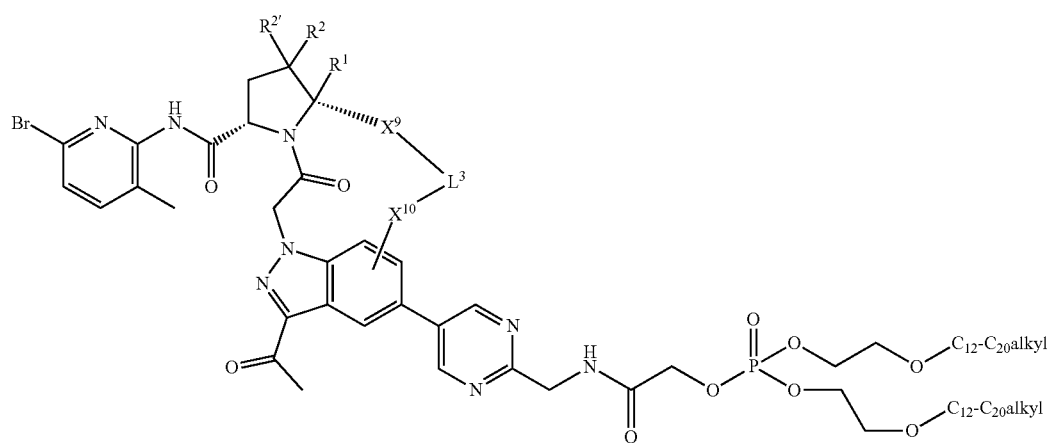
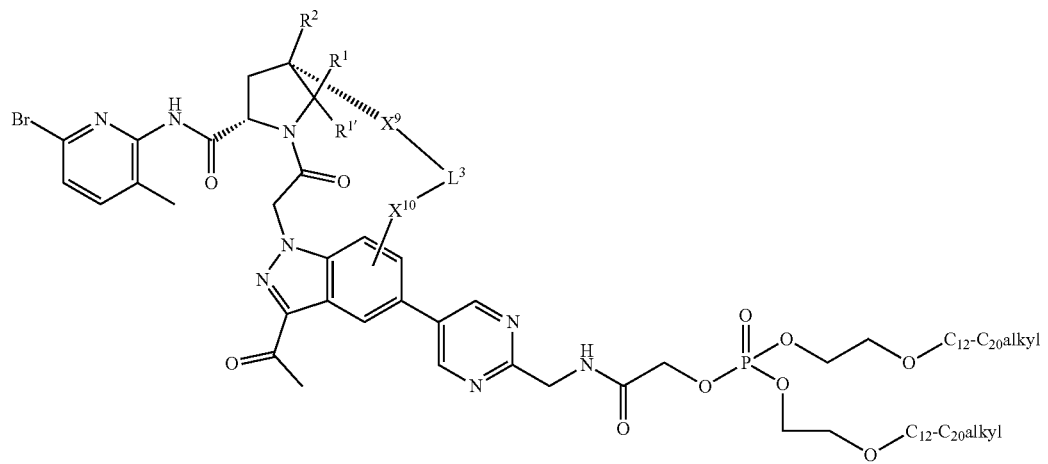

-continued
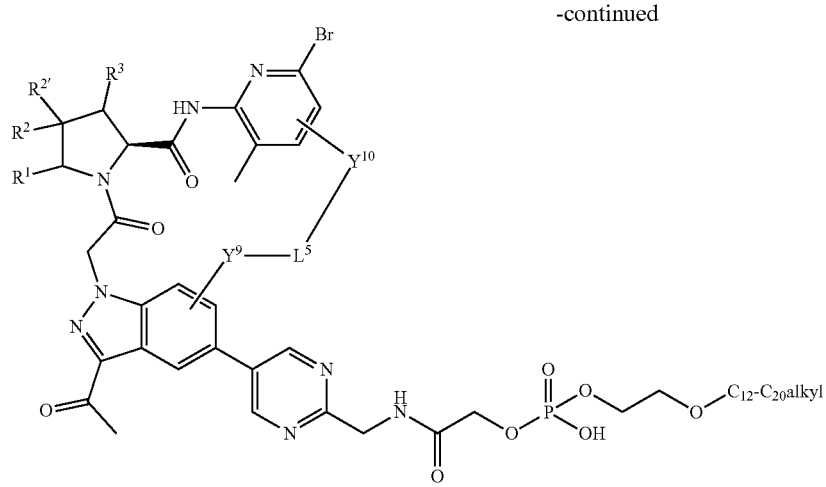
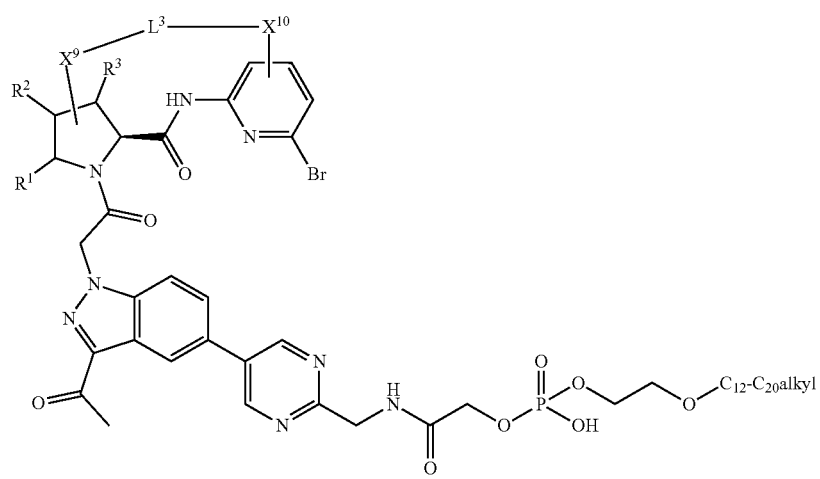
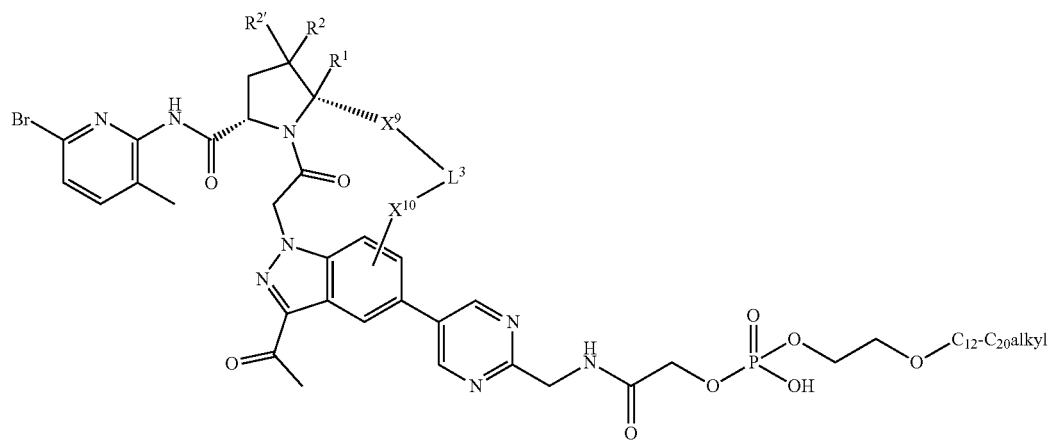

-continued

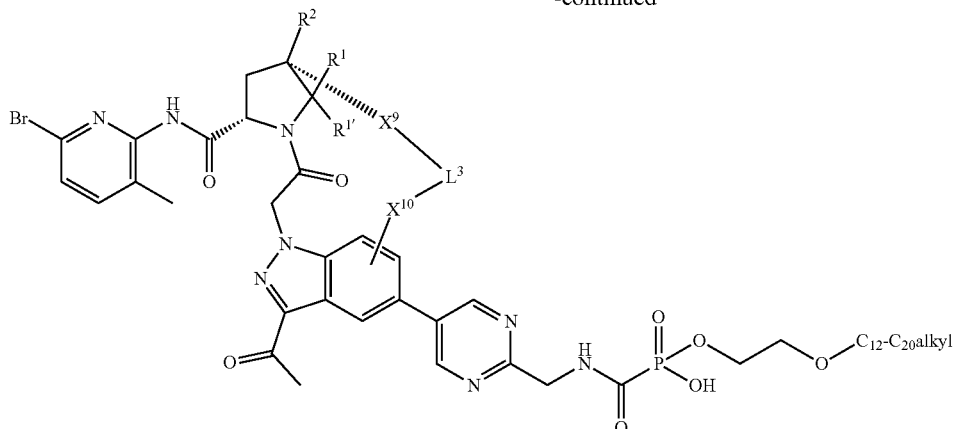

In one embodiment $R^{32}$ is:

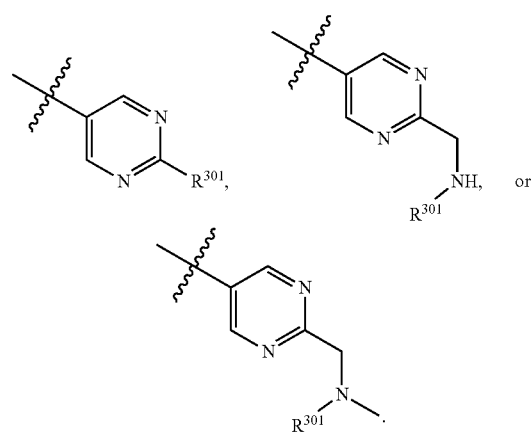

N-Oxides

In certain embodiments, any of the active compounds can be provided in its N-oxide form to a patient in need thereof. In one embodiment, an N-oxide of an active compound or a precursor of the active compound is used in a manufacturing scheme. In yet another embodiment, the N-oxide is a metabolite of administration of one of the active compounds herein, and may have independent activity. The N-oxide can be formed by treating the compound of interest with an oxidizing agent, for example a suitable peroxyacid or peroxide, to generate an N-oxide compound. For example, a heteroaryl group, for example a pyridyl group, can be treated with an oxidizing agent such as sodium percarbonate in the presence of a rhenium-based catalyst under mild reaction conditions to generate an N-oxide compound. A person skilled in the art will understand that appropriate protecting groups may be necessary to carry out the chemistry. See, Jain, S. L. et al., "Rhenium-Catalyzed Highly Efficient Oxidations of Tertiary Nitrogen Compounds to N-Oxides Using Sodium Percarbonate as Oxygen Source, Synlett, 2261-2663, 2006.

In one embodiment the N-oxide is in the A-Ring. In one embodiment the N-oxide is in the B-Ring. In one embodiment the N-oxide is on the $R^{32}$ group.

In other embodiments, any of the active compounds with a sulfur can be provided in its sulfoxide or sulfone form to a patient in need thereof. In a different embodiment, a sulfoxide or sulfone of one of the active compounds or a precursor of the active compound is used in a manufacturing scheme. A sulfur atom in a selected compound as described herein can be oxidized to form a sulfoxide

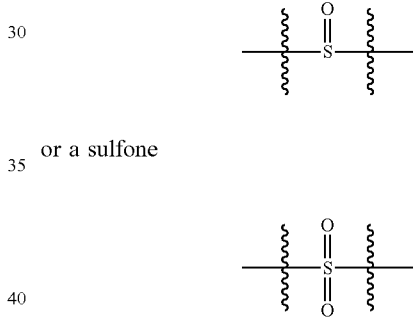

or a sulfone using known methods. For example, the compound 1,3,5-triazo-2,4,6-triphosphorine-2,2,4,4,6,6-tetrachloride (TAPC) is an efficient promoter for the oxidation of sulfides to sulfoxides. See, Bahrami, M. et al., "TAPC-Promoted Oxidation of sulfides and Deoxygenation of Sulfoxides", J. Org. Chem., 75, 6208-6213 (2010). Oxidation of sulfides with 30% hydrogen peroxide catalyzed by tantalum carbide provides sulfoxides in high yields, see, Kirihara, A., et al., "Tantalum Carbide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Sulfides can be oxidized to sulfones using, for example, niobium carbide as the catalyst, see, Kirihara, A., et al., "Tantalum Cardide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Urea-hydrogen peroxide adduct is a stable inexpensive and easily handled reagent for the oxidation of sulfides to sulfones, see Varma, R. S. and Naicker, K. P., "The Urea-Hydrogen Peroxide Complex: Solid-State Oxidative Protocols for Hydroxylated Aldehydes and Ketones (Dakin Reaction), Nitriles, Sulfides, and Nitrogen Heterocycles", Org. Lett., 1, 189-191 (1999). One skilled in the art will appreciate that other heteroatoms, such as nitrogen, may need to be protected and then deprotected while carrying out the oxidation of a sulfur atom to produce the desired compound.

Embodiments of Formula I

In one embodiment, $R^{53}$ is cyano, nitro, hydroxyl or $C_1$-$C_6$alkoxy.

In one embodiment, $Z^3$ is $C(R^1R^{1'})$.

In one embodiment, $Z^{4a}$ is N, CH or CZ.

In the below embodiments $L^6$ is

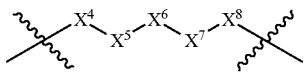

In one embodiment the compound of Formula I is selected from:

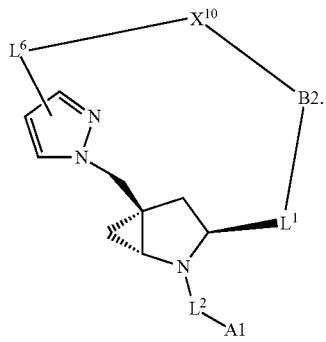

In one embodiment the compound of Formula I is selected from:

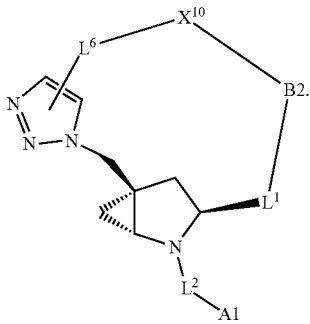

In one embodiment the compound of Formula I is selected from:

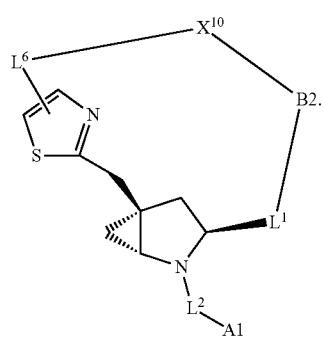

In one embodiment the compound of Formula I is selected from:

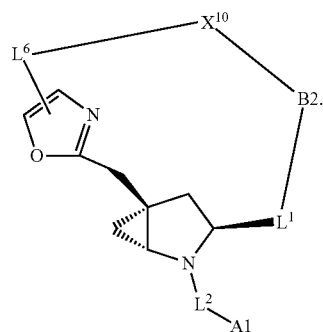

In one embodiment the compound of Formula I is selected from:

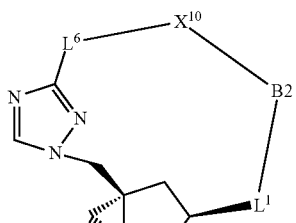

and

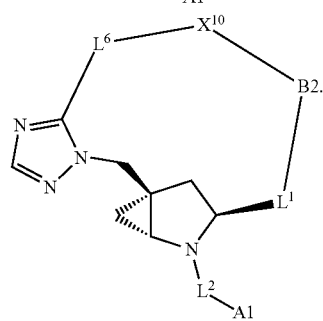

In one embodiment the compound of Formula I is selected from:

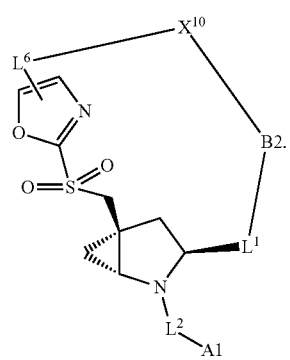

In one embodiment the compound of Formula I is selected from:

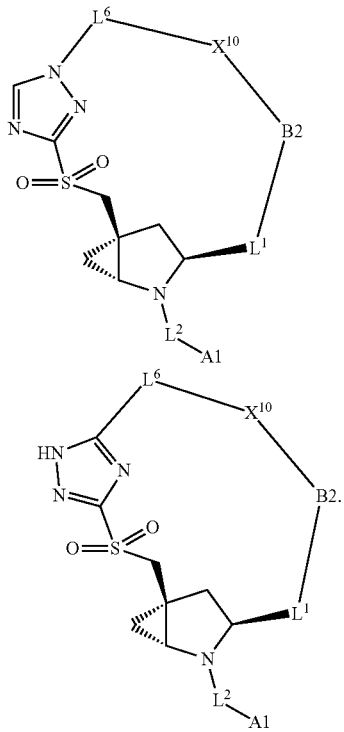

and

In one embodiment the compound of Formula I is selected from:

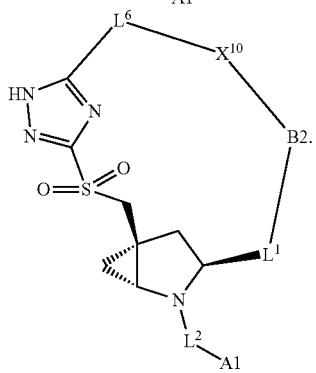

In one embodiment the compound of Formula I is selected from:

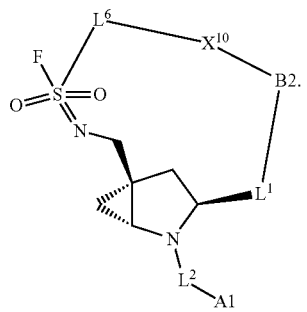

In one embodiment the compound of Formula I is selected from:

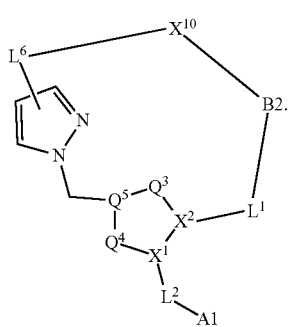

In one embodiment the compound of Formula I is selected from:

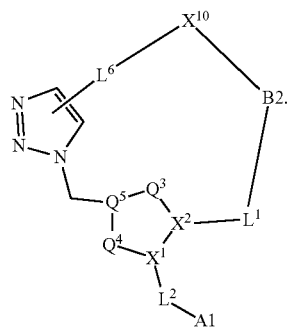

In one embodiment the compound of Formula I is selected from:

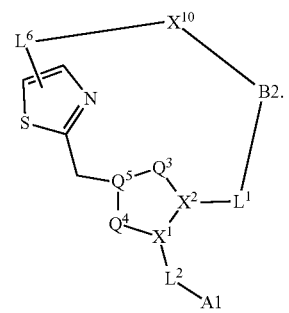

In one embodiment the compound of Formula I is selected from:

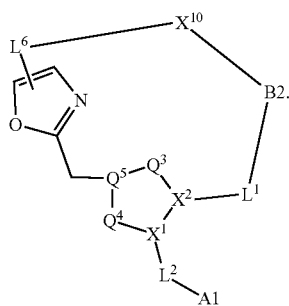

In one embodiment the compound of Formula I is selected from:

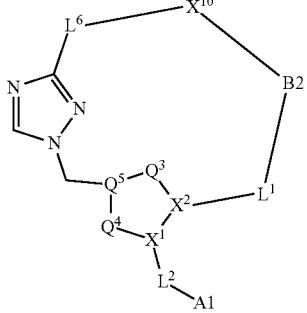

and

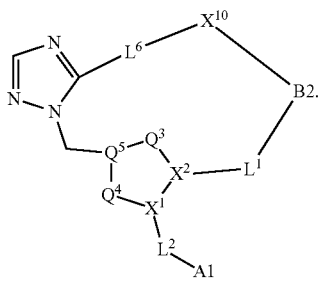

In one embodiment the compound of Formula I is selected from:

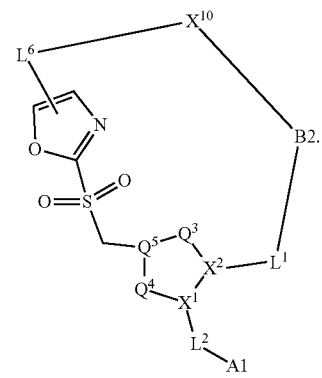

In one embodiment the compound of Formula I is selected from:

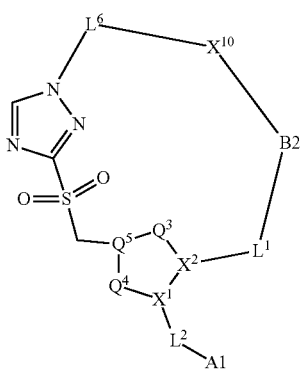

and

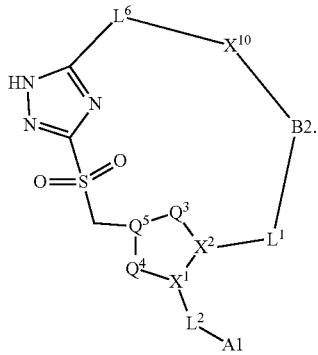

In one embodiment the compound of Formula I is selected from:

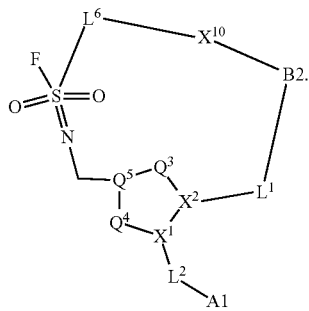

In one embodiment the compound of Formula I is selected from:

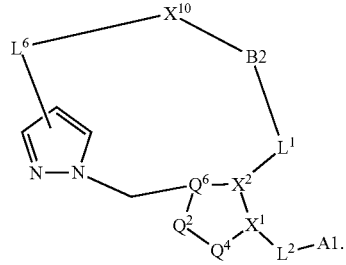

In one embodiment the compound of Formula I is selected from:

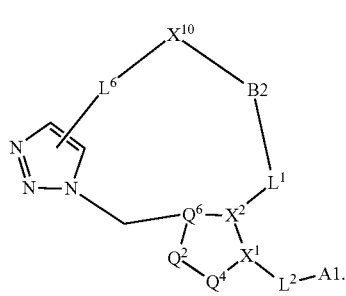

In one embodiment the compound of Formula I is selected from:

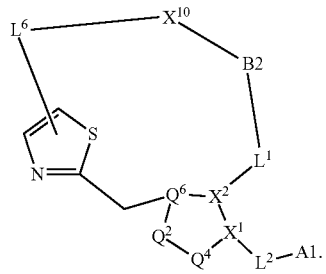

In one embodiment the compound of Formula I is selected from:

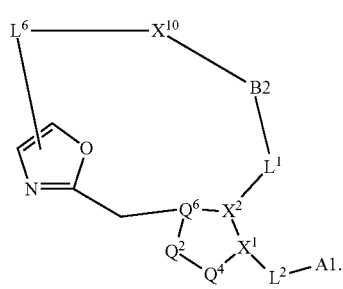

In one embodiment the compound of Formula I is selected from:

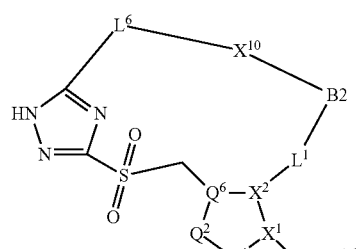

and

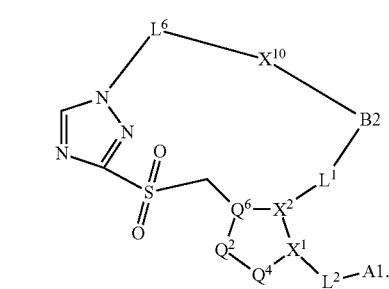

In one embodiment the compound of Formula I is selected from:

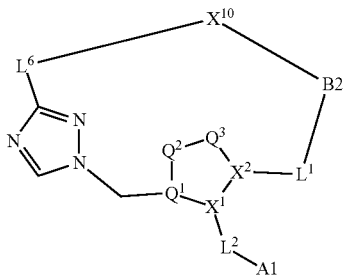

and

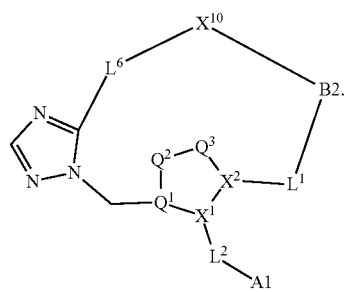

In one embodiment the compound of Formula I is selected from:

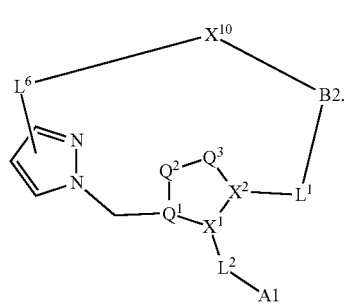

In one embodiment the compound of Formula I is selected from:

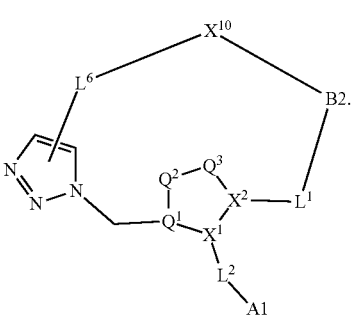

In one embodiment the compound of Formula I is selected from:

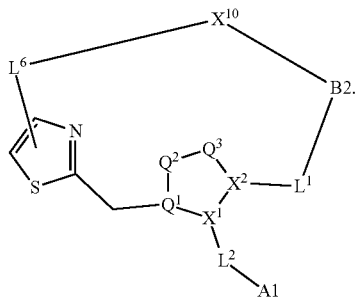

In one embodiment the compound of Formula I is selected from:

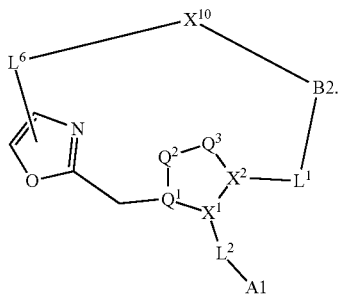

In one embodiment the compound of Formula I is selected from:

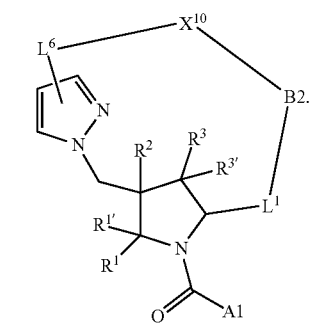

In one embodiment the compound of Formula I is selected from:

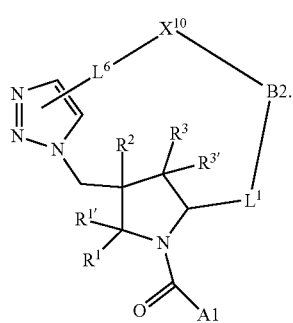

In one embodiment the compound of Formula I is selected from:

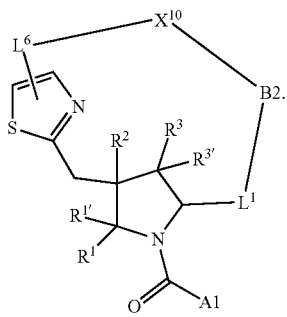

In one embodiment the compound of Formula I is selected from:

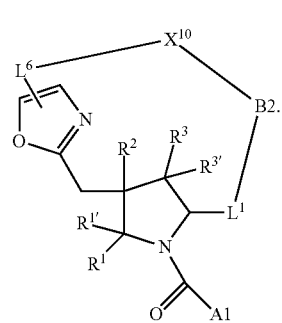

In one embodiment the compound of Formula I is selected from:

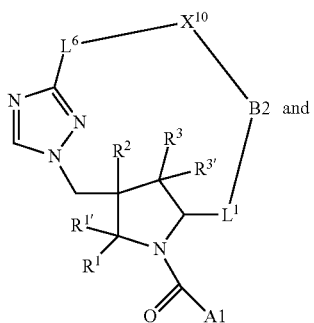

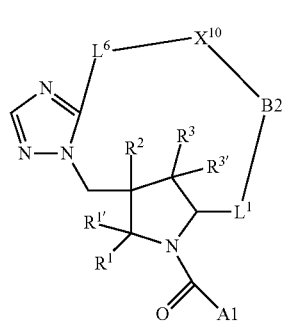

In one embodiment the compound of Formula I is selected from:

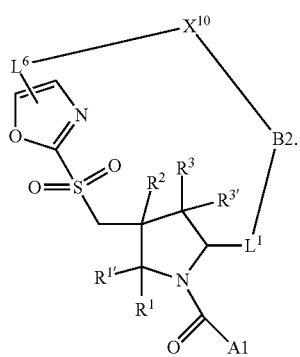

In one embodiment the compound of Formula I is selected from:

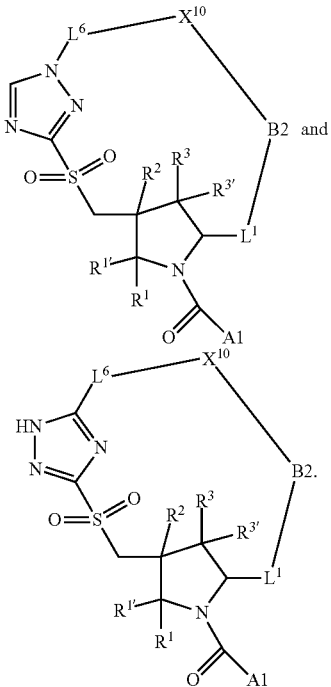

In one embodiment the compound of Formula I is selected from:

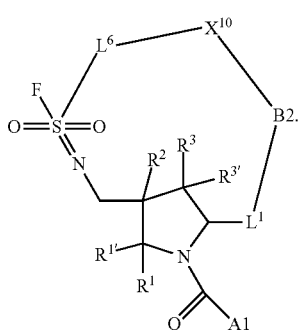

Embodiments of Formula II

In the below embodiments $L^6$ is

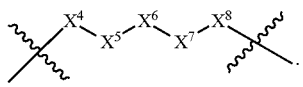

In one embodiment the compound of Formula II is selected from:

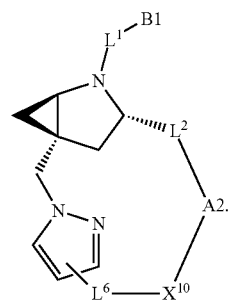

In one embodiment the compound of Formula II is selected from:

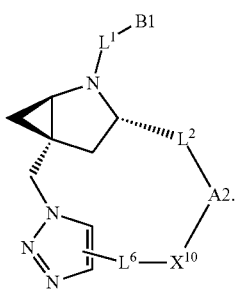

In one embodiment the compound of Formula II is selected from:

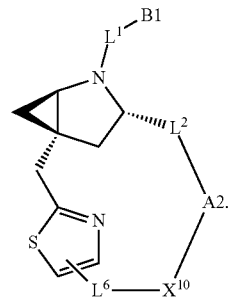

In one embodiment the compound of Formula II is selected from:

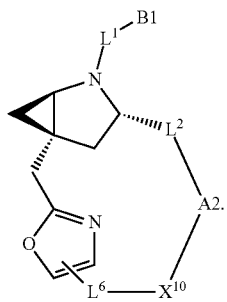

In one embodiment the compound of Formula II is selected from:

 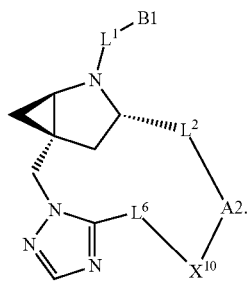

In one embodiment the compound of Formula II is selected from:

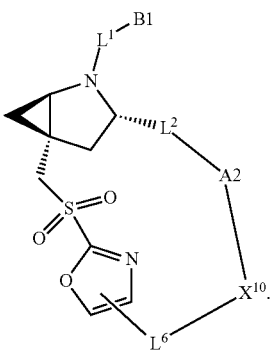

In one embodiment the compound of Formula II is selected from:

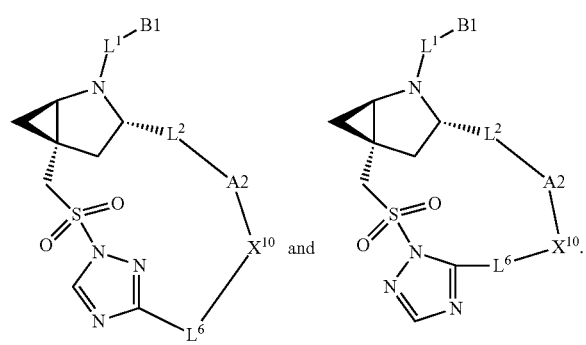

In one embodiment the compound of Formula II is selected from:

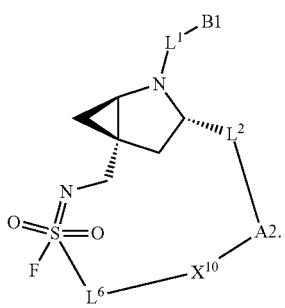

In one embodiment the compound of Formula II is selected from:

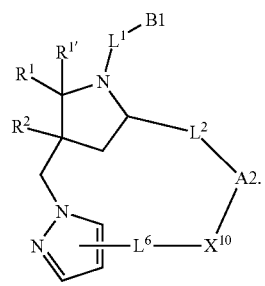

In one embodiment the compound of Formula II is selected from:

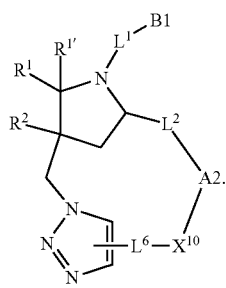

In one embodiment the compound of Formula II is selected from:

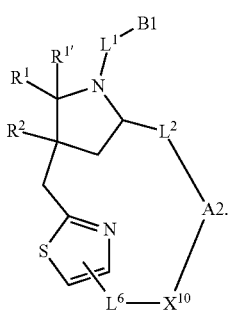

In one embodiment the compound of Formula II is selected from:

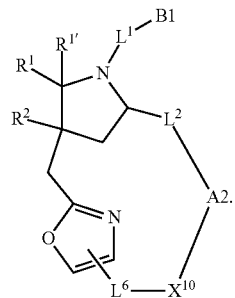

In one embodiment the compound of Formula II is selected from:

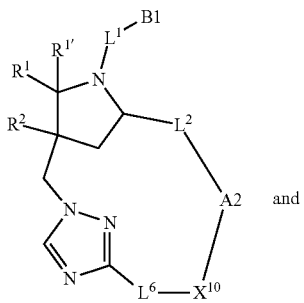

In one embodiment the compound of Formula II is selected from:

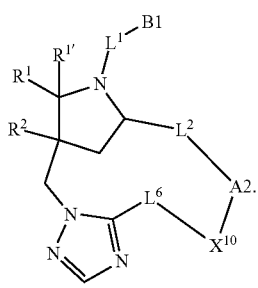

In one embodiment the compound of Formula II is selected from:

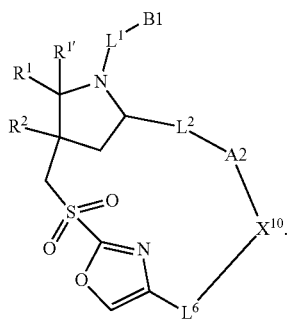

In one embodiment the compound of Formula II is selected from:

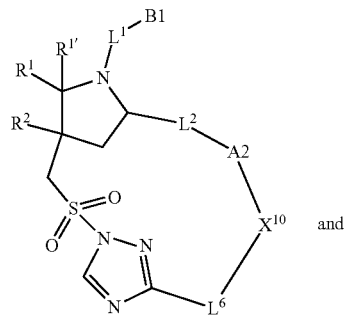

and

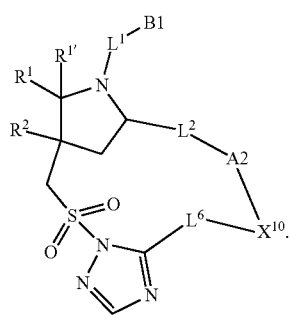

In one embodiment the compound of Formula II is selected from:

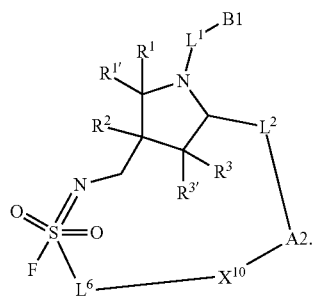

Additional Compounds of the Present Invention

In the below embodiments $L^6$ is

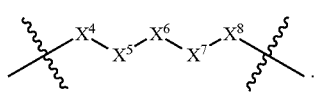

In one embodiment the compound of the present invention is selected from:
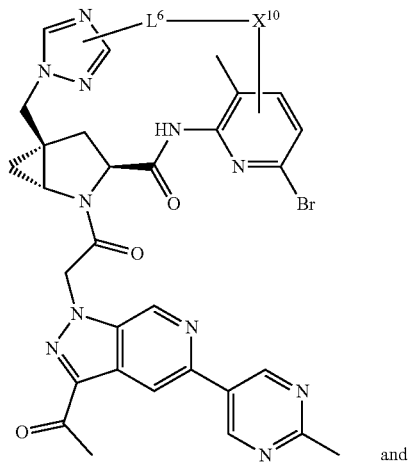
and
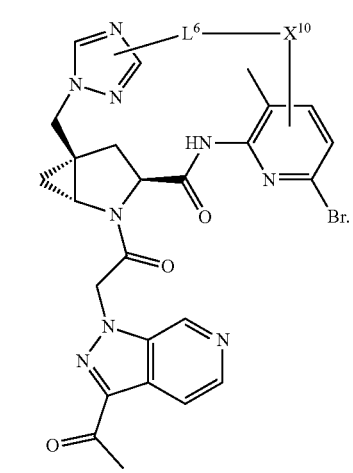
In one embodiment the compound of the present invention is selected from:
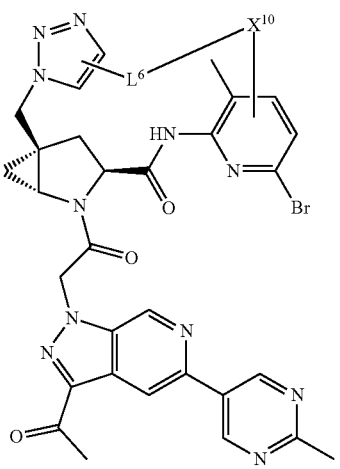
and
-continued
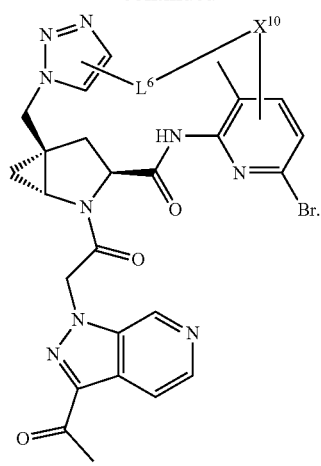
In one embodiment the compound of the present invention is selected from:
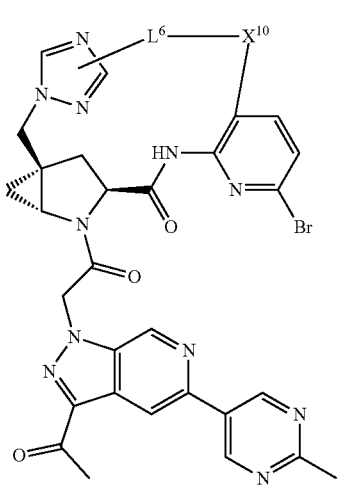
and
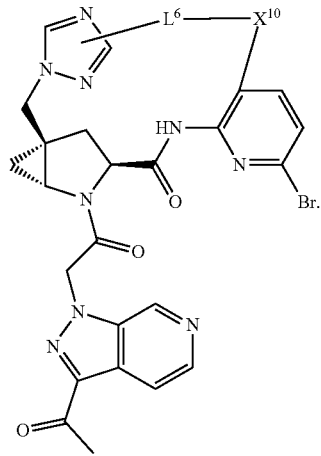

In one embodiment the compound of the present invention is selected from:
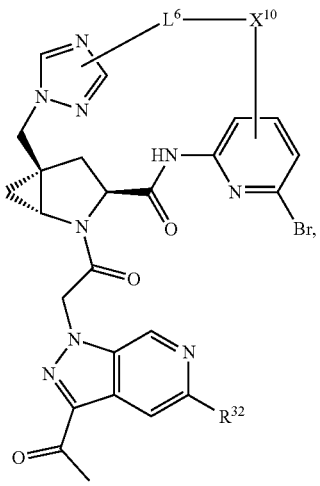
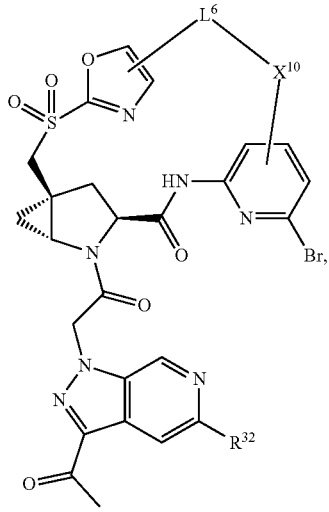
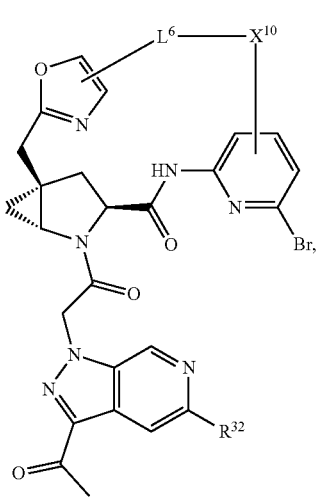
and
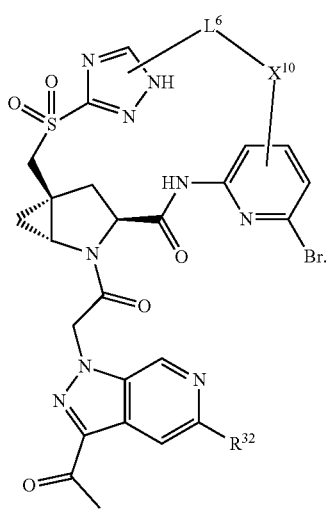

In one embodiment the compound of the present invention is selected from:
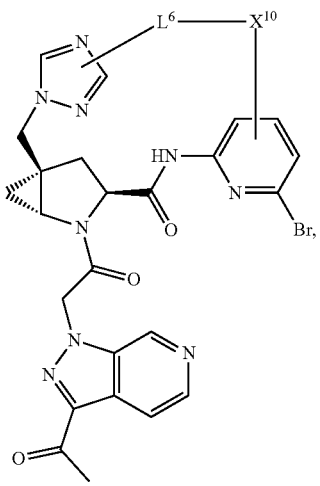
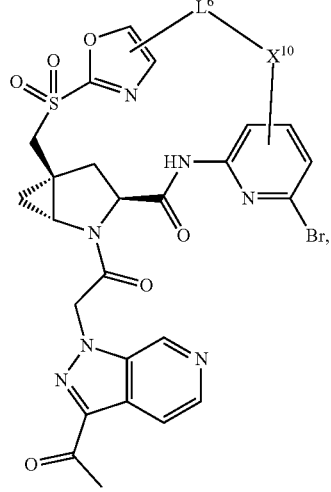

In one embodiment the compound of the present invention is selected from:

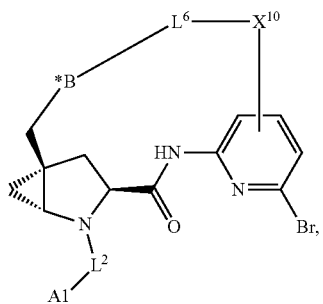

wherein *B is a moiety selected from B1 in a divalent form.

In one embodiment the compound of the present invention is selected from:

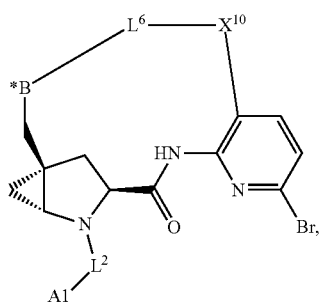

wherein *B is a moiety selected from B1 in a divalent form.

In one embodiment the compound of the present invention is selected from:

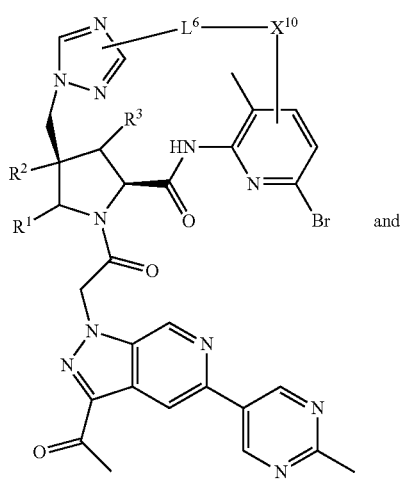

and

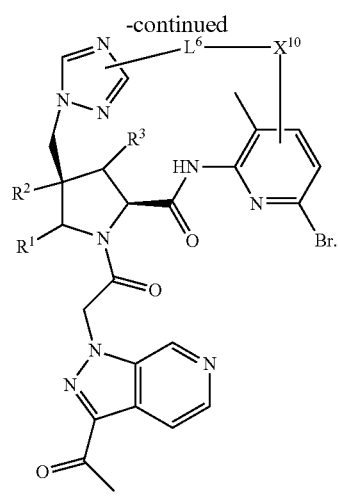

-continued

In one embodiment the compound of the present invention is selected from:

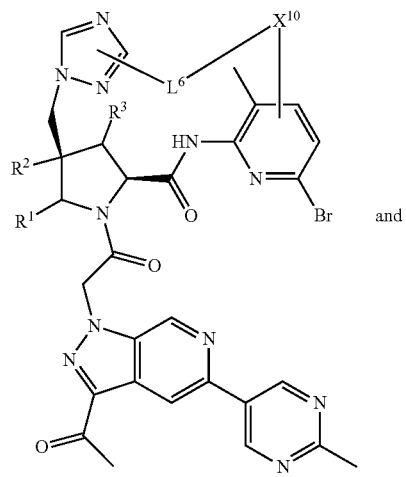

and

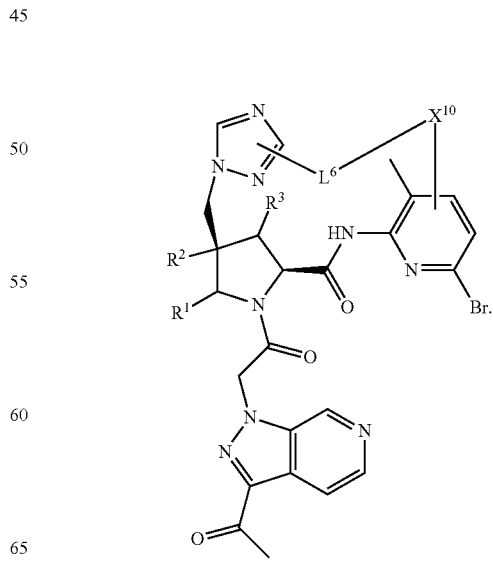

333
In one embodiment the compound of the present invention is selected from:
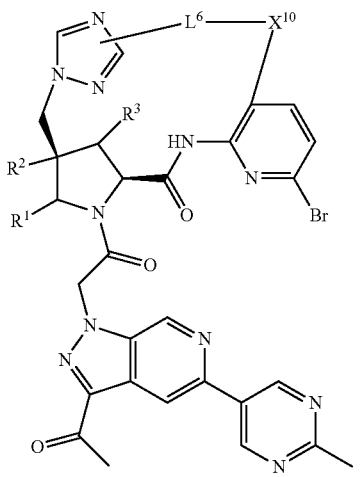
and
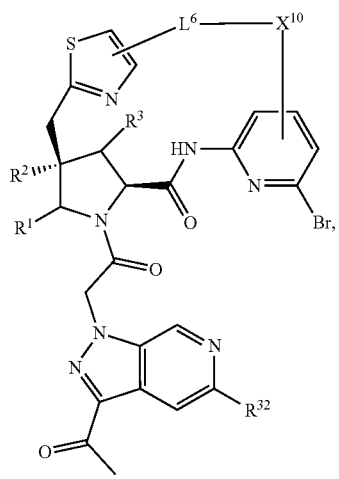
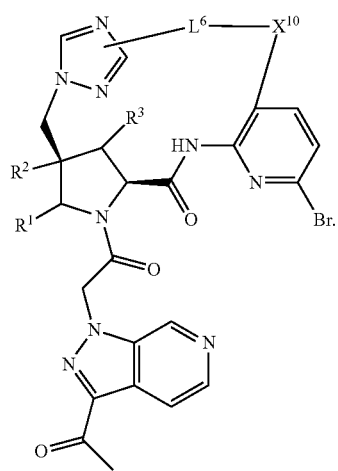
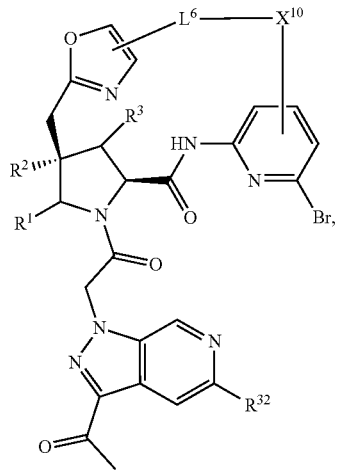
In one embodiment the compound of the present invention is selected from:
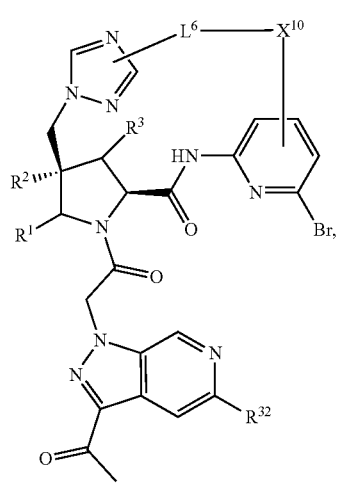
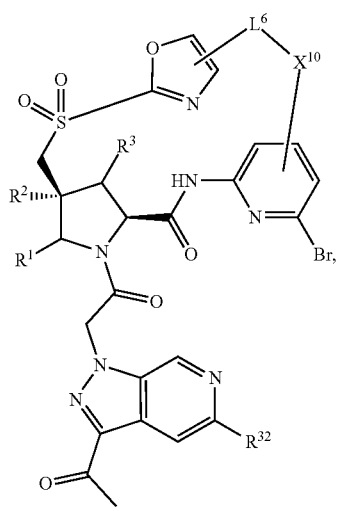
334
-continued 335
-continued
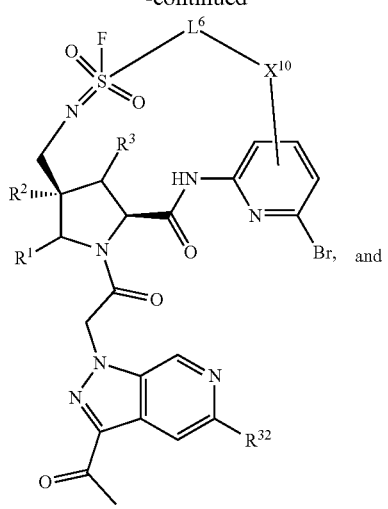
336
-continued
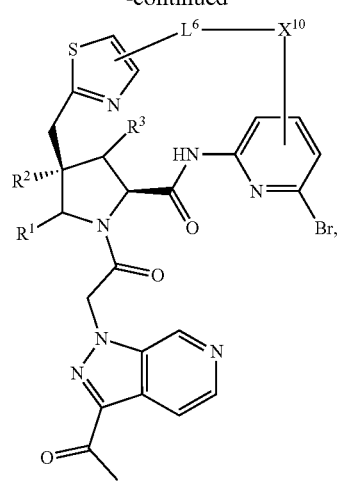
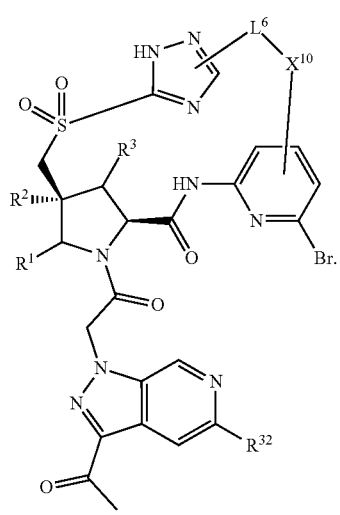
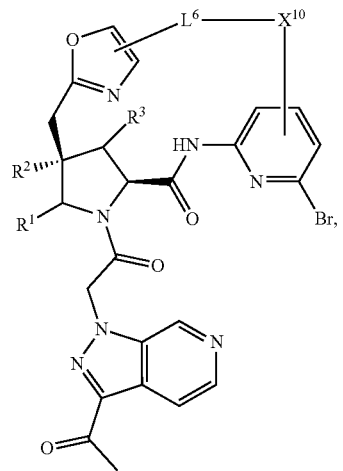
In one embodiment the compound of the present invention is selected from:
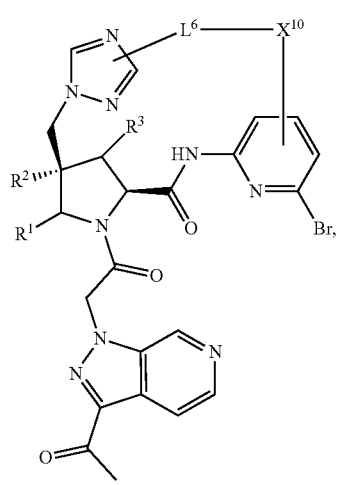
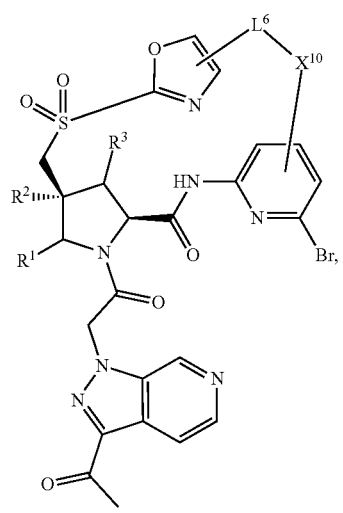

337
-continued
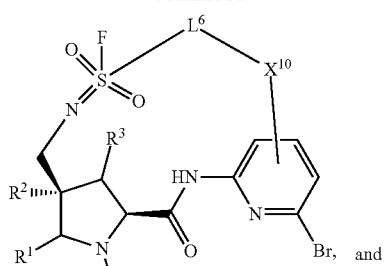
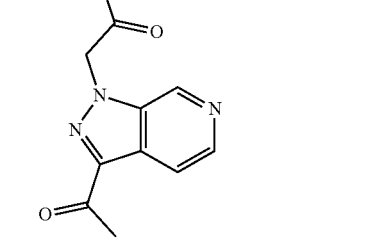
In one embodiment the compound of the present invention is selected from:
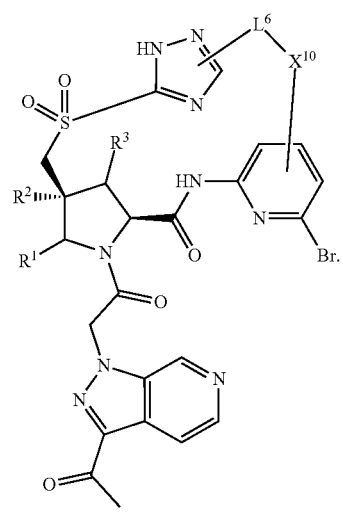
338
-continued
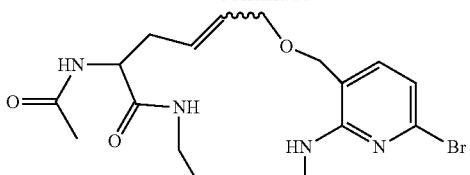
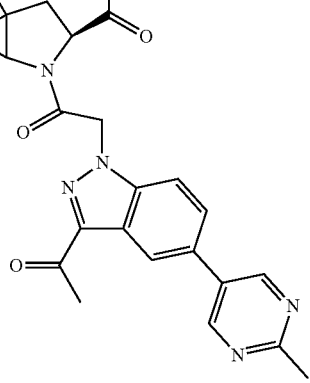
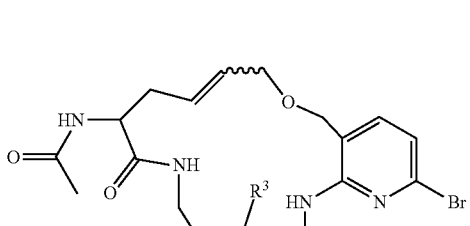
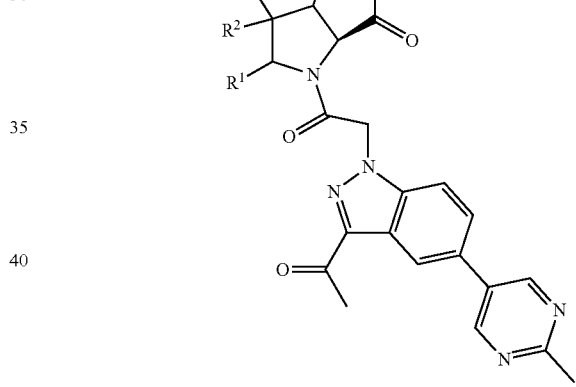
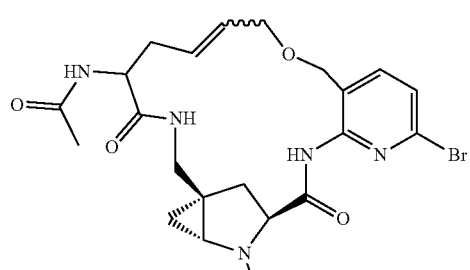
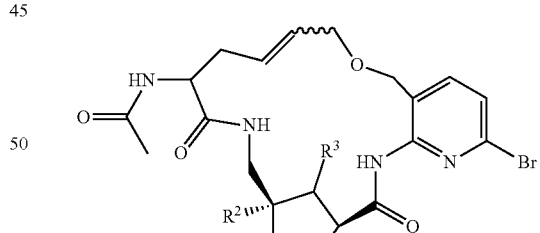
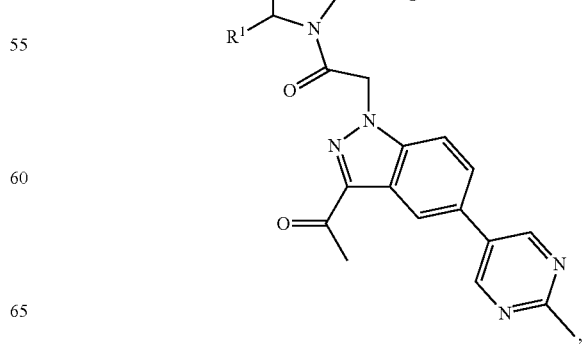

-continued

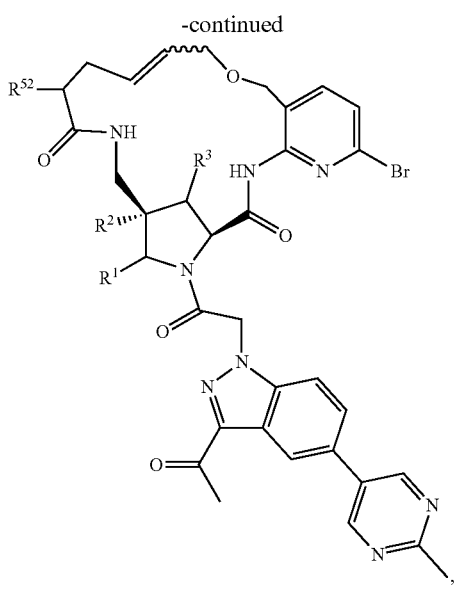

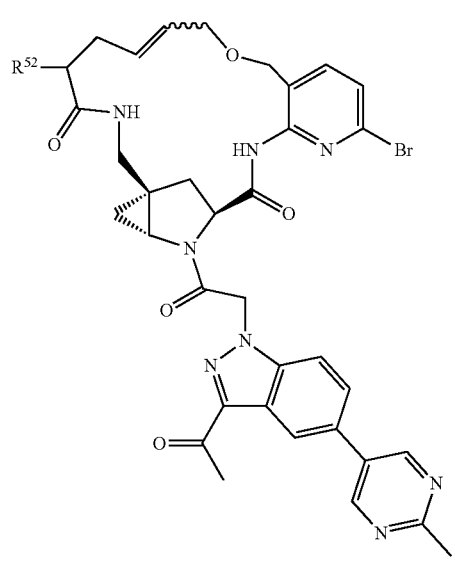

In one embodiment the compound of the present invention is selected from:

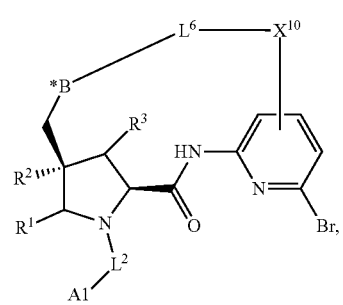

wherein *B is a moiety selected from B1 in a divalent form.

In one embodiment the compound of the present invention is selected from:

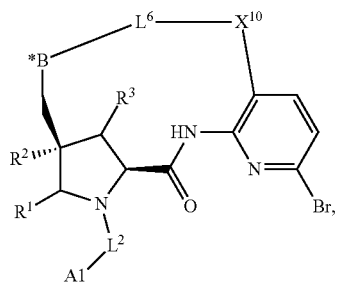

wherein *B is a moiety selected from B1 in a divalent form.

Additional Formulas

TABLE 1

Additional Exemplary Formulas within the Present Invention.

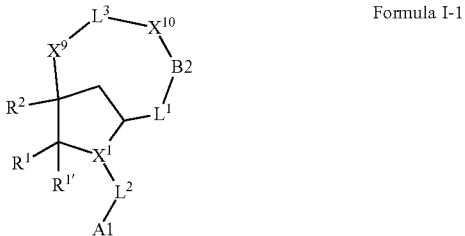

Formula I-1

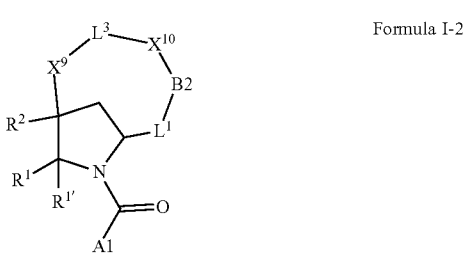

Formula I-2

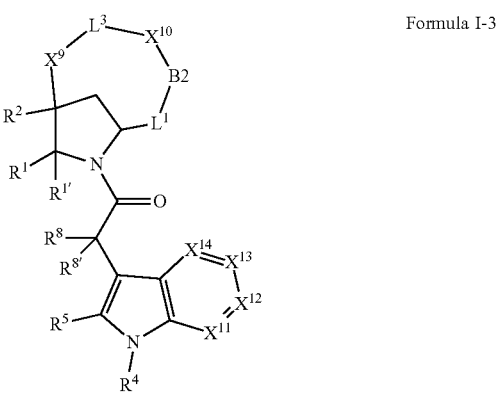

Formula I-3

TABLE 1-continued
Additional Exemplary Formulas within the Present Invention.
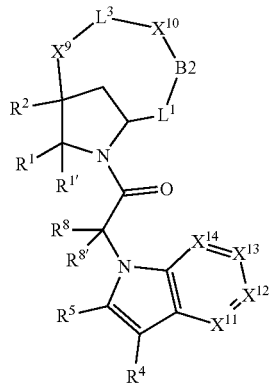
Formula I-4
Formula I-5
Formula I-6
Formula I-7
TABLE 1-continued
Additional Exemplary Formulas within the Present Invention.
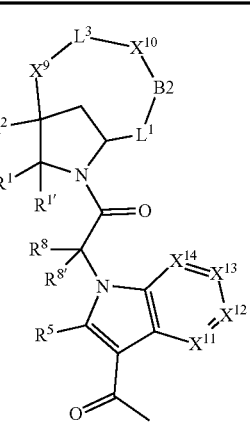
Formula I-8
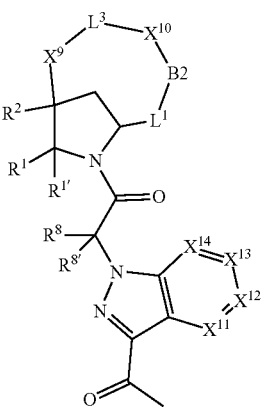
Formula I-9
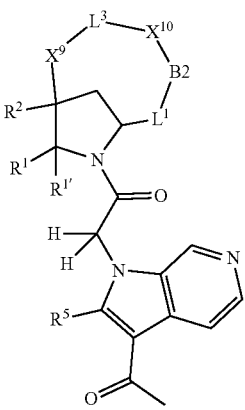
Formula I-10

TABLE 1-continued
Additional Exemplary Formulas within the Present Invention.
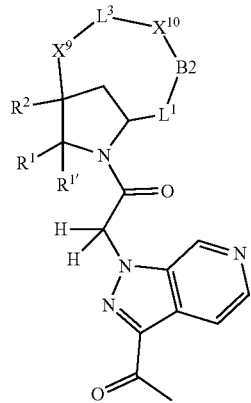
Formula I-11
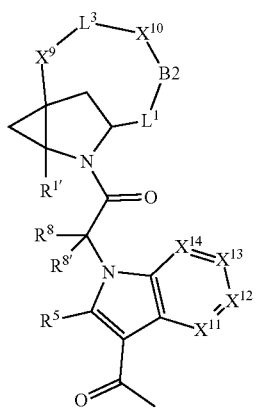
Formula I-12
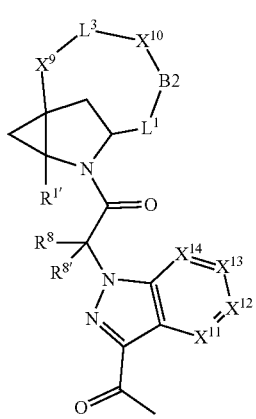
Formula I-13
TABLE 1-continued
Additional Exemplary Formulas within the Present Invention.
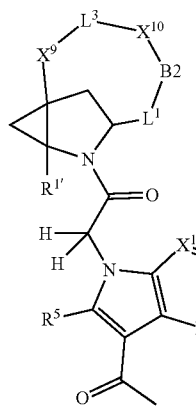
Formula I-14
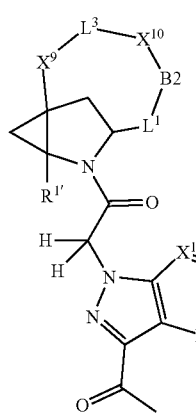
Formula I-15
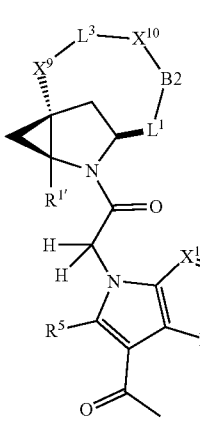
Formula I-16

TABLE 1-continued
Additional Exemplary Formulas within the Present Invention.
Formula I-17
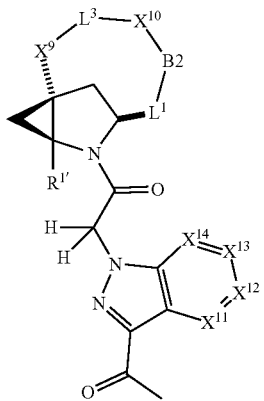
Formula I-18
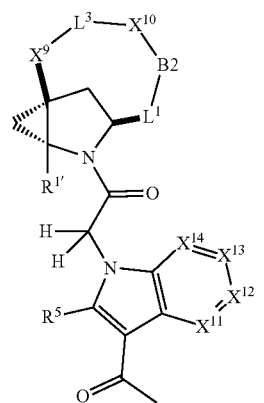
Formula I-19
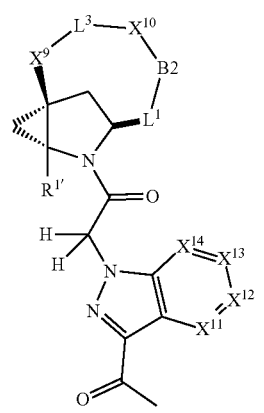
Formula I-20
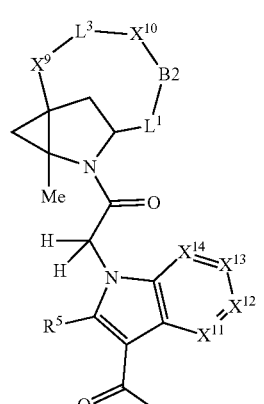
TABLE 1-continued
Additional Exemplary Formulas within the Present Invention.
Formula I-21
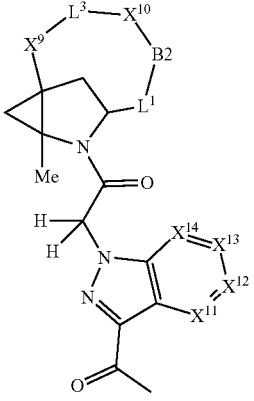
Formula I-22
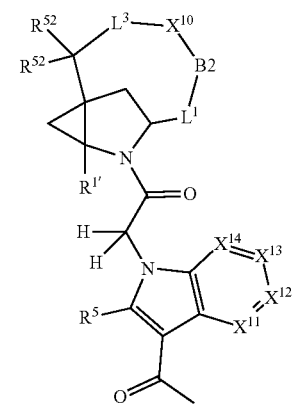
Formula I-23
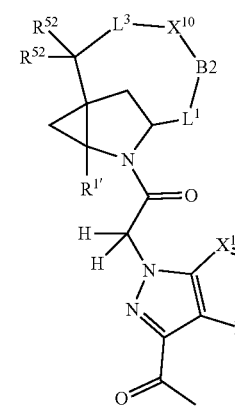

TABLE 1-continued
Additional Exemplary Formulas within the Present Invention.
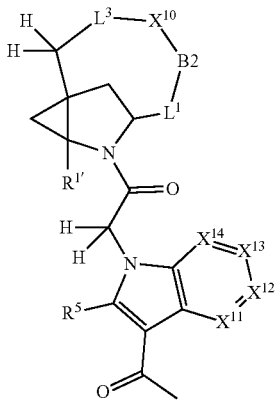
Formula I-24
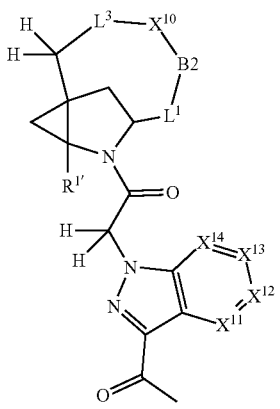
Formula I-25
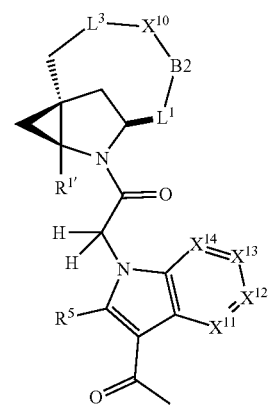
Formula I-26
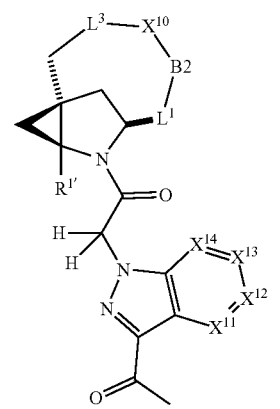
Formula I-27
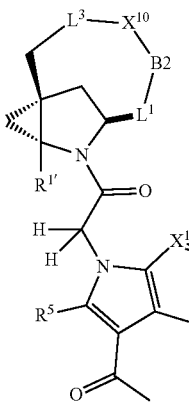
Formula I-28
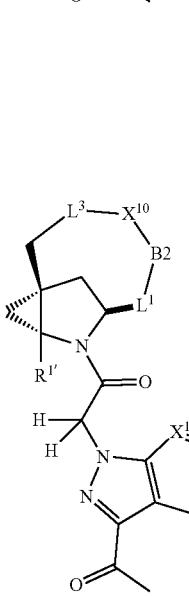
Formula I-29
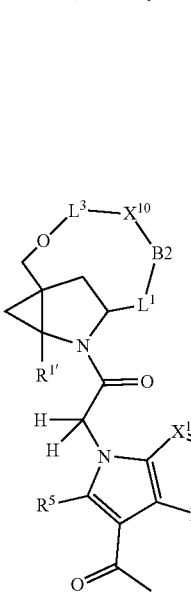
Formula I-30

TABLE 1-continued
Additional Exemplary Formulas within the Present Invention.
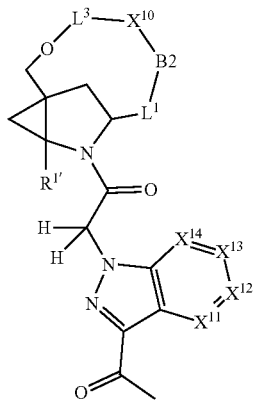
Formula I-31
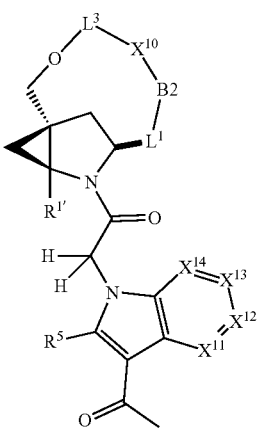
Formula I-32
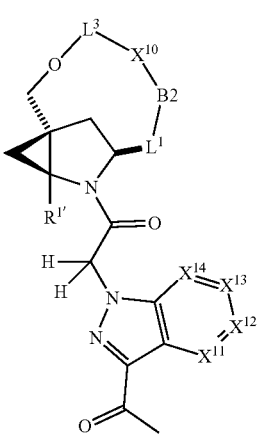
Formula I-33
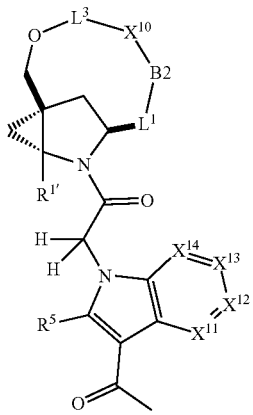
Formula I-34
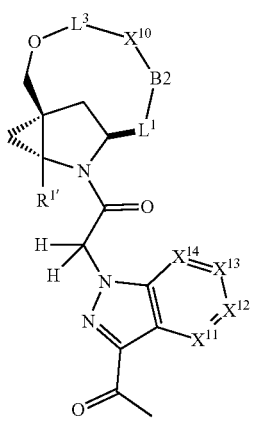
Formula I-35
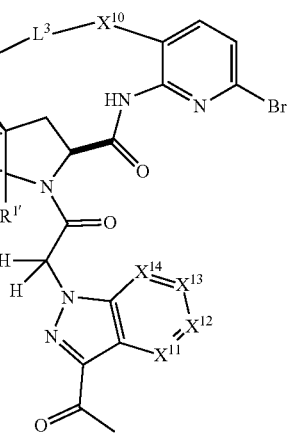
Formula I-36

TABLE 1-continued
Additional Exemplary Formulas within the Present Invention.
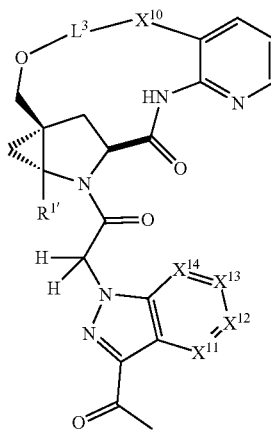
Formula I-37
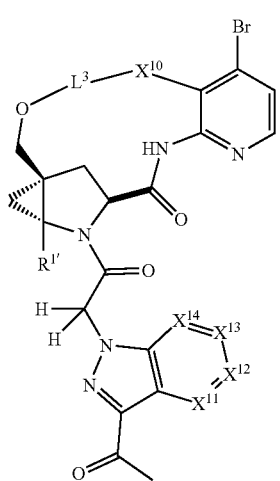
Formula I-38
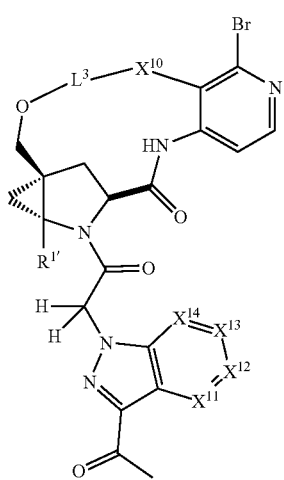
Formula I-39
TABLE 1-continued
Additional Exemplary Formulas within the Present Invention.
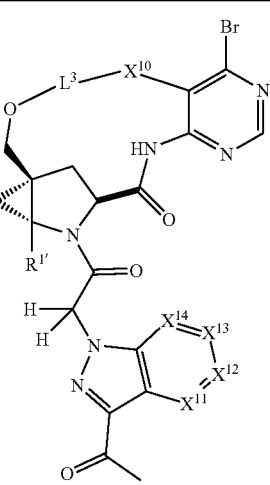
Formula I-40
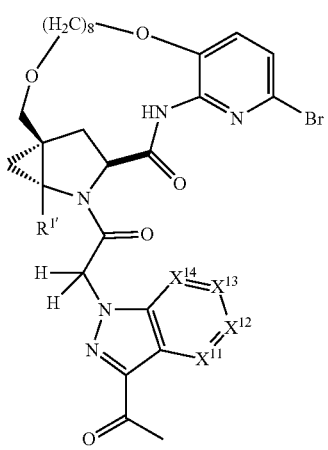
Formula I-41
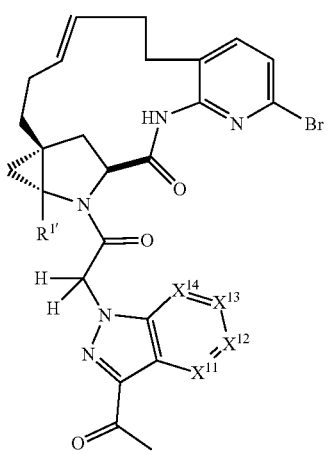
Formula I-42

TABLE 1-continued
Additional Exemplary Formulas within the Present Invention.
Formula I-43
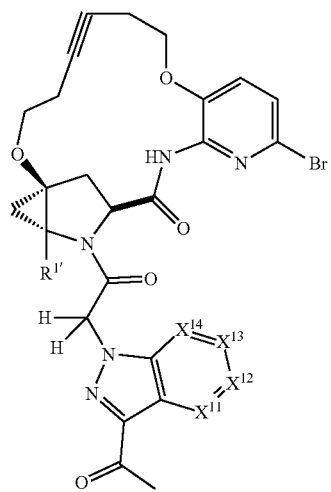
Formula I-44
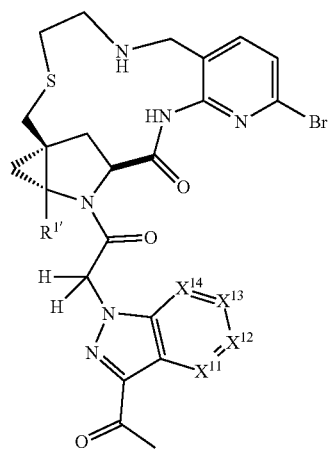
Formula I-45
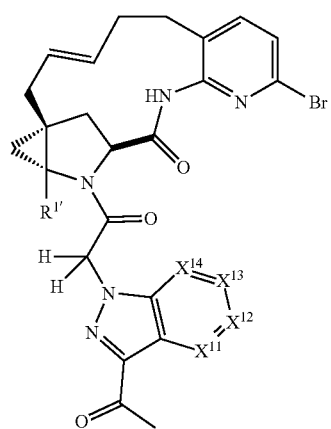
TABLE 2
Additional Exemplary Formulas within the Present Invention.
Formula II-1
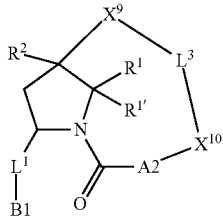
Formula II-2
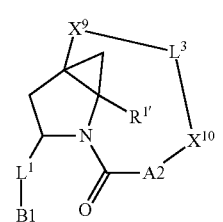
Formula II-3
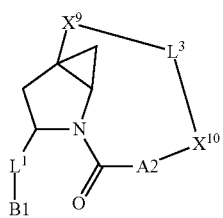
Formula II-4
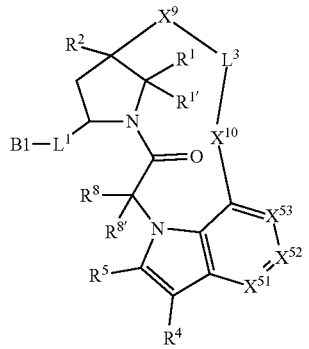
Formula II-5
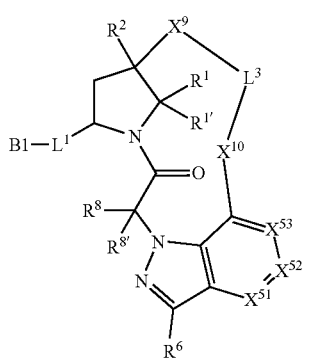

TABLE 2-continued
Additional Exemplary Formulas within the Present Invention.
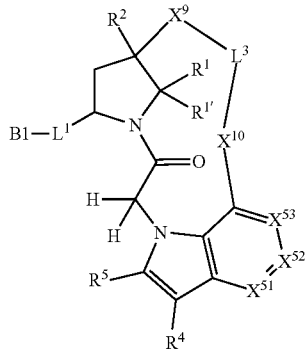
Formula II-6
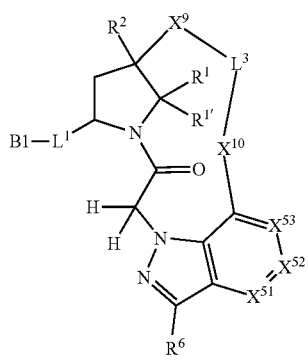
Formula II-7
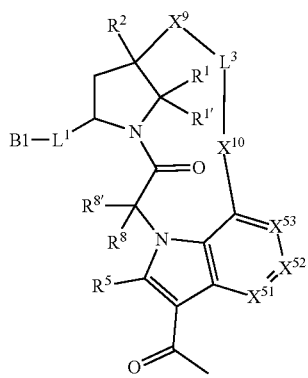
Formula II-8
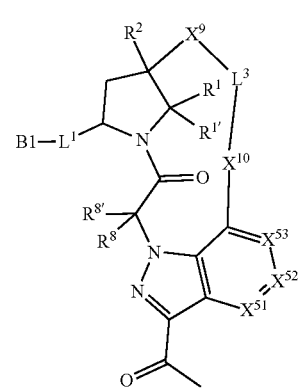
Formula II-9
TABLE 2-continued
Additional Exemplary Formulas within the Present Invention.
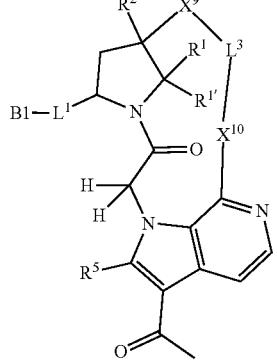
Formula II-10
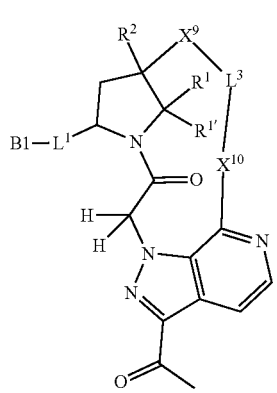
Formula II-11
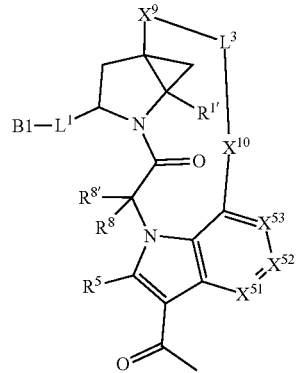
Formula II-12
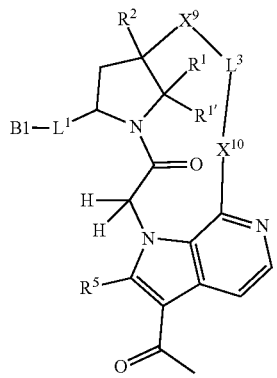
Formula II-13

TABLE 2-continued
Additional Exemplary Formulas within the Present Invention.
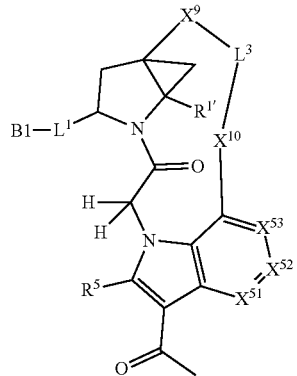
Formula II-14
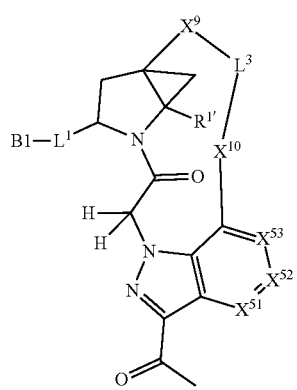
Formula II-15
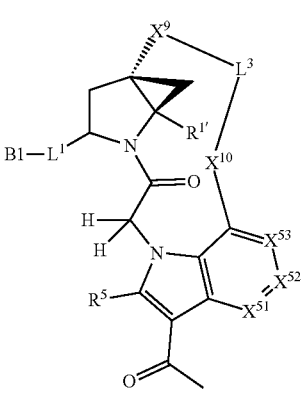
Formula II-16
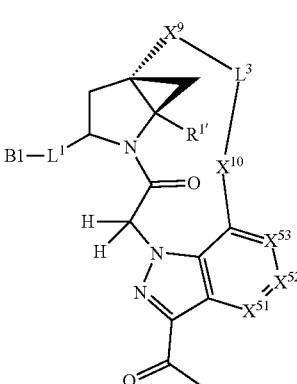
Formula II-17
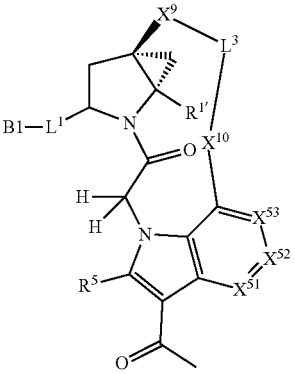
Formula II-18
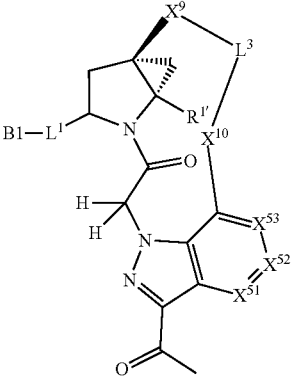
Formula II-19
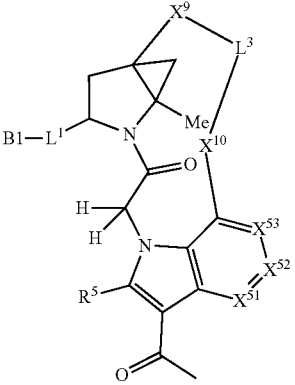
Formula II-20
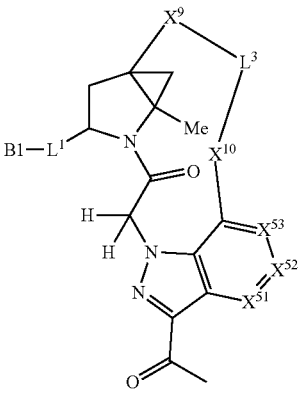
Formula II-21

TABLE 2-continued
Additional Exemplary Formulas within the Present Invention.
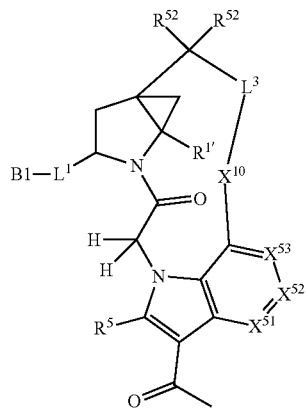 Formula II-22
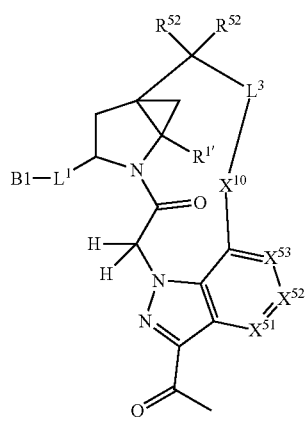 Formula II-23
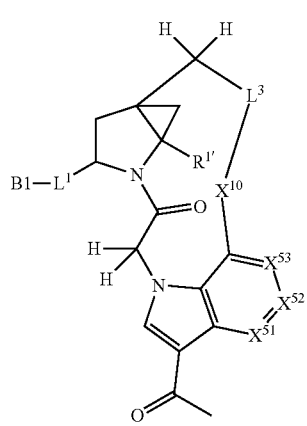 Formula II-24
TABLE 2-continued
Additional Exemplary Formulas within the Present Invention.
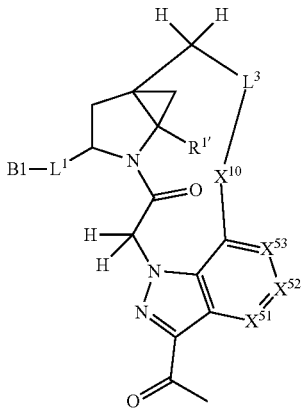 Formula II-25
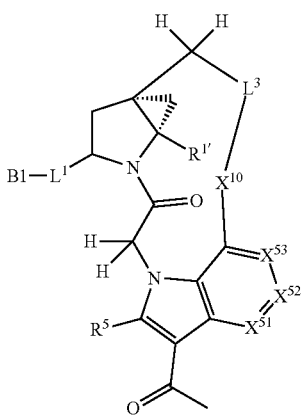 Formula II-26
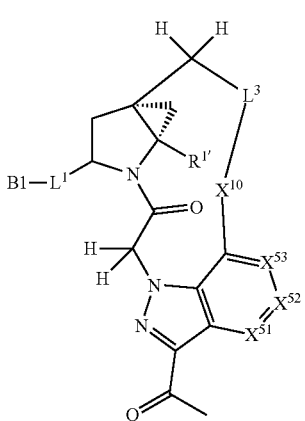 Formula II-27

TABLE 2-continued
Additional Exemplary Formulas within the Present Invention.
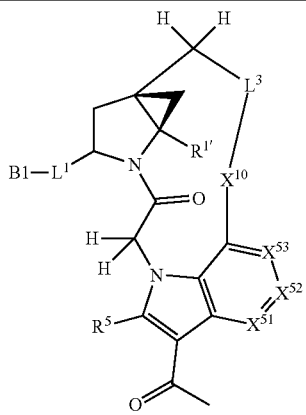
Formula II-28
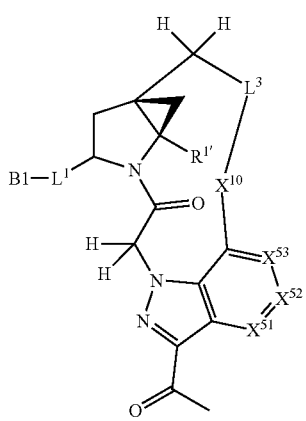
Formula II-29
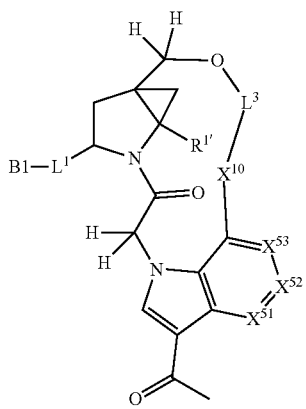
Formula II-30
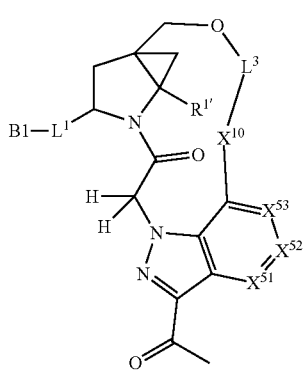
Formula II-31
TABLE 2-continued
Additional Exemplary Formulas within the Present Invention.
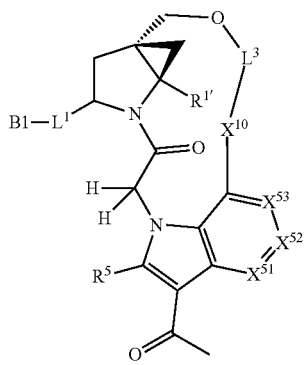
Formula II-32
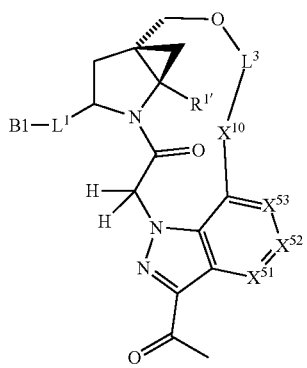
Formula II-33
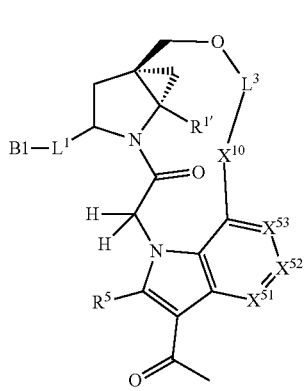
Formula II-34
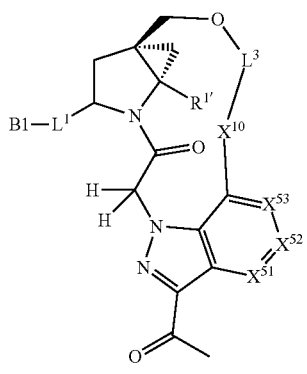
Formula II-35

TABLE 2-continued
Additional Exemplary Formulas within the Present Invention.
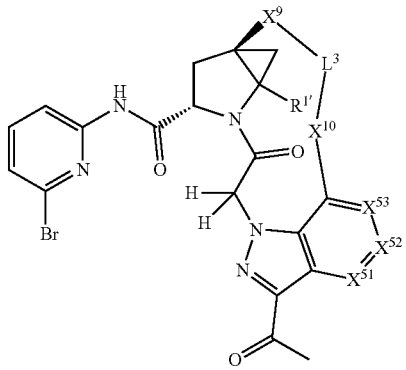
Formula II-36
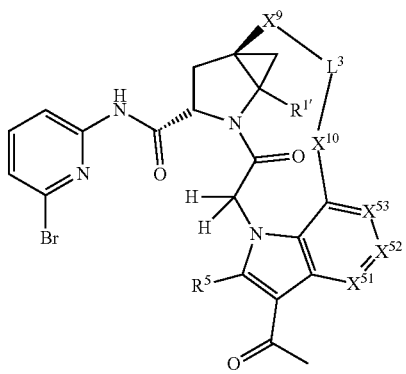
Formula II-37
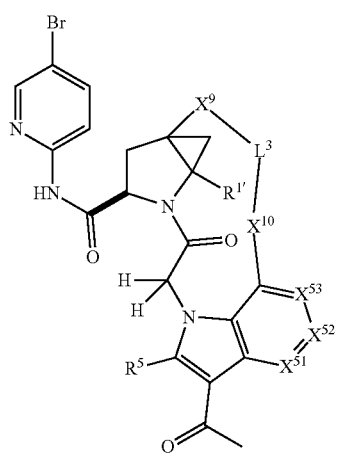
Formula II-38
TABLE 2-continued
Additional Exemplary Formulas within the Present Invention.
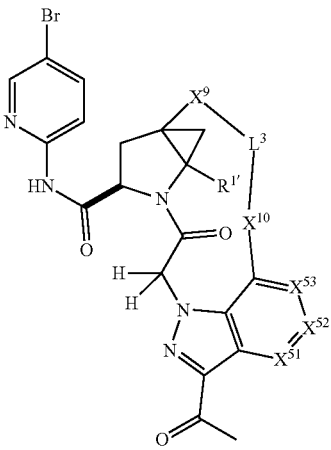
Formula II-39
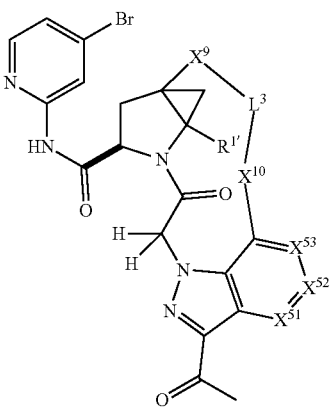
Formula II-40
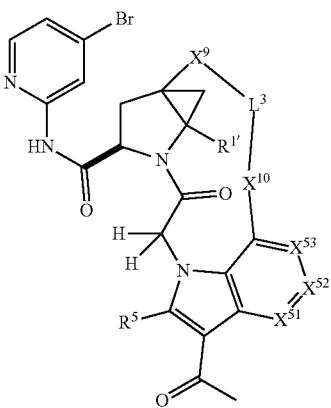
Formula II-41

TABLE 2-continued
Additional Exemplary Formulas within the Present Invention.
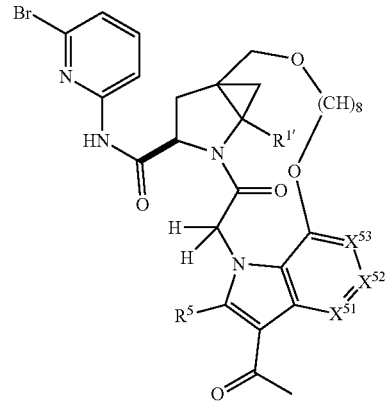
Formula II-41
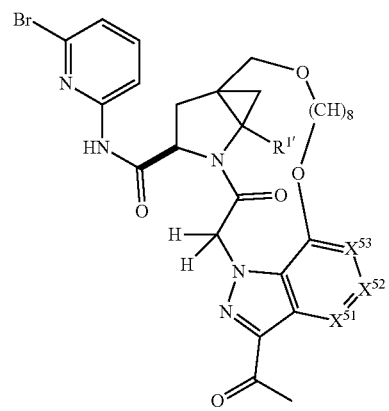
Formula II-42
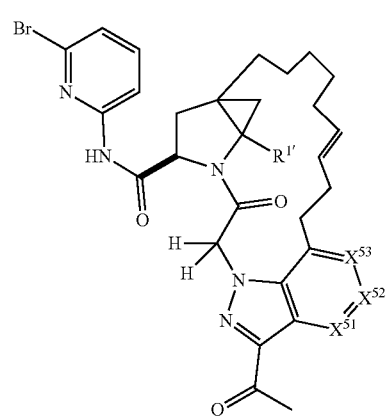
Formula II-43
TABLE 2-continued
Additional Exemplary Formulas within the Present Invention.
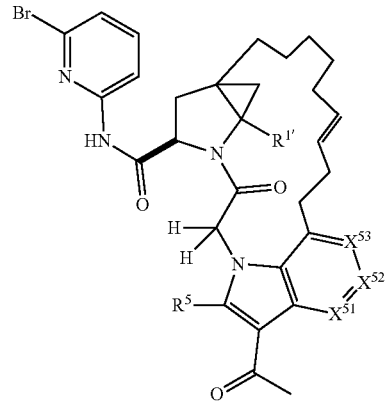
Formula II-44
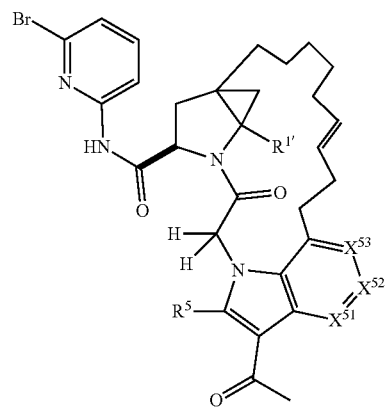
Formula II-44
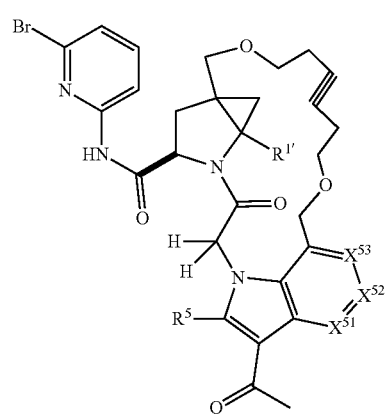
Formula II-45

TABLE 2-continued
Additional Exemplary Formulas within the Present Invention.
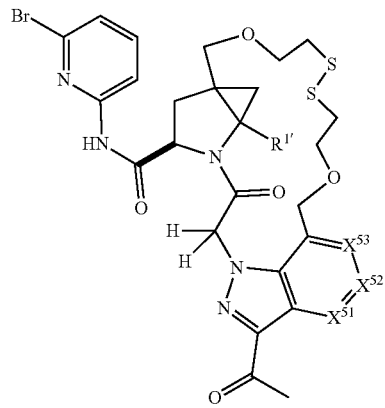
Formula II-46
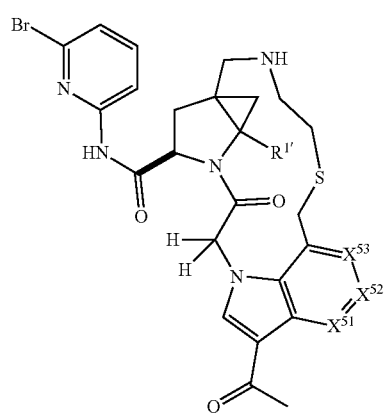
Formula II-47
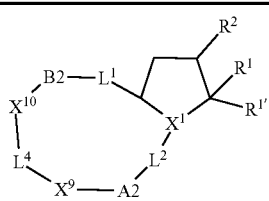
Formula II-48
TABLE 3
Additional Exemplary Formulas within the Present Invention.
Formula III-1
TABLE 3-continued
Additional Exemplary Formulas within the Present Invention.
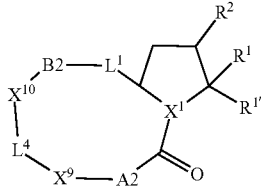
Formula III-2
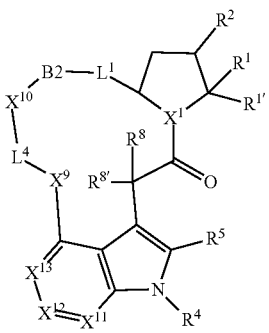
Formula III-3
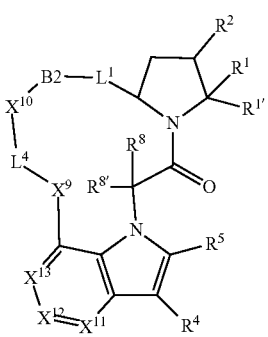
Formula III-4
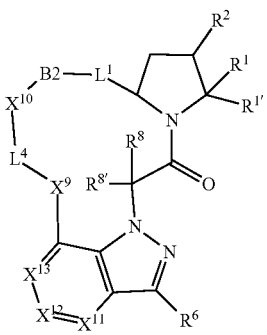
Formula III-5
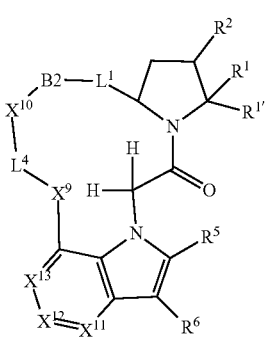
Formula III-6

TABLE 3-continued
Additional Exemplary Formulas within the Present Invention.
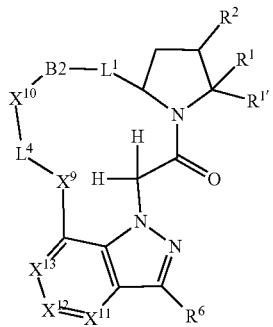
Formula III-7
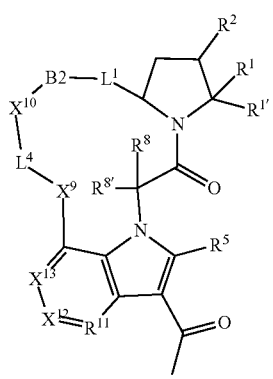
Formula III-8
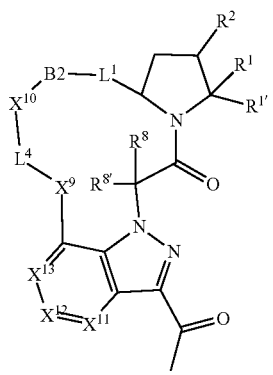
Formula III-9
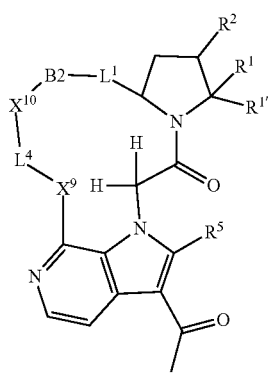
Formula III-10
TABLE 3-continued
Additional Exemplary Formulas within the Present Invention.
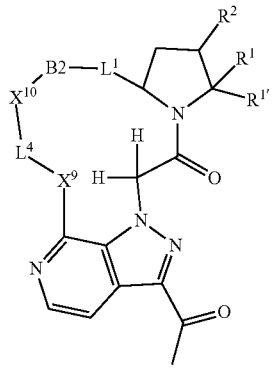
Formula III-11
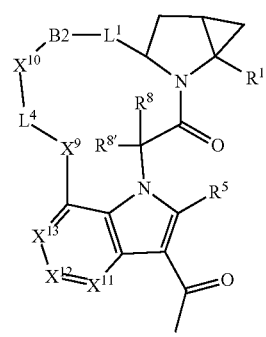
Formula III-12
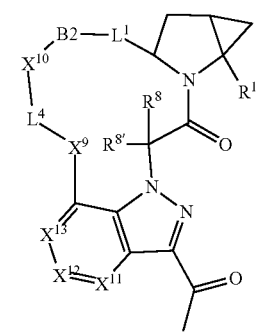
Formula III-13
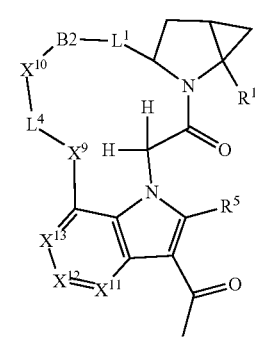
Formula III-14

TABLE 3-continued
Additional Exemplary Formulas within the Present Invention.
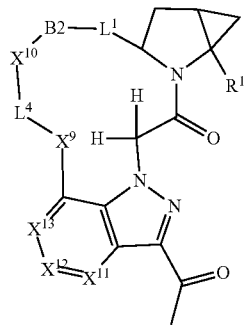
Formula III-15

Formula III-16

Formula III-17
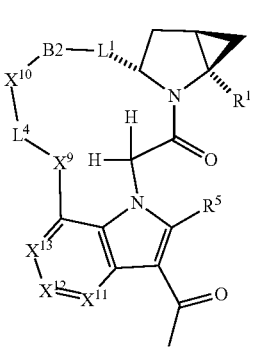
Formula III-18
TABLE 3-continued
Additional Exemplary Formulas within the Present Invention.
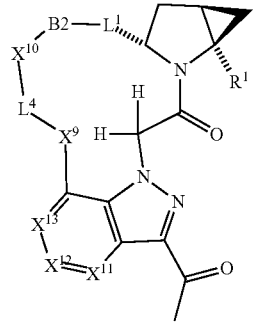
Formula III-19
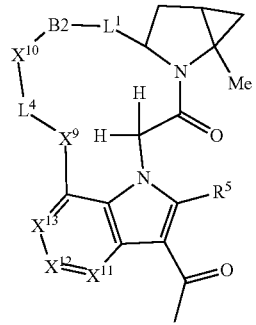
Formula III-20
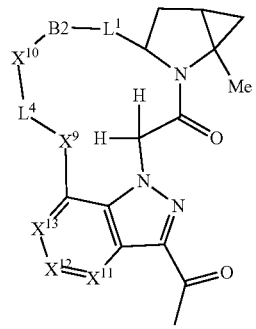
Formula III-21
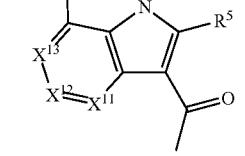
Formula III-22

TABLE 3-continued
Additional Exemplary Formulas within the Present Invention.
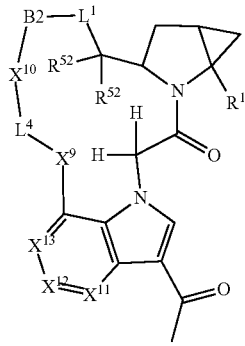
Formula III-23
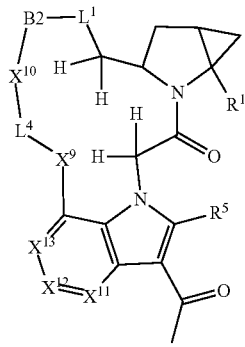
Formula III-24
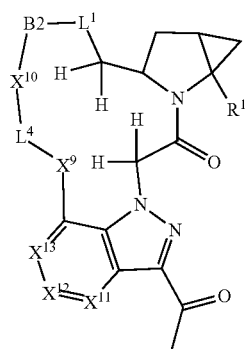
Formula III-25
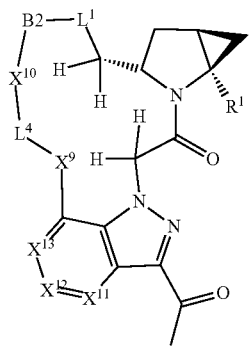
Formula III-26
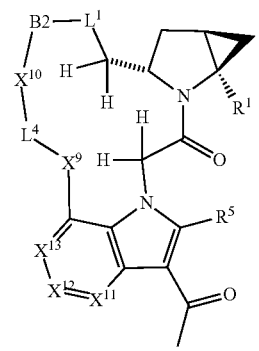
Formula III-27
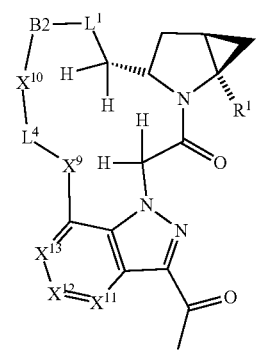
Formula III-28
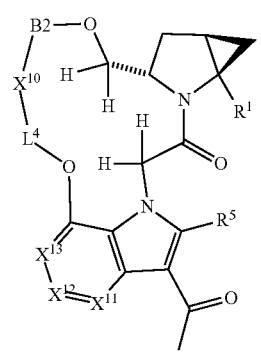
Formula III-29
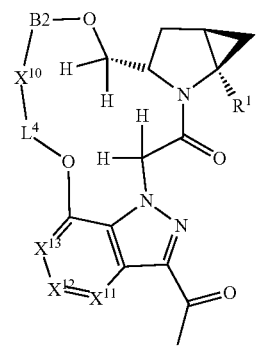
Formula III-30

TABLE 3-continued
Additional Exemplary Formulas within the Present Invention.
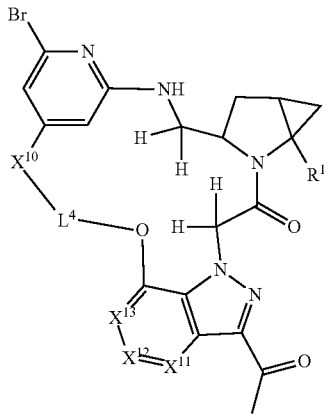
Formula III-31
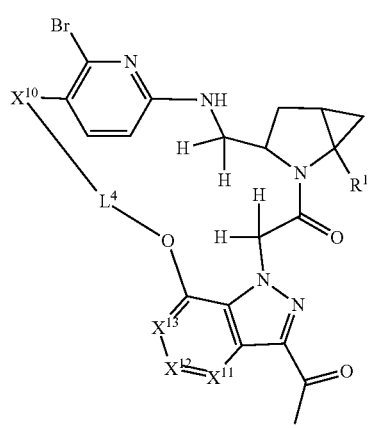
Formula III-32
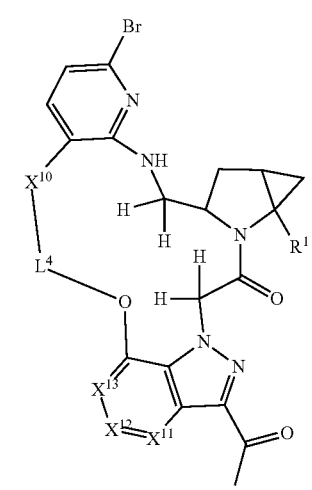
Formula III-33
TABLE 3-continued
Additional Exemplary Formulas within the Present Invention.
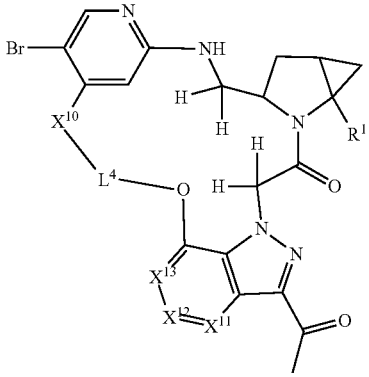
Formula III-34
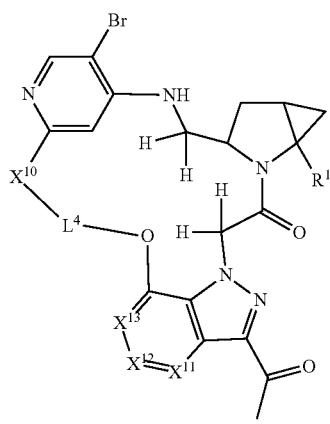
Formula III-35
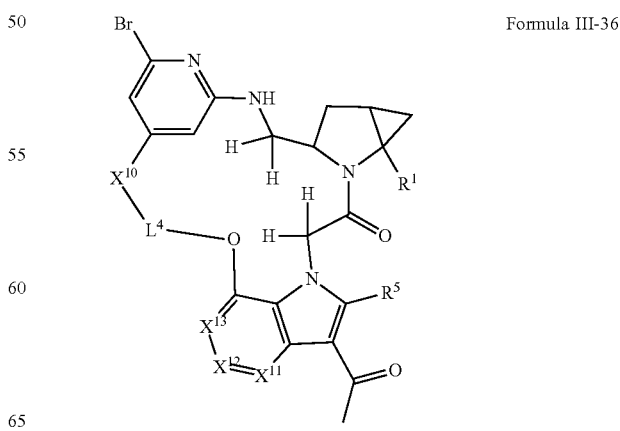
Formula III-36

TABLE 3-continued
Additional Exemplary Formulas within the Present Invention.
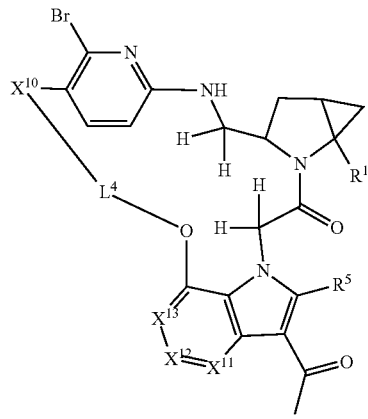
Formula III-37
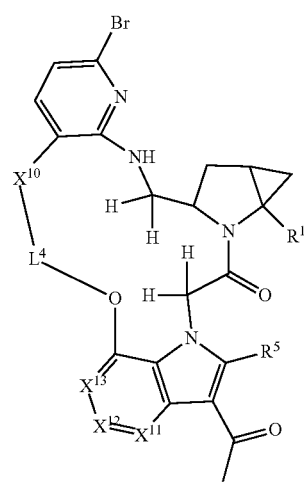
Formula III-38
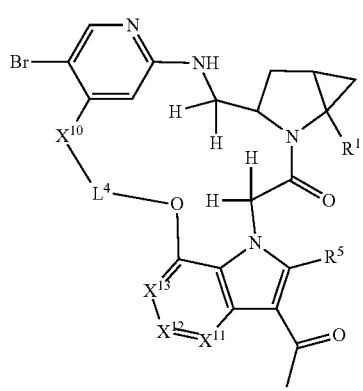
Formula III-39
TABLE 3-continued
Additional Exemplary Formulas within the Present Invention.
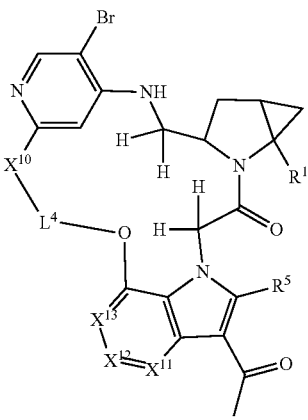
Formula III-40
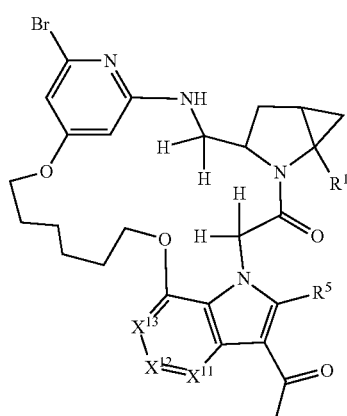
Formula III-41
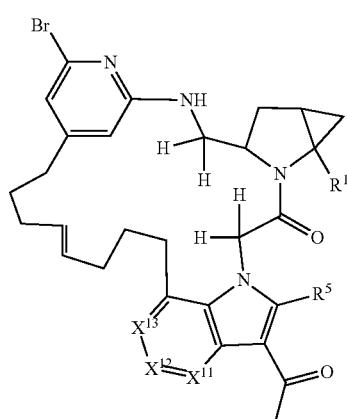
Formula III-42
TABLE 4
Additional Exemplary Formulas within the Present Invention.
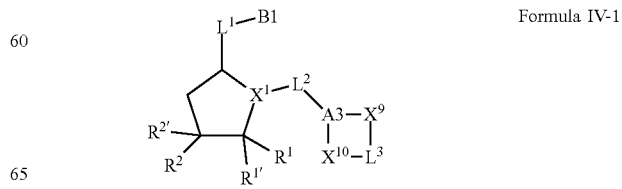
Formula IV-1

TABLE 4-continued
Additional Exemplary Formulas within the Present Invention.
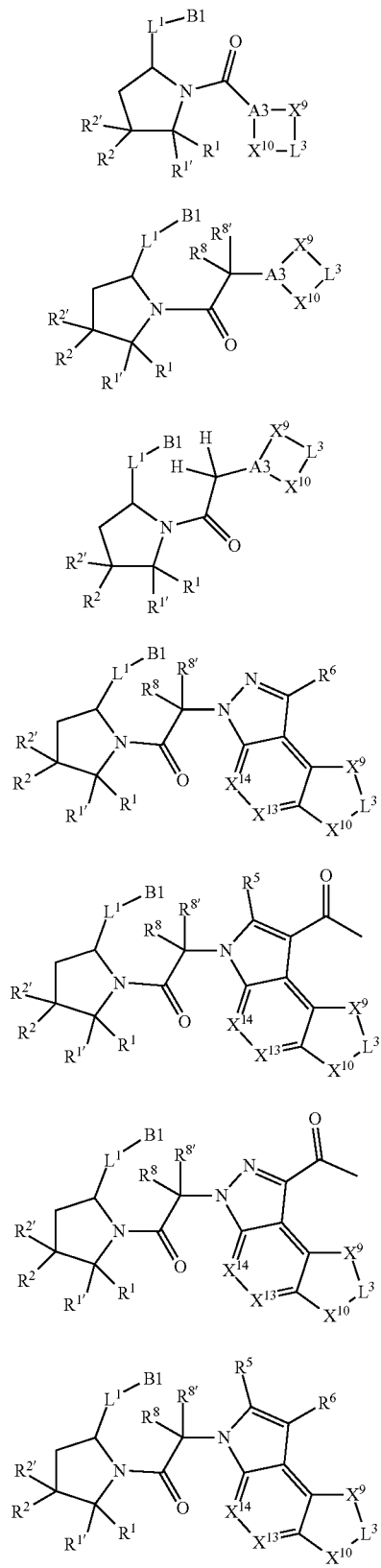
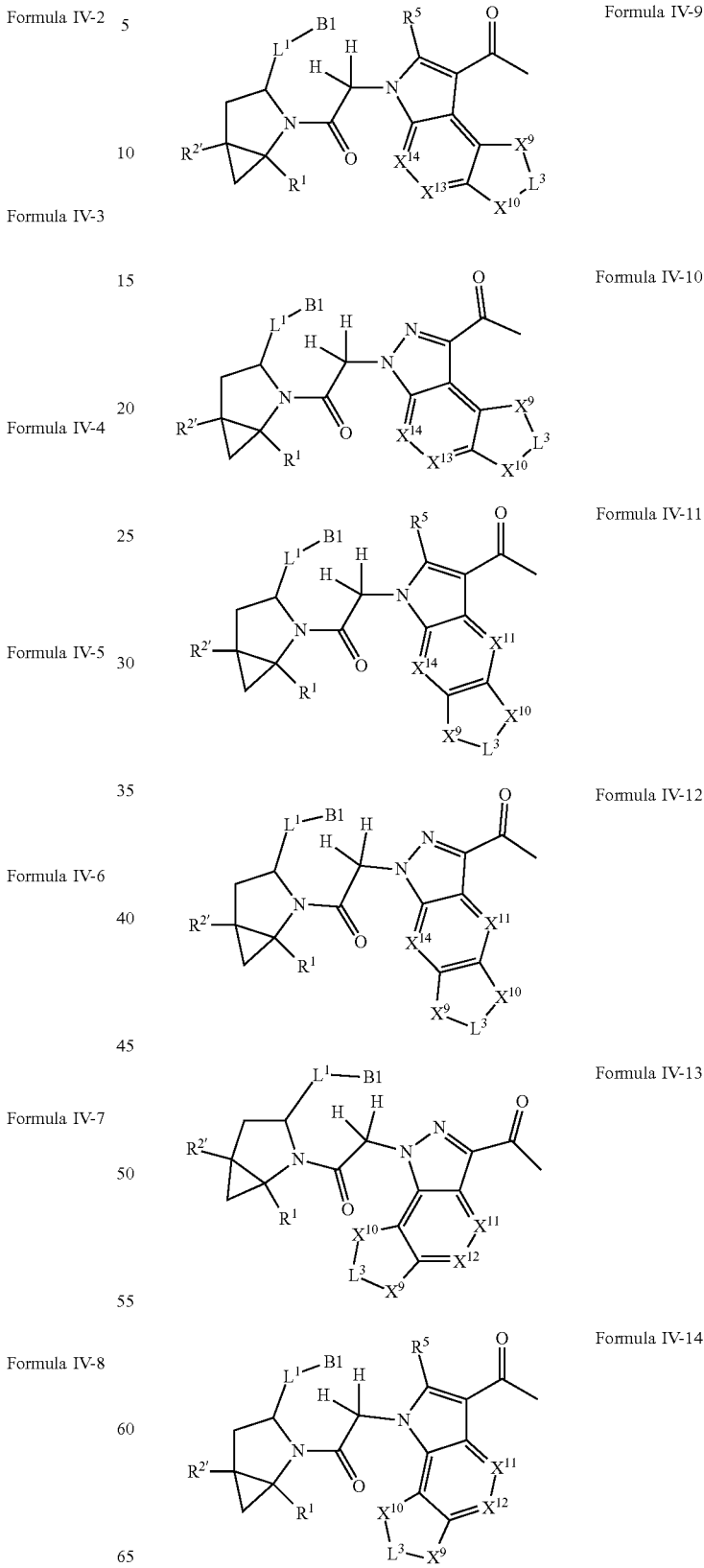

TABLE 4-continued
Additional Exemplary Formulas within the Present Invention.
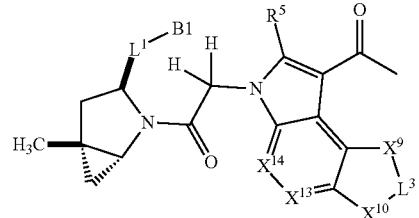 Formula IV-15
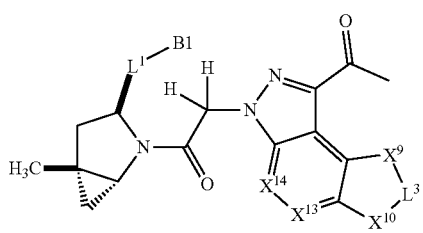 Formula IV-16
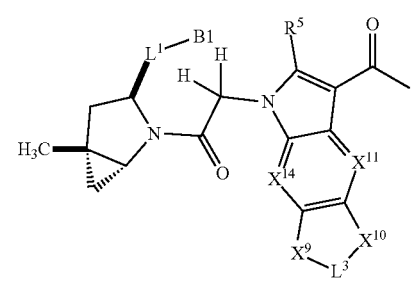 Formula IV-17
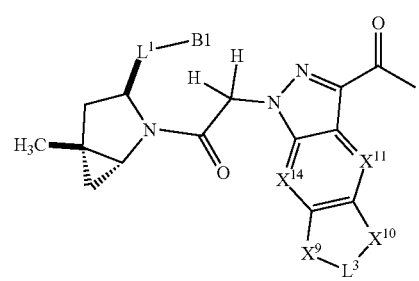 Formula IV-18
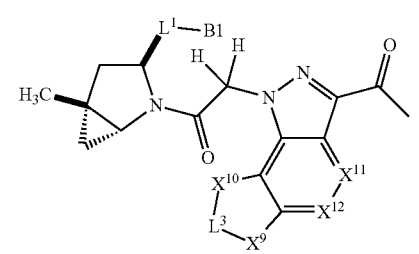 Formula IV-19
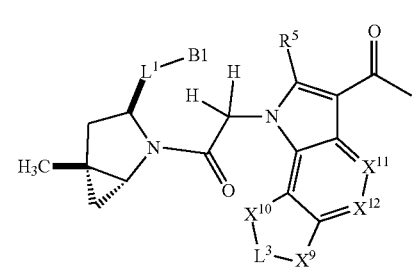 Formula IV-20
TABLE 4-continued
Additional Exemplary Formulas within the Present Invention.
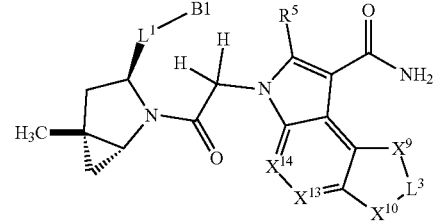 Formula IV-21
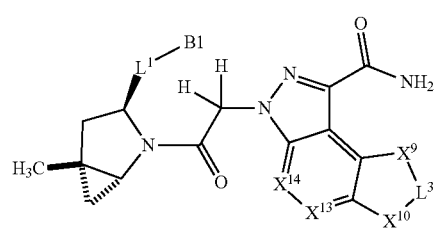 Formula IV-22
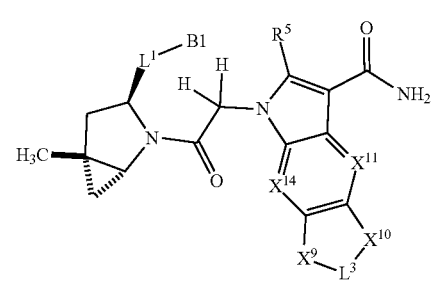 Formula IV-23
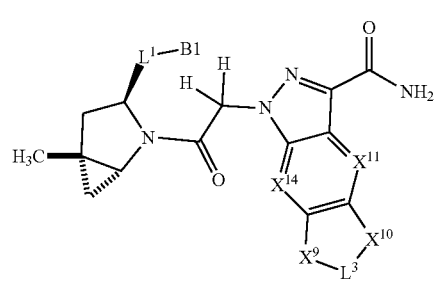 Formula IV-24
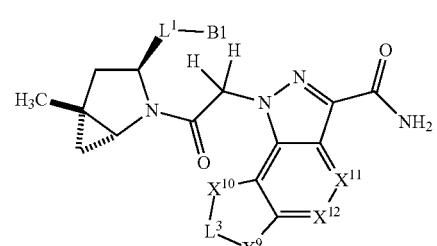 Formula IV-25
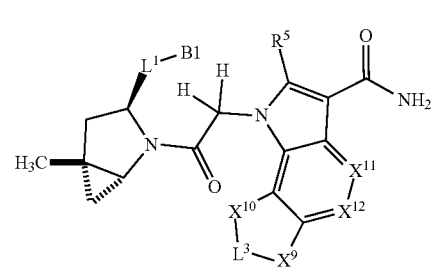 Formula IV-26

TABLE 5
Additional Exemplary Formulas within the Present Invention.
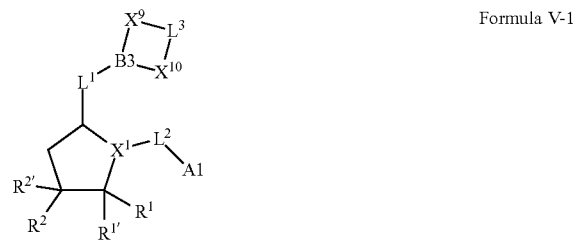
Formula V-1
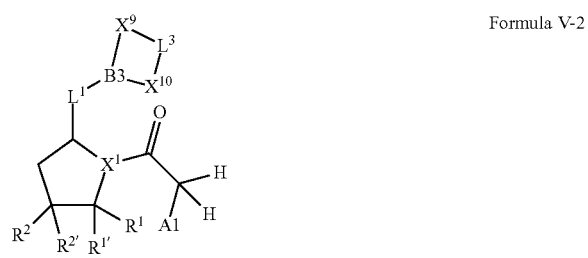
Formula V-2
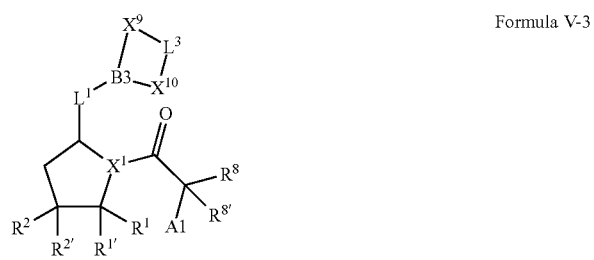
Formula V-3
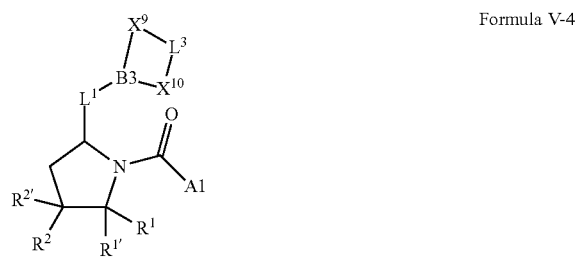
Formula V-4
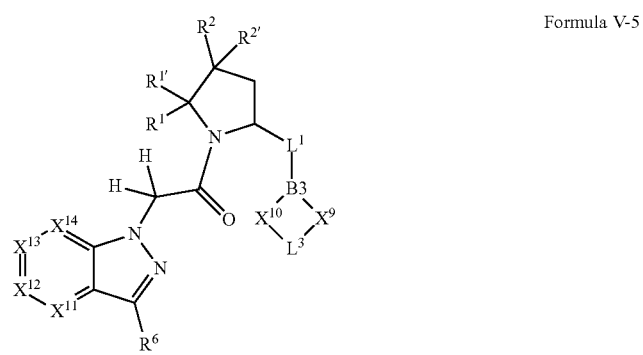
Formula V-5

TABLE 5-continued
*Additional Exemplary Formulas within the Present Invention.*
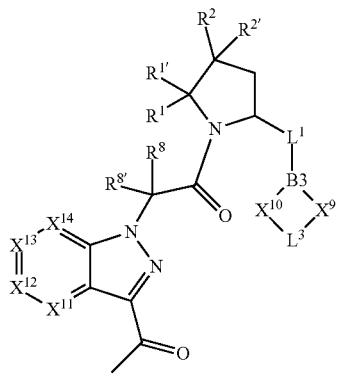
Formula V-6
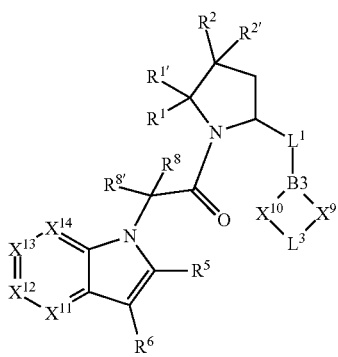
Formula V-7
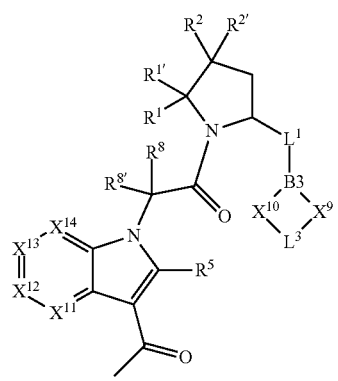
Formula V-8
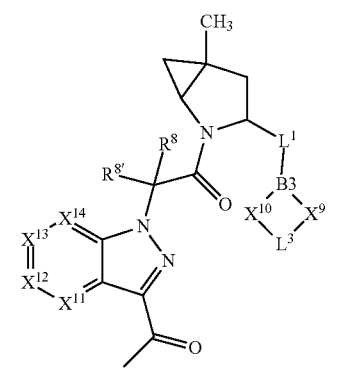
Formula V-9

TABLE 5-continued
*Additional Exemplary Formulas within the Present Invention.*
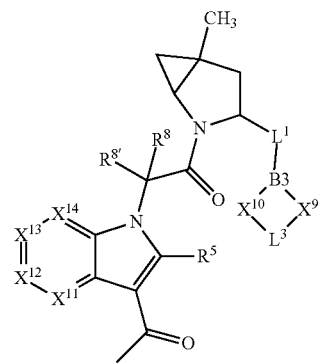
Formula V-10
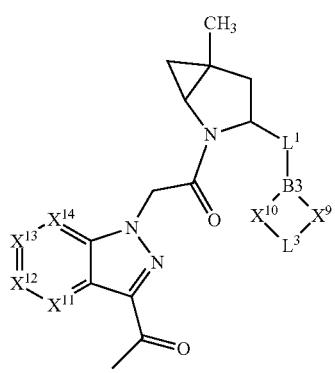
Formula V-11
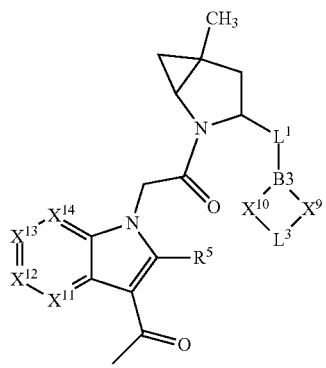
Formula V-12
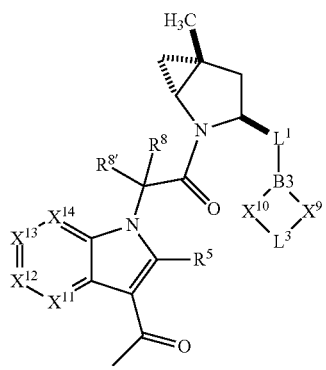
Formula V-13

TABLE 5-continued
*Additional Exemplary Formulas within the Present Invention.*
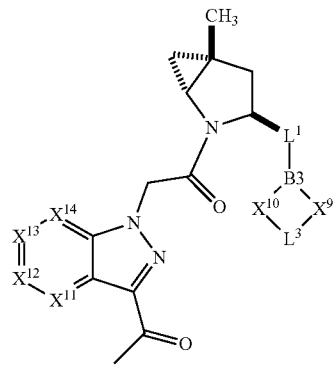
Formula V-14
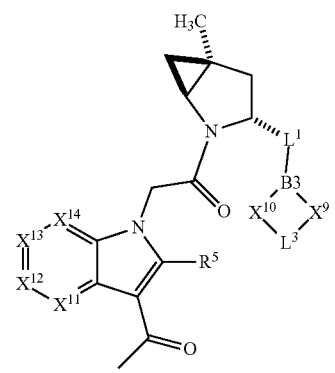
Formula V-15
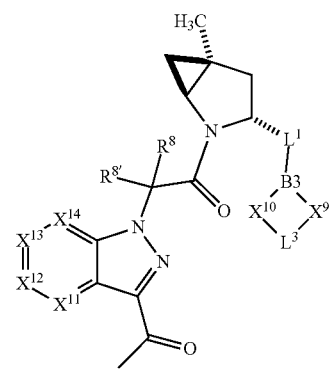
Formula V-16
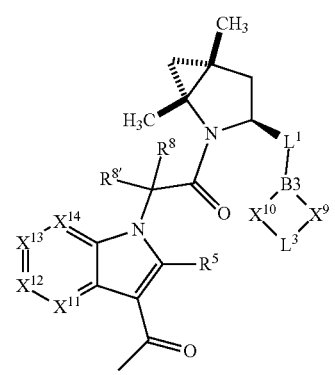
Formula V-17

TABLE 5-continued
*Additional Exemplary Formulas within the Present Invention.*
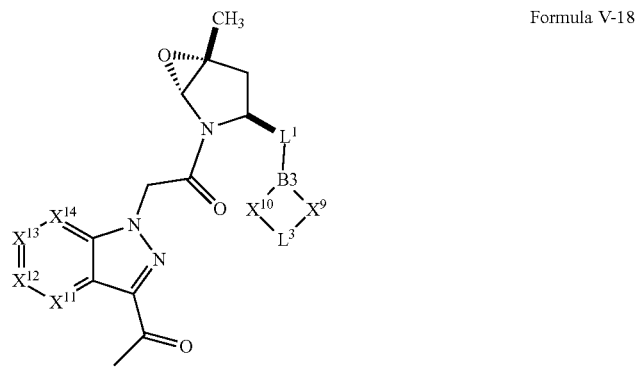
Formula V-18
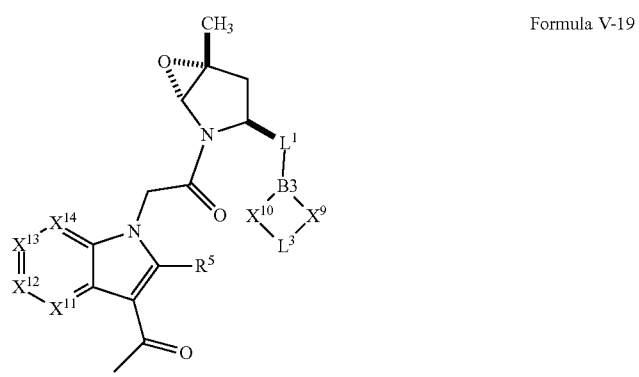
Formula V-19
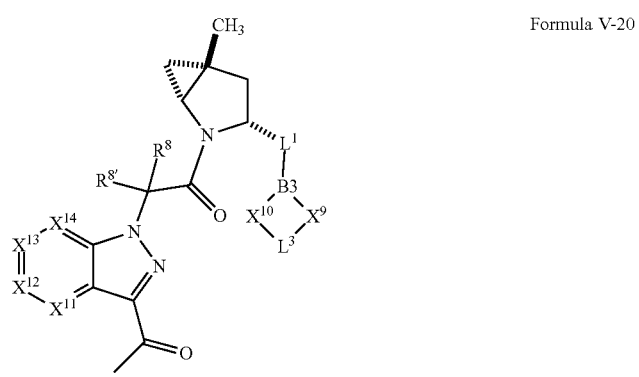
Formula V-20
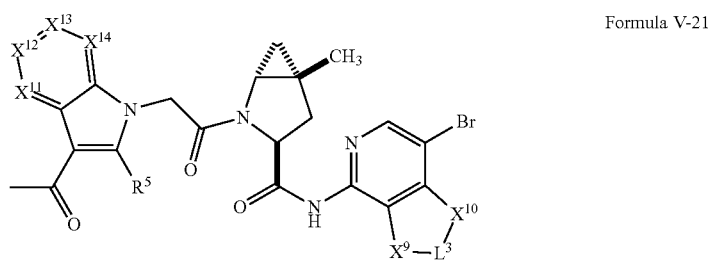
Formula V-21

TABLE 5-continued
Additional Exemplary Formulas within the Present Invention.
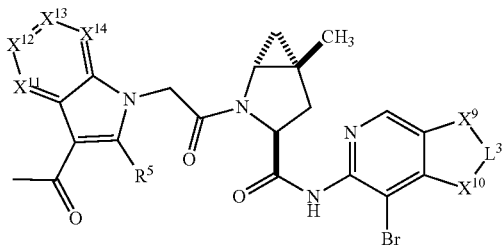 Formula V-22
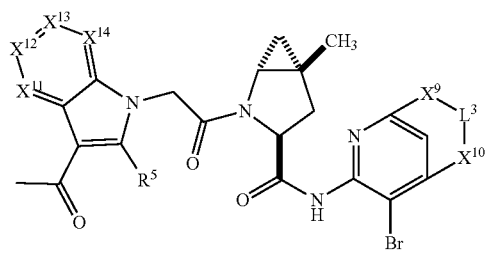 Formula V-23
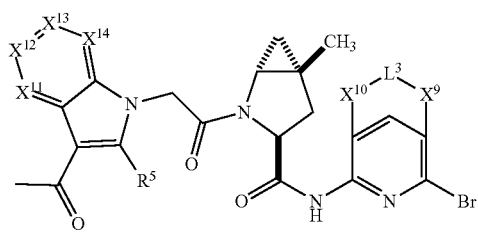 Formula V-24
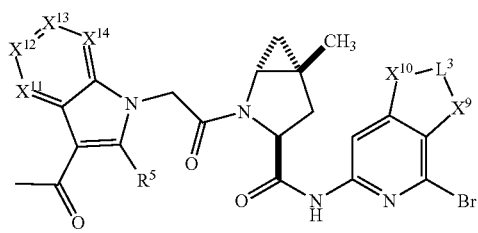 Formula V-25
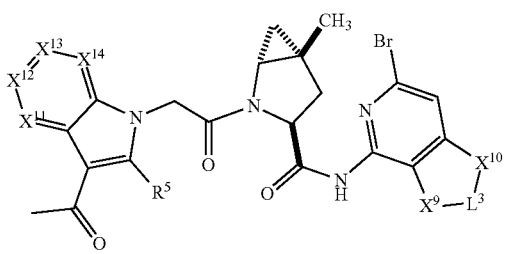 Formula V-26
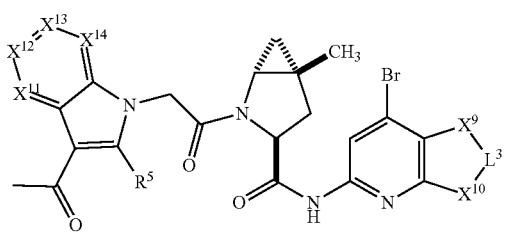 Formula V-27

TABLE 5-continued
Additional Exemplary Formulas within the Present Invention.
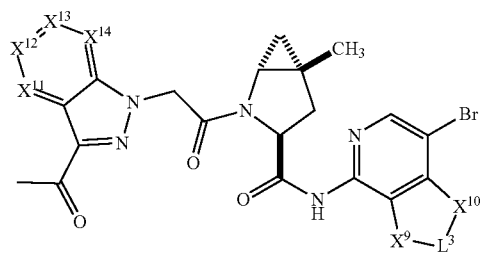
Formula V-28
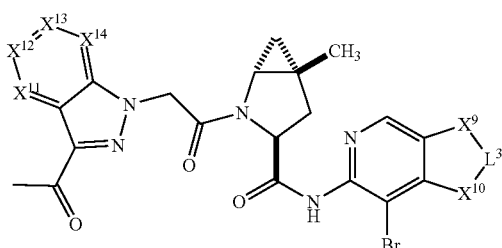
Formula V-29
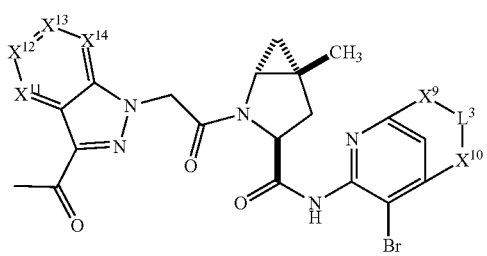
Formula V-30
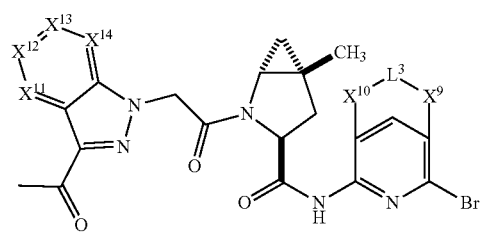
Formula V-31
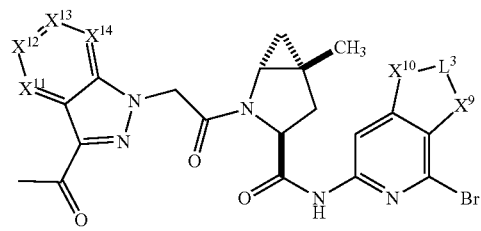
Formula V-32
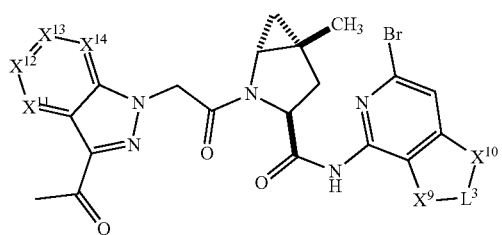
Formula V-33

TABLE 5-continued
Additional Exemplary Formulas within the Present Invention.
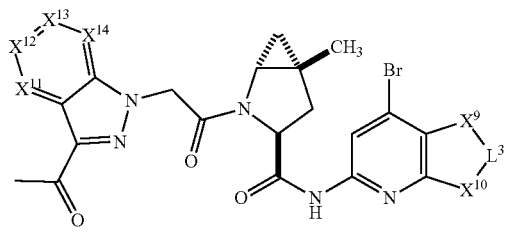
Formula V-34
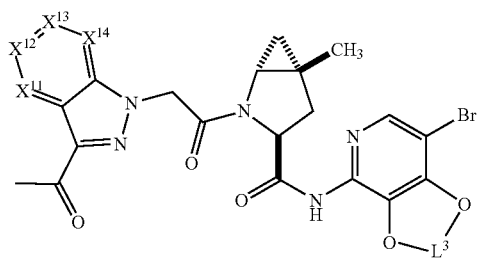
Formula V-35
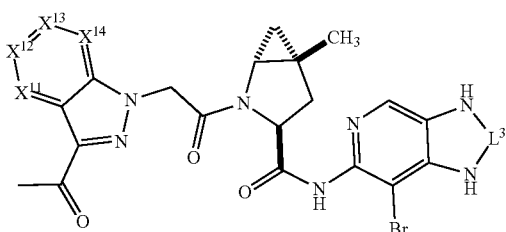
Formula V-36
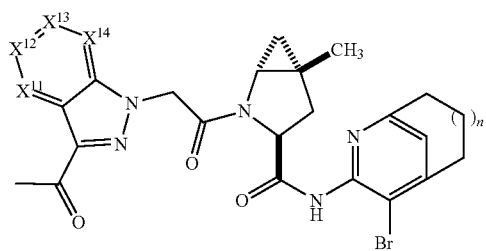
Formula V-37
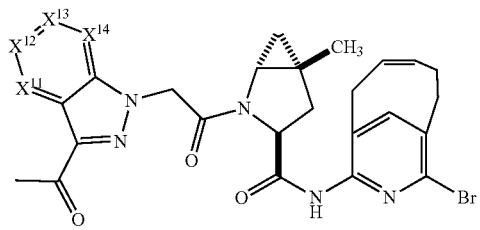
Formula V-38
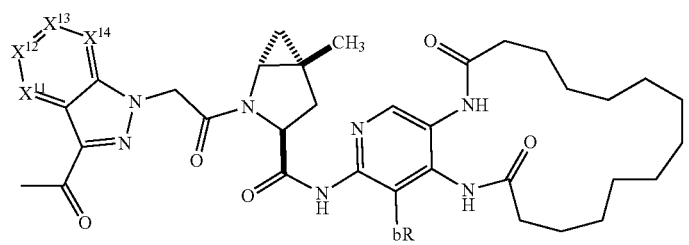
Formula V-39

TABLE 6
Additional Exemplary Formulas within the Present Invention.
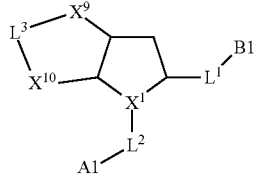
Formula VI-1
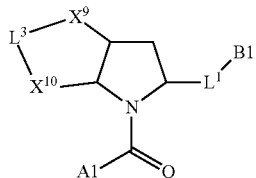
Formula VI-2
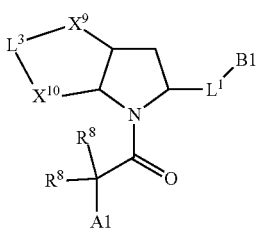
Formula VI-3
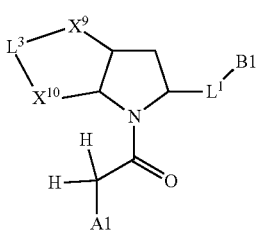
Formula VI-4
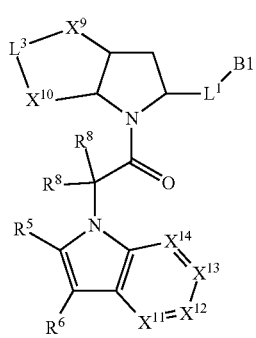
Formula VI-5
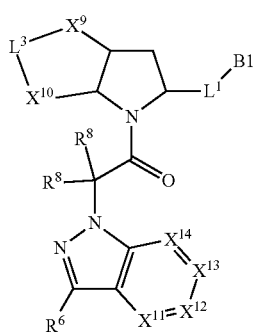
Formula VI-6
TABLE 6-continued
Additional Exemplary Formulas within the Present Invention.
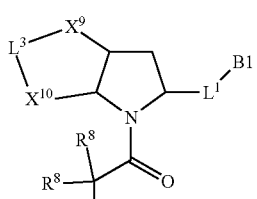
Formula VI-6
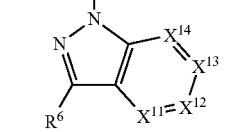
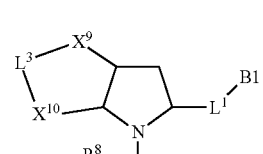
Formula VI-7
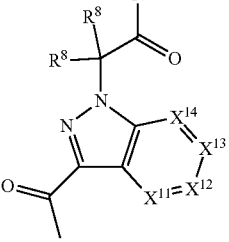
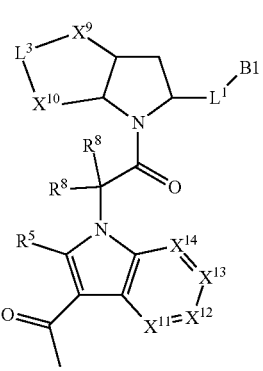
Formula VI-8
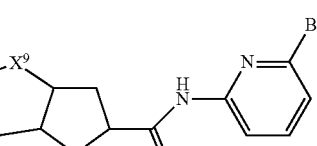
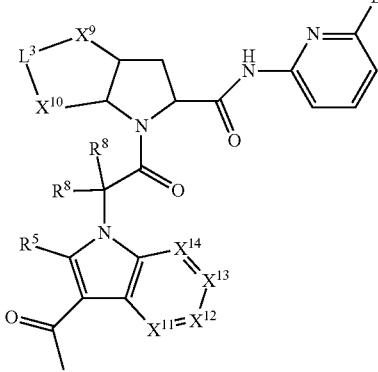
Formula VI-9

TABLE 6-continued

Additional Exemplary Formulas within the Present Invention.

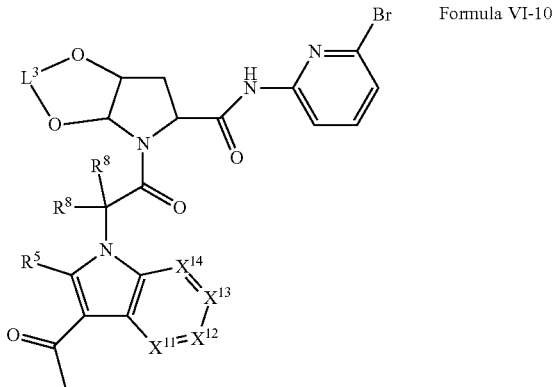
Formula VI-10

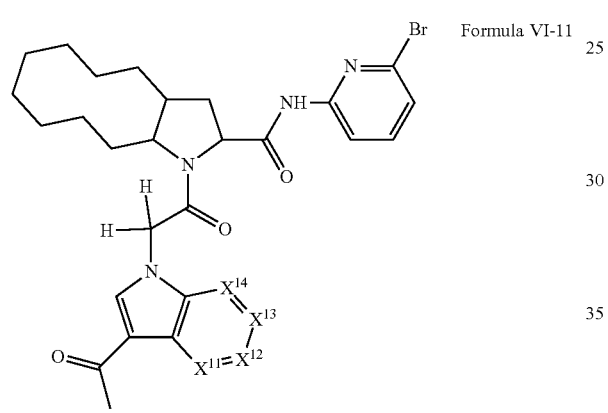
Formula VI-11

TABLE 7

Additional Exemplary Formulas within the Present Invention.

The Compound of Formula VIII is selected from:

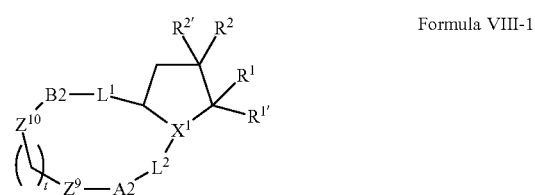
Formula VIII-1

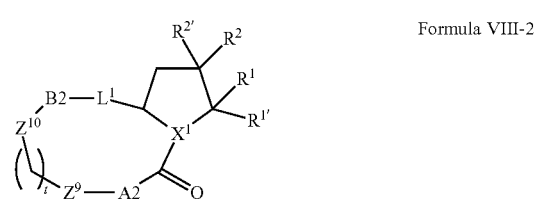
Formula VIII-2

TABLE 7-continued

Additional Exemplary Formulas within the Present Invention.

The Compound of Formula VIII is selected from:

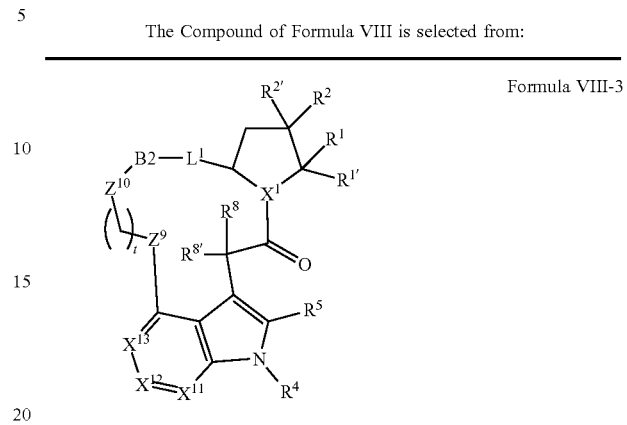
Formula VIII-3

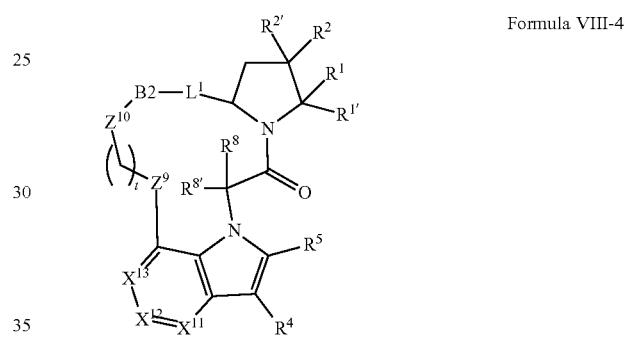
Formula VIII-4

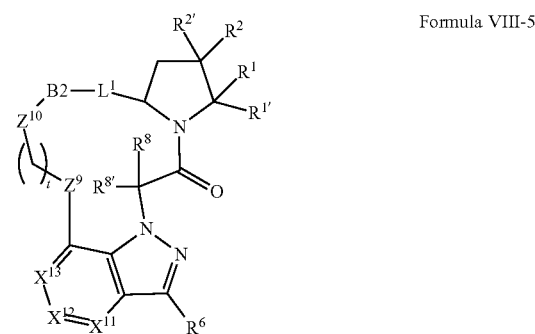
Formula VIII-5

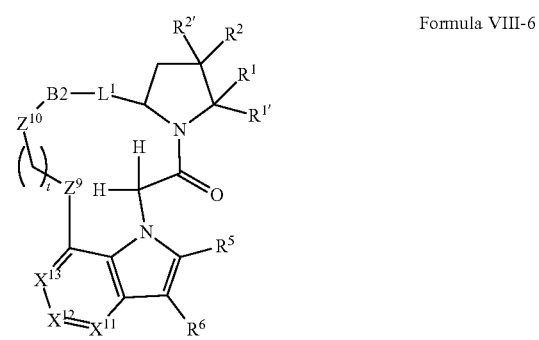
Formula VIII-6

TABLE 7-continued
Additional Exemplary Formulas within the Present Invention.
The Compound of Formula VIII is selected from:
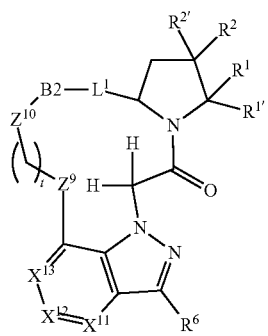
Formula VIII-7
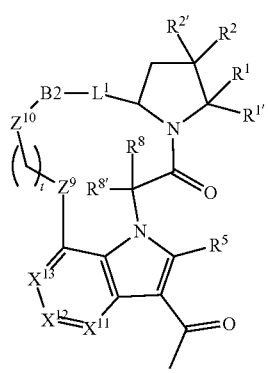
Formula VIII-8
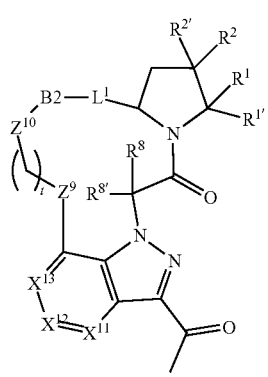
Formula VIII-9
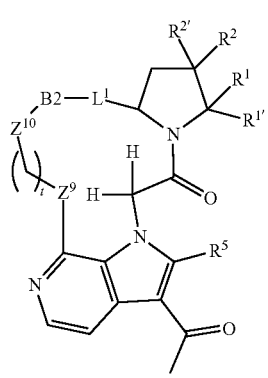
Formula VIII-10
TABLE 7-continued
Additional Exemplary Formulas within the Present Invention.
The Compound of Formula VIII is selected from:
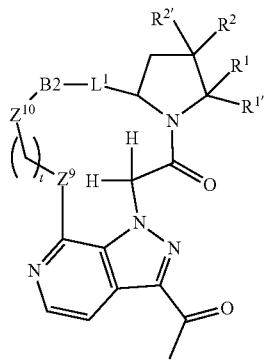
Formula VIII-11
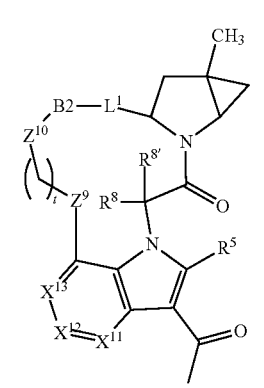
Formula VIII-12
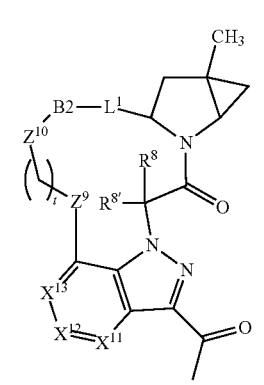
Formula VIII-13
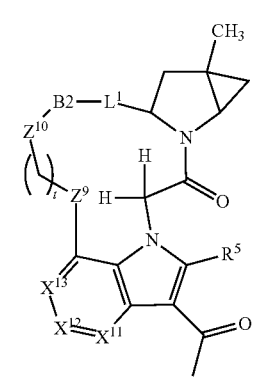
Formula VIII-14

TABLE 7-continued
Additional Exemplary Formulas within the Present Invention.
The Compound of Formula VIII is selected from:
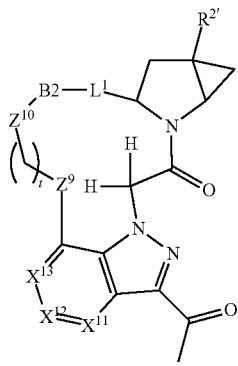
Formula VIII-15
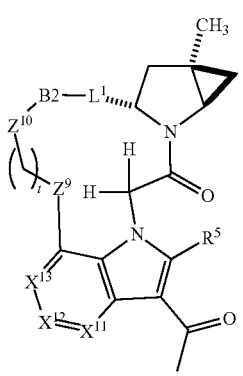
Formula VIII-16
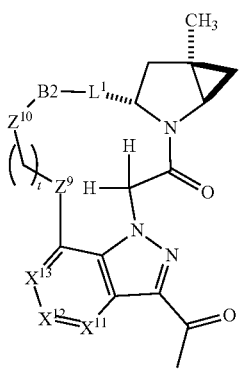
Formula VIII-17
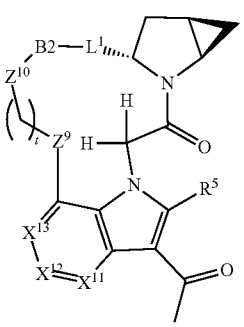
Formula VIII-18
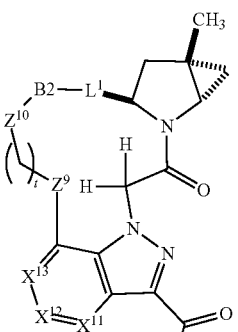
Formula VIII-19
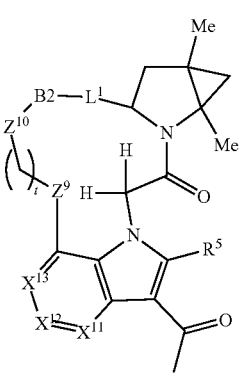
Formula VIII-20
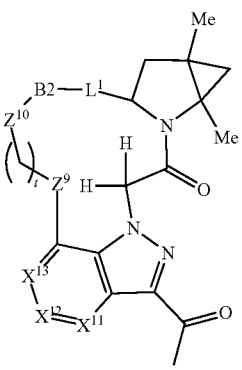
Formula VIII-21
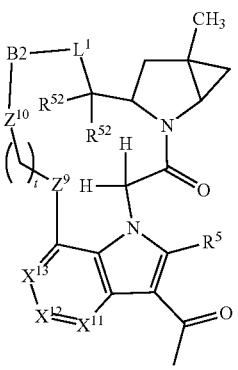
Formula VIII-22

TABLE 7-continued
Additional Exemplary Formulas within the Present Invention.
The Compound of Formula VIII is selected from:
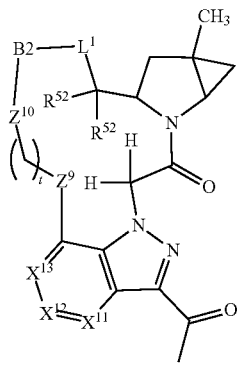
Formula VIII-23
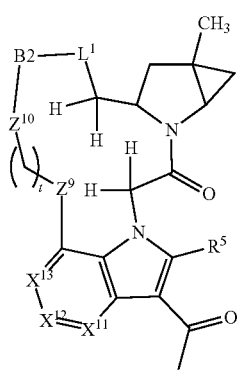
Formula VIII-24
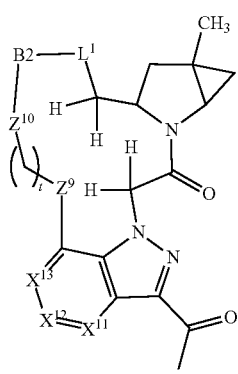
Formula VIII-25
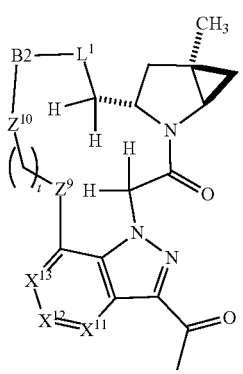
Formula VIII-26
TABLE 7-continued
Additional Exemplary Formulas within the Present Invention.
The Compound of Formula VIII is selected from:
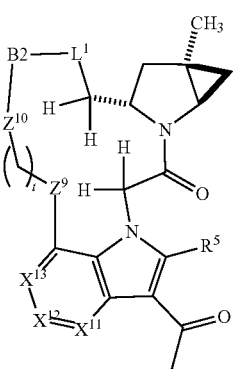
Formula VIIII-27
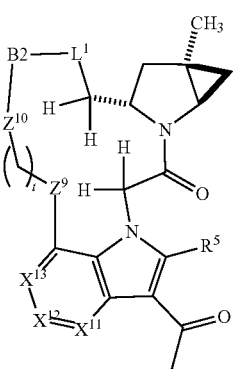
Formula VIII-28
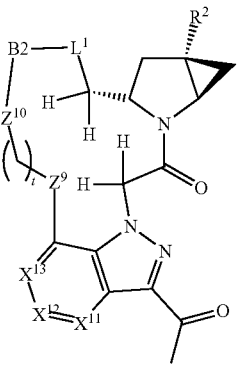
Formula VIII-29

TABLE 7-continued
Additional Exemplary Formulas within the Present Invention.
The Compound of Formula VIII is selected from:
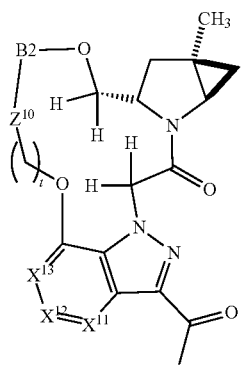
Formula VIII-30
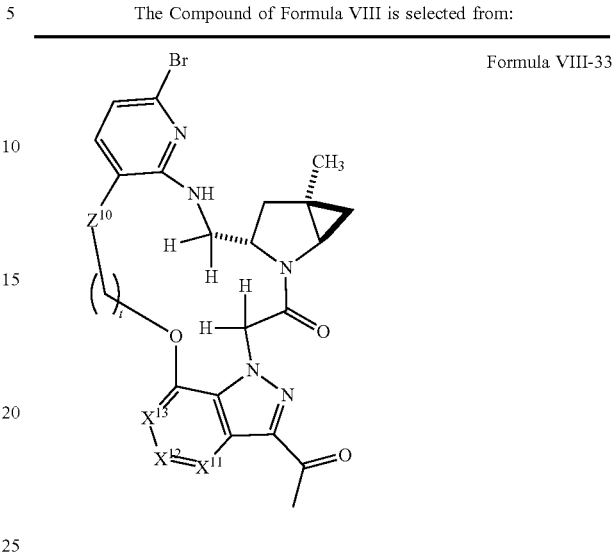
Formula VIII-33
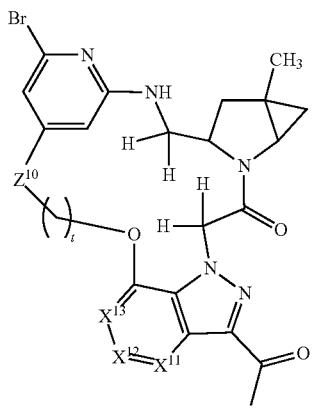
Formula VIII-31
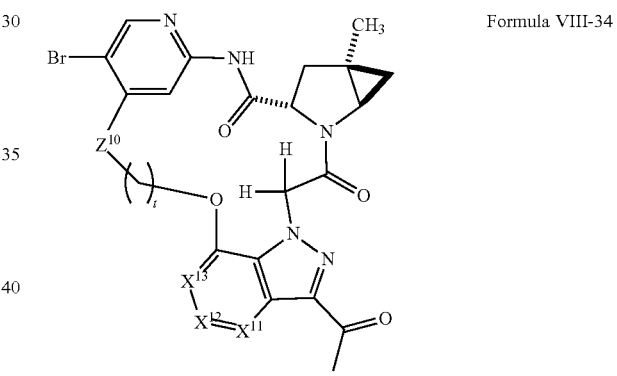
Formula VIII-34
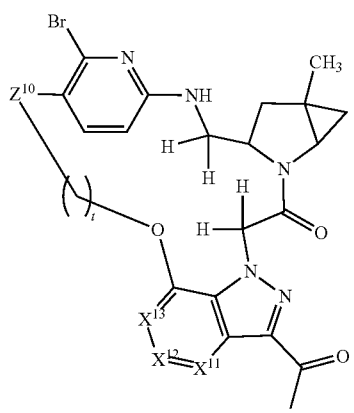
Formula VIII-32
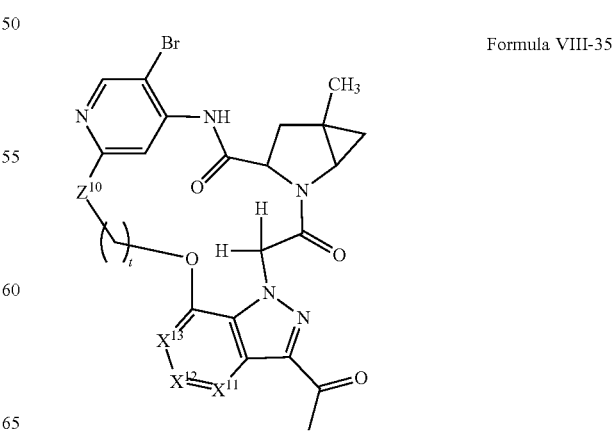
Formula VIII-35

TABLE 7-continued

Additional Exemplary Formulas within the Present Invention.

The Compound of Formula VIII is selected from:

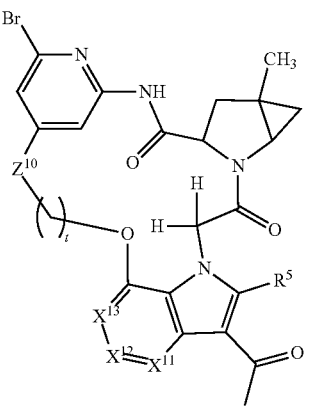

Formula VIII-36

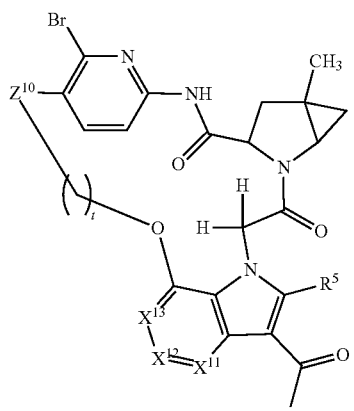

Formula VIII-37

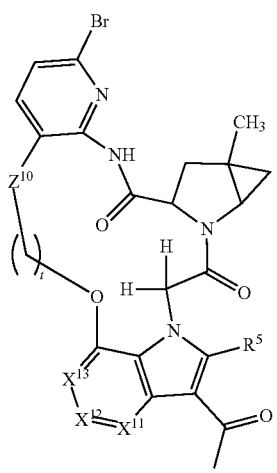

Formula VIII-38

TABLE 7-continued

Additional Exemplary Formulas within the Present Invention.

The Compound of Formula VIII is selected from:

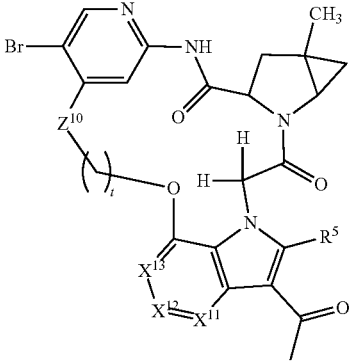

Formula VIII-39

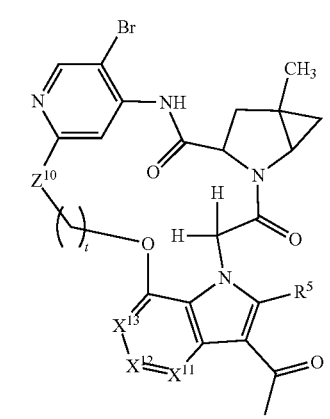

Formula VIII-40

In one aspect, the disclosure includes compounds and salts of Formulas in Table 1 for any use and in any composition described in this application.

In one embodiment the compound of the present invention is selected from:

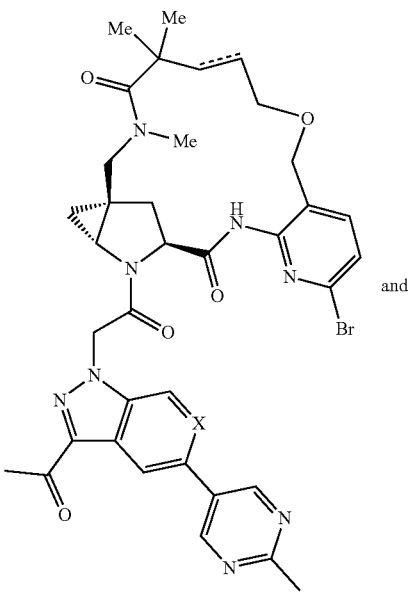

and

X = C, and N

413
-continued
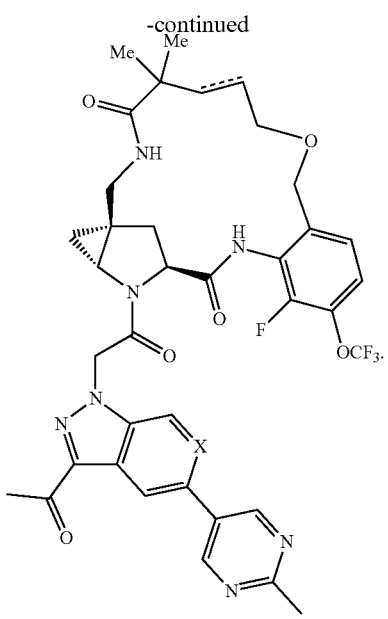
In one embodiment the compound of the present invention is selected from:
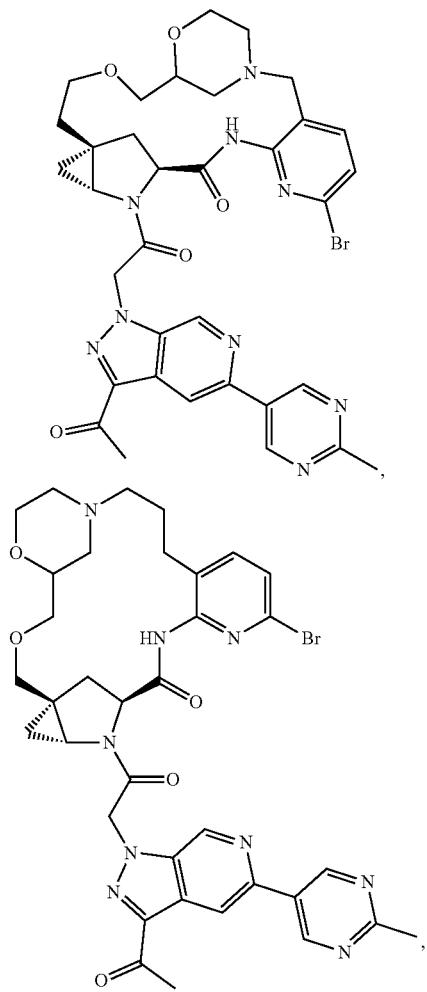
414
-continued
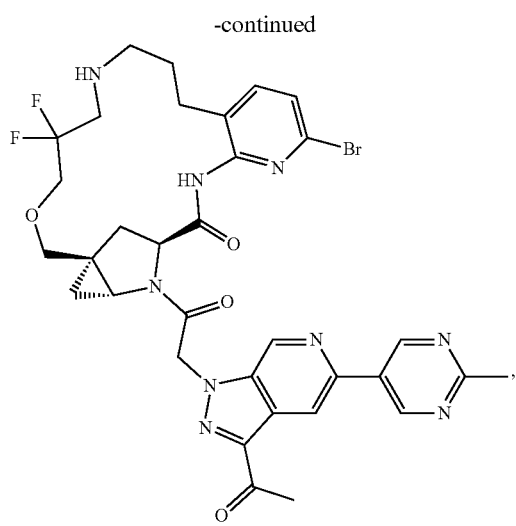
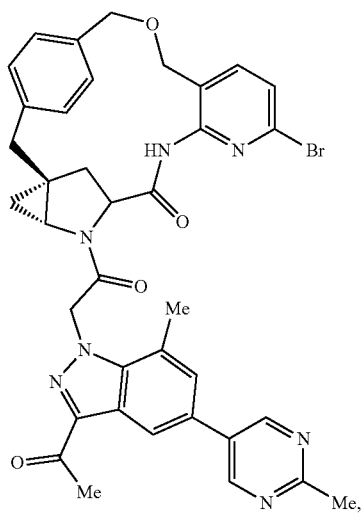
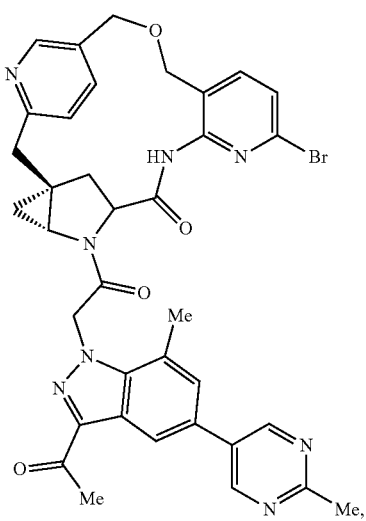

415
-continued
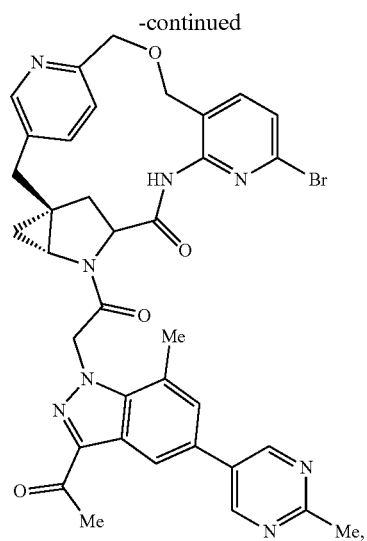
416
-continued
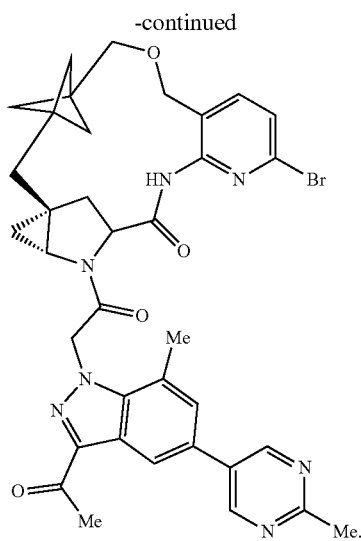
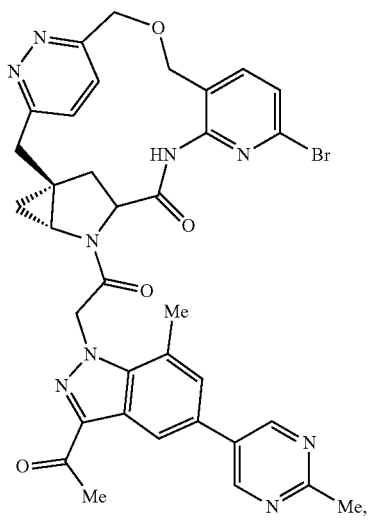
In one embodiment the compound of the present invention is selected from:
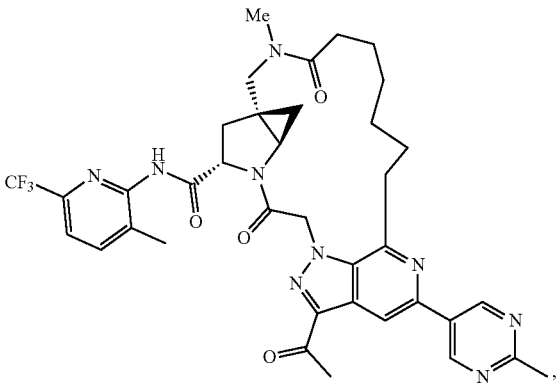
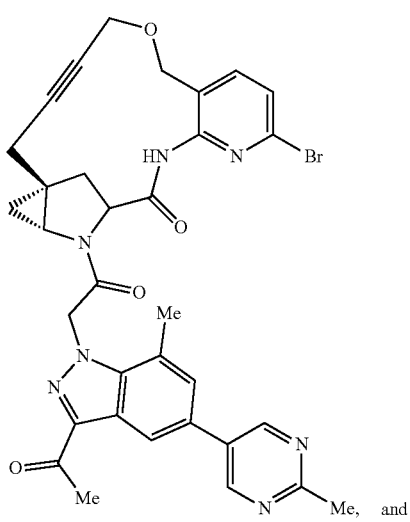
, and
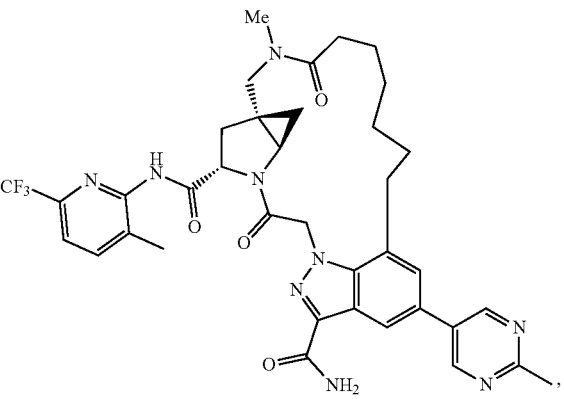

-continued
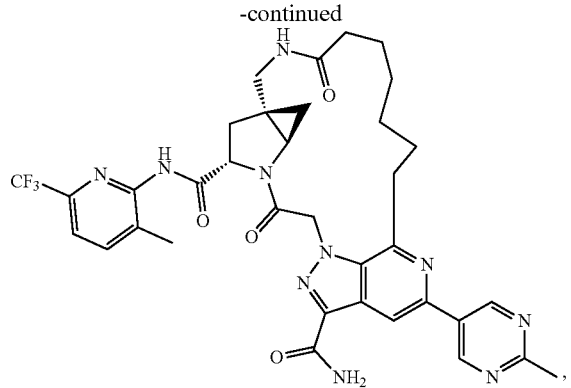
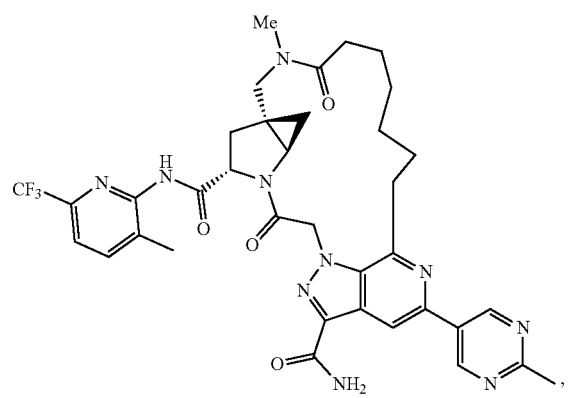
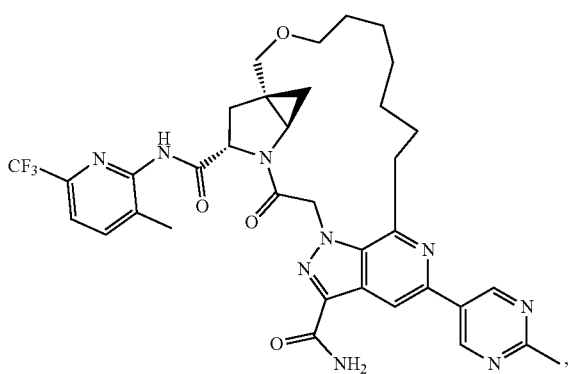
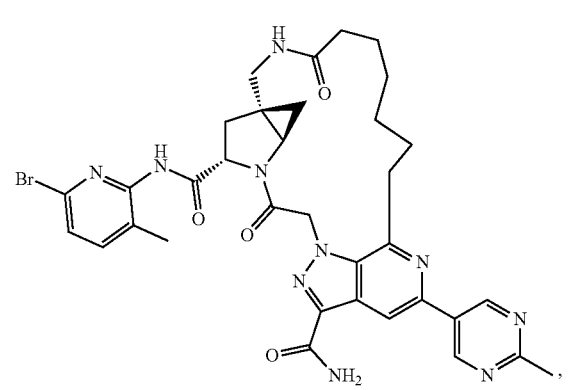
-continued
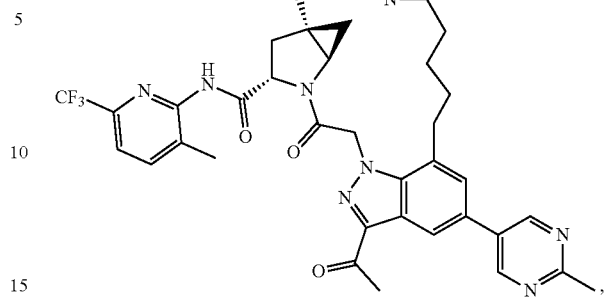
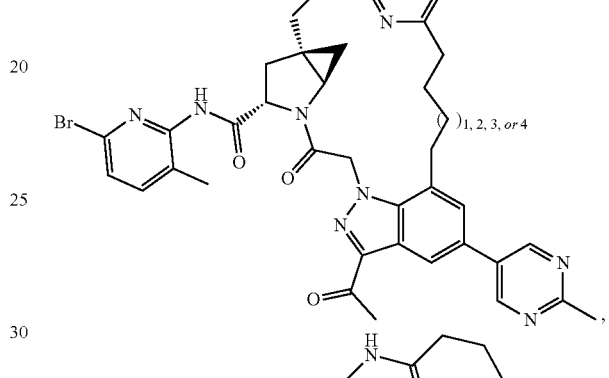
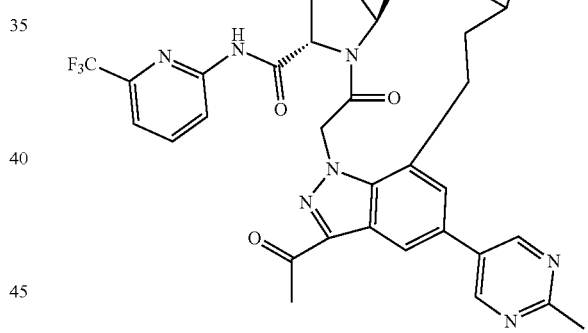
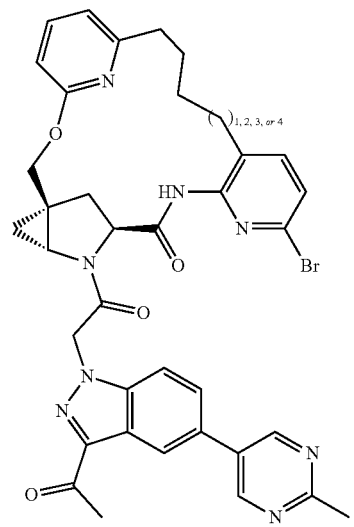

419
-continued
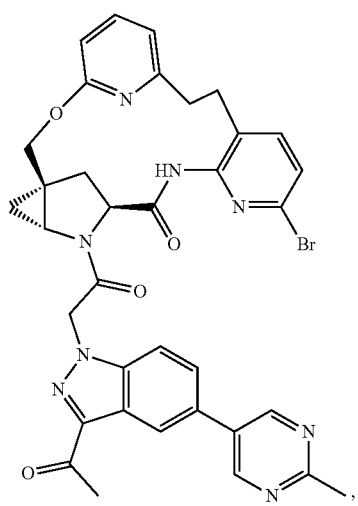
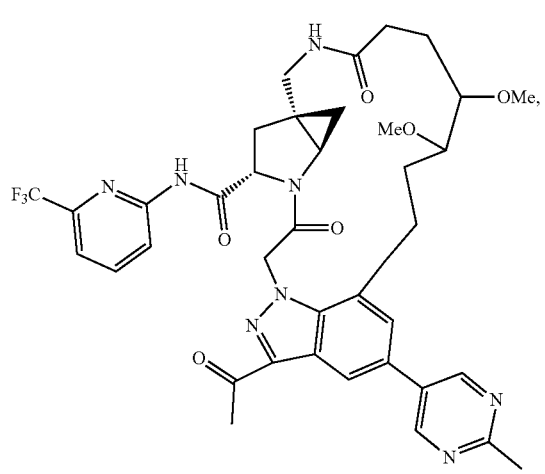
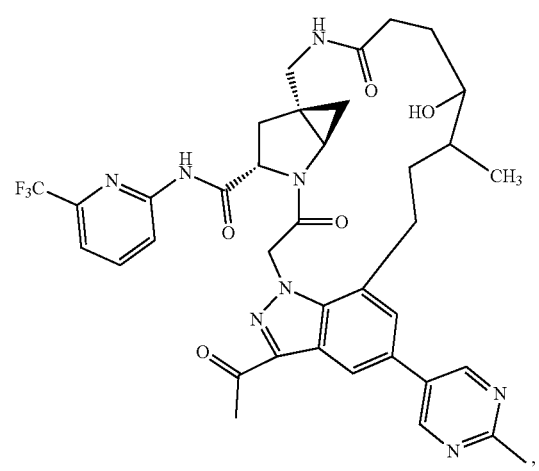
420
-continued
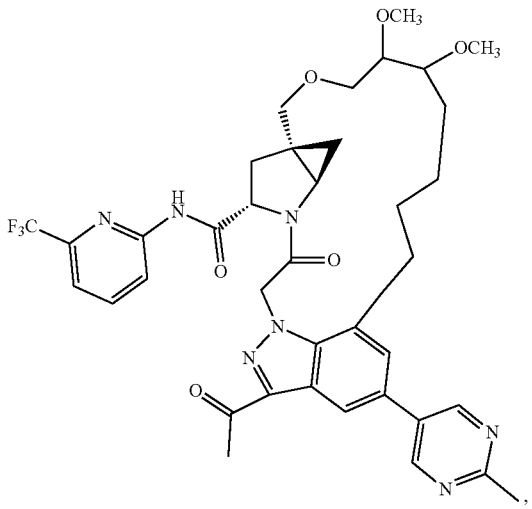
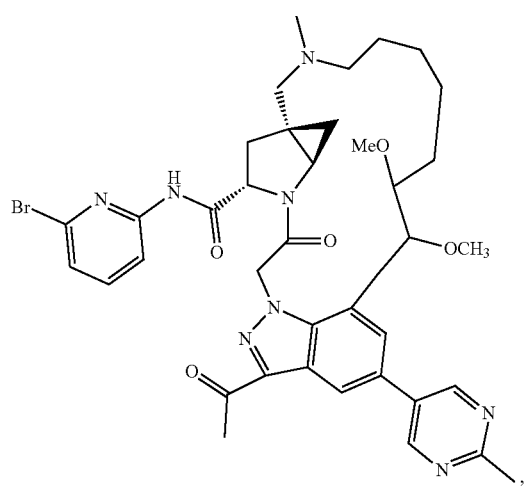
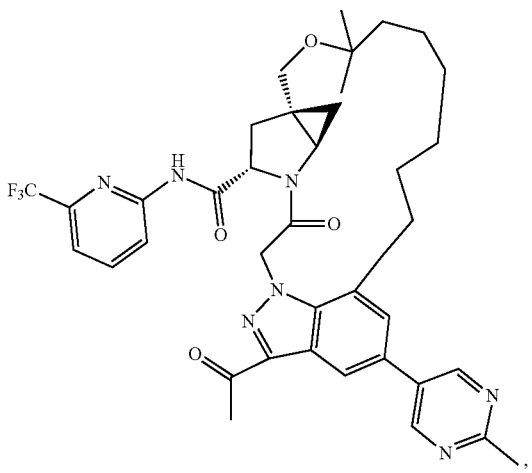

421
-continued
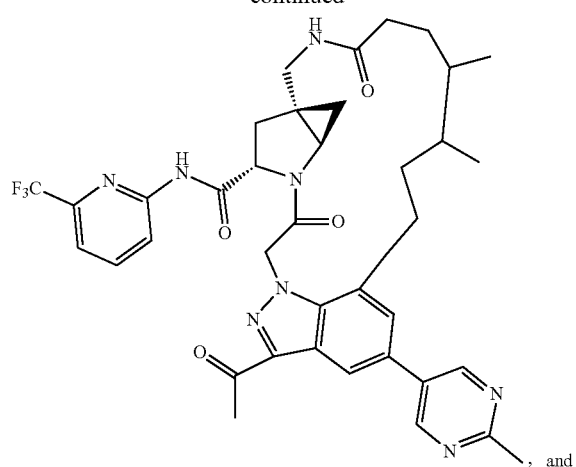
, and
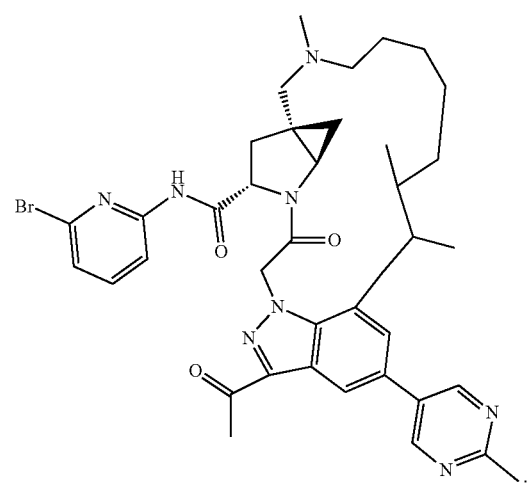
In one embodiment the compound of the present invention is selected from:
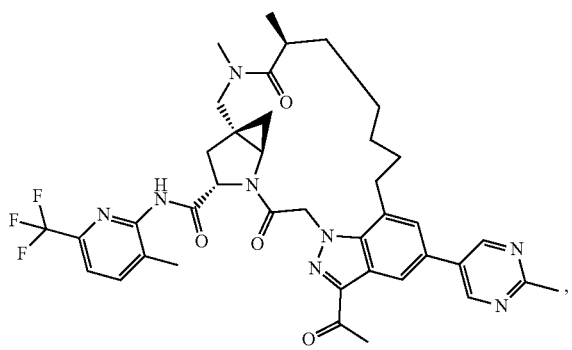
422
-continued
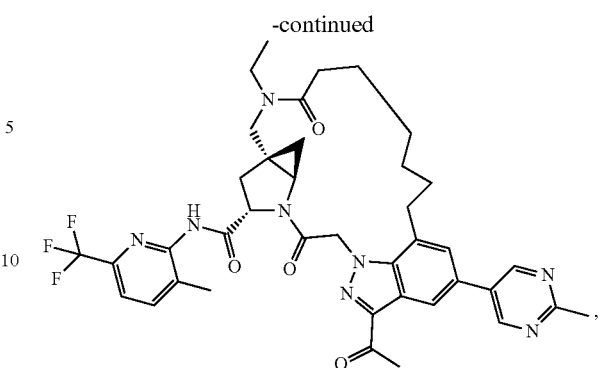
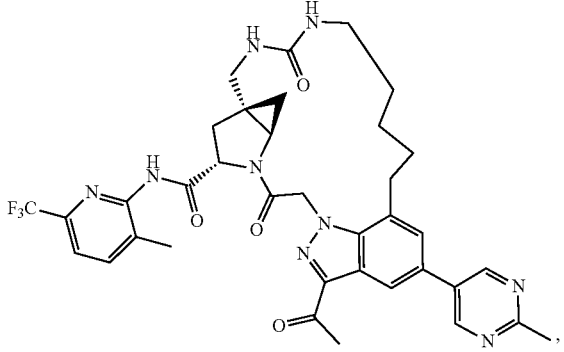

423
-continued
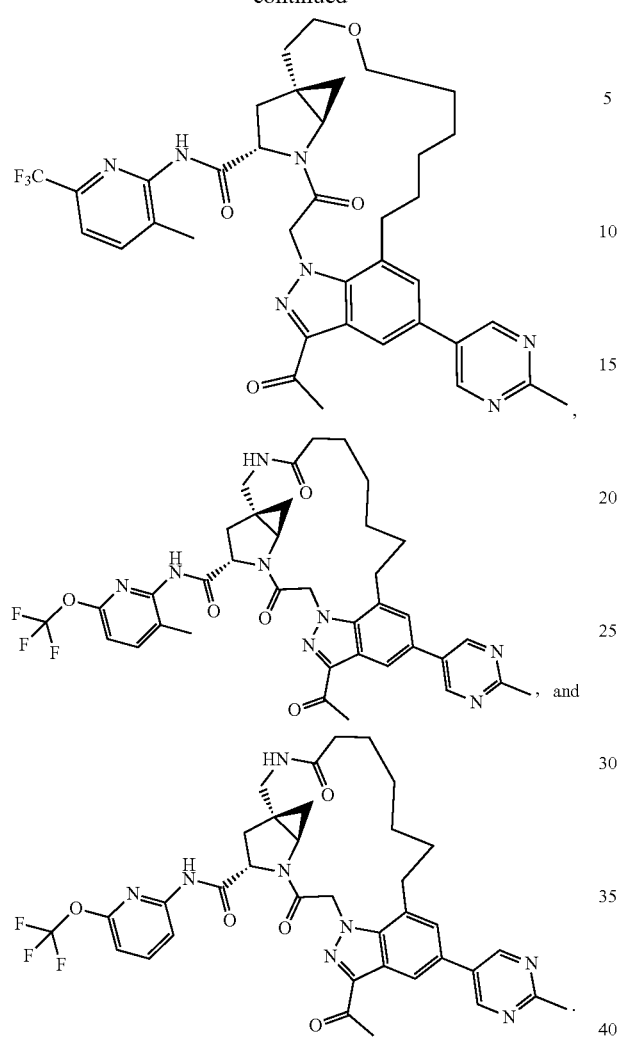
In one embodiment the compound of the present invention is selected from:
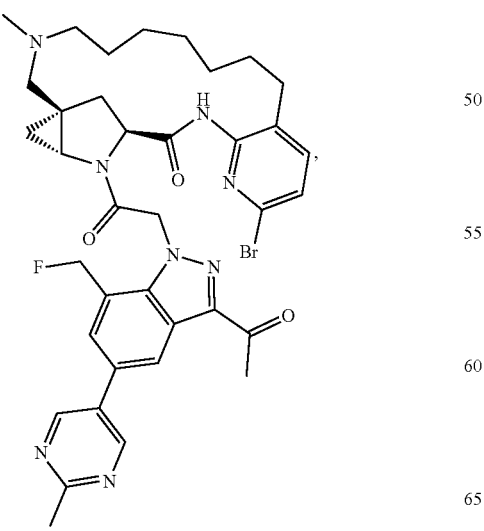
424
-continued
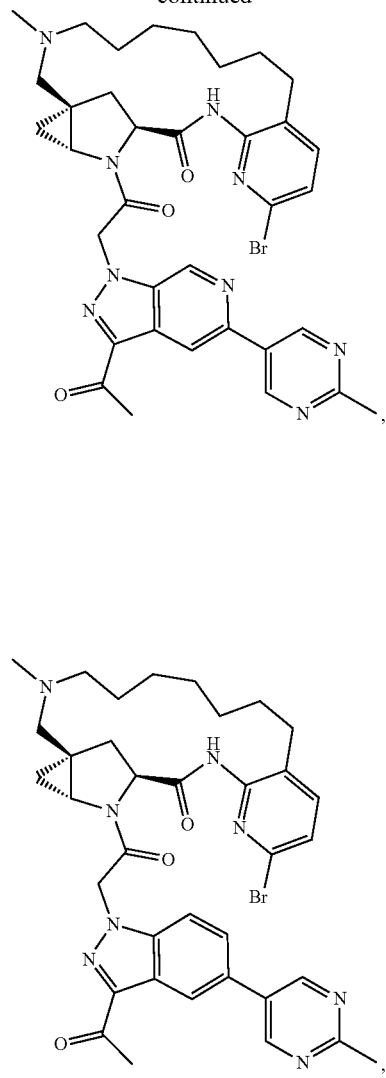
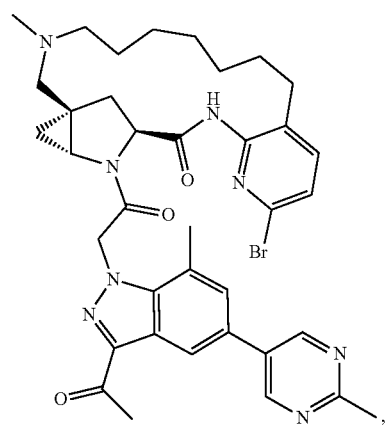

425
-continued
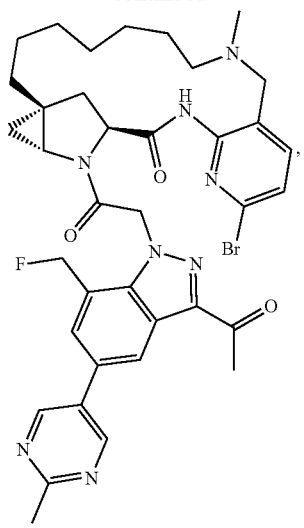
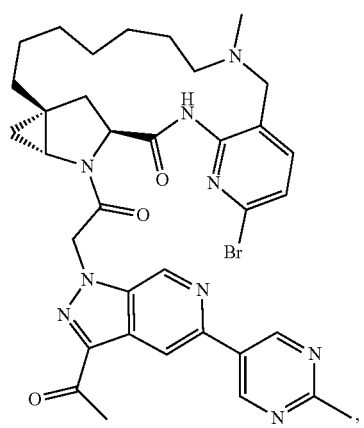
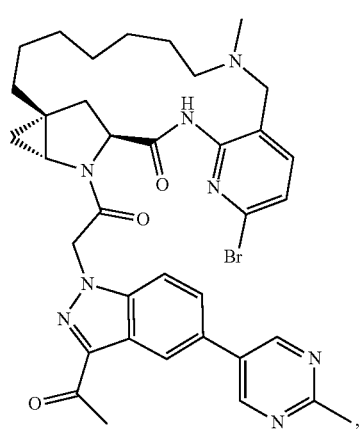
426
-continued
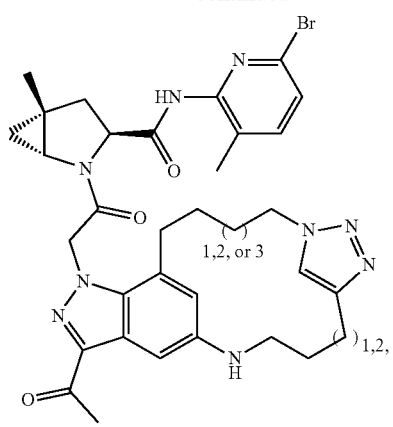
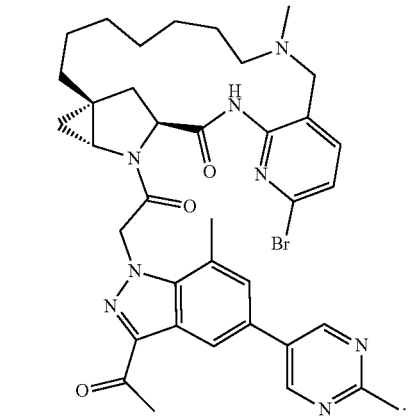
In one embodiment the compound of the present invention is selected from:
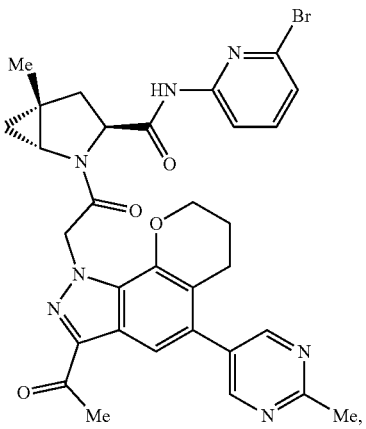

427
-continued
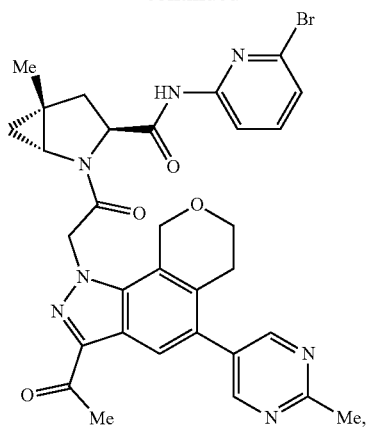
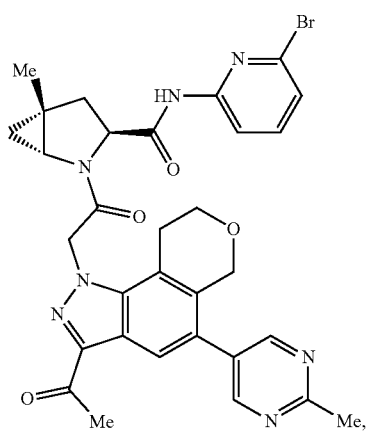
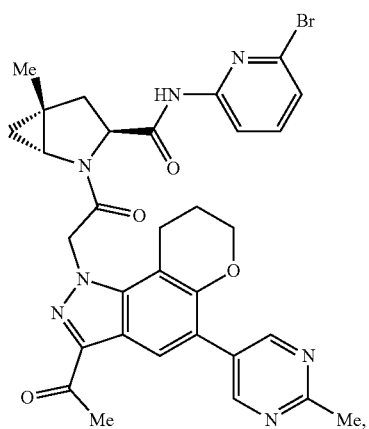
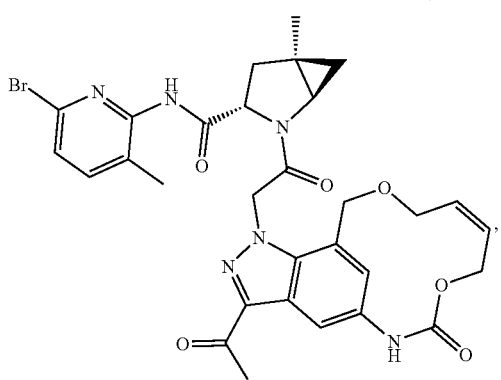
428
-continued
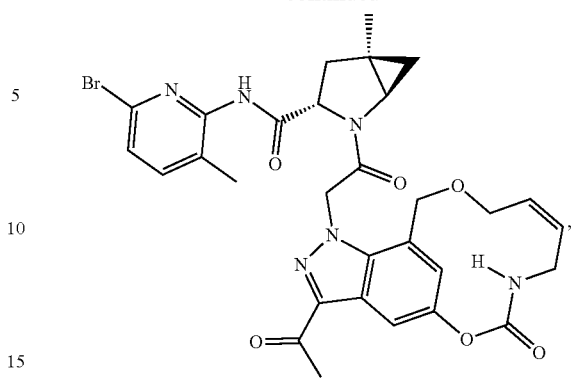
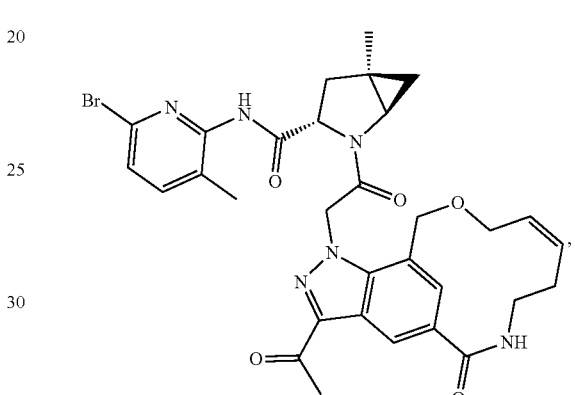
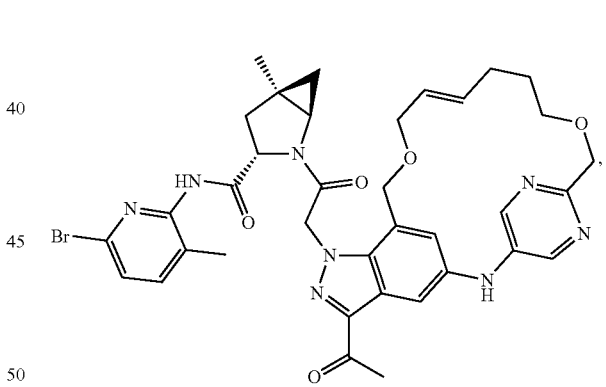
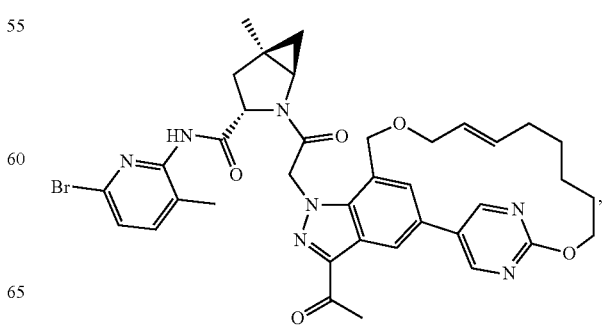

-continued
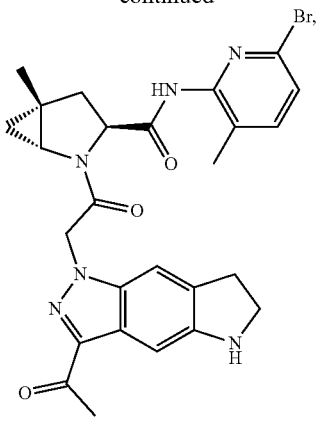
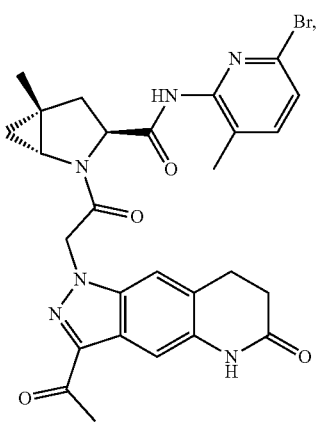
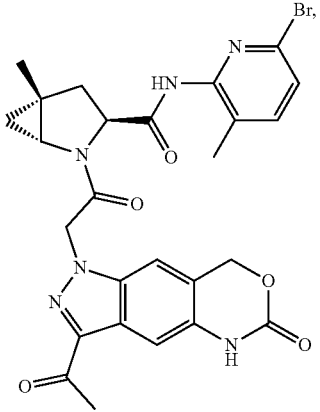
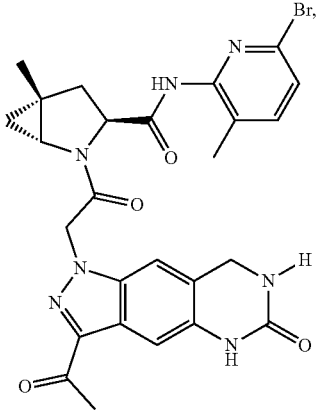
-continued
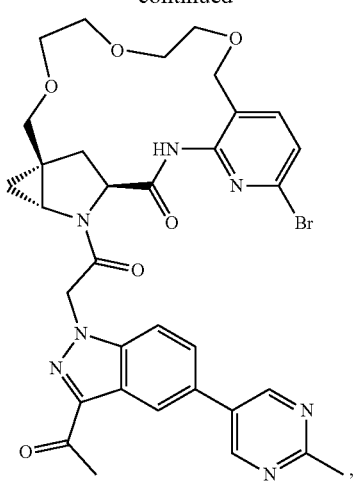
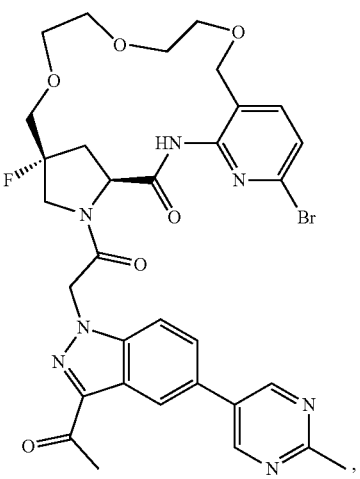
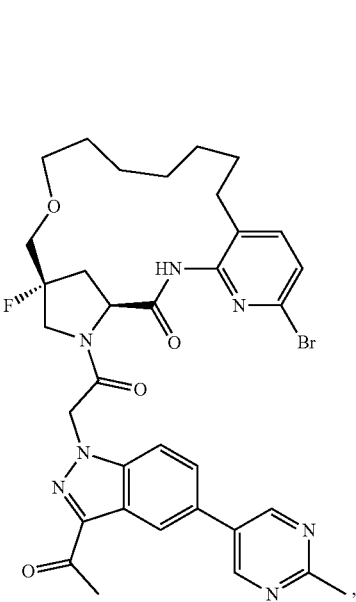

431
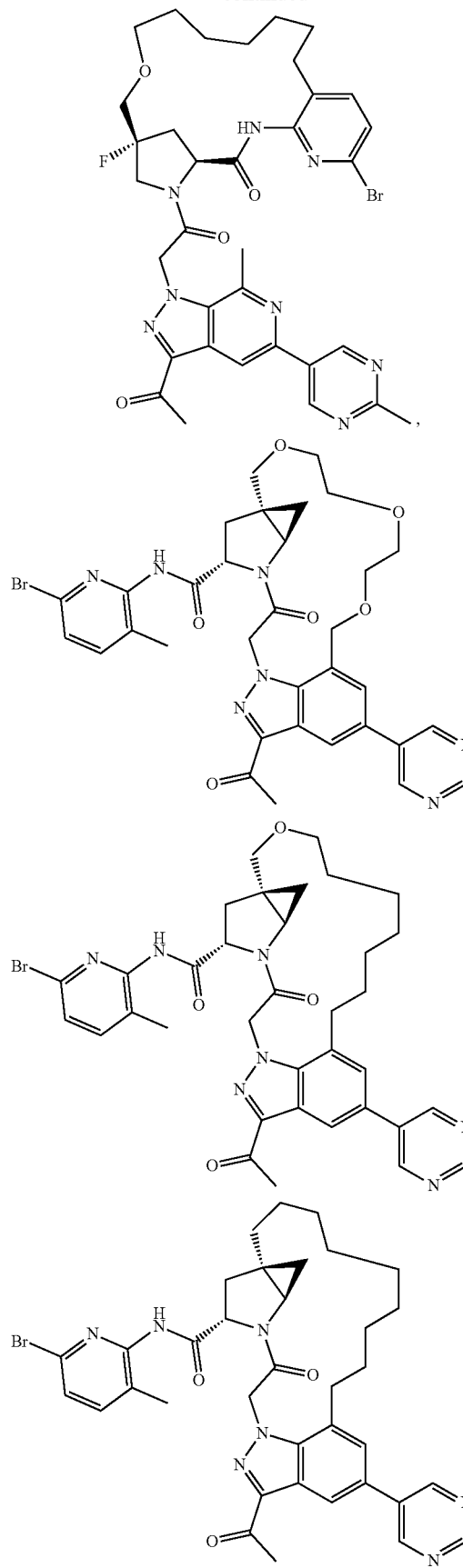
432
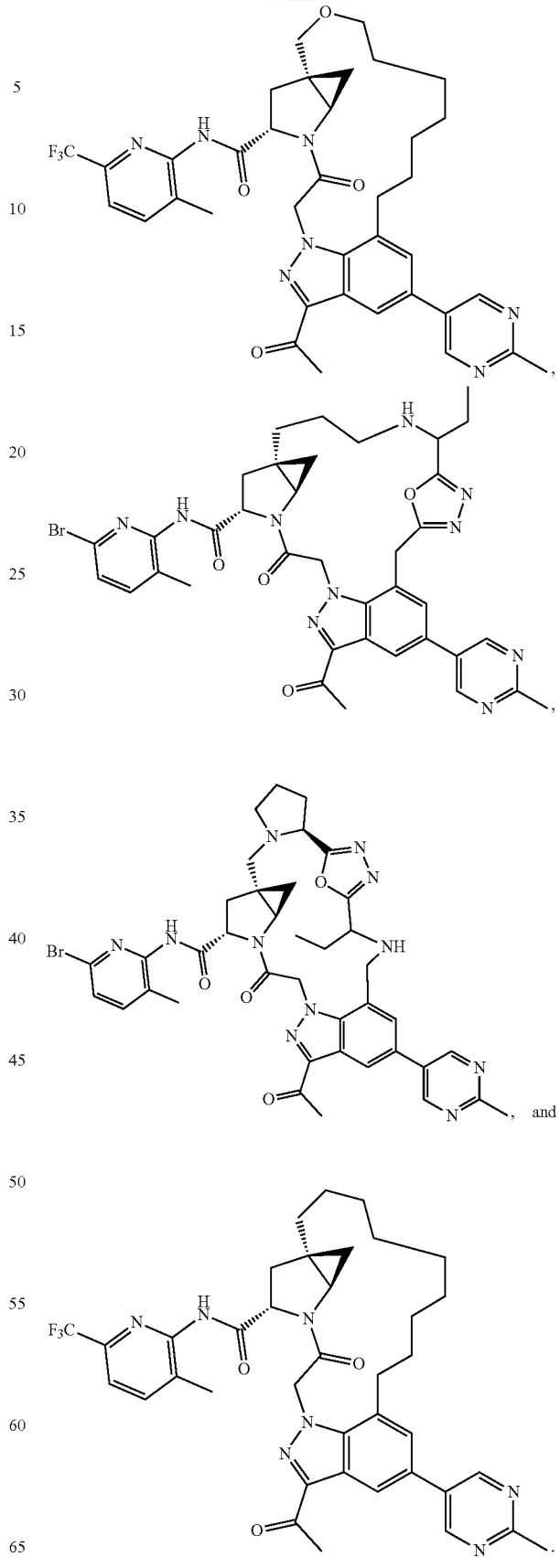

Additional Embodiments
In another embodiment $X^9$-$L^3$-$X^{10}$ or $X^{10}$-$L^3$-$X^9$ is selected from:
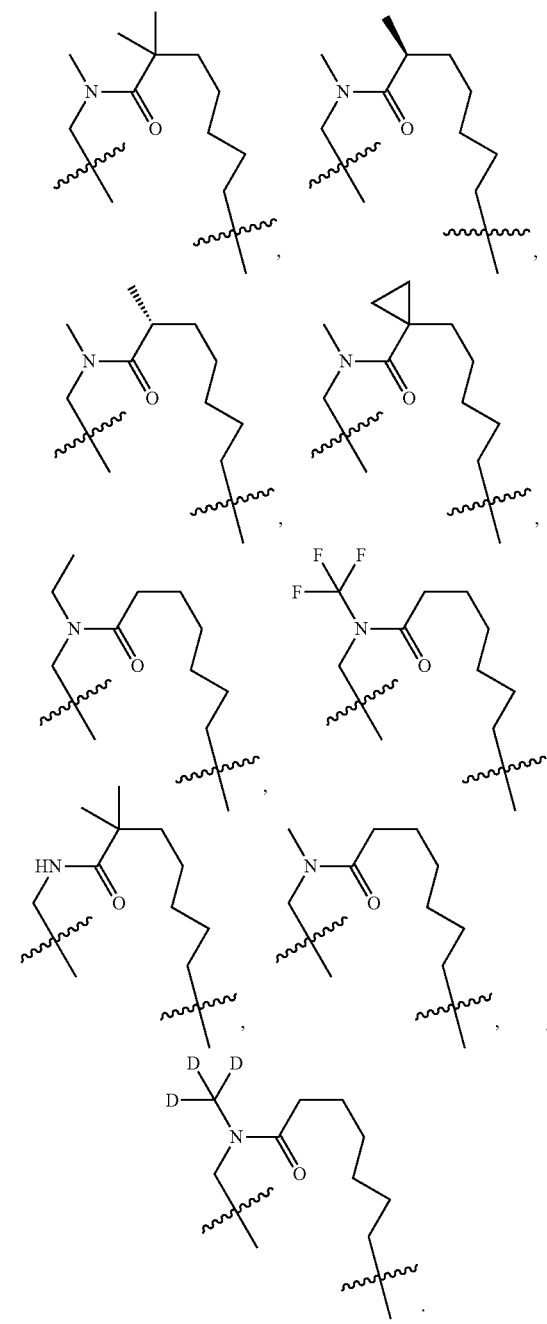
In another embodiment $X^9$-$L^3$-$X^{10}$ or $X^{10}$-$L^3$-$X^9$ is
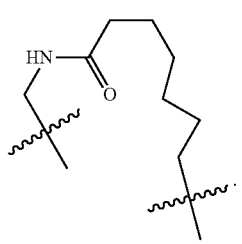 [SMILES: *CCCCCCC(=O)NC*]
In another embodiment $X^9$-$L^3$-$X^{10}$ or $X^{10}$-$L^3$-$X^9$ is selected from:
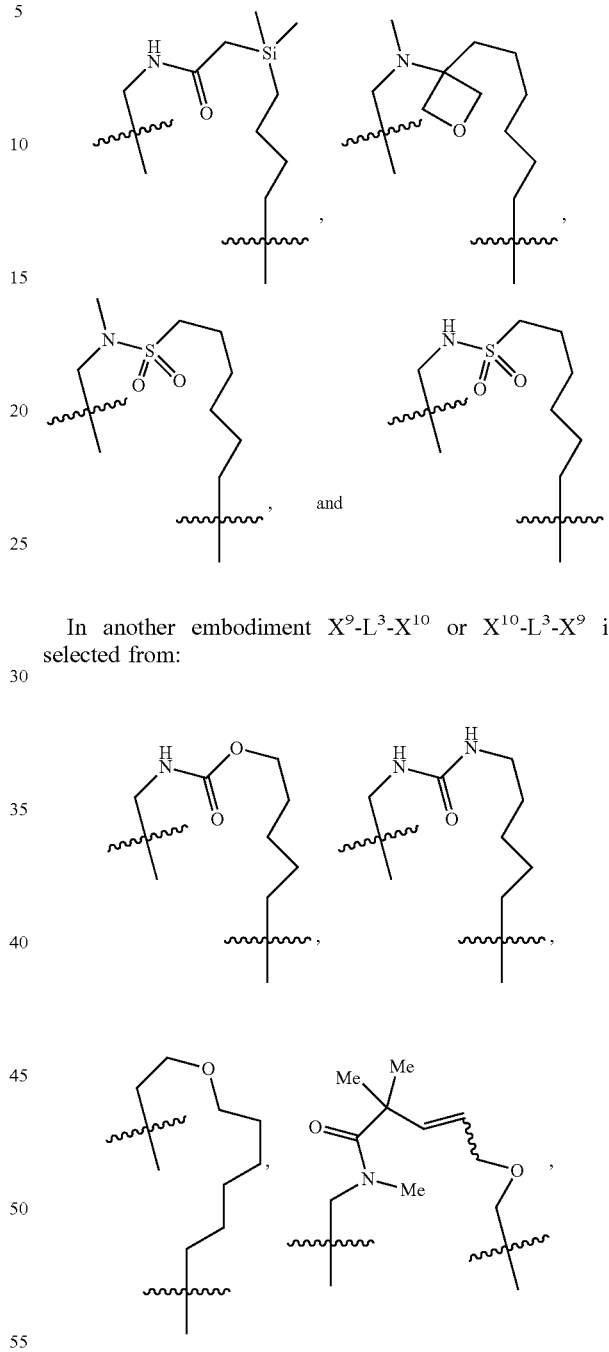
In another embodiment $X^9$-$L^3$-$X^{10}$ or $X^{10}$-$L^3$-$X^9$ is selected from:
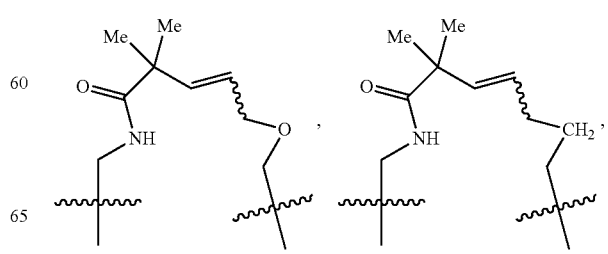

435
-continued
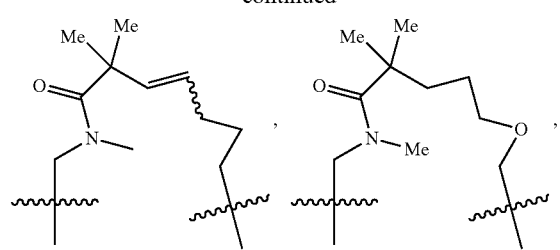
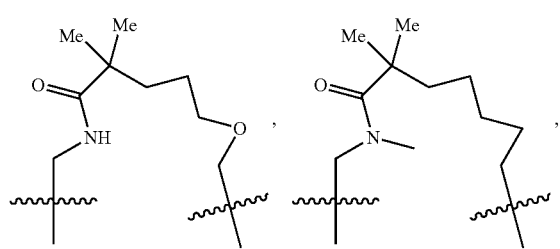
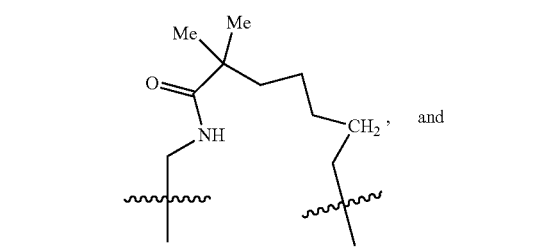
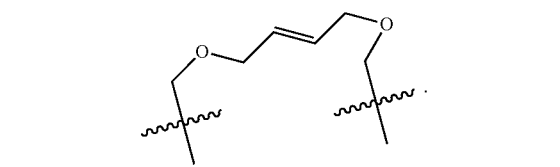
In another embodiment $X^9$-$L^3$-$X^{10}$ or $X^{10}$-$L^3$-$X^9$ is selected from:
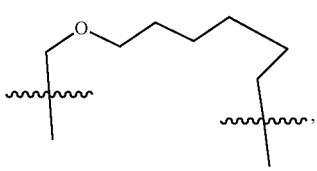
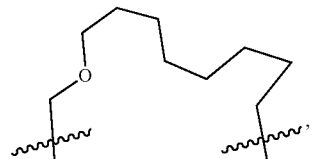
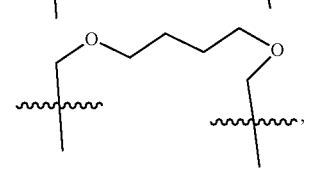
436
-continued
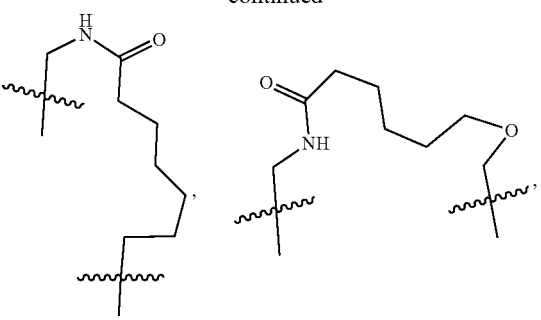
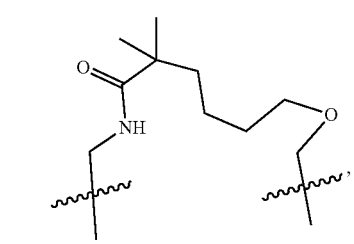
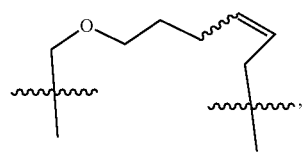
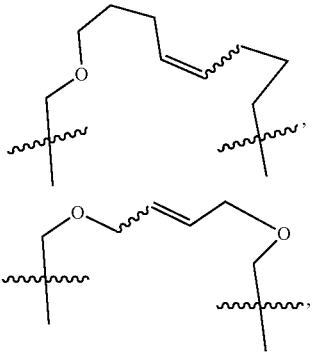
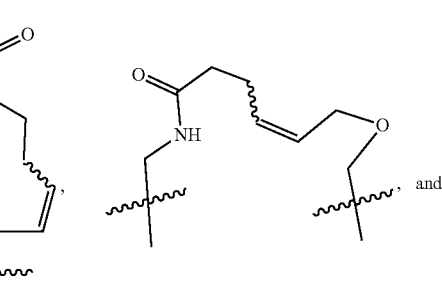
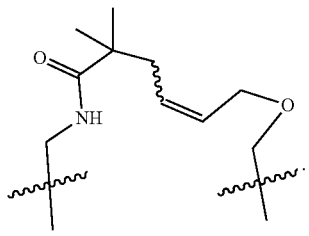

In another embodiment $X^9$-$L^3$-$X^{10}$ or $X^{10}$-$L^3$-$X^9$ is selected from:
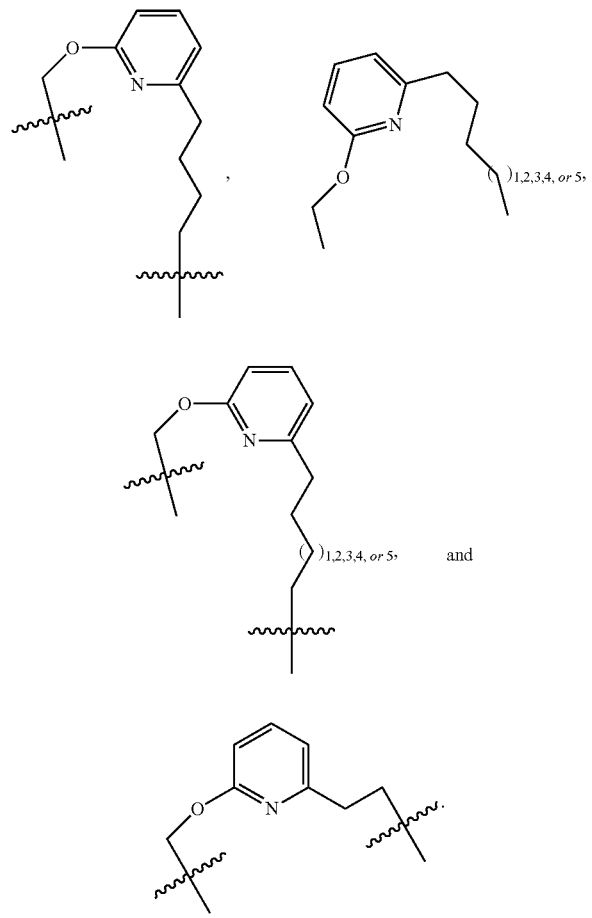
In another embodiment $X^9$-$L^3$-$X^{10}$ or $X^{10}$-$L^3$-$X^9$ is selected from:
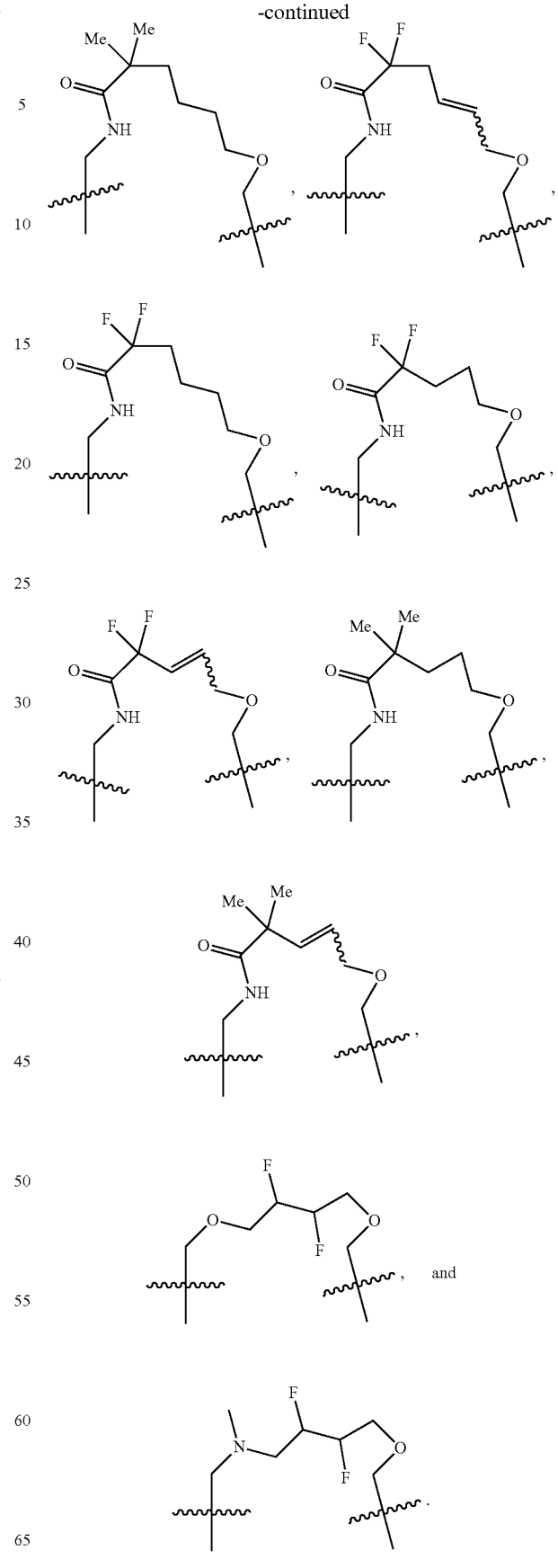

In another embodiment $X^9$-$L^3$-$X^{10}$ or $X^{10}$-$L^3$-$X^9$ is selected from:
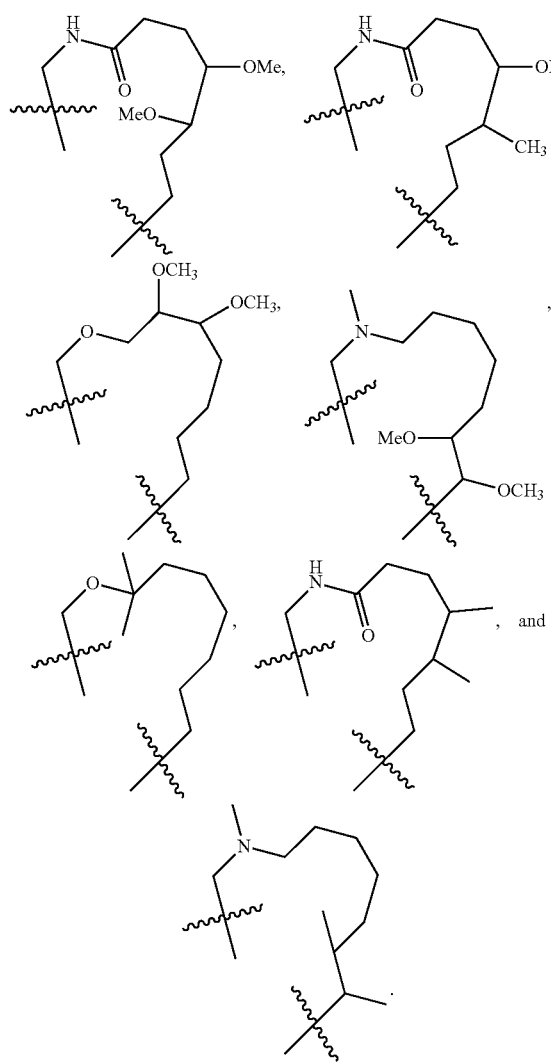
In another embodiment $X^9$-$L^3$-$X^{10}$ or $X^{10}$-$L^3$-$X^9$ is selected from:
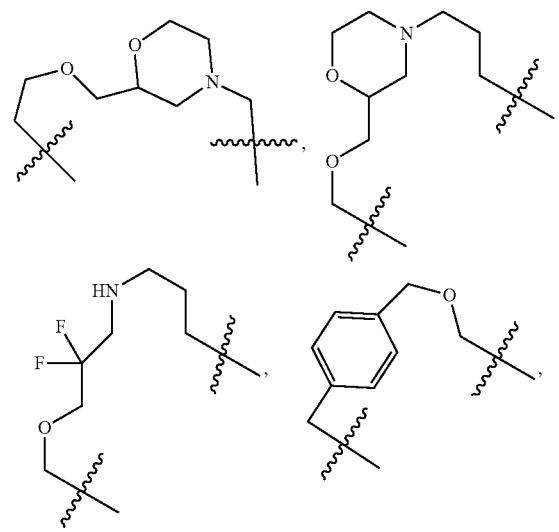
In another embodiment $X^9$-$L^3$-$X^{10}$ or $X^{10}$-$L^3$-$X^9$ is selected from:
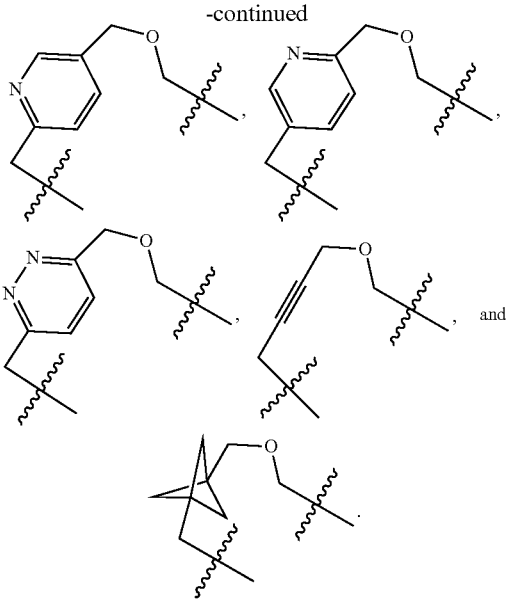
In another embodiment $X^9$-$L^3$-$X^{10}$ or $X^{10}$-$L^3$-$X^9$ is selected from:
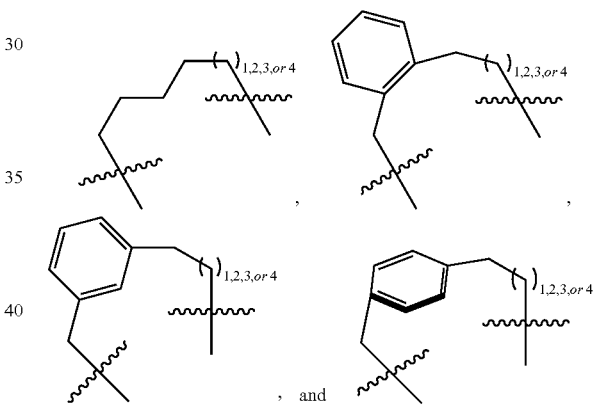
In another embodiment $X^9$-$L^3$-$X^{10}$ or $X^{10}$-$L^3$-$X^9$ is selected from:
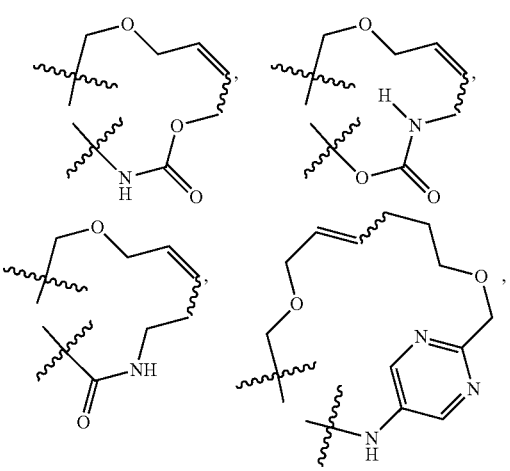

-continued
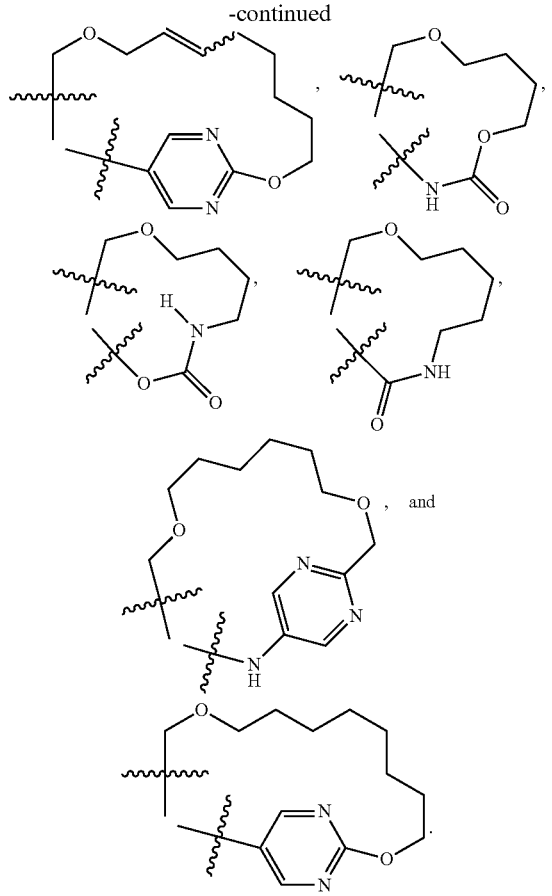
In another embodiment $X^9$-$L^3$-$X^{10}$ or $X^{10}$-$L^3$-$X^9$ is selected from:
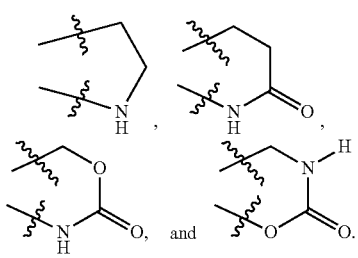
In another embodiment $X^9$-$L^3$-$X^{10}$ or $X^{10}$-$L^3$-$X^9$ is selected from:
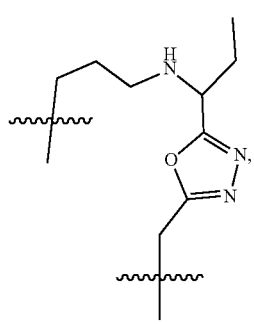
-continued
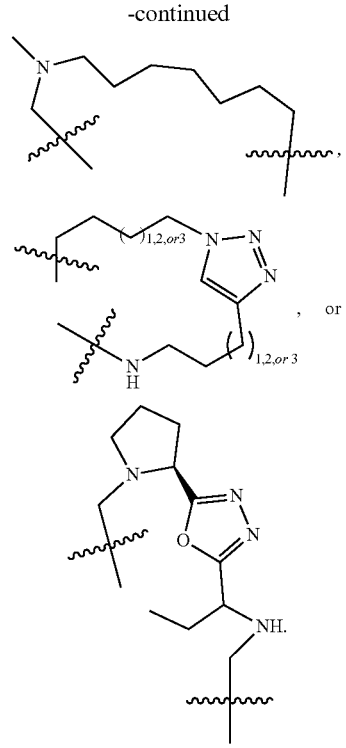
In one embodiment $R^{32}$ is selected from:
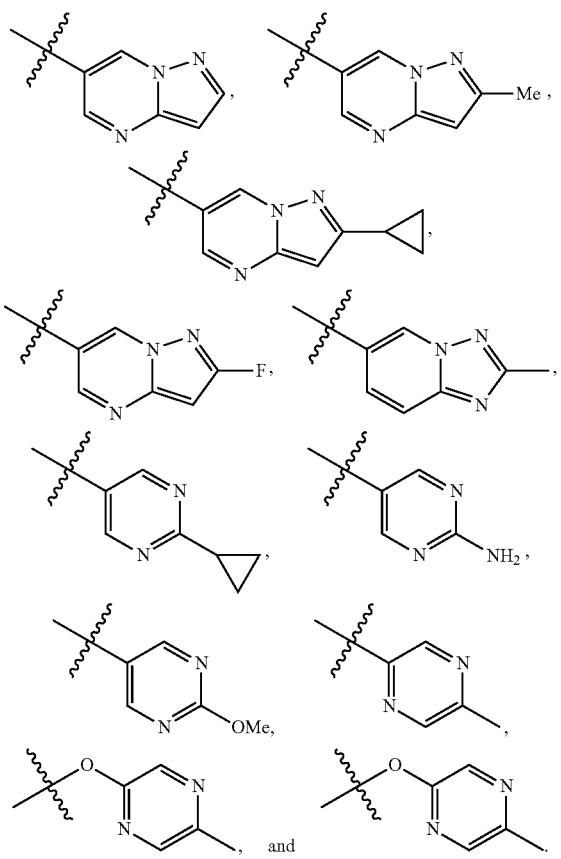

In an alternative embodiment $R^{32}$ is selected from:

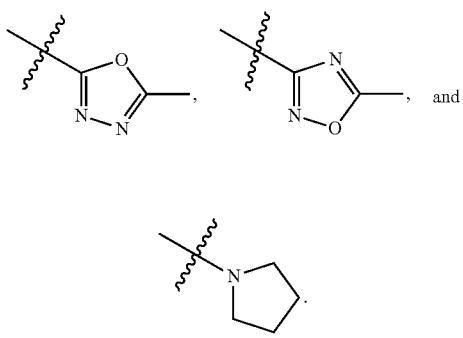

In an alternative embodiment $R^{11}$, $R^{12}$, $R^{13}$, $R^{14}$, or $R^{15}$ is -alkyl-$R^{32}$ or —O-alkyl-$R^{32}$.

In an alternative embodiment $R^{11}$, $R^{12}$, $R^{13}$, $R^{14}$, or $R^{15}$ is

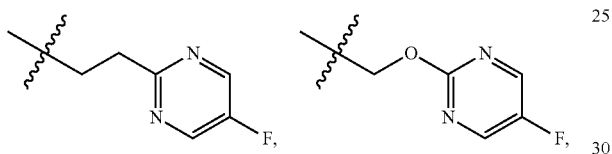

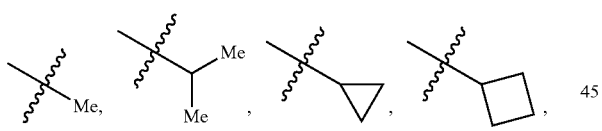

In one embodiment $R^{11}$, $R^{12}$, $R^{13}$, $R^{14}$, or $R^{15}$ is

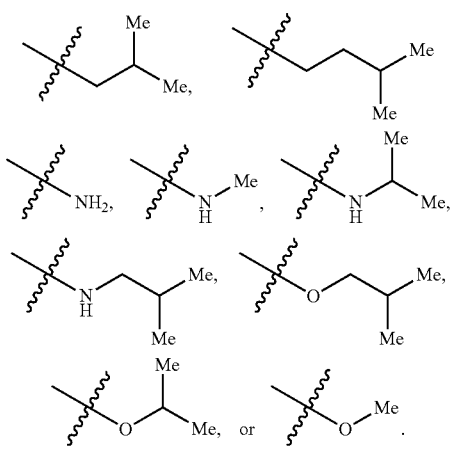

In one embodiment a compound of Formula:

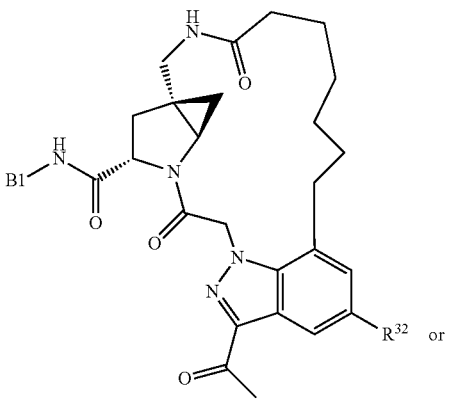

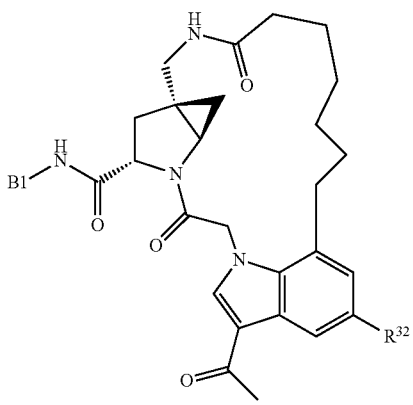

is provided, wherein B1 and $R^{32}$ are as defined above.

In another embodiment a compound of Formula:

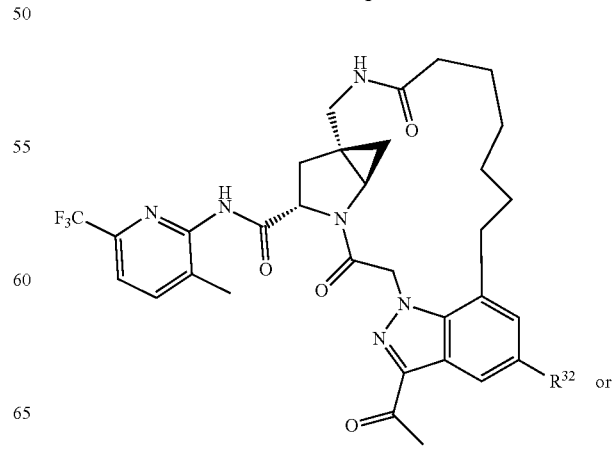

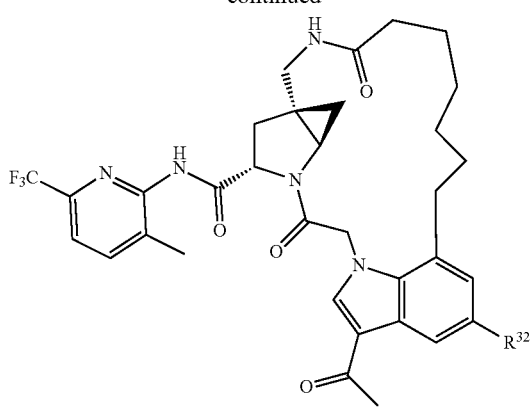

is provided, wherein $R^{32}$ is as defined above.

In another embodiment a compound of Formula:

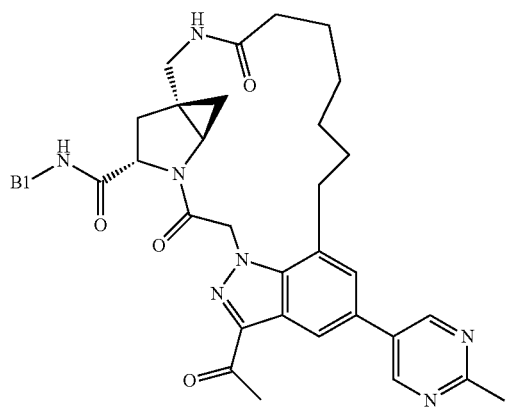

is provided, wherein B1 is as defined above.

In another embodiment, B1 is selected from:

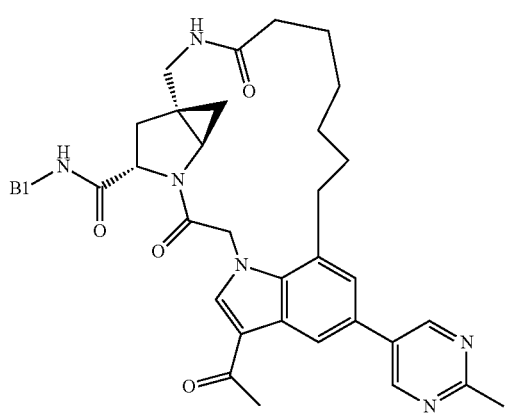

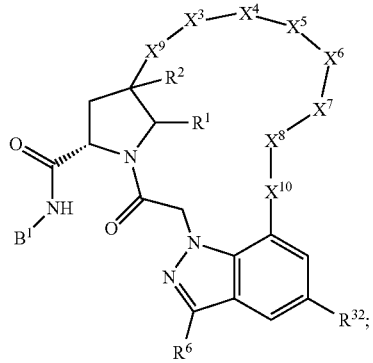

In an alternative embodiment $R^9$ is haloalkyl.

In an alternative embodiment $X^3$, $X^4$, $X^5$, $X^6$, $X^7$, or $X^8$ is —Si(alkyl)$_2$—.

In an alternative embodiment $R^{104}$ is alkoxy or haloalkoxy.

In one embodiment, provided is a compound of formula:

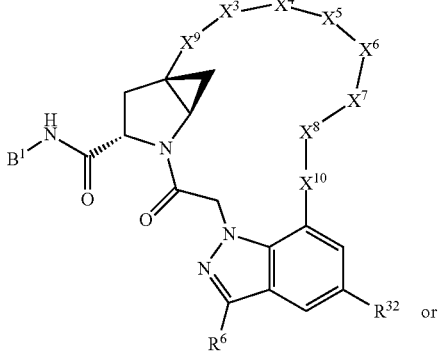

or a pharmaceutically acceptable salt, isotopic analog, prodrug, or isolated isomer thereof; wherein all variables are as defined herein.

In another embodiment, provided is a compound of formula:

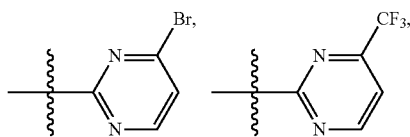

-continued

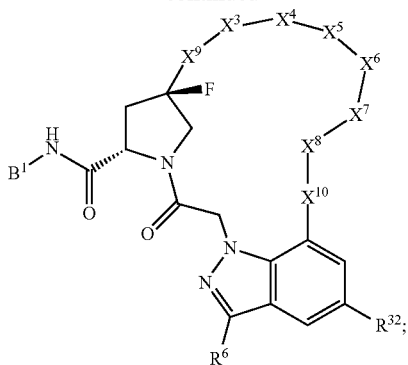

or a pharmaceutically acceptable salt, isotopic analog, prodrug, or isolated isomer thereof; wherein all variables are as defined herein.

In another embodiment, provided is a compound of one of the following formulas:

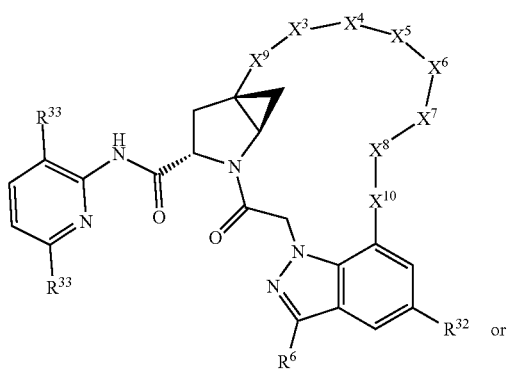

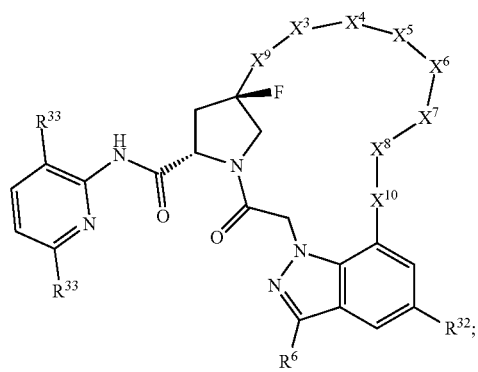

or a pharmaceutically acceptable salt, isotopic analog, prodrug, or isolated isomer thereof; wherein all variables are as defined herein.

In another embodiment, provided is a compound of formula:

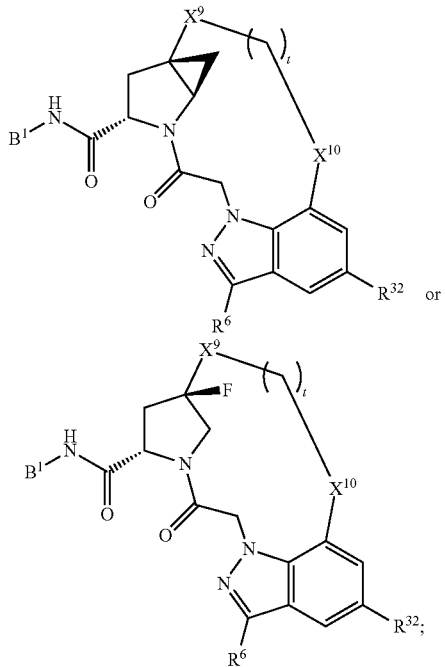

or a pharmaceutically acceptable salt, isotopic analog, prodrug, or isolated isomer thereof;
wherein t is 1, 2, 3, 4, 5, or 6; and
all other variables are as defined herein.

In another embodiment, provided is a compound of formula:

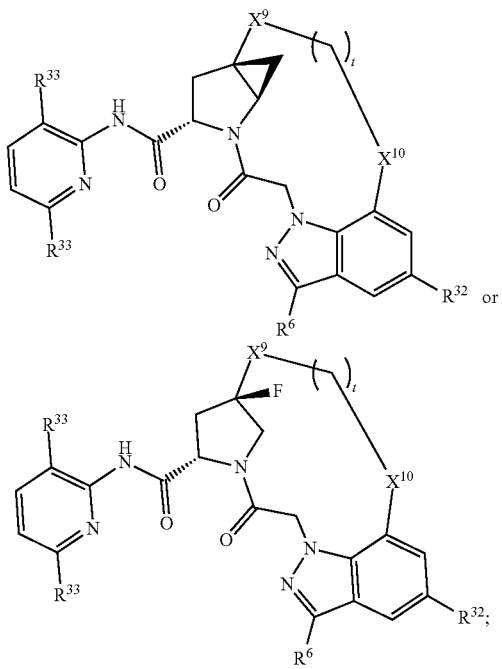

or a pharmaceutically acceptable salt, isotopic analog, prodrug, or isolated isomer thereof;
wherein t is 1, 2, 3, 4, 5, or 6; and
all other variables are as defined herein.

In another embodiment, provided is a compound of formula:

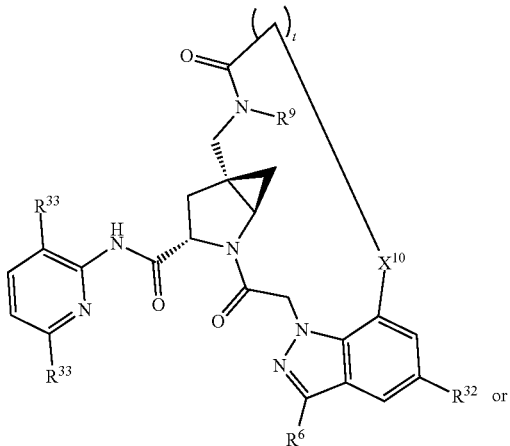

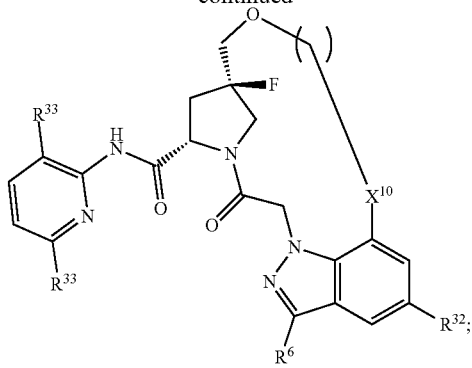

or a pharmaceutically acceptable salt, isotopic analog, prodrug, or isolated isomer thereof;
wherein t is 1, 2, 3, 4, 5, or 6; and
all other variables are as defined herein.

In another embodiment, provided is a compound of formula:

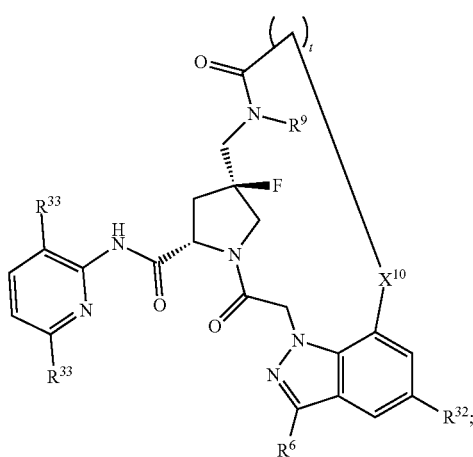

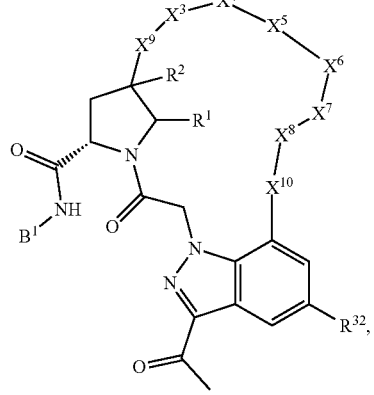

or a pharmaceutically acceptable salt, isotopic analog, prodrug, or isolated isomer thereof;
wherein t is 1, 2, 3, 4, 5, or 6; and
all other variables are as defined herein.

In another embodiment, provided is a compound of formula:

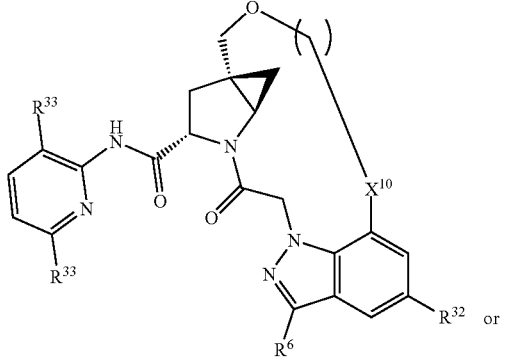

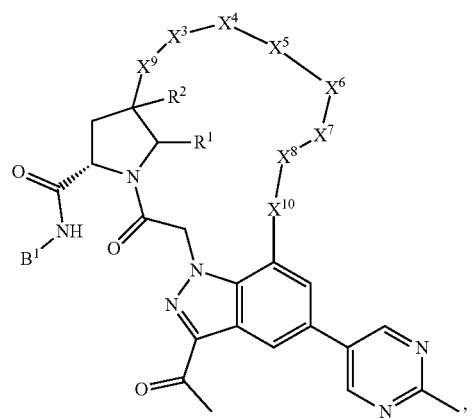

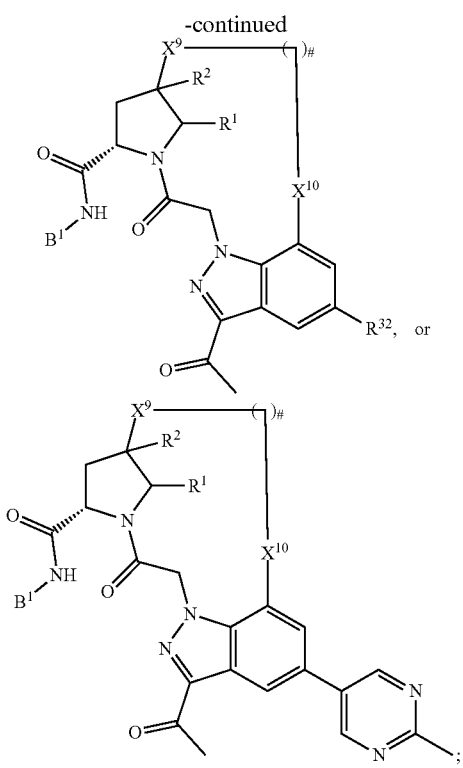

or a pharmaceutically acceptable salt, isotopic analog, prodrug, or isolated isomer thereof;
wherein # is 3, 4, 5, 6, 7, 8, 9, or 10 and
all other variables are as defined herein.
In an alternative embodiment Z is haloalkyl.

The $R^{12}$ and $R^{13}$ Heteroaryl, and Heterocycle Substituents

In one embodiment this invention includes a compound of Formula I, Formula II, Formula III, Formula IV, Formula V, Formula VI, Formula VII, or Formula VIII a pharmaceutically acceptable salt, prodrug, isotopic analog, N-oxide, or isolated isomer thereof, optionally in a pharmaceutically acceptable composition, wherein at least one of $R^{12}$ or $R^{13}$ on the A1 or A2 group is an heteroaryl, or heterocycle for example, $R^{32}$.

In one embodimnt one of $R^{12}$ and $R^{13}$ is selected from $R^{31}$ and the other of $R^{12}$ and $R^{13}$ is selected from $R^{32}$. In another embodiment, each of $R^{12}$ and $R^{13}$ can be independently selected from $R^{32}$.

$R^{31}$ is selected from hydrogen, halogen, hydroxyl, nitro, cyano, amino, —COOH, haloalkyl including $C_1$-$C_6$haloalkyl, haloalkoxy including $C_1$-$C_6$haloalkoxy, alkyl including $C_1$-$C_6$alkyl, -$C_0$-$C_4$alkyl($C_3$-$C_7$cycloalkyl), alkenyl including $C_2$-$C_6$alkenyl, alkanoyl including $C_2$-$C_6$alkanoyl, alkoxy including $C_1$-$C_6$alkoxy, alkenyloxy including $C_2$-$C_6$alkenyloxy, —C(O)OR$^9$, thioalkyl including $C_1$-$C_6$thioalkyl, -$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, haloalkyl including $C_1$-$C_6$haloalkyl, and haloalkoxy including $C_1$-$C_6$haloalkoxy is unsubstituted or substituted with one or more substituents independently selected from halogen, hydroxyl, nitro, cyano, amino, —COOH, —CONH$_2$, haloalkyl including $C_1$-$C_6$haloalkyl, and haloalkoxy including $C_1$-$C_6$haloalkoxy, and each of which $R^{31}$ is also optionally substituted with one substituent selected from phenyl and 4- to 7-membered heterocycle containing 1, 2, or 3 heteroatoms independently selected from N, O, and S; which phenyl or 4- to 7-membered heterocycle is unsubstituted or substituted with one or more substituents independently selected from halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, (mono- and di-$C_1$-$C_6$alkylamino) $C_0$-$C_4$alkyl, $C_1$-$C_6$alkylester, -$C_0$-$C_4$alkyl)($C_3$-$C_7$cycloalkyl), haloalkyl including $C_1$-$C_6$haloalkyl, and haloalkoxy including $C_1$-$C_6$haloalkoxy;

In one embodiment $R^{32}$ is selected from heteroaryl; saturated heterocycle or partially unsaturated heterocycle; wherein the heteroaryl, saturated heterocycle or partially unsaturated heterocycle ring can be optionally substituted.

Non-Limiting $R^{12}$/$R^{13}$ Embodiments

In one embodiment, $R^{12}$ is $R^{32}$.
In one embodiment, $R^{13}$ is $R^{32}$.
In one embodiment, $R^{12}$ is an optionally substituted heteroaryl.
In one embodiment, $R^{13}$ is an optionally substituted heteroaryl.
In one embodiment, $R^{12}$ is $R^{32}$.
In one embodiment, $R^{12}$ is $R^{32}$, which is (4- to 7-membered heterocycloalkyl) having 1, 2, or 3 heteroatoms independently selected from N, O, and S.
In one embodiment, the disclosure provides compounds of Formula I, Formula II, Formula III, Formula IV, Formula V, Formula VI, Formula VII, or Formula VIII, wherein;
one of $R^{12}$ and $R^{13}$ is H and the other of $R^{12}$ and $R^{13}$ is $R^{32}$, where
$R^{32}$ is selected from heteroaryl; saturated heterocycle or partially unsaturated heterocycle; wherein the heteroaryl; saturated heterocycle or partially unsaturated heterocycle ring can be optionally substituted.

In another embodiment, the disclosure provides compounds of Formula I, Formula II, Formula III, Formula IV, Formula V, Formula VI, Formula VII, or Formula VIII wherein;
$R^1$, $R^{1'}$, $R^2$, and $R^{3'}$ are all hydrogen;
$R^2$ is fluoro and $R^3$ is hydrogen, -$C_0$-$C_4$alkyl($C_3$-$C_7$cycloalkyl), or —O-$C_0$-$C_4$alkyl($C_3$-$C_7$cycloalkyl);
$R^5$ is hydrogen, halogen, or $C_1$-$C_6$alkyl;
$R^{11}$, $R^{13}$, $R^{14}$, and $R^{15}$ if present, are independently selected at each occurrence from hydrogen, halogen, hydroxyl, amino, $C_1$-$C_4$alkyl, $C_1$-$C_4$alkoxy, -$C_0$-$C_2$alkyl (mono- and di-$C_1$-$C_6$alkylamino), trifluoromethyl, and trifluoromethoxy;
$X^{12}$ is CR$^{12}$; and
$R^{12}$ is selected from heteroaryl; saturated heterocycle or partially unsaturated heterocycle; wherein the heteroaryl; saturated heterocycle or partially unsaturated heterocycle ring can be optionally substituted.

In one embodiment, the disclosure provides compounds of Formula I, Formula II, Formula III, Formula IV, Formula V, Formula VI, Formula VII, or Formula VIII, wherein;
m is 0 or 1;
$R^2$ is halogen, $R^{2'}$ is hydrogen or halogen, and $R^3$ is hydrogen, halogen, -$C_0$-$C_4$alkyl($C_3$-$C_7$cycloalkyl), or —O-$C_0$-$C_4$alkyl($C_3$-$C_7$cycloalkyl);
$R^6$ is —C(O)$C_1$-$C_4$alkyl, —C(O)NH$_2$, —C(O)CF$_3$, —C(O)($C_3$-$C_7$cycloalkyl), or -ethyl(cyanoimino);

one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ is $R^{32}$, where $R^{32}$ is selected from aryl, heteroaryl; saturated or unsaturated heterocycle; wherein the aryl, heteroaryl, saturated or unsaturated heterocycle ring can be optionally substituted.

In one embodiment, the disclosure provides compounds of Formula I, Formula II, Formula III, Formula IV, Formula V, Formula VI, Formula VII, or Formula VIII, wherein one of $R^{12}$ and $R^{13}$ is hydrogen, hydroxyl, halogen, methyl, or methoxy; and the other of $R^{12}$ and $R^{13}$ is $R^{32}$, where $R^{32}$ is selected from heteroaryl; saturated heterocycle or partially unsaturated heterocycle; wherein the heteroaryl; saturated heterocycle or partially unsaturated heterocycle ring, can be optionally substituted.

In one embodiment, $R^{32}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, alkoxy including $C_1$-$C_6$alkoxy, -$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, haloalkyl including $C_1$-$C_6$haloalkyl, and haloalkoxy including $C_1$-$C_6$haloalkoxy.

In one embodiment, $R^{31}$ is hydrogen and $R^{32}$ is pyrimidinyl.

In another embodiment, $R^{31}$ is hydrogen and $R^{32}$ is pyrimidine substituted with a methyl group.

Non-Limiting L-B Embodiments

In one embodiment, -L1-B1- is:

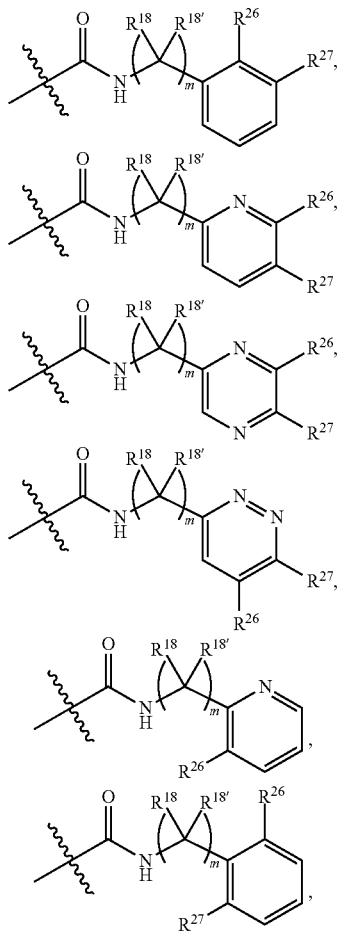

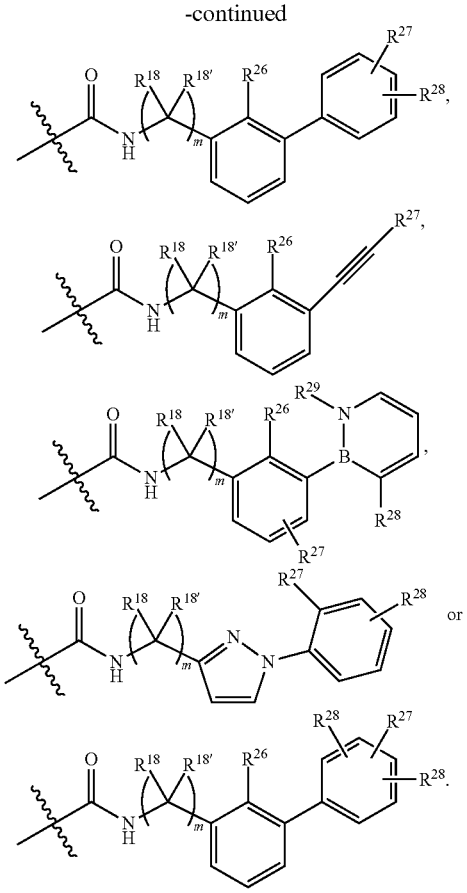

wherein $R^{18}$ and $R^{18'}$ are independently selected from hydrogen, halogen, hydroxymethyl, and methyl; and m is 0 or 1; and $R^{26}$, $R^{27}$, and $R^{28}$ are independently selected from hydrogen, halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, thioalkyl including $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and -$C_0$-$C_4$alkoxy($C_3$-$C_7$cycloalkyl); each of which $R^{26}$, $R^{27}$, and $R^{28}$ other than hydrogen, halogen, hydroxyl, nitro, cyano, is unsubstituted or substituted with one or more substituents independently selected from halogen, hydroxyl, amino, alkoxy including $C_1$-$C_6$alkoxy, haloalkyl including $C_1$-$C_6$haloalkyl, ($C_3$-$C_7$cycloalkyl)$C_0$-$C_4$alkyl-, and haloalkoxy including $C_1$-$C_6$haloalkoxy; and $R^{29}$ is hydrogen, alkyl including $C_1$-$C_6$alkyl, $C_1C_2$haloalkyl or —Si(CH$_3$)$_2$C(CH$_3$)$_3$.

In one embodiment, -L-B1- moiety is selected:

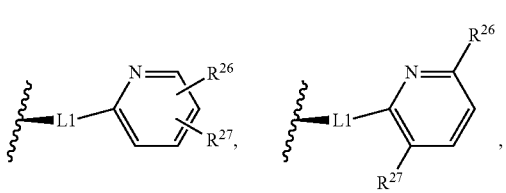

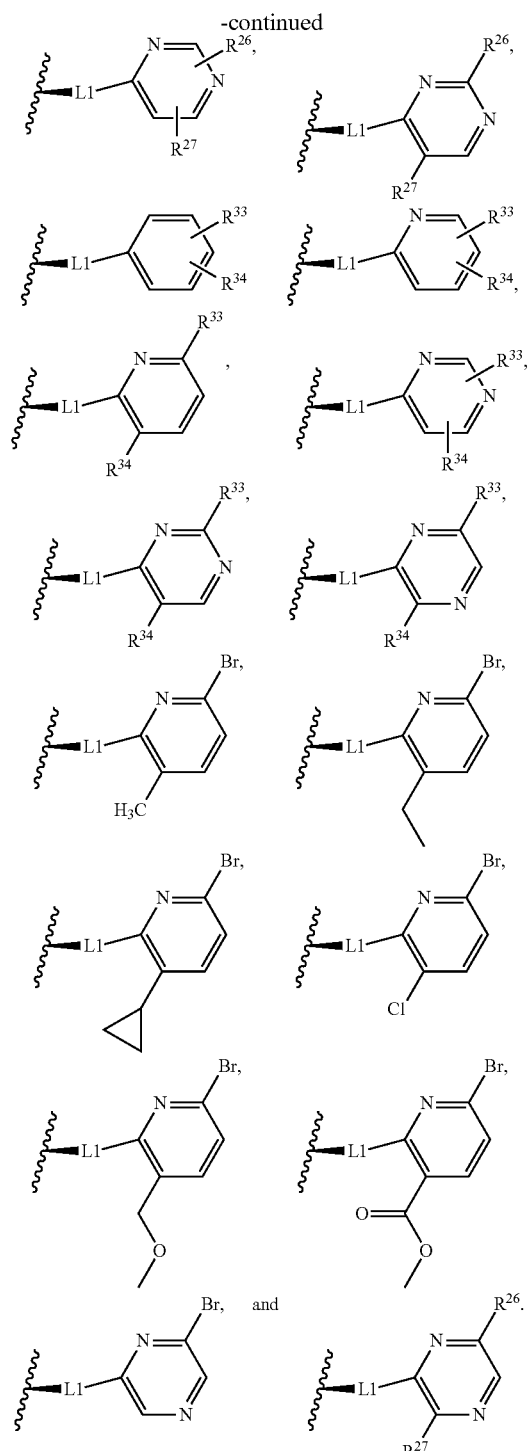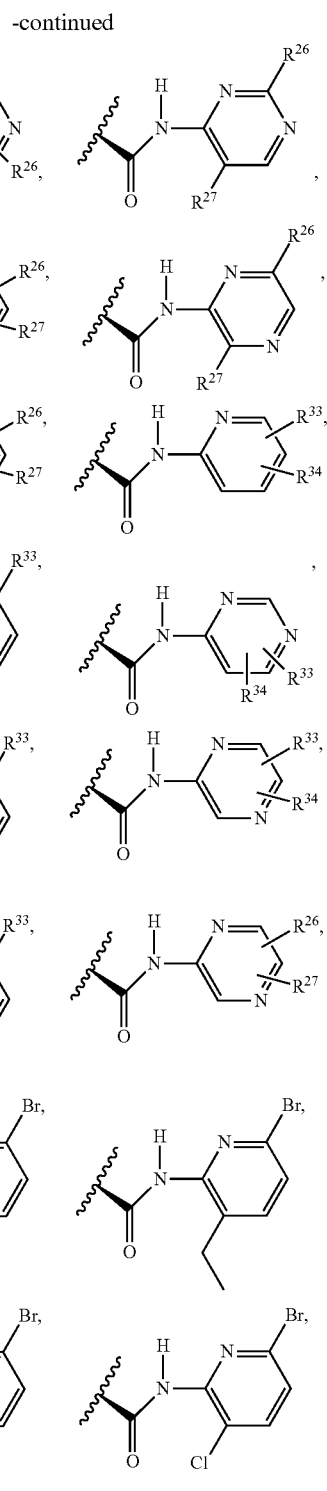
In one embodiment, -L1-B1- moiety is selected:
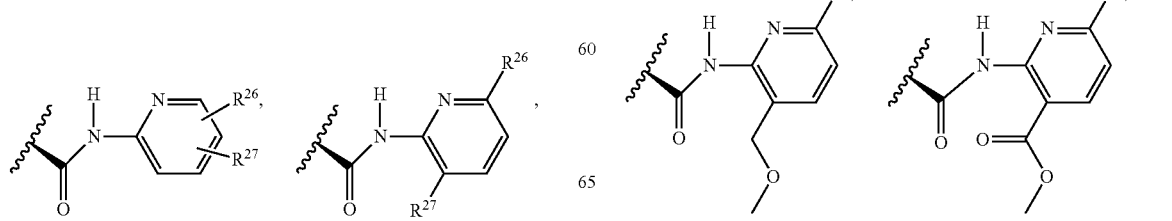

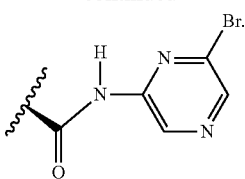
In one embodiment, -L1-B1- moiety is selected:
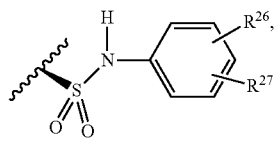 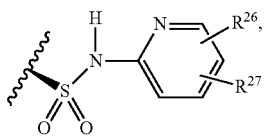
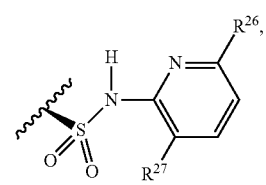 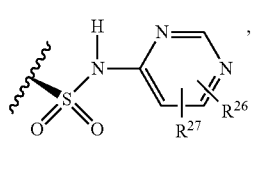
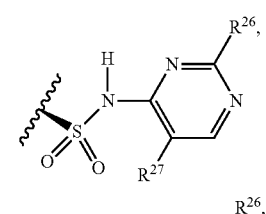 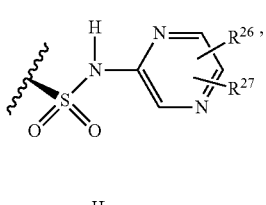
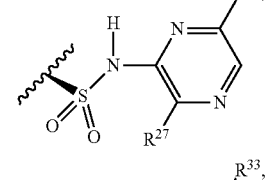 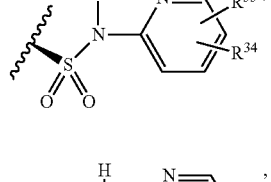
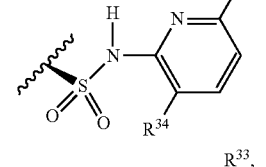 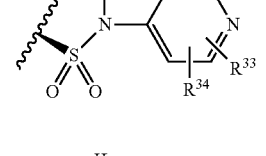
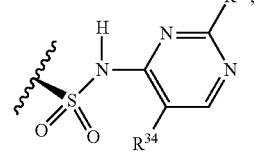 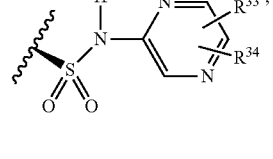
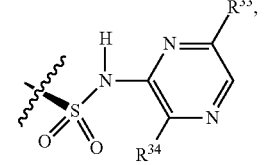 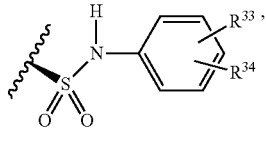
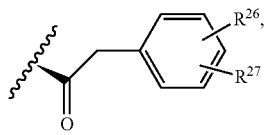 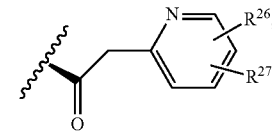
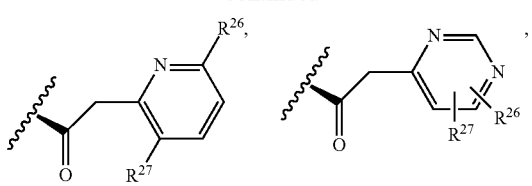 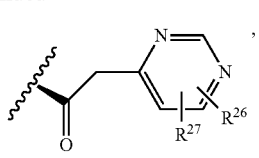
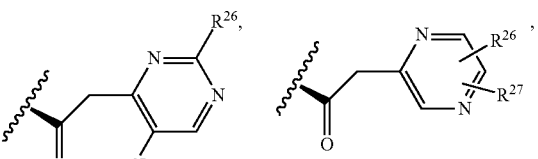 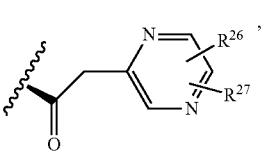
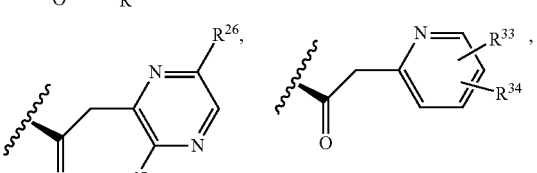 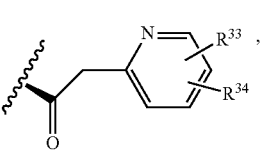
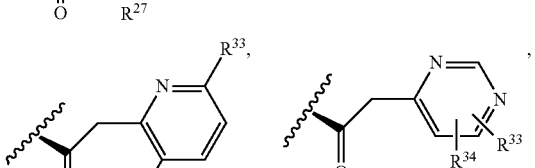 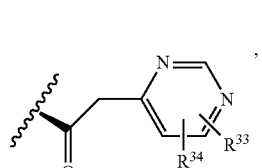
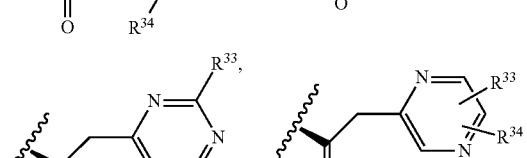 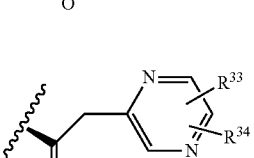
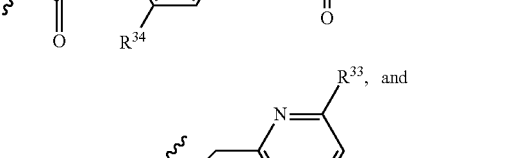 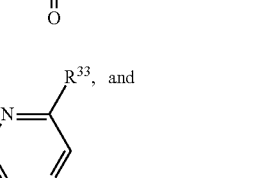
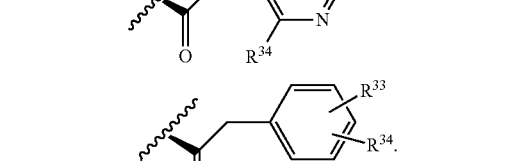
In one embodiment, -L1-B1- moiety is selected:
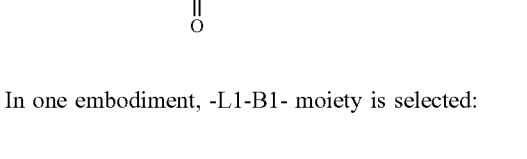 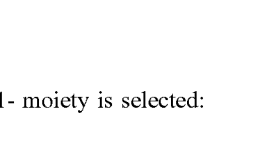
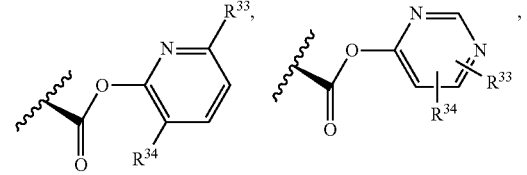 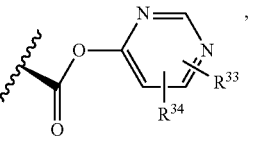
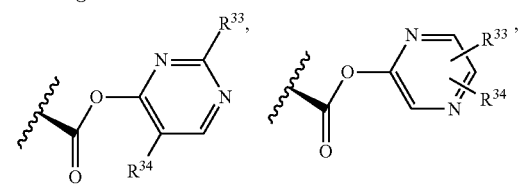 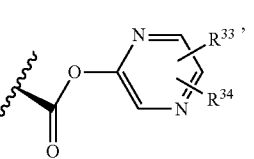

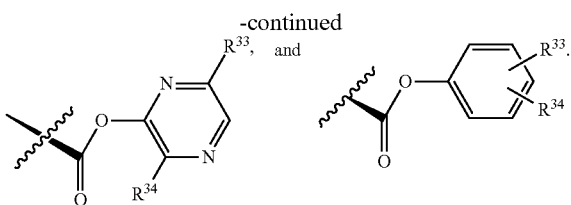

In one embodiment, m is 0.

In one embodiment, the disclosure further includes compounds and salts in which B1 is 2-fluoro-3-chlorophenyl. In another embodiment, another carbocyclic, aryl, heterocyclic, or heteroaryl group such as 2-bromo-pyridin-6-yl, 1-(2,2,2-trifluoroethyl)-1H-pyrazol-3-yl, 2,2-dichlorocyclopropylmethyl, or 2-fluoro-3-trimethylsilylphenyl is used.

In another embodiment, B1 is phenyl, pyridyl, or indanyl each of which is unsubstituted or substituted with one or more substituents independently selected from hydrogen, halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, thioalkyl including $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, -$C_0$-$C_4$alkoxy ($C_3$-$C_7$cycloalkyl), (phenyl)$C_0$-$C_2$alkyl, (pyridyl)$C_0$-$C_2$alkyl; each of which substituents other than hydrogen, halogen, hydroxyl, nitro, cyano, is unsubstituted or substituted with one or more substituents independently selected from halogen, hydroxyl, amino, alkyl including $C_1$-$C_6$alkyl, alkoxy including $C_1$-$C_6$alkoxy, —OSi(CH$_3$)$_2$C(CH$_3$)$_3$, —Si(CH$_3$)$_2$C(CH$_3$)$_3$, haloalkyl including $C_1$-$C_6$haloalkyl, and haloalkoxy including $C_1$-$C_6$haloalkoxy.

In another embodiment, B1 is phenyl or pyridyl substituted with 1, 2, or 3 substituents selected from chloro, bromo, hydroxyl, —SCF$_3$, $C_1$-$C_6$alkyl, $C_1$-$C_6$alkoxy, trifluoromethyl, phenyl and trifluoromethoxy each of which substituents other than chloro, bromo, hydroxyl, —SCF$_3$, can be optionally substituted.

In certain embodiments, B1 is a 2-fluoro-3-chlorophenyl or a 2-fluoro-3-trifluoromethoxyphenyl group.

In one embodiment, B1 is pyridyl, optionally substituted with halogen, $C_1$-$C_6$alkoxy, and trifluoromethyl.

In one embodiment, B1 is phenyl, substituted with 1, 2, or 3 substituents independently selected from halogen, $C_1$-$C_6$alkyl, $C_1$-$C_6$alkoxy, trifluoromethyl, and optionally substituted phenyl.

In one embodiment, $R^{23}$ is independently selected at each occurrence from ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S.

In one embodiment, L1-B1 is:

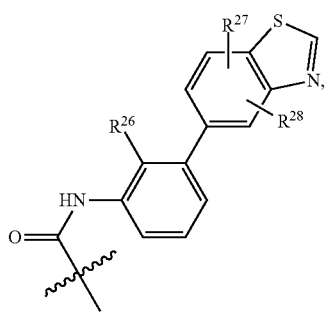

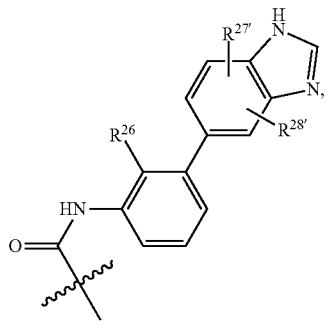

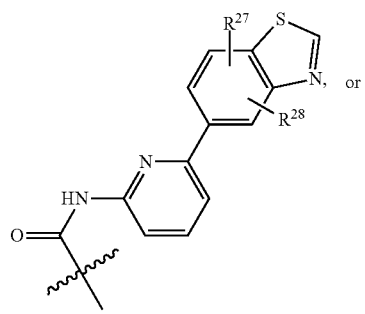

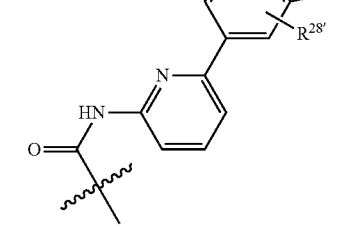

$R^{27'}$, and $R^{28'}$ are independently selected from hydrogen, fluoro, bromo, iodo, hydroxyl, nitro, cyano, alkyl including $C_1$-$C_6$alkyl, alkenyl including $C_2$-$C_6$alkenyl, alkanoyl including $C_2$-$C_6$alkanoyl, $C_2$-$C_6$alkoxy, $C_2$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and -$C_0$-$C_4$alkoxy($C_3$-$C_7$cycloalkyl); each of which $R^{27'}$, and $R^{28'}$ other than hydrogen, fluoro, bromo, iodo, hydroxyl, nitro, and cyano, is unsubstituted or substituted with one or more substituents independently selected from halogen, hydroxyl, amino, alkoxy including $C_1$-$C_6$alkoxy, haloalkyl including $C_1$-$C_6$haloalkyl, ($C_3$-$C_7$cycloalkyl)$C_0$-$C_4$alkyl-, and haloalkoxy including $C_1$-$C_6$haloalkoxy.

Exemplary Compounds of the Present Invention
Exemplary compounds of the present invention include:
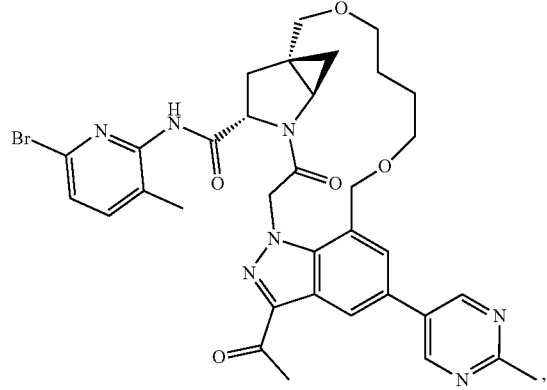
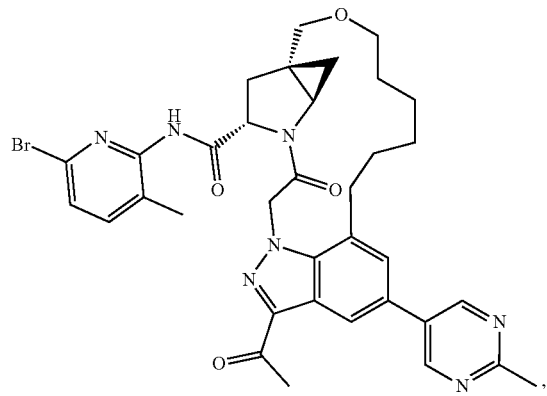
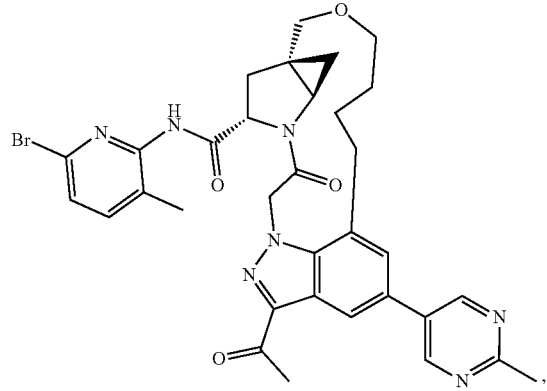
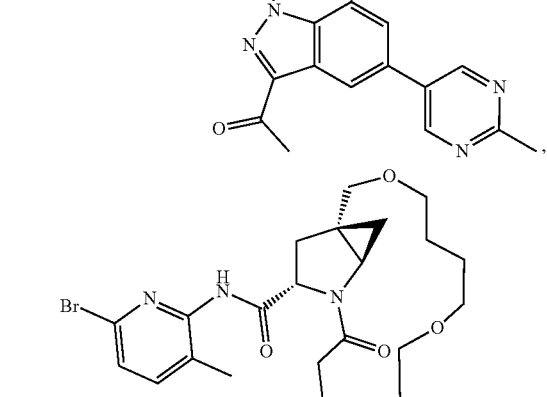
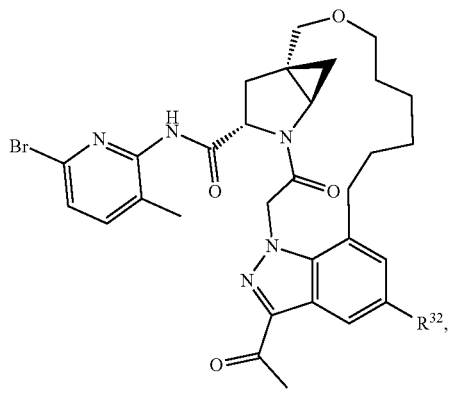
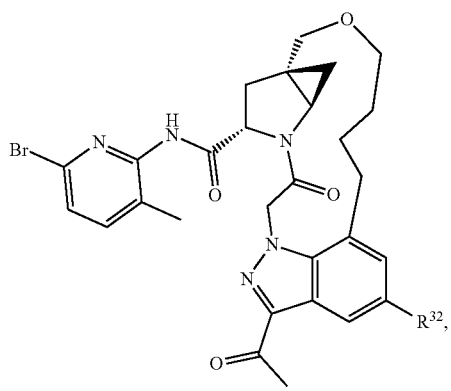
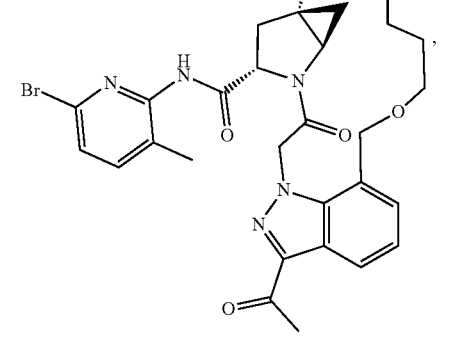
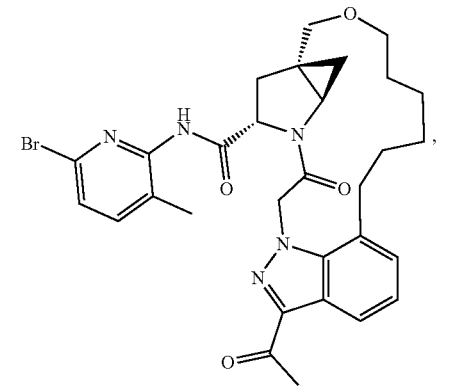

463
-continued
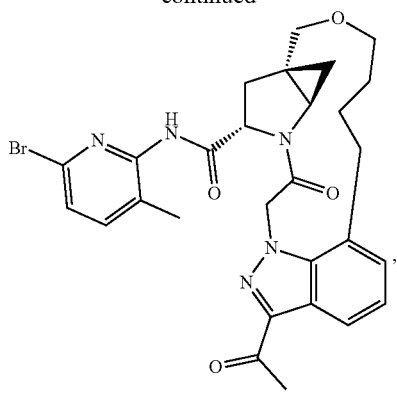
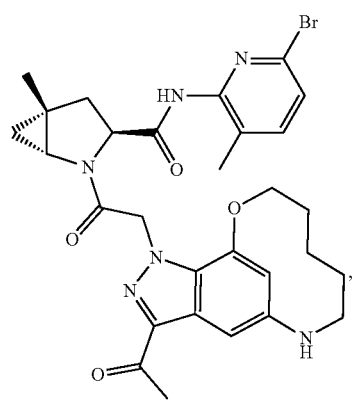
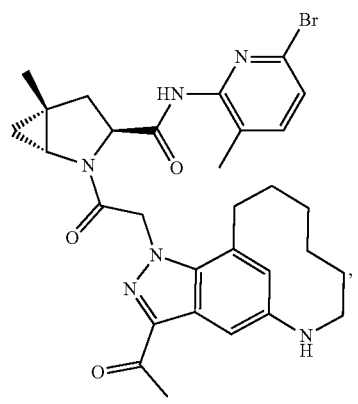
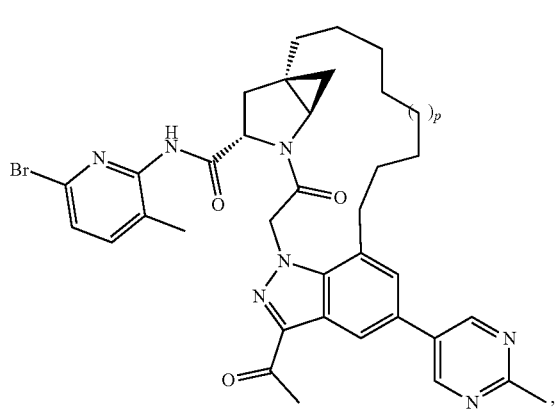
464
-continued
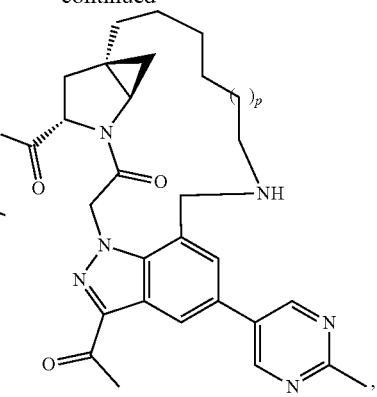
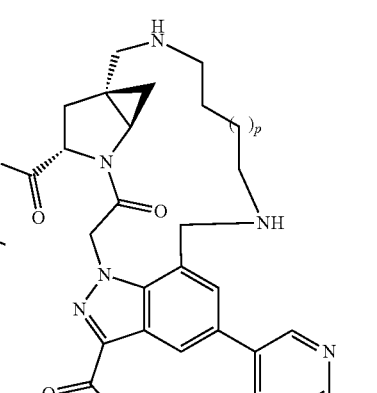
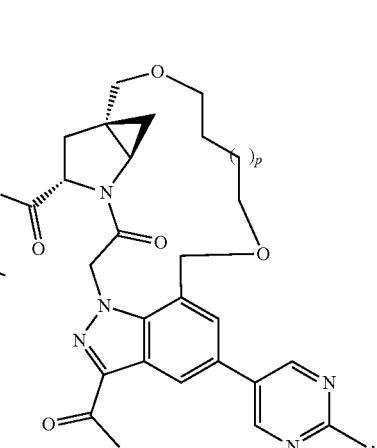
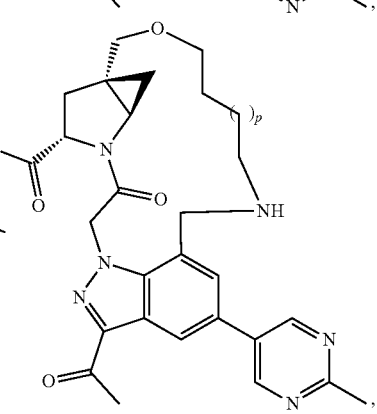

-continued

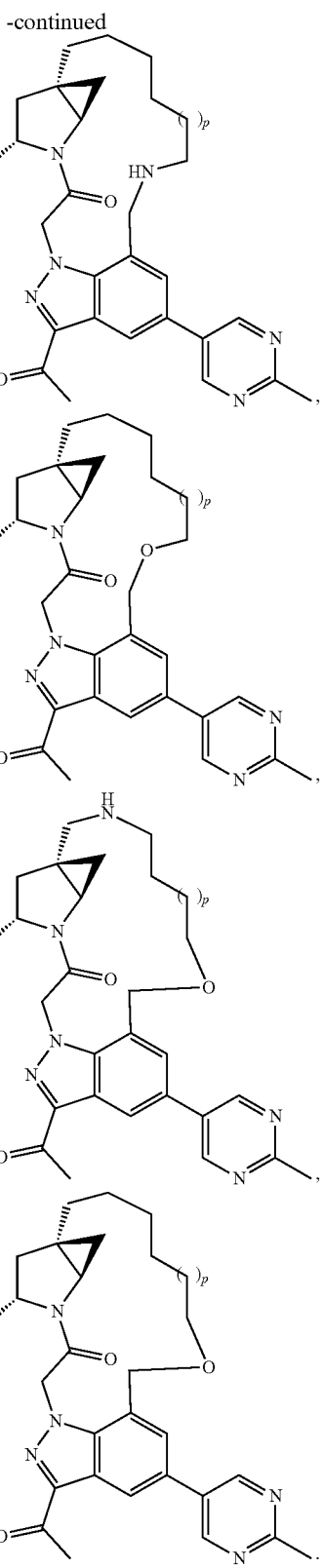

Pharmaceutical Preparations

Active compounds described herein can be administered to a host in need thereof as the neat chemical, but are more typically administered as a pharmaceutical composition that includes an effective amount for a host, typically a human, in need of such treatment of an active compound as described herein or its pharmaceutically acceptable salt, prodrug, isotopic analog, N-oxide, or isolated isomer thereof. Thus, in one embodiment, the disclosure provides pharmaceutical compositions comprising an effective amount of a compound or its pharmaceutically acceptable salt, prodrug, isotopic analog, N-oxide, or isolated isomer thereof together with at least one pharmaceutically acceptable carrier for any of the uses described herein. The pharmaceutical composition may contain a compound or salt as the only active agent, or, in an alternative embodiment, the compound and at least one additional active agent.

An effective amount of an active compound as described herein, or the active compound described herein in combination or alternation with, or preceded by, concomitant with or followed by another active agent, can be used in an amount sufficient to (a) inhibit the progression of a disorder mediated by the complement pathway, including an inflammatory, immune, including an autoimmune, disorder or Complement Factor D related disorder; (b) cause a regression of an inflammatory, immune, including an autoimmune, disorder or Complement Factor D related disorder; (c) cause a cure of an inflammatory, immune, including an autoimmune, disorder or Complement Factor D related disorder; or inhibit or prevent the development of an inflammatory, immune, including an autoimmune, disorder or Complement Factor D related disorder. Accordingly, an effective amount of an active compound or its salt or composition described herein will provide a sufficient amount of the active agent when administered to a patient to provide a clinical benefit.

The exact amount of the active compound or pharmaceutical composition described herein to be delivered to the host, typically a human, in need thereof, will be determined by the health care provider to achieve the desired clinical benefit.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound, or its salt or prodrug. In one embodiment, the dosage form has at least about 1mg, 5 mg, 10 mg, 25 mg, 50 mg, 75 mg, 100 mg, 200 mg, 400 mg, 500 mg, 600 mg, 1000 mg, 1200 mg, or 1600 mg of active compound, or its salt. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include a molar ratio of the active compound and an additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent: active compound), or its salt, described herein. In one embodiment, the additional active agent is an anti-inflammatory or immunosuppressing agent.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, sub-tenon, sub-retinal, retro-bulbar, peribulbar, suprachorodial, subchorodial, chorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The pharmaceutical compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Classes of carriers include, but are not limited to binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

In certain embodiments, the pharmaceutical composition for administration further includes a compound or salt of Formula I, Formula II, Formula III, Formula IV, Formula V, Formula VI, Formula VII, or Formula VIII and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidyl choline; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the pharmaceutical preparation may include polymers for controlled delivery of the described compounds, including, but not limited to pluronic polymers, polyesters (e.g., polylactic acid, poly(lactic-co-glycolic acid), polycaprolactone, polyvalerolactone, poly(1, 3-dioxan-2one)); polyanhydrides (e.g., poly(sebacic anhydride)); polyethers (e.g., polyethylene glycol); polyurethanes; polymethacrylates; polyacrylates; and polycyanoacrylates. In some embodiments, polymers may be modified with polyethylene glycol (PEG), with a carbohydrate, and/or with acyclic polyacetals derived from polysaccharides. See, e.g., Papisov, 2001, ACS Symposium Series, 786:301, incorporated by reference herein.

The compounds of the present invention can be formulated as particles. In one embodiment the particles are or include microparticles. In an alternative embodiment the particles are or include nanoparticles.

In an additional alternative embodiment, common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer. Nanoparticles with different sizes and morphologies can be obtained by this method.

Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles from a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment an active compound as described herein is administered to a patient in need thereof as particles formed by solvent removal. In another embodiment the present invention provides particles formed by solvent removal comprising a compound of the present invention and one or more pharmaceutically acceptable excipients as defined herein. In another embodiment the particles formed by solvent removal comprise a compound of the present invention and an additional therapeutic agent. In a further embodiment the particles formed by solvent removal comprise a compound of the present invention, an additional therapeutic agent, and one or more pharmaceutically acceptable excipients. In another embodiment any of the described particles formed by solvent removal can be formulated into a tablet and then coated to form a coated tablet. In an alternative embodiment the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment an active compound as described herein is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional therapeutic agent. In a further embodiment the SDD comprises a compound of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated.

Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In one embodiment, an active compound as described herein is administered to a patient in need thereof as particles formed by phase inversion. In another embodiment the present invention provides particles formed by phase inversion comprising a compound of the present invention and one or more pharmaceutically acceptable excipients as defined herein. In another embodiment the particles formed by phase inversion comprise a compound of the present invention and an additional therapeutic agent. In a further embodiment the particles formed by phase inversion comprise a compound of the present invention, an additional therapeutic agent, and one or more pharmaceutically acceptable excipients. In another embodiment any of the described particles formed by phase inversion can be formulated into a tablet and then coated to form a coated tablet. In an alternative embodiment the particles formed by phase inversion are formulated into a tablet but the tablet is uncoated.

Techniques for particle formation using coacervation are known in the art, for example, as described in GB-B-929 406; GB-B-929 40 1; and U.S. Pat. Nos. 3,266,987, 4,794, 000, and 4,460,563. Coacervation involves the separation of a compound (or polymer matrix and one or more compounds) solution into two immiscible liquid phases. One phase is a dense coacervate phase, which contains a high concentration of the compound, while the second phase contains a low concentration of the compound. Within the dense coacervate phase, the compound forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment an active compound as described herein is administered to a patient in need thereof as particles formed by coacervation. In another embodiment the present invention provides particles formed by coacervation comprising a compound of the present invention and one or more pharmaceutically acceptable excipients as defined herein. In another embodiment the particles formed by coacervation comprise a compound of the present invention and an additional therapeutic agent. In a further embodiment the particles formed by coacervation comprise a compound of the present invention, an additional therapeutic agent, and one or more pharmaceutically acceptable excipients. In another embodiment any of the described particles formed by coacervation can be formulated into a tablet and then coated to form a coated tablet. In an alternative embodiment the particles formed by coacervation are formulated into a tablet but the tablet is uncoated.

Methods for very low temperature casting of controlled release microspheres are described in U.S. Pat. No. 5,019, 400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present invention is administered to a patient in need thereof as particles formed by low temperature casting. In another embodiment the present invention provides particles formed by low temperature casting comprising a compound of the present invention and one or more pharmaceutically acceptable excipients as defined herein. In another embodiment the particles formed by low temperature casting comprise a compound of the present invention and an additional therapeutic agent. In a further embodiment the particles formed by low temperature casting comprise a compound of the present invention, an additional therapeutic agent, and one or more pharmaceutically acceptable excipients. In another embodiment any of the described particles formed by low temperature casting can be formulated into a tablet and then coated to form a coated tablet. In an alternative embodiment the particles formed by low temperature casting are formulated into a tablet but the tablet is uncoated.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based compound delivery can be used to release compounds at a sustained rate and thus lower the frequency of administration, deliver drugs in a targeted manner to minimize systemic side effects, or deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Methods for producing nanoparticles are known in the art. For example, see Muller, R. H., et al., Solid lipid nanoparticles (SLN) for controlled drug delivery—a review of the state of the art, Eur. H. Pharm. Biopharm., 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. No. 8,465,775; U.S. Pat. No. 8,444,899; U.S. Pat. No. 8,420,124; U.S. Pat. No. 8,263,129; U.S. Pat. No. 8,158,728; U.S. Pat. No. 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007, 845; P. Paolicelli et al., "Surface-modified PLGA-based Nanoparticles that can Efficiently Associate and Deliver Virus-like Particles" Nanomedicine. 5(6):843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7;(PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658;

and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. No. 6,123,727; U.S. Pat. No. 5,804,178; U.S. Pat. No. 5,770,417; U.S. Pat. No. 5,736,372; U.S. Pat. No. 5,716,404; U.S. Pat. No. 6,095,148; U.S. Pat. No. 5,837,752; U.S. Pat. No. 5,902,599; U.S. Pat. No. 5,696,175; U.S. Pat. No. 5,514,378; U.S. Pat. No. 5,512,600; U.S. Pat. No. 5,399,665; U.S. Pat. No. 5,019,379; U.S. Pat. No. 5,010,167; U.S. Pat. No. 4,806,621; U.S. Pat. No. 4,638,045; and U.S. Pat. No. 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390: 386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-C$_0$-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6): 843-853 (2010); U.S. Pat. No. 6,632,671 to Unger Oct. 14, 2003, all incorporated herein by reference.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticle.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S. Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. No. 6,582,678, U.S. Pat. No. 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. No. 5,710,182 and U.S. Pat. No. 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. No. 8,367,097 and U.S. Pat. No. 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. No. 9,066,779 and U.S. Pat. No. 8,623,395 titled "Implantable therapeutic device", WO/2014/160884 titled "Ophthalmic Implant for Delivering Therapeutic Substances", U.S. Pat. No. 8,399,006, U.S. Pat. No. 8,277,830, U.S. Pat. No. 8,795,712, U.S. Pat. No. 8,808,727, U.S. Pat. No. 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. No. 8,905,963 and U.S. Pat. No. 9,033,911 titled "Injector apparatus and method for drug delivery", WO/2015/057554 titled "Formulations and Methods for Increasing or Reducing Mucus", U.S. Pat. No. 8,715,712 and U.S. Pat. No. 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled " Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion" , WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved inj ectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. No. 6,007,845 and U.S. Pat. No. 5,578,325 titled "Nanoparticles and microparticles of non-linear hydrophilichydrophobic multi-block copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

Uses of Active Compounds for Treatment of Selected Disorders

In one aspect, an effective amount of an active compound or its salt or composition as described herein is used to treat a medical disorder which is an inflammatory or immune condition, a disorder mediated by the complement cascade (including a dysfunctional cascade) including a Complement Factor D-related disorder or alternative complement pathway-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

In one embodiment, the disorder is selected from fatty liver and conditions stemming from fatty liver, such as nonalcoholic steatohepatitis (NASH), liver inflammation, cirrhosis and liver failure. In one embodiment of the present invention, a method is provided for treating fatty liver disease in a host by administering an effective amount of an active compound or its salt or composition as described herein.

In another embodiment, an active compound or its salt or composition as described herein is used to modulate an immune response prior to or during surgery or other medical procedure. One non-limiting example is use in connection with acute or chronic graft versus host disease, which is a common complication as a result of allogeneic tissue transplant, and can also occur as a result of a blood transfusion.

In one embodiment, the present invention provides a method of treating or preventing dermatomyositis by administering to a subject in need thereof an effective amount of an active compound or its salt or composition as described herein.

In one embodiment, the present invention provides a method of treating or preventing amyotrophic lateral sclerosis by administering to a subject in need thereof an effective amount of an active compound or its salt or composition as described herein.

In one embodiment, the present invention provides a method of treating or preventing abdominal aortic aneurysm, hemodialysis complications, hemolytic anemia, or hemodialysis by administering to a subject in need thereof an effective amount of an active compound or its salt or composition as described herein.

In another embodiment, a method is provided for the treatment or prevention of cytokine or inflammatory reactions in response to the administration of pharmaceutical or biotherapeutic (e.g. CAR T-cell therapy or monoclonal antibody therapy) in a host by administering an effective amount of an active compound or its salt or composition as described herein. Various types of cytokine or inflammatory reactions may occur in response to a number of factors, such as the administrations of biotherapeutics. In one embodiment, the cytokine or inflammatory reaction is cytokine release syndrome. In one embodiment, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as cytokine storm, and can be fatal.

Fatal cytokine storms have been observed in response to infusion with several monoclonal antibody therapeutics. See, Abramowicz D, et al. "Release of tumor necrosis factor, interleukin-2, and gamma-interferon in serum after injection of OKT3 monoclonal antibody in kidney transplant recipients" *Transplantation* (1989) 47(4):606-8; Chatenoud L, et al. "In vivo cell activation following OKT3 administration. Systemic cytokine release and modulation by corticosteroids" *Transplantation* (1990) 49(4):697-702; and Lim L C, Koh L P, and Tan P. "Fatal cytokine release syndrome with chimeric anti-CD20 monoclonal antibody rituximab in a 71-year-old patient with chronic lymphocytic leukemia" *J. Clin Oncol.* (1999) 17(6):1962-3.

Also contemplated herein, is the use of an active compound or its salt or composition as described herein to mediate an adverse immune response in patients receiving bi-specific T-cell engagers (BiTE). A bi-specific T-cell engager directs T-cells to target and bind with a specific antigen on the surface of a cancer cell. For example, Blinatumomab (Amgen), a BiTE has recently been approved as a second line therapy in Philadelphia chromosome-negative relapsed or refractory acute lymphoblastic leukemia. Blinatumomab is given by continuous intravenous infusion in 4-week cycles. The use of BiTE agents has been associated with adverse immune responses, including cytokine release syndrome. The most significantly elevated cytokines in the CRS associated with ACT include IL-10, IL-6, and IFN-γ (Klinger et al., Immunopharmacologic response of patients with B-lineage acute lymphoblastic leukemia to continuous infusion of T cell-engaging CD19/CD3-bispecific BiTE antibody blinatumomab. Blood (2012) 119:6226-6233).

In another embodiment, the disorder is episcleritis, idiopathic episcleritis, anterior episcleritis, or posterior episcleritis. In one embodiment, the disorder is idiopathic anterior uveitis, HLA-B27 related uveitis, herpetic keratouveitis, Posner Schlossman syndrome, Fuch's heterochromic iridocyclitis, or cytomegalovirus anterior uveitis.

In one embodiment, the present invention provides a method of treating or preventing a C3 glomurenopathy by administering to a subject in need thereof an effective amount of an active compound or its salt or composition as described herein. In one embodiment, the disorder is selected from dense deposit disease (DDD) and C3 glomerulonephritis (C3GN).

In one embodiment, the present invention provides a method of treating or preventing a IC-MPGN by administering to a subject in need thereof an effective amount of an active compound or its salt or composition as described herein.

In one embodiment, the present invention provides a method of treating or preventing a paroxysmal nocturnal hemoglobinuria (PNH) by administering to a subject in need thereof an effective amount of an active compound or its salt or composition as described herein.

In one embodiment, the present invention provides a method of treating or preventing age-related macular degeneration (AMD) by administering to a subject in need thereof an effective amount of an active compound or its salt or composition as described herein.

In one embodiment, the present invention provides a method of treating or preventing rheumatoid arthritis by administering to a subject in need thereof an effective amount of an active compound or its salt or composition as described herein.

In one embodiment, the present invention provides a method of treating or preventing multiple sclerosis by administering to a subject in need thereof an effective amount of an active compound or its salt or composition as described herein.

In one embodiment, the present invention provides a method of treating or preventing myasthenia gravis by administering to a subject in need thereof an effective amount of an active compound or its salt or composition as described herein.

In one embodiment, the present invention provides a method of treating or preventing atypical hemolytic uremic syndrome (aHUS) by administering to a subject in need thereof an effective amount of an active compound or its salt or composition as described herein.

In one embodiment, the present invention provides a method of treating or preventing neuromyelitis optica (NMO) by administering to a subject in need thereof an effective amount of an active compound or its salt or composition as described herein.

In yet another embodiment, the present invention provides a method of treating or preventing a disorder as described below by administering to a subject in need thereof an effective amount of an active compound or its salt or composition as described herein, including:

a. vitritis, sarcoidosis, syphilis, tuberculosis, or Lyme disease;
b. retinal vasculitis, Eales disease, tuberculosis, syphilis, or toxoplasmosis;
c. neuroretinitis, viral retinitis, or acute retinal necrosis;
d. varicella zoster virus, herpes simplex virus, cytomegalovirus, Epstein-Barr virus, lichen planus, or Dengue-associated disease (e.g., hemorraghic Dengue Fever);
e. Masquerade syndrome, contact dermatitis, trauma induced inflammation, UVB induced inflammation, eczema, granuloma annulare, or acne.

In an additional embodiment, the disorder is selected from:

a. acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA);
b. antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy;
c. allergic bronchopulmonary aspergillosis, allergic neuritis, drug allergy, radiation-induced lung injury, eosinophilic pneumonia, radiographic contrast media allergy, bronchiolitis obliterans, or interstitial pneumonia;
d. parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia;
e. Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In one embodiment, the disorder is selected from:

a. atopic dermatitis, dermatitis, dermatomyositis bullous pemphigoid, scleroderma, sclerodermatomyositis, psoriatic arthritis, pemphigus vulgaris, Discoid lupus erythematosus, cutaneous lupus, chilblain lupus erythematosus, or lupus erythematosus-lichen planus overlap syndrome.;
b. cryoglobulinemic vasculitis, mesenteric/enteric vascular disorder, peripheral vascular disorder, antineutrophil cytoplasm antibody (ANCA)-associated vasculitis (AAV), IL-2 induced vascular leakage syndrome, or immune complex vasculitis;
c. angioedema, low platelets (HELLP) syndrome, sickle cell disease, platelet refractoriness, red cell casts, or typical or infectious hemolytic uremic syndrome (tHUS);
d. hematuria, hemorrhagic shock, drug-induced thrombocytopenia, autoimmune hemolytic anemia (AIHA), azotemia, blood vessel and/or lymph vessel inflammation, rotational atherectomy, or delayed hemolytic transfusion reaction;

e. British type amyloid angiopathy, Buerger's disease, bullous pemphigoid, C1q nephropathy, cancer, or catastrophic antiphospholipid syndrome.

In another embodiment, the disorder is selected from:
a. wet (exudative) AMD, dry (non-exudative) AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, pathological myopia, or RPE degeneration;
b. pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen;
c. chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita;
d. essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch- Schonlein purpura nephritis, or abnormal urinary sediments;
e. hepatitis, hepatitis A, hepatitis B, hepatitis C or human immunodeficiency virus (HIV),
f. a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae;

*Neisseria meningitidis*, shiga toxin *E. coli*-related hemolytic uremic syndrome (STEC-HUS), hemolytic uremic syndrome (HUS); *Streptococcus*, or poststreptococcal glomerulonephritis.

In a further embodiment, the disorder is selected from: hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis;
a. inclusion body myositis, intestinal ischemia, iridocyclitis, iritis, juvenile chronic arthritis, Kawasaki's disease (arteritis), or lipiduria;
b. membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis nodosa (PAN), progressive subcortical gliosis, proteinuria, reduced glomerular filtration rate (GFR), or renovascular disorder;
c. multiple organ failure, multiple system atrophy (MSA), myotonic dystrophy, Niemann-Pick disease type C, chronic demyelinating diseases, or progressive supranuclear palsy;

spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thyroiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis; von Hippel-Lindau disease, histoplasmosis of the eye, hard drusen, soft drusen, pigment clumping, or photoreceptor and/or retinal pigmented epithelia (RPE) loss,.

In one embodiment, an active compound or its salt or composition as described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitonial fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, pityriasis lichenoides et varioliformis acuta, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton mysathenic syndrome, Oshtoran syndrome, pediatric autoimmune neuropsychiatric disorder associated with streptococcus (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis or ischemic-reperfusion injury of the eye.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In a further embodiment, the disorder is selected from glaucoma, diabetic retinopathy, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, diabetic macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion, or central retinal vein occulusion (CVRO).

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

Disorders that may be treated or prevented by an active compound or its salt or composition as described herein also include, but are not limited to:
 a. hereditary angioedema, capillary leak syndrome, hemolytic uremic syndrome (HUS),
 b. neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome;
 c. inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), lupus nephritides, arthritis, immune complex disorders and autoimmune diseases, systemic lupus, or lupus erythematosus;
 d. ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes;
 e. Alzheimer's dementia, stroke, schizophrenia, traumatic brain injury, trauma, Parkinson's disease, epilepsy, transplant rejection, prevention of fetal loss, biomaterial reactions (e.g. in hemodialysis, inplants), hyperacute allograft rejection, xenograft rejection, transplantation, psoriasis, burn injury, thermal injury including burns or frostbite, or crush injury;
 f. asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In one embodiment, a method for the treatment of sickle cell in a host is provided that includes the administration of an effective amount of an active compound or its salt or composition as described herein. In one embodiment, a method for the treatment of immunothrombocytopenic purpura (ITP), thrombotic thrombocytopenic purpura (TTP), or idiopathic thrombocytopenic purpura (ITP) in a host is provided that includes the administration of an effective amount of an active compound or its salt or composition as described herein. In one embodiment, a method for the treatment of ANCA-vasculitis in a host is provided that includes the administration of an effective amount of an active compound or its salt or composition as described herein. In one embodiment, a method for the treatment of IgA nephropathy in a host is provided that includes the administration of an effective amount of an active compound or its salt or composition as described herein. In one embodiment, a method for the treatment of rapidly progressing glomerulonephritis (RPGN), in a host is provided that includes the administration of an effective amount of an active compound or its salt or composition as described herein. In one embodiment, a method for the treatment of lupus nephritis, in a host is provided that includes the administration of an effective amount of an active compound or its salt or composition as described herein. In one embodiment, a method for the treatment of hemorraghic dengue fever, in a host is provided that includes the administration of an effective amount of an active compound or its salt or composition as described herein.

In an additional alternative embodiment, an active compound or its salt or composition as described herein is used in the treatment of an autoimmune disorder.

The complement pathway enhances the ability of antibodies and phagocytic cells to clear microbes and damaged cells from the body. It is part of the innate immune system and in healthy individuals is an essential process. Inhibiting the complement pathway will decrease the body's immune system response. Therefore, it is an object of the present invention to treat autoimmune disorders by administering an effective does of an active compound or its salt or composition as described herein to a subject in need thereof.

In one embodiment the autoimmune disorder is caused by activity of the complement system. In one embodiment the autoimmune disorder is caused by activity of the alternative complement pathway. In one embodiment the autoimmune disorder is caused by activity of the classical complement pathway. In another embodiment the autoimmune disorder is caused by a mechanism of action that is not directly related to the complement system, such as the over-proliferation of T-lymphocytes or the over-production of cytokines.

Non-limiting examples of autoimmune disorders include: lupus, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In one embodiment, an active compound or its salt or composition as described herein is used in the treatment of lupus. Non-limiting examples of lupus include lupus erythematosus, cutaneous lupus, discoid lupus erythematosus, chilblain lupus erythematosus, or lupus erythematosus-lichen planus overlap syndrome.

Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple Sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in MRI scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In one embodiment an active compound or its salt or composition as described herein is provided at an effective dose to treat a patient with type 1 diabetes. In one embodiment an active compound or its salt or composition as described herein is provided at an effective dose to treat a patient with type 2 diabetes.

Type 1 diabetes is an autoimmune disease. An autoimmune disease results when the body's system for fighting infection (the immune system) turns against a part of the body. The pancreas then produces little or no insulin.

Combination Therapy

In one embodiment an active compound or its salt or composition as described herein may be provided in combination or alternation with or preceded by, concomitant with or followed by, an effective amount of at least one additional therapeutic agent, for example, for treatment of a disorder listed herein. Non-limiting examples of second active agents for such combination therapy are provided below.

In one embodiment, an active compound or its salt or composition as described herein may be provided in combination or alternation with at least one additional inhibitor of the complement system or a second active compound with a different biological mechanism of action. In the description below and herein generally, whenever any of the terms referring to an active compound or its salt or composition as described herein are used, it should be understood that pharmaceutically acceptable salts, prodrugs or compositions are considered included, unless otherwise stated or inconsistent with the text.

In non-limiting embodiments, an active compound or its salt or composition as described herein may be provided together with a protease inhibitor, a soluble complement regulator, a therapeutic antibody (monoclonal or polyclonal), complement component inhibitor, receptor agonist, or siRNA.

In other embodiments, an active compound described herein is administered in combination or alternation with an antibody against tumor necrosis factor (TNF), including but not limited to infliximab (Remicade), adalimumab, certolizumab, golimumab, or a receptor fusion protein such as etanercept (Embrel).

In another embodiment, an active compound as described herein can be administered in combination or alternation with an anti-CD20 antibody, including but not limited to rituximab (Rituxan), adalimumab (Humira), ofatumumab (Arzerra), tositumomab (Bexxar), obinutuzumab (Gazyva), or ibritumomab (Zevalin).

In an alternative embodiment, an active compound as described herein can be administered in combination or alternation with an anti-IL6 antibody, including but not limited to tocilizumab (Actemra) and siltuximab (Sylvant).

In an alternative embodiment, an active compound as described herein can be administered in combination or alternation with an IL17 inhibitor, including but not limited to secukibumab (Cosentyx).

In an alternative embodiment, an active compound as described herein can be administered in combination or alternation with a p40 (IL12/IL23) inhibitor, including but not limited to ustekinumab (Stelara).

In an alternative embodiment, an active compound as described herein can be administered in combination or alteration with an IL23 inhibitor, including but not limited to risankizumab.

In an alternative embodiment, an active compound as described herein can be administered in combination or alteration with an anti-interferon a antibody, for example but not limited to sifalimumab.

In an alternative embodiment, an active compound as described herein can be administered in combination or alteration with a kinase inhibitor, for example but not limited to a JAK1/JAK3 inhibitor, for example but not limited to tofacitinib (Xelianz). In an alternative embodiment, an active compound as described herein can be administered in combination or alteration with a JAK1/JAK2 inhibitor, for example but not limited to baracitibib.

In an alternative embodiment, an active compound as described herein can be administered in combination or alteration with an anti-VEGF agent, for example but not limited to: aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids.

In another embodiment, an active compound as described herein can be administered in combination or alternation with an immune checkpoint inhibitor. Non-limiting examples of checkpoint inhibitors include anti-PD-1 or anti-PDL1 antibodies, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.), atezolizumab, durvalumab, and KN035, or anti-CTLA4 antibodies, for example Ipilimumab, Tremelimumab, AGEN1884 and AGEN2041 (Agenus).

Non-limiting examples of active agents that can be used in combination with active compounds described herein are:

Protease inhibitors: plasma-derived C1-INH concentrates, for example Cetor® (Sanquin), Berinert-P® (CSL Behring, Lev Pharma), and Cinryze®; recombinant human C1-inhibitors, for example Rhucin®; ritonavir (Norvir®, Abbvie, Inc.);

Soluble complement regulators: Soluble complement receptor 1 (TP10) (Avant Immunotherapeutics); sCR1-sLex/TP-20 (Avant Immunotherapeutics); MLN-2222/CAB-2 (Millenium Pharmaceuticals); Mirococept (Inflazyme Pharmaceuticals);

Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix); 4(1MEW)APL-1,APL-2 (Appelis); CP40/AMY-101,PEG-Cp40 (Amyndas);

PDGF inhibitors: Sorafenib Tosylate; Imatinib Mesylate (STI571); Sunitinib Malate; Ponatinib (AP24534); Axitinib; Imatinib (STI571); Nintedanib (BIBF 1120); Pazopanib HC1 (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil;

Anti-factor H or anti-factor B agents: Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas);

Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH;

Anti-CR3, anti-MASP2, anti C1s, and anti-C1n molecules: Cynryze (ViroPharma/Baxter); TNT003 (True North); OMS721 (Omeros); OMS906 (Omeros); and Imprime PGG (Biothera);

Receptor agonists: PMX-53 (Peptech Ltd.); JPE-137 (Jerini); JSM-7717 (Jerini);

Others: Recombinant human MBL (rhMBL; Enzon Pharmaceuticals);

Imides and glutarimide derivatives such as thalidomide, lenalidomide, pomalidomide;

Additional non-limiting examples that can be used in combination or alternation with an active compound or its salt or composition as described herein include the following.

Non-limiting examples of potential therapeutics for combination therapy

| Name | Target | Company | Class of Molecule |
| --- | --- | --- | --- |
| LFG316 | C5 | Novartis/Morphosys | Monoclonal antibody |
| 4(1MEW)APL-1, APL-2 | C3/C3b | Apellis | Compstatin Family |
| 4(1MeW)POT-4 | C3/C3b | Potentia | Compstatin Family |
| Anti-C5 siRNA | C5 | Alnylam | Si-RNA |
| Anti-FB siRNA | CFB | Alnylam | SiRNA |
| ARC1005 | C5 | Novo Nor disk | Aptamers |
| ATA | C5 | N.A. | Chemical |

Non-limiting examples of potential therapeutics for combination therapy

| Name | Target | Company | Class of Molecule |
|---|---|---|---|
| Coversin | C5 | Volution Immuno-Pharmaceuticals | Small animal protein |
| CP40/AMY-101, PEG-Cp40 | C3/C3b | Amyndas | Compstatin Family |
| CRIg/CFH | CAP C3 convertase | NA | CFH-based protein |
| Cynryze | C1n/C1s | ViroPharma/Baxter | Human purified protein |
| FCFD4514S | CFD | Genentech/Roche | Monoclonal antibody |
| H17 | C3 (C3b/iC3b) | EluSys Therapeutics | Monoclonal antibody |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 | C5 | Rapharma | Small molecule |
| sCR1 (CDX-1135) | CAP and CP C3 | Celldex | CR1-based protein |
| SOBI002 | C5 | Swedish Orphan Biovitrum | Affibody |
| SOMAmers | C5 | SomaLogic | Aptamers |
| SOMAmers | CFB and CFD | SomaLogic | Aptamers (SELEX) |
| TA106 | CFB | Alexion Pharmaceuticals | Monoclonal antibody |
| TNT003 | C1s | True North | Monoclonal antibody |
| TT30 (CR2/CFH) | CAP C3 convertase | Alexion | CFH-based protein |
| TT32 (CR2/CR1) | CAP and CCP C3 | Alexion Pharmaceuticals | CR1-based protein |
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-2 | Omeros | Monoclonal antibody |
| Bikaciomab, NM9308 | CFB | Novelmed | Monoclonal antibody |
| NM9401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |
| rFH | C3-conv, C3b | Optherion | Regulator |
| 5C6, AMY-301 | CFH | Amyndas | Regulator |
| Erdigna | C5 | Adienne Pharma | Antibody |
| ARC 1905 | C5 | Opthotech | Monoclonal Antibody |
| MEDI7814 | C5/C5a | MedImmune | Monoclonal Antibody |
| NOX-D19 | C5a | Noxxon | Aptamer (Spiegelmer) |
| IFX-1, CaCP29 | C5a | InflaRx | Monoclonal Antibody |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-C5aR-151, NN8209; Anti-C5aR-215, NN8210 | C5aR | Novo Nordisk | Monoclonal Antibody |
| Imprime PGG | CR3 | Biothera | Soluble beta-glucan |

In one embodiment, an active compound or its salt or composition as described herein may be provided together with a compound that inhibits an enzyme that metabolizes an administered protease inhibitor. In one embodiment, a compound or salt may be provided together with ritonavir.

In one embodiment, an active compound or its salt or composition as described herein may be provided in combination with a complement C5 inhibitor or C5 convertase inhibitor. In another embodiment, an active compound or its salt or composition as described herein may be provided in combination with eculizumab, a monoclonal antibody directed to the complement factor C5 and manufactured and marketed by Alexion Pharmaceuticals under the tradename Soliris. Eculizumab has been approved by the U.S. FDA for the treatment of PNH and aHUS.

In one embodiment, an active compound or its salt or composition as described herein may be provided together with a compound that inhibits Complement Factor D. In one embodiment of the invention, an active compound or its salt or composition as described herein as described herein can be used in combination or alternation with a compound described in Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D; Novartis PCT patent publication WO2012/093101 titled "Indole compounds or analogues thereof useful for the treatment of age- related macular degeneration" describes certain Factor D inhibitors; Novartis PCT patent publications WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/

009977, WO2015/066241, Bristol-Myers Squibb PCT patent publication WO2004/045518 titled "Open chain prolyl urea-related modulators of androgen receptor function"; Japan Tobacco Inc. PCT patent publication WO1999/048492 titled "Amide derivatives and nociceptin antagonists"; Ferring B. V. and Yamanouchi Pharmaceutical Co. LTD. PCT patent publication WO1993/020099 titled "CCK and/or gastrin receptor ligands"; Alexion Pharmaceuticals PCT patent publication WO1995/029697 titled "Methods and compositions for the treatment of glomerulonephritis and other inflammatory diseases"; or Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

In one embodiment, an active compound or its salt or composition as described herein is administered in combination with an anti-inflammatory drug, antimicrobial agent, anti-angiogenesis agent, immunosuppressant, antibody, steroid, ocular antihypertensive drug or combinations thereof. Examples of such agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus, anti-PDGFR molecule, and combinations thereof In one embodiment of the present invention, an active compound or its salt or composition as described herein can be administered in combination or alternation with at least one immunosuppressive agent. The immunosuppressive agent as non-limiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g.ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA41g (Abatacept), belatacept, LFA31g, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, tocilizumab (Actemra), siltuximab (Sylvant), secukibumab (Cosentyx), ustekinumab (Stelara), risankizumab, sifalimumab, aspirin and ibuprofen.

Examples of anti-inflammatory agents include methotrexate, dexamethasone, dexamethasone alcohol, dexamethasone sodium phosphate, fluromethalone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, an active compound or its salt or composition as described herein is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In one embodiment, an active compound or its salt or composition as described herein is administered in combination or alteration with an omega-3 fatty acid or a peroxisome proliferator-activated receptor (PPARs) agonist. Omega-3 fatty acids are known to reduce serum triglycerides by inhibiting DGAT and by stimulating peroxisomal and mitochondrial beta oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark Omacor®. Such a form of omega-3 fatty acid is described, for example, in U.S. Pat. Nos. 5,502,077, 5,656,667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methyl-propanoic acid, 1-methylethyl ester, has been known for many years as a medicinally active principle because of its efficacy in lowering blood triglyceride and cholesterol levels.

In one embodiment, the present invention provides a method of treating or preventing age-related macular degeneration (AMD) by administering to a subject in need thereof an effective amount of an active compound or its salt or composition as described herein in combination with an anti-VEGF agent. Non-limiting examples of anti-VEGF agents include, but are not limited to, aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); Cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids, including, but not limited to, triamcinolone acetonide.

In one embodiment, the present invention provides a method of treating or preventing age-related macular degeneration (AMD) by administering to a subject in need thereof an effective amount of an active compound or its salt or composition as described herein in combination with a complement C5 inhibitor, for example, a complement C5 inhibitor described herein and in the table above titled Non-limiting examples of potential therapeutics for combination therapy, including, but not limited to, eculizumab; LFG316 (Novartis/Morphosys); Anti-C5 siRNA (Alnylam); ARC1005 (Novo Nordisk); Coversin (Volution Immuno-Pharmaceuticals); Mubodine (Adienne Pharma); RA101348 (Ra Pharma); SOBI002 (Swedish Orphan Biovitrum); SOMAmers (SomaLogic); Erdigna (Adienne Pharma); ARC1905 (Opthotech); MEDI7814 (MedImmune); NOX-D19 (Noxxon); IFX-1, CaCP29 (InflaRx); PMX53, PMX205 (Cephalon, Teva); CCX168 (ChemoCentryx); ADC-1004 (Alligator Bioscience); and Anti-C5aR-151, NN8209; Anti-C5aR-215, NN8210 (Novo Nordisk).

In one embodiment, the present invention provides a method of treating or preventing age-related macular degeneration (AMD) by administering to a subject in need thereof an effective amount of an active compound or its salt or composition as described herein in combination with anti-properidin agent, for example, an anti-properidin agent as described above, including but not limited to NM9401 (Novelmed).

In one embodiment, the present invention provides a method of treating or preventing age-related macular degeneration (AMD) by administering to a subject in need thereof an effective amount of an active compound or its salt or composition as described herein in combination with a complement C3 inhibitor for example, a complement C3 inhibitor described above, including, but not limited to, a compstatin or compstatin analogue, for example Compstatin/POT-4 (Potentia Pharmaceuticals); ARC1905 (Archemix); 4(1MEW)APL-1,APL-2 (Appelis); CP40/AMY-101, PEG-Cp40 (Amyndas) Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); and CRIg/CFH.

In one embodiment, the present invention provides a method of treating or preventing age-related macular degeneration (AMD) by administering to a subject in need thereof an effective amount of an active compound or its salt or composition as described herein in combination with an anti-factor H or anti-factor B agent selected from Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas).

In one embodiment, the present invention provides a method of treating or preventing age-related macular degeneration (AMD) by administering to a subject in need thereof an effective amount of an active compound or its salt or composition as described herein in combination with an anti-MASP2, anti-C1s or anti-CR3 molecules, for example, but not limited to: Cynryze (ViroPharma/Baxter); TNT003 (True North); OMS721 (Omeros); OMS906 (Omeros); and Imprime PGG (Biothera).

In one embodiment, the present invention provides a method of treating or preventing age-related macular degeneration (AMD) by administering to a subject in need thereof an effective amount of an active compound or its salt or composition as described herein in combination with an PDGF inhibitor, for example as described herein including but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid;

MK-2461; Tyrphostin (AG 1296); Dovitinib (TKI258) Lactate; Sennoside B; Sunitinib; AZD2932; and Trapidil.

In one embodiment, the present invention provides a method of treating or preventing paroxysmal nocturnal hemoglobinuria (PNH) by administering to a subject in need thereof an effective amount of an active compound or its salt or composition as described herein with an additional inhibitor of the complement system or another active compound with a different biological mechanism of action. In another embodiment, the present invention provides a method of treating or preventing paroxysmal nocturnal hemoglobinuria (PNH) by administering to a subject in need thereof an effective amount of an active compound or its salt or composition as described herein in combination or alternation with eculizumab. In another embodiment, the present invention provides a method of treating or preventing paroxysmal nocturnal hemoglobinuria (PNH) by administering to a subject in need thereof an effective amount of an active compound or its salt or composition as described herein in combination or alternation with CP40. In one embodiment, the additional agent is PEGylated-CP40. CP40 is a peptide inhibitor that shows a strong binding affinity for C3b and inhibits hemolysis of paroxysmal nocturnal hemoglobinuria (PNH) erythrocytes. In one embodiment, the additional agent is a complement component inhibitor, for example but not limited to Compstatin/POT-4 (Potentia Pharmaceuticals); ARC1905 (Archemix); 4(1MEW)APL-1,APL-2 (Appelis); CP40/AMY-101,PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera)

In one embodiment, the present invention provides a method of treating or preventing rheumatoid arthritis by administering to a subject in need thereof an effective amount of a composition comprising an active compound or its salt or composition as described herein in combination or alternation with an additional inhibitor of the complement system, or an active agent that functions through a different mechanism of action. In another embodiment, the present invention provides a method of treating or preventing rheumatoid arthritis by administering to a subject in need thereof an effective amount of an active compound or its salt or composition as described herein in combination or alternation with methotrexate. In certain embodiments, an active compound or its salt or composition as described herein is administered in combination or alternation with at least one additional therapeutic agent selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a subject in need thereof an effective amount of an active compound or its salt or composition as described herein in combination or alternation with an additional inhibitor of the complement system, or an active agent that functions through a different mechanism of action. In another embodiment, the present invention provides a method of treating or preventing multiple sclerosis by administering to a subject in need thereof an effective amount of an active compound or its salt or composition as described herein in combination or alternation with a corticosteroid. Examples of corticosteroids include, but are not limited to, prednisone, dexamethasone, solumedrol, and methylprednisolone. In one embodiment, an active compound or its salt or composition as described herein is combined with at least one anti-multiple sclerosis drug, for example, selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), Solu-Medrol (methylprednisolone), High-dose oral Deltasone (prednisone), H.P. Acthar Gel (ACTH), or a combination thereof.

In one embodiment, an active compound or its salt or composition as described herein is useful in a combination with another pharmaceutical agent to ameliorate or reduce a side effect of the agent. For example, in one embodiment, an active compound or its salt or composition as described herein may be used in combination with adoptive cell transfer therapies to reduce an associated inflammatory response associated with such therapies, for example, a cytokine mediated response such as cytokine release syndrome. In one embodiment, the adoptive cell transfer therapy includes the use of a chimeric antigen receptor T-Cell (CAR T). In one embodiment, the adoptive cell transfer therapy includes the use of a chimeric antigen receptor T-Cell (CAR T) or a dendritic cell to treat a hematologic or solid tumor, for example, a B-cell related hematologic cancer. In one embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19.

In an additional alternative embodiment, an active compound or its salt or composition as described herein may be provided in combination with eculizumab for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, an active compound or its salt or composition as described herein may be provided in combination with compstatin or a compstatin derivative for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, the additional agent is a complement component inhibitor, for example but not limited to Compstatin/POT-4 (Potentia Pharmaceuticals); ARC 1905 (Archemix); 4(1MEW)APL-1,APL-2 (Appelis); CP40/AMY-101,PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HC1 (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera)

In one embodiment, an active compound or its salt or composition as described herein may be provided in combination with rituxan for the treatment of a complement mediated disorder. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein may be provided in combination with cyclophosphamide for the treatment of a complement mediated disorder. In one embodiment, the disorder is an autoimmune disease. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein is dosed in combination with a conventional DLE treatment for the treatment of lupus to a subject in need thereof.

Examples of conventional DLE treatments include topical corticosteroid ointments or creams, such as triamcinolone acetonide, fluocinolone, flurandrenolide, betamethasone valerate, or betamethasone dipropionate. Resistant plaques can be injected with an intradermal corticosteroid. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL).

In one embodiment, an active compound or its salt or composition as described herein may be provided in combination with methotrexate for the treatment of Lupus.

In one embodiment, an active compound or its salt or composition as described herein may be provided in combination with azathioprine for the treatment of Lupus.

In one embodiment, an active compound or its salt or composition as described herein may be provided in combination with a non-steroidal anti-inflammatory drug for the treatment of Lupus.

In one embodiment, an active compound or its salt or composition as described herein may be provided in combination with a corticosteroid for the treatment of Lupus.

In one embodiment, an active compound or its salt or composition as described herein may be provided in combination with a belimumab (Benlysta) for the treatment of Lupus.

In one embodiment, an active compound or its salt or composition as described herein may be provided in combination with hydroxychloroquine (Plaquenil) for the treatment of Lupus.

In one embodiment, an active compound or its salt or composition as described herein may be provided in combination with sifalimumab for the treatment of Lupus.

In one embodiment, an active compound or its salt or composition as described herein may be provided in combination with OMS721 (Omeros) for the treatment of a complement mediated disorder. In one embodiment, an active compound or its salt or composition as described herein may be provided in combination with OMS906 (Omeros) for the treatment of a complement mediated disorder. In one embodiment, the complement mediated disorder is, for example, thrombotic thrombocytopenic purpura (TTP) or aHUS.

In one embodiment, an active compound or its salt or composition as described herein may be provided in combination with an anti-inflammatory agent, immunosuppressive agent, or anti-cytokine agent for the treatment or prevention of cytokine or inflammatory reactions in response to the administration of pharmaceuticals or biotherapeutics (e.g. adoptive T-cell therapy (ACT) such as CAR T-cell therapy, or monoclonal antibody therapy). In one embodiment, an active compound or its salt or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ. In one embodiment, an active compound or its salt or composition as described herein may be provided in combination with an anti-cytokine inhibitor including, but are not limited to, adalimumab, infliximab, etanercept, protopic, efalizumab, alefacept, anakinra, siltuximab, secukibumab, ustekinumab, golimumab, and tocilizumab, or a combination thereof. Additional anti-inflammatory agents that can be used in combination with an active compound or its salt or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline); DAB 486-IL-2 and/or DAB 389-IL-2 (IL-2 fusion proteins; Seragen); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibiton); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1β converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine).

In a specific embodiment, an active compound or its salt or composition as described herein may be provided in combination with a corticosteroid for the treatment or prevention of cytokine or inflammatory reactions in response to the administration of pharmaceuticals or biotherapeutics. In another embodiment, an active compound or its salt or composition as described herein may be provided in combination with etanercept for the treatment or prevention of cytokine or inflammatory reactions in response to the administration of pharmaceuticals or biotherapeutics. In another embodiment, an active compound or its salt or composition as described herein may be provided in combination with tocilizumab for the treatment or prevention of cytokine or inflammatory reactions in response to the administration of pharmaceuticals or biotherapeutics. In another embodiment, an active compound or its salt or composition as described herein may be provided in combination with etanercept and tocilizumab for the treatment or prevention of cytokine or inflammatory reactions in response to the administration of pharmaceuticals or biotherapeutics. In another embodiment, an active compound or its salt or composition as described herein may be provided in combination with infliximab for the treatment or prevention of cytokine or inflammatory reactions in response to the administration of pharmaceuticals or biotherapeutics. In another embodiment, an active compound or its salt or composition as described herein may be provided in combination with golimumab for the treatment or prevention of cytokine or inflammatory reactions in response to the administration of pharmaceuticals or biotherapeutics.

Combinations for Prophylactic or Concomitant Anti-Bacterial Therapy

In one aspect of the present invention, a method is provided for treating a host in need thereof that comprises administering an effective amount of a prophylactic anti-bacterial vaccine prior to administration of an active compound or its salt or composition for any of the disorders described herein. In another aspect of the present invention, a method is provided for treating a host in need thereof that comprises administering an effective amount of a prophylactic anti-bacterial drug, such as a pharmaceutical drug, prior to administration of an active compound or its salt or composition for any of the disorders described herein. In one aspect of the present invention, a method is provided for treating a host in need thereof that comprises administering an effective amount of an anti-bacterial vaccine after administration of an active compound or its salt or composition for any of the disorders described herein. In another aspect of the present invention, a method is provided for treating a host in need thereof that comprises administering an effective amount of an anti-bacterial drug, such as a pharmaceutical drug, after administration of an active compound or its salt or composition for any of the disorders described herein. In one embodiment, the disorder is PNH, C3G, or aHUS. In one embodiment, the host has received an organ or other tissue or biological fluid transplant. In one embodiment, the host is also administered eculizumab.

In one aspect of the present invention, an active compound or its salt or composition as described herein is administered to a host concomitantly to a subject following the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject concomitantly with the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject and, during the administration period of the compound or salt, a vaccine against a bacterial infection is administered to the subject. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, the subject is administered an active compound or its salt or composition as described herein in combination with an antibiotic compound for the duration of Factor D inhibitor administration. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject following the prophylactic administration of a vaccine against a bacterial infection, and in combination with an antibiotic compound for the duration of Factor D inhibitor administration. In one embodiment, the complement mediated disorder is PNH or aHUS. In one embodiment, the subject has received an organ or other tissue or biological fluid transplant. In one embodiment, the subject is also administered eculizumab.

In one embodiment, the subject, prior to receiving an active compound or its salt or composition as described herein, is vaccinated against a bacterial infection caused by the bacterium *Neisseria meningitidis*. In one embodiment, the subject is vaccinated against a bacterial infection caused by the bacterium *Haemophilus influenzae*. In one embodiment, the *Haemophilus influenzae* is *Haemophilus influenzae* serotype B (Hib). In one embodiment, the subject is vaccinated against a bacterial infection caused by *Streptococcus pneumoniae*. In one embodiment, the subject is vaccinated against a bacterial infection caused by the bacterium *Nisseria meningitidis*, *Haemophilus influenzae*, or *Streptococcus pneumoniae*, or a combination of one or more of *Nisseria meningitidis*, *Haemophilus influenzae*, or *Streptococcus pneumoniae*. In one embodiment, the subject is vaccinated against a bacterial infection caused by the bacterium *Nisseria meningitidis*, *Haemophilus influenzae*, and *Streptococcus pneumoniae*.

In other embodiments, the subject is vaccinated against a bacterial infection caused by a bacterium selected from a Gram-negative bacterium. In one embodiment, the subject is vaccinated against a bacterial infection caused by a bacterium selected from a Gram-positive bacterium. In one embodiment, the subject is vaccinated against a bacterial infection caused by the bacterium *Nisseria meningitidis*, *Haemophilus influenzae*, or *Streptococcus pneunemoniae*, or a combination of one or more of *Nisseria meningitidis*, *Haemophilus influenzae*, or *Streptococcus pneumoniae*, and one or more of, but not limited to, *Bacillus anthracis*, *Bordetella pertussis*, *Clostridium tetani*, *Corynebacterium diphtheria*, *Coxiella burnetii*, *Mycobacterium tuberculosis*, *Salmonella typhi*, *Vibrio cholerae*, *Anaplasma phagocytophilum*, *Ehrlichia ewingii*, *Ehrlichia chaffeensis*, *Ehrlichia canis*, *Neorickettsia sennetsu*, *Mycobacterium leprae*, *Borrelia burgdorferi*, *Borrelia mayonii*, *Borrelia afzelii*, *Borrelia garinii*, *Mycobacterium bovis*, *Staphylococcus aureus*, *Streptococcus pyogenes*, *Treponema pallidum*, *Francisella tularensis*, *Yersinia pestis*, In one embodiment, the subject is vaccinated with one or more vaccines selected from, but not limited to, typhoid vaccine, live (Vivotif Berna Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (Prevnar 13, Pfizer), haemophilus b conjugate (prp-t) vaccine (ActHIB, Sanofi; Hibrix, GSK), haemophilus b conjugate (hboc) vaccine (HibTITER, Neuron Biotech), haemophilus b conjugate (prp-omp) vaccine (PedvaxHIB, Merck), haemophilus b conjugate (prp-t) vaccine/meningococcal conjugate vaccine (MenHibrix, GSK), haemophilus b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal Berna, Hendricks Regional Health), *Bacillus* Calmette and Guerin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/ polio (Kinrix, GSK; Quadracel, Sanofi), diphtheria and tetanus toxois and pertussis tetanus/hepatitis B/polio (Pediarix, GSK), diphtheria and tetanus toxois and pertussis/polio, haemophilus influenza tybe b (Pentacel, Sanofi), and/or diphtheria, and pertussis (Tdap; Boostrix, GSK; Adacel, Sanofi), or a combination thereof.

As described above, a subject receiving a compound of the present invention to treat a disorder is prophylactically administered an antibiotic compound in addition to a Factor D inhibitor described herein. In one embodiment, the subject is administered an antibiotic compound for the duration of administration of the active compound to reduce the development of a bacterial infection. Antibiotic compounds for concomitant administration with a Factor D inhibitor described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Surnamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen),azlocillin, carbenicillin (Geocillin), cloxacillin (Tegopen), dicloxacillin (Dynapen), flucloxacillin (Floxapen), mezlocillin (Mezlin), methicillin (Staphcillin), nafcillin (Unipen),oxacillin (Prostaphlin), penicillin G (Pentids), penicillin V (Veetids (Pen-Vee-K), piperacillin (Pipracil), penicillin G (Pfizerpen), temocillin (Negaban), ticarcillin (Ticar), amoxicillin/clavulanate (Augmentin), ampicillin/sulbactam (Unasyn), piperacillin/tazobactam (Zosyn), ticarcillin/clavulanate (Timentin), bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (NegGram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (Micro-Sulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole ($C_0$-trimoxazole) (TMP-SMX) (Bactrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the subject is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenem, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

VII. Process of Preparation of Compounds of Formula I, Formula II, Formula III, Formula IV, Formula V, Formula VI, Formula VII, or Formula VIII

ABBREVIATIONS

ACN Acetonitrile
Ac Acetyl
$Ac_2O$ Acetic anhydride
AcOEt, EtOAc ethyl acetate
AcOH Acetic acid
$Boc_2O$ di-tert-butyl decarbonate
Bu Butyl
CAN Ceric ammonium nitrate
CBz Carboxybenzyl
CDI Carbonyldiimidazole
$CH_3OH$, MeOH Methanol
CsF Cesium fluoride
CuI Cuprous iodide
DCM, $CH_2Cl_2$ Dichloromethane
DIEA, DIPEA N,N-diisopropylethylamine
DMA N,N-dimethylacetamide
DMAP 4-Dimethylaminopyridine
DMF N,N-dimethylformamide
DMS Dimethyl sulfide
DMSO Dimethylsulfoxide
DPPA Diphenyl phosphoryl azide
EDCI 1-Ethyl-3-(3-dimethylaminopropyl)carbodiimide
Et Ethyl
$Et_3N$, TEA Triethylamine
EtOAc Ethylacetate
EtOH Ethanol
HATU 1-[Bis(dimethylamino)methylene]-1H-1,2,3-triazolo[4,5-b]pyridinium3-oxide hexafluorophosphate
HCl Hydrochloric acid
HOBT Hydroxybenzotriazole
iBu, i-Bu, isoBu Isobutyl
iPr, i-Pr, isoPr Isopropyl
$^iPr_2NEt$ N,N-diisopropylethylamine
$K_2CO_3$ Potassium carbonate
$K_2CO_3$ Potassium carbonate
LiOH Lithium hydroxide
Me Methyl
MeI Methyl iodide
Ms Mesyl
MSCl Mesylchloride
MTBE Methyl $^t$butylether
$Na_2SO_4$ Sodium sulfate
NaCl Sodium chloride
NaH Sodium hydride
$NaHCO_3$ Sodium bicarbonate
NBS N-bromo succinimide
NCS N-chloro succinimide
$NEt_3$ Trimethylamine
NMP N-Methyl-2-pyrrolidone
PCC Pyridinium chlorochromate
$Pd(OAc)_2$ Palladium acetate
$Pd(dppf)Cl_2$ [1,1'-Bis(diphenylphosphino)ferrocene]dichloropalladium(II)
$Pd(PPh_3)_2Cl_2$ Bis(triphenylphosphine)palladium(II) dichloride
$Pd(PPh_3)_4$ Tetrakis(triphenylphosphine)palladium(0)
Pd/C Palladium on carbon
$Pd_2(dba)_3$ Tris(dibenzylideneacetone)dipalladium(0)
PMB 4-Methoxybenzyl ether
$PPh_3$ Triphenylphosphine
Pr Propyl
Py, py Pyridine
RT Room temperature
TBAF Tetra-n-butyl ammonium fluoride
TBAT Tetrabutylammonium difluorotriphenylsilicate
tBu, t-Bu Tertbutyl
tBuOK Potassium tert-butoxide
TEA Trimethylamine
$Tf_2O$ Trifluoromethanesulfonic anhydride
TFA Trifluoroacetic acid
THF Tetrahydrofuran
TMS Trimethylsilane
TMSBr Bromotrimethylsilane
$t_R$ Retention time
Troc 2,2,2-Trichlorethoxycarbonyl chloride
$Zn(CN)_2$ Zinc cyanide

General Methods

All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

LC Method A
Instrument: Waters Acquity Ultra Performance LC
Column: ACQUITY UPLC BEH C18 2.1×50 mm, 1.7 μm
Column Temperature: 40° C.
Mobile Phase: Solvent A: $H_2O$+0.05% FA; Solvent B :$CH_3CN$+0.05% FA
Flow Rate: 0.8 mL/min
Gradient: 0.24 min @ 15% B, 3.26 min gradient (15-85% B), then 0.5 min @ 85% B.
Detection: UV (PDA), ELS, and MS (SQ in EI mode)

LC Method B
Instrument: Shimadzu LC-2010A HT
Column: Athena, C18-WP, 50×4.6 mm, 5 μm
Column Temperature: 40° C.
Mobile Phase: Solvent A: $H_2O/CH_3OH/FA$=90/10/0.1; Solvent B: $H_2O/CH_3OH/FA$=10/90/0.1
Flow Rate: 3 mL/min
Gradient: 0.4 min @ 30% B, 3.4 min gradient (30-100% B), then 0.8 min @ 100% B
Detection: UV (220/254 nm)

LC Method C
Instrument: Agilent 1100/1200 series LC system with DAD detector
Column: Atlantis dC18 (250×4.6) mm, 5 μm
Column Temperature: Ambient
Mobile Phase A: 0.1% TFA in water, Mobile Phase B: Acetonitrile
Flow Rate: 1.0 mL/min
Gradient:

| Time (min) | 0.0 | 15 | 20 | 23 | 30 |
|---|---|---|---|---|---|
| % B | 10 | 100 | 100 | 10 | 10 |

Detection: (210-400 nm)

LC Method D
Instrument: Shimadzu LC 20AD system with PDA detector
Column: Phenomenex Gemini NX C18 (150×4.6) mm, 5 μm
Column Temperature: Ambient
Mobile Phase A: 10 mM $NH_4OAC$ in water, Mobile Phase B: Acetonitrile
Flow Rate: 1.0 mL/min
Gradient:

| Time (min) | 0.0 | 15 | 20 | 23 | 30 |
|---|---|---|---|---|---|
| % B | 10 | 100 | 100 | 10 | 10 |

Detection: (210-400 nm)

Examples of Central Synthons

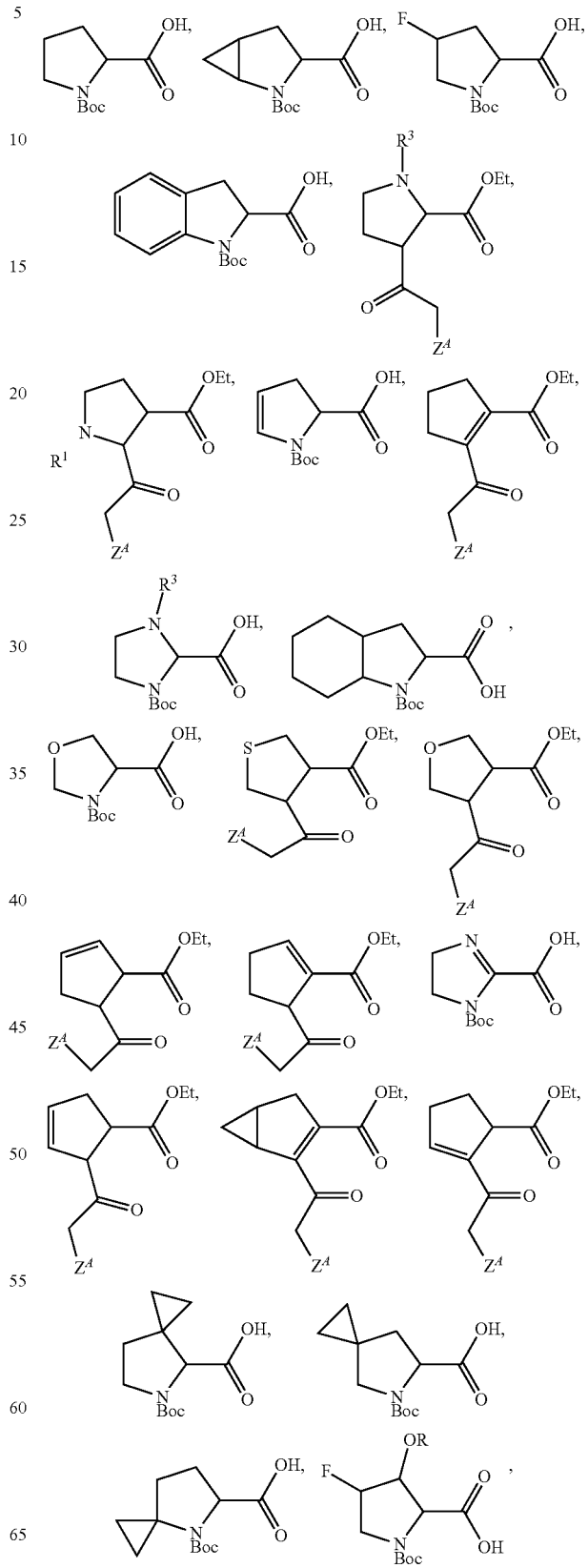

507
-continued
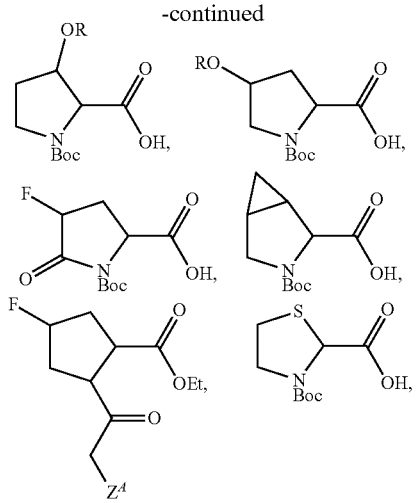
508
-continued
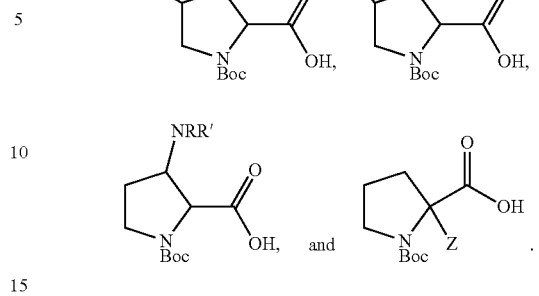
$Z^A$ is halogen.
In one embodiment, deuterated L-proline synthons are disclosed. Deuterated synthons include, but are not limited to, for example, the following compounds:
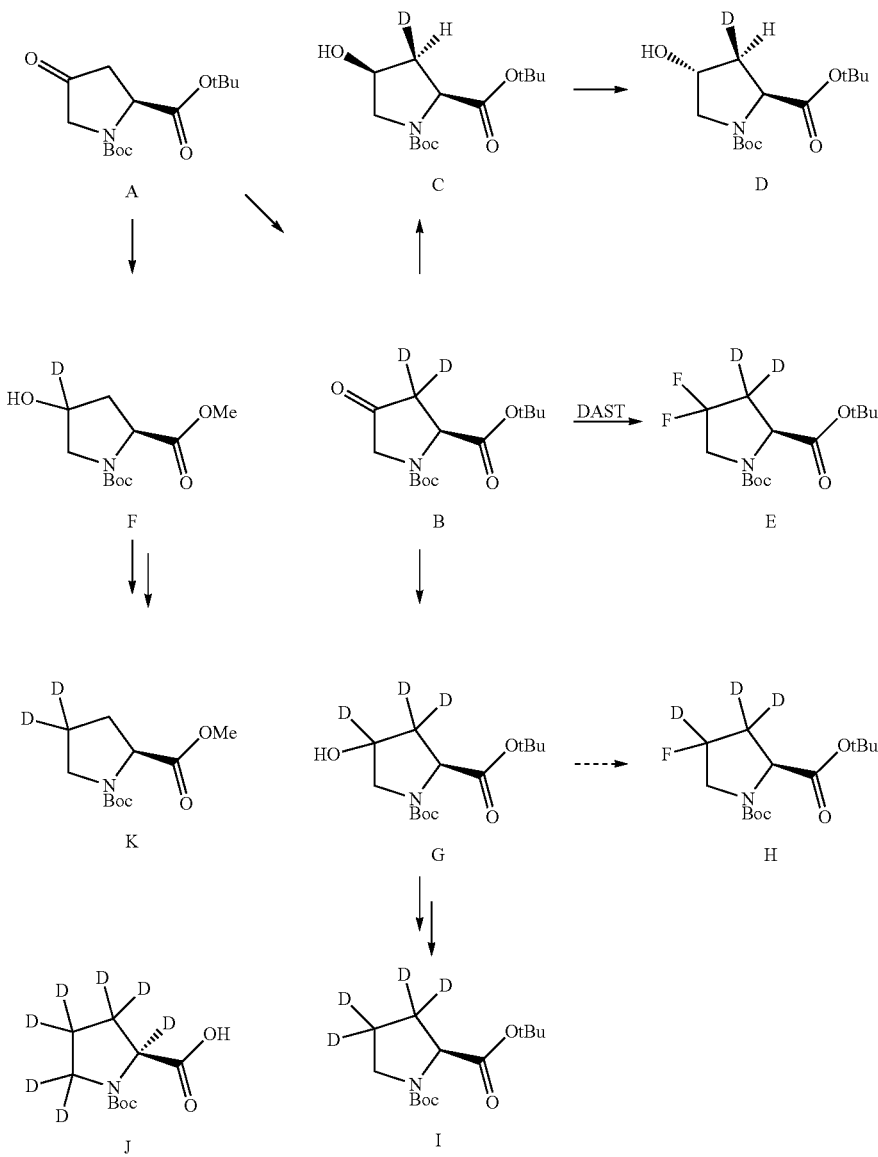

Structure A can be treated with deuterium oxide to generate Structure B. See, Barraclough, P. et al. Tetrahedron Lett. 2005, 46, 4653-4655; Barraclough, P. et al. Org. Biomol. Chem. 2006, 4, 1483-1491 and WO 2014/037480 (p.103). Structure B can be reduced to generate Structure C. See, Barraclough, P. et al. Tetrahedron Lett. 2005, 46, 4653-4655; Barraclough, P. et al. Org. Biomol. Chem. 2006, 4, 1483-1491. Structure C can be treated with Mitsunobu reaction conditions to generate Structure D. Structure B can be treated with DAST to generate Structure E. See, WO 2014/037480. Structure A can be treated with sodium borodeuteride to generate Structure F. See, Dormoy, J. -R.; Castro, B. Synthesis 1986, 81-82. Compound F can be used to generate Structure K. See, Dormoy, J. -R.; Castro, B. Synthesis 1986, 81-82. Structure B can be treated with a deuterated reducing agent, for example sodium borodeuteride to generate Structure G. Structure G can be treated with DAST to generate Structure H. Structure F can be used to generate Structure K. See, Dormoy, J. -R.; Castro, B. Synthesis 1986, 81-82. Structure G can be used to generate Structure I. Structure J can be prepared according to Hruby, V. J. et al. J. Am. Chem. Soc. 1979, 101, 202-212. Structures A-J can be used to prepare compounds of Formula I.

Preparation of Central-L-B Synthons

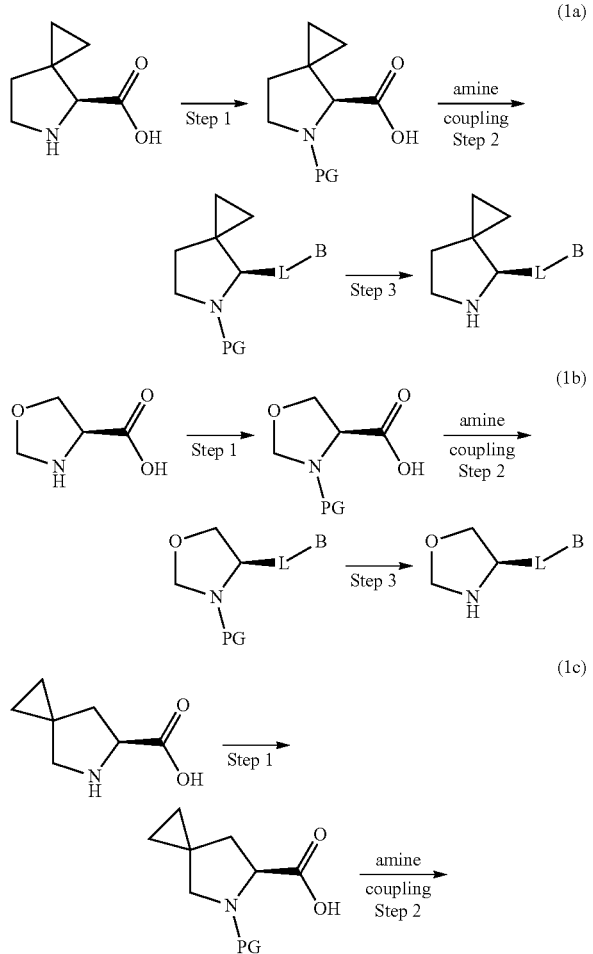

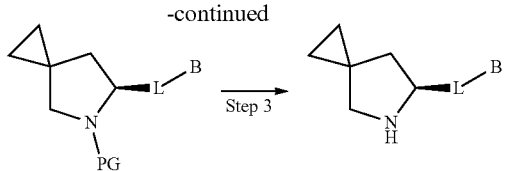

Routes 1a, 1b and 1c.

In Route 1a, 5-azaspiro[2.4]heptane-4,5-dicarboxylic acid, 5-(1,1-dimethylethyl) ester, (4S)-, CAS 209269-08-9, can be prepared as described in Tandon, M. et al. Bioorg. Med. Chem. Lett. 1998, 8, 1139-1144. In Step 2, the protected azaspiro[2.4]heptane is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1b, (4S) 4-oxazolidinecarboxylic acid, hydrochloride is treated with an amine protecting reagent. In one embodiment, the amine protecting reagent is di-tert-butyl dicarbonate. In another embodiment, 3,4-oxazolidinedicarboxylic acid, 3-(1,1-dimethylethyl) ester, (4S)-, is commercially available from JPM2 Pharmaceuticals. In one embodiment the reaction is carried out in an organic solvent in the presence of a base. In one embodiment, the organic solvent is acetonitrile. In one embodiment, the base is 4-dimentylaminopyridine (DMAP). In Step 2, the protected 4-oxazolidinecarboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1c, (S)-5-(tert-Butoxycarbonyl)-5-azaspiro[2.4]heptane-6-caboxylic acid, CAS 1129634-44-1, is commercially available from Ark Pharm. In Step 2, the carboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

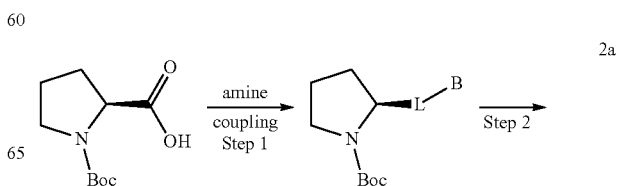

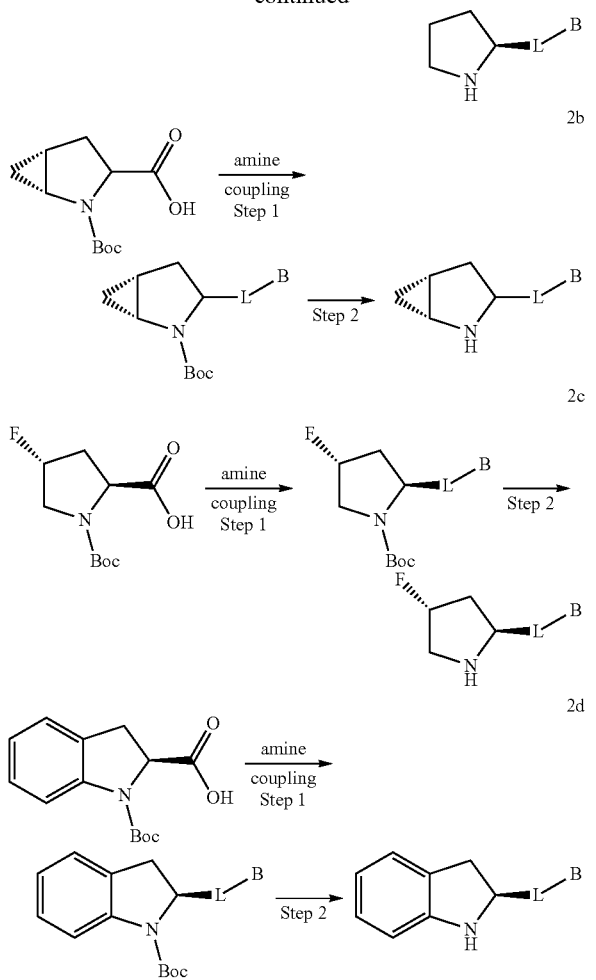

Routes 2a, 2b, 2c, and 2d.

In Route 2a, commercially available Boc-L-proline is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2b, commercially available (1R,3S,5R)-2-[(tert-butoxy)carbonyl]-2-azabicyclo[3.1.0]hexane-3-carboxylic acid, from Enamine, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2c, commercially available (2S,4R)-1-(tert-butoxycarbonyl)-4-fluoropyrrolidine-2-carboxylic acid, from Manchester Organics, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2d, commercially available (S)-1-(tert-butoxycarbonyl)indoline-2-carboxylic acid, from Chem-Impex, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane. This chemistry is illustrated in Scheme 2.

Additional starting materials that can readily be converted to Central-L-B-Synthons include, but are not limited to: (S)-1-(tert-butoxycarbonyl)-2,3-dihydro-1H-pyrrole-2-carboxylic acid, CAS 90104-21-5, available from Ark Pharm; cyclopent-1-ene-1,2-dicarboxylic acid, CAS 3128-15-2, purchased from Ark Pharm; imidazole, 1H-imidazole-1,2-dicarboxylic acid, 1-(1,1-dimethylethyl)2-ethyl ester, CAS 553650-00-3, commercially available from FCH Group; Boc-L-octahydroindole-2-carboxylic acid can be purchased from Chem Impex. The compound,

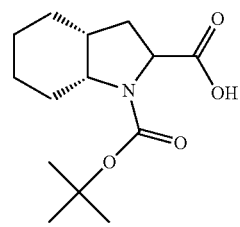 [SMILES: CC(C)(C)OC(=O)N1C(C(=O)O)C[C@H]2CCCC[C@H]21]

can be prepared according to the procedures disclosed in WO 2004/111041; (S)-Boc-5-oxopyrrolidine-2-carboxylic acid is available from the Aldrich Chemical Co.; (1S,2S,5R)-3-(tert-butoxycarbonyl)-3-azabicyclo[3.3.0]hexane-2-carboxylic acid is available from Ark Pharm; (S)-3-Boc-thiazolidine-2-carboxylic acid is available from Alfa Aesar; (2S,4R)-1-(tert-butoxycarbonyl)-4-chloropyrrolidine-2-carboxylic acid is available from Arch Bioscience; (1S,3aR,6aS)-2-(tert-butoxycarbonyl)octahydrocyclopenta[c]pyrrole-1-carboxylic acid is available from Ark Pharm; 1,2-pyrrolidinedicarboxylic acid, 3-[[(phenylmethoxy)carbonyl]amino]-, 1-(1,1-dimethylethyl) ester, (2S,3R) can be prepared as disclosed in WO 2004/007501. The Cbz group can be removed and the amino group can be alkylated to generate central core compounds of the present invention.

The compound

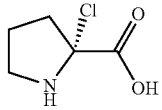

can be prepared as disclosed by Braun, J. V.; Heymons, Albrecht Berichte der Deutschen Chemischen Gesellschaft [Abteilung] B: Abhandlungen (1930) 63B, 502-7.

The compounds (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester can be prepared as a mixture according to WO 2012/093101 to Novartis and the regioisomers can be ultimately separated once coupled to generate the central core-L-B synthons. The compound (S)-Boc-5-oxopyrrolidine-2-carboxylic acid is available from the Aldrich Chemical Co.

Scheme 1.
Synthesis of (4$^1$R,4$^3$S,4$^5$R,E)-4$^2$-(2-(3-Acetyl-5-(2-methylpyrimidin-5-yl)-1H-indazol-1-yl)acetyl)-1$^6$-bromo-13-oxa-4$^2$,2,6-triaza-1(2,3)-pyridina-4(3,5)-bicyclo[3.1.0]hexanacyclotetradecaphan-10-ene-3,7-dione (2)

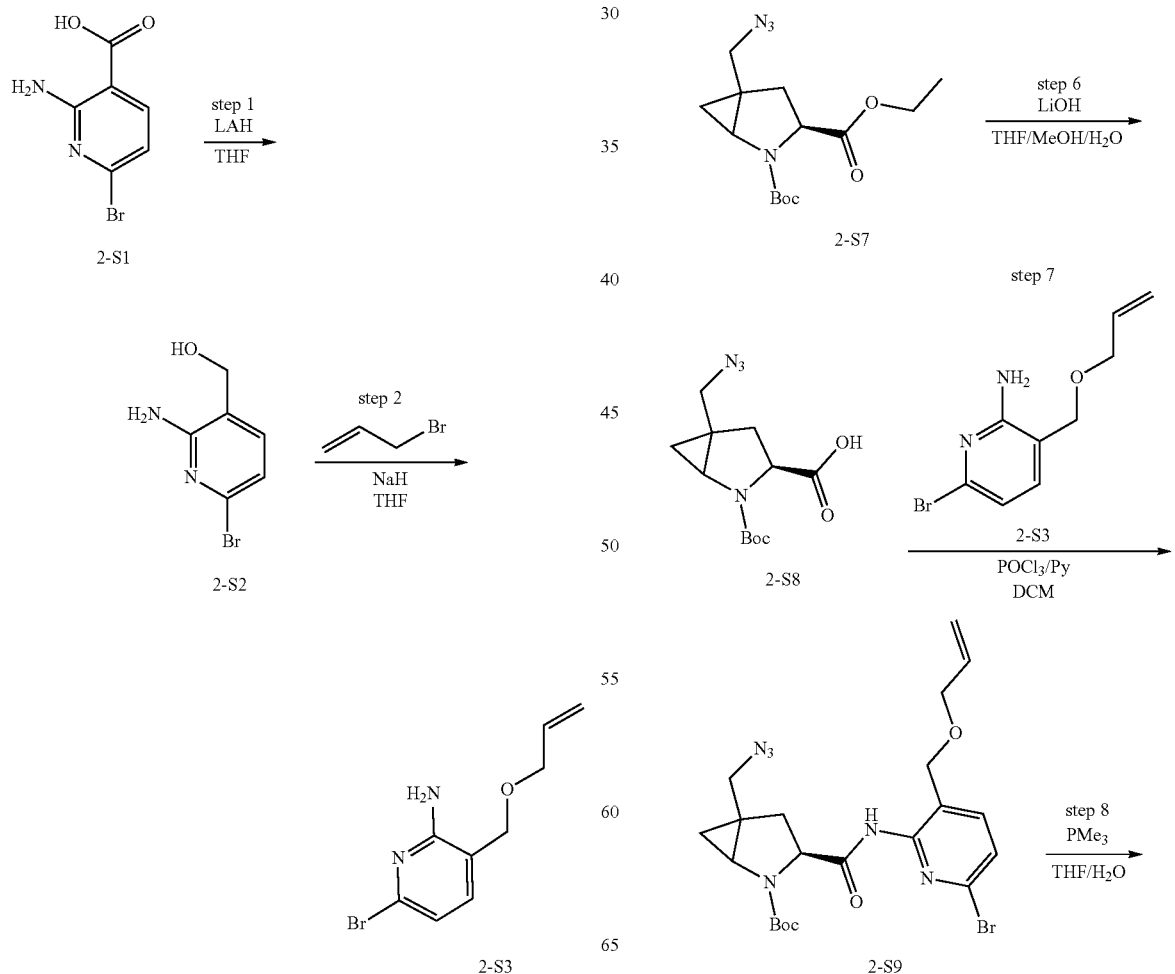

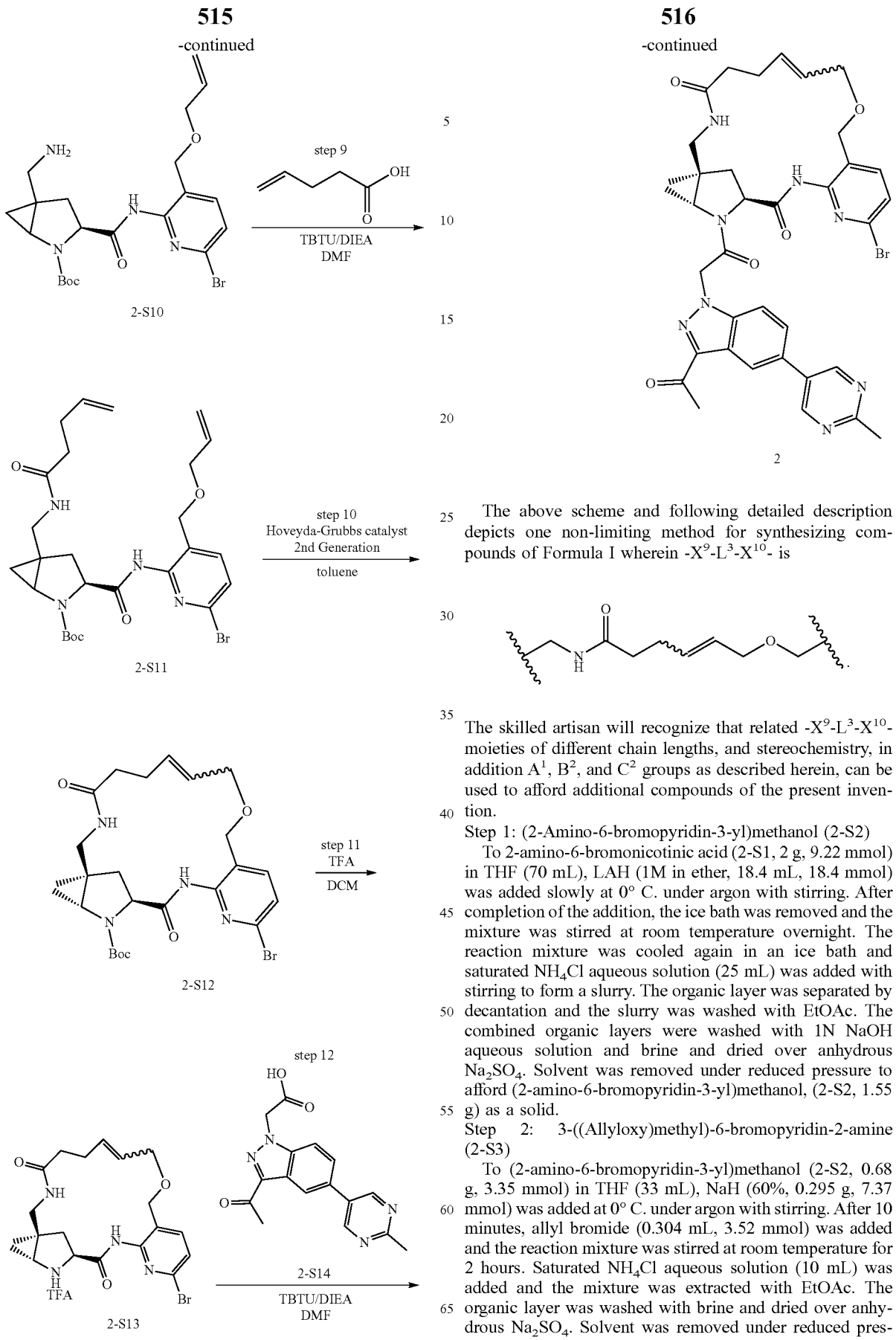

The above scheme and following detailed description depicts one non-limiting method for synthesizing compounds of Formula I wherein -X$^9$-L$^3$-X$^{10}$- is The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1: (2-Amino-6-bromopyridin-3-yl)methanol (2-S2)

To 2-amino-6-bromonicotinic acid (2-S1, 2 g, 9.22 mmol) in THF (70 mL), LAH (1M in ether, 18.4 mL, 18.4 mmol) was added slowly at 0° C. under argon with stirring. After completion of the addition, the ice bath was removed and the mixture was stirred at room temperature overnight. The reaction mixture was cooled again in an ice bath and saturated NH$_4$Cl aqueous solution (25 mL) was added with stirring to form a slurry. The organic layer was separated by decantation and the slurry was washed with EtOAc. The combined organic layers were washed with 1N NaOH aqueous solution and brine and dried over anhydrous Na$_2$SO$_4$. Solvent was removed under reduced pressure to afford (2-amino-6-bromopyridin-3-yl)methanol, (2-S2, 1.55 g) as a solid.

Step 2: 3-((Allyloxy)methyl)-6-bromopyridin-2-amine (2-S3)

To (2-amino-6-bromopyridin-3-yl)methanol (2-S2, 0.68 g, 3.35 mmol) in THF (33 mL), NaH (60%, 0.295 g, 7.37 mmol) was added at 0° C. under argon with stirring. After 10 minutes, allyl bromide (0.304 mL, 3.52 mmol) was added and the reaction mixture was stirred at room temperature for 2 hours. Saturated NH$_4$Cl aqueous solution (10 mL) was added and the mixture was extracted with EtOAc. The organic layer was washed with brine and dried over anhydrous Na$_2$SO$_4$. Solvent was removed under reduced pressure, and the residue was purified by column chromatography on silica gel with EtOAc in hexanes (0-30%) as the eluent to afford 3-((allyloxy)methyl)-6-bromopyridin-2-amine (2-S3, 0.276 g) as a yellow solid.

Step 3: 2-(tert-Butyl) 3-ethyl (3S)-5-(hydroxymethyl)-2-azabicyclo[3.1.0]hexane-2,3-dicarboxylate (2-S5)

To a solution of 1-(tert-butyl) 2-ethyl (S)-4-(hydroxyethyl)-2,3-dihydro-1H-pyrrole-1,2-dicarboxylate (2-S4, 0.492 g, 1.82 mmol) in DCM (15 mL) under argon at −25° C., diethylzinc (1M in hexanes, 3.63 mL, 3.63 mmol) was added with stirring followed by diiodomethane (0.0.323 mL, 4 mmol). The reaction mixture was stirred at −10° C. for 2 hours. Saturated $NH_4Cl$ aqueous solution (10 mL) was added at 0° C. and stirred at room temperature for 10 minutes. The solid was removed by filtration and the filtrate was extracted twice with DCM. The combined organic layers were washed with brine and dried over anhydrous $Na_2SO_4$. The solution was filtered and the solvent was removed under reduced pressure. The remaining residue was purified by column chromatography on silica gel with EtOAc in hexanes (0-50%) as the eluent to afford a diastereomeric mixture of 2-(tert-butyl) 3-ethyl (3S)-5-(hydroxymethyl)-2-azabicyclo[3.1.0]hexane-2,3-dicarboxylate (2-S5, 0.39 g) as a colorless oil.

Step 4: 2-(tert-Butyl) 3-ethyl (3S)-5-(((methylsulfonyl)oxy)methyl)-2-azabicyclo[3.1.0]hexane-2,3-dicarboxylate (2-S6)

To solution of 2-(tert-butyl) 3-ethyl (3S)-5-(hydroxymethyl)-2-azabicyclo[3.1.0]hexane-2,3-dicarboxylate (2-S5, 0.39 g, 1.37 mmol) in DCM (15 mL), DIEA (0.286 mL, 1.64 mmol) was added followed by MSCl (0.128 mL, 1.64 mmol) at 0° C. under argon. After the reaction mixture was stirred at room temperature for 4 hours, water was added. The organic layer was separated, washed with brine, and dried over anhydrous $Na_2SO_4$. The solution was filtered and the solvent was removed under reduced pressure to afford 2-(tert-butyl) 3-ethyl (3S)-5-(((methylsulfonyl)oxy)methyl)-2-azabicyclo[3.1.0]hexane-2,3-dicarboxylate (2-S6, 0.405 g) and carried forward in the next step without additional purification.

Step 5: 2-(tert-Butyl) 3-ethyl (3S)-5-(azidomethyl)-2-azabicyclo[3.1.0]hexane-2,3-dicarboxylate (2-S7)

2-(tert-Butyl) 3-ethyl (3S)-5-(((methylsulfonyl)oxy)methyl)-2-azabicyclo[3.1.0]hexane-2,3-dicarboxylate (2-S6, 0.2 g, 0.55 mmol) was treated with sodium azide (0.18 g, 2.75 mmol) in DMF (5 mL). The reaction was stirred at 60° C. overnight. Water was added and the mixture was extracted with EtOAc. The organic layer was washed with brine, dried over anhydrous $Na_2SO_4$, and the solvent was removed under reduced pressure. The residue was purified by column chromatography on silica gel with EtOAc in hexanes (0-50%) as the eluent to afford 2-(tert-butyl) 3-ethyl (3S)-5-(azidomethyl)-2-azabicyclo[3.1.0]hexane-2,3-dicarboxylate (2-S7, 27 mg).

Step 6: (3S)-5-(Azidomethyl)-2-(tert-butoxycarbonyl)-2-azabicyclo [3.1.0]hexane-3-carboxylic acid (2-S8)

2-(tert-Butyl) 3-ethyl (3S)-5-(azidomethyl)-2-azabicyclo[3.1.0]hexane-2,3-dicarboxylate (2-S7, 27 mg, 0.087 mmol) was dissolved in a mixed solvent of THF-MeOH-water (2 mL-0.1 ml-0.1 mL) and treated with LiOH monohydrate (7.3 mg). The reaction stirred at 50° C. for 2 hours before the mixture was cooled to room temperature and acidified with 1N HCl. The reaction was extracted with EtOAc, washed with brine, dried over anhydrous $Na_2SO_4$, and the volatiles were removed under reduced pressure to afford (3S)-5-(azidomethyl)-2-(tert-butoxycarbonyl)-2-azabicyclo[3.1.0]hexane-3-carboxylic acid (2-S8, 19 mg).

Step 7: tert-Butyl (3S)-3-((3-((allyloxy)methyl)-6-bromopyridin-2-yl)carbamoyl)-5-(azidomethyl)-2-azabicyclo[3.1.0]hexane-2-carboxylate (2-S9)

$POCl_3$ (0.013 mL, 0.134 mmol) was added to a mixture of (3S)-5-(azidomethyl)-2-(tert-butoxycarbonyl)-2-azabicyclo[3.1.0]hexane-3-carboxylic acid (2-S8, 19 mg, 0.067 mmol), 2-S3 (16 mg, 0.067 mmol), and pyridine (0.054 mL, 0.67 mmol) in DCM (3 mL) at 0° C. under an atmosphere of argon. The reaction mixture was stirred at room temperature for 6 hours before water was added and the mixture was extracted with DCM. The organic layer was washed with brine, dried over anhydrous $Na_2SO_4$, and the solvent was removed under reduced pressure. The residue was purified by column chromatography on silica gel with MeOH in DCM (0-10%) as the eluent to afford tert-butyl (3S)-3-((3-((allyloxy)methyl)-6-bromopyridin-2-yl)carbamoyl)-5-(azidomethyl)-2-azabicyclo[3.1.0]hexane-2-carboxylate (2-S9, 25 mg) as a yellow oil.

Step 8: tert-Butyl (3S)-3-((3-((allyloxy)methyl)-6-bromopyridin-2-yl)carbamoyl)-5-(aminomethyl)-2-azabicyclo [3.1.0] hexane-2-carboxylate (2-S10)

tert-Butyl (3S)-3-((3-((allyloxy)methyl)-6-bromopyridin-2-yl)carbamoyl)-5-(azidomethyl)-2-azabicyclo[3.1.0]hexane-2-carboxylate (2-S9, 25 mg, 0.049 mmol) was treated with trimethylphosphine (1.0 M in THF, 0.098 mL, 0.098 mmol) in THF (5 mL) and water (0.0018 mL, 0.098 mmol). The reaction stirred at room temperature overnight. The mixture was diluted with water and extracted with EtOAc. The organic layer was washed with brine, dried over anhydrous $Na_2SO_4$, and the solvent was removed under reduced pressure. The residue was purified by column chromatography on silica gel with MeOH in DCM (0-30%) as the eluent to afford tert-butyl (3S)-3-((3-((allyloxy)methyl)-6-bromopyridin-2-yl)carbamoyl)-5-(aminomethyl)-2-azabicyclo[3.1.0]hexane-2-carboxylate (2-S10).

Step 9: tert-Butyl (3S)-3-((3-((allyloxy)methyl)-6-bromopyridin-2-yl)carbamoyl)-5-(pent-4-enamidomethyl)-2-azabicyclo [3.1.0] hexane-2-carboxylate (2-S11)

To the mixture of tert-butyl (3S)-3-((3-((allyloxy)methyl)-6-bromopyridin-2-yl)carbamoyl)-5-(aminomethyl)-2-azabicyclo[3.1.0]hexane-2-carboxylate (2-S10) and pent-4-enoic acid (0.006 mL, 0.06 mmol) in DMF (3 mL), TBTU (32 mg, 0.1 mmol) was added followed by DIEA (0.043 mL, 0.25 mmol) with stirring. After stirring for 1 hour at room temperature, the reaction was subject to aqueous workup with EtOAc extraction. The organic layer was washed with brine, dried over anhydrous $Na_2SO_4$, and the solvent was removed under reduced pressure. The residue was purified by column chromatography on silica gel with MeOH in DCM (0-10%) as the eluent to afford tert-butyl (3S)-3-((3-((allyloxy)methyl)-6-bromopyridin-2-yl)carbamoyl)-5-(pent-4-enamidomethyl)-2-azabicyclo[3 1.0]hexane-2-carboxylate (2-S11, 12 mg).

Step 10: tert-Butyl $(4^1R,4^3S,4^5R,E)$-$1^6$-bromo-3,7-dioxo-13-oxa-$4^2$,2,6-triaza-1(2,3)-pyridina-4(3,5)-bicyclo[3.1.0]hexanacyclotetradecaphan-10-ene-$4^2$-carboxylate (2-12)

tert-Butyl (3S)-3-((3-((allyloxy)methyl)-6-bromopyridin-2-yl)carbamoyl)-5-(pent-4-enamidomethyl)-2-azabicyclo [3.1.0]hexane-2-carboxylate (2-S11, 12 mg, 0.02 mmol) in toluene (3 mL) was treated with Hoveyda-Grubbs catalyst $2^{nd}$ generation (2 mg). The reaction was stirred at 80° C. under argon for 2 hours. Solvent was removed under reduced pressure and the residue was purified by column chromatography on silica gel with MeOH in DCM (0-10%) as the eluent to afford tert-butyl $(4^1R,4^3S,4^5R,E)$-$1^6$-bromo- 3,7-dioxo-13-oxa-4²,2,6-triaza-1(2,3)-pyridina-4(3,5)-bicyclo[3.1.0]hexanacyclotetradecaphan-10-ene-4²-carboxylate (2-S12, 6 mg).

Step 11: (4¹R,4³S,4⁵R,E)-1⁶-Bromo-13-oxa-4²,2,6-triaza-1(2,3)-pyridina-4(3,5)-bicyclo[3.1.0]hexanacyclotetradecaphan-10-ene-3,7-dione TFA salt (2-S13)

tert-Butyl (4¹R,4³S,4⁵R,E)-1⁶-bromo-3,7-dioxo-13-oxa-4²,2,6-triaza-1(2,3)-pyridina-4(3,5)-bicyclo[3.1.0]hexanacyclotetradecaphan-10-ene-4²-carboxylate (2-S12, 6 mg, 0.0112 mmol) in DCM (4 mL) was treated with TFA (2 mL). The reaction was stirred at room temperature for 2 hours before the volatiles were removed under reduced pressure and the residue was co-evaporated with toluene (5 mL) twice to afford (4¹R,4³S,4⁵R,E)-1⁶-bromo-13-oxa-4²,2,6-triaza-1(2,3)-pyridina-4(3,5)-bicyclo[3.1.0]hexanacyclotetradecaphan-10-ene-3,7-dione TFA salt (S13). The material was carried forward in the next step without additional purification.

Step 12: (4¹R,4³S,4⁵R,E)-4²-(2-(3-Acetyl-5-(2-methylpyrimidin-5-yl)-1H-indazol-1-yl)acetyl)-1⁶-bromo-13-oxa-4², 2,6-triaza-1(2,3)-pyridina-4(3,5)-bicyclo[3.1.0]hexanacyclotetradecaphan-10-ene-3,7-dione (2)

To a mixture of (4¹R,4³S,4⁵R,E)-1⁶-bromo-13-oxa-4²,2, 6-triaza-1(2,3)-pyridina-4(3,5)-bicyclo[3.1.0]hexanacyclotetradecaphan-10-ene-3,7-dione TFA salt (2-S13) and 2-(3-acetyl-5-(2-methylpyrimidin-5-yl)-1H-indazol-1-yl)acetic acid (2-S14, 5 mg, 0.015 mmol) in DMF (2 mL), TBTU (9.6 mg) was added followed by DIEA (0.016 mL) with stirring. After the reaction was complete (as monitored by HPLC), the reaction mixture was purified by HPLC to afford 2 (5 mg). ¹H NMR (400 MHz, Methanol-d₄) δ 8.93 (s, 2H), 8.43 (d, J=1.3 Hz, 1H), 7.70 (d, J=1.2 Hz, 2H), 7.60 (d, J=7.9 Hz, 1H), 7.31 (d, J=8.0 Hz, 1H), 5.69 (d, J=17.2 Hz, 1H), 5.63-5.52 (m, 3H), 4.34-4.06 (m, 1H), 4.01 (d, J=12.4 Hz, 1H), 3.67 (dd, J=2.6, 5.7 Hz, 1H), 3.54-3.37 (m, 1H), 2.91 (d, J=14.8 Hz, 1H), 2.67 (s, 3H), 2.62 (s, 4H), 2.58-2.46 (m, 1H), 2.30 (s, 5H), 1.16 (s, 1H), 1.06 (dd, J=2.6, 6.0 Hz, 1H). LC (method A): t_R=1.51 min. LC/MS (EI) m/z: [M+H]⁺727.

Scheme 2. Synthesis of (4¹R,4³S,4⁵S,E)-4²-(2-(3-Acetyl-5-(2-methylpyrimidin-5-yl)-1H-indazol-1-yl)-1⁶-bromo-6,11-dioxa-4²,2-diaza-1(2,3)-pyridina-4(3,5)-bicyclo[3.1.0] hexanacyclododecaphan-8-en-3-one(3)

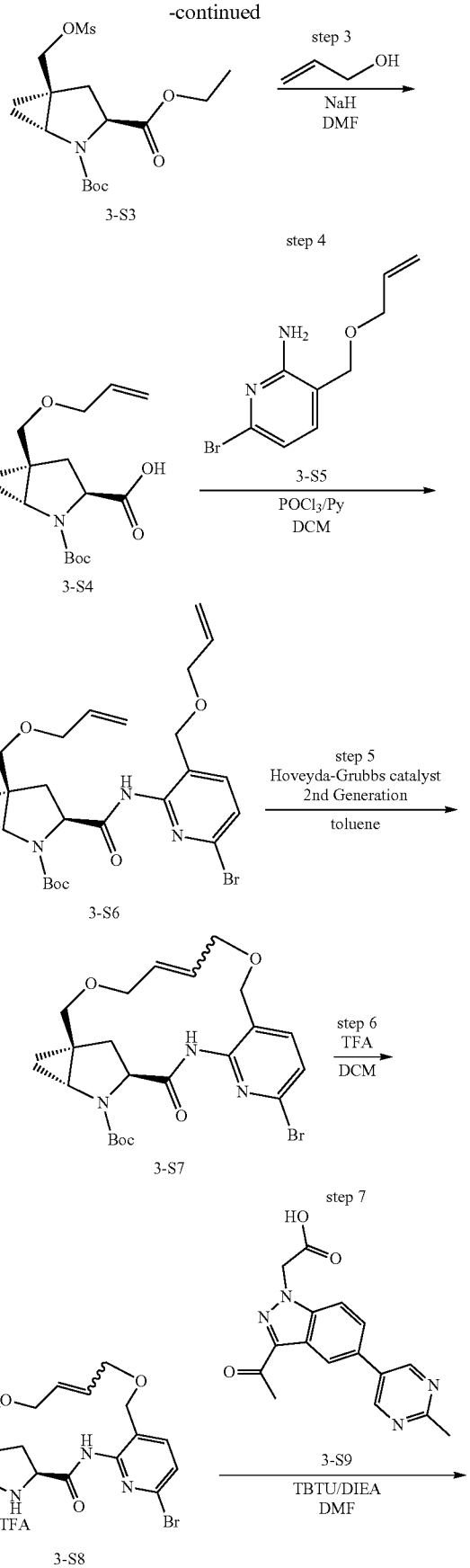

-continued

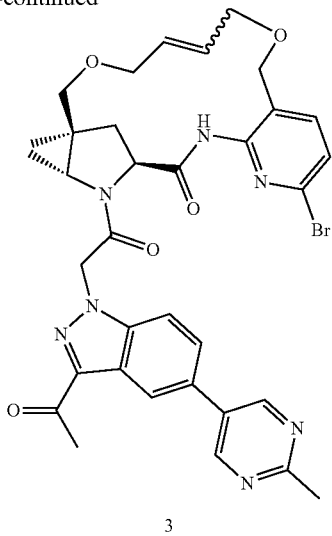

3

The above scheme and following detailed description depicts one non-limiting method for synthesizing compounds of Formula I wherein -$X^9$-$L^3$-$X^{10}$- is

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: 2-(tert-Butyl) 3-ethyl (1R,3S,5S)-5-(hydroxymethyl)-2-azabicyclo[3.1.0]hexane-2,3-dicarboxylate (3-S2) Method 1

To a solution of 1-(tert-butyl) 2-ethyl (S)-4-(hydroxymethyl)-2,3-dihydro-1H-pyrrole-1,2-dicarboxylate (3-S1, 0.246 g, 0.91 mmol) in DCM (9 mL) under argon at −25° C., diethylzinc (1M in hexanes, 2 mL, 2.0 mmol) was added with stirring followed by diiodomethane (0.184 mL, 2.28 mmol). The reaction mixture was stirred at −5° C. for 2 hours before additional diethylzinc (1M in hexanes, 0.6 mL) and diiodomethane (0.055 mL) were added and the reaction was kept at −5° C. for an additional 1 hour. Saturated $NH_4Cl$ aqueous solution (10 mL) was added at 0° C. and the reaction was stirred at room temperature for 10 minutes. The reaction mixture was filtered to remove solid before the aqueous layer was extracted with DCM and the combined organic layer was washed with brine and dried over anhydrous $Na_2SO_4$. The solution was filtered and the solvent was removed under reduced pressure. The remaining residue was purified by column chromatography on silica gel with EtOAc in hexanes (0-50%) as the eluent to afford 2-(tert-butyl) 3-ethyl (1R,3S,5S)-5-(hydroxymethyl)-2-azabicyclo [3.1.0]hexane-2,3-dicarboxylate, (3-S2) as the diastereoisomer with the longest retention time.

Method 2: Adapted from Charette et al. JACS 1998, 120, 11943.

Under argon, DME (2.12 mL, 20.45 mmol) and diethlyzinc (1M in hexanes, 2.045 mL, 20.45 mmol) were added followed by diiodomethane (3.3 mL, 40.89 mmol) slowly with stirring to a solution of DCM (50 mL) cooled to −15° C. After 10 minutes, a solution of butylboronic acid N,N, N',N'-tetramethyl-D-tartaric acid diamide ester (1.85 mL, 7.5 mmol) in DCM (5 mL) followed by 1-(tert-butyl) 2-ethyl (S)-4-(hydroxymethyl)-2,3-dihydro-1H-pyrrole-1,2-dicarboxylate (3-S1, 1.85 g, 6.82 mmol) in DCM (5 mL) was added. The reaction mixture was stirred at room temperature for 2 hours and then cooled in an ice bath. Saturated $NH_4Cl$ aqueous solution (10 mL) was added and the reaction was stirred at room temperature for 10 minutes. The aqueous layer was extracted with DCM and the organic layer was washed with brine and dried over anhydrous $Na_2SO_4$. The solution was filtered and the solvent was removed under reduced pressure. The remaining residue was purified by column chromatography on silica gel with EtOAc in hexanes (0-50%) as the eluent to afford 2-(tert-butyl) 3-ethyl (1R,3S,5S)-5-(hydroxymethyl)-2-azabicyclo[3.1.0]hexane-2,3-dicarboxylate (3-S2, 1.224 g).

Step 2: 2-(tert-Butyl) 3-ethyl (1R,3S,5S)-5-(((methylsulfonyl)oxy)methyl)-2-azabicyclo[3.1.0]hexane-2,3-dicarboxylate (3-S3)

To a solution of 2-(tert-butyl) 3-ethyl (1R,3S,5S)-5-(hydroxymethyl)-2-azabicyclo[3.1.0]hexane-2,3-dicarboxylate (3-S2, 0.743 g, 2.61 mmol) in DCM (25 mL), DIEA (0.682 mL, 3.92 mmol) was added followed by MSCl (0.305 mL, 3.92 mmol) at 0° C. under argon. After the reaction mixture was stirred at room temperature for 2 hours, $NaHCO_3$ aqueous solution was added. The organic layer was washed with brine and dried over anhydrous $Na_2SO_4$. The solution was filtered and the solvent was removed under reduced pressure to afford 2-(tert-butyl) 3-ethyl (1R,3S,5S)-5-(((methylsulfonyl)oxy)methyl)-2-azabicyclo[3.1.0]hexane-2,3-dicarboxylate (3-S3) as a yellow syrup. The material was used in the next step without additional purification.

Step 3: (1R,3S,5S)-5-((Allyloxy)methyl)-2-(tert-butoxycarbonyl)-2-azabicyclo [3.1.0]hexane-3-carboxylic acid (3-S4)

To a suspension of NaH (60%, 0.522 g, 13.05 mmol) in DMF (10 mL), allyl alcohol (0.886 mL, 13.05 mmol) was added at 0° C. under argon. After stirring at room temperature for 10 minutes and then cooling in an ice bath, 2-(tert-butyl) 3-ethyl (1R,3S,5S)-5-(((methylsulfonyl)oxy)methyl)-2-azabicyclo[3.1.0]hexane-2,3-dicarboxylate 3-S3 in DMF (10 mL) was added to the reaction mixture. After stirring at room temperature for 1 hour, water (0.18 mL, 10 mmol) was added and the mixture was stirred at room temperature for an additional 30 minutes. The mixture was then cooled with an ice bath and 1N HCl aqueous solution (20 mL) and water (80 mL) were added. After extracting with EtOAc, the organic layer was washed with brine and dried over anhydrous $Na_2SO_4$. Solvent was removed under reduced pressure and the residue was purified by column chromatography on silica gel with MeOH in DCM (0-10%) as the eluent to afford (1R,3S,5S)-5-((allyloxy)methyl)-2-(tert-butoxycarbonyl)-2-azabicyclo[3.1.0]hexane-3-carboxylic acid (3-S4, 0.624 g) as a yellow solid.

Step 4: tert-Butyl (1R,3S,5S)-5-((allyloxy)methyl)-3-((3-((allyloxy)methyl)-6-bromopyridin-2-yl)carbamoyl)-2-azabicyclo[3.1.0]hexane-2-carboxylate (3-S6)

To a mixture of (1R,3S,5S)-5-((allyloxy)methyl)-2-(tert-butoxycarbonyl)-2-azabicyclo[3.1.0]hexane-3-carboxylic acid (3-S4, 117 mg, 0.394 mmol) and 3-S5 (96 mg, 0.394 mmol) in DCM (5 mL), pyridine (0.159 mL, 1.97 mmol) was added followed by $POCl_3$ (0.037 mL, 0.394 mmol) at 0° C. under argon. The reaction mixture was stirred overnight at room temperature before water was added and the mixture was extracted with AcOEt. After washing with brine, the organic layer was dried over anhydrous $Na_2SO_4$. The solution was filtered and the solvent was removed under reduced pressure. The remaining residue was purified by column chromatography on silica gel with EtOAc in hexane (0-50%) as the eluent to afford tert-butyl (1R,3S,5S)-5-((allyloxy) methyl)-3-((3-((allyloxy)methyl)-6-bromopyridin-2-yl)carbamoyl)-2-azabicyclo[3.1.0]hexane-2-carboxylate (3-S6, 118 mg).

Step 5: tert-Butyl (4$^1$R,4$^3$S,4$^5$S,E)-1$^6$-bromo-3-oxo-6,11-dioxa-4$^2$,2-diaza-1(2,3)-pyridina-4(3,5)-bicyclo[3.1.0] hexanacyclododecaphan-8-ene-4$^2$-carboxylate (3-S7)

tert-Butyl (1R,3S,5S)-5-((allyloxy)methyl)-3-((3-((allyloxy)methyl)-6-bromopyridin-2-yl)carbamoyl)-2-azabicyclo[3.1.0]hexane-2-carboxylate (3-S6, 118 mg, 0.23 mmol) in toluene (23 mL) was treated with Hoveyda-Grubbs catalyst 2$^{nd}$ generation (7.1 mg, 0.011 mmol) at 80° C. under argon and the reaction was stirred for 2 hours. Additional catalyst (3 mg) was added and the mixture was heated for an additional 1 hour. The solvent was removed under reduced pressure and the residue was purified by column chromatography on silica gel with EtOAc in hexane (0-100%) as the eluent to afford tert-butyl (4$^1$R,4$^3$S,4$^5$S,E)-1$^6$-bromo-3-oxo-6,11-dioxa-4$^2$,2-diaza-1(2,3)-pyridina-4(3,5)-bicyclo[3.1.0] hexanacyclododecaphan-8-ene-4$^2$-carboxylate (3-S7, 44 mg) as a solid.

Step 6: (4$^1$R,4$^3$S,4$^5$S,E)-1$^6$-Bromo-6,11-dioxa-4$^2$,2-diaza-1 (2,3)-pyridina-4(3,5)-bicyclo[3.1.0]hexanacyclododecaphan-8-en-3-one Trifluoroacetic Acid Salt (3-S8)

tert-Butyl (4$^1$R,4$^3$S,4$^5$S,E)-1$^6$-bromo-3-oxo-6,11-dioxa-4$^2$,2-diaza-1(2,3)-pyridina-4(3,5)-bicyclo[3.1.0]hexanacyclododecaphan-8-ene-4$^2$-carboxylate (3-S7, 22 mg, 0.0445 mmol) in DCM (2 mL) was treated with TFA (1 mL) at room temperature for 1 hour. The volatiles were removed under reduced pressure and the residue was co-evaporated with toluene (5 mL) twice to afford (4$^1$R,4$^3$S,4$^5$S,E)-1$^6$-bromo-6,11-dioxa-4$^2$,2-diaza-1(2,3)-pyridina-4(3,5)-bicyclo[3.1.0] hexanacyclododecaphan-8-en-3-one TFA salt (3-S8), which was carried forward in the next step without additional purification.

Step 7: (4$^1$R,4$^3$S,4$^5$S,E)-4$^2$-(2-(3-Acetyl-5-(2-methylpyrimidin-5-yl)-1H-indazol-1-yl)acetyl)-1$^6$-bromo-6,11-dioxa-4$^2$,2-diaza-1(2,3)-pyridina-4(3,5)-bicyclo[3.1.0] hexanacyclododecaphan-8-en-3-one (3)

To a mixture of (4$^1$R,4$^3$S,4$^5$S,E)-1$^6$-bromo-6,11-dioxa-4$^2$, 2-diaza-1(2,3)-pyridina-4(3,5)-bicyclo[3.1.0]hexanacyclododecaphan-8-en-3-one TFA salt 3-S8 and 2-(3-acetyl-5-(2-methylpyrimidin-5-yl)-1H-indazol-1-yl)acetic acid (3-S9, 14 mg, 0.0445 mmol) in DMF (1 mL), TBTU (31.5 mg) was added followed by DIEA (0.059 mL) at room temperature with stirring. After the reaction was complete, NaHCO3 aqueous solution (10 mL) was added to form a precipitate that was collected by filtration and purified by column chromatography on silica gel with MeOH in DCM (0-10%) as the eluent to afford (4$^1$R,4$^3$S,4$^5$S,E)-4$^2$-(2-(3-acetyl-5-(2-methylpyrimidin-5-yl)-1H-indazol-1-yl)acetyl)-1$^6$-bromo-6,11-dioxa-4$^2$,2-diaza-1(2,3)-pyridina-4(3,5)-bicyclo[3.1.0]hexanacyclododecaphan-8-en-3-one (3, 16 mg) as a white solid. $^1$H NMR (400 MHz, Chloroform-d) δ 8.89 (s, 2H), 8.72 (s, 1H), 8.56 (t, J=1.3 Hz, 1H), 7.73 (d, J=8.1 Hz, 1H), 7.59 (d, J=1.3 Hz, 2H), 7.33 (d, J=8.0 Hz, 1H), 5.81-5.66 (m, 2H), 5.60-5.39 (m, 2H), 4.87 (d, J=8.6 Hz, 1H), 4.27 (d, J=13.6 Hz, 1H), 4.15-4.10 (m, 2H), 4.08-3.97 (m, 3H), 3.92-3.84 (m, 1H), 3.58 (q, J=10.3 Hz, 2H), 3.34 (dd, J=5.7, 2.8 Hz, 1H), 2.80 (s, 3H), 2.70 (s, 3H), 2.61-2.53 (m, 1H), 2.27 (dd, J=13.9, 8.8 Hz, 1H), 1.36 (t, J=5.7 Hz, 1H), 1.05 (dd, J=5.7, 2.7 Hz, 1H). LC (method A): t$_R$=1.75 min. LC/MS (EI) m/z: [M+H]$^+$686.

Scheme 3. Synthesis of (4$^1$R,4$^3$S,4$^5$S)-4$^2$-(2-(3-Acetyl-5-(2-methylpyrimidin-5-yl)-1H-indazol-1-yl)acetyl)-1$^6$-bromo-6,11-dioxa-4$^2$,2-diaza-1(2,3)-pyridina-4(3,5)-bicyclo[3.1.0]hexanacyclododecaphan-3-one (4)

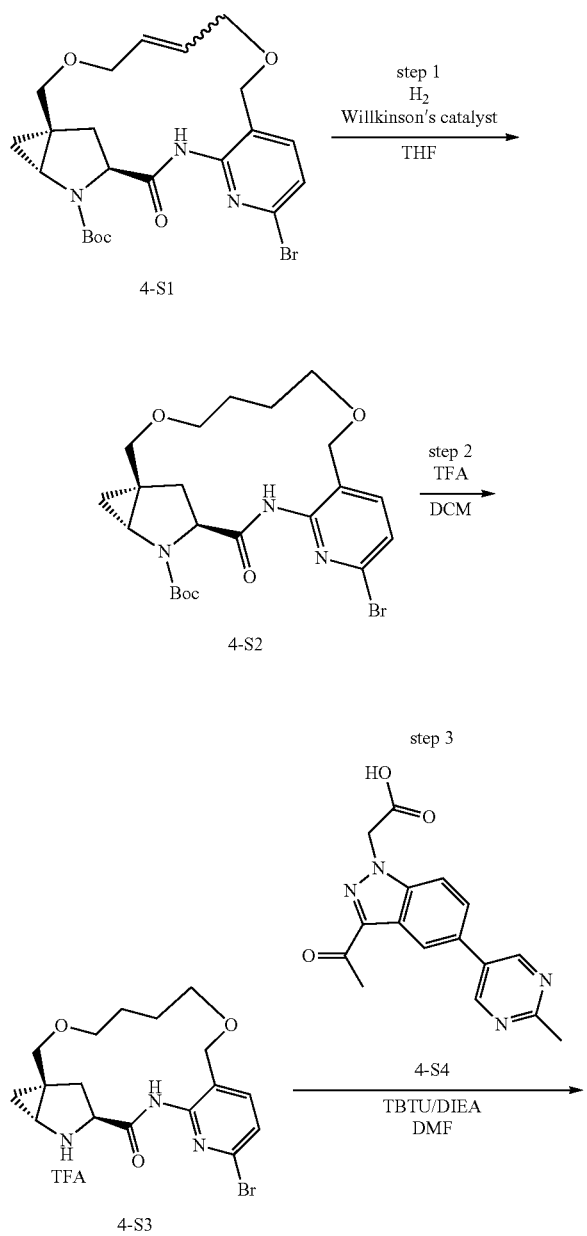

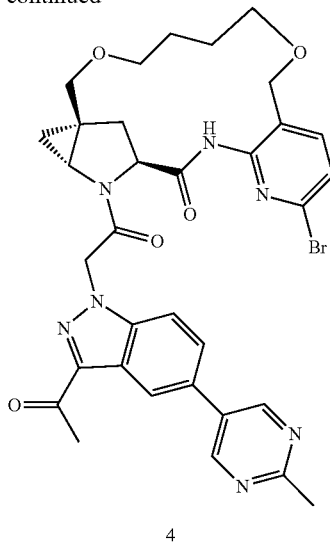

4

The above scheme and following detailed description depicts one non-limiting method for synthesizing compounds of Formula I wherein -X$^9$-L$^3$-X$^{10}$- is

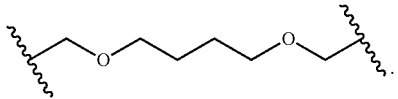 [SMILES: *COCCCCOC*]

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1: tert-Butyl (4$^1$R,4$^3$S,4$^5$S)-1$^6$-bromo-3-oxo-6,11-dioxa-4$^2$,2-diaza-1(2,3)-pyridina-4(3,5)-bicyclo[3.1.0]hexanacyclododecaphane-4$^2$-carboxylate (4-S2)

tert-Butyl (4$^1$R,4$^3$S,4$^5$S,E)-1$^6$-bromo-3-oxo-6,11-dioxa-4$^2$,2-diaza-1(2,3)-pyridina-4(3,5)-bicyclo[3.1.0]hexanacyclododecaphan-8-ene-4$^2$-carboxylate (4-S1, 23 mg, 0.0466 mmol) in THF (1.5 mL) was hydrogenated under 20 psi hydrogen atmosphere in the presence of Wilkinson's catalyst (9 mg) overnight. The mixture was filtered through Celite and the solvent was removed under reduced pressure. The residue was purified by column chromatography on silica gel with EtOAc in hexane (0-85%) as the eluent to afford tert-butyl (4$^1$R,4$^3$S,4$^5$S)-1$^6$-bromo-3-oxo-6,11-dioxa-4$^2$,2-diaza-1(2,3)-pyridina-4(3,5)-bicyclo[3.1.0]hexanacyclododecaphane-4$^2$-carboxylate (4-S2, 11.8 mg).

Step 2: (4$^1$R,4$^3$S,4$^5$S)-1$^6$-Bromo-6,11-dioxa-4$^2$,2-diaza-1(2,3)-pyridina-4(3,5)-bicyclo[3.1.0]hexanacyclododecaphan-3-one Trifluoroacetic Acid Salt (4-S3)

tert-butyl (4$^1$R,4$^3$S,4$^5$S)-1$^6$-bromo-3-oxo-6,11-dioxa-4$^2$,2-diaza-1(2,3)-pyridina-4(3,5)-bicyclo[3.1.0]hexanacyclododecaphane-4$^2$-carboxylate (4-S2, 11.8 mg) in DCM (2 mL) was treated with TFA (2 mL) at room temperature for 1 hour. The volatiles were removed under reduced pressure and the residue was co-evaporated with toluene (5 mL) twice to afford (4$^1$R,4$^3$S,4$^5$S)-1$^6$-bromo-6,11-dioxa-4$^2$,2-diaza-1(2,3)-pyridina-4(3,5)-bicyclo[3.1.0]hexanacyclododecaphan-3-one TFA salt (4-S3). The crude material was carried forward in the next step without additional purification.

Step 3: (4$^1$R,4$^3$S,4$^5$S)-4$^2$-(2-(3-Acetyl-5-(2-methylpyrimidin-5-yl)-1H-indazol-1-yl)acetyl)-1$^6$-bromo-6,11-dioxa-4$^2$,2-diaza-1(2,3)-pyridina-4(3,5)-bicyclo[3.1.0]hexanacyclododecaphan-3-one (4)

To a mixture of (4$^1$R,4$^3$S,4$^5$S)-1$^6$-bromo-6,11-dioxa-4$^2$,2-diaza-1(2,3)-pyridina-4(3,5)-bicyclo[3.1.0]hexanacyclododecaphan-3-one TFA salt 4-S3 and 2-(3-acetyl-5-(2-methylpyrimidin-5-yl)-1H-indazol-1-yl)acetic acid (4-S4, 9.4 mg) in DMF (0.5 mL), TBTU (18 mg) was added followed by DIEA (0.025 mL)=at room temperature with stirring. After reaction the reaction was complete, NaHCO$_3$ aqueous solution (15 mL) was added to form a precipitate that was collected by filtration and purified by column chromatography on silica gel with MeOH in DCM (0-10%) as the eluent to afford (4$^1$R,4$^3$S,4$^5$S)-4$^2$-(2-(3-acetyl-5-(2-methylpyrimidin-5-yl)-1H-indazol-1-yl)acetyl)-1$^6$-bromo-6,11-dioxa-4$^2$,2-diaza-1(2,3)-pyridina-4(3,5)-bicyclo[3.1.0] hexanacyclododecaphan-3-one (4, 9.3 mg) as a white solid. $^1$H NMR (400 MHz, Chloroform-d) δ 8.90 (s, 2H), 8.62-8.53 (m, 2H), 7.71-7.59 (m, 3H), 7.29 (d, J=8.0 Hz, 1H), 5.60-5.45 (m, 2H), 4.94 (s, 1H), 4.37-4.26 (m, 2H), 3.83 (d, J=10.5 Hz, 1H), 3.58-3.45 (m, 4H), 3.37 (d, J=6.4 Hz, 1H), 2.89 (d, J=10.5 Hz, 1H), 2.80 (s, 4H), 2.70 (s, 5H), 2.44 (dd, J=13.8, 9.6 Hz, 1H), 1.69 (d, J=46.6 Hz, 5H), 1.18 (t, J=5.7 Hz, 1H), 0.94 (dd, J=5.8, 2.7 Hz, 1H). LC (method A): t$_R$=1.85 min. LC/MS (EI) m/z: [M+H]$^+$688.

Scheme 4.
Synthesis of (4$^1$R,4$^3$S,4$^5$S,E)-4$^2$-(2-(3-Acetyl-5-(2-methylpyrimidin-5-yl)-1H-indazol-1-yl)acetyl)-6,11-dioxa-4$^2$,2-diaza-1(2,3)-pyridina-4(3,5)-bicyclo[3.1.0]hexanacyclododecaphan-8-en-3-one (5)

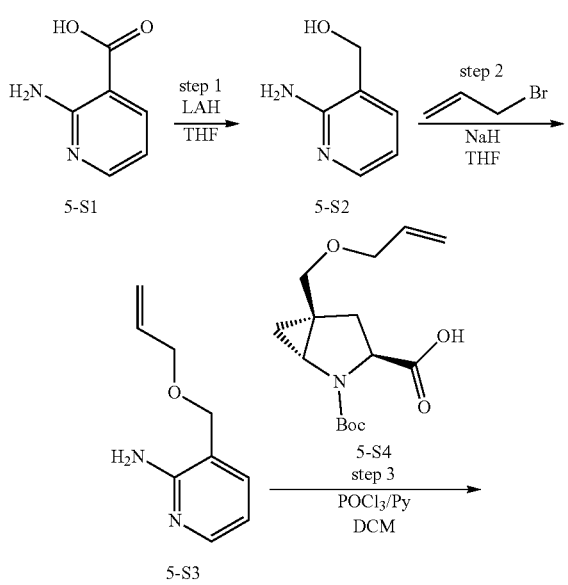

-continued

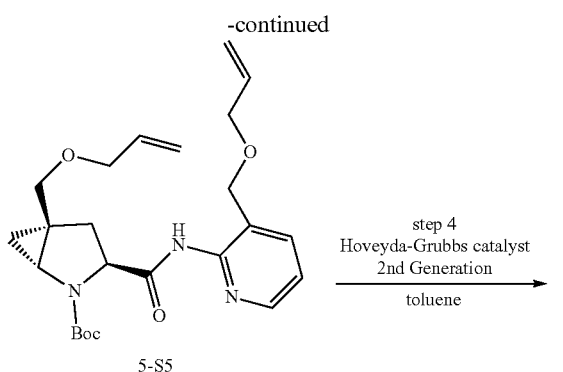

5-S5 step 4
Hoveyda-Grubbs catalyst
2nd Generation
toluene
→

5-S6 step 5
TFA
DCM
→

5-S7

5-S8
step 6
TBTU/DIEA
DMF
→

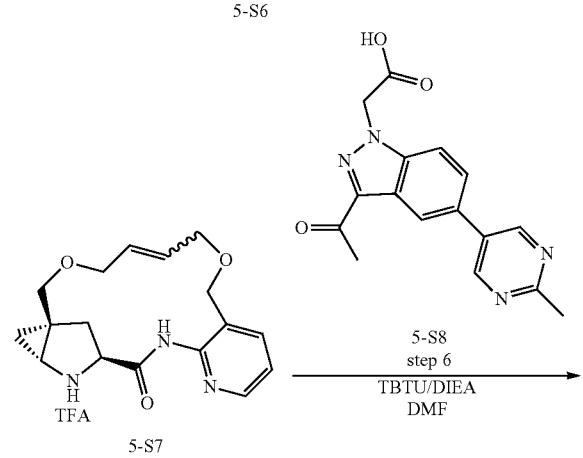

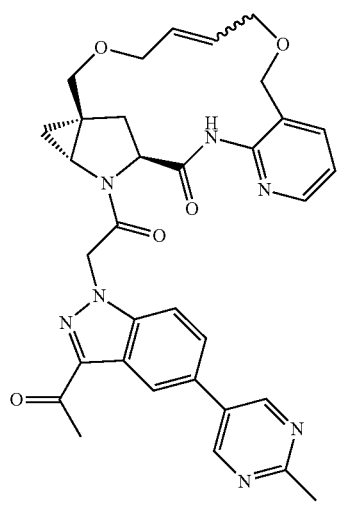

5

The above scheme and following detailed description depicts one non-limiting method for synthesizing compounds of Formula I wherein -$X^9$-$L^3$-$X^{10}$- is

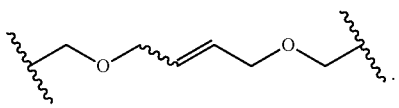 [SMILES: *COCC=CCOC*]

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: (2-Aminopyridin-3-yl)methanol (5-S2)

To a suspension of 2-aminonicotinic acid (5-S1, 1.58 g, 11.45 mmol) in THF (80 mL), LAH (1M in ether, 22.9 mL, 22.9 mmol) was added slowly at 0° C. under argon with stirring. After completion of the addition, the ice bath was removed and the mixture was stirred at room temperature. Additional LAH (1M in ether, 11.4 mL) was added after 48 hours and the reaction was again cooled with an ice bath before saturated NH$_4$Cl aqueous solution (20 mL) was added with stirring to form slurry. The organic layer was separated by decantation and the slurry was washed with EtOAc. The combined organic layer was washed with 1N NaOH aqueous solution, brine, and dried over anhydrous Na$_2$SO$_4$. Solvent was removed under reduced pressure to afford (2-aminopyridin-3-yl)methanol (5-S2, 0.74 g) as an off-white solid.

Step 2: 3-((Allyloxy)methyl)pyridin-2-amine (5-S3)

To (2-aminopyridin-3-yl)methanol (5-S2, 0.25 g, 2.02 mmol) in THF (10 mL), NaH (60%, 0.162 g, 4.04 mmol) was added at 0° C. under argon with stirring. After 10 minutes, allyl bromide (0.175 mL, 2.02 mmol) was added and the reaction mixture was stirred at 50° C. overnight. Water (30 mL) was added and the mixture was extracted with EtOAc. The organic layer was washed with brine and dried over anhydrous Na$_2$SO$_4$. Solvent was removed under reduced pressure and the residue was purified by column chromatography on silica gel with EtOAc in hexanes (0-50%) as the eluent to afford 3-((allyloxy)methyl)pyridin-2-amine (5-S3, 0.16 g) as a solid.

Step 3: tert-Butyl (1R,3S,5S)-5-((allyloxy)methyl)-3-((3-((allyloxy)methyl)pyridin-2-yl)carbamoyl)-2-azabicyclo[3.1.0]hexane-2-carboxylate (5-S5)

To a mixture of 5-S3 (40.6 mg, 0.248 mmol) and 5-S4 (73.6 mg, 0.248 mmol) in DCM (5 mL), pyridine (0.1 mL, 1.24 mmol) was added followed by POCl$_3$ (0.0233 mL, 0.25 mmol) at 0° C. under argon. The reaction mixture was stirred overnight at room temperature. Water was added and the mixture was extracted with DCM. After washing with brine, the organic layer was dried over anhydrous Na$_2$SO$_4$. The solution was filtered and the solvent was removed under reduced pressure. The remaining residue was purified by preparation TLC on silica gel with EtOAc in hexane (40%) as the eluent to afford tert-butyl (1R,3S,5S)-5-((allyloxy)methyl)-3-((3-((allyloxy)methyl)pyridin-2-yl)carbamoyl)-2-azabicyclo[3.1.0]hexane-2-carboxylate (5-S5, 20 mg).

Step 4: tert-Butyl (4¹R,4³S,4⁵S,E)-3-oxo-6,11-dioxa-4²,2-diaza-1(2,3)-pyridina-4(3,5)-bicyclo[3.1.0]hexanacyclodo-decaphan-8-ene-4²-carboxylate (5-S6)

tert-butyl (1R,3S,5S)-5-((allyloxy)methyl)-3-((3-((allyloxy)methyl)pyridin-2-yl)carbamoyl)-2-azabicyclo[3.1.0]hexane-2-carboxylate (5-S5, 20 mg) in toluene (23 mL) was treated with Hoveyda-Grubbs catalyst $2^{nd}$ generation (1.4 mg) at 60° C. under argon for 4 hours. Solvent was removed under reduced pressure and the residue was purified by column chromatography on silica gel with MeOH in DCM (0-10%) as the eluent to afford tert-butyl (4¹R,4³S,4⁵S,E)-3-oxo-6,11-dioxa-4²,2-diaza-1(2,3)-pyridina-4(3,5)-bicyclo[3.1.0]hexanacyclododecaphan-8-ene-4²-carboxylate (5-S6, 11.3 mg) as a yellow oil.

Step 5: (4¹R,4³S,4⁵S,E)-6,11-Dioxa-4²,2-diaza-1(2,3)-pyridina-4(3,5)-bicyclo[3.1.0]hexanacyclododecaphan-8-en-3-one Trifluoroacetic Acid Salt (5-S7)

tert-Butyl (4¹R,4³S,4⁵S,E)-3-oxo-6,11-dioxa-4²,2-diaza-1(2,3)-pyridina-4(3,5)-bicyclo[3.1.0]hexanacyclododecaphan-8-ene-4²-carboxylate (5-S6, 11.3 mg, 0.027 mmol) in DCM (2 mL) was treated with TFA (2 mL) at room temperature and the reaction was stirred for 1 hour. The volatiles were removed under reduced pressure and the residue was co-evaporated with toluene (5 mL) twice to afford (4¹R,4³S,4⁵S,E)-6,11-dioxa-4²,2-diaza-1(2,3)-pyridina-4(3,5)-bicyclo[3.1.0]hexanacyclododecaphan-8-en-3-one TFA salt (5-S7), which was carried forward in the next step without additional purification.

Step 6: (4¹R,4³S,4⁵S,E)-4²-(2-(3-Acetyl-5-(2-methylpyrimidin-5-yl)-1H-indazol-1-yl)acetyl)-6,11-dioxa-4²,2-diaza-1(2,3)-pyridina-4(3,5)-bicyclo[3.1.0]hexanacyclododecaphan-8-en-3-one (5)

To a mixture of (4¹R,4³S,4⁵S,E)-6,11-dioxa-4²,2-diaza-1(2,3)-pyridina-4(3,5)-bicyclo[3.1.0]hexanacyclododecaphan-8-en-3-one TFA salt 5-S7 and 2-(3-acetyl-5-(2-methylpyrimidin-5-yl)-1H-indazol-1-yl)acetic acid (5-S8, 8.4 mg, 0.027 mmol) in DMF (1 mL), TBTU (13 mg) was added followed by DIEA (0.024 mL) at room temperature with stirring. After the reaction was complete, NaHCO₃ aqueous solution (5 mL) was added and the mixture was extracted with EtOAc. The organic layer was washed with 1N HCl aqueous solution. The aqueous solution was lyophilized and the residue was treated with NaHCO₃ aqueous solution and extracted with DCM. The organic layer was washed with brine and dried over anhydrous Na₂SO₄. The solution was filtered and the solvent was removed under reduced pressure. The remaining residue was purified by column chromatography on silica gel with MeOH in DCM (0-10%) as the eluent to afford (4¹R,4³S,4⁵S,E)-4²-(2-(3-acetyl-5-(2-methylpyrimidin-5-yl)-1H-indazol-1-yl)acetyl)-6,11-dioxa-4²,2-diaza-1(2,3)-pyridina-4(3,5)-bicyclo[3 1.0]hexanacyclododecaphan-8-en-3-one (5, 8.3 mg) as a white powder. ¹H NMR (400 MHz, Chloroform-d) δ 8.97 (s, 1H), 8.88 (s, 2H), 8.60-8.53 (m, 1H), 8.28 (dd, J=4.7, 1.8 Hz, 1H), 7.83 (dd, J=7.8, 1.8 Hz, 1H), 7.62-7.53 (m, 2H), 7.15 (dd, J=7.7, 4.8 Hz, 1H), 5.83-5.72 (m, 2H), 5.58-5.38 (m, 2H), 4.79 (d, J=8.3 Hz, 1H), 4.37 (d, J=13.4 Hz, 1H), 4.22 (d, J=13.4 Hz, 1H), 4.15-4.06 (m, 2H), 4.05-3.97 (m, 1H), 3.91-3.83 (m, 1H), 3.65-3.53 (m, 2H), 3.37 (dd, J=5.7, 2.7 Hz, 1H), 2.80 (s, 4H), 2.69 (s, 3H), 2.57 (dd, J=13.9, 3.0 Hz, 1H), 2.29 (dd, J=13.9, 8.8 Hz, 1H), 1.27 (q, J=4.8, 3.9 Hz, 1H), 0.99 (dd, J=5.7, 2.7 Hz, 1H). LC (method A): $t_R$=1.38 min. LC/MS (EI) m/z: [M+H]⁺608.

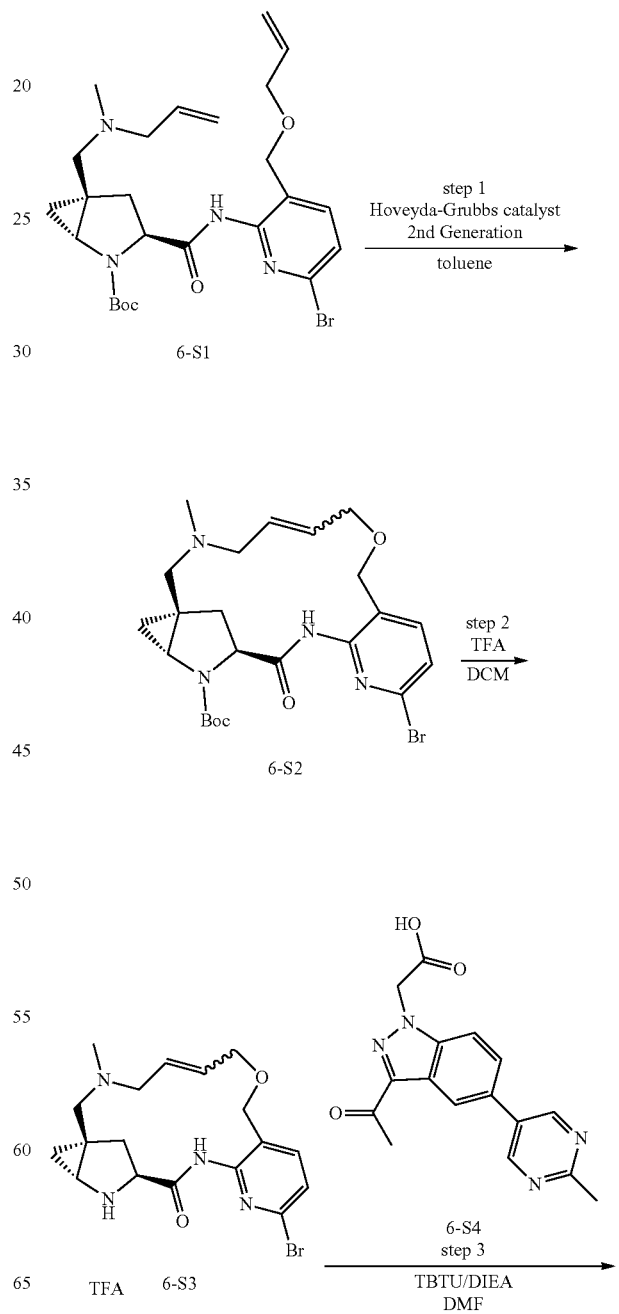

Scheme 5. Synthesis of (4¹R,4³S,4⁵S,E)-4²-(2-(3-Acetyl-5-(2-methylpyrimidin-5-yl)-1H-indazol-1-yl)acetyl)-1⁶-bromo-6-methyl-11-oxa-4²,2,6-triaza-1(2,3)-pyridina-4(3,5)-bicyclo[3.1.0]hexanacyclododecaphan-8-en-3-one (6)

-continued

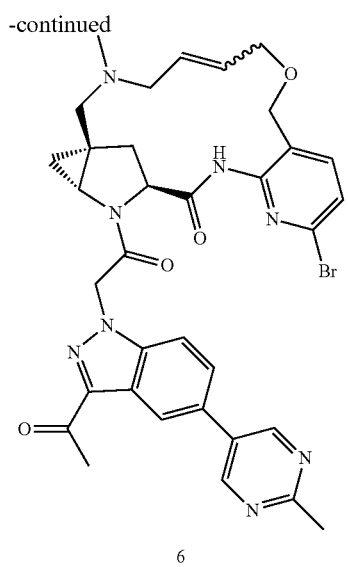

6

The above scheme and following detailed description depicts one non-limiting method for synthesizing compounds of Formula I wherein -X$^9$-L$^3$-X$^{10}$- is

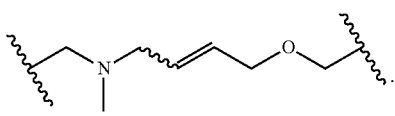 [SMILES: *COCC=CCN(C)C*]

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1: tert-Butyl (4$^1$R,4$^3$S,4$^5$R,E)-1$^6$-bromo-6-methyl-3-oxo-11-oxa-4$^2$,2,6-triaza-1(2,3)-pyridina-4(3,5)-bicyclo[3.1.0]hexanacyclododecaphan-8-ene-4$^2$-carboxylate (6-S2)

tert-Butyl (1R,3S,5R)-5-((allyl(methyl)amino)methyl)-3-((3-((allyloxy)methyl)-6-bromopyridin-2-yl)carbamoyl)-2-azabicyclo[3.1.0]hexane-2-carboxylate (6-S1, 144 mg, 0.269 mmol) in toluene (27 mL) was treated with Hoveyda-Grubbs catalyst 2nd generation (8.4 mg, 0.011 mmol) at 80° C. under argon and the reaction was stirred for 2 hours. Additional catalyst (5 mg) was added every 30 minutes until the reaction was complete. Solvent was removed under reduced pressure and the residue was purified by column chromatography on silica gel with MeOH in DCM (0-10%) as the eluent to afford tert-butyl (4$^1$R,4$^3$S,4$^5$R,E)-1$^6$-bromo-6-methyl-3-oxo-11-oxa-4$^2$,2,6-triaza-1(2,3)-pyridina-4(3,5)-bicyclo[3.1.0]hexanacyclododecaphan-8-ene-4$^2$-carboxylate (6-S2, 93 mg).

Step 2: (4$^1$R,4$^3$S,4$^5$R,E)-1$^6$-Bromo-6-methyl-11-oxa-4$^2$,2,6-triaza-1(2,3)-pyridina-4(3,5)-bicyclo[3.1.0]hexanacyclododecaphan-8-en-3-one Trifluoroacetic Acid Salt (6-S3)

tert-Butyl (4$^1$R,4$^3$S,4$^5$R,E)-1$^6$-bromo-6-methyl-3-oxo-11-oxa-4$^2$,2,6-triaza-1(2,3)-pyridina-4(3,5)-bicyclo[3.1.0]hexanacyclododecaphan-8-ene-4$^2$-carboxylate (6-S2, 40 mg, 0.079 mmol) in DCM (2 mL) was treated with TFA (2 mL) at room temperature for 1 hour. The volatiles were removed under reduced pressure and the residue was co-evaporated with toluene (5 mL) twice to afford (4$^1$R,4$^3$S,4$^5$R,E)-1$^6$-bromo-6-methyl-11-oxa-4$^2$,2,6-triaza-1(2,3)-pyridina-4(3,5)-bicyclo[3.1.0]hexanacyclododecaphan-8-en-3-one TFA salt (6-S3), which was carried forward in the next step without additional purification.

Step 3: (4$^1$R,4$^3$S,4$^5$R,E)-4$^2$-(2-(3-Acetyl-5-(2-methylpyrimidin-5-yl)-1H-indazol-1-yl)acetyl)-1$^6$-bromo-6-methyl-11-oxa-4$^2$,2,6-triaza-1(2,3)-pyridina-4(3,5)-bicyclo[3.1.0]hexanacyclododecaphan-8-en-3-one (6)

To a mixture of (4$^1$R,4$^3$S,4$^5$R,E)-1$^6$-bromo-6-methyl-11-oxa-4$^2$,2,6-triaza-1(2,3)-pyridina-4(3,5)-bicyclo[3.1.0]hexanacyclododecaphan-8-en-3-one TFA salt 6-S3 and 2-(3-acetyl-5-(2-methylpyrimidin-5-yl)-1H-indazol-1-yl)acetic acid (6-S4, 25 mg, 0.08 mmol) in DMF (1 mL), TBTU (39 mg) was added followed by DIEA (0.14 mL) at room temperature with stirring. After the reaction was complete, NaHCO$_3$ aqueous solution (10 mL) was added to form a precipitate that was collected by filtration and purified by column chromatography on silica gel with MeOH in DCM (0-15%) as the eluent to afford (4$^1$R,4$^3$S,4$^5$R,E)-4$^2$-(2-(3-acetyl-5-(2-methylpyrimidin-5-yl)-1H-indazol-1-yl)acetyl)-1$^6$-bromo-6-methyl-11-oxa-4$^2$,2,6-triaza-1(2,3)-pyridina-4(3,5)-bicyclo[3.1.0]hexanacyclododecaphan-8-en-3-one (6, 27.4 mg) as an off-white solid. $^1$H NMR (400 MHz, Chloroform-d) δ 8.89 (s, 3H), 8.65 (s, 1H), 8.56 (t, J=1.2 Hz, 1H), 7.81 (d, J=8.1 Hz, 1H), 7.58 (d, J=1.3 Hz, 2H), 7.35 (d, J=8.0 Hz, 1H), 5.72 (ddd, J=13.8, 8.6, 4.8 Hz, 1H), 5.63-5.53 (m, 1H), 5.52-5.37 (m, 2H), 4.91 (d, J=8.8 Hz, 1H), 4.26-4.16 (m, 3H), 3.94 (dd, J=12.7, 8.1 Hz, 1H), 3.24 (d, J=12.9 Hz, 1H), 3.13 (dd, J=12.7, 4.7 Hz, 1H), 3.06 (dd, J=5.7, 2.7 Hz, 1H), 2.80 (s, 3H), 2.74-2.63 (m, 4H), 2.54 (d, J=14.2 Hz, 1H), 2.34 (s, 3H), 2.30-2.18 (m, 1H), 1.63 (d, J=12.9 Hz, 1H), 1.23 (t, J=5.7 Hz, 1H), 1.11 (dd, J=5.7, 2.7 Hz, 1H). LC (method A): t$_R$=1.08 min. LC/MS (EI) m/z: [M+H]$^+$699.

Scheme 6. Synthesis of (4$^1$R,4$^3$S,4$^5$R)-4$^2$-(2-(3-Acetyl-5-(2-methylpyrimidin-5-yl)-1H-indazol-1-yl)acetyl)-1$^6$-bromo-6-methyl-11-oxa-4$^2$,2,6-triaza-1(2,3)-pyridina-4(3,5)-bicyclo[3.1.0]hexanacyclododecaphan-3-one (7)

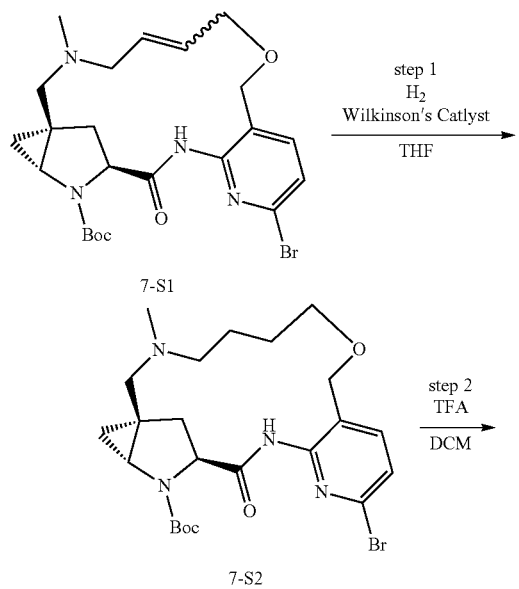

-continued step 3

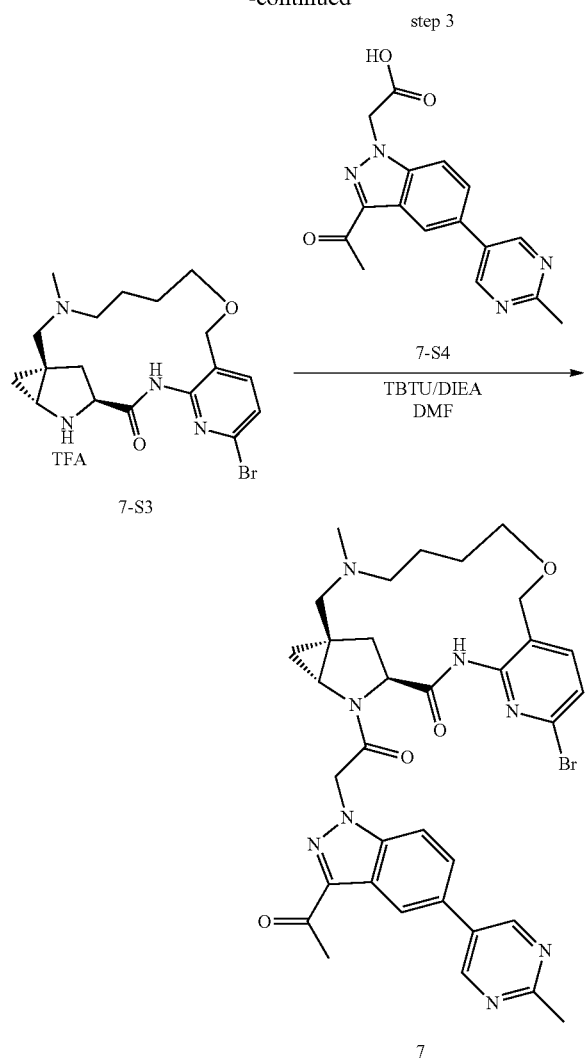

The above scheme and following detailed description depicts one non-limiting method for synthesizing compounds of Formula I wherein -X$^9$-L$^3$-X$^{10}$- is

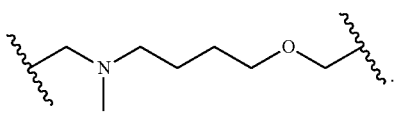 [SMILES: *COCCCCN(C)C*]

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1: tert-Butyl (4$^1$R,4$^3$S,4$^5$R)-1$^6$-bromo-6-methyl-3-oxo-11-oxa-4$^2$,2,6-triaza-1(2,3)-pyridina-4(3,5)-bicyclo[3.1.0] hexanacyclododecaphane-4$^2$-carboxylate (7-S2)

tert-Butyl ((4$^1$R,4$^3$S,4$^5$R)-1$^6$-bromo-6-methyl-3-oxo-11-oxa-4$^2$,2,6-triaza-1(2,3)-pyridina-4(3,5)-bicyclo[3.1.0] hexanacyclododecaphane-8-ene-4$^2$-carboxylate (7-S1, 57 mg, 0.112) in THF (3 mL) was hydrogenated under 20 psi hydrogen atmosphere in the presence of Wilkinson's catalyst (20 mg) overnight. The mixture was filtered through Celite and the solvent was removed under reduced pressure. The residue was purified by column chromatography on silica gel with MeOH in DCM (0-10%) as the eluent to afford tert-butyl (4$^1$R,4$^3$S,4$^5$R)-1$^6$-bromo-6-methyl-3-oxo-11-oxa-4$^2$,2,6-triaza-1(2,3)-pyridina-4(3,5)-bicyclo[3.1.0]hexana-cyclododecaphane-4$^2$-carboxylate (7-S2, 40 mg).

Step 2: (4$^1$R,4$^3$S,4$^5$R)-1$^6$-Bromo-6-methyl-11-oxa-4$^2$,2,6-triaza-1(2,3)-pyridina-4(3,5)-bicyclo[3.1.0]hexanacyclodo-decaphan-3-one Trifluoroacetic acid salt. salt (7-S3)

tert-Butyl (4$^1$R,4$^3$S,4$^5$R)-1$^6$-bromo-6-methyl-3-oxo-11-oxa-4$^2$,2,6-triaza-1(2,3)-pyridina-4(3,5)-bicyclo[3.1.0] hexanacyclododecaphan-8-ene-42-carboxylate 7-S2 (40 mg, 0.079 mmol) in DCM (2 mL) was treated with TFA (2 mL) at room temperature for 1 hour. The volatiles were removed under reduced pressure and the residue was co-evaporated with toluene (5 mL) twice to afford (4$^1$R,4$^3$S,4$^5$R)-1$^6$-bromo-6-methyl-11-oxa-4$^2$,2,6-triaza-1(2,3)-pyridina-4(3,5)-bicyclo[3.1.0]hexanacyclododecaphan-3-one TFA salt (7-S3) for next step.

Step 3: (4$^1$R,4$^3$S,4$^5$R)-4$^2$-(2-(3-Acetyl-5-(2-methylpyrimi-din-5-yl)-1H-indazol-1-yl)acetyl)-1$^6$-bromo-6-methyl-11-oxa-4$^2$,2,6-triaza-1(2,3)-pyridina-4(3,5)-bicyclo[3.1.0] hexanacyclododecaphan-3-one (7)

To a mixture of (4$^1$R,4$^3$S,4$^5$R)-1$^6$-bromo-6-methyl-11-oxa-4$^2$,2,6-triaza-1(2,3)-pyridina-4(3,5)-bicyclo[3.1.0] hexanacyclododecaphan-3-one TFA salt 7-S3 and 2-(3-acetyl-5-(2-methylpyrimidin-5-yl)-1H-indazol-1-yl)acetic acid (7-S4, 24 mg, 0.077 mmol) in DMF (1 mL), TBTU (37 mg) was added followed by DIEA (0.134 mL) at room temperature with stirring. After the reaction was complete, NaHCO$_3$ aqueous solution (10 mL) was added to form a precipitate that was collected by filtration and purified by column chromatography on silica gel with MeOH in DCM (0-15%) as the eluent to afford (4$^1$R,4$^3$S,4$^5$R)-4$^2$-(2-(3-acetyl-5-(2-methylpyrimidin-5-yl)-1H-indazol-1-yl)acetyl)-1$^6$-bromo-6-methyl-11-oxa-4$^2$,2,6-triaza-1(2,3)-pyridina-4 (3,5)-bicyclo[3.1.0]hexanacyclododecaphan-3-one (7, 21.4 mg) as off-white solid. $^1$H NMR (400 MHz, Chloroform-d) δ 8.96 (s, 1H), 8.90 (s, 2H), 8.57 (s, 1H), 7.69-7.58 (m, 2H), 7.42 (d, J=7.9 Hz, 1H), 7.23 (d, J=7.8 Hz, 1H), 5.61 (d, J=16.3 Hz, 1H), 5.47 (d, J=16.3 Hz, 1H), 4.64 (s, 1H), 4.34 (d, J=13.3 Hz, 1H), 4.11 (d, J=13.3 Hz, 1H), 3.57-3.46 (m, 2H), 3.33 (s, 1H), 2.80 (s, 4H), 2.72 (s, 3H), 2.61 (d, J=13.4 Hz, 1H), 2.47-2.28 (m, 3H), 2.24 (s, 3H), 1.79 (d, J=25.5 Hz, 4H), 1.59-1.36 (m, 4H), 1.04 (t, J=5.8 Hz, 1H), 0.94 (dd, J=5.7, 2.6 Hz, 1H). LC (method A): t$_R$=1.05 min. LC/MS (EI) m/z: [M+H]$^+$701.

Scheme 7. Synthesis of (4$^1$R,4$^3$S,4$^5$R,E)-4$^2$-(2-(3-Acetyl-5-(2-methylpyrimidin-5-yl)-1H-indazol-1-yl)acetyl)-1$^6$-bromo-6-methyl-4$^2$,2,6-triaza-1(2,3)-pyridina-4(3,5)-bicyclo[3.1.0]hexanacyclododecaphan-11-en-3-one (8)

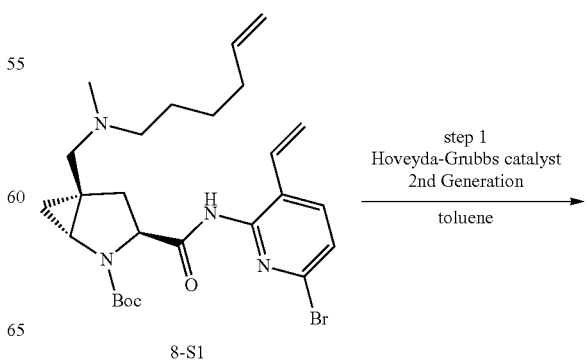

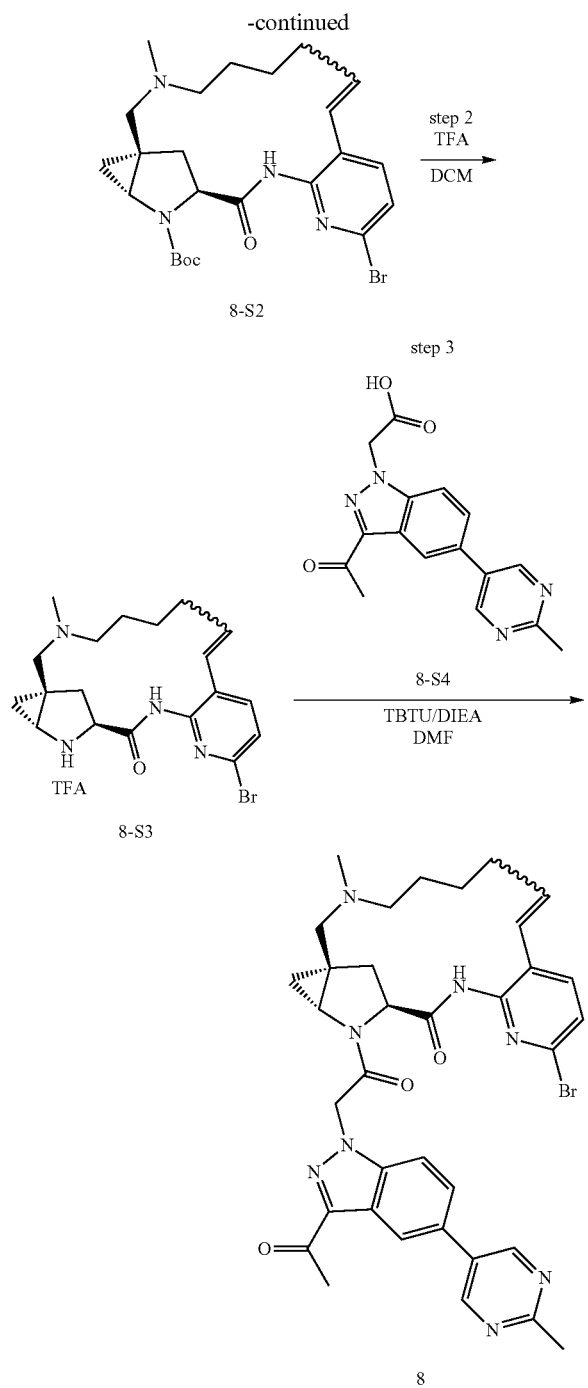

8-S2 step 2
TFA
DCM step 3

8-S4

TBTU/DIEA
DMF

8-S3

8

The above scheme and following detailed description depicts one non-limiting method for synthesizing compounds of Formula I wherein -X$^9$-L$^3$-X$^{10}$- is

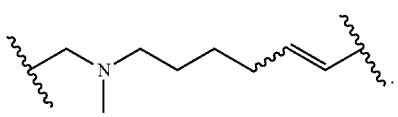 [SMILES: *C=CCCCCN(C)C*]

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1: tert-Butyl (4$^1$R,4$^3$S,4$^5$R,E)-1$^6$-bromo-6-methyl-3-oxo-4$^2$,2,6-triaza-1(2,3)-pyridina-4(3,5)-bicyclo[3.1.0]hexanacyclododecaphan-11-ene-42-carboxylate (8-S2)

tert-Butyl (1R,3S,5R)-3-((6-bromo-3-vinylpyridin-2-yl)carbamoyl)-5-((hex-5-en-1-yl(methyl)amino)methyl)-2-azabicyclo[3.1.0]hexane-2-carboxylate (8-S1, 83 mg, 0.156 mmol) in toluene (20 mL) was treated with Hoveyda-Grubbs catalyst 2nd generation (5 mg) at 70° C. under argon and the reaction was stirred for 2 hours. Additional catalyst (5 mg) was added every 30 minutes until the reaction was complete. Solvent was removed under reduced pressure and the residue was purified by HPLC to afford tert-butyl (4$^1$R,4$^3$S,4$^5$R, E)-1$^6$-bromo-6-methyl-3-oxo-4$^2$,2,6-triaza-1(2,3)-pyridina-4(3,5)-bicyclo[3.1.0]hexanacyclododecaphan-11-ene-42-carboxylate (8-S2, 16 mg).

Step 2: (4$^1$R,4$^3$S,4$^5$R,E)-1$^6$-Bromo-6-methyl-4$^2$,2,6-triaza-1(2,3)-pyridina-4(3,5)-bicyclo[3.1.0]hexanacyclododecaphan-11-en-3-one TFA salt (8-S3)

tert-Butyl (4$^1$R,4$^3$S,4$^5$R,E)-1$^6$-bromo-6-methyl-3-oxo-4$^2$,2,6-triaza-1(2,3)-pyridina-4(3,5)-bicyclo[3.1.0]hexanacyclododecaphan-11-ene-42-carboxylate (8-S2, 16 mg) (16 mg) in DCM (1.5 mL) was treated with TFA (1.5 mL) at room temperature for 1 hour. The volatiles were removed under reduced pressure and the residue was co-evaporated with toluene (5 mL) twice to afford (4$^1$R,4$^3$S,4$^5$R,E)-1$^6$-bromo-6-methyl-4$^2$,2,6-triaza-1(2,3)-pyridina-4(3,5)-bicyclo[3.1.0]hexanacyclododecaphan-11-en-3-one TFA salt (8-S3) for next step.

Step 3: (4$^1$R,4$^3$S,4$^5$R,E)-4$^2$-(2-(3-acetyl-5-(2-methylpyrimidin-5-yl)-1H-indazol-1-yl)acetyl)-1$^6$-bromo-6-methyl-4$^2$,2,6-triaza-1(2,3)-pyridina-4(3,5)-bicyclo[3.1.0]hexanacyclododecaphan-11-en-3-one (8)

To a mixture of (4$^1$R,4$^3$S,4$^5$R,E)-1$^6$-bromo-6-methyl-4$^2$,2,6-triaza-1(2,3)-pyridina-4(3,5)-bicyclo[3.1.0]hexanacyclododecaphan-11-en-3-one TFA salt TFA salt (8-S3, 0.016 mmol) and 2-(3-acetyl-5-(2-methylpyrimidin-5-yl)-1H-indazol-1-yl)acetic acid (8-S4, 5 mg) in DMF (1.0 mL), TBTU (10 mg) was added followed by DIEA (0.028 mL) at room temperature with stirring. After the reaction was complete, NaHCO$_3$ aqueous solution (5 mL) was added to form a precipitate that was collected by filtration and purified by preparative TLC on silica gel with MeOH in DCM (10%) as the eluent to afford (4$^1$R,4$^3$S,4$^5$R,E)-4$^2$-(2-(3-acetyl-5-(2-methylpyrimidin-5-yl)-1H-indazol-1-yl)acetyl)-1$^6$-bromo-6-methyl-4$^2$,2,6-triaza-1(2,3)-pyridina-4(3,5)-bicyclo[3.1.0]hexanacyclododecaphan-11-en-3-one (8, 5.3 mg) as white solid. $^1$H NMR (400 MHz, Chloroform-d) δ 8.85 (s, 2H), 8.79 (s, 1H), 8.55 (dd, J=0.8, 1.7 Hz, 1H), 7.64-7.55 (m, 2H), 7.52 (dd, J=1.7, 8.8 Hz, 1H), 7.30-7.26 (m, 1H), 6.15 (ddd, J=4.9, 7.4, 16.0 Hz, 1H), 5.74 (d, J=16.1 Hz, 1H), 5.59 (d, J=16.1 Hz, 1H), 5.45 (d, J=16.1 Hz, 1H), 4.90 (dd, J=2.3, 9.0 Hz, 1H), 3.31 (s, 1H), 3.14 (d, J=13.7 Hz, 1H), 2.80 (s, 4H), 2.71 (s, 3H), 2.54 (s, 1H), 2.29 (s, 5H), 2.01 (ddd, J=8.0, 14.4, 32.6 Hz, 4H), 1.52 (ddt, J=10.9, 17.2, 46.1 Hz, 3H), 1.22 (d, J=32.2 Hz, 4H), 0.96-0.81 (m, 2H). LC (method A): t$_R$=1.24 min. LC/MS (EI) m/z: [M+H]$^+$697.

Scheme 8. Synthesis of (4¹R,4³S,4⁵R,E)-4²-(2-(3-Acetyl-5-(2-methylpyrimidin-5-yl)-1H-indazol-1-yl)acetyl)-1⁶-bromo-7-thia-4²,2,6-triaza-1(2,3)-pyridina-4(3,5)-bicyclo[3.1.0]hexanacycloundecaphan-10-en-3-one 7,7-dioxide (9)

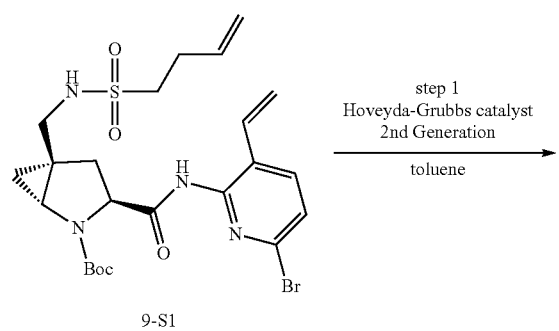

9-S1 step 1
Hoveyda-Grubbs catalyst
2nd Generation
toluene

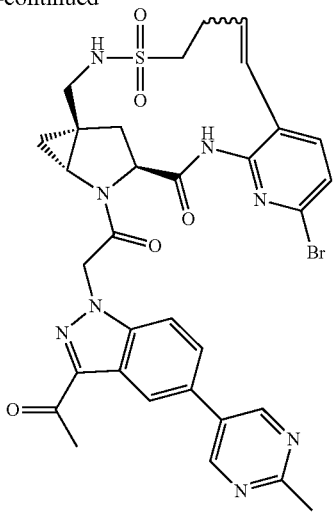

9

-continued

9-S2 step 2
TFA
DCM

9-S3 step 3

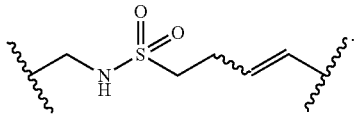 [SMILES: *C=CCCS(=O)(=O)NC*]

9-S4

TBTU/DIEA
DMF

The above scheme and following detailed description depicts one non-limiting method for synthesizing compounds of Formula I wherein -X⁹-L³-X¹⁰- is The skilled artisan will recognize that related -X⁹-L³-X¹⁰- moieties of different chain lengths, and stereochemistry, in addition A¹, B², and C² groups as described herein, can be used to afford additional compounds of the present invention.

Step 1: tert-Butyl (4¹R,4³S,4⁵R,E)-1⁶-bromo-3-oxo-7-thia-4²,2,6-triaza-1(2,3)-pyridina-4(3,5)-bicyclo[3.1.0]hexanacycloundecaphan-10-ene-4²-carboxylate 7,7-dioxide (9-S2)

tert-Butyl (1R,3S,5R)-3-((6-bromo-3-vinylpyridin-2-yl)carbamoyl)-5-((but-3-en-1-ylsulfonamido)methyl)-2-azabicyclo[3.1.0]hexane-2-carboxylate (9-S1, 95 mg, 0.17 mmol) in toluene (20 mL) was treated with Hoveyda-Grubbs catalyst 2nd generation (5 mg) at 70° C. under argon and the reaction was stirred for 2 hours. Additional catalyst (5 mg) was added every 30 minutes until the reaction was complete. Solvent was removed under reduced pressure and the residue was purified by column chromatography on silica gel with EtOAc in hexanes (0-75%) as the eluent to afford tert-butyl (4¹R,4³S,4⁵R,E)-1⁶-bromo-3-oxo-7-thia-4²,2,6-triaza-1(2,3)-pyridina-4(3,5)-bicyclo[3.1.0]hexanacycloundecaphan-10-ene-4²-carboxylate 7,7-dioxide (9-S2, 30.9 mg) as a pale yellow solid.

Step 2: (4¹R,4³S,4⁵R,E)-1⁶-Bromo-7-thia-4²,2,6-triaza-1(2,3)-pyridina-4(3,5)-bicyclo[3.1.0]hexanacycloundecaphan-10-en-3-one 7,7-dioxide TFA salt (9-S3)

tert-Butyl (4¹R,4³S,4⁵R,E)-1⁶-bromo-3-oxo-7-thia-4²,2,6-triaza-1(2,3)-pyridina-4(3,5)-bicyclo[3.1.0]hexanacycloundecaphan-10-ene-4²-carboxylate 7,7-dioxide (9-S2, 30.9 mg) in DCM (1 mL) was treated with TFA (1 mL) at room temperature and the reaction stirred for 1 hour. The volatiles were removed under reduced pressure and the residue was co-evaporated with toluene (5 mL) twice to afford (4¹R,4³S,4⁵R,E)-1⁶-bromo-7-thia-4²,2,6-triaza-1(2, 3)-pyridina-4(3,5)-bicyclo[3.1.0]hexanacycloundecaphan-10-en-3-one 7,7-dioxide TFA salt (9-S3), which was carried forward in the next step without additional purificarion.

Step 3: (4¹R,4³S,4⁵R,E)-4²-(2-(3-Acetyl-5-(2-methylpyrimidin-5-yl)-1H-indazol-1-yl)acetyl)-1⁶-bromo-7-thia-4²,2,6-triaza-1(2,3)-pyridina-4(3,5)-bicyclo[3.1.0]hexanacycloundecaphan-10-en-3-one 7,7-dioxide (9)

To a mixture of (4¹R,4³S,4⁵R,E)-1⁶-bromo-7-thia-4²,2,6-triaza-1(2,3)-pyridina-4(3,5)-bicyclo[3.1.0]hexanacycloundecaphan-10-en-3-one 7,7-dioxide TFA salt (9-S3, 0.029 mmol) and 2-(3-acetyl-5-(2-methylpyrimidin-5-yl)-1H-indazol-1-yl)acetic acid (9-S4, 9 mg) in DMF (1.5 mL), TBTU (19 mg) was added followed by DIEA (0.025 mL) at room temperature with stirring. After the reaction was complete, NaHCO₃ aqueous solution (10 mL) was added to form a precipitate that was collected by filtration and purified by column chromatography on silica gel with MeOH in DCM (0-10%) as the eluent to afford (4¹R,4³S,4⁵R,E)-4²-(2-(3-acetyl-5-(2-methylpyrimidin-5-yl)-1H-indazol-1-yl)acetyl)-1⁶-bromo-7-thia-4²,2,6-triaza-1(2,3)-pyridina-4(3,5)-bicyclo[3.1.0]hexanacycloundecaphan-10-en-3-one 7,7-dioxide (9, 12 mg) as white solid.

¹H NMR (400 MHz, Chloroform-d) δ 8.99 (s, 1H), 8.83 (s, 2H), 8.49 (d, J=1.3 Hz, 1H), 7.45 (t, J=4.0 Hz, 3H), 7.21 (d, J=8.0 Hz, 1H), 6.18-6.05 (m, 1H), 6.01 (d, J=15.9 Hz, 1H), 5.72 (s, 1H), 5.48-5.26 (m, 2H), 4.86 (d, J=8.1 Hz, 1H), 3.67 (dd, J=5.4, 12.7 Hz, 1H), 3.39 (dd, J=2.7, 5.7 Hz, 1H), 3.33 (q, J=5.8 Hz, 2H), 2.79 (s, 3H), 2.77-2.70 (m, 1H), 2.67 (s, 2H), 2.64 (d, J=6.4 Hz, 1H), 2.50 (d, J=13.9 Hz, 1H), 2.11 (dd, J=8.3, 14.0 Hz, 1H), 1.03 (dd, J=2.9, 5.7 Hz, 1H). LC (method A): $t_R$=1.49 min. LC/MS (EI) m/z: [M+H]⁺719.

Scheme 9.
Synthesis of (18aS,19aR,20aR,E)-2-Acetyl-15-bromo-19a-methyl-5,6,7,10,12,17,19,19a,20,20a-decahydro-4H-cyclopropa[4,5]pyrrolo[2,1-g]pyrazolo[1,5-k]pyrido[3,2-c][1]oxa[5,8,11,14]tetraazacyclononadecine-4,18,22(18aH,23H)-trione (14) and (18aS,19aR,20aR,Z)-2-Acetyl-15-bromo-19a-methyl-5,6,7,10,12,17,19,19a,20,20a-decahydro-4H-cyclopropa[4,5]pyrrolo[2,1-g]pyrazolo[1,5-k]pyrido[3,2-c][1]oxa[5,8,11,14]tetraazacyclononadecine-4,18,22(18aH,23H)-trione (15)

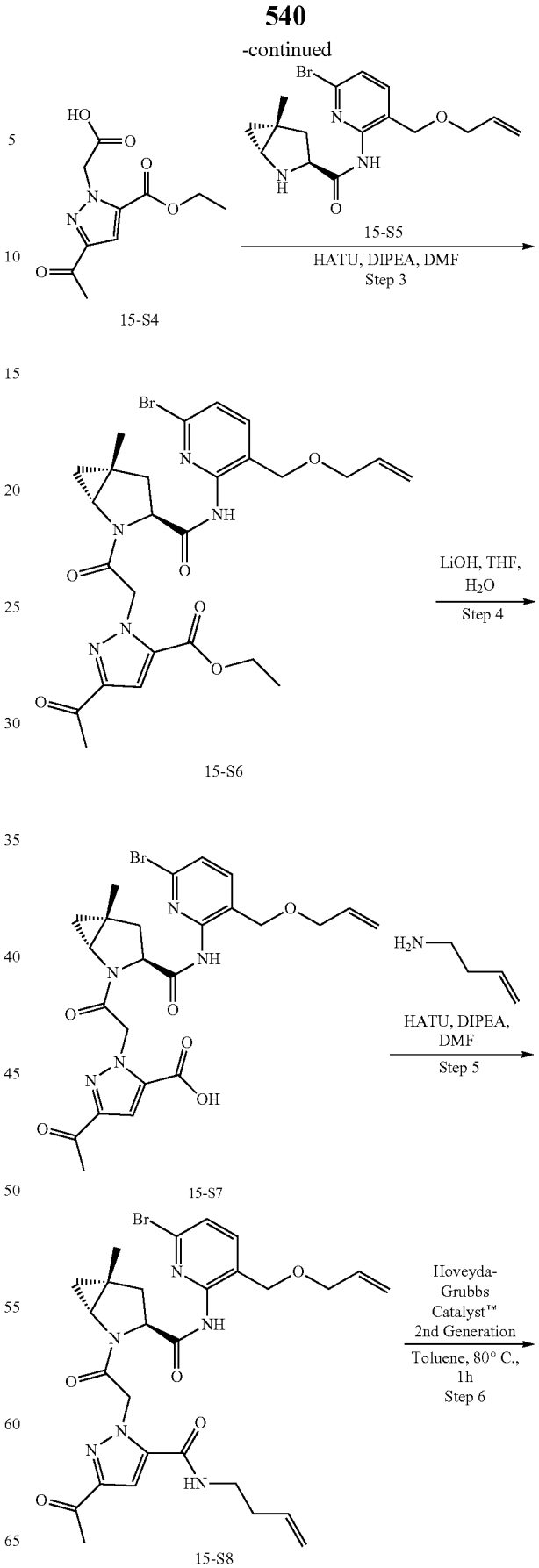

-continued

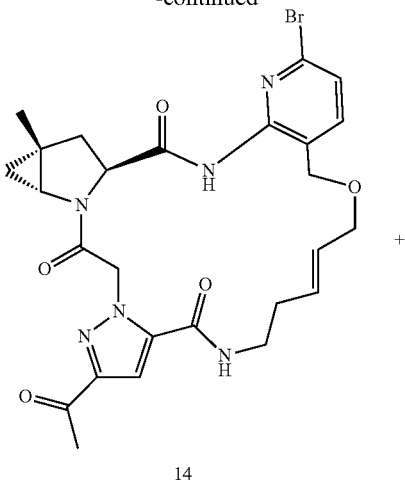

14

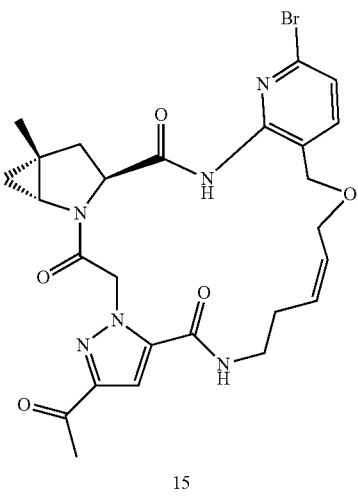

15

The above scheme and following detailed description depicts one non-limiting method for synthesizing compounds of Formula III wherein -$Y^9$-$L^5$-$Y^{10}$- is

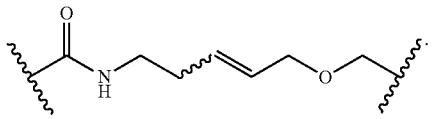 [SMILES: *COCC=CCCNC(*)=O]

The skilled artisan will recognize that related -$Y^9$-$L^5$-$Y^{10}$- moieties of different chain lengths, and stereochemistry, in addition $A^1$, $B^2$, and $C^2$ groups as described herein, can be used to afford additional compounds of the present invention.

Step 1: Ethyl 3-acetyl-1-(2-(tert-butoxy)-2-oxoethyl)-1H-pyrazole-5-carboxylate (15-S3)

To a solution of ethyl 3-acetyl-1H-pyrazole-5-carboxylate (1 equiv) in CH₃CN (10 vol) was added tert-butyl 2-bromoacetate (1.1 equiv) and potassium carbonate (1.1 equiv). The mixture was refluxed overnight under an atmosphere of argon. After cooling the reaction mixture to room temperature, the mixture was filtered through Celite and washed with CH₃CN. The filtrate was concentrated under reduced pressure and the remaining residue was purified by column chromatography on silica gel (eluted with DCM/MeOH) to afford compound 15-S3.

Step 2: 2-(3-Acetyl-5-(ethoxycarbonyl)-1H-pyrazol-1-yl)acetic acid (15-S4)

To a solution of compound 15-S3 (1 equiv) in DCM (10 vol) at 0° C. under an atmosphere of argon was added TFA (5 vol). The reaction mixture was stirred at room temperature for 3 hours and then concentrated to dryness. The remaining material was used directly in the next synthetic step without additional purification.

Step 3: Ethyl 3-acetyl-1-(2-(((1R,3S,5R)-3-((3-((allyloxy)methyl)-6-bromopyridin-2-yl)carbamoyl)-5-methyl-2-azabicyclo[3.1.0]hexan-2-yl)-2-oxoethyl)-1H-pyrazole-5-carboxylate (15-S6)

To a solution of compound 15-S4 (1 equiv) in DMF (10 vol) at 0° C. under an atmosphere of argon was added (1R,3S,5R)-N-(3-((allyloxy)methyl)-6-bromopyridin-2-yl)-5-methyl-2-azabicyclo[3.1.0]hexane-3-carboxamide (15-S5, 1 equiv), HATU (2.1 equiv), and DIPEA (5 equiv). The reaction mixture was stirred at room temperature for 3 hours and then quenched with water (30 vol). The resulting mixture was extracted with DCM. The organic layer was washed with brine, dried over anhydrous Na₂SO₄, filtered, and concentrated to dryness. The remaining residue was purified by column chromatography on silica gel (eluted with DCM/MeOH) to afford compound 15-S6.

Step 4: 3-Acetyl-1-(2-(((1R,3S,5R)-3-((3-((allyloxy)methyl)-6-bromopyridin-2-yl)carbamoyl)-5-methyl-2-azabicyclo[3.1.0]hexan-2-yl)-2-oxoethyl)-1H-pyrazole-5-carboxylic acid (15-S7)

To a solution of ethyl 3-acetyl-1-(2-(((1R,3S,5R)-3-((3-((allyloxy)methyl)-6-bromopyridin-2-yl)carbamoyl)-5-methyl-2-azab cyclo[3.1.0]hexan-2-yl)-2-oxoethyl)-1H-pyrazole-5-carboxylate (15-S6, 1 equiv) in THF/H₂O (3:1, 10 vol) was added LiOH (2.1 equiv). The reaction mixture was stirred at room temperature for 5 hours and concentrated under reduced pressure. The remaining residue was neutralized using 2N HCl before the solid was filtered and used directly in the next synthetic step without additional purification.

Step 5: (1R,3S,5R)-2-(2-(3-acetyl-5-(but-3-en-1-ylcarbamoyl)-1H-pyrazol-1-yl)acetyl)-N-(3-((allyloxy)methyl)-6-bromopyridin-2-yl)-5-methyl-2-azabicyclo[3.1.0]hexane-3-carboxamide (15-S8)

To a solution of compound 15-S7 (1 equiv) in DMF (10 vol) at 0° C. under an atmosphere of argon was added but-3-en-1-amine (5, 1 equiv), HATU (2.1 equiv), and DIPEA (5 equiv). The reaction mixture was stirred at room temperature for 3 hours. The reaction was quenched with water (30 vol), extracted with DCM, washed with brine, dried over anhydrous Na₂SO₄, filtered, and concentrated to dryness. The remaining residue was purified by column chromatography on silica gel (eluted with DCM/MeOH) to afford compound 15-S8.

Step 6: (18aS,19aR,20aR,E)-2-Acetyl-15-bromo-19a-methyl-5,6,7,10,12,17,19,19a,20,20a-decahydro-4H-cyclopropa[4,5]pyrrolo[2,1-g]pyrazolo[1,5-k]pyrido[3,2-c][1]oxa[5,8,11,14]tetraazacyclononadecine-4,18,22(18aH,23H)-trione (14) and (18aS,19aR,20aR,Z)-2-Acetyl-15-bromo-19a-methyl-5,6,7,10,12,17,19,19a,20,20a-decahydro-4H-cyclopropa[4,5]pyrrolo[2,1-g]pyrazolo[1,5-k]pyrido[3,2-c][1]oxa[5,8,11,14]tetraazacyclononadecine-4,18,22(18aH,23H)-trione (15)

To a solution of compound 15-58 (1 equiv) in toluene (200 vol) under an atmosphere of argon was added Hoveyda-Grubbs Catalyst 2nd Generation (0.05 equiv). The reaction mixture was stirred at 80° C. for 1 hour and concentrated to dryness. The remaining residue was purified by column chromatography on silica gel (eluted with DCM/MeOH) to afford compounds 14 and 15.

Compound 14: $^1$H NMR (400 MHz, Methanol-d4) δ 0.93-1.00 (m, 1H), 1.03-1.09 (m, 1H), 1.38 (s, 3H), 2.15-2.24 (m, 2H), 2.28-2.35 (m, 1H), 2.49-2.60 (m, 4H), 3.03-3.13 (m, 1H), 3.41-3.59 (m, 2H), 3.76-3.87 (m, 1H), 4.04-4.14 (m, 1H), 4.26-4.49 (m, 4H), 5.38 (d, J=16.5 Hz, 1H), 5.43-5.59 (m, 2H), 6.01 (d, J=16.4 Hz, 1H), 7.23-7.31 (m, 1H), 7.45-7.58 (m, 1H), 7.75-7.89 (m, 1H), 8.36-8.53 (m, 1H).

Compound 15: $^1$H NMR (400 MHz, Methanol-d4) δ 0.96-1.11 (m, 2H), 1.38 (s, 3H), 1.95-2.17 (m, 2H), 2.26-2.35 (m, 1H), 2.47-2.67 (m, 4H), 2.89-3.01 (m, 1H), 3.07-3.19 (m, 1H), 3.40-3.48 (m, 1H), 3.72-3.94 (m, 2H), 4.17-4.32 (m, 2H), 4.44-4.59 (m, 2H), 5.35-5.50 (m, 2H), 5.57 (d, J=16.8 Hz, 1H), 5.68-5.81 (m, 1H), 7.10-7.23 (m, 1H), 7.44 (t, J=8.9 Hz, 1H), 7.72 (dd, J=7.8, 16.0 Hz, 1H), 8.14 (s, 1H).

Scheme 10. ($3^1$R,$3^3$S,$3^5$R,Z)-$3^2$-(2-(3-Acetyl-5-(2-methylpyrimidin-5-yl)-1H-indazol-1-yl)acetyl-$6^6$-bromo-$1^1$H-8-oxo-$3^2$,5-diaza-6(2,3)-pyridina-1(1,4)-triazola-3(5,3)-bicyclo[3.1.0]hexanacyclononaphan-4-one (18)

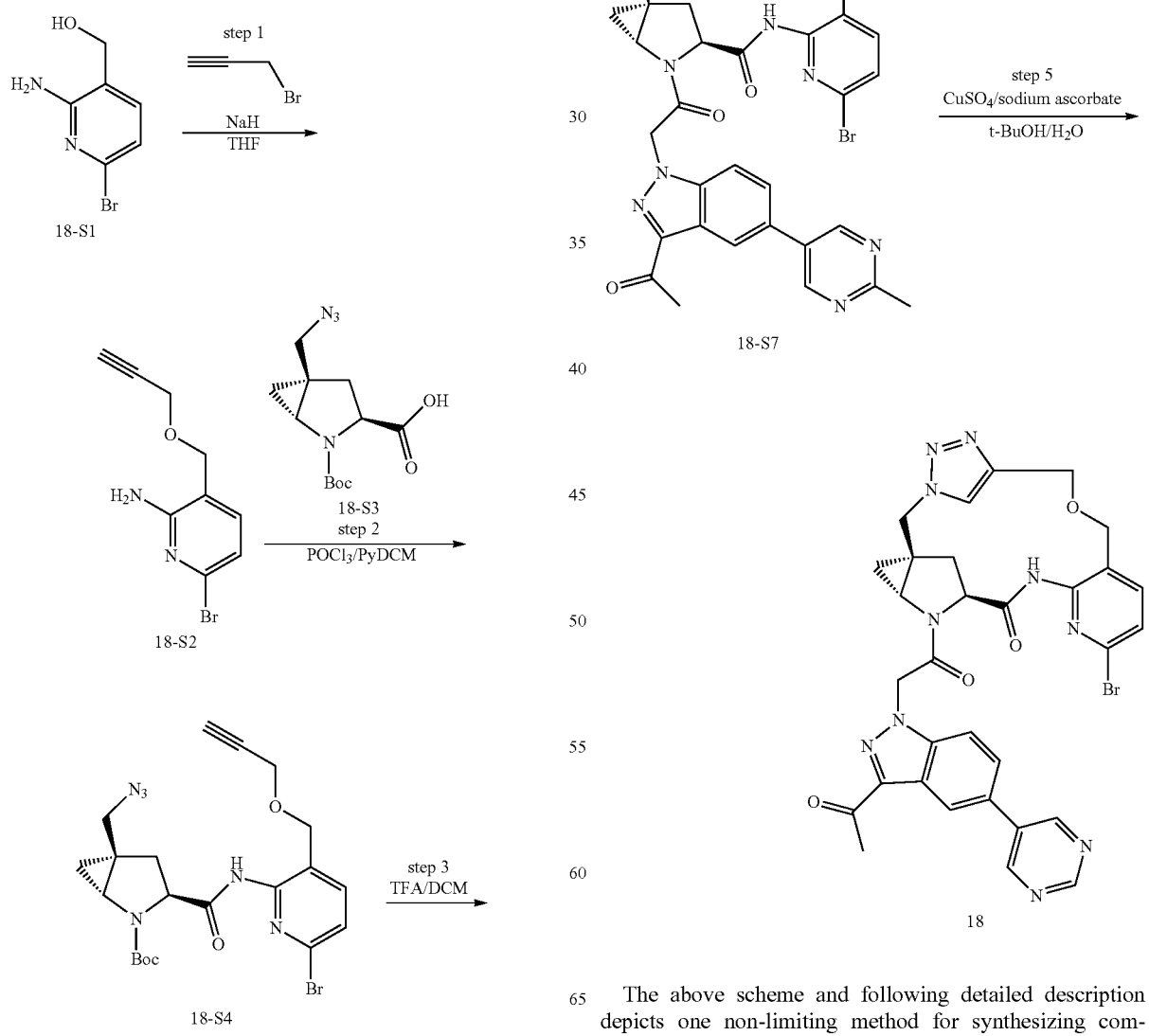

The above scheme and following detailed description depicts one non-limiting method for synthesizing compounds of Formula I wherein -$X^9$-$L^3$-$X^{10}$- is

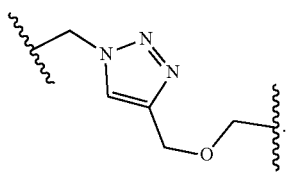 [SMILES: *COCc1cn(C*)nn1]

The skilled artisan will recognize that related -X⁹-L³-X¹⁰- moieties of different chain lengths, (including different 5-membered heteroarylene moieties), and stereochemistry, in addition to A¹, B², and C² groups described herein, can be used to afford additional compounds of the present invention.

Step 1: 6-Bromo-3-((prop-2-yn-1-yloxy)methyl)pyridin-2-amine (18-S2)

Sodium hydride (43 mg, 1.0 mmol) was added to a solution of 2-amino-6-bromopyridin-3-yl)methanol (18-S1, 110 mg, 0.54 mmol) in THF (5 mL) with stirring. The mixture was cooled in an ice bath and 3-bromo-1-propyne (80.6 mg, 0.54 mmol, 80% in toluene) was added. The mixture was stirred and allowed to warm to room temperature overnight. Aqueous NH₄Cl (10 mL) was added to quench the reaction. The mixture was extracted with EtOAc, washed with water, washed with brine, and dried over anhydrous Na₂SO₄. Solvent was evaporated, and the crude material was purified by column chromatography on silica gel with EtOAc in hexane (0-50%) as eluent to afford 6-bromo-3-((prop-2-yn-1-yloxy)methyl)pyridin-2-amine (18-S2, 36 mg) as a pale yellow solid.

Step 2: tert-Butyl (1R,3S,5R)-5-(azidomethyl)-3-((6-bromo-3-((prop-2-yn-1-yloxy)methyl)pyridin-2-yl)carbamoyl)-2-azabicyclo[3.1.0]hexane-2-carboxylate (18-S4)

Pyridine (0.06 mL, 0.75 mmol) followed by phosphorus oxychloride (0.014 mL, 0.15 mmol) was added to a mixture of (1R,3S,5R)-5-(azidomethyl)-2-(tert-butoxycarbonyl)-2-azabicyclo[3.1.0]hexane-3-carboxylic acid (18-S3, 42 mg, 0.15 mmol) and 6-bromo-3-[(prop-2-yn-1-yloxy)methyl]pyridin-2-amine (18-S2, 36 mg, 0.15 mmol) in DCM (3 mL) at 0° C. with stirring. The ice bath was removed and the reaction mixture was stirred at room temperature under argon. Once the reaction was complete (as monitored by LC-MS), aqueous NaHCO₃ was added and the mixture was extracted with DCM. The organic layer was washed with brine and dried over anhydrous Na₂SO₄. Solvent was removed under reduced pressure. The residue was purified by column chromatography on silica gel with EtOAc in hexane as eluent to afford tert-butyl (1R,3S,5R)-5-(azidomethyl)-3-((6-bromo-3-((prop-2-yn-1-yloxy)methyl)pyridin-2-yl)carbamoyl)-2-azabicyclo[3.1.0]hexane-2-carboxylate (18-S4, 63 mg).

Step 3: (1R,3S,5R)-5-(Azidomethyl)-N-(6-bromo-3-((prop-2-yn-1-yloxy)methyl)pyridin-2-yl)-2-azabicyclo[3.1.0]hexane-3-carboxamide Trifluoroacetic Acid Salt (18-S5)

tert-Butyl (1R,3S,5R)-5-(azidomethyl)-3-((6-bromo-3-((prop-2-yn-1-yloxy)methyl)pyridin-2-yl)carbamoyl)-2-azabicyclo[3.1.0]hexane-2-carboxylate (18-S4, 34 mg, 0.067 mmol) was treated with TFA (2 mL) in DCM (2 mL) at room temperature with stirring for 1 hour. Solvent was removed under reduced pressure and (1R,3S,5R)-5-(azidomethyl)-N-(6-bromo-3 -((prop-2-yn-1-yloxy)methyl)pyridin-2-yl)-2-azabicyclo[3.1.0]hexane-3-carboxamide TFA salt (18-S5) was co-evaporated with toluene (5 mL×2). The material was carried forward in the next step without additional purification.

Step 4: (1R,3S,5R)-2-(2-(3-Acetyl-5-(2-methylpyrimidin-5-yl)-1H-indazol-1-yl)acetyl)-5-(azidomethyl)-N-(6-bromo-3-((prop-2-yn-1-yloxy)methyl)pyridin-2-yl)-2-azabicyclo[3.1.0]hexane-3-carboxamide (18-S7)

O-(Benzotriazol-1-yl)-N,N,N,N-tetramethyluronium tetrafluoroborate (32 mg, 0.10 mmol) followed by diisopropylethylamine (0.058 mL, 0.335 mmol) was added to a mixture of (1R,3S,5R)-5-(azidomethyl)-N-(6-bromo-3-((prop-2-yn-1-yloxy)methyl)pyridin-2-yl)-2-azabicyclo[3.1.0]hexane-3-carboxamide TFA salt (18-S5) and 2-(3-acetyl-5-(2-methylpyrimidin-5-yl)-1H-indazol-1-yl)acetic acid (18-S6, 21 mg, 0.067 mmol) in DMF (1 mL) with stirring. After the reaction was complete, aqueous NaHCO₃ was added and the mixture was extracted with EtOAc. The organic layer was washed with water, washed with brine, and dried over anhydrous Na₂SO₄. Solvent was removed under reduced pressure and the residue was purified by column chromatography on silica gel (MeOH in DCM 0-10%) to afford (1R,3S,5R)-2-(2-(3-acetyl-5-(2-methylpyrimidin-5-yl)-1H-indazol-1-yl)acetyl)-5-(azidomethyl)-N-(6-bromo-3-((prop-2-yn-1-yloxy)methyl)pyridin-2-yl)-2-azabicyclo[3 1.0] hexane-3-carboxamide (18-S7, 14 mg).

Step 5: (3¹R,3³S,3⁵R,Z)-3²-(2-(3-Acetyl-5-(2-methylpyrimidin-5-yl)-1H-indazol-1-yl)acetyl)-6⁶-bromo-1¹H-8-oxa-3²,5-diaza-6(2,3)-pyridina-1(1,4)-triazola-3(5,3)-bicyclo[3.1.0]hexanacyclononaphan-4-one (18)

(1R,3S,5R)-2-(2-(3-acetyl-5-(2-methylpyrimidin-5-yl)-1H-indazol-1-yl)acetyl)-5-(azidomethyl)-N-(6-bromo-3-((prop-2-yn-1-yloxy)methyl)pyridin-2-yl)-2-azabicyclo[3.1.0]hexane-3-carboxamide (18-S7, 14 mg, 0.02 mmol) was dissolved in 2-methyl-2-propanol (2 mL) and water (2 mL). The solution was heated to 100° C. in the presence of CuSO4 (0.5 mg, 0.002 mmol) and sodium ascorbate (2 mg, 0.01 mmol) for 1 hour. The volatiles were evaporated and the residue was purified by column chromatography on silica gel (MeOH in DCM 0-15%) to afford (3¹R,3³S,3⁵R, Z)-3²-(2-(3 -acetyl-5-(2-methylpyrimidin-5-yl)-1H-indazol-1-yl)acetyl)-6⁶-bromo-1¹H-8-oxa-3²,5-diaza-6(2,3)-pyridina-1(1,4)-triazola-3(5,3)-bicyclo[3.1.0]hexanacyclononaphan-4-one (18, 8.7 mg) as a white solid. ¹H NMR (400 MHz, Chloroform-d) δ 8.90 (s, 2H), 8.56 (d, J=1.4 Hz, 1H), 8.44 (s, 1H), 7.88 (s, 1H), 7.69-7.61 (m, 2H), 7.57 (d, J=8.8 Hz, 1H), 7.36 (d, J=8.0 Hz, 1H), 5.52 (d, J=16.6 Hz, 1H), 5.35 (d, J=16.6 Hz, 1H), 4.90 (d, J=14.6 Hz, 1H), 4.74 (s, 3H), 4.05-3.87 (m, 2H), 3.59 (s, 1H), 2.80 (s, 4H), 2.73 (s, 3H), 2.45 (d, J=12.0 Hz, 2H), 2.33 (s, 1H), 1.38 (s, 1H), 1.12 (dd, J=3.0, 5.9 Hz, 1H). LC (method A): $t_R$=1.29 min. LC/MS (EI) m/z: [M+H]⁺699.

Scheme 11. Synthesis of (41R,43S,45R,E)-42-(2-(3-Acetyl-5-(2-methylpyrimidin-5-yl)-1H-indazol-1-yl)acetyl)-16-bromo-11-methyl-42,2,11-triaza-1(2,3)-pyridina-4(3,5)-bicyclo[3.1.0]hexanacyclotridecaphan-5-en-3,12-dione (19)

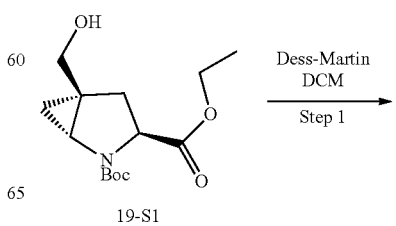

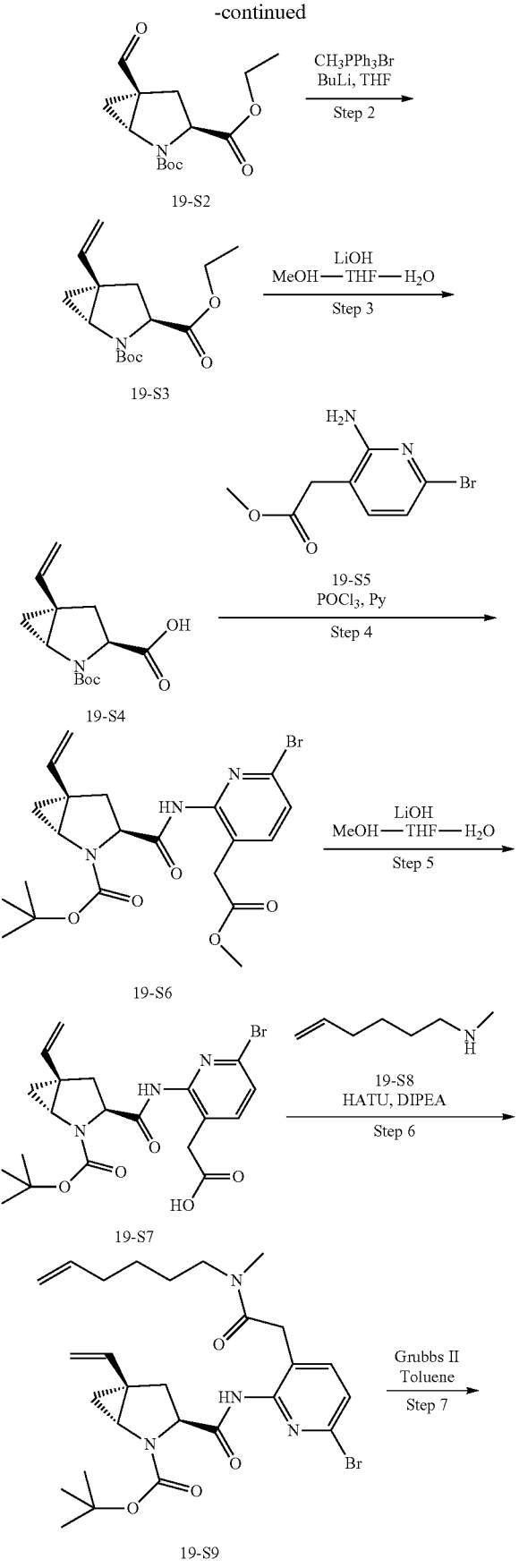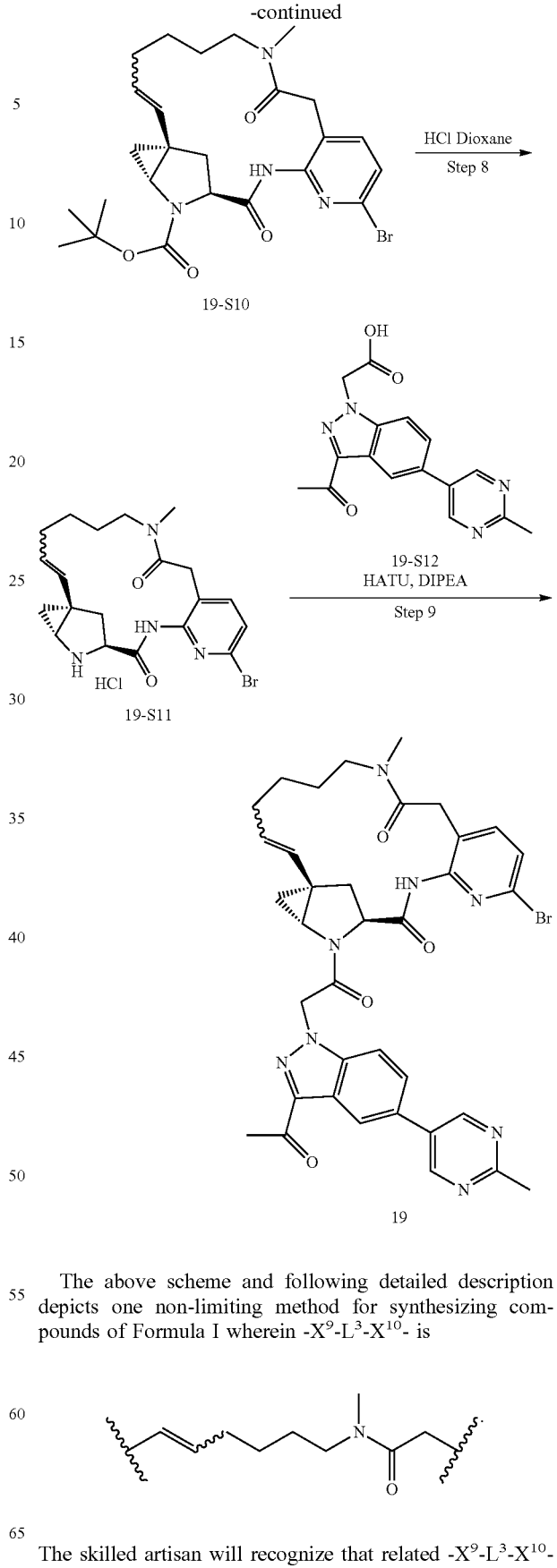
The above scheme and following detailed description depicts one non-limiting method for synthesizing compounds of Formula I wherein -X⁹-L³-X¹⁰- is
The skilled artisan will recognize that related -X⁹-L³-X¹⁰- moieties of different chain lengths, and stereochemistry, in addition A¹, B², and C² groups as described herein, can be used to afford additional compounds of the present invention.

Step 1: 2-(tert-Butyl) 3-ethyl (1R,3S,5S)-5-formyl-2-azabicyclo[3.1.0]hexane-2,3-dicarboxylate (19-S2)

To the solution of 2-(tert-butyl) 3-ethyl (1R,3S,5S)-5-(hydroxymethyl)-2-azabicyclo[3.1.0]hexane-2,3-dicarboxylate (19-S1, 67 mg, 0.23 mmol) in DCM (4 mL) was added Dess-Martin reagent (0.31 mmol) at 0° C. under argon. After stirring for 3 hours, the reaction was diluted with DCM (20 mL) and quenched with aqueous $NaHCO_3$ (10%, 15 mL). The DCM layer was collected and the aqueous phase was extracted with DCM (15 mL×2). The DCM phase was combined, washed with brine, and dried over magnesium sulfate. The solution was filtered and concentrated to afford crude product (19-S2, 62 mg) that was carried forward in the next step without further purification.

Step 2: 2-(tert-Butyl) 3-ethyl (1R,3S,5R)-5-vinyl-2-azabicyclo[3.1.0]hexane-2,3-dicarboxylate (19-S3)

To the suspension of methyltriphenylphosphonium bromide (111 mg, 0.31 mmol) in 5 mL dry THF BuLi (1.6M in hexane, 0.31 mmol) was added dropwise at 0° C. under argon. The mixture was stirred for 1 hour before a solution of aldehyde (19-S2, 62 mg) in THF (2 mL) was added dropwise. The mixture was warmed to room temperature and stirred overnight. The reaction was quenched with water (10 ml) and extracted with ethyl acetate (15 mL×3). The organic phases were combined, washed with brine, and dried over magnesium sulfate. The solution was filtered, concentrated and purified to afford 31mg of 19-S3. $^1$H NMR (400 MHz, $CDCl_3$) δ 0.89-0.94 (m, 1H), 1.04-1.08 (m, 1H), 1.28 (t, J=7.2 Hz, 3H), 1.44 (s, 9H), 2.32 (dd, J=13.2, 7.0 Hz, 1H), 2.43 (dd, J=13.1, 8.8 Hz, 1H), 3.43 (s, 1H), 3.97-4.09 (m, 1H), 4.16-4.26 (m, 2H), 4.99 (d, J=7.8 Hz, 1H), 5.02 (s, 1H), 5.70 (dd, J=17.0, 10.7 Hz, 1H) ppm.

Step 3: (1R,3S,5R)-2-(tert-Butoxycarbonyl)-5-vinyl-2-azabicyclo[3.1.0]hexane-3-carboxylic acid (19-S4)

Compound 19-S3 (171 mg, 0.42 mmol) was dissolved in a mixture of $CH_3OH$-THF-$H_2O$ (2 mL-2 mL-2 mL) and treated with LiOH (24 mg). The reaction mixture was stirred overnight at room temperature. The volatiles were evaporated under reduced pressure and the remaining residue was acidified with 10% citric acid (10 mL). The mixture was extracted with ethyl acetate (15 mL×3), the combined organic layers were washed with water, washed with brine, and dried over $MgSO_4$. The solution was filtered and the filtrate was concentrated. The residue (19-S4, 101.4 mg) was dried and carried forward in the next step.

Step 4: tert-Butyl (1R,3S,5R)-3-((6-bromo-3-(2-methoxy-2-oxoethyl)pyridin-2-yl)carbamoyl)-5-vinyl-2-azabicyclo[3.1.0]hexane-2-carboxylate (19-S6)

A solution of (1R,3S,5R)-2-(tert-butoxycarbonyl)-5-vinyl-2-azabicyclo[3.1.0]hexane-3-carboxylic acid (19-S4, 101 mg, 0.40 mmol, 1.equiv) and methyl 2-(2-amino-6-bromopyridin-3-yl)acetate (19-S5, 103 mg, 0.42 mmol) in DCM (10 mL) was cooled to 0-5° C. before pyridine (5 equiv) was added followed by the dropwise addition of $POCl_3$ (2 equiv) under an atmosphere of argon. The reaction mixture was warmed to room temperature and stirred overnight. The reaction was diluted with DCM (10 mL) and neutralized with saturated aqueous NaHCO3 solution (10 mL). The aqueous layer was extracted with DCM (2×10 mL). The combined organic layers were washed with brine (10 mL), dried over $Na_2SO_4$, and concentrated to dryness. The residue was purified by column chromatography on silica gel (eluted by 5% MeOH in DCM gradient) to afford 19-S6 (126 mg, 66% yield).

Step 5: 2-(6-Bromo-2-((1R,3S,5R)-2-(tert-butoxycarbonyl)-5-vinyl-2-azabicyclo[3.1.0]hexane-3-carboxamido)pyridin-3-yl)acetic acid (19-S7)

Compound 19-S6 (126 mg, 0.26 mmol) was dissolved in a mixture of $CH_3OH$-THF-$H_2O$ (2 mL-2 mL-2 mL) and treated with LiOH (24 mg). The reaction mixture was stirred overnight at room temperature. The volatiles were evaporated under reduced pressure and the remaining residue was acidified with 10% citric acid (10 mL). The mixture was extracted with ethyl acetate (15 mL×3), the combined organic layers were washed with water, washed with brine, and dried over $MgSO_4$. The solution was filtered and the filtrate was concentrated. The residue (19-S7, 114 mg) was dried and carried forward in the next step.

Step 6: tert-Butyl (1R,3S,5R)-3-((6-bromo-3-(2-(hex-5-en-1-yl(methyl)amino)-2-oxoethyl)pyridin-2-yl)carbamoyl)-5-vinyl-2-azabicyclo[3.1.0]hexane-2-carboxylate (19-S9)

To a solution of 2-(6-bromo-2-((1R,3S,5R)-2-(tert-butoxycarbonyl)-5-vinyl-2-azabicyclo[3.1.0]hexane-3-carboxamido)pyridin-3-yl)acetic acid (19-S7, 36.5 mg, 0.078 mmol), N-methylhex-5-en-1-amine (19-S8, 11.7 mg, 0.078 mmol) and HATU (35.6 mg, 0.094 mmol) in DMF (4.0 mL), DIPEA (5 equiv) was added at 0° C. under an atmosphere of argon. The reaction mixture was stirred at room temperature for 3 hours. After completion of the reaction, the reaction mixture was diluted with EtOAc (20 mL) and water (10 mL) and the aqueous layers were extracted with EtOAC (15 mL). The combined organic layers were washed with saturated aqueous $NaHCO_3$ (15 mL) and brine, dried over anhydrous $Na_2SO_4$, filtered, and concentrated to dryness. The residue was purified by column chromatography on silica gel to afford 19-29 (22 mg).

Step 7: tert-Butyl (41R,43S,45R,E)-16-bromo-11-methyl-3,12-dioxo-42,2,11-triaza-1(2,3)-pyridina-4(3,5)-bicyclo[3.1.0]hexanacyclotridecaphan-5-ene-42-carboxylate (19-S10)

tert-Butyl (1R,3S,5R)-3-((6-bromo-3-(2-(hex-5-en-1-yl(methyl)amino)-2-oxoethyl)pyridin-2-yl)carbamoyl)-5-vinyl-2-azabicyclo[3.1.0]hexane-2-carboxylate (19-S9, 22 mg, 0.039 mmol) in toluene (5.5 mL) was treated with Hoveyda-Grubbs catalyst $2^{nd}$ generation (2.5 mg). The reaction was allowed to stir overnight at room temperature under argon before additional catalyst (1.0 mg) was added and the mixture was stirred for 4 hours. Solvent was removed under reduced pressure and the residue was purified by column chromatography on silica gel with MeOH in DCM (0-100%) as eluent to afford 19-S10 (9.4 mg).

Step 8: (41R,43S,45R,E)-16-Bromo-11-methyl-42,2,11-triaza-1(2,3)-pyridina-4(3,5)-bicyclo[3.1.0]hexanacyclotridecaphan-5-ene-3,12-dione hydrochloride (19-S11)

tert-Butyl (41R,43S,45R,E)-16-bromo-11-methyl-3,12-dioxo-42,2,11-triaza-1(2,3)-pyridina-4(3,5)-bicyclo[3.1.0] hexanacyclotridecaphan-5-ene-42-carboxylate (19-S10, 9.4 mg, 0.018 mmol) was taken up in 4N HCl dioxane (1.0 mL) and the resulting reaction mixture was stirred at room temperature for 3 hours. After completion of the reaction monitored (as monitored by HPLC), the solvent was removed under reduced pressure. The remaining residue (19-S11, 8.2 mg) was used directly in the next step without further purification.

Step 9: (41R,43S,45R,E)-42-(2-(3-Acetyl-5-(2-methylpyrimidin-5-yl)-1H-indazol-1-yl)acetyl)-16-bromo-11-methyl-42,2,11-triaza-1(2,3)-pyridina-4(3,5)-bicyclo[3.1.0] hexanacyclotridecaphan-5-ene-3,12-dione (19)

To the solution of (41R,43S,45R,E)-16-bromo-11-methyl-42,2,11-triaza-1(2,3)-pyridina-4(3,5)-bicyclo[3.1.0] hexanacyclotridecaphan-5-ene-3,12-dione hydrochloride (19-S11, 8.2 mg, 0.017 mmol, 1 equiv.), [3-acetyl-5-(2-methylpyrimidin-5-yl)indazol-1-yl]acetic acid (19-S12, 5.96 mg, 0.019 mmol, 1.1 equiv.) in DMF (2.0 mL), HATU (1.5 eqiv, 10.3 mg, 0.27 mmol) was added followed by the dropwise addition of DIPEA (4.0 equiv) at room temperature. The mixture was stirred for 1 hour at room temperature and the volatiles were evaporated. The residue was diluted with 10% sodium carbonate (50 mL) and extracted with ethyl acetate. The combined organic solution was successively washed with water and brine and dried over MgSO$_4$. The solution was filtered and the solvent was removed. The residue was purified by column chromatography on silica gel (eluted by 5% MeOH in DCM gradient) to afford 19 (4.5 mg). $^1$H NMR (400 MHz, DMSO-d$_6$, 300 K): (major rotamer) δ 1.32 (t, J=5.4 Hz, 1H), 1.37-1.56 (m, 5H), 1.95-2.04 (m, 1H), 2.10-2.19 (m, 1H), 2.42-2.48(m, 2H), 2.65 (s, 3H), 2.66-2.67 (m, 2H), 2.69 (s, 3H), 2.87 (s, 3H), 3.52 (d, J=17.4 Hz, 1H), 3.66 (d, J=17.5 Hz, 1H), 3.78-3.85 (m, 1H), 4.75 (t, J=5.7 Hz, 1H), 5.40-5.55 (m, 2H), 5.80 (d, J=17.4Hz, 1H), 5.90 (d, J=17.4 Hz, 1H), 7.49 (d, J=8.1 Hz, 1H), 7.56 (d, J=8.1 Hz, 1H), 7.87 (s, 2H), 8.44 (s, 1H), 9.04 (s, 2H), 10.33 (s, 1H) ppm. LC (method A): t$_R$=1.87 min. LC/MS (0) m/z: [M+H]$^+$727.04.

Scheme 12: Synthesis of (41R,43S,45R,Z)-13-Acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotetradecaphan-11-ene-43-carboxamide (20) and (41R,43S,45R,Z)-13-Acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide (21)

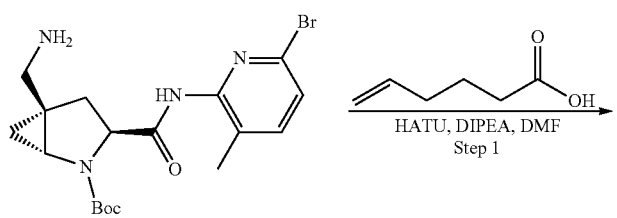

21-S1

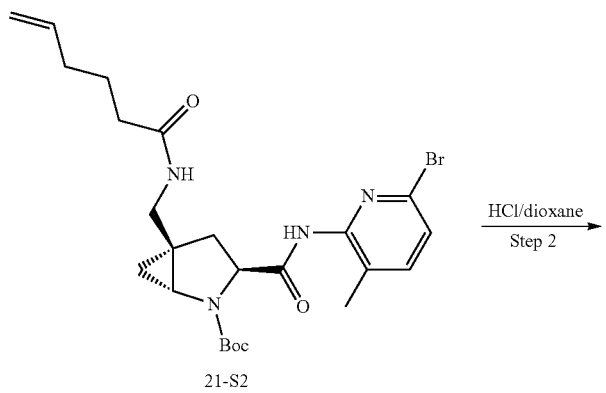

21-S2

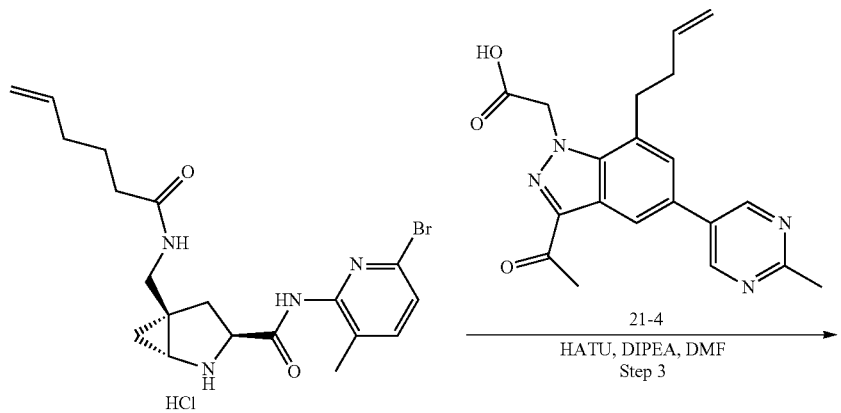

21-S3

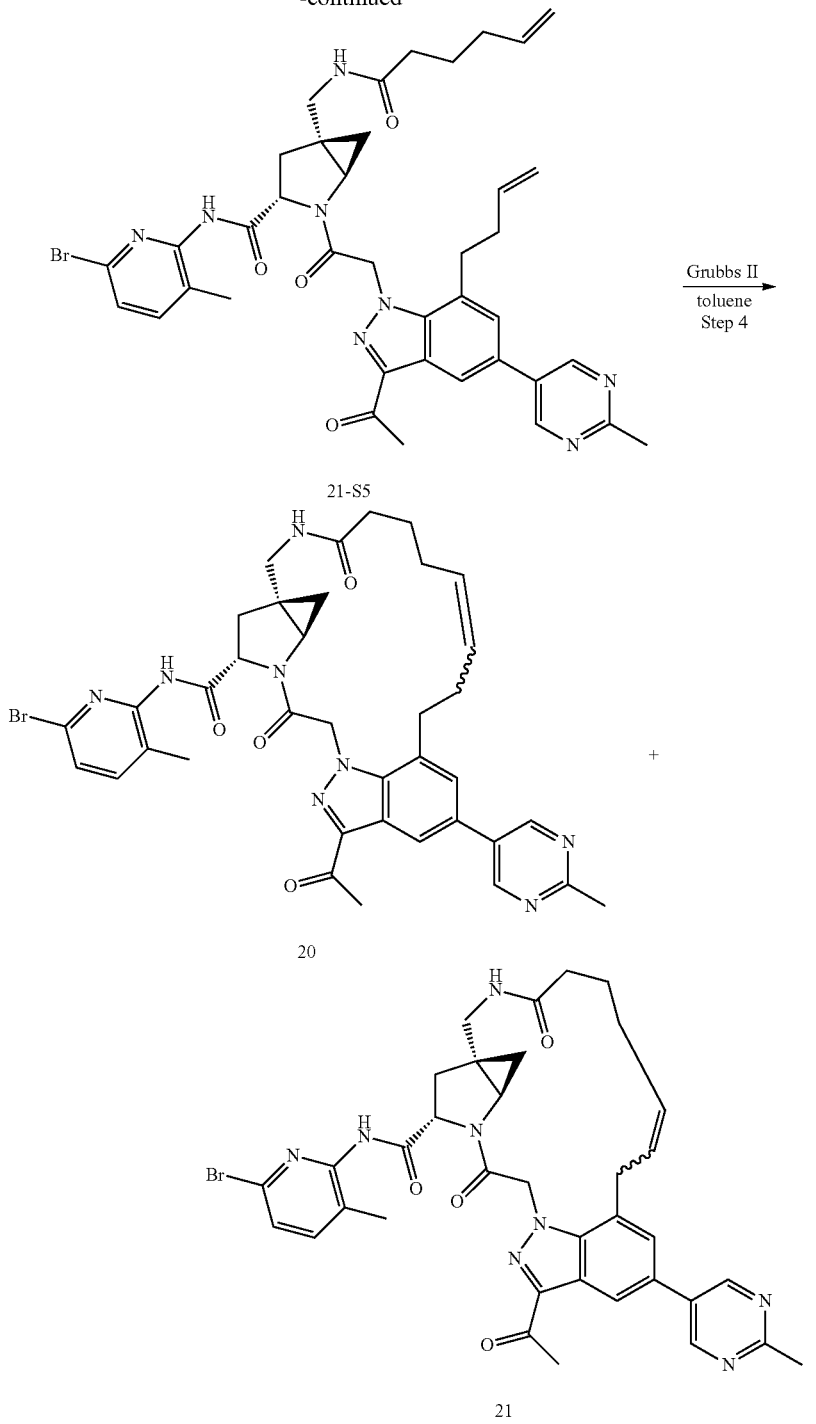

The above scheme and following detailed description depicts one non-limiting method for synthesizing compounds of Formula II wherein -X⁹-L³-X¹⁰- is

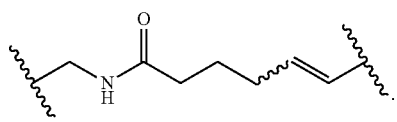 [SMILES: *C=CCCCC(=O)NC*]

The skilled artisan will recognize that related -X⁹-L³-X¹⁰- moieties of different chain lengths, and stereochemistry, in addition A¹, B², and C² groups as described herein, can be used to afford additional compounds of the present invention.

Step 1: (1R,3S,5R)-tert-Butyl 3-(6-bromo-3-methylpyridin-2-ylcarbamoyl)-5-(hex-5-enamidomethyl)-2-azabicyclo[3.1.0]hexane-2-carboxylate (21-S2)

To a mixture of 21-51 (90 mg, 0.22 mmol), hex-5-enoic acid (30 mg, 0.264 mmol) and HATU (126 mg, 0.33 mmol)

in DMF (2 mL) was added DIPEA (143 mg, 1.1 mmol). The reaction was stirred at room temperature for 1 hour. The mixture was then diluted with EtOAc, washed with 10% aqueous LiCl solution and brine, dried, and concentrated to afford crude product. The residue was purified by a silica gel column (eluted with DCM:EtOAc=4:1) to afford 21-S2 (82 mg, 71.7% yield) as a colorless oil. LC/MS (ESI) m/z: 521/523 (M+H)$^+$.

Step 2: (1R,3S,5R)-N-(6-Bromo-3-methylpyridin-2-yl)-5-(hex-5-enamidomethyl)-2-azabicyclo[3.1.0]hexane-3-carboxamide Hydrochloride (21-S3)

A solution of 21-S2 (82 mg, 0.157 mmol) in HCl/dioxane solution (2 mL, 4 M) was stirred at 0° C. for 1 hour under N$_2$ atmosphere. The reaction mixture was concentrated to dryness and the residue was washed with ether. The residue was dried under vacuum to afford crude 21-S3 (70 mg, 97.4% yield) as a white solid. The crude product was carried forward in the next step without additional purification. LC/MS (ESI) m/z: 421/423 (M+H)$^+$.

Step 3: (1R,3S,5R)-2-(2-(3-Acetyl-7-(but-3-enyl)-5-(2-methylpyrimidin-5-yl)-1H-indazol-1-yl)acetyl)-N-(6-bromo-3-methylpyridin-2-yl)-5-(hex-5-enamidomethyl)-2-azabicyclo[3.1.0]hexane-3-carboxamide (21-S5)

To a mixture of 21-S3 (70 mg, 0.153 mmol), 21-S4 (58 mg, 0.157 mmol) and HATU (90 mg, 0.24 mmol) in DMF (2 mL) was added DIPEA (103 mg, 0.79 mmol). The reaction mixture was stirred at room temperature for 1 hour. The mixture was then diluted with EtOAc and washed with 10% aqueous LiCl solution and brine, dried, and concentrated to afford crude product that was purified by silica gel column (eluted with DCM:MeOH=50:1) to afford 19-S5 (70 mg, 58.2% yield) as brown solid. $^1$H-NMR (400 MHz, DMSO-d$_6$) δ 10.30 (s, 1H), 8.97-9.10 (m, 2H), 8.34-8.42 (m, 1H), 7.92-8.02 (m, 1H), 7.54-7.69 (m, 2H), 7.45 (d, J=7.9 Hz, 1H), 5.64-5.95 (m, 4H), 4.88-5.19 (m, 4H), 4.38-4.48 (m, 1H), 3.84-4.01 (m, 1H), 3.57-3.73 (m, 2H), 2.69 (s, 3H), 2.65 (s, 3H), 2.17-2.24 (m, 1H), 2.08-2.15 (m, 2H), 2.05 (s, 3H), 1.93-2.02 (m, 2H), 1.63-1.70 (m, 1H), 1.54-1.62 (m, 2H), 1.48 (d, J=6.8 Hz, 1H), 1.42 (d, J=6.8 Hz, 1H), 1.16-1.27 (m, 2H), 0.94-1.00 (m, 1H), 0.87-0.93 (m, 1H).LC/MS (ESI) m/z: 767/769 (M+H)$^+$.

Step 4: (41R,43S,45R,Z)-13-Acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotetradecaphan-11-ene-43-carboxamide (20) and (41R,43S,45R,Z)-13-Acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide (21)

To a solution of 19-S5 (27 mg, 0.035 mmol) in anhydrous toluene (5 mL) was added Grubbs II catalyst (5 mg, 0.00525 mmol). The resulting mixture was stirred at 80° C. for 2.5 hours under N$_2$ atmosphere. The mixture was then cooled and diluted with water (20 mL) and extracted with EtOAc/MeOH (30:1). The organic phase was washed with brine, dried over anhydrous Na$_2$SO$_4$, filtered, and concentrated to afford crude product. The residue was purified by pre-TLC (eluted with DCM:MeOH=20:1) and further purified via pre-HPLC to afford Compound 20 (3 mg, 11.6% yield) and Compound 21 (4 mg, 15.8% yield) as white solids.

Compound 20: $^1$H-NMR (400 MHz, CD$_3$OD) δ 9.00 (s, 2H), 8.44-8.49 (m, 1H), 7.67-7.75 (m, 1H), 7.47-7.57 (m, 1H), 7.34-7.42 (m, 1H), 5.62-5.81 (m, 2H), 5.46-5.54 (m, 1H), 5.31-5.38 (m, 1H), 4.41-4.47 (m, 1H), 4.15-4.22 (m, 1H), 3.54-3.58 (m, 1H), 3.45-3.53 (m, 1H), 2.75 (s, 3H), 2.68 (s, 3H), 2.46-2.60 (m, 3H), 2.26-2.42 (m, 3H), 2.12 (s, 3H), 1.91-1.97 (m, 1H), 1.63-1.72 (m, 1H), 1.32-1.48 (m, 4H), 1.23-1.30 (m, 1H), 1.11-1.16 (m, 1H). LC/MS (ESI) m/z: 739/741 (M+H)$^+$.

Compound 21: $^1$H-NMR (400 MHz, CD$_3$OD) δ 8.99 (s, 2H), 8.44-8.47 (m, 1H), 7.53-7.59 (m, 1H), 7.47-7.52 (m, 1H), 7.32-7.39 (m, 1H), 5.58-5.88 (m, 2H), 5.45-5.57 (m, 2H), 4.37-4.42 (m, 1H), 3.98-4.06 (m, 1H), 3.64-3.71 (m, 1H), 3.43-3.49 (m, 1H), 2.74 (s, 3H), 2.68 (s, 3H), 2.51-2.58 (m, 2H), 2.41-2.47 (m, 1H), 2.31-2.39 (m, 2H), 2.15-2.24 (m, 1H), 2.02 (s, 3H), 1.90-1.96 (m, 1H), 1.72-1.78 (m, 1H), 1.35-1.41 (m, 1H), 1.26-1.34 (m, 1H), 1.19-1.25 (m, 1H), 1.10-1.14 (m, 1H). LC/MS (ESI) m/z: 725/727 (M+H)$^+$.

Scheme 13. Synthesis of N-((41R,43S,45R,8S)-42-(2-(3-Acetyl-5-(2-methylpyrimidin-5-yl)-1H-indazol-1-yl)acetyl)-16-bromo-3,7-dioxo-13-oxo-42,2,6-triaza-1(2,3)-pyridina-4(3,5)-bicyclo[3.1.0]hexanacyclotetradecaphan-10-en-8-yl)acetamide (22)

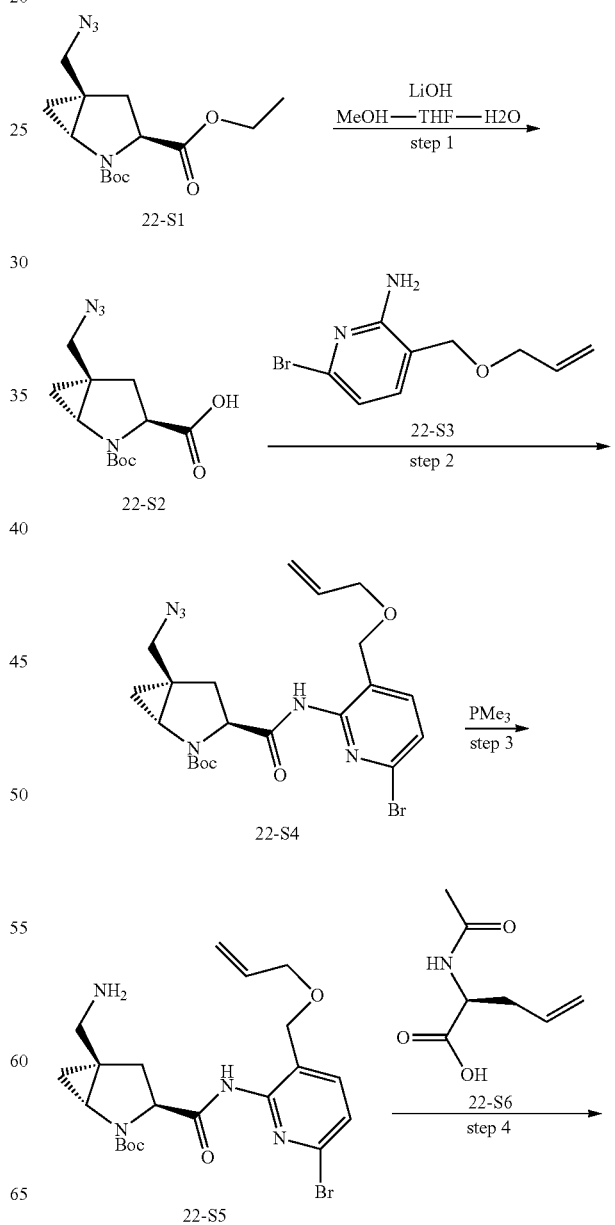

557
-continued

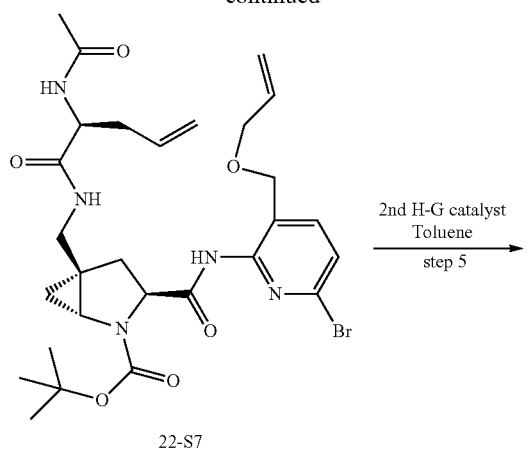

22-S7

2nd H-G catalyst
Toluene
step 5

558
-continued

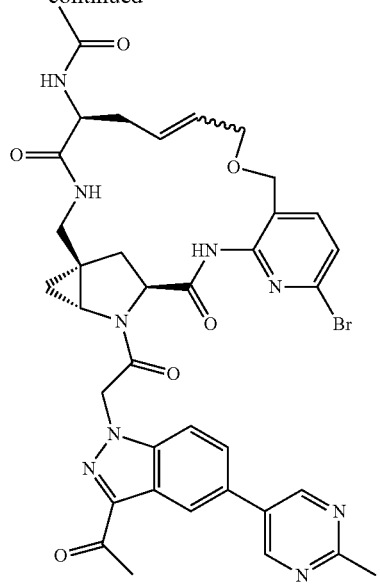

22

The above scheme and following detailed description depicts one non-limiting method for synthesizing compounds of Formula I wherein -$X^9$-$L^3$-$X^{10}$- is

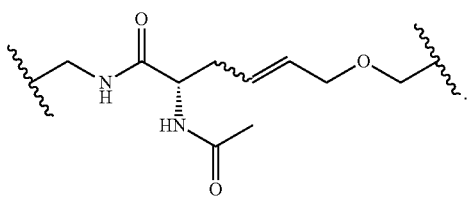 [SMILES: *CNC(=O)[C@H](CC=CCOC*)NC(C)=O]

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: (1R,3S,5R)-5-(Azidomethyl)-2-(tert-butoxycarbonyl)-2-azabicyclo[3.1.0]hexane-3-carboxylic acid (22-S2)

2-(tert-Butyl) 3-ethyl (1R,3S,5R)-5-(azidomethyl)-2-azabicyclo[3.1.0]hexane-2,3-dicarboxylate (22-S1, 92 mg, 0.296 mmol) was treated with LiOH (14 mg) in a mixed solvent of THF-MeOH-water (2 mL-2 ml-2 mL) at room temperature overnight. The volatiles were evaporated and the residue was acidified with 10% aqueous citric acid (5 mL) and extracted with EtOAc. The organic layer was washed with brine, dried over anhydrous $Na_2SO_4$, and the solvent was removed under reduced pressure to afford (1R,3S,5R)-5-(azidomethyl)-2-(tert-butoxycarbonyl)-2-azabicyclo[3.1.0]hexane-3-carboxylic acid (22-S2, 78 mg).

Step 2: tert-Butyl (1R,3S,5R)-3-((3-((allyloxy)methyl)-6-bromopyridin-2-yl)carbamoyl)-5-(azidomethyl)-2-azabicyclo[3.1.0]hexane-2-carboxylate (22-S4)

Into a mixture of (1R,3S,5R)-5-(azidomethyl)-2-(tert-butoxycarbonyl)-2-azabicyclo[3.1.0]hexane-3-carboxylic acid (22-S2, 78 mg, 0.276 mmol), 3-((allyloxy)methyl)-6-bromopyridin-2-amine (22-S3, 74 mg, 0.305 mmol), pyridine (0.5 mL, 6.0 mmol) in DCM (5.0 mL) was added $POCl_3$ (0.02 mL, 2.0 mmol) at 0° C. under an atmosphere of argon.

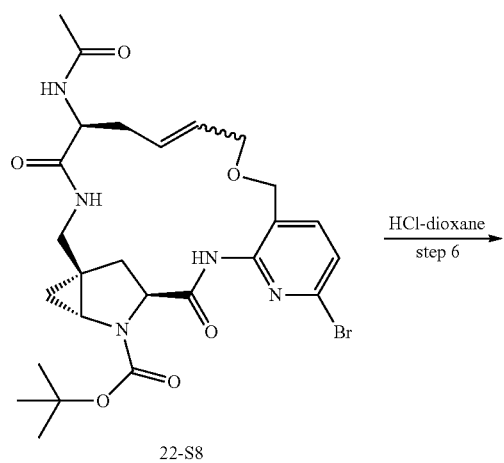

22-S8

HCl-dioxane
step 6

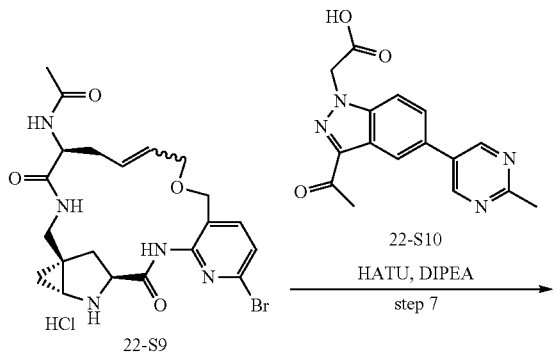

22-S9

22-S10

HATU, DIPEA
step 7

The reaction mixture was stirred at room temperature for 6 hours. Water was added and the mixture was extracted with DCM. The organic layer was washed with brine, dried over anhydrous Na$_2$SO$_4$, and the solvent was removed under reduced pressure. The residue was purified by column chromatography on silica gel with MeOH in DCM (0-10%) as the eluent to afford tert-butyl (3S)-3-((3-((allyloxy)methyl)-6-bromopyridin-2-yl)carbamoyl)-5-(azidomethyl)-2-azabicyclo[3.1.0]hexane-2-carboxylate (22-S4, 88 mg) as a yellow oil.

Step 3: tert-Butyl (1R,3S,5R)-3-((3-((allyloxy)methyl)-6-bromopyridin-2-yl)carbamoyl)-5-(aminomethyl)-2-azabicyclo[3.1.0]hexane-2-carboxylate (22-S5)

tert-Butyl (1R,3S,5R)-3-((3-((allyloxy)methyl)-6-bromopyridin-2-yl)carbamoyl)-5-(azidomethyl)-2-azabicyclo[3.1.0]hexane-2-carboxylate (22-S4, 88 mg, 0.173 mmol) was treated with trimethylphosphane (1.0 M in THF, 0.45 mL, 0.45 mmol) in THF (10 mL) in the presence of water (0.0081 mL, 0.45 mmol) at 50° C. for 5 hours. The reaction was cooled to room temperature and the volatiles were evaporated. The residue was diluted with EtOAc (30 mL) and water (20 mL). The EtOAc layer was collected and the aqueous layer was extracted with EtOAc (20 mL×3). The combined organic layers were washed with brine, dried over anhydrous Na$_2$SO$_4$, and the solvent was removed under reduced pressure. The residue was purified by column chromatography on silica gel with MeOH in DCM (0-30%) as the eluent to afford 22-S5 (52 mg).

Step 4: tert-Butyl (1R,3S,5R)-5-((((S)-2-acetamidopent-4-enamido)methyl)-3-((3-((allyloxy)methyl)-6-bromopyridin-2-yl)carbamoyl)-2-azabicyclo[3.1.0]hexane-2-carboxylate (22-S7)

To the solution of tert-butyl (1R,3S,5R)-5-(aminomethyl)-3-({6-bromo-3-[(prop-2-en-1-yloxy)methyl]pyridin-2-yl}carbamoyl)-2-azabicyclo[3.1.0]hexane-2-carboxylate (22-S5, 52 mg, 0.108 mmol), (2S)-2-acetamidopent-4-enoic acid (22-S6, 0.025 g, 0.162 mmol) in DMF (2.0 mL), HATU (61.6 mg, 0.162 mmol) was added followed by the dropwise addition of DIEA (5.0 eq) at 0° C. The mixture was stirred for 1 hour at 0° C. and then warmed to room temperature overnight. An additional batch of 22-S6 (25 mg), HATU (62 mg) and DIPEA was added before the reaction was stirred for 2 hours at room temperature. The volatiles were evaporated and the residue was diluted with 10% sodium carbonate (50 mL) and extracted with ethyl acetate. The combined organic layers was successively washed with water and brine and dried over MgSO$_4$. The solution was filtered and the solvent was removed. The residue was purified by column chromatography on silica gel with MeOH in DCM (0-10%) as the eluent to afford 22-S7 (27.5 mg).

Step 5: tert-Butyl (41R,43S,45R,8S)-8-acetamido-16-bromo-3,7-dioxo-13-oxa-42,2,6-triaza-1(2,3)-pyridina-4(3,5)-bicyclo[3.1.0]hexanacyclotetradecaphan-10-ene-42-carboxylate (22-S8)

A solution of tert-butyl (1R,3S,5R)-5-(((S)-2-acetamidopent-4-enamido)methyl)-3-((3-((allyloxy)methyl)-6-bromopyridin-2-yl)carbamoyl)-2-azabicyclo[3.1.0]hexane-2-carboxylate (22-S7, 26 mg, 0.042 mmol) in toluene (5.0 mL) was degassed and refilled with argon three times and the solution was treated with Hoveyda-Grubbs catalyst 2$^{nd}$ generation (3.5 mg) at 55° C. under argon for 3 hours. The reaction was cooled to room temperature and the volatiles were removed under reduced pressure. The residue was purified by column chromatography on silica gel with MeOH in DCM (0-10%) as the eluent to afford 22-S8 (13.3 mg).

Step 6: N-((41R,43S,45R,8S)-16-Bromo-3,7-dioxo-13-oxa-42,2,6-triaza-1(2,3)-pyridina-4(3,5)-bicyclo[3.1.0]hexanacyclotetradecaphan-10-en-8-yl)acetamide hydrochloride (22-S9)

tert-Butyl (41R,43S,45R,8S)-8-acetamido-16-bromo-3,7-dioxo-13-oxa-42,2,6-triaza-1(2,3)-pyridina-4(3,5)-bicyclo[3.1.0]hexanacyclotetradecaphan-10-ene-42-carboxylate (22-S8, 12.8 mg, 0.022 mmol) was taken up in 4N HCl dioxane (2.0 mL) and the resulting reaction mixture was stirred at room temperature for 2 hours. After completion of the reaction (as monitored by HPLC), the solvent was removed under reduced pressure. The remaining residue 22-S9 was used directly in the next step without additional purification.

Step 7: N-((41R,43S,45R,8S)-42-(2-(3-Acetyl-5-(2-methylpyrimidin-5-yl)-1H-indazol-1-yl)acetyl)-16-bromo-3,7-dioxo-13-oxa-42,2,6-triaza-1(2,3)-pyridina-4(3,5)-bicyclo[3.1.0]hexanacyclotetradecaphan-10-en-8-yl)acetamide (22)

To a solution of [3-acetyl-5-(2-methylpyrimidin-5-yl)indazol-1-yl]acetic acid (22-S10), 8.192 mg, 0.026 mmol), N-((41R,43S,45R,8S)-16-bromo-3,7-dioxo-13-oxa-42,2,6-triaza-1(2,3)-pyridina-4(3,5)-bicyclo[3.1.0]hexanacyclotetradecaphan-10-en-8-yl)acetamide hydrochloride (22-S9, 11.6 mg, 0.022 mmol) in DMF (2.0 mL), HATU (1.5 equiv, 12.5 mg, 0.033 mmol) was added followed by the dropwise addition of DIEA (5.0 equiv) at room temperature. The mixture was stirred for 1 hour at room temperature. The volatiles were then evaporated and the residue was diluted with 10% sodium carbonate (50 mL) and extracted with ethyl acetate. The combined organic layers was successively washed with water and brine and dried over MgSO$_4$. The solution was filtered and the solvent was removed. The residue was purified by column chromatography on silica gel with MeOH in DCM (0-10%) as the eluent to afford 22 (6.7 mg). LC (method A): $t_R$=1.37 min. LC/MS (EI) m/z: [M+H]$^+$786.

Scheme 14. Synthesis of (41R,43S,45S)-13-Acetyl-N-(6-bromo-3-methylpyridin-2-yl)-15-(2-methylpyrimidin-5-yl)-3-oxo-11H-6-oxo-42-aza-1(7)-indazola-(2,5)-bicyclo[3.1.0]hexanacyclotetradecaphane-43-carboxamide (23) and (41R,43S,45S)-13-Acetyl-N-(6-bromo-3-methylpyridin-2-yl)-15-(2-methylpyrimidin-5-yl)-3-oxo-11H-6-oxa-42-aza-1(7)-indazola-(2,5)-bicyclo[3.1.0]hexanacyclopentadecaphane-43-carboxamide (24)

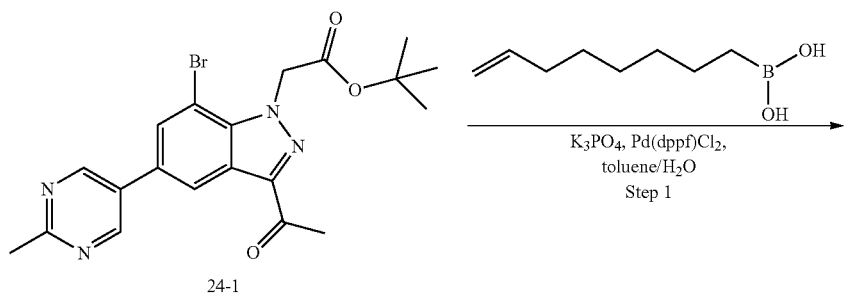

24-1

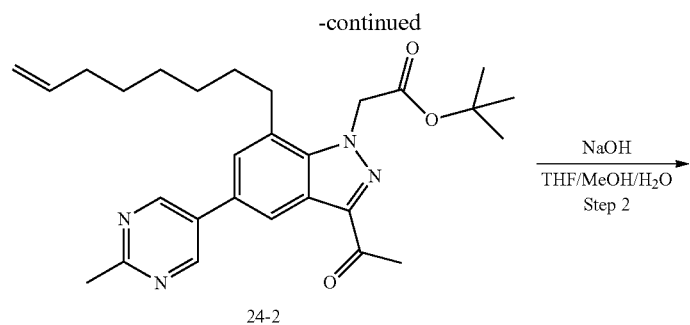
24-2
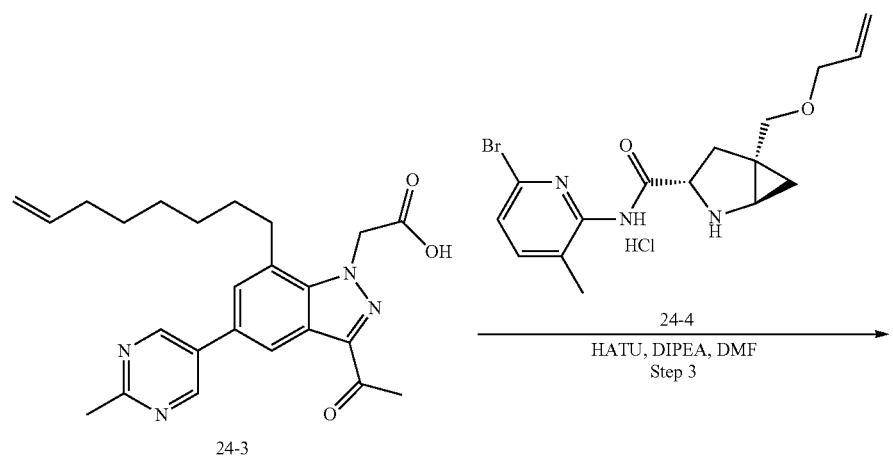
24-3
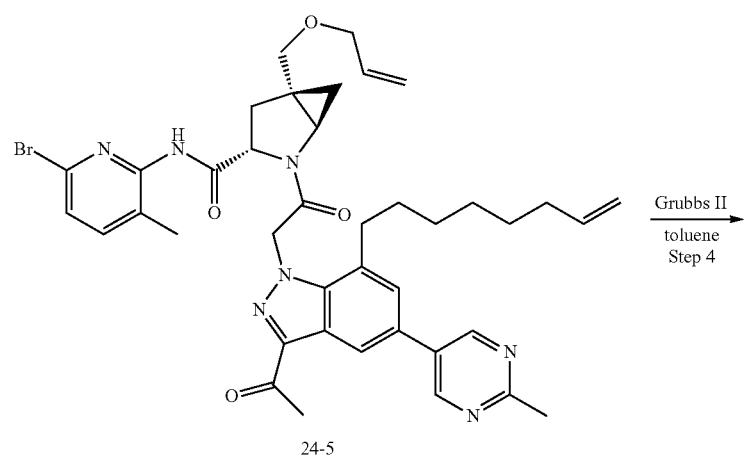
24-5
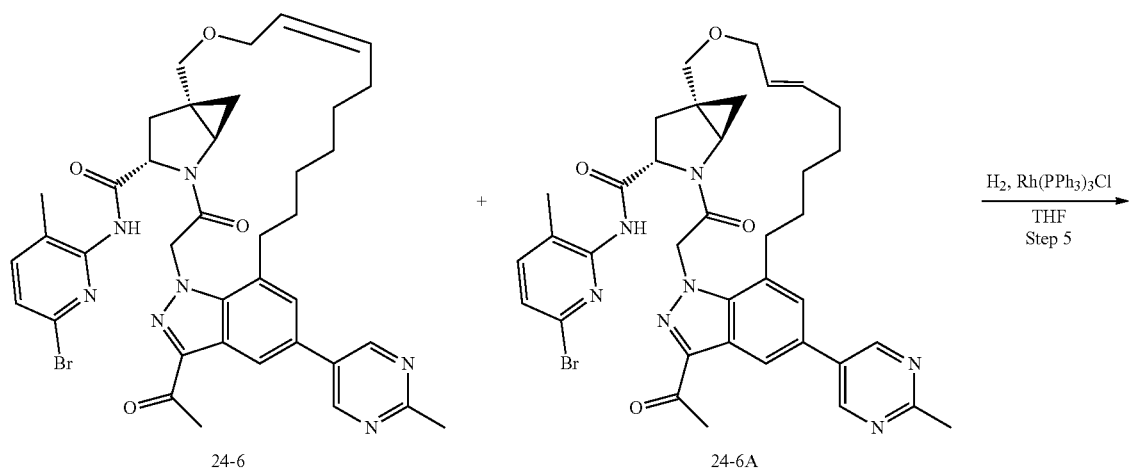
24-6 + 24-6A

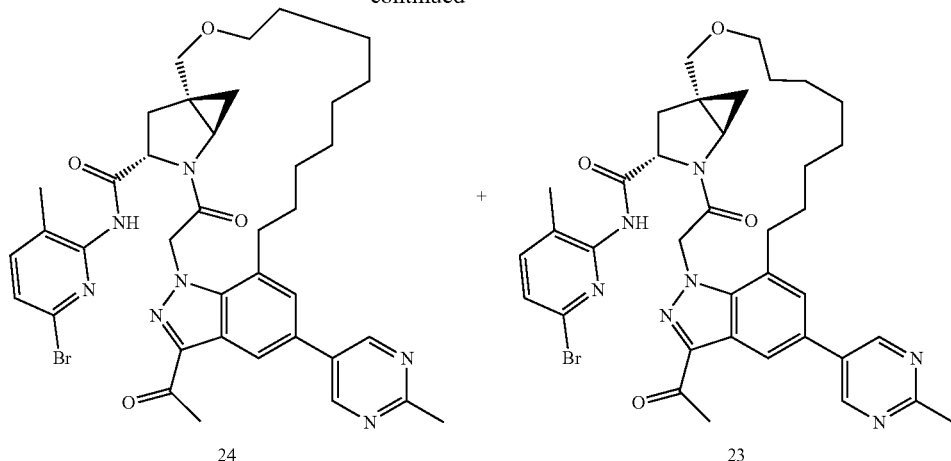

The above scheme and following detailed description depicts one non-limiting method for synthesizing compounds of Formula II wherein -X$^9$-L$^3$-X$^{10}$- is

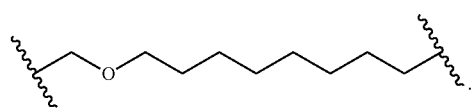 [SMILES: *CCCCCCCCOC*]

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1: tert-Butyl 2-(3-acetyl-5-(2-methylpyrimidin-5-yl)-7-(oct-7-enyl)-1H-indazol-1-yl)acetate (24-2)

To a mixture of 24-1 (240 mg, 0.54 mmol) and K$_3$PO$_4$ (344 mg, 1.62 mmol) in toluene/H$_2$O (6 mL, v/v=5:1) was added oct-7-enylboronic acid (169 mg, 1.08 mmol) and Pd(dppf)Cl$_2$ (40 mg, 0.054 mmol) and the resulting mixture was stirred at 100° C. overnight under N$_2$ atmosphere. The mixture was diluted with water and extracted with EtOAc twice. The combined organic layers were washed with brine, dried over anhydrous Na$_2$SO$_4$, and concentrated. The residue was purified by column chromatography on silica gel (eluted with petroleum ether/EtOAc=100:1 to 5:1) to afford 24-2 (140 mg, 54.5% yield) as a colorless oil. LC/MS (ESI) m/z: 477 (M+H)$^+$.

Step 2: 2-(3-Acetyl-5-(2-methylpyrimidin-5-yl)-7-(oct-7-enyl)-1H-indazol-1-yl) acetic acid (24-3)

To a solution of compound 24-2 (140 mg, 0.29 mmol) in THF/MeOH/H$_2$O (v/v/v=1:1:1, 3 mL) was added NaOH (24 mg, 0.59 mmol) and the resulting mixture was stirred at room temperature for 3 hours. The mixture was then washed with ether and the aqueous layer was acidified with 1N HCl solution to pH=5 and extracted with CHCl$_3$/i-PrOH (3:1). The organic layer was washed with brine, dried over Na$_2$SO$_4$, filtered, and concentrated to afford 24-3 (105 mg, 97.2% yield) as a white solid. LC/MS (ESI) m/z: 421 (M+H)$^+$.

Step 3: (1R,3S,5S)-2-(2-(3-Acetyl-5-(2-methylpyrimidin-5-yl)-7-(oct-7-enyl)-1H-indazol-1-yl)acetyl)-5-(allyloxymethyl)-N-(6-bromo-3-methylpyridin-2-yl)-2-azabicyclo[3.1.0]hexane-3-carboxamide (24-5)

To a mixture of 24-3 (100 mg, 0.24 mmol) and 24-4 (87 mg, 0.24 mmol) in DMF (2 mL) was added DIPEA (154 mg, 1.19 mmol) followed by HATU (136 mg, 0.36 mmol). The reaction was stirred at room temperature for 2 hours. The mixture was diluted with EtOAc and washed with 10% aqueous LiCl solution and brine, dried, and concentrated to afford crude product. The residue was purified by column chromatography on silica gel (eluted with DCM to DCM/MeOH=200:1) to afford 24-5 (120 mg, 65.7% yield) as a light yellow solid. LC/MS (ESI) m/z: 768/770 (M+H)$^+$.

Step 4: (41R,43S,45S,Z)-13-Acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclopentadecaphan-8-ene-43-carboxamide (24-6) and (41R,43S,45S,E)-13-Acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclotetradecaphan-8-ene-43-carboxamide (24-6A)

To a solution of 24-5 (46 mg, 0.06 mmol) in dry toluene (20 mL) was added Grubbs II catalyst (12 mg, 0.015 mmol) and the resulting mixture was stirred at 80° C. for 4 hours under N$_2$ atmosphere. The mixture was then cooled and diluted with water (20 mL) and extracted with EtOAc/MeOH (30:1) twice. The combined organic layers were washed with brine, dried over anhydrous Na$_2$SO$_4$, filtered, and concentrated to afford crude product. The residue was purified by pre-TLC (eluted with DCM:EtOAc=2:1) to afford a mixture of 24-6 and compound 24-6A (40 mg, 88.7% yield) as brown solids. LC/MS (ESI) m/z: 740/742 (M+H)$^+$, 726/728 (M+H)$^+$.

Step 5: (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclotetradecaphane-43-carboxamide (23) and (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclopentadecaphane-43-carboxamide (24)

To a mixture of 24-6 and 24-6A (40 mg, 0.054 mmol) in THF (8 mL) was added Rh(PPh$_3$)$_3$Cl (13 mg, 0.0135 mmol) and the resulting mixture was stirred at 70° C. for 16 hours under 25 psi of H$_2$ atmosphere. The mixture was then cooled and diluted with water (20 mL) and extracted with EtOAc/MeOH (30:1). The organic phase was washed with brine, dried over anhydrous Na$_2$SO$_4$, filtered, and concentrated to afford crude product. The residue was purified by pre-TLC (eluted with DCM:MeOH=20:1) and further purified via pre-HPLC to afford 24 (5 mg, 12.5% yield) and 23 (2 mg, 5% yield) as white solids.

Compound 24: $^1$H-NMR (400 MHz, CD$_3$OD) δ 9.00 (s, 2H), 8.44 (s, 1H), 7.50-7.58 (m, 2H), 7.35 (d, J=7.8 Hz, 1H), 5.80 (d, J=18.1 Hz, 1H), 5.73 (d, J=18.1 Hz, 1H), 4.62-4.68 (m, 1H), 3.86 (d, J=9.8 Hz, 1H), 3.57-3.66 (m, 2H), 3.46-3.55 (m, 2H), 3.10-3.15 (m, 1H), 2.88-2.94 (m, 1H), 2.74 (s, 3H), 2.69 (s, 3H), 2.51-2.56 (m, 2H), 2.10 (s, 3H), 1.71-1.78 (m, 2H), 1.55-1.67 (m, 4H), 1.25-1.53 (m, 9H), 1.06-1.11 (m, 1H). LC/MS (ESI) m/z: 742/744 (M+H)$^+$.

Compound 23: $^1$H-NMR (400 MHz, CD$_3$OD) δ 9.00 (s, 2H), 8.44 (s, 1H), 7.47-7.58 (m, 2H), 7.34 (d, J=8.1 Hz, 1H), 5.88 (d, J=17.5 Hz, 1H), 5.71 (d, J=17.6 Hz, 1H), 4.52-4.58 (s, 1H), 4.01 (d, J=11.1 Hz, 1H), 3.73-3.78 (m, 1H), 3.54-3.60 (m, 2H), 3.46-3.49 (m, 1H), 3.12-3.16 (m, 1H), 2.91-2.95 (m, 1H), 2.74 (s, 3H), 2.69 (s, 3H), 2.51-2.60 (m, 2H), 2.10 (s, 3H), 1.75-1.86 (m, 2H), 1.37-1.67 (m, 8H), 1.27-1.35 (m, 2H), 1.21-1.25 (m, 1H), 1.02-1.06 (m, 1H). LC/MS (ESI) m/z: 728/730 (M+H)$^+$.

Scheme 15. Synthesis of (1S,5E,18S,20R)-19-{2-[3-Acetyl-5-(2-methylpyrimidin-5-yl)pyrazolo[3,4-c]pyridin-1-yl]acetyl}-13-bromo-3,8-dioxa-14,16,19-triazatetracyclo[16.3.1.0$^{1,20}$.0$^{10,15}$]docosa-5,10,12,14-tetraen-17-one (25) and (1S,5Z,18S,20R)-19-{2-[3-Acetyl-5-(2-methylpyrimidin-5-yl)pyrazolo[3,4-c]pyridin-1-yl]acetyl}-13-bromo-3,8-dioxa-14,16,19-triazatetracyclo[16.3.1.0$^{1,20}$.0$^{10,15}$]docosa-5,10,12,14-tetraen-17-one (26)

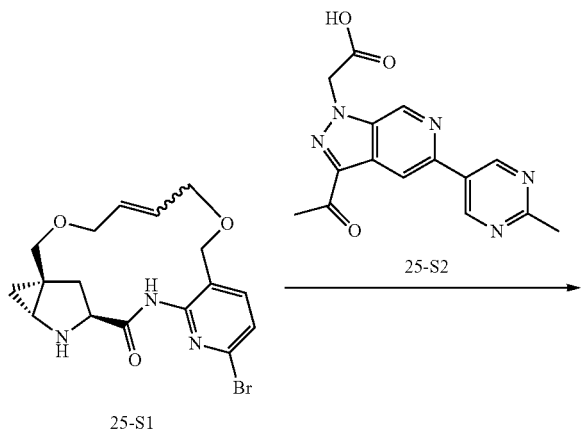

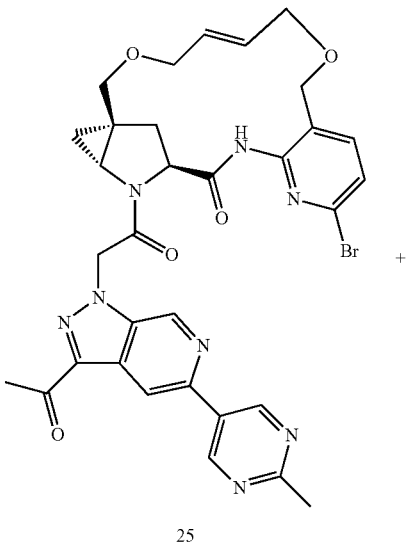

25

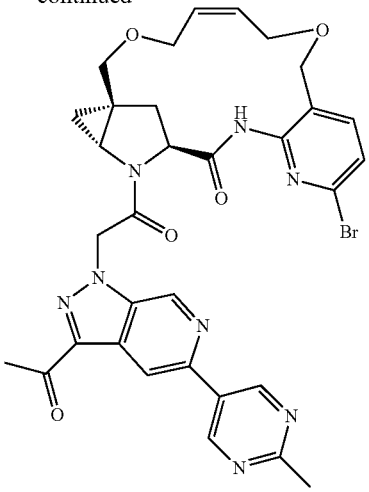

26

The above scheme and following detailed description depicts one non-limiting method for synthesizing compounds of Formula I wherein -X$^9$-L$^3$-X$^{10}$- is

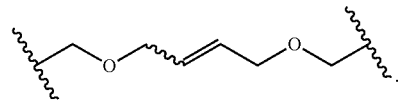 [SMILES: *COCC=CCOC*]

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

To a mixture of (1S,18S,20R)-13-bromo-3,8-dioxa-14,16,19-triazatetracyclo[16.3.1.0$^{1,20}$.0$^{10,15}$]docosa-5,10,12,14-tetraen-17-one 25-S1 (0.037 g, 0.072 mmol) and [3-acetyl-5-(2-methylpyrimidin-5-yl)pyrazolo[3,4-c]pyridin-1-yl] acetic acid 25-S2 (0.022 g, 0.072 mmol) in DMF (1.5 mL) was added O-(benzotriazol-1-yl)-N,N,N,N-tetramethyluronium tetrafluoroborate (0.035 g, 0.108 mmol) followed by NN-diisopropylethylamine (0.047 g, 0.063 mL, 0.36 mmol) with stirring at room temperature. After the reaction was completed, the mixture was purified by HPLC to provide 25 (5.7 mg) and 26 (1.5 mg).

25: $^1$H NMR (400 MHz, Chloroform-d) δ 9.29 (s, 2H), 9.09 (d, J=1.3 Hz, 1H), 8.86 (s, 1H), 8.62 (d, J=1.2 Hz, 1H), 7.72 (dd, J=3.9, 8.1 Hz, 1H), 7.34 (d, J=8.0 Hz, 1H), 5.78 (q, J=5.1 Hz, 2H), 5.69-5.50 (m, 2H), 4.88 (d, J=8.6 Hz, 1H), 4.48-4.00 (m, 6H), 3.94-3.80 (m, 1H), 3.59 (d, J=1.5 Hz, 2H), 3.42 (dd, J=2.7, 5.6 Hz, 1H), 2.82 (s, 3H), 2.71 (s, 3H), 2.69-2.49 (m, 1H), 2.32 (td, J=8.9, 12.9, 13.4 Hz, 1H), 1.37 (t, J=5.7 Hz, 1H), 1.11 (dd, J=2.7, 5.7 Hz, 1H). LC (method A): t$_R$=1.61 min. LC/MS (EI) m/z: [M+H]$^+$687.

26: $^1$H NMR (400 MHz, Chloroform-d) δ 9.30 (s, 2H), 9.08 (s, 1H), 8.63 (d, J=1.0 Hz, 1H), 7.74 (d, J=8.0 Hz, 1H), 7.34 (d, J=8.0 Hz, 1H), 6.03-5.90 (m, 1H), 5.83-5.71 (m, 1H), 5.68-5.51 (m, 2H), 4.89 (s, 1H), 4.50-4.26 (m, 2H), 4.25-4.12 (m, 1H), 3.99 (dd, J=9.1, 20.7 Hz, 3H), 3.53-3.47 (m, 1H), 3.12 (d, J=10.5 Hz, 1H), 2.82 (s, 4H), 2.71 (s, 3H), 2.46-2.34 (m, 1H), 1.32 (t, J=5.6 Hz, 1H), 1.05 (dd, J=2.7, 5.8 Hz, 1H). LC (method A): t$_R$=1.66 min. LC/MS (EI) m/z: [M+H]$^+$687.

Scheme 16. Synthesis of (1R,19S,21R)-20-{2-[3-Acetyl-5-(2-methylpyrimidin-5-yl)pyrazolo[3,4-c]pyridin-1-yl]acetyl}-14-bromo-7-methylidene-9-oxa-3,4,15,17,20-pentaazapentacyclo[17.3.1.1³,⁶.0¹,²¹.0¹¹,¹⁶]tetracosa-4,6(24),11,13,15,-pentaen-18-one (27)

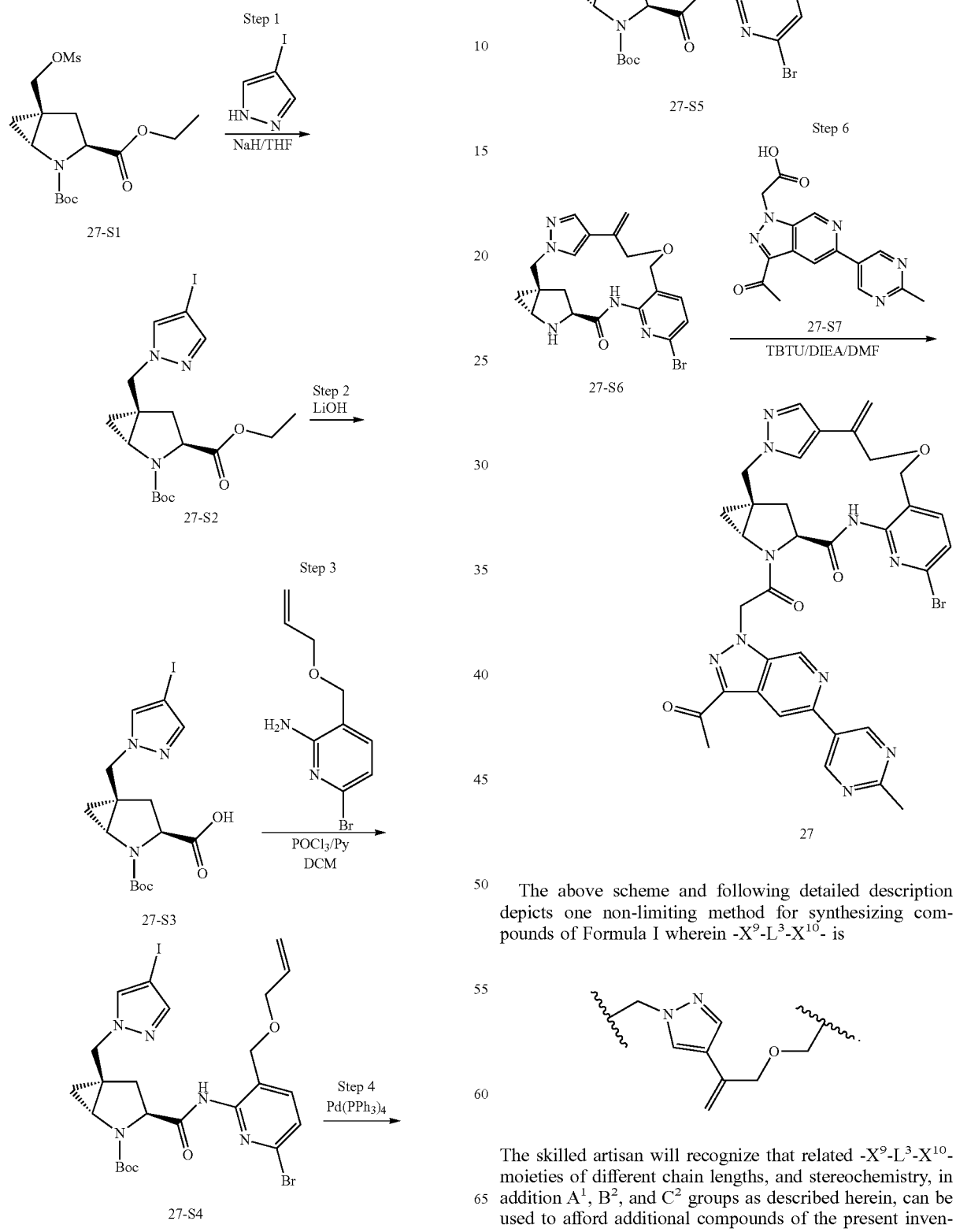

The above scheme and following detailed description depicts one non-limiting method for synthesizing compounds of Formula I wherein -$X^9$-$L^3$-$X^{10}$- is

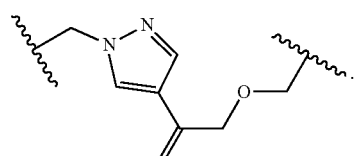

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: 2-tert-Butyl 3-Ethyl (1R,3S,5R)-5-[(4-Iodopyrazol-1-yl)methyl]-2-azabicyclo[3.1.0]hexane-2,3-dicarboxylate (27-S2)

To a solution of 4-iodopyrazole (0.494 g, 2.548 mmol) in tetrahydrofuran (10 mL) was added sodium hydride (0.094 g, 2.352 mmol) with stirring at 0 20 C. After 15 minutes, 2-tert-butyl 3-ethyl (1R,3S,5S)-5-[(methanesulfonyloxy)methyl]-2-azabicyclo[3.1.0]hexane-2,3-dicarboxylate 27-S1 (0.712 g, 1.96 mmol) in THF (5 mL) was added, and the mixture was stirred from 0° C. to room temperature overnight. NH$_4$Cl aqueous solution was added, and the mixture was extracted with EtOAc. The organic layer was washed with brine and dried over anhydrous Na$_2$SO$_4$. The solvent was removed under reduced pressure, and the residue was purified by column chromatography on silica gel (MeOH in DCM 0-10%) to provide 2-tert-butyl 3-ethyl (1R,3S,5R)-5-[(4-iodopyrazol-1-yl)methyl]-2-azabicyclo[3.1.0]hexane-2,3-dicarboxylate 27-S2 (280 mg) as colorless syrup.

Step 2: (1R,3S,5R)-2-(tert-Butoxycarbonyl)-5-[1(4-iodopyrazol-1-yl)methyl]-2-azabicyclo[3.1.0]hexane-3-carboxylic Acid (27-S3)

2-tert-Butyl 3-ethyl (1R,3S,5R)-5-[(4-iodopyrazol-1-yl)methyl]-2-azabicyclo[3.1.0]hexane-2,3-dicarboxylate 27-S2 (280 mg, 0.607 mmol) was treated with lithium hydroxide (1.5 N, 0.607 mL, 0.91 mmol) in tetrahydrofuran (5 mL) and methanol (0.6 mL) at room temperature overnight. Amberlite CG-50 (0.6 g) was added. After stirring at room temperature for 20 minutes, the resin was removed by filtration and washed with MeOH. The solvent was removed under reduced pressure, and the residue was co-evaporated with toluene (10 mL×2) to give (1R,3S,5R)-2-(tert-butoxycarbonyl)-5-[(4-iodopyrazol-1-yl)methyl]-2-azabicyclo[3.1.0]hexane-3-carboxylic acid 27-S3 as white solid.

Step 3: tert-Butyl (1R,3S,5R)-3-({6-Bromo-3-[(prop-2-en-1-yloxy)methyl]pyridin-2-yl}carbamoyl)-5-[(4-iodopyrazol-1-yl)methyl]-2-azabicyclo[3.1.0]hexane-2-carboxylate (27-S4)

To a mixture of (1R,3S,5R)-2-(tert-butoxycarbonyl)-5-[(4-iodopyrazol-1-yl)methyl]-2-azabicyclo[3.1.0]hexane-3-carboxylic acid 27-S3 (0.263 g, 0.607 mmol) and 6-bromo-3-[(prop-2-en-1-yloxy)methyl]pyridin-2-amine (0.148 g, 0.607 mmol) in dichloromethane (6 mL) was added pyridine (0.245 mL, 3.035 mmol) followed by phosphoryl chloride (0.057 mL, 0.607 mmol) with stirring at 0° C. After stirring at room temperature for 2 hours, NaHCO$_3$ aqueous solution was added. The organic layer was washed with brine and dried over anhydrous Na$_2$SO$_4$. The solvent was removed under reduced pressure, and the residue was purified by column chromatography on silica gel (MeOH in DCM, 0-10%) to provide tert-butyl (1R,3S,5R)-3-({6-bromo-3-[(prop-2-en-1-yloxy)methyl]pyridin-2-yl}carbamoyl)-5-[(4-iodopyrazol-1-yl)methyl]-2-azabicyclo[3.1.0]hexane-2-carboxylate 27-S4 (366 mg).

Step 4: tert-Butyl (1R,19S,21R)-14-Bromo-7-methylidene-18-oxo-9-oxa-3,4,15,17,20-pentaazapentacyclo[17.3.1.1$^{3,6}$.0$^{1,21}$.0$^{11,14}$]tetracosa-4,6(24),11,13,15-pentaene-20-carboxylate (27-S5)

A mixture of tert-butyl (1R,3S,5R)-3-({6-bromo-3-[(prop-2-en-1-yloxy)methyl]pyridin-2-yl}carbamoyl)-5-[(4-iodopyrazol-1-yl)methyl]-2-azabicyclo[3.1.0]hexane-2-carboxylate 27-S4 (50 mg, 0.076 mmol, 1 equiv.), potassium carbonate (0.021 g, 0.152 mmol), potassium acetate (0.007 g, 0.076 mmol) and tetrakis(triphenylphosphine)palladium (0) (45 mg) in acetonitrile (8 mL) was stirred at 60° C. under argon overnight. The solvent was removed under reduced pressure, and the residue was purified by HPLC to provide tert-butyl (1R,19S,21R)-14-bromo-7-methylidene-18-oxo-9-oxa-3,4,15,17,20-pentaazapentacyclo[17.3.1.1$^{3,6}$.0$^{1,21}$.0$^{11,16}$]tetracosa-4,6(24),11,13,15-pentaene-20-carboxylate 27-S5 (3.5 mg).

Step 5: (1R,19S,21R)-14-Bromo-7-methylidene-9-oxa-3,4,15,17,20-pentaazapentacyclo[17.3.1.1$^{3,6}$.0$^{1,21}$.0$^{11,16}$]tetracosa-4,6(24),11,13,15-pentaen-18-one Trifluoroacetic Acid Salt (27-S6)

tert-Butyl (1R,19S,21R)-14-bromo-7-methylidene-18-oxo-9-oxa-3,4,15,17,20-pentaazapentacyclo[17.3.1.1$^{3,6}$.0$^{1,21}$.0$^{11,16}$]tetracosa-4,6(24),11,13,15-pentaene-20-carboxylate 27-S5 (3.5 mg, 0.007 mmol) was treated with trifluoroacetic acid (2 mL) in dichloromethane (2 mL) at room temperature. After the reaction was completed, the solvent was removed under reduced pressure to provide (1R,19S,21R)-14-bromo-7-methylidene-9-oxa-3,4,15,17,20-pentaazapentacyclo[17.3.1.1$^{3,6}$.0$^{1,21}$.0$^{11,16}$]tetracosa-4,6(24),11,13,15-pentaen-18-one TFA salt 27-S6.

Step 6: (1R,19S,21R)-20-{2-[3-acetyl-5-(2-methylpyrimidin-5-yl)pyrazolo[3,4-c]pyridin-1-yl]acetyl}-14-bromo-7-methylidene-9-oxa-3,4,15,17,20-pentaazapentacyclo[17.3.1.1$^{3,6}$.0$^{1,21}$.0$^{11,16}$]tetracosa-4,6(24),11,13,15-pentaen-18-one (27)

To a mixture of (1R,19S,21R)-14-bromo-7-methylidene-9-oxa-3,4,15,17,20-pentaazapentacyclo[17.3.1.1$^{3,6}$.0$^{1,21}$.0$^{11,16}$]tetracosa-4,6(24),11,13,15-pentaen-18-one trifluoroacetic acid salt 27-S6 (0.01 mmol) and [3-acetyl-5-(2-methylpyrimidin-5-yl)pyrazolo[3,4-c]pyridin-1-yl]acetic acid 27-S7 (3 mg) in N,N-dimethylformamide (1 mL) was added O-(benzotriazol-1-yl)-N,N,N,N-tetramethyluronium tetrafluoroborate (4 mg) followed by N,N-diisopropylethylamine (0.012 mL) with stirring. After the reaction was completed, the mixture was purified by HPLC to provide (1R,19S,21R)-20-{2-[3-acetyl-5-(2-methylpyrimidin-5-yl)pyrazolo[3,4-c]pyridin-1-yl]acetyl}-14-bromo-7-methylidene-9-oxa-3,4,15,17,20-pentaazapentacyclo[17.3.1.1$^{3,6}$.0$^{1,21}$.0$^{11,16}$]tetracosa-4,6(24),11,13,15-pentaen-18-one 27. $^1$H NMR (400 MHz, Chloroform-d) δ 9.29 (s, 2H), 9.11 (s, 1H), 8.63 (s, 1H), 8.00 (s, OH), 7.66 (d, J=12.5 Hz, 1H), 7.59-7.43 (m, 3H), 7.21 (d, J=7.8 Hz, 1H), 5.72-5.55 (m, 2H), 5.46 (s, 1H), 5.18 (s, 1H), 4.59 (d, J=14.7 Hz, 1H), 4.37 (t, J=11.8 Hz, 2H), 4.31-4.17 (m, 1H), 3.81 (d, J=15.4 Hz, 2H), 2.82 (d, J=4.0 Hz, 4H), 2.75 (s, 3H), 2.52-2.36 (m, 1H), 1.21 (d, J=5.9 Hz, 1H). LC (method A): t$_R$=2.09 min. LC/MS (EI) m/z: [M+H]$^+$723.

Scheme 17. Synthesis of (1R,7E,20S,22R)-21-{2-[3-Acetyl-5-(2-methylpyrimidin-5-yl)indazol-1-yl]acetyl}-15-bromo-10-oxa-3,16,18,21,25-pentaazapentacyclo[18.3.1.1$^{3,6}$.0$^{1,22}$.0$^{12,17}$]pentacosa-4,6(25),7,12,14,16-hexaen-19-one (28)

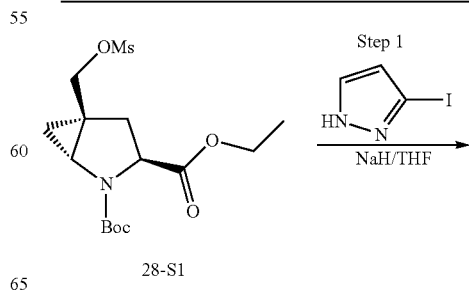

571
-continued

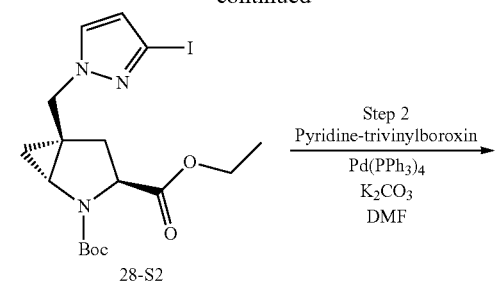
28-S2

Step 2
Pyridine-trivinylboroxin
Pd(PPh₃)₄
K₂CO₃
DMF

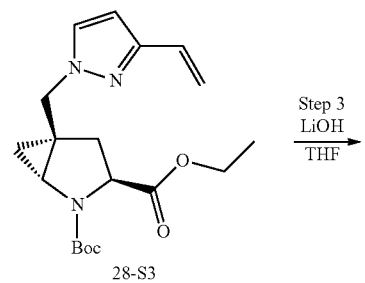
28-S3

Step 3
LiOH
THF

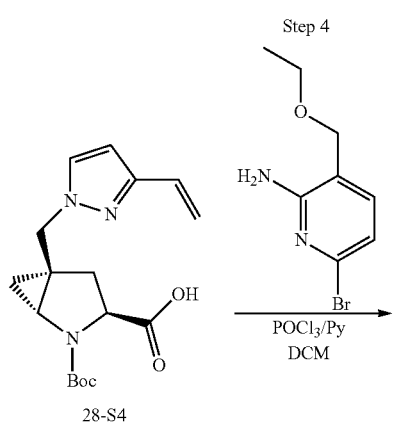
28-S4

Step 4

POCl₃/Py
DCM

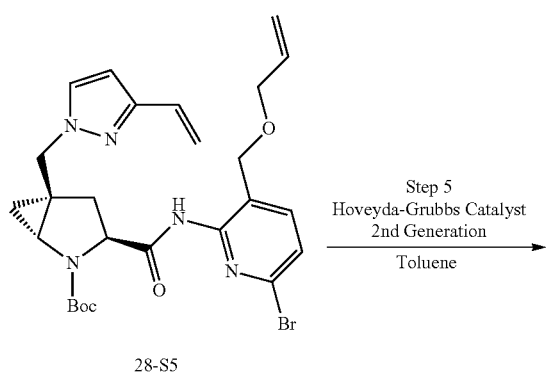
28-S5

Step 5
Hoveyda-Grubbs Catalyst
2nd Generation
Toluene

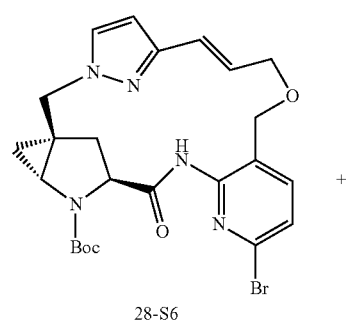
28-S6

+

572
-continued

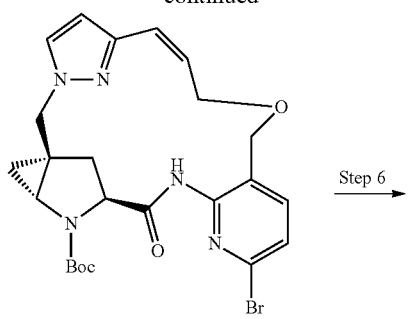
28-S7

Step 6

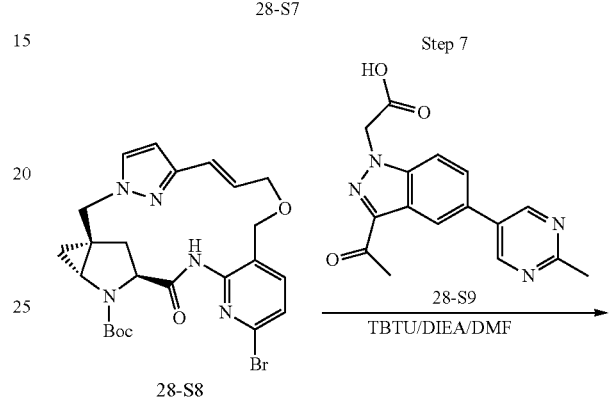
28-S8

Step 7

TBTU/DIEA/DMF

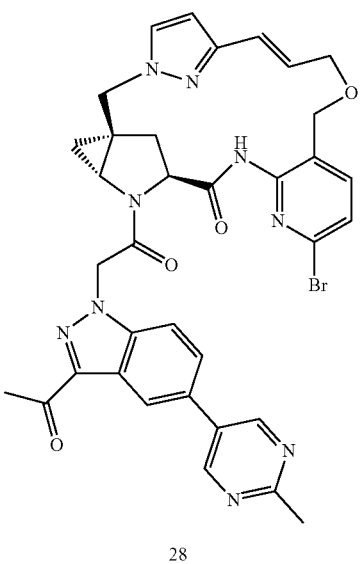
28

The above scheme and following detailed description depicts one non-limiting method for synthesizing compounds of Formula I wherein -$X^9$-$L^3$-$X^{10}$- is The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: 2-tert-Butyl 3-Ethyl (1R,3S,5R)-5-[(3-Iodopyrazol-1-yl)methyl]-2-azabicyclo[3.1.0]hexane-2,3-dicarboxylate (28-S2)

To a solution of 3-iodo-1H-pyrazole (0.653 g, 3.367 mmol) in THF (10 mL) was added sodium hydride (0.124 g, 3.108 mmol) with stirring at room temperature under argon. After 15 minutes, 2-tert-butyl 3-ethyl (1R,3S,5S)-5-[(methanesulfonyloxy)methyl]-2-azabicyclo[3.1.0]hexane-2,3-dicarboxylate 28-S1 (0.941 g, 2.59 mmol) in THF (10 mL) was added. The reaction mixture was stirred at room temperature for 2 days. $NH_4Cl$ aqueous solution was added, and the organic phase was washed with brine and dried over anhydrous $Na_2SO_4$. The solvent was removed under reduced pressure, and the residue was purified by column chromatography on silica gel (MeOH in DCM 0-10%) to provide 2-tert-butyl 3-ethyl (1R,3S,5R)-5-[(3-iodopyrazol-1-yl)methyl]-2-azabicyclo[3.1.0]hexane-2,3-dicarboxylate 28-S2 (0.448 g) as an oil.

Step 2: 2-tert-Butyl 3-Ethyl (1R,3S,5R)-5-[(3-Ethenylpyrazol-1-yl)methyl]-2-azabicyclo[3.1.0]hexane-2,3-dicarboxylate (28-S3)

To a mixture of 2-tert-butyl 3-ethyl (1R,3S,5R)-5-[(3-iodopyrazol-1-yl)methyl]-2-azabicyclo[3.1.0]hexane-2,3-dicarboxylate 28-S2 (0.448 g, 0.971 mmol), pyridine-trivinylboroxin complex (1:1) (0.234 g, 0.971 mmol), and potassium carbonate (0.268 g) in N,N-dimethylformamide (9 mL) and water (1 mL) was added tetrakis(triphenylphosphine)palladium(0) (0.056 g, 0.049 mmol). The reaction mixture was stirred at 70° C. under argon overnight. Water was added at room temperature, and the mixture was extracted with EtOAc. The organic layer was washed with $NH_4Cl$ aqueous solution, brine, and dried over anhydrous $Na_2SO_4$. The solvent was removed under reduced pressure, and the residue was purified by column chromatography on silica gel (MeOH in DCM 0-10%) to provide 2-tert-butyl 3-ethyl (1R,3S, 5R)-5-[(3-ethenylpyrazol-1-yl)methyl]-2-azabicyclo[3.1.0]hexane-2,3-dicarboxylate 28-S3 (0.248 g) as oil.

Step 3: (1R,3S,5R)-2-(tert-Butoxycarbonyl)-5-[(3-ethenylpyrazol-1-yl)methyl]-2-azabicyclo[3.1.0]hexane-3-carboxylic Acid (28-S4)

2-tert-butyl 3-ethyl (1R,3S,5R)-5-[(3-ethenylpyrazol-1-yl)methyl]-2-azabicyclo[3.1.0]hexane-2,3-dicarboxylate 28-S3 (0.248 g, 0.686 mmol) in THF (5 mL) and methanol (0.7 mL) was treated with lithium hydroxide (1.5 N, 0.686 mL, 1.029 mmol) at room temperature. After the reaction was completed, Amberlite CG-50 (0.686 g) was added, and the reaction was stirred for 10 minutes. The resin was removed by filtration and washed with MeOH. The solvent was removed under reduced pressure, and the residue was co-evaporated with toluene to provide (1R,3 S,5R)-2-(tert-butoxycarbonyl)-5-[(3-ethenylpyrazol-1-yl)methyl]-2-azabicyclo[3.1.0]hexane-3-carboxylic acid 28-S4 (0.247 g, 0.741 mmol) as white foam.

Step 4: tert-Butyl (1R,3S,5R)-3-({6-bromo-3-[(prop-2-en-1-yloxy)methyl]pyridin-2-yl}carbamoyl)-5-[(3-ethenylpyrazol-1-yl)methyl]-2-azabicyclo[3.1.0]hexane-2-carboxylate (28-S5)

To a mixture of (1R,3S,5R)-2-(tert-butoxycarbonyl)-5-[(3-ethenylpyrazol-1-yl)methyl]-2-azabicyclo[3.1.0]hexane-3-carboxylic acid 28-S4 (0.114 g, 0.343 mmol) and 6-bromo-3-[(prop-2-en-1-yloxy)methyl]pyridin-2-amine (0.083 g, 0.343 mmol) in dichloromethane (5 mL) was added pyridine (0.136 g, 0.138 mL, 1.715 mmol) followed by phosphoryl chloride (0.035 mL, 0.377 mmol) with stirring at 0° C. After the reaction mixture was stirred at room temperature for 2 hours, $NaHCO_3$ aqueous solution was added. The organic layer was washed with brine and dried over anhydrous $Na_2SO_4$. The solvent was removed under reduced pressure, and the residue was purified by column chromatography on silica gel (MeOH in DCM, 0-10%) to provide tert-butyl (1R,3S,5R)-3-({6-bromo-3-[(prop-2-en-1-yloxy)methyl]pyridin-2-yl}carbamoyl)-5-[(3-ethenylpyrazol-1-yl)methyl]-2-azabicyclo[3.1.0]hexane-2-carboxylate 28-S5 (177.7 mg) as a yellow syrup.

Step 5: tert-Butyl (1R,7E,20S,22R)-15-Bromo-19-oxo-10-oxa-3,16,18,21,25-pentaazapentacyclo[18.3.1.1$^{3,6}$.0$^{1,22}$.0$^{12,17}$]pentacosa-4,6(25),7,12,14,16-hexaene-21-carboxylate (28-S6) and tert-Butyl (1R,7Z,20S,22R)-15-bromo-19-oxo-10-oxa-3,16,18,21,25-pentaazapentacyclo[18.3.1.1$^{3,6}$.0$^{1,22}$.0$^{12,17}$]pentacosa-4,6(25),7,12,14,16-hexaene-21-carboxylate (28-S7)

tert-Butyl (1R,3S,5R)-3-({6-bromo-3-[(prop-2-en-1-yloxy)methyl]pyridin-2-yl}carbamoyl)-5-[(3-ethenylpyrazol-1-yl)methyl]-2-azabicyclo[3.1.0]hexane-2-carboxylate 28-S5 (122 mg, 0.218 mmol) was dissolved in toluene (22 mL) and treated with Hoveyda-Grubbs Catalyst $2^{nd}$ Generation (0.007 g, 0.011 mmol) at 60° C. under argon. Additional catalyst (8 mg) was added after 2 hours, and the reaction was stirred overnight. The solvent was removed under reduced pressure, and the residue was purified by column chromatography on silica gel with MeOH in DCM (0-10%) to provide tert-butyl (1R,7E,20S,22R)-15-bromo-19-oxo-10-oxa-3,16,18,21,25-pentaazapentacyclo[18.3.1.1$^{3,6}$.0$^{1,22}$.0$^{12,17}$]pentacosa-4,6(25),7,12,14,16-hexaene-21-carboxylate 28-S6 (27 mg), and tert-butyl (1R,7Z,20S,22R)-15-bromo-19-oxo-10-oxa-3,16,18,21,25-pentaazapentacyclo[18.3.1.1$^{3,6}$.0$^{1,22}$.0$^{12,17}$]pentacosa-4,6(25),7,12,14,16-hexaene-21-carboxylate 28-S7 (109 mg).

Step 6: (1R,7E,20S,22R)-15-Bromo-10-oxa-3,16,18,21,25-pentaazapentacyclo[18.3.1.1$^{3,6}$.0$^{1,22}$.0$^{12,17}$]pentacosa-4,6(25),7,12,14,16-hexaen-19-one Trifluoroacetic Acid Salt (29-S8)

tert-Butyl (1R,7E,20S,22R)-15-bromo-19-oxo-10-oxa-3,16,18,21,25-pentaazapentacyclo[18.3.1.1$^{3,6}$.0$^{1,22}$.0$^{12,17}$]pentacosa-4,6(25),7,12,14,16-hexaene-21-carboxylate 28-S6 (27 mg, 0.051 mmol) in DCM (2 mL) was treated with trifluoroacetic acid (2 mL) at room temperature for 1 hour. The solvent was evaporated, and the residue was co-evaporated with toluene to provide (1R,7E,20S,22R)-15-bromo-10-oxa-3,16,18,21,25-pentaazapentacyclo[18.3.1.1$^{3,6}$.0$^{1,22}$.0$^{12,17}$]pentacosa-4,6(25),7,12,14,16-hexaen-19-one trifluoroacetic acid salt 28-S8.

Step 7: (1R,7E,20S,22R)-21-{2-[3-acetyl-5-(2-methylpyrimidin-5-yl)indazol-1-yl]acetyl}-15-bromo-10-oxa-3,16,18,21,25-pentaazapentacyclo[18.3.1.1$^{3,6}$.0$^{1,22}$.0$^{2,17}$]pentacosa-4,6(25),7,12,14,16-hexaen-19-one (28)

To a mixture of (1R,7E,20S,22R)-15-bromo-10-oxa-3,16,18,21,25-pentaazapentacyclo[18.3.1.1$^{3,6}$.0$^{1,22}$.0$^{12,17}$]pentacosa-4,6(25),7,12,14,16-hexaen-19-one trifluoroacetic acid salt 28-S8 (0.025 mmol) and [3-acetyl-5-(2-methylpyrimidin-5-yl)indazol-1-yl]acetic acid 28-S9 (0.008 g, 0.025 mmol) in N,N-dimethylformamide (1 mL) was added O-(benzotriazol-1-yl)-N,N,N,N-tetramethyluronium tetrafluoroborate (0.016 g, 0.05 mmol) followed by N,N-diisopropylethylamine (0.044 mL, 0.25 mmol), and the mixture was stirred at room temperature. After the reaction was completed, the mixture was applied to HPLC for purification to provide (1R,7E,20S,22R)-21-{2-[3-acetyl-5-(2-methylpyrimidin-5-yl)indazol-1-yl]acetyl}-15-bromo-10-oxa-3,16,18,21,25-pentaazapentacyclo[18.3.1.1$^{3,6}$.

$O^{1,22}.O^{12,17}$]pentacosa-4,6(25),7,12,14,16-hexaen-19-one 28 (5.7 mg) as a white powder. $^1$H NMR (400 MHz, Chloroform-d) δ 8.93 (d, J=12.6 Hz, 2H), 8.87 (d, J=2.9 Hz, 2H), 8.55 (s, 1H), 7.57 (s, 2H), 7.50-7.36 (m, 3H), 6.53 (d, J=15.9 Hz, 1H), 6.37 (s, 1H), 6.31-6.19 (m, 1H), 5.49 (d, J=29.0 Hz, 2H), 4.46 (d, J=13.0 Hz, 1H), 4.37 (d, J=12.9 Hz, 1H), 4.22 (d, J=13.1 Hz, 1H), 4.14-3.92 (m, 2H), 3.67 (s, 1H), 2.79 (s, 4H), 2.70 (d, J=3.6 Hz, 5H), 1.24 (d, J=7.5 Hz, 1H), 1.01 (s, 1H). LC (method A): $t_R$=2.18 min. LC/MS (0EI m/z: [M+H]$^+$724.

Scheme 18. Synthesis of (1R,7Z,20S,22R)-21-{2-[3-Acetyl-5-(2-methylpyrimidin-5-yl)pyrazolo[3,4-c]pyridin-1-yl]acetyl}-15-bromo-10-oxa-3,16,18,21,25-pentaazapentacyclo[18.3.1.1$^{3,6}$.0$^{1,22}$.0$^{12,17}$]pentacosa-4,6(25),7,12,14,16-hexaen-19-one (29)

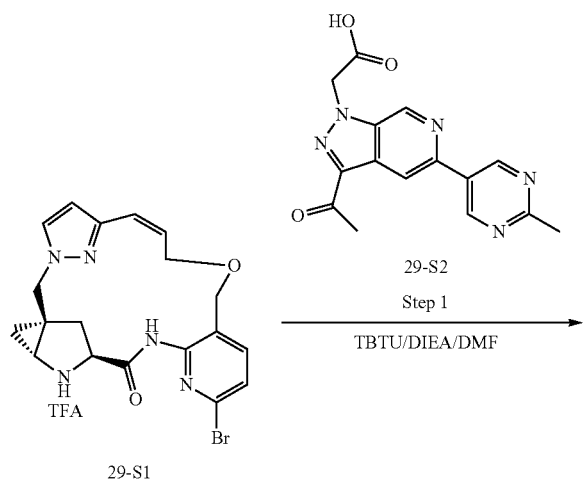

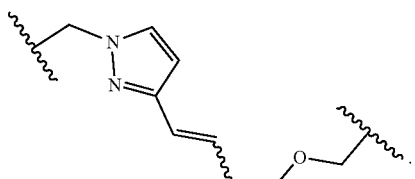

The skilled artisan will recognize that related -X$^9$-L$^3$-X$^{10}$-moieties of different chain lengths, and stereochemistry, in addition A$^1$, B$^2$, and C$^2$ groups as described herein, can be used to afford additional compounds of the present invention.

To a mixture of (1R,7Z,20S,22R)-15-bromo-10-oxa-3,16,18,21,25-pentaazapentacyclo[18.3.1.1$^{3,6}$.0$^{1,22}$.0$^{12,17}$]pentacosa-4,6(25),7,12,14,16-hexaen-19-one trifluoroacetic acid salt 29-S1 (0.035 mmol) and [3-acetyl-5-(2-methylpyrimidin-5-yl)pyrazolo[3,4-c]pyridin-1-yl]acetic acid 29-S2 (0.011 g, 0.035 mmol) in N,N-dimethylformamide (1 mL) was added O-(benzotriazol-1-yl)-N,N,N,N-tetramethyluronium tetrafluoroborate (0.022 g, 0.07 mmol) followed by N,N-diisopropylethylamine (0.061 mL, 0.35 mmol) with stirring at room temperature. After 1 hourr, the mixture was applied to HPLC for purification to provide (1R,7Z,20S,22R)-21-{2-[3-acetyl-5-(2-methylpyrimidin-5-yl)pyrazolo[3,4-c]pyridin-1-yl]acetyl}-15-bromo-10-oxa-3,16,18,21,25-pentaazapentacyclo[18.3.1.1$^{3,6}$.0$^{1,22}$.0$^{12,17}$]pentacosa-4,6(25),7,12,14,16-hexaen-19-one 29 (2.2 mg) as a white powder. $^1$H NMR (400 MHz, Chloroform-d) δ 9.48 (s, 1H), 9.30 (s, 2H), 9.10 (d, J=1.2 Hz, 1H), 8.64 (s, 1H), 7.46-7.35 (m, 2H), 7.19 (d, J=7.9 Hz, 1H), 6.33 (d, J=11.6 Hz, 1H), 6.17 (d, J=2.2 Hz, 1H), 5.81-5.56 (m, 3H), 4.91 (s, 1H), 4.56 (dd, J=14.3, 28.7 Hz, 2H), 4.39 (d, J=11.7 Hz, 1H), 4.17 (d, J=14.2 Hz, 1H), 3.97 (s, 1H), 3.74 (d, J=14.5 Hz, 1H), 2.82 (s, 3H), 2.75 (s, 3H), 2.49 (d, J=7.7 Hz, 2H), 1.44 (t, J=5.8 Hz, 1H), 1.14 (dd, J=3.0, 6.1 Hz, 1H). LC (method A): $t_R$=1.76 min. LC/MS (EI) m/z: [M+H]$^+$725.

Scheme 19: Synthesis of (41R,43S,45R)-13-Acetyl-N-(6-bromo-3-methylpyridin-2-yl)-15-(2-methylpyrimidin-5-yl)-3-oxo-11H-42-aza-1(1,7)-indazola-4(2,5)-bicyclo[3.1.0]hexanacyclotridecaphane-43-carboxamide (30)

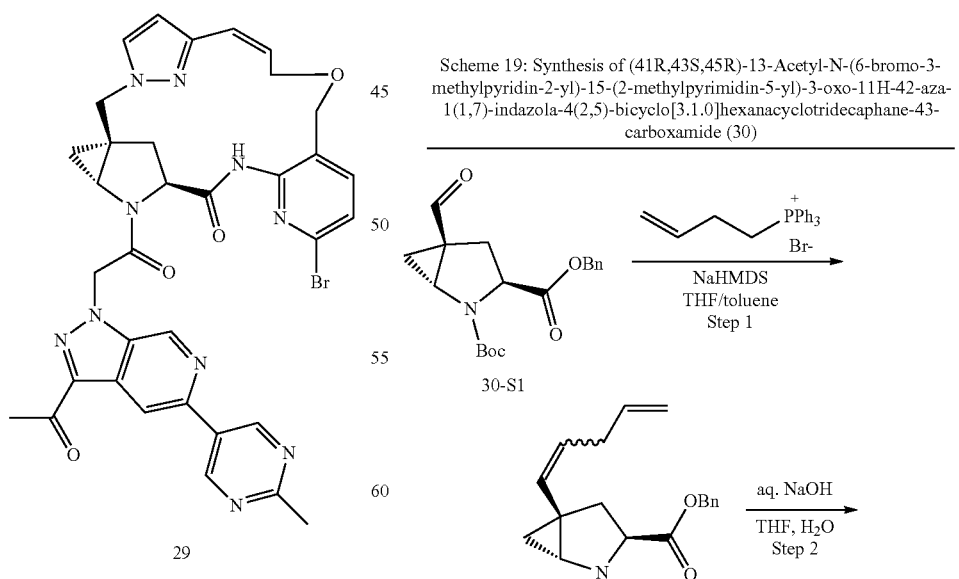

The above scheme and following detailed description depicts one non-limiting method for synthesizing compounds of Formula I wherein -X$^9$-L$^3$-X$^{10}$- is

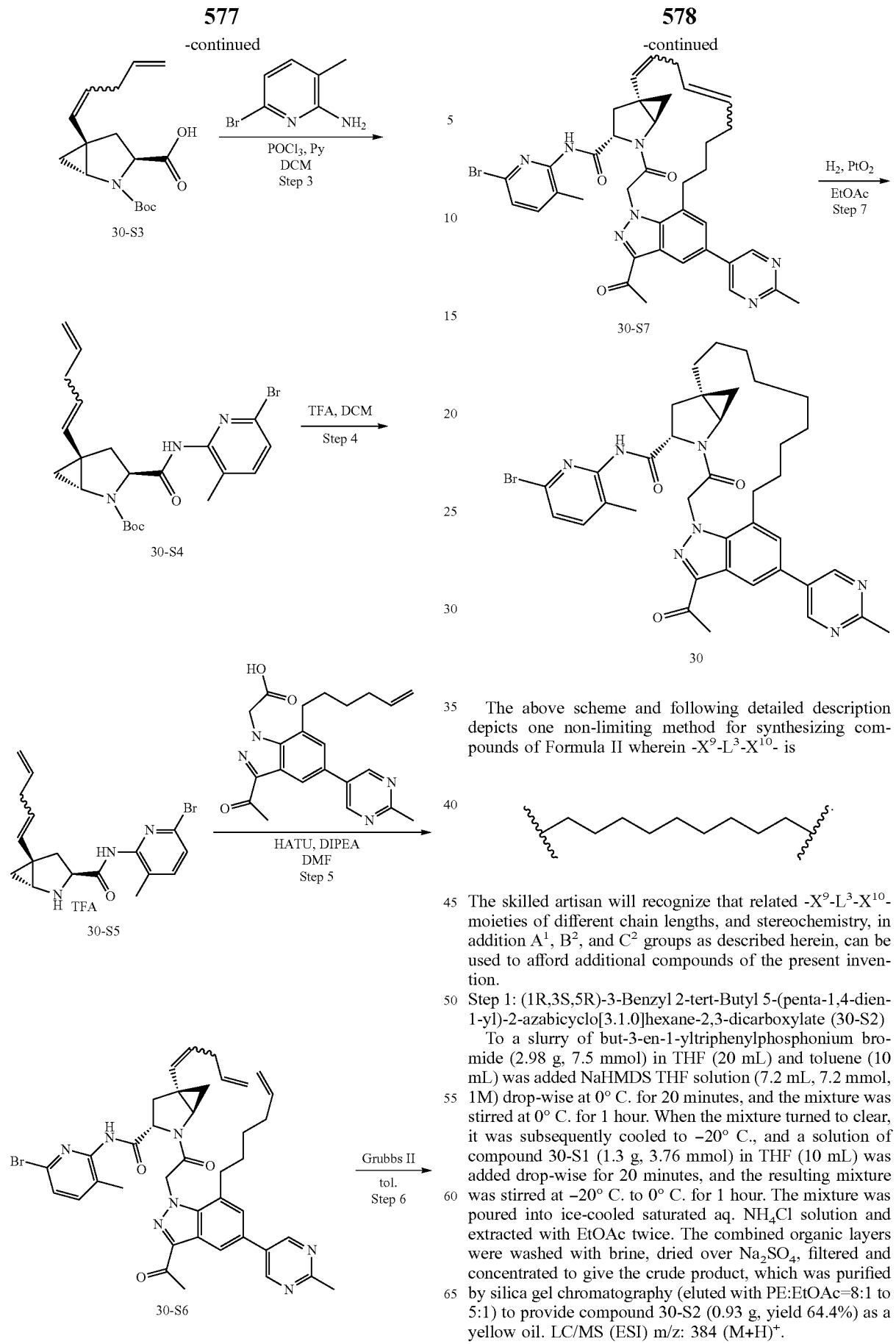

The above scheme and following detailed description depicts one non-limiting method for synthesizing compounds of Formula II wherein -$X^9$-$L^3$-$X^{10}$- is The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: (1R,3S,5R)-3-Benzyl 2-tert-Butyl 5-(penta-1,4-dien-1-yl)-2-azabicyclo[3.1.0]hexane-2,3-dicarboxylate (30-S2)

To a slurry of but-3-en-1-yltriphenylphosphonium bromide (2.98 g, 7.5 mmol) in THF (20 mL) and toluene (10 mL) was added NaHMDS THF solution (7.2 mL, 7.2 mmol, 1M) drop-wise at 0° C. for 20 minutes, and the mixture was stirred at 0° C. for 1 hour. When the mixture turned to clear, it was subsequently cooled to −20° C., and a solution of compound 30-S1 (1.3 g, 3.76 mmol) in THF (10 mL) was added drop-wise for 20 minutes, and the resulting mixture was stirred at −20° C. to 0° C. for 1 hour. The mixture was poured into ice-cooled saturated aq. NH$_4$Cl solution and extracted with EtOAc twice. The combined organic layers were washed with brine, dried over Na$_2$SO$_4$, filtered and concentrated to give the crude product, which was purified by silica gel chromatography (eluted with PE:EtOAc=8:1 to 5:1) to provide compound 30-S2 (0.93 g, yield 64.4%) as a yellow oil. LC/MS (ESI) m/z: 384 (M+H)$^+$.

Step 2: (1R,3S,5R)-2-(tert-Butoxycarbonyl)-5-(penta-1,4-dien-1-yl)-2-azabicyclo[3.1.0]hexane-3-carboxylic Acid (30-S3)

To a solution of compound 30-S2 (0.91 g, 2.37 mmol) in THF (10 mL) and MeOH (10 mL) was added a solution of NaOH (0.19 g, 4.74 mmol) in water (5 mL) at 0° C., and the mixture was stirred at this temperature for 2 hours. The mixture was concentrated to dryness, and the residue was diluted with water and washed with EtOAc twice. The aqueous layer was acidified by adding 0.5 N HCl to pH~3 and extracted with DCM twice. The combined organic layer was washed with brine, dried over anhydrous $Na_2SO_4$, filtered and concentrated to dryness to give compound 30-S3 (0.63 g, yield 90.5%) as light yellow solid. LC/MS (ESI) m/z: 294 (M+H)+.

Step 3: (1R,3S,5R)-tert-Butyl 3-((6-bromo-3-methylpyridin-2-yl)carbamoyl)-5-(penta-1,4-dien-1-yl)-2-azabicyclo[3.1.0]hexane-2-carboxylate (30-S4)

To a mixture of compound 30-S3 (0.15 g, 0.51 mmol) and 6-bromo-3-methylpyridin-2-amine (96 mg, 0.51) in dichloromethane (5 mL) was added pyridine (0.202 g, 2.56 mmol) followed by drop-wise addition of phosphoryl chloride (0.157 g, 1.023 mmol) at 0° C., and the reaction was stirred at 0° C. for 2 hours. The mixture was diluted with DCM and washed with saturated aq. $NH_4Cl$ solution, 0.5 N aq. HCl, and brine successively, dried, and concentrated to dryness. The residue was purified by silica gel chromatography (eluted with PE:EtOAc=5:1 to 3:1) to provide compound 30-S4 (0.12 g, yield 50.76%) as a light yellow solid. LC/MS (ESI) m/z: 462/464 (M+H)+.

Step 4: (1R,3S,5R)-N-(6-Bromo-3-methylpyridin-2-yl)-5-(penta-1,4-dien-1-yl)-2-azabicyclo[3.1.0]hexane-3-carboxamide Trifluoroacetic Acid Salt (30-S5)

To a solution of compound 30-S4 (0.12 g, 0.26 mmol) in dichloromethane (4 mL) was added Trifluoroacetic acid (2 mL) at 0° C., and the mixture was stirred at 25° C. for 2 hours. The mixture was concentrated to dryness, washed with ether, and dried under vacuum to give compound 30-S5 (0.15 g, yield 100%) as yellow oil. LC/MS (ESI) m/z: 362/364 (M+H)+.

Step 5: (1R,3S,5R)-2-(2-(3-Acetyl-7-(hex-5-en-1-yl)-5-(2-methylpyrimidin-5-yl)-1H-indazol-1-yl)acetyl)-N-(6-bromo-3-methylpyridin-2-yl)-5-(penta-1,4-dien-1-yl)-2-azabicyclo[3.1.0]hexane-3-carboxamide (30-S6)

To a mixture of compound 30-S5 (0.15 g, 0.25 mmol) and [3-acetyl-7-(hex-5-en-1-yl)-5-(2-methylpyrimidin-5-yl)indazol-1-yl]acetic acid (0.1 g, 0.25) in DMF (5 mL) was added HATU (0.145 g, 0.38 mmol) followed by DIPEA (99 mg, 0.76 mmol) at 0° C., and the reaction was stirred at 25° C. for 2 hours. The mixture was diluted with EtOAc and washed with saturated aq. $NH_4Cl$ solution and brine, dried over $Na_2SO_4$, filtered and concentrated to dryness. The residue was purified by silica gel chromatography (eluted with PE:EtOAc=3:1 to 1:1) to provide compound 30-S6 (0.15 g, yield 80.1%) as a yellow solid. LC/MS (ESI) m/z: 736/738 (M+H)+.

Step 6: (41R,43S,45R)-13-Acetyl-N-(6-bromo-3-methylpyridin-2-yl)-15-(2-methylpyrimidin-5-yl)-3-oxo-11H-42-aza-1(1,7)-indazola-4(2,5)-bicyclo[3.1.0]hexanacyclotridecaphane-5,8-diene-43-carboxamide (30-S7)

To a solution of compound 30-S6 (0.1 g, 0.136 mmol, 1 equiv.) in degassed toluene (60 mL) was added Grubbs Catalyst 2nd Generation (23 mg, 0.027 mmol) under $N_2$ atmosphere, the mixture was degassed under $N_2$ atmosphere three times, and stirred at 80° C. for 16 hours under $N_2$ atmosphere. The mixture was concentrated to dryness and the residue was purified by silica gel chromatography (eluted with PE:EtOAc=3:1 to 1:1) to provide compound 30S-7 (21 mg, yield 21.8%) as a yellow solid. LC/MS (ESI) m/z: 708/710 (M+H)+.

Step 7: (41R,43S,45R)-13-Acetyl-N-(6-bromo-3-methylpyridin-2-yl)-15-(2-methylpyrimidin-5-yl)-3-oxo-11H-42-aza-1(1,7)-indazola-4(2,5)-bicyclo[3.1.0]hexanacyclotridecaphane-43-carboxamide (30)

To a solution of compound 30S-7 (20 mg, 0.028 mmol) in ethyl acetate (2 mL) was added $PtO_2$ (1 mg), the mixture was degassed under $N_2$ for three times and stirred under a $H_2$ balloon for 10 minutes. The mixture was filtered, and the filtrate was concentrated to dryness. The residue was purified by preparatory HPLC to provide 30 (2.5 mg, yield 12.5%) as a white solid. $^1$H-NMR (400 MHz, DMSO-$d_6$) δ 10.35 (s, 1H), 9.01 (s, 2H), 8.30-8.31 (d, J=1.6 Hz, 1H), 7.58-7.60 (d, J=8.4 Hz, 1H), 7.56-7.57 (m, 1H), 7.39-7.41 (d, J=7.6 Hz, 1H), 5.88-5.92 (d, J=17.6 Hz, 1H), 5.49-5.54 (d, J=18 Hz, 1H), 4.37-4.40 (m, 1H), 3.64-3.65 (m, 1H), 3.13-3.17 (m, 1H), 2.72-2.79 (m, 1H), 2.67 (s, 3H), 2.64 (s, 3H), 2.31-2.34 (m, 1H), 2.15-2.20 (m, 1H), 1.96-2.05 (m, 2H), 2.01 (s, 3H), 1.80-1.84 (m, 1H), 1.55-1.68 (m, 4H), 1.23-1.55 (m, 9H), 1.11-1.17 (m, 1H), 0.90-0.92 (m, 1H). LC/MS (ESI) m/z: 712/714 (M+H)+.

Scheme 20: Synthesis of (41R,43S,45R)-42-(2-(3-Acetyl-5-(2-methylpyrimidin-5-yl)-1H-pyrazolo[3,4-c]pyridin-1-yl)acetyl)-16-bromo-8,8-dimethyl-13-oxa-42,2,6-triaza-1(2,3)-pyridina-4(3,5)-bicyclo[3.1.0]hexanacyclotetradecaphane-3,7-dione (31)

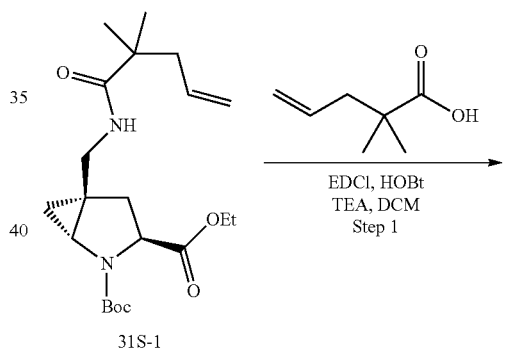

31S-1

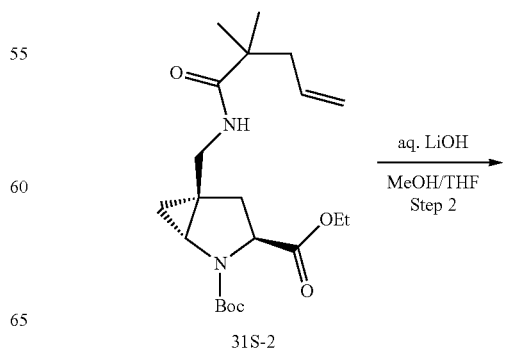

31S-2

581
-continued

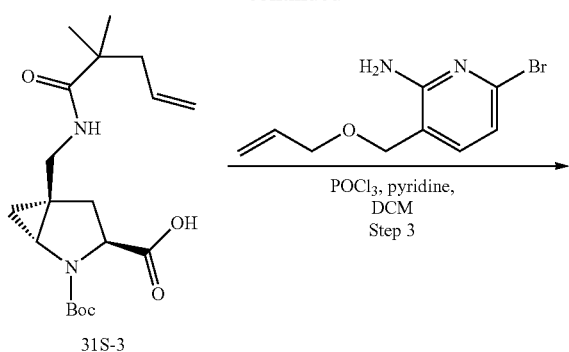
31S-3

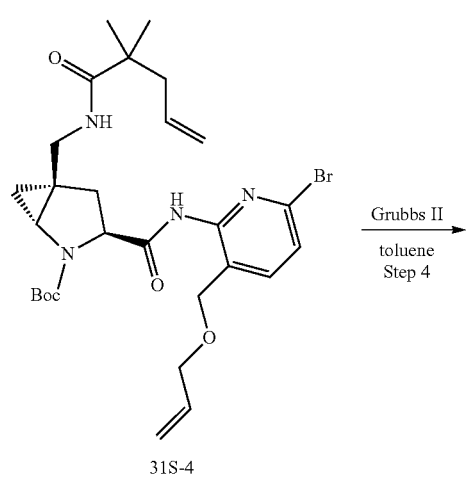
31S-4

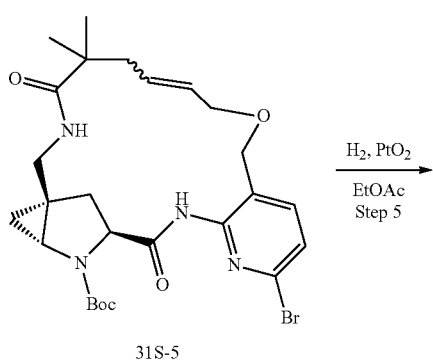
31S-5

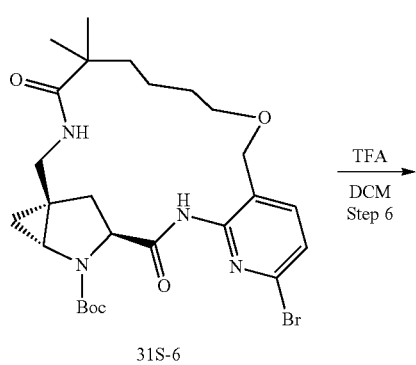
31S-6

582
-continued

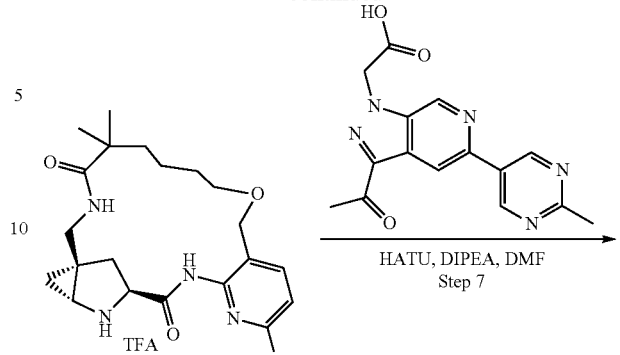
31S-7

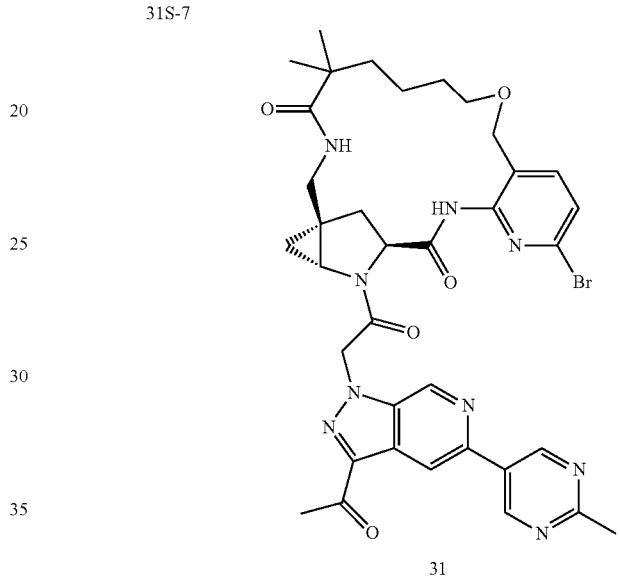
31

The above scheme and following detailed description depicts one non-limiting method for synthesizing compounds of Formula I wherein -$X^9$-$L^3$-$X^{10}$- is

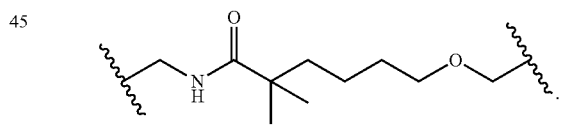

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: (1R,3S,5R)-2-tert-Butyl 3-Ethyl 5-((2,2-Dimethylpent-4-enamido)methyl)-2-azabicyclo[3.1.0]hexane-2,3-dicarboxylate (31S-2)

To a mixture of compound 31S-1 (0.13 g, 0.46 mmol) and 2,2-dimethylpent-4-enoic acid (71 mg, 0.55 mmol) in dichloromethane (3 mL) was added EDCI (0.131 g, 0.69 mmol) and HOBt (62 mg, 0.46 mmol) followed by triethylamine (0.139 g, 1.37 mmol) at 0° C., and the reaction was stirred at room temperature for 2 hours. The mixture was diluted with DCM, washed with saturated aq. NH₄Cl solution and brine, dried over anhydrous Na₂SO₄, filtered and concentrated to dryness. The residue was purified by silica gel chromatography (eluted with PE:EtOAc=3:1 to 1:1) to provide compound 31S-2 (0.14 g, yield 77.1%) as a light yellow oil. LC/MS (ESI) m/z: 395 (M+H)+.

Step 2: (1R,3S,5R)-2-(tert-Butoxycarbonyl)-5-((2,2-dimethylpent-4-enamido)methyl)-2-azabicyclo[3.1.0]hexane-3-carboxylic Acid (31S-3)

To a solution of compound 31S-2 (140 mg, 0.355 mmol) in MeOH/THF (6 mL, 2:1) was added a solution of LiOH (71 mg, 1.78 mmol) in water (2 mL), and the mixture was stirred at room temperature for 2 hours. The mixture was diluted with water, washed with ether, and the aqueous layer was collected and acidified with 0.5 N aq. HCl solution to pH~3. The mixture was extracted with DCM twice, and the combined organic layers were washed with brine, dried over anhydrous $Na_2SO_4$, filtered and concentrated to provide compound 31S-3 (120 mg, yield 92.3%) as a colorless oil. LC/MS (ESI) m/z: 367(M+H)+.

Step 3: (1R,3S,5R)-tert-Butyl 3-(3-(Allyloxymethyl)-6-bromopyridin-2-ylcarbamoyl)-5-((2,2-dimethylpent-4-enamido)methyl)-2-azabicyclo[3.1.0]hexane-2-carboxylate (31S-4)

To a solution of compound 31S-3 (120 mg, 0.33 mmol) and 3-(allyloxymethyl)-6-bromopyridin-2-amine (88 mg, 0.36 mmol) in anhydrous DCM (14 mL) was added pyridine (131 mg, 1.65 mmol) followed by drop-wise addition of $POCl_3$ (61 mg, 0.396 mmol) under $N_2$ atmosphere at 0° C. The reaction mixture was stirred at room temperature for 1 hour. The reaction mixture was quenched with ice-cooled water and extracted with DCM twice. The combined organic phases were washed with brine, dried over anhydrous $Na_2SO_4$, filtered and concentrated to dryness. The residue was purified by silica gel column chromatography (eluted with PE:EtOAc=3:1 to 1:1) to provide compound 31S-4 (130 mg, yield 66.8%) as a colorless oil. LC/MS (ESI) m/z: 591/593 (M+H)+.

Step 4: tert-Butyl (41R,43S,45R)-16-Bromo-8,8-dimethyl-3,7-dioxo-13-oxa-42,2,6-triaza-1(2,3)-pyridina-4(3,5)-bicyclo[3.1.0]hexanacyclotetradecaphan-10-ene-42-carboxylate (31S-5)

To a solution of compound 31S-4 (130 mg, 0.22 mmol) in degassed toluene (70 mL) was added Grubbs II catalyst (47 mg, 0.055 mmol), and the resulting mixture was stirred at 80° C. for 16 hours under $N_2$ atmosphere. The mixture was concentrated to dryness, and the residue was purified by silica gel column chromatography (eluted with PE:EtOAc=2:1 to 1:1) to provide compound 31S-5 (103 mg, yield 83.1%) as a brown solid. LC/MS (ESI) m/z: 563/565 (M+H)+.

Step 5: tert-Butyl (41R,43S,45R)-16-Bromo-8,8-dimethyl-3,7-dioxo-13-oxa-42,2,6-triaza-1(2,3)-pyridina-4(3,5)-bicyclo[3.1.0]hexanacyclotetradecaphane-42-carboxylate (XS-6)

To a solution of compound 31S-5 (70 mg, 0.125 mmol) in EtOAc (10 mL) was added $PtO_2$ (20 mg), and the mixture was stirred at room temperature for 10 minutes under a $H_2$ balloon. Then the mixture was filtered, and the filtrate was concentrated to dryness. The residue was purified by silica gel column chromatography (eluted with PE:EtOAc=1:1) to provide compound 31S-6 (58 mg, yield 66.8%) as a yellow solid. LC/MS (ESI) m/z: 565/567 (M+H)+.

Step 6: (41R,43S,45R)-16-Bromo-8,8-dimethyl-13-oxa-42,2,6-triaza-1(2,3)-pyridina-4(3,5)-bicyclo[3.1.0]hexanacyclotetradecaphane-3,7-dione Trifluoroacetic Acid Salt (31S-7)

To a solution of compound 31S-6 (58 mg, 0.103 mmol) in DCM (2 mL) was added TFA (1 mL) drop-wise at 0° C. under $N_2$ atmosphere, and the mixture was stirred at room temperature for 1 hour. The mixture was concentrated to dryness, washed with ether, and dried under vacuum to give compound 31S-7 (55 mg, yield 92.4%) as a brown solid. LC/MS (ESI) m/z: 465/467 (M+H)+.

Step 7: (41R,43S,45R)-42-(2-(3-Acetyl-5-(2-methylpyrimidin-5-yl)-1H-pyrazolo[3,4-c]pyridin-1-yl)acetyl)-16-bromo-8,8-dimethyl-13-oxa-42,2,6-triaza-1(2,3)-pyridina-4(3,5)-bicyclo[3.1.0]hexanacyclotetradecaphane-3,7-dione (31)

To a mixture of compound 31S-7 (29 mg, 0.052 mmol), 2-(3-acetyl-5-(2-methylpyrimidin-5-yl)-1H-pyrazolo[3,4-c]pyridin-1-yl)acetic acid (19 mg, 0.057 mmol), and HATU (32 mg, 0.084 mmol) in DMF (2 mL) was added DIPEA (34 mg, 0.26 mmol), and the reaction mixture was stirred at room temperature for 1 hour. The mixture was diluted with EtOAc and washed with 10% aq. LiCl solution and brine, dried over anhydrous $Na_2SO_4$, filtered and concentrated to dryness. The residue was purified via preparatory HPLC to provide compound 31 (4 mg, yield 10.2%) as a white solid. $^1$H-NMR (400 MHz, DMSO-$d_6$) δ 9.79 (s, 1H), 9.31-9.42 (m, 3H), 8.62 (d, J=1.2 Hz, 1H), 7.69 (d, J=7.9 Hz, 1H), 7.43 (d, J=7.9 Hz, 1H), 6.03 (d, J=17.4 Hz, 1H), 5.82 (d, J=17.3 Hz, 1H), 4.17-4.32 (m, 2H), 3.73-3.82 (m, 1H), 3.39-3.59 (m, 2H), 2.93-3.24 (m, 3H), 2.71 (s, 3H), 2.69 (s, 3H), 2.43-2.48 (m, 1H), 2.26-2.33 (m, 1H), 1.22-1.71 (m, 6H), 1.11-1.22 (m, 2H), 1.09 (s, 3H), 1.07 (s, 3H). LC/MS (ESI) m/z: 758/760 (M+H)+.

Scheme 21: Synthesis of (41R,43S,45R)-42-(2-(3-Acetyl-5-(2-methylpyrimidin-5-yl)-1H-pyrazolo[3,4-c]pyridin-1-yl)acetyl)-16-bromo-8,8-dimethyl-13-oxa-42,2,6-triaza-1(2,3)-pyridina-4(3,5)-bicyclo[3.1.0]hexanacyclotetradecaphan-10-ene-3,7-dione (32)

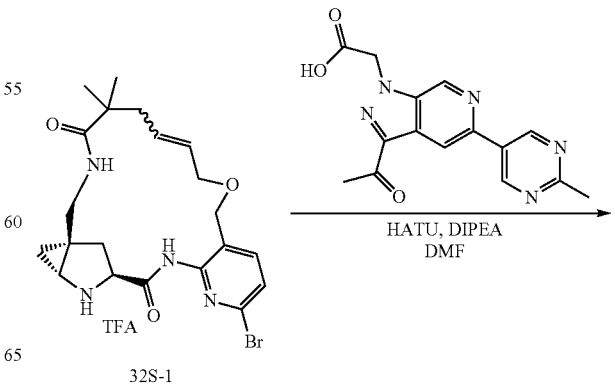

32S-1

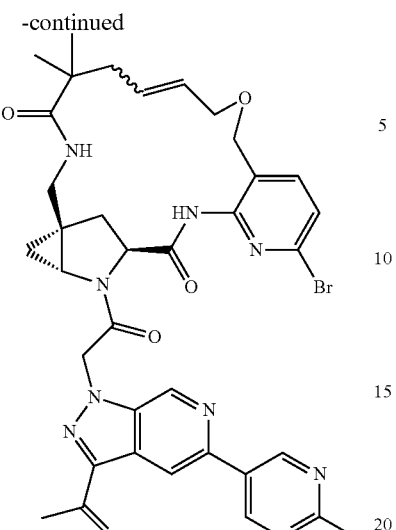

32

The above scheme and following detailed description depicts one non-limiting method for synthesizing compounds of Formula II wherein -X$^9$-L$^3$-X$^{10}$- is

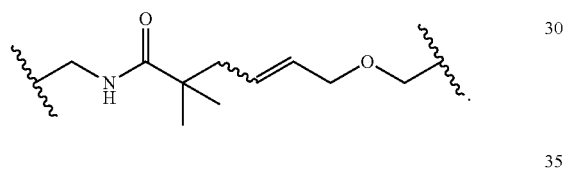

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

To a mixture of 2-(3-acetyl-5-(2-methylpyrimidin-5-yl)-1H-pyrazolo[3,4-c]pyridin-1-yl)acetic acid (17 mg, 0.054 mmol) and compound 32S-1 (30 mg, 0.054 mmol) in DMF (1 mL) was added HATU (31 mg, 0.081 mmol) and DIPEA (21 mg, 0.16 mmol) at 0° C., and the mixture was stirred at 25° C. for 1 hour. The mixture was diluted with EtOAc, washed with 10% aq. LiCl solution and brine, dried, and concentrated to dryness. The residue was purified by preparatory HPLC to give compound 32 (5 mg, yield 12.3%) as white solid. $^1$H-NMR (400 MHz, DMSO-d$_6$) δ 9.36 (s, 2H), 9.34 (d, J=1.2 Hz, 1H), 8.62 (d, J=1.2 Hz, 1H), 7.78 (d, J=8.1 Hz, 1H), 7.50 (d, J=8.0 Hz, 1H), 7.31 (d, J=3.6 Hz, 1H), 5.97 (d, J=17.3 Hz, 1H), 5.82 (d, J=17.1 Hz, 1H), 5.64-5.57 (m, 1H), 5.56-5.48 (m, 1H), 4.39 (d, J=14.3 Hz, 2H), 4.25-4.19 (m, 1H), 3.96-3.89 (m, 1H), 3.85 (s, 1H), 3.81-3.77 (m, 1H), 3.77-3.70 (m, 1H), 2.68 (dd, J=10.5, 3.4 Hz, 6H), 2.64-2.58 (m, 1H), 2.47-2.42 (m, 2H), 2.39-2.27 (m, 1H), 2.13-2.07 (m, 1H), 2.00-1.94 (m, 1H), 1.19 (s, 3H), 1.18-1.13 (m, 2H), 1.12 (s, 3H). LC/MS (ESI) 756/758 m/z: (M+H)$^+$.

Scheme 22:
Synthesis of (41R,43S,45R)-42-(2-(3-Acetyl-5-(2-methylpyrimidin-5-yl)-1H-pyrazolo[3,4-c]pyridin-1-yl]acetyl)-16-bromo-8,8-difluoro-13-oxa-42,2,6-triaza-1(2,3)-pyridina-4(3,5)-bicyclo[3.1.0]hexanacyclotetradecaphane-3,7-dione (33) and (41R,43S,45R)-42-(2-(3-acetyl-5-(2-methylpyrimidin-5-yl)-1H-indazol-1-yl)acetyl)-16-bromo-8,8-difluoro-13-oxa-42,2,6-triaza-1(2,3)-pyridina-4(3,5)-bicyclo[3.1.0]hexanacyclotetradecaphane-3,7-dione (34)

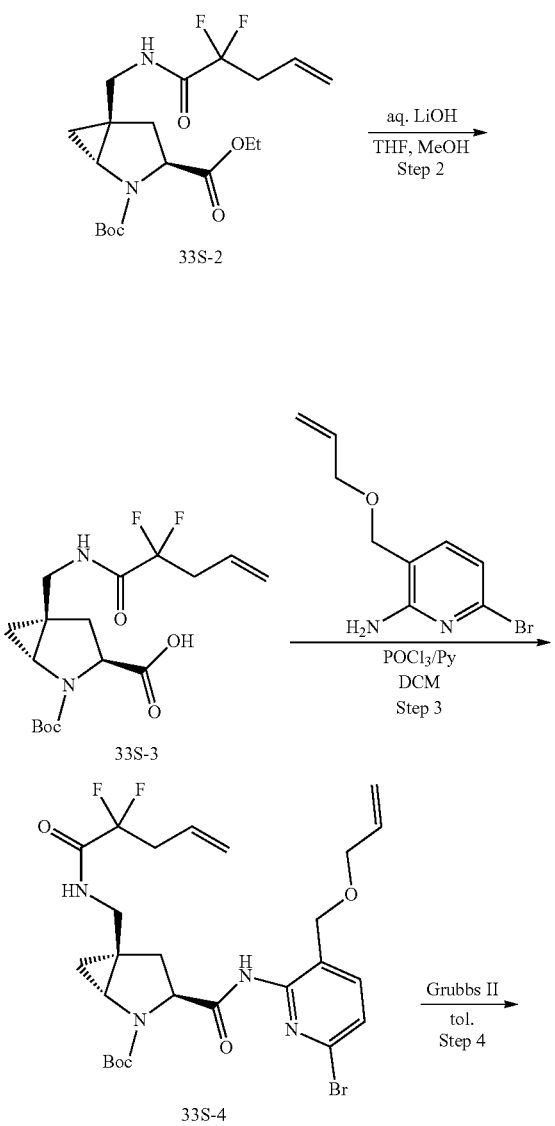

587

-continued

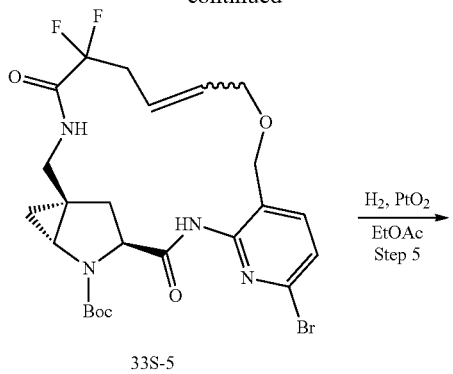

33S-5

H₂, PtO₂
EtOAc
Step 5

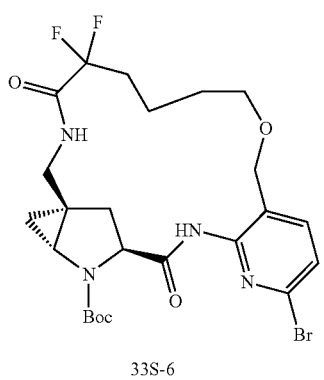

33S-6

TFA
DCM
Step 6

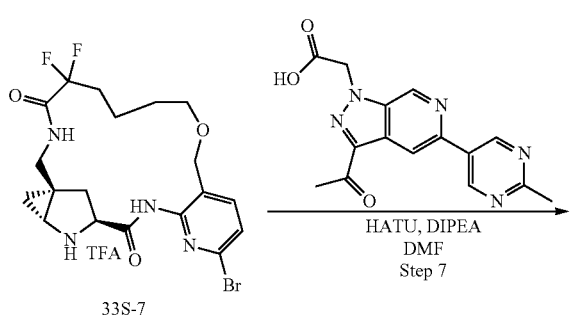

33S-7

HATU, DIPEA
DMF
Step 7

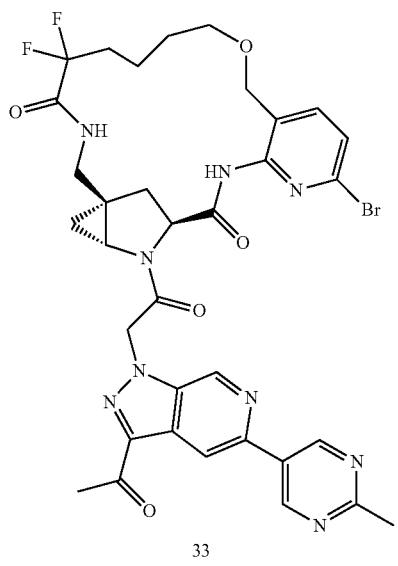

33

588

-continued

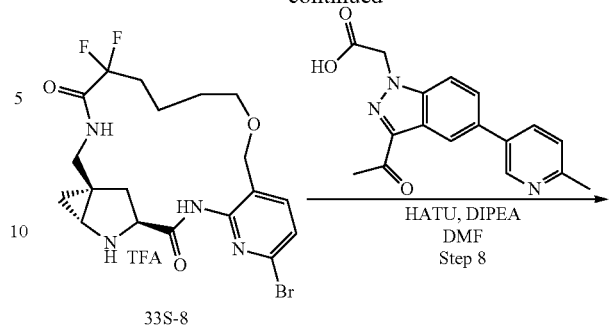

33S-8

HATU, DIPEA
DMF
Step 8

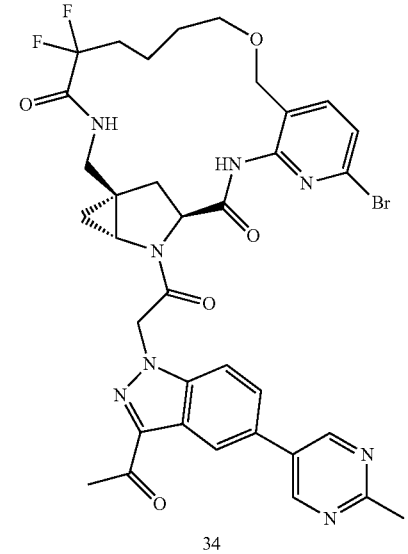 [SMILES: CC(=O)c1nn(CC(=O)N2[C@H]3C[C@@]4(CNC(=O)C(F)(F)CCCCOCc5ccc(Br)nc5NC3=O)C[C@@H]24)c2ccc(-c3cnc(C)nc3)cc12]

34

The above scheme and following detailed description depicts one non-limiting method for synthesizing compounds of Formula I wherein -X⁹-L³-X¹⁰- is The skilled artisan will recognize that related -X⁹-L³-X¹⁰- moieties of different chain lengths, and stereochemistry, in addition A¹, B², and C² groups as described herein, can be used to afford additional compounds of the present invention.

Step 1: (1R,3S,5R)-2-tert-Butyl 3-Ethyl 5-((2,2-Difluoropent-4-enamido)methyl)-2-azabicyclo[3.1.0]hexane-2,3-dicarboxylate (33S-2)

To a mixture of compound 33S-1 (350 mg, 1.23 mmol) and 2,2-difluoropent-4-enoic acid (167 mg, 1.23 mmol) in DCM (5 mL) was added TEA (373 mg, 3.69 mmol) followed by HOBt (166 mg, 1.23 mmol) and EDCI (425 mg, 2.2 mmol) at 0° C., and the mixture was stirred at room temperature overnight. The mixture was diluted with DCM and washed with water and brine, dried with anhydrous Na₂SO₄, filtered and concentrated to dryness. The residue was purified by chromatography on silica gel (PE:EtOAc=4:1) to give compound 33S-2 (254 mg, yield 51.4%) as light yellow oil. LC/MS (ESI) m/z: 403 (M+H)⁺.

Step 2: (1R,3S,5R)-2-(tert-Butoxycarbonyl)-5-((2,2-difluoropent-4-enamido)methyl)-2-azabicyclo[3.1.0]hexane-3-carboxylic Acid (33S-3)

To a solution of compound 33S-2 (254 mg, 0.63 mmol) in MeOH/THF (6 mL, v/v=2/1) was added a solution of lithium hydroxide (80 mg, 1.89 mmol) in water (2 mL) at 0° C., and the mixture was stirred at room temperature for 1 hour. The reaction mixture was concentrated to dryness, and the residue was diluted with water and washed with ether twice. The aqueous layer was acidified by adding 1N aq. HCl and extracted with DCM twice. The combined organic layer was washed with brine, dried and concentrated to dryness to provide compound 33S-3 (214 mg, yield 91.1%) as a light yellow solid. LC/MS (ESI) m/z: 375 (M+H)$^+$.

Step 3: (1R,3S,5R)-tert-Butyl 3-((3-((Allyloxy)methyl)-6-bromopyridin-2-yl)carbamoyl)-5-((2,2-difluoropent-4-enamido)methyl)-2-azabicyclo[3.1.0]hexane-2-carboxylate (33S-4)

To a mixture of compound 33S-3 (214 mg, 0.57 mmol) and 3-((allyloxy)methyl)-6-bromopyridin-2-amine (138 mg, 0.57 mmol) in DCM (5 mL) was added pyridine (225 mg, 2.85 mmol) followed by phosphoryl chloride (95 mg, 0.60 mmol) at 0° C., and the mixture was stirred at room temperature for 1 hour under N$_2$ atmosphere. The mixture was poured into ice water and extracted with DCM twice. The combined organic layers were washed with brine, dried with anhydrous Na$_2$SO$_4$, filtered and concentrated to dryness. The residue was purified by chromatography on silica gel (PE:EtOAc=15:1) to provide compound 33S-4 (123 mg, yield 57.7%) as a yellow solid. LC/MS (ESI) m/z: 599/601 (M+H)$^+$.

Step 4: tert-Butyl (41R,43S,45R,E)-16-Bromo-8,8-difluoro-3,7-dioxo-13-oxa-42,2,6-triaza-1(2,3)-pyridina-4(3,5)-bicyclo[3.1.0]hexanacyclotetradecaphan-10-ene-42-carboxylate (33S-5)

To a solution of compound 33S-4 (123 mg, 0.2 mmol) in degassed toluene (100 mL) was added Grubbs II catalyst (44 mg, 0.05 mmol) at 0° C. under N$_2$ atmosphere, and the mixture was stirred at 80° C. overnight under N$_2$ atmosphere. The mixture was concentrated to dryness, and the residue was purified by chromatography on silica gel (PE:EtOAc=3:1) to provide compound 33S-5 (110 mg, yield 96.5%) as a brown solid. LC/MS (ESI) m/z: 571/573 (M+H)$^+$.

Step 5: tert-Butyl (41R,43S,45R)-16-Bromo-8,8-difluoro-3,7-dioxo-13-oxa-42,2,6-triaza-1(2,3)-pyridina-4(3,5)-bicyclo[3.1.0]hexanacyclotetradecaphane-42-carboxylate (33S-6)

To a solution of compound 33S-5 (70 mg, 0.12 mmol) in ethyl acetate (3 mL) was added PtO$_2$ (18 mg, 25% wt), and the resulting mixture was stirred at room temperature for 10 minutes under a H$_2$ balloon. The mixture was filtered, and the filtrate was concentrated to dryness to give compound 33S-6 (60 mg, yield 85.4%) as a brown solid. LC/MS (ESI) m/z: 573/575 (M+H)$^+$.

Step 6: (1R,20S,22R)-15-Bromo-5,5-difluoro-10-oxa-3,16,18,21-tetraazatetracyclo[18.3.1.0$^{1,22}$.0$^{12,17}$]tetracosa-12,14,16-triene-4,19-dione Trifluoroacetic Acid Salt (33S-7)

To a solution of compound 33S-6 (60 mg, 0.11 mmol) in DCM (3 mL) was added TFA (1 mL) at 0° C., and the mixture was stirred at room temperature for 1 hour. The reaction mixture was concentrated to dryness, washed with ether and dried under vacuum to give compound 33S-7 (60 mg, yield 100%) as a yellow oil. LC/MS (ESI) m/z: 473/475 (M+H)$^+$.

Step 7: (41R,43S,45R)-42-(2-(3-Acetyl-5-(2-methylpyrimidin-5-yl)-1H-pyrazolo[3,4-c]pyridin-1-yl)acetyl)-16-bromo-8,8-difluoro-13-oxa-42,2,6-triaza-1(2,3)-pyridina-4(3,5)-bicyclo[3.1.0]hexanacyclotetradecaphane-3,7-dione (33)

To a mixture of compound 33S-7 (30 mg, 0.053 mmol) and 2-(3-acetyl-5-(2-methylpyrimidin-5-yl)-1H-pyrazolo[3,4-c]pyridin-1-yl)acetic acid (16 mg, 0.053 mmol) in DMF (3 mL) was added DIPEA (34 mg, 0.26 mmol) followed by HATU (30 mg, 0.079 mmol) at 0° C., and the mixture was stirred at room temperature for 1 hour. The mixture was diluted with water and extracted with EtOAc twice. The combined organic layers were washed with 10% aq. LiCl solution and brine, dried over Na$_2$SO$_4$, filtered and concentrated to dryness. The residue was purified by preparatory HPLC to give 33 (5 mg, yield 12.5%) as a white solid. $^1$H-NMR (400 MHz, DMSO-d$_6$) δ 9.82 (s, 1H), 9.37 (s, 2H), 9.36 (d, J=1.2 Hz, 1H), 9.09-9.00 (m, 1H), 8.62 (d, J=1.6 Hz, 1H), 7.70 (d, J=7.6 Hz, 1H), 7.45 (d, J=8.0 Hz, 1H), 6.08 (d, J=17.2 Hz, 1H), 5.83 (d, J=17.2 Hz, 1H), 4.32 (d, J=12.8 Hz, 1H), 4.18-4.23 (m, 1H), 3.81 (m, 1H), 3.69-3.72 (m, 1H), 3.43-3.45 (m, 1H), 3.23-3.25 (m, 1H), 3.05-3.07 (m, 1H), 2.70 (s, 3H), 2.69 (s, 3H), 1.97-2.26 (m, 4H), 1.60-1.64 (m, 1H), 1.45-1.51 (m, 2H), 1.25-1.29 (m, 2H), 1.14-1.17 (m, 2H). LC/MS (ESI) m/z: 766/768 (M+H)$^+$.

Step 8: 41R,43S,45R)-42-(2-(3-acetyl-5-(2-methylpyrimidin-5-yl)-1H-indazol-1-yl)acetyl)-16-bromo-8,8-difluoro-13-oxa-42,2,6-triaza-1(2,3)-pyridina-4(3,5)-bicyclo[3.1.0]hexanacyclotetradecaphane-3,7-dione (34)

To a mixture of compound 33S-7 (30 mg, 0.053mmol) and 2-(3-acetyl-5-(2-methylpyrimidin-5-yl)-1H-indazol-1-yl)acetic acid (16 mg, 0.053 mmol) in DMF (3 mL) was added DIPEA (34 mg, 0.26 mmol) followed by HATU (30 mg, 0.079 mmol) at 0° C., and the mixture was stirred at room temperature for 1 hour. The mixture was diluted with water and extracted with EtOAc twice. The combined organic layers were washed with 10% aq. LiCl solution and brine, dried over Na$_2$SO$_4$, filtered and concentrated to dryness. The residue was purified by preparatry HPLC to give 34 (8 mg, yield 19.8%) as a white solid. $^1$H-NMR (400 MHz, DMSO-d$_6$) δ 9.78 (s, 1H), 9.06 (s, 2H), 8.45 (t, J=1.2 Hz, 1H), 7.91 (d, J=1.2 Hz, 2H), 7.69 (d, J=8.0 Hz, 1H), 7.65-7.54 (m, 1H), 7.46 (d, J=7.6 Hz, 1H), 5.93 (d, J=17.6 Hz, 1H), 5.67 (d, J=17.6 Hz, 1H), 4.34 (d, J=12.4 Hz, 1H), 4.16-4.22 (m, 1H), 3.80 (m, 1H), 3.69-3.72 (m, 1H), 3.43-3.47 (m, 1H), 3.27-3.28 (m, 1H), 3.02-3.08 (m, 1H), 2.68 (s, 3H), 2.67 (s, 3H), 1.99-2.27 (m, 4H), 1.37-1.68 (m, 3H), 1.16-1.28 (m, 4H). LC/MS (ESI) m/z: 765/767 (M+H)$^+$.

Scheme 23:
Synthesis of (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclotridecaphane-43-carboxamide (35)

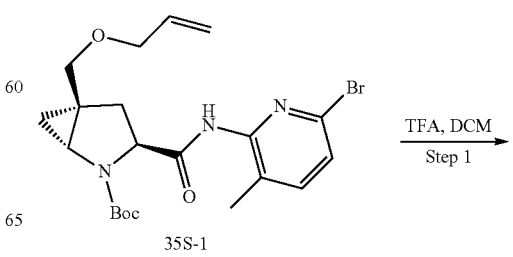

35S-1

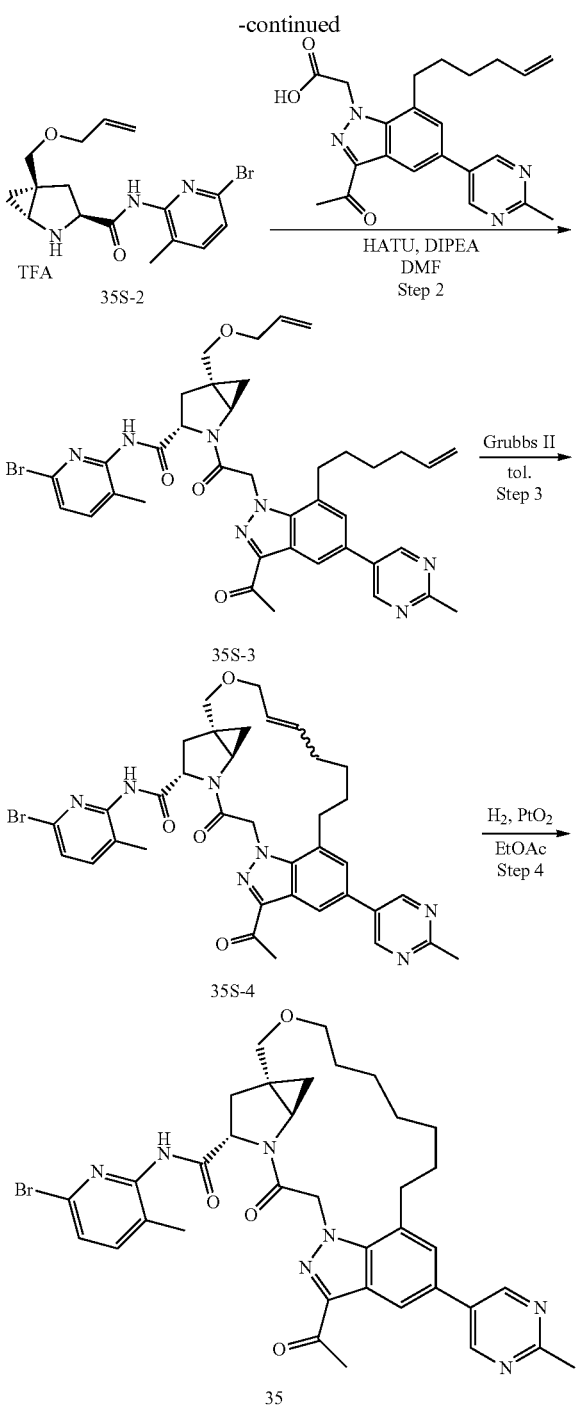

addition $A^1$, $B^2$, and $C^2$ groups as described herein, can be used to afford additional compounds of the present invention.

Step 1: (1R,3S,5S)-5-((Allyloxy)methyl)-N-(6-bromo-3-methylpyridin-2-yl)-2-azabicyclo[3.1.0]hexane-3-carboxamide Trifluoroacetic Acid Salt(35S-2)

To a solution of compound 35S-1 (113 mg, 0.24 mmol) in DCM (4 mL) was added TFA (2 mL) at 0° C., and the reaction was stirred at 25° C. for 1 hour. The mixture was concentrated to dryness, and the residue was washed with ether and dried under vacuum to give compound 35S-2 (89 mg, yield 100%) as a brown syrup. LC/MS (ESI) m/z: 366/368 (M+H)⁺.

Step 2: (1R,3S,5S)-2-(2-(3-Acetyl-7-(hex-5-en-1-yl)-5-(2-methylpyrimidin-5-yl)-1H-indazol-1-yl)acetyl)-5-((allyloxy)methyl)-N-(6-bromo-3-methylpyridin-2-yl)-2-azabicyclo[3.1.0]hexane-3-carboxamide (35S-3)

To a mixture of compound 35S-2 (89 mg, 0.24 mmol) and 2-(3-acetyl-7-(hex-5-en-1-yl)-5-(2-methylpyrimidin-5-yl)-1H-indazol-1-yl)acetic acid (113 mg, 0.29 mmol) in DMF (5 mL) was added DIPEA (154 mg, 1.2 mmol) and HATU (137 mg, 0.36 mmol) at 0° C., and the mixture was stirred at 25° C. for 1 hour. The mixture was diluted with EtOAc and washed with 10% aq. LiCl solution and brine, dried over Na₂SO₄ and concentrated to dryness. The residue was purified by column chromatography on silica gel (eluted with PE:EtOAc=1:2) to provide compound 35S-3 (115 mg, 83.9% yield) as a white solid. LC/MS (ESI) m/z: 740/742 (M+H)⁺.

Step 3: (41R,43S,45S,E)-13-Acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclotridecaphan-8-ene-43-carboxamide (35S-4)

To a solution of compound 35S-3 (115 mg, 0.16 mmol) in toluene (100 mL) was added Grubb's second generation catalyst (26.4 mg, 0.031 mmol) under N₂ atmosphere. The mixture was degassed under N₂ atmosphere three times and stirred under N₂ atmosphere at 80° C. overnight. The mixture was concentrated to dryness, and the residue was purified by column chromatography on silica gel (eluted with DCM:MeOH=40:1) to provide compound 35S-4 (50 mg, 44.0% yield) as a brown solid. LC/MS (ESI) m/z: 712/714 (M+H)⁺.

Step 4: (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclotridecaphane-43-carboxamide (35)

To a solution of compound 35S-4 (50 mg, 0.07 mmol) in ethyl acetate (3 mL) was added PtO₂ (15 mg, 30% wt) at 0° C., and the mixture was degassed under N₂ atmosphere three times and stirred at 25° C. under a H₂ balloon for 20 minutes. The mixture was filtered, and the filtrate was concentrated to dryness. The residue was purified by preparatory HPLC to give compound 35 (4.6 mg, yield 9.2%) as a white solid. ¹H-NMR (400 MHz, DMSO-d₆) δ 10.37 (s, 1H), 9.01 (s, 2H), 8.30 (d, J=1.6 Hz, 1H), 7.59 (d, J=7.6 Hz, 1H), 7.54 (d, J=2.0 Hz, 1H), 7.40 (d, J=8.0 Hz, 1H), 6.05 (d, J=18.0 Hz, 1H), 5.51 (d, J=17.6 Hz, 1H), 4.35 (t, J=8.0 Hz, 1H), 3.99-3.94 (m, 2H), 3.68 (d, J=8.8 Hz, 1H), 3.60-3.54 (m, 1H), 3.23-3.18 (m, 1H), 3.03 (d, J=12.8 Hz, 1H), 2.90-2.84 (m, 1H), 2.67 (s, 3H), 2.64 (s, 3H), 2.37 (q, J=7.5, 5.9 Hz, 2H), 2.00 (s, 3H), 1.89-1.56 (m, 8H), 1.43-1.40 (m, 2H), 1.00 (dd, J=5.6, 5.6 Hz, 1H), 0.93 (t, J=5.6 Hz, 1H). LC/MS (ESI) m/z: 714/716 (M+H)⁺.

The above scheme and following detailed description depicts one non-limiting method for synthesizing compounds of Formula II wherein -X⁹-L³-X¹⁰- is

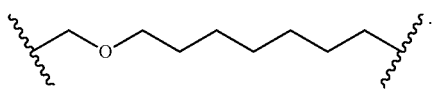 [SMILES: *CCCCCCCOC*]

The skilled artisan will recognize that related -X⁹-L³-X¹⁰- moieties of different chain lengths, and stereochemistry, in

593

Scheme 24: Synthesis of (41R,43S,45R)-42-(2-(3-Acetyl-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexanacyclotridecaphan-3-one (36)

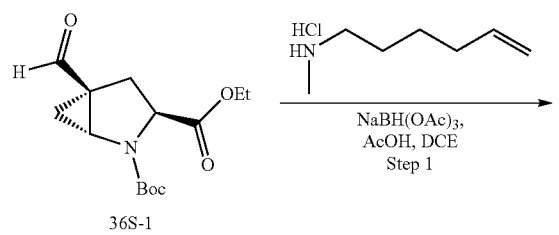

36S-1

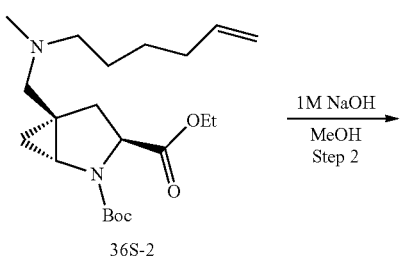

36S-2

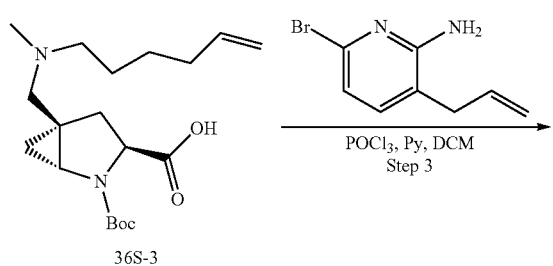

36S-3

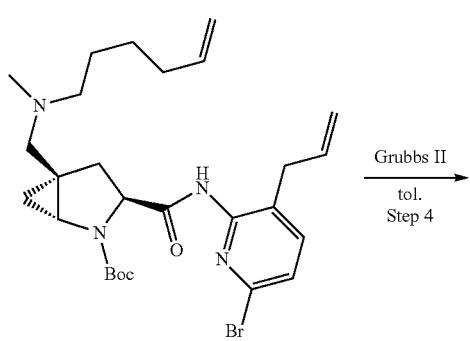

36S-4

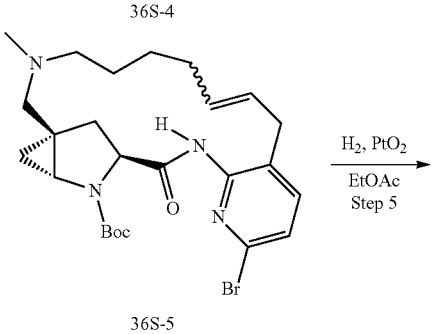

36S-5

594

-continued

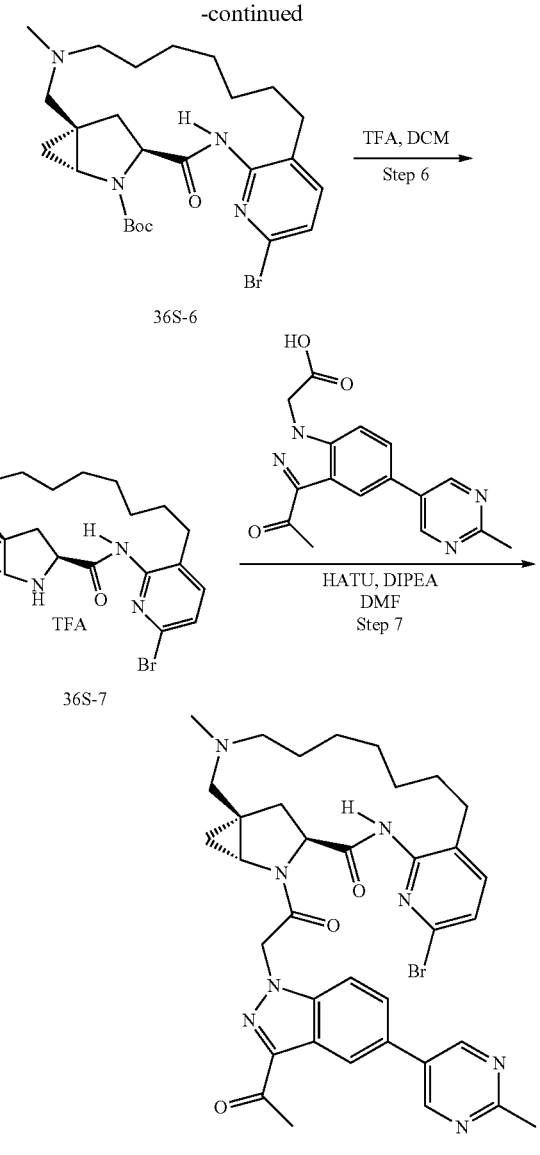

36

The above scheme and following detailed description depicts one non-limiting method for synthesizing compounds of Formula I wherein $-X^9-L^3-X^{10}-$ is

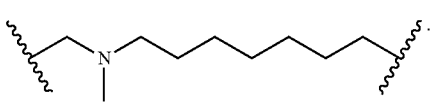 [SMILES: *CCCCCCCN(C)C*]

The skilled artisan will recognize that related $-X^9-L^3-X^{10}-$ moieties of different chain lengths, different chain lengths, and stereochemistry, in addition $A^1$, $B^2$, and $C^2$ groups as described herein, can be used to afford additional compounds of the present invention.

Step 1: (1R,3S,5R)-2-tert-butyl 3-ethyl 5-((hex-5-en-1-yl(methyl)amino)methyl)-2-azabicyclo[3.1.0]hexane-2,3-dicarboxylate (46S-2)

To a mixture of compound 36S-1 (380 mg, 1.34 mmol) and N-methylhex-5-en-1-amine hydrochloride (227 mg, 2.01mmol) and 4 Å molecular sieves (600 mg) in anhydrous 1,2-dichloroethane (10 mL,) was stirred at 0° C. for 40 minutes under N₂ atmosphere. Sodium triacetoxyborohydride (852 mg, 4.02 mmol) was added to the mixture followed by acetic acid (one drop), and the mixture was stirred at 25° C. for 16 hours. The mixture was diluted with H₂O and extracted with EtOAc twice. The combined organic layers were washed with brine, dried with anhydrous Na₂SO₄, filtered and concentrated to dryness. The residue was purified by chromatography on silica gel (PE: EtOAc=5:1 to 1:1) to provide compound 36S-2 (100 mg, yield 19.6%) as a yellow oil. LC/MS (ESI) m/z: 381 (M+H)⁺.

Step 2: (1R,3S,5R)-2-(tert-Butoxycarbonyl)-5-((hex-5-en-1-yhmethyl)amino)methyl)-2-azabicyclo[3.1.0]hexane-3-carboxylic Acid (36S-3)

To a solution of compound 36S-2 (100 mg, 0.26 mmol) in methanol (1.6 mL) was added aq. NaOH solution (0.52 mL, 0.52 mmol) at 0° C., and the mixture was stirred at 25° C. for 4 hours. The mixture was diluted with water and washed with ether twice. The aqueous layer was acidified by adding 0.5N aq. HCl to pH~4 and extracted with DCM twice. The combined organic layers were washed with brine, dried and concentrated to dryness to give compound 36S-3 (79 mg, yield 86.3%) as a yellow oil. LC/MS (ESI) m/z: 353 (M+H)⁺.

Step 3: (1R,3S,5R)-tert-Butyl 3-((3-Allyl-6-bromopyridin-2-yl)carbamoyl)-5-((hex-5-en-1-yl(methyl)amino)methyl)-2-azabicyclo[3.1.0]hexane-2-carboxylate (36S-4)

To a mixture of compound 36S-3 (79 mg, 0.22 mmol) and 3-allyl-6-bromopyridin-2-amine (47 mg, 0.22 mmol) in DCM (3 mL) was added pyridine (87 mg, 1.1 mmol) and POCl₃ (37 mg, 0.24 mmol) at 0° C. After addition, the mixture was stirred at 25° C. for 1 hour. The mixture was poured into ice-cooled water and extracted with DCM twice. The combined organic layers were washed with water and brine, dried over Na₂SO₄, filtered and evaporated to dryness. The residue was purified by column chromatography on silica gel (eluted with DCM:MeOH=20:1) to provide compound 36S-4 (36 mg, 30.0% yield) as a white solid. LC/MS (ESI) m/z: 547/549 (M+H)⁺.

Step 4: tert-Butyl (41R,43S,45R,E)-16-Bromo-6-methyl-3-oxo-42,2,6-triaza-1(2,3)-pyridina-4(3,5)-bicyclo[3.1.0] hexanacyclotridecaphan-11-ene-42-carboxylate (36S-5)

To a solution of compound 36S-4 (36 mg, 0.066 mmol) in toluene (36 mL) was added Grubbs second generation catalyst (11 mg, 0.013 mmol) under N₂ atmosphere. The mixture was degassed under N₂ atmosphere three times and stirred under N₂ atmosphere at 80° C. overnight. The mixture was concentrated to dryness, and the residue was purified by column chromatography on silica gel (eluted with DCM:MeOH=50:1) to provide compound 36S-5 (32 mg, 93.5% yield) as a brown solid. LC/MS (ESI) m/z: 519/521 (M+H)⁺.

Step 5: tert-Butyl (41R,43S,45R)-16-Bromo-6-methyl-3-oxo-42,2,6-triaza-1(2,3)-pyridina-4(3,5)-bicyclo[3.1.0] hexanacyclotridecaphane-42-carboxylate (36S-6)

To a solution of compound 36S-5 (32 mg, 0.062 mmol) in ethyl acetate (3 mL) was added PtO₂ (10 mg, 30% wt) at 0° C. The mixture was degassed under N₂ atmosphere three times and stirred at 25° C. under a H₂ balloon for 15 minutes. The mixture was filtered, and the filtrate was concentrated to dryness to give compound 36S-6 (25 mg, yield 78.1%) as a brown solid. LC/MS (ESI) m/z: 521/523 (M+H)⁺.

Step 6: (41R,43S,45R)-16-Bromo-6-methyl-42,2,6-triaza-1 (2,3)-pyridina-4(3,5)-bicyclo[3.1.0]hexanacyclotridecaphan-3-one Trifluoroacetic Acid Salt (365-7)

To a solution of compound 36S-6 (25 mg, 0.048 mmol) in DCM (2 mL) was added TFA (1 mL) at 0° C., and the reaction was stirred at 25° C. for 1 hour. The mixture was concentrated to dryness, and the residue was washed with ether and dried under vacuum to give compound 36S-7 (20 mg, yield 99.1%) as a brown syrup. LC/MS (ESI) m/z: 421/423 (M+H)⁺.

Step 7: Synthesis of (41R,43S,45R)-42-(2-(3-Acetyl-5-(2-methylpyrimidin-5-yl)-1H-indazol-1-yl)acetyl)-16-bromo-6-methyl-42,2,6-triaza-1(2,3)-pyridina-4(3,5)-bicyclo [3.1.0]hexanacyclotridecaphan-3-one (36)

To a mixture of compound 36S-7 (20 mg, 0.048 mmol) and 2-(3-acetyl-5-(2-methylpyrimidin-5-yl)-1H-indazol-1-yl)acetic acid (15 mg, 0.048 mmol) in DMF (3 mL) was added DIPEA (31 mg, 0.24 mmol) and HATU (27 mg, 0.072 mmol) at 0° C., and the mixture was stirred at 25° C. for 1 hour. The mixture was diluted with EtOAc and washed with 10% aq. LiCl solution and brine, dried over Na₂SO₄, and concentrated to dryness. The residue was purified by preparatory HPLC to provide compound 36 (4.4 mg, 12.9% yield) as a white solid. ¹H-NMR (400 MHz, DMSO-d₆) δ 10.28 (s, 1H), 9.05 (s, 2H), 8.44 (t, J=1.6 Hz, 1H), 7.87 (t, J=2.0 Hz, 2H), 7.65 (d, J=8.0 Hz, 1H), 7.46 (d, J=8.0 Hz, 1H), 5.96 (d, J=17.2 Hz, 1H), 5.58 (d, J=17.2 Hz, 1H), 4.52-4.46 (m, 1H), 3.70-3.66 (m, 1H), 2.67 (d, J=12.4 Hz, 6H), 2.42-2.38 (m, 2H), 2.34-2.27 (m, 2H), 2.24 (s, 3H), 1.81-1.73 (m, 8H), 1.67-1.63 (m, 2H), 1.48-1.41 (m, 4H), 1.13-1.09 (m, 1H), 0.98 (t, J=5.6 Hz, 1H). LC/MS (ESI) m/z: 713/715 (M+H)⁺.

Scheme 25: Synthesis of (14Z,31R,33S,35R)-32-(2-(3-acetyl-7-methyl-5-(2-methylpyrimidin-5-yl)-1H-indazol-1-yl)acetyl)-66-bromo-8-oxa-32,5-diaza-1(5,3)-oxadiazola-6(2,3)pyridina-3(5,3)-bicyclo[3.1.0] hexanacycloundecaphan-10-en-4-one (37)

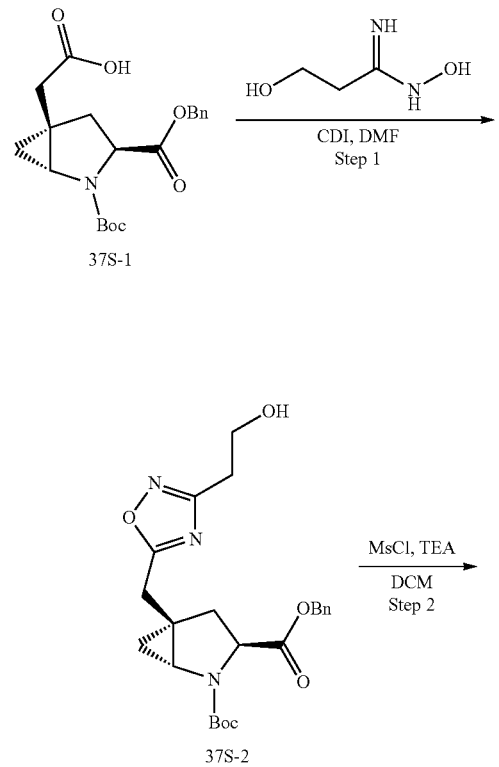

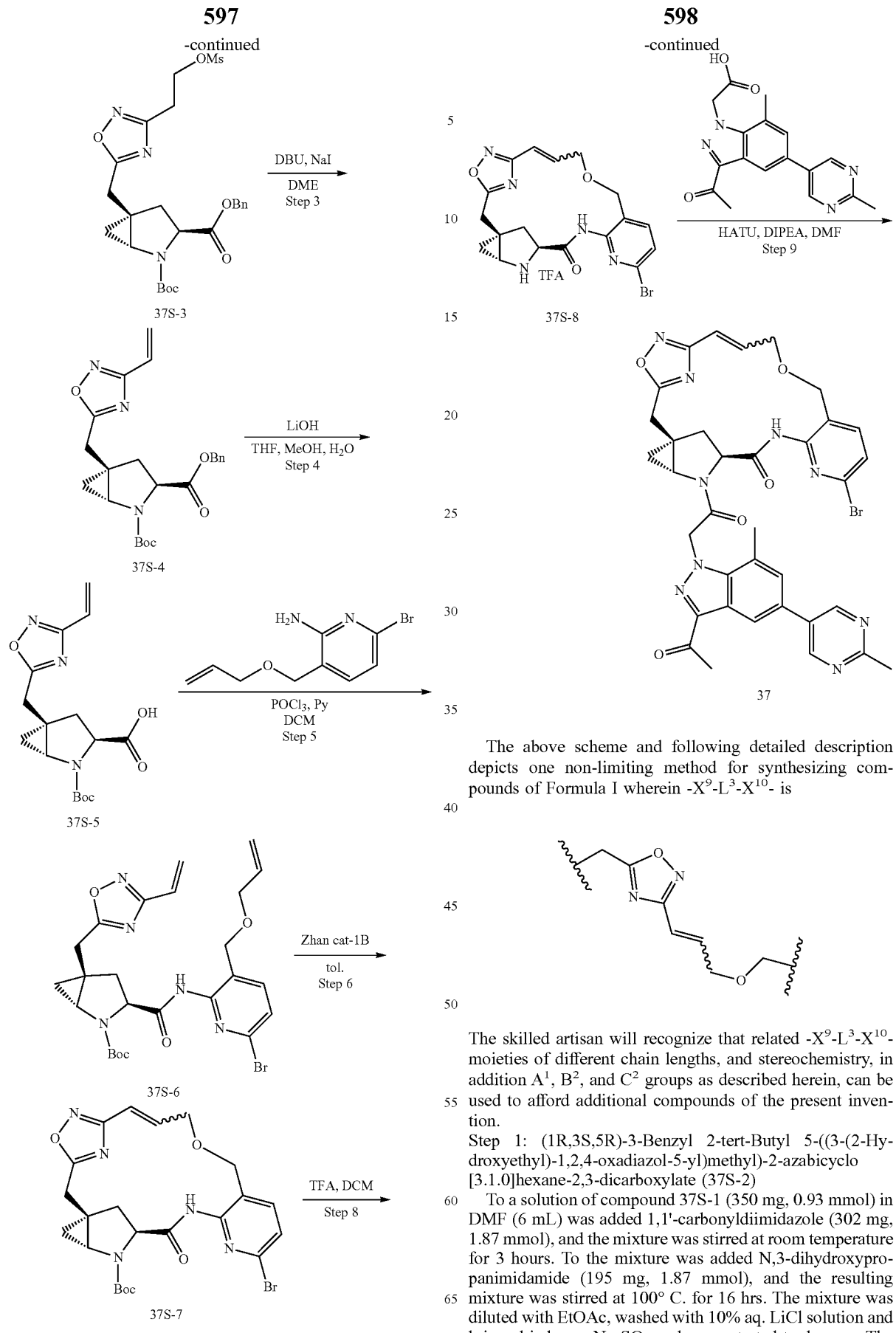

The above scheme and following detailed description depicts one non-limiting method for synthesizing compounds of Formula I wherein $-X^9-L^3-X^{10}-$ is The skilled artisan will recognize that related $-X^9-L^3-X^{10}-$ moieties of different chain lengths, and stereochemistry, in addition $A^1$, $B^2$, and $C^2$ groups as described herein, can be used to afford additional compounds of the present invention.

Step 1: (1R,3S,5R)-3-Benzyl 2-tert-Butyl 5-((3-(2-Hydroxyethyl)-1,2,4-oxadiazol-5-yl)methyl)-2-azabicyclo[3.1.0]hexane-2,3-dicarboxylate (37S-2)

To a solution of compound 37S-1 (350 mg, 0.93 mmol) in DMF (6 mL) was added 1,1'-carbonyldiimidazole (302 mg, 1.87 mmol), and the mixture was stirred at room temperature for 3 hours. To the mixture was added N,3-dihydroxypropanimidamide (195 mg, 1.87 mmol), and the resulting mixture was stirred at 100° C. for 16 hrs. The mixture was diluted with EtOAc, washed with 10% aq. LiCl solution and brine, dried over $Na_2SO_4$ and concentrated to dryness. The residue was purified by silica gel column chromatography (eluted with PE:EtOAc=6:1) to provide compound 37S-2 (250 mg, yield 60.5%) as a yellow oil. LC/MS (ESI) m/z: 444 [M+H]$^+$.

Step 2: (1R,3S,5R)-3-Benzyl 2-tert-Butyl 5-((3-(2-((Methylsulfonyl)oxy)ethyl)-1,2,4-oxadiazol-5-yl)methyl)-2-azabicyclo[3.1.0]hexane-2,3-dicarboxylate (37S-3)

To a solution of compound 37S-2 (250 mg, 0.56 mmol) in anhydrous DCM (5 mL) was added TEA (0.23 mL, 1.68 mmol) followed by methanesulfonyl chloride (96 mg, 1.12 mmol) at 0° C. The reaction was stirred at 0° C. for 1 hour. The reaction mixture was poured into ice-cooled saturated aq. NH$_4$Cl solution (5 mL) and extracted with DCM twice. The combined organic phases were washed with brine, dried over anhydrous Na$_2$SO$_4$, filtered and concentrated to provide compound 37S-3 (320 mg, yield 100%) as a yellow oil. LC/MS (ESI) m/z: 522 (M+H)$^+$.

Step 3: (1R,3S,5R)-3-Benzyl 2-tert-Butyl 5-((3-Vinyl-1,2,4-oxadiazol-5-yl)methyl)-2-azabicyclo[3.1.0]hexane-2,3-dicarboxylate (37S-4)

To a solution of compound 37S-3 (320 mg, 0.56 mmol) in DME (5 mL) was added DBU (216 mg, 1.42 mmol) and NaI (320 mg, 2.13 mmol), and the reaction was stirred at 80° C. for 2 hours. The reaction mixture was diluted with EtOAc, washed with water and brine, dried over anhydrous Na$_2$SO$_4$, filtered and concentrated to dryness. The residue was purified by column chromatography on silica gel (DCM:MeOH=100:1) to provide compound 37S-4 (100 mg, yield 41.8%) as a yellow oil. LC/MS (ESI) m/z: 431 (M+H)$^+$.

Step 4: (1R,3S,5R)-2-(tert-Butoxycarbonyl)-5-((3-vinyl-1,2,4-oxadiazol-5-yl)methyl)-2-azabicyclo[3.1.0]hexane-3-carboxylic Acid (37S-5)

To a solution of compound 37S-4 (100 mg, 0.24 mmol) in THF (2 mL), MeOH (2 mL), and water (1 mL) was added LiOH (29.6 mg, 0.72 mmol), and the mixture was stirred at room temperature for 2 hours. The mixture was concentrated to dryness, diluted with water, and washed with EtOAc twice. The aqueous layer was acidified by adding 1 N aq. HCl to pH~3 at 0° C., and extracted with DCM twice. The combined organic layers were washed with brine, dried over anhydrous Na$_2$SO$_4$, filtered and concentrated to dryness to give compound 37S-5 (78 mg, yield 98.0%) as a colorless oil. LC/MS (ESI) m/z: 336 (M+H)$^+$.

Step 5: (1R,3S,5R)-tert-Butyl 3-((3-(((Allyloxy)methyl)-6-bromopyridin-2-yl)carbamoyl)-5-((3-vinyl-1,2,4-oxadiazol-5-yl)methyl)-2-azabicyclo[3.1.0]hexane-2-carboxylate (37S-6)

To a solution of compound 37S-5 (78 mg, 0.24 mmol) and 3-((allyloxy)methyl)-6-bromopyridin-2-amine (58 mg, 0.24 mmol) in DCM (10 mL) was added pyridine (94.8 mg, 1.2 mmol) and POCl$_3$ (55.3 mg, 0.36 mmol) at 0° C. After addition, the mixture was stirred at 25° C. for 1 hour. The mixture was diluted with DCM, washed with ice-cooled water and brine, dried over Na$_2$SO$_4$, filtered and evaporated to dryness. The residue was purified by column chromatography on silica gel (PE:EtOAc=3:1) to provide compound 37S-6 (80 mg, yield 60.2%) as a yellow oil. LC/MS (ESI) m/z: 560/562 (M+H)$^+$.

Step 6: tert-Butyl (14Z,31R,33S,35R)-66-Bromo-4-oxo-8-oxa-32,5-diaza-1(5,3)-oxadiazola-6(2,3)-pyridina-3(5,3)-bicyclo[3.1.0]hexacycloundecaphan-10-ene-32-carboxylate (37S-7)

To a solution of compound 37S-6 (80 mg, 0.14 mmol) in toluene (80 mL) was added Zhan catalyst-1B (42.4 mg, 0.05 mmol). The mixture was degassed under N$_2$ atmosphere three times and stirred at 80° C. under N$_2$ atmosphere for 16 hours. The mixture was concentrated to dryness, and the residue was purified by silica gel column chromatography (eluted with DCM:MeOH=30:1) to provide compound 37S-7 (40 mg, yield 56.2%) as a white solid. LC/MS (ESI) m/z: 532/534 (M+H)$^+$.

Step 7: (14Z,31R,33S,35R)-66-Bromo-8-oxa-32,5-diaza-1(5,3)-oxadiazola-6(2,3)-pyridina-3(5,3)-bicyclo[3.1.0]hexanacycloundecaphan-10-en-4-one Trifluoroacetic Acid Salt (37S-8)

To a solution of compound 37S-7 (40 mg, 0.075 mmol) in DCM (2 mL) was added TFA (1 mL), and the reaction mixture was stirred at 25° C. for 2 hours. The mixture was concentrated to dryness, washed with ether and dried under vacuum to give compound 37S-8 (60 mg, yield 100%) as a brown solid. LCMS: LC/MS (ESI) m/z: 432/434 (M+H)$^+$.

Step 8: (14Z,31R,33S,35R)-32-(2-(3-acetyl-7-methyl-5-(2-methylpyrimidin-5-yl)-1H-indazol-1-yl)acetyl)-66-bromo-8-oxa-32,5-diaza-1(5,3)-oxadiazola-6(2,3)-pyridina-3(5,3)-bicyclo[3.1.0]hexanacycloundecaphan-10-en-4-one (37)

To a mixture of compound 37S-8 (60 mg, 0.075 mmol), 2-(3-acetyl-7-methyl-5-(2-methylpyrimidin-5-yl)-1H-indazol-1-yl)acetic acid (24 mg, 0.075 mmol) and HATU (57 mg, 0.15 mmol) in DMF (2 mL) was added DIPEA (0.052 mL, 0.30 mmol) at 0° C., and the reaction was stirred at room temperature for 1 hour. The mixture was diluted with EtOAc, washed with 10% aq. LiCl solution and brine, dried over Na$_2$SO$_4$ and concentrated to dryness. The residue was purified by preparatory HPLC to provide 37 (2.1 mg, yield 3.8%) as a white solid. $^1$H-NMR (400 MHz, CD$_3$OD) δ: 8.98 (s, 2H), 8.40 (s, 1H), 7.78 (d, J=6.4 Hz, 1H), 7.51 (s, 1H), 7.41 (d, J=8.1 Hz, 1H), 6.68 (d, J=12.0 Hz, 1H), 6.34-6.24 (m, 1H), 5.96 (d, J=17.7 Hz, 1H), 5.79 (d, J=17.5 Hz, 1H), 5.24-5.15 (m, 1H), 4.67-4.34 (m, 3H), 4.23 (m, 1H), 3.86 (m, 1H), 3.65 (d, J=15.0 Hz, 1H), 3.48 (m, 0.5H), 3.13 (m, 0.5H), 2.82 (d, J=7.6 Hz, 2H), 2.73 (d, J=5.7 Hz, 6H), 2.68 (s, 3H), 1.49 (t, J=5.7 Hz, 1H), 1.23-1.21 (m, 1H). LC/MS (ESI) m/z: 738/740 (M+H)$^+$.

Scheme 26: Synthesis of (41R,43S,45R)-13-Acetyl-N-(6-bromo-3-methylpyridin-2-yl)-6-methyl-15-(2-methylpyrimidin-5-yl)-3-oxo-11H-42,6-diaza-1(1,7)-indazola-4(2,5)-bicyclo[3.1.0]hexanacyclotridecaphane-43-carboxamide (38)

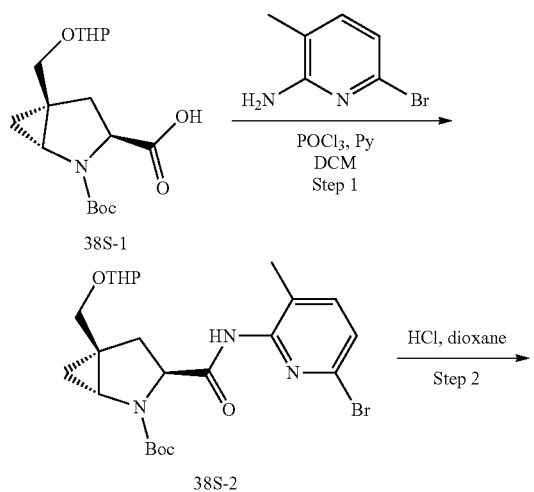

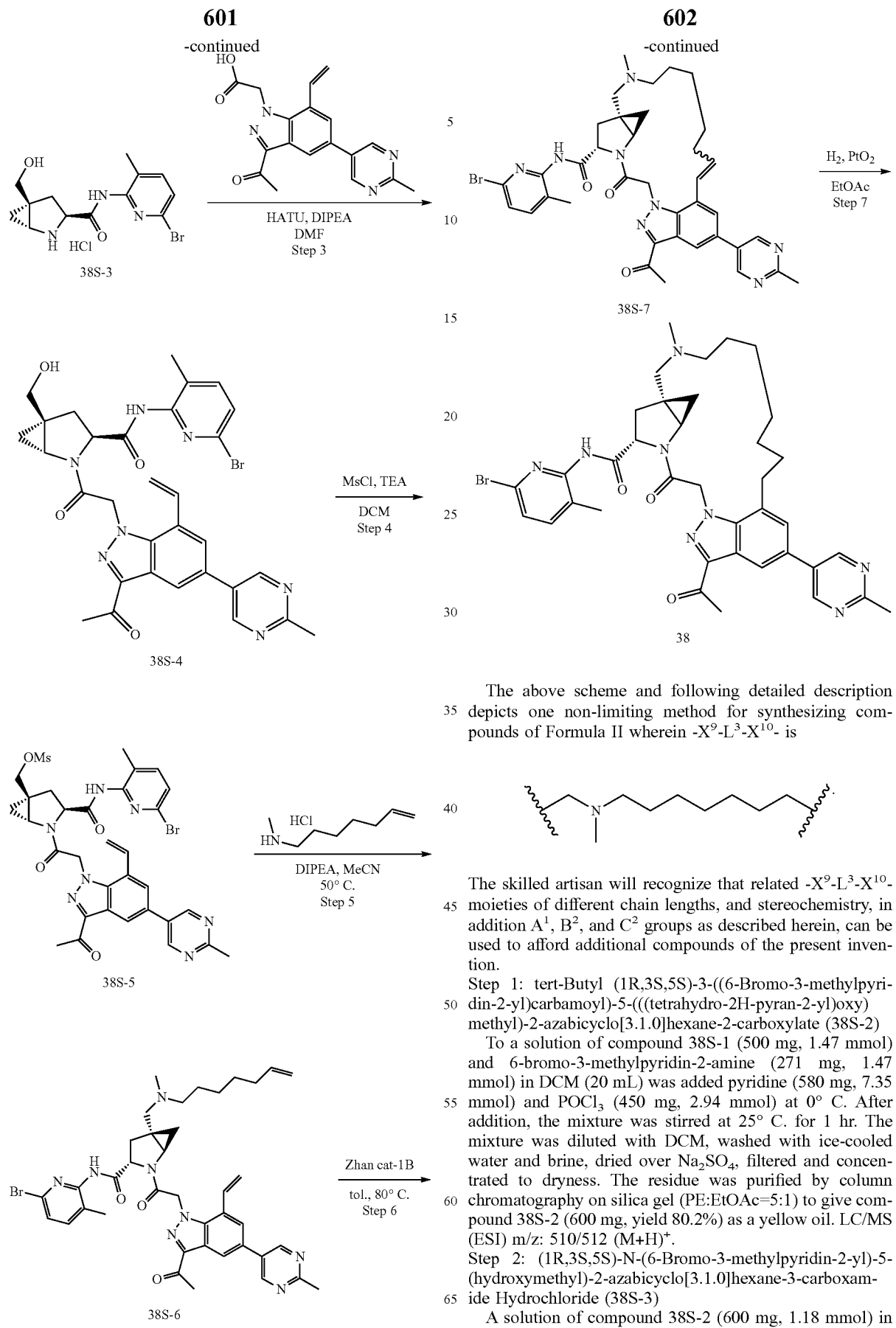

The above scheme and following detailed description depicts one non-limiting method for synthesizing compounds of Formula II wherein -$X^9$-$L^3$-$X^{10}$- is The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: tert-Butyl (1R,3S,5S)-3-((6-Bromo-3-methylpyridin-2-yl)carbamoyl)-5-((((tetrahydro-2H-pyran-2-yl)oxy)methyl)-2-azabicyclo[3.1.0]hexane-2-carboxylate (38S-2)

To a solution of compound 38S-1 (500 mg, 1.47 mmol) and 6-bromo-3-methylpyridin-2-amine (271 mg, 1.47 mmol) in DCM (20 mL) was added pyridine (580 mg, 7.35 mmol) and $POCl_3$ (450 mg, 2.94 mmol) at 0° C. After addition, the mixture was stirred at 25° C. for 1 hr. The mixture was diluted with DCM, washed with ice-cooled water and brine, dried over $Na_2SO_4$, filtered and concentrated to dryness. The residue was purified by column chromatography on silica gel (PE:EtOAc=5:1) to give compound 38S-2 (600 mg, yield 80.2%) as a yellow oil. LC/MS (ESI) m/z: 510/512 (M+H)+.

Step 2: (1R,3S,5S)-N-(6-Bromo-3-methylpyridin-2-yl)-5-(hydroxymethyl)-2-azabicyclo[3.1.0]hexane-3-carboxamide Hydrochloride (38S-3)

A solution of compound 38S-2 (600 mg, 1.18 mmol) in HCl/1,4-dioxane (10 mL, 4M) was stirred at room temperature for 1 hour. The mixture was concentrated to dryness to give compound 38S-3 (600 mg, yield 100%) as a brown syrup. LC/MS (ESI) m/z: 326/328 [M+H]+.

Step 3: (1R,3S,5S)-2-(2-(3-Acetyl-5-(2-methylpyrimidin-5-yl)-7-vinyl-1H-indazol-1-yl)acetyl)-N-(6-bromo-3-methylpyridin-2-yl)-5-(hydroxymethyl)-2-azabicyclo[3.1.0]hexane-3-carboxamide (38S-4)

To a mixture of the compound 38S-3 (410 mg, 0.89 mmol), 2-(3-acetyl-5-(2-methylpyrimidin-5-yl)-7-vinyl-1H-indazol-1-yl)acetic acid (300 mg, 0.89 mmol) and HATU (609 mg, 1.60 mmol) in DMF (10 mL) was added DIPEA (0.61 mL, 3.57 mmol) at 0° C., and the reaction was stirred at room temperature for 2 hours. The mixture was diluted with EtOAc, washed with 10% aq. LiCl solution and brine, dried over Na2SO4 and concentrated to dryness. The residue was purified by column chromatography on silica gel (DCM:MeOH=50:1) to give compound 38S-4 (350 mg, yield 61.2%) as a yellow oil. LC/MS (ESI) m/z: 644/646 (M+H)+.

Step 4: ((1R,3S,5S)-2-(2-(3-Acetyl-5-(2-methylpyrimidin-5-yl)-7-vinyl-1H-indazol-1-yl)acetyl)-3-((6-bromo-3-methylpyridin-2-yl)carbamoyl)-2-azabicyclo[3.1.0]hexan-5-yl)methyl Methanesulfonate (38S-5)

To a solution of compound 38S-4 (350 mg, 0.54 mmol) in anhydrous DCM (10 mL) was added TEA (0.23 mL, 1.63 mmol) followed methanesulfonyl chloride (93 mg, 0.81 mmol) at 0° C., and the reaction was stirred at 0° C. for 1 hour. The mixture was diluted with DCM, washed with water and brine, dried over anhydrous Na2SO4, filtered and concentrated to dryness to give compound 38S-5 (410 mg, yield 100%) as a yellow solid. LC/MS (ESI) m/z: 722/724 (M+H)+.

Step 5: (1R,3S,5R)-2-(2-(3-Acetyl-5-(2-methylpyrimidin-5-yl)-7-vinyl-1H-indazol-1-yl)acetyl)-N-(6-bromo-3-methylpyridin-2-yl)-5-((hept-6-en-1-yl(methyl)amino)methyl)-2-azabicyclo[3.1.0]hexane-3-carboxamide (38S-6)

To a solution of compound 38S-5 (410 mg, 0.54 mmol) in MeCN (5 mL) was added DIPEA (0.37 mL, 2.16 mmol), NaI (14 mg, 0.16 mmol), and N-methylhept-6-en-1-amine hydrochloride (177 mg, 1.08 mmol), and the reaction mixture was stirred at 50° C. overnight. The mixture was diluted with DCM, washed with water and brine, dried over anhydrous Na2SO4 and concentrated to dryness. The residue was purified by column chromatography on silica gel (DCM:MeOH=60:1) to give compound 38S-6 (260 mg, yield 64.0%) as a white solid. LC/MS (ESI) m/z: 753/755 (M+H)+.

Step 6: (41R,43S,45R)-13-Acetyl-N-(6-bromo-3-methylpyridin-2-yl)-6-methyl-15-(2-methylpyrimidin-5-yl)-3-oxo-11H-42,6-diaza-1(1,7)-indazola-4(2,5)-bicyclo[3.1.0]hexanacyclotridecaphan-12-ene-43-carboxamide (38S-7)

To a solution of compound 38S-6 (260 mg, 0.35 mmol) in toluene (80 mL) was added Zhan catalyst-1B (42.4 mg, 0.05 mmol). The mixture was degassed under N2 atmosphere three times and stirred under N2 atmosphere at 80° C. overnight. The mixture was concentrated under reduced pressure to dryness, and the residue was purified by column chromatography on silica gel (DCM:MeOH=40:1) to give compound 38S-7 (120 mg, yield 47.4%) as a white solid. LC/MS (ESI) m/z: 725/727 (M+H)+.

Step 8: (41R,43S,45R)-13-Acetyl-N-(6-bromo-3-methylpyridin-2-yl)-6-methyl-15-(2-methylpyrimidin-5-yl)-3-oxo-11H-42,6-diaza-1(1,7)-indazola-4(2,5)-bicyclo[3.1.0]hexanacyclotridecaphane-43-carboxamide (38)

A solution of compound 38S-7 (30 mg, 0.04 mmol) in EtOH (3 mL) and EtOAc (3 mL) was degassed three times under N2 atmosphere, and PtO2 (12 mg) was added. The mixture was stirred under a H2 balloon at room temperature for 50 minutes. The mixture was filtered and the filtrate was concentrated to dryness. The residue product was purified by preparatory HPLC to give X (4 mg, yield 13.3%) as a white solid. 1H-NMR (400 MHz, CD3OD) δ 8.99 (s, 2H), 8.44 (d, J=1.8 Hz, 1H), 7.55 (s, 1H), 7.50 (d, J=8.0 Hz, 1H), 7.33 (d, J=7.9 Hz, 1H), 5.86 (d, J=17.9 Hz, 1H), 5.72 (d, J=17.7 Hz, 1H), 4.56-4.43 (m, 1H), 3.81 (t, J=6.1 Hz, 1H), 3.66-3.61 (m, 1H), 3.48 (dd, J=4.4, 2.7 Hz, 1H), 3.13 (t, J=3.5 Hz, 1H), 2.74 (s, 3H), 2.69 (s, 3H), 2.43-2.38 (m, 2H), 2.21-2.17 (m, 5H), 2.07 (s, 3H), 2.03 (d, J=5.7 Hz, 4H), 1.62-1.58 (m, 4H), 1.47-1.41 (m, 5H), 1.04 (dd, J=4.7, 2.7 Hz, 1H), 1.01-0.96 (m, 1H). LC/MS (ESI) m/z: 727/729 (M+H)+.

Scheme 27: Synthesis of (41R,43S,45R)-13-Acetyl-N-(6-bromo-3-methylpyridin-2-yl)-12,13-dihydroxy-6-methyl-15-(2-methylpyrimidin-5-yl)-3-oxo-11H-42,6-diaza-1(1,7)-indazola-4(2,5)-bicyclo[3.1.0]hexanacyclotridecaphane-43-carboxamide (39)

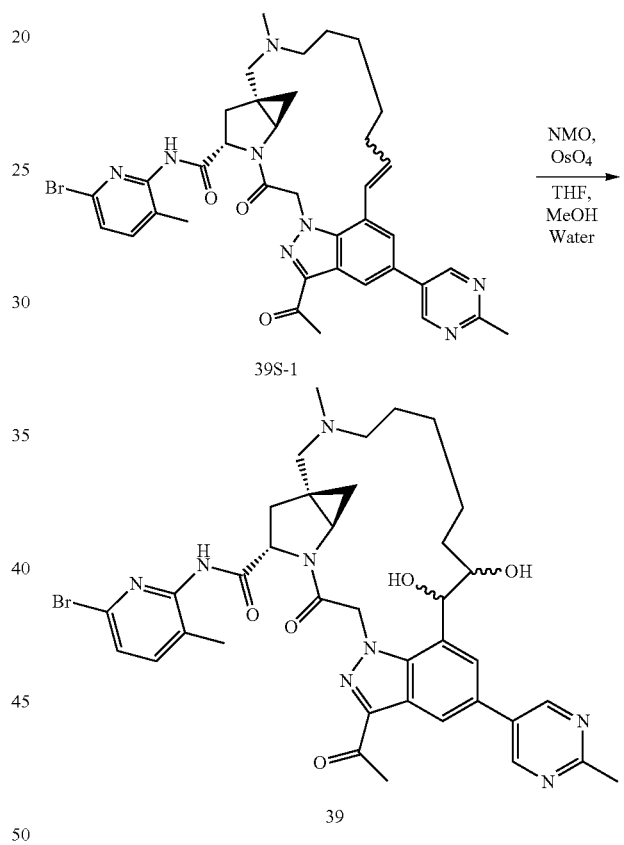

The above scheme and following detailed description depicts one non-limiting method for synthesizing compounds of Formula II wherein -X9-L3-X10- is

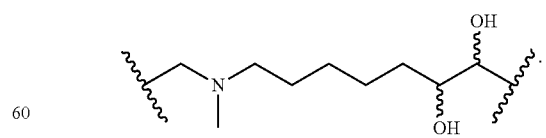

The skilled artisan will recognize that related -X9-L3-X10- moieties of different chain lengths, and stereochemistry, in addition A1, B2, and C2 groups as described herein, can be used to afford additional compounds of the present invention.

To a solution of compound 39S-1 (60 mg, 0.080 mmol) in MeOH (3 mL), THF (3 mL), and water (1mL) was added NMO (14.4 mg, 0.12 mmol) and OsO$_4$ (1 mol/L in THF) (0.5 mL). After addition, the mixture was stirred at room temperature for 16 hours. To the mixture was added ice-cooled aq. Na$_2$SO$_3$ solution and extracted with DCM. The organic layer was washed with water and brine, dried over Na$_2$SO$_4$, filtered and evaporated to dryness. The residue was purified by preparatory HPLC to give 39 (1.1 mg, yield 1.8%) as a yellow solid. $^1$H-NMR (400 MHz, CD$_3$OD) δ: 9.02 (s, 2H), 8.54 (d, J=1.7 Hz, 1H), 8.09 (s, 1H), 7.47 (d, J=7.7 Hz, 1H), 7.30 (d, J=7.8 Hz, 1H), 6.47 (d, J=16.5 Hz, 1H), 5.56 (d, J=26.4 Hz, 1H), 5.26 (s, 1H), 4.57 (s, 1H), 4.09 (d, J=5.7 Hz, 1H), 3.80 (d, J=9.9 Hz, 1H), 3.48 (s, 1H), 3.13 (s, 1H), 2.74 (s, 3H), 2.70 (s, 3H), 2.60-2.43 (m, 2H), 2.39-2.30 (m, 2H), 2.26-2.12 (m, 1H), 2.05 (s, 3H), 1.96-1.73 (m, 3H), 1.70-1.55 (m, 3H), 1.48-1.46 (m, 2H), 1.35-1.28 (m, 1H), 1.06-1.02 (m, 1H). LCMS: LC/MS (ESI) m/z: 759/761 (M+H)$^+$.

Scheme 28: Synthesis of (41R,43S,45R)-13-Acetyl-N-(3-methyl-6-(trifluoromethyl)pyridin-2-yl)-15-(2-methylpyrimidin-5-yl)-3,7-dioxo-11H-42,6-diaza-1(1,7)-pyrazolo[3,4-c]pyridina-4(2,5)-bicyclo[3.1.0]hexanacyclotridecaphan-11-ene-43-carboxamide (40) and (41R,43S,45R)-13-Acetyl-N-(3-methyl-6-(trifluoromethyl)pyridin-2-yl)-15-(2-methylpyrimidin-5-yl)-3,7-dioxo-11H-42,6-diaza-1(1,7)-pyrazolo[3,4-c]pyridina-4(2,5)-bicyclo[3.1.0]hexanacyclotridecaphane-43-carboxamide (41)

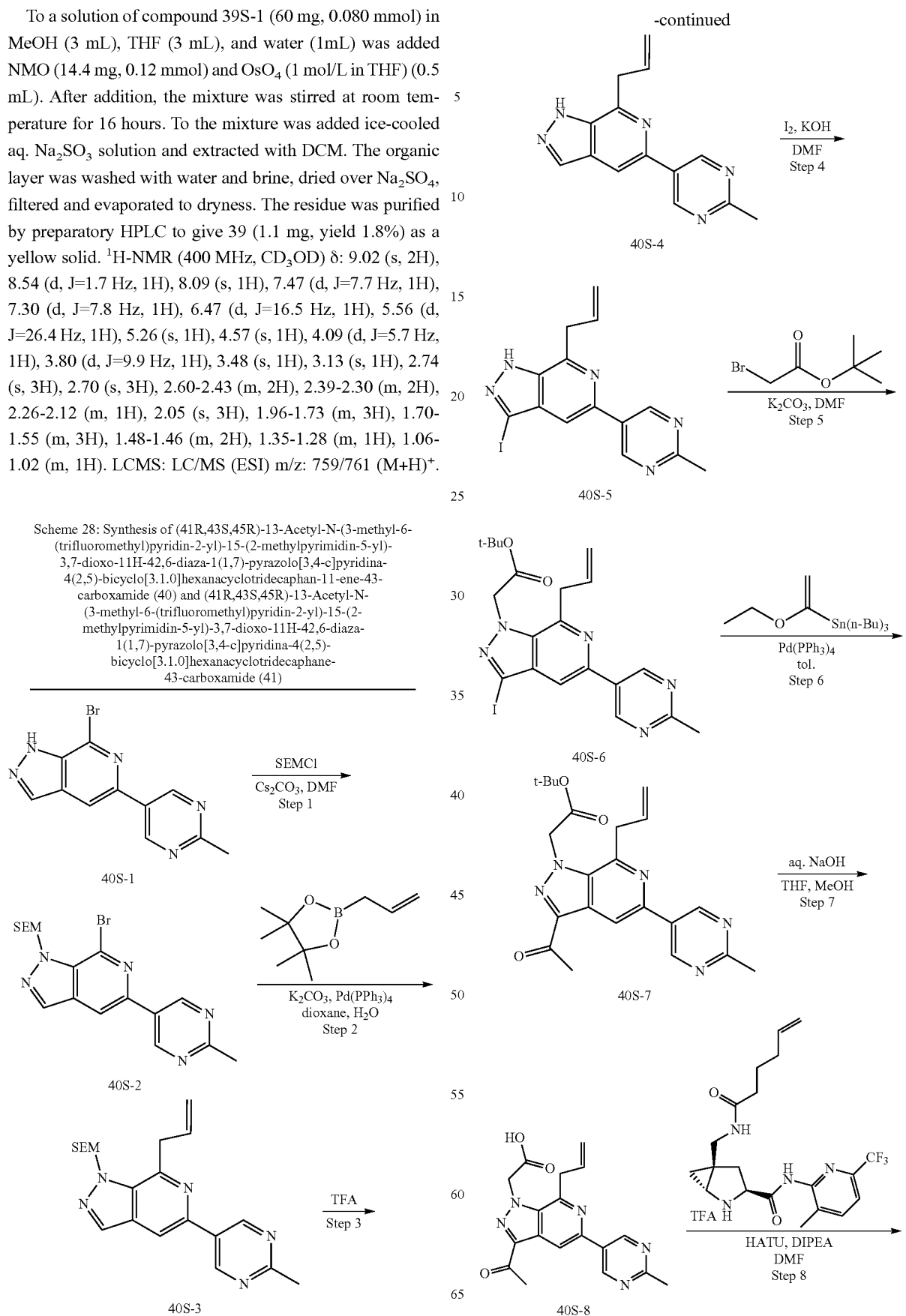

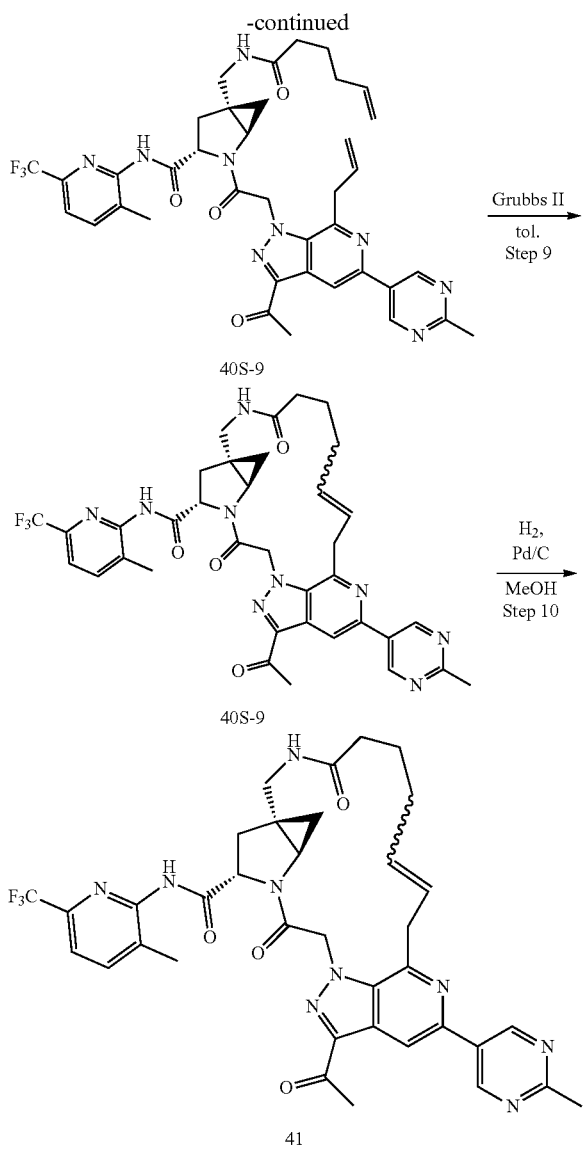

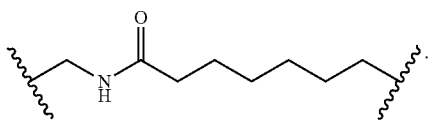 [SMILES: *CCCCCCC(=O)NC*]

The above scheme and following detailed description depicts one non-limiting method for synthesizing compounds of Formula II wherein -X$^9$-L$^3$-X$^{10}$- is The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1: 7-Bromo-5-(2-methylpyrimidin-5-yl)-1-((2-(trimethylsilyl)ethoxy)methyl)-1H-pyrazolo[3,4-c]pyridine (40S-2)

To a solution of compound 40S-1 (5 g, 17.3 mmol) in anhydrous DMF (50 mL) was added CsCO$_3$ (14.15 g, 43.25 mmol) followed by drop-wise addition of SEMCl (5.23 g, 31.14 mmol) at 0° C., and the mixture was stirred at 25° C. for 3 hours. The reaction mixture was poured into ice-cooled saturated aq. NH$_4$Cl solution and extracted with EtOAc twice. The combined organic phases were washed with brine, dried over anhydrous Na$_2$SO$_4$, filtered and concentrated to dryness. The residue was purified by column chromatography on silica gel (PE:EtOAc=2:1) to give compound 40S-2 (3.6 g, 49.7% yield) as a yellow oil. LC/MS (ESI) m/z: 420/422 (M+H)$^+$.

Step 2: 7-Allyl-5-(2-methylpyrimidin-5-yl)-1-((2-(trimethylsilyl)ethoxy)methyl)-1H-pyrazolo[3,4-c]pyridine (3)

To a mixture of compound 40S-2 (3.6 g, 8.59 mmol) and 2-allyl-4,4,5,5-tetramethyl-1,3,2-dioxaborolane (1.88 g, 11.17 mmol) in 1,4-dioxane (40 mL) and water (4 mL) was added K$_2$CO$_3$ (2.96 g, 21.48 mmol) and Pd(PPh$_3$)$_4$ (992 mg, 0.86 mmol) at 0° C. The mixture was degassed under N$_2$ atmosphere three times and stirred at 95° C. under N$_2$ atmosphere for 16 hours. The mixture was diluted with EtOAc, washed with water and brine, dried over anhydrous Na$_2$SO$_4$, filtered and concentrated to dryness. The residue was purified by column chromatography on silica gel (PE:EtOAc=2 1) to give compound 40S-3 (2.6 g, 79.3% yield) as a yellow oil. LC/MS (ESI) m/z: 382 (M+H)$^+$.

Step 3: 7-Allyl-5-(2-methylpyrimidin-5-yl)-1H-pyrazolo[3,4-c]pyridine (40S-4)

A solution of compound 40S-3 (2.6 g, 6.8 mmol) in TFA (25 mL) was stirred at 25° C. for 2 hours. The mixture was concentrated to dryness and the residue was poured into ice-cooled saturated aq. NaHCO$_3$ solution and extracted with DCM twice. The combined organic layers were washed with brine, dried over anhydrous Na$_2$SO$_4$, filtered and concentrated to dryness. The residue was purified by column chromatography on silica gel (PE:EtOAc=1:1) to give compound 40S-4 (1.3 g, 76.5% yield) as a yellow solid. LC/MS (ESI) m/z: 252 (M+H)$^+$.

Step 4: 7-Allyl-3-iodo-5-(2-methylpyrimidin-5-yl)-1H-pyrazolo[3,4-c]pyridine (40S-5)

To a solution of compound 40S-4 (1.3 g, 5.18 mmol) in DMF (15 mL) was added KOH (654 mg, 11.65 mmol) and iodine (1.97 g, 7.77 mmol) at 0° C., and the reaction mixture was stirred at room temperature overnight. The mixture was diluted with EtOAc, washed with saturated aq. Na$_2$S$_2$O$_3$ solution and brine, dried over Na$_2$SO$_4$, and concentrated to dryness. The residue was purified by column chromatography on silica gel (eluted with petroleum ether:ethyl acetate=1:1) to give compound 40S-5 (1.6 g, 81.7% yield) as a yellow solid. LC/MS (ESI) m/z: 378 (M+H)$^+$.

Step 5: tert-Butyl 2-(7-Allyl-3-iodo-5-(2-methylpyrimidin-5-yl)-1H-pyrazolo[3,4-c]pyridin-1-yl)acetate (40S-6)

To a solution of compound 40S-5 (1.6 g, 4.2 mmol) in DMF (20 mL) was added K$_2$CO$_3$ (1.16 g, 8.4 mmol) and tert-butyl 2-bromoacetate (900 mg, 4.6 mmol) at 0° C. The reaction mixture was stirred at room temperature overnight. The mixture was diluted with EtOAc, washed with saturated aq. NH$_4$Cl solution and brine, dried over Na$_2$SO$_4$, and concentrated to dryness. The residue was purified by column chromatography on silica gel (eluted with petroleum ether:ethyl acetate=3:1) to give the compound 40S-6 (1.4 g, 82.5% yield) as a yellow solid. LC/MS (ESI) m/z: 492 (M+H)$^+$.

Step 6: tert-Butyl 2-(3-Acetyl-7-allyl-5-(2-methylpyrimidin-5-yl)-1H-pyrazolo[3,4-c]pyridin-1-yl)acetate (40S-7)

To a solution of the compound 40S-6 (500 mg, 1.02 mmol) in toluene (5 mL) was added tributyl(1-ethoxyvinyl)stannane (367 mg, 1.02 mmol) and Pd(PPh$_3$)$_4$ (117 mg, 0.10 mmol). The mixture was degassed under N$_2$ atmosphere three times and stirred at 100° C. under N$_2$ atmosphere overnight. The mixture was concentrated to dryness, and the residue was purified by column chromatography on silica gel (eluted with petroleum ether:ethyl acetate=2:1) to give compound 40S-7 (400 mg, 96.4% yield) as a brown solid. LC/MS (ESI) m/z: 408 (M+H)$^+$.

Step 7: 2-(3-Acetyl-7-allyl-5-(2-methylpyrimidin-5-yl)-1H-pyrazolo[3,4-c]pyridin-1-yl)acetic Acid (40S-8)

To a solution of compound 40S-7 (400 mg, 0.98 mmol) in THF (5 mL), MeOH (5 mL), and water (5 mL) was added NaOH (123 mg, 2.94 mmol), and the mixture was stirred at room temperature for 2 hours. The mixture was concentrated to dryness, and the residue was diluted with water and washed with EtOAc twice. The aqueous layer was acidified by adding 1 N aq. HCl to pH~3 at 0° C., and extracted with DCM twice. The combined organic layers were washed with brine, dried over anhydrous Na$_2$SO$_4$, filtered and concentrated to dryness to give compound 40S-8 (300 mg, 95.2% yield) as a yellow solid. LC/MS (ESI) m/z: 352 (M+H)$^+$.

Step 8: (1R,3S,5R)-2-(2-(3-Acetyl-7-allyl-5-(2-methylpyrimidin-5-yl)-1H-pyrazolo[3,4-c]pyridin-1-yl)acetyl)-5-(hex-5-enamidomethyl)-N-(3-methyl-6-(trifluoromethyl)pyridin-2-yl)-2-azabicyclo[3.1.0]hexane-3-carboxamide (40S-9)

To a mixture of the compound 40S-8 (36.4 mg, 0.10 mmol) and (1R,3S,5R)-5-(hex-5-enamidomethyl)-N-(3-methyl-6-(trifluoromethyl)pyridin-2-yl)-2-azabicyclo[3.1.0]hexane-3-carboxamide (52 mg, 0.10 mmol) in DMF (3 mL) was added DIPEA (0.086 mL, 0.5 mmol) and HATU (76.0 mg, 0.20 mmol) at 0° C. After addition, the reaction mixture was stirred at room temperature for 2 hours. The mixture was diluted with EtOAc, washed with saturated aq. NH$_4$Cl solution and brine, dried over Na$_2$SO$_4$ and concentrated to dryness. The residue was purified by column chromatography on silica gel (eluted with DCM:MeOH=50:1) to give compound 40S-9 (52 mg, 69.9% yield) as a yellow solid. LC/MS (ESI) m/z: 744 (M+H)$^+$.

Step 13: (41R,43S,45R)-13-Acetyl-N-(3-methyl-6-(trifluoromethyl)pyridin-2-yl)-15-(2-methylpyrimidin-5-yl)-3,7-dioxo-11H-42,6-diaza-1(1,7)-pyrazolo[3,4-c]pyridina-4(2,5)-bicyclo[3.1.0]hexanacyclotridecaphan-11-ene-43-carboxamide (40)

To a solution of compound 40S-9 (52 mg, 0.070 mmol) in toluene (50 mL) was added Grubb's second generation catalyst (14.8 mg, 0.018 mmol). After addition, the reaction mixture was stirred at 80° C. overnight. The mixture was concentrated to dryness and the residue was purified by preparatory HPLC to give 40 (13.5 mg, 26.9% yield) as a white solid. $^1$H-NMR (400 MHz, CD$_3$OD) δ 9.36 (s, 2H), 8.57 (s, 1H), 7.73 (d, J=7.9 Hz, 1H), 7.50 (d, J=7.8 Hz, 1H), 7.19 (d, J=14.9 Hz, 1H), 7.09-6.99 (m, 1H), 6.12 (d, J=17.5 Hz, 1H), 5.61 (d, J=17.3 Hz, 1H), 4.46-4.42 (m, 1H), 3.93-3.86 (m, 1H), 3.45 (d, J=15.8 Hz, 2H), 2.76 (s, 3H), 2.71 (s, 3H), 2.69-2.52 (m, 4H), 2.28 (t, J=5.0 Hz, 2H), 2.10 (m, 1H), 2.05 (s, 3H), 1.97-1.90 (m, 1H), 1.35 (m, 1H), 1.32-1.29 (m, 1H), 1.19-1.15 (m, 1H). LC/MS (ESI) m/z: 702 (M+H)$^+$.

Step 14: (41R,43S,45R)-13-Acetyl-N-(3-methyl-6-(trifluoromethyl)pyridin-2-yl)-15-(2-methylpyrimidin-5-yl)-3,7-dioxo-11H-42,6-diaza-1(1,7)-pyrazolo[3,4-c]pyridina-4(2,5)-bicyclo[3.1.0]hexanacyclotridecaphane-43-carboxamide (41)

To a solution of 40 (10 mg, 0.014 mmol) in MeOH (1 mL) and THF (1 mL) was degassed three times under N$_2$ atmosphere, and Pd/C (2 mg, 10% wt) was added. The mixture was degassed again and stirred under a H$_2$ balloon at room temperature over 30 minutes. The mixture was filtered, and the filtrate was concentrated to dryness. The residue was purified by preparatory HPLC to give 41 (1.5 mg, 15.0% yield) as a white solid. $^1$H-NMR (400 MHz, CD$_3$OD) δ 9.34 (s, 2H), 8.57 (s, 1H), 7.78 (d, J=7.8 Hz, 1H), 7.53 (d, J=7.8 Hz, 1H), 5.88 (d, J=17.7 Hz, 1H), 5.70 (d, J=17.5 Hz, 1H), 4.35 (m, 1H), 3.81 (m, 1H), 3.54 (d, J=14.6 Hz, 1H), 3.48 (m, 1H), 3.13 (m, 1H), 2.75 (s, 3H), 2.71 (s, 3H), 2.70-2.63 (m, 1H), 2.52 (dd, J=13.5, 8.1 Hz, 1H), 2.24 (t, J=5.5 Hz, 2H), 2.13 (s, 3H), 2.09-1.99 (m, 1H), 1.88-1.69 (m, 5H), 1.35 (d, J=6.9 Hz, 1H), 1.29 (m, 1H), 1.20-1.14 (m, 1H). LC/MS (ESI) m/z: 704 [M+H]$^+$.

Scheme 29: Synthesis of 42 and 43

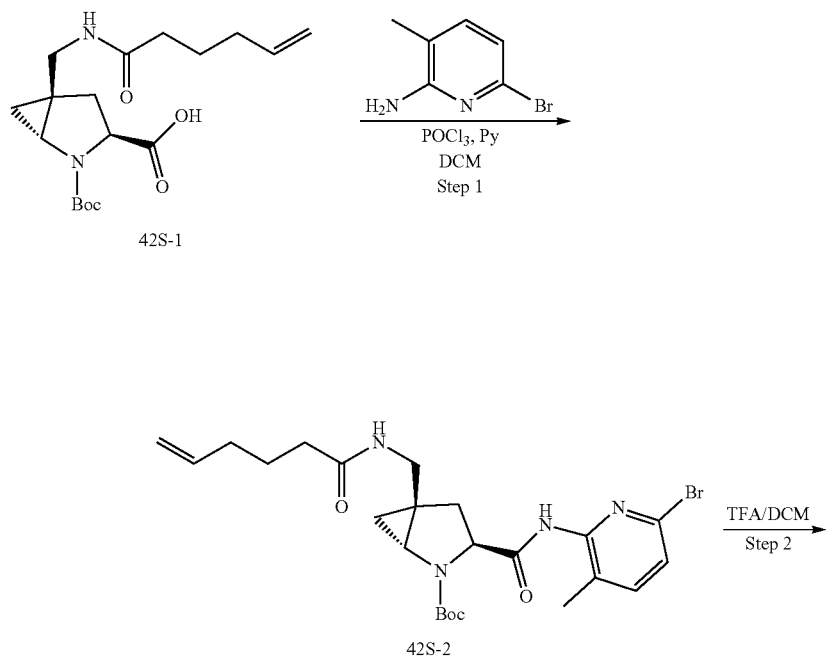

-continued
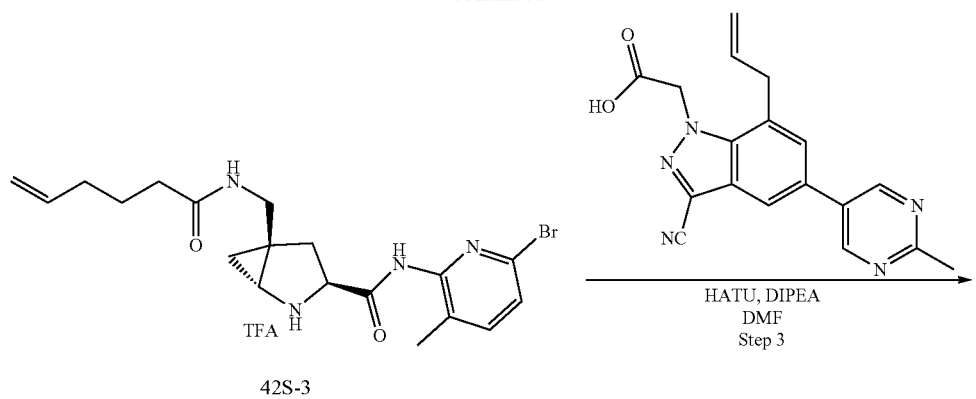
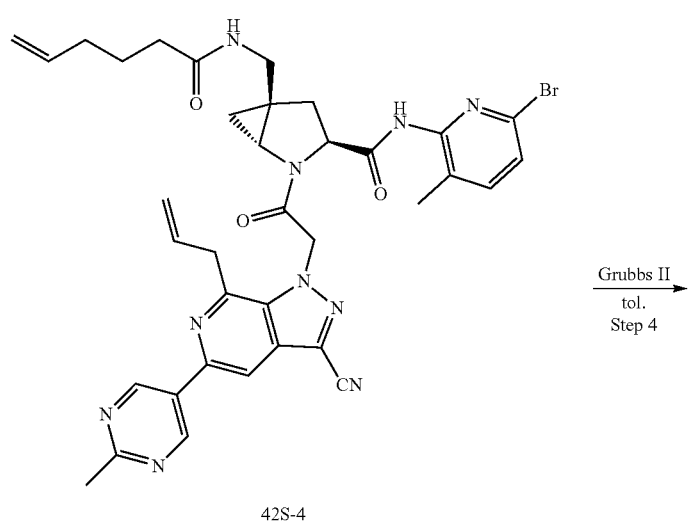
42S-4
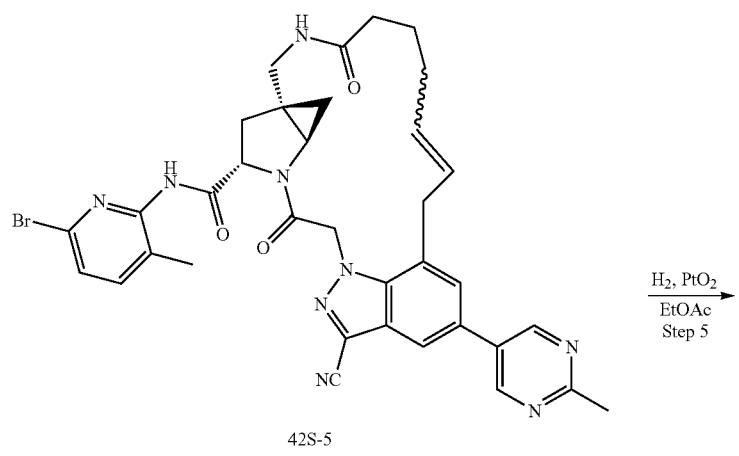
42S-5

-continued
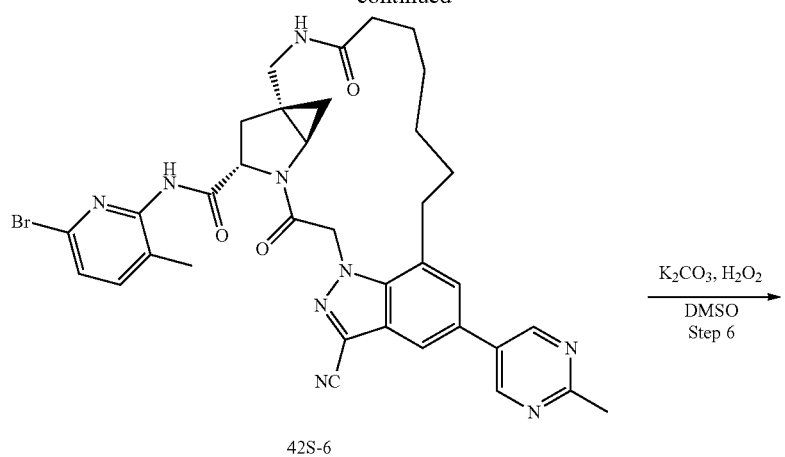
42S-6
K$_2$CO$_3$, H$_2$O$_2$
DMSO
Step 6
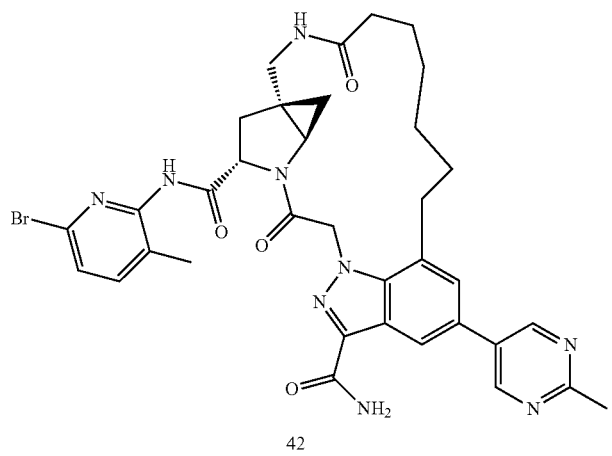
42
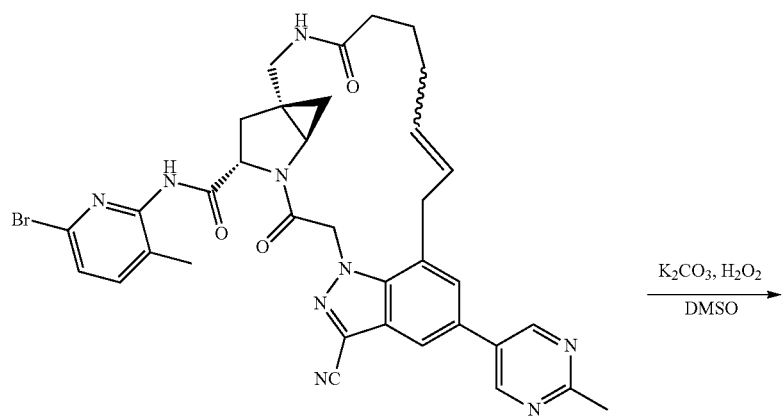
42S-5
K$_2$CO$_3$, H$_2$O$_2$
DMSO

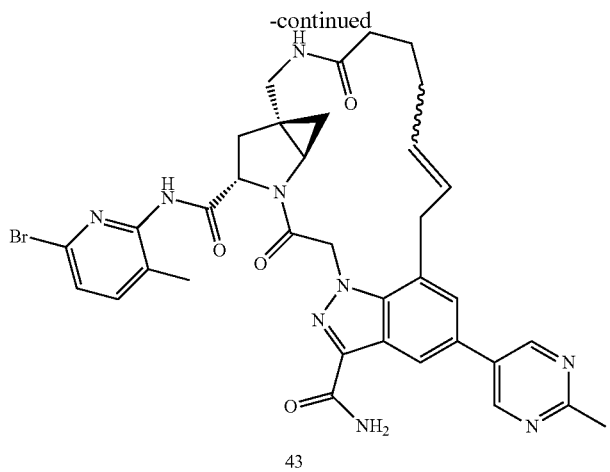

43

The above scheme and following detailed description depicts one non-limiting method for synthesizing compounds of Formula II wherein -X$^9$-L$^3$-X$^{10}$-is The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1: (1R,3S,5R)-tert-Butyl 3-((6-Bromo-3-methylpyridin-2-yl)carbamoyl)-5-(hex-5-enamidomethyl)-2-azabicyclo[3.1.0]hexane-2-carboxylate (42S-2)

To a mixture of compound 42S-1 (280 mg, 0.80 mmol) and 6-bromo-3-methylpyridin-2-amine (149 mg, 0.80 mmol) in DCM (10 mL) was added pyridine (314 mg, 3.98 mmol) and POCl$_3$ (183 mg, 1.19 mmol) at 0° C. After addition, the mixture was stirred at 25° C. for 1 hour. The mixture was quenched with ice-cooled water and extracted with DCM twice. The combined organic layers were washed with water and brine, dried over Na$_2$SO$_4$, filtered and evaporated to dryness. The residue was purified by column chromatography on silica gel (PE:EtOAc=1:1) to give compound 42S-2 (250 mg, 60.1% yield) as a yellow oil. LC/MS (ESI) m/z: 521/523 (M+H)$^+$.

Step 2: (1R,3S,5R)-N-(6-Bromo-3-methylpyridin-2-yl)-5-(hex-5-enamidomethyl)-2-azabicyclo[3.1.0]hexane-3-carboxamide Trifluoroacetic Acid Salt (42S-3)

To a solution of compound 42S-2 (250 mg, 0.48 mmol) in DCM (3 mL) was added TFA (2 mL) at 0° C. After addition, the reaction mixture was stirred at 25° C. for 2 hours. The mixture was concentrated under reduced pressure to give compound 42S-3 (300 mg, 100% yield) as a yellow oil. LC/MS (ESI) m/z: 421/423 (M+H)$^+$.

Step 3: (1R,3S,5R)-2-(2-(7-Allyl-3-cyano-5-(2-methylpyrimidin-5-yl)-1H-pyrazolo[3,4-c]pyridin-1-yl)acetyl)-N-(6-bromo-3-methylpyridin-2-yl)-5-(hex-5-enamidomethyl)-2-azabicyclo[3.1.0]hexane-3-carboxamide (42S-4)

To a mixture of the compound 42S-3 (150 mg, 0.24 mmol), 2-(7-allyl-3-cyano-5-(2-methylpyrimidin-5-yl)-1H-indazol-1-yl)acetic acid (90 mg, 0.24 mmol) and HATU (164 mg, 0.43 mmol) in DMF (3 mL) was added DIPEA (0.165 mL, 0.96 mmol) at 0° C. After addition, the reaction mixture stirred at room temperature for 2 hours. The mixture was diluted with EtOAc, washed with saturated aq. NH$_4$Cl solution and brine, dried over Na$_2$SO$_4$ and concentrated to dryness. The residue was purified by column chromatography on silica gel (eluted with DCM:MeOH=60:1) to give compound 42S-4 (140 mg, 79.5% yield) as a yellow solid. LC/MS (ESI) m/z: 736/738 (M+H)$^+$.

Step 4: (41R,43S,45R)-N-(6-Bromo-3-methylpyridin-2-yl)-13-cyano-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide (42S-5)

To a solution of compound 42S-4 (140 mg, 0.19 mmol) in degassed toluene (150 mL) was added Grubb's second generation catalyst (40.3 mg, 0.048 mmol) under N$_2$ atmosphere. After addition, the reaction mixture was stirred at 80° C. under N$_2$ atmosphere for 16 hours. The mixture was concentrated to dryness, and the residue was purified by column chromatography on silica gel (eluted with DCM:MeOH=60:1) to give compound 42S-5 (60 mg, 44.8% yield) as yellow solid. LC/MS (ESI) m/z: 708/710 (M+H)$^+$.

Step 5: (41R,43S,45R)-N-(6-Bromo-3-methylpyridin-2-yl)-13-cyano-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide (XS-6)

A solution of compound 42S-5 (40 mg, 0.056 mmol) in EtOAc (3 mL) was degassed three times under N$_2$ atmosphere, and PtO$_2$ (5 mg) was added. The mixture was degassed again and stirred under a H$_2$ balloon at room temperature for 1 hour. The mixture was filtered, and the filtrate was concentrated to dryness to give compound 42S-6 (40 mg, 100% yield) as a brown solid. LC/MS (ESI) m/z: 710/712 [M+H]$^+$.

Step 6: 42

To a solution of compound 42S-6 (40 mg, 0.056 mmol) in DMSO (3 mL) was added K$_2$CO$_3$ (49.0 mg, 0.36 mmol) and 30% aq. H$_2$O$_2$ (40.8 mg, 0.36 mmol). After addition, the mixture was stirred at room temperature for 15 minutes. The mixture was diluted with EtOAc, washed with water and brine, dried over Na$_2$SO$_4$ and concentrated to dryness. The residue was purified by preparatory HPLC to give 42 (8.2 mg, 20.0% yield) as a white solid. $^1$H-NMR (400 MHz, DMSO-$d_6$) δ 9.00 (s, 2H), 8.30 (d, J=1.6 Hz, 1H), 8.21 (s, 1H), 7.72 (s, 1H), 7.57 (s, 1H), 7.48 (d, J=16.4 Hz, 2H), 7.40 (s, 1H), 5.82 (d, J=17.9 Hz, 1H), 5.39 (d, J=18.1 Hz, 1H), 4.26 (t, J=8.0 Hz, 1H), 3.65-3.46 (m, 1H), 3.11 (m, 3H), 2.87-2.75 (m, 1H), 2.68 (s, 3H), 2.41 (m, 2H), 2.21-2.10 (m, 2H), 1.98 (s, 3H), 1.81-1.72 (m, 2H), 1.71-1.60 (m, 3H), 1.52-1.38 (m, 3H), 1.23-1.18 (m, 1H), 1.04-1.00 (m, 1H). LC/MS (ESI) m/z: 728/730 (M+H)$^+$.

Step 7: 43

To a solution of compound 42S-5 (20 mg, 0.028 mmol) in DMSO (3 mL) was added $K_2CO_3$ (49.0 mg, 0.36 mmol) and 30% aq. $H_2O_2$ (40.8 mg, 0.36 mmol). After addition, the mixture was stirred at room temperature for 15 min. The mixture was diluted with EtOAc, washed with water and brine, dried over $Na_2SO_4$ and concentrated to dryness. The residue was purified by preparatory HPLC to give 43 (4.3 mg, 21.1% yield) as a white solid. $^1$H-NMR (400 MHz, DMSO-$d_6$) δ 9.01 (s, 2H), 8.36 (s, 1H), 8.33 (s, 1H), 7.98 (m, 1H), 7.72 (s, 1H), 7.64-7.55 (m, 2H), 7.49 (s, 1H), 7.46-7.38 (m, 1H), 6.08-5.87 (m, 1H), 5.73-5.60 (m, 1H), 5.45-5.31 (m, 1H), 4.46-4.23 (m, 1H), 3.85-3.64 (m, 1H), 2.68 (s, 3H), 2.9-2.33 (m, 3H), 2.30-2.17 (m, 3H), 2.17-2.09 (m, 2H), 2.05 (s, 3H), 2.00 (m, 1H), 1.79 (dd, J=11.2, 8.6 Hz, 1H), 1.71-1.51 (m, 3H), 1.05 (m, 1H), 1.05-0.94 (m, 1H), 0.85 (t, J=7.8 Hz, 1H). LC/MS (ESI) m/z: 726/728 (M+H)$^+$.

Scheme 30: Synthesis of (41R,43S,45R)-13-Acetyl-8,8-difluoro-N-(3-methyl-6-(trifluoromethyl)pyridin-2-yl)-15-(2-methylpyrimidin-5-yl)-3,7-dioxo-11H-12-oxa-42,6-diaza-1(1,7)-indazola-4(2,5)-bicyclo[3.1.0]hexanacyclotridecaphan-9-ene-43-carboxamide (44)

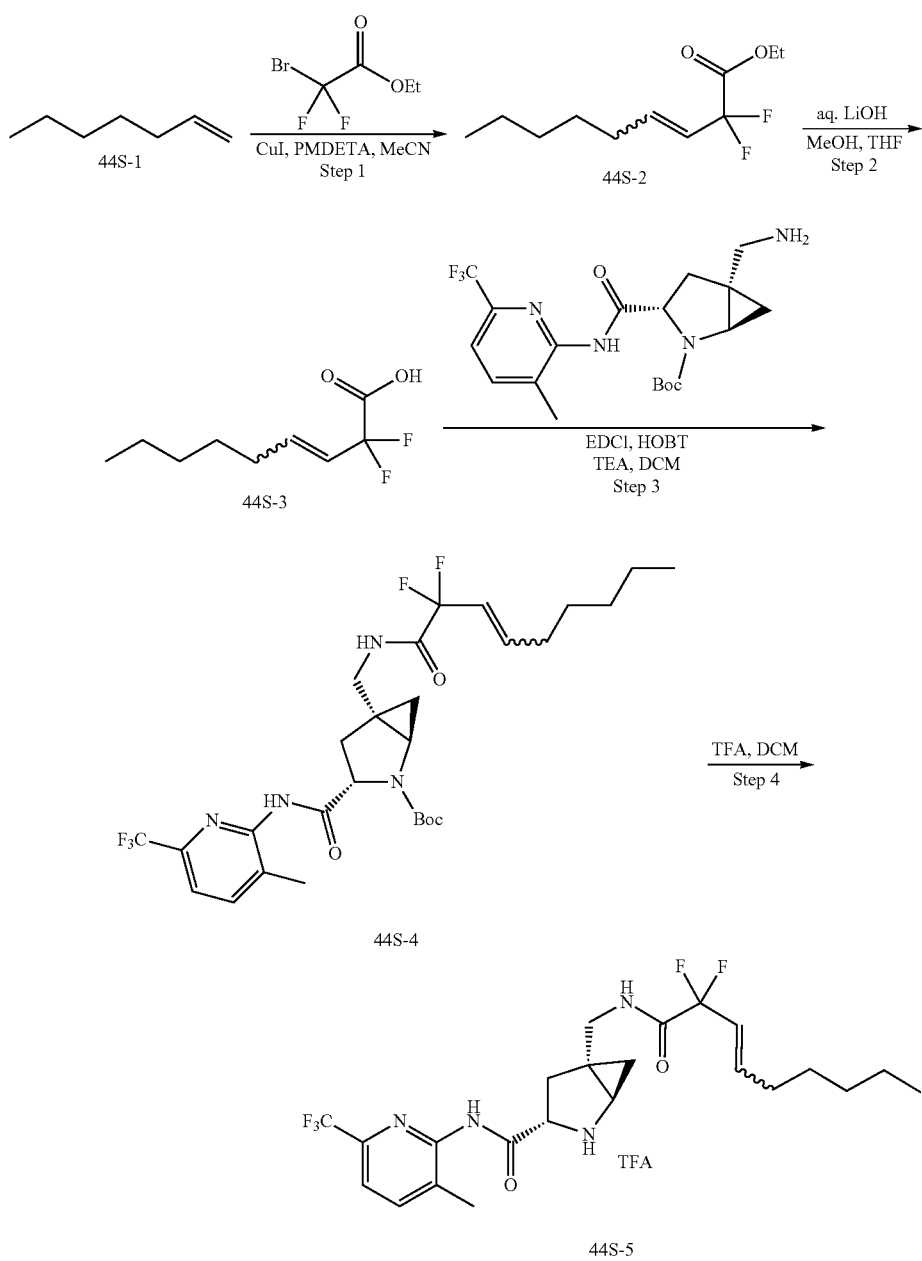

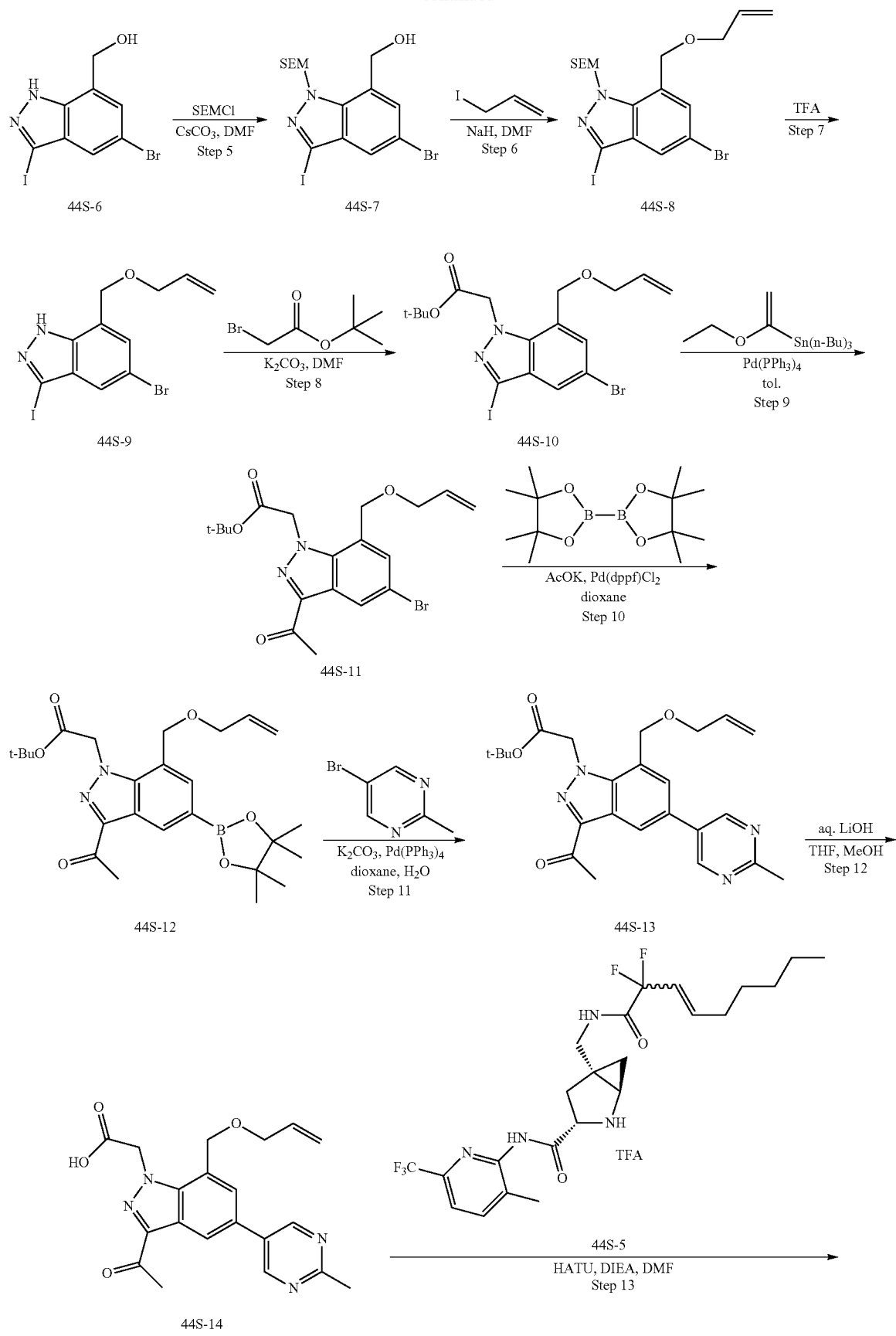

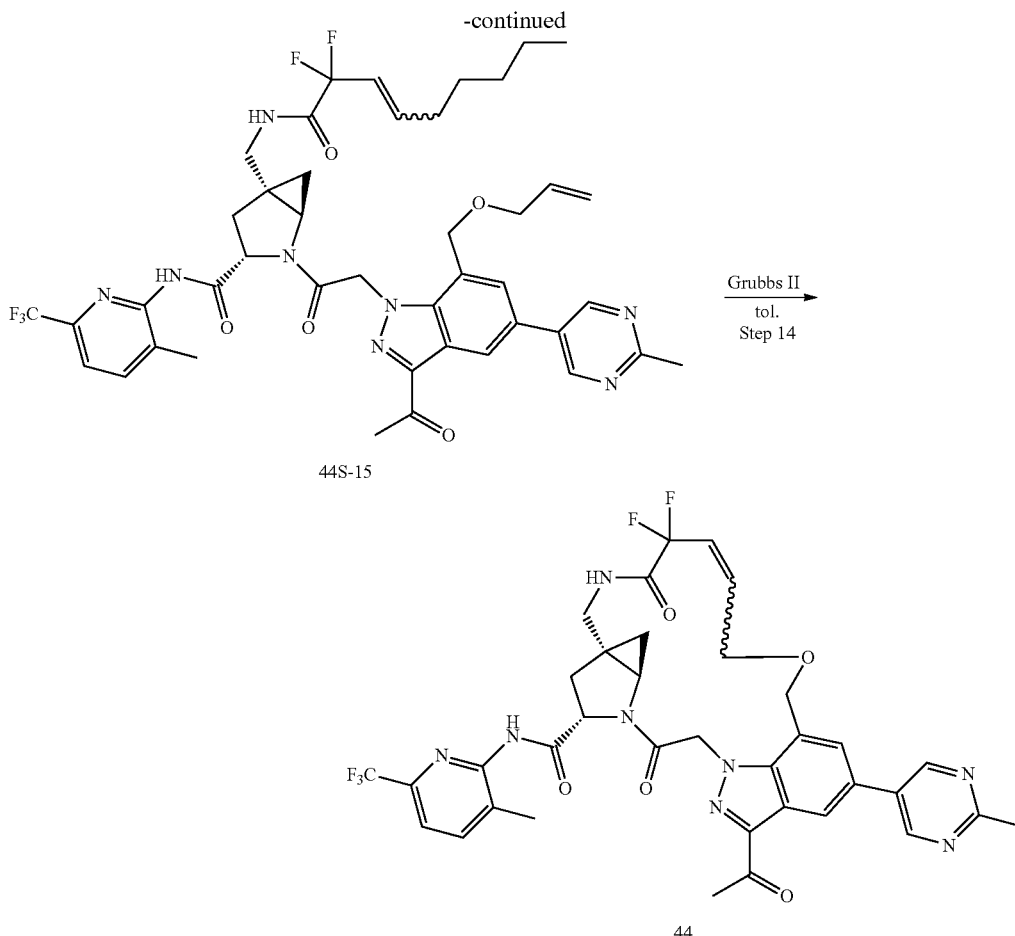

The above scheme and following detailed description depicts one non-limiting method for synthesizing compounds of Formula II wherein -$X^9$-$L^3$-$X^{10}$- is

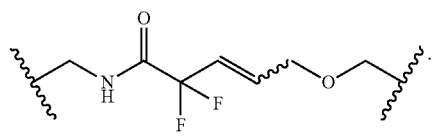 [SMILES: *CNC(=O)C(F)(F)C=CCOC*]

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: Ethyl 2,2-Difluoronon-3-enoate (44S-2)

To a mixture of hept-1-ene (1 g, 10.2 mmol) and ethyl 2-bromo-2,2-difluoroacetate (3.08 g, 15.3 mmol) in acetonitrile (15 mL) was added $N^1$-(2-(dimethylamino)ethyl)-$N^1$,$N^2$,$N^2$-trimethylethane-1,2-diamine (2.65 g, 15.3 mmol), and the mixture was degassed under $N_2$ atmosphere three times. CuI (194 mg, 0.10 mmol) was added to the mixture under $N_2$ atmosphere, and the resulting mixture was stirred at 80° C. under $N_2$ atmosphere for 16 hours. The mixture was diluted with EtOAc and filtered. The filtrate was concentrated to dryness, and the residue was purified by column chromatography on silica gel (eluted with PE:EtOAc=60:1) to give compound 44S-2 (1.8 g, 80.2% yield) as a colorless oil.

Step 2: 2,2-Difluoronon-3-enoic Acid (44S-3)

To a solution of compound 44S-2 (1.8 g, 8.2 mmol) in THF (10 mL), MeOH (10 mL) and water (10 mL) was added LiOH (1.38 g, 32.8 mmol), and the mixture was stirred at room temperature for 2 hours. The mixture was concentrated to dryness, and the residue was diluted with water and washed with EtOAc twice. The aqueous layer was acidified by adding 1 N aq. HCl to pH~3 at 0° C. and extracted with DCM twice. The combined organic layers were washed with brine, dried over anhydrous $Na_2SO_4$, filtered and concentrated to dryness to give compound 44S-3 (1.5 g, 95.5% yield) as a colorless oil.

Step 3: (1R,3S,5R)-5-((2,2-Difluoronon-3-enamido)methyl)-N-(3-methyl-6-(trifluoromethyl)pyridin-2-yl)-2-azabicyclo[3.1.0]hexane-3-carboxamide (44S-4)

To a mixture of compound 44S-3 (123 mg, 0.64 mmol) and (1R,3S,5R)-tert-butyl 5-(aminomethyl)-3-((3-methyl-6-(trifluoromethyl)pyridin-2-yl)carbamoyl)-2-azabicyclo[3.1.0]hexane-2-carboxylate (140 mg, 0.32 mmol) in DCM (10 mL) was added EDCI (91.2 mg, 0.48 mmol), HOBt (43.2 mg, 0.32 mmol) and triethyl amine (0.18 mL, 1.28 mmol), and the mixture was stirred at 25° C. for 16 hours. The mixture was diluted with DCM, washed with water and brine, dried over anhydrous $Na_2SO_4$, filtered and concentrated to dryness. The residue was purified by column chromatography on silica gel (PE:EtOAc=2:1) to give compound 44S-4 (147 mg, 39.1% yield) as a colorless oil. LC/MS (ESI) m/z: 589 (M+H)$^+$.

Step 4: (1R,3S,5R)-5-((2,2-Difluoronon-3-enamido) methyl)-N-(3-methyl-6-(trifluoromethyl)pyridin-2-yl)-2-azabicyclo[3.1.0]hexane-3-carboxamide Trifluoroacetic Acid Salt (44S-5)

To a solution of compound 44S-4 (147 mg, 0.25 mmol) in DCM (3 mL) was added TFA (2 mL) at 0° C., and the reaction mixture was stirred at 25° C. for 2 hours. The mixture was concentrated under reduced pressure to give compound 44S-5 (150 mg, 100% yield) as a yellow oil. LCMS: LC/MS (ESI) m/z: 489 (M+H)$^+$.

Step 5: (5-Bromo-3-iodo-1-((2-(trimethylsilyl)ethoxy) methyl)-1H-indazol-7-yl)methanol (44S-7)

To a solution of compound 44S-6 (3.9 g, 11.0 mmol) in anhydrous DMF (50 mL) was added Cs$_2$CO$_3$ (8.98 g, 27.5 mmol) followed by drop-wise addition of SEMCl (3.33 g, 19.8 mmol) at 0° C., and the mixture was stirred at 25° C. for 16 hours. The reaction mixture diluted with EtOAc, washed with water and brine, dried over anhydrous Na$_2$SO$_4$, filtered and concentrated to dryness. The residue was purified by column chromatography on silica gel (PE:EtOAc=8: 1) to give compound 44S-7 (3.6 g, 67.9% yield) as a yellow oil. LC/MS (ESI) m/z: 483/485 (M+H)$^+$.

Step 6: (5-Bromo-3-iodo-1-((2-(trimethylsilyl)ethoxy) methyl)-1H-indazol-7-yl)methanol (44S-8)

To a solution of compound 44S-7 (3.6 g, 7.5 mmol) in anhydrous DMF (50 mL) was added NaH (600 mg, 15.0 mmol, 60% dispersion in mineral oil) in portions at 0° C. After addition, the mixture was stirred at 0° C. for 30 minutes. 3-iodoprop-1-ene (1.39 g, 8.25 mmol) was added, and the resulting mixture was stirred at 25° C. for 16 hours. The reaction mixture was poured into ice-cooled saturated aq. NH$_4$Cl solution and extracted with EtOAc twice. The combined organic phases were washed with brine, dried over anhydrous Na$_2$SO$_4$, filtered and concentrated to dryness. The residue was purified by column chromatography on silica gel (PE:EtOAc=20:1) to give compound 44S-8 (2.8 g, 71.5% yield) as a yellow oil.

Step 7: (5-Bromo-3-iodo-1-((2-(trimethylsilyl)ethoxy) methyl)-1H-indazol-7-yl)methanol (44S-9)

A solution of compound 44S-8 (2.8 g, 5.36 mmol) in TFA (20 mL) was stirred at 25° C. for 2 hours. The mixture was concentrated to dryness, and the residue was poured into ice-cooled saturated aq. NaHCO$_3$ solution. The mixture was extracted with DCM twice, and the combined organic phases were washed with brine, dried over anhydrous Na$_2$SO$_4$, filtered and concentrated to dryness. The residue was purified by column chromatography on silica gel (PE:EtOAc=2: 1) to give compound 44S-9 (1.4 g, 66.7% yield) as a yellow solid. LC/MS (ESI) m/z: 393/395 (M+H)$^+$.

Step 8: tert-Butyl 2-(7-((Allyloxy)methyl)-5-bromo-3-iodo-1H-indazol-1-yl)acetate (44S-10)

To a solution of compound 44S-9 (1.4 g, 3.57 mmol) in DMF (20 mL) was added K$_2$CO$_3$ (986 mg, 7.14 mmol) and tert-butyl 2-bromoacetate (766 mg, 3.93 mmol) at 0° C., and the reaction mixture was stirred at room temperature overnight. The mixture was diluted with EtOAc, washed with saturated aq. NH$_4$Cl solution and brine, dried over Na$_2$SO$_4$ and concentrated to dryness. The residue was purified by column chromatography on silica gel (eluted with petroleum ether:ethyl acetate=8:1) to give compound 44S-10 (1.5 g, 83.1% yield) as a yellow solid. LC/MS (ESI) m/z: 507/509 (M+H)$^+$.

Step 9: tert-Butyl 2-(3-Acetyl-7-((allyloxy)methyl)-5-bromo-1H-indazol-1-yl)acetate (44S-11)

To a solution of compound 44S-10 (1.5 g, 2.96 mmol) in toluene (5 mL) was added tributyl(1-ethoxyvinyl)stannane (1.07 g, 2.96 mmol) and Pd(PPh$_3$)$_4$ (342 mg, 0.30 mmol). The mixture was degassed under N$_2$ atmosphere three times and stirred at 100° C. under N$_2$ atmosphere for 16 hours. The mixture was concentrated to dryness, and the residue was dissolved in THF (10 mL). 1N aq. HCl (10 mL) was added to the solution, and the mixture was stirred at room temperature for 1 hour. The mixture was diluted with EtOAc, washed with water and brine, dried over anhydrous Na$_2$SO$_4$, filtered and concentrated to dryness. The residue was purified by column chromatography on silica gel (eluted with petroleum ether:ethyl acetate=6:1) to give compound 44S-11 (800 mg, 64.1% yield) as a brown solid. LC/MS (ESI) m/z: 423/425 (M+H)$^+$.

Step 10: tert-Butyl 2-(3-Acetyl-7-((allyloxy)methyl)-5-(4,4, 5,5-tetramethyl-1,3,2-dioxaborolan-2-yl)-1H-indazol-1-yl) acetate (44S-12)

To a mixture of compound 44S-11 (170 mg, 0.40 mmol) and 4,4,4',4',5,5,5',5'-octamethyl-2,2'-bi(1,3,2-dioxaborolane) (123 mg, 0.48 mmol) in 1,4-dioxane (5 mL) was added AcOK (100 mg, 1.02 mmol) and Pd(dppf)Cl$_2$ (29.3 mg, 0.04 mmol), and the mixture was degassed and stirred at 115° C. under N$_2$ atmosphere for 4 hours. The mixture was directly used in the next reaction without any work-up. LC/MS (ESI) m/z: 471 (M+H)$^+$.

Step 11: tert-Butyl 2-(3-Acetyl-7-((allyloxy)methyl)-5-(2-methylpyrimidin-5-yl)-1H-indazol-1-yl)acetate (44S-13)

To the above mixture, 5-bromo-2-methylpyrimidine (75.7 mg, 0.44 mmol) was added followed by water (1 mL) and K$_2$CO$_3$ (110.4 mg, 0.80 mmol), and the mixture was degassed under N$_2$ three times. Pd(PPh$_3$)$_4$ (46.2 mg, 0.04 mmol) was added, and the resulting mixture was stirred at 95° C. under N$_2$ atmosphere for 16 hours. The reaction mixture was concentrated to dryness and diluted with EtOAc, washed with water and brine, dried over Na$_2$SO$_4$ and concentrated to dryness. The residue was purified by column chromatography on silica gel (PE:EtOAc=2:1) to give compound 44S-13 (110 mg, 62.9% yield) as a white solid. LC/MS (ESI) m/z: 437 (M+H)$^+$.

Step 12: 2-(3-Acetyl-7-((allyloxy)methyl)-5-(2-methylpyrimidin-5-yl)-1H-indazol-1-yl)acetic Acid (44S-14)

To a solution of compound 44S-13 (110 mg, 0.25 mmol) in THF (5 mL), MeOH (5 mL), and water (5 mL) was added LiOH (31.8 mg, 0.76 mmol), and the mixture was stirred at room temperature for 2 hours. The mixture was concentrated to dryness, and the residue was diluted with water and washed with EtOAc twice. The aqueous layer was acidified by adding 1 N aq. HCl to pH~3 and extracted with DCM twice. The combined organic layers were washed with brine, dried over anhydrous Na$_2$SO$_4$, filtered and concentrated to dryness to give compound 44S-14 (95 mg, 99.7% yield) as a yellow solid. LCMS: LC/MS (ESI) m/z: 381 (M+H)$^+$.

Step 13: (1R,3S,5R)-2-(2-(3-Acetyl-7-((allyloxy)methyl)-5-(2-methylpyrimidin-5-yl)-1H-indazol-1-yl)acetyl)-5-((2,2-difluoronon-3-enamido)methyl)-N-(3-methyl-6-(trifluoromethyl)pyridin-2-yl)-2-azabicyclo[3.1.0]hexane-3-carboxamide (44S-15)

To a mixture of the compound 44S-14 (95 mg, 0.25 mmol), compound 44S-5 (150 mg, 0.25 mmol), and HATU (171 mg, 0.45 mmol) in DMF (3 mL) was added DIPEA (0.215 mL, 1.25 mmol) at 0° C., and the reaction mixture was stirred at room temperature for 2 hours. The mixture was diluted with EtOAc, washed with saturated aq. NH$_4$Cl solution and brine, dried over Na$_2$SO$_4$ and concentrated to dryness. The residue was purified by column chromatography on silica gel (eluted with DCM:MeOH=50:1) to give compound XS-15 (140 mg, 66.0% yield) as a light yellow solid. LC/MS (ESI) m/z: 851 (M+H)+.

Step 14: (41R,43S,45R)-13-Acetyl-8,8-difluoro-N-(3-methyl-6-(trifluoromethyl)pyridin-2-yl)-15-(2-methylpyrimidin-5-yl)-3,7-dioxo-11H-12-oxa-42,6-diaza-1(1,7)-indazola-4(2,5)-bicyclo[3.1.0]hexanacyclotridecaphan-9-ene-43-carboxamide (44)

To a solution of compound 44S-15 (140 mg, 0.16 mmol) in toluene (150 mL) was added Grubb's second generation catalyst (34.9 mg, 0.041 mmol). After addition, the reaction mixture was degassed under N₂ atmosphere and stirred at 80° C. under N₂ atmosphere for 16 hours. The mixture was concentrated to dryness and the residue was purified by preparatory HPLC to give 44 (1.5 mg, 1.26% yield) as a white solid. ¹H-NMR (400 MHz, CD₃OD) δ 9.01 (s, 2H), 8.53 (s, 1H), 7.83 (s, 2H), 7.58 (s, 1H), 6.55-6.28 (m, 1H), 5.96 (d, J=32.8 Hz, 1H), 5.62 (d, J=16.1 Hz, 1H), 5.17 (d, J=13.7 Hz, 1H), 4.78 (d, J=12.5 Hz, 1H), 4.50-4.42 (m, 2H), 3.76-3.70 (m, 1H), 3.47 (dd, J=22.4, 11.1 Hz, 3H), 2.75 (s, 3H), 2.69 (s, 3H), 2.65-2.58 (m, 1H), 2.22 (s, 3H), 1.36 (d, J=4.3 Hz, 1H), 1.32-1.28 (m, 2H), 1.13-1.10 (m, 1H), 0.95-0.80 (m, 1H). LC/MS (ESI) m/z: 753 (M+H)+.

Scheme 31: Synthesis of (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclotridecaphan-9-ene-43-carboxamide (45), (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclotetradecaphane-43-carboxamide (46), (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclotridecaphane-43-carboxamide (47), (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclododecaphane-43-carboxamide (48)

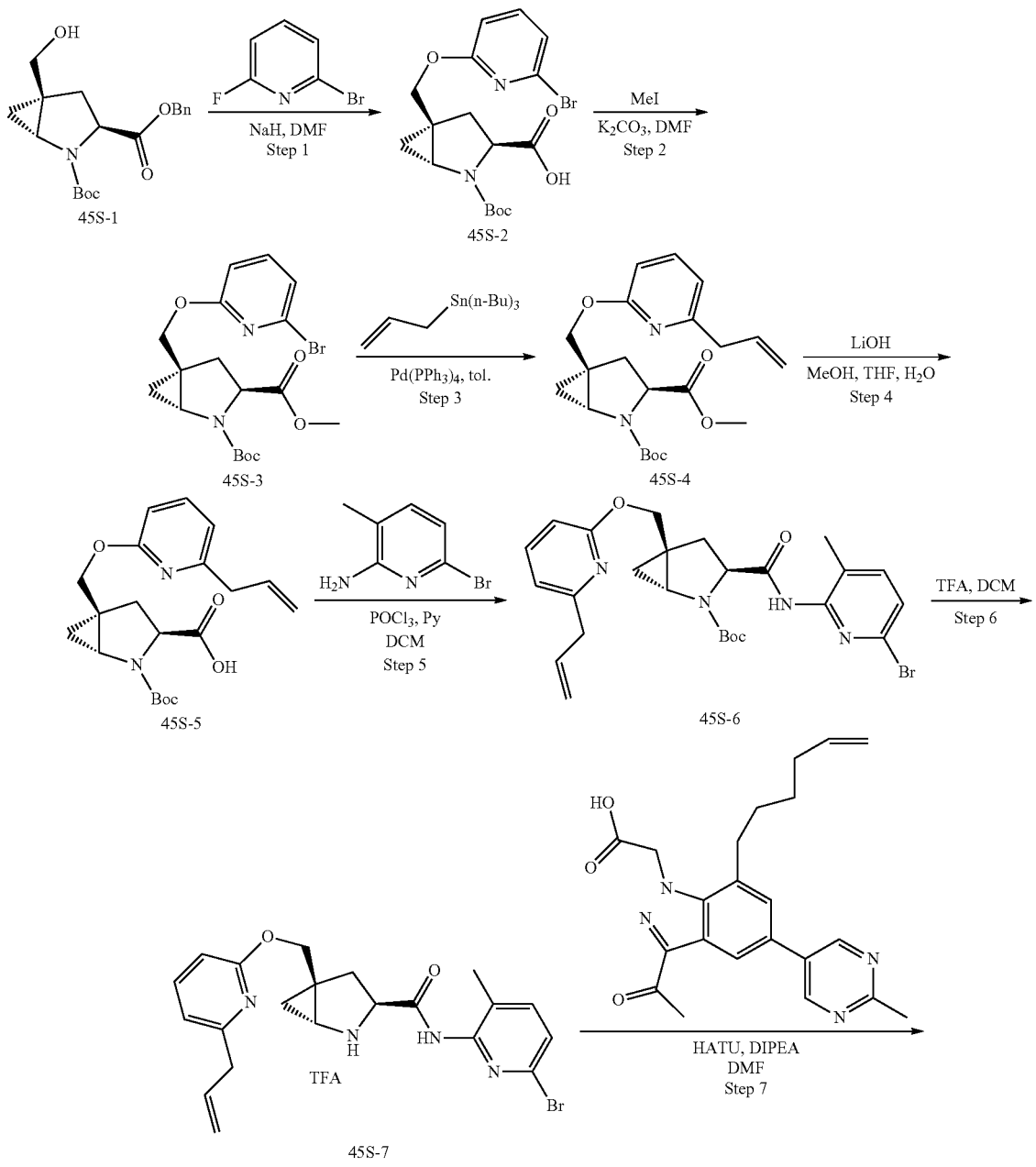

-continued
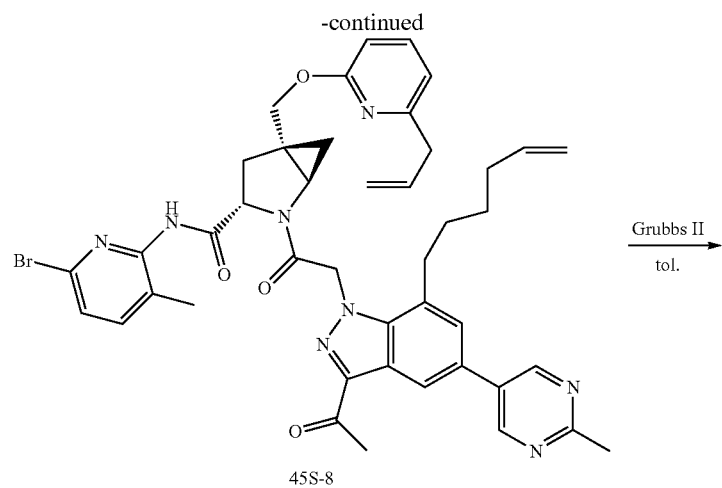
45S-8
Grubbs II
tol.
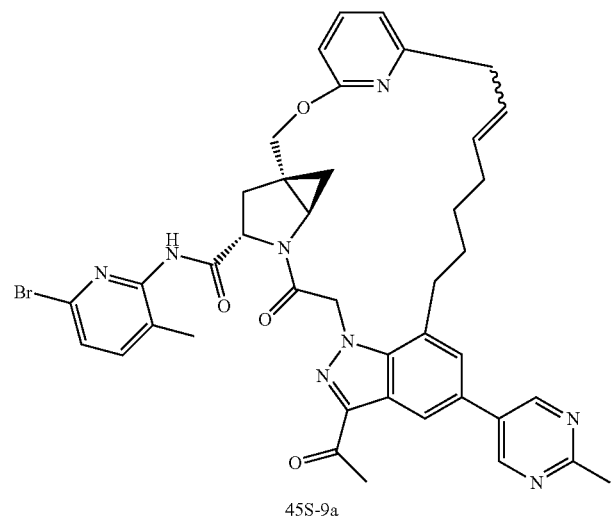
45S-9a
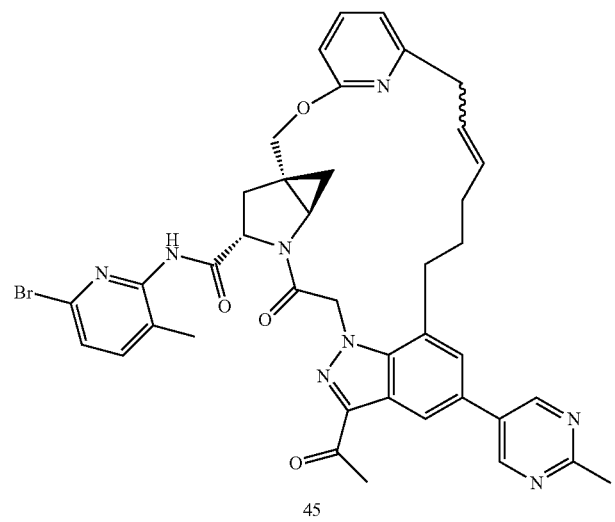 [SMILES: CC(=O)c1nn2c3c(cc(-c4cnc(C)nc4)cc13)CCCCCc1cccc(n1)OC[C@@]13C[C@@H](C(=O)Nc4nc(Br)ccc4C)N(C(=O)C2)[C@@H]1C3]
45

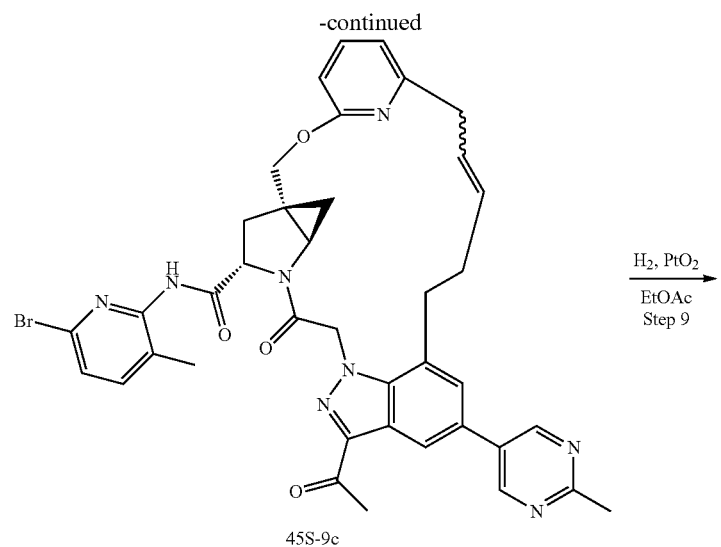
45S-9c
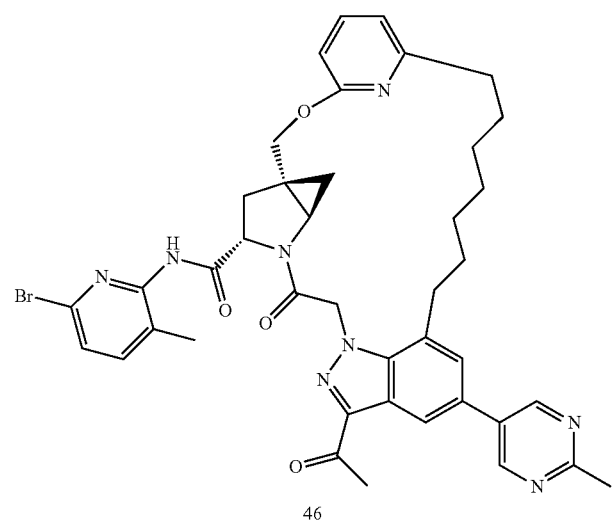
46
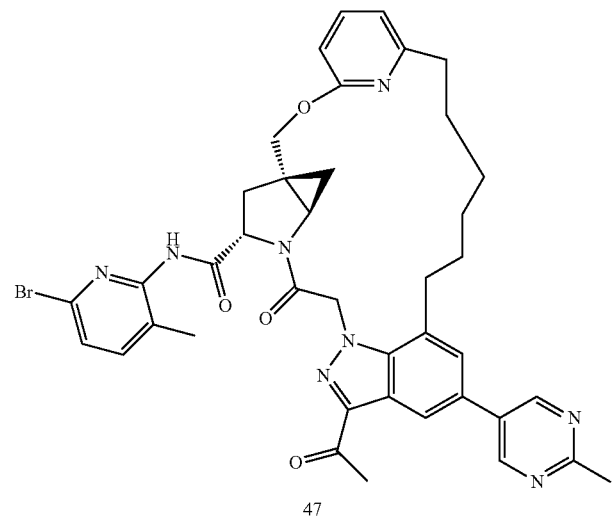
47

-continued

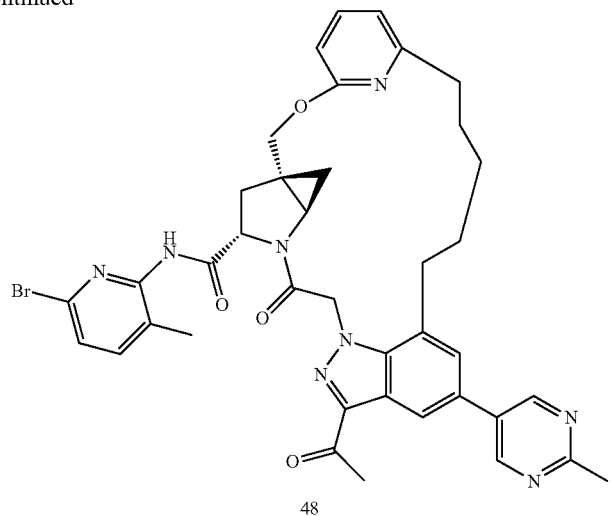

48

The above scheme and following detailed description depicts one non-limiting method for synthesizing compounds of Formula II wherein -$X^9$-$L^3$-$X^{10}$- is

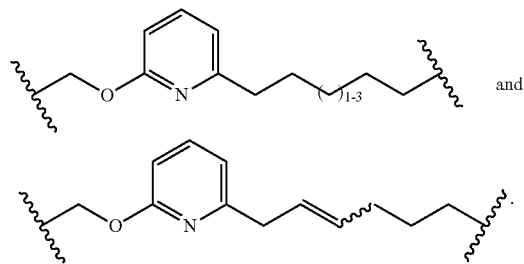

and

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: (1R,3S,5S)-5-(((6-Bromopyridin-2-yl)oxy)methyl)-2-(tert-butoxycarbonyl)-2-azabicyclo[3.1.0]hexane-3-carboxylic Acid (45S-2)

To a solution of compound 45S-1 (500 mg, 1.44 mmol) in DMF (10 mL) was added NaH (87 mg, 2.16 mmol, 60% dispersion in mineral oil) in portions at 0° C., and the mixture was stirred at this temperature for 1 hour. A solution of 2-bromo-6-fluoropyridine (380 mg, 2.16 mmol) in DMF (2 ml) was added to the mixture at 0° C., and the resulting mixture was stirred at 40° C. for 16 hours. After cooling to room temperature, the reaction mixture was quenched with 1N aq. HCl and extracted with EtOAc three times. The combined organic layers were washed with aq. NH$_4$Cl solution and brine, dried over Na$_2$SO$_4$, filtered and concentrated to dryness. The residue was purified by silica gel column chromatography (eluted with DCM:MeOH=50:1 to 10:1) to give compound 45S-2 (400 mg, yield 67.3%) as a yellow solid. LC/MS (ESI) 413/415 m/z (m+H)$^+$.

Step 2: (1R,3S,5S)-2-tert-Butyl 3-Methyl 5-(((6-Bromopyridin-2-yl)oxy)methyl)-2-azabicyclo[3.1.0]hexane-2,3-dicarboxylate (45S-3)

To a mixture of compound 45S-2 (200 mg, 0.48 mmol) and K$_2$CO$_3$ (167 mg, 1.21 mmol) in DMF (5 mL) was added MeI (103 mg, 0.73 mmol), and the mixture was stirred at room temperature for 2 hours. The mixture was diluted with EtOAc, washed with saturated aq. NH$_4$Cl solution and brine, dried over Na$_2$SO$_4$, filtered and concentrated to dryness. The residue was purified by silica gel column chromatography (eluted with PE:EtOAc=50:1 to 10:1) to give compound 45S-3 (200 mg, yield 96.7%) as a yellow oil. LC/MS (ESI) 427/429 m/z (m+H)$^+$.

Step 3: (1R,3S,5S)-2-tert-Butyl 3-Methyl 5-(((6-Allylpyridin-2-yl)oxy)methyl)-2-azabicyclo[3.1.0]hexane-2,3-dicarboxylate (45S-4)

To a mixture of compound 45S-3 (200 mg, 0.47 mmol) and allyltributylstannane (309 mg, 0.94 mmol) in toluene (10 mL) was added Pd(PPh$_3$)$_4$ (54 mg, 0.05 mmol). The mixture was degassed under N$_2$ atmosphere three times and stirred under N$_2$ atmosphere at 100° C. for 16 hours. The mixture was diluted with EtOAc, washed with aq. KF solution and brine, dried over anhydrous Na$_2$SO$_4$ and concentrated to dryness. The residue was purified by silica gel chromatography (eluted with PE:EtOAc=20:0 to 6:1) to give compound 45S-4 (120 mg, 66.0% yield) as a yellow oil. LC/MS (ESI) 389 m/z: (M+H)$^+$.

Step 4: (1R,3S,5S)-5-(((6-Allylpyridin-2-yl)oxy)methyl)-2-(tert-butoxycarbonyl)-2-azabicyclo[3.1.0]hexane-3-carboxylic Acid (45S-5)

To a solution of compound 45S-4 (120 mg, 0.31 mmol) in MeOH (1 mL), THF (1 mL) and water (1 mL) was added LiOH (37 mg, 1.54 mmol), and the mixture was stirred at room temperature for 2 hours. The mixture was concentrated to dryness, and the residue was dissolved in water and washed with ether twice. The aqueous layer was acidified by adding 1N aq. HCl to pH~4 and extracted with EtOAc twice. The combined organic layers were washed with brine, dried over Na$_2$SO$_4$ and concentrated under reduced pressure to give compound 45S-5 (103 mg, yield 89.1%) as a white solid. LC/MS (ESI) 373 m/z: (M−H)$^-$.

Step 5: (1R,3S,5S)-tert-Butyl 3-((6-Bromo-3-methylpyridin-2-yl)carbamoyl)-5-(((6-bromopyridin-2-yl)oxy)methyl)-2-azabicyclo[3.1.0]hexane-2-carboxylate (45S-6)

To a mixture of compound 45S-5 (103 mg, 0.28 mmol) and 6-bromo-3-methylpyridin-2-amine (51 mg, 0.28 mmol) in DCM (2 mL) was added pyridine (109 mg, 1.38 mmol) followed by POCl$_3$ (63 mg, 0.42 mmol), and the mixture was stirred at room temperature for 1 hour. The mixture was quenched with saturated aq. NaHCO₃ solution and extracted with DCM. The organic layer was separated, washed with saturated 0.5 N aq. HCl solution and brine, dried over Na₂SO₄, filtered and concentrated to dryness. The residue was purified by silica gel chromatography (eluted with PE:EtOAc=15:1 to 3:1) to give compound 45S-6 (100 mg, yield 66.9%) as a white solid. LC/MS (ESI) 543/545 m/z: (M+H)⁺.

Step 6: (1R,3S,5S)-5-(((6-Allylpyridin-2-yl)oxy)methyl)-N-(6-bromo-3-methylpyridin-2-yl)-2-azabicyclo[3.1.0] hexane-3-carboxamide Trifluoroacetic Acid Salt (45S-7)

To a solution of compound 45S-6 (100 mg, 0.18 mmol) in DCM (2 mL) was added TFA (1 mL) at 0° C., and the mixture was stirred at room temperature for 1 hour. The mixture was concentrated to dryness, washed with ether, and dried under vacuum to give to give compound 45S-7 (95 mg, 95.8% yield TFA salt) as a brown solid. LC/MS (ESI) m/z: 443/445 (M+H)⁺.

Step 7: (1R,3S,5S)-2-(2-(3-Acetyl-7-(hex-5-en-1-yl)-5-(2-methylpyrimidin-5-yl)-1H-indazol-1-yl)acetyl)-5-(((6-allylpyridin-2-yl)oxy)methyl)-N-(6-bromo-3-methylpyridin-2-yl)-2-azabicyclo[3.1.0]hexane-3-carboxamide (45S-8)

To a mixture of 2-(3-acetyl-7-(hex-5-en-1-yl)-5-(2-methylpyrimidin-5-yl)-1H-indazol-1-yl)acetic acid (69 mg, 0.176 mmol) and compound 45S-7 (95 mg, 0.176 mmol) in DMF (3 mL) was added HATU (122 mg, 0.321 mmol) and DIPEA (97 mg, 0.749 mmol) at 0° C., and the mixture was stirred at 25° C. for 1 hour. The mixture was diluted with EtOAc, washed with 10% aq. LiCl solution and brine, dried and concentrated to dryness. The residue was purified by silica gel chromatography (eluted with PE:EtOAc=20:1 to 1:1) to give compound 45S-8 (130 mg, yield 90.3%) as white solid. LC/MS (ESI) 817/819 m/z: (M+H)⁺.

Step 8: (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclotetradecaphan-9-ene-43-carboxamide (45S-9a), (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclotridecaphan-9-ene-43-carboxamide (45), and (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclododecaphan-9-ene-43-carboxamide (45S-9c)

To a solution of compound 45S-8 (130 mg, 0.16 mmol) in degassed toluene (100 mL) was added Grubbs 2$^{nd}$ catalyst (34 mg, 0.04 mmol), and the mixture was stirred under N₂ atmosphere at 80° C. for 16 hours. The mixture was concentrated to dryness, and the residue was purified by preparatory HPLC to give a mixture of 45S-9a, 45, and 45S-9c (98 mg, yield 78.1%) as a white solid. 45: ¹H-NMR (400 MHz, CD₃OD) δ 9.00 (s, 2H), 8.45 (s, 1H), 7.59-7.50 (m, 3H), 7.40-7.34 (m, 1H), 6.78 (s, 1H), 6.64-6.55 (m, 1H), 5.85-5.81 (m, 2H), 5.74-5.59 (m, 1H), 4.83-4.81 (m, 1H), 4.60-4.52 (m, 2H), 3.93-3.86 (m, 1H), 3.45-3.41 (m, 1H), 2.74 (s, 3H), 2.68 (s, 3H), 2.67-2.62 (m, 2H), 2.22-2.15 (m, 2H), 2.12 (s, 3H), 1.97-1.93 (m, 1H), 1.90-1.83 (m, 1H), 1.82-1.75 (m, 2H), 1.75-1.70 (m, 1H), 1.69-1.60 (m, 1H), 1.33-1.27 (m, 2H), 1.11-1.07 (m, 1H), 1.01-0.95 (m, 1H).

Step 9: (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclotetradecaphane-43-carboxamide (46), (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0] hexanacyclotridecaphane-43-carboxamide (47), and (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0] hexanacyclododecaphane-43-carboxamide (48)

To a mixture of 45S-9a, 45, and 45-S9c (19 mg) in EtOAc (2 mL) was added PtO₂ (4 mg). The mixture was degassed under N₂ atmosphere three times and stirred under a H₂ balloon at room temperature for 1 hour. The mixture was filtered and concentrated to dryness. The residue was purified by preparatory HPLC to give 46 (2.1 mg), 47 (2 mg), and 48 (1.2 mg) as a white solid.

46: ¹H-NMR (400 MHz, CD₃OD) δ 8.99 (s, 2H), 8.44 (d, J=1.5 Hz, 1H), 7.54 (s, 1H), 7.52 (d, J=4.2 Hz, 1H), 7.50 (d, J=7.6 Hz, 1H), 7.36 (d, J=8.0 Hz, 1H), 6.77 (d, J=7.3 Hz, 1H), 6.58 (d, J=8.2 Hz, 1H), 5.89 (d, J=17.6 Hz, 1H), 5.75 (d, J=17.8 Hz, 1H), 4.78-4.75 (m, 1H), 4.59-4.54 (m, 1H), 3.90-3.86 (m, 1H), 3.00-2.97 (m, 1H), 2.74 (s, 3H), 2.68 (s, 3H), 2.22-2.16 (m, 1H), 2.08 (s, 3H), 2.04-2.00 (m, 1H), 1.71-1.64 (m, 2H), 1.58-1.54 (m, 2H), 1.33-1.27 (m, 10H), 1.16-1.12 (m, 1H), 0.91-0.88 (m, 1H). LC/MS (ESI) 791/793 m/z: (M+H)⁺.

47: ¹H-NMR (400 MHz, DMSO-d₆) δ 10.21 (s, 1H), 9.01 (s, 2H), 8.31 (d, J=1.6 Hz, 1H), 7.65-7.54 (m, 3H), 7.42 (d, J=7.9 Hz, 1H), 6.87 (d, J=7.3 Hz, 1H), 6.55 (d, J=8.2 Hz, 1H), 5.56 (s, 2H), 4.90 (d, J=12.1 Hz, 1H), 4.63-4.54 (m, 1H), 4.41 (d, J=12.0 Hz, 1H), 3.54-3.45 (m, 1H), 2.91-2.78 (m, 2H), 2.77-2.69 (m, 1H), 2.67 (s, 3H), 2.63 (s, 3H), 2.58-2.54 (m, 1H), 2.39-2.33 (m, 1H), 2.02 (s, 3H), 1.92-1.85 (m, 1H), 1.82-1.74 (m, 1H), 1.61-1.58 (m, 1H), 1.51-1.39 (m, 3H), 1.33-1.30 (m, 1H), 1.27-1.22 (m, 3H), 1.17-1.13 (m, 1H). LC/MS (ESI) 777/779 m/z: (M+H)⁺.

48: ¹H-NMR (400 MHz, DMSO-d₆) δ 10.10 (s, 1H), 9.01 (s, 2H), 8.31 (d, J=1.6 Hz, 1H), 7.60-7.47 (m, 3H), 7.38 (d, J=8.0 Hz, 1H), 6.79 (d, J=7.3 Hz, 1H), 6.54 (d, J=8.3 Hz, 1H), 5.89 (d, J=17.8 Hz, 1H), 5.55 (d, J=18.1 Hz, 1H), 4.60-4.52 (m, 1H), 4.49-4.39 (m, 2H), 3.87-3.79 (m, 1H), 3.05-2.97 (m, 1H), 2.83-2.72 (m, 2H), 2.67 (s, 3H), 2.64 (s, 3H), 2.62-2.54 (m, 1H), 2.44-2.39 (m, 1H), 2.07-1.98 (m, 2H), 1.85-1.82 (m, 2H), 1.50-1.44 (m, 2H), 1.25-1.21 (m, 5H), 0.86 (t, J=6.7 Hz, 1H). LC/MS (ESI) 763/765 m/z: (M+H)⁺.

Scheme 32: Synthesis of (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexana-8(1,3)-benzenacyclopentadecaphane-43-carboxamide (49)

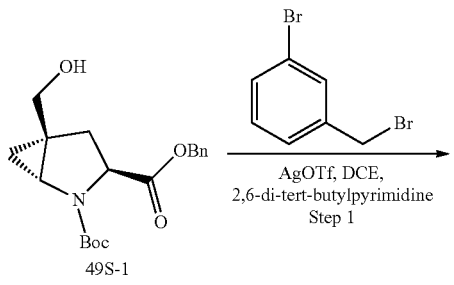

635
-continued
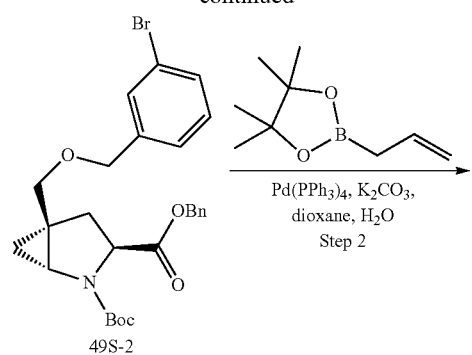
49S-2
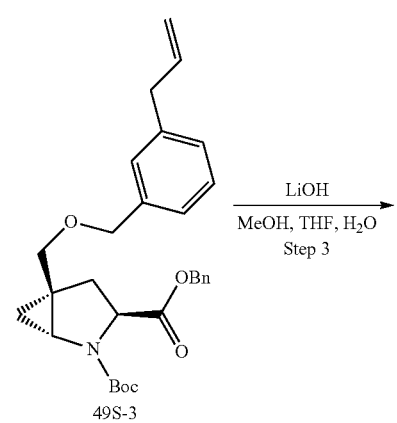
49S-3
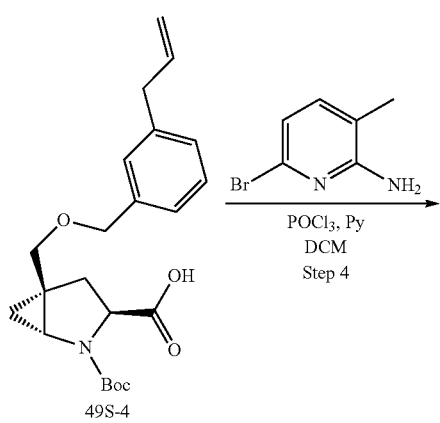
49S-4
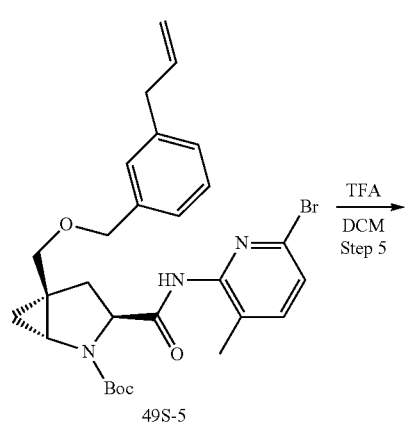
49S-5
636
-continued
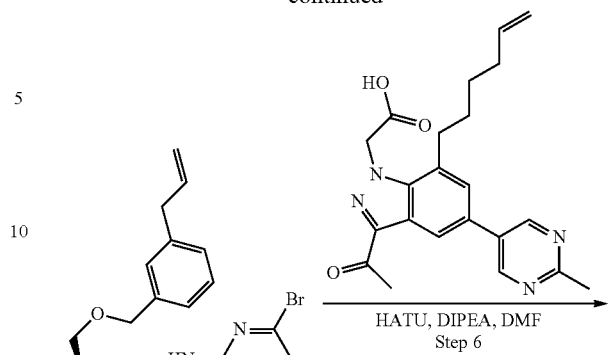
49S-6
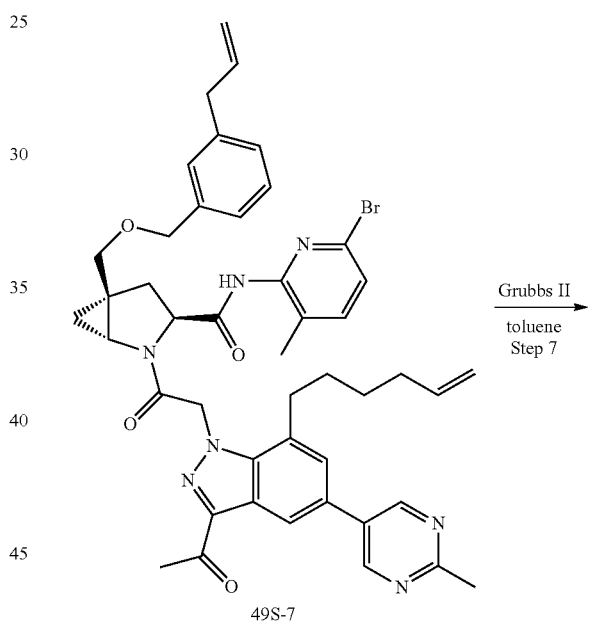
49S-7
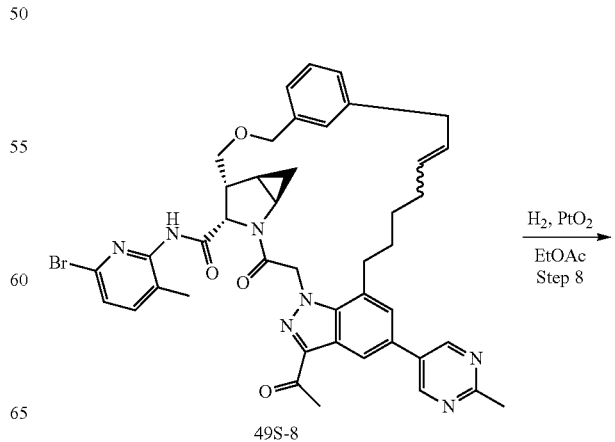
49S-8

-continued

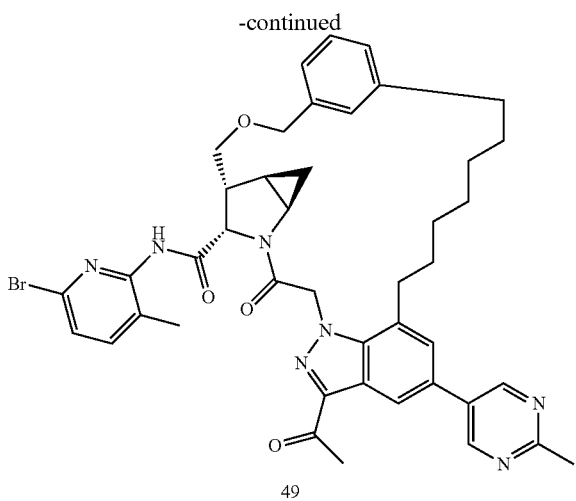

49

The above scheme and following detailed description depicts one non-limiting method for synthesizing compounds of Formula II wherein -X$^9$-L$^3$-X$^{10}$- is

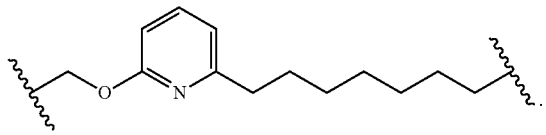 [SMILES: *CCCCCCCc1cccc(OC*)n1]

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1: (1R,3S,5S)-3-Benzyl 2-tert-Butyl 5-(((3-Bromobenzyl)oxy)methyl)-2-azabicyclo[3.1.0]hexane-2,3-dicarboxylate (49S-2)

To a suspension of compound 49S-1 (522 mg, 1.5 mmol) and AgOTf (579 mg, 2.25 mmol) in anhydrous DCE (30 mL) was added 2,6-di-tert-butylpyridine (634 mg, 3.3 mmol) and 1-bromo-3-(bromomethyl)benzene (600 mg, 2.4 mmol) at 0° C., and the mixture was stirred at room temperature for 4 hours under N$_2$ atmosphere. The mixture was filtered, and the filtrate was concentrated to dryness. The residue was purified by silica gel column chromatography (eluted with PE:EtOAc=50:1 to 20:1) to give compound 49S-2 (270 mg, 35.0% yield) as a colorless oil. LC/MS (ESI) m/z: 416/418 (M−100)$^+$.

Step 2: (1R,3S,5S)-3-Benzyl 2-tert-Butyl 5-(((3-Allylbenzyl)oxy)methyl)-2-azabicyclo[3.1.0]hexane-2,3-dicarboxylate (49-S3)

To a mixture of compound 49S-2 (216 mg, 0.42 mmol) and 2-allyl-4,4,5,5-tetramethyl-1,3,2-dioxaborolane (106 mg, 0.63 mmol) in 1,4-dioxane (18 mL) and water (2 mL) was added K$_2$CO$_3$ (117 mg, 0.84 mmol) followed by addition of Pd(PPh$_3$)$_4$ (49 mg, 0.04 mmol), and the reaction was stirred at 95° C. under N$_2$ atmosphere for 16 hours. The mixture was diluted with EtOAc, washed with water and brine, dried over Na$_2$SO$_4$, filtered and concentrated to dryness. The residue was purified by silica gel column chromatography (eluted with PE:EtOAc=100:1 to 25:1) to give compound 49S-3 (140 mg, 69.9% yield) as a yellow oil. LC/MS (ESI) m/z: 500 (M+Na)$^+$.

Step 3: (1R,3S,5S)-5-(((3-Allylbenzyl)oxy)methyl)-2-(tert-butoxycarbonyl)-2-azabicyclo[3.1.0]hexane-3-carboxylic Acid (49S-4)

To a solution of compound 49S-3 (140 mg, 0.3 mmol) in MeOH/THF (6 mL, 2/1) was added a solution of LiOH (38 mg, 0.9 mmol) in water (1 mL), and the mixture was stirred at room temperature for 16 hours. The mixture was diluted with water and washed with ether, and the aqueous layer was acidified with 1N aq. HCl solution to pH-4 and extracted with DCM twice. The combined organic phases were washed with brine, dried over anhydrous Na$_2$SO$_4$, filtered and concentrated to dryness to give compound 49S-4 (110 mg, yield 94.7%) as a colorless oil. LC/MS (ESI) m/z: 386 (M−H)$^−$.

Step 4: (1R,3S,5S)-tert-Butyl 5-(((3-Allylbenzyl)oxy)methyl)-3-((6-bromo-3-methylpyridin-2-yl)carbamoyl)-2-azabicyclo[3.1.0]hexane-2-carboxylate (49S-5)

To a solution of compound 49S-4 (110 mg, 0.284 mmol) and 6-bromo-3-methylpyridin-2-amine (54 mg, 0.284 mmol) in anhydrous DCM (14 mL) was added pyridine (112 mg, 1.42 mmol) followed by drop-wise addition of POCl$_3$ (48 mg, 0.31 mmol) at 0° C. under N2 atmosphere. The reaction mixture was stirred at room temperature for 1 hour. The reaction mixture was quenched with ice-cooled water and extracted with DCM twice. The combined organic phases were washed with brine, dried over anhydrous Na$_2$SO$_4$, filtered and concentrated to dryness. The residue was purified by silica gel column chromatography (eluted with PE:EtOAc=20:1 to 5:1) to give compound 49S-5 (95 mg, 60.3% yield) as a yellow solid. LC/MS (ESI) m/z: 556/558 (M+H)$^+$.

Step 5: (1R,3S,5S)-5-(((3-Allylbenzyl)oxy)methyl)-N-(6-bromo-3-methylpyridin-2-yl)-2-azabicyclo[3.1.0]hexane-3-carboxamide Trifluoroacetic Acid Salt (49S-6)

To a solution of compound XS-5 (95 mg, 0.171 mmol) in DCM (2 mL) was added TFA (1 mL) drop-wise at 0° C., and the mixture was stirred at room temperature for 1 hour. The mixture was concentrated to dryness, and the residue was washed with ether and dried under vacuum to give compound 49S-6 (96 mg, 100% yield) as a light-red solid. LC/MS (ESI) m/z: 456/458 (M+H)$^+$.

Step 6: (1R,3S,5S)-2-(2-(3-Acetyl-7-(hex-5-en-1-yl)-5-(2-methylpyrimidin-5-yl)-1H-indazol-1-yl)acetyl)-5-(((3-allylbenzyl)oxy)methyl)-N-(6-bromo-3-methylpyridin-2-yl)-2-azabicyclo[3.1.0]hexane-3-carboxamide (49S-7)

To a mixture of compound 49S-6 (92 mg, 0.171 mmol), 2-(3-acetyl-7-(hex-5-en-1-yl)-5-(2-methylpyrimidin-5-yl)-1H-indazol-1-yl)acetic acid (68 mg, 0.171 mmol) and HATU (104 mg, 0.274 mmol) in DMF (2 mL) was added DIPEA (112 mg, 0.816 mmol), and the reaction mixture was stirred at room temperature for 1 hour. Then the mixture was diluted with EtOAc, washed with 10% aq. LiCl solution and brine. The organic layer was separated, dried over anhydrous Na$_2$SO$_4$, filtered and concentrated to give crude product. The residue was purified by silica gel column chromatography (eluted with DCM:MeOH=200:1 to 70:1) to give compound 49S-7 (80 mg, 56.4% yield) as a yellow solid. LC/MS (ESI) m/z: 830/832 (M+H)$^+$.

Step 7: (41R,43S,45S,E)-13-acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexana-8(1,3)-benzenacyclopentadecaphan-10-ene-43-carboxamide (49S-8)

To a solution of compound 49S-7 (90 mg, 0.11 mmol) in degassed toluene (60 mL) was added Grubbs II catalyst (23 mg, 0.0275 mmol), and the mixture was stirred at 80° C. under N$_2$ atmosphere for 16 hours. The mixture was concentrated under reduced pressure, and the residue was purified by silica gel column chromatography (eluted with PE:EtOAc=10:1 to 1:1) to give compound 49S-8 (36 mg, 40.9% yield) as brown solid. LC/MS (ESI) m/z: 802/804 (M+H)$^+$.

Step 8: (41R,43S,45S)-13-Acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexana-8(1,3)-benzenacyclopentadecaphane-43-carboxamide (49)

To a solution of compound 49S-8 (36 mg, 0.045 mmol) in EtOAc (15 mL) was added PtO$_2$ (11 mg), and the mixture was stirred at room temperature for 30 minutes under a H$_2$ balloon. The mixture was filtered, and the filtrate was concentrated to dryness. The residue was purified by preparatory HPLC to give 49 (10 mg, 27.7% yield) as a white solid. $^1$H-NMR (400 MHz, DMSO-d$_6$) δ 10.29 (s, 1H), 9.03 (s, 2H), 8.33 (s, 1H), 7.60 (s, 2H), 7.38-7.46 (m, 1H), 7.30 (s, 1H), 7.20-7.26 (m, 1H), 7.03-7.12 (m, 2H), 5.91 (d, J=17.0 Hz, 1H), 5.58 (d, J=17.4 Hz, 1H), 4.43-4.60 (m, 3H), 3.64-3.71 (m, 1H), 3.52-3.57 (m, 1H), 3.21-3.29 (m, 1H), 2.86-3.00 (m, 2H), 2.68 (s, 3H), 2.64 (s, 3H), 2.57-2.60 (m, 1H), 2.16-2.37 (m, 3H), 2.00 (s, 3H), 1.61-1.74 (m, 3H), 1.45-1.60 (m, 3H), 1.36-1.44 (m, 2H), 1.24-1.31 (m, 2H), 1.14-1.19 (m, 1H), 1.03-1.08 (m, 1H). LC/MS (ESI) m/z: 804/806 (M+H)$^+$.

Scheme 33: Synthesis of (41R,43S,45R,E)-42-(2-(3-Acetyl-7-(fluoromethyl)-5-(2-methylpyrimidin-5-yl)-1H-indazol-1-yl)acetyl)-16-bromo-11-oxa-42,2-diaza-1(2,3)-pyridina-4(3,5)-bicyclo[3.1.0]hexanacyclododecaphan-8-en-3-one (50)

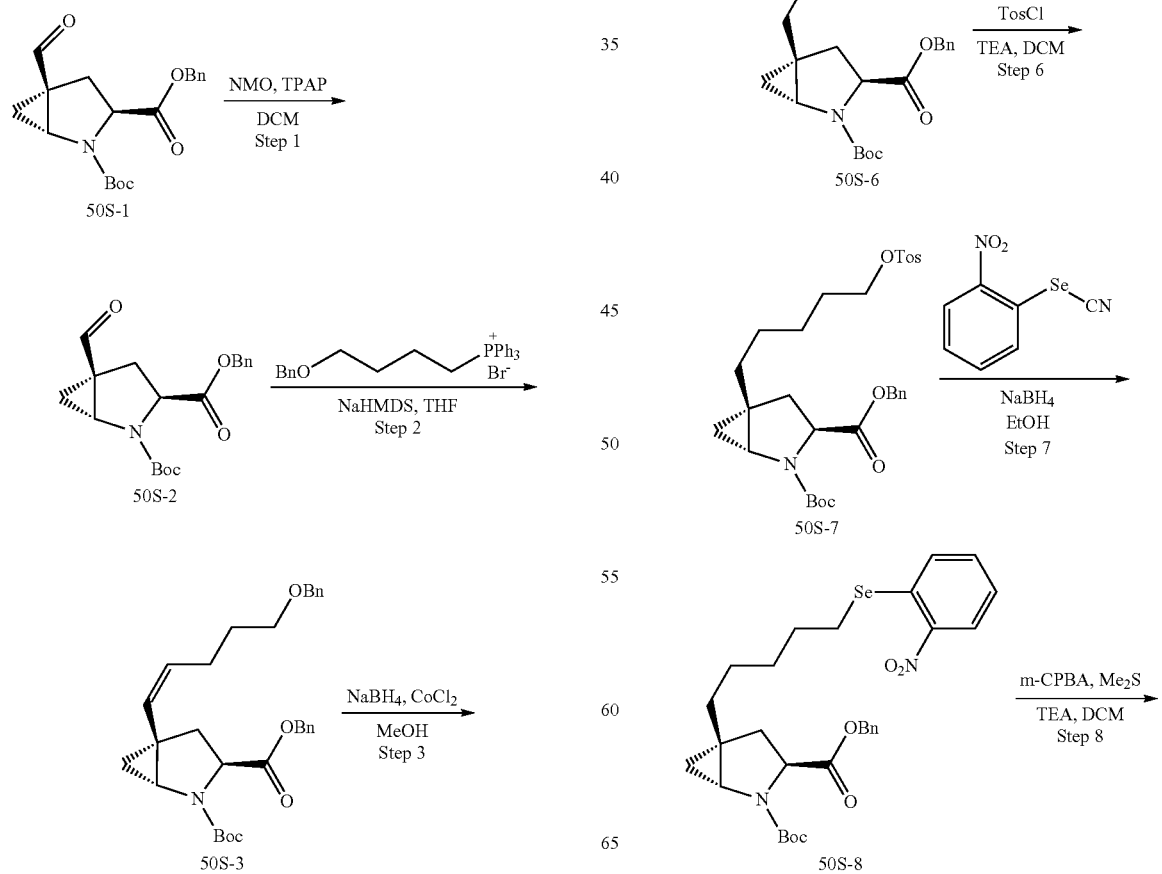

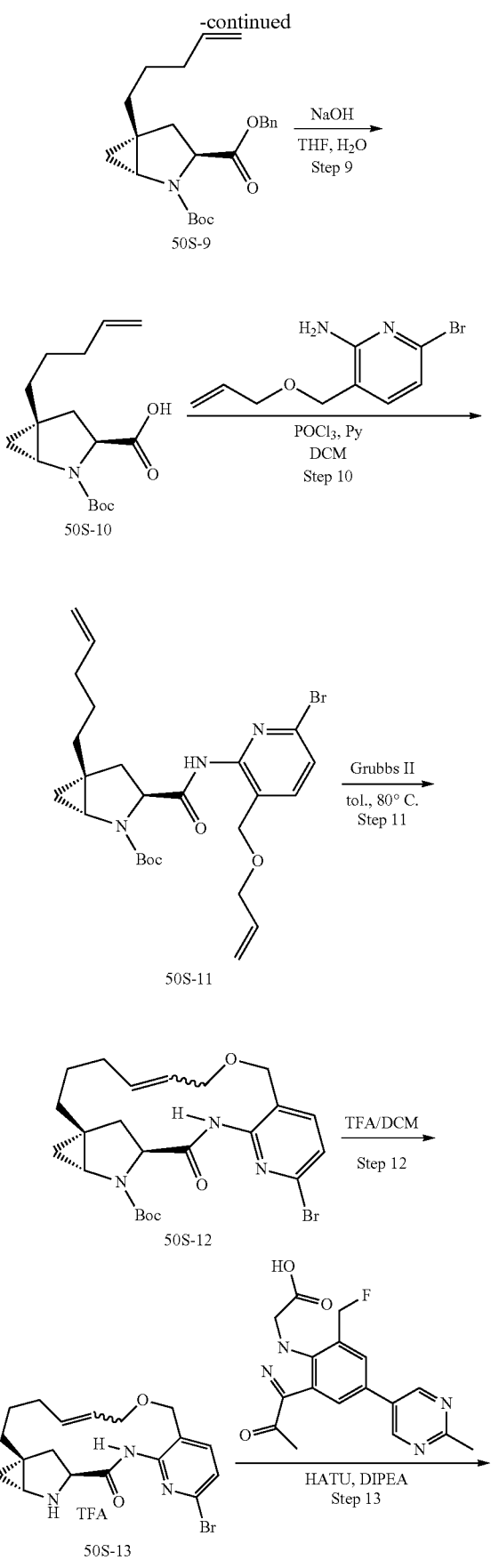
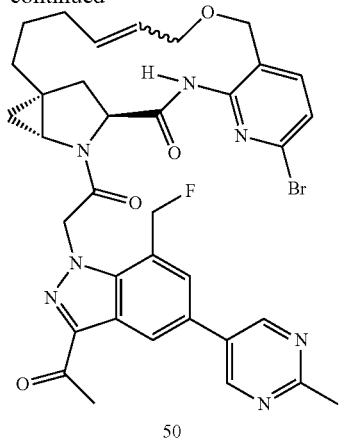

The above scheme and following detailed description depicts one non-limiting method for synthesizing compounds of Formula I wherein -X⁹-L³-X¹⁰- is

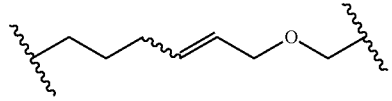 [SMILES: *CCCC=CCOC*]

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: (1R,3S,5S)-3-Benzyl 2-tert-Butyl 5-Formyl-2-azabicyclo[3.1.0]hexane-2,3-dicarboxylate (50S-2)

To a solution of compound 50S-1 (1.2 g, 3.46 mmol) in DCM (100 mL) was added NMO (607 mg, 5.19 mmol), TPAP (121 mg, 0.35 mmol) and 4A MS (1.6 g) at 0° C. After addition, the reaction mixture was stirred at room temperature for 1 hour. The mixture was concentrated to dryness and purified by silica gel chromatography (eluted with PE:EtOAc=3:1) to give compound 50S-2 (0.92 g, yield 77.3%) as a colorless oil. LC/MS (ESI) m/z: 346 (M+H)⁺.

Step 2: (1R,3S,5R)-3-benzyl 2-tert-butyl 5-((Z)-5-(benzyloxy)pent-1-en-1-yl)-2-azabicyclo[3.1.0]hexane-2,3-dicarboxylate (50S-3)

To a solution of (4-(benzyloxy)butyl)triphenylphosphonium bromide (3.9 g, 7.80 mmol) in THF (30 mL) was drop-wise added NaHMDS (7.15 mL, 7.15 mmol, 1M in THF) at −78° C. After addition, the reaction mixture was stirred at −40° C. for 1 hour, and a solution of compound 50S-2 (900 mg, 2.60 mmol) in THF (5 mL) was added to the mixture drop-wise at −78° C. The reaction mixture was stirred at 25° C. for 1.5 hours. The reaction mixture was poured into ice-cooled saturated aq. NH₄Cl solution and extracted with EtOAc twice. The combined organic phases were washed with brine, dried over anhydrous Na₂SO₄, filtered and concentrated to dryness. The residue was purified by silica gel chromatography (eluted with PE:EtOAc=25:1) to give compound 50S-3 (400 mg, yield 31.5%) as a colorless oil. LC/MS (ESI) m/z: 492 (M+H)⁺.

Step 3: (1R,3S,5R)-3-Benzyl 2-tert-Butyl 5-(5-(Benzyloxy)pentyl)-2-azabicyclo[3.1.0]hexane-2,3-dicarboxylate (50S-4)

To a solution of compound 50S-3 (400 mg, 0.81 mmol) in MeOH (5 mL) was added $CoCl_2$ (105 mg, 0.81 mmol) and $NaBH_4$ (92 mg, 2.43 mmol) at 0° C., and the reaction mixture was stirred at 0° C. for 1 hour. The reaction mixture was poured into ice-cooled saturated aq. $NH_4Cl$ solution (5 mL) and extracted with DCM. The combined organic phases are washed with brine, dried over anhydrous $Na_2SO_4$, filtered and concentrated to dryness to give compound 50S-4 (400 mg, yield 100%) as a colorless oil. LC/MS (ESI) m/z: 494 $(M+H)^+$.

Step 4: (1R,3S,5R)-2-(tert-Butoxycarbonyl)-5-(5-hydroxypentyl)-2-azabicyclo[3.1.0]hexane-3-carboxylic Acid (50S-5)

A solution of compound 50S-4 (400 mg, 0.81 mmol) in MeOH (10 mL) was degassed three times under $N_2$ atmosphere, and Pd/C (40 mg) was added. The mixture was degassed again and stirred under a $H_2$ balloon at room temperature over 2 hours. The mixture was filtered and evaporated to dryness to give the title compound 50S-5 (240 mg, 97.8% yield) as a colorless oil. LC/MS (ESI) m/z: 314 $(M+H)^+$.

Step 5: (1R,3S,5R)-3-Benzyl 2-tert-Butyl 5-(5-Hydroxypentyl)-2-azabicyclo[3.1.0]hexane-2,3-dicarboxylate (50S-6)

To a solution of compound 50S-5 (240 mg, 0.77 mmol) in MeCN (10 mL) was added $K_2CO_3$ (266 mg, 1.93 mmol) and BnBr (159 mg, 0.92 mmol), and the mixture was stirred at 25° C. overnight. The mixture was diluted with EtOAc, washed with water and brine, dried over $Na_2SO_4$, filtered and concentrated to dryness. The residue was purified by column chromatography on silica gel (eluted with PE:EtOAc=30:1) to give compound 50S-6 (230 mg, 74.2% yield) as a colorless oil. LC/MS (ESI) m/z: 404 $(M+H)^+$.

Step 6: (1R,3S,5R)-3-Benzyl 2-tert-Butyl 5-(5-(Tosyloxy)pentyl)-2-azabicyclo[3.1.0]hexane-2,3-dicarboxylate (50S-7)

To a solution of compound 50S-6 (230 mg, 0.73 mmol) in anhydrous DCM (10 mL) was added TEA (0.30 mL, 2.13 mmol) followed tosyl chloride (208 mg, 1.10 mmol) at 0° C., and the reaction was stirred at 25° C. for 2 hours. The reaction mixture was poured into ice-cooled saturated aq. $NH_4Cl$ solution and extracted with DCM twice. The combined organic phases were washed with brine, dried over anhydrous $Na_2SO_4$, filtered and concentrated to dryness. The residue was purified by column chromatography on silica gel (eluted with PE:EtOAc=30:1 to 10:1) to give compound 50S-7 (230 mg, 56.7% yield) as a colorless oil. LC/MS (ESI) m/z: 558 $(M+H)^+$.

Step 7: (1R,3S,5R)-3-Benzyl 2-tert-Butyl 5-(5-((2-Nitrophenyl)selanyl)pentyl)-2-azabicyclo[3.1.0]hexane-2,3-dicarboxylate (50S-8)

To a solution of compound 50S-7 (230 mg, 0.41 mmol) in EtOH (5 mL) was added 1-nitro-2-selenocyanatobenzene (280 mg, 1.24 mmol) at 0° C., and the reaction mixture was stirred at 0° C. for 1 hour. Then $NaBH_4$ (47 mg, 1.24 mmol) was added, and the reaction mixture was stirred at 0° C. to room temperature for 1 hour. The mixture was quenched with ice-cooled water and extracted with DCM. The organic phase was washed with brine, dried over anhydrous $Na_2SO_4$, filtered and concentrated to dryness. The residue was purified by column chromatography on silica gel (eluted with PE:EtOAc=40:1 to 10:1) to give compound 50S-8 (220 mg, 91.3% yield) as a yellow solid. LC/MS (ESI) m/z: 589 $(M+H)^+$.

Step 8: (1R,3S,5R)-3-Benzyl 2-tert-Butyl 5-(Pent-4-en-1-yl)-2-azabicyclo[3.1.0]hexane-2,3-dicarboxylate (50S-9)

To a solution of compound 50S-8 (220 mg, 0.39 mmol) in DCM (5 mL) was added m-CPBA (81 mg, 0.47 mmol) at −70° C., and the mixture was stirred at room temperature for 2 hours. A solution of $Me_2S$-THF (3.9 mL, 3.9 mmol) and TEA (990 mg, 9.80 mmol) was added to the mixture at −70° C. The resulting mixture was stirred at room temperature for 16 hours. The mixture was quenched with ice-cooled saturated aq. $NaHCO_3$ solution and extracted with DCM twice. The combined organic phases were washed with brine, dried over anhydrous $Na_2SO_4$, filtered and concentrated to dryness. The residue was purified by column chromatography on silica gel (eluted with PE:EtOAc=5:1) to give compound 50S-9 (100 mg, 66.7% yield) as a white solid. LC/MS (ESI) m/z: 386 $(M+H)^+$.

Step 9: (1R,3S,5R)-2-(tert-Butoxycarbonyl)-5-(pent-4-en-1-yl)-2-azabicyclo[3.1.0]hexane-3-carboxylic Acid (50S-10)

To a solution of compound 50S-9 (120 mg, 0.31 mmol) in THF (1 mL), MeOH (1 mL) and water (1 mL) was added LiOH (52.7 mg, 1.26 mmol), and the mixture was stirred at room temperature for 2 hours. The mixture was concentrated to dryness, diluted with water, and washed with EtOAc twice. The aqueous layer was acidified by adding 1 N aq. HCl to pH~3 at 0° C. and extracted with DCM twice. The combined organic layers were washed with brine, dried over anhydrous $Na_2SO_4$, filtered and concentrated to dryness to give compound 50S-10 (85 mg, 92.9% yield) as a yellow oil. LC/MS (ESI) m/z: 296 $(M+H)^+$.

Step 10: (1R,3S,5R)-tert-butyl 3-((3-((allyloxy)methyl)-6-bromopyridin-2-yl)carbamoyl)-5-(pent-4-en-1-yl)-2-azabicyclo[3.1.0]hexane-2-carboxylate (50S-11)

To a mixture of compound 50-S10 (85 mg, 0.29 mmol) and 3-((allyloxy)methyl)-6-bromopyridin-2-amine (70 mg, 0.29 mmol) in DCM (10 mL) was added Pyridine (115 mg, 1.45 mmol) and $POCl_3$ (67 mg, 0.44 mmol) at 0° C. After addition, the mixture was stirred at 25° C. for 1 hr. The mixture was poured into ice-cooled water and extracted with DCM twice. The combine organic layers were washed with water and brine, dried over $Na_2SO_4$, filtered and evaporated to dryness. The residue was purified by column chromatography on silica gel (eluted with PE:EtOAc=10:1) to give compound 50-511 (75 mg, 49.8% yield) as yellow oil. LC/MS (ESI) m/z: 520/522 $(M+H)^+$.

Step 11: tert-Butyl (41R,43S,45R,E)-16-Bromo-3-oxo-11-oxa-42,2-diaza-1(2,3)-pyridina-4(3,5)-bicyclo [3.1.0] hexanacyclododecaphan-8-ene-42-carboxylate (50S-12)

To a solution of compound 50S-11 (75 mg, 0.14 mmol) in toluene (75 mL) was added Grubb's second generation catalyst (30.6 mg, 0.036 mmol) under $N_2$ atmosphere. The mixture was degassed under $N_2$ three times and stirred at 80° C. under $N_2$ atmosphere overnight. The mixture was concentrated to dryness, and the residue was purified by column chromatography on silica gel (eluted with PE:EtOAc=3:1) to give compound 50S-12 (50 mg, 70.4% yield) as a brown solid. LC/MS (ESI) m/z: 492/494 $(M+H)^+$.

Step 12: (41R,43S,45R,E)-16-Bromo-11-oxa-42,2-diaza-1(2,3)-pyridina-4(3,5)-bicyclo[3.1.0]hexanacyclododecaphan-8-en-3-one Trifluoroacetic Acid Salt (50S-13)

To a solution of compound 50S-12 (50 mg, 0.10 mmol) in DCM (2 mL) was added TFA (1 mL). After addition, the reaction mixture was stirred at 25° C. for 2 hours. The mixture was concentrated to dryness to give compound 50S-13 (60 mg, 100% yield) as a brown solid. LC/MS (ESI) m/z: 392/394 $(M+H)^+$.

Step 13: (41R,43S,45R,E)-42-(2-(3-Acetyl-7-(fluoromethyl)-5-(2-methylpyrimidin-5-yl)-1H-indazol-1-yl)acetyl)-16-bromo-11-oxa-42,2-diaza-1(2,3)-pyridina-4(3,5)-bicyclo [3.1.0]hexanacyclododecaphan-8-en-3-one (50)

To a solution of the compound 50S-13 (60 mg, 0.10 mmol), 2-(3-acetyl-7-(fluoromethyl)-5-(2-methylpyrimidin- 5-yl)-1H-indazol-1-yl)acetic acid (35 mg, 0.10 mmol) and HATU (76 mg, 0.20 mmol) in DMF (2 mL) was added DIPEA (0.07 mL, 0.40 mmol) at 0° C., and the reaction was stirred at room temperature for 2 hours. The mixture was diluted with EtOAc, washed with 10% aq. LiCl solution and brine, dried over $Na_2SO_4$, and concentrated to dryness. The residue was purified by preparatory HPLC to give 50 (3.5 mg, 4.9% yield) as a white solid. $^1$H-NMR (400 MHz, DMSO-$d_6$) δ 10.60 (s, 1H), 9.08 (s, 2H), 8.59 (s, 1H), 8.02 (s, 1H), 7.91 (d, J=8.1 Hz, 1H), 7.61 (d, J=8.1 Hz, 1H), 5.97-5.61 (m, 5H), 5.52-5.42 (m, 1H), 4.65 (d, J=8.1 Hz, 1H), 4.30 (d, J=13.9 Hz, 2H), 4.08 (d, J=13.6 Hz, 1H), 3.99 (dd, J=12.4, 8.8 Hz, 1H), 2.69 (s, 6H), 2.37 (d, J=29.0 Hz, 2H), 2.22 (s, 1H), 2.12-1.99 (m, 2H), 1.88 (d, J=10.2 Hz, 1H), 1.59 (m, 1H), 1.35 (d, J=10.3 Hz, 1H), 1.20 (d, J=24.1 Hz, 3H), 1.08 (m, 1H). LC/MS (ESI) m/z: 716/718 (M+H)$^+$.

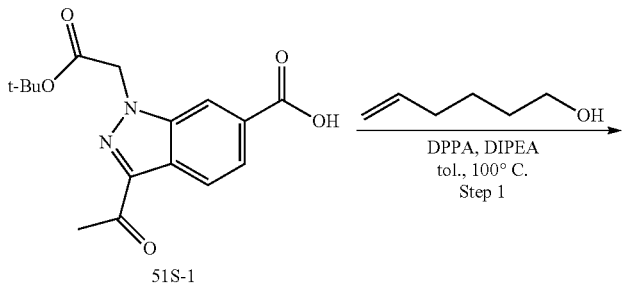

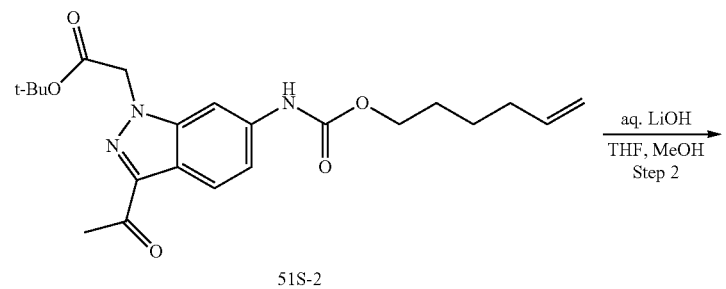

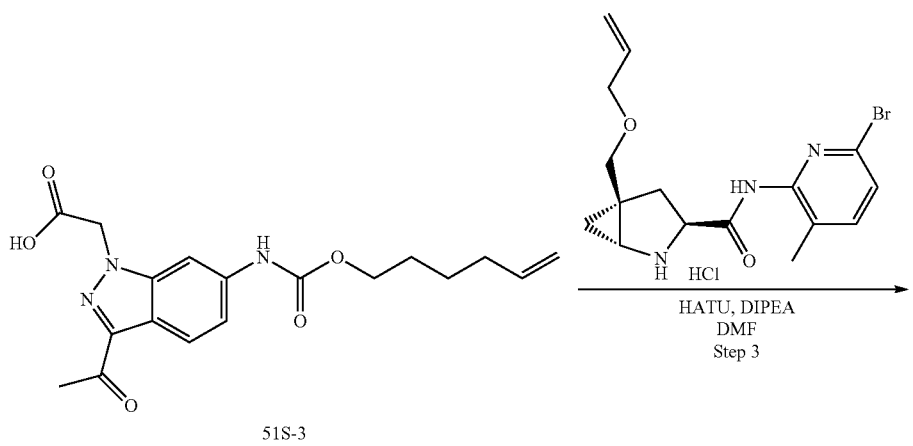

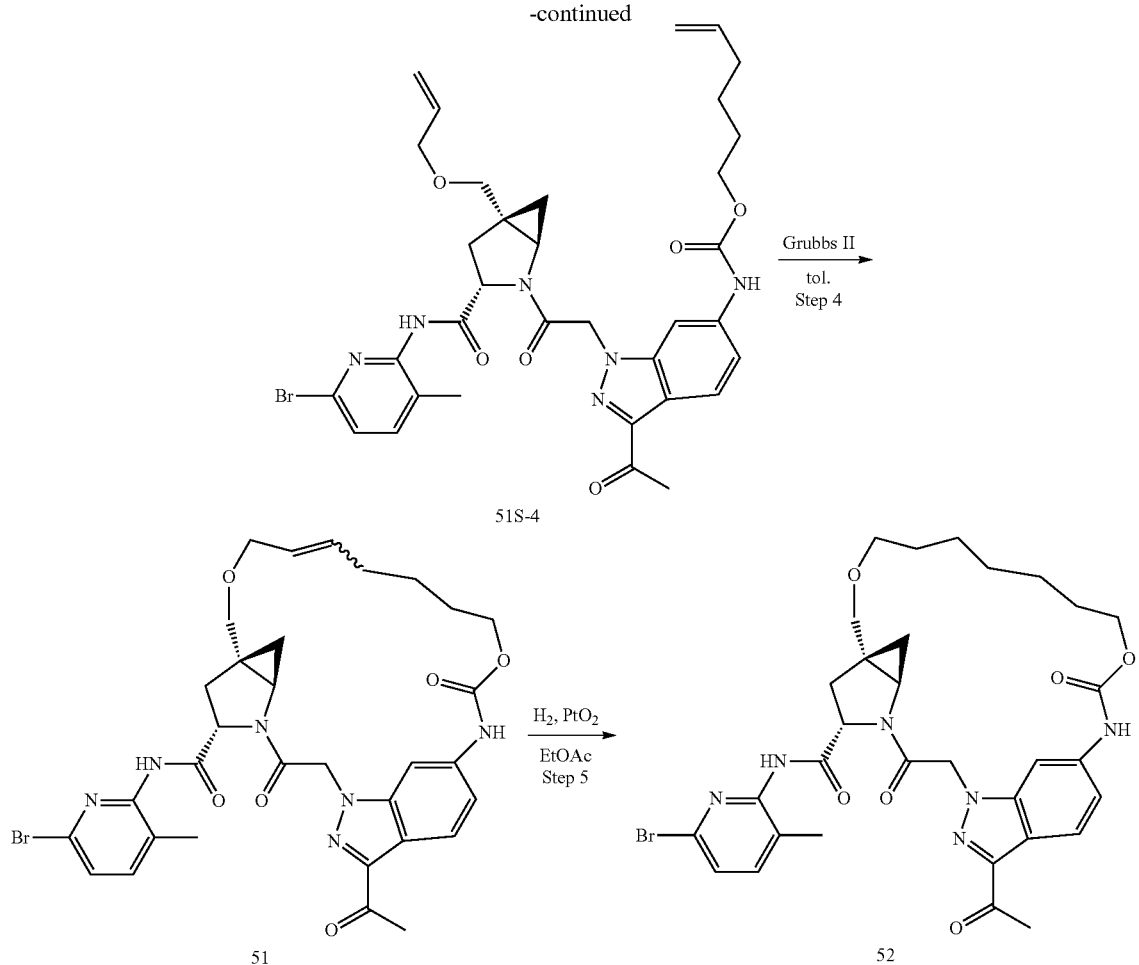

51S-4

51

52

The above scheme and following detailed description depicts one non-limiting method for synthesizing compounds of Formula II wherein -$X^9$-$L^3$-$X^{10}$- is The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: tert-Butyl 2-(3-Acetyl-6-(((hex-5-en-1-yloxy)carbonyl)amino)-1H-indazol-1-yl)acetate (51S-2)

To a solution of compound 51S-1 (0.2 g, 0.63 mmol) in toluene (10 mL) was added piphenyl phosphorazidate (0.259 g, 0.94 mmol) and DIPEA (0.325 g, 2.513 mmol), and the mixture was stirred at 100° C. under $N_2$ atmosphere for 1 hour. Hex-5-en-1-ol (0.126 g, 1.257 mmol) was added, and the mixture was stirred at 100° C. for another 3 hours. The mixture was concentrated to dryness and the residue was purified by silica gel chromatography (eluted with PE:E-tOAc=5:1 to 3:1) to give compound 51S-2 (0.13 g, yield 49.8%) as an off-white solid. LC/MS (ESI) m/z: 416 (M+H)+.

Step 2: 2-(3-Acetyl-6-(((hex-5-en-1-yloxy)carbonyl)amino)-1H-indazol-1-yl)acetic Acid (51S-3)

To a solution of compound 51S-2 (0.13 g, 0.313 mmol) in tetrahydrofuran (2 mL), methanol (1 mL), and Water (1 mL) was added lithium hydroxide (0.022 g, 0.939 mmol), and the mixture was stirred at 0° C. for 3 hours. The mixture was diluted with water and washed with ether twice. The aqueous layer was acidified by adding 0.5 N aq. HCl to pH~4 and extracted with DCM twice. The combined organic layers were washed with brine, dried and concentrated to dryness to give compound XS-3 (89 mg, yield 79.2%) as a light yellow solid. LC/MS (ESI) m/z: 360 (M+H)+.

Step 3: Hex-5-en-1-yl (3-Acetyl-1-(2-((1R,3S,5S)-5-((allyloxy)methyl)-3-((6-bromo-3-methylpyridin-2-yl)carbamoyl)-2-azabicyclo[3.1.0]hexan-2-yl)-2-oxoethyl)-1H-indazol-6-yl)carbamate (51S-4)

To a mixture of compound 51S-3 (89 mg, 0.248 mmol) and (1R,3S,5S)-N-(6-bromo-3-methylpyridin-2-yl)-5-[(prop-2-en-1-yloxy)methyl]-2-azabicyclo[3.1.0]hexane-3-carboxamide (0.109 g, 0.248 mmol) in DMF (3 mL) was added DIPEA (0.112 g, 0.867 mmol) followed by HATU (0.122 g, 0.322 mmol) at 0° C., and the reaction mixture was stirred at 25° C. for 2 hours . The mixture was diluted with EtOAc, washed with saturated aq. $NH_4Cl$ solution and brine, dried and concentrated to dryness. The residue was purified by silica gel chromatography (eluted with PE:EtOAc=3:1 to 1:1) to give compound 51S-4 (0.12 g, yield 68.5%) as a light yellow solid. LC/MS (ESI) m/z: 707/709 (M+H)+.

Step 4: (41R,43S,45S,E)-13-Acetyl-N-(6-bromo-3-methylpyridin-2-yl)-3,15-dioxo-11H-6,14-dioxa-42,16-diaza-1(1,6)-indazola-4(2,5)-bicyclo[3.1.0]hexanacyclohexadecaphan-8-ene-43-carboxamide (51)

A solution of compound 51S-4 (0.12 g, 0.17 mmol) in toluene (100 mL) was degassed under $N_2$ three times, and Grubbs Catalyst $2^{nd}$ Generation (14 mg, 0.017 mmol) was added. The resulting mixture was degassed again and stirred at 80° C. under $N_2$ atmosphere for 16 hours. The mixture was concentrated to dryness, and the residue was purified by silica gel chromatography (eluted with PE:EtOAc=4:1 to 1:1) to give 51 (59 mg, yield 51.2%) as a brown solid. $^1$H-NMR (400 MHz, DMSO-$d_6$) δ 9.94 (br, 1H), 9.91 (br, 1H), 8.22 (br, 1H), 8.00-8.02 (d, J=8.8 Hz, 1H), 7.60-7.62 (d, J=7.6 Hz, 1H), 7.43-7.45 (d, J=8.0 Hz, 1H), 7.05-7.07 (dd, J=8.4 Hz, 1H), 5.61-5.69 (m, 2H), 5.58-5.53 (m, 1H), 5.35-5.39 (m, 1H), 4.37-4.47 (m, 2H), 3.88-4.15 (m, 4H), 3.76 (m, 1H), 3.57 (m, 1H), 2.59 (s, 3H), 2.43-2.45 (m, 1H), 2.20-2.25 (m, 1H), 2.03-2.06 (m, 3H), 2.00 (s, 3H), 1.61-1.65 (m, 2H), 1.39-1.43 (m, 2H), 1.23 (m, 1H), 0.56-0.62 (m, 1H). LC/MS (ESI) m/z: 679/681 (M+H)$^+$.

Step 5: (41R,43S,45S)-13-Acetyl-N-(6-bromo-3-methylpyridin-2-yl)-3,15-dioxo-11H-6,14-dioxa-42,16-diaza-1(1,6)-indazola-4(2,5)-bicyclo[3.1.0]hexanacyclohexadecaphane-43-carboxamide (52)

To a degassed solution of 51 (30 mg, 0.044 mmol) in tetrahydrofuran (5 mL) was added tris(triphenylphosphine)rhodium(I) chloride (6 mg, 0.007 mmol), and the mixture was degassed under $N_2$ atmosphere three times and stirred under a $H_2$ balloon at 70° C. for 5 hours. The mixture was concentrated to dryness to give crude product, which was purified by preparatory HPLC to give 52 (5 mg, yield 16.6%) as a white solid. $^1$H-NMR (400 MHz, DMSO-$d_6$) δ 9.91 (br, 1H), 9.86 (br, 1H), 8.03 (br, 1H), 8.00-8.02 (d, J=8.8 Hz, 1H), 7.60-7.62 (d, J=7.6 Hz, 1H), 7.42-7.44 (d, J=8.0 Hz, 1H), 7.04-7.07 (dd, J=8.4 Hz, 1.6 Hz, 1H), 5.55 (m, 2H), 4.43-4.46 (m, 1H), 3.99-4.07 (m, 2H), 3.77 (m, 1H), 3.39-3.51 (m, 4H), 2.60 (s, 3H), 2.41-2.47 (m, 1H), 2.26-2.33 (m, 1H), 2.01 (s, 3H), 1.67 (m, 2H), 1.34-1.48 (m, 8H), 0.99 (m, 1H), 0.92 (m, 1H). LC/MS (ESI) m/z: 681/683 (M+H)$^+$.

Scheme 35: Synthesis of (41R,43S,45S,E)-13-Acetyl-N-(6-bromo-3-methylpyridin-2-yl)-3,14-dioxo-11H-6,15 dioxo-42,13-diaza-1(1,6)-indazola-4(2,5)-bicyclo[3.1.0]hexanacyclopentadecaphan-8-ene-43-carboxamide (53)

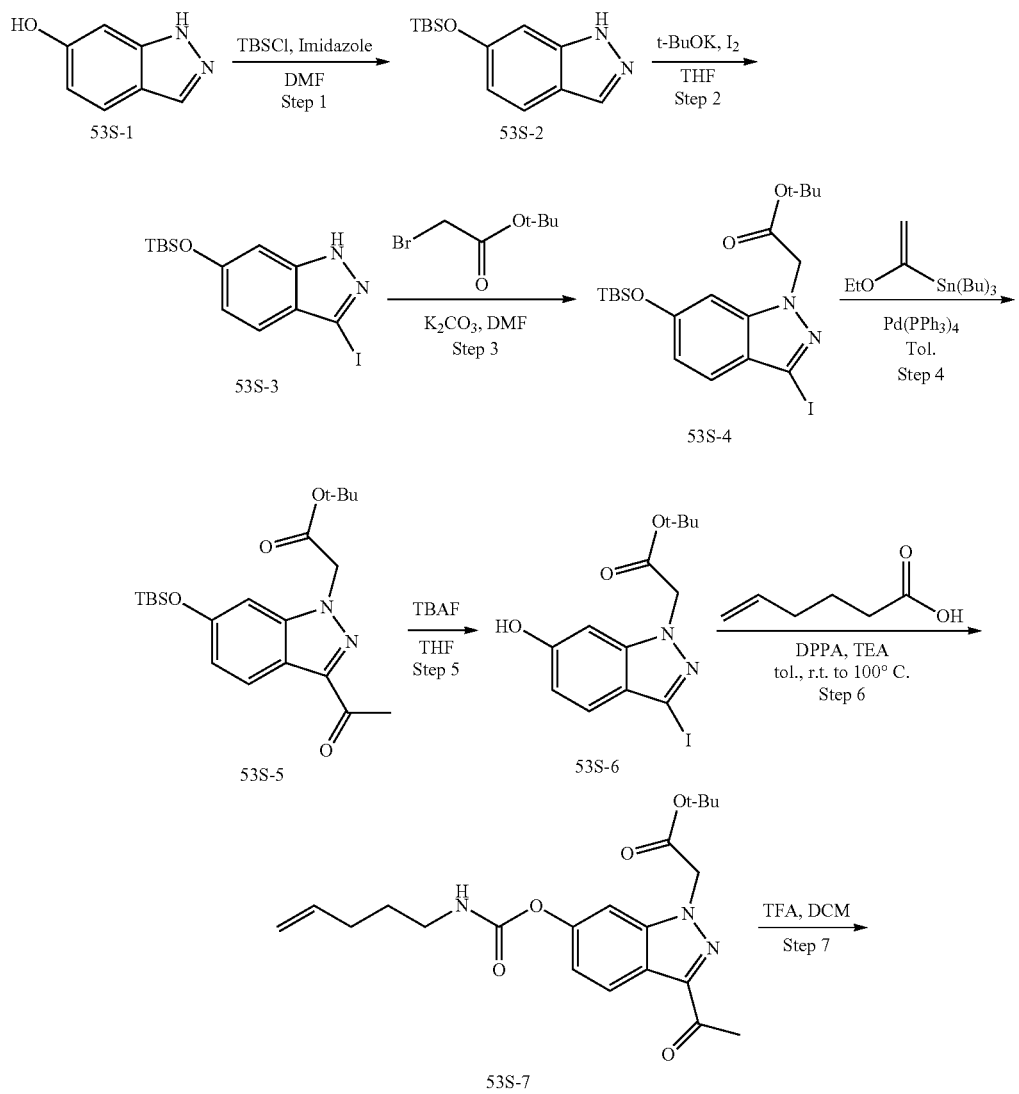

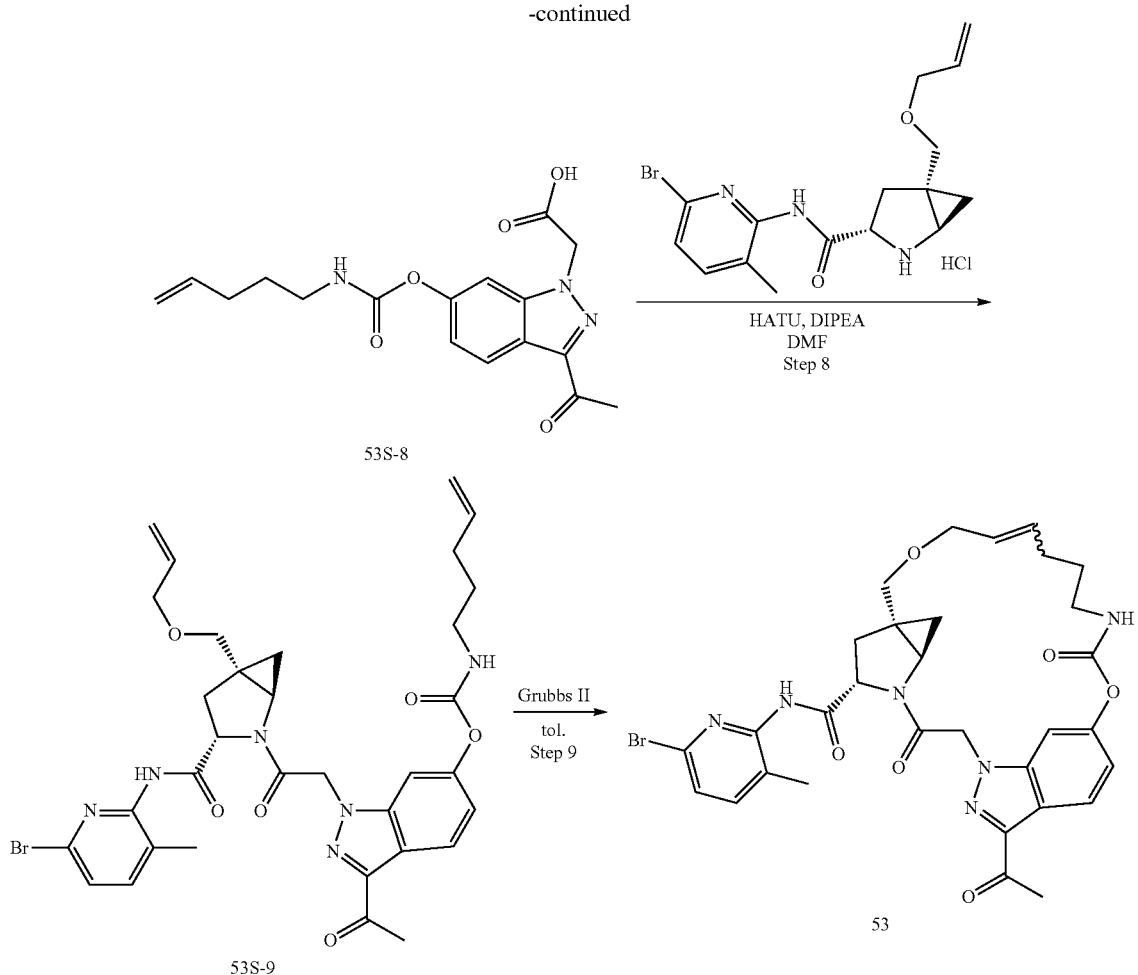

The above scheme and following detailed description depicts one non-limiting method for synthesizing compounds of Formula II wherein -$X^9$-$L^3$-$X^{10}$- is

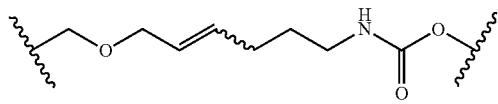 [SMILES: *COCC=CCCCNC(=O)O*]

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: 6-((tert-Butyldimethylsilyl)oxy)-1H-indazole (53S-2)

To a solution of 1H-indazol-6-ol (2.0 g, 14.9 mmol) in DMF (20 mL) was added imidazole (2.03 g, 29.8 mmol) and tert-butyl dimethylchlorosilane (3.37 g, 22.37 mmol) at 0° C., and the mixture was stirred at room temperature under $N_2$ atmosphere overnight. The mixture was diluted with ice water and extracted with EtOAc twice. The combined organic layers were washed with 10% aq. LiCl solution and brine, dried and concentrated to dryness. The residue was purified by chromatography on silica gel (PE:EtOAc=10:1) to give compound 53S-2 (3.55 g, yield 96.0%) as a light oil. LC/MS (ESI) m/z: 249 (M+H)+.

Step 2: 6-[(tert-Butyldimethylsilyl)oxy]-3-iodo-1H-indazole (53S-3)

To a solution of compound 53S-2 (3.55 g, 14.31 mmol) in THF (40 mL) was added potassium tert-butoxide (2.68 g, 23.90 mmol) and $I_2$(6.05 g, 23.85 mmol) at 0° C., and the reaction was stirred at room temperature for 2 hours. The mixture was diluted with water and extracted with EtOAc twice. The combined organic layers were washed with 5% aq. $Na_2S_2O_3$ solution and brine, dried and concentrated to give compound 53S-3 (4.39 g, yield 82.1%) as a white solid, which was used directly in the next step. LC/MS (ESI) m/z: 375 (M+H)+.

Step 3: tert-Butyl 2-{6-[(tert-butyldimethylsilyl)oxy]-3-iodoindazol-1-yl}acetate(53S-4)

To a solution of compound 53S-3 (4.39 g, 11.74 mmol) in DMF (45 mL) was added $K_2CO_3$ (4.86 g, 35.22 mmol) followed by tert-butyl 2-bromoacetate (2.75 g, 14.09 mmol) and the reaction mixture was stirred at room temperature overnight. The mixture was diluted with water and extracted with EtOAc twice. The combined organic layers were washed with brine, dried and concentrated under reduced pressure. The residue was purified by chromatography on silica gel (eluted with PE:EtOAc=100:1 to 50:1) to give compound 53S-4 (3.8 g, 66.3% yield) as a white oil. LC/MS (ESI) m/z: 489(M+H)+.

Step 4: tert-Butyl 2-{3-Acetyl-6-[(tert-butyldimethylsilyl)oxy]indazol-1-yl}acetate (53S-5)

To a mixture of compound 53S-4 (3.8 g, 7.78 mmol) and tributyl(1-ethoxyethenyl)stannane (3.65 g, 10.1 mmol) in toluene (40 mL) was added Pd(PPh$_3$)$_4$ (900 mg, 0.78 mmol). The mixture was degassed under N$_2$ atmosphere three times and stirred at 100° C. under N$_2$ atmosphere overnight. The mixture was concentrated to dryness and the residue was dissolved in THF (25 mL). 0.5 N aq. HCl solution (10 mL) was added, and the mixture was stirred at room temperature for 1 hour. The mixture was extracted with EtOAc, washed with brine, dried and concentrated to dryness. The residue was purified by silica gel chromatography (eluted with PE:EtOAc=30:1) to give compound 53S-5 (3.0 g, yield 95.3%) as a yellow oil. LC/MS (ESI) m/z: 405 (M+H)$^+$.

Step 5: tert-Butyl 2-(3-Acetyl-6-hydroxyindazol-1-yl)acetate (53S-6)

To a solution of compound 53S-5 (3.0 g, 7.4 mmol) in tetrahydrofuran (30 mL) was added a solution of TBAF in THF (14.8 mL, 14.8 mmol, 1M in THF) at 0° C., and the reaction was stirred at room temperature for 30 minutes. The mixture was diluted with water and extracted with EtOAc twice. The combined organic layers were washed with brine, dried with anhydrous Na$_2$SO$_4$ and concentrated to dryness. The residue was purified by chromatography on silica gel (eluted with PE:EtOAc=20:1 to 7:1) to give compound 53S-6 (1.84 g, yield 85.47%) as a white solid. LC/MS (ESI) m/z: 291 (M+H)$^+$.

Step 6: tert-Butyl 2-(3-Acetyl-6-{[(pent-4-en-1-yl)carbamoyl]oxy}indazol-1-yl)acetate (53S-7)

To a solution of 5-hexenoic acid (708 mg, 6.2 mmol) in toluene (10 mL) was added triethylamine (1.88 g, 18.6 mmol) and DPPA (2.56 g, 9.3 mmol) at 0° C., and the mixture was stirred at room temperature for 1 hour. Compound 53S-6 (600 mg, 2.07 mmol) was added to above mixture and the resulting mixture was stirred at 80° C. under N$_2$ atmosphere overnight. The mixture was extracted with EtOAc twice and the combined organic layers were washed with saturated aq. NaHCO$_3$ solution and brine, dried and concentrated to dryness. The residue was purified by column chromatography on silica gel (eluted with PE:Acetone=10:1) to give compound 53S-7 (134 mg, yield 16.15%) as a white solid. LC/MS (ESI) m/z: 402 (M+H)$^+$.

Step 7: (3-Acetyl-6-{[(pent-4-en-1-yl)carbamoyl]oxy}indazol-1-yl)acetic Acid (53S-8)

To a solution of compound 53S-7 (134 mg, 0.32 mmol) in DCM (2 mL) was added TFA (2 mL) at 0° C., and the reaction was stirred at room temperature for 1 hr. The mixture was concentrated to dryness, and the residue was washed with ether and dried under vacuum to give compound 53S-8 (110 mg, yield 98.36%) as a yellow oil, which was used directly in the next step. LC/MS (ESI) m/z: 346 (M+H)$^+$.

Step 8: 3-Acetyl-1-{2-[(1R,3S,5S)-3-[(6-bromo-3-methylpyridin-2-yl)carbamoyl]-5-[(prop-2-en-1-yloxy)methyl]-2-azabicyclo[3.1.0]hexan-2-yl]-2-oxoethyl}indazol-6-yl N-(pent-4-en-1-yl)carbamate (53S-9)

To a mixture of compound 53S-8 (87 mg, 0.25 mmol) and (1R,3S,5S)-5-((allyloxy)methyl)-N-(6-bromo-3-methylpyridin-2-yl)-2-azabicyclo[3.1.0]hexane-3-carboxamide hydrochloride (100.7 mg, 0.25 mmol) in DMF (3 mL) was added DIPEA (163 mg, 1.26 mmol) and HATU (144 mg, 0.38 mmol) at 0° C., and the mixture was stirred at room temperature for 1 hour. The mixture was diluted with water and extracted with EtOAc. The organic layer was washed with brine, dried and concentrated. The residue was purified by chromatography on silica gel (eluted with PE:EtOAc=1:1) to give compound 53S-9 (60 mg, yield 34.34%) as a white solid. LC/MS (ESI) m/z: 693/695 (M+H)$^+$.

Step 9: (41R,43S,45S,E)-13-Acetyl-N-(6-bromo-3-methylpyridin-2-yl)-3,14-dioxo-11H-6,15-dioxa-42,13-diaza-1(1,6)-indazola-4(2,5)-bicyclo[3.1.0]hexanacyclopentadecaphan-8-ene-43-carboxamide (53)

To a solution of compound 53S-9 (60 mg, 0.089 mmol) in degassed toluene (60 mL) was added Grubbs 2$^{nd}$ catalyst (15 mg, 0.018 mmol) under N$_2$ atmosphere, and the mixture was stirred at 80° C. under N$_2$ atmosphere overnight. The mixture was concentrated to dryness, and the residue was purified by preparatory TLC to give 53 (2.4 mg, yield 4.1%) as a white solid. $^1$H-NMR (400 MHz, DMSO-d$_6$) δ 10.22 (s, 1H), 8.12 (d, J=8.8 Hz, 1H), 7.67 (d, J=1.6 Hz, 1H), 7.64-7.59 (m, 1H), 7.43 (d, J=7.6 Hz, 1H), 7.07 (dd, J=2.0, 2.0 Hz, 1H), 5.79 (d, J=15.6 Hz, 1H), 5.68-5.54 (m, 2H), 5.33 (t, J=3.2 Hz, 1H), 4.36 (dd, J=5.2, 5.2 Hz, 1H), 3.95 (t, J=5.4 Hz, 1H), 3.81-3.77 (m, 1H), 3.31-3.28 (m, 1H), 3.24-3.16 (m, 1H), 3.06-2.98 (m, 1H), 2.62 (s, 2H), 2.05 (s, 2H), 2.03-1.95 (m, 3H), 1.67-1.57 (m, 2H), 1.23 (s, 6H), 0.86 (d, J=6.4 Hz, 1H), 0.55-0.46 (m, 1H), 0.27-0.19 (m, 1H). LC/MS (ESI) m/z: 665/667 (M+H)$^+$.

Scheme 36: Synthesis of (41R,43S,45R)-13-acetyl-6-methyl-N-(3-methyl-6-(trifluoromethyl)pyridin-2-yl)-15-(2-methylpyrimi-5-yl)-3,7-dioxo-11H-42,6-diaza-1(1,7)-indazola-4(2,5)-bicyclo[3.1.0]hexanacyclotridecaphane-43-carboxamide (54)

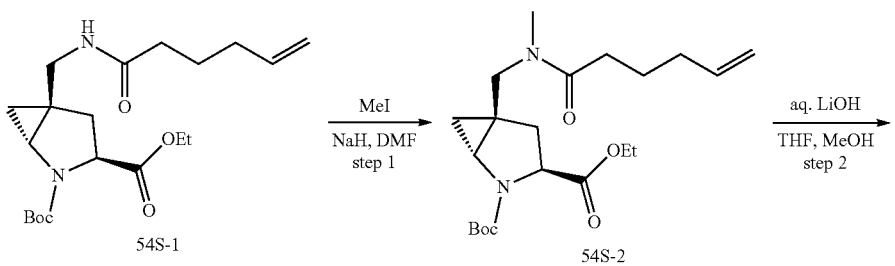

-continued
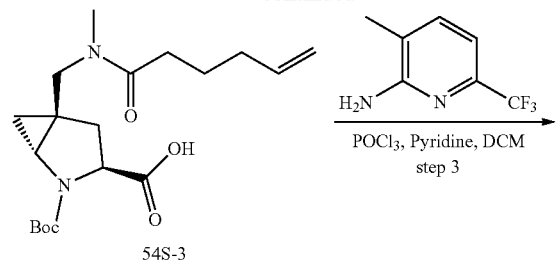
54S-3
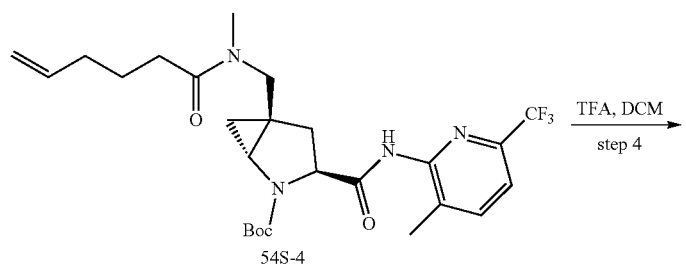
54S-4
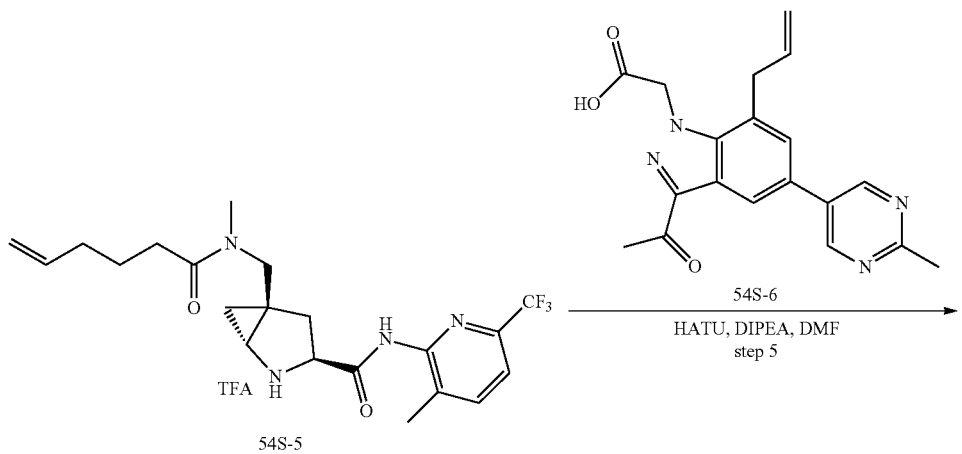
54S-5
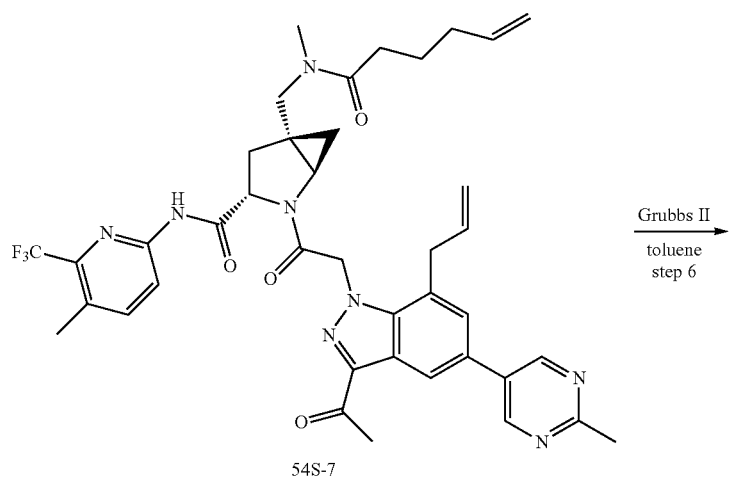
54S-7

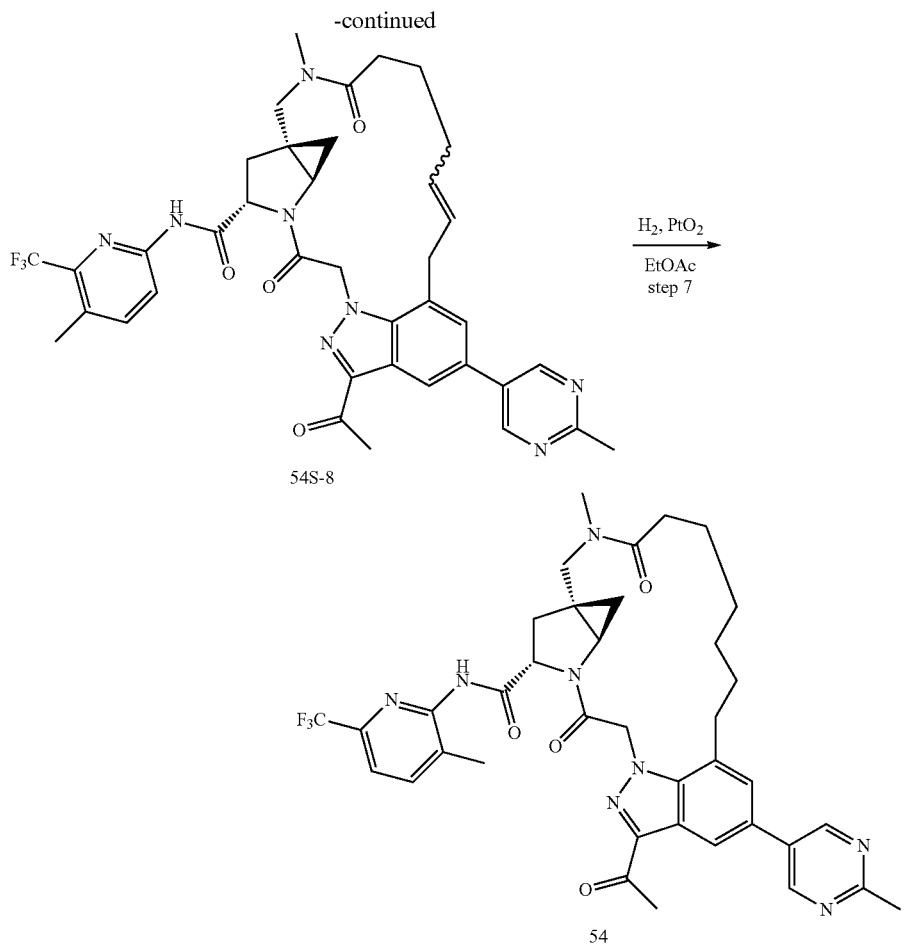

54S-8

54

The above scheme and following detailed description depicts one non-limiting method for synthesizing compounds of Formula II wherein -$X^9$-$L^3$-$X^{10}$- is

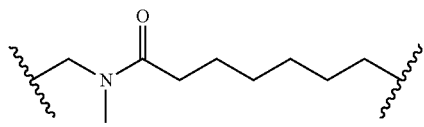 [SMILES: *CCCCCCC(=O)N(C)C*]

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1 : (1R,3S,5R)-2-tert-Butyl 3-Ethyl 5-((N-Methylhex-5-enamido)methyl)-2-azabicyclo[3.1.0]hexane-2,3-dicarboxylate (54S-2)

To a solution of compound 54S-1 (0.1 g, 0.27 mmol) in DMF (3 mL) was added portion-wise sodium hydride (26 mg, 1.09 mmol) at 0° C., and the mixture was stirred at 0° C. for 1 hour under $N_2$ atmosphere. MeI (0.12 g, 0.82 mmol) was added, and the mixture was stirred at room temperature under $N_2$ atmosphere overnight. The mixture was poured into iced saturated aq. $NH_4Cl$ solution and extracted with EtOAc twice. The combined organic layers were washed with brine, dried with anhydrous $Na_2SO_4$, filtered and concentrated to dryness. The residue was purified by chromatography on silica gel (PE:EtOAc=10:1 to 2:1) to give compound 54S-2 (0.1 g, yield 77.05%) as brown solid. LC/MS (ESI) m/z: 395 $(M+H)^+$.

Step 2: (1R,3S,5R)-2-(tert-Butoxycarbonyl)-5-((N-methylhex-5-enamido)methyl)-2-azabicyclo[3.1.0]hexane-3-carboxylic Acid (54S-3)

To a solution of compound 54S-2 (0.15 g, 0.38 mmol) in methanol (3 mL) and tetrahydrofuran (3 mL) was added a solution of LiOH (0.048 g, 1.14 mmol) in water (1 mL) at 0° C., and the mixture was stirred at room temperature for 2 hours. The mixture was washed with $Et_2O$ and water. The aqueous layer was acidified with 0.5 M aq. HCl solution and extracted with DCM/MeOH (v/v=20:1). The combined organic layers were washed with brine, dried with anhydrous $Na_2SO_4$, filtered and concentrated to dryness to give compound 54S-3 (0.13 g, yield 93.30%) as a yellow oil. LC/MS (ESI) m/z: 367 $(M+H)^+$.

Step 3: (1R,3S,5R)-tert-Butyl 3-(3-Methyl-6-(trifluoromethyl)pyridin-2-ylcarbamoyl)-5-((N-methylhex-5-enamido) methyl)-2-azabicyclo[3.1.0]hexane-2-carboxylate (54S-4)

To a mixture of compound 54S-3 (0.13 g, 0.36 mmol) and 3-methyl-6-(trifluoromethyl)pyridin-2-amine (0.062 g, 0.36 mmol) in DCM (5 mL) was added pyridine (0.14 g, 1.77 mmol) followed by phosphoryl chloride (0.06 g, 0.39 mmol) at 0° C., and the mixture was stirred at room temperature for 30 minutes under $N_2$ atmosphere. The mixture was poured into iced water and extracted with DCM twice. The combined organic layers were washed with brine, dried with anhydrous Na$_2$SO$_4$, filtered and concentrated to dryness. The residue was purified by chromatography on silica gel (PE:EtOAc=10:1 to 2 1) to give compound 54S-4 (0.06 g, yield 32.24%) as a yellow solid. LC/MS (ESI) m/z: 525 (M+H)$^+$.

Step 4: (1R,3S,5R)-N-(3-Methyl-6-(trifluoromethyl)pyridin-2-yl)-5-((N-methylhex-5-enamido)methyl)-2-azabicyclo[3.1.0]hexane-3-carboxamide Trifluoroacetic Acid Salt (54S-5)

To a solution of compound 54S-4 (0.06 g, 0.11 mmol) in DCM (3 mL) was added TFA (1 mL) at 0° C., and the mixture was stirred at room temperature for 1 hour. The reaction mixture was concentrated to dryness, washed with ether and dried under vacuum to give compound 54S-5 (0.045 g, yield 92.65%) as a yellow oil, which was used directly in the next step. LC/MS (ESI) m/z: 425 (M+H)$^+$.

Step 5: (1R,3S,5R)-2-(2-(3-acetyl-7-allyl-5-(2-methylpyrimidin-5-yl)-1H-indazol-1-yl)acetyl)-N-(5-methyl-6-(trifluoromethyl)pyridin-2-yl)-5-((N-methylhex-5-enamido)methyl)-2-azabicyclo[3.1.0]hexane-3-carboxamide (54S-7)

To a mixture of compound 54S-5 (0.045 g, 0.1 mmol) and compound 54S-6 (0.037 g, 0.11 mmol) in DMF (2 mL) was added DIPEA (0.068 g, 0.53 mmol) followed by HATU (0.08 g, 0.21 mmol) at 0° C., and the mixture was stirred at room temperature for 1 hour. The mixture was diluted with H$_2$O and extracted with EtOAc twice. The combined organic layers were washed with 10% aq. LiCl solution and brine, dried with anhydrous Na$_2$SO$_4$, filtered and concentrated to dryness. The residue was purified by chromatography on silica gel (DCM:MeOH=100:1 to 60:1) to give compound 54S-7 (0.075 g, yield 93.70%) as a yellow solid. LC/MS (ESI) m/z: 757 (M+H)$^+$.

Step 6: (4$^1$R,4$^3$S,4$^5$R,E)-13-acetyl-6-methyl-N-(5-methyl-6-(trifluoromethyl)pyridin-2-yl)-15-(2-methylpyrimidin-5-yl)-3,7-dioxo-11H-4$^2$,6-diaza-1(1,7)-indazola-4(2,5)-bicyclo[3.1.0]hexanacyclotridecaphan-11-ene-4$^3$-carboxamide (54S-8)

To a solution of compound 54S-7 (75 mg, 0.099 mmol) in degassed toluene (80 mL) was added Grubbs II catalyst (17 mg, 0.02 mmol) at 0° C. under N$_2$ atmosphere, and the mixture was stirred at 80° C. overnight under N$_2$ atmosphere. The mixture was concentrated to dryness and the residue was purified by chromatography on silica gel (DCM:MeOH=80:1 to 60:1) to give compound 54S-8 (50 mg, yield 70.59%) as a brown oil. LC/MS (ESI) m/z: 729 (M+H)$^+$.

Step 7: (4$^1$R,4$^3$S,4$^5$R)-13-acetyl-6-methyl-N-(3-methyl-6-(trifluoromethyl)pyridin-2-yl)-15-(2-methylpyrimidin-5-yl)-3,7-dioxo-11H-4$^2$,6-diaza-1(1,7)-indazola-4(2,5)-bicyclo[3.1.0]hexanacyclotridecaphane-4$^3$-carboxamide (54)

To a solution of compound 54S-8 (50 mg, 0.069 mmol) in methanol (5 mL) was added 10% Pd/C (10 mg) at 0° C. The mixture was degassed under N$_2$ atmosphere three times and stirred under a H$_2$ balloon at room temperature for 1 hour. The mixture was filtered, and the filtrate was concentrated to dryness. The residue was purified by preparatory HPLC to give 54 (5.5 mg, yield 10.9%) as white solid. $^1$H-NMR (400 MHz, DMSO-d$_6$) δ 10.66 (s, 1H), 9.01 (d, J=17.2 Hz, 2H), 8.31 (d, J=12.0 Hz, 1H), 7.97-7.87 (m, 1H), 7.71-7.51 (m, 2H), 5.91 (d, J=17.2 Hz, 1H), 5.73 (d, J=18.0 Hz, 1H), 5.64-5.35 (m, 2H), 4.75-4.60 (m, 1H), 4.51-4.36 (m, 1H), 4.01 (d, J=4.0 Hz, 1H), 3.85-3.74 (m, 1H), 3.16 (s, 3H), 2.84 (s, 3H), 2.67 (s, 3H), 2.63 (s, 3H), 2.15 (d, J=16.4 Hz, 4H), 1.88-1.35 (m, 8H), 1.25-1.19 (m, 1H), 1.13-1.04 (m, 1H). LC/MS (ESI) m/z: 731 (M+H)$^+$.

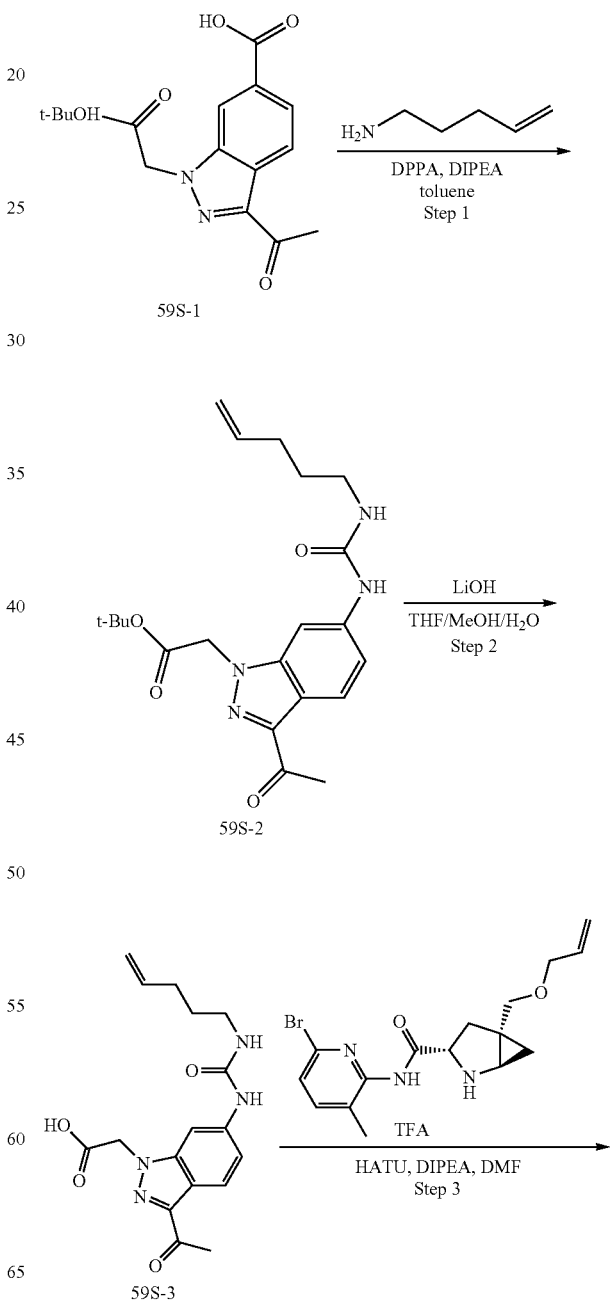

Scheme 37: Synthesis of (4$^1$R,4$^3$S,4$^5$S,Z)-1$^3$-acetyl-N-(6-bromo-3-methylpyridin-2-yl)-3,14-dioxo-1$^1$H-6-oxa-4$^2$,13,15-triaza-1(1,6)-indazola-4(2,5)-bicyclo[3.1.0]hexanacyclopentadecaphan-8-ene-4$^3$-carboxamide (59)

-continued

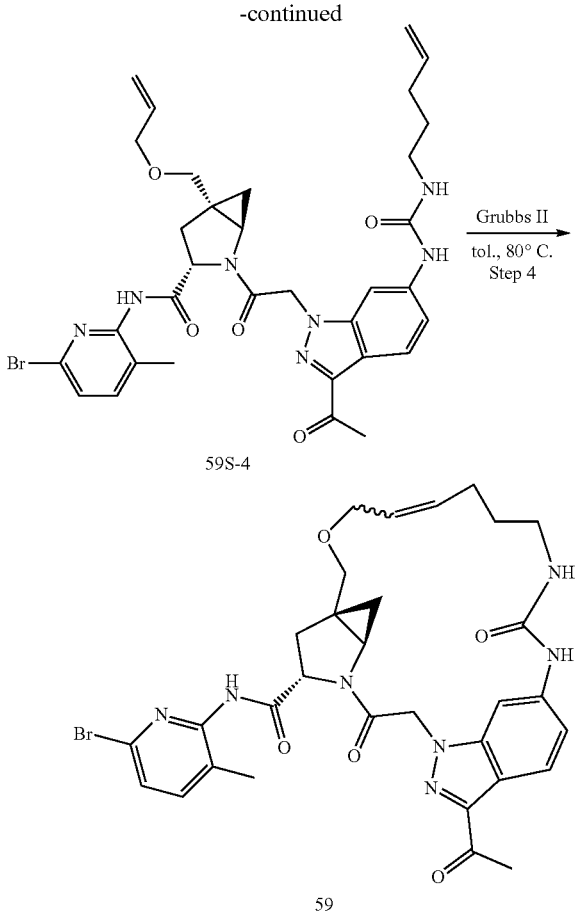

The above scheme and following detailed description depicts one non-limiting method for synthesizing compounds of Formula II wherein -X$^9$-L$^3$-X$^{10}$- is

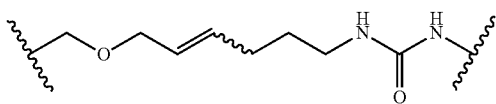 [SMILES: *COCC=CCCCNC(=O)N*]

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 3: tert-butyl 2-(3-acetyl-6-(3-(pent-4-en-1-yl)ureido)-1H-indazol-1-yl)acetate (59S-2)

To a mixture of compound 59S-1 (200 mg, 0.63 mmol) in toluene (10 mL) was added DIPEA (243 mg, 1.89 mmol) followed by DPPA (260 mg, 0.95 mmol), and the mixture was stirred at 100° C. for 1 hour under N$_2$ atmosphere. Then pent-4-en-1-amine hydrochloride (383 mg, 3.15 mmol) was added into the mixture. The reaction mixture was stirred at 100° C. for 2 hours under N$_2$ atmosphere. The mixture was diluted with EtOAc, washed with brine, dried over Na$_2$SO$_4$, filtered and concentrated to give crude product, which was purified by column chromatography on silica gel (eluted with PE:EtOAc=20:1 to 10:1) to give compound 59S-2 (120 mg, yield 47.4%) as a white solid. LC/MS (ESI) m/z: 401 (M+H)$^+$.

Step 4: 2-(3-acetyl-6-(3-(pent-4-en-1-yl)ureido)-1H-indazol-1-yl)acetic acid (59S-3)

To a solution of compound 59S-2 (120 mg, 0.30 mmol) in THF (2 mL), MeOH (2 mL) and water (1 mL) was added LiOH (92 mg, 2.19 mmol) at 0° C., and the reaction mixture was stirred at room temperature for 2 hours. The mixture was concentrated to dryness, and the residue was dissolved in water and washed with EtOAc twice. The aqueous layer was acidified by adding 1N HCl to pH~3. The mixture was extracted with DCM twice. The combined organic layers were washed with brine, dried over Na$_2$SO$_4$, filtered and concentrated to dryness to give compound 59S-3 (90 mg, 86.5% yield) as a white solid. LC/MS (ESI) m/z: 345 (M+H)$^+$.

Step 5: (1R,3S,5S)-2-(2-(3-acetyl-6-(3-(pent-4-en-1-yl)ureido)-1H-indazol-1-yl)acetyl)-5-((allyloxy)methyl)-N-(6-bromo-3-methylpyridin-2-yl)-2-azabicyclo[3.1.0] hexane-3-carboxamide (59S-4)

To a mixture of compound 59S-3 (90 mg, 0.26 mmol) and (1R,3S,5S)-5-((allyloxy)methyl)-N-(6-bromo-3-methylpyridin-2-yl)-2-azabicyclo[3.1.0]hexane-3-carboxamide TFA salt (121 mg, 0.26 mmol) in DMF (5 mL) was added DIPEA (101 mg, 0.78 mmol) at 0° C. followed by HATU (148 mg, 0.39 mmol), and the mixture was stirred at 25° C. for 2 hours. The mixture was diluted with EtOAc, washed with saturated aq. NH$_4$Cl solution and brine successively, dried over Na$_2$SO$_4$, filtered and concentrated to give crude product, which was purified by silica gel chromatography (eluted with DCM:MeOH=40:1) to give compound 59S-4 (54 mg, 30.0% yield) as white solid. LC/MS (ESI) m/z: 692/694 (M+H)$^+$.

Step 6: (4$^1$R,4$^3$S,4$^5$S,Z)-1$^3$-acetyl-N-(6-bromo-3-methylpyridin-2-yl)-3,14-dioxo-1$^1$H-6-oxa-4$^2$,13,15-triaza-1(1,6)-indazola-4(2,5)-bicyclo[3.1.0]hexanacyclopentadecaphan-8-ene-43-carboxamide (59)

To a solution of compound 59S-4 (54 mg, 0.08 mmol) in anhydrous toluene (50 mL) was added Grubbs II catalyst (17 mg, 0.02 mmol), and the resulting mixture was stirred at 80° C. for 16 hours under N$_2$ atmosphere. The reaction mixture was concentrated to dryness. The residue was purified by silica gel chromatography (DCM:MeOH=30:1) and re-purified by preparatory HPLC to give 59 (1.1 mg, Yield 2.1%) as a white solid. $^1$H-NMR (400 MHz, CD$_3$OD) δ 8.59 (s, 1H), 7.97 (m, 1H), 7.43-7.26 (m, 2H), 6.66 (s, 1H), 5.82-5.59 (m, 3H), 5.28 m, 1H), 4.46-4.37 (m, 1H), 4.21-4.12 (m, 1H), 4.10-3.98 (m, 2H), 3.82-3.72 (m, 2H), 3.05-2.98 (m, 1H), 2.66 (s, 3H), 2.62-2.60 (m, 1H), 2.12-2.02 (m, 2H), 1.56 (s, 5H), 1.32-1.27 (m, 3H), 1.06-0.97 (m, 1H). LC/MS (ESI) m/z: 664/666 (M+H)$^+$.

Scheme 38: Synthesis of (41R,43S,45R)-42-(2-(3-acetyl-7-(fluoromethyl)-5-(2-methylpyrimidin-5-yl)-1H-indazol-1-yl)acetyl)-16-bromo-12-methyl-42,2,12-triaza-1(2,3)-pyridina-4(3,5)-bicyclo[3.1.0] hexanacyclotridecaphan-3-one (60) and (41R,43S,45R)-42-(2-(3-acetyl-5-(2-methylpyrimidin-5-yl)-1H-pyrazolo[3,4-c]pyridin-1-yl)acetyl)-16-bromo-12-methyl-42,2,12-triaza-1(2,3)-pyridina-4(3,5)-bicyclo[3.1.0]hexanacyclotridecaphan-3-one (61)

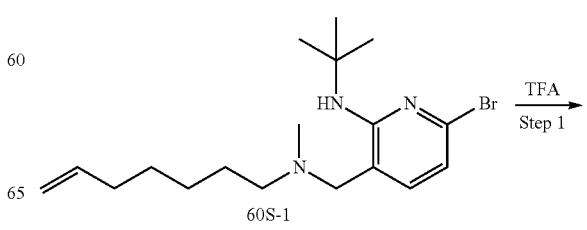

-continued

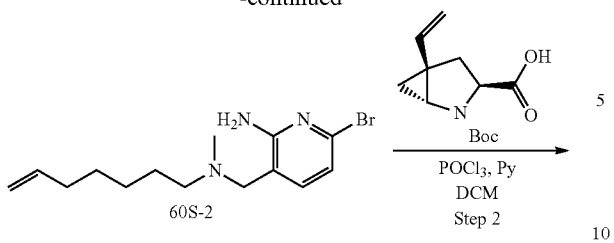

Step 2

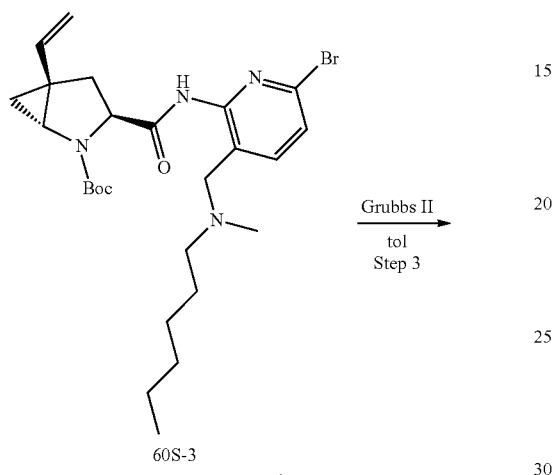

Step 3

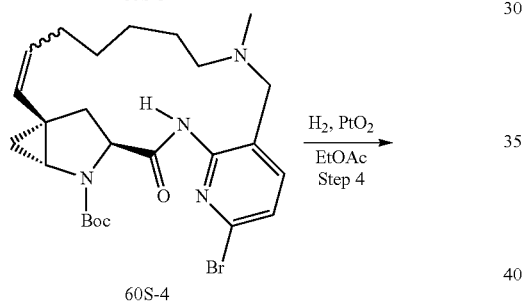

Step 4

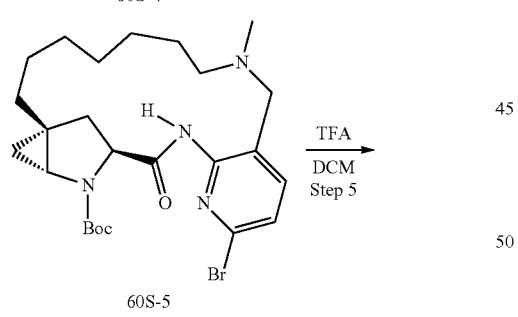

Step 5

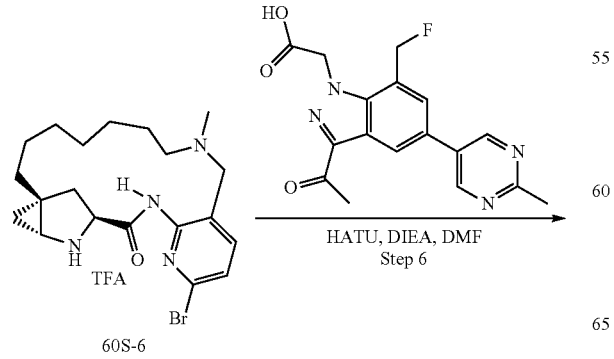

Step 6

-continued

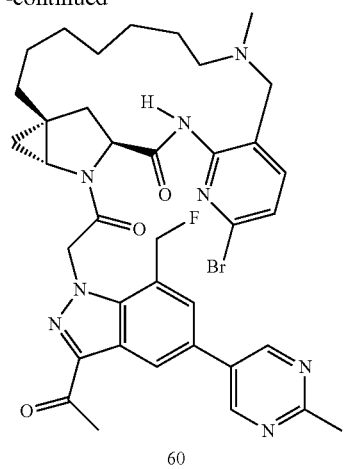

60

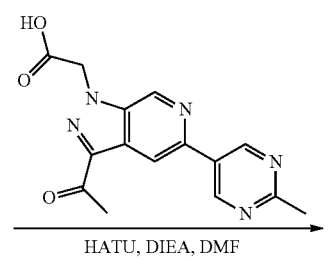

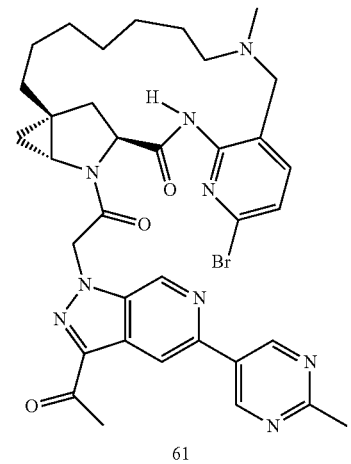

61

The above scheme and following detailed description depicts one non-limiting method for synthesizing compounds of Formula I wherein -$X^9$-$L^3$-$X^{10}$- is

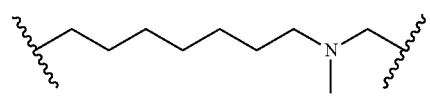 [SMILES: *CCCCCCCN(C)C*]

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: 6-Bromo-3-((hept-6-en-1-yl(methyl)amino)methyl)pyridin-2-amine (60S-2)

A solution of compound 60S-1 (380 mg, 1.04 mmol) in TFA (5 mL) was stirred at 70° C. for 2 hours. The mixture was concentrated to dryness, and the residue was poured into ice-cooled sat. aq. NaHCO$_3$ solution (10 mL) and extracted with DCM twice. The combined organic layers were washed with brine, dried over Na$_2$SO$_4$, filtered and concentrated to dryness. The residue was purified by column chromatography on silica gel (eluted with PE:EtOAc=5:1) to give compound 60S-2 (227 mg, 70.3% yield) as a white solid. LCMS: LC/MS (ESI) m/z: 312/314 (M+H)$^+$.

Step 2: (1R,3S,5R)-tert-Butyl 3-((6-Bromo-3-((hept-6-en-1-yl(methyl)amino)methyl)pyridin-2-yl)carbamoyl)-5-vinyl-2-azabicyclo[3.1.0]hexane-2-carboxylate (60S-3)

To a mixture of compound 60S-2 (200 mg, 0.64 mmol) and (1R,3S,5R)-2-(tert-butoxycarbonyl)-5-vinyl-2-azabicyclo[3.1.0]hexane-3-carboxylic acid (163 mg, 0.64 mmol) in dichloromethane (10 mL) was added pyridine (254 mg, 3.22 mmol) followed by drop-wise addition of POCl$_3$ (148 mg, 0.09 mmol) at 0° C., and the mixture was stirred at 0° C. for 1 hour. The mixture was diluted with DCM, washed with ice-cooled 0.5 N aq. HCl and brine, dried over Na$_2$SO$_4$, filtered and concentrated to dryness. The residue was purified by column chromatography on silica gel (eluted with PE:EtOAc=3:1) to give compound 60S-3 (90 mg, 25.8% yield) as a white solid. LCMS: LC/MS (ESI) m/z: 547/549 (M+H)$^+$.

Step 3: tert-Butyl (41R,43S,45R,Z)-16-Bromo-12-methyl-3-oxo-42,2,12-triaza-1(2,3)-pyridina-4(3,5)-bicyclo[3.1.0]hexanacyclotridecaphan-5-ene-42-carboxylate (60S-4)

To a solution of compound 60S-3 (90 mg, 0.16 mmol) in anhydrous toluene (90 mL) was added Grubbs II catalyst (8 mg, 0.01 mmol) and the resulting mixture was stirred at 80° C. for 16 hours under N$_2$ atmosphere. The reaction mixture was concentrated to dryness. The residue was purified by silica gel chromatography (DCM:MeOH=40:1 to 30:1) to give compound 60S-4 (60 mg, 72.4% yield) as a brown solid. LC/MS (ESI) m/z: 519/521 (M+H)$^+$.

Step 4: tert-Butyl (41R,43S,45R)-16-Bromo-12-methyl-3-oxo-42,2,12-triaza-1(2,3)-pyridina-4(3,5)-bicyclo[3.1.0]hexanacyclotridecaphane-42-carboxylate (60S-5)

To a solution of compound 60S-4 (60 mg, 0.12 mmol) in ethyl acetate (10 mL) was added PtO$_2$ (15 mg, 0.07 mmol), and the resulting mixture was stirred at room temperature for 10 minutes under a H$_2$ balloon. The mixture was filtered and concentrated to dryness to give compound 60S-5 (60 mg, 99.5% yield) as a brown solid. LC/MS (ESI) m/z: 521/523 (M+H)$^+$.

Step 5: (41R,43S,45R)-16-Bromo-12-methyl-42,2,12-triaza-1(2,3)-pyridina-4(3,5)-bicyclo[3.1.0]hexanacyclotridecaphan-3-one Trifluoroacetic Acid Salt (60S-6)

To a solution of compound 60S-5 (60 mg, 0.12 mmol) in dichloromethane (2 mL) was added TFA (1 mL) at 0° C., and the mixture was stirred at 0° C. for 2 hours. The mixture was concentrated to dryness to give compound 60S-6 (60 mg, crude) as a yellow syrup, which was directly used to the next reaction without purification. LC/MS (ESI) m/z: 421/423 (M+H)$^+$.

Step 6: (41R,43S,45R)-42-(2-(3-Acetyl-7-(fluoromethyl)-5-(2-methylpyrimidin-5-yl)-1H-indazol-1-yl)acetyl)-16-bromo-12-methyl-42,2,12-triaza-1(2,3)-pyridina-4(3,5)-bicyclo[3.1.0]hexanacyclotridecaphan-3-one (60)

To a mixture of compound 60S-6 (24 mg, 0.06 mmol) and 2-(3-acetyl-7-(fluoromethyl)-5-(2-methylpyrimidin-5-yl)-1H-indazol-1-yl)acetic acid (24 mg, 0.06 mmol) in DMF (2 mL) was added DIPEA (23 mg, 0.18 mmol) at 0° C. followed by HATU (34 mg, 0.09 mmol), and the mixture was stirred at 25° C. for 2 hours. The mixture was diluted with EtOAc, washed with saturated aq. NH$_4$Cl solution and brine successively, dried over Na$_2$SO$_4$, filtered and concentrated to give crude product, which was purified by preparatory HPLC to give 60 (5.2 mg, yield 11.6%) as a white solid. $^1$H-NMR (400 MHz, DMSO-d$_6$) δ 10.55 (s, 1H), 9.07 (s, 2H), 8.58 (s, 1H), 8.02 (s, 1H), 7.69 (d,J=8.0 Hz, 1H), 7.41 (d, J=7.9 Hz, 1H), 6.01-5.95 (m, 2H), 5.85-5.79 (m, 1H), 5.72-5.66 (m, 2H), 4.74-4.66 (m, 1H), 3.62-3.58 (m, 1H), 3.52-3.45 (m, 2H), 2.69 (s, 3H), 2.67 (s, 3H), 2.44-2.31 (m, 3H), 2.24-2.16 (m, 4H), 1.72-1.66 (m, 1H), 1.49-1.25 (m, 11H), 1.04 (m, 2H). LC/MS (ESI) m/z: 745/747 (M+H)$^+$.

Step 7: (41R,43S,45R)-42-(2-(3-Acetyl-5-(2-methylpyrimidin-5-yl)-1H-pyrazolo[3,4-c]pyridin-1-yl)acetyl)-16-bromo-12-methyl-42,2,12-triaza-1(2,3)-pyridina-4(3,5)-bicyclo[3.1.0]hexanacyclotridecaphan-3-one (61)

To a mixture of compound 60S-6 (24 mg, 0.06 mmol) and 2-(3-acetyl-5-(2-methylpyrimidin-5-yl)-1H-pyrazolo[3,4-c]pyridin-1-yl)acetic acid (19 mg, 0.06 mmol) in DMF (2 mL) was added DIPEA (23 mg, 0.18 mmol) at 0° C. followed by HATU (34 mg, 0.09 mmol), and the mixture was stirred at 2° C. for 2 hours. The mixture was diluted with EtOAc, washed with saturated aq. NH$_4$Cl solution and brine successively, dried over Na$_2$SO$_4$, filtered and concentrated to give crude product, which was purified by preparatory HPLC to give 61 (2.5 mg, yield 5.8%) as a white solid. $^1$H-NMR (400 MHz, CD$_3$OD) δ 9.35 (s, 2H), 9.28 (s, 1H), 8.69 (s, 1H), 7.51 (m, 1H), 7.31-7.23 (m, 1H), 6.03 (m, 1H), 5.81 (m, 1H), 4.84-4.74 (m, 1H), 3.67-3.48 (m, 3H), 2.76 (s, 3H), 2.72 (s, 3H), 2.58-2.51 (m, 1H), 2.41 (s, 3H), 2.37-2.25 (m, 3H), 1.93-1.83 (m, 1H), 1.65-1.43 (m, 5H), 1.42-1.28 (m, 5H), 1.21-1.05 (m, 3H). LC/MS (ESI) m/z: 714/716 (M+H)$^+$.

Scheme 39: Synthesis of (42S,44R)-41-(2-(3-acetyl-5-(2-methylpyrimidin-5-yl)-1H-indazol-1-yl)acetyl)-16-bromo-44-fluoro-6-oxa-2-aza-1(2,3)-pyridina-4(2,4)-pyrrolidinacyclotridecaphan-3-one (62)

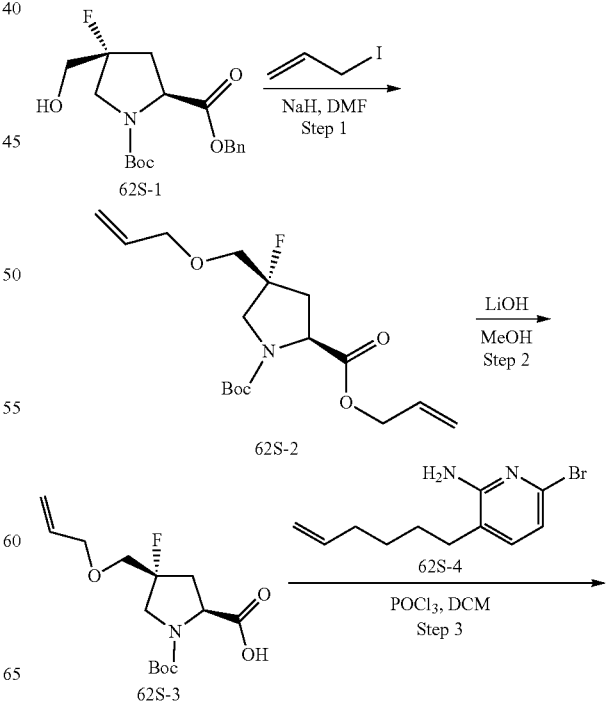

667
-continued

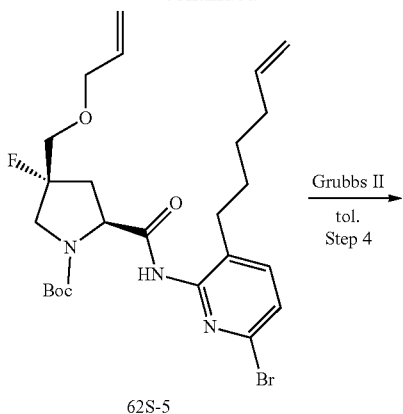
62S-5

Grubbs II
tol.
Step 4

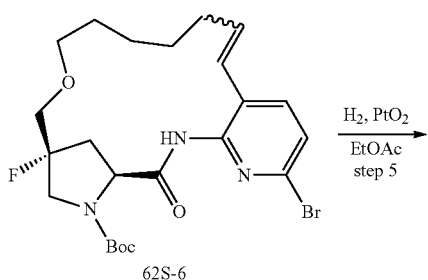
62S-6

H₂, PtO₂
EtOAc
step 5

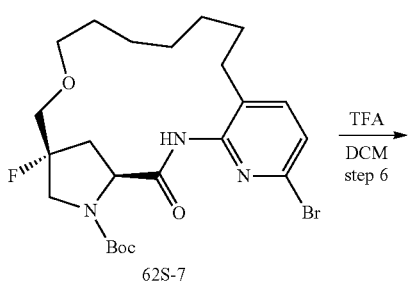
62S-7

TFA
DCM
step 6

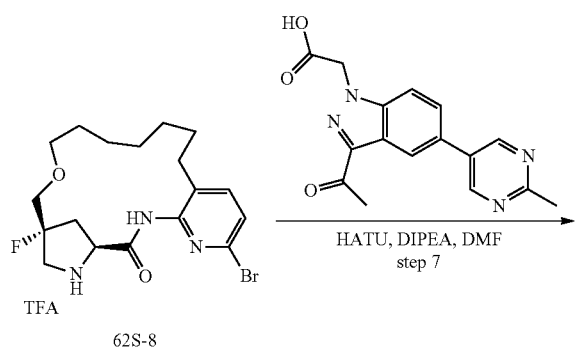
62S-8

HATU, DIPEA, DMF
step 7

668
-continued

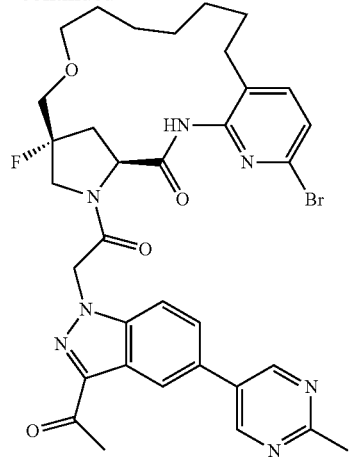
62

The above scheme and following detailed description depicts one non-limiting method for synthesizing compounds of Formula I wherein -X$^9$-L$^3$-X$^{10}$- is $$\text{\raisebox{-0.5ex}{\scalebox{1.2}{$\sim$}}}\!\!-\!\text{CH}_2\text{O}(\text{CH}_2)_7\!-\!\text{\raisebox{-0.5ex}{\scalebox{1.2}{$\sim$}}}$$

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1: (2S,4R)-2-Allyl 1-tert-Butyl-((allyloxy)methyl)-4-fluoropyrrolidine-1,2-dicarboxylate (62S-2)

To a solution of compound 62S-1 (460 mg, 1.302 mmol) in anhydrous DMF (5 mL) was added NaH (130 mg, 3.255 mmol) at 0° C. under N₂ atmosphere, and the mixture was stirred at 0° C. for 1 hour. 3-iodoprop-1-ene (656 mg, 3.905 mmol) was added at 0 20 C., and the resulting mixture was stirred at room temperature for 1 hour. The mixture was poured into ice-cooled sat. NH₄Cl solution and extracted with EtOAc twice. The combined organic layers were washed with brine, dried over anhydrous Na₂SO₄ and concentrated under reduced pressure. The residue was purified by chromatography on silica gel (eluted with PE:EtOAc=25:1 to 20:1) to give compound 62S-2 (150 mg, yield 33.5%) as a light yellow oil. LC/MS (ESI) m/z: 344 (M+H)⁺.

Step 2: (2S,4R)-4-((Allyloxy)methyl)-1-(tert-butoxycarbonyl)-4-fluoropyrrolidine-2-carboxylic Acid (62S-3)

To a solution of compound 62S-2 (150 mg, 0.437 mmol) in THF (1 mL) and methanol (1 mL) was added a solution of lithium hydroxide (31 mg, 1.31 mmol) in water (1 mL) at 0° C., and the reaction mixture was stirred at room temperature for 2 hours. The mixture was diluted with water and washed with ether twice. The aqueous layer was acidified with 1 N aq. HCl solution until pH~3 and extracted with EtOAc twice. The combined organic layers were dried over anhydrous Na₂SO₄ and concentrated to dryness to give compound 62S-3 (81 mg, yield 61.1%) as a light oil, which was directly used to the next reaction without further purification. LC/MS (ESI) m/z: 304 (M+H)⁺.

Step 3: (2S,4R)-tert-Butyl 4-((Allyloxy)methyl)-2-((6-bromo-3-(hex-5-en-1-yl)pyridin-2-yl)carbamoyl)-4-fluoro-pyrrolidine-1-carboxylate (62S-5)

To a mixture of compound 62S-3 (77 mg, 0.255 mmol) and compound 62S-4 (65 mg, 0.255 mmol) in anhydrous DCM (4 mL) was added pyridine (101 mg, 1.274 mmol) followed by POCl$_3$ (43 mg, 0.28 mmol) at 0° C. under N$_2$ atmosphere, and the reaction mixture was stirred at room temperature for 30 minutes. The mixture was poured into ice water and extracted with DCM twice. The combined organic layers were washed with brine, dried over anhydrous Na$_2$SO$_4$ and concentrated under reduced pressure. The residue was purified by chromatography on silica gel (eluted with PE:EtOAc=20:1 to 5:1) to give compound 62S-5 (89 mg, yield 64.6%) as a light oil. LC/MS (ESI) m/z: 540 (M+H)$^+$.

Step 4: tert-Butyl (4²S,4⁴R,E)-1⁶-Bromo-4⁴-fluoro-3-oxo-6-oxa-2-aza-1(2,3)-pyridina-4(2,4)-pyrrolidinacyclotride-caphan-1²-ene-4¹-carboxylate (62S-6)

To a solution of compound 62S-5 (89 mg, 0.165 mmol) in degassed toluene (90 mL) was added Grubbs 2$^{nd}$ catalyst (35 mg, 0.41 mmol). The reaction mixture was degassed under N$_2$ atmosphere three times and stirred at 80° C. overnight under N$_2$ atmosphere. The mixture was concentrated to dryness and the residue was purified chromatography on silica gel (eluted with PE:EtOAc=20:1 to 6:1) to give compound 62S-6 (50 mg, yield 59.3%) as a light brown oil. LC/MS (ESI) m/z: 512 (M+H)$^+$.

Step 5: tert-Butyl (4²S,4⁴R)-1⁶-Bromo-4⁴-fluoro-3-oxo-6-oxa-2-aza-1(2,3)-pyridina-4(2,4)-pyrrolidinacyclotride-caphane-4¹-carboxylate (62S-7)

To a solution of compound 62S-6 (50 mg, 0.098 mmol) in degassed EtOAc (3 mL) was added PtO$_2$ (7 mg), and the mixture was stirred under a H$_2$ balloon at room temperature for 20 minutes. The mixture was filtered, and the filtrate was evaporated to dryness to give compound 62S-7 (50 mg, yield 99.6%) as a light brown oil, which was directly used in the next reaction without further purification. LC/MS (ESI) m/z: 514 (M+H)$^+$.

Step 6: (4²S,4⁴R)-1⁶-Bromo-4⁴-fluoro-6-oxa-2-aza-1(2,3)-pyridina-4(2,4)-pyrrolidinacyclotridecaphan-3-one Trifluoroacetic Acid Salt (62S-8)

To a solution of compound 62S-7 (50 mg) in DCM (2 mL) was added TFA (1 mL) at 0° C., and the reaction mixture was stirred at room temperature for 1 hour. The mixture was evaporated to dryness to give compound 62S-8 (40 mg, crude) as a yellow oil, which was directly used in the next reaction without further purification. LC/MS (ESI) m/z: 352 (M+H)$^+$.

Step 7: (4²S,4⁴R)-4¹-(2-(3-acetyl-5-(2-methylpyrimidin-5-yl)-1H-indazol-1-yl)acetyl)-1⁶-bromo-4⁴-fluoro-6-oxa-2-aza-1(2,3)-pyridina-4(2,4)-pyrrolidinacyclotridecaphan-3-one (62)

To a mixture of compound 62S-8 (20 mg, 0.048 mmol) and 2-(3-acetyl-5-(2-methylpyrimidin-5-yl)-1H-indazol-1-yl)acetic acid (15 mg, 0.048 mmol) in DMF (3 mL) was added DIPEA (19 mg, 0.145 mmol) followed by HATU (28 mg, 0.072 mmol), and the reaction mixture was stirred at room temperature for 1 hour. The mixture was poured into ice water and extracted with EtOAc twice. The organic layers were washed with brine, dried over anhydrous Na$_2$SO$_4$ and concentrated under reduced pressure. The residue was purified by preparatory HPLC to give compound 62 (4 mg, yield 10.2%) as a white solid. $^1$H-NMR (400 MHz, DMSO-d$_6$) δ 10.41 (s, 1H), 9.04 (s, 2H), 8.44 (s, 1H), 7.89-7.82 (m, 2H), 7.69 (d, J=8.1 Hz, 1H), 7.48 (d, J=8.0 Hz, 1H), 5.84 (d, J=17.3 Hz, 1H), 5.65 (d, J=17.2 Hz, 1H), 4.76 (t, J=8.7 Hz, 1H), 4.27-4.20 (m, 1H), 4.09-3.98 (m, 2H), 3.78-3.60 (m, 4H), 3.55-3.51 (m, 1H), 2.68 (s, 3H), 2.65 (s, 3H), 2.42-2.32 (m, 2H), 1.62-1.56 (m, 2H), 1.52-1.46 (m, 2H), 1.44-1.33 (m, 6H). LC/MS (ESI) m/z: 706 (M+H)$^+$.

Scheme 40: Synthesis of (1⁴Z,3¹R,3³S,3⁵R,13E)-6³-acetyl-N-(6-bromo-3-methylpyridin-2-yl)-6⁵-(2-methylpyrimidin-5-yl)-4-oxo-1¹H,6¹H-3²-aza-6(1,7)-indazola-1(1,4)-triazola-3(5,2)-bicyclo[3.1.0]hexanacyclotetradecaphan-13-ene-3³-carboxamide (62), (1⁴Z,3¹R,3³S,3⁵R,13Z)-6³-acetyl-N-(6-bromo-3-methylpyridin-2-yl)-6⁵-(2-methylpyrimidin-5-yl)-4-oxo-1¹H,6¹H-3²-aza-6(1,7)-indazola-1(1,4)-triazola-3(5,2)-bicyclo[3.1.0]hexanacyclotetradecaphan-13-ene-3³-carboxamide (64), and (3¹R,3³S,3⁵R,Z)-6³-acetyl-N-(6-bromo-3-methylpyridin-2-yl)-6⁵-(2-methylpyrimidin-5-yl)-4-oxo-1¹H,6¹H-3²-aza-6(1,7)-indazola-1(1,4)-triazola-3(5,2)-bicyclo[3.1.0]hexanacyclotetradecaphan-3³-carboxamide (65)

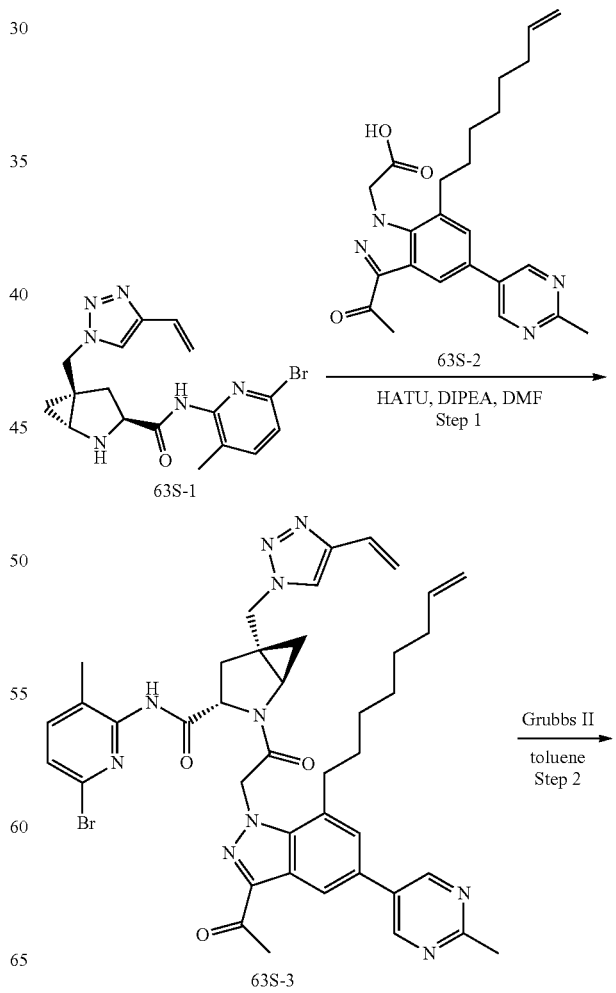

-continued

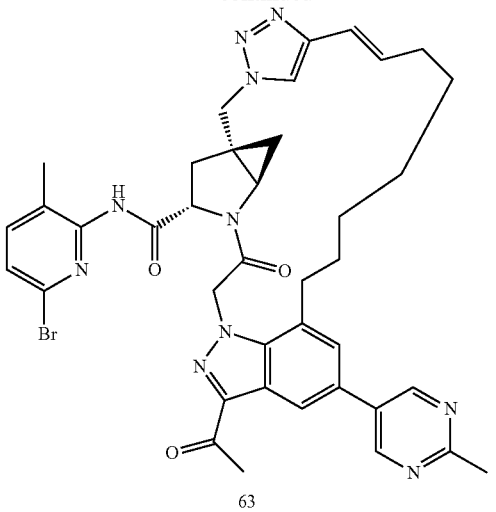

63

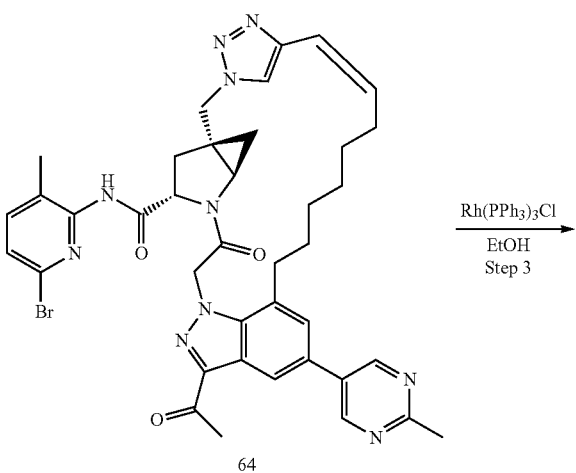

64

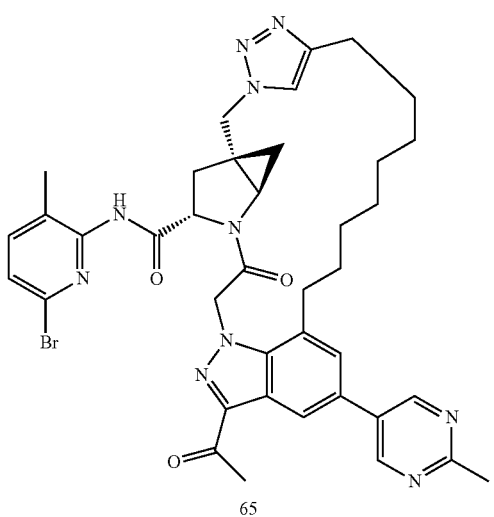

65

The above scheme and following detailed description depicts one non-limiting method for synthesizing compounds of Formula II wherein -$X^9$-$L^3$-$X^{10}$- is

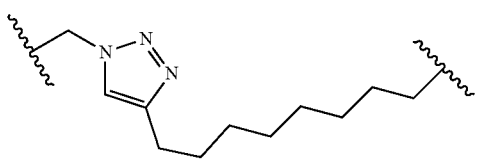 [SMILES: *CCCCCCCCc1cn(C*)nn1]

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: (1R,3S,5R)-2-(2-(3-Acetyl-5-(2-methylpyrimidin-5-yl)-7-(oct-7-en-1-yl)-1H-indazol-1-yl)acetyl)-N-(6-bromo-3-methylpyridin-2-yl)-5-((4-vinyl-1H-1,2,3-triazol-1-yl)methyl)-2-azabicyclo[3.1.0]hexane-3-carboxamide (63S-3)

To a mixture of compound 63S-1 (110 mg, 0.275 mmol), compound 63S-2 (103 mg, 0.25 mmol) and HATU (171 mg, 0.45 mmol) in DMF (5 mL) was added DIPEA (163 mg, 1.25 mmol), and the reaction mixture was stirred at room temperature for 1 hour. The mixture was diluted with EtOAc and washed with 10% aq. LiCl solution and brine, dried over anhydrous $Na_2SO_4$, filtered and concentrated to dryness. The residue was purified via preparatory TLC (eluted with DCM:MeOH=15:1) to give compound 63S-3 (105 mg, yield 52.2%) as a brown solid. LC/MS (ESI) m/z: 805/807 (M+H)$^+$.

Step 2: bicyclo[3.1.0]hexanacyclotetradecaphan-13-ene-3$^3$-carboxamide (X1) and (1$^4$Z,3$^1$R,3$^3$S,3$^5$R,13Z)-6$^3$-acetyl-N-(6-bromo-3-methylpyridin-2-yl)-6$^5$-(2-methylpyrimidin-5-yl)-4-oxo-1$^1$H,6$^1$H-3$^2$-aza-6(1,7)-indazola-1(1,4)-triazola-3(5,2)-bicyclo[3.1.0]hexanacyclotetradecaphan-13-ene-3$^3$-carboxamide (63)

To a solution of compound 63S-3 (105 mg, 0.13 mmol) in degassed toluene (50 mL) was added Grubbs 2$^{nd}$ catalyst (23 mg, 0.026 mmol), and the mixture was stirred at 80° C. for 16 hours under $N_2$ atmosphere. The mixture was concentrated to dryness, and the residue was purified by silica gel column (eluted with DCM:MeOH=45:1) to give a mixture of 63 and 64 (60 mg, yield 59.4%) as a dark red solid. 20 mg of the mixture was further purified by preparatory HPLC to give pure 63 (4 mg, 3.97% yield) and 64 (7 mg, yield 6.93%) as a white solid.

63: $^1$H-NMR (400 MHz, DMSO-$d_6$) δ 10.20 (s, 1H), 9.02 (s, 2H), 8.51 (s, 1H), 8.29 (s, 1H), 7.55 (d, J=8.1 Hz, 1H), 7.49 (s, 1H), 7.36 (d, J=7.9 Hz, 1H), 6.47-6.54 (m, 1H), 6.25-6.38 (m, 2H), 5.57 (d, J=17.7 Hz, 1H), 5.03 (d, J=15.0 Hz, 1H), 4.31-4.42 (m, 2H), 4.03 (d, J=15.2 Hz, 1H), 2.88-3.02 (m, 2H), 2.67 (s, 3H), 2.64 (s, 3H), 2.48 (s, 3H), 2.18-2.28 (m, 2H), 1.46-1.87 (m, 10H), 1.39-1.44 (m, 1H), 1.28-1.33 (m, 1H). LC/MS (ESI) m/z: 777/779 (M+H)$^+$.

64: $^1$H-NMR (400 MHz, DMSO-$d_6$) δ 10.25 (s, 1H), 9.02 (s, 2H), 8.32 (s, 1H), 8.22 (s, 1H), 7.48-7.62 (m, 2H), 7.35 (d, J=7.9 Hz, 1H), 6.40 (d, J=11.4 Hz, 1H), 5.96 (d, J=17.9 Hz, 1H), 5.75 (dt, J=11.3, 7.2 Hz, 1H), 5.64 (d, J=17.9 Hz, 1H), 5.08 (d, J=14.9 Hz, 1H), 4.44-4.52 (m, 1H), 4.34-4.41 (m, 1H), 4.04 (d, J=15.0 Hz, 1H), 3.02-3.10 (m, 1H), 2.87-2.95 (m, 1H), 2.68 (s, 3H), 2.65 (s, 3H), 2.47 (s, 3H), 2.31-2.40 (m, 2H), 1.43-1.82 (m, 10H), 1.30-1.40 (m, 2H). LC/MS (ESI) m/z: 777/779 (M+H)$^+$.

Step 3: $(3^1R,3^3S,3^5R,Z)$-$6^3$-acetyl-N-(6-bromo-3-methylpyridin-2-yl)-$6^5$-(2-methylpyrimidin-5-yl)-4-oxo-$1^1H$, $6^1H$-$3^2$-aza-6(1,7)-indazola-1(1,4)-triazola-3(5,2)-bicyclo[3.1.0]hexanacyclotetradecaphane-$3^3$-carboxamide (65)

To a mixture of 63 and 64 (40 mg, 0.052 mmol) in EtOH (20 mL) was added Rh(PPh$_3$)$_3$Cl (12 mg, 0.013 mmol), and the mixture was stirred under a H$_2$ balloon at 70° C. for 3 hours. The mixture was cooled and concentrated to dryness, and the residue was purified via preparatory HPLC to give compound 65 (8 mg, yield 19.8%) as a white solid. $^1$H-NMR (400 MHz, DMSO-d$_6$) δ 10.18 (s, 1H), 9.01 (s, 2H), 8.31 (d, J=1.5 Hz, 1H), 7.92 (s, 1H), 7.57 (d, J=10.1 Hz, 2H), 7.38 (d, J=7.9 Hz, 1H), 5.95 (d, J=17.8 Hz, 1H), 5.59 (d, J=17.8 Hz, 1H), 4.96 (d, J=14.7 Hz, 1H), 4.38-4.44 (m, 1H), 4.14 (d, J=14.6 Hz, 1H), 4.06-4.11 (m, 1H), 2.97-3.02 (m, 1H), 2.89-2.95 (m, 1H), 2.67 (s, 3H), 2.65 (s, 3H), 2.55-2.63 (m, 2H), 1.93-2.05 (m, 2H), 1.85 (s, 3H), 1.59-1.78 (m, 4H), 1.50-1.59 (m, 2H), 1.38-1.44 (m, 2H), 1.29-1.36 (m, 2H), 1.23-1.28 (m, 2H), 1.13-1.22 (m, 2H). LC/MS (ESI) m/z: 779/781 (M+H)$^+$.

Scheme 41: Synthesis of 66, 67, and 68

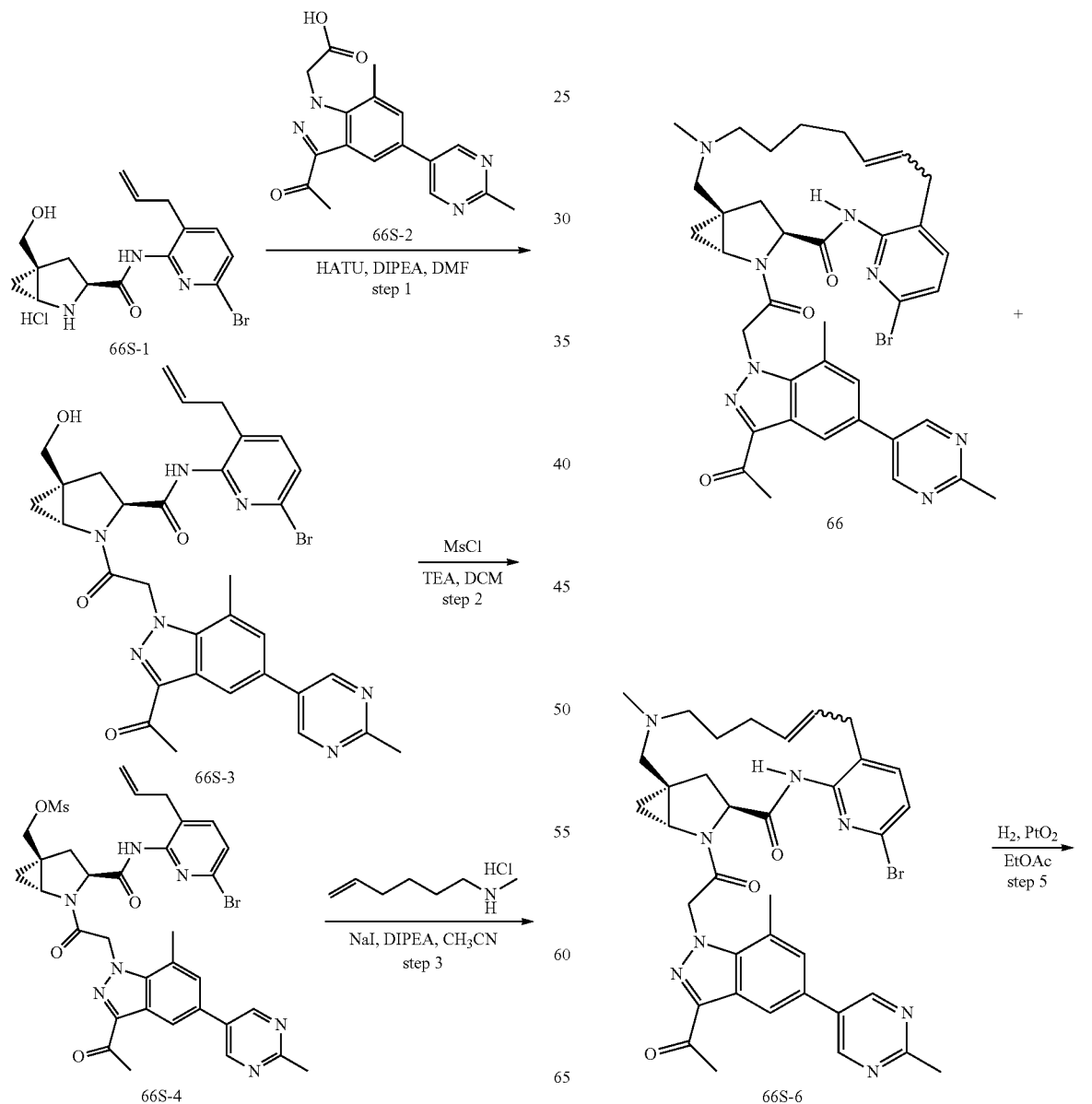

-continued

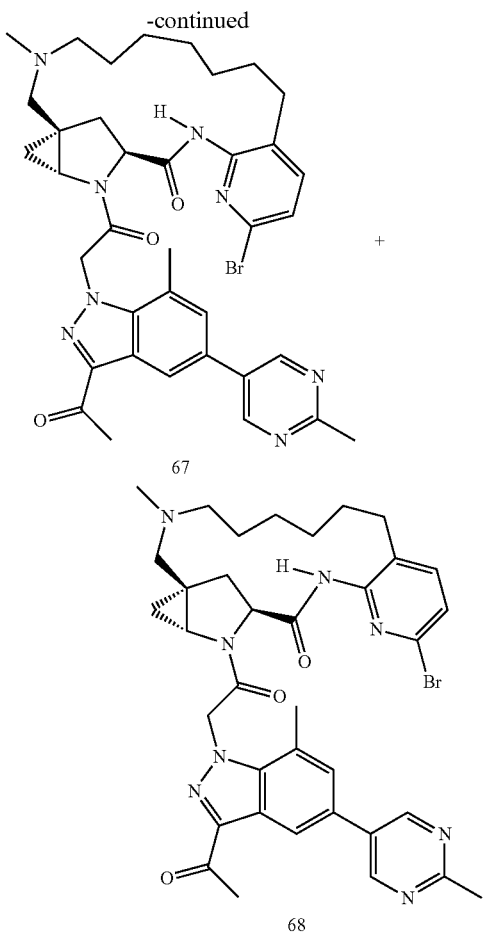

The above scheme and following detailed description depicts one non-limiting method for synthesizing compounds of Formula I wherein -$X^9$-$L^3$-$X^{10}$- is

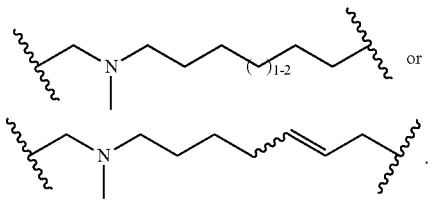

The skilled artisan will recognize that related -$X^9$-$L^3$-$X^{10}$- moieties of different chain lengths, and stereochemistry, in addition $A^1$, $B^2$, and $C^2$ groups as described herein, can be used to afford additional compounds of the present invention.

Step 1: (1R,3S,5S)-2-(2-(3-Acetyl-7-methyl-5-(2-methylpyrimidin-5-yl)-1H-indazol-1-yl)acetyl)-N-(3-allyl-6-bromopyridin-2-yl)-5-(hydroxymethyl)-2-azabicyclo[3.1.0]hexane-3-carboxamide (66S-3)

To a mixture of compound 66S-1 (180 mg, 0.463 mmol) and compound 66S-2 (120 mg, 0.37 mmol) in DMF (5 mL) was added HATU (264 mg, 0.7 mmol) followed by DIPEA (241 mg, 1.85 mmol) at 0° C., and the reaction mixture was stirred at room temperature for 1 hour. The mixture was poured into ice water and extracted with EtOAc twice. The organic layers were washed with brine, dried over anhydrous $Na_2SO_4$ and concentrated under reduced pressure. The residue was purified by chromatography on silica gel (eluted with DCM:MeOH=50:1) to give compound 66S-3 (134 mg, yield 44.1%) as a yellow solid. LC/MS (ESI) m/z: 658/660 (M+H)$^+$.

Step 2: ((1R,3S,5S)-2-(2-(3-acetyl-7-methyl-5-(2-methylpyrimidin-5-yl)-1H-indazol-1-yl)acetyl)-3-((3-allyl-6-bromopyridin-2-yl)carbamoyl)-2-azabicyclo[3.1.0]hexan-5-yl) methyl methanesulfonate (66S-4)

To a solution of compound 66S-3 (0.134 g, 0.2 mmol) in anhydrous dichloromethane (10 mL) was added triethylamine (0.04 g, 0.4 mmol) followed by MSCl (0.035 g, 0.3 mmol) at 0° C., and the reaction mixture was stirred at 0° C. for 30 minutes. The mixture was poured into ice-cooled saturated aq. $NH_4Cl$ solution and extracted with DCM twice. The combined organic layers were washed with water, dried over anhydrous $Na_2SO_4$ and concentrated under reduced pressure to give compound 66S-4 (130 mg, yield 89.9%) as a light oil, which was directly used to the next reaction without further purification. LC/MS (ESI) m/z: 736 (M+H)$^+$.

Step 3: (1R,3S,5R)-2-(2-(3-Acetyl-7-methyl-5-(2-methylpyrimidin-5-yl)-1H-indazol-1-yl)acetyl)-N-(3-allyl-6-bromopyridin-2-yl)-5-((hex-5-en-1-yl(methyl)amino)methyl)-2-azabicyclo[3.1.0]hexane-3-carboxamide (66S-5)

To a solution of compound 66S-4 (0.156 g, 0.212 mmol) in acetonitrile (15 mL) was added N-methylhex-5-en-1-amine hydrochloride (0.064 g, 0.424 mmol), DIPEA (110 mg, 0.85 mmol) followed by NaI (0.032 g, 0.212 mmol) at 0° C., and the reaction mixture was stirred at 45° C. overnight in a sealed tube. The mixture was partitioned with DCM and water. The organic layer was dried over $Na_2SO_4$ and concentrated under reduced pressure. The residue was purified by chromatography on silica gel (eluted with DCM:MeOH=50:1) to give compound 66S-5 (0.115 g, yield 72.3%) as a yellow solid. LC/MS (ESI) m/z: 753 (M+H)$^+$.

Step 4: 66 and 66S-6

To a solution of compound 66S-5 (115 mg, 0.153 mmol) in degassed toluene (60 mL) was added Grubbs $2^{nd}$ catalyst (26 mg, 0.031 mmol). The reaction mixture was degassed under Ar atmosphere three times and stirred at 80° C. under Ar atmosphere for 18 hours. The mixture was concentrated under reduced pressure, and the residue was purified by chromatography on silica gel (eluted with DCM:MeOH=40:1) to give a mixture of compound 66 and compound 66S-6 (70 mg, yield 63.1%) as brown solid. 66: LC/MS (ESI) m/z: 725/727 (M+H)$^+$, compound 66S-6: LC/MS (ESI) m/z: 711/713 (M+H)$^+$.

Step 5: 67 and 68

To a mixture of 66 and compound 66S-6 (35 mg, 0.048 mmol) in EtOAc was added $PtO_2$ (7 mg), and the resulting mixture was stirred under a $H_2$ balloon at room temperature for 1 hour. The mixture was filtered, and the filtrate was concentrated to dryness. The residue was purified via preparatory HPLC to give 67 (6 mg, yield 17.1%) and 68 (4 mg, yield 11.4%) as a white solid.

67: $^1$H-NMR (400 MHz, DMSO-$d_6$) δ 10.29 (s, 1H), 9.02 (s, 2H), 8.31 (s, 1H), 7.65 (d, J=8.1 Hz, 1H), 7.60 (s, 1H), 7.46 (d, J=8.0 Hz, 1H), 6.10 (d, J=17.9 Hz, 1H), 5.65 (d, J=17.9 Hz, 1H), 4.47-4.53 (m, 1H), 3.66-3.69 (m, 1H), 2.70 (s, 3H), 2.67 (s, 3H), 2.64 (s, 3H), 2.34-2.48 (m, 6H), 2.26-2.34 (m, 2H), 2.21 (s, 3H), 1.28-1.58 (m, 10H), 0.98-1.06 (m, 2H). LC/MS (ESI) m/z: 727/729 (M+H)$^+$.

68: $^1$H-NMR (400 MHz, DMSO-$d_6$) δ 10.28 (s, 1H), 9.03 (s, 2H), 8.32 (s, 1H), 7.74 (d, J=8.1 Hz, 1H), 7.63 (s, 1H), 7.50 (d, J=8.0 Hz, 1H), 6.05 (d, J=18.0 Hz, 1H), 5.74 (d, J=17.7 Hz, 1H), 4.56-4.61 (m, 1H), 3.56-3.61 (m, 1H), 2.70 (s, 3H), 2.68 (s, 3H), 2.66 (s, 3H), 2.52-2.60 (m, 2H), 2.29-2.46 (m, 5H), 2.20 (s, 3H), 1.99 (d, J=11.9 Hz, 1H), 1.42-1.70 (m, 6H), 1.28-1.35 (m, 2H), 1.06-1.15 (m, 2H). LC/MS (ESI) m/z: 713/715 (M+H)$^+$.

Scheme 42: Synthesis of (4¹R,4³S,4⁵S,E)-1³-Acetyl-N-(6-bromo-3-methylpyridin-2-yl)-1⁵-(2-methylpyrimidin-5-yl)-3-oxo-1¹H-6,13-dioxa-4²-aza-1(1,6)-indazola-4(2,5)-bicyclo[3.1.0]hexanacyclotridecaphan-8-ene-4³-carboxamide (69), (4¹R,4³S,4⁵S,Z)-13-acetyl-N-(6-bromo-3-methylpyridin-2-yl)-1⁵-(2-methylpyrimidin-5-yl)-3-oxo-1¹H-6,13-dioxa-4²-aza-1(1,6)-indazola-4(2,5)-bicyclo[3.1.0]hexanacyclotridecaphan-8-ene-4³-carboxamide (70), and (4¹R,4³S,4⁵S)-1³-acetyl-N-(6-bromo-3-methylpyridin-2-yl)-1⁵-(2-methylpyrimidin-5-yl)-3-oxo-1¹H-6,13-dioxa-4²-aza-1(1,6)-indazola-4(2,5)-bicyclo[3.1.0]hexanacyclotridecaphane-4³-carboxamide (71)

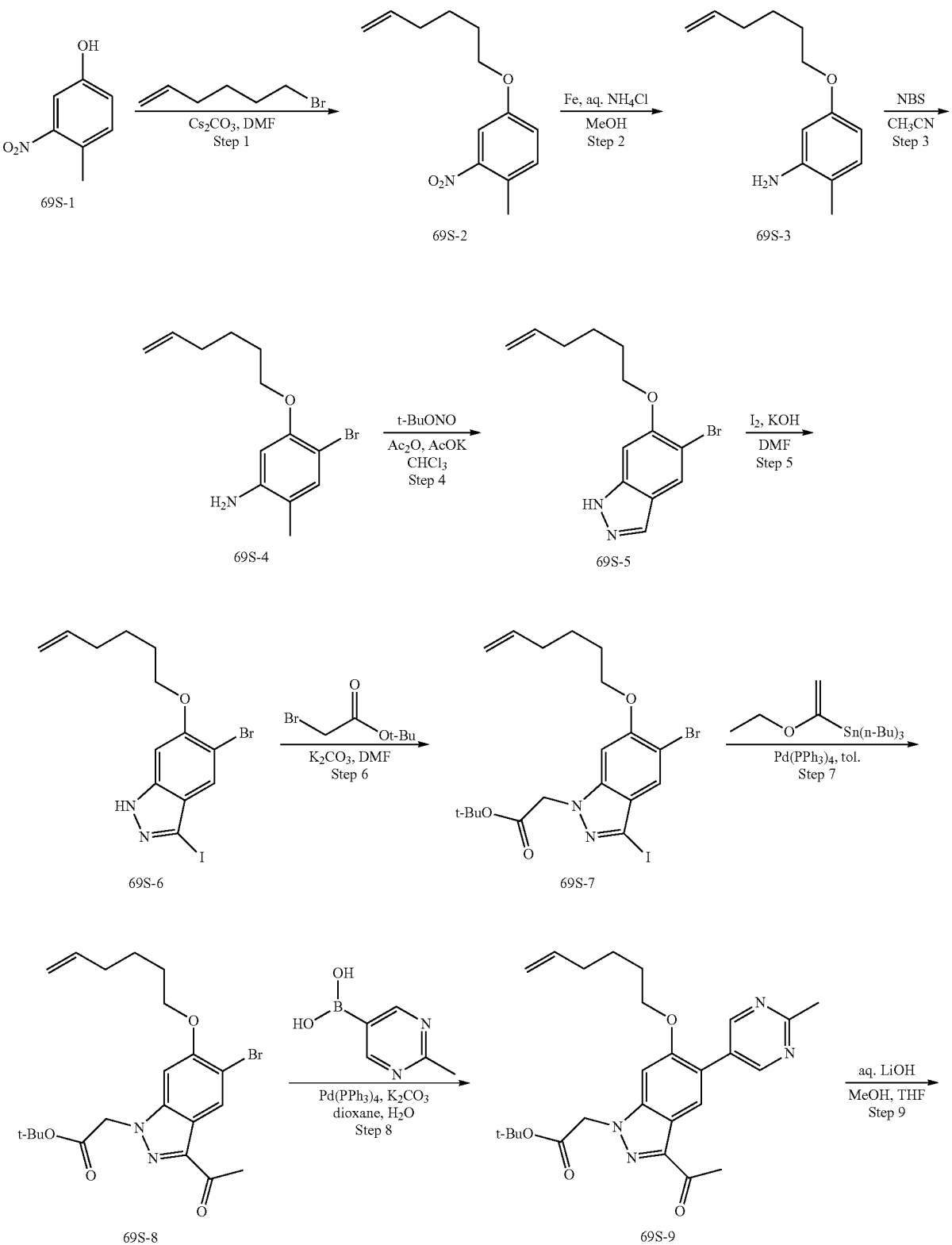

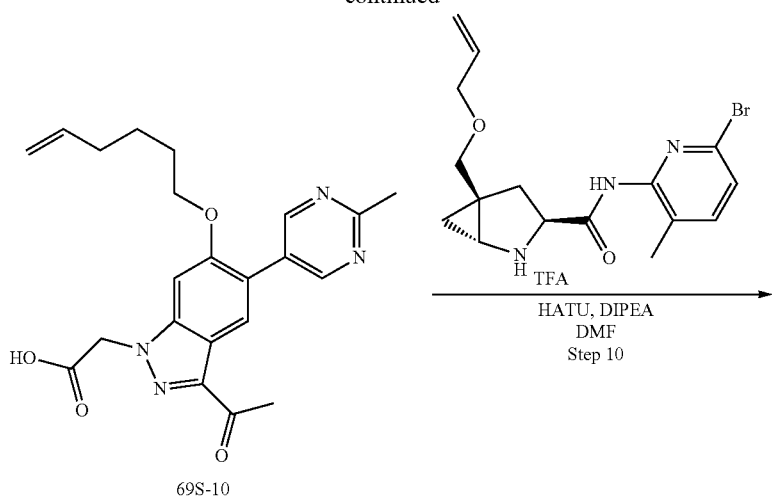
69S-10
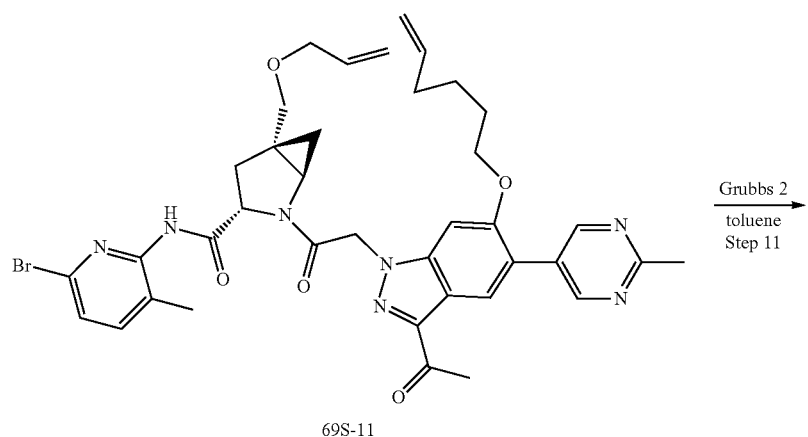
69S-11
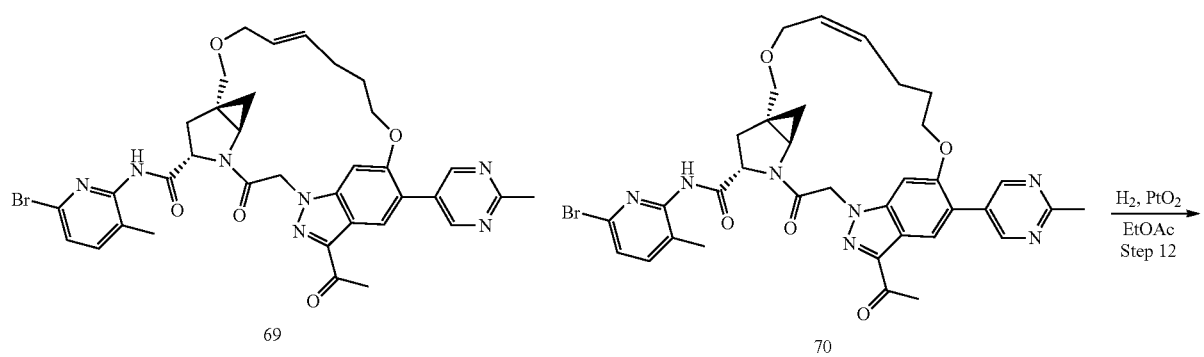
69      70
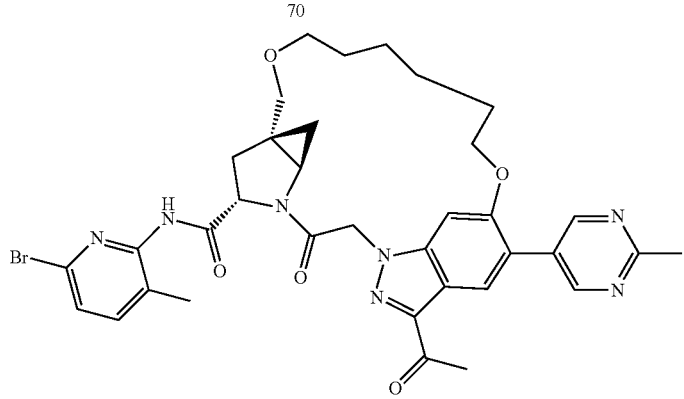
71

The above scheme and following detailed description depicts one non-limiting method for synthesizing compounds of Formula II wherein -X$^9$-L$^3$-X$^{10}$- is

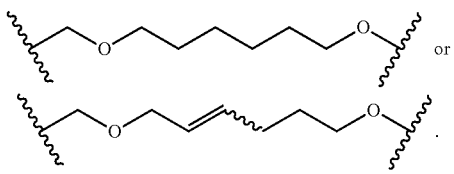

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention. %ps Step 1: 4-(Hex-5-en-1-yloxy)-1-methyl-2-nitrobenzene (69S-2)

Compound 69S-1 (8 g, 52.2 mmol) in dry DMF (80 mL) was treated with cesium carbonate (42.55 g , 130.6 mmol) followed by 6-bromohex-1-ene (12.78 g, 78.36 mmol), and the mixture heated to 80° C. for 30 minutes. After cooling to room temperature, the reaction mixture was treated with water and extracted with EtOAc twice. The combined organic layers were washed with 5% aq. LiOH solution and brine, dried over Na$_2$SO$_4$, filtered and concentrated to dryness. The residue was purified by silica gel column chromatography (eluted with petroleum ether:EtOAc=200:1 to 100:1) to give compound 69S-2 (9 g, yield 73.2%) as a yellow solid.

Step 2: 5-(Hex-5-en-1-yloxy)-2-methylaniline (69S-3)

Compound 69S-2 (9 g, 38.25 mmol) in ethanol (90 mL) and water (15 mL) was treated with ammonium chloride (20.46 g, 0.38 mol) and iron (10.68 g , 0.19 mmol), and the mixture was stirred at 70° C. for 2 hours. The mixture was filtered through celite, and the filter cake was washed with EtOAc. The filtrate was washed with brine, dried over Na$_2$SO$_4$, filtered and concentrated to dryness to give compound 69S-3 (7.5 g, yield 95.5%) as a brown oil, which was directly used to the next reaction without purification.

Step 3: 4-Bromo-5-(hex-5-en-1-yloxy)-2-methylaniline (XS-4)

To a solution of compound 69S-3 (7.5 g, 36.53 mmol) in DMF (80 mL) was added NBS (6.50 g, 36.53 mmol) in portions at 0° C., and the mixture was stirred at room temperature for 1 hour. The mixture was diluted with EtOAc and washed with saturated aq. NH$_4$Cl solution and brine, dried over Na$_2$SO$_4$, filtered and concentrated to dryness. The residue was purified by silica gel chromatography (eluted with petroleum ether:EtOAc=100:1 to 30:1) to give compound 69S-4 (6.5 g, yield 62.6%) as a brown oil.

Step 4: 5-Bromo-6-(hex-5-en-1-yloxy)-1H-indazole (69S-5)

To a mixture of compound 69S-4 (2 g, 7.04 mmol) and potassium acetate (0.2 g, 2.04 mmol) in chloroform (30 mL) was added acetic anhydride (1.63 g, 15.98 mmol) drop-wise at 0° C., and the mixture was stirred at room temperature for 1 hour. The temperature of the mixture was raised to 60° C. and tert-butyl nitrite (1.1 g, 10.6 mmol) was added drop-wise. The resulting mixture was stirred at 60° C. for 16 hours. The mixture was cooled to room temperature, diluted with DCM, washed with water and brine, dried over Na$_2$SO$_4$, filtered and concentrated to dryness. The residue was dissolved in aq. HCl (20 mL, 6M) and the mixture was stirred at room temperature for 4 hrs. The mixture was basified by adding ice-cooled saturated aq. NaHCO$_3$ solution and extracted with EtOAc twice. The combined organic layers were washed with brine, dried over Na$_2$SO$_4$, filtered and concentrated to dryness. The residue was purified by silica gel column chromatography (eluted with petroleum ether:EtOAc=20:1 to 7:1) to give compound 69S-5 (0.65 g, yield 31.3%) as a white solid. LC/MS (ESI) 295/297 m/z: (M+H)$^+$.

Step 5: 5-Bromo-6-(hex-5-en-1-yloxy)-3-iodo-1H-indazole (69S-6)

To a mixture of compound XS-5 (0.65 g, 2.20 mmol) and potassium hydroxide (0.28 g, 4.96 mmol) in DMF (10 mL) was added iodine (0.84 g, 3.30 mmol) at 0° C., and the mixture was stirred at room temperature for 1 hour . The mixture was quenched with saturated aq. Na$_2$S$_2$O$_3$ solution, and EtOAc was added. The organic layer was separated, washed with saturated aq.NH$_4$Cl solution and brine, dried over Na$_2$SO$_4$, filtered and concentrated to dryness to give compound 69S-6 (0.6 g, yield 64.7%) as a brown solid, which was directly used to the next reaction without purification. LC/MS (ESI) 420/422 m/z: (M+H)$^+$.

Step 6: tert-Butyl 2-(5-Bromo-6-(hex-5-en-1-yloxy)-3-iodo-1H-indazol-1-yl)acetate (69S-7)

To a mixture of compound 69S-6 (600 mg, 1.42 mmol) and K$_2$CO$_3$ (492 mg, 3.56 mmol) in DMF (5 mL) was added tert-butyl bromoacetate (306 mg, 1.57 mmol), and the mixture was stirred at room temperature for 16 hours. The mixture was diluted with EtOAc, washed with water and saturated aq. NH$_4$Cl solution, dried over Na$_2$SO$_4$, filtered and concentrated to dryness. The residue was purified by silica gel chromatography (eluted with petroleum ether: EtOAc=30:1 to 15:1) to give compound 69S-7 (465 mg, yield 61.0%) as a white solid. LC/MS (ESI) 535/537 m/z: (M+H)$^+$.

Step 7: tert-Butyl 2-(3-Acetyl-5-bromo-6-(hex-5-en-1-yloxy)-1H-indazol-1-yl)acetate (69S-8)

To a mixture of compound 69S-7 (0.465 g, 0.87 mmol) and tributyl(1-ethoxyvinyl)stannane (345 mg, 0.96 mmol) in toluene (10 mL) was added Pd(PPh$_3$)$_4$ (100 mg, 0.09 mmol). The mixture was degassed under N$_2$ atmosphere three times and stirred at 100° C. under N$_2$ atmosphere for 16 hours. THF (10 mL) and 1N aq. HCl (10 mL) was added to the mixture, and the resulting mixture was stirred at room temperature for 2 hours. The mixture was diluted with EtOAc, washed with water and brine, dried over anhydrous Na$_2$SO$_4$ and concentrated to dryness. The residue was purified by silica gel chromatography (petroleum ether:ethyl acetate=20:0 to 6:1) to give compound 69S-8 (0.18 g, yield 45.9%) as a white solid. LC/MS (ESI) 451/453 m/z: (M+H)$^+$.

Step 8: tert-Butyl 2-(3-Acetyl-6-(hex-5-en-1-yloxy)-5-(2-methylpyrimidin-5-yl)-1H-indazol-1-yl)acetate (69S-9)

To a mixture of compound 69S-8 (0.18 g, 0.40 mmol) and (2-methylpyrimidin-5-yl)boronic acid (65 mg, 0.44 mmol) in 1,4-dioxane (9 mL) and water (1 mL) was added K$_2$CO$_3$ (0.14 g, 0.997 mmol) followed by Pd(PPh$_3$)$_4$ (46 mg, 0.04 mmol). The mixture was degassed under N$_2$ atmosphere three times and stirred at 90° C. under N$_2$ atmosphere overnight. The mixture was partitioned between EtOAc and water, and the separated organic layers were washed with brine, dried over Na$_2$SO$_4$, and concentrated under reduced pressure. The residue was purified by silica gel chromatography (petroleum ether:ethyl acetate=20:1 to 3:1) to give compound 69S-9 (116 mg, yield 62.6%) as a white solid. LC/MS (ESI) 465m/z: (M+H)$^+$.

Step 9: 2-(3-Acetyl-6-(hex-5-en-1-yloxy)-5-(2-methylpyrimidin-5-yl)-1H-indazol-1-yl)acetic Acid (69S-10)

To a solution of compound 69S-9 (116 mg ,0.25 mmol) in MeOH (1 mL),THF (1 mL), and water (1 mL) was added LiOH (30 mg, 1.25 mmol), and the mixture was stirred at room temperature for 2 hours. The mixture was concentrated to dryness, and the residue was dissolved in water and washed with ether twice. The aqueous layer was acidified by adding 1N aq. HCl to pH~4 and extracted with EtOAc twice. The combined organic layers were washed with brine, dried over $Na_2SO_4$, and concentrated under reduced pressure to give compound 69S-10 (100 mg, yield 98.1%) as a white solid. LC/MS (ESI) 409 m/z: $(M+H)^+$.

Step 10: (1R,3S,5S)-2-(2-(3-acetyl-6-(hex-5-en-1-yloxy)-5-(2-methylpyrimidin-5-yl)-1H-indazol-1-yl)acetyl)-5-((allyloxy)methyl)-N-(6-bromo-3-methylpyridin-2-yl)-2-azabicyclo[3.1.0]hexane-3-carboxamide (69S-11)

To a mixture of (1R,3S,5S)-5-((allyloxy)methyl)-N-(6-bromo-3-methylpyridin-2-yl)-2-azabicyclo[3.1.0]hexane-3-carboxamide (101 mg, 0.274 mmol) and compound 69S-10 (102 mg, 0.250 mmol) in DMF (3 mL) was added HATU (142 mg, 0.375 mmol) and DIPEA (97 mg, 0.749 mmol) at 0° C., and the mixture was stirred at 25° C. for 1 hour. The mixture was diluted with EtOAc, washed with 10% aq. LiCl solution and brine, dried and concentrated to dryness. The residue was purified by silica gel chromatography (petroleum ether:ethyl acetate=20:1 to 1:1) to give compound 69S-11 (150 mg, yield 79.4%) as a white solid. LC/MS (ESI) 756 m/z: $(M+H)^+$.

Step 11: $(4^1R,4^3S,4^5S,E)$-$1^3$-Acetyl-N-(6-bromo-3-methylpyridin-2-yl)-$1^5$-(2-methylpyrimidin-5-yl)-3-oxo-$1^1$H-6,13-dioxa-$4^2$-aza-1(1,6)-indazola-4(2,5)-bicyclo[3.1.0]hexanacyclotridecaphan-8-ene-$4^3$-carboxamide (69) and $(4^1R,4^3S,4^5S,Z)$-13-acetyl-N-(6-bromo-3-methylpyridin-2-yl)-$1^5$-(2-methylpyrimidin-5-yl)-3-oxo-$1^1$H-6,13-dioxa-$4^2$-aza-1(1,6)-indazola-4(2,5)-bicyclo[3.1.0]hexanacyclotridecaphan-8-ene-$4^3$-carboxamide (70)

To a solution of compound 69S-11 (150 mg, 0.198 mmol) in degassed toluene (150 mL) was added Grubbs $2^{nd}$ generation catalyst (34 mg, 0.04 mmol), and the mixture was stirred at 80° C. under $N_2$ atmosphere for 16 hours. The mixture was concentrated to dryness and the residue was purified by preparatory HPLC to give 69 (15 mg, Yield 10.6%) and 70 (10 mg, Yield 7.07%) as white solids.

69: $^1$H-NMR (400 MHz, $CD_3OD$) δ 8.82 (s, 2H), 8.16 (s, 1H), 7.47 (d, J=8.0 Hz, 1H), 7.31 (d, J=7.9 Hz, 1H), 7.24 (s, 1H), 5.75 (d, J=16.0 Hz, 1H), 5.68-5.50 (m, 3H), 5.42 (d, J=15.9 Hz, 1H), 4.57 (s, 1H), 4.39-4.33 (m, 1H), 4.20-4.14 (m, 2H), 4.14-4.06 (m, 2H), 4.01 (d, J=11.4 Hz, 1H), 3.22 (d, J=11.4 Hz, 1H), 2.74 (s, 3H), 2.67 (s, 3H), 2.60-2.49 (m, 2H), 2.42-2.28 (m, 2H), 2.21-2.11 (m, 2H), 1.98 (s, 3H), 1.29 (s, 3H), 0.99-0.94 (m, 1H), 0.92-0.84 (m, 2H). LC/MS (ESI) 714 /716 m/z: $(M+H)^+$.

70: $^1$H-NMR (400 MHz, DMSO-$d_6$) δ 10.34 (s, 1H), 8.82 (s, 2H), 8.07 (s, 1H), 7.68 (s, 1H), 7.64 (d, J=7.9 Hz, 1H), 7.45 (d, J=8.0 Hz, 1H), 6.00 (d, J=15.3 Hz, 1H), 5.57-5.29 (m, 3H), 5.07 (d, J=15.0 Hz, 1H), 4.40 (dd, J=9.1, 4.8 Hz, 1H), 4.16 (dd, J=9.1, 4.8 Hz, 1H), 4.08-4.02 (m, 1H), 3.76-3.67 (m, 2H), 3.58-3.53 (m, 1H), 3.48 (d, J=9.4 Hz, 1H), 2.68 (s, 3H), 2.60 (s, 3H), 2.34-2.21 (m, 2H), 2.11 (s, 3H), 2.06-1.81 (m, 4H), 1.76-1.69 (m, 1H). LC/MS (ESI) 714/716 m/z: $(M+H)^+$.

Step 12: $(4^1R,4^3S,4^5S)$-$1^3$-acetyl-N-(6-bromo-3-methylpyridin-2-yl)-$1^5$-(2-methylpyrimidin-5-yl)-3-oxo-$1^1$H-6,13-dioxa-$4^2$-aza-1(1,6)-indazola-4(2,5)-bicyclo[3.1.0]hexanacyclotridecaphane-$4^3$-carboxamide (71)

To a mixture of 69 and 70 (19 mg, 0.027 mmol) in EtOAc (2 mL) was added $PtO_2$ (4 mg). The mixture was degassed under $N_2$ atmosphere three times and stirred under a $H_2$ balloon at room temperature for 1 hour. The mixture was filtered and concentrated to dryness. The residue was purified by preparatory HPLC to give 71 (2 mg, yield 10.5%). $^1$H-NMR (400 MHz, DMSO-$d_6$) δ 10.33 (s, 1H), 8.77 (s, 2H), 8.04 (s, 1H), 7.61 (d, J=8.2 Hz, 1H), 7.52 (s, 1H), 7.41 (d, J=7.9 Hz, 1H), 5.72 (d, J=15.5 Hz, 1H), 5.46 (d, J=15.6 Hz, 1H), 4.48 (dd, J=9.3, 4.4 Hz, 1H), 4.38-4.31 (m, 1H), 4.21-4.14 (m, 1H), 3.98-3.92 (m, 1H), 3.71 (d, J=10.0 Hz, 1H), 3.10 (d, J=10.0 Hz, 1H), 2.67 (s, 3H), 2.61 (s, 3H), 2.38-2.27 (m, 2H), 2.23-2.10 (m, 2H), 2.07 (s, 3H), 1.92-1.76 (m, 2H), 1.76-1.61 (m, 2H), 1.51-1.44 (m, 2H), 1.32-1.20 (m, 2H), 0.53-0.47 (m, 1H), 0.37-0.31 (m, 1H). LC/MS (ESI) 716/718 m/z: $(M+H)^+$.

Scheme 43: Synthesis of $(4^1R,4^3S,4^5S,E)$-13-Acetyl-N-(6-bromo-3-methylpyridin-2-yl)-3,14-dioxo-$1^1$H-6,13-dioxa-$4^2$,15-diaza-1(1,6)-indazola-4(2,5)-bicyclo[3.1.0]hexanacyclopentadecaphan-8-ene-4-carboxamide (72) and $(4^1R,4^3S,4^5S)$-13-Acetyl-N-(6-bromo-3-methylpyridin-2-yl)-3,14-dioxo-$1^1$H-6,13-dioxa-$4^2$,15-diaza-1(1,6)-indazola-4(2,5)-bicyclo[3.1.0]hexanacyclopentadecaphane-$4^3$-carboxamide (73)

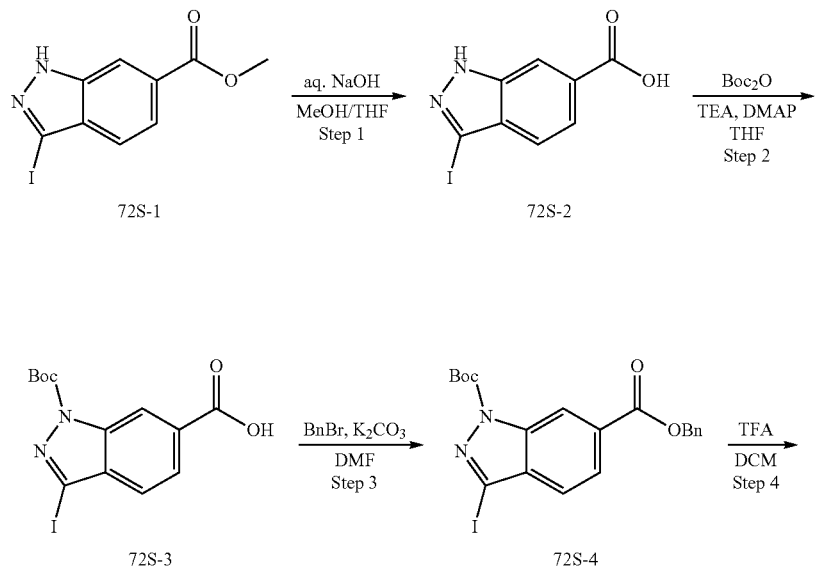

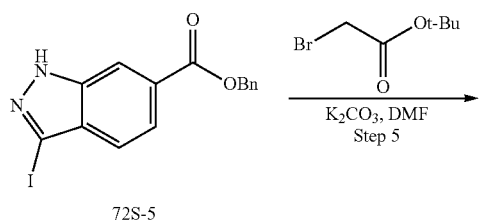
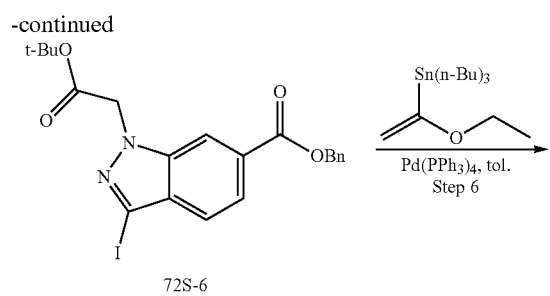
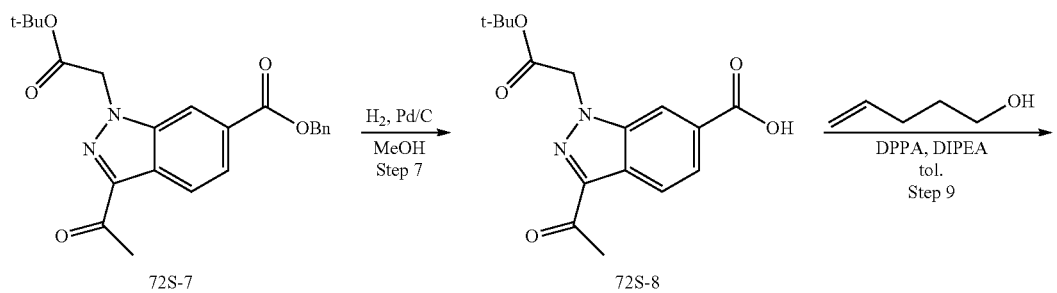
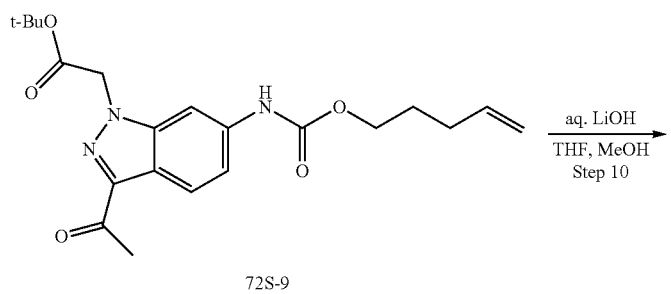
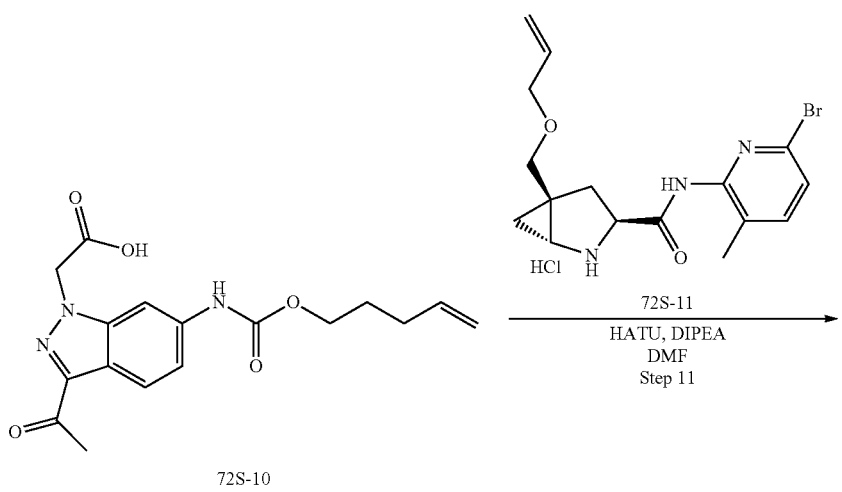

-continued

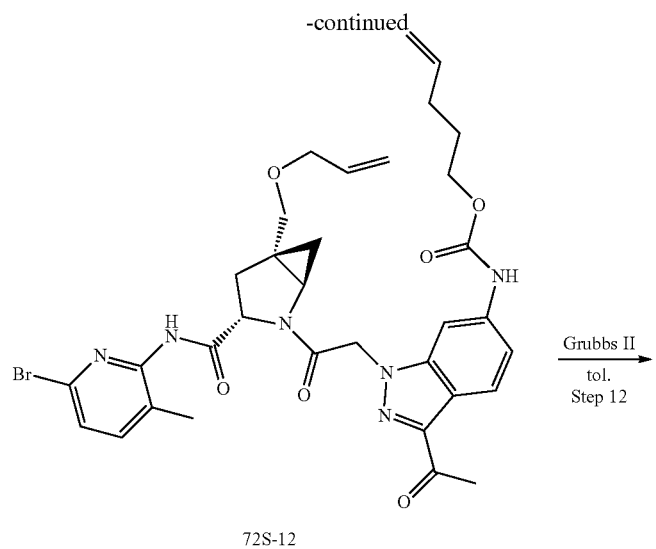

72S-12

Grubbs II
tol.
Step 12

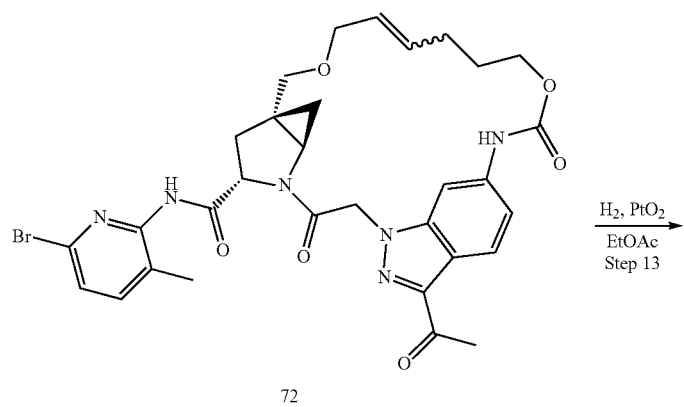

72

H₂, PtO₂
EtOAc
Step 13

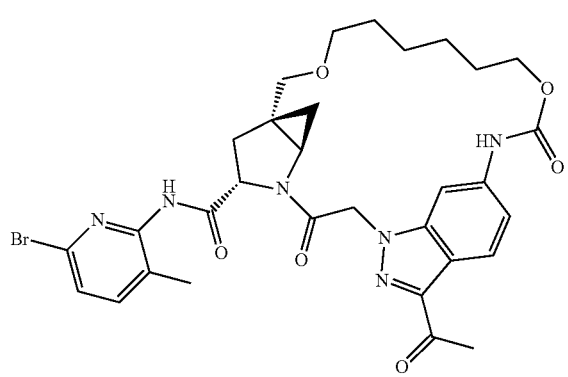

73

The above scheme and following detailed description depicts one non-limiting method for synthesizing compounds of Formula II wherein -X⁹-L³-X¹⁰- is

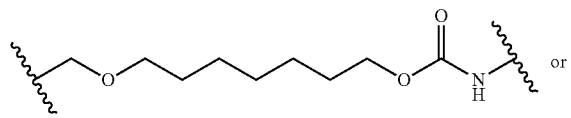

or

-continued

The skilled artisan will recognize that related -X⁹-L³-X¹⁰- moieties of different chain lengths, and stereochemistry, in addition A¹, B², and C² groups as described herein, can be used to afford additional compounds of the present invention.

Step 1: 3-Iodo-1H-indazole-6-carboxylic Acid (72S-2)

To a solution of methyl 3-iodo-1H-indazole-6-carboxylate (15 g, 49.6 mmol) in methanol (30 mL), tetrahydrofuran (30 mL), and water (30 mL) was added sodium hydroxide (7.9 g, 198.6 mmol), and the mixture was stirred at room temperature for 8 hours. The pH was adjusted to ~5 by adding 1N aq. HCl, and the slurry was filtered. The filter cake was washed with water and dried under vacuum to give 3-iodo-1H-indazole-6-carboxylic acid (14 g, yield 97.9%) as a white solid, which was directly used to the next reaction without purification. LC/MS (ESI) m/z: 289 (M+H)$^+$.

Step 2: 1-(tert-Butoxycarbonyl)-3-iodo-1H-indazole-6-carboxylic Acid (72S-3)

To a solution of 3-iodo-1H-indazole-6-carboxylic acid (13 g, 45.1 mmol) in THF (100 mL) was added di-tert-butyl dicarbonate (14.8 g, 67.7 mmol), DMAP (0.55 g, 4.5 mmol) and triethylamine (5.02 g, 49.6 mmol), and the mixture was stirred at room temperature for 2 hours. The mixture was diluted with EtOAc, washed with water and brine, dried and concentrated to give compound XS-3 (17.1 g, Yield 97.7%) as a yellow solid, which was used directly in the next step. LC/MS (ESI) m/z: 389 (M+H)$^+$.

Step 3: 6-Benzyl 1-tert-Butyl 3-iodo-1H-indazole-1,6-dicarboxylate (72S-4)

To a solution of compound XS-3 (17 g, 43.8 mmol) in DMF (100 mL) was added Cs$_2$CO$_3$ (18.5 g, 56.9 mmol) and benzyl bromide (8.9 g, 52.5 mmol) at 0° C., and the mixture was stirred at room temperature for 1 hour. The reaction mixture was diluted with EtOAc, washed with saturated aq. NH$_4$Cl solution and brine, dried over anhydrous Na$_2$SO$_4$, filtered and concentrated to give 6-benzyl 1-tert-butyl 3-iodoindazole-1,6-dicarboxylate (18.9 g, yield 90.2%) as a yellow solid. LC/MS (ESI) m/z: 479 (M+H)$^+$.

Step 4: Benzyl 3-Iodo-1H-indazole-6-carboxylate (72S-5)

To a solution of 6-benzyl 1-tert-butyl 3-iodoindazole-1,6-dicarboxylate (18.9 g, 38.2 mmol) in DCM (100 mL) was added TFA (33 mL) at 0° C., and the mixture was stirred at room temperature for 2 hours. The reaction mixture was concentrated to dryness, and the residue was basified with saturated aq. NaHCO$_3$ solution. The mixture was extracted with EtOAc, and the organic layer was dried over anhydrous Na$_2$SO$_4$, filtered and concentrated to dryness to give benzyl 3-iodo-1H-indazole-6-carboxylate (8.6 g, yield 59.5%) as a yellow solid, which was used directly in the next step. LC/MS (ESI) m/z: 379 (M+H)$^+$.

Step 5: Benzyl 1-[2-(tert-Butoxy)-2-oxoethyl]-3-iodoindazole-6-carboxylate (72S-6)

To a solution of benzyl 3-iodo-1H-indazole-6-carboxylate (8 g, 21.2 mmol) in DMF (80 mL) was added tert-butyl 2-bromoacetate (10.7 g, 55.0 mmol) and potassium carbonate (8.77 g, 63.5 mmol) at 0° C., and the mixture was stirred at room temperature for 16 hours. The mixture was diluted with EtOAc, washed with water, saturated aq. NH$_4$Cl solution and brine successively, dried over anhydrous Na$_2$SO$_4$, filtered and concentrated to dryness. The residue product was purified by silica gel chromatography (eluted with PE:EtOAc=20:1) to give benzyl 1-[2-(tert-butoxy)-2-oxoethyl]-3-iodoindazole-6-carboxylate (6.5 g, yield 62.2%) as a yellow solid. LC/MS (ESI) m/z: 493 (M+H)$^+$.

Step 6: Benzyl 3-Acetyl-1-[2-(tert-butoxy)-2-oxoethyl]indazole-6-carboxylate (72S-7)

To a solution of benzyl 1-[2-(tert-butoxy)-2-oxoethyl]-3-iodoindazole-6-carboxylate (2.7 g, 5.48 mmol) in toluene (30 mL) was added tributyl(1-ethoxyethenyl)stannane (2.57 g, 7.13 mmol) and Pd(PPh$_3$)$_4$ (0.634 g, 0.55 mmol). The mixture was degassed under N$_2$ atmosphere three times and stirred at 100° C. under N$_2$ atmosphere for 16 hours. The mixture was concentrated to dryness, and the residue was dissolved in THF (10 mL). 1N aq. HCl solution (10 mL) was added, and the mixture was stirred at room temperature for 1 hour. The mixture was extracted with EtOAc, washed with brine, dried over anhydrous Na$_2$SO$_4$, filtered and concentrated to dryness. The residue was purified by silica gel chromatography (eluted with PE:EtOAc=20:1) to give benzyl 3-acetyl-1-[2-(tert-butoxy)-2-oxoethyl]indazole-6-carboxylate (2 g, yield 89.3%) as a yellow solid. LC/MS (ESI) m/z: 409 (M+H)$^+$.

Step 7: 3-Acetyl-1-[2-(tert-butoxy)-2-oxoethyl]indazole-6-carboxylic Acid (72S-8)

To a solution of benzyl 3-acetyl-1-[2-(tert-butoxy)-2-oxoethyl]indazole-6-carboxylate (2 g, 4.897 mmol) in MeOH (30 mL) was added Pd/C (0.2 g, 10% wt). The mixture was degassed under N$_2$ three times and stirred under a H$_2$ balloon at room temperature for 2 hours. The mixture was filtered and the filtrate was concentrated to dryness to give 3-acetyl-1-[2-(tert-butoxy)-2-oxoethyl]indazole-6-carboxylic acid (1.5 g, yield 96.2%) as a yellow solid. LC/MS (ESI) m/z: 319 (M+H)$^+$.

Step 8: tert-Butyl 2-(3-Acetyl-6-{[(pent-4-en-1-yloxy)carbonyl]amino}indazol-1-yl)acetate (72S-9)

To a solution of 3-acetyl-1[2-(tert-butoxy)-2-oxoethyl]indazole-6-carboxylic acid (0.3 g, 0.94 mmol) in toluene (20 mL) was added DPPA (0.39 g, 1.4 mmol) and DIPEA (0.49 mL, 2.83 mmol), and mixture was stirred at room temperature for 1 hour. 4-Penten-1-ol (0.081 g, 0.94 mmol) was added, and the resulting mixture was stirred at 100° C. under N$_2$ atmosphere for 16 hours. The mixture was diluted with EtOAc, washed with saturated aq.NaHCO$_3$ solution and brine, dried over anhydrous Na$_2$SO$_4$, and concentrated to dryness. The residue was purified by column chromatography on silica gel (eluted with PE:EtOAc=10:1) to give tert-butyl 2-(3-acetyl-6-{[(pent-4-en-1-yloxy)carbonyl]amino}indazol-1-yl)acetate (0.17 g, yield 44.9%). LC/MS (ESI) m/z: 402 (M+H)$^+$.

Step 9: (3-Acetyl-6-{[(pent-4-en-1-yloxy)carbonyl]amino}indazol-1-yl)acetic Acid (72S-10)

To a solution of tert-butyl 2-(3-acetyl-6-{[(pent-4-en-1-yloxy)carbonyl]amino}indazol-1-yl)acetate (0.1 g, 0.25 mmol) in MeOH (2 mL) and THF (2 mL) was added a solution of LiOH (0.024 g, 0.1 mmol) in water (1 mL), and the mixture was stirred at 0° C. for 1 hour. The mixture was concentrated to dryness, and the residue was diluted with water and washed with ether twice. The aqueous layer was acidified by 1 N aq. HCl to pH ~3 and extracted with DCM twice. The combined organic layers were dried with anhydrous Na$_2$SO$_4$, filtered and concentrated to dryness to give (3-acetyl-6-{[(pent-4-en-1-yloxy)carbonyl]amino}indazol-1-yl)acetic acid (80 mg, yield 93%) as a yellow solid. LC/MS (ESI) m/z: 346 (M+H)$^+$.

Step 10: (1R,2S,5S)-3-{2-[3-Acetyl-5-(2-methylpyrimidin-5-yl)indazol-1-yl]acetyl}-N-[(3-chloro-2-fluorophenyl)methyl]-3-azabicyclo[3.1.0]hexane-2-carboxamide (72S-12)

To a solution of (1R,2S,5S)-N-[(3-Chloro-2-fluorophenyl)methyl]-3-azabicyclo[3.1.0]hexane-2-carboxamide (50 mg, 0.18 mmol) in DMF (3 mL) was added [3-acetyl-5-(2-methylpyrimidin-5-yl)indazol-1-yl]acetic acid (64 mg, 0.205 mmol), HATU (0.106 g, 0.28 mmol) and DIPEA (0.072 g, 0.56 mmol), and the mixture was stirred at 25° C. for 1 hour. The mixture was diluted with EtOAc, washed with saturated aq.NH$_4$Cl solution and brine successively, dried over anhydrous Na$_2$SO$_4$, and concentrated to dryness. The residue was purified by column chromatography on silica gel (eluted with PE:EtOAc=2:1) to give compound XS-12 (55 mg, yield 44%) as a yellow solid. LC/MS (ESI) m/z: 694 (M+H)$^+$.

Step 12: ($4^1$R,$4^3$S,$4^5$S,E)-13-Acetyl-N-(6-bromo-3-methylpyridin-2-yl)-3,14-dioxo-$1^1$H-6,13-dioxa-$4^2$,15-diaza-1(1,6)-indazola-4(2,5)-bicyclo[3.1.0]hexanacyclopentadecaphan-8-ene-4-carboxamide (72)

To a solution of 72S-12 (0.14 g, 0.20 mmol) in degassed toluene (100 mL) was added Grubbs $2^{nd}$ generation catalyst (0.034 g, 0.04 mmol). The mixture was degassed under N$_2$ atmosphere three times and stirred at 80° C. under N$_2$ atmosphere for 2 hours. The mixture was concentrated to dryness, and the residue was purified by silica gel chromatography (eluted with PE:EtOAc=1:1) and further purified by preparatory HPLC to give 72 (92 mg, yield 68.5%) as a white solid. $^1$H-NMR (400 MHz, DMSO-d$_6$) δ 10.09 (s, 1H), 9.86-9.72 (m, 1H), 8.02-7.98 (m, 1H), 7.87-7.69 (m, 1H), 7.61-7.56 (m, 1H), 7.44-7.39 (m, 1H), 7.05-7.00 (m, 1H), 6.20-6.05 (m, 1H), 5.75 (s, 1H), 5.65-5.39 (m, 3H), 4.92-4.78 (m, 1H), 4.53-4.41 (m, 1H), 4.41-4.31 (m, 1H), 4.31-4.21 (m, 1H), 4.16-4.04 (m, 2H), 3.97 (s, 1H), 3.91-3.85 (m, 1H), 3.77 (s, 1H), 2.70-2.57 (m, 4H), 2.40-2.33 (m, 1H), 2.07-1.94 (m, 4H), 1.37 (d, J=6.6 Hz, 2H), 1.15 (m, 1H), 1.04-0.92 (m, 1H). LC/MS (ESI) m/z: 667 (M+H)$^+$.

Step 13: ($4^1$R,$4^3$S,$4^5$S)-13-Acetyl-N-(6-bromo-3-methylpyridin-2-yl)-3,14-dioxo-$1^1$H-6,13-dioxa-$4^2$,15-diaza-1(1,6)-indazola-4(2,5)-bicyclo[3.1.0]hexanacyclopentadecaphane-$4^3$-carboxamide (73)

To a solution of 72 (35 mg, 0.0526 mmol) in EtOAc (3 mL) was added platinum dioxide (5 mg, 0.022 mmol) at 0° C. The mixture was degassed under N$_2$ atmosphere and stirred under a H$_2$ balloon at room temperature for 10 minutes. The reaction mixture was filtered and concentrated to dryness. The residue was purified by preparatory HPLC to give 73 (3 mg, yield 8.5%). $^1$H-NMR (400 MHz, DMSO-d$_6$) δ 10.06 (s, 1H), 9.79 (s, 1H), 8.00 (d, J=8.7 Hz, 1H), 7.59 (d, J=8.0 Hz, 1H), 7.41 (d, J=7.9 Hz, 1H), 7.08-7.02 (m, 1H), 5.60 (d, J=17.0 Hz, 1H), 5.48 (d, J=16.4 Hz, 1H), 4.45-4.38 (m, 1H), 4.16-4.06 (m, 2H), 3.82-3.71 (m, 2H), 3.58-3.43 (m, 3H), 3.15 (d, J=11.0 Hz, 1H), 2.60 (s, 3H), 2.44-2.37 (m, 1H), 2.33-2.26 (m, 1H), 2.00 (s, 3H), 1.73 (d, J=18.0 Hz, 2H), 1.55 (s, 2H), 1.38 (s, 3H), 1.23 (m, 1H), 0.92-0.80 (m, 2H). LC/MS (ESI) m/z: 667 (M+H)$^+$.

Scheme 44: Synthesis of ($4^1$R,$4^3$S,$4^5$S,E)-$1^3$-Acetyl-N-(6-bromo-3-methylpyridin-2-yl)-3,15-dioxo-$1^1$H-6-oxa-$4^2$,14-diaza-1(1,6)-indazola-4(2,5)-bicyclo[3.1.0]hexanacyclopentadecaphan-8-ene-$4^3$-carboxamide (74) and ($4^1$R,$4^3$S,$4^5$S)-$1^3$-Acetyl-N-(6-bromo-3-methylpyridin-2-yl)-3,15-dioxo-$1^1$H-6-oxa-$4^2$,$1^4$-diaza-1(1,6)-indazola-4(2,5)-bicyclo[3.1.0]hexanacyclopentadecaphane-$4^3$-carboxamide (75)

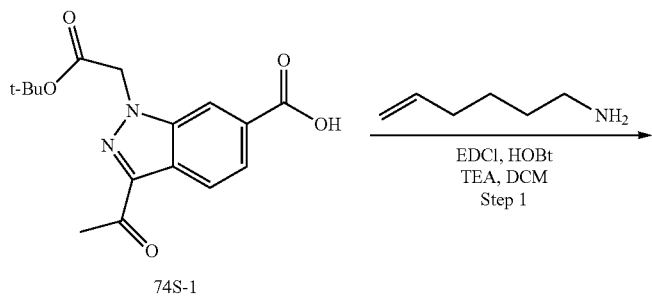

74S-1

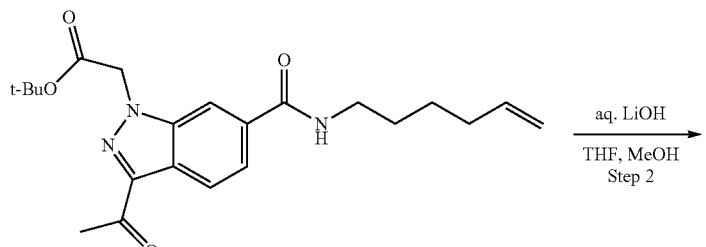

74S-2

-continued
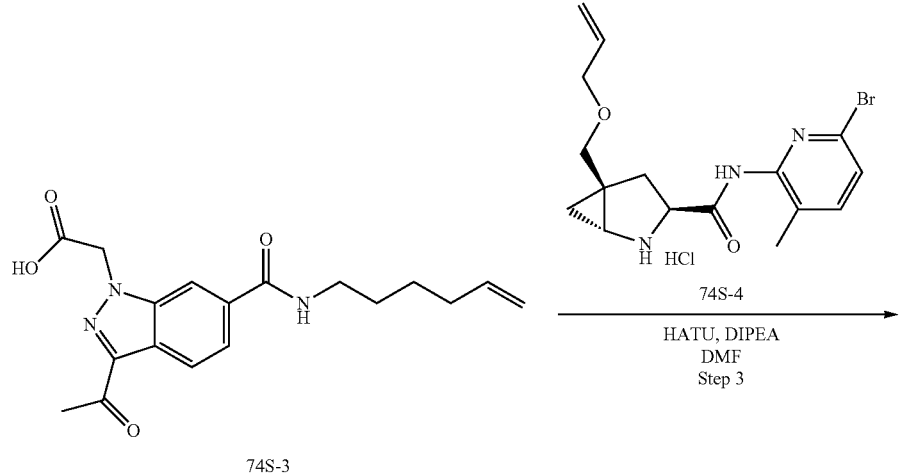
74S-3
74S-4
HATU, DIPEA
DMF
Step 3
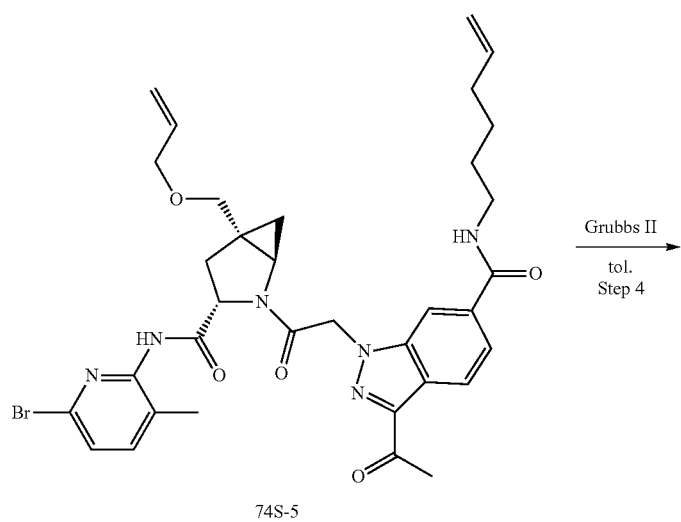
74S-5
Grubbs II
tol.
Step 4
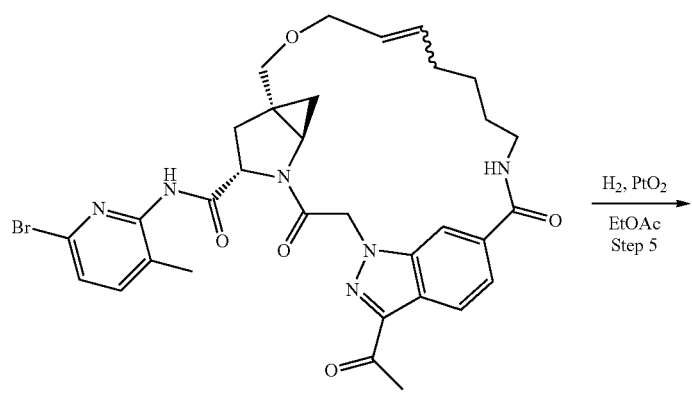
74
H₂, PtO₂
EtOAc
Step 5

-continued

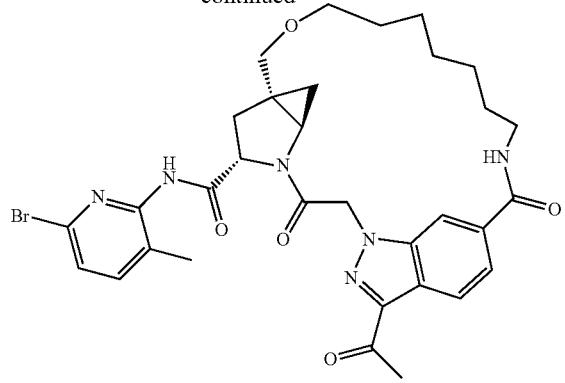

75

The above scheme and following detailed description depicts one non-limiting method for synthesizing compounds of Formula II wherein -X$^9$-L$^3$-X$^{10}$- is

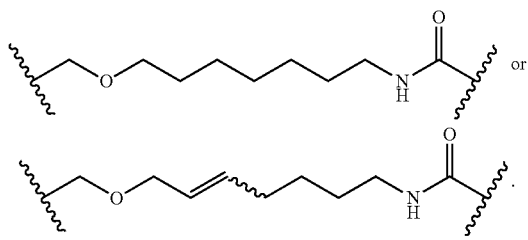

The skilled artisan will recognize that related -X$^9$-L$^3$-X$^{10}$- moieties of different chain lengths, and stereochemistry, in addition A$^1$, B$^2$, and C$^2$ groups as described herein, can be used to afford additional compounds of the present invention.

Step 1 : tert-Butyl 2-{3-acetyl-6-[(hex-5-en-1-yl)carbamoyl]indazol-1-yl}acetate (74S-2)

To a solution of 3-acetyl-1-[2-(tert-butoxy)-2-oxoethyl]indazole-6-carboxylic acid (200 mg, 0.63 mmol) in dichloromethane (3 mL) was added triethylamine (318 mg, 3.14 mmol) and hex-5-en-1-amine hydrochloride (85 mg, 0.63 mmol) followed by EDCI (181 mg, 0.94 mmol) and 1-Hydroxybenzotriazole (144 mg, 1.07 mmol) at 0° C., and the reaction was stirred at room temperature for 1 hour. The mixture was diluted with water and extracted with DCM twice. The combined organic layers were washed with saturated aq. NH$_4$Cl solution and brine, dried with anhydrous Na$_2$SO$_4$ and concentrated to dryness. The residue was purified by chromatography on silica gel (eluted with PE:EtOAc=6:1) to give tert-butyl 2-{3-acetyl-6-[(hex-5-en-1-yl)carbamoyl]indazol-1-yl}acetate (110 mg, yield 43.83%) as a light yellow oil. LC/MS (ESI) m/z: 400 (M+H)$^+$.

Step 2 : {3-Acetyl-6-[(hex-5-en-1-yl)carbamoyl]indazol-1-yl}acetic Acid (74S-3)

To a solution of tert-butyl 2-{3-acetyl-6-[(hex-5-en-1-yl)carbamoyl]indazol-1-yl}acetate (110 mg, 0.28 mmol) in MeOH/THF (4 mL, v/v=1:1) was added a solution of lithium hydroxide (46 mg, 1.10 mmol) in water (2 mL) at 0° C., and the mixture was stirred at room temperature for 1 hour. The reaction mixture was concentrated to dryness, and the residue was diluted with water and washed with ether twice. The aqueous layer was acidified by adding 1N aq. HCl and extracted with DCM twice. The combined organic layer was washed with brine, dried and concentrated to dryness to give {3-acetyl-6-[(hex-5-en-1-yl)carbamoyl]indazol-1-yl}acetic acid (95 mg, yield 100%), which was used directly in the next step. LC/MS (ESI) m/z: 344 (M+H)$^+$.

Step 3: 3-Acetyl-1-{2-[(1R,3S,5S)-3-[(6-bromo-3-methylpyridin-2-yl)carbamoyl]-5-[(prop-2-en-1-yloxy)methyl]-2-azabicyclo[3.1.0]hexan-2-yl]-2-oxoethyl}-N-(hex-5-en-1-yl)indazole-6-carboxamide (74S-5)

To a mixture of {3-acetyl-6-[(hex-5-en-1-yl)carbamoyl]indazol-1-yl}acetic acid (99 mg, 0.28 mmol) and (1R,3S,5S)-N-(6-bromo-3-methylpyridin-2-yl)-5-[(prop-2-en-1-yloxy)methyl]-2-azabicyclo[3.1.0]hexane-3-carboxamide hydrochloride (113 mg, 0.28 mmol) in DMF (3 mL) was added DIPEA (186 mg, 1.44 mmol) and HATU (164 mg, 0.43 mmol) at 0° C., and the mixture was stirred at room temperature for 1 hour. The mixture was diluted with water and extracted with EtOAc. The organic layer was washed with brine, dried and concentrated. The residue was purified by silica gel chromatography (eluted with PE:EtOAc=1:1) to give compound XS-5 (160 mg, yield 82.6%) as a white solid. LC/MS (ESI) m/z: 691/693 (M+H)$^+$.

Step 4: (4$^1$R,4$^3$S,4$^5$S,E)-1$^3$-Acetyl-N-(6-bromo-3-methylpyridin-2-yl)-3,15-dioxo-1$^1$H-6-oxa-4$^2$,14-diaza-1(1,6)-indazola-4(2,5)-bicyclo[3.1.0]hexanacyclopentadecaphan-8-ene-4$^3$-carboxamide (74)

To a solution of 3-acetyl-1-{2-[(1R,3S,5S)-3-[(6-bromo-3-methylpyridin-2-yl)carbamoyl]-5-[(prop-2-en-1-yloxy)methyl]-2-azabicyclo[3.1.0]hexan-2-yl]-2-oxoethyl}-N-(hex-5-en-1-yl)indazole-6-carboxamide (160 mg, 0.23 mmol) in degassed toluene (160 mL) was added Grubbs 2$^{nd}$ generation catalyst (39 mg, 0.05 mmol) under N$_2$ atmosphere, and the mixture was stirred at 80° C. under N$_2$ atmosphere for 16 hours. The mixture was concentrated to dryness, and the residue was purified by chromatography on silica gel (PE:EtOAc=10:1 to 1:1) to give 74 (70 mg, yield 45.60%) as a white solid. $^1$H-NMR (400 MHz, DMSO-d$_6$) δ 10.52 (s, 1H), 8.20 (dd, J=0.7, 0.7 Hz, 1H), 8.17-8.12 (m, 1H), 7.99 (t, J=2.2 Hz, 1H), 7.76 (dd, J=1.3, 1.3 Hz, 1H), 7.64-7.60 (m, 1H), 7.45 (d, J=7.9 Hz, 1H), 6.15 (d, J=6.2 Hz, 1H), 5.98 (d, J=16.5 Hz, 1H), 5.58 (d, J=16.2 Hz, 1H), 4.50 (dd, J=5.6, 5.6 Hz, 1H), 4.28-4.23 (m, 1H), 4.20 (m, 1H), 4.16 (d, J=11.6 Hz, 1H), 3.38 (d, J=4.7 Hz, 1H), 2.65 (s, 3H), 2.59-2.52 (m, 2H), 2.46-2.42 (m, 1H), 2.14-1.99 (m, 2H), 1.90 (s, 3H), 1.88-1.82 (m, 1H), 1.31-1.14 (m, 6H), 1.07 (t, J=5.8 Hz, 1H), 0.98 (dd, J=2.6, 2.6 Hz, 1H). LC/MS (ESI) m/z: 663/665 (M+H)$^+$.

Step 5: (4[1]R,4[3]S,4[5]S)-1[3]-Acetyl-N-(6-bromo-3-methylpyridin-2-yl)-3,15-dioxo-1[1]H-6-oxa-4[2],1[4]-diaza-1(1,6)-indazola-4(2,5)-bicyclo[3.1.0]hexanacyclopentadecaphane-4[3]-carboxamide (75)

To a solution of 74 (30 mg, 0.045 mmol) in Ethyl acetate (3 mL) was added PtO$_2$ (9 mg, 30% wt) at 0° C. The mixture was degassed under N$_2$ three times and stirred under a H$_2$ balloon at room temperature for 10 minutes. The mixture was filtered, and the filtrate was concentrated to dryness. The residue was purified by preparatory HPLC to give 75 (4.0 mg, yield 13.3%) as a white solid. $^1$H-NMR (400 MHz, DMSO-d$_6$) δ 10.46 (s, 1H), 8.21 (dd, J=0.72, 0.72 Hz, 1H), 8.09-8.03 (m, 1H), 8.01 (d, J=12.2 Hz, 1H), 7.77 (dd, J=1.4, 1.4 Hz, 1H), 7.66-7.60 (m, 1H), 7.46 (d, J=8.0 Hz, 1H), 5.92 (d, J=16.4 Hz, 1H), 5.62 (d, J=16.4 Hz, 1H), 4.54 (dd, J=5.0, 5.0 Hz, 1H), 4.26-4.14 (m, 1H), 3.98 (dd, J=2.6, 2.6 Hz, 1H), 3.80 (d, J=11.3 Hz, 1H), 3.60-3.54 (m, 1H), 3.04 (d, J=11.3 Hz, 1H), 2.77-2.69 (m, 1H), 2.65 (s, 3H), 2.46 (d, J=9.5 Hz, 1H), 2.38 (dd, J=5.2, 5.2 Hz, 1H), 2.34-2.21 (m, 1H), 1.97 (s, 3H), 1.49-1.41 (m, 2H), 1.35-1.28 (m, 2H), 1.27-1.18 (m, 4H), 1.14-0.93 (m, 2H), 0.92-0.83 (m, 2H). LC/MS (ESI) m/z: 665/667 (M+H)$^+$.

Example 1. Non-Limiting Examples of Compounds of Formula I, Formula II, Formula III, Formula IV, Formula V, Formula VI, Formula VII, or Formula VIII Table 4 and Table 5 show illustrative Factor D inhibitors with characterizing data. The assay of Example 2 was used to determine the IC$_{50}$'s of the compounds. Other standard Factor D inhibition assays are also available. Three *s are used to denote compounds with an IC$_{50}$ less than 1 micromolar; two s indicate compound with an IC$_{50}$ between 1 micromolar and 10 micromolar, and one * denotes compounds with an IC$_{50}$ greater than 10 micromolar.

TABLE 4

Non-limiting Examples of Compounds of the Present Invention

| Cmp No. | Structure | Name | IC$_{50}$ (Stars) | RT min (Method A, B, C, or D) | MS (M + 1) |
|---|---|---|---|---|---|
| T-1 | 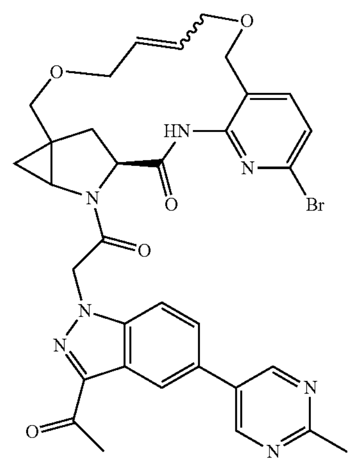 [SMILES: CC(=O)c1nn(CC(=O)N2C3CC34COCC=CCOCc3ccc(Br)nc3NC(=O)[C@@H]2C4)c2ccc(-c3cnc(C)nc3)cc12] | (43S)-44-(2-(3-acetyl-5-(2-methylpyrimidin-5-yl)-1H-indazol-1-yl)acetyl)-16-bromo-6,11-dioxa-44,2-diaza-1(2,3)-pyridina-4(3,1)-bicyclo[3.1.0]hexana-cyclododecaphan-8-en-3-one | *** | 1.72 (A) | 688 |
| T-2 | 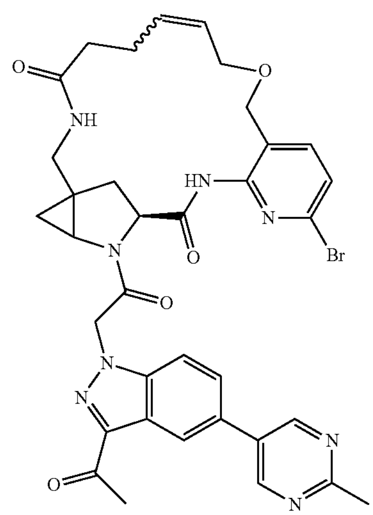 [SMILES: CC(=O)c1nn(CC(=O)N2C3CC34CNC(=O)CCC=CCOCc3ccc(Br)nc3NC(=O)[C@@H]2C4)c2ccc(-c3cnc(C)nc3)cc12] | (43S)-44-(2-(3-acetyl-5-(2-methylpyrimidin-5-yl)-1H-indazol-1-yl)acetyl)-16-bromo-13-oxa-44,2,6-triaza-1(2,3)-pyridina-4(3,1)-bicyclo[3.1.0]hexana-cyclotetradecaphan-10-ene-3,7-dione | *** | 1.50 (A) | 729 |

TABLE 4-continued

Non-limiting Examples of Compounds of the Present Invention

| Cmp No. | Structure | Name | IC$_{50}$ (Stars) | RT min (Method A, B, C, or D) | MS (M + 1) |
|---|---|---|---|---|---|
| T-3 | 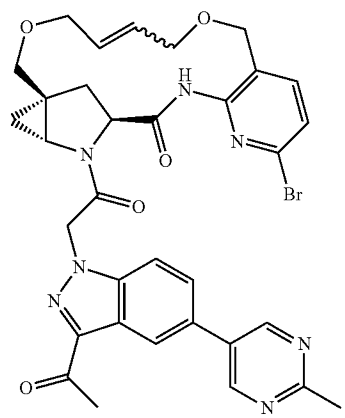 [SMILES: CC(=O)c1nn(CC(=O)N2[C@H]3C[C@@]4(COCC=CCOCc5ccc(Br)nc5NC3=O)C[C@@H]24)c2ccc(-c3cnc(C)nc3)cc12] | (41R,43S,45S)-42-(2-(3-acetyl-5-(2-methylpyrimidin-5-yl)-1H-indazol-1-yl)acetyl)-16-bromo-6,11-dioxa-42,2-diaza-1(2,3)-pyridina-4(3,5)-bicyclo[3.1.0]hexana-cyclododecaphan-8-en-3-one | *** | 1.75 (A) | 686 |
| T-4 | 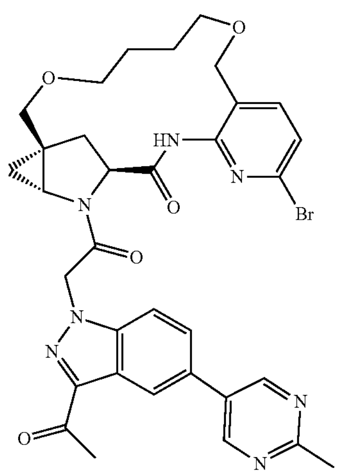 [SMILES: CC(=O)c1nn(CC(=O)N2[C@H]3C[C@@]4(COCCCCOCc5ccc(Br)nc5NC3=O)C[C@@H]24)c2ccc(-c3cnc(C)nc3)cc12] | (41R,43S,45S)-42-(2-(3-acetyl-5-(2-methylpyrimidin-5-yl)-1H-indazol-1-yl)acetyl)-16-bromo-6,11-dioxa-42,2-diaza-1(2,3)-pyridina-4(3,5)-bicyclo[3.1.0]hexana-cyclododecaphan-3-one | *** | 1.85 (A) | 688 |
| T-5 | 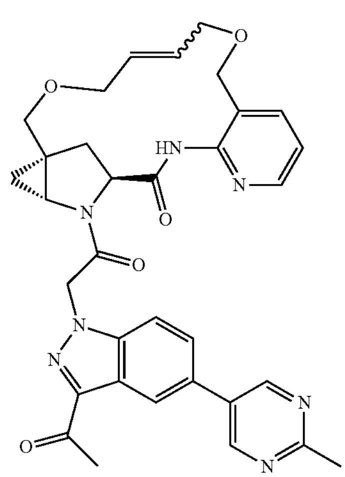 [SMILES: CC(=O)c1nn(CC(=O)N2[C@H]3C[C@@]4(COCC=CCOCc5cccnc5NC3=O)C[C@@H]24)c2ccc(-c3cnc(C)nc3)cc12] | (41R,43S,45S)-42-(2-(3-acetyl-5-(2-methylpyrimidin-5-yl)-1H-indazol-1-yl)acetyl)-6,11-dioxa-42,2-diaza-1(2,3)-pyridina-4(3,5)-bicyclo[3.1.0]hexana-cyclododecaphan-8-en-3-one | *** | 1.38 (A) | 608 |

TABLE 4-continued

Non-limiting Examples of Compounds of the Present Invention

| Cmp No. | Structure | Name | IC$_{50}$ (Stars) | RT min (Method A, B, C, or D) | MS (M + 1) |
|---|---|---|---|---|---|
| T-6 | 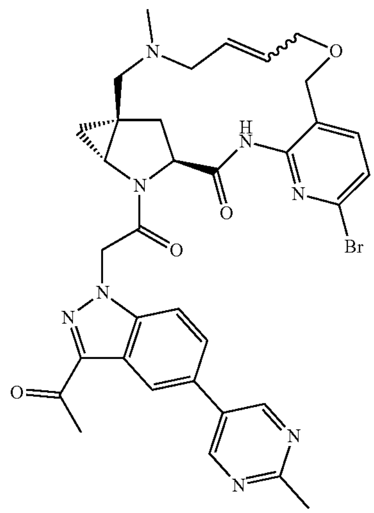 [SMILES: CC(=O)c1nn(CC(=O)N2[C@H]3C[C@]4(C[C@@H]24)CN(C)CC=CCOCc2ccc(Br)nc2NC3=O)c2ccc(-c3cnc(C)nc3)cc12] | (41R,43S,45R)-42-(2-(3-acetyl-5-(2-methylpyrimidin-5-yl)-1H-indazol-1-yl)acetyl)-16-bromo-6-methyl-11-oxa-42,2,6-triaza-1(2,3)-pyridina-4(3,5)-bicyclo[3.1.0]hexana-cyclododecaphan-8-en-3-one | *** | 1.07 (A) | 699 |
| T-7 | 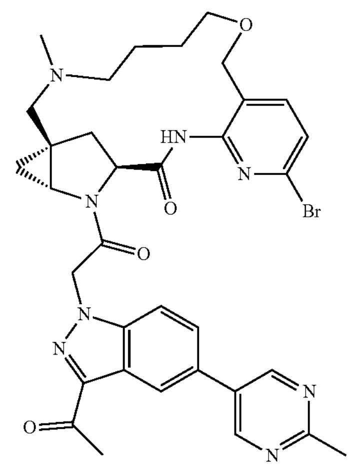 [SMILES: CC(=O)c1nn(CC(=O)N2[C@H]3C[C@]4(C[C@@H]24)CN(C)CCCCOCc2ccc(Br)nc2NC3=O)c2ccc(-c3cnc(C)nc3)cc12] | (41R,43S,45R)-42-(2-(3-acetyl-5-(2-methylpyrimidin-5-yl)-1H-indazol-1-yl)acetyl)-16-bromo-6-methyl-11-oxa-42,2,6-triaza-1(2,3)-pyridina-4(3,5)-bicyclo[3.1.0]hexana-cyclododecaphan-3-one | *** | 1.05 (A) | 701 |
| T-8 | 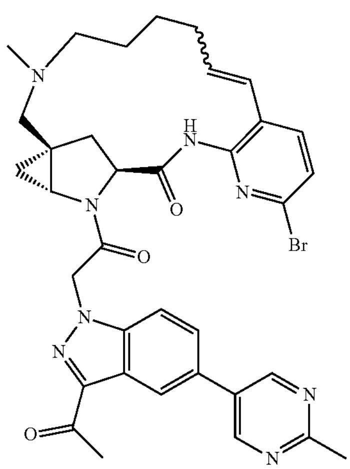 | (41R,43S,45R)-42-(2-(3-acetyl-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexana-cyclododecaphan-11-en-3-one | *** | 1.24 (A) | 697 |

TABLE 4-continued

Non-limiting Examples of Compounds of the Present Invention

| Cmp No. | Structure | Name | IC$_{50}$ (Stars) | RT min (Method A, B, C, or D) | MS (M + 1) |
|---|---|---|---|---|---|
| T-9 | 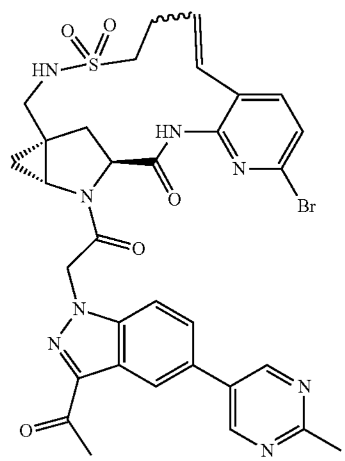 [SMILES: CC(=O)c1nn(CC(=O)N2[C@H]3C[C@@]4(CNS(=O)(=O)CCC=Cc5ccc(Br)nc5NC3=O)C[C@@H]24)c2ccc(-c3cnc(C)nc3)cc12] | (41R,43S,45R)-42-(2-(3-acetyl-5-(2-methylpyrimidin-5-yl)-1H-indazol-1-yl)acetyl)-16-bromo-7-thia-42,2,6-triaza-1(2,3)-pyridina-4(3,5)-bicyclo[3.1.0]hexana-cycloundecaphan-10-en-3-one 7,7-dioxide | *** | 1.49 (A) | 719 |
| T-10 | 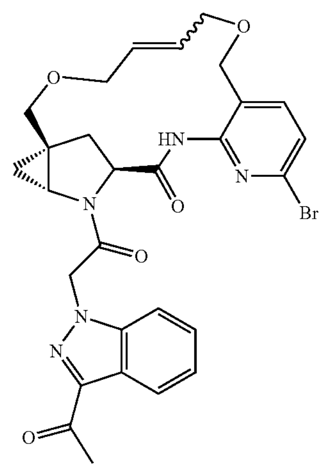 [SMILES: CC(=O)c1nn(CC(=O)N2[C@H]3C[C@@]4(COCC=CCOCc5ccc(Br)nc5NC3=O)C[C@@H]24)c2ccccc12] | (41R,43S,45S)-42-(2-(3-acetyl-1H-indazol-1-yl)acetyl)-16-bromo-6,11-dioxa-42,2-diaza-1(2,3)-pyridina-4(3,5)-bicyclo[3.1.0]hexana-cyclododecaphan-8-en-3-one | *** | 1.90 (A) | 594 |
| T-11 | 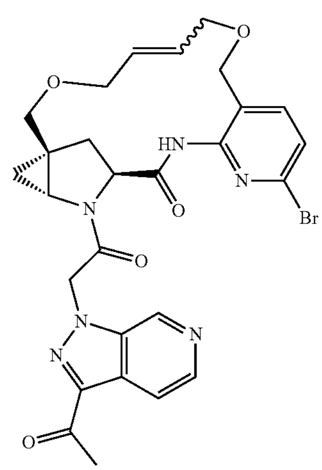 [SMILES: CC(=O)c1nn(CC(=O)N2[C@H]3C[C@@]4(COCC=CCOCc5ccc(Br)nc5NC3=O)C[C@@H]24)c2cnccc12] | (41R,43S,45S)-42-(2-(3-acetyl-1H-pyrazolo[3,4-c]pyridin-1-yl)acetyl)-16-bromo-6,11-dioxa-42,2-diaza-1(2,3)-pyridina-4(3,5)-bicyclo[3.1.0]hexana-cyclododecaphan-8-en-3-one | *** | 1.38 (A) | 595 |

TABLE 4-continued

Non-limiting Examples of Compounds of the Present Invention

| Cmp No. | Structure | Name | IC$_{50}$ (Stars) | RT min (Method A, B, C, or D) | MS (M + 1) |
|---|---|---|---|---|---|
| T-12 | 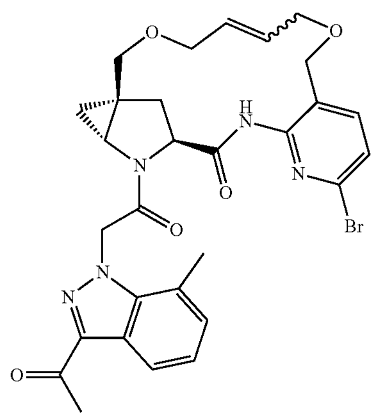 [SMILES: CC(=O)c1nn(CC(=O)N2[C@H]3C[C@@]4(COCC=CCOCc5ccc(Br)nc5NC3=O)C[C@@H]24)c2c(C)cccc12] | (41R,43S,45S)-42-(2-(3-acetyl-7-methyl-1H-indazol-1-yl)acetyl)-16-bromo-6,11-dioxa-42,2-diaza-1(2,3)-pyridina-4(3,5)-bicyclo[3.1.0]hexana-cyclododecaphan-8-en-3-one | *** | 2.03 (A) | 608 |
| T-13 | 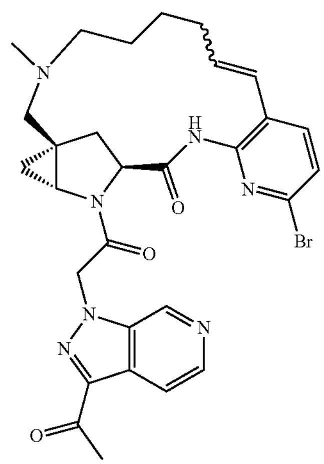 [SMILES: CC(=O)c1nn(CC(=O)N2[C@H]3C[C@]4(C[C@@H]24)CN(C)CCCCC=Cc2ccc(Br)nc2NC3=O)c2cnccc12] | (41R,43S,45R)-42-(2-(3-acetyl-1H-pyrazolo[3,4-c]pyridin-1-yl)acetyl)-16-bromo-6-methyl-42,2,6-triaza-1(2,3)-pyridina-4(3,5)-bicyclo[3.1.0]hexana-cyclododecaphan-11-en-3-one | *** | 1.00 (A) | 606 |
| T-14 | 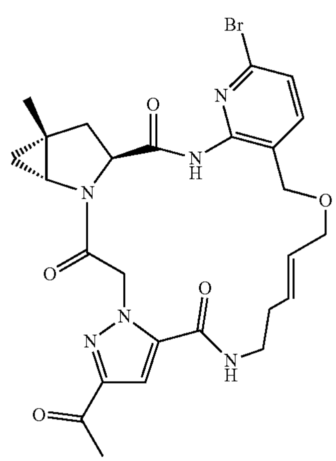 [SMILES: CC(=O)c1cc2n(n1)CC(=O)N1[C@@H](C[C@@]3(C)C[C@@H]13)C(=O)Nc1nc(Br)ccc1COC/C=C/CCNC2=O] | (18aS,19aR,20aR,E)-2-acetyl-15-bromo-19a-methyl-6,7,12,17,18a,19,19a,20,20a,23-decahydro-4H-cyclopropa[4,5]pyrrolo[2,1-g]pyrazolo[1,5-k]pyrido[3,2-c][1,5,8,11,14]oxatetra-azacyclononadecine-4,18,22(5H,10H)-trione | * | 1.66 (A) | 585 |

TABLE 4-continued

Non-limiting Examples of Compounds of the Present Invention

| Cmp No. | Structure | Name | IC$_{50}$ (Stars) | RT min (Method A, B, C, or D) | MS (M + 1) |
|---|---|---|---|---|---|
| T-15 | 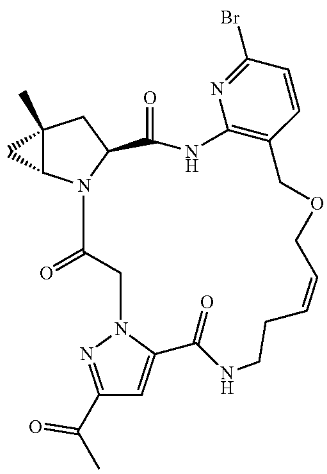 [SMILES: CC(=O)c1cc2n(n1)CC(=O)N1[C@@H](C[C@@]3(C)C[C@@H]13)C(=O)Nc1nc(Br)ccc1COC/C=C\CCNC2=O] | (18aS,19aR,20aR,Z)-2-acetyl-15-bromo-19a-methyl-6,7,12,17,18a,19,19a,20,20a,23-decahydro-4H-cyclopropa[4,5]pyrrolo[2,1-g]pyrazolo[1,5-k]pyrido[3,2-c][1,5,8,11,14]oxatetra-azacyclononadecine-4,18,22(5H,10H)-trione | * | 2.47 (A) | 585 |
| T-16 | 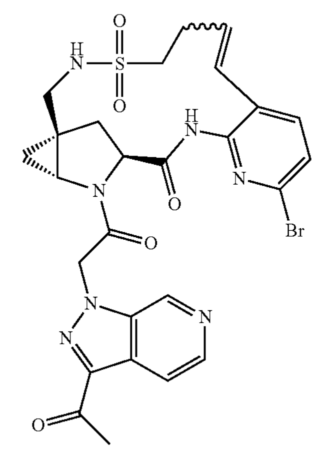 [SMILES: CC(=O)c1nn(CC(=O)N2[C@H]3C[C@@]4(CNS(=O)(=O)CCC=Cc5ccc(Br)nc5NC3=O)C[C@@H]24)c2cnccc12] | (41R,43S,45R)-42-(2-(3-acetyl-1H-pyrazolo[3,4-c]pyridin-1-yl)acetyl)-16-bromo-7-thia-42,2,6-triaza-1(2,3)-pyridina-4(3,5)-bicyclo[3.1.0]hexana-cycloundecaphan-10-en-3-one 7,7-dioxide | *** | 1.14 (A) | 628 |
| T-17 | 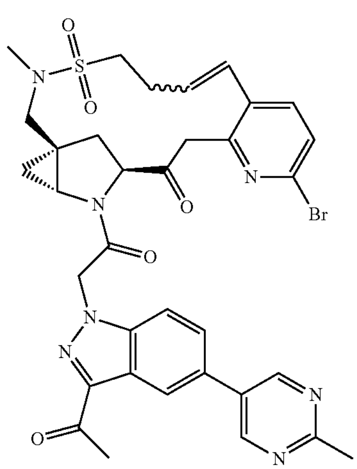 | (41R,43S,45R)-42-(2-(3-acetyl-5-(2-methylpyrimidin-5-yl)-1H-indazol-1-yl)acetyl)-16-bromo-6-methyl-7-thia-42,6-diaza-1(2,3)-pyridina-4(3,5)-bicyclo[3.1.0]hexana-cycloundecaphan-10-en-3-one 7,7-dioxide | *** | 1.54 (A) | 733 |

TABLE 5

Additional Non-limiting Examples of Compounds of the Present Invention

| Cmp No. | Structure | Name | IC$_{50}$ (Stars) | RT min (Method A, B, C, or D) | MS (M + 1) |
|---|---|---|---|---|---|
| T-18 | 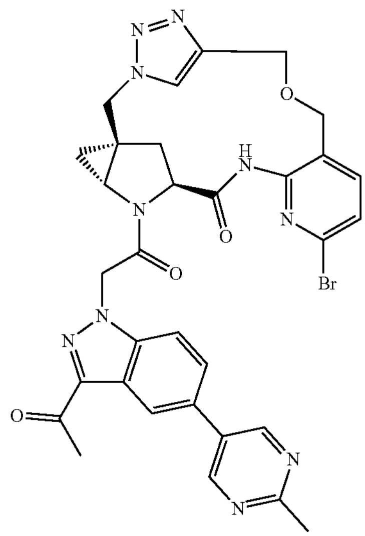 [SMILES: CC(=O)c1nn(CC(=O)N2[C@H]3C[C@]4(C[C@@H]24)Cn2cc(nn2)COCc2ccc(Br)nc2NC3=O)c2ccc(-c3cnc(C)nc3)cc12] | (31R,33S,35R,Z)-32-(2-(3-acetyl-5-(2-methylpyrimidin-5-yl)-1H-indazol-1-yl)acetyl)-66-bromo-11H-8-oxa-32,5-diaza-6(2,3)-pyridina-1(1,4)-triazola-3(5,3)-bicyclo[3.1.0]hexanacyclononaphan-4-one | *** | 1.56 (A) | 699 |
| T-19 | 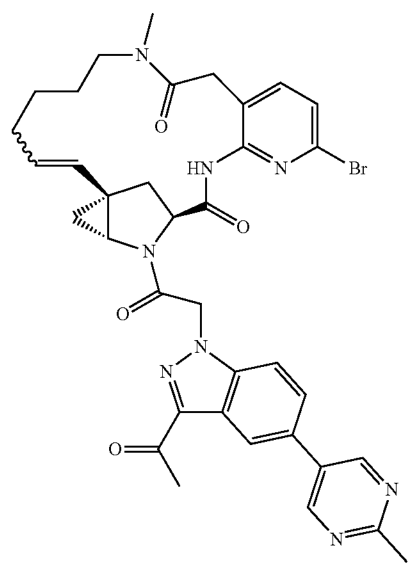 [SMILES: CC(=O)c1nn(CC(=O)N2[C@H]3C[C@@]4(C=CCCCCN(C)C(=O)Cc5ccc(Br)nc5NC3=O)C[C@@H]24)c2ccc(-c3cnc(C)nc3)cc12] | (41R,43S,45R)-42-(2-(3-acetyl-5-(2-methylpyrimidin-5-yl)-1H-indazol-1-yl)acetyl)-16-bromo-11-methyl-42,2,11-triaza-1(2,3)-pyridina-4(3,5)-bicyclo[3.1.0]hexanacyclotridecaphan-5-ene-3,12-dione | *** | 1.87 (A) | 727 |
| T-20 | 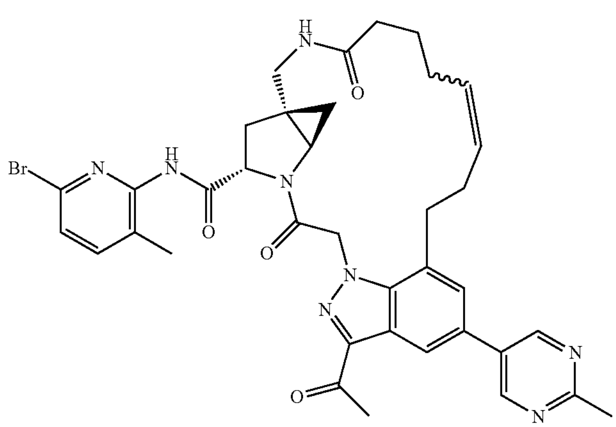 [SMILES: CC(=O)c1nn2c3c(cc(-c4cnc(C)nc4)cc13)CCC=CCCCC(=O)NC[C@@]13C[C@@H](C(=O)Nc4nc(Br)ccc4C)N(C(=O)C2)[C@@H]1C3] | (41R,43S,45R)-13-acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotetradecaphan-11-ene-43-carboxamide | *** | 3.79 (B) | 739 |

TABLE 5-continued

Additional Non-limiting Examples of Compounds of the Present Invention

| Cmp No. | Structure | Name | IC$_{50}$ (Stars) | RT min (Method A, B, C, or D) | MS (M + 1) |
|---|---|---|---|---|---|
| T-21 | 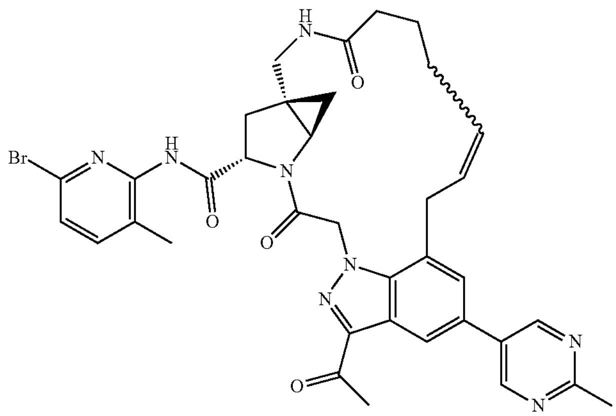 [SMILES: CC(=O)c1nn2c3c(cc(-c4cnc(C)nc4)cc13)CC=CCCCC(=O)NC[C@@]13C[C@@H](C(=O)Nc4nc(Br)ccc4C)N(C(=O)C2)[C@@H]1C3] | (41R,43S,45R)-13-acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | 3.66 (B) | 725 |
| T-22 | 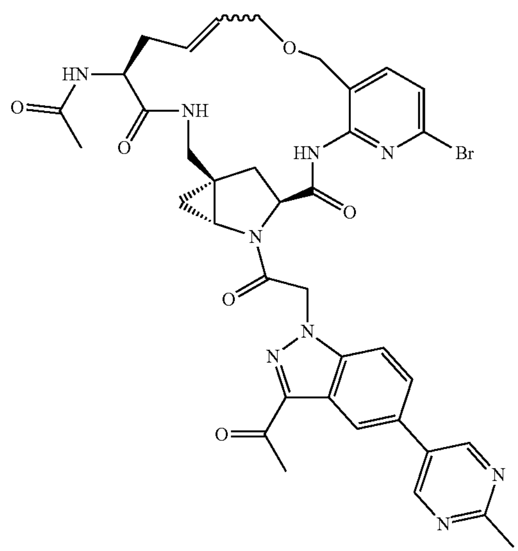 [SMILES: CC(=O)N[C@H]1CC=CCOCc2ccc(Br)nc2NC(=O)[C@@H]2C[C@@]3(CNC1=O)C[C@H]3N2C(=O)Cn1nc(C(C)=O)c2cc(-c3cnc(C)nc3)ccc21] | N-((41R,43S,45R,8S)-42-(2-(3-acetyl-5-(2-methylpyrimidin-5-yl)-1H-indazol-1-yl)acetyl)-16-bromo-3,7-dioxo-13-oxa-42,2,6-triaza-1(2,3)-pyridina-4(3,5)-bicyclo[3.1.0]hexanacyclotetradecaphan-10-en-8-yl)acetamide | *** | 1.37 (A) | 786 |
| T-23 | 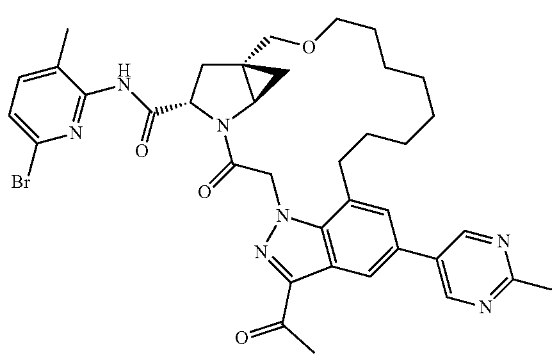 [SMILES: CC(=O)c1nn2c3c(cc(-c4cnc(C)nc4)cc13)CCCCCCCCOC[C@@]13C[C@@H](C(=O)Nc4nc(Br)ccc4C)N(C(=O)C2)[C@@H]1C3] | (41R,43S,45S)-13-acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclotetradecaphane-43-carboxamide | *** | 4.37 (B) | 728 |

TABLE 5-continued

Additional Non-limiting Examples of Compounds of the Present Invention

| Cmp No. | Structure | Name | IC$_{50}$ (Stars) | RT min (Method A, B, C, or D) | MS (M + 1) |
|---|---|---|---|---|---|
| T-24 | 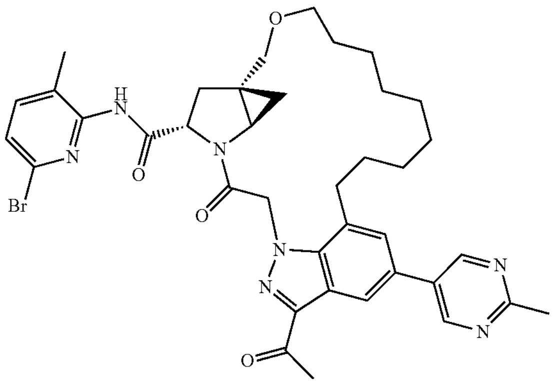 [SMILES: CC(=O)c1nn2c3c(cc(-c4cnc(C)nc4)cc13)CCCCCCCCCOC[C@@]13C[C@@H](C(=O)Nc4nc(Br)ccc4C)N(C(=O)C2)[C@@H]1C3] | (41R,43S,45S)-13-acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclopentadecaphane-43-carboxamide | *** | 4.68 (B) | 742 |
| T-25 | 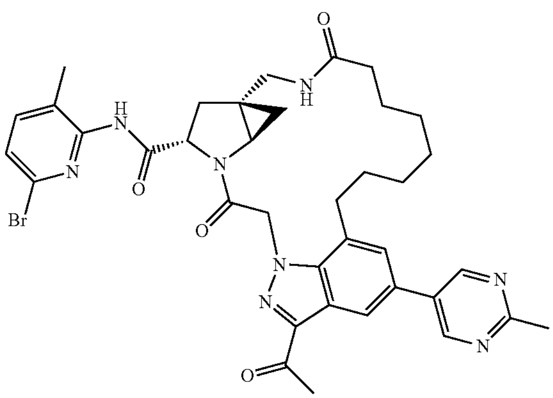 [SMILES: CC(=O)c1nn2c3c(cc(-c4cnc(C)nc4)cc13)CCCCCCCC(=O)NC[C@@]13C[C@@H](C(=O)Nc4nc(Br)ccc4C)N(C(=O)C2)[C@@H]1C3] | (41R,43S,45R)-13-acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotetradecaphane-43-carboxamide | | 3.84 (B) | 741 |
| T-26 | 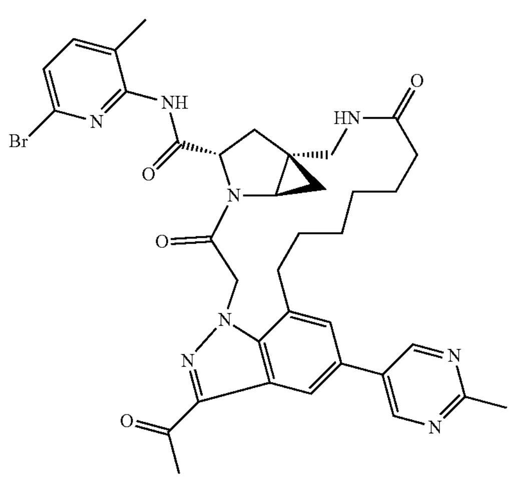 [SMILES: CC(=O)c1nn2c3c(cc(-c4cnc(C)nc4)cc13)CCCCCCC(=O)NC[C@@]13C[C@@H](C(=O)Nc4nc(Br)ccc4C)N(C(=O)C2)[C@@H]1C3] | (41R,43S,45R)-13-acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | | 3.71 (B) | 727 |

TABLE 5-continued

Additional Non-limiting Examples of Compounds of the Present Invention

| Cmp No. | Structure | Name | IC₅₀ (Stars) | RT min (Method A, B, C, or D) | MS (M + 1) |
|---|---|---|---|---|---|
| T-27 | 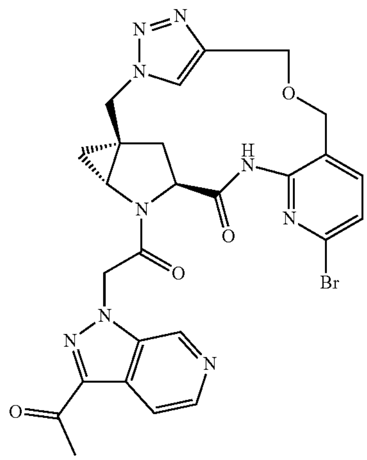 [SMILES: CC(=O)c1nn(CC(=O)N2[C@H]3C[C@]4(C[C@@H]24)Cn2cc(nn2)COCc2ccc(Br)nc2NC3=O)c2cnccc12] | (31R,33S,35R,Z)-32-(2-(3-acetyl-1H-pyrazolo[3,4-c]pyridin-1-yl)acetyl)-66-bromo-11H-8-oxa-32,5-diaza-6(2,3)-pyridina-1(1,4)-triazola-3(5,3)-bicyclo[3.1.0]hexanacyclononaphan-4-one | *** | 0.89 (A) | 608 |

TABLE 6

Additional Non-limiting Examples of Compounds of the Present Invention

| Cmp No. | Structure and Name | IC₅₀ (Stars) | RT min (Method A, B, C, or D) | MS (M + 1) |
|---|---|---|---|---|
| T-28 | (31R,33S,35R,Z)-32-(2-(3-acetyl-5-(2-methylpyrimidin-5-yl)-1H-indazol-1-yl)acetyl)-66-bromo-11H-8-oxa-32,5-diaza-6(2,3)-pyridina-1(1,4)-triazola-3(5,3)-bicyclo[3.1.0]hexanacyclononaphan-4-one | *** | 1.29 (A) | 699 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-29 | 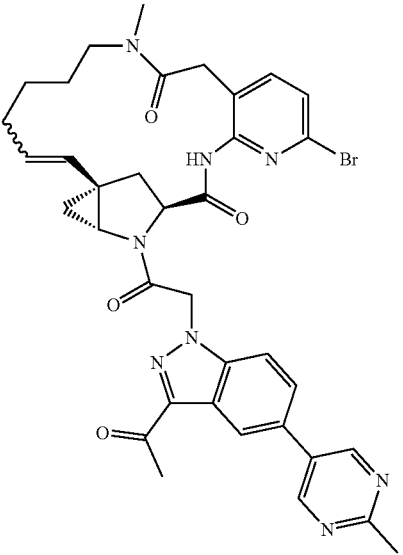 [SMILES: CC(=O)c1nn(CC(=O)N2[C@H]3C[C@@]4(C=CCCCCN(C)C(=O)Cc5ccc(Br)nc5NC3=O)C[C@@H]24)c2ccc(-c3cnc(C)nc3)cc12]<br>(41R,43S,45R)-42-(2-(3-acetyl-5-(2-methylpyrimidin-5-yl)-1H-indazol-1-yl)acetyl)-16-bromo-11-methyl-42,2,11-triaza-1(2,3)-pyridina-4(3,5)-bicyclo[3.1.0]hexanacyclotridecaphan-5-ene-3,12-dione | *** | 1.87 (A) | 727 |
| T-30 | 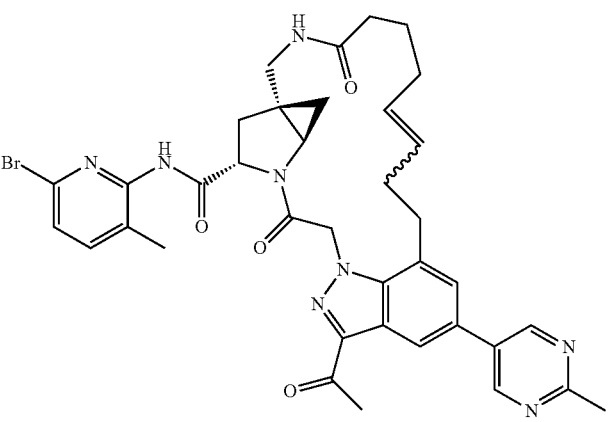 [SMILES: CC(=O)c1nn2c3c(cc(-c4cnc(C)nc4)cc13)CCC=CCCCC(=O)NC[C@@]13C[C@@H](C(=O)Nc4nc(Br)ccc4C)N(C(=O)C2)[C@@H]1C3]<br>(41R,43S,45R)-13-acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotetradecaphan-11-ene-43-carboxamide | *** | 3.79 (B) | 739 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-31 | 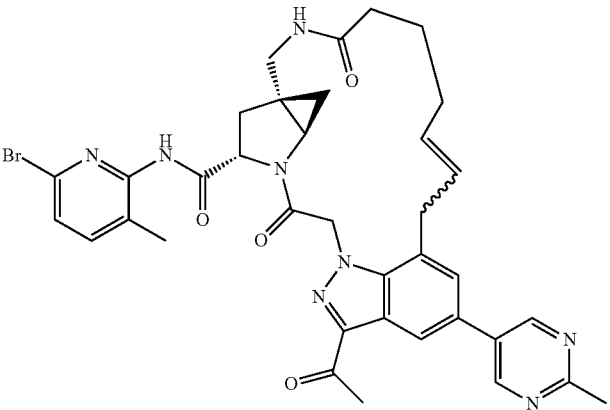 [SMILES: CC(=O)c1nn2c3c(cc(-c4cnc(C)nc4)cc13)CC=CCCCC(=O)NC[C@@]13C[C@@H](C(=O)Nc4nc(Br)ccc4C)N(C(=O)C2)[C@@H]1C3] (41R,43S,45R)-13-acetyl-N-(6-bromo-3-methylpyridin-2-yl)-15-(2-methylpyrimidin-5-yl)-3,7-dioxo-11H-42,6-diaza-1(1,7)-indazola-4(2,5-bicyclo[3.1.0]hexanacyclotridecaphan-11-ene-43-carboxamide | *** | 3.66 (B) | 725 |
| T-32 | 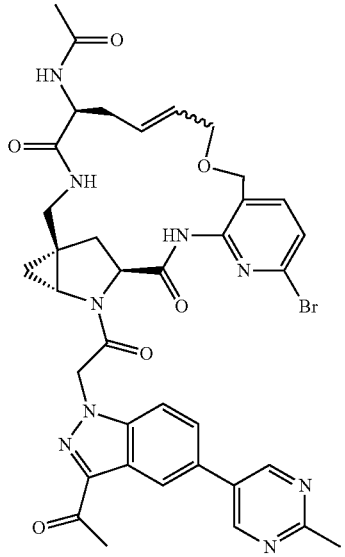 [SMILES: CC(=O)N[C@H]1CC=CCOCc2ccc(Br)nc2NC(=O)[C@@H]2C[C@@]3(CNC1=O)C[C@H]3N2C(=O)Cn1nc(C(C)=O)c2cc(-c3cnc(C)nc3)ccc21] N-((41R,43S,45R,8S)-42-(2-(3-acetyl-5-(2-methylpyrimidin-5-yl)-1H-indazol-1-yl)acetyl)-16-bromo-3,7-dioxo-13-oxa-42,2,6-triaza-1(2,3)-pyridina-4(3,5)-bicyclo[3.1.0]hexanacyclotetradecaphan-10-en-8-yl)acetamide | *** | 1.37 (A) | 786 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-33 | 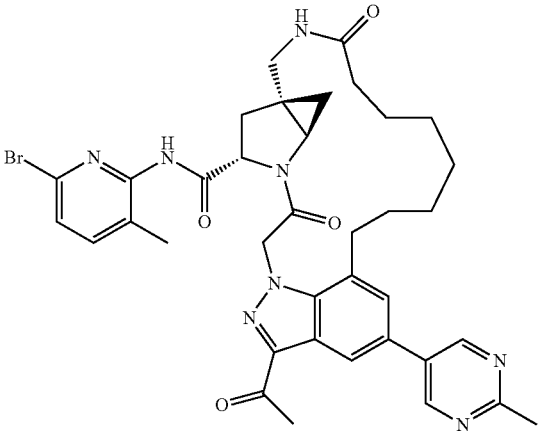 [SMILES: CC(=O)c1nn2c3c(cc(-c4cnc(C)nc4)cc13)CCCCCCCC(=O)NC[C@@]13C[C@@H](C(=O)Nc4nc(Br)ccc4C)N(C(=O)C2)[C@@H]1C3]<br>(41R,43S,45R)-13-acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotetradecaphane-43-carboxamide | ND | 3.84 (B) | 741 |
| T-34 | 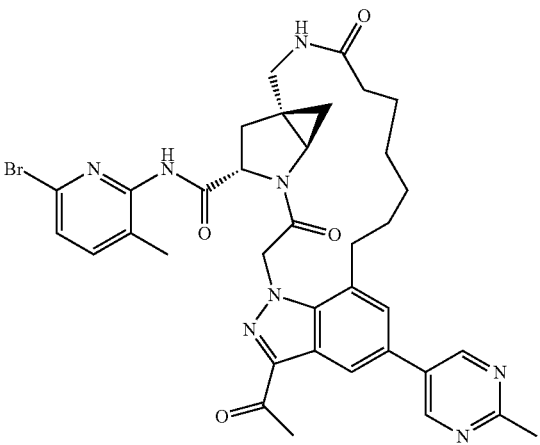 [SMILES: CC(=O)c1nn2c3c(cc(-c4cnc(C)nc4)cc13)CCCCCCC(=O)NC[C@@]13C[C@@H](C(=O)Nc4nc(Br)ccc4C)N(C(=O)C2)[C@@H]1C3]<br>(41R,43S,45R)-13-acetyl-N-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | ND | 3.71 (B) | 727 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-35 | 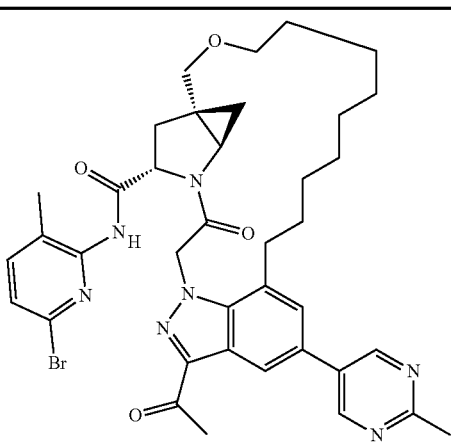<br>(41R,43S,45R)-13-acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclotridecaphane-43-carboxamide | *** | 4.68 (B) | 742 |
| T-36 | 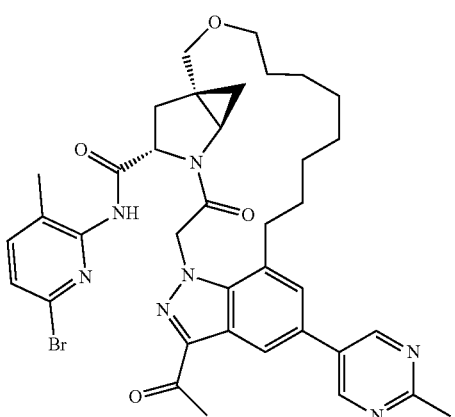<br>(41R,43S,45S)-13-acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclotetradecaphane-43-carboxamide | *** | 4.37 (B) | 728 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-37 | 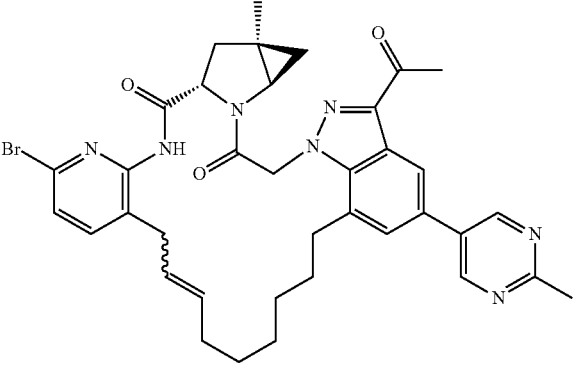 [SMILES: CC(=O)c1nn2c3c(cc(-c4cnc(C)nc4)cc13)CCCCCCC=CCc1ccc(Br)nc1NC(=O)[C@@H]1C[C@@]3(C)C[C@H]3N1C(=O)C2]<br>(18aS,19aR,20aR)-26-acetyl-15-bromo-19a-methyl-2-(2-methylpyrimidin-5-yl)-4,5,6,7,8,9,18a,19,19a,20,20a,23-dodecahydrocyclopropa[4',5']pyrrolo[1',2':4,5]pyrido[2',3':8,9][1,4,7]triazacycloicosino[19,20,1-hi]indazole-18,22(12H,17H)-dione | *** | 4.42 (B) | 710 |
| T-38 | 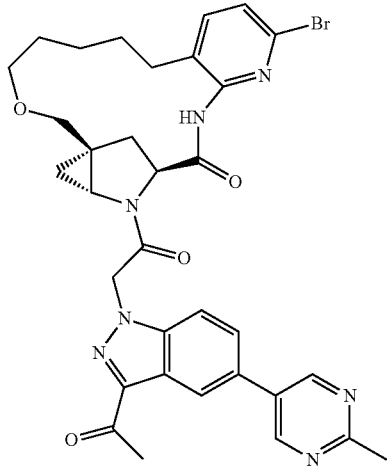 [SMILES: CC(=O)c1nn(CC(=O)N2[C@H]3C[C@@]4(COCCCCCc5ccc(Br)nc5NC3=O)C[C@@H]24)c2ccc(-c3cnc(C)nc3)cc12]<br>(41R,43S,45S)-42-(2-(3-acetyl-5-(2-methylpyrimidin-5-yl)-1H-indazol-1-yl)acetyl)-16-bromo-6-oxa-42,2-diaza-1(2,3)-pyridina-4(3,5)-bicyclo[3.1.0]hexanacycloundecaphan-3-one | *** | 3.50 (B) | 672 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-39 | 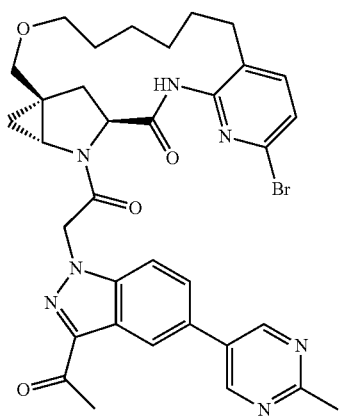 [SMILES: CC(=O)c1nn(CC(=O)N2[C@H]3C[C@@]4(COCCCCCCc5ccc(Br)nc5NC3=O)C[C@@H]24)c2ccc(-c3cnc(C)nc3)cc12]<br>(41R,43S,45S)-42-(2-(3-acetyl-5-(2-methylpyrimidin-5-yl)-1H-indazol-1-yl)acetyl)-16-bromo-6-oxa-42,2-diaza-1(2,3)-pyridina-4(3,5)-bicyclo[3.1.0]hexanacyclododecaphan-3-one | *** | 3.79 (B) | 686 |
| T-40 | 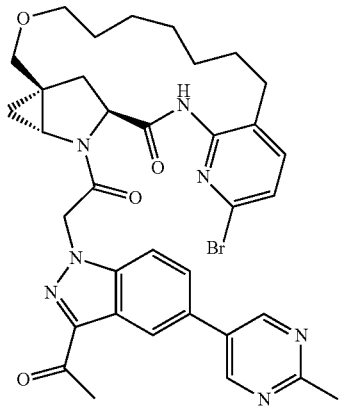<br>(41R,43S,45S)-42-(2-(3-acetyl-5-(2-methylpyrimidin-5-yl)-1H-indazol-1-yl)acetyl)-16-bromo-6-oxa-42,2-diaza-1(2,3)-pyridina-4(3,5)-bicyclo[3.1.0]hexanacyclotridecaphan-3-one | *** | 3.97 (B) | 700 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-41 | 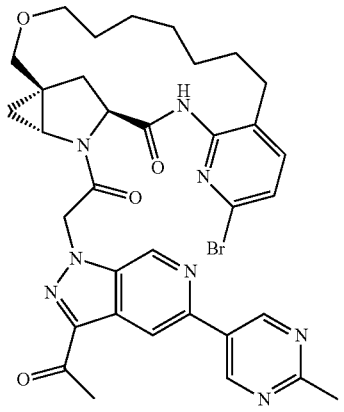 [SMILES: CC(=O)c1nn(CC(=O)N2[C@H]3C[C@@]4(COCCCCCCCc5ccc(Br)nc5NC3=O)C[C@@H]24)c2cnc(-c3cnc(C)nc3)cc12] (41R,43S,45S)-42-(2-(3-acetyl-5-(2-methylpyrimidin-5-yl)-1H-pyrazolo[3,4-c]pyridin-1-yl)acetyl)-16-bromo-6-oxa-42,2-diaza-1(2,3)-pyridina-4(3,5)-bicyclo[3.1.0]hexanacyclotridecaphan-3-one | *** | 3.67 (B) | 701 |
| T-42 | 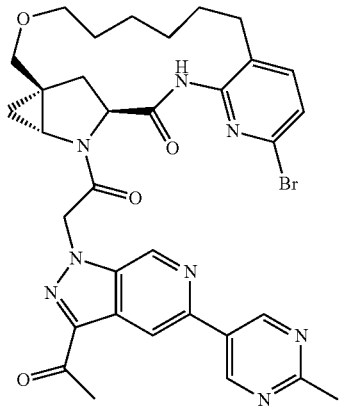 [SMILES: CC(=O)c1nn(CC(=O)N2[C@H]3C[C@@]4(COCCCCCCc5ccc(Br)nc5NC3=O)C[C@@H]24)c2cnc(-c3cnc(C)nc3)cc12] (41R,43S,45S)-42-(2-(3-acetyl-5-(2-methylpyrimidin-5-yl)-1H-pyrazolo[3,4-c]pyridin-1-yl)acetyl)-16-bromo-6-oxa-42,2-diaza-1(2,3)-pyridina-4(3,5)-bicyclo[3.1.0]hexanacyclododecaphan-3-one | *** | 3.48 (B) | 687 |

US 11,718,626 B2

731                                                                                        732

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-43 | 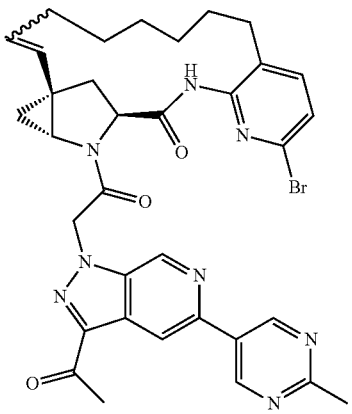 [SMILES: CC(=O)c1nn(CC(=O)N2[C@H]3C[C@@]4(C=CCCCCCCc5ccc(Br)nc5NC3=O)C[C@@H]24)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-16-bromo-42,2-diaza-1(2,3)-pyridina-4(3,5)-bicyclo[3.1.0]hexanacyclododecaphan-5-en-3-one | *** | 4.12 (B) | 683 |
| T-44 | 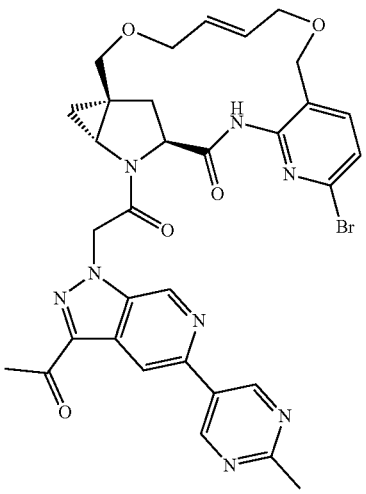 [SMILES: CC(=O)c1nn(CC(=O)N2[C@H]3C[C@@]4(COC/C=C/COCc5ccc(Br)nc5NC3=O)C[C@@H]24)c2cnc(-c3cnc(C)nc3)cc12]<br>(41R,43S,45S,E)-42-(2-(3-acetyl-5-(2-methylpyrimidin-5-yl)-1H-pyrazolo[3,4-c]pyridin-1-yl)acetyl)-16-bromo-6,11-dioxa-42,2-diaza-1(2,3)-pyridina-4(3,5)-bicyclo[3.1.0]hexanacyclododecaphan-8-en-3-one | *** | 1.61 (A) | 689 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-45 | 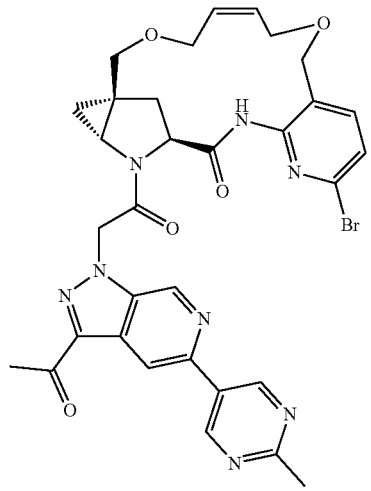 [SMILES: CC(=O)c1nn(CC(=O)N2[C@H]3C[C@@]4(COC/C=C\COCc5ccc(Br)nc5NC3=O)C[C@@H]24)c2cnc(-c3cnc(C)nc3)cc12]<br>(41R,43S,45S,Z)-42-(2-(3-acetyl-5-(2-methylpyrimidin-5-yl)-1H-pyrazolo[3,4-c]pyridin-1-yl)acetyl)-16-bromo-6,11-dioxa-42,2-diaza-1(2,3)-pyridina-4(3,5)-bicyclo[3.1.0]hexanacyclododecaphan-8-en-3-one | *** | 1.66 (A) | 689 |
| T-46 | 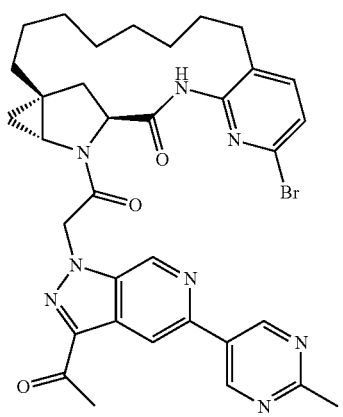 [SMILES: CC(=O)c1nn(CC(=O)N2[C@H]3C[C@@]4(CCCCCCCCc5ccc(Br)nc5NC3=O)C[C@@H]24)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-16-bromo-42,2-diaza-1(2,3)-pyridina-4(3,5)-bicyclo[3.1.0]hexanacyclododecaphan-3-one | *** | 3.90 (B) | 685 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-47 | 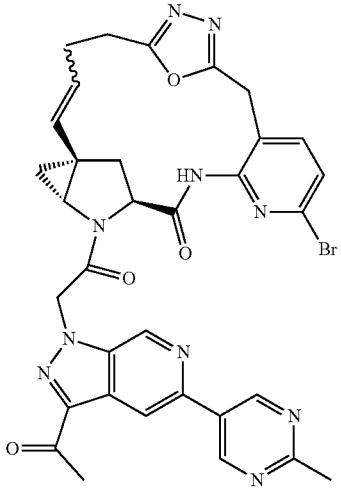 [SMILES: CC(=O)c1nn(CC(=O)N2[C@H]3C[C@@]4(C=CCCC5=NN=C(Cc6ccc(Br)nc6NC3=O)O5)C[C@@H]24)c2cnc(-c3cnc(C)nc3)cc12]<br>(61R,63S,65R)-62-(2-(3-acetyl-5-(2-methylpyrimidin-5-yl)-1H-pyrazolo[3,4-c]pyridin-1-yl)acetyl)-36-bromo-62,4-diaza-1(2,5)-oxadiazola-3(3,2)-pyridina-6(3,5)-bicyclo[3.1.0]hexanacyclodecaphan-7-en-5-one | *** | 1.45 (A) | 711 |
| T-48 | 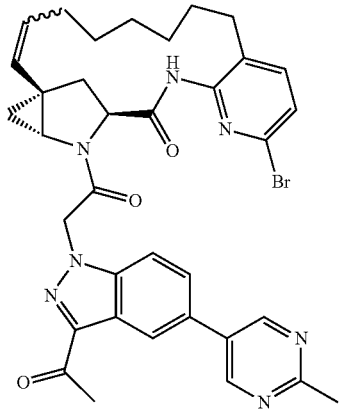 [SMILES: CC(=O)c1nn(CC(=O)N2[C@H]3C[C@@]4(C=CCCCCCCc5ccc(Br)nc5NC3=O)C[C@@H]24)c2ccc(-c3cnc(C)nc3)cc12]<br>(41R,43S,45R)-42-(2-(3-acetyl-5-(2-methylpyrimidin-5-yl)-1H-indazol-1-yl)acetyl)-16-bromo-42,2-diaza-1(2,3)-pyridina-4(3,5)-bicyclo[3.1.0]hexanacyclododecaphan-5-en-3-one | *** | 3.82 (B) | 682 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-49 | 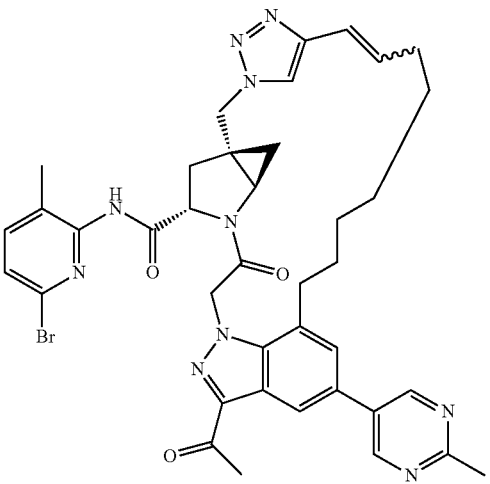 [SMILES: CC(=O)c1nn2c3c(cc(-c4cnc(C)nc4)cc13)CCCCCCC=Cc1cn(nn1)C[C@@]13C[C@@H](C(=O)Nc4nc(Br)ccc4C)N(C(=O)C2)[C@@H]1C3]<br>(14Z,31R,33S,35R)-63-acetyl-N-(6-bromo-3-methylpyridin-2-yl)-65-(2-methylpyrimidin-5-yl)-4-oxo-11H,61H,32-aza-6(1,7)-indazola-1(1,4)-triazola-3(5,2)-bicyclo[3.1.0]hexanacyclotetradecaphan-13-ene-33-carboxamide | *** | 4.09 (B) | 777 |
| T-50 | 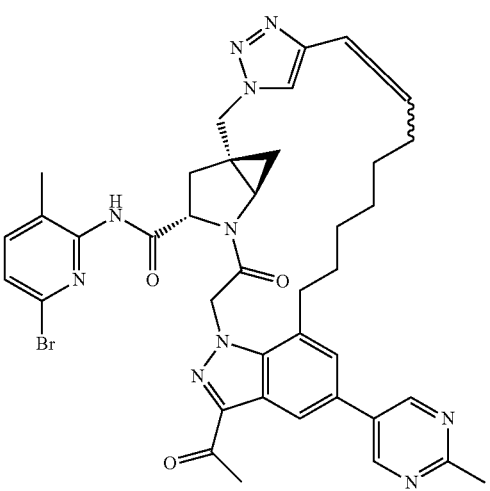 [SMILES: CC(=O)c1nn2c3c(cc(-c4cnc(C)nc4)cc13)CCCCCCC=Cc1cn(nn1)C[C@@]13C[C@@H](C(=O)Nc4nc(Br)ccc4C)N(C(=O)C2)[C@@H]1C3]<br>(14Z,31R,33S,35R)-63-acetyl-N-(6-bromo-3-methylpyridin-2-yl)-65-(2-methylpyrimidin-5-yl)-4-oxo-11H,61H,32-aza-6(1,7)-indazola-1(1,4)-triazola-3(5,2)-bicyclo[3.1.0]hexanacyclotetradecaphan-13-ene-33-carboxamide | *** | 4.11 (B) | 777 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-51 | (41R,43S,45R)-13-acetyl-N-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-12-ene-43-carboxamide | *** | 3.32 (B) | 715 |
| T-52 | (41R,43S,45R)-13-acetyl-N-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | 3.34 (B) | 715 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-53 | 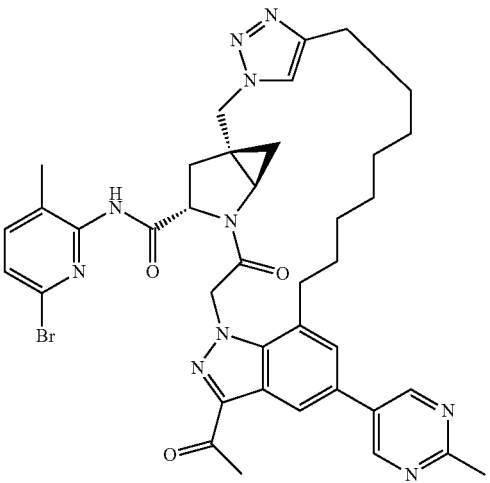 [SMILES: CC(=O)c1nn2c3c(cc(-c4cnc(C)nc4)cc13)CCCCCCCCc1cn(nn1)C[C@@]13C[C@@H](C(=O)Nc4nc(Br)ccc4C)N(C(=O)C2)[C@@H]1C3]<br>(31R,33S,35R,Z)-63-acetyl-N-(6-bromo-3-methylpyridin-2-yl)-65-(2-methylpyrimidin-5-yl)-4-oxo-11H,61H-32-aza-6(1,7)-indazola-1(1,4)-triazola-3(5,2)-bicyclo[3.1.0]hexanacyclotetradecaphane-33-carboxamide | *** | 3.76 (B) | 779 |
| T-54 | 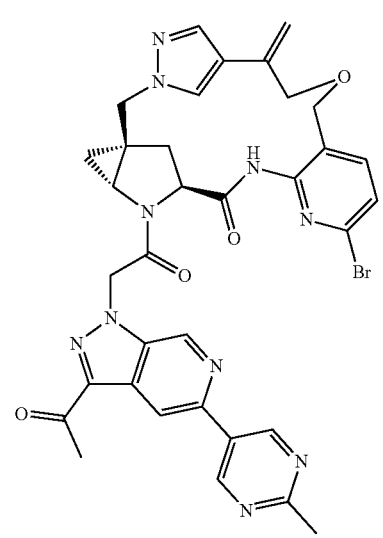 [SMILES: C=C1COCc2ccc(Br)nc2NC(=O)[C@@H]2C[C@]3(C[C@H]3N2C(=O)Cn2nc(C(C)=O)c3cc(-c4cnc(C)nc4)ncc32)Cn2cc1cn2]<br>(31R,33S,35R,Z)-32-(2-(3-acetyl-5-(2-methylpyrimidin-5-yl)-1H-pyrazolo[3,4-c]pyridin-1-yl)acetyl)-66-bromo-10-methylene-11H-8-oxa-32,5-diaza-6(2,3)-pyridina-1(1,4)-pyrazola-3(5,3)-bicyclo[3.1.0]hexanacyclodecaphan-4-one | *** | 2.09 (A) | 722 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-55 | 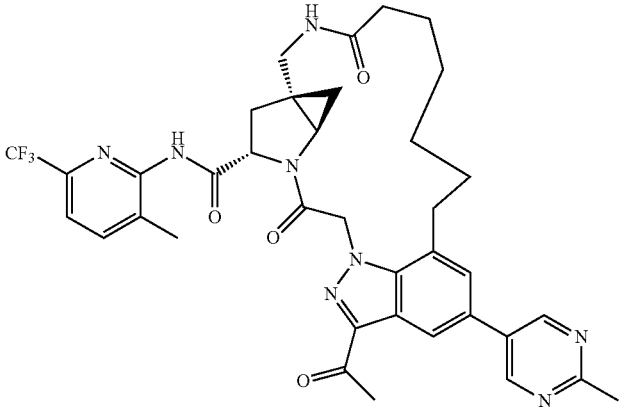 [SMILES: CC(=O)c1nn2c3c(cc(-c4cnc(C)nc4)cc13)CCCCCCC(=O)NC[C@@]13C[C@@H](C(=O)Nc4nc(C(F)(F)F)ccc4C)N(C(=O)C2)[C@@H]1C3]<br>(41R,43S,45R)-13-acetyl-N-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | 3.68 (B) | 717 |
| T-56 | 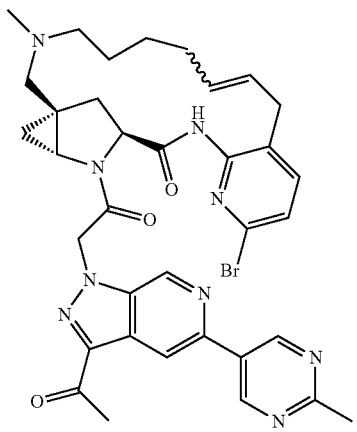<br>(41R,43S,45R)-42-(2-(3-acetyl-5-(2-methylpyrimidin-5-yl)-1H-pyrazolo[3,4-c]pyridin-1-yl)acetyl)-16-bromo-6-methyl-42,2,6-triaza-1(2,3)-pyridina-4(3,5)-bicyclo[3.1.0]hexanacyclotridecaphan-11-en-3-one | *** | 2.63 (B) | 712 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-57 | 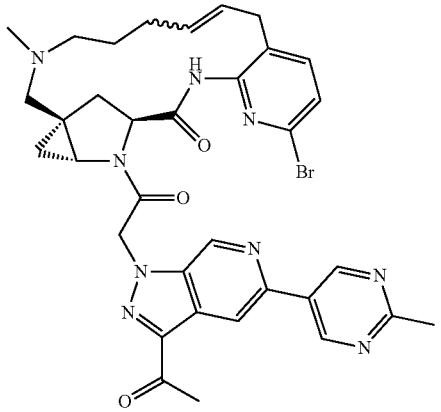<br>(41R,43S,45R)-42-(2-(3-acetyl-5-(2-methylpyrimidin-5-yl)-1H-pyrazolo[3,4-c]pyridin-1-yl)acetyl)-16-bromo-6-methyl-42,2,6-triaza-1(2,3)-pyridina-4(3,5)-bicyclo[3.1.0]hexanacyclododecaphan-10-en-3-one | *** | 3.15 (B) | 698 |
| T-58 | 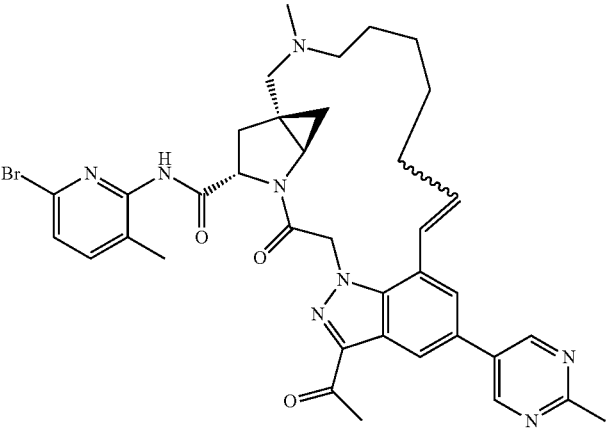 [SMILES: CC(=O)c1nn2c3c(cc(-c4cnc(C)nc4)cc13)C=CCCCCCN(C)C[C@@]13C[C@@H](C(=O)Nc4nc(Br)ccc4C)N(C(=O)C2)[C@@H]1C3]<br>(41R,43S,45R)-13-acetyl-N-(6-bromo-3-methylpyridin-2-yl)-6-methyl-15-(2-methylpyrimidin-5-yl)-3-oxo-11H-42,6-diaza-1(1,7)-indazola-4(2,5)-bicyclo[3.1.0]hexanacyclotridecaphan-12-ene-43-carboxamide | *** | 2.61 (B) | 725 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-59 | 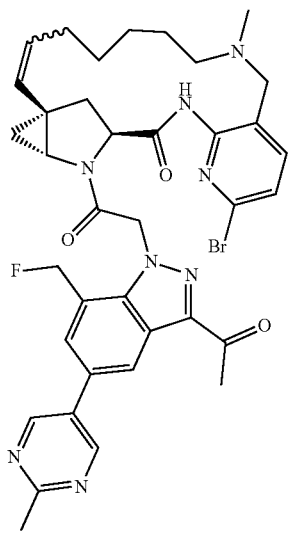 [SMILES: CC(=O)c1nn(CC(=O)N2[C@H]3C[C@@]4(C=CCCCCCN(C)Cc5ccc(Br)nc5NC3=O)C[C@@H]24)c2c(CF)cc(-c3cnc(C)nc3)cc12]<br>(41R,43S,45R)-42-(2-(3-acetyl-7-(fluoromethyl)-5-(2-methylpyrimidin-5-yl)-1H-indazol-1-yl)acetyl)-16-bromo-12-methyl-42,2,12-triaza-1(2,3)-pyridina-4(3,5)-bicyclo[3.1.0]hexanacyclotridecaphan-5-en-3-one | *** | 3.21 (B) | 743 |
| T-60 | 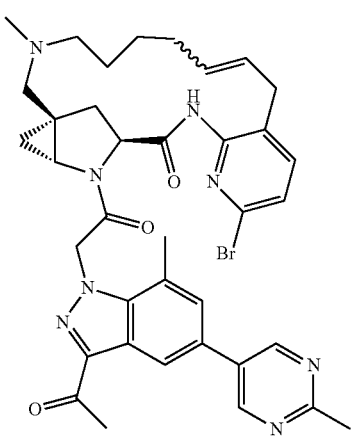<br>(41R,43S,45R)-42-(2-(3-acetyl-7-methyl-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexanacyclotridecaphan-11-en-3-one | *** | 2.87 (B) | 725 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-62 | 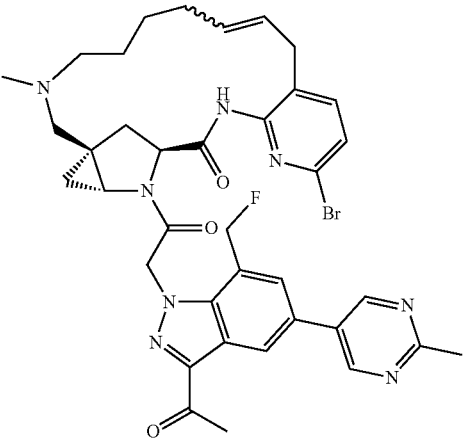<br>(41R,43S,45R)-42-(2-(3-acetyl-7-(fluoromethyl)-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexanacyclotridecaphan-11-en-3-one | *** | 2.86 (B) | 743 |
| T-63 | 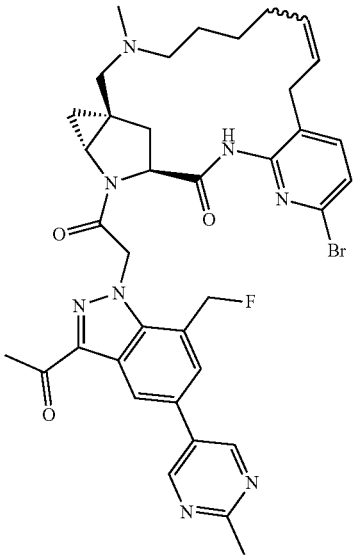 [SMILES: CC(=O)c1nn(CC(=O)N2[C@H]3C[C@]4(C[C@@H]24)CN(C)CCCCC=CCc2ccc(Br)nc2NC3=O)c2c(CF)cc(-c3cnc(C)nc3)cc12]<br>(41R,43S,45R)-42-(2-(3-acetyl-7-(fluoromethyl)-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexanacyclotridecaphan-11-en-3-one | *** | 2.73 (B) | 743 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-64 | 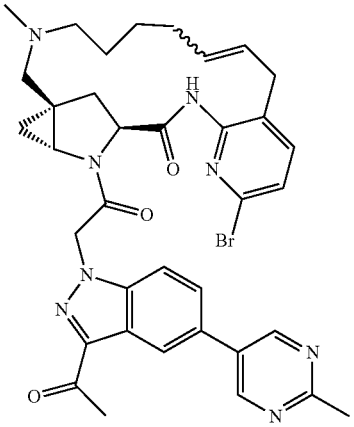<br>(41R,43S,45R)-42-(2-(3-acetyl-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexanacyclotridecaphan-11-en-3-one | *** | 2.66 (B) | 711 |
| T-65 | 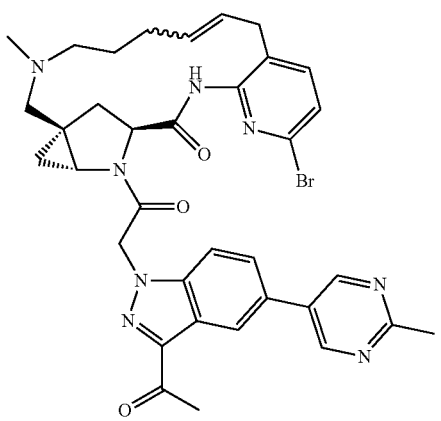<br>(41R,43S,45R)-42-(2-(3-acetyl-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexanacyclododecaphan-10-en-3-one | *** | 2.61 (B) | 697 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-66 | 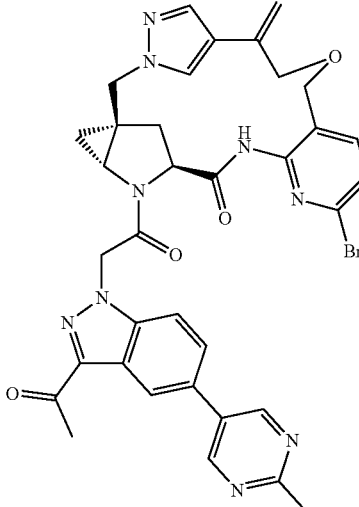<br>(31R,33S,35R,Z)-32-(2-(3-acetyl-5-(2-methylpyrimidin-5-yl)-1H-indazol-1-yl)acetyl)-66-bromo-10-methylene-11H-8-oxa-32,5-diaza-6(2,3)-pyridina-1(1,4)-pyrazola-3(5,3)-bicyclo[3.1.0]hexanacyclodecaphan-4-one | *** | 1.67 (A) | 722 |
| T-67 | 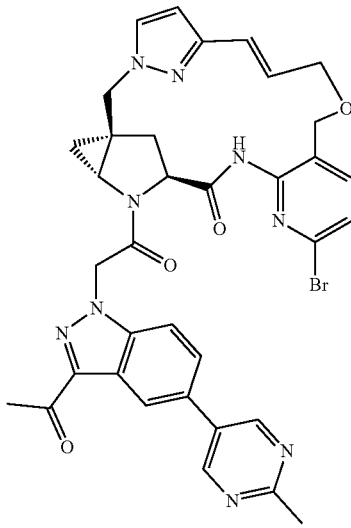 [SMILES: CC(=O)c1nn(CC(=O)N2[C@H]3C[C@]4(C[C@@H]24)Cn2ccc(n2)/C=C/COCc2ccc(Br)nc2NC3=O)c2ccc(-c3cnc(C)nc3)cc12]<br>(12Z,31R,33S,35R,10E)-32-(2-(3-acetyl-5-(2-methylpyrimidin-5-yl)-1H-indazol-1-yl)acetyl)-66-bromo-11H-8-oxa-32,5-diaza-6(2,3)-pyridina-1(1,3)-pyrazola-3(5,3)-bicyclo[3.1.0]hexanacycloundecaphan-10-en-4-one | *** | 2.18 (A) | 723 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-68 | 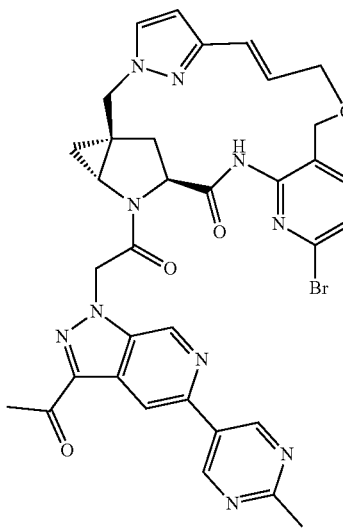<br>(12Z,31R,33S,35R,10E)-32-(2-(3-acetyl-5-(2-methylpyrimidin-5-yl)-1H-pyrazolo[3,4-c]pyridin-1-yl)acetyl)-66-bromo-11H-8-oxa-32,5-diaza-6(2,3)-pyridina-1(1,3)-pyrazola-3(5,3)-bicyclo[3.1.0]hexanacycloundecaphan-10-en-4-one | *** | 2.07 (A) | 724 |
| T-69 | 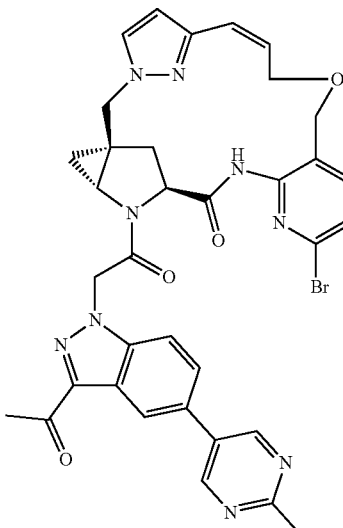<br>(12Z,31R,33S,35R,10Z)-32-(2-(3-acetyl-5-(2-methylpyrimidin-5-yl)-1H-indazol-1-yl)acetyl)-66-bromo-11H-8-oxa-32,5-diaza-6(2,3)-pyridina-1(1,3)-pyrazola-3(5,3)-bicyclo[3.1.0]hexanacycloundecaphan-10-en-4-one | *** | 1.86 (A) | 724 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-70 | 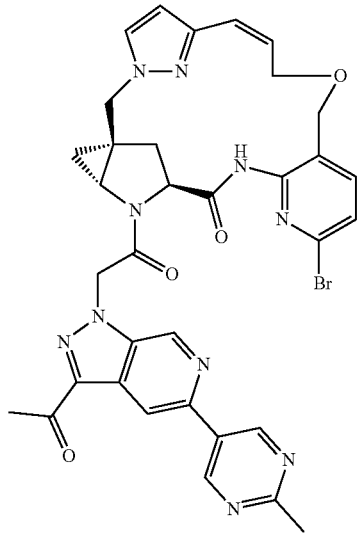 [SMILES: CC(=O)c1nn(CC(=O)N2[C@H]3C[C@]4(C[C@@H]24)Cn2ccc(n2)/C=C\COCc2ccc(Br)nc2NC3=O)c2cnc(-c3cnc(C)nc3)cc12]<br>(12Z,31R,33S,35R,10Z)-32-(2-(3-acetyl-5-(2-methylpyrimidin-5-yl)-1H-pyrazolo[3,4-c]pyridin-1-yl)acetyl)-66-bromo-11H-8-oxa-32,5-diaza-6(2,3)-pyridina-1(1,3)-pyrazola-3(5,3)-bicyclo[3.1.0]hexanacycloundecaphan-10-en-4-one | *** | 1.76 (A) | 723 |
| T-71 | 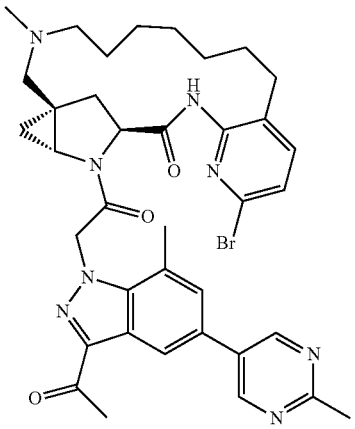<br>(41R,43S,45R)-42-(2-(3-acetyl-7-methyl-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexanacyclotridecaphan-3-one | *** | 2.63 (B) | 727 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-72 | 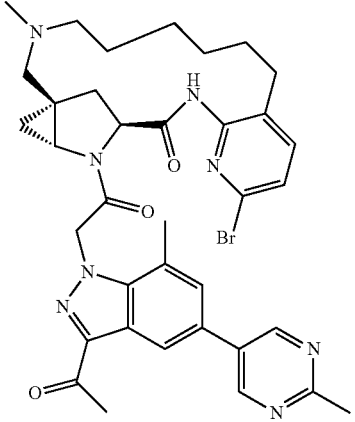<br>(41R,43S,45R)-42-(2-(3-acetyl-7-methyl-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexanacyclododecaphan-3-one | *** | 2.31 (B) | 713 |
| T-73 | 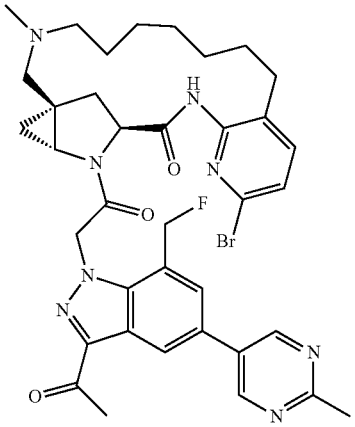<br>(41R,43S,45R)-42-(2-(3-acetyl-7-(fluoromethyl)-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexanacyclotridecaphan-3-one | ND | 2.90 (B) | 745 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-74 | 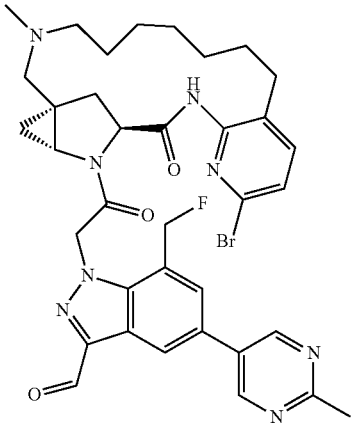<br>1-(2-((41R,43S,45R)-16-bromo-6-methyl-3-oxo-42,2,6-triaza-1(2,3)-pyridina-4(3,5)-bicyclo[3.1.0]hexanacyclotridecaphane-42-yl)-2-oxoethyl)-7-(fluoromethyl)-5-(2-methylpyrimidin-5-yl)-1H-indazole-3-carbaldehyde | *** | 2.69 (B) | 731 |
| T-75 | 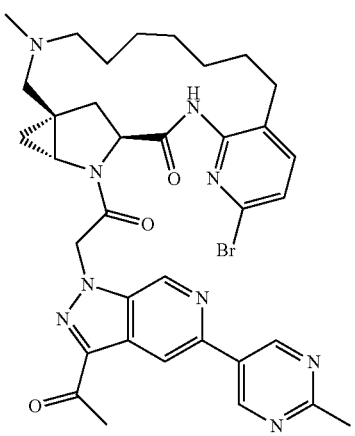<br>(41R,43S,45R)-42-(2-(3-acetyl-5-(2-methylpyrimidin-5-yl)-1H-pyrazolo[3,4-c]pyridin-1-yl)acetyl)-16-bromo-6-methyl-42,2,6-triaza-1(2,3)-pyridina-4(3,5)-bicyclo[3.1.0]hexanacyclotridecaphan-3-one | *** | 2.75 (B) | 714 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-76 | 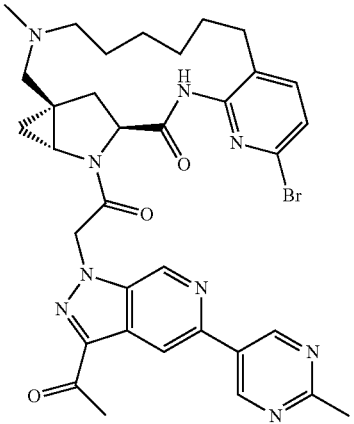<br>(41R,43S,45R)-42-(2-(3-acetyl-5-(2-methylpyrimidin-5-yl)-1H-pyrazolo[3,4-c]pyridin-1-yl)acetyl)-16-bromo-6-methyl-42,2,6-triaza-1(2,3)-pyridina-4(3,5)-bicyclo[3.1.0]hexanacyclododecaphan-3-one | *** | 2.49 (B) | 700 |
| T-77 | 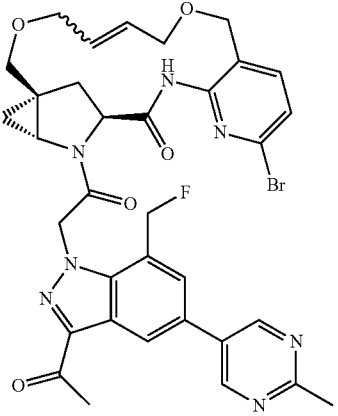 [SMILES: CC(=O)c1nn(CC(=O)N2[C@H]3C[C@@]4(COCC=CCOCc5ccc(Br)nc5NC3=O)C[C@@H]24)c2c(CF)cc(-c3cnc(C)nc3)cc12]<br>(41R,43S,45S)-42-(2-(3-acetyl-7-(fluoromethyl)-5-(2-methylpyrimidin-5-yl)-1H-indazol-1-yl)acetyl)-16-bromo-6,11-dioxa-42,2-diaza-1(2,3)-pyridina-4(3,5)-bicyclo[3.1.0]hexanacyclododecaphan-8-en-3-one | *** | 3.27 (B) | 718 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-78 | 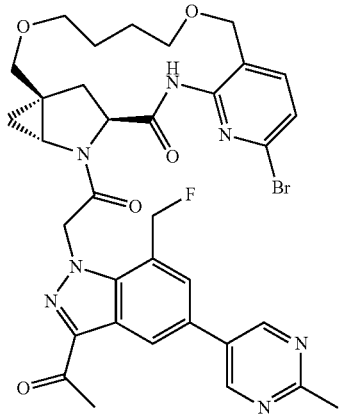 [SMILES: CC(=O)c1nn(CC(=O)N2[C@H]3C[C@@]4(COCCCCOCc5ccc(Br)nc5NC3=O)C[C@@H]24)c2c(CF)cc(-c3cnc(C)nc3)cc12]<br>(41R,43S,45S)-42-(2-(3-acetyl-7-(fluoromethyl)-5-(2-methylpyrimidin-5-yl)-1H-indazol-1-yl)acetyl)-16-bromo-6,11-dioxa-42,2-diaza-1(2,3)-pyridina-4(3,5)-bicyclo[3.1.0]hexanacyclododecaphan-3-one | *** | 3.64 (B) | 720 |
| T-79 | 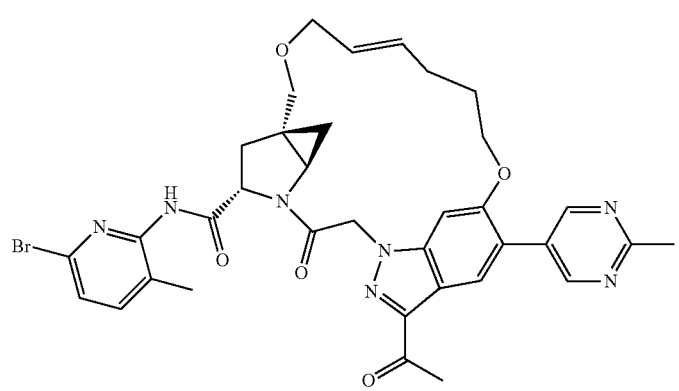 [SMILES: CC(=O)c1nn2c3cc(c(-c4cnc(C)nc4)cc13)OCCC/C=C/COC[C@@]13C[C@@H](C(=O)Nc4nc(Br)ccc4C)N(C(=O)C2)[C@@H]1C3]<br>(41R,43S,45S,E)-13-acetyl-N-(6-bromo-3-methylpyridin-2-yl)-15-(2-methylpyrimidin-5-yl)-3-oxo-11H-6,13-dioxa-42-aza-1(1,6)-indazola-4(2,5)-bicyclo[3.1.0]hexanacyclotridecaphan-8-ene-43-carboxamide | *** | 3.62 (B) | 714 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-80 | (41R,43S,45S,Z)-13-acetyl-N-(6-bromo-3-methylpyridin-2-yl)-15-(2-methylpyrimidin-5-yl)-3-oxo-11H-6,13-dioxa-42-aza-1(1,6)-indazola-4(2,5)-bicyclo[3.1.0]hexanacyclotridecaphan-8-ene-43-carboxamide | *** | 3.71 (B) | 714 |
| T-81 | (41R,43S,45S)-13-acetyl-N-(6-bromo-3-methylpyridin-2-yl)-15-(2-methylpyrimidin-5-yl)-3-oxo-11H-6,13-dioxa-42-aza-1(1,6)-indazola-4(2,5)-bicyclo[3.1.0]hexanacyclotridecaphane-43-carboxamide | ND | 3.82 (B) | 716 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-82 | 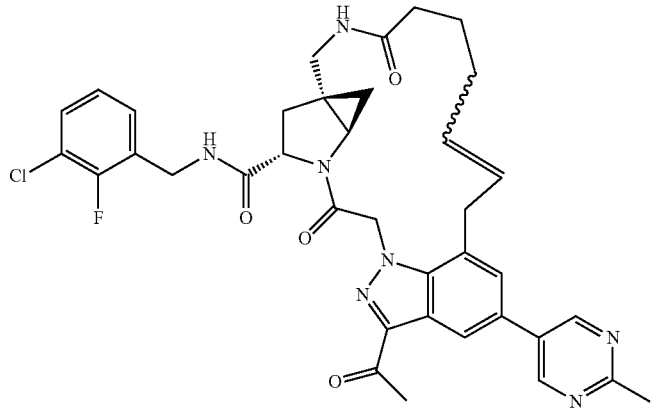 [SMILES: CC(=O)c1nn2c3c(cc(-c4cnc(C)nc4)cc13)CC=CCCCC(=O)NC[C@@]13C[C@@H](C(=O)NCc4cccc(Cl)c4F)N(C(=O)C2)[C@@H]1C3]<br>(41R,43S,45R)-13-acetyl-N-(3-chloro-2-fluorobenzyl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | 3.69 (B) | 698 |
| T-83 | 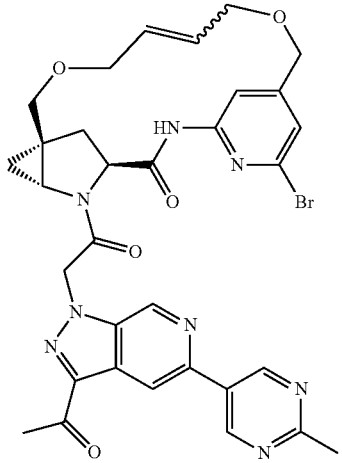 [SMILES: CC(=O)c1nn(CC(=O)N2[C@H]3C[C@@]4(COCC=CCOCc5cc(Br)nc(c5)NC3=O)C[C@@H]24)c2cnc(-c3cnc(C)nc3)cc12]<br>(41R,43S,45S)-42-(2-(3-acetyl-5-(2-methylpyrimidin-5-yl)-1H-pyrazolo[3,4-c]pyridin-1-yl)acetyl)-16-bromo-6,11-dioxa-42,2-diaza-1(2,4)-pyridina-4(3,5)-bicyclo[3.1.0]hexanacyclododecaphan-8-en-3-one | *** | 1.84 (A) | 688 |

TABLE 6-continued

Additional Non-limiting Examples of Compounds of the Present Invention

| Cmp No. | Structure and Name | IC₅₀ (Stars) | RT min (Method A, B, C, or D) | MS (M + 1) |
|---|---|---|---|---|
| T-84 | 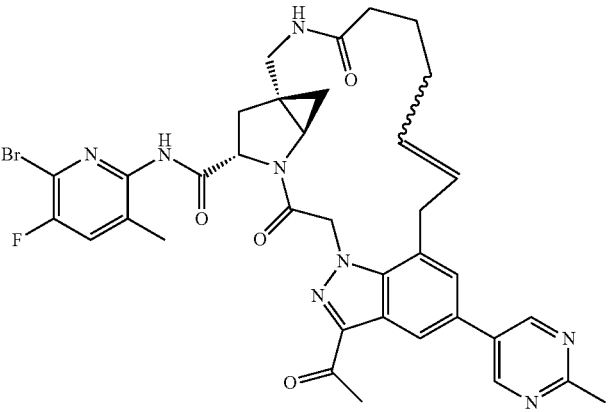 [SMILES: CC(=O)c1nn2c3c(cc(-c4cnc(C)nc4)cc13)CC=CCCCC(=O)NC[C@@]13C[C@@H](C(=O)Nc4nc(Br)c(F)cc4C)N(C(=O)C2)[C@@H]1C3]<br>(41R,43S,45R)-13-acetyl-N-(6-bromo-5-fluoro-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | 3.34 (B) | 743 |
| T-85 | 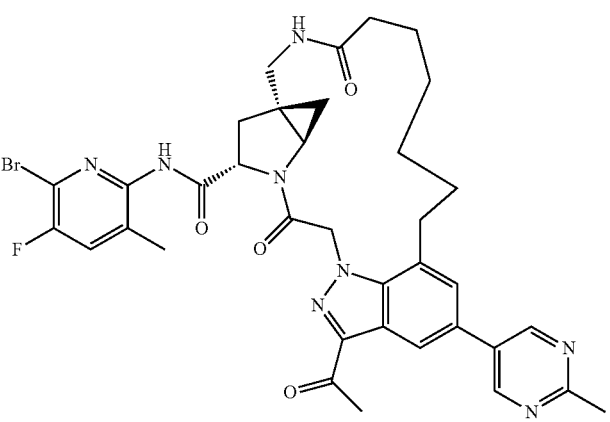 [SMILES: CC(=O)c1nn2c3c(cc(-c4cnc(C)nc4)cc13)CCCCCCC(=O)NC[C@@]13C[C@@H](C(=O)Nc4nc(Br)c(F)cc4C)N(C(=O)C2)[C@@H]1C3]<br>(41R,43S,45R)-13-acetyl-N-(6-bromo-5-fluoro-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | 3.46 (B) | 745 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-86 | 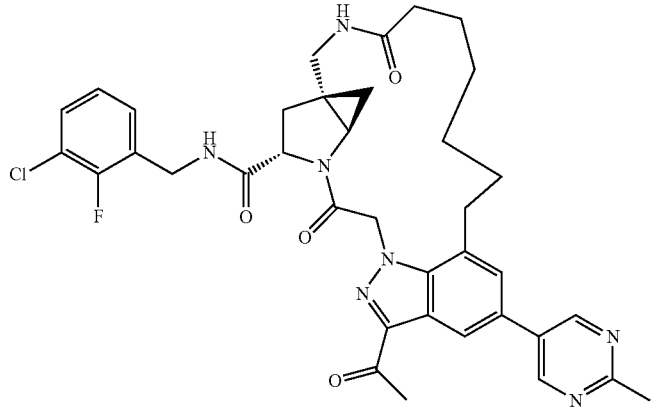 [SMILES: CC(=O)c1nn2c3c(cc(-c4cnc(C)nc4)cc13)CCCCCCC(=O)NC[C@@]13C[C@@H](C(=O)NCc4cccc(Cl)c4F)N(C(=O)C2)[C@@H]1C3]<br>(41R,43S,45R)-13-acetyl-N-(3-chloro-2-fluorobenzyl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | 3.90 (B) | 700 |
| T-87 | 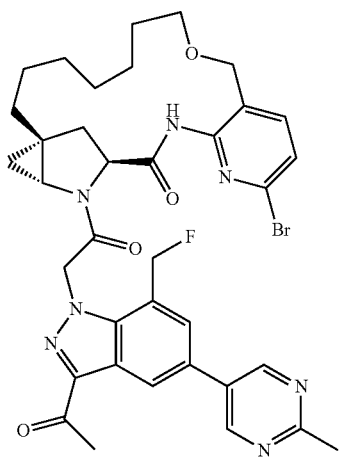 [SMILES: CC(=O)c1nn(CC(=O)N2[C@H]3C[C@@]4(CCCCCCCOCc5ccc(Br)nc5NC3=O)C[C@@H]24)c2c(CF)cc(-c3cnc(C)nc3)cc12]<br>(41R,43S,45R)-42-(2-(3-acetyl-7-(fluoromethyl)-5-(2-methylpyrimidin-5-yl)-1H-indazol-1-yl)acetyl)-16-bromo-12-oxa-42,2-diaza-1(2,3)-pyridina-4(3,5)-bicyclo[3.1.0]hexanacyclotridecaphan-3-one | *** | 3.99 (B) | 732 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-88 | 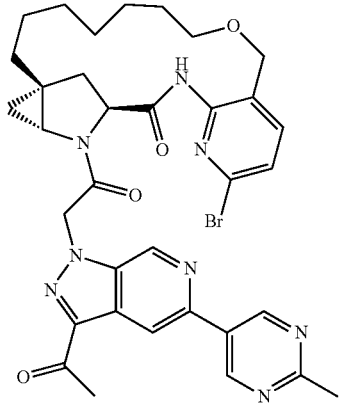 [SMILES: CC(=O)c1nn(CC(=O)N2[C@H]3C[C@@]4(CCCCCCCOCc5ccc(Br)nc5NC3=O)C[C@@H]24)c2cnc(-c3cnc(C)nc3)cc12](41R,43S,45R)-42-(2-(3-acetyl-5-(2-methylpyrimidin-5-yl)-1H-pyrazolo[3,4-c]pyridin-1-yl)acetyl)-16-bromo-12-oxa-42,2-diaza-1(2,3)-pyridina-4(3,5)-bicyclo[3.1.0]hexanacyclotridecaphan-3-one | *** | 3.67 (B) | 701 |
| T-89 | 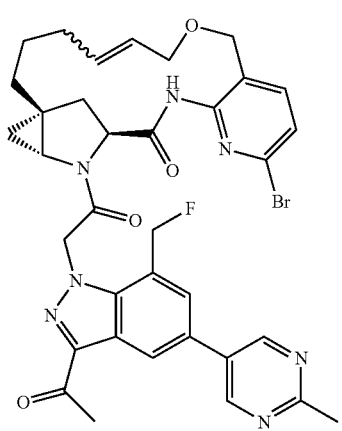(41R,43S,45R)-42-(2-(3-acetyl-7-(fluoromethyl)-5-(2-methylpyrimidin-5-yl)-1H-indazol-1-yl)acetyl)-16-bromo-11-oxa-42,2-diaza-1(2,3)-pyridina-4(3,5)-bicyclo[3.1.0]hexanacyclododecaphan-8-en-3-one | *** | 3.76 (B) | 716 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-90 | (41R,43S,45R)-13-acetyl-N-(6-bromo-4-fluoropyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | 3.83 (B) | 731 |
| T-91 | (41R,43S,45R)-13-acetyl-15-(2-methylpyrimidin-5-yl)-3,7-dioxo-N-(1-(2,2,2-trifluoroethyl)-1H-pyrazol-3-yl)-11H-42,6-diaza-1(1,7)-indazola-4(2,5)-bicyclo[3.1.0]hexanacyclotridecaphan-11-ene-43-carboxamide | *** | 3.33 (B) | 704 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-92 | 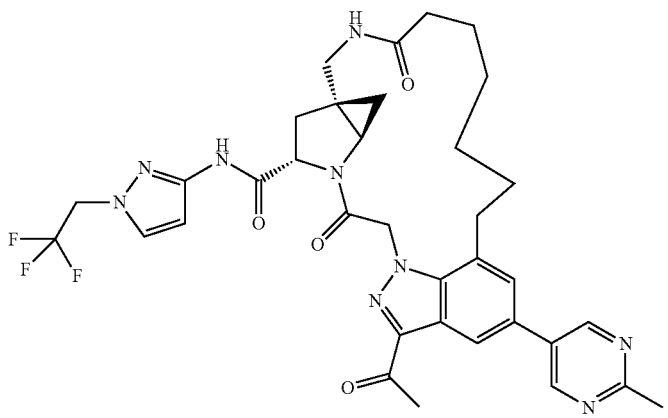 [SMILES: CC(=O)c1nn2c3c(cc(-c4cnc(C)nc4)cc13)CCCCCCC(=O)NC[C@@]13C[C@@H](C(=O)Nc4ccn(CC(F)(F)F)n4)N(C(=O)C2)[C@@H]1C3]<br>(41R,43S,45R)-13-acetyl-15-(2-methylpyrimidin-5-yl)-3,7-dioxo-N-(1-(2,2,2-trifluoroethyl)-1H-pyrazol-3-yl)-11H-42,6-diaza-1(1,7)-indazola-4(2,5)-bicyclo[3.1.0]hexanacyclotridecaphane-43-carboxamide | *** | 3.37 (B) | 706 |
| T-93 | 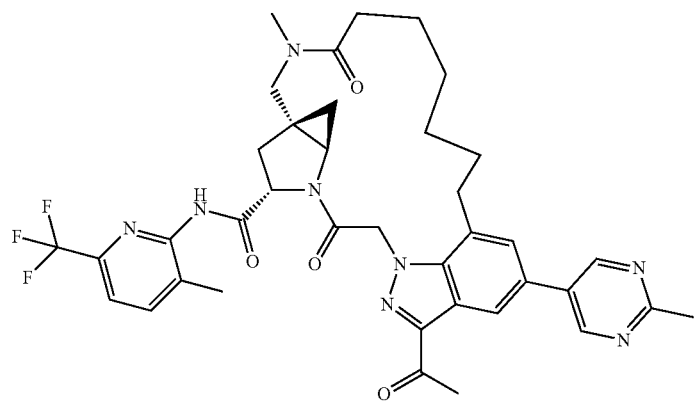 [SMILES: CC(=O)c1nn2c3c(cc(-c4cnc(C)nc4)cc13)CCCCCCC(=O)N(C)C[C@@]13C[C@@H](C(=O)Nc4nc(C(F)(F)F)ccc4C)N(C(=O)C2)[C@@H]1C3]<br>(41R,43S,45R)-13-acetyl-6-methyl-N-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | 3.55 (B) | 731 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-94 | 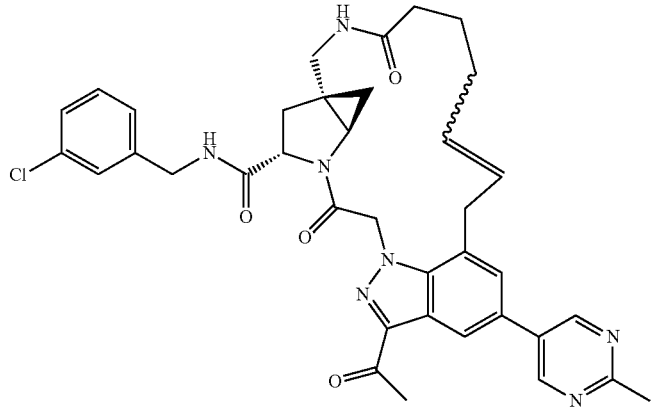 [SMILES: CC(=O)c1nn2c3c(cc(-c4cnc(C)nc4)cc13)CC=CCCCC(=O)NC[C@@]13C[C@@H](C(=O)NCc4cccc(Cl)c4)N(C(=O)C2)[C@@H]1C3]<br>(41R,43S,45R)-13-acetyl-N-(3-chlorobenzyl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | 3.48 (B) | 680 |
| T-95 | 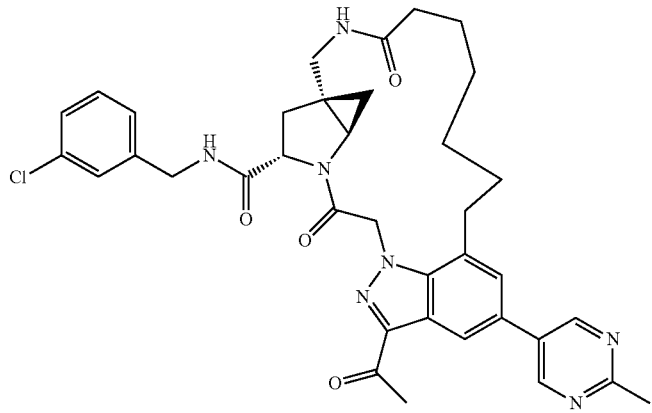 [SMILES: CC(=O)c1nn2c3c(cc(-c4cnc(C)nc4)cc13)CCCCCCC(=O)NC[C@@]13C[C@@H](C(=O)NCc4cccc(Cl)c4)N(C(=O)C2)[C@@H]1C3]<br>(41R,43S,45R)-13-acetyl-N-(3-chlorobenzyl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | 3.63 (B) | 682 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-96 | 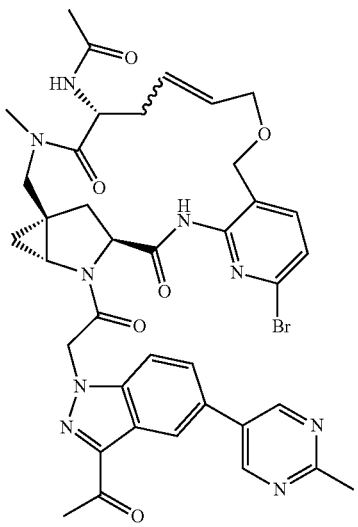<br>N-((41R,43S,45R,8R)-42-(2-(3-acetyl-5-(2-methylpyrimidin-5-yl)-1H-indazol-1-yl)acetyl)-16-bromo-6-methyl-3,7-dioxo-13-oxa-42,2,6-triaza-1(2,3)-pyridina-4(3,5)-bicyclo[3.1.0]hexanacyclotetradecaphan-10-en-8-yl)acetamide | *** | 1.44 (A) | 800 |
| T-97 | 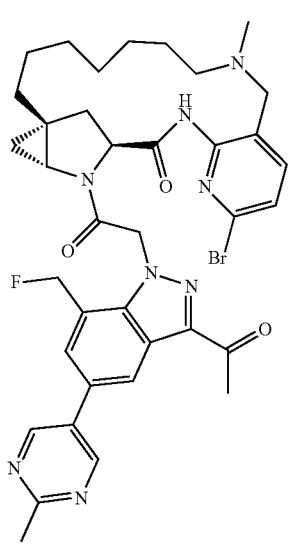 [SMILES: CC(=O)c1nn(CC(=O)N2[C@H]3C[C@@]4(CCCCCCCN(C)Cc5ccc(Br)nc5NC3=O)C[C@@H]24)c2c(CF)cc(-c3cnc(C)nc3)cc12]<br>(41R,43S,45R)-42-(2-(3-acetyl-7-(fluoromethyl)-5-(2-methylpyrimidin-5-yl)-1H-indazol-1-yl)acetyl)-16-bromo-12-methyl-42,2,12-triaza-1(2,3)-pyridina-4(3,5)-bicyclo[3.1.0]hexanacyclotridecaphan-3-one | *** | 2.94 (B) | 745 |

TABLE 6-continued

Additional Non-limiting Examples of Compounds of the Present Invention

| Cmp No. | Structure and Name | IC₅₀ (Stars) | RT min (Method A, B, C, or D) | MS (M + 1) |
|---|---|---|---|---|
| T-98 | 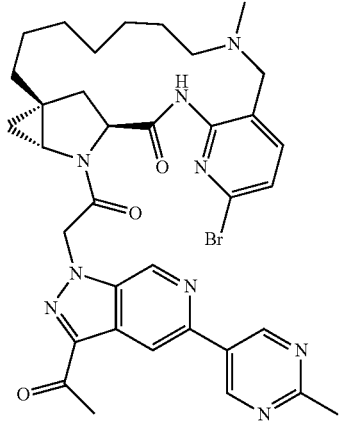 [SMILES: CC(=O)c1nn(CC(=O)N2[C@H]3C[C@@]4(CCCCCCCN(C)Cc5ccc(Br)nc5NC3=O)C[C@@H]24)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-16-bromo-12-methyl-42,2,12-triaza-1(2,3)-pyridina-4(3,5)-bicyclo[3.1.0]hexanacyclotridecaphan-3-one | *** | 2.40 (B) | 714 |
| T-99 | 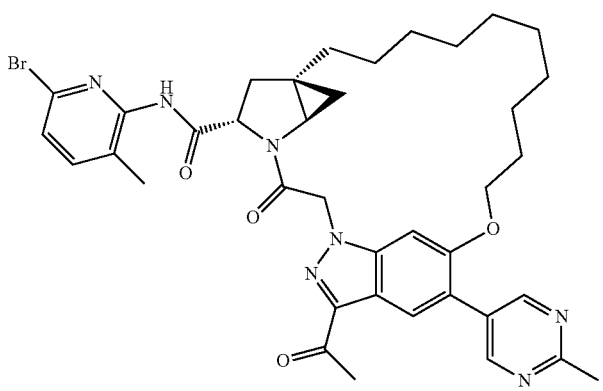 [SMILES: CC(=O)c1nn2c3cc(c(-c4cnc(C)nc4)cc13)OCCCCCCCCCC[C@@]13C[C@@H](C(=O)Nc4nc(Br)ccc4C)N(C(=O)C2)[C@@H]1C3]<br>(41R,43S,45R)-13-acetyl-N-(6-bromo-3-methylpyridin-2-yl)-15-(2-methylpyrimidin-5-yl)-3-oxo-11H-15-oxa-42-aza-1(1,6)-indazola-4(2,5)-bicyclo[3.1.0]hexanacyclopentadecaphane-43-carboxamide | *** | 4.54 (B) | 742 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-100 | 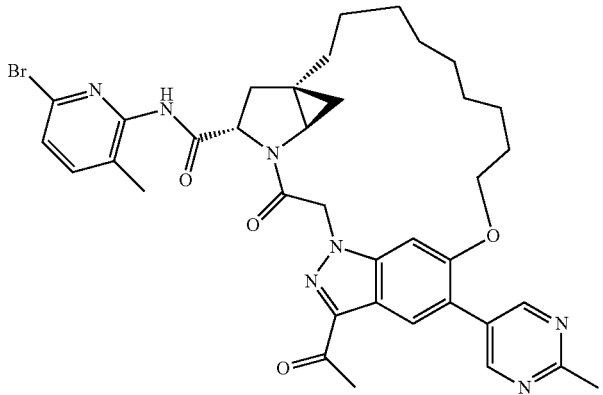 [SMILES: CC(=O)c1nn2c3cc(c(-c4cnc(C)nc4)cc13)OCCCCCCCCC[C@@]13C[C@@H](C(=O)Nc4nc(Br)ccc4C)N(C(=O)C2)[C@@H]1C3]<br>(41R,43S,45R)-13-acetyl-N-(6-bromo-3-methylpyridin-2-yl)-15-(2-methylpyrimidin-5-yl)-3-oxo-11H-14-oxa-42-aza-1(1,6)-indazola-4(2,5)-bicyclo[3.1.0]hexanacycloteradecaphane-43-carboxamide | *** | 4.42 (B) | 728 |
| T-101 | 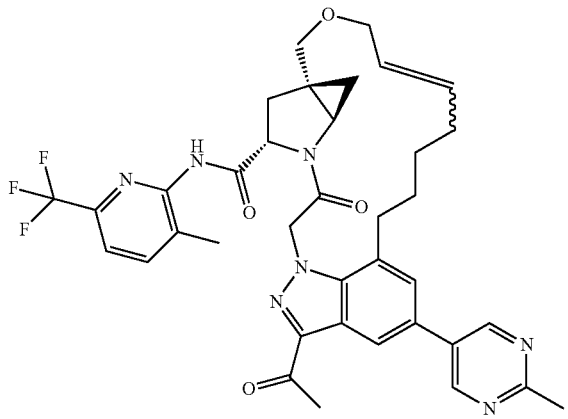 [SMILES: CC(=O)c1nn2c3c(cc(-c4cnc(C)nc4)cc13)CCCCC=CCOC[C@@]13C[C@@H](C(=O)Nc4nc(C(F)(F)F)ccc4C)N(C(=O)C2)[C@@H]1C3]<br>(41R,43S,45S)-13-acetyl-N-(3-methyl-6-(trifluoromethyl)pyridin-2-yl)-15-(2-methylpyrimidin-5-yl)-3-oxo-11H-6-oxa-42-aza-1(1,7)-indazola-4(2,5)-bicyclo[3.1.0]hexanacyclotridecaphan-8-ene-43-carboxamide | *** | 4.01 (B) | 702 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-102 | 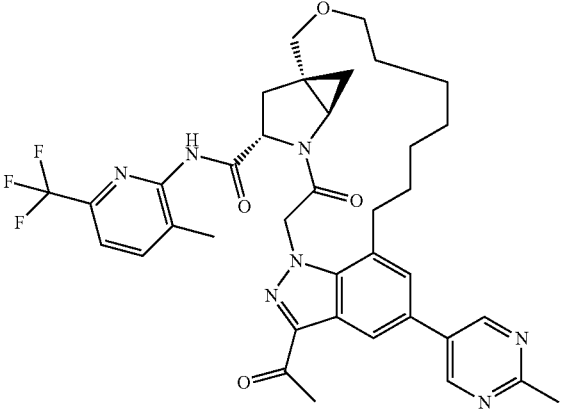 [SMILES: CC(=O)c1nn2c3c(cc(-c4cnc(C)nc4)cc13)CCCCCCCOC[C@@]13C[C@@H](C(=O)Nc4nc(C(F)(F)F)ccc4C)N(C(=O)C2)[C@@H]1C3] (41R,43S,45S)-13-acetyl-N-(3-methyl-6-(trifluoromethyl)pyridin-2-yl)-15-(2-methylpyrimidin-5-yl)-3-oxo-11H-6-oxa-42-aza-1(1,7)-indazola-4(2,5)-bicyclo[3.1.0]hexanacyclotridecaphane-43-carboxamide | *** | 4.07 (B) | 704 |
| T-103 | 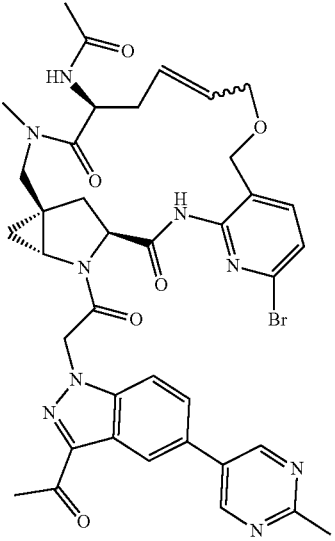 N-((41R,43S,45R,8S)-42-(2-(3-acetyl-5-(2-methylpyrimidin-5-yl)-1H-indazol-1-yl)acetyl)-16-bromo-6-methyl-3,7-dioxo-13-oxa-42,2,6-triaza-1(2,3)-pyridina-4(3,5)-bicyclo[3.1.0]hexanacyclotetradecaphan-10-en-8-yl)acetamide | *** | 1.38 (A) | 800 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-104 | 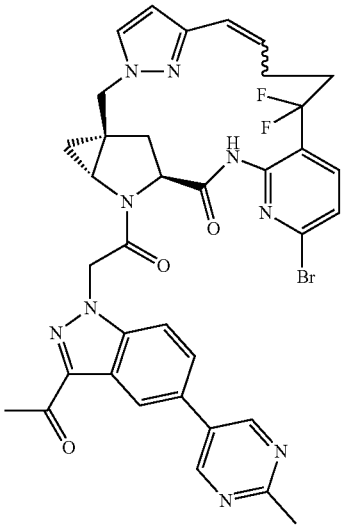 [SMILES: CC(=O)c1nn(CC(=O)N2[C@H]3C[C@]4(C[C@@H]24)Cn2ccc(n2)C=CCCC(F)(F)c2ccc(Br)nc2NC3=O)c2ccc(-c3cnc(C)nc3)cc12]<br>(12Z,31R,33S,35R)-32-(2-(3-acetyl-5-(2-methylpyrimidin-5-yl)-1H-indazol-1-yl)acetyl)-66-bromo-7,7-difluoro-11H-32,5-diaza-6(2,3)-pyridina-1(1,3)-pyrazola-3(5,3)-bicyclo[3.1.0]hexanacycloundeaphan-10-en-4-one | *** | 2.04 (A) | 756 |
| T-105 | 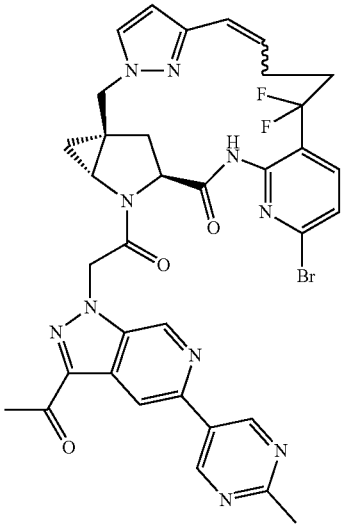 [SMILES: CC(=O)c1nn(CC(=O)N2[C@H]3C[C@]4(C[C@@H]24)Cn2ccc(n2)C=CCCC(F)(F)c2ccc(Br)nc2NC3=O)c2cnc(-c3cnc(C)nc3)cc12]<br>(12Z,31R,33S,35R)-32-(2-(3-acetyl-5-(2-methylpyrimidin-5-yl)-1H-pyrazolo[3,4-c]pyridin-1-yl)acetyl)-66-bromo-7,7-difluoro-11H-32,5-diaza-6(2,3)-pyridina-1(1,3)-pyrazola-3(5,3)-bicyclo[3.1.0]hexanacycloundecaphan-10-en-4-one | *** | 1.96 (A) | 757 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-106 | 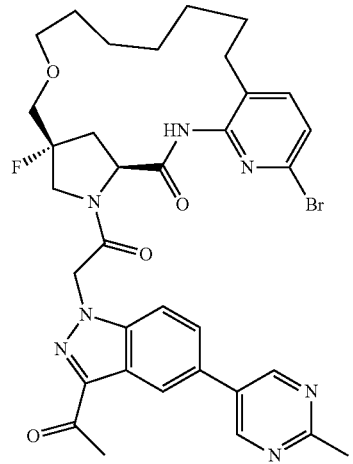 [SMILES: CC(=O)c1nn(CC(=O)N2C[C@@]3(F)COCCCCCCCc4ccc(Br)nc4NC(=O)[C@@H]2C3)c2ccc(-c3cnc(C)nc3)cc12] (42S,44R)-41-(2-(3-acetyl-5-(2-methylpyrimidin-5-yl)-1H-indazol-1-yl)acetyl)-16-bromo-44-fluoro-6-oxa-2-aza-1(2,3)-pyridina-4(2,4)-pyrrolidinacyclotridecaphan-3-one | *** | 3.61 (B) | 706 |
| T-107 | 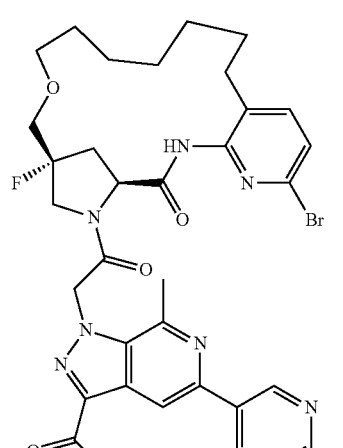 (42S,44R)-41-(2-(3-acetyl-7-methyl-5-(2-methylpyrimidin-5-yl)-1H-pyrazolo[3,4-c]pyridin-1-yl)acetyl)-16-bromo-44-fluoro-6-oxa-2-aza-1(2,3)-pyridina-4(2,4)-pyrrolidinacyclotridecaphan-3-one | *** | 3.84 (B) | 721 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-108 | 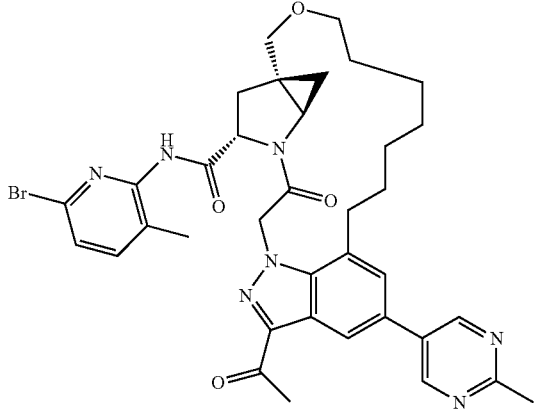 [SMILES: CC(=O)c1nn2c3c(cc(-c4cnc(C)nc4)cc13)CCCCCCCOC[C@@]13C[C@@H](C(=O)Nc4nc(Br)ccc4C)N(C(=O)C2)[C@@H]1C3]<br>(41R,43S,45S)-13-acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexanacyclotridecaphane-43-carboxamide | *** | 4.01 (B) | 714 |
| T-109 | 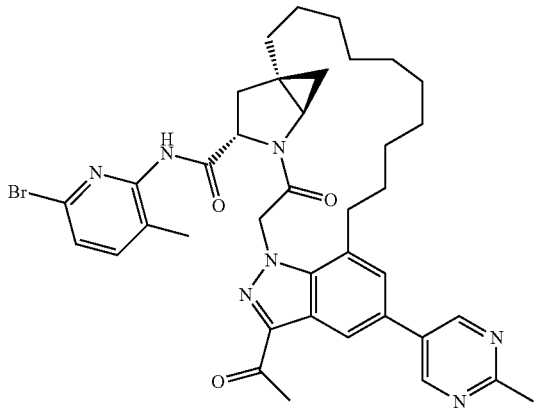 [SMILES: CC(=O)c1nn2c3c(cc(-c4cnc(C)nc4)cc13)CCCCCCCCCC[C@@]13C[C@@H](C(=O)Nc4nc(Br)ccc4C)N(C(=O)C2)[C@@H]1C3]<br>(41R,43S,45R)-13-acetyl-N-(6-bromo-3-methylpyridin-2-yl)-15-(2-methylpyrimidin-5-yl)-3-oxo-11H-42-aza-1(1,7)-indazola-4(2,5)-bicyclo[3.1.0]hexanacyclotetradecaphane-43-carboxamide | *** | 4.75 (B) | 726 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-110 | 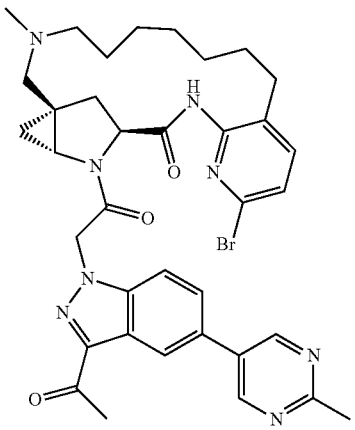<br>(41R,43S,45R)-42-(2-(3-acetyl-5-(2-methylpyrimidin-5-yl)-1H-indazol-1-yl)acetyl)-16-bromo-6-methyl-42,2,6-triaza-1(2,3)-pyridina-4(3,5)-bicyclo[3.1.0]hexanacyclotridecaphan-3-one | *** | 2.74 (B) | 713 |
| T-111 | 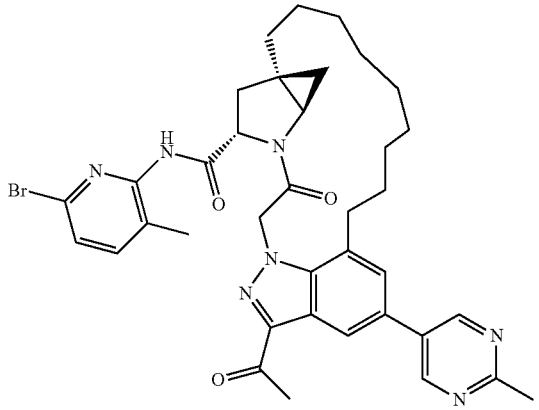 [SMILES: CC(=O)c1nn2c3c(cc(-c4cnc(C)nc4)cc13)CCCCCCCCC[C@@]13C[C@@H](C(=O)Nc4nc(Br)ccc4C)N(C(=O)C2)[C@@H]1C3]<br>(41R,43S,45R)-13-acetyl-N-(6-bromo-3-methylpyridin-2-yl)-15-(2-methylpyrimidin-5-yl)-3-oxo-11H-42-aza-1(1,7)-indazola-4(2,5)-bicyclo[3.1.0]hexanacyclotridecaphane-43-carboxamide | *** | 4.21 (B) | 712 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-112 | 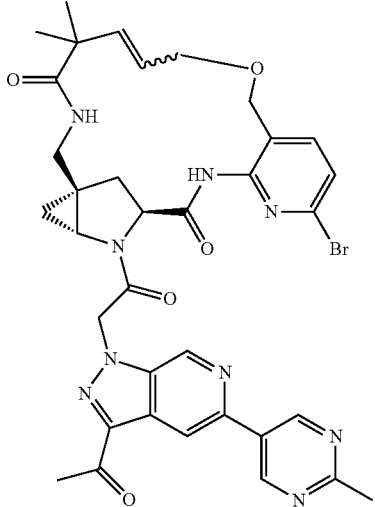 [SMILES: CC(=O)c1nn(CC(=O)N2[C@H]3C[C@@]4(CNC(=O)C(C)(C)C=CCOCc5ccc(Br)nc5NC3=O)C[C@@H]24)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-16-bromo-8,8-dimethyl-12-oxa-42,2,6-triaza-1(2,3)-pyridina-4(3,5)-bicyclo[3.1.0]hexanacyclotridecaphan-9-ene-3,7-dione | *** | 3.04 (B) | 742 |
| T-113 | 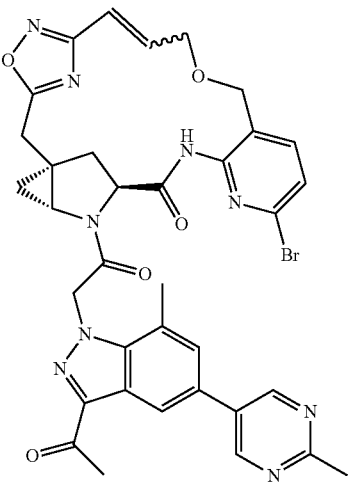 [SMILES: CC(=O)c1nn(CC(=O)N2[C@H]3C[C@@]4(Cc5nc(no5)C=CCOCc5ccc(Br)nc5NC3=O)C[C@@H]24)c2c(C)cc(-c3cnc(C)nc3)cc12]<br>(14Z,31R,33S,35R)-32-(2-(3-acetyl-7-methyl-5-(2-methylpyrimidin-5-yl)-1H-indazol-1-yl)acetyl)-66-bromo-8-oxa-32,5-diaza-1(5,3)-oxadiazola-6(2,3)-pyridina-3(5,3)-bicyclo[3.1.0]hexanacycloundecaphan-10-en-4-one | *** | 3.38 (B) | 738 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-114 | 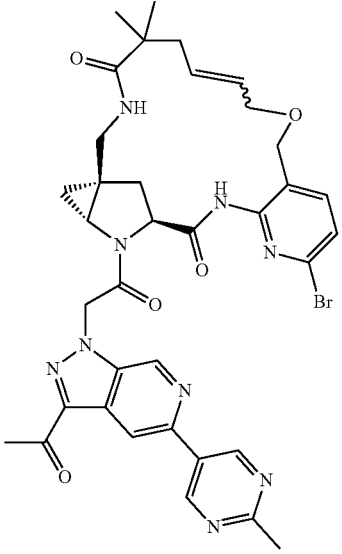 [SMILES: CC(=O)c1nn(CC(=O)N2[C@H]3C[C@@]4(CNC(=O)C(C)(C)CC=CCOCc5ccc(Br)nc5NC3=O)C[C@@H]24)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-16-bromo-8,8-dimethyl-13-oxa-42,2,6-triaza-1(2,3)-pyridina-4(3,5)-bicyclo[3.1.0]hexanacyclotetradecaphan-10-ene-3,7-dione | *** | 3.51 (B) | 756 |
| T-115 | 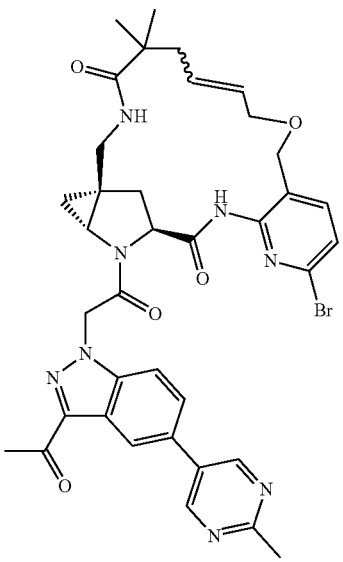 [SMILES: CC(=O)c1nn(CC(=O)N2[C@H]3C[C@@]4(CNC(=O)C(C)(C)CC=CCOCc5ccc(Br)nc5NC3=O)C[C@@H]24)c2ccc(-c3cnc(C)nc3)cc12]<br>(41R,43S,45R)-42-(2-(3-acetyl-5-(2-methylpyrimidin-5-yl)-1H-indazol-1-yl)acetyl)-16-bromo-8,8-dimethyl-13-oxa-42,2,6-triaza-1(2,3)-pyridina-4(3,5)-bicyclo[3.1.0]hexanacyclotetradecaphan-10-ene-3,7-dione | *** | 3.58 (B) | 755 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-116 | 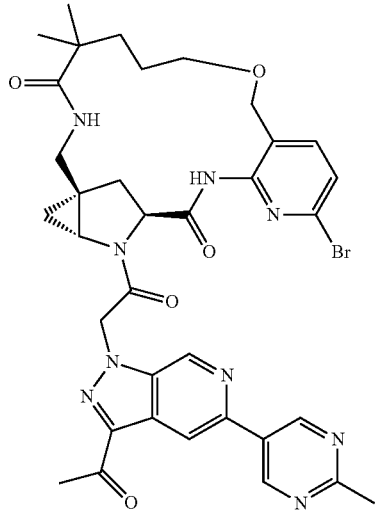 [SMILES: CC(=O)c1nn(CC(=O)N2[C@H]3C[C@@]4(CNC(=O)C(C)(C)CCCOCc5ccc(Br)nc5NC3=O)C[C@@H]24)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-16-bromo-8,8-dimethyl-12-oxa-42,2,6-triaza-1(2,3)-pyridina-4(3,5)-bicyclo[3.1.0]hexanacyclotridecaphane-3,7-dione | *** | 2.94 (B) | 744 |
| T-117 | 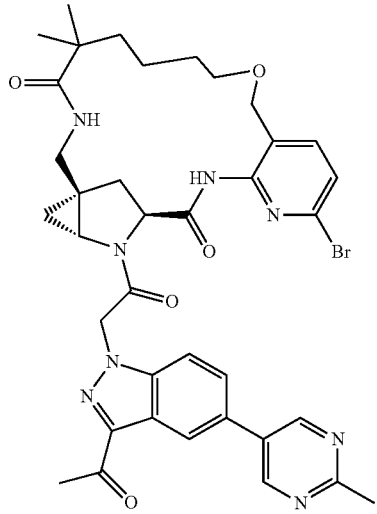 [SMILES: CC(=O)c1nn(CC(=O)N2[C@H]3C[C@@]4(CNC(=O)C(C)(C)CCCCOCc5ccc(Br)nc5NC3=O)C[C@@H]24)c2ccc(-c3cnc(C)nc3)cc12]<br>(41R,43S,45R)-42-(2-(3-acetyl-5-(2-methylpyrimidin-5-yl)-1H-indazol-1-yl)acetyl)-16-bromo-8,8-dimethyl-13-oxa-42,2,6-triaza-1(2,3)-pyridina-4(3,5)-bicyclo[3.1.0]hexanacyclotetradecaphane-3,7-dione | *** | 3.60 (B) | 757 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-118 | 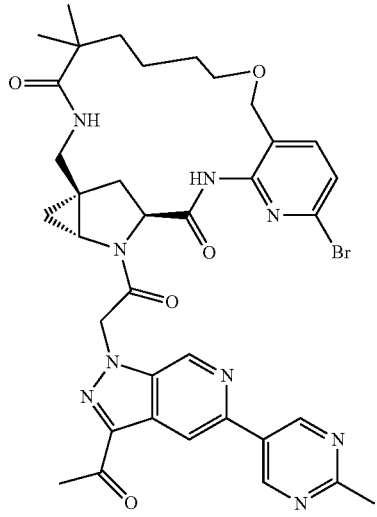 [SMILES: CC(=O)c1nn(CC(=O)N2[C@H]3C[C@@]4(CNC(=O)C(C)(C)CCCCOCc5ccc(Br)nc5NC3=O)C[C@@H]24)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-16-bromo-8,8-dimethyl-13-oxa-42,2,6-triaza-1(2,3)-pyridina-4(3,5)-bicyclo[3.1.0]hexanacyclotetradecaphane-3,7-dione | *** | 3.53 (B) | 758 |
| T-119 | 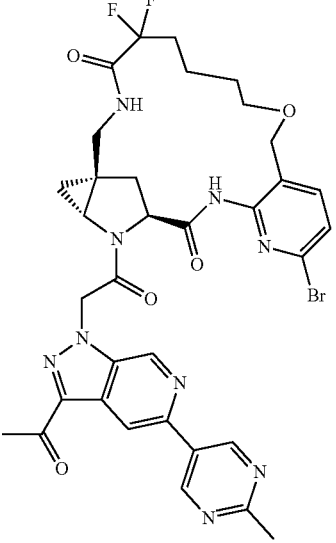<br>(41R,43S,45R)-42-(2-(3-acetyl-5-(2-methylpyrimidin-5-yl)-1H-pyrazolo[3,4-c]pyridin-1-yl)acetyl)-16-bromo-8,8-difluoro-13-oxa-42,2,6-triaza-1(2,3)-pyridina-4(3,5)-bicyclo[3.1.0]hexanacyclotetradecaphane-3,7-dione | *** | 2.97 (B) | 766 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-120 | (41R,43S,45R)-42-(2-(3-acetyl-5-(2-methylpyrimidin-5-yl)-1H-indazol-1-yl)acetyl)-16-bromo-8,8-difluoro-13-oxa-42,2,6-triaza-1(2,3)-pyridina-4(3,5)-bicyclo[3.1.0]hexanacyclotetradecaphane-3,7-dione | *** | 3.02 (B) | 765 |
| T-121 | (41R,43S,45R)-13-acetyl-N-(6-bromo-3-methylpyridin-2-yl)-12,13-dihydroxy-6-methyl-15-(2-methylpyrimidin-5-yl)-3-oxo-11H-42,6-diaza-1(1,7)-indazola-4(2,5)-bicyclo[3.1.0]hexanacyclotridecaphane-43-carboxamide | *** | 2.50 (B) | 759 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-122 | 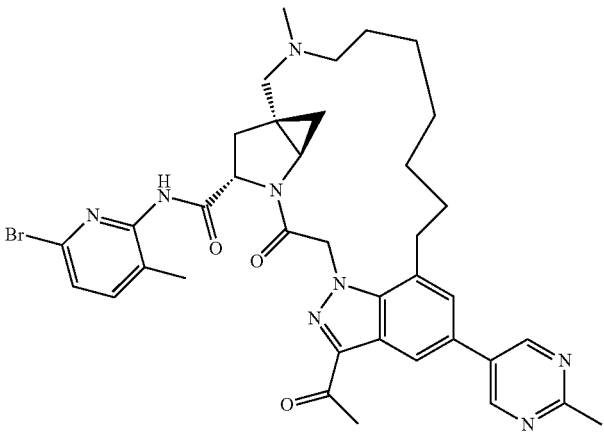 [SMILES: CC(=O)c1nn2c3c(cc(-c4cnc(C)nc4)cc13)CCCCCCCN(C)C[C@@]13C[C@@H](C(=O)Nc4nc(Br)ccc4C)N(C(=O)C2)[C@@H]1C3](41R,43S,45R)-13-acetyl-N-(6-bromo-3-methylpyridin-2-yl)-6-methyl-15-(2-methylpyrimidin-5-yl)-3-oxo-11H-42,6-diaza-1(1,7)-indazola-4(2,5)-bicyclo[3.1.0]hexanacyclotridecaphane-43-carboxamide | ** | 2.73 (B) | 727 |
| T-123 | 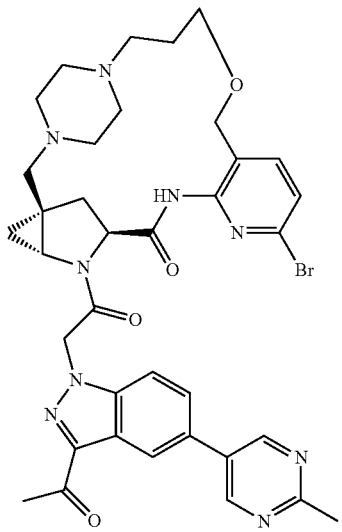 [SMILES: CC(=O)c1nn(CC(=O)N2[C@H]3C[C@]4(C[C@@H]24)CN2CCN(CCCOCc4ccc(Br)nc4NC3=O)CC2)c2ccc(-c3cnc(C)nc3)cc12](31R,33S,35R)-32-(2-(3-acetyl-5-(2-methylpyrimidin-5-yl)-1H-indazol-1-yl)acetyl)-66-bromo-8-oxa-32,5-diaza-1(1,4)-piperazina-6(2,3)-pyridina-3(5,3)-bicyclo[3.1.0]hexanacycloundecaphan-4-one | ** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-124 | 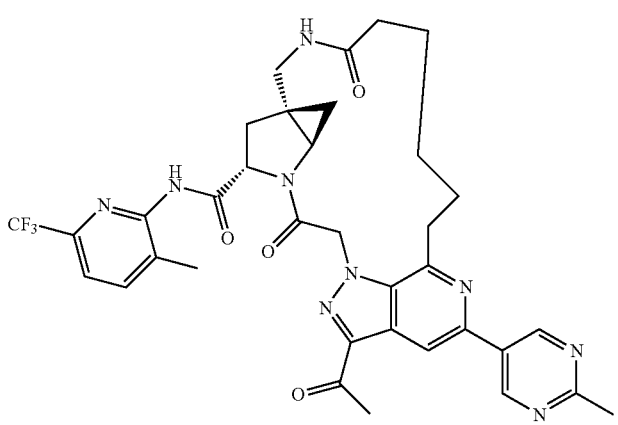 [SMILES: CC(=O)c1nn2c3c(nc(-c4cnc(C)nc4)cc13)CCCCCC(=O)NC[C@@]13C[C@@H](C(=O)Nc4nc(C(F)(F)F)ccc4C)N(C(=O)C2)[C@@H]1C3]<br>(41R,43S,45R)-13-acetyl-N-(3-methyl-6-(trifluoromethyl)pyridin-2-yl)-15-(2-methylpyrimidin-5-yl)-3,7-dioxo-11H-42,6-diaza-1(1,7)-pyrazolo[3,4-c]pyridina-4(2,5)-bicyclo[3.1.0]hexanacyclododecaphane-43-carboxamide | *** | 3.29 (B) | 704 |
| T-125 | 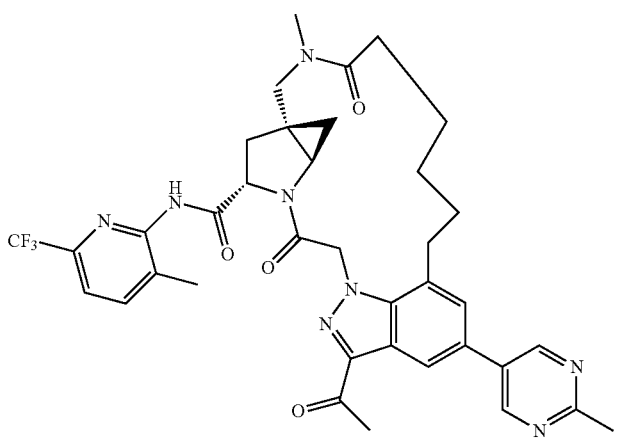 [SMILES: CC(=O)c1nn2c3c(cc(-c4cnc(C)nc4)cc13)CCCCCC(=O)N(C)C[C@@]13C[C@@H](C(=O)Nc4nc(C(F)(F)F)ccc4C)N(C(=O)C2)[C@@H]1C3]<br>(41R,43S,45R)-13-acetyl-6-methyl-N-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclododecaphane-43-carboxamide | *** | 3.54 (B) | 717 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-126 | 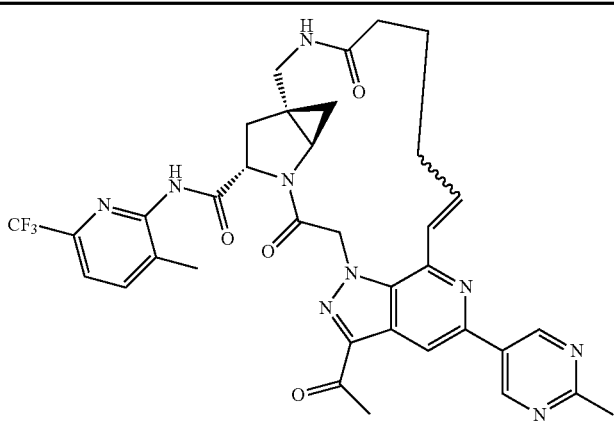 (41R,43S,45R)-13-acetyl-N-(3-methyl-6-(trifluoromethyl)pyridin-2-yl)-15-(2-methylpyrimidin-5-yl)-3,7-dioxo-11H-42,6-diaza-1(1,7)-pyrazolo[3,4-c]pyridina-4(2,5)-bicyclo[3.1.0]hexanacyclododecaphan-11-ene-43-carboxamide | *** | 3.15 (B) | 702 |
| T-127 | 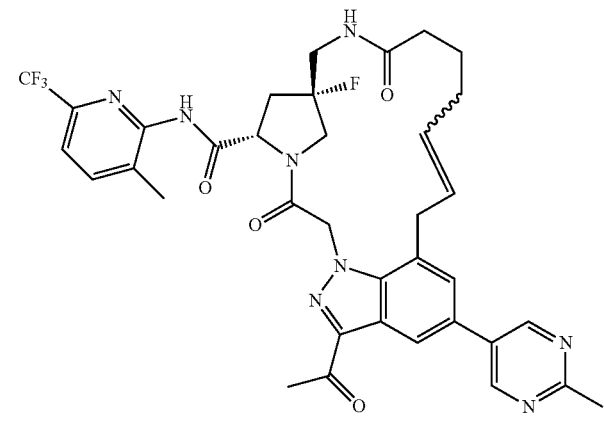 [SMILES: CC(=O)c1nn2c3c(cc(-c4cnc(C)nc4)cc13)CC=CCCCC(=O)NC[C@]1(F)C[C@@H](C(=O)Nc3nc(C(F)(F)F)ccc3C)N(C1)C(=O)C2] (43R,45S)-13-acetyl-43-fluoro-N-(3-methyl-6-(trifluoromethyl)pyridin-2-yl)-15-(2-methylpyrimidin-5-yl)-3,7-dioxo-11H-6-aza-1(1,7)-indazola-4(1,3)-pyrrolidinacyclotridecaphan-11-ene-45-carboxamide | * | 3.99 (B) | 721 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-128 | (43R,45S)-13-acetyl-43-fluoro-N-(3-methyl-6-(trifluoromethyl)pyridin-2-yl)-15-(2-methylpyrimidin-5-yl)-3,7-dioxo-11H-6-aza-1(1,7)-indazola-4(1,3)-pyrrolidinacyclotridecaphane-45-carboxamide | *** | 3.32 (B) | 723 |
| T-129 | (43R,45S)-13-acetyl-43-fluoro-N-(3-methyl-6-(trifluoromethyl)pyridin-2-yl)-15-(2-methylpyrimidin-5-yl)-3,7-dioxo-11H-6-aza-1(1,7)-indazola-4(1,3)-pyrrolidinacyclododecaphane-45-carboxamide | ** | 3.17 (B) | 709 |

| Cmp No. | Structure and Name | IC$_{50}$ (Stars) | RT min (Method A, B, C, or D) | MS (M + 1) |
|---|---|---|---|---|
| T-130 | 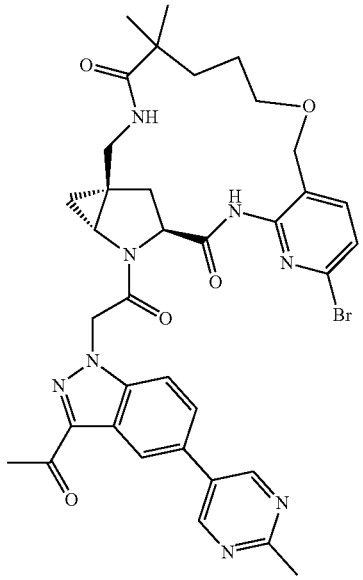 [SMILES: CC(=O)c1nn(CC(=O)N2[C@H]3C[C@@]4(CNC(=O)C(C)(C)CCCOCc5ccc(Br)nc5NC3=O)C[C@@H]24)c2ccc(-c3cnc(C)nc3)cc12]<br>(41R,43S,45R)-42-(2-(3-acetyl-5-(2-methylpyrimidin-5-yl)-1H-indazol-1-yl)acetyl)-16-bromo-8,8-dimethyl-12-oxa-42,2,6-triaza-1(2,3)-pyridina-4(3,5)-bicyclo[3.1.0]hexanacyclotridecaphane-3,7-dione | *** | 2.96 (B) | 743 |
| T-131 | 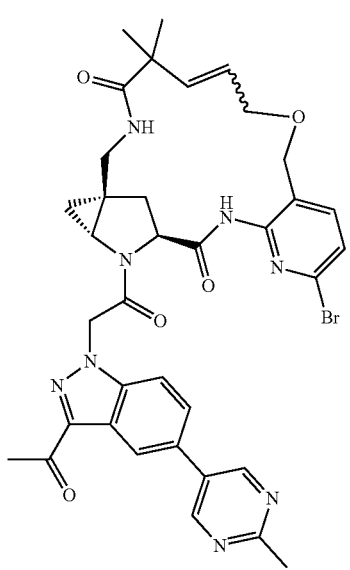 [SMILES: CC(=O)c1nn(CC(=O)N2[C@H]3C[C@@]4(CNC(=O)C(C)(C)C=CCOCc5ccc(Br)nc5NC3=O)C[C@@H]24)c2ccc(-c3cnc(C)nc3)cc12]<br>(41R,43S,45R)-42-(2-(3-acetyl-5-(2-methylpyrimidin-5-yl)-1H-indazol-1-yl)acetyl)-16-bromo-8,8-dimethyl-12-oxa-42,2,6-triaza-1(2,3)-pyridina-4(3,5)-bicyclo[3.1.0]hexanacyclotridecaphan-9-ene-3,7-dione | *** | 3.06 (B) | 741 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-132 | (41R,43S,45R)-13-acetyl-N-(3-methyl-6-(trifluoromethyl)pyridin-2-yl)-15-(2-methylpyrimidin-5-yl)-3,7-dioxo-11H-42,6-diaza-1(1,7)-pyrazolo[3,4-c]pyridina-4(2,5)-bicyclo[3.1.0]hexanacyclotridecaphane-43-carboxamide | *** | 3.43 (B) | 718 |
| T-133 | (41R,43S,45R)-13-cyano-N-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | 3.39 (B) | 698 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-134 | 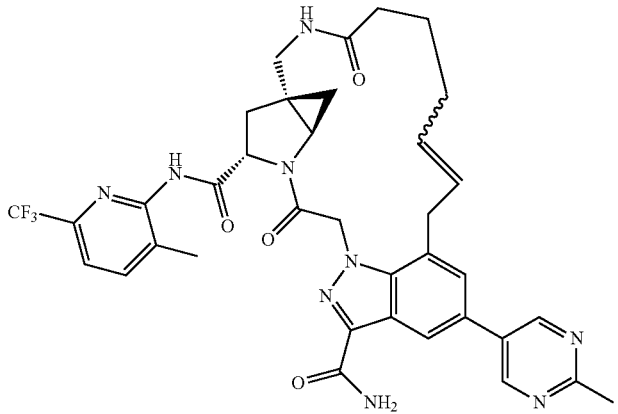 [SMILES: Cc1ncc(-c2cc3c4c(c2)c(C(N)=O)nn4CC(=O)N2[C@H](C(=O)Nc4nc(C(F)(F)F)ccc4C)C[C@@]4(CNC(=O)CCCC=CC3)C[C@@H]24)cn1]<br>(41R,43S,45R)-N43-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-13,43-dicarboxamide | *** | 3.43 (B) | 716 |
| T-135 | 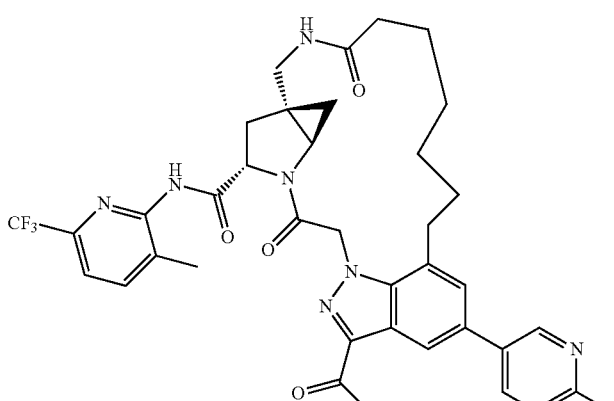<br>(41R,43S,45R)-N43-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-13,43-dicarboxamide | ND | 3.48 (B) | 718 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-136 | 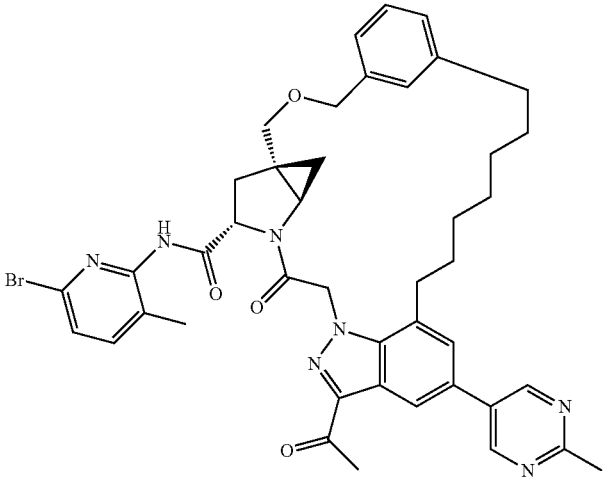 [SMILES: CC(=O)c1nn2c3c(cc(-c4cnc(C)nc4)cc13)CCCCCCCc1cccc(c1)COC[C@@]13C[C@@H](C(=O)Nc4nc(Br)ccc4C)N(C(=O)C2)[C@@H]1C3]<br>(41R,43S,45S)-13-acetyl-N-(6-bromo-3-methylpyridin-2-yl)-15-(2-methylpyrimidin-5-yl)-3-oxo-11H-6-oxa-42-aza-1(1,7)-indazola-4(2,5)-bicyclo[3.1.0]hexana-8(1,3)-benzenacyclopentadecaphane-43-carboxamide | *** | 4.92 (B) | 804 |
| T-137 | 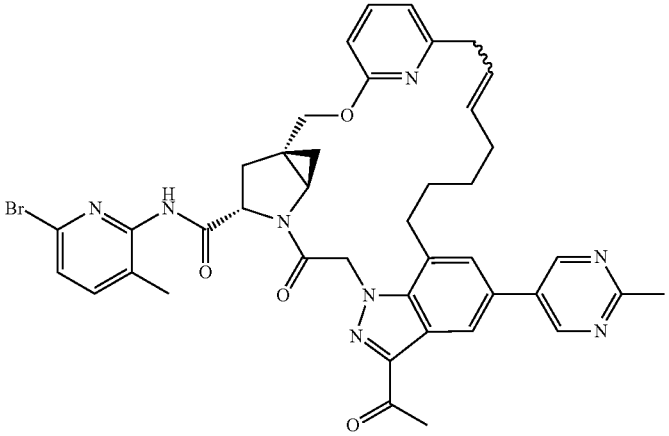 [SMILES: CC(=O)c1nn2c3c(cc(-c4cnc(C)nc4)cc13)CCCCC=CCc1cccc(n1)OC[C@@]13C[C@@H](C(=O)Nc4nc(Br)ccc4C)N(C(=O)C2)[C@@H]1C3]<br>(41R,43S,45S)-13-acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclotetradecaphan-9-ene-43-carboxamide | *** | 4.44 (B) | 789 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-138 | 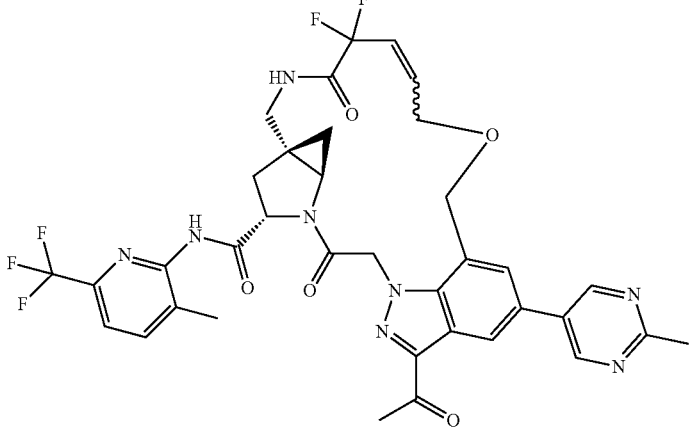 41R,43S,45R)-13-acetyl-8,8-difluoro-N-(3-methyl-6-(trifluoromethyl)pyridin-2-yl)-15-(2-methylpyrimidin-5-yl)-3,7-dioxo-11H-12-oxa-42,6-diaza-1(1,7)-indazola-4(2,5)-bicyclo[3.1.0]hexanacyclotridecaphan-9-ene-43-carboxamide | *** | 3.48 (B) | 753 |
| T-139 | 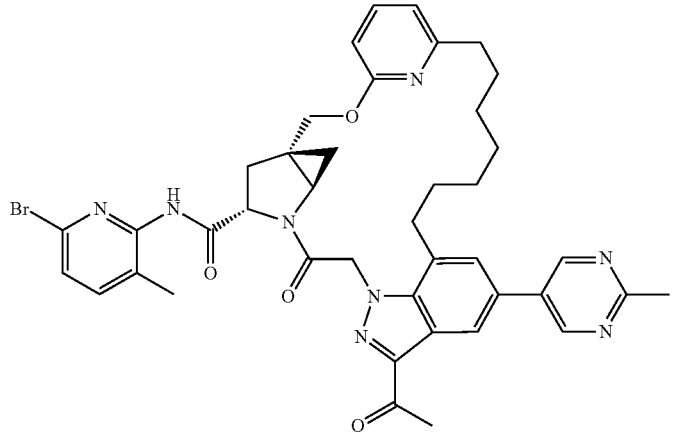 [SMILES: CC(=O)c1nn2c3c(cc(-c4cnc(C)nc4)cc13)CCCCCCCc1cccc(n1)OC[C@@]13C[C@@H](C(=O)Nc4nc(Br)ccc4C)N(C(=O)C2)[C@@H]1C3] (41R,43S,45S)-13-acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclotetradecaphane-43-carboxamide | *** | 4.69 (B) | 791 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-140 | 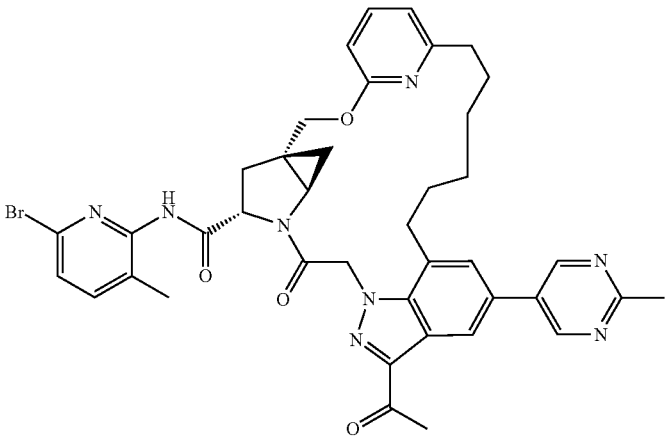 [SMILES: CC(=O)c1nn2c3c(cc(-c4cnc(C)nc4)cc13)CCCCCCc1cccc(n1)OC[C@@]13C[C@@H](C(=O)Nc4nc(Br)ccc4C)N(C(=O)C2)[C@@H]1C3]<br>(41R,43S,45S)-13-acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclotridecaphane-43-carboxamide | *** | 4.59 (B) | 777 |
| T-141 | 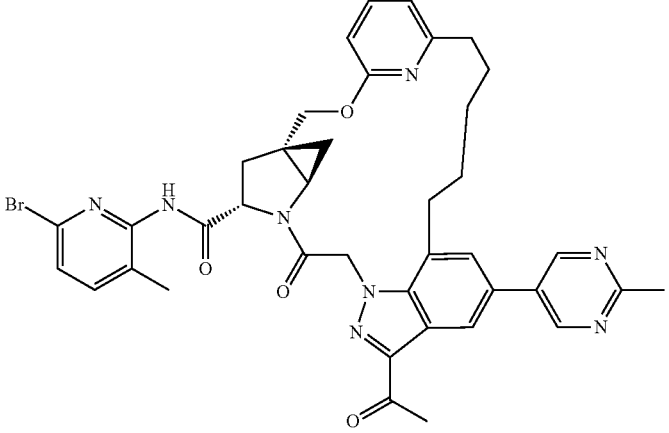 [SMILES: CC(=O)c1nn2c3c(cc(-c4cnc(C)nc4)cc13)CCCCCc1cccc(n1)OC[C@@]13C[C@@H](C(=O)Nc4nc(Br)ccc4C)N(C(=O)C2)[C@@H]1C3]<br>(41R,43S,45S)-13-acetyl-N-(6-bromo-3-methylpyridin-2-yl)-15-(2-methylpyrimidin-5-yl)-3-oxo-11H-6-oxa-42-aza-1(1,7)-indazola-7(2,6)-pyridina-4(2,5)-bicyclo[3.1.0]hexanacyclododecaphane-43-carboxamide | *** | 4.48 (B) | 765 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-152 | 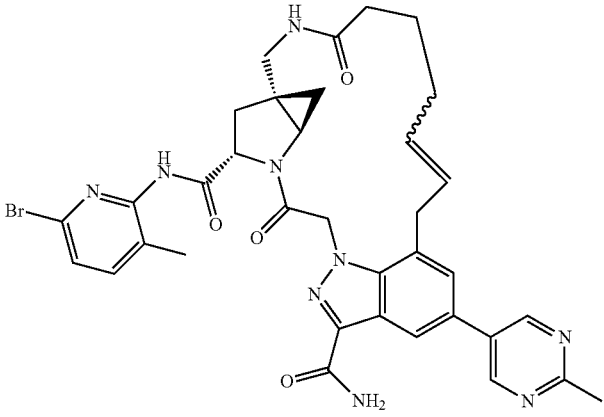 [SMILES: Cc1ncc(-c2cc3c4c(c2)c(C(N)=O)nn4CC(=O)N2[C@H](C(=O)Nc4nc(Br)ccc4C)C[C@@]4(CNC(=O)CCCC=CC3)C[C@@H]24)cn1]<br>(41R,43S,45R)-N43-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-13,43-dicarboxamide | *** | 3.17 (B) | 726 |
| T-153 | 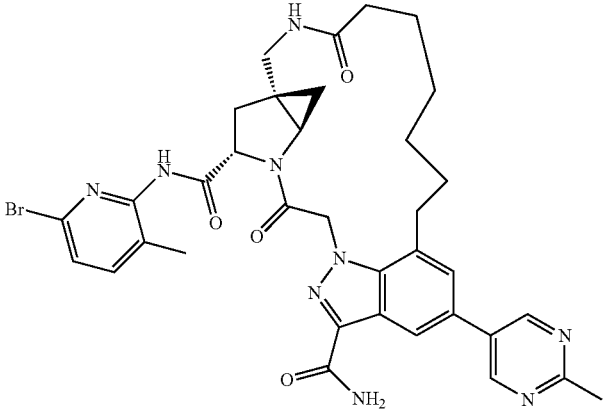 [SMILES: Cc1ncc(-c2cc3c4c(c2)c(C(N)=O)nn4CC(=O)N2[C@H](C(=O)Nc4nc(Br)ccc4C)C[C@@]4(CNC(=O)CCCCCC3)C[C@@H]24)cn1]<br>(41R,43S,45R)-N43-(6-bromo-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-13,43-dicarboxamide | *** | 3.40 (B) | 728 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-154 | 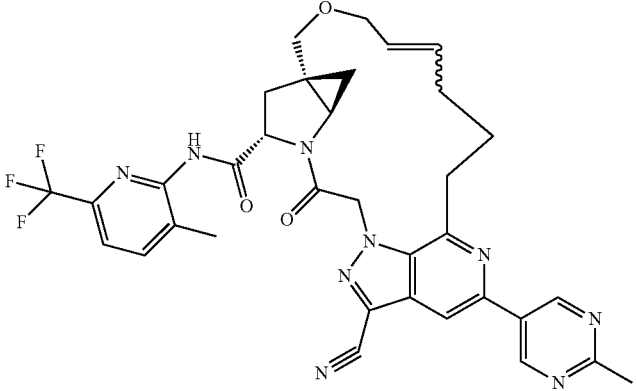 [SMILES: Cc1ncc(-c2cc3c(C#N)nn4c3c(n2)CCCC=CCOC[C@@]23C[C@@H](C(=O)Nc5nc(C(F)(F)F)ccc5C)N(C(=O)C4)[C@@H]2C3)cn1]<br>(41R,43S,45S)-13-cyano-N-(3-methyl-6-(trifluoromethyl)pyridin-2-yl)-15-(2-methylpyrimidin-5-yl)-3-oxo-11H-6-oxa-42-aza-1(1,7)-pyrazolo[3,4-c]pyridina-4(2,5)-bicyclo[3.1.0]hexanacyclododecaphan-8-ene-43-carboxamide | *** | 3.03 (B) | 672 |
| T-155 | 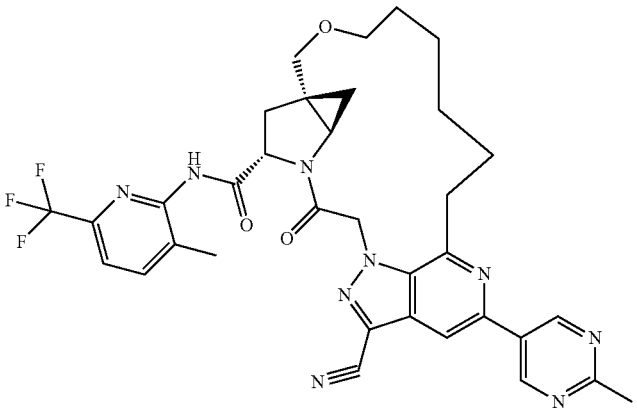 [SMILES: Cc1ncc(-c2cc3c(C#N)nn4c3c(n2)CCCCCCOC[C@@]23C[C@@H](C(=O)Nc5nc(C(F)(F)F)ccc5C)N(C(=O)C4)[C@@H]2C3)cn1]<br>(41R,43S,45S)-13-cyano-N-(3-methyl-6-(trifluoromethyl)pyridin-2-yl)-15-(2-methylpyrimidin-5-yl)-3-oxo-11H-6-oxa-42-aza-1(1,7)-pyrazolo[3,4-c]pyridina-4(2,5)-bicyclo[3.1.0]hexanacyclododecaphane-43-carboxamide | *** | 3.57 (B) | 674 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-156 | 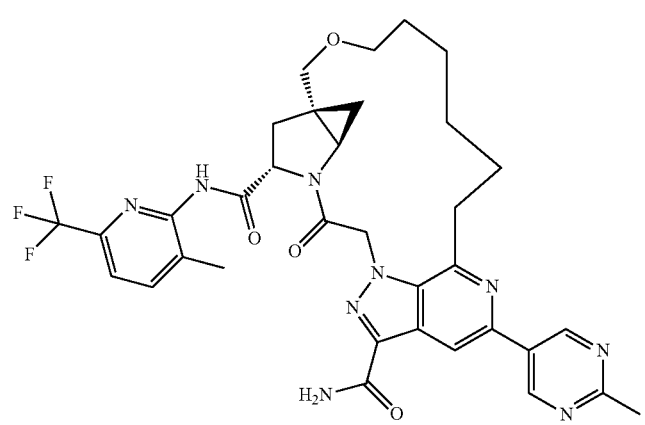 [SMILES: Cc1ncc(-c2cc3c(C(N)=O)nn4c3c(n2)CCCCCCOC[C@@]23C[C@@H](C(=O)Nc5nc(C(F)(F)F)ccc5C)N(C(=O)C4)[C@@H]2C3)cn1] (41R,43S,45S)-N43-(3-methyl-6-(trifluoromethyl)pyridin-2-yl)-15-(2-methylpyrimidin-5-yl)-3-oxo-11H-6-oxa-42-aza-1(1,7)-pyrazolo[3,4-c]pyridina-4(2,5)-bicyclo[3.1.0]hexanacyclododecaphane-13,43-dicarboxamide | *** | 3.72 (B) | 692 |
| T-157 | 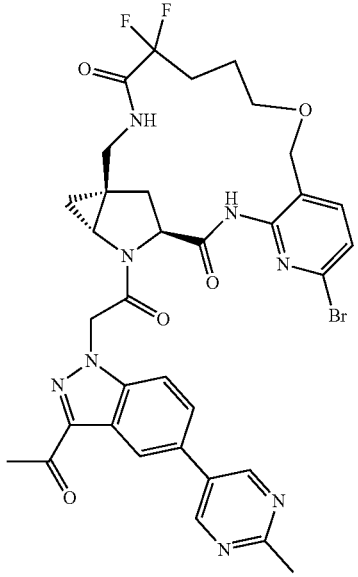 [SMILES: CC(=O)c1nn(CC(=O)N2[C@H]3C[C@@]4(CNC(=O)C(F)(F)CCCOCc5ccc(Br)nc5NC3=O)C[C@@H]24)c2ccc(-c3cnc(C)nc3)cc12] (41R,43S,45R)-42-(2-(3-acetyl-5-(2-methylpyrimidin-5-yl)-1H-indazol-1-yl)acetyl)-16-bromo-8,8-difluoro-12-oxa-42,2,6-triaza-1(2,3)-pyridina-4(3,5)-bicyclo[3.1.0]hexanacyclotridecaphane-3,7-dione | *** | 2.97 (B) | 751 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-158 | (41R,43S,45R)-13-acetyl-N-(3-methyl-6-(trifluoromethyl)pyridin-2-yl)-15-(2-methylpyrimidin-5-yl)-3,7-dioxo-11H-42,6-diaza-1(1,7)-indola-4(2,5)-bicyclo[3.1.0]hexanacyclotridecaphan-11-ene-43-carboxamide | ND | 3.53 (B) | 714 |
| T-159 | (41R,43S,45R)-13-acetyl-N-(3-methyl-6-(trifluoromethyl)pyridin-2-yl)-15-(2-methylpyrimidin-5-yl)-3,7-dioxo-11H-42,6-diaza-1(1,7)-indola-4(2,5)-bicyclo[3.1.0]hexanacyclotridecaphane-43-carboxamide | *** | 3.65 (B) | 716 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-160 | 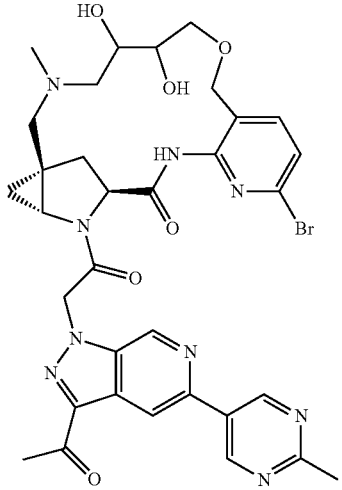 [SMILES: CC(=O)c1nn(CC(=O)N2[C@H]3C[C@]4(C[C@@H]24)CN(C)CC(O)C(O)COCc2ccc(Br)nc2NC3=O)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-16-bromo-8,9-dihydroxy-6-methyl-11-oxa-42,2,6-triaza-1(2,3)-pyridina-4(3,5)-bicyclo[3.1.0]hexanacyclododecaphan-3-one | *** | 3.36 (B) | 736 |
| T-161 | 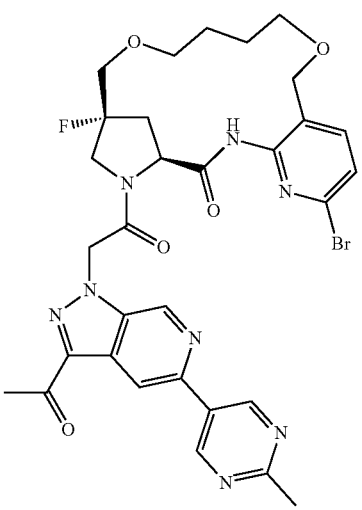 [SMILES: CC(=O)c1nn(CC(=O)N2C[C@@]3(F)COCCCCOCc4ccc(Br)nc4NC(=O)[C@@H]2C3)c2cnc(-c3cnc(C)nc3)cc12]<br>(42S,44R)-41-(2-(3-acetyl-5-(2-methylpyrimidin-5-yl)-1H-pyrazolo[3,4-c]pyridin-1-yl)acetyl)-16-bromo-44-fluoro-6,11-dioxa-2-aza-1(2,3)-pyridina-4(2,4)-pyrrolidinacyclododecaphan-3-one | *** | 3.35 (B) | 695 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-162 | 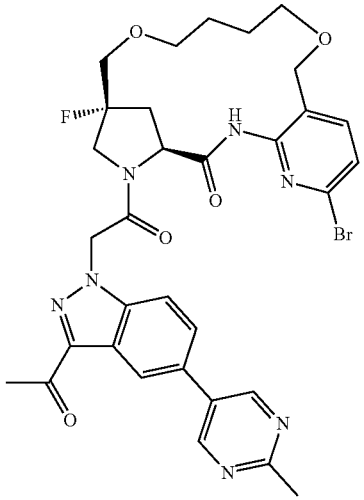 [SMILES: CC(=O)c1nn(CC(=O)N2C[C@@]3(F)COCCCCOCc4ccc(Br)nc4NC(=O)[C@@H]2C3)c2ccc(-c3cnc(C)nc3)cc12]<br>(42S,44R)-41-(2-(3-acetyl-5-(2-methylpyrimidin-5-yl)-1H-indazol-1-yl)acetyl)-16-bromo-44-fluoro-6,11-dioxa-2-aza-1(2,3)-pyridina-4(2,4)-pyrrolidinacyclododecaphan-3-one | *** | 3.44 (B) | 694 |
| T-163 | 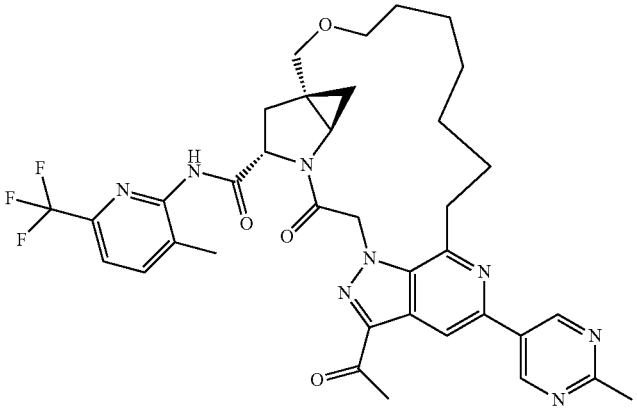 [SMILES: CC(=O)c1nn2c3c(nc(-c4cnc(C)nc4)cc13)CCCCCCCOC[C@@]13C[C@@H](C(=O)Nc4nc(C(F)(F)F)ccc4C)N(C(=O)C2)[C@@H]1C3]<br>(41R,43S,45S)-13-acetyl-N-(3-methyl-6-(trifluoromethyl)pyridin-2-yl)-15-(2-methylpyrimidin-5-yl)-3-oxo-11H-6-oxa-42-aza-1(1,7)-pyrazolo[3,4-c]pyridina-4(2,5)-bicyclo[3.1.0]hexanacyclotridecaphane-43-carboxamide | *** | 4.21 (B) | 705 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-164 | 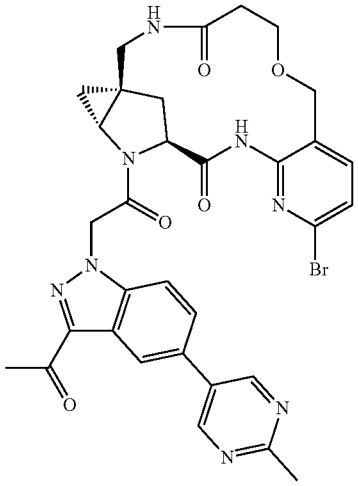 [SMILES: CC(=O)c1nn(CC(=O)N2[C@H]3C[C@@]4(CNC(=O)CCOCc5ccc(Br)nc5NC3=O)C[C@@H]24)c2ccc(-c3cnc(C)nc3)cc12](41R,43S,45R)-42-(2-(3-acetyl-5-(2-methylpyrimidin-5-yl)-1H-indazol-1-yl)acetyl)-16-bromo-10-oxa-42,2,6-triaza-1(2,3)-pyridina-4(3,5)-bicyclo[3.1.0]hexanacycloundecaphane-3,7-dione | *** | 1.26 (A) | 689 |
| T-165 | 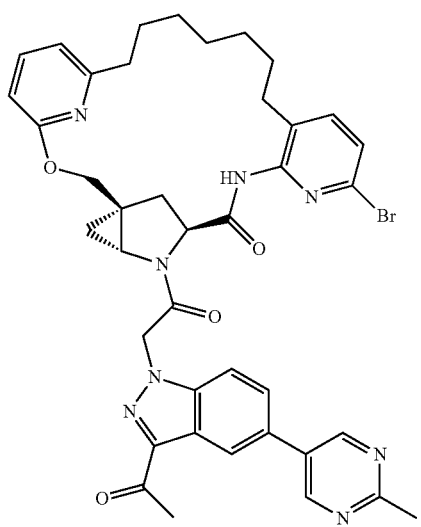 [SMILES: CC(=O)c1nn(CC(=O)N2[C@H]3C[C@@]4(COc5cccc(n5)CCCCCCCc5ccc(Br)nc5NC3=O)C[C@@H]24)c2ccc(-c3cnc(C)nc3)cc12](41R,43S,45S)-42-(2-(3-acetyl-5-(2-methylpyrimidin-5-yl)-1H-indazol-1-yl)acetyl)-16-bromo-6-oxa-42,2-diaza-1(2,3),7(2,6)-dipyridina-4(3,5)-bicyclo[3.1.0]hexanacyclotetradecaphan-3-one | *** | 4.34 (B) | 777 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-166 | 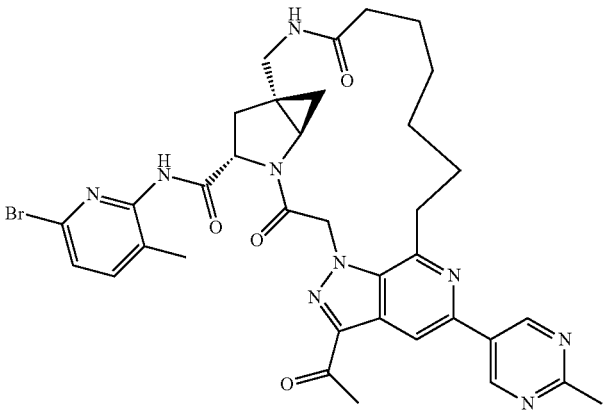 [SMILES: CC(=O)c1nn2c3c(nc(-c4cnc(C)nc4)cc13)CCCCCCC(=O)NC[C@@]13C[C@@H](C(=O)Nc4nc(Br)ccc4C)N(C(=O)C2)[C@@H]1C3] (41R,43S,45R)-13-acetyl-N-(6-bromo-3-methylpyridin-2-yl)-15-(2-methylpyrimidin-5-yl)-3,7-dioxo-11H-42,6-diaza-1(1,7)-pyrazolo[3,4-c]pyridina-4(2,5)-bicyclo[3.1.0]hexanacyclotridecaphane-43-carboxamide | *** | 3.88 (B) | 728 |
| T-167 | 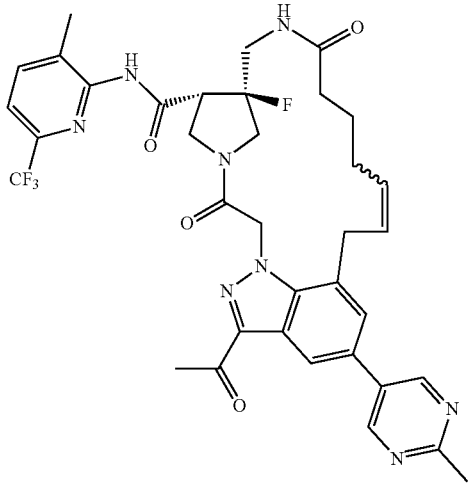 [SMILES: CC(=O)c1nn2c3c(cc(-c4cnc(C)nc4)cc13)CC=CCCCC(=O)NC[C@]1(F)CN(C[C@@H]1C(=O)Nc1nc(C(F)(F)F)ccc1C)C(=O)C2] (43S,45S)-13-acetyl-43-fluoro-N-(3-methyl-6-(trifluoromethyl)pyridin-2-yl)-15-(2-methylpyrimidin-5-yl)-3,7-dioxo-11H-6-aza-1(1,7)-indazola-4(1,3)-pyrrolidinacyclotridecaphan-11-ene-45-carboxamide | *** | 3.18 (B) | 721 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-168 | 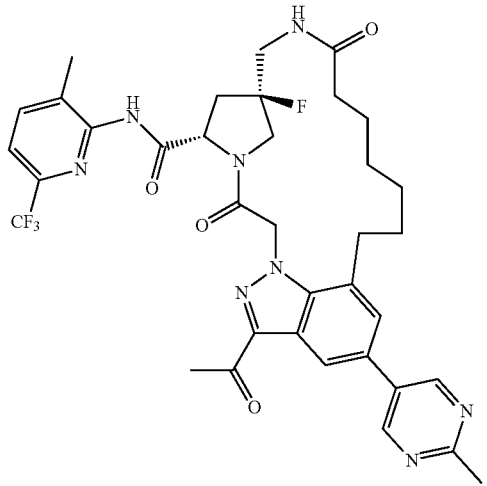 (43S,45S)-13-acetyl-43-fluoro-N-(3-methyl-6-(trifluoromethyl)pyridin-2-yl)-15-(2-methylpyrimidin-5-yl)-3,7-dioxo-11H-6-aza-1(1,7)-indazola-4(1,3)-pyrrolidinacyclotridecaphane-45-carboxamide | *** | 3.30 (B) | 723 |
| T-169 | 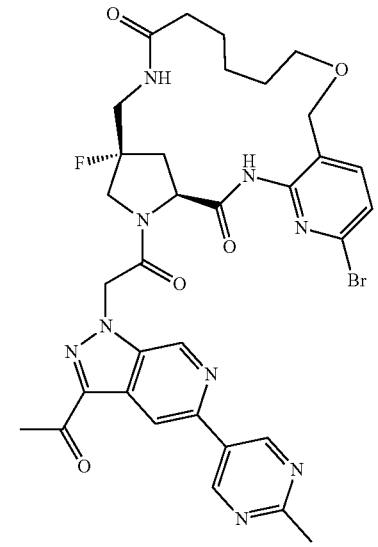 [SMILES: CC(=O)c1nn(CC(=O)N2C[C@@]3(F)CNC(=O)CCCCCOCc4ccc(Br)nc4NC(=O)[C@@H]2C3)c2cnc(-c3cnc(C)nc3)cc12] (42S,44S)-41-(2-(3-acetyl-5-(2-methylpyrimidin-5-yl)-1H-pyrazolo[3,4-c]pyridin-1-yl)acetyl)-16-bromo-44-fluoro-13-oxa-2,6-diaza-1(2,3)-pyridina-4(2,4)-pyrrolidinacyclotetradecaphane-3,7-dione | *** | 2.94 (B) | 736 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-170 | 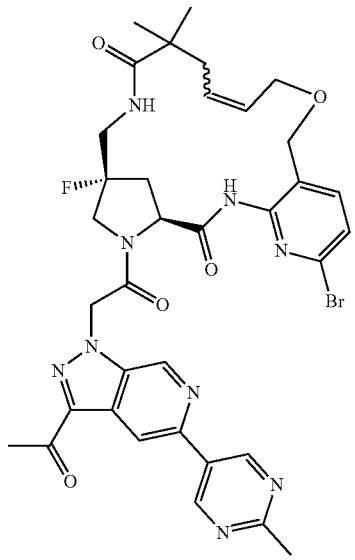 [SMILES: CC(=O)c1nn(CC(=O)N2C[C@@]3(F)CNC(=O)C(C)(C)CC=CCOCc4ccc(Br)nc4NC(=O)[C@@H]2C3)c2cnc(-c3cnc(C)nc3)cc12]<br>(42S,44S)-41-(2-(3-acetyl-5-(2-methylpyrimidin-5-yl)-1H-pyrazolo[3,4-c]pyridin-1-yl)acetyl)-16-bromo-44-fluoro-8,8-dimethyl-13-oxa-2,6-diaza-1(2,3)-pyridina-4(2,4)-pyrrolidinacyclotetradecaphan-10-ene-3,7-dione | *** | 2.93 (B) | 762 |
| T-171 | 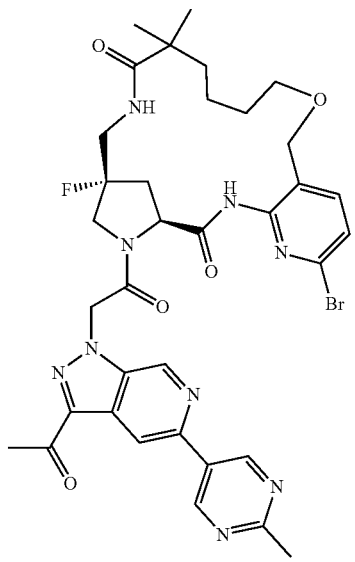 [SMILES: CC(=O)c1nn(CC(=O)N2C[C@@]3(F)CNC(=O)C(C)(C)CCCCOCc4ccc(Br)nc4NC(=O)[C@@H]2C3)c2cnc(-c3cnc(C)nc3)cc12]<br>(42S,44S)-41-(2-(3-acetyl-5-(2-methylpyrimidin-5-yl)-1H-pyrazolo[3,4-c]pyridin-1-yl)acetyl)-16-bromo-44-fluoro-8,8-dimethyl-13-oxa-2,6-diaza-1(2,3)-pyridina-4(2,4)-pyrrolidinacyclotetradecaphane-3,7-dione | *** | 3.49 (B) | 764 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-172 | 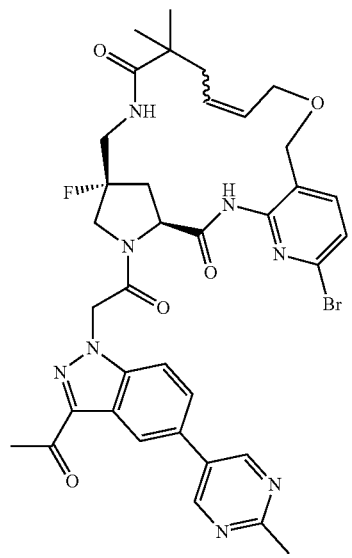 [SMILES: CC(=O)c1nn(CC(=O)N2C[C@@]3(F)CNC(=O)C(C)(C)CC=CCOCc4ccc(Br)nc4NC(=O)[C@@H]2C3)c2ccc(-c3cnc(C)nc3)cc12]<br>(42S,44S)-41-(2-(3-acetyl-5-(2-methylpyrimidin-5-yl)-1H-indazol-1-yl)acetyl)-16-bromo-44-fluoro-8,8-dimethyl-13-oxa-2,6-diaza-1(2,3)-pyridina-4(2,4)-pyrrolidinacyclotetradecaphan-10-ene-3,7-dione | *** | 3.45 (B) | 761 |
| T-173 | 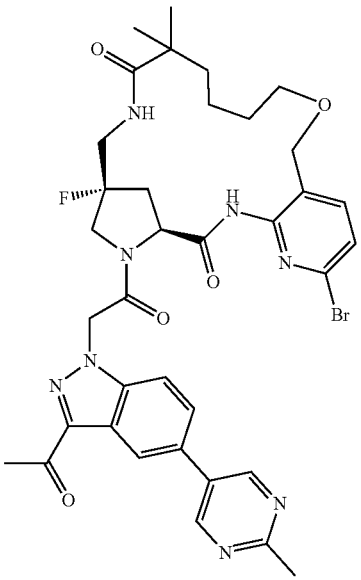 [SMILES: CC(=O)c1nn(CC(=O)N2C[C@@]3(F)CNC(=O)C(C)(C)CCCCOCc4ccc(Br)nc4NC(=O)[C@@H]2C3)c2ccc(-c3cnc(C)nc3)cc12]<br>(42S,44S)-41-(2-(3-acetyl-5-(2-methylpyrimidin-5-yl)-1H-indazol-1-yl)acetyl)-16-bromo-44-fluoro-8,8-dimethyl-13-oxa-2,6-diaza-1(2,3)-pyridina-4(2,4)-pyrrolidinacyclotetradecaphane-3,7-dione | *** | 3.34 (B) | 763 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-174 | (43S,45S)-13-acetyl-N-(6-bromo-3-methylpyridin-2-yl)-43-fluoro-15-(2-methylpyrimidin-5-yl)-3,7-dioxo-11H-6-aza-1(1,7)-indazola-4(1,3)-pyrrolidinacyclotridecaphan-11-ene-45-carboxamide | *** | | |
| T-175 | (43S,45S)-13-acetyl-N-(6-bromo-3-methylpyridin-2-yl)-43-fluoro-15-(2-methylpyrimidin-5-yl)-3,7-dioxo-11H-6-aza-1(1,7)-indazola-4(1,3)-pyrrolidinacyclotridecaphane-45-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-176 | (41R,43S,45R)-13-acetyl-15-(2-methylpyrimidin-5-yl)-3,7-dioxo-N-((S)-1-phenylethyl)-11H-42,6-diaza-1(1,7)-indazola-4(2,5)-bicyclo[3.1.0]hexanacyclotridecaphane-43-carboxamide | *** | | |
| T-177 | (41R,43S,45R)-13-acetyl-N-(3,3-dimethylbutyl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-178 | 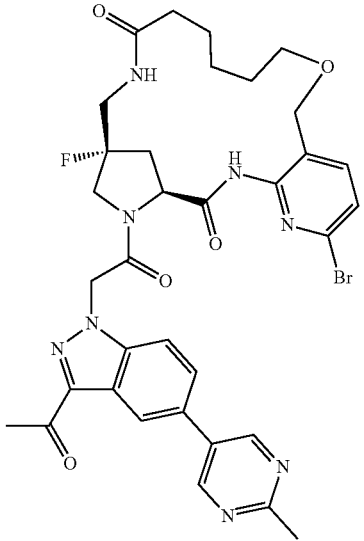 [SMILES: CC(=O)c1nn(CC(=O)N2C[C@@]3(F)CNC(=O)CCCCCOCc4ccc(Br)nc4NC(=O)[C@@H]2C3)c2ccc(-c3cnc(C)nc3)cc12]<br>(42S,44S)-41-(2-(3-acetyl-5-(2-methylpyrimidin-5-yl)-1H-indazol-1-yl)acetyl)-16-bromo-44-fluoro-13-oxa-2,6-diaza-1(2,3)-pyridina-4(2,4)-pyrrolidinacyclotetradecaphane-3,7-dione | *** | | |
| T-179 | 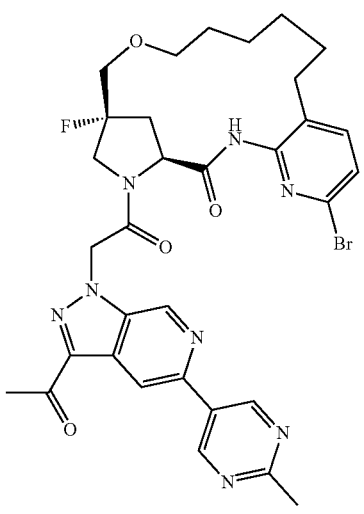 [SMILES: CC(=O)c1nn(CC(=O)N2C[C@@]3(F)COCCCCCCc4ccc(Br)nc4NC(=O)[C@@H]2C3)c2cnc(-c3cnc(C)nc3)cc12]<br>(42S,44R)-41-(2-(3-acetyl-5-(2-methylpyrimidin-5-yl)-1H-pyrazolo[3,4-c]pyridin-1-yl)acetyl)-16-bromo-44-fluoro-6-oxa-2-aza-1(2,3)-pyridina-4(2,4)-pyrrolidinacyclododecaphan-3-one | *** | | |

TABLE 6-continued

Additional Non-limiting Examples of Compounds of the Present Invention

| Cmp No. | Structure and Name | IC₅₀ (Stars) | RT min (Method A, B, C, or D) | MS (M + 1) |
|---|---|---|---|---|
| T-180 | 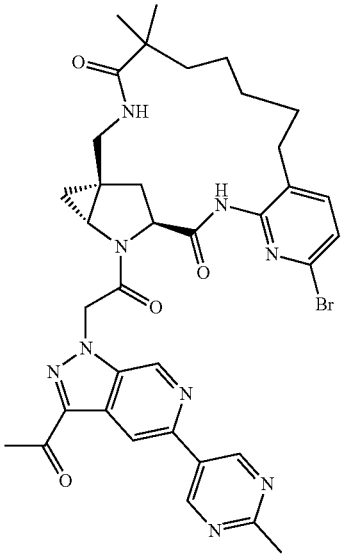 [SMILES: CC(=O)c1nn(CC(=O)N2[C@H]3C[C@@]4(CNC(=O)C(C)(C)CCCCCc5ccc(Br)nc5NC3=O)C[C@@H]24)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-16-bromo-8,8-dimethyl-42,2,6-triaza-1(2,3)-pyridina-4(3,5)-bicyclo[3.1.0]hexanacyclotridecaphane-3,7-dione | *** | | |
| T-181 | 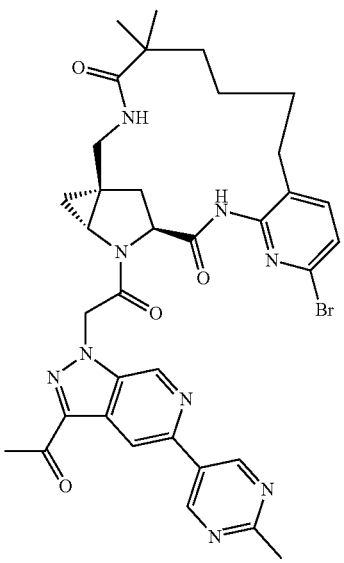 [SMILES: CC(=O)c1nn(CC(=O)N2[C@H]3C[C@@]4(CNC(=O)C(C)(C)CCCCc5ccc(Br)nc5NC3=O)C[C@@H]24)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-16-bromo-8,8-dimethyl-42,2,6-triaza-1(2,3)-pyridina-4(3,5)-bicyclo[3.1.0]hexanacyclododecaphane-3,7-dione | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-182 | 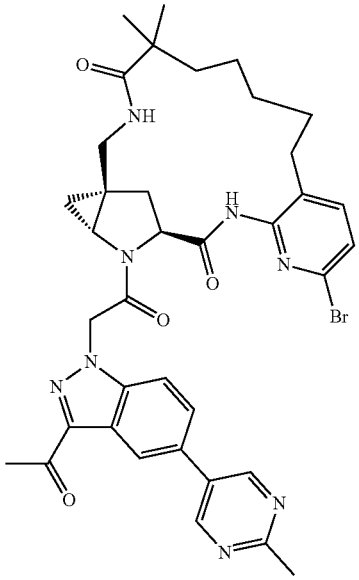 [SMILES: CC(=O)c1nn(CC(=O)N2[C@H]3C[C@@]4(CNC(=O)C(C)(C)CCCCCc5ccc(Br)nc5NC3=O)C[C@@H]24)c2ccc(-c3cnc(C)nc3)cc12]<br>(41R,43S,45R)-42-(2-(3-acetyl-5-(2-methylpyrimidin-5-yl)-1H-indazol-1-yl)acetyl)-16-bromo-8,8-dimethyl-42,2,6-triaza-1(2,3)-pyridina-4(3,5)-bicyclo[3.1.0]hexanacyclotridecaphane-3,7-dione | *** | | |
| T-183 | 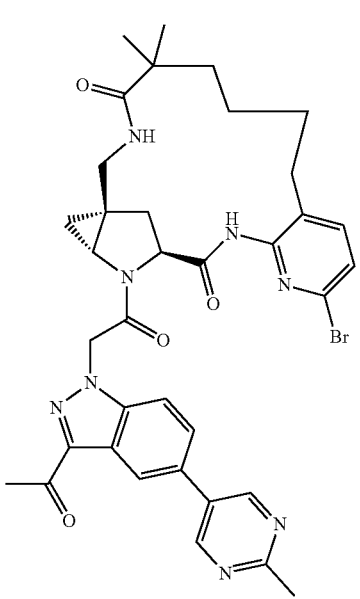 [SMILES: CC(=O)c1nn(CC(=O)N2[C@H]3C[C@@]4(CNC(=O)C(C)(C)CCCCc5ccc(Br)nc5NC3=O)C[C@@H]24)c2ccc(-c3cnc(C)nc3)cc12]<br>(41R,43S,45R)-42-(2-(3-acetyl-5-(2-methylpyrimidin-5-yl)-1H-indazol-1-yl)acetyl)-16-bromo-8,8-dimethyl-42,2,6-triaza-1(2,3)-pyridina-4(3,5)-bicyclo[3.1.0]hexanacyclododecaphane-3,7-dione | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-184 | (41R,43S,45R)-13-acetyl-8,8-dimethyl-15-(2-methylpyrimidin-5-yl)-3,7-dioxo-N-(1-(2,2,2-trifluoroethyl)-1H-pyrazol-3-yl)-11H-42,6-diaza-1(1,7)-indazola-4(2,5)-bicyclo[3.1.0]hexanacyclotridecaphan-11-ene-43-carboxamide | *** | | |
| T-185 | (41R,43S,45R)-13-acetyl-8,8-dimethyl-15-(2-methylpyrimidin-5-yl)-3,7-dioxo-N-(1-(2,2,2-trifluoromethyl)-1H-pyrazol-3-yl)-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-186 | 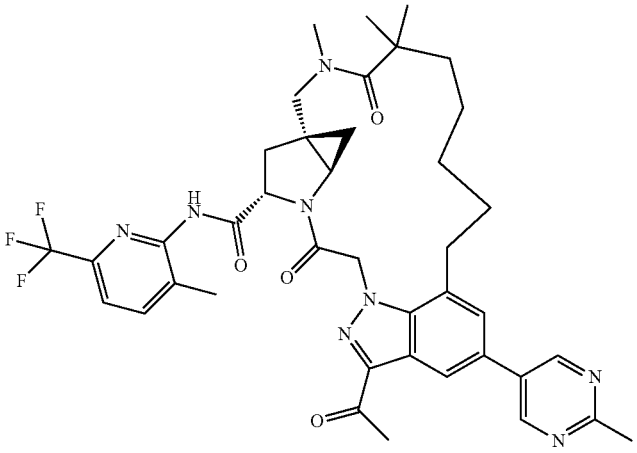 [SMILES: CC(=O)c1nn2c3c(cc(-c4cnc(C)nc4)cc13)CCCCCC(C)(C)C(=O)N(C)C[C@@]13C[C@@H](C(=O)Nc4nc(C(F)(F)F)ccc4C)N(C(=O)C2)[C@@H]1C3]<br>(41R,43S,45R)-13-acetyl-6,8,8-trimethyl-N-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-187 | 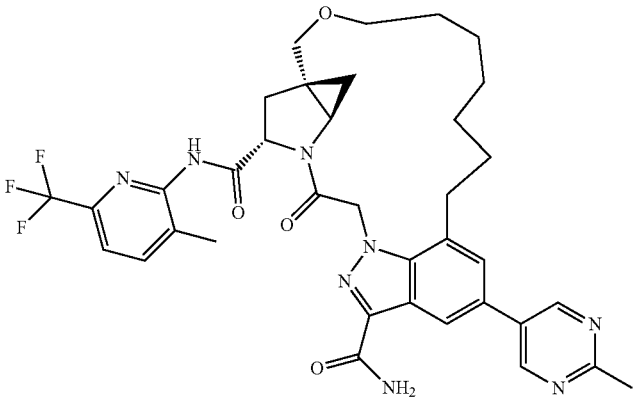 [SMILES: Cc1ncc(-c2cc3c4c(c2)c(C(N)=O)nn4CC(=O)N2[C@H](C(=O)Nc4nc(C(F)(F)F)ccc4C)C[C@@]4(COCCCCCCC3)C[C@@H]24)cn1]<br>(41R,43S,45S)-N43-(3-methyl-6-(trifluoromethyl)pyridin-2-yl)-15-(2-methylpyrimidin-5-yl)-3-oxo-11H-6-oxa-42-aza-1(1,7)-indazola-4(2,5)-bicyclo[3.1.0]hexanacyclotridecaphane-13,43-dicarboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-188 | 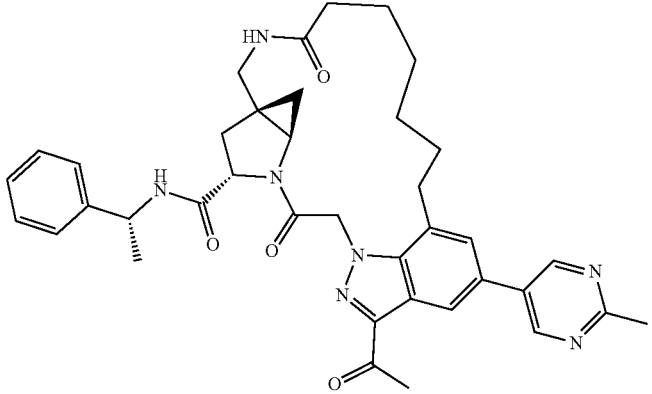 [SMILES: CC(=O)c1nn2c3c(cc(-c4cnc(C)nc4)cc13)CCCCCCC(=O)NC[C@@]13C[C@@H](C(=O)N[C@H](C)c4ccccc4)N(C(=O)C2)[C@@H]1C3]<br>(41R,43S,45R)-13-acetyl-15-(2-methylpyrimidin-5-yl)-3,7-dioxo-N-((R)-1-phenylethyl)-11H-42,6-diaza-1(1,7)-indazola-4(2,5)-bicyclo[3.1.0]hexanacyclotridecaphane-43-carboxamide | *** | | |
| T-189 | 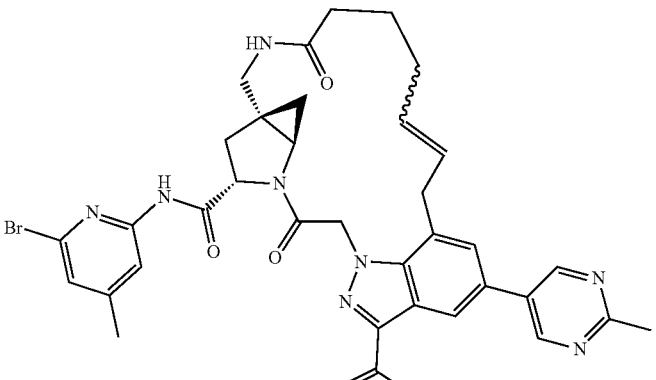<br>(41R,43S,45R)-13-acetyl-N-(6-bromo-4-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-190 | 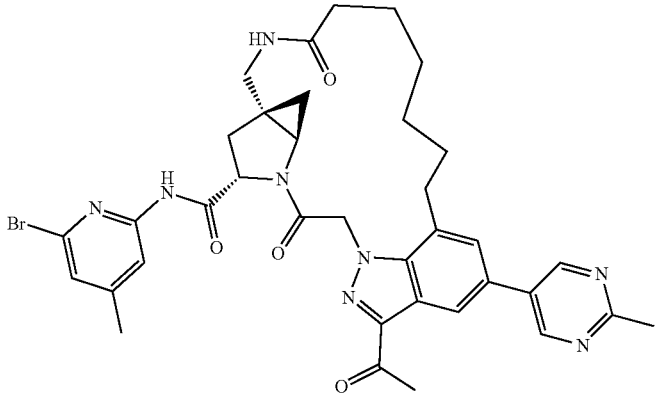 [SMILES: CC(=O)c1nn2c3c(cc(-c4cnc(C)nc4)cc13)CCCCCCC(=O)NC[C@@]13C[C@@H](C(=O)Nc4cc(C)cc(Br)n4)N(C(=O)C2)[C@@H]1C3]<br>(41R,43S,45R)-13-acetyl-N-(6-bromo-4-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-191 | 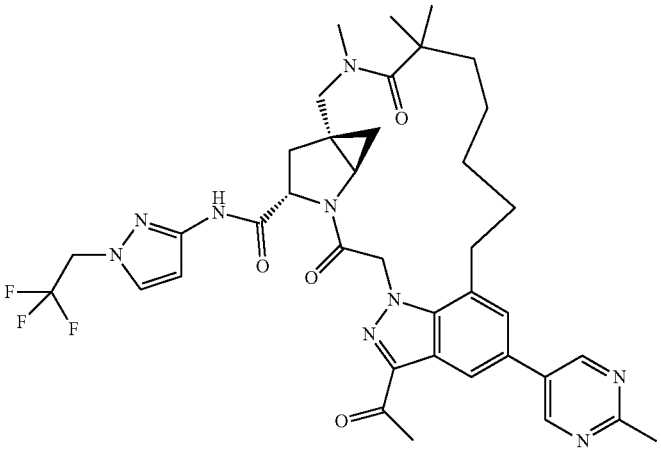 [SMILES: CC(=O)c1nn2c3c(cc(-c4cnc(C)nc4)cc13)CCCCCC(C)(C)C(=O)N(C)C[C@@]13C[C@@H](C(=O)Nc4ccn(CC(F)(F)F)n4)N(C(=O)C2)[C@@H]1C3]<br>(41R,43S,45R)-13-acetyl-6,8,8-trimethyl-15-(2-methylpyrimidin-5-yl)-3,7-dioxo-N-(1-(2,2,2-trifluoroethyl)-1H-pyrazol-3-yl)-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-192 | 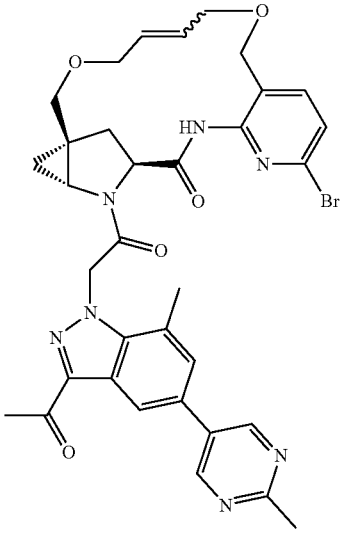 [SMILES: CC(=O)c1nn(CC(=O)N2[C@H]3C[C@@]4(COCC=CCOCc5ccc(Br)nc5NC3=O)C[C@@H]24)c2c(C)cc(-c3cnc(C)nc3)cc12]<br>(41R,43S,45S)-42-(2-(3-acetyl-7-methyl-5-(2-methylpyrimidin-5-yl)-1H-indazol-1-yl)acetyl)-16-bromo-6,11-dioxa-42,2-diaza-1(2,3)-pyridina-4(3,5)-bicyclo[3.1.0]hexanacyclododecaphan-8-en-3-one | *** | | |
| T-193 | 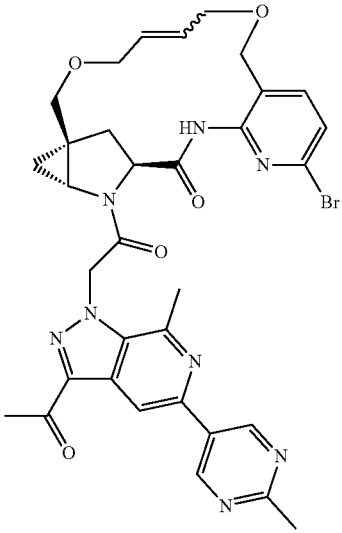 [SMILES: CC(=O)c1nn(CC(=O)N2[C@H]3C[C@@]4(COCC=CCOCc5ccc(Br)nc5NC3=O)C[C@@H]24)c2c(C)nc(-c3cnc(C)nc3)cc12]<br>(41R,43S,45S)-42-(2-(3-acetyl-7-methyl-5-(2-methylpyrimidin-5-yl)-1H-pyrazolo[3,4-c]pyridin-1-yl)acetyl)-16-bromo-6,11-dioxa-42,2-diaza-1(2,3)-pyridina-4(3,5)-bicyclo[3.1.0]hexanacyclododecaphan-8-en-3-one | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-194 | 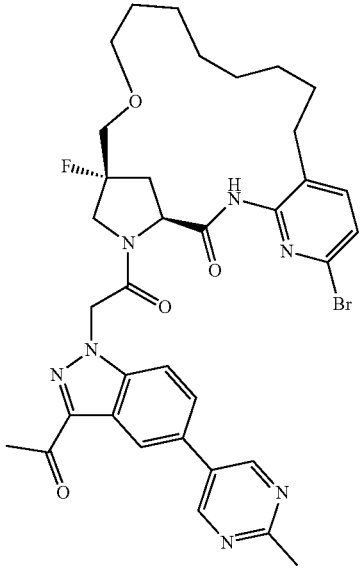 [SMILES: CC(=O)c1nn(CC(=O)N2C[C@@]3(F)COCCCCCCCCc4ccc(Br)nc4NC(=O)[C@@H]2C3)c2ccc(-c3cnc(C)nc3)cc12]<br>(42S,44R)-41-(2-(3-acetyl-5-(2-methylpyrimidin-5-yl)-1H-indazol-1-yl)acetyl)-16-bromo-44-fluoro-6-oxa-2-aza-1(2,3)-pyridina-4(2,4)-pyrrolidinacyclotetradecaphan-3-one | *** | | |
| T-195 | 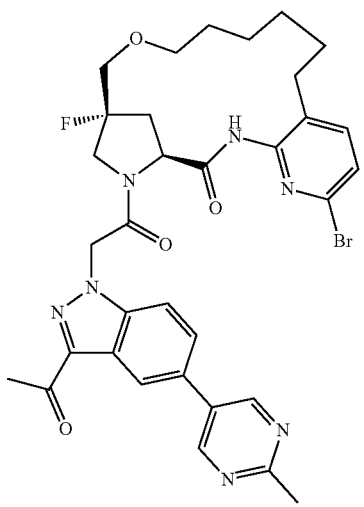 [SMILES: CC(=O)c1nn(CC(=O)N2C[C@@]3(F)COCCCCCCc4ccc(Br)nc4NC(=O)[C@@H]2C3)c2ccc(-c3cnc(C)nc3)cc12]<br>(42S,44R)-41-(2-(3-acetyl-5-(2-methylpyrimidin-5-yl)-1H-indazol-1-yl)acetyl)-16-bromo-44-fluoro-6-oxa-2-aza-1(2,3)-pyridina-4(2,4)-pyrrolidinacyclododecaphan-3-one | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-196 | 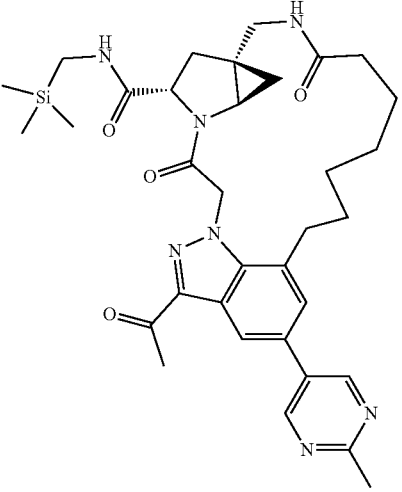 [SMILES: CC(=O)c1nn2c3c(cc(-c4cnc(C)nc4)cc13)CCCCCCC(=O)NC[C@@]13C[C@@H](C(=O)NC[Si](C)(C)C)N(C(=O)C2)[C@@H]1C3]<br>(41R,43S,45R)-13-acetyl-15-(2-methylpyrimidin-5-yl)-3,7-dioxo-N-((trimethylsilyl)methyl)-11H-42,6-diaza-1(1,7)-indazola-4(2,5)-bicyclo[3.1.0]hexanacyclotridecaphane-43-carboxamide | ** | | |
| T-197 | 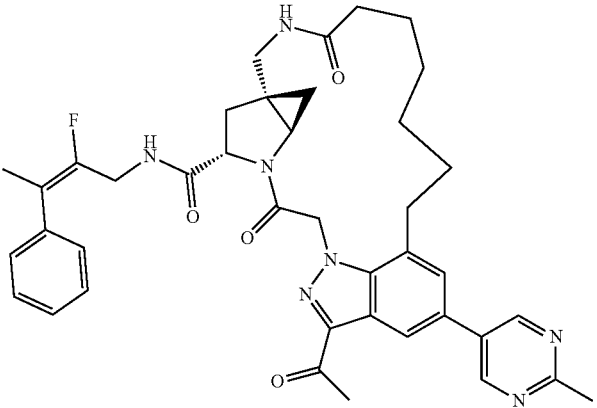 [SMILES: CC(=O)c1nn2c3c(cc(-c4cnc(C)nc4)cc13)CCCCCCC(=O)NC[C@@]13C[C@@H](C(=O)NC/C(F)=C(/C)c4ccccc4)N(C(=O)C2)[C@@H]1C3]<br>(41R,43S,45R)-13-acetyl-N-((E)-2-fluoro-3-phenylbut-2-en-1-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-198 | 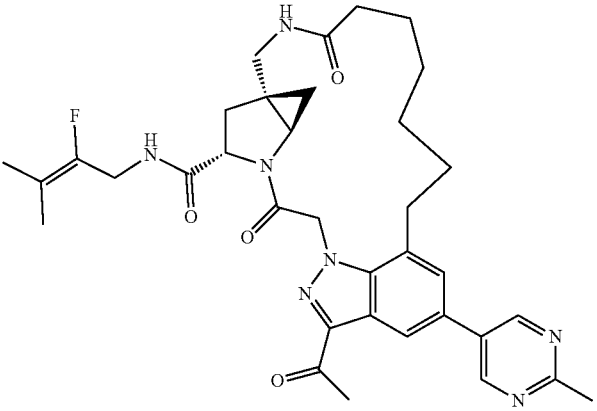 [SMILES: CC(=O)c1nn2c3c(cc(-c4cnc(C)nc4)cc13)CCCCCCC(=O)NC[C@@]13C[C@@H](C(=O)NCC(F)=C(C)C)N(C(=O)C2)[C@@H]1C3]<br>(41R,43S,45R)-13-acetyl-N-(2-fluoro-3-methylbut-2-en-1-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-199 | 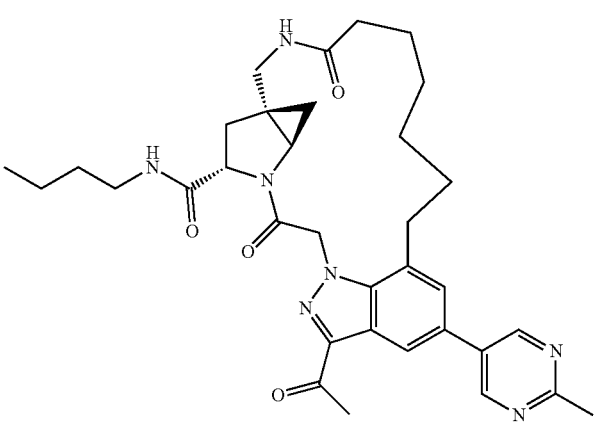 [SMILES: CCCCNC(=O)[C@@H]1C[C@]23CNC(=O)CCCCCCc4cc(-c5cnc(C)nc5)cc5c(C(C)=O)nn(c45)CC(=O)N1[C@@H]2C3]<br>(41R,43S,45R)-13-acetyl-N-butyl-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-200 | 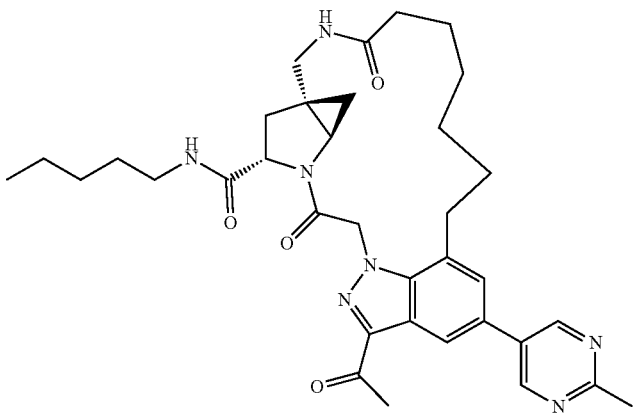 [SMILES: CCCCCNC(=O)[C@@H]1C[C@]23CNC(=O)CCCCCCc4cc(-c5cnc(C)nc5)cc5c(C(C)=O)nn(c45)CC(=O)N1[C@@H]2C3]<br>(41R,43S,45R)-13-acetyl-15-(2-methylpyrimidin-5-yl)-3,7-dioxo-N-pentyl-11H-42,6-diaza-1(1,7)-indazola-4(2,5)-bicyclo[3.1.0]hexanacyclotridecaphane-43-carboxamide | *** | | |
| T-201 | 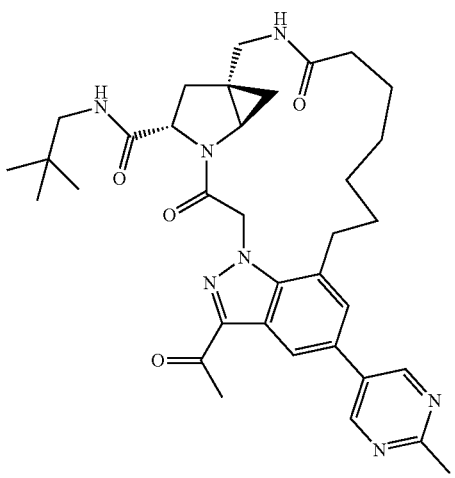 [SMILES: CC(=O)c1nn2c3c(cc(-c4cnc(C)nc4)cc13)CCCCCCC(=O)NC[C@@]13C[C@@H](C(=O)NCC(C)(C)C)N(C(=O)C2)[C@@H]1C3]<br>(41R,43S,45R)-13-acetyl-15-(2-methylpyrimidin-5-yl)-N-neopentyl-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-202 | 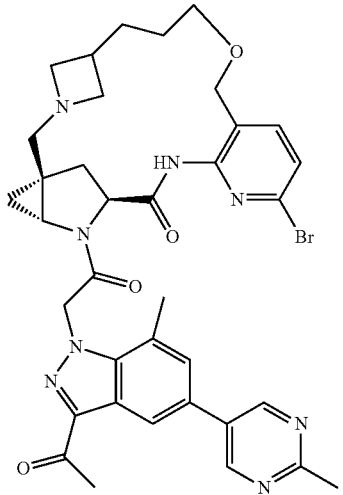 [SMILES: CC(=O)c1nn(CC(=O)N2[C@H]3C[C@]4(C[C@@H]24)CN2CC(CCCOCc4ccc(Br)nc4NC3=O)C2)c2c(C)cc(-c3cnc(C)nc3)cc12]<br>(31R,33S,35R)-32-(2-(3-acetyl-7-methyl-5-(2-methylpyrimidin-5-yl)-1H-indazol-1-yl)acetyl)-66-bromo-8-oxa-32,5-diaza-6(2,3)-pyridina-1(1,3)-azetidina-3(5,3)-bicyclo[3.1.0]hexanacycloundecaphan-4-one | *** | 1.53 (A) | 728 |
| T-203 | 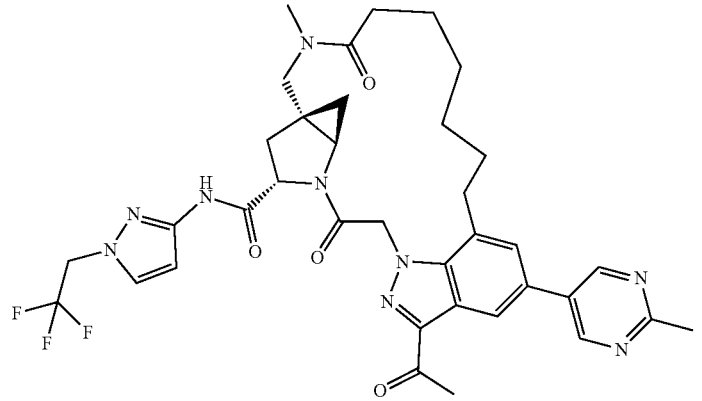 [SMILES: CC(=O)c1nn2c3c(cc(-c4cnc(C)nc4)cc13)CCCCCCC(=O)N(C)C[C@@]13C[C@@H](C(=O)Nc4ccn(CC(F)(F)F)n4)N(C(=O)C2)[C@@H]1C3]<br>(41R,43S,45R)-13-acetyl-6-methyl-15-(2-methylpyrimidin-5-yl)-3,7-dioxo-N-(1-(2,2,2-trifluoroethyl)-1H-pyrazolo-3-yl)-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-204 | 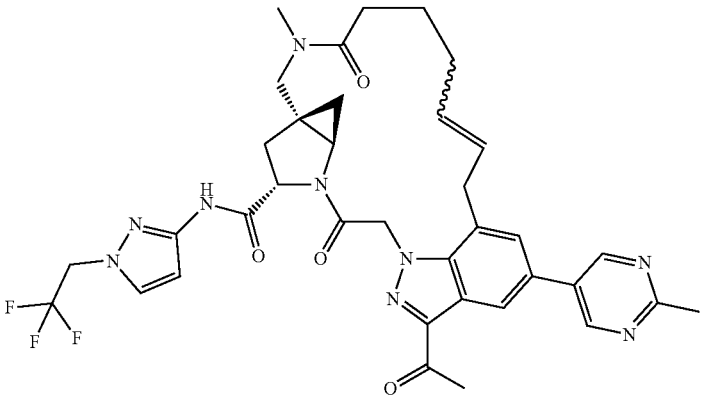 [SMILES: CC(=O)c1nn2c3c(cc(-c4cnc(C)nc4)cc13)CC=CCCCC(=O)N(C)C[C@@]13C[C@@H](C(=O)Nc4ccn(CC(F)(F)F)n4)N(C(=O)C2)[C@@H]1C3]<br>(41R,43S,45R)-13-acetyl-6-methyl-15-(2-methylpyrimidin-5-yl)-3,7-dioxo-N-(1-(2,2,2-trifluoroethyl)-1H-pyrazol-3-yl)-11H-42,6-diaza-1(1,7)-indazola-4(2,5)-bicyclo[3.1.0]hexanacyclotridecaphan-11-ene-43-carboxamide | *** | | |
| T-205 | 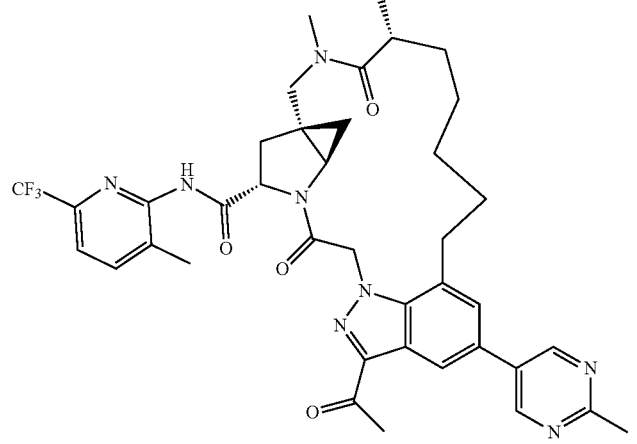 [SMILES: CC(=O)c1nn2c3c(cc(-c4cnc(C)nc4)cc13)CCCCC[C@@H](C)C(=O)N(C)C[C@@]13C[C@@H](C(=O)Nc4nc(C(F)(F)F)ccc4C)N(C(=O)C2)[C@@H]1C3]<br>(41R,43S,45R,8R)-13-acetyl-6,8-dimethyl-N-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-206 | 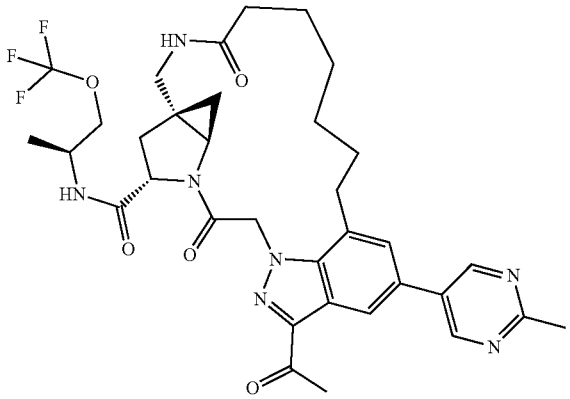 [SMILES: CC(=O)c1nn2c3c(cc(-c4cnc(C)nc4)cc13)CCCCCCC(=O)NC[C@@]13C[C@@H](C(=O)N[C@@H](C)COC(F)(F)F)N(C(=O)C2)[C@@H]1C3]<br>(41R,43S,45R)-13-acetyl-15-(2-methylpyrimidin-5-yl)-3,7-dioxo-N-((S)-1-(trifluoromethoxy)propan-2-yl)-11H-42,6-diaza-1(1,7)-indazola-4(2,5)-bicyclo[3.1.0]hexanacyclotridecaphane-43-carboxamide | *** | | |
| T-207 | 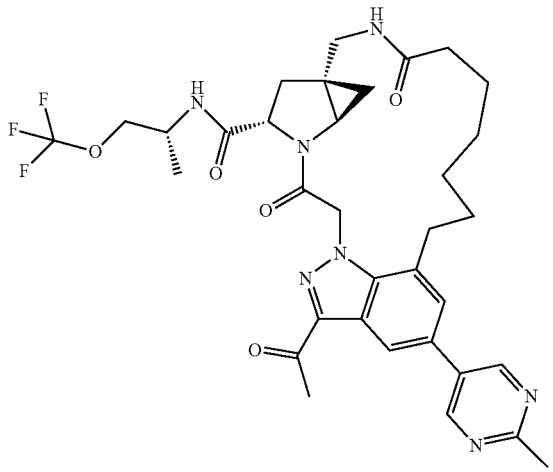 [SMILES: CC(=O)c1nn2c3c(cc(-c4cnc(C)nc4)cc13)CCCCCCC(=O)NC[C@@]13C[C@@H](C(=O)N[C@H](C)COC(F)(F)F)N(C(=O)C2)[C@@H]1C3]<br>(41R,43S,45R)-13-acetyl-15-(2-methylpyrimidin-5-yl)-3,7-dioxo-N-((R)-1-(trifluoromethoxy)propan-2-yl)-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-208 | (41R,43S,45R)-13-acetyl-15-(2-methylpyrimidin-5-yl)-3,7-dioxo-N-(2-(trifluoromethoxy)ethyl)-11H-42,6-diaza-1(1,7)-indazola-4(2,5)-bicyclo[3.1.0]hexanacyclotridecaphane-43-carboxamide | *** | | |
| T-209 | (41R,43S,45R)-13-acetyl-N-(6-bromo-4-methoxypyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-210 | 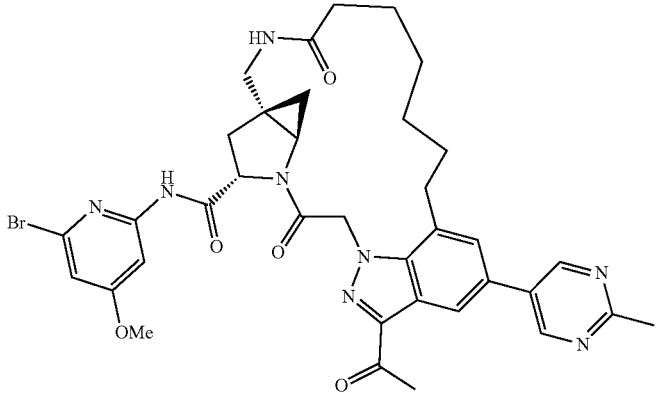 [SMILES: COc1cc(Br)nc(NC(=O)[C@@H]2C[C@]34CNC(=O)CCCCCCc5cc(-c6cnc(C)nc6)cc6c(C(C)=O)nn(c56)CC(=O)N2[C@@H]3C4)c1]<br>(41R,43S,45R)-13-acetyl-N-(6-bromo-4-methoxypyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-211 | 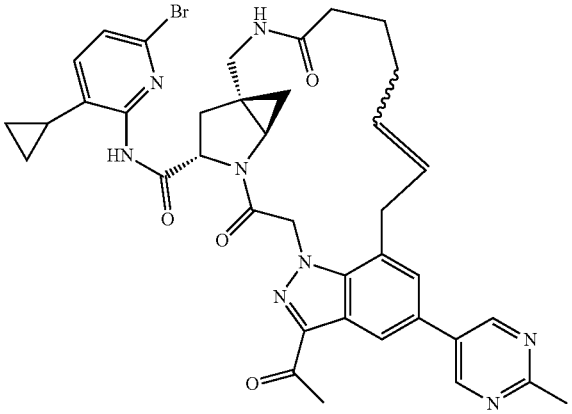 [SMILES: CC(=O)c1nn2c3c(cc(-c4cnc(C)nc4)cc13)CC=CCCCC(=O)NC[C@@]13C[C@@H](C(=O)Nc4nc(Br)ccc4C4CC4)N(C(=O)C2)[C@@H]1C3]<br>(41R,43S,45R)-13-acetyl-N-(6-bromo-3-cyclopropylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-212 | 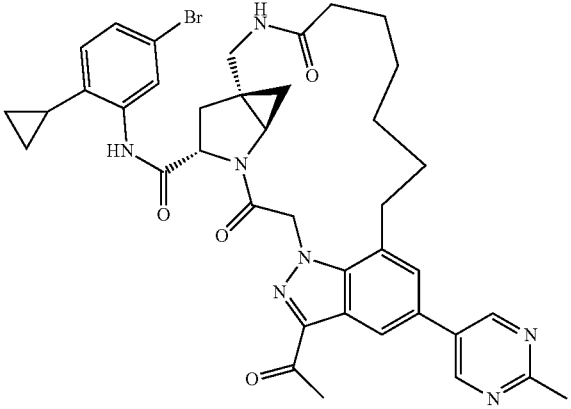 [SMILES: CC(=O)c1nn2c3c(cc(-c4cnc(C)nc4)cc13)CCCCCCC(=O)NC[C@@]13C[C@@H](C(=O)Nc4cc(Br)ccc4C4CC4)N(C(=O)C2)[C@@H]1C3]<br>(41R,43S,45R)-13-acetyl-N-(6-bromo-3-cyclopropylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-213 | 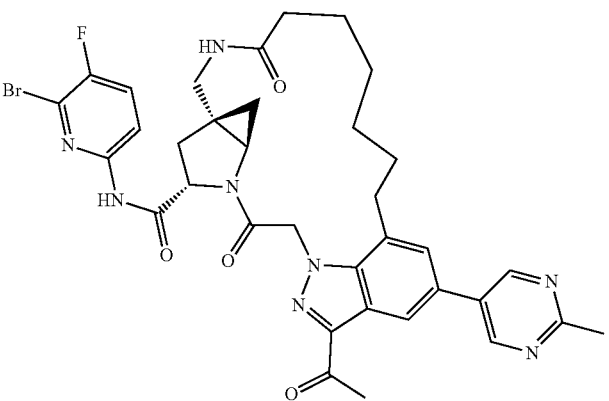 [SMILES: CC(=O)c1nn2c3c(cc(-c4cnc(C)nc4)cc13)CCCCCCC(=O)NC[C@@]13C[C@@H](C(=O)Nc4ccc(F)c(Br)n4)N(C(=O)C2)[C@@H]1C3]<br>(41R,43S,45R)-13-acetyl-N-(6-bromo-5-fluoropyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-214 | 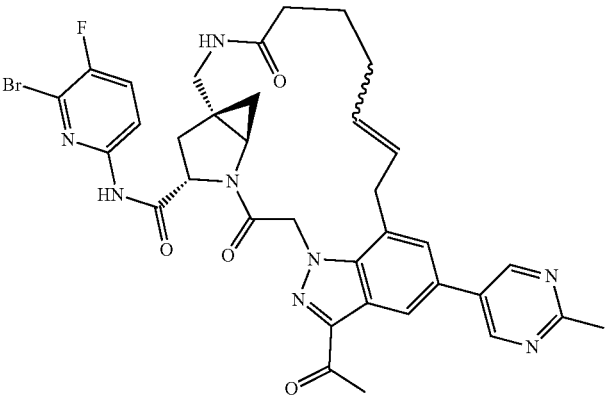 [SMILES: CC(=O)c1nn2c3c(cc(-c4cnc(C)nc4)cc13)CC=CCCCC(=O)NC[C@@]13C[C@@H](C(=O)Nc4ccc(F)c(Br)n4)N(C(=O)C2)[C@@H]1C3]<br>41R,43S,45R)-13-acetyl-N-(6-bromo-5-fluoropyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | | |
| T-215 | 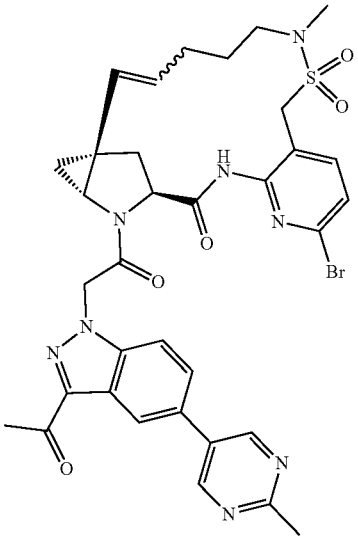 [SMILES: CC(=O)c1nn(CC(=O)N2[C@H]3C[C@@]4(C=CCCCN(C)S(=O)(=O)Cc5ccc(Br)nc5NC3=O)C[C@@H]24)c2ccc(-c3cnc(C)nc3)cc12]<br>(41R,43S,45R)-42-(2-(3-acetyl-5-(2-methylpyrimidin-5-yl)-1H-indazol-1-yl)acetyl)-16-bromo-10-methyl-11-thia-42,2,10-triaza-1(2,3)-pyridina-4(3,5)-bicyclo[3.1.0]hexanacyclododecaphan-5-en-3-one 11,11-dioxide | *** | 1.88 (A) | 748 |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-216 | (41R,43S,45R)-42-(2-(3-acetyl-7-methyl-5-(2-methylpyrimidin-5-yl)-1H-indazol-1-yl)acetyl)-16-bromo-10-methyl-11-thia-42,2,10-triaza-1(2,3)-pyridina-4(3,5)-bicyclo[3.1.0]hexanacyclododecaphan-5-en-3-one 11,11-dioxide | *** | 1.98 (A) | 760 |
| T-217 | (41R,43S,45R)-13-acetyl-N-(6-bromo-5-fluoro-4-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-218 | 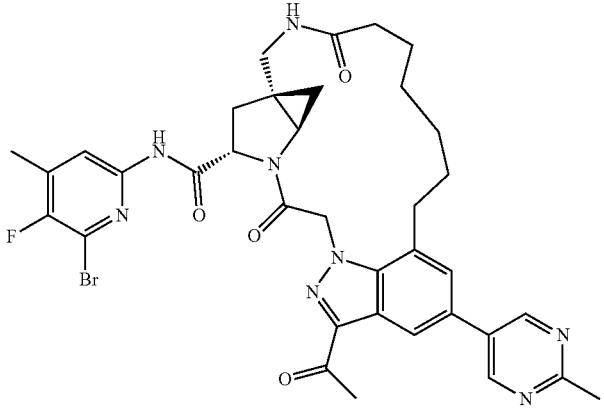 [SMILES: CC(=O)c1nn2c3c(cc(-c4cnc(C)nc4)cc13)CCCCCCC(=O)NC[C@@]13C[C@@H](C(=O)Nc4cc(C)c(F)c(Br)n4)N(C(=O)C2)[C@@H]1C3]<br>(41R,43S,45R)-13-acetyl-N-(6-bromo-5-fluoro-4-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-219 | 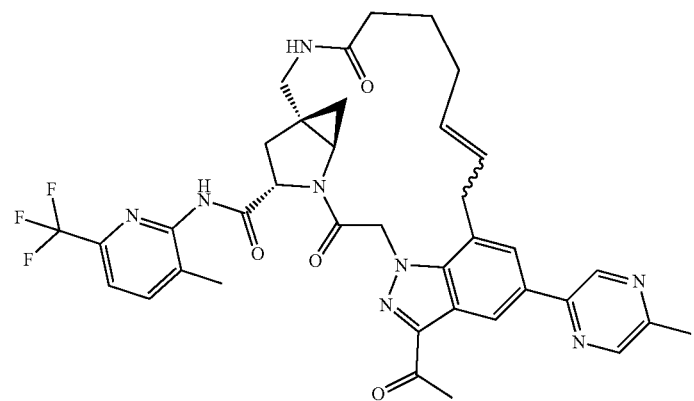 [SMILES: CC(=O)c1nn2c3c(cc(-c4cnc(C)cn4)cc13)CC=CCCCC(=O)NC[C@@]13C[C@@H](C(=O)Nc4nc(C(F)(F)F)ccc4C)N(C(=O)C2)[C@@H]1C3]<br>(41R,43S,45R)-13-acetyl-N-(3-methyl-6-(trifluoromethyl)pyridin-2-yl)-15-(5-methylpyrazin-2-yl)-3,7-dioxo-11H-42,6-diaza-1(1,7)-indazola-4(2,5)-bicyclo[3.1.0]hexanacyclotridecaphan-11-ene-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-220 | 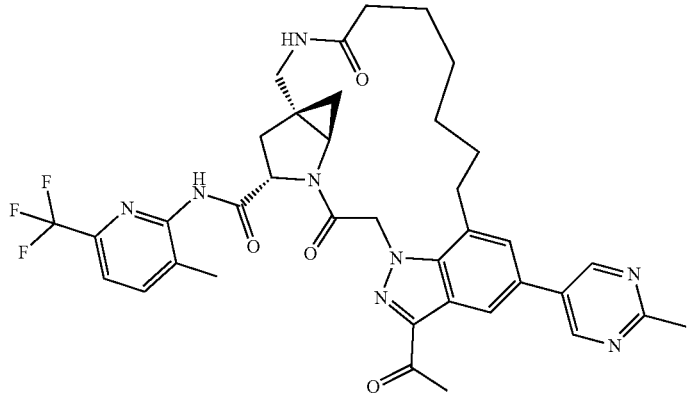 [SMILES: CC(=O)c1nn2c3c(cc(-c4cnc(C)nc4)cc13)CCCCCCC(=O)NC[C@@]13C[C@@H](C(=O)Nc4nc(C(F)(F)F)ccc4C)N(C(=O)C2)[C@@H]1C3]<br>(41R,43S,45R)-13-acetyl-N-(3-methyl-6-(trifluoromethyl)pyridin-2-yl)-15-(5-methylpyrazin-2-yl)-3,7-dioxo-11H-42,6-diaza-1(1,7)-indazola-4(2,5)-bicyclo[3.1.0]hexanacyclotridecaphane-43-carboxamide | *** | | |
| T-221 | 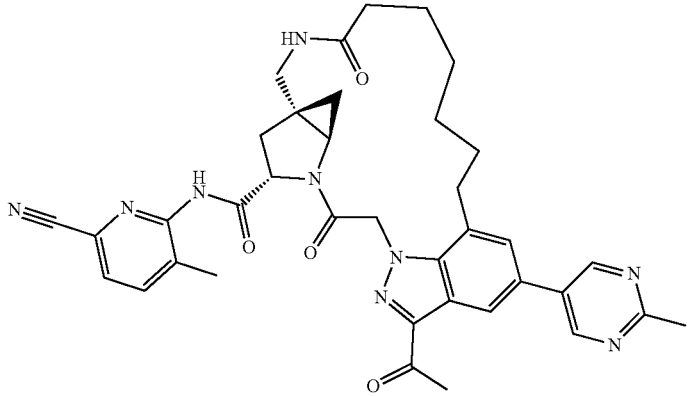 [SMILES: CC(=O)c1nn2c3c(cc(-c4cnc(C)nc4)cc13)CCCCCCC(=O)NC[C@@]13C[C@@H](C(=O)Nc4nc(C#N)ccc4C)N(C(=O)C2)[C@@H]1C3]<br>(41R,43S,45R)-13-acetyl-N-(6-cyano-3-methylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-222 | 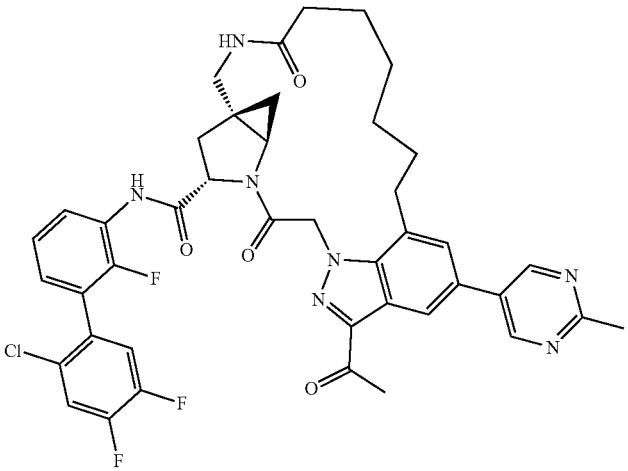 [SMILES: CC(=O)c1nn2c3c(cc(-c4cnc(C)nc4)cc13)CCCCCCC(=O)NC[C@@]13C[C@@H](C(=O)Nc4cccc(-c5cc(F)c(F)cc5Cl)c4F)N(C(=O)C2)[C@@H]1C3]<br>(41R,43S,45R)-13-acetyl-N-(2'-chloro-2,4',5'-trifluoro-[1,1'-biphenyl]-3-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-223 | 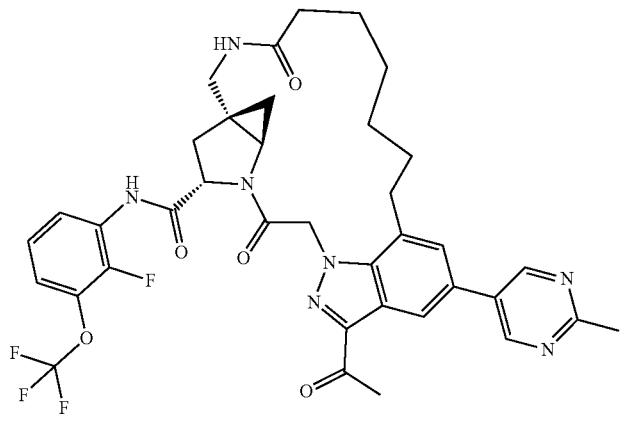 [SMILES: CC(=O)c1nn2c3c(cc(-c4cnc(C)nc4)cc13)CCCCCCC(=O)NC[C@@]13C[C@@H](C(=O)Nc4cccc(OC(F)(F)F)c4F)N(C(=O)C2)[C@@H]1C3]<br>(41R,43S,45R)-13-acetyl-N-(2-fluoro-3-(trifluoromethoxy)phenyl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-224 | 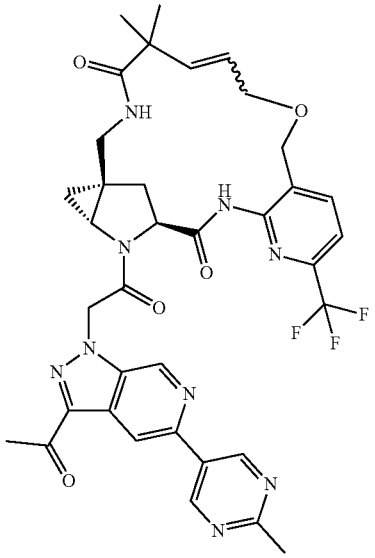 [SMILES: CC(=O)c1nn(CC(=O)N2[C@H]3C[C@@]4(CNC(=O)C(C)(C)C=CCOCc5ccc(C(F)(F)F)nc5NC3=O)C[C@@H]24)c2cnc(-c3cnc(C)nc3)cc12]<br>(41R,43S,45R)-42-(2-(3-acetyl-5-(2-methylpyrimidin-5-yl)-1H-pyrazolo[3,4-c]pyridin-1-yl)acetyl)-8,8-dimethyl-16-(trifluoromethyl)-12-oxa-42,2,6-triaza-1(2,3)-pyridina-4(3,5)-bicyclo[3.1.0]hexanacyclotridecaphan-9-ene-3,7-dione | *** | | |
| T-225 | 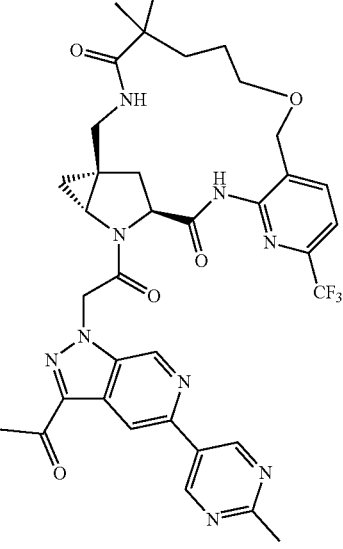<br>(41R,43S,45R)-42-(2-(3-acetyl-5-(2-methylpyrimidin-5-yl)-1H-pyrazolo[3,4-c]pyridin-1-yl)acetyl)-8,8-dimethyl-16-(trifluoromethyl)-12-oxa-42,2,6-triaza-1(2,3)-pyridina-4(3,5)-bicyclo[3.1.0]hexanacyclotridecaphane-3,7-dione | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-226 | 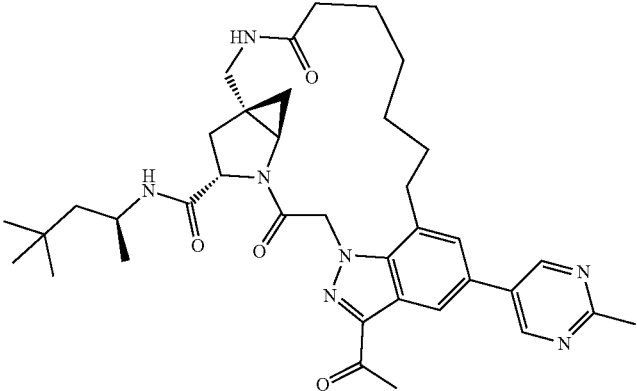 [SMILES: CC(=O)c1nn2c3c(cc(-c4cnc(C)nc4)cc13)CCCCCCC(=O)NC[C@@]13C[C@@H](C(=O)N[C@@H](C)CC(C)(C)C)N(C(=O)C2)[C@@H]1C3]<br>(41R,43S,45R)-13-acetyl-N-((S)-4,4-dimethylpentan-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-227 | 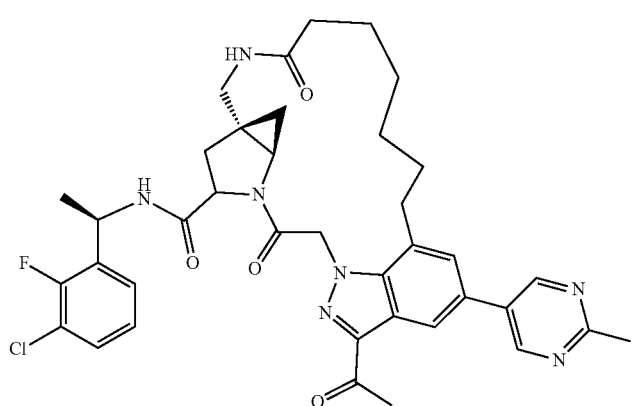 [SMILES: CC(=O)c1nn2c3c(cc(-c4cnc(C)nc4)cc13)CCCCCCC(=O)NC[C@@]13CC(C(=O)N[C@H](C)c4cccc(Cl)c4F)N(C(=O)C2)[C@@H]1C3]<br>(41R,45R)-13-acetyl-N-((R)-1-(3-chloro-2-fluorophenyl)ethyl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-228 | 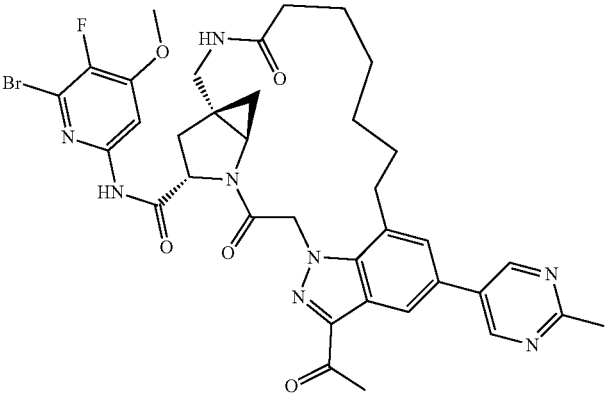 [SMILES: COc1cc(NC(=O)[C@@H]2C[C@]34CNC(=O)CCCCCCc5cc(-c6cnc(C)nc6)cc6c(C(C)=O)nn(c56)CC(=O)N2[C@@H]3C4)nc(Br)c1F]<br>(41R,43S,45R)-13-acetyl-N-(6-bromo-5-fluoro-4-methoxypyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-229 | 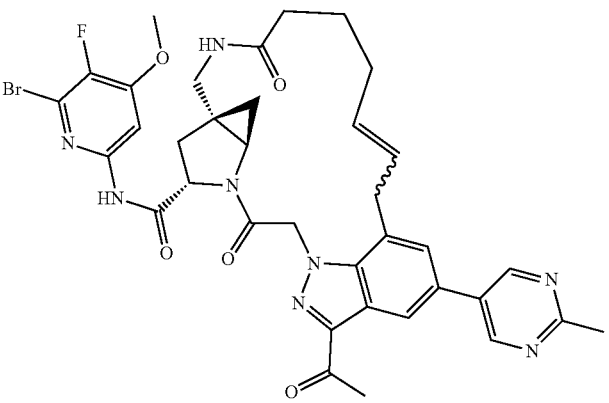 [SMILES: COc1cc(NC(=O)[C@@H]2C[C@]34CNC(=O)CCCC=CCc5cc(-c6cnc(C)nc6)cc6c(C(C)=O)nn(c56)CC(=O)N2[C@@H]3C4)nc(Br)c1F]<br>(41R,43S,45R)-13-acetyl-N-(6-bromo-5-fluoro-4-methoxypyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-230 | 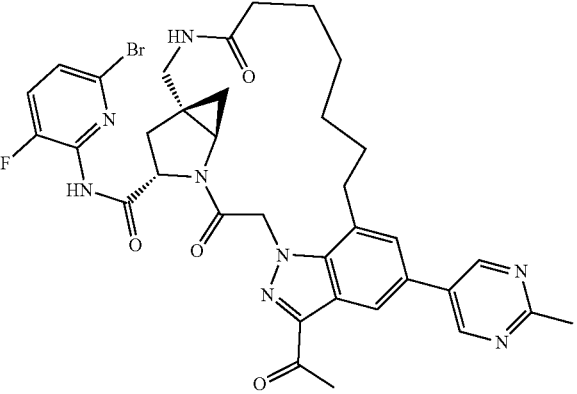 [SMILES: CC(=O)c1nn2c3c(cc(-c4cnc(C)nc4)cc13)CCCCCCC(=O)NC[C@@]13C[C@@H](C(=O)Nc4nc(Br)ccc4F)N(C(=O)C2)[C@@H]1C3]<br>(41R,43S,45R)-13-acetyl-N-(6-bromo-3-fluoropyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-231 | 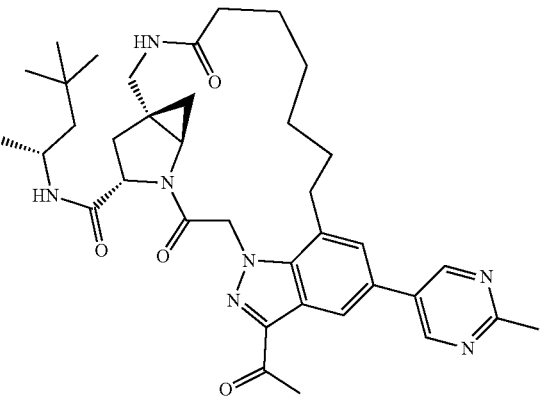 [SMILES: CC(=O)c1nn2c3c(cc(-c4cnc(C)nc4)cc13)CCCCCCC(=O)NC[C@@]13C[C@@H](C(=O)N[C@H](C)CC(C)(C)C)N(C(=O)C2)[C@@H]1C3]<br>(41R,43S,45R)-13-acetyl-N-((R)-4,4-dimethylpentan-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-232 | 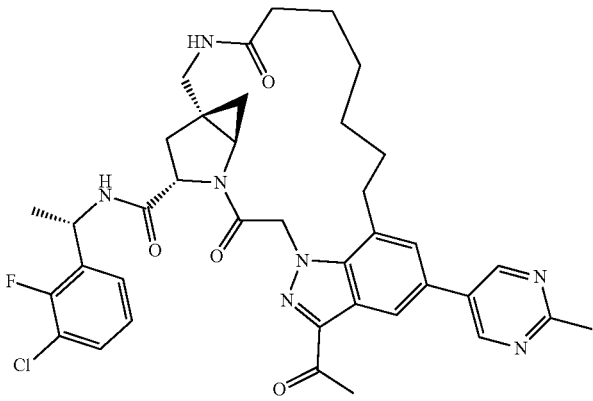 [SMILES: CC(=O)c1nn2c3c(cc(-c4cnc(C)nc4)cc13)CCCCCCC(=O)NC[C@@]13C[C@@H](C(=O)N[C@@H](C)c4cccc(Cl)c4F)N(C(=O)C2)[C@@H]1C3]<br>(41R,43S,45R)-13-acetyl-N-((S)-1-(3-chloro-2-fluorophenyl)ethyl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-233 | 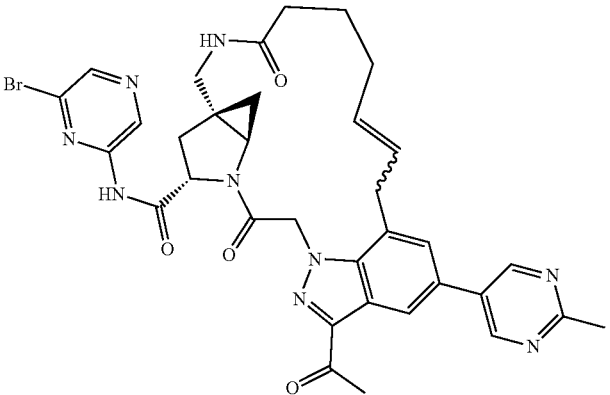 [SMILES: CC(=O)c1nn2c3c(cc(-c4cnc(C)nc4)cc13)CC=CCCCC(=O)NC[C@@]13C[C@@H](C(=O)Nc4cncc(Br)n4)N(C(=O)C2)[C@@H]1C3]<br>(41R,43S,45R)-13-acetyl-N-(6-bromopyrazin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | | |

…TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-234 | 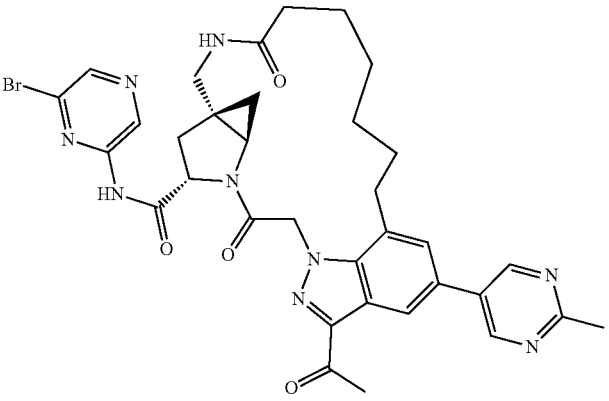 [SMILES: CC(=O)c1nn2c3c(cc(-c4cnc(C)nc4)cc13)CCCCCCC(=O)NC[C@@]13C[C@@H](C(=O)Nc4cncc(Br)n4)N(C(=O)C2)[C@@H]1C3]<br>(41R,43S,45R)-13-acetyl-N-(6-bromopyrazin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-235 | 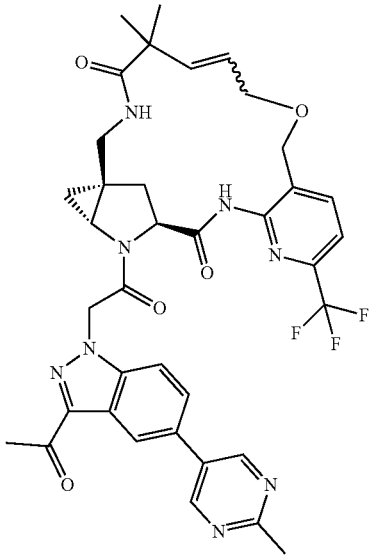 [SMILES: CC(=O)c1nn(CC(=O)N2[C@H]3C[C@@]4(CNC(=O)C(C)(C)C=CCOCc5ccc(C(F)(F)F)nc5NC3=O)C[C@@H]24)c2ccc(-c3cnc(C)nc3)cc12]<br>(41R,43S,45R)-42-(2-(3-acetyl-5-(2-methylpyrimidin-5-yl)-1H-indazol-1-yl)acetyl)-8,8-dimethyl-16-(trifluoromethyl)-12-oxa-42,2,6-triaza-1(2,3)-pyridina-4(3,5)-bicyclo[3.1.0]hexanacyclotridecaphan-9-ene-3,7-dione | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-236 | (41R,43S,45R)-42-(2-(3-acetyl-5-(2-methylpyrimidin-5-yl)-1H-indazol-1-yl)acetyl)-8,8-dimethyl-16-(trifluoromethyl)-12-oxa-42,2,6-triaza-1(2,3)-pyridina-4(3,5)-bicyclo[3.1.0]hexanacyclotridecaphane-3,7-dione | *** | | |
| T-237 | (41R,43S,45R)-13-acetyl-N-(3-methyl-6-(trifluoromethyl)pyridin-2-yl)-15-(2-methylpyrimidin-5-yl)-3,7-dioxo-11H-42,6,8-triaza-1(1,7)-indazola-4(2,5)-bicyclo[3.1.0]hexanacyclododecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-238 | 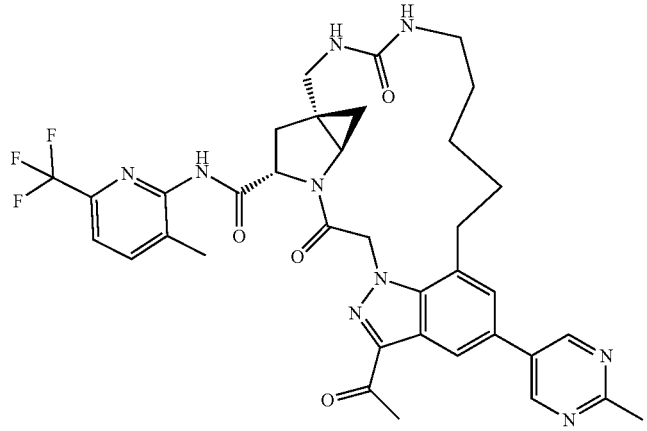 [SMILES: CC(=O)c1nn2c3c(cc(-c4cnc(C)nc4)cc13)CCCCCNC(=O)NC[C@@]13C[C@@H](C(=O)Nc4nc(C(F)(F)F)ccc4C)N(C(=O)C2)[C@@H]1C3]<br>(41R,43S,45R)-13-acetyl-N-(3-methyl-6-(trifluoromethyl)pyridin-2-yl)-15-(2-methylpyrimidin-5-yl)-3,7-dioxo-11H-42,6,8-triaza-1(1,7)-indazola-4(2,5)-bicyclo[3.1.0]hexanacyclotridecaphane-43-carboxamide | *** | | |
| T-239 | 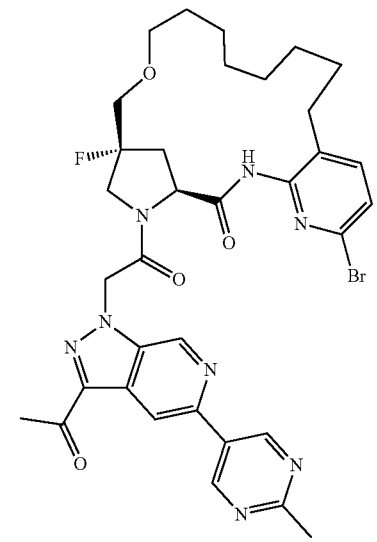 [SMILES: CC(=O)c1nn(CC(=O)N2C[C@@]3(F)COCCCCCCCCc4ccc(Br)nc4NC(=O)[C@@H]2C3)c2cnc(-c3cnc(C)nc3)cc12]<br>(42S,44R)-41-(2-(3-acetyl-5-(2-methylpyrimidin-5-yl)-1H-pyrazolo[3,4-c]pyridin-1-yl)acetyl)-16-bromo-44-fluoro-6-oxa-2-aza-1(2,3)-pyridina-4(2,4)-pyrrolidinacyclotetradecaphan-3-one | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-240 | 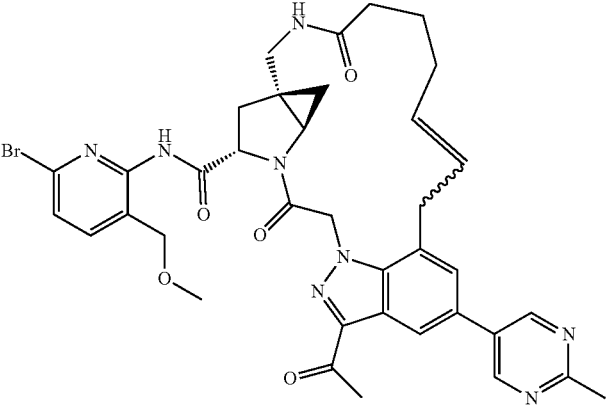 [SMILES: COCc1ccc(Br)nc1NC(=O)[C@@H]1C[C@]23CNC(=O)CCCC=CCc4cc(-c5cnc(C)nc5)cc5c(C(C)=O)nn(c45)CC(=O)N1[C@@H]2C3](41R,43S,45R)-13-acetyl-N-(6-bromo-3-(methoxymethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | | |
| T-241 | 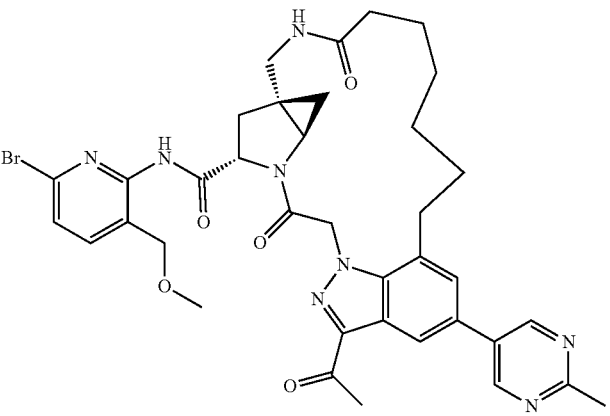 [SMILES: COCc1ccc(Br)nc1NC(=O)[C@@H]1C[C@]23CNC(=O)CCCCCCc4cc(-c5cnc(C)nc5)cc5c(C(C)=O)nn(c45)CC(=O)N1[C@@H]2C3](41R,43S,45R)-13-acetyl-N-(6-bromo-3-(methoxymethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-242 | 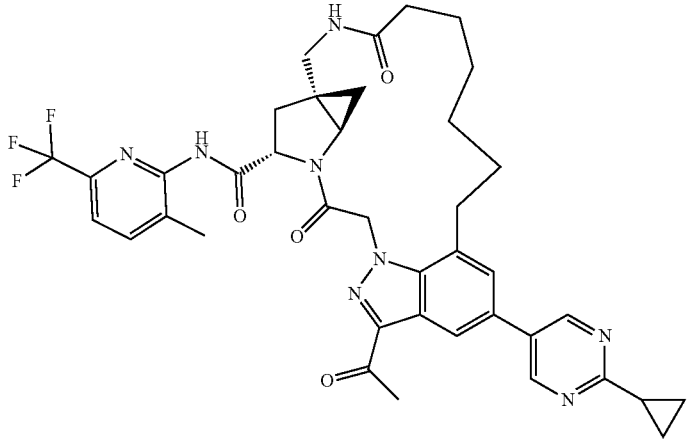 [SMILES: CC(=O)c1nn2c3c(cc(-c4cnc(C5CC5)nc4)cc13)CCCCCCC(=O)NC[C@@]13C[C@@H](C(=O)Nc4nc(C(F)(F)F)ccc4C)N(C(=O)C2)[C@@H]1C3](41R,43S,45R)-13-acetyl-15-(2-cyclopropylpyrimidin-5-yl)-N-(3-methyl-6-(trifluoromethyl)pyridin-2-yl)-3,7-dioxo-11H-42,6-diaza-1(1,7)-indazola-4(2,5)-bicyclo[3.1.0]hexanacyclotridecaphane-43-carboxamide | *** | | |
| T-243 | 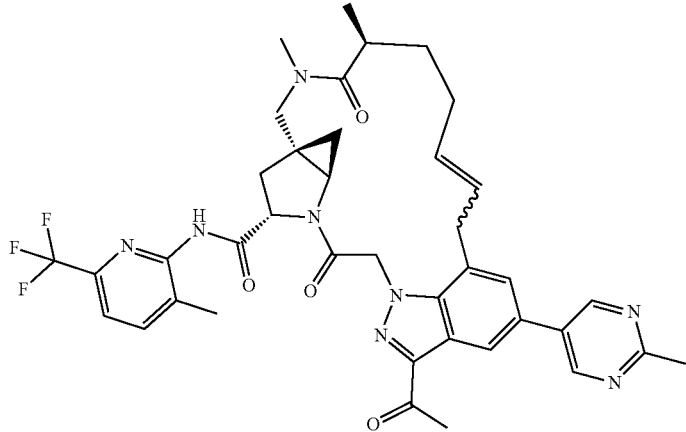 [SMILES: CC(=O)c1nn2c3c(cc(-c4cnc(C)nc4)cc13)CC=CCC[C@H](C)C(=O)N(C)C[C@@]13C[C@@H](C(=O)Nc4nc(C(F)(F)F)ccc4C)N(C(=O)C2)[C@@H]1C3](41R,43S,45R,8S)-13-acetyl-6,8-dimethyl-N-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-244 | 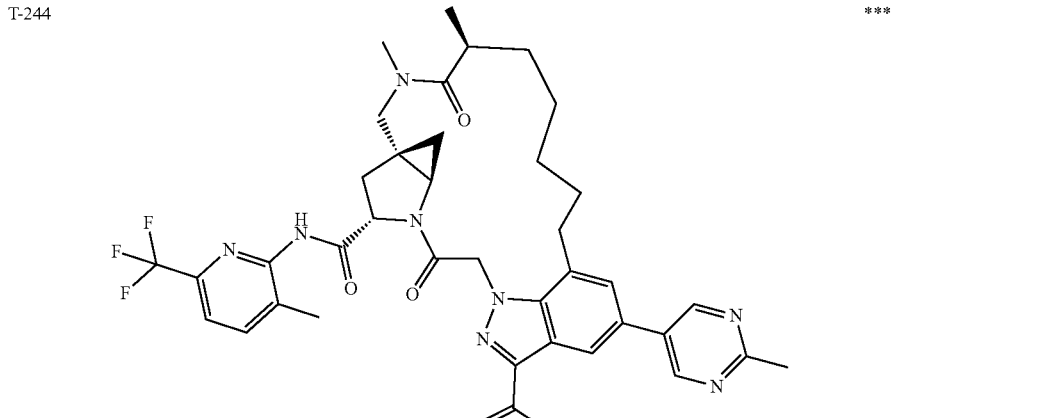<br>(41R,43S,45R,8S)-13-acetyl-6,8-dimethyl-N-(3-methyl-6-(trifluoromethyl)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-245 | 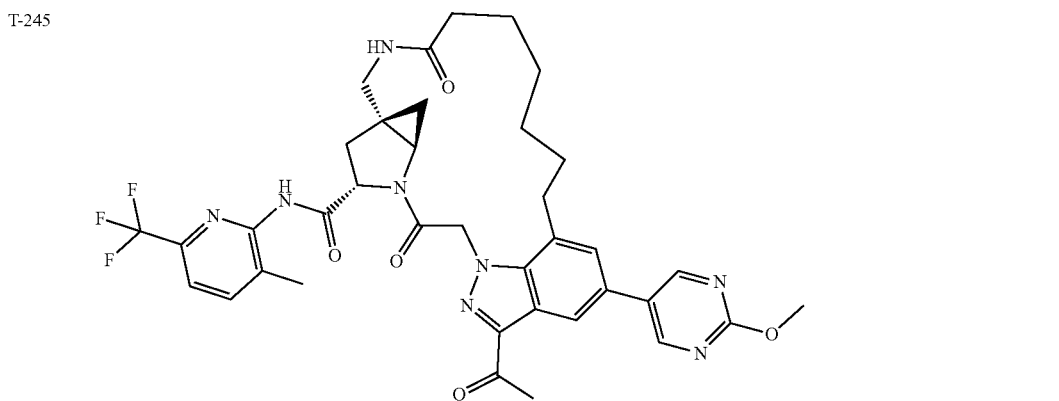<br>(41R,43S,45R)-13-acetyl-15-(2-methoxypyrimidin-5-yl)-N-(3-methyl-6-(trifluoromethyl)pyridin-2-yl)-3,7-dioxo-11H-42,6-diaza-1(1,7)-indazola-4(2,5)-bicyclo[3.1.0]hexanacyclotridecaphane-43-carboxamide | | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-246 | 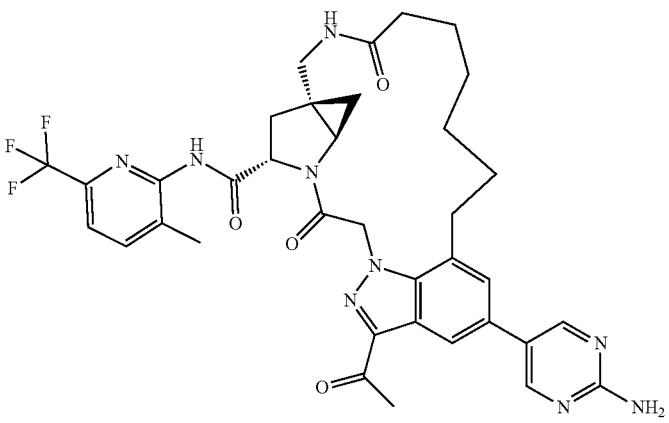 [SMILES: CC(=O)c1nn2c3c(cc(-c4cnc(N)nc4)cc13)CCCCCCC(=O)NC[C@@]13C[C@@H](C(=O)Nc4nc(C(F)(F)F)ccc4C)N(C(=O)C2)[C@@H]1C3]<br>(41R,43S,45R)-13-acetyl-15-(2-aminopyrimidin-5-yl)-N-(3-methyl-6-(trifluoromethyl)pyridin-2-yl)-3,7-dioxo-11H-42,6-diaza-1(1,7)-indazola-4(2,5)-bicyclo[3.1.0]hexanacyclotridecaphane-43-carboxamide | | | |
| T-247 | 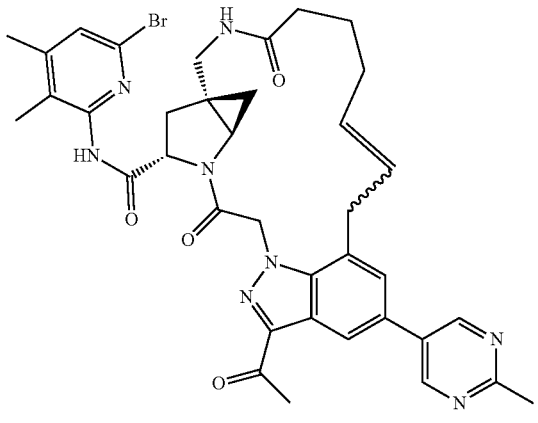<br>(41R,43S,45R)-13-acetyl-N-(6-bromo-3,4-dimethylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphan-11-ene-43-carboxamide | | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-248 | 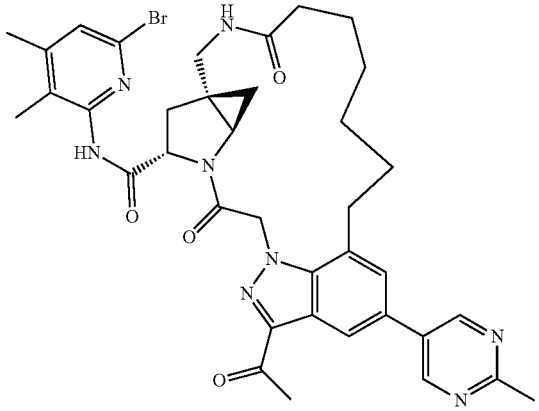(41R,43S,45R)-13-acetyl-N-(6-bromo-3,4-dimethylpyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | | | |
| T-249 | 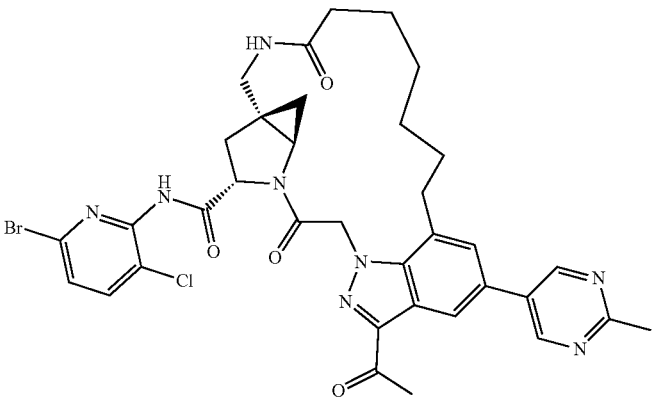 [SMILES: CC(=O)c1nn2c3c(cc(-c4cnc(C)nc4)cc13)CCCCCCC(=O)NC[C@@]13C[C@@H](C(=O)Nc4nc(Br)ccc4Cl)N(C(=O)C2)[C@@H]1C3](41R,43S,45R)-13-acetyl-N-(6-bromo-3-chloropyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-250 | 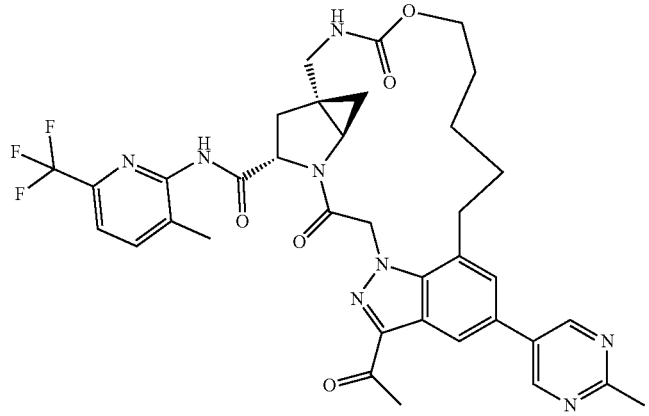 [SMILES: CC(=O)c1nn2c3c(cc(-c4cnc(C)nc4)cc13)CCCCCOC(=O)NC[C@@]13C[C@@H](C(=O)Nc4nc(C(F)(F)F)ccc4C)N(C(=O)C2)[C@@H]1C3]<br>(41R,43S,45R)-13-acetyl-N-(3-methyl-6-(trifluoromethyl)pyridin-2-yl)-15-(2-methylpyrimidin-5-yl)-3,7-dioxo-11H-8-oxa-42,6-diaza-1(1,7)-indazola-4(2,5)-bicyclo[3.1.0]hexanacyclotridecaphane-43-carboxamide | | | |
| T-251 | 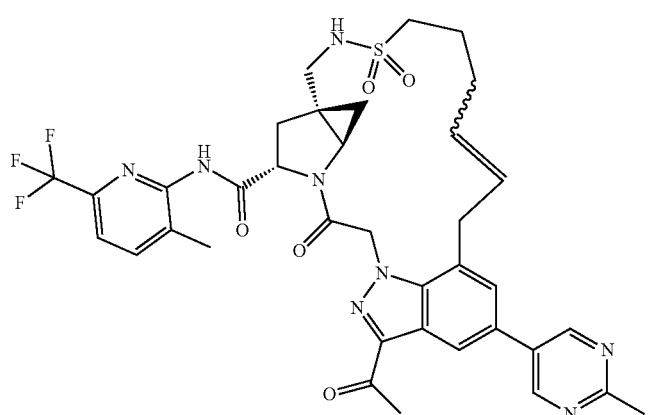<br>(41R,43S,45R)-13-acetyl-N-(3-methyl-6-(trifluoromethyl)pyridin-2-yl)-15-(2-methylpyrimidin-5-yl)-3-oxo-11H-7-thia-42,6-diaza-1(1,7)-indazola-4(2,5)-bicyclo[3.1.0]hexanacyclotridecaphan-11-ene-43-carboxamide 7,7-dioxide | | | |

| Cmp No. | Structure and Name | IC$_{50}$ (Stars) | RT min (Method A, B, C, or D) | MS (M + 1) |
|---|---|---|---|---|
| T-252 | 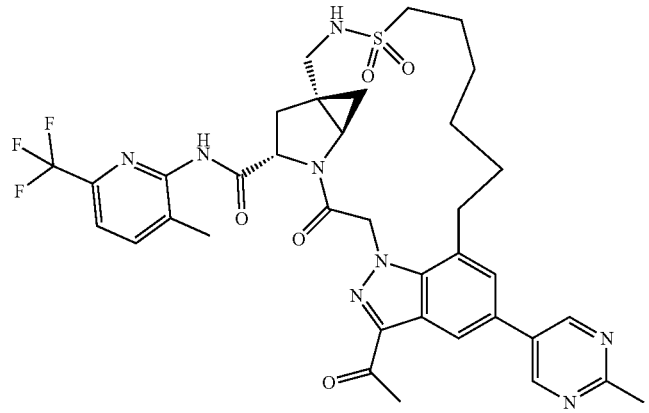 [SMILES: CC(=O)c1nn2c3c(cc(-c4cnc(C)nc4)cc13)CCCCCCS(=O)(=O)NC[C@@]13C[C@@H](C(=O)Nc4nc(C(F)(F)F)ccc4C)N(C(=O)C2)[C@@H]1C3]<br>(41R,43S,45R)-13-acetyl-N-(3-methyl-6-(trifluoromethyl)pyridin-2-yl)-15-(2-methylpyrimidin-5-yl)-3-oxo-11H-7-thia-42,6-diaza-1(1,7)-indazola-4(2,5)-bicyclo[3.1.0]hexanacyclotridecaphane-43-carboxamide 7,7-dioxide | | | |
| T-253 | 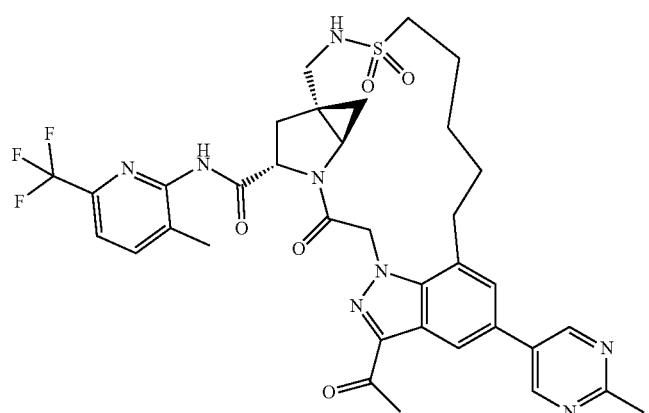<br>(41R,43S,45R)-13-acetyl-N-(3-methyl-6-(trifluoromethyl)pyridin-2-yl)-15-(2-methylpyrimidin-5-yl)-3-oxo-11H-7-thia-42,6-diaza-1(1,7)-indazola-4(2,5)-bicyclo[3.1.0]hexanacyclododecaphane-43-carboxamide 7,7-dioxide | | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-254 | (41R,43S,45R)-13-acetyl-N-(3-methyl-6-(trifluoromethoxy)pyridin-2-yl)-15-(2-methylpyrimidin-5-yl)-3,7-dioxo-11H-42,6-diaza-1(1,7)-indazola-4(2,5)-bicyclo[3.1.0]hexanacyclotridecaphane-43-carboxamide | | | |
| T-255 | (41R,43S,45R)-13-acetyl-N-(3-methyl-6-(trifluoromethyl)pyridin-2-yl)-3,7-dioxo-15-(pyrazolo[1,5-a]pyrimidin-6-yl)-11H-42,6-diaza-1(1,7)-indazola-4(2,5)-bicyclo[3.1.0]hexanacyclotridecaphane-43-carboxamide | *** | | |

| Cmp No. | Structure and Name | IC₅₀ (Stars) | RT min (Method A, B, C, or D) | MS (M + 1) |
|---|---|---|---|---|
| T-256 | 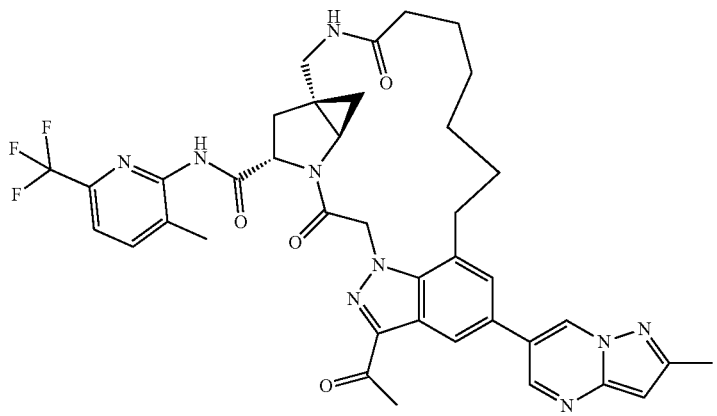 [SMILES: CC(=O)c1nn2c3c(cc(-c4cnc5cc(C)nn5c4)cc13)CCCCCCC(=O)NC[C@@]13C[C@@H](C(=O)Nc4nc(C(F)(F)F)ccc4C)N(C(=O)C2)[C@@H]1C3] (41R,43S,45R)-13-acetyl-N-(3-methyl-6-(trifluoromethyl)pyridin-2-yl)-15-(2-methylpyrazolo[1,5-a]pyrimidin-5-yl)-3,7-dioxo-11H-42,6-diaza-1(1,7)-indazola-4(2,5)-bicyclo[3.1.0]hexanacyclotridecaphane-43-carboxamide | *** | | |
| T-257 | 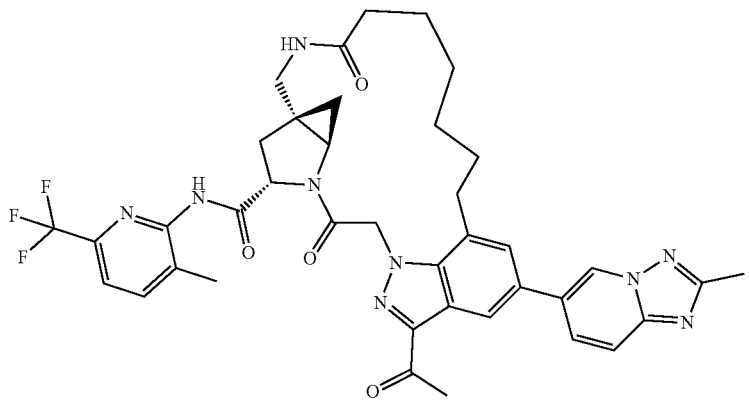 [SMILES: CC(=O)c1nn2c3c(cc(-c4ccc5nc(C)nn5c4)cc13)CCCCCCC(=O)NC[C@@]13C[C@@H](C(=O)Nc4nc(C(F)(F)F)ccc4C)N(C(=O)C2)[C@@H]1C3] (41R,43S,45R)-13-acetyl-N-(3-methyl-6-(trifluoromethyl)pyridin-2-yl)-15-(2-methyl-[1,2,4]triazolo[1,5-a]pyridin-6-yl)-3,7-dioxo-11H-42,6-diaza-1(1,7)-indazola-4(2,5)-bicyclo[3.1.0]hexanacyclotridecaphane-43-carboxamide | *** | | |

TABLE 6-continued

Additional Non-limiting Examples of Compounds of the Present Invention

| Cmp No. | Structure and Name | IC$_{50}$ (Stars) | RT min (Method A, B, C, or D) | MS (M + 1) |
|---|---|---|---|---|
| T-258 | 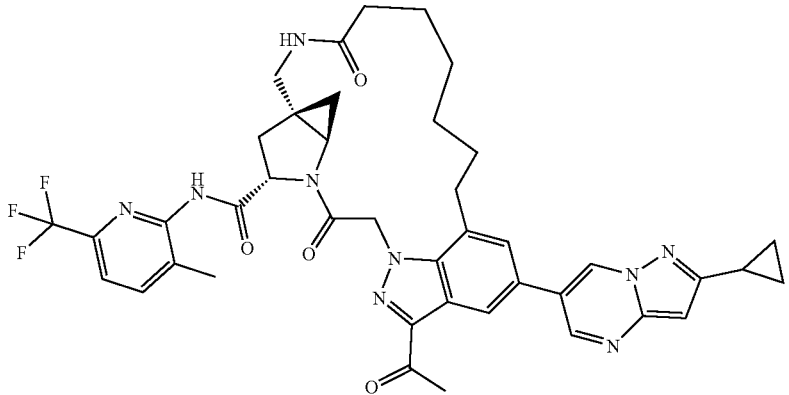 [SMILES: CC(=O)c1nn2c3c(cc(-c4cnc5cc(C6CC6)nn5c4)cc13)CCCCCCC(=O)NC[C@@]13C[C@@H](C(=O)Nc4nc(C(F)(F)F)ccc4C)N(C(=O)C2)[C@@H]1C3]<br>(41R,43S,45R)-13-acetyl-15-(2-cyclopropylpyrazolo[1,5-a]pyrimidin-6-yl)-N-(3-methyl-6-(trifluoromethyl)pyridin-2-yl)-3,7-dioxo-11H-42,6-diaza-1(1,7)-indazola-4(2,5)-bicyclo[3.1.0]hexanacyclotridecaphane-43-carboxamide | *** | | |

Example 2. Human Factor D Assay

Human Factor D (purified from human serum, Complement Technology, Inc.) at 80 nM final concentration is incubated with test compound at various concentrations for 5 min at room temperature in 50 mM Tris, 1M NaCl, pH 7.5. A synthetic substrate Z-L-Lys-SBzl and DTNB (Ellman's reagent) are added to final concentrations of 100 μM each. Absorbance at 405 nm ($A_{405}$) is recorded at 30 second intervals for 30 minutes using a microplate spectrophotometer. IC$_{50}$ values are calculated by nonlinear regression of Complement Factor D reaction rates as a function of test compound concentration.

Example 3. Hemolysis Assay

The hemolysis assay was previously described by G. Ruiz-Gomez, et al., J. Med. Chem. (2009) 52: 6042-6052. Prior to the assay, the optimum concentration of Normal Human Serum (NHS) needed to achieve 100% lysis of rabbit erythrocytes (RE) is determined by titration. In the assay, NHS (Complement Technology) is diluted in GVB⁰ Buffer (0.1% gelatin, 5 mM Veronal, 145 mM NaCl, 0.025% NaN$_3$, pH 7.3, Complement Technology) plus 10 mM Mg-EGTA and incubated with test compound at various concentrations for 15 min at 37° C. RE (Complement Technology) freshly suspended in GVB⁰ plus 10 mM Mg-EGTA are added to a final concentration of 1×10⁸ cells/mL and reactions are incubated for 30 min at 37° C. Positive control reactions (100% lysis) consist of GVB⁰ plus 10 mM Mg-EGTA with NHS and RE but without test compound; negative control reactions (0% lysis) consist of GVB⁰ plus 10 mM Mg-EGTA with RE only. Samples are centrifuged at 2000 g for 3 min and supernatants collected. Absorbance at 405 nm ($A_{405}$) is recorded using a microplate spectrophotometer. IC$_{50}$ values are calculated by nonlinear regression from the percentage of hemolysis as a function of test compound concentration.

This specification has been described with reference to embodiments of the invention. However, one of ordinary skill in the art appreciates that various modifications and changes can be made without departing from the scope of the invention as set forth in the claims below. Accordingly, the specification was to be regarded in an illustrative rather than a restrictive sense, and all such modifications are intended to be included within the scope of invention.

We claim:

1. A compound selected from Formula:

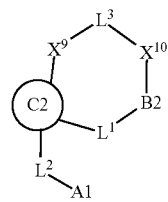

or a pharmaceutically acceptable salt thereof;
wherein:
C2 is

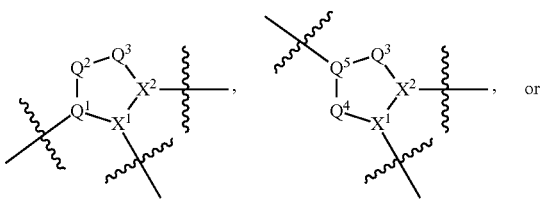

-continued

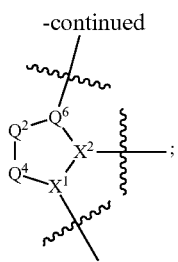

X$^1$ and X$^2$ are independently N, CH, or CZ, wherein X$^1$ is directly bound to L$^2$ and X$^2$ is directly bound to L$^1$;
Q$^1$ is N or C(R$^1$), wherein Q$^1$ is directly bound to X$^9$;
Q$^2$ is C(R$^2$R$^{2'}$);
Q$^3$ is C(R$^3$R$^{3'}$);
Q$^4$ is C(R$^1$R$^1$);
Q$^5$ is C(R$^2$) or N wherein Q$^5$ is directly bound to X$^9$;
Q$^6$ is N or C(R$^3$), wherein Q$^6$ is directly bound to X$^9$;
Z is F, Cl, NH$_2$, CH$_3$, CH$_2$D, CHD$_2$, or CD$_3$;
R$^1$, R$^{1'}$, R$^2$, R$^{2'}$, R$^3$, and R$^{3'}$ are independently selected from hydrogen, R$^{201}$, halogen, hydroxyl, nitro, cyano, amino, C$_1$-C$_6$alkyl, C$_2$-C$_6$alkenyl, C$_2$-C$_6$alkynyl, C$_1$-C$_6$alkoxy, C$_2$-C$_6$alkanoyl, C$_1$-C$_6$alkylthio-, hydroxyC$_1$-C$_6$alkyl-, aminoC$_1$-C$_6$alkyl-, -C$_0$-C$_4$alkylNR$^9$R$^{10}$, —C(O)OR$^9$, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, —OR', —NR'R'', C$_1$-C$_6$haloalkyl, and C$_1$-C$_6$haloalkoxy;
or R$^1$ and R$^2$ are taken together to form a 3-membered carbocyclic ring, a 4- to 6-membered carbocyclic or aryl ring, or a 4- to 6-membered heterocyclic or heteroaryl ring containing 1 or 2 heteroatoms independently selected from N, O, and S;
or R$^2$ and R$^3$ are taken together to form a 3- to 6-membered carbocyclic or aryl ring or a 3- to 6-membered heterocyclic or heteroaryl ring;
R' and R'' are independently selected from H, R$^{201}$, alkyl, cycloalkyl, cycloalkylalkyl, heterocycle, heterocycloalkyl, aryl, arylalkyl, heteroaryl, and heteroarylalkyl;
A1 is

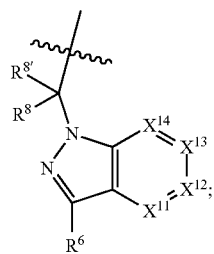

L$^1$ is a bond,

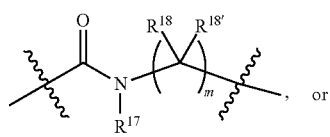

-continued

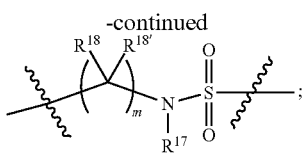

L$^2$ is —C(O)—, —C(S)—, —P(O)OH—, —S(O)—, —S(O)$_2$—, or —C(R$^{52}$)$_2$—;
L$^3$ is

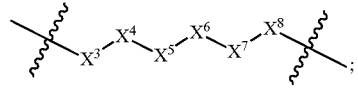

X$^3$, X$^4$, X$^5$, X$^6$, X$^7$, and X$^8$ are each independently selected from alkyl, bond, —C(R$^{52}$)$_2$—, —C(R$^{52}$)$_2$C(R$^{52}$)$_2$—, —C(R$^{52}$)$_2$C(R$^{52}$)$_2$C(R$^{52}$)$_2$—, —C(O)—, —C(S)—, —P(O)OR$^9$—, —S(O)—, —S(O)$_2$—, —O—, —S—, R$^{201}$ in a divalent state, alkenylene, alkynylene, heterocycle, heteroalkylene, heteroalkynylene, heteroalkenylene, arylalkyl, heterocycloalkyl, heteroarylalkyl, aryl, heteroaryl, cycloalkyl, and —NR$^9$—;
X$^9$ and X$^{10}$ are independently selected from alkylene, —C(R$^{52}$)$_2$, —C(R$^{52}$)$_2$O—, —C(R$^{52}$)$_2$NR$^9$—, —C(R$^{52}$)$_2$OC(O)—, —C(R$^{52}$)$_2$NR$^9$C(O)—, —O—, —S—, —C(O)—, —C(S)—, —P(O)OR$^9$—, —S(O)—, —S(O)$_2$—, alkenylene, alkynylene, R$^{201}$ in a divalent state, R$^{32}$ in a divalent state, —NR$^9$—, —CH$_2$O—, —CH$_2$N(H)—, —CH$_2$OC(O)—, —CH$_2$N(H)C(O)—, —CH$_2$N(CH$_3$)—, and —CH$_2$N(CH$_3$)C(O)—; or
X$^9$-L$^3$-X$^{10}$ or X$^{10}$-L$^3$-X$^9$ is

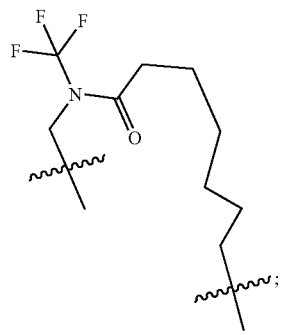 [SMILES: *CCCCCCC(=O)N(C*)C(F)(F)F]

X$^{11}$ is CR$^{11}$;
X$^{12}$ is CR$^{12}$;
X$^{13}$ is CR$^{13}$;
X$^{14}$ is CR$^{14}$;
R$^6$ are independently is selected from hydrogen, halogen, —CHO, —C(O)NH$_2$, -C$_2$-C$_6$alkanoyl, —C(O)NH(CH$_3$), —COON, —P(O)(OR$^9$)$_2$, —OC(O)R$^9$, —C(O)OR$^9$, nitro, hydroxyl, phenyl, 5- to 6-membered heteroaryl, cyano, amino, and C$_1$-C$_6$alkyl;
R$^8$ and R$^{8'}$ are independently selected from hydrogen, halogen, hydroxyl, C$_1$-C$_6$alkyl, -C$_0$-C$_4$alkyl(C$_3$-C$_7$cycloalkyl), C$_1$-C$_6$alkoxy, and (C$_1$-C$_4$alkylamino)C$_0$-C$_2$alkyl;
or R$^8$ and R$^{8'}$ are taken together to form an oxo group;

or $R^8$ and $R^{8'}$ are taken together to form a 3-membered carbocyclic ring;

$R^9$ and $R^{10}$ are independently selected at each occurrence from hydrogen, $C_1$-$C_6$alkyl, ($C_3$-$C_7$cycloalkyl)$C_0$-$C_4$alkyl, -$C_0$-$C_4$alkyl($C_3$-$C_7$cycloalkyl), and —O-$C_0$-$C_4$alkyl($C_3$-$C_7$cycloalkyl);

$R^{11}$, $R^{12}$, $R^{13}$, and $R^{14}$ are independently selected at each occurrence from hydrogen, $R^{201}$, halogen, hydroxyl, nitro, cyano, —O(PO)(OR$^9$)$_2$, —(PO)(OR$^9$)$_2$, $C_1$-$C_6$alkyl, $C_2$-$C_6$alkenyl, $C_2$-$C_6$alkynyl, -$C_2$-$C_6$alkenyl-aryl, -$C_2$-$C_6$alkenyl-cycloalkyl, -$C_2$-$C_6$alkenyl-heterocycle, -$C_2$-$C_6$alkenyl-heteroaryl, $C_2$-$C_6$alkynyl, -$C_2$-$C_6$alkynyl-aryl, -$C_2$-$C_6$alkynyl-cycloalkyl, -$C_2$-$C_6$alkynyl(heterocycle), -$C_2$-$C_6$alkynyl-heteroaryl, $C_2$-$C_6$alkanoyl, $C_1$-$C_6$alkoxy, $C_1$-$C_6$thioalkyl, -$C_0$-$C_4$alkyl(mono- and di-alkylamino), -$C_0$-$C_4$alkyl($C_3$-$C_7$cycloalkyl), -$C_0$-$C_4$alkoxy($C_3$-$C_7$cycloalkyl), $C_1$-$C_6$haloalkyl, $C_1$-$C_6$haloalkoxy, amino, —COON, -$C_0$-$C_4$alkyl($C_3$-$C_7$cycloalkyl), $C_2$-$C_6$alkenyloxy, —C(O)OR$^9$, $C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, —C(NR$^9$)NR$^9$R$^{10}$, and $R^{32}$, each of which other than hydrogen, halogen, hydroxyl, nitro, cyano, haloalkyl, and haloalkoxy is optionally substituted with one or more substituents independently selected from halogen, hydroxyl, nitro, cyano, amino, —COON, —CONH$_2$, $C_1$-$C_6$haloalkyl, $C_1$-$C_6$haloalkoxy, phenyl, 4- to 7-membered heterocycle containing 1, 2, or 3 heteroatoms independently selected from N, O, and S, each of which phenyl or 4- to 7-membered heterocycle is optionally substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-alkylamino)$C_0$-$C_4$alkyl, $C_1$-$C_6$alkylester, -$C_0$-$C_4$alkyl($C_3$-$C_7$cycloalkyl), $C_1$-$C_6$haloalkyl, and $C_1$-$C_6$haloalkoxy;

$R^{17}$ is hydrogen, $C_1$-$C_6$alkyl, or -$C_0$-$C_4$alkyl($C_3$-$C_7$cycloalkyl);

$R^{18}$ and $R^{18'}$ are independently selected from hydrogen, halogen, hydroxymethyl, and methyl;

$R^{21}$ and $R^{22}$ are independently selected from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, -$C_1$-$C_4$alkylOC(O)OC$_1$-$C_6$alkyl, -$C_1$-$C_4$alkylOC(O)$C_1$-$C_6$alkyl, -$C_1$-$C_4$alkylC(O)OC$_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S;

or $R^{21}$ and $R^{22}$ can be taken together to form a carbocyclic or heterocyclic ring;

$R^{23}$ is independently selected from $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S;

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings;

$R^{32}$ is selected from hydrogen, aryl, heteroaryl, heterocycle,

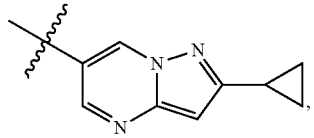 [SMILES: *c1cnc2cc(C3CC3)nn2c1]

and

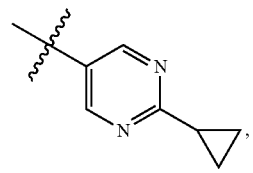 [SMILES: *c1cnc(C2CC2)nc1]

wherein the aryl, heteroaryl, and heterocycle can be optionally substituted with 1, 2, 3, or 4 substituents independently selected from halogen, hydroxyl, amino, cyano, —CHO, —COON, —CONH$_2$, $C_1$-$C_6$alkyl, $C_2$-$C_6$alkenyl, $C_2$-$C_6$alkynyl, $C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_6$haloalkyl, hydroxy$C_1$-$C_6$alkyl, -$C_0$-$C_6$alkyl-heterocycle, -$C_0$-$C_6$alkyl-heteroaryl, $C_1$-$C_6$haloalkoxy, and $R^{201}$;

B2 is a heteroaryl, heterocycle, or aryl group directly bound to both $L^1$ and $X^{10}$ at two independent positions; wherein, each of which B2 is optionally substituted with one or more substituents independently selected from $R^{33}$, $R^{34}$, $R^{35}$, $R^{36}$, and $R^{201}$;

$R^{33}$ is independently selected from halogen, hydroxyl, —COON, cyano, $C_1$-$C_6$alkyl, $C_2$-$C_6$alkanoyl, $C_1$-$C_6$alkoxy, -$C_0$-$C_4$alkylNR$^9$R$^{10}$, —SO$_2$R$^9$, $C_1$-$C_6$haloalkyl, and $C_1$-$C_6$haloalkoxy;

$R^{34}$ is independently selected from nitro, $C_2$-$C_6$alkenyl, $C_2$-$C_6$alkynyl, $C_1$-$C_6$thioalkyl, -JC$_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$R$^{22}$), -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$S0$_2$R$^{22}$, -JC(NH$_2$)=NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)NR$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, and -JC(O)OR$^{23}$; each of which $R^{34}$ is optionally substituted with one or more substituents independently selected from halogen, hydroxyl, nitro, cyano, amino, oxo, —B(OH)$_2$, —Si(CH$_3$)$_3$, —COON, —CONH$_2$, —P(O)(OH)$_2$, $C_1$-$C_6$alkyl, -$C_0$-$C_4$alkyl($C_3$-$C_7$cycloalkyl), $C_1$-$C_6$alkoxy, -$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_6$haloalkyl, and $C_1$-$C_6$haloalkoxy;

R³⁵ is independently selected from naphthyl, naphthyloxy, indanyl, (4- to 7-membered heterocycloalkyl)C₀-C₄alkyl containing 1 or 2 heteroatoms selected from N, O, and S, and bicyclic heterocycle containing 1, 2, or 3 heteroatoms independently selected from N, O, and S, and containing 4- to 7-ring atoms in each ring; each of which R³⁵ is optionally substituted with one or more substituents independently selected from halogen, hydroxyl, nitro, cyano, C₁-C₆alkyl, C₂-C₆alkenyl, C₂-C₆alkanoyl, C₁-C₆alkoxy, (mono- and di-alkylamino)C₀-C₄alkyl, C₁-C₆alkylester, -C₀-C₄alkyl(C₃-C₇cycloalkyl), —SO₂R⁹, C₁-C₆haloalkyl, and C₁-C₆haloalkoxy;

R³⁶ is independently selected from tetrazolyl, (phenyl)C₀-C₂alkyl, (phenyl)C₁-C₆alkoxy, phenoxy, and heteroaryl containing 1, 2, or 3 heteroatoms independently selected from N, O, B, and S, each of which R³⁶ is optionally substituted with one or more substituents independently selected from halogen, hydroxyl, nitro, cyano, C₁-C₆alkyl, C₂-C₆alkenyl, C₂-C₆alkanoyl, C₁-C₆alkoxy, (mono- and di-alkylamino)C₀-C₄alkyl, C₁-C₆alkylester, -C₀-C₆alkyl(C₃-C₇cycloalkyl), —SO₂R⁹, —OSi(CH₃)₂C(CH₃)₃, —Si(CH₃)₂C(CH₃)₃, C₁-C₆haloalkyl, and C₁-C₆haloalkoxy;

R⁵² is independently selected from halo, hydrogen, or C₁-C₆alkyl, amino, hydroxyl, aminoalkyl, alkenyl, alkynyl, C₂-C₆alkenyl(aryl), C₂-C₆alkenyl(cycloalkyl), C₂-C₆alkenyl(heterocycle), C₂-C₆alkenyl(heteroaryl), alkynyl, C₂-C₆alkynyl(aryl), C₂-C₆alkynyl(cycloalkyl), C₂-C₆alkynyl(heterocycle), C₂-C₆alkynyl(heteroaryl), alkanoyl, C₁-C₆alkoxy, C₁-C₆thioalkyl, -C₀-C₄alkyl(mono- and di-alkylamino), -C₀-C₄alkyl(C₃-C₇cycloalkyl), -C₀-C₄alkoxy(C₃-C₇cycloalkyl), haloalkyl, haloalkoxy, —COON, -C₀-C₄alkyl(C₃-C₇cycloalkyl), C₂-C₆alkenyloxy, —C(O)OR⁹, -C₀-C₄alkylNR⁹R¹⁰, —C(O)NR⁹R¹⁰, —SO₂R⁹, —SO₂NR⁹R¹⁰, —OC(O)R⁹, R²⁰¹, and N(R⁹)C(O)R¹⁰;

or two R⁵² groups can be taken together to form an oxo or alkene group;

or two R⁵² groups can be taken together to form a 3- to 6-membered carbocyclic spiro ring or a 3- to 6-membered heterocyclic spiro ring containing 1 or 2 heteroatoms independently selected from N, O, or S;

R²⁰¹ is selected from aminoalkyl-, alkylaminoalkyl-, heterocycloalkyl-, hydroxyalkyl, -alkyl—O-alkyl, -alkyl—S-alkyl, -alkyl—N(alkyl)-alkyl, -alkyl—NH-alkyl, -aliphatic—O-aliphatic, -aliphatic—S-aliphatic, -aliphatic—N(aliphatic)-aliphatic, -aliphatic—NH-aliphatic, -aliphatic—O-heterocycle, -aliphatic—S-heterocycle, -aliphatic—N(aliphatic)-heterocycle, -aliphatic—NH-heterocycle, -alkyl—NHC(O)haloalkyl, -alkyl—NR⁹C(O)haloalkyl, -alkyl—C(O)NHhaloalkyl, -alkyl—C(O)NR⁹haloalkyl, -alkyl—NHC(O)haloalkyl, -alkyl—NR⁹C(O)aliphatic, -alkyl—C(O)NHaliphatic, -alkyl—NR⁹C(O)aliphatic, -alkyl—NHC(O)aliphatic, alkyl—O-haloalkyl, alkyl-heteroaryl, heteroaryl, heterocycle, alkyl-heterocycle, and —N(aliphatic)₂;

J is independently selected from a covalent bond, C₁-C₄alkylene, —OC₁-C₄alkylene, C₂-C₄alkenylene, and C₂-C₄alkynylene; and m is 0, 1, 2, or 3.

2. The compound of claim 1, wherein R³² is

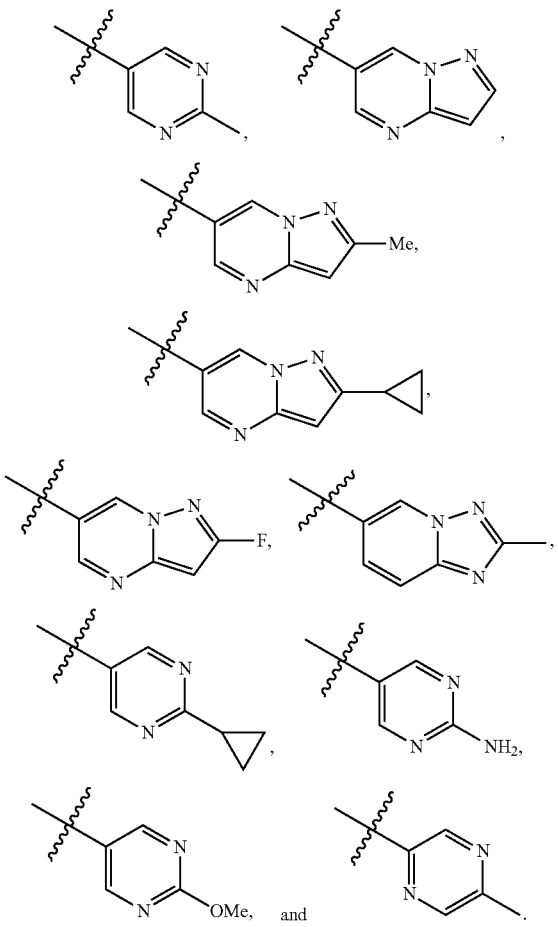

3. The compound of claim 1, wherein X⁹-L³-X¹⁰ or X¹⁰-L³-X⁹ is selected from:

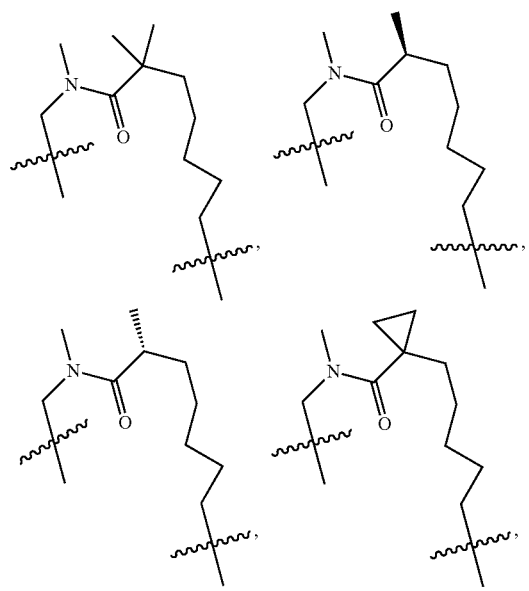

943
-continued
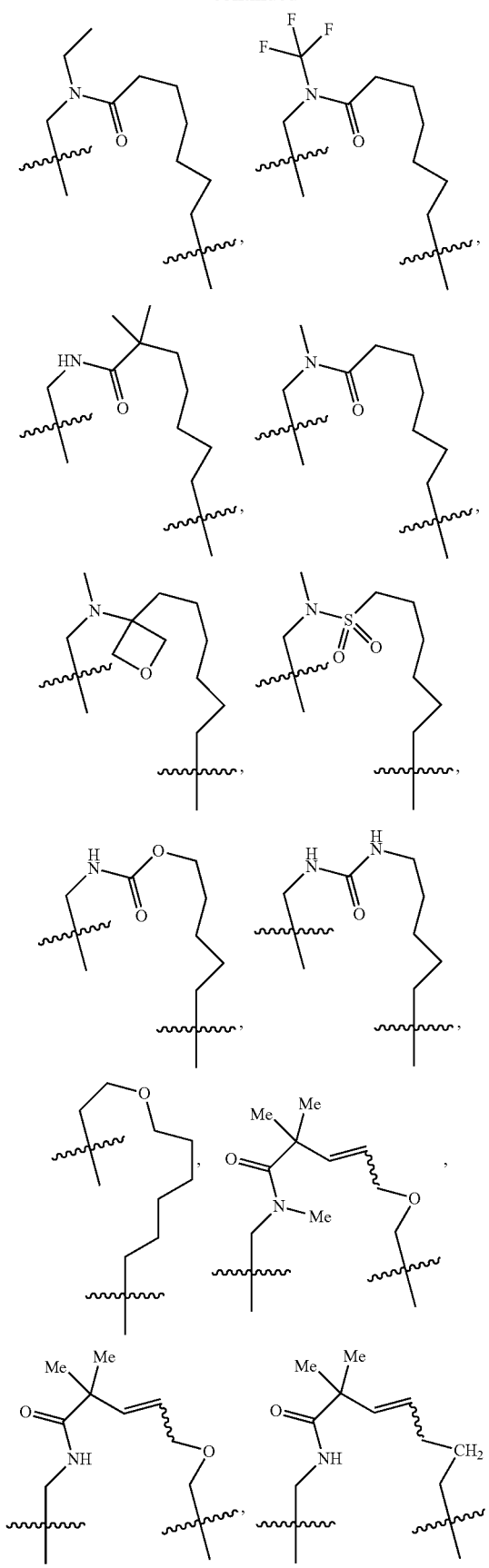
944
-continued
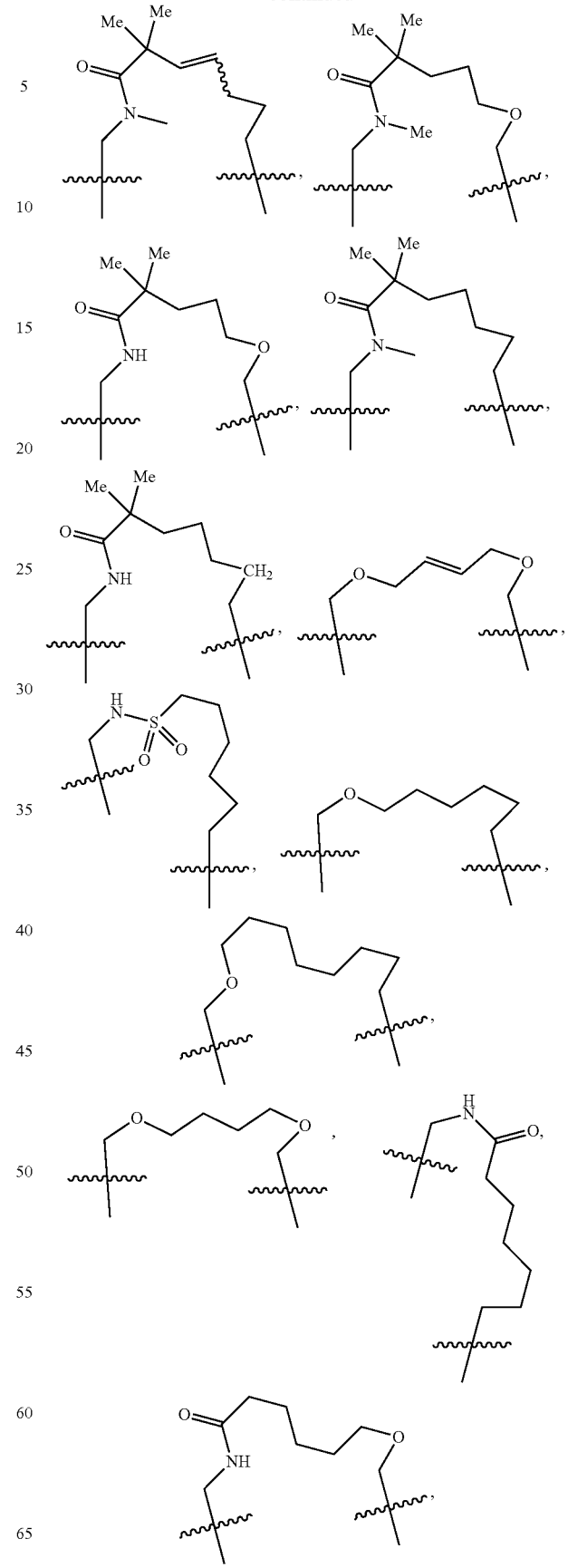

945
-continued
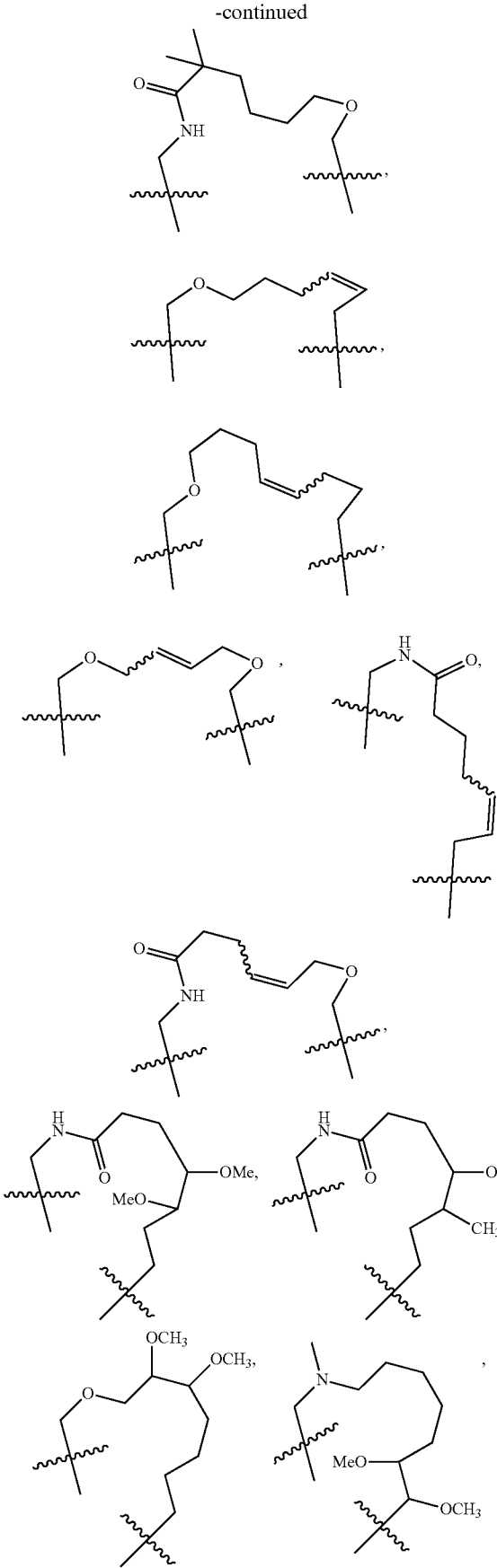
946
-continued
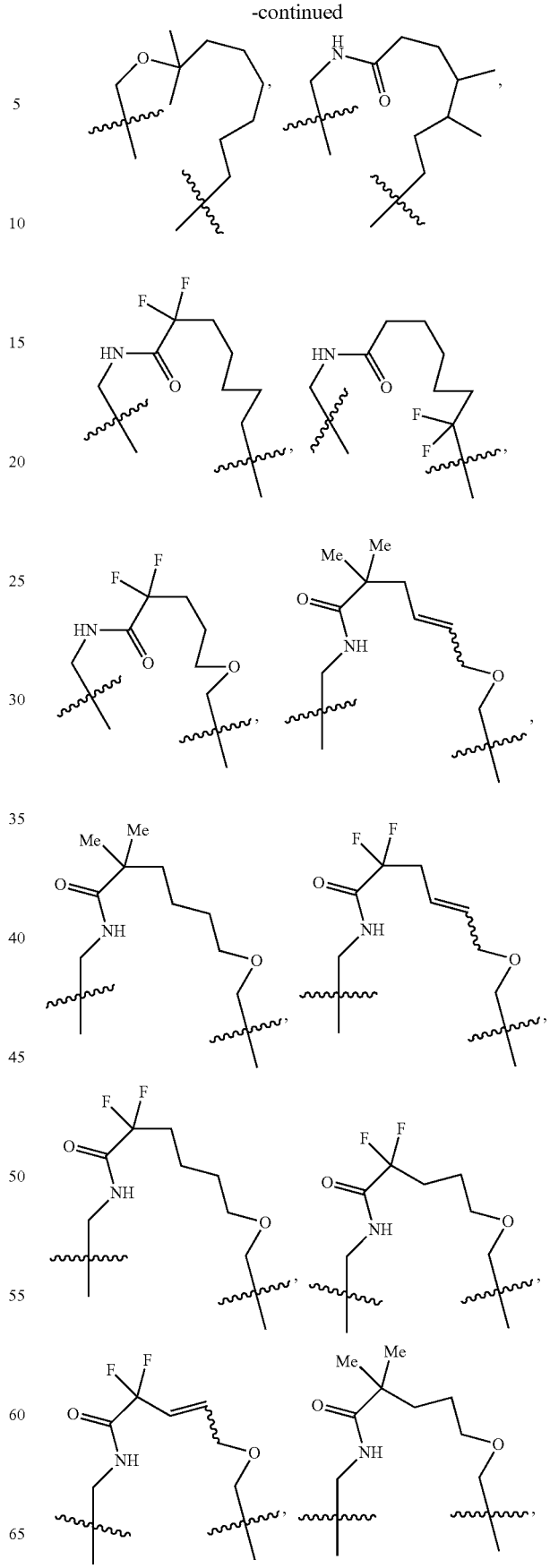

-continued
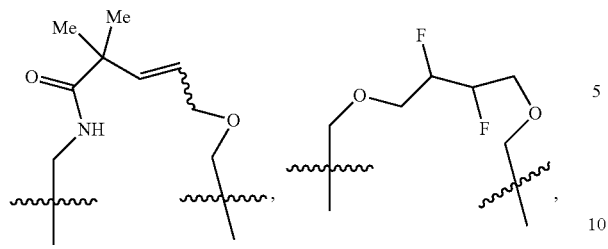
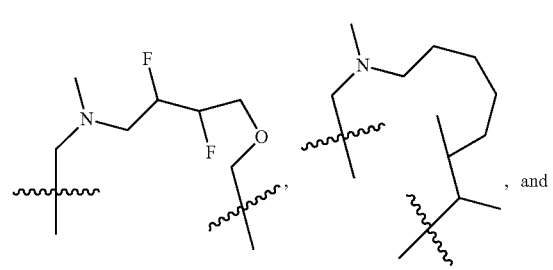
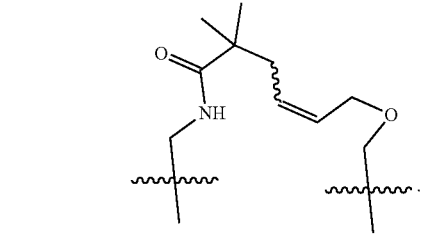
4. The compound of claim 1, wherein $X^9$-$L^3$-$X^{10}$ or $X^{10}$-$L^3$-$X^9$ is selected from:
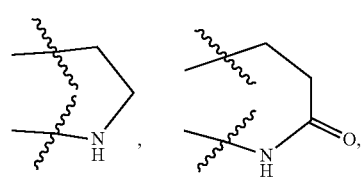
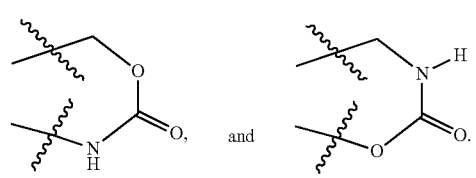
5. The compound of claim 1, wherein B2 is a six membered heteroaryl substituted with 1 or 2 groups selected from $R^{33}$.
6. The compound of claim 1, wherein the compound is:
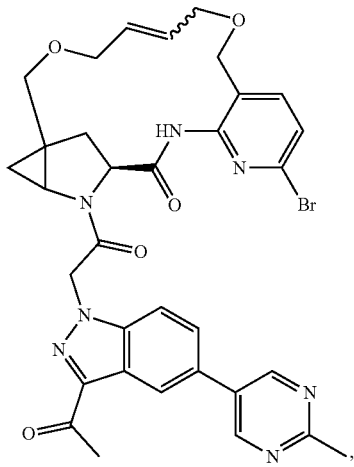
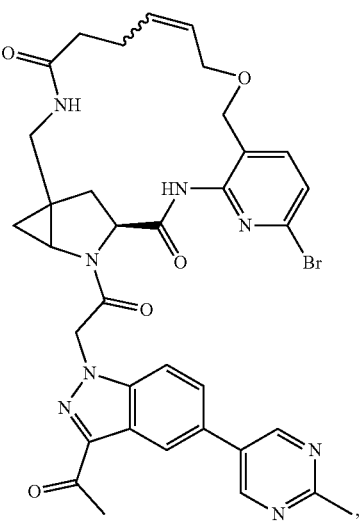
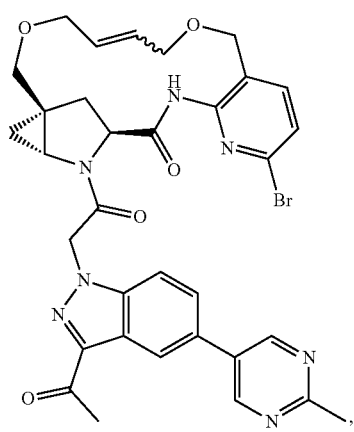

949
-continued
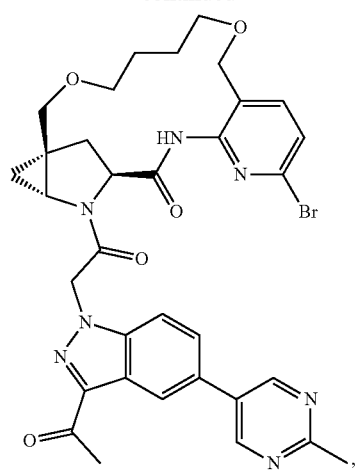
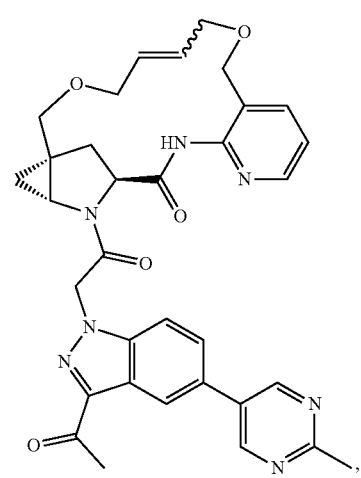
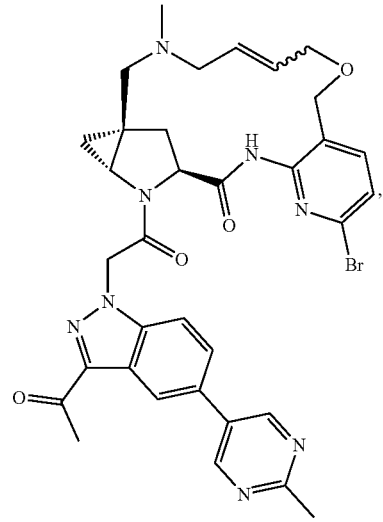
950
-continued
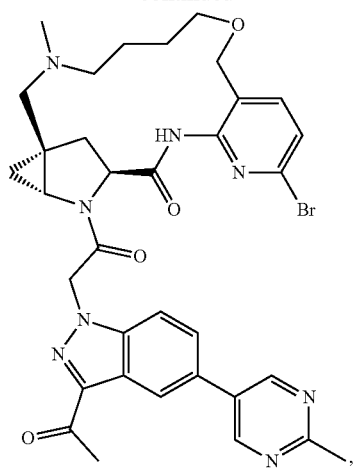
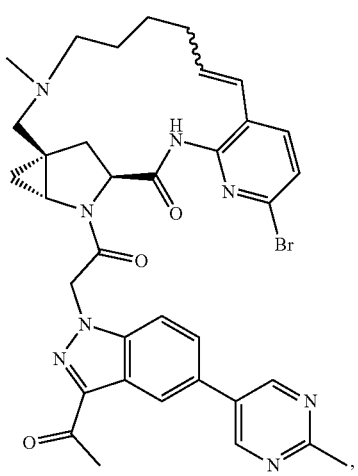
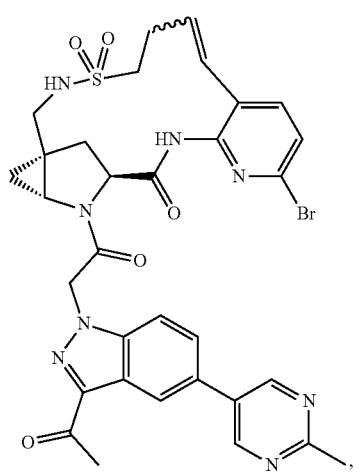

951
-continued
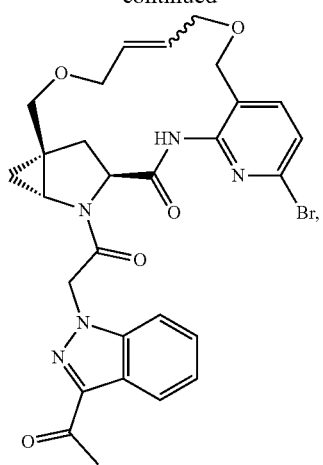
Br,
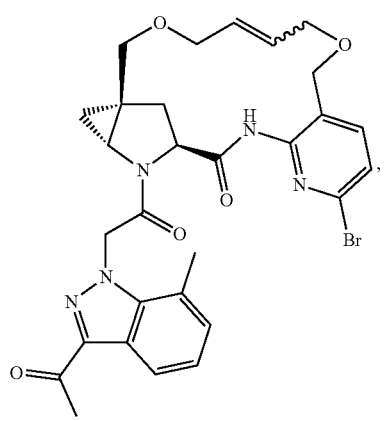
Br,
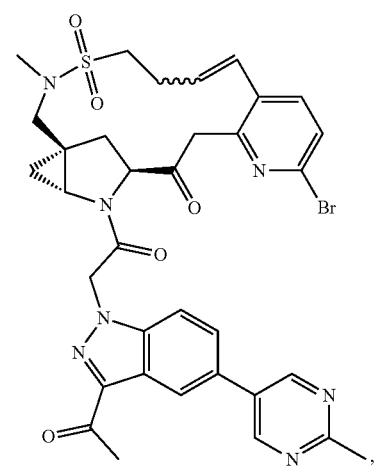
952
-continued
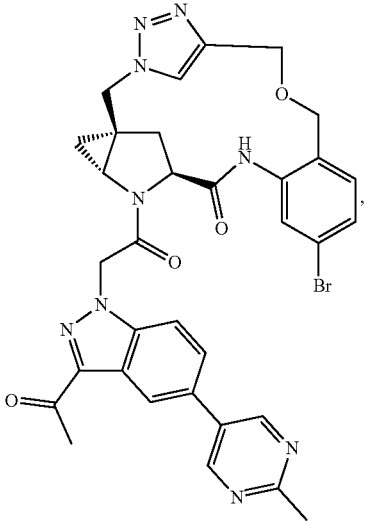
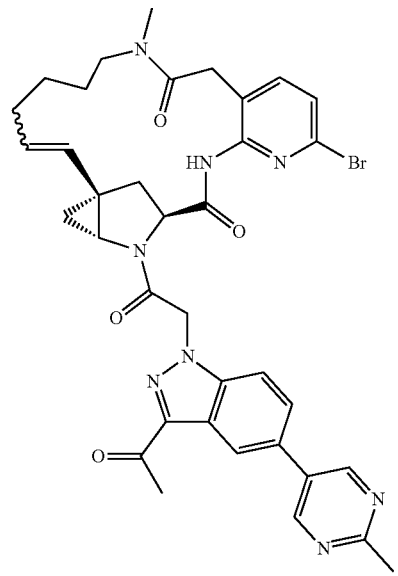
,
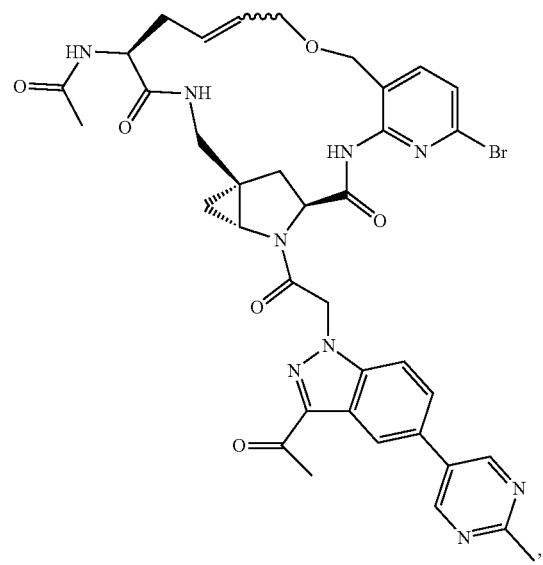
, 953
-continued
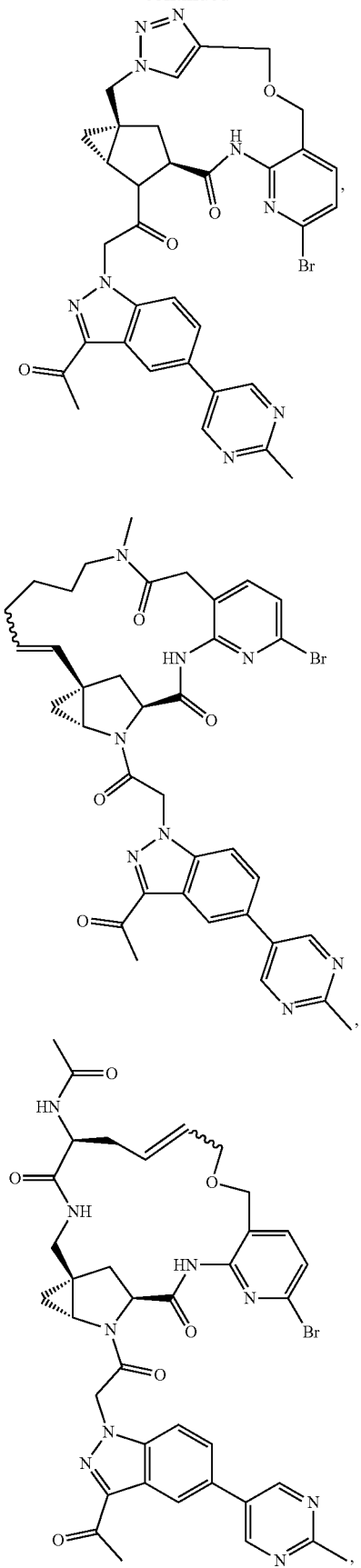
954
-continued
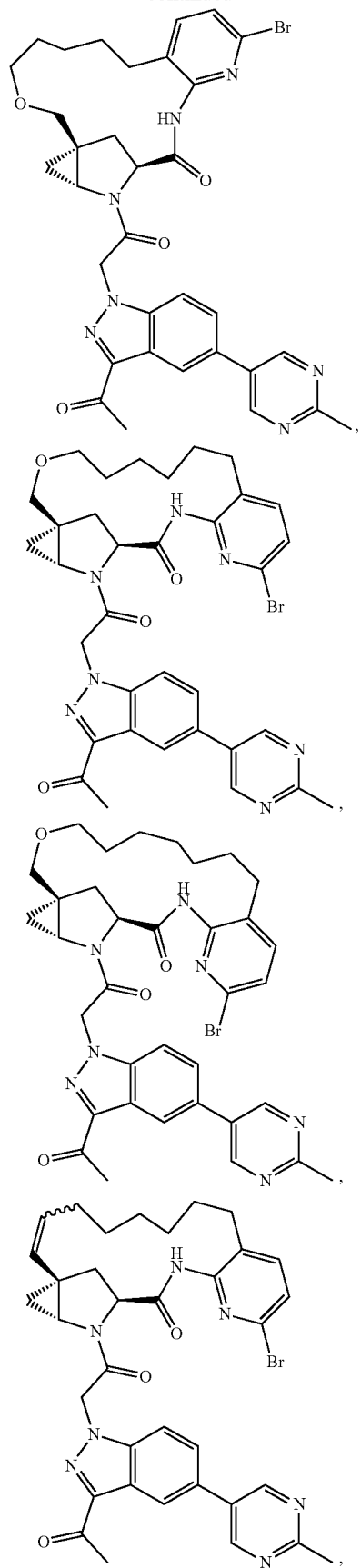

955
-continued
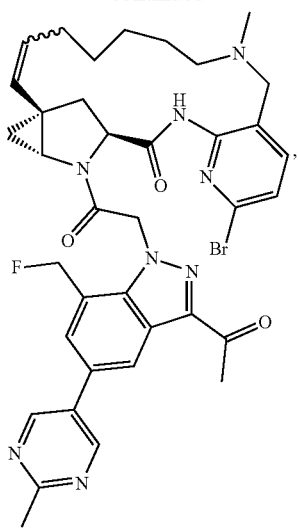
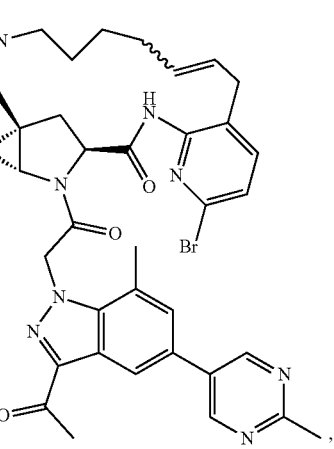
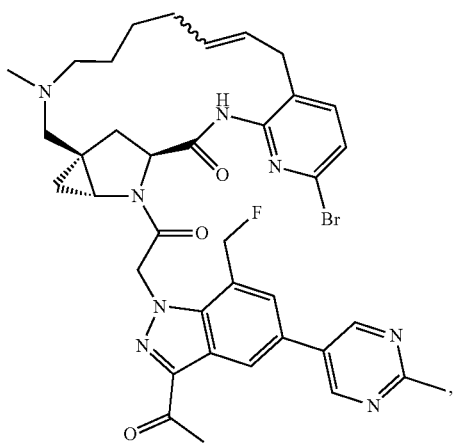
956
-continued
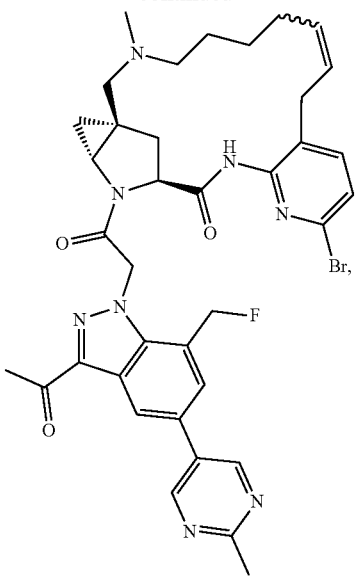
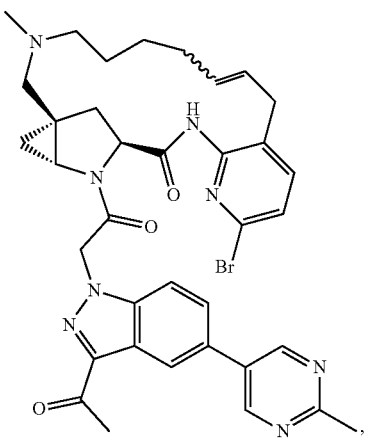
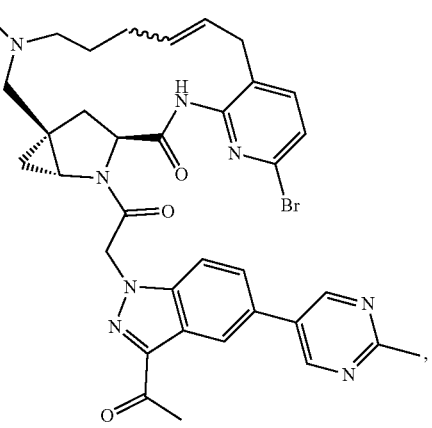

957
-continued
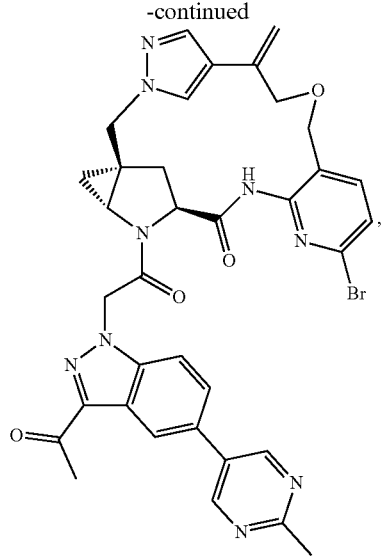
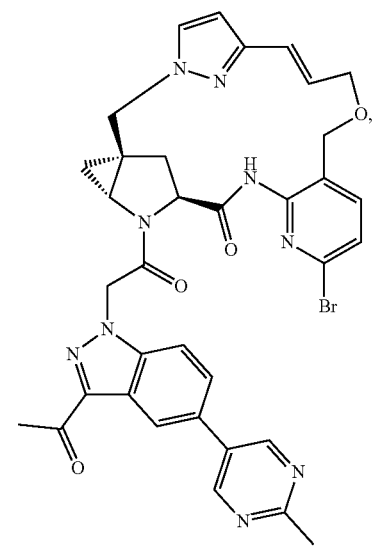
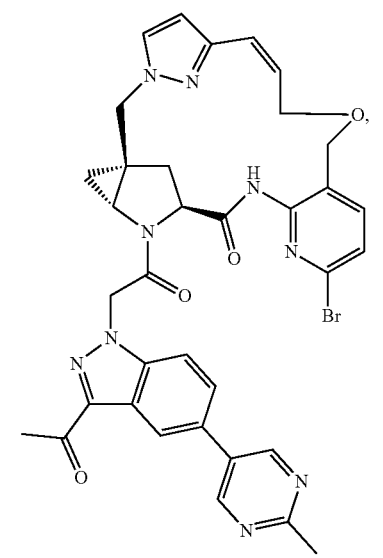
958
-continued
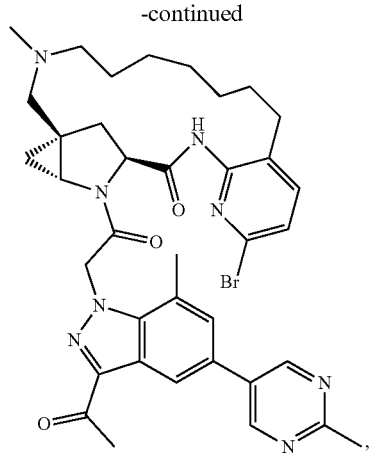
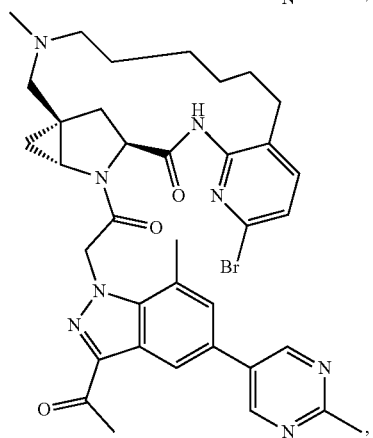
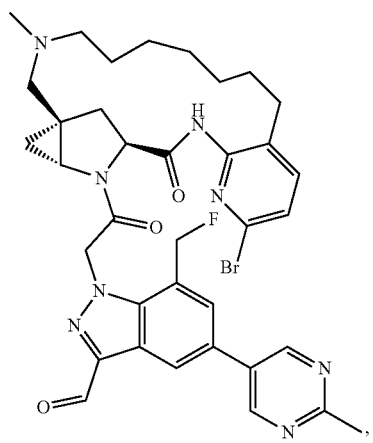
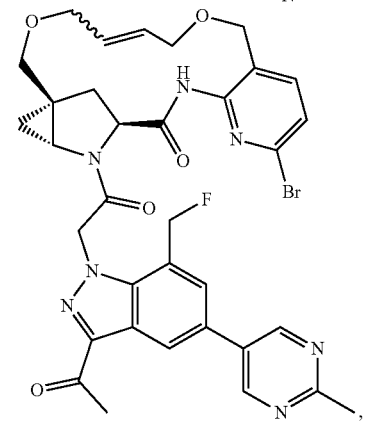

959 -continued
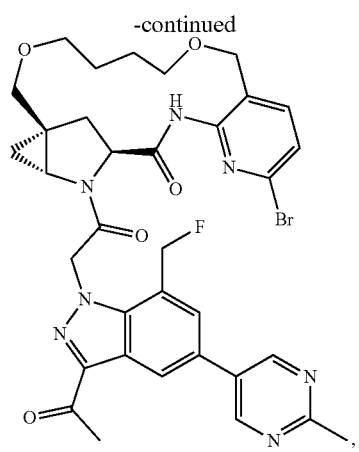
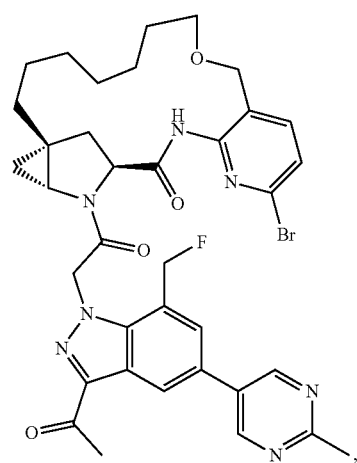
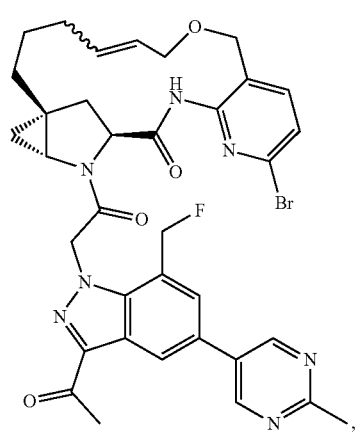
960 -continued
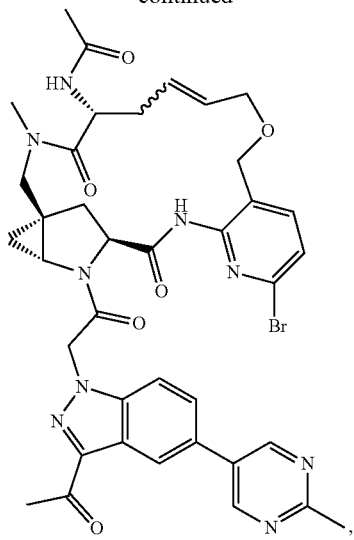
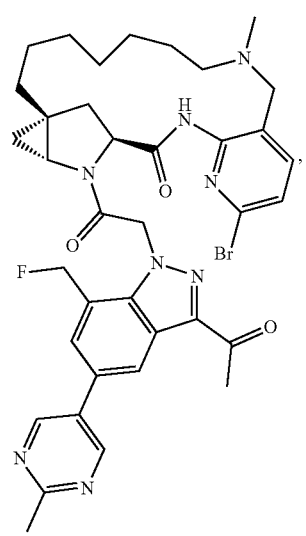
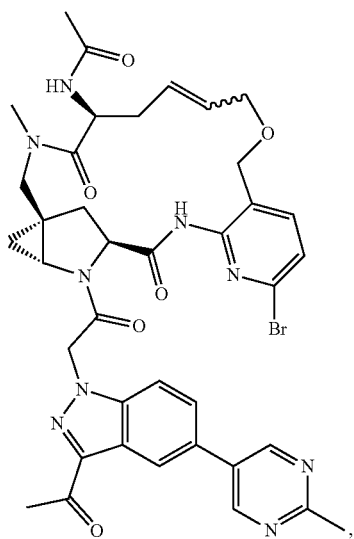

961
-continued
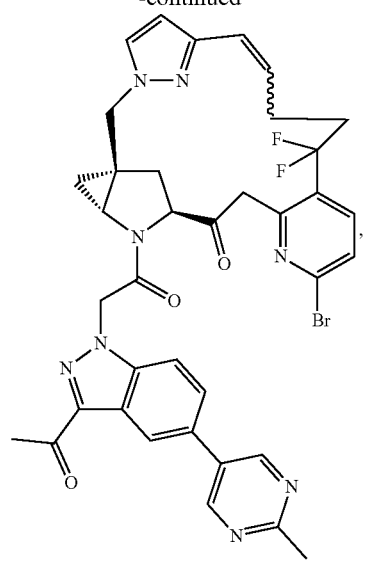
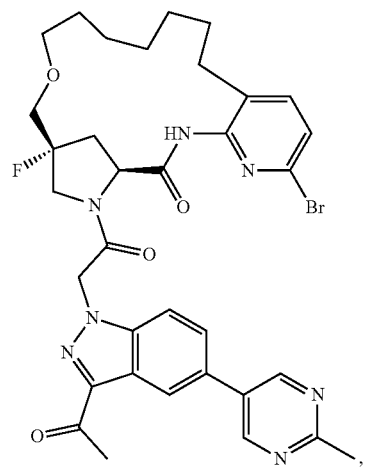
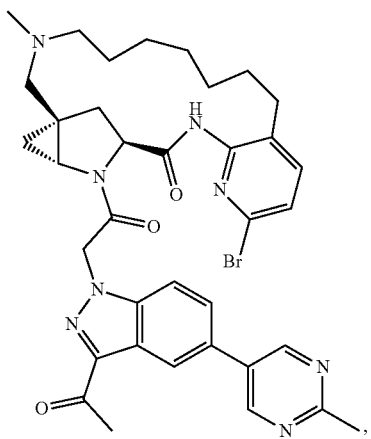
962
-continued
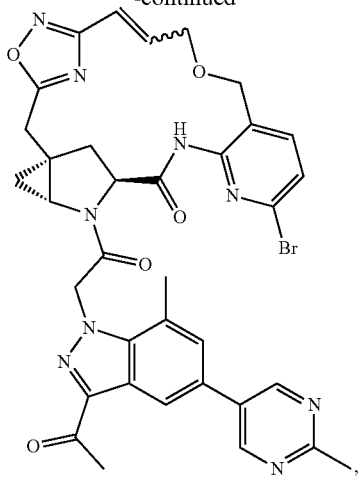
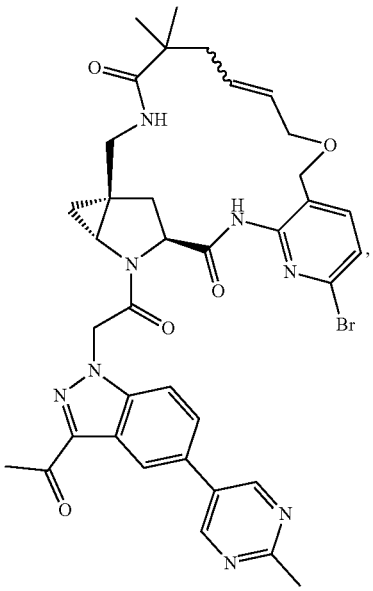
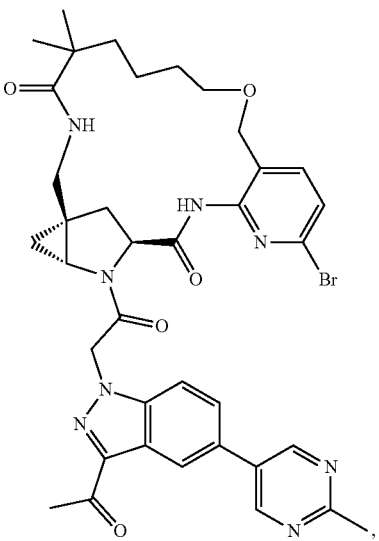

963
-continued
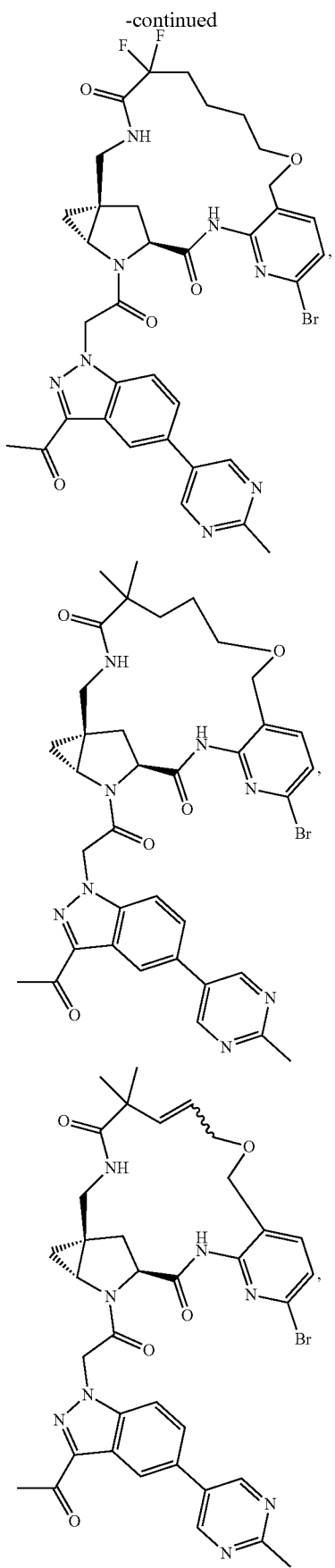
964
-continued
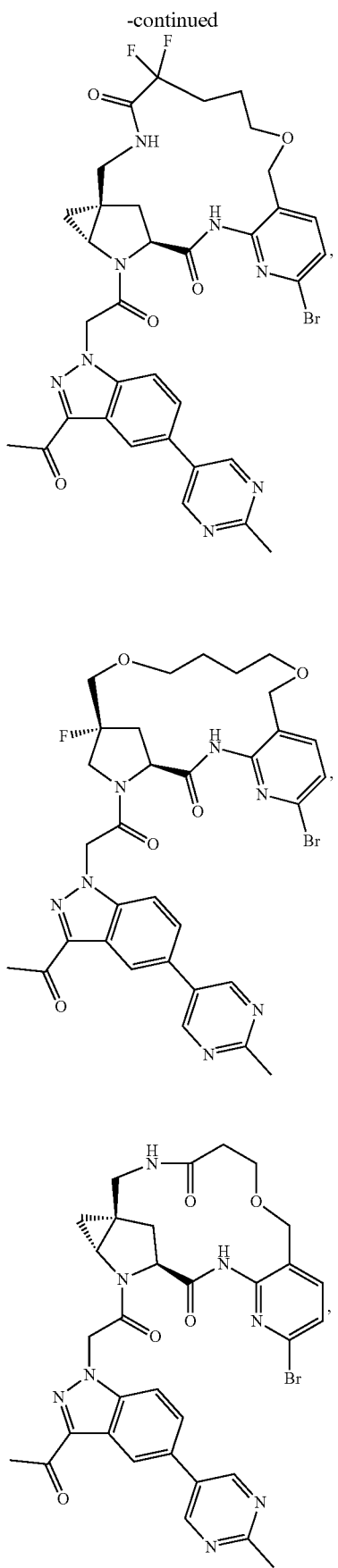

965
-continued

966
-continued

967
-continued
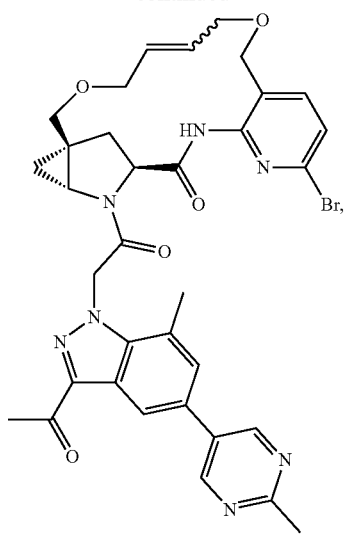
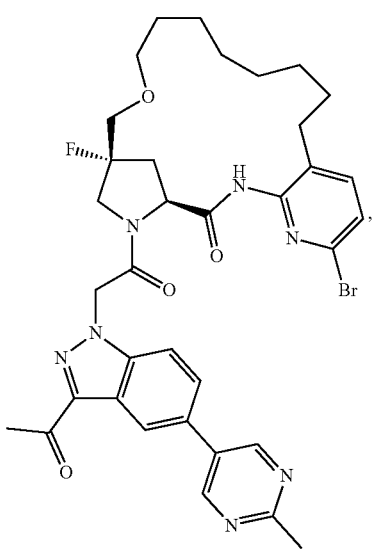
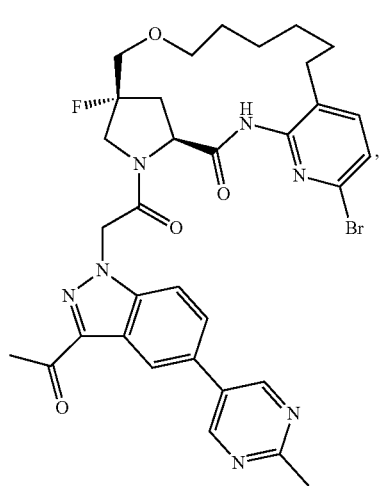
968
-continued
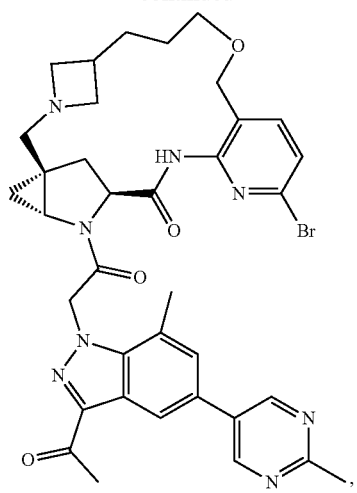
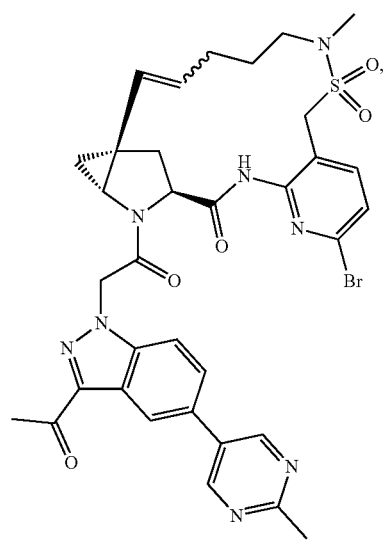
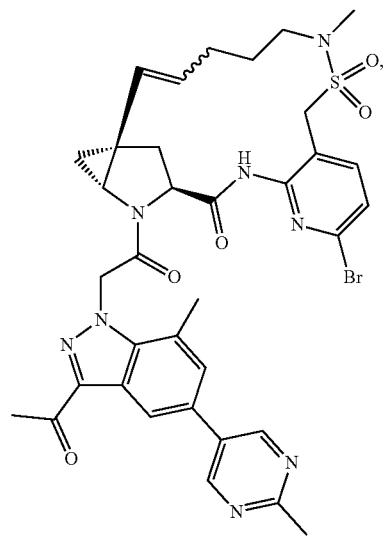

969

-continued

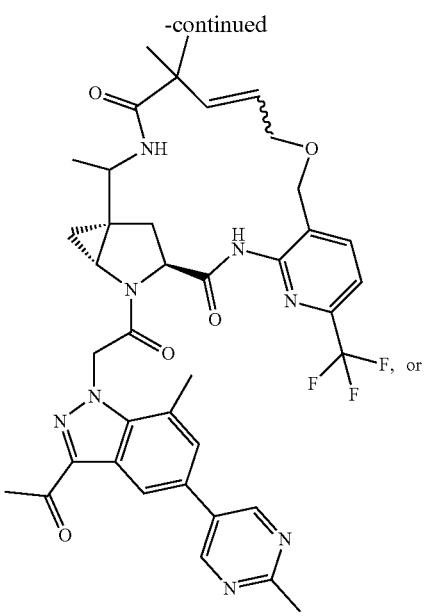

F, or

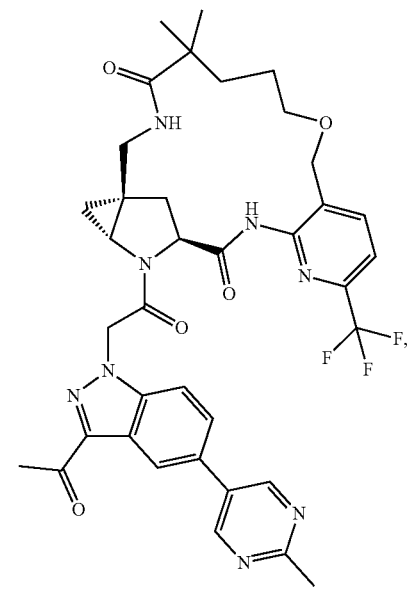 [SMILES: CC(=O)c1nn(CC(=O)N2[C@H]3C[C@@]4(CNC(=O)C(C)(C)CCCOCc5ccc(C(F)(F)F)nc5NC3=O)C[C@@H]24)c2ccc(-c3cnc(C)nc3)cc12]

or a pharmaceutically acceptable salt thereof.

970

7. The compound of claim 6, wherein the compound is

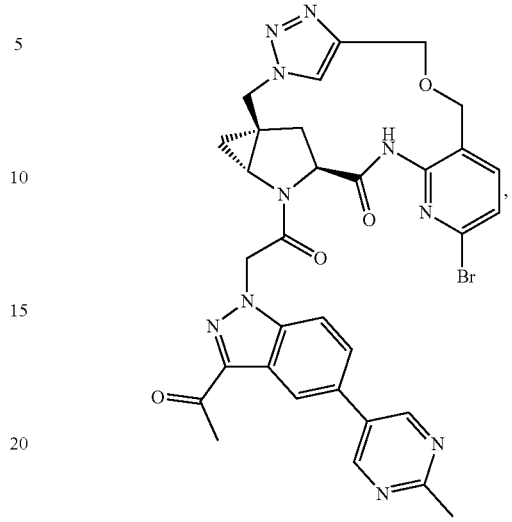

or a pharmaceutically acceptable salt thereof.

8. A pharmaceutical composition comprising a compound of claim 1 or a pharmaceutically acceptable salt thereof, and a pharmaceutically acceptable carrier.

9. A method of inhibiting complement factor D, comprising administering to a patient in need thereof an effective amount of the compound of claim 1 or a pharmaceutically acceptable salt thereof.

10. The method of claim 9, wherein the patient is human.

11. The method of claim 9, wherein the patient has a complement factor D disorder is selected from acute respiratory distress syndrome, age-related macular degeneration, arthritis, asthma, Alzheimer's dementia, amyotrophic lateral sclerosis, antibody-mediated transplant rejection, antineutrophil cytoplasm antibody-associated vasculitis, antiphospholipid syndrome, atypical or typical hemolytic uremic syndrome, cardiovascular disease, cold agglutinin disease, complement 3 glomerulopathy, chronic obstructive pulmonary disease, cirrhosis, Crohn's disease, C3 glomerulonephritis, diabetic retinopathy, dermatomyositis, dermatitis, epidermolysis bullosa acquisita, fatty liver, focal segmental glomerulosclerosis, geographic atrophy, glomerulonephritis, graft versus host disease, Guillain Barre syndrome, hemolytic anemia, hidradenitis suppurativa, IgA nephropathy, ischemia/reperfusion injury, liver failure, liver inflammation, lupus nephritis, membrane proliferative glomerulonephritis, multifocal motor neuropathy, multiple sclerosis, myasthenia gravis, neuromyelitis optica, nonalcoholic steatohepatitis, ocular disorder, ophthalmic disease, pancreatitis, paroxysmal nocturnal hemoglobinuria, pemphigoid, pemphigus vulgaris, pre-eclampsia, reduced glomerular filtration rate, renovascular disorder, respiratory disease, retinal detachment, rheumatoid arthritis, scleroderma, sepsis, Shiga toxin *E. coli*-related hemolytic uremic syndrome, spinal cord injury, sickle cell disease, traumatic brain injury, ulcerative colitis, and viral infection.

12. The method of claim 11, wherein the disorder is a renovascular disorder.

13. The method of claim 11, wherein the disorder is paroxysmal nocturnal hemoglobinuria.

14. The method of claim 11, wherein the disorder is an ophthalmic disease.

15. The method of claim 11, wherein the disorder is age-related macular degeneration or retinal degeneration.

16. The method of claim 11, wherein the disorder is geographic atrophy.

17. The method of claim 11, wherein the disorder is sickle cell disease.

18. The method of claim 11, wherein the disorder is myasthenia gravis.

19. The method of claim 11, wherein the disorder is lupus nephritis.

20. The method of claim 11, wherein the disorder is IgA nephropathy.

21. The method of claim 11, wherein the disorder is a viral infection.

\* \* \* \* \*

UNITED STATES PATENT AND TRADEMARK OFFICE
CERTIFICATE OF CORRECTION

Page 1 of 3

PATENT NO. : 11,718,626 B2
APPLICATION NO. : 17/314155
DATED : August 8, 2023
INVENTOR(S) : Jason Allan Wiles et al.

It is certified that error appears in the above-identified patent and that said Letters Patent is hereby corrected as shown below:

In the Claims

Column 937, Claim 1, Line 16 replace "$(C(R^2R^{2\prime})$" with --$C(R^2R^{2\prime})$--;
Line 17 replace "$C(R^3R^3)$" with --$C(R^3R^{3\prime})$--;
Line 18 replace "$C(R^1R^1)$" with --$C(R^1R^{1\prime})$--;
Line 23 replace "$R^{1\prime\prime}$" with --$R^{1\prime}$--;
Line 23 replace "$R^{2\prime\prime}$" with --$R^{2\prime}$--;
Line 23 replace "$R^{3\prime\prime}$" with --$R^{3\prime}$--.

Column 938, Claim 1, Line 29 replace "-$C(R^{52})_2$" with -- -$C(R^{52})_2$- --;
Line 58 replace "$R^6$ are independently is selected" with --$R^6$ is selected--;
Line 60 replace "—COON" with -- -COOH--;
Line 63 replace "$R^{8\prime\prime}$" with --$R^{8\prime}$--;
Line 67 replace "$R^{8\prime\prime}$" with --$R^{8\prime}$--.

Column 939, Claim 1, Line 1 replace "$R^{8\prime\prime}$" with --$R^{8\prime}$--;
Line 20 replace "—COON" with -- -COOH--;
Line 27 replace "—COON" with -- -COOH--;
Line 40 replace "$R^{18\prime\prime}$" with --$R^{18\prime}$--.

Column 940, Claim 1, Line 26 replace "—COON" with -- -COOH--;
Line 38 replace "—COON" with -- -COOH--;
Line 47 replace "-$JOP(O)(OR^{21}R^{22})$" with -- -$JOP(O)(OR^{21})R^{22}$--;
Line 54 replace "-$JC(O)NR^{21}SO_2R^{22}$" with -- -$JC(O)NR^{21}SO_2R^{22}$--;
Line 62 replace "—COON" with -- -COOH--.

Column 941, Claim 1, Line 23 replace "-$C_0$-$C_6$alkyl($C_3$-$C_7$cycloalkyl)" with -- -$C_0$-$C_4$alkyl($C_3$-$C_7$cycloalkyl)--;
Line 36 replace "—COON" with -- -COOH--.

Signed and Sealed this
Twenty-fourth Day of September, 2024

Katherine Kelly Vidal
*Director of the United States Patent and Trademark Office*

CERTIFICATE OF CORRECTION (continued)
U.S. Pat. No. 11,718,626 B2

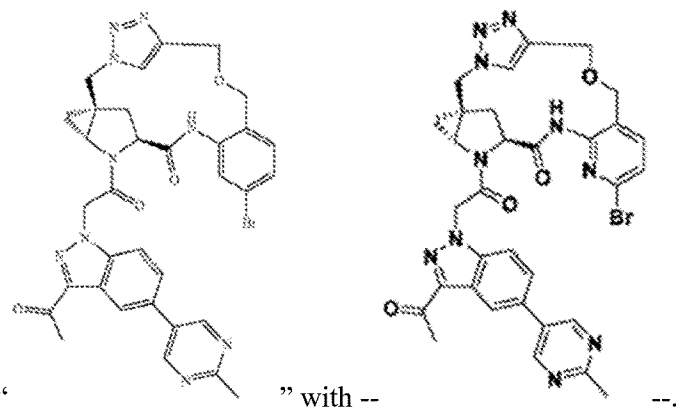

Column 952, Claim 6, Line 10 replace " " with -- --.

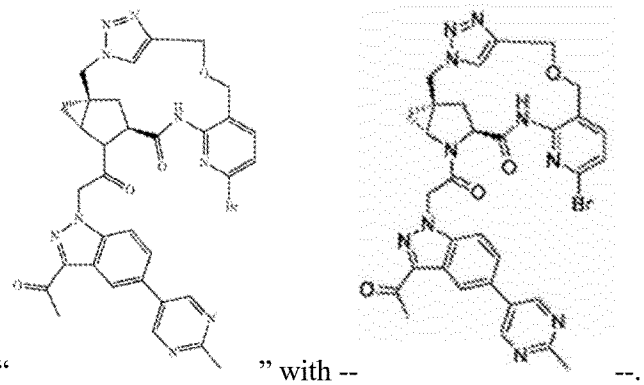

Column 953, Claim 6, Line 9 replace " " with -- --.

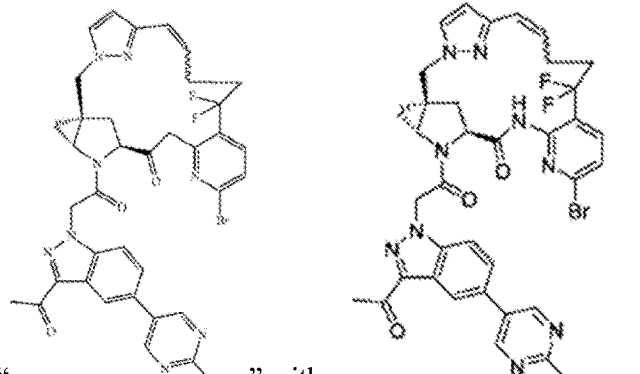

Column 961, Claim 6, Line 8 replace " " with -- --.

CERTIFICATE OF CORRECTION (continued)
U.S. Pat. No. 11,718,626 B2

Page 3 of 3

Column 969, Claim 6, Line 16 replace " 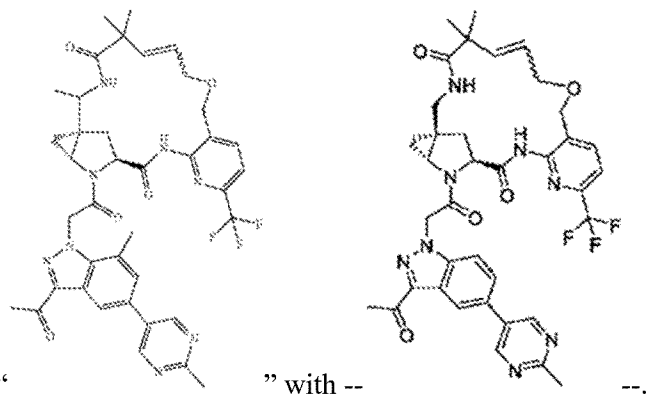 " with -- --.

Column 970, Claim 11, Line 36 replace "complement factor D disorder is selected from" with --complement factor D disorder selected from--.